United States Patent
Wu et al.

(10) Patent No.: US 12,195,465 B2
(45) Date of Patent: Jan. 14, 2025

(54) MACROCYCLIC HETEROCYCLES AND USES THEREOF

(71) Applicant: Kumquat Biosciences Inc., San Diego, CA (US)

(72) Inventors: Baogen Wu, San Diego, CA (US); Pingda Ren, San Diego, CA (US); Zhiyong Chen, San Diego, CA (US); Yi Liu, San Diego, CA (US)

(73) Assignee: Kumquat Biosciences Inc., San Diego, CA (US)

( * ) Notice: Subject to any disclaimer, the term of this patent is extended or adjusted under 35 U.S.C. 154(b) by 0 days.

(21) Appl. No.: 18/497,515

(22) Filed: Oct. 30, 2023

(65) Prior Publication Data

US 2024/0208975 A1 Jun. 27, 2024

Related U.S. Application Data

(63) Continuation of application No. 18/328,109, filed on Jun. 2, 2023, now Pat. No. 11,912,708, which is a continuation of application No. PCT/US2023/065963, filed on Apr. 19, 2023.

(60) Provisional application No. 63/486,922, filed on Feb. 24, 2023, provisional application No. 63/404,482, filed on Sep. 7, 2022, provisional application No. 63/332,794, filed on Apr. 20, 2022.

(51) Int. Cl.
| | | |
|---|---|---|
| *C07D 471/22* | (2006.01) | |
| *A61K 45/06* | (2006.01) | |
| *C07D 495/22* | (2006.01) | |
| *C07D 498/22* | (2006.01) | |

(52) U.S. Cl.
CPC ............ *C07D 471/22* (2013.01); *A61K 45/06* (2013.01); *C07D 495/22* (2013.01); *C07D 498/22* (2013.01)

(58) Field of Classification Search
CPC .. C07D 471/22; C07D 495/22; C07D 498/22; C07D 237/30; C07D 239/72; A61P 35/00
See application file for complete search history.

(56) References Cited

U.S. PATENT DOCUMENTS

| | | | | |
|---|---|---|---|---|
| 11,168,102 | B1 | 11/2021 | Gill et al. | |
| 11,648,254 | B2 * | 5/2023 | Wu ..................... | C07D 487/04 |
| | | | | 514/290 |
| 11,912,708 | B2 * | 2/2024 | Wu ..................... | C07D 495/22 |
| 2021/0139517 | A1 | 5/2021 | Gill et al. | |
| 2021/0188857 | A1 * | 6/2021 | Marx ................... | C07D 498/04 |
| 2023/0064360 | A1 | 3/2023 | Wu et al. | |
| 2023/0339952 | A1 | 10/2023 | Wu et al. | |

FOREIGN PATENT DOCUMENTS

| | | |
|---|---|---|
| CN | 106565684 A | 4/2017 |
| CN | 113801114 A | 12/2021 |
| CN | 114436976 A | 5/2022 |
| CN | 114539245 A | 5/2022 |
| EP | 3783000 A1 | 2/2021 |
| WO | WO-2005061497 A1 | 7/2005 |
| WO | WO-2011011522 A2 | 1/2011 |
| WO | WO-2014145512 A2 | 9/2014 |
| WO | WO-2015018797 A2 | 2/2015 |
| WO | WO-2018115380 A1 | 6/2018 |
| WO | WO-2018134685 A2 | 7/2018 |
| WO | WO-2018172250 A1 | 9/2018 |
| WO | WO-2019122129 A1 | 6/2019 |
| WO | WO-2019201848 A1 | 10/2019 |
| WO | WO-2019231271 A1 | 12/2019 |
| WO | WO-2020259513 A1 | 12/2020 |
| WO | WO-2021074227 A1 | 4/2021 |
| WO | WO-2021092115 A1 | 5/2021 |
| WO | WO-2021249519 A1 | 12/2021 |
| WO | WO-2022058344 A1 | 3/2022 |
| WO | WO-2022081912 A2 | 4/2022 |
| WO | WO-2022083657 A1 | 4/2022 |
| WO | WO-2022160931 A1 | 8/2022 |
| WO | WO-2022161461 A1 | 8/2022 |
| WO | WO-2022187411 A1 | 9/2022 |
| WO | WO-2022271562 A1 | 12/2022 |
| WO | WO-2023205701 | 10/2023 |

OTHER PUBLICATIONS

Co-pending U.S. Appl. No. 18/187,997, inventors Wu; Baogen et al., filed Mar. 22, 2023.
Co-pending U.S. Appl. No. 18/469,444, inventors Wu; Baogen et al., filed Sep. 18, 2023.
International Search Report and Written Opinion dated Jul. 12, 2023 for PCT/US2023/065963.
U.S. Appl. No. 18/328,109 Notice of Allowance dated Sep. 27, 2023.

\* cited by examiner

*Primary Examiner* — Theodore R. Howell
*Assistant Examiner* — George W Kosturko
(74) *Attorney, Agent, or Firm* — Wilson Sonsini Goodrich & Rosati

(57) ABSTRACT

The present disclosure provides compounds and pharmaceutically acceptable salt thereof, and methods of using the same. The compounds and methods have a range of utilities as therapeutics, diagnostics, and research tools. In particular, the subject compositions and methods are useful for reducing signaling output of oncogenic proteins.

21 Claims, No Drawings

Specification includes a Sequence Listing.

MACROCYCLIC HETEROCYCLES AND USES THEREOF

CROSS-REFERENCE

This application is a continuation of U.S. application Ser. No. 18/328,109, filed Jun. 2, 2023, which is a continuation of International Application No. PCT/US2023/065963, filed Apr. 19, 2023, which claims the benefit of U.S. Provisional Application No. 63/332,794, filed Apr. 20, 2022; U.S. Provisional Application No. 63/404,482, filed Sep. 7, 2022; and U.S. Provisional Application No. 63/486,922, filed Feb. 24, 2023, each incorporated herein by reference in its entirety.

SEQUENCE LISTING

The instant application contains a Sequence Listing which has been submitted electronically in XML format and is hereby incorporated by reference in its entirety. Said XML copy, created on Oct. 2, 2023, is named 56690_748_302_SL.xml and is 7,954 bytes in size.

BACKGROUND

Cancer (e.g., tumor, neoplasm, metastases) is the second leading cause of death worldwide estimated to be responsible for about 10 million deaths each year. Many types of cancers are marked with mutations in one or more proteins involved in various signaling pathways leading to unregulated growth of cancerous cells. In some cases, about 25 to 30 percent (%) of tumors are known to harbor Rat sarcoma (Ras) mutations.

Activated by guanine nucleotide exchange factors (GEFs), Ras in its GTP-bound state interacts with a number of effectors. Return to the inactive state is driven by GTPase-activating proteins (GAPs), which down-regulate active Ras by accelerating the weak intrinsic GTPase activity. For oncogenic Ras mutants, however, the GAP activity is impaired or greatly reduced, resulting in persistent activation, which drives the oncogenic Ras signaling through, e.g., the RAS-RAF-MEK-ERK and RAS-PI3K-PDK1-AKT pathways, both essential to cell survival and proliferation.

The most-studied GEF for Ras is the protein Son of Sevenless (SOS) for which two human isoforms, SOS1 and SOS2, are known. SOS1 is a human homologue of the originally identified *Drosophila* protein Son of Sevenless. SOS1 has two binding sites for Ras proteins; a catalytic site that binds GDP-bound Ras proteins to promote guanine nucleotide exchange and an allosteric site that binds GTP-bound Ras to further promote activation of Ras proteins. Son of Sevenless 2 (SOS2) is a homolog of SOS1 in mammalian cells. Double SOS1 and SOS2 knockout leads to rapid lethality in adult mice (Baltanas et al., Mol. Cell. Biol., 2013, 33(22):4562-78).

Ras proteins have long been considered to be "undruggable", due to, in part, high affinity to their substrate guanosine-5'-triphosphate (GTP) and/or their smooth surfaces without any obvious targeting region. A specific G12C Ras gene mutation has been identified as a druggable target to which a number of G12C specific inhibitors have been developed. However, such therapeutics are still of limited application, as the G12C mutation in Ras exhibits a much lower prevalence rate as compared to other known Ras mutations, including G12D and G12V. Drug resistance and lack of durability impose further limitations to such therapeutics.

SUMMARY

In view of the foregoing, there remains a considerable need for a new design of therapeutics and diagnostics that can specifically inhibit Ras pathway signaling by, e.g., inhibiting a GEF such as a SOS protein. Such compositions and methods can be particularly useful for treating a variety of the diseases including, but not limited to, cancers and neoplasia conditions. The present disclosure addresses these needs, and provides additional advantages applicable for diagnosis, prognosis, and treatment for a wide diversity of diseases.

In certain aspects, the present disclosure provides a compound of Formula (I):

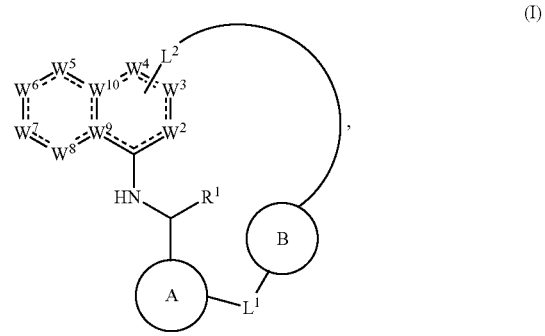

or a pharmaceutically acceptable salt or solvate thereof, wherein:

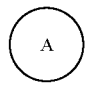

is selected from $C_{5-7}$ carbocycle and 5- to 7-membered heterocycle, each of which is optionally substituted with one or more $R^{11}$;

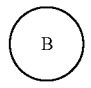

is absent or selected from $C_{3-8}$ carbocycle and 3- to 8-membered heterocycle, each of which is optionally substituted with one or more $R^{11a}$;

$L^1$ is selected from a bond, $C_{1-6}$ alkylene, and $C_{1-6}$ haloalkylene;

$L^2$ is selected from $C_{5-25}$ alkylene, $C_{5-25}$ alkenylene, $C_{5-25}$ alkynylene, 5- to 25-membered heteroalkylene, and 5- to 25-membered heteroalkenylene, each of which is optionally substituted with one or more $R^{11b}$, wherein $L^2$ is covalently bound to one of $W^3$, $W^4$, $W^5$, $W^6$, or $W^7$; or $L^2$ is $-L^3-D-L^4-$, wherein $L^4$ is covalently bound to one of $W^3$, $W^4$, $W^5$, $W^6$, or $W^7$;

$L^3$ is selected from $C_{1-10}$ alkylene, $C_{1-10}$ alkenylene, $C_{1-10}$ alkynylene, 2- to 10-membered heteroalkylene, and 2- to 10-membered heteroalkenylene, each of which is optionally substituted with one or more $R^{11b}$;

D is absent or selected from $C_{3-12}$ carbocycle and 3- to 12-membered heterocycle, each of which is optionally substituted with one or more $R^{11d}$;

$L^4$ is selected from $C_{1-10}$ alkylene, $C_{1-10}$ alkenylene, $C_{1-10}$ alkynylene, 2- to 10-membered heteroalkylene, and 2- to 10-membered heteroalkenylene, each of which is optionally substituted with one or more $R^{11b}$;

$W^2$ is selected from $N(R^{2b})$, N, $C(R^2)$, $C(R^2)(R^{2a})$, and $C(O)$;

$W^3$ is selected from $N(R^{3b})$, N, $C(R^3)$, $C(R^3)(R^{3a})$, and $C(O)$;

$W^4$ is selected from $N(R^{4b})$, N, $C(R^4)$, $C(R^4)(R^{4a})$, and $C(O)$;

$W^5$ is selected from $N(R^{5b})$, N, $C(R^5)$, $C(R^5)(R^{5a})$, and $C(O)$;

$W^6$ is selected from $N(R^{6b})$, N, $C(R^6)$, $C(R^6)(R^{6a})$, and $C(O)$;

$W^7$ is selected from $N(R^{7b})$, N, $C(R^7)$, $C(R^7)(R^{7a})$, and $C(O)$;

$W^8$ is selected from $N(R^{8b})$, N, $C(R^8)$, $C(R^8)(R^{8a})$, and $C(O)$;

$W^9$ is selected from N, $C(R^9)$, and C;

$W^{10}$ is selected from N, $C(R^{10})$, and C;

$R^1$ is $C_{1-3}$ alkyl optionally substituted with one or more $R^{11}$;

$R^2$, $R^{2a}$, $R^{3a}$, $R^{4a}$, $R^{5a}$, $R^{6a}$, $R^{7a}$, $R^8$, and $R^{8a}$ are each independently selected from hydrogen, halogen, —CN, $C_{1-6}$ alkyl, $C_{2-6}$ alkenyl, $C_{2-6}$ alkynyl, $C_{3-10}$ carbocycle, 3- to 10-membered heterocycle, —$OR^{12}$, —$SR^{12}$, —$N(R^{12})(R^{13})$, —$C(O)OR^{12}$, —$OC(O)N(R^{12})(R^{13})$, —$N(R^{14})C(O)N(R^{12})(R^{13})$, —$N(R^{14})C(O)OR^{15}$, —$N(R^{14})S(O)_2R^{15}$, —$C(O)R^{15}$, —$S(O)R^{15}$, —$OC(O)R^{15}$, —$C(O)N(R^{12})(R^{13})$, —$C(O)C(O)N(R^{12})(R^{13})$, —$N(R^{14})C(O)R^{15}$, —$S(O)_2R^{15}$, —$S(O)_2N(R^{12})(R^{13})$, —$S(=O)(=NH)N(R^{12})(R^{13})$, —$CH_2C(O)N(R^{12})(R^{13})$, —$CH_2N(R^{14})C(O)R^{15}$, —$CH_2S(O)_2R^{15}$, and —$CH_2S(O)_2N(R^{12})(R^{13})$, wherein each $C_{1-6}$ alkyl, $C_{2-6}$ alkenyl, $C_{2-6}$ alkynyl, $C_{3-10}$ carbocycle, and 3- to 10-membered heterocycle is independently optionally substituted with one, two, or three $R^{20}$;

$R^3$, $R^4$, $R^5$, $R^6$, and $R^7$ are each independently selected from a bond to $L^2$, hydrogen, halogen, —CN, $C_{1-6}$ alkyl, $C_{2-6}$ alkenyl, $C_{2-6}$ alkynyl, $C_{3-10}$ carbocycle, 3- to 10-membered heterocycle, —$OR^{12}$, —$SR^{12}$, —$N(R^{12})(R^{13})$, —$C(O)OR^{12}$, —$OC(O)N(R^{12})(R^{13})$, —$N(R^{14})C(O)N(R^{12})(R^{13})$, —$N(R^{14})C(O)OR^{15}$, —$N(R^{14})S(O)_2R^{15}$, —$C(O)R^{15}$, —$S(O)R^{15}$, —$OC(O)R^{15}$, —$C(O)N(R^{12})(R^{13})$, —$C(O)C(O)N(R^{12})(R^{13})$, —$N(R^{14})C(O)R^{15}$, —$S(O)_2R^{15}$, —$S(O)_2N(R^{12})(R^{13})$, —$S(=O)(=NH)N(R^{12})(R^{13})$, —$CH_2C(O)N(R^{12})(R^{13})$, —$CH_2N(R^{14})C(O)R^{15}$, —$CH_2S(O)_2R^{15}$, and —$CH_2S(O)_2N(R^{12})(R^{13})$, wherein each $C_{1-6}$ alkyl, $C_{2-6}$ alkenyl, $C_{2-6}$ alkynyl, $C_{3-10}$ carbocycle, and 3- to 10-membered heterocycle is independently optionally substituted with one, two, or three $R^{20}$;

$R^{2b}$ and $R^{8b}$ are each independently selected from hydrogen, —CN, $C_{1-6}$ alkyl, $C_{2-6}$ alkenyl, $C_{2-6}$ alkynyl, $C_{3-10}$ carbocycle, 3- to 10-membered heterocycle, —$OR^{12}$, —$SR^{12}$, —$C(O)OR^{12}$, —$OC(O)N(R^{12})(R^{13})$, —$C(O)R^{15}$, —$S(O)R^{15}$, —$OC(O)R^{15}$, —$C(O)N(R^{12})(R^{13})$, —$C(O)C(O)N(R^{12})(R^{13})$, —$S(O)_2R^{15}$, —$S(O)_2N(R^{12})(R^{13})$, —$S(=O)(=NH)N(R^{12})(R^{13})$, —$CH_2C(O)N(R^{12})(R^{13})$, —$CH_2N(R^{14})C(O)R^{15}$, —$CH_2S(O)_2R^{15}$, and —$CH_2S(O)_2N(R^{12})(R^{13})$, wherein each $C_{1-6}$ alkyl, $C_{2-6}$ alkenyl, $C_{2-6}$ alkynyl, $C_{3-10}$ carbocycle and 3- to 10-membered heterocycle is independently optionally substituted with one, two, or three $R^{20}$;

$R^{3b}$, $R^{4b}$, $R^{5b}$, $R^{6b}$, and $R^{7b}$ are each independently selected from a bond to $L^2$, hydrogen, —CN, $C_{1-6}$ alkyl, $C_{2-6}$ alkenyl, $C_{2-6}$ alkynyl, $C_{3-10}$ carbocycle, 3- to 10-membered heterocycle, —$OR^{12}$, —$SR^{12}$, —$C(O)OR^{12}$, —$OC(O)N(R^{12})(R^{13})$, —$C(O)R^{15}$, —$S(O)R^{15}$, —$OC(O)R^{15}$, —$C(O)N(R^{12})(R^{13})$, —$C(O)C(O)N(R^{12})(R^{13})$, —$S(O)_2R^{15}$, —$S(O)_2N(R^{12})(R^{13})$, —$S(=O)(=NH)N(R^{12})(R^{13})$, —$CH_2C(O)N(R^{12})(R^{13})$, —$CH_2N(R^{14})C(O)R^{15}$, —$CH_2S(O)_2R^{15}$, and —$CH_2S(O)_2N(R^{12})(R^{13})$, wherein each $C_{1-6}$ alkyl, $C_{2-6}$ alkenyl, $C_{2-6}$ alkynyl, $C_{3-10}$ carbocycle and 3- to 10-membered heterocycle is independently optionally substituted with one, two, or three $R^{20}$;

$R^9$ and $R^{10}$ are each independently selected from hydrogen, $C_{1-6}$ alkyl, $C_{2-6}$ alkenyl, $C_{2-6}$ alkynyl, $C_{3-10}$ carbocycle, —$CH_2$—($C_{3-10}$ carbocycle), 3- to 10-membered heterocycle, and —$CH_2$-(3- to 10-membered heterocycle), wherein each $C_{1-6}$ alkyl, $C_{2-6}$ alkenyl, $C_{2-6}$ alkynyl, $C_{3-10}$ carbocycle, —$CH_2$—($C_{3-10}$ carbocycle), 3- to 10-membered heterocycle, and —$CH_2$-(3- to 10-membered heterocycle) is independently optionally substituted with one, two, or three $R^{20}$;

$R^{11}$, $R^{11a}$, and $R^{11d}$ are each independently selected at each occurrence from halogen, —CN, $C_{1-6}$ alkyl, $C_{2-6}$ alkenyl, $C_{2-6}$ alkynyl, $C_{3-10}$ carbocycle, 3- to 10-membered heterocycle, —$OR^{12}$, —$SR^{12}$, —$N(R^{12})(R^{13})$, —$C(O)OR^{12}$, —$OC(O)N(R^{12})(R^{13})$, —$N(R^{14})C(O)N(R^{12})(R^{13})$, —$N(R^{14})C(O)OR^{15}$, —$N(R^{14})S(O)_2R^{15}$, —$C(O)R^{15}$, —$S(O)R^{15}$, —$OC(O)R^{15}$, —$C(O)N(R^{12})(R^{13})$, —$C(O)C(O)N(R^{12})(R^{13})$, —$N(R^{14})C(O)R^{15}$, —$S(O)_2R^{15}$, —$S(O)_2N(R^{12})(R^{13})$, —$S(=O)(=NH)N(R^{12})(R^{13})$, —$CH_2C(O)N(R^{12})(R^{13})$, —$CH_2N(R^{14})C(O)R^{15}$, —$CH_2S(O)_2R^{15}$, —$CH_2S(O)_2N(R^{12})(R^{13})$, —$CH_2N(R^{12})S(O)_2(R^{13})$, and —$P(O)(R^{17})(R^{17a})$, wherein $C_{1-6}$ alkyl, $C_{2-6}$ alkenyl, $C_{2-6}$ alkynyl, $C_{3-10}$ carbocycle, and 3- to 10-membered heterocycle are optionally substituted with one, two, or three $R^{20}$;

$R^{11b}$ is independently selected at each occurrence from halogen, oxo, —CN, $C_{1-6}$ alkyl, $C_{2-6}$ alkenyl, $C_{2-6}$ alkynyl, $C_{3-10}$ carbocycle, 3- to 10-membered heterocycle, —$OR^{12}$, —$SR^{12}$, —$N(R^{12})(R^{13})$, —$C(O)OR^{12}$, —$OC(O)N(R^{12})(R^{13})$, —$N(R^{14})C(O)N(R^{12})(R^{13})$, —$N(R^{14})C(O)OR^{15}$, —$N(R^{14})S(O)_2R^{15}$, —$C(O)R^{15}$, —$S(O)R^{15}$, —$OC(O)R^{15}$, —$C(O)N(R^{12})(R^{13})$, —$C(O)C(O)N(R^{12})(R^{13})$, —$N(R^{14})C(O)R^{15}$, —$S(O)_2R^{15}$, —$S(O)_2N(R^{12})(R^{13})$, —$S(=O)(=NH)N(R^{12})(R^{13})$, —$CH_2C(O)N(R^{12})(R^{13})$, —$CH_2N(R^{14})C(O)R^{15}$, —$CH_2S(O)_2R^{15}$, —$CH_2S(O)_2N(R^{12})(R^{13})$, —$CH_2N(R^{12})S(O)_2(R^{13})$, and —$P(O)(R^{17})(R^{17a})$, wherein $C_{1-6}$ alkyl, $C_{2-6}$ alkenyl, $C_{2-6}$ alkynyl, $C_{3-10}$ carbocycle, and 3- to 10-membered heterocycle are optionally substituted with one, two, or three $R^{20}$;

$R^{11c}$ is independently selected at each occurrence from halogen, —$OR^{12}$, and —$N(R^{12})(R^{13})$;

$R^{12}$ is independently selected at each occurrence from hydrogen, $C_{1-6}$ alkyl, $C_{1-6}$ haloalkyl, $C_{2-6}$ alkenyl, $C_{2-6}$ alkynyl, $C_{3-10}$ carbocycle, and 3- to 10-membered heterocycle, wherein $C_{1-6}$ alkyl, $C_{2-6}$ alkenyl, $C_{2-6}$ alkynyl, $C_{3-10}$ carbocycle, and 3- to 10-membered heterocycle are optionally substituted with one, two, or three $R^{20}$;

$R^{13}$ is independently selected at each occurrence from hydrogen, $C_{1-6}$ alkyl, and $C_{1-6}$ haloalkyl; or $R^{12}$ and $R^{13}$, together with the nitrogen atom to which they are attached, form a 3- to 10-membered heterocycle optionally substituted with one, two, or three $R^{20}$;

$R^{14}$ is independently selected at each occurrence from hydrogen, $C_{1-6}$ alkyl, and $C_{1-6}$ haloalkyl;

$R^{15}$ is independently selected at each occurrence from $C_{1-6}$ alkyl, $C_{2-6}$ alkenyl, $C_{2-6}$ alkynyl, $C_{3-10}$ carbocycle, and 3- to 10-membered heterocycle, wherein $C_{1-6}$ alkyl, $C_{2-6}$ alkenyl, $C_{2-6}$ alkynyl, $C_{3-10}$ carbocycle, and 3- to 10-membered heterocycle are optionally substituted with one, two, or three $R^{20}$;

$R^{17}$ and $R^{17a}$ are each independently selected at each occurrence from $C_{1-6}$ alkyl and $C_{3-6}$ cycloalkyl, wherein $C_{1-6}$ alkyl and $C_{3-6}$ cycloalkyl are optionally substituted with one, two or three $R^{20}$; or $R^{17}$ and $R^{17a}$, together with the phosphorous atom to which they are attached, form a 3- to 10-membered heterocycle;

$R^{20}$ is independently selected at each occurrence from halogen, oxo, =NH, —CN, $C_{1-6}$ alkyl, $C_{2-6}$ alkenyl, $C_{2-6}$ alkynyl, $C_{3-10}$ carbocycle, —CH$_2$—($C_{3-10}$ carbocycle), 3- to 10-membered heterocycle, —CH$_2$-(3- to 10-membered heterocycle), —OR$^{21}$, —SR$^{21}$, —N(R$^{22}$)(R$^{23}$), —C(O)OR$^{22}$, —C(O)N(R$^{22}$)(R$^{23}$), —C(O)C(O)N(R$^{22}$)(R$^{23}$), —OC(O)N(R$^{22}$)(R$^{23}$), —N(R$^{22}$)C(O)N(R$^{22}$)(R$^{23}$), —N(R$^{24}$)C(O)OR$^{25}$, —N(R$^{24}$)C(O)R$^{25}$, —N(R$^{22}$)S(O)$_2$R$^{25}$, —C(O)R$^{25}$, —S(O)$_2$R$^{25}$, —S(O)$_2$N(R$^{22}$)(R$^{23}$), —OCH$_2$C(O)OR$^{22}$, and —OC(O)R$^{25}$, wherein $C_{1-6}$ alkyl, $C_{2-6}$ alkenyl, $C_{2-6}$ alkynyl, $C_{3-10}$ carbocycle, —CH$_2$—($C_{3-10}$ carbocycle), 3- to 10-membered heterocycle, and —CH$_2$-(3- to 10-membered heterocycle) are optionally substituted with one, two, or three groups independently selected from halogen, oxo, =NH, —CN, $C_{1-6}$ alkyl, $C_{1-6}$ haloalkyl, $C_{1-6}$ alkoxy, $C_{1-6}$ haloalkoxy, —OR$^{21}$, —SR$^{21}$, —N(R$^{22}$)(R$^{23}$), —C(O)OR$^{22}$, —C(O)N(R$^{22}$)(R$^{23}$), —C(O)C(O)N(R$^{22}$)(R$^{23}$), —OC(O)N(R$^{22}$)(R$^{23}$), —N(R$^{24}$)C(O)N(R$^{22}$)(R$^{23}$), —N(R$^{24}$)C(O)OR$^{25}$, —N(R$^{24}$)C(O)R$^{25}$, —N(R$^{22}$)S(O)$_2$R$^{25}$, —C(O)R$^{25}$, —S(O)$_2$R$^{25}$, —S(O)$_2$N(R$^{22}$)(R$^{23}$), and —OC(O)R$^{25}$;

$R^{21}$ is independently selected at each occurrence from H, $C_{1-6}$ alkyl, $C_{1-6}$ haloalkyl, $C_{2-6}$ alkenyl, $C_{2-6}$ alkynyl, $C_{3-10}$ carbocycle, and 3- to 10-membered heterocycle, wherein $C_{3-10}$ carbocycle and 3- to 10-membered heterocycle are optionally substituted with one, two, or three groups independently selected from halogen and $C_{1-6}$ alkyl;

$R^{22}$ is independently selected at each occurrence from H, $C_{1-6}$ alkyl, $C_{1-6}$ haloalkyl, $C_{2-6}$ alkenyl, $C_{2-6}$ alkynyl, $C_{3-10}$ carbocycle, and 3- to 10-membered heterocycle, wherein $C_{3-10}$ carbocycle and 3- to 10-membered heterocycle are optionally substituted with one, two, or three groups independently selected from halogen and $C_{1-6}$ alkyl;

$R^{23}$ is independently selected at each occurrence from H and $C_{1-6}$ alkyl;

$R^{4}$ is independently selected at each occurrence from H and $C_{1-6}$ alkyl;

$R^{25}$ is independently selected at each occurrence from $C_{1-6}$ alkyl, $C_{2-6}$ alkenyl, $C_{2-6}$ alkynyl, $C_{3-10}$ carbocycle, and 3- to 10-membered heterocycle, wherein $C_{1-6}$ alkyl, $C_{3-10}$ carbocycle, and 3- to 10-membered heterocycle are optionally substituted with one, two, or three groups independently selected from halogen, $C_{1-6}$ alkyl, $C_{1-6}$ haloalkyl, $C_{1-6}$ alkoxy, $C_{3-10}$ carbocycle, and 3- to 10-membered heterocycle; and ----- indicates a single or double bond such that all valences are satisfied.

In certain aspects, the present disclosure provides a compound of Formula (I):

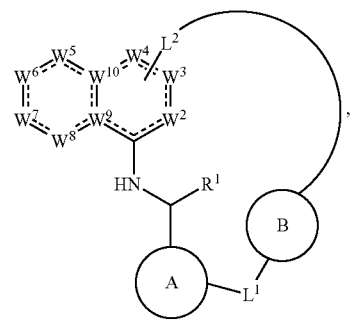

or a pharmaceutically acceptable salt or solvate thereof, wherein:

is selected from $C_{5-7}$ carbocycle and 5- to 7-membered heterocycle, each of which is optionally substituted with one or more $R^{11}$;

is absent or selected from $C_{3-8}$ carbocycle and 3- to 8-membered heterocycle, each of which is optionally substituted with one or more $R^{11a}$;

$L^1$ is selected from a bond, $C_{1-6}$ alkylene, and $C_{1-6}$ haloalkylene;

$L^2$ is selected from $C_{5-25}$ alkylene, $C_{5-25}$ alkenylene, $C_{5-25}$ alkynylene, 5- to 25-membered heteroalkylene, and 5- to 25-membered heteroalkenylene, each of which is optionally substituted with one or more $R^{11b}$, wherein $L^2$ is covalently bound to one of $W^3$, $W^4$, $W^5$, $W^6$, or $W^7$.

$W^2$ is selected from N(R$^{2b}$), N, C(R$^2$), C(R$^2$)(R$^{2a}$), and C(O);

$W^3$ is selected from N(R$^{3b}$), N, C(R$^3$), C(R$^3$)(R$^{3a}$), and C(O);

$W^4$ is selected from N(R$^{4b}$), N, C(R$^4$), C(R$^4$)(R$^{4a}$), and C(O);

$W^5$ is selected from N(R$^{5b}$), N, C(R$^5$), C(R$^5$)(R$^{5a}$), and C(O);

$W^6$ is selected from N(R$^{6b}$), N, C(R$^6$), C(R$^6$)(R$^{6a}$), and C(O);

$W^7$ is selected from N(R$^{7b}$), N, C(R$^7$), C(R$^7$)(R$^{7a}$), and C(O);

$W^8$ is selected from N(R$^{8b}$), N, C(R$^8$), C(R$^8$)(R$^{8a}$), and C(O);

$W^9$ is selected from N, C(R$^9$), and C;

$W^{10}$ is selected from N, C(R$^{10}$), and C;

$R^1$ is $C_{1-3}$ alkyl optionally substituted with one or more $R^{11}$;

$R^2$, $R^{2a}$, $R^{3a}$, $R^{4a}$, $R^{5a}$, $R^{6a}$, $R^{7a}$, $R^8$, and $R^{8a}$ are each independently selected from hydrogen, halogen, CN, $C_{1-6}$ alkyl, $C_{2-6}$ alkenyl, $C_{2-6}$ alkynyl, $C_{3-10}$ carbocycle, 3- to 10-membered heterocycle, —OR$^{12}$, —SR$^{12}$, —N(R$^{12}$)(R$^{13}$), —C(O)OR$^{12}$, —OC(O)N(R$^{12}$)(R$^{13}$), —N(R$^{14}$)C(O)N(R$^{12}$)(R$^{13}$), —N(R$^{14}$)C(O)R$^{15}$, —N(R$^{14}$)S(O)$_2$R$^{15}$, —C(O)R$^{15}$, —S(O)R$^{15}$, —OC(O)R$^{15}$, —C(O)N(R$^{12}$)(R$^{13}$), —C(O)C(O)N(R$^{12}$)(R$^{13}$), —N(R$^{14}$)C(O)R$^{15}$, —S(O)$_2$R$^{15}$, —S(O)$_2$N(R$^{12}$)(R$^{13}$), —S(=O)(=NH)N(R$^{12}$)(R$^{13}$), —CH$_2$C(O)N(R$^{12}$)(R$^{13}$), —CH$_2$N(R$^{14}$)C(O)R$^{15}$, —CH$_2$S(O)$_2$R$^{15}$, and —CH$_2$S(O)$_2$N(R$^{12}$)(R$^{13}$), wherein each C$_{1-6}$ alkyl, C$_{2-6}$ alkenyl, C$_{2-6}$ alkynyl, C$_{3-10}$ carbocycle, and 3- to 10-membered heterocycle is independently optionally substituted with one, two, or three R$^{20}$;

R$^3$, R$^4$, R$^5$, R$^6$, and R$^7$ are each independently selected from a bond to L$^2$, hydrogen, halogen, —CN, C$_{1-6}$ alkyl, C$_{2-6}$ alkenyl, C$_{2-6}$ alkynyl, C$_{3-10}$ carbocycle, 3- to 10-membered heterocycle, —OR$^{12}$, —SR$^{12}$, —N(R$^{12}$)(R$^{13}$), —C(O)OR$^{12}$, —OC(O)N(R$^{12}$)(R$^{13}$), —N(R$^{14}$)C(O)N(R$^{12}$)(R$^{13}$), —N(R$^{14}$)C(O)OR$^{15}$, —N(R$^{14}$)S(O)$_2$R$^{15}$, —C(O)R$^{15}$, —S(O)R$^{15}$, —OC(O)R$^{15}$, —C(O)N(R$^{12}$)(R$^{13}$), —C(O)C(O)N(R$^{12}$)(R$^{13}$), —N(R$^{14}$)C(O)R$^{15}$, —S(O)$_2$R$^{15}$, —S(O)$_2$N(R$^{12}$)(R$^{13}$), —S(=O)(=NH)N(R$^{12}$)(R$^{13}$), —CH$_2$C(O)N(R$^{12}$)(R$^{13}$), —CH$_2$N(R$^{14}$)C(O)R$^{15}$, —CH$_2$S(O)$_2$R$^{15}$, and —CH$_2$S(O)$_2$N(R$^{12}$)(R$^{13}$), wherein each C$_{1-6}$ alkyl, C$_{2-6}$ alkenyl, C$_{2-6}$ alkynyl, C$_{3-10}$ carbocycle, and 3- to 10-membered heterocycle is independently optionally substituted with one, two, or three R$^{20}$;

R$^{2b}$ and R$^{8b}$ are each independently selected from hydrogen, —CN, C$_{1-6}$ alkyl, C$_{2-6}$ alkenyl, C$_{2-6}$ alkynyl, C$_{3-10}$ carbocycle, 3- to 10-membered heterocycle, —OR$^{12}$, —SR$^{12}$, —C(O)OR$^{12}$, —OC(O)N(R$^{12}$)(R$^{13}$), —C(O)R$^{15}$, —S(O)R$^{15}$, —OC(O)R$^{15}$, —C(O)N(R$^{12}$)(R$^{13}$), —C(O)C(O)N(R$^{12}$)(R$^{13}$), —S(O)$_2$R$^{15}$, —S(O)$_2$N(R$^{12}$)(R$^{13}$), —S(=O)(=NH)N(R$^{12}$)(R$^{13}$), —CH$_2$C(O)N(R$^{12}$)(R$^{13}$), —CH$_2$N(R$^{14}$)C(O)R$^{15}$, —CH$_2$S(O)$_2$R$^{15}$, and —CH$_2$S(O)$_2$N(R$^{12}$)(R$^{13}$), wherein each C$_{1-6}$ alkyl, C$_{2-6}$ alkenyl, C$_{2-6}$ alkynyl, C$_{3-10}$ carbocycle and 3- to 10-membered heterocycle is independently optionally substituted with one, two, or three R$^{20}$;

R$^{3b}$, R$^{4b}$, R$^{5b}$, R$^{6b}$, and R$^{7b}$ are each independently selected from a bond to L$^2$, hydrogen, —CN, C$_{1-6}$ alkyl, C$_{2-6}$ alkenyl, C$_{2-6}$ alkynyl, C$_{3-10}$ carbocycle, 3- to 10-membered heterocycle, —OR$^{12}$, —SR$^{12}$, —C(O)OR$^{12}$, —OC(O)N(R$^{12}$)(R$^{13}$), —C(O)R$^{15}$, —S(O)R$^{15}$, —OC(O)R$^{15}$, —C(O)N(R$^{12}$)(R$^{13}$), —C(O)C(O)N(R$^{12}$)(R$^{13}$), —S(O)$_2$R$^{15}$, —S(O)$_2$N(R$^{12}$)(R$^{13}$), —S(=O)(=NH)N(R$^{12}$)(R$^{13}$), —CH$_2$C(O)N(R$^{12}$)(R$^{13}$), —CH$_2$N(R$^{14}$)C(O)R$^{15}$, —CH$_2$S(O)$_2$R$^{15}$, and —CH$_2$S(O)$_2$N(R$^{12}$)(R$^{13}$), wherein each C$_{1-6}$ alkyl, C$_{2-6}$ alkenyl, C$_{2-6}$ alkynyl, C$_{3-10}$ carbocycle and 3- to 10-membered heterocycle is independently optionally substituted with one, two, or three R$^{20}$;

R$^9$ and R$^{10}$ are each independently selected from hydrogen, C$_{1-6}$ alkyl, C$_{2-6}$ alkenyl, C$_{2-6}$ alkynyl, C$_{3-10}$ carbocycle, —CH$_2$—(C$_{3-10}$ carbocycle), 3- to 10-membered heterocycle, and —CH$_2$-(3- to 10-membered heterocycle), wherein each C$_{1-6}$ alkyl, C$_{2-6}$ alkenyl, C$_{2-6}$ alkynyl, C$_{3-10}$ carbocycle, —CH$_2$—(C$_{3-10}$ carbocycle), 3- to 10-membered heterocycle, and —CH$_2$-(3- to 10-membered heterocycle) is independently optionally substituted with one, two, or three R$^{20}$;

R$^{11}$ and R$^{11a}$ are each independently selected at each occurrence from halogen, —CN, C$_{1-6}$ alkyl, C$_{2-6}$ alkenyl, C$_{2-6}$ alkynyl, C$_{3-10}$ carbocycle, 3- to 10-membered heterocycle, —OR$^{12}$, —SR$^{12}$, —N(R$^{12}$)(R$^{13}$), —C(O)OR$^{12}$, —OC(O)N(R$^{12}$)(R$^{13}$), —N(R$^{14}$)C(O)N(R$^{12}$)(R$^{13}$), —N(R$^{14}$)C(O)OR$^{15}$, —N(R$^{14}$)S(O)$_2$R$^{15}$, —C(O)R$^{15}$, —S(O)R$^{15}$, —OC(O)R$^{15}$, —C(O)N(R$^{12}$)(R$^{13}$), —C(O)C(O)N(R$^{12}$)(R$^{13}$), —N(R$^{14}$)C(O)R$^{15}$, —S(O)$_2$R$^{15}$, —S(O)$_2$N(R$^{12}$)(R$^{13}$), —S(=O)(=Ni)N(R$^{12}$)(R$^{13}$), —CH$_2$C(O)N(R$^{12}$)(R$^{13}$), —CH$_2$N(R$^{14}$)C(O)R$^{15}$, —CH$_2$S(O)$_2$R$^{15}$, —CH$_2$S(O)$_2$N(R$^{12}$)(R$^{13}$), —CH$_2$N(R$^{12}$)S(O)$_2$(R$^{13}$), and —P(O)(R$^{17}$)(R$^{17a}$), wherein C$_{1-6}$ alkyl, C$_{2-6}$ alkenyl, C$_{2-6}$ alkynyl, C$_{3-10}$ carbocycle, and 3- to 10-membered heterocycle are optionally substituted with one, two, or three R$^{20}$;

R$^{11b}$ is independently selected at each occurrence from halogen, oxo, —CN, C$_{1-6}$ alkyl, C$_{2-6}$ alkenyl, C$_{2-6}$ alkynyl, C$_{3-10}$ carbocycle, 3- to 10-membered heterocycle, —OR$^{12}$, —SR$^{12}$, —N(R$^{12}$)(R$^{13}$), —C(O)OR$^{12}$, —OC(O)N(R$^{12}$)(R$^{13}$), —N(R$^{14}$)C(O)N(R$^{12}$)(R$^{13}$), —N(R$^{14}$)C(O)OR$^{15}$, —N(R$^{14}$)S(O)$_2$R$^{15}$, —C(O)R$^{15}$, —S(O)R$^{15}$, —OC(O)R$^{15}$, —C(O)N(R$^{12}$)(R$^{13}$), —C(O)C(O)N(R$^{12}$)(R$^{13}$), —N(R$^{14}$)C(O)R$^{15}$, —S(O)$_2$R$^{15}$, —S(O)$_2$N(R$^{12}$)(R$^{13}$), —S(=O)(=NH)N(R$^{12}$)(R$^{13}$), —CH$_2$C(O)N(R$^{12}$)(R$^{13}$), —CH$_2$N(R$^{14}$)C(O)R$^{15}$, —CH$_2$S(O)$_2$R$^{15}$, —CH$_2$S(O)$_2$N(R$^{12}$)(R$^{13}$), —CH$_2$N(R$^{12}$)S(O)$_2$(R$^{13}$), and —P(O)(R$^{17}$)(R$^{17a}$), wherein C$_{1-6}$ alkyl, C$_{2-6}$ alkenyl, C$_{2-6}$ alkynyl, C$_{3-10}$ carbocycle, and 3- to 10-membered heterocycle are optionally substituted with one, two, or three R$^{20}$;

R$^{11c}$ is independently selected at each occurrence from halogen, —OR$^{12}$, and —N(R$^{12}$)(R$^{13}$);

R$^{12}$ is independently selected at each occurrence from hydrogen, C$_{1-6}$ alkyl, C$_{1-6}$ haloalkyl, C$_{2-6}$ alkenyl, C$_{2-6}$ alkynyl, C$_{3-10}$ carbocycle, and 3- to 10-membered heterocycle, wherein C$_{1-6}$ alkyl, C$_{2-6}$ alkenyl, C$_{2-6}$ alkynyl, C$_{3-10}$ carbocycle, and 3- to 10-membered heterocycle are optionally substituted with one, two, or three R$^{20}$;

R$^{13}$ is independently selected at each occurrence from hydrogen, C$_{1-6}$ alkyl, and C$_{1-6}$ haloalkyl; or R$^{12}$ and R$^{13}$, together with the nitrogen atom to which they are attached, form a 3- to 10-membered heterocycle optionally substituted with one, two, or three R$^{20}$;

R$^{14}$ is independently selected at each occurrence from hydrogen, C$_{1-6}$ alkyl, and C$_{1-6}$ haloalkyl;

R$^{15}$ is independently selected at each occurrence from C$_{1-6}$ alkyl, C$_{2-6}$ alkenyl, C$_{2-6}$ alkynyl, C$_{3-10}$ carbocycle, and 3- to 10-membered heterocycle, wherein C$_{1-6}$ alkyl, C$_{2-6}$ alkenyl, C$_{2-6}$ alkynyl, C$_{3-10}$ carbocycle, and 3- to 10-membered heterocycle are optionally substituted with one, two, or three R$^{20}$;

R$^{17}$ and R$^{17a}$ are each independently at each occurrence from C$_{1-6}$ alkyl and C$_{3-6}$ cycloalkyl, wherein C$_{1-6}$ alkyl and C$_{3-6}$ cycloalkyl are optionally substituted with one, two or three R$^{20}$; or R$^{17}$ and R$^{17a}$, together with the phosphorous atom to which they are attached, form a 3- to 10-membered heterocycle;

R$^{20}$ is independently selected at each occurrence from halogen, oxo, =NH, —CN, C$_{1-6}$ alkyl, C$_{2-6}$ alkenyl, C$_{2-6}$ alkynyl, C$_{3-10}$ carbocycle, —CH$_2$—(C$_{3-10}$ carbocycle), 3- to 10-membered heterocycle, —CH$_2$-(3- to 10-membered heterocycle), —OR$^{21}$, —SR$^{21}$, —N(R$^{22}$)(R$^{23}$), —C(O)OR$^{22}$, —C(O)N(R$^{22}$)(R$^{23}$), —C(O)C(O)N(R$^{22}$)(R$^{23}$), —OC(O)N(R$^{22}$)(R$^{23}$), —N(R$^{22}$)C(O)N(R$^{22}$)(R$^{23}$), —N(R$^{24}$)C(O)OR$^{25}$, —N(R$^{24}$)C(O)R$^{25}$, —N(R$^{22}$)S(O)$_2$R$^{25}$, —C(O)R$^{25}$, —S(O)$_2$R$^{25}$, —S(O)$_2$N(R$^{22}$)(R$^{23}$), —OCH$_2$C(O)OR$^{22}$, and —OC(O)R$^{25}$, wherein C$_{1-6}$ alkyl, C$_{2-6}$ alkenyl, C$_{2-6}$ alkynyl, C$_{3-10}$ carbocycle, —CH$_2$—(C$_{3-10}$ carbocycle), 3- to 10-membered heterocycle, and —CH$_2$-(3- to 10-membered heterocycle) are optionally substituted with one, two, or three groups independently selected from halogen, oxo, =NH, —CN, C$_{1-6}$ alkyl, C$_{1-6}$ haloalkyl, C$_{1-6}$ alkoxy, C$_{1-6}$ haloalkoxy, —OR$^{21}$, —$SR^{21}$, —$N(R^{22})(R^{23})$, —$C(O)OR^{22}$, —$C(O)N(R^{22})(R^{23})$, —$C(O)C(O)N(R^{22})(R^{23})$, —$OC(O)N(R^{22})(R^{23})$, —$N(R^{24})C(O)N(R^{22})(R^{23})$, —$N(R^{24})C(O)OR^{25}$, —$N(R^{24})C(O)R^{25}$, —$N(R^{24})S(O)_2R^{25}$, —$C(O)R^{25}$, —$S(O)_2R^{25}$, —$S(O)_2N(R^{22})(R^{23})$, and —$OC(O)R^{25}$;

$R^{21}$ is independently selected at each occurrence from H, $C_{1-6}$ alkyl, $C_{1-6}$ haloalkyl, $C_{2-6}$ alkenyl, $C_{2-6}$ alkynyl, $C_{3-10}$ carbocycle, and 3- to 10-membered heterocycle, wherein $C_{3-10}$ carbocycle and 3- to 10-membered heterocycle are optionally substituted with one, two, or three groups independently selected from halogen and $C_{1-6}$alkyl;

$R^{22}$ is independently selected at each occurrence from H, $C_{1-6}$ alkyl, $C_{1-6}$ haloalkyl, $C_{2-6}$ alkenyl, $C_{2-6}$ alkynyl, $C_{3-10}$ carbocycle, and 3- to 10-membered heterocycle, wherein $C_{3-10}$ carbocycle and 3- to 10-membered heterocycle are optionally substituted with one, two, or three groups independently selected from halogen and $C_{1-6}$alkyl;

$R^{23}$ is independently selected at each occurrence from H and $C_{1-6}$ alkyl;

$R^{24}$ is independently selected at each occurrence from H and $C_{1-6}$ alkyl;

$R^{25}$ is independently selected at each occurrence from $C_{1-6}$ alkyl, $C_{2-6}$ alkenyl, $C_{2-6}$ alkynyl, $C_{3-10}$ carbocycle, and 3- to 10-membered heterocycle, wherein $C_{1-6}$ alkyl, $C_{3-10}$ carbocycle, and 3- to 10-membered heterocycle are optionally substituted with one, two, or three groups independently selected from halogen, $C_{1-6}$ alkyl, $C_{1-6}$ haloalkyl, $C_{1-6}$ alkoxy, $C_{3-10}$ carbocycle, and 3- to 10-membered heterocycle; and ----- indicates a single or double bond such that all valences are satisfied.

The compound of Formula (I) may be a compound of Formula (I-A):

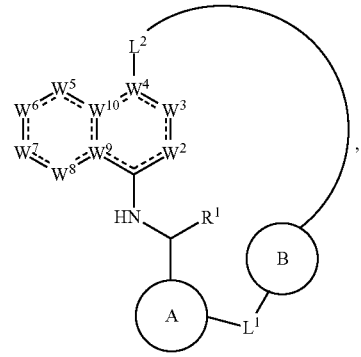

(I-A)

or a pharmaceutically acceptable salt or solvate thereof.

The compound of Formula (I) may be a compound of Formula (I-B):

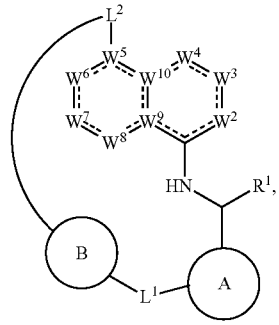

(I-B)

or a pharmaceutically acceptable salt or solvate thereof.

The compound of Formula (I) may be a compound of Formula (I-C):

(I-C)

or a pharmaceutically acceptable salt or solvate thereof.

The compound of Formula (I) may be a compound of Formula (I-D):

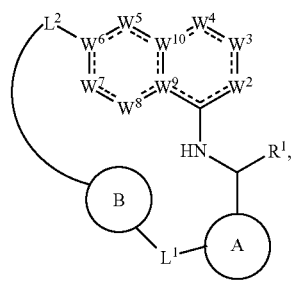

(I-D)

or a pharmaceutically acceptable salt or solvate thereof.

The compound of Formula (I) may be a compound of Formula (I-E):

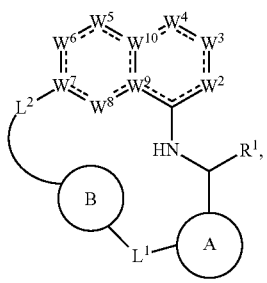

(I-E)

or a pharmaceutically acceptable salt or solvate thereof.

For a compound of Formula (I), (I-A), (I-B), (I-C), (I-D), or (I-E), $L^2$ may be selected from $C_{5-25}$ alkylene, $C_{5-25}$ alkenylene, $C_{5-25}$ alkynylene, 5- to 25-membered heteroalkylene, and 5- to 25-membered heteroalkenylene, each of which is optionally substituted with one or more $R^{11b}$, wherein $L^2$ is covalently bound to one of $W^3$, $W^4$, $W^5$, $W^6$, or $W^7$.

In some embodiments, for a compound of Formula (I), (I-A), (I-B), (I-C), (I-D), or (I-E):

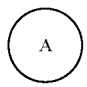

is selected from $C_{5-7}$ cycloalkyl, 5- to 7-membered heterocycloalkyl, 5- to 7-membered heteroaryl, and phenyl, each of which is optionally substituted with one or more $R^{11}$;

$L^1$ is selected from a bond, $C_{1-2}$ alkylene, and $C_{1-2}$ haloalkylene; and $R^1$ is $C_{1-2}$ alkyl optionally substituted with one or more $R^{11c}$.

In some embodiments, for a compound of Formula (I), (I-A), (I-B), (I-C), (I-D), or (I-E):

$R^7$ is selected from a bond to $L^2$, halogen, —CN, $C_{1-6}$ alkyl, $C_{2-6}$ alkenyl, $C_{2-6}$ alkynyl, $C_{3-10}$ carbocycle, 3- to 10-membered heterocycle, —$OR^{12}$, —$SR^{12}$, —$N(R^{12})(R^{13})$, —$C(O)OR^{12}$, —$OC(O)N(R^{12})(R^{13})$, —$N(R^{14})C(O)N(R^{12})(R^{13})$, —$N(R^{14})C(O)OR^{15}$, —$N(R^{14})S(O)_2R^{15}$, —$C(O)R^{15}$, —$S(O)R^{15}$, —$OC(O)R^{15}$, —$C(O)N(R^{12})(R^{13})$, —$C(O)C(O)N(R^{12})(R^{13})$, —$N(R^{14})C(O)R^{15}$, —$S(O)_2R^{15}$, —$S(O)_2N(R^{12})(R^{13})$, —$S(=O)(=NH)N(R^{12})(R^{13})$, —$CH_2C(O)N(R^{12})(R^{13})$, —$CH_2N(R^{14})C(O)R^{15}$, —$CH_2S(O)_2R^{15}$, and —$CH_2S(O)_2N(R^{12})(R^{13})$, wherein each $C_{1-6}$ alkyl, $C_{2-6}$ alkenyl, $C_{2-6}$ alkynyl, $C_{3-10}$ carbocycle, and 3- to 10-membered heterocycle is independently optionally substituted with one, two, or three $R^{20}$; and $R^{7b}$ is selected from a bond to $L^2$, —CN, $C_{1-6}$ alkyl, $C_{2-6}$ alkenyl, $C_{2-6}$ alkynyl, $C_{3-10}$ carbocycle, 3- to 10-membered heterocycle, —$OR^{12}$, —$SR^{12}$, —$C(O)OR^{12}$, —$OC(O)N(R^{12})(R^{13})$, —$C(O)R^{15}$, —$S(O)R^{15}$, —$OC(O)R^{15}$, —$C(O)N(R^{12})(R^{13})$, —$C(O)C(O)N(R^{12})(R^{13})$, —$S(O)_2R^{15}$, —$S(O)_2N(R^{12})(R^{13})$, —$S(=O)(=NH)N(R^{12})(R^{13})$, —$CH_2C(O)N(R^{12})(R^{13})$, —$CH_2N(R^{14})C(O)R^{15}$, —$CH_2S(O)_2R^{15}$, and —$CH_2S(O)_2N(R^{12})(R^{13})$, wherein each $C_{1-6}$ alkyl, $C_{2-6}$ alkenyl, $C_{2-6}$ alkynyl, $C_{3-10}$ carbocycle and 3- to 10-membered heterocycle is independently optionally substituted with one, two, or three $R^{20}$.

For a compound of Formula (I), (I-A), (I-B), (I-C), (I-D), or (I-E), $W^2$ may be N. In some embodiments, $W^3$ is selected from $N(R^{3b})$, N, $C(R^3)$, and C(O), such as $W^3$ is selected from $C(R^3)$ and C(O). In some embodiments, $W^4$ is selected from $N(R^{4b})$, N, $C(R^4)$, and C(O), such as $W^4$ is selected from $N(R^{4b})$ and N. In some embodiments, $W^5$ is selected from $N(R^{5b})$, N, $C(R^5)$, and C(O), such as $W^5$ is selected from $N(R^{5b})$, N, and $C(R^5)$. In some embodiments, $W^5$ is selected from $N(R^{5b})$ and $C(R^5)$. In some embodiments, $W^6$ is selected from $C(R^6)$ and C(O). In some embodiments, $W^7$ is $C(R^7)$. In some embodiments, $W^8$ is $C(R^8)$, such as CH. In some embodiments, $W^9$ is C. In some embodiments, $W^{10}$ is C. In some embodiments, $W^2$ is N; $W^3$ is $N(R^{3b})$; $W^4$ is C(O); and $W^9$ and $W^{10}$ are each C. In some embodiments, $W^2$ is N; $W^3$ is C(O); $W^4$ is $N(R^{4b})$; and $W^9$ and $W^{10}$ are each C. In some embodiments, $W^2$ is N; $W^3$ is $C(R^3)$; $W^4$ is N; and $W^9$ and $W^{10}$ are each C. In some embodiments, $W^5$ is $C(R^5)$; $W^6$ is $C(R^6)$; $W^7$ is $C(R^7)$; $W^8$ is $C(R^8)$; and $W^9$ and $W^{10}$ are each C. In some embodiments, $W^5$ is $N(R^b)$; $W^6$ is C(O); $W^7$ is $C(R^7)$; $W^8$ is $C(R^8)$; and $W^9$ and $W^{10}$ are each C. In some embodiments, $W^5$ is N; $W^6$ is $C(R^6)$; $W^7$ is $C(R^7)$; $W^8$ is $C(R^8)$; and $W^9$ and $W^{10}$ are each C. In some embodiments, $W^2$ is N; $W^3$ is selected from $N(R^{3b})$, N, $C(R^3)$, and C(O); $W^4$ is selected from $N(R^{4b})$, N, $C(R^4)$, and C(O); $W^5$ is selected from $N(R^{5b})$, N, and $C(R^5)$; $W^6$ is selected from $C(R^6)$ and C(O); $W^7$ is $C(R^7)$; $W^8$ is $C(R^8)$; and $W^9$ and $W^{10}$ are each C. In some embodiments, $W^2$ is N; $W^3$ is selected from $C(R^3)$ and C(O); $W^4$ is selected from $N(R^{4b})$ and N; $W^5$ is selected from $N(R^{5b})$ and $C(R^5)$; $W^6$ is selected from $C(R^6)$ and C(O); $W^7$ is $C(R^7)$; $W^8$ is CH; and $W^9$ and $W^{10}$ are each C.

The compound of Formula (I-B) may be a compound of Formula (I-B1) or (I-B2):

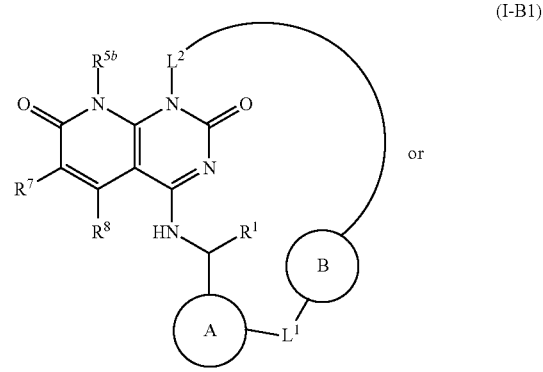

(I-B1)

or

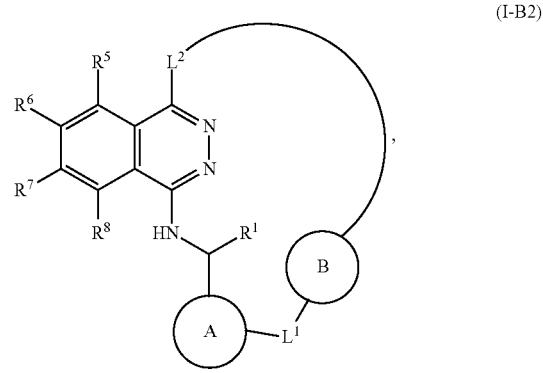

(I-B2)

or a pharmaceutically acceptable salt or solvate thereof.

The compound of Formula (I-C) may be a compound of Formula (I-C1), (I-C2), or (I-C3):

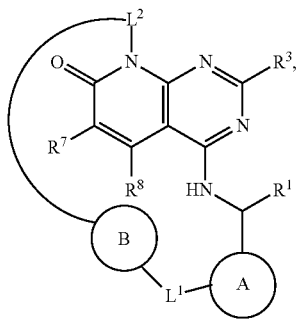
(I-C1)

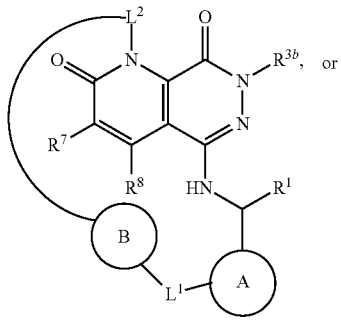
(I-C2)

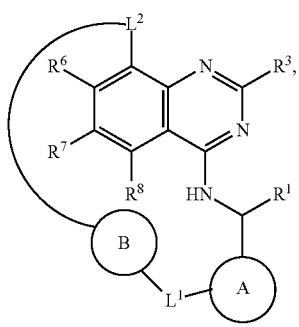
(I-C3)

or a pharmaceutically acceptable salt or solvate thereof.

The compound of Formula (I-D) may be a compound of Formula (I-D1) or (I-D2):

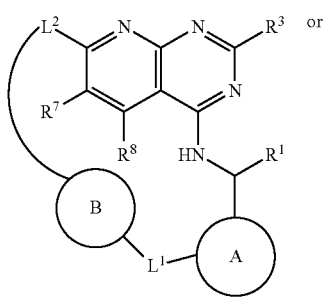
(I-D1)

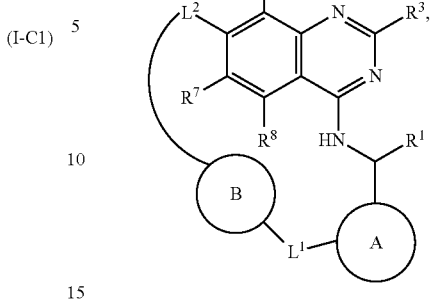
(I-D2)

or a pharmaceutically acceptable salt or solvate thereof.

The compound of Formula (I-E) may be a compound of Formula (I-E1):

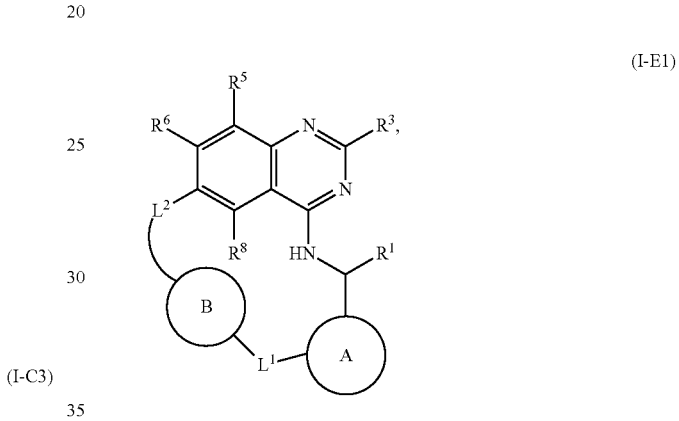
(I-E1)

or a pharmaceutically acceptable salt or solvate thereof.

For a compound of Formula (I), (I-A), (I-B), (I-B1), (I-B2), (I-C), (I-C1), (I-C2), (I-C3), (I-D), (I-D1), (I-D2), (I-E), or (I-E1), $R^1$ may be unsubstituted $C_{1-2}$ alkyl, such as —$CH_3$. In some embodiments, $R^3$ is selected from hydrogen, halogen, —CN, —$OR^{12}$, and $C_{1-6}$ alkyl optionally substituted with one, two, or three $R^{20}$. In some embodiments, $R^3$ is $C_{1-6}$ alkyl optionally substituted with one, two, or three $R^{20}$. In some embodiments, $R^3$ is hydrogen or —$CH_3$. In some embodiments, $R^{3b}$ is —$CH_3$. In some embodiments, $R^5$ is selected from hydrogen, —$OR^{12}$, and $C_{1-6}$ alkyl optionally substituted with one, two, or three $R^{20}$. In some embodiments, $R^5$ is hydrogen. In some embodiments, $R^1$ is selected from hydrogen and $C_{1-6}$ alkyl optionally substituted with one, two, or three $R^{20}$. In some embodiments, $R^1$ is —$CH_3$. In some embodiments, $R^6$ is selected from hydrogen, —$OR^{12}$, and $C_{1-6}$ alkyl optionally substituted with one, two, or three $R^{20}$, and wherein $R^{12}$ is selected from $C_{1-6}$ alkyl. In some embodiments, $R^6$ is selected from hydrogen and —$OCH_3$.

For a compound of Formula (I), (I-A), (I-B), (I-B1), (I-B2), (I-C), (I-C1), (I-C2), (I-C3), (I-D), (I-D1), (I-D2), (I-E), or (I-E1), $R^7$ may be selected from $C_{1-6}$ alkyl, $C_{3-10}$ carbocycle, 3- to 10-membered heterocycle, —$N(R^{12})(R^{13})$, —$C(O)R^{15}$, —$C(O)N(R^{12})(R^{13})$, —$S(O)_2R^{15}$, —$SO_2N(R^{12})(R^{13})$, wherein $C_{1-6}$ alkyl, $C_{3-10}$ carbocycle, and 3- to 10-membered heterocycle are optionally substituted with one, two, or three $R^{20}$. In some embodiments, $R^7$ is selected from $C_{1-6}$ alkyl, $C_{3-10}$ cycloalkyl, 3- to 10-membered heterocycloalkyl, and —$N(R^{12})(R^{13})$, wherein $C_{1-6}$ alkyl, $C_{3-10}$ cycloalkyl, and 3- to 10-membered heterocycloalkyl are optionally substituted with one, two, or three $R^{20}$. In some embodiments, $R^7$ is 3- to 10-membered heterocycloalkyl optionally substituted with one, two, or three $R^{20}$. In some embodiments, $R^7$ is $C_{3-10}$ cycloalkyl optionally substituted with one, two, or three $R^{20}$. In some embodiments, $R^7$ is $C_{3-4}$ cycloalkyl optionally substituted with one $R^{20}$. In some embodiments, $R^{20}$ is —CN. In some embodiments, $R^7$ is

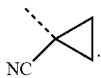

In some embodiments, $R^7$ is $C_{1-6}$ alkyl optionally substituted with one, two, or three $R^{20}$. In some embodiments, $R^7$ is —N($R^{12}$)($R^{13}$). In some embodiments, $R^7$ is selected from

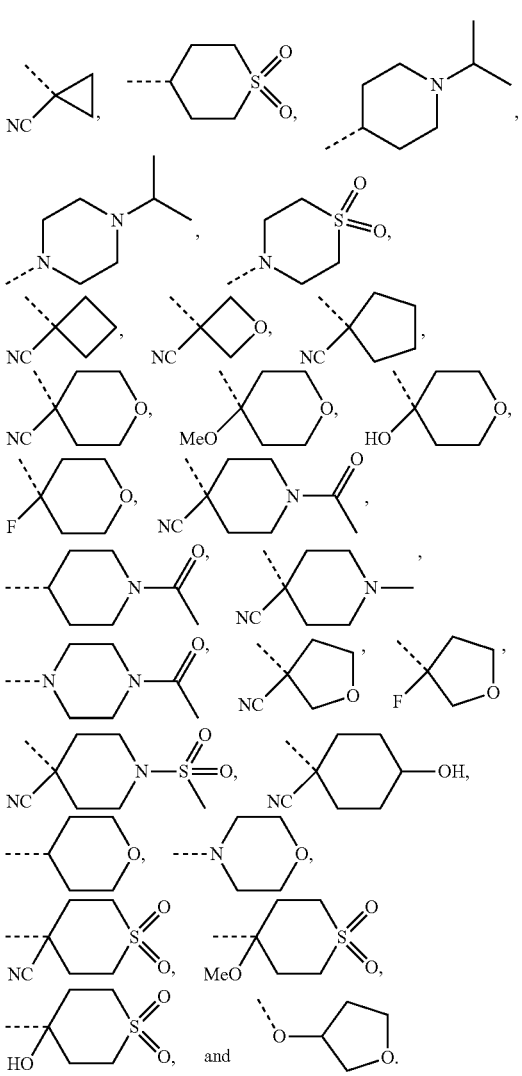

In some embodiments, $R^7$ is selected from

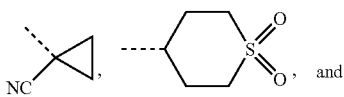

-continued

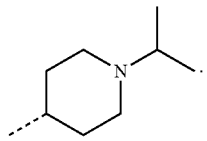

For a compound of Formula (I), (I-A), (I-B), (I-B1), (I-B2), (I-C), (I-C1), (I-C2), (I-C3), (I-D), (I-D1), (I-D2), (I-E), or (I-E1), $R^8$ may be selected from hydrogen, halogen, and $C_{1-6}$ alkyl optionally substituted with one, two, or three $R^{20}$. In some embodiments, $R^8$ is hydrogen.

For a compound of Formula (I), (I-A), (I-B), (I-B1), (I-B2), (I-C), (I-C1), (I-C2), (I-C3), (I-D), (I-D1), (I-D2), (I-E), or (I-E1),

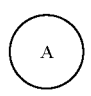

may be selected from phenyl and 5- to 7-membered heteroaryl, each of which is optionally substituted with one or more $R^{11}$. In some embodiments,

is selected from phenyl, pyridyl, and thiophenyl, each of which is optionally substituted with one or more $R^{11}$. In some embodiments,

is selected from

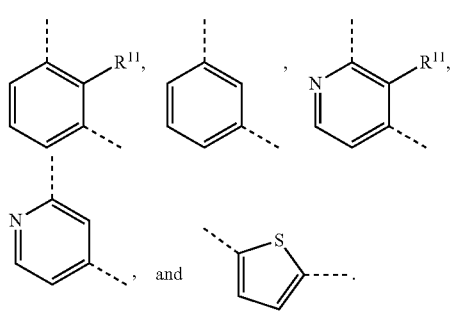

In some embodiments, $R^{11}$, when present, is independently selected at each occurrence from fluorine and —$CH_3$.

For a compound of Formula (I), (I-A), (I-B), (I-B1), (I-B2), (I-C), (I-C1), (I-C2), (I-C3), (I-D), (I-D1), (I-D2), (I-E), or (I-E1), $L^1$ may be selected from a bond and $C_{1-3}$ haloalkylene. In some embodiments, $L^1$ is $C_{1-3}$ haloalkylene. In some embodiments, $L^1$ is selected from —$CF_2$—, —$CF_2CH_2$—, and —$CF_2CH_2CH_2$—.

For a compound of Formula (I), (I-A), (I-B), (I-B1), (I-B2), (I-C), (I-C1), (I-C2), (I-C3), (I-D), (I-D1), (I-D2), (I-E), or (I-E1),

is selected from absent, phenyl, and 4- to 8-membered heterocycle, wherein the phenyl and 4- to 8-membered heterocycle are optionally substituted with one or more $R^{11a}$. In some embodiments,

is selected from absent, phenyl, azetidine, pyrrolidine, and piperidine, wherein the phenyl, azetidine, pyrrolidine, and piperidine are optionally substituted with one or more $R^{11a}$. In some embodiments,

is selected from azetidine, pyrrolidine, and piperidine, each of which is optionally substituted with one or more —$CH_3$.

For a compound of Formula (I), (I-A), (I-B), (I-B1), (I-B2), (I-C), (I-C1), (I-C2), (I-C3), (I-D), (I-D1), (I-D2), (I-E), or (I-E1), $L^2$, together with the atoms to which it is attached, may form a 16- to 36-membered macrocyclic ring. In some embodiments, $L^2$, together with the atoms to which it is attached, forms a 16- to 24-membered macrocyclic ring. In some embodiments, $L^2$ is selected from $C_{6-15}$ alkylene, $C_{6-15}$ alkenylene, $C_{6-15}$ alkynylene, 6- to 15-membered heteroalkylene, and 6- to 15-membered heteroalkenylene, each of which is optionally substituted with one or more $R^{11b}$. In some embodiments, $L^2$ is selected from $C_{5-10}$ alkylene, $C_{5-10}$ alkenylene, 5- to 10-membered heteroalkylene, and 5- to 10-membered heteroalkenylene, each of which is optionally substituted with one or more $R^{11b}$. The alkenylene and heteroalkenylene may comprise one carbon-carbon double bond. The heteroalkylene and heteroalkenylene may comprise at least one oxygen or nitrogen atom. In some embodiments, $R^{11b}$ is selected from halogen, oxo, $C_{1-6}$ alkyl, $C_{1-6}$ haloalkyl, ($C_{1-6}$ alkyl)-OH, and —OH. In some embodiments, $R^{11b}$ is selected from —F, =O, —$CH_3$, —$CH_2F$, —$CHF_2$, —$CF_3$, —$CH_2CH_2F$, —$CH_2CHF_2$, —$CH_2OH$, and —OH.

In some embodiments, for a compound of Formula (I), (I-A), (I-B), (I-B1), (I-B2), (I-C), (I-C1), (I-C2), (I-C3), (I-D), (I-D1), (I-D2), (I-E), or (I-E1), $R^5$ is hydrogen; $R^{5b}$ is —$CH_3$; $R^6$ is selected from hydrogen and —$OCH_3$; $R^7$ is selected from $C_{1-6}$ alkyl, $C_{3-10}$ carbocycle, 3- to 10-membered heterocycle, —$N(R^{12})(R^{13})$, —$C(O)R^{15}$, —$C(O)N(R^{12})(R^{13})$, —$S(O)_2R^{15}$, and —$SO_2N(R^{12})(R^{13})$, wherein $C_{1-6}$ alkyl, $C_{3-10}$ carbocycle, and 3- to 10-membered heterocycle are optionally substituted with one, two, or three $R^{20}$; and $R^1$ is hydrogen. In some embodiments, $R^3$ is hydrogen or —$CH_3$; $R^{3b}$ is —$CH_3$; $R^6$ is selected from hydrogen and —$OCH_3$; $R^7$ is selected from $C_{1-6}$ alkyl, $C_{3-10}$ carbocycle, 3- to 10-membered heterocycle, —$N(R^{12})(R^{13})$, —$C(O)R^{15}$, —$C(O)N(R^{12})(R^{13})$, —$S(O)_2R^{35}$, and —$SO_2N(R^{12})(R^{13})$, wherein $C_{1-6}$ alkyl, $C_{3-10}$ carbocycle, and 3- to 10-membered heterocycle are optionally substituted with one, two, or three $R^{20}$; and $R^8$ is hydrogen. In some embodiments, $R^7$ is selected from

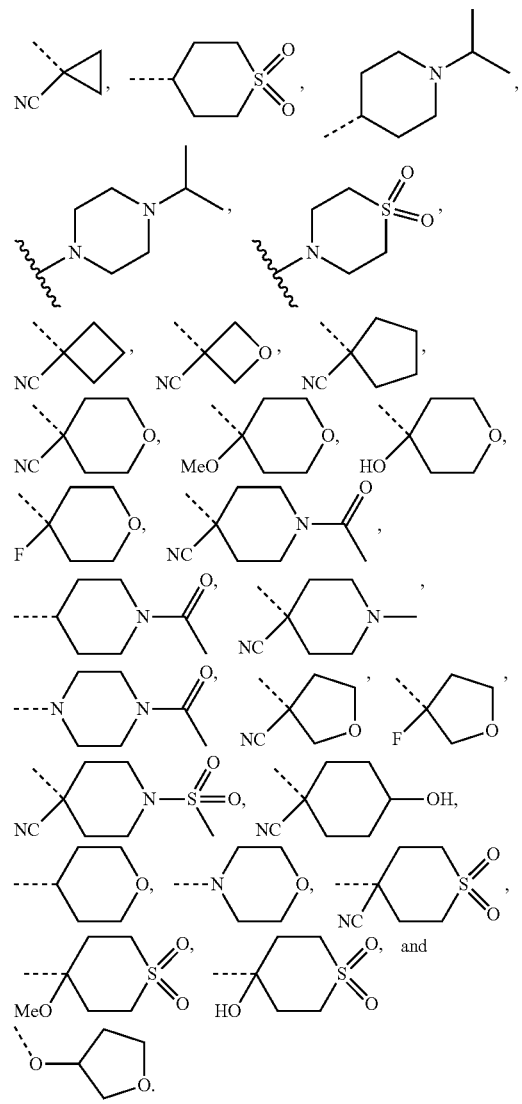

In some embodiments, $R^1$ is —$CH_3$;

is selected from phenyl and 5- to 7-membered heteroaryl, each of which is optionally substituted with one or more $R^{11}$; $L^1$ is selected from a bond and $C_{1-3}$ haloalkylene;

is selected from absent, phenyl, and 4- to 8-membered heterocycle, wherein the phenyl and 4- to 8-membered heterocycle are optionally substituted with one or more R$^{11a}$; and L$^2$ is selected from C$_{5-10}$ alkylene, C$_{5-10}$ alkenylene, 5- to 10-membered heteroalkylene, and 5- to 10-membered heteroalkenylene, each of which is optionally substituted with one or more R$^{11b}$. In some embodiments, R$^{11}$, when present, is fluorine; R$^{11a}$, when present, is —CH$_3$; and R$^{11b}$, when present, is selected from halogen, oxo, C$_{1-6}$ alkyl, C$_{1-6}$ haloalkyl, (C$_{1-6}$ alkyl)-OH, and —OH.

A compound of Formula (I), (I-A), (I-B), (I-B1), (I-B2), (I-C), (I-C1), (I-C2), (I-C3), (I-D), (I-D1), (I-D2), (I-E), or (I-E1) may be a compound having the structure:

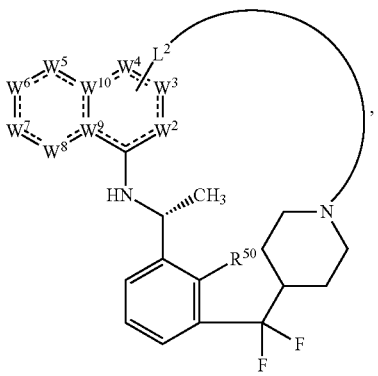

or a pharmaceutically acceptable salt or solvate thereof.

In some embodiments, the present disclosure provides a compound of Formula (I-C1), or a pharmaceutically acceptable salt or solvate thereof, wherein:

is selected from

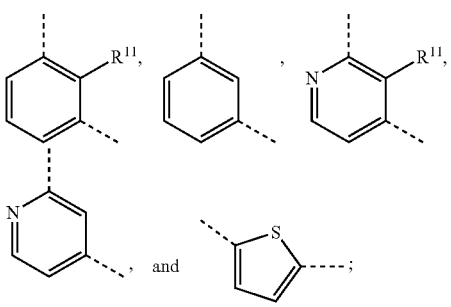

is selected from azetidine, pyrrolidine, and piperidine, each of which is optionally substituted with one or more —CH$_3$;

L$^1$ is C$_{1-3}$ haloalkylene;

L$^2$ is C$_{5-10}$ alkenylene optionally substituted with one or more R$^{11b}$;

R$^1$ is —CH$_3$;

R$^3$ is —CH$_3$;

R$^7$ is selected from

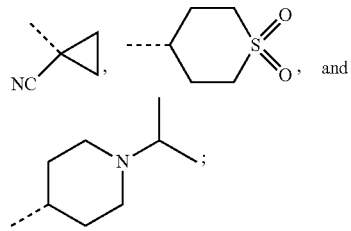

R$^8$ is hydrogen;

R$^{11}$ is selected from fluorine and —CH$_3$; and

R$^{11b}$ is selected from halogen, oxo, C$_{1-6}$ alkyl, C$_{1-6}$ haloalkyl, (C$_{1-6}$ alkyl)-OH, and —OH.

In some embodiments, the present disclosure provides a compound of Formula (I-C1), or a pharmaceutically acceptable salt or solvate thereof, wherein:

is selected from

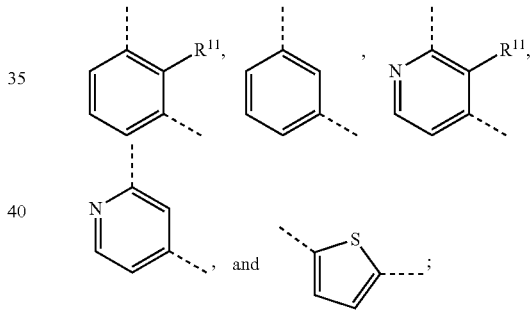

is selected from azetidine, pyrrolidine, and piperidine, each of which is optionally substituted with one or more —CH$_3$;

L$^1$ is C$_{1-3}$ haloalkylene;

L$^2$ is selected from 5- to 10-membered heteroalkylene optionally substituted with one or more R$^{11b}$;

R$^1$ is —CH$_3$;

R$^3$ is hydrogen or —CH$_3$;

R$^7$ is selected from

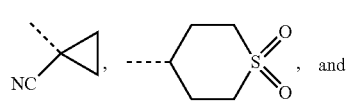

-continued

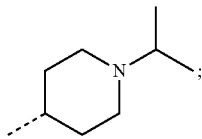

R[8] is hydrogen;
R[11] is selected from fluorine and —CH$_3$; and
R[11b] is selected from halogen, oxo, C$_{1-6}$ alkyl, C$_{1-6}$ haloalkyl, (C$_{1-6}$ alkyl)-OH, and —OH.

In certain aspects, the present disclosure provides a compound of Formula (III):

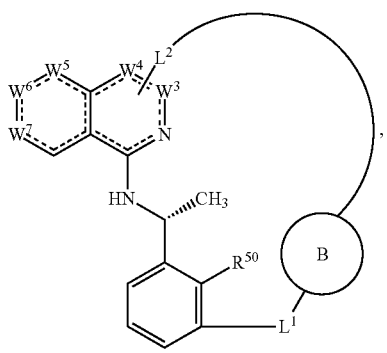

(III)

or a pharmaceutically acceptable salt or solvate thereof, wherein:

is selected from 3- to 8-membered heterocycle, optionally substituted with one or more R[11a];

L[1] is selected from a bond, C$_{1-6}$ alkylene, and C$_{1-6}$ haloalkylene;

L[2] is selected from C$_{5-25}$ alkylene, C$_{5-25}$ alkenylene, C$_{5-25}$ alkynylene, 5- to 25-membered heteroalkylene, and 5- to 25-membered heteroalkenylene, each of which is optionally substituted with one or more R[11b], wherein L[2] is covalently bound to one of W[3], W[4], W[5], W[6], or W[7]; or L[2] is -L[3]-D-L[4]-, wherein L[4] is covalently bound to one of W[3], W[4], W[5], W[6], or W[7].

L[3] is selected from C$_{1-10}$ alkylene, C$_{1-10}$ alkenylene, C$_{1-10}$ alkynylene, 2- to 10-membered heteroalkylene, and 2- to 10-membered heteroalkenylene, each of which is optionally substituted with one or more R[11b].

D is absent or selected from C$_{3-12}$ carbocycle and 3- to 12-membered heterocycle, each of which is optionally substituted with one or more R[11d].

L[4] is selected from C$_{1-10}$ alkylene, C$_{1-10}$ alkenylene, C$_{1-10}$ alkynylene, 2- to 10-membered heteroalkylene, and 2- to 10-membered heteroalkenylene, each of which is optionally substituted with one or more R[11b];

W[3] is selected from N(R[3b]) and N and W[4] is selected from C(R[4]) and C(O); or W[3] is selected from C(R[3]) and C(O), and W[4] is selected from N(R[4b]) and N;

W[5] is selected from N(R[5b]), N, and C(R[5]);

W[6] is selected from N, C(R[6]), and C(O);

W[7] is selected from N, C(R[7]), and C(O);

R[50] is hydrogen or halogen;

R[3], R[4], R[5], R[6], and R[7] are each independently selected from a bond to L[2], hydrogen, halogen, —CN, C$_{1-6}$ alkyl, C$_{2-6}$ alkenyl, C$_{2-6}$ alkynyl, C$_{3-10}$ carbocycle, 3- to 10-membered heterocycle, —OR[12], —SR[12], —N(R[12])(R[13]), —C(O)OR[12], —OC(O)N(R[12])(R[13]), —N(R[14])C(O)N(R[12])(R[13]), —N(R[14])C(O)OR[15], —N(R[14])S(O)$_2$R[15], —C(O)R[15], —S(O)R[15], —OC(O)R[15], —C(O)N(R[12])(R[13]), —C(O)C(O)N(R[12])(R[13]), —N(R[14])C(O)R[15], —S(O)$_2$R[15], —S(O)$_2$N(R[12])(R[13]), —S(=O)(=NH)N(R[12])(R[13]), —CH$_2$C(O)N(R[12])(R[13]), —CH$_2$N(R[14])C(O)R[15], —CH$_2$S(O)$_2$R[15], and —CH$_2$S(O)$_2$N(R[12])(R[13]), wherein each C$_{1-6}$ alkyl, C$_{2-6}$ alkenyl, C$_{2-6}$ alkynyl, C$_{3-10}$ carbocycle, and 3- to 10-membered heterocycle is independently optionally substituted with one, two, or three R[20];

R[3b], R[4b], and R[5b] are each independently selected from a bond to L[2], hydrogen, —CN, C$_{1-6}$ alkyl, C$_{2-6}$ alkenyl, C$_{2-6}$ alkynyl, C$_{3-10}$ carbocycle, 3- to 10-membered heterocycle, —OR[12], —SR[12], —C(O)OR[12], —OC(O)N(R[12])(R[13]), —C(O)R[15], —S(O)R[15], —OC(O)R[15], —C(O)N(R[12])(R[13]), —C(O)C(O)N(R[12])(R[13]), —S(O)$_2$R[15], —S(O)$_2$N(R[12])(R[13]), —S(=O)(=NH)N(R[12])(R[13]), —CH$_2$C(O)N(R[12])(R[13]), —CH$_2$N(R[14])C(O)R[15], —CH$_2$S(O)$_2$R[15], and —CH$_2$S(O)$_2$N(R[12])(R[13]), wherein each C$_{1-6}$ alkyl, C$_{2-6}$ alkenyl, C$_{2-6}$ alkynyl, C$_{3-10}$ carbocycle and 3- to 10-membered heterocycle is independently optionally substituted with one, two, or three R[20];

R[11a] and R[11d] are each independently selected at each occurrence from halogen, —CN, C$_{1-6}$ alkyl, C$_{2-6}$ alkenyl, C$_{2-6}$ alkynyl, C$_{3-10}$ carbocycle, 3- to 10-membered heterocycle, —OR[12], —SR[12], —N(R[12])(R[13]), —C(O)OR[12], —OC(O)N(R[12])(R[13]), —N(R[14])C(O)N(R[12])(R[13]), —N(R[14])C(O)OR[15], —N(R[14])S(O)$_2$R[15], —C(O)R[15], —S(O)R[15], —OC(O)R[15], —C(O)N(R[12])(R[13]), —C(O)C(O)N(R[12])(R[13]), —N(R[14])C(O)R[15], —S(O)$_2$R[15], —S(O)$_2$N(R[12])(R[13]), —S(=O)(=Ni)N(R[12])(R[13]), —CH$_2$C(O)N(R[12])(R[13]), —CH$_2$N(R[14])C(O)R[15], —CH$_2$S(O)$_2$R[15], —CH$_2$S(O)$_2$N(R[12])(R[13]), —CH$_2$N(R[12])S(O)$_2$(R[13]), and —P(O)(R[17])(R[17a]), wherein C$_{1-6}$ alkyl, C$_{2-6}$ alkenyl, C$_{2-6}$ alkynyl, C$_{3-10}$ carbocycle, and 3- to 10-membered heterocycle are optionally substituted with one, two, or three R[20];

R[11b] is independently selected at each occurrence from halogen, oxo, —CN, C$_{1-6}$ alkyl, C$_{2-6}$ alkenyl, C$_{2-6}$ alkynyl, C$_{3-10}$ carbocycle, 3- to 10-membered heterocycle, —OR[12], —SR[12], —N(R[12])(R[13]), —C(O)OR[12], —OC(O)N(R[12])(R[13]), —N(R[14])C(O)N(R[12])(R[13]), —N(R[14])C(O)OR[15], —N(R[14])S(O)$_2$R[15], —C(O)R[15], —S(O)R[15], —OC(O)R[15], —C(O)N(R[12])(R[13]), —C(O)C(O)N(R[12])(R[13]), —N(R[14])C(O)R[15], —S(O)$_2$R[15], —S(O)$_2$N(R[12])(R[13]), —S(=O)(=NH)N(R[12])(R[13]), —CH$_2$C(O)N(R[12])(R[13]), —CH$_2$N(R[14])C(O)R[15], —CH$_2$S(O)$_2$R[15], —CH$_2$S(O)$_2$N(R[12])(R[13]), —CH$_2$N(R[12])S(O)$_2$(R[13]), and —P(O)(R[17])(R[17a]), wherein C$_{1-6}$ alkyl, C$_{2-6}$ alkenyl, C$_{2-6}$ alkynyl, C$_{3-10}$ carbocycle, and 3- to 10-membered heterocycle are optionally substituted with one, two, or three R[20];

R[12] is independently selected at each occurrence from hydrogen, C$_{1-6}$ alkyl, C$_{1-6}$ haloalkyl, C$_{2-6}$ alkenyl, C$_{2-6}$ alkynyl, C$_{3-10}$ carbocycle, and 3- to 10-membered heterocycle, wherein C$_{1-6}$ alkyl, C$_{2-6}$ alkenyl, C$_{2-6}$ alkynyl, C$_{3-10}$ carbocycle, and 3- to 10-membered heterocycle are optionally substituted with one, two, or three R[20];

$R^{13}$ is independently selected at each occurrence from hydrogen, $C_{1-6}$ alkyl, and $C_{1-6}$ haloalkyl; or $R^{12}$ and $R^{13}$, together with the nitrogen atom to which they are attached, form a 3- to 10-membered heterocycle optionally substituted with one, two, or three $R^{20}$;

$R^{14}$ is independently selected at each occurrence from hydrogen, $C_{1-6}$ alkyl, and $C_{1-6}$ haloalkyl;

$R^{15}$ is independently selected at each occurrence from $C_{1-6}$ alkyl, $C_{2-6}$ alkenyl, $C_{2-6}$ alkynyl, $C_{3-10}$ carbocycle, and 3- to 10-membered heterocycle, wherein $C_{1-6}$ alkyl, $C_{2-6}$ alkenyl, $C_{2-6}$ alkynyl, $C_{3-10}$ carbocycle, and 3- to 10-membered heterocycle are optionally substituted with one, two, or three $R^{20}$;

$R^{17}$ and $R^{17a}$ are each independently selected at each occurrence from $C_{1-6}$ alkyl and $C_{3-6}$ cycloalkyl, wherein $C_{1-6}$ alkyl and $C_{3-6}$ cycloalkyl are optionally substituted with one, two or three $R^{20}$; or $R^{17}$ and $R^{17a}$, together with the phosphorous atom to which they are attached, form a 3- to 10-membered heterocycle;

$R^{20}$ is independently selected at each occurrence from halogen, oxo, =NH, —CN, $C_{1-6}$ alkyl, $C_{2-6}$ alkenyl, $C_{2-6}$ alkynyl, $C_{3-10}$ carbocycle, —CH$_2$—($C_{3-10}$ carbocycle), 3- to 10-membered heterocycle, —CH$_2$-(3- to 10-membered heterocycle), —OR$^{21}$, —SR$^{21}$, —N(R$^{22}$)(R$^{23}$), —C(O)OR$^{22}$, —C(O)N(R$^{22}$)(R$^{23}$), —C(O)C(O)N(R$^{22}$)(R$^{23}$), —OC(O)N(R$^{22}$)(R$^{23}$), —N(R$^{22}$)C(O)N(R$^{22}$)(R$^{23}$), —N(R$^{24}$)C(O)OR$^{25}$, —N(R$^{24}$)C(O)R$^{25}$, —N(R$^{22}$)S(O)$_2$R$^{25}$, —C(O)R$^{25}$, —S(O)$_2$R$^{25}$, —S(O)$_2$N(R$^{22}$)(R$^{23}$), —OCH$_2$C(O)OR$^{22}$, and —OC(O)R$^{25}$, wherein $C_{1-6}$ alkyl, $C_{2-6}$ alkenyl, $C_{2-6}$ alkynyl, $C_{3-10}$ carbocycle, —CH$_2$—($C_{3-10}$ carbocycle), 3- to 10-membered heterocycle, and —CH$_2$-(3- to 10-membered heterocycle) are optionally substituted with one, two, or three groups independently selected from halogen, oxo, =NH, —CN, $C_{1-6}$ alkyl, $C_{1-6}$ haloalkyl, $C_{1-6}$ alkoxy, $C_{1-6}$ haloalkoxy, —OR$^{21}$, —SR$^{21}$, —N(R$^{22}$)(R$^{23}$), —C(O)OR$^{22}$, —C(O)N(R$^{22}$)(R$^{23}$), —C(O)C(O)N(R$^{22}$)(R$^{23}$), —OC(O)N(R$^{22}$)(R$^{23}$), —N(R$^{24}$)C(O)N(R$^{22}$)(R$^{23}$), —N(R$^{24}$)C(O)OR$^{25}$, —N(R$^{24}$)C(O)R$^{25}$, —N(R$^{22}$)S(O)$_2$R$^{25}$, —C(O)R$^{25}$, —S(O)$_2$R$^{25}$, —S(O)$_2$N(R$^{22}$)(R$^{23}$), and —OC(O)R$^{25}$;

$R^{21}$ is independently selected at each occurrence from H, $C_{1-6}$ alkyl, $C_{1-6}$ haloalkyl, $C_{2-6}$ alkenyl, $C_{2-6}$ alkynyl, $C_{3-10}$ carbocycle, and 3- to 10-membered heterocycle, wherein $C_{3-10}$ carbocycle and 3- to 10-membered heterocycle are optionally substituted with one, two, or three groups independently selected from halogen and $C_{1-6}$ alkyl;

$R^{22}$ is independently selected at each occurrence from H, $C_{1-6}$ alkyl, $C_{1-6}$ haloalkyl, $C_{2-6}$ alkenyl, $C_{2-6}$ alkynyl, $C_{3-10}$ carbocycle, and 3- to 10-membered heterocycle, wherein $C_{3-10}$ carbocycle and 3- to 10-membered heterocycle are optionally substituted with one, two, or three groups independently selected from halogen and $C_{1-6}$ alkyl;

$R^{23}$ is independently selected at each occurrence from H and $C_{1-6}$ alkyl;

$R^2$ is independently selected at each occurrence from H and $C_{1-6}$ alkyl;

$R^{25}$ is independently selected at each occurrence from $C_{1-6}$ alkyl, $C_{2-6}$ alkenyl, $C_{2-6}$ alkynyl, $C_{3-10}$ carbocycle, and 3- to 10-membered heterocycle, wherein $C_{1-6}$ alkyl, $C_{3-10}$ carbocycle, and 3- to 10-membered heterocycle are optionally substituted with one, two or three groups independently selected from halogen, $C_{1-6}$ alkyl, $C_{1-6}$ haloalkyl, $C_{1-6}$ alkoxy, $C_{3-10}$ carbocycle, and 3- to 10-membered heterocycle; and ----- indicates a single or double bond such that all valences are satisfied.

In certain aspects, the present disclosure provides a compound of Formula (III):

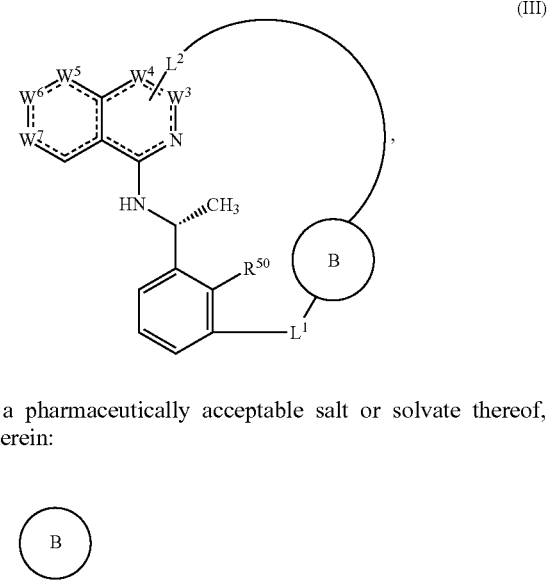

or a pharmaceutically acceptable salt or solvate thereof, wherein:

B is selected from 3- to 8-membered heterocycle, optionally substituted with one or more $R^{11a}$;

$L^1$ is selected from a bond, $C_{1-6}$ alkylene, and $C_{1-6}$ haloalkylene;

$L^2$ is selected from $C_{5-25}$ alkylene, $C_{5-25}$ alkenylene, $C_{5-25}$ alkynylene, 5- to 25-membered heteroalkylene, and 5- to 25-membered heteroalkenylene, each of which is optionally substituted with one or more $R^{11b}$, wherein $L^2$ is covalently bound to one of $W^3$, $W^4$, $W^5$, $W^6$, or $W^7$;

$W^3$ is selected from $N(R^{3b})$ and N and $W^4$ is selected from $C(R^4)$ and $C(O)$; or $W^3$ is selected from $C(R^3)$ and $C(O)$, and $W^4$ is selected from $N(R^{4b})$ and N;

$W^5$ is selected from $N(R^{5b})$, N, and $C(R^5)$;

$W^6$ is selected from N, $C(R^6)$, and $C(O)$;

$W^7$ is selected from N, $C(R^7)$, and $C(O)$;

$R^{50}$ is hydrogen or halogen;

$R^3$, $R^4$, $R^5$, $R^6$, and $R^7$ are each independently selected from a bond to $L^2$, hydrogen, halogen, —CN, $C_{1-6}$ alkyl, $C_{2-6}$ alkenyl, $C_{2-6}$ alkynyl, $C_{3-10}$ carbocycle, 3- to 10-membered heterocycle, —OR$^{12}$, —SR$^{12}$, —N(R$^{12}$)(R$^{13}$), —C(O)OR$^{12}$, —OC(O)N(R$^{12}$)(R$^{13}$), —N(R$^{14}$)C(O)N(R$^{12}$)(R$^{13}$), —N(R$^{14}$)C(O)OR$^{15}$, —N(R$^{14}$)S(O)$_2$R$^{15}$, —C(O)R$^{15}$, —S(O)R$^{15}$, —OC(O)R$^{15}$, —C(O)N(R$^{12}$)(R$^{13}$), —C(O)C(O)N(R$^{12}$)(R$^{13}$), —N(R$^{14}$)C(O)R$^{15}$, —S(O)$_2$R$^{15}$, —S(O)$_2$N(R$^{12}$)(R$^{13}$), —S(=O)(=NH)N(R$^{12}$)(R$^{13}$), —CH$_2$C(O)N(R$^{12}$)(R$^{13}$), —CH$_2$N(R$^{14}$)C(O)R$^{15}$, —CH$_2$S(O)$_2$R$^{15}$, and —CH$_2$S(O)$_2$N(R$^{12}$)(R$^{13}$), wherein each $C_{1-6}$ alkyl, $C_{2-6}$ alkenyl, $C_{2-6}$ alkynyl, $C_{3-10}$ carbocycle, and 3- to 10-membered heterocycle is independently optionally substituted with one, two, or three $R^{20}$;

$R^{3b}$, $R^{4b}$, and $R^{5b}$ are each independently selected from a bond to $L^2$, hydrogen, —CN, $C_{1-6}$ alkyl, $C_{2-6}$ alkenyl, $C_{2-6}$ alkynyl, $C_{3-10}$ carbocycle, 3- to 10-membered heterocycle, $-OR^{12}$, $-SR^{12}$, $-C(O)OR^{12}$, $-OC(O)N(R^{12})(R^{13})$, $-C(O)R^{15}$, $-S(O)R^{15}$, $-OC(O)R^{15}$, $-C(O)N(R^{12})(R^{13})$, $-C(O)C(O)N(R^{12})(R^{13})$, $-S(O)_2R^{15}$, $-S(O)_2N(R^{12})(R^{13})$, $-S(=O)(=NH)N(R^{12})(R^{13})$, $-CH_2C(O)N(R^{12})(R^{13})$, $-CH_2N(R^{14})C(O)R^{15}$, $-CH_2S(O)_2R^{15}$, and $-CH_2S(O)_2N(R^{12})(R^{13})$, wherein each $C_{1-6}$ alkyl, $C_{2-6}$ alkenyl, $C_{2-6}$ alkynyl, $C_{3-10}$ carbocycle and 3- to 10-membered heterocycle is independently optionally substituted with one, two, or three $R^{20}$;

$R^{11a}$ is independently selected at each occurrence from halogen, $-CN$, $C_{1-6}$ alkyl, $C_{2-6}$ alkenyl, $C_{2-6}$ alkynyl, $C_{3-10}$ carbocycle, 3- to 10-membered heterocycle, $-OR^{12}$, $-SR^{12}$, $-N(R^{12})(R^{13})$, $-C(O)OR^{12}$, $-OC(O)N(R^{12})(R^{13})$, $-N(R^{14})C(O)N(R^{12})(R^{13})$, $-N(R^{14})C(O)OR^{15}$, $-N(R^{14})S(O)_2R^{15}$, $-C(O)R^{15}$, $-S(O)R^{15}$, $-OC(O)R^{15}$, $-C(O)N(R^{12})(R^{13})$, $-C(O)C(O)N(R^{12})(R^{13})$, $-N(R^{14})C(O)R^{15}$, $-S(O)_2R^{15}$, $-S(O)_2N(R^{12})(R^{13})$, $-S(=O)(=NH)N(R^{12})(R^{13})$, $-CH_2C(O)N(R^{12})(R^{13})$, $-CH_2N(R^{14})C(O)R^{15}$, $-CH_2S(O)_2R^{15}$, $-CH_2S(O)_2N(R^{12})(R^{13})$, $-CH_2N(R^{12})S(O)_2(R^{13})$, and $-P(O)(R^{17})(R^{17a})$, wherein $C_{1-6}$ alkyl, $C_{2-6}$ alkenyl, $C_{2-6}$ alkynyl, $C_{3-10}$ carbocycle, and 3- to 10-membered heterocycle are optionally substituted with one, two, or three $R^{20}$;

$R^{11b}$ is independently selected at each occurrence from halogen, oxo, $-CN$, $C_{1-6}$ alkyl, $C_{2-6}$ alkenyl, $C_{2-6}$ alkynyl, $C_{3-10}$ carbocycle, 3- to 10-membered heterocycle, $-OR^{12}$, $-SR^{12}$, $-N(R^{12})(R^{13})$, $-C(O)OR^{12}$, $-OC(O)N(R^{12})(R^{13})$, $-N(R^{14})C(O)N(R^{12})(R^{13})$, $-N(R^{14})C(O)OR^{15}$, $-N(R^{14})S(O)_2R^{15}$, $-C(O)R^{15}$, $-S(O)R^{15}$, $-OC(O)R^{15}$, $-C(O)N(R^{12})(R^{13})$, $-C(O)C(O)N(R^{12})(R^{13})$, $-N(R^{14})C(O)R^{15}$, $-S(O)_2R^{15}$, $-S(O)_2N(R^{12})(R^{13})$, $-S(=O)(=NH)N(R^{12})(R^{13})$, $-CH_2C(O)N(R^{12})(R^{13})$, $-CH_2N(R^{14})C(O)R^{15}$, $-CH_2S(O)_2R^{15}$, $-CH_2S(O)_2N(R^{12})(R^{13})$, $-CH_2N(R^{12})S(O)_2(R^{13})$, and $-P(O)(R^{17})(R^{17a})$, wherein $C_{1-6}$ alkyl, $C_{2-6}$ alkenyl, $C_{2-6}$ alkynyl, $C_{3-10}$ carbocycle, and 3- to 10-membered heterocycle are optionally substituted with one, two, or three $R^{20}$;

$R^{12}$ is independently selected at each occurrence from hydrogen, $C_{1-6}$ alkyl, $C_{1-6}$ haloalkyl, $C_{2-6}$ alkenyl, $C_{2-6}$ alkynyl, $C_{3-10}$ carbocycle, and 3- to 10-membered heterocycle, wherein $C_{1-6}$ alkyl, $C_{2-6}$ alkenyl, $C_{2-6}$ alkynyl, $C_{3-10}$ carbocycle, and 3- to 10-membered heterocycle are optionally substituted with one, two, or three $R^{20}$;

$R^{13}$ is independently selected at each occurrence from hydrogen, $C_{1-6}$ alkyl, and $C_{1-6}$ haloalkyl; or $R^{12}$ and $R^{13}$, together with the nitrogen atom to which they are attached, form a 3- to 10-membered heterocycle optionally substituted with one, two, or three $R^{20}$;

$R^{14}$ is independently selected at each occurrence from hydrogen, $C_{1-6}$ alkyl, and $C_{1-6}$ haloalkyl;

$R^{15}$ is independently selected at each occurrence from $C_{1-6}$ alkyl, $C_{2-6}$ alkenyl, $C_{2-6}$ alkynyl, $C_{3-10}$ carbocycle, and 3- to 10-membered heterocycle, wherein $C_{1-6}$ alkyl, $C_{2-6}$ alkenyl, $C_{2-6}$ alkynyl, $C_{3-10}$ carbocycle, and 3- to 10-membered heterocycle are optionally substituted with one, two, or three $R^{20}$;

$R^{17}$ and $R^{17a}$ are each independently selected at each occurrence from $C_{1-6}$ alkyl and $C_{3-6}$ cycloalkyl, wherein $C_{1-6}$ alkyl and $C_{3-6}$ cycloalkyl are optionally substituted with one, two or three $R^{20}$; or $R^{17}$ and $R^{17a}$, together with the phosphorous atom to which they are attached, form a 3- to 10-membered heterocycle;

$R^{20}$ is independently selected at each occurrence from halogen, oxo, $=NH$, $-CN$, $C_{1-6}$ alkyl, $C_{2-6}$ alkenyl, $C_{2-6}$ alkynyl, $C_{3-10}$ carbocycle, $-CH_2-(C_{3-10}$ carbocycle), 3- to 10-membered heterocycle, $-CH_2-$(3- to 10-membered heterocycle), $-OR^{21}$, $-SR^{21}$, $-N(R^{22})(R^{23})$, $-C(O)OR^{22}$, $-C(O)N(R^{22})(R^{23})$, $-C(O)C(O)N(R^{22})(R^{23})$, $-OC(O)N(R^{22})(R^{23})$, $-N(R^{22})C(O)N(R^{22})(R^{23})$, $-N(R^{24})C(O)OR^{25}$, $-N(R^{24})C(O)R^{25}$, $-N(R^{22})S(O)_2R^{25}$, $-C(O)R^{25}$, $-S(O)_2R^{25}$, $-S(O)_2N(R^{22})(R^{23})$, $-OCH_2C(O)OR^{22}$, and $-OC(O)R^{25}$, wherein $C_{1-6}$ alkyl, $C_{2-6}$ alkenyl, $C_{2-6}$ alkynyl, $C_{3-10}$ carbocycle, $-CH_2-(C_{3-10}$ carbocycle), 3- to 10-membered heterocycle, and $-CH_2-$(3- to 10-membered heterocycle) are optionally substituted with one, two, or three groups independently selected from halogen, oxo, $=NH$, $-CN$, $C_{1-6}$ alkyl, $C_{1-6}$ haloalkyl, $C_{1-6}$ alkoxy, $C_{1-6}$ haloalkoxy, $-OR^{21}$, $-SR^{21}$, $-N(R^{22})(R^{23})$, $-C(O)OR^{22}$, $-C(O)N(R^{22})(R^{23})$, $-C(O)C(O)N(R^{22})(R^{23})$, $-OC(O)N(R^{22})(R^{23})$, $-N(R^{24})C(O)N(R^{22})(R^{23})$, $-N(R^{24})C(O)OR^{25}$, $-N(R^{24})C(O)R^{25}$, $-N(R^{22})S(O)_2R^{25}$, $-C(O)R^{25}$, $-S(O)_2R^{25}$, $-S(O)_2N(R^{22})(R^{23})$, and $-OC(O)R^{25}$;

$R^{21}$ is independently selected at each occurrence from H, $C_{1-6}$ alkyl, $C_{1-6}$ haloalkyl, $C_{2-6}$ alkenyl, $C_{2-6}$ alkynyl, $C_{3-10}$ carbocycle, and 3- to 10-membered heterocycle, wherein $C_{3-10}$ carbocycle and 3- to 10-membered heterocycle are optionally substituted with one, two, or three groups independently selected from halogen and $C_{1-6}$ alkyl;

$R^{22}$ is independently selected at each occurrence from H, $C_{1-6}$ alkyl, $C_{1-6}$ haloalkyl, $C_{2-6}$ alkenyl, $C_{2-6}$ alkynyl, $C_{3-10}$ carbocycle, and 3- to 10-membered heterocycle, wherein $C_{3-10}$ carbocycle and 3- to 10-membered heterocycle are optionally substituted with one, two, or three groups independently selected from halogen and $C_{1-6}$ alkyl;

$R^{23}$ is independently selected at each occurrence from H and $C_{1-6}$ alkyl;

$R^{24}$ is independently selected at each occurrence from H and $C_{1-6}$ alkyl;

$R^{25}$ is independently selected at each occurrence from $C_{1-6}$ alkyl, $C_{2-6}$ alkenyl, $C_{2-6}$ alkynyl, $C_{3-10}$ carbocycle, and 3- to 10-membered heterocycle, wherein $C_{1-6}$ alkyl, $C_{3-10}$ carbocycle, and 3- to 10-membered heterocycle are optionally substituted with one, two, or three groups independently selected from halogen, $C_{1-6}$ alkyl, $C_{1-6}$ haloalkyl, $C_{1-6}$ alkoxy, $C_{3-10}$ carbocycle, and 3- to 10-membered heterocycle; and ----- indicates a single or double bond such that all valences are satisfied.

In certain aspects, the present disclosure provides a compound described herein, or a pharmaceutically acceptable salt or solvate thereof. In certain aspects, the present disclosure provides a pharmaceutical composition comprising a compound described herein, or a pharmaceutically acceptable salt or solvate thereof, and a pharmaceutically acceptable excipient.

In certain aspects, the present disclosure provides a method of treating cancer in a subject in need thereof, comprising administering to the subject a therapeutically effective amount of a compound described herein, or a pharmaceutically acceptable salt or solvate thereof. In some embodiments, the cancer is a solid tumor or a hematological cancer. In some embodiments, the subject is administered with an additional agent or therapy.

In certain aspects, the present disclosure provides a method of reducing Ras signaling output, comprising contacting a SOS1 protein with an effective amount of a compound described herein, or a pharmaceutically acceptable salt or solvate thereof, thereby reducing the Ras signaling output. In some embodiments, the compound disrupts interaction between a Ras protein and SOS1. In some embodiments, the Ras protein is a wildtype K-Ras or a mutant K-Ras.

In certain aspects, the present disclosure provides a method of inhibiting cell growth, comprising administering a cell expressing SOS1 with an effective amount of a compound described herein, or a pharmaceutically acceptable salt or solvate thereof, thereby inhibiting growth of said cells.

In certain aspects, the present disclosure provides a method of reducing Ras signaling output of a cell, comprising contacting the cell with an effective amount of a compound described herein, or a pharmaceutically acceptable salt or solvate thereof, in combination with an additional agent, wherein the additional agent is a chemotherapeutic agent, a radioactive agent, an immune modulator, or an inhibitor against one or more targets selected from: MEK, epidermal growth factor receptor (EGFR), FGFR1, FGFR2, FGFR3, FGFR4, mitotic kinase, topoisomerase, ALK, c-MET, ErbB2, AXL, NTRK1, RET, A-Raf, B-Raf, C-Raf, ERK, MDM2, mTOR, BET, IGF1/2, IGF1-R, CDK9, SHC, GAB, GRB, PI3-kinase, MAPK, SHIP1, SHIP2, SHP1, SHP2, SRC, JAK, PARP, BTK, FLT3, HDAC, VEGFR, PDGFR, LCK, Bcr-Abl, AKT, wildtype KRas, KRas mutant (e.g., KrasG12C, KRas G12D, KRas G12S, KRas G12V, KRas G13D, KRas G13C, or KRas G13V), ROS1, CDK4/6, and a mutant of the one or more target thereof. In some embodiments, the additional agent is an inhibitor against one or more targets selected from MEK, epidermal growth factor receptor (EGFR), A-Raf, B-Raf, C-Raf, SHP2, wildtype KRas, a KRas mutant, and CDK4/6. In some embodiments, the additional agent is a chemotherapeutic agent, a radioactive agent, or an immune modulator.

In certain aspects, the present disclosure provides a SOS1 protein bound by a compound described herein, or a pharmaceutically acceptable salt or solvate thereof, wherein interaction of the SOS1 protein with a Ras protein is reduced as compared to a SOS1 protein unbound to said compound.

In certain aspects, the present disclosure provides a compound having the formula A-$L^{AB}$-B, wherein:
A is a monovalent form of a compound described herein;
$L^{AB}$ is a covalent linker bonded to A and B; and
B is a monovalent form of a degradation enhancer.

In some embodiments, the degradation enhancer is capable of binding a protein selected from E3A, mdm2, APC, EDD1, SOCS/BC-box/eloBC/CUL5/RING, LNXp80, CBX4, CBLL1, HACE1, HECTD1, HECTD2, HECTD3, HECTD4, HECW1, HECW2, HERC1, HERC2, HERC3, HERC4, HER5, HERC6, HUWE1, ITCH, NEDD4, NEDD4L, PPIL2, PRPF19, PIAS1, PIAS2, PIAS3, PIAS4, RANBP2, RNF4, RBX1, SMURF1, SMURF2, STUB1, TOPORS, TRIP12, UBE3A, UBE3B, UBE3C, UBE3D, UBE4A, UBE4B, UBOX5, UBR5, VHL (von-Hippel-Lindau ubiquitin ligase), WWP1, WWP2, Parkin, MKRN1, CMA (chaperon-mediated autophage), SCFb-TRCP (Skip-Cullin-F box (Beta-TRCP) ubiquitin complex), b-TRCP (b-transducing repeat-containing protein), cIAP1 (cellular inhibitor of apoptosis protein 1), APC/C (anaphase-promoting complex/cyclosome), CRBN (cereblon), CUL4-RBX1-DDB1-CRBN ($CRL4C^{RBN}$) ubiquitin ligase, XIAP, IAP, KEAP1, DCAF15, RNF114, DCAF16, AhR, SOCS2, KLHL12, UBR2, SPOP, KLHL3, KLHL20, KLHDC2, SPSB1, SPSB2, SPSB4, SOCS6, FBXO4, FBXO31, BTRC, FBW7, CDC20, PML, TRIM21, TRIM24, TRIM33, GID4, avadomide, iberdomide, and CC-885. In some embodiments, the degradation enhancer is capable of binding a protein selected from UBE2A, UBE2B, UBE2C, UBE2D1, UBE2D2, UBE2D3, UBE2DR, UBE2E1, UBE2E2, UBE2E3, UBE2F, UBE2G1, UBE2G2, UBE2H, UBE2I, UBE2J1, UBE2J2, UBE2K, UBE2L3, UBE2L6, UBE2L1, UBE2L2, UBE2L4, UBE2M, UBE2N, UBE20, UBE2Q1, UBE2Q2, UBE2R1, UBE2R2, UBE2S, UBE2T, UBE2U, UBE2V1, UBE2V2, UBE2W, UBE2Z, ATG3, BIRC6, and UFC1.

In some embodiments, $L^{AB}$ is -$L^{AB1}$-$L^{AB2}$-$L^{AB3}$-$L^{AB4}$-$L^{AB5}$-;

$L^{AB1}$, $L^{AB2}$, $L^{AB3}$, $L^{AB4}$, and $L^{AB5}$ are independently selected from a bond, —O—, —N($R^{10}$)—, —C(O)—, —N($R^{100}$)C(O)—, —C(O)N($R^{100}$)—, —S—, —S(O)$_2$—, —S(O)—, —S(O)$_2$N($R^{100}$)—, —S(O)N(R)—, —N($R^{100}$)S(O)—, —N($R^{100}$)S(O)$_2$—, $C_{1-6}$ alkylene, —(O—$C_{1-6}$ alkyl)$_x$-, —($C_{1-6}$ alkyl-)$_x$-, $C_{2-6}$ alkenylene, $C_{2-6}$ alkynylene, $C_{1-6}$ haloalkylene, $C_{3-12}$ carbocyclene, and 3- to 10-membered heterocyclene, wherein $C_{1-6}$ alkylene, $C_{2-6}$ alkenylene, $C_{2-6}$ alkynylene, $C_{1-6}$ haloalkylene, $C_{3-12}$ carbocyclene, and 3- to 10-membered heterocyclene are optionally substituted with one, two, or three $R^{20}$; and wherein each $C_{1-6}$ alkyl of —(O—$C_{1-6}$ alkyl)$_z$- and —($C_{1-6}$ alkyl-O)$_z$— is optionally substituted with one, two, or three $R^{20}$;

z is independently an integer from 0 to 10;

each $R^{100}$ is independently selected from hydrogen, $C_{1-6}$ alkyl, $C_{2-6}$ alkenyl, $C_{2-6}$ alkynyl, $C_{3-10}$ carbocycle, —CH$_2$—($C_{3-10}$ carbocycle), 3- to 10-membered heterocycle, and —CH$_2$-(3- to 10-membered heterocycle), wherein $C_{1-6}$ alkyl, $C_{2-6}$ alkenyl, $C_{2-6}$ alkynyl, $C_{3-10}$ carbocycle, —CH$_2$—($C_{3-10}$ carbocycle), 3- to 10-membered heterocycle, and —CH$_2$-(3- to 10-membered heterocycle) are optionally substituted with one, two, or three $R^{20}$;

$R^{20}$ is independently selected at each occurrence from halogen, oxo, =NH, —CN, $C_{1-6}$ alkyl, $C_{2-6}$ alkenyl, $C_{2-6}$ alkynyl, $C_{3-10}$ carbocycle, —CH$_2$—($C_{3-10}$ carbocycle), 3- to 10-membered heterocycle, —CH$_2$-(3- to 10-membered heterocycle), —OR$^{21}$, —SR$^{21}$, —N($R^{22}$)($R^{23}$), —C(O)OR$^{22}$, —C(O)N($R^{22}$)($R^{23}$), —C(O)C(O)N($R^{22}$)($R^{23}$), —OC(O)N($R^{22}$)($R^{23}$), —N($R^{24}$)C(O)N($R^{22}$)($R^{23}$), —N($R^{24}$)C(O)OR$^{25}$, —N($R^{24}$)C(O)R$^{25}$, —N($R^{24}$)S(O)$_2$R$^{25}$, —C(O)R$^{25}$, —S(O)$_2$R$^{25}$, —S(O)$_2$N($R^{22}$)($R^{23}$), —OCH$_2$C(O)OR$^{22}$, and —OC(O)R$^{25}$, wherein $C_{1-6}$ alkyl, $C_{2-6}$ alkenyl, $C_{2-6}$ alkynyl, $C_{3-10}$ carbocycle, —CH$_2$—($C_{3-10}$ carbocycle), 3- to 10-membered heterocycle, and —CH$_2$-(3- to 10-membered heterocycle) are optionally substituted with one, two, or three groups independently selected from halogen, oxo, =NH, —CN, $C_{1-6}$ alkyl, $C_{1-6}$ haloalkyl, $C_{1-6}$ alkoxy, $C_{1-6}$ haloalkoxy, —OR$^{21}$, —SR$^{21}$, —N($R^{22}$)($R^{23}$), —C(O)OR$^{22}$, —C(O)N($R^{22}$)($R^{23}$), —C(O)C(O)N($R^{22}$)($R^{23}$), —OC(O)N($R^{22}$)($R^{23}$), —N($R^{24}$)C(O)N($R^{22}$)($R^{23}$), —N($R^{24}$)C(O)OR$^{25}$, —N($R^{24}$)C(O)R$^{25}$, —N($R^{24}$)S(O)$_2$R$^{25}$, —C(O)R$^{25}$, —S(O)$_2$R$^{25}$, —S(O)$_2$N($R^{22}$)($R^{23}$), and —OC(O)R$^{25}$;

$R^{21}$ is independently selected at each occurrence from H, $C_{1-6}$ alkyl, $C_{1-6}$ haloalkyl, $C_{2-6}$ alkenyl, $C_{2-6}$ alkynyl, $C_{3-10}$ carbocycle, and 3- to 10-membered heterocycle, wherein $C_{3-10}$ carbocycle and 3- to 10-membered heterocycle are optionally substituted with one, two, or three groups independently selected from halogen and $C_{1-6}$alkyl;

$R^{22}$ is independently selected at each occurrence from H, $C_{1-6}$ alkyl, $C_{1-6}$ haloalkyl, $C_{2-6}$ alkenyl, $C_{2-6}$ alkynyl, $C_{3-10}$ carbocycle, and 3- to 10-membered heterocycle, wherein $C_{3-10}$ carbocycle and 3- to 10-membered heterocycle are optionally substituted with one, two, or three groups independently selected from halogen and $C_{1-6}$alkyl;

$R^{23}$ is independently selected at each occurrence from H and $C_{1-6}$ alkyl;

$R^{24}$ is independently selected at each occurrence from H and $C_{1-6}$ alkyl; and $R^{25}$ is independently selected at each occurrence from $C_{1-6}$ alkyl, $C_{2-6}$ alkenyl, $C_{2-6}$ alkynyl, $C_{3-10}$ carbocycle, and 3- to 10-membered heterocycle, wherein $C_{1-6}$ alkyl, $C_{3-10}$ carbocycle, and 3- to 10-membered heterocycle are optionally substituted with one, two, or three groups independently selected from halogen, $C_{1-6}$ alkyl, $C_{1-6}$ haloalkyl, $C_{1-6}$ alkoxy, $C_{3-10}$ carbocycle, and 3- to 10-membered heterocycle.

In some embodiments, $L^{AB}$ is $-(O-C_2 \text{ alkyl})_z-$ and z is an integer from 1 to 10. In some embodiments, L, is $-(C_2 \text{ alkyl-O}-)_z-$ and z is an integer from 1 to 10. In some embodiments, $L^{AB}$ is $-(CH_2)_{xx1}L^{AB2}(CH_2O)_{xx2}-$, wherein $L^{AB2}$ is selected from a bond, 5- to 6-membered heterocyclene, phenylene, $-C_{2-4}$ alkynylene, $-SO_2-$, and $-NH-$; and zz1 and zz2 are independently an integer from 0 to 10. In some embodiments, $L^{AB}$ is $-(CH_2)_{zz1}(CH_2O)_{xx2}-$, wherein zz1 and zz2 are each independently an integer from 0 to 10. In some embodiments, $L^{AB}$ is a PEG linker. In some embodiments, B is a monovalent form of a compound selected from -continued

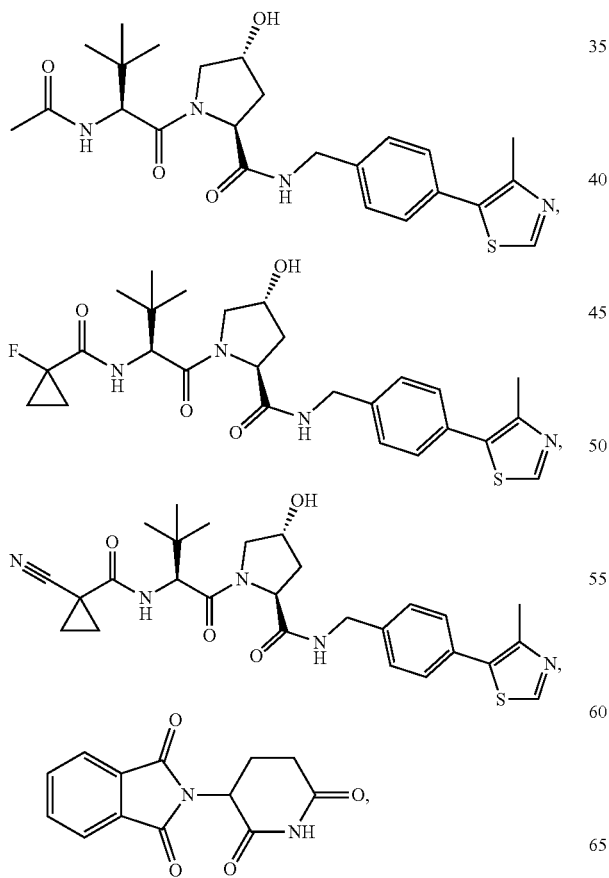

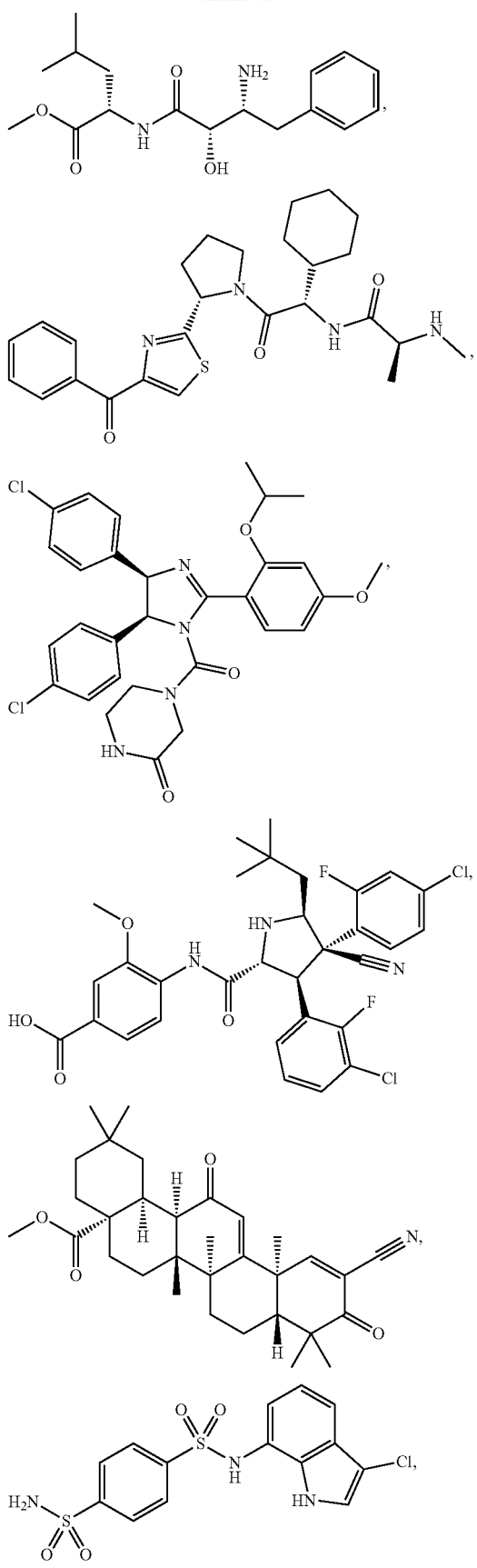

-continued

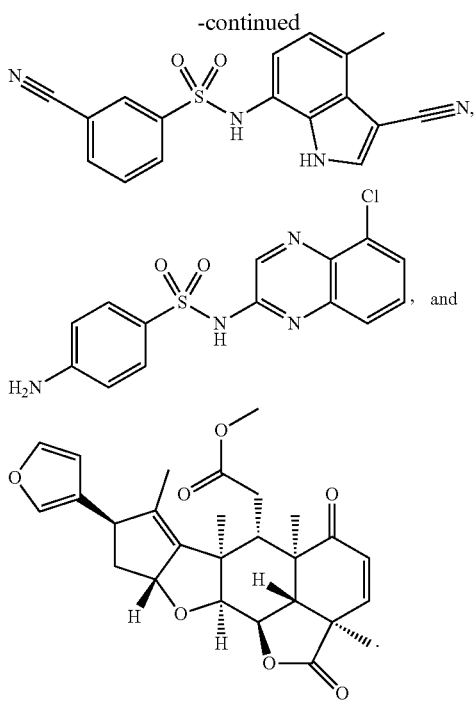

INCORPORATION BY REFERENCE

All publications, patents, and patent applications mentioned in this specification are herein incorporated by reference to the same extent as if each individual publication, patent, or patent application was specifically and individually indicated to be incorporated by reference.

DETAILED DESCRIPTION

Unless defined otherwise, all technical and scientific terms used herein have the same meaning as is commonly understood by one of skill in the art to which this disclosure belongs. In the event that there are a plurality of definitions for terms herein, those in this section prevail. All patents, patent applications, publications and published nucleotide and amino acid sequences (e.g., sequences available in GenBank or other databases) referred to herein are incorporated by reference. Chemical structures are named herein according to IUPAC conventions as implemented in ChemDraw® software (Perkin Elmer, Inc., Cambridge, MA). The section headings used herein are for organizational purposes only and are not to be construed as limiting the subject matter described. As used in the specification and claims, the singular forms "a", "an" and "the" include plural references unless the context clearly dictates otherwise.

The term "$C_{x-y}$" or "$C_x$-$C_y$" when used in conjunction with a chemical moiety, such as alkyl, alkenyl, or alkynyl, is meant to include groups that contain from x to y carbons in the chain. For example, the term "$C_{x-y}$ alkyl" refers to substituted or unsubstituted saturated hydrocarbon groups, including straight-chain alkyl and branched-chain alkyl groups, that contain from x to y carbons in the chain.

"Alkyl" refers to substituted or unsubstituted saturated hydrocarbon groups, including linear and branched alkyl groups. An alkyl group may contain from one to twelve carbon atoms (e.g., $C_{1-12}$ alkyl), such as one to eight carbon atoms ($C_{1-8}$ alkyl) or one to six carbon atoms ($C_{1-6}$ alkyl). Exemplary alkyl groups include methyl, ethyl, n-propyl, isopropyl, n-butyl, isobutyl, sec-butyl, tert-butyl, pentyl, isopentyl, neopentyl, hexyl, septyl, octyl, nonyl, and decyl. An alkyl group is attached to the rest of the molecule by a single bond. Unless stated otherwise specifically in the specification, an alkyl group is optionally substituted by one or more substituents such as those substituents described herein.

"Haloalkyl" refers to an alkyl group that is substituted by one or more halogens. Exemplary haloalkyl groups include trifluoromethyl, difluoromethyl, trichloromethyl, 2,2,2-trifluoroethyl, 1,2-difluoroethyl, 3-bromo-2-fluoropropyl, and 1,2-dibromoethyl.

"Alkenyl" refers to substituted or unsubstituted hydrocarbon groups, including linear and branched alkenyl groups, containing at least one double bond. An alkenyl group may contain from two to twelve carbon atoms (e.g., $C_{2-12}$ alkenyl), such as two to eight carbon atoms ($C_{2-8}$ alkenyl) or two to six carbon atoms ($C_{2-6}$ alkenyl). Exemplary alkenyl groups include ethenyl (i.e., vinyl), prop-1-enyl, but-1-enyl, pent-1-enyl, penta-1,4-dienyl, and the like. Unless stated otherwise specifically in the specification, an alkenyl group is optionally substituted by one or more substituents such as those substituents described herein.

"Alkynyl" refers to substituted or unsubstituted hydrocarbon groups, including linear and branched alkynyl groups, containing at least one triple bond. An alkynyl group may contain from two to twelve carbon atoms (e.g., $C_{2-12}$ alkynyl), such as two to eight carbon atoms ($C_{2-8}$ alkynyl) or two to six carbon atoms ($C_{2-6}$ alkynyl). Exemplary alkynyl groups include ethynyl, propynyl, butynyl, pentynyl, hexynyl, and the like. Unless stated otherwise specifically in the specification, an alkynyl group is optionally substituted by one or more substituents such as those substituents described herein.

"Alkylene" or "alkylene chain" refers to substituted or unsubstituted divalent saturated hydrocarbon groups, including linear alkylene and branched alkylene groups, that contain from one to twelve carbon atoms (e.g., $C_{1-12}$ alkylene), such as one to eight carbon atoms ($C_{1-8}$ alkylene) or one to six carbon atoms ($C_{1-6}$ alkylene). Exemplary alkylene groups include methylene, ethylene, propylene, and n-butylene. Similarly, "alkenylene" and "alkynylene" refer to alkylene groups, as defined above, which comprise one or more carbon-carbon double or triple bonds, respectively. The points of attachment of the alkylene, alkenylene or alkynylene chain to the rest of the molecule can be through one carbon or any two carbons of the chain. Unless stated otherwise specifically in the specification, an alkylene, alkenylene, or alkynylene group is optionally substituted by one or more substituents such as those substituents described herein.

"Heteroalkyl", "heteroalkenyl" and "heteroalkynyl" refer to substituted or unsubstituted alkyl, alkenyl and alkynyl groups, respectively, in which one or more, such as 1, 2 or 3, of the carbon atoms are replaced with a heteroatom, such as O, N, P, Si, S, or combinations thereof. Any nitrogen, phosphorus, and sulfur heteroatoms present in the chain may optionally be oxidized, and any nitrogen heteroatoms may optionally be quaternized. If given, a numerical range refers to the chain length in total. For example, a 3- to 8-membered heteroalkyl group has a chain length of 3 to 8 atoms. Connection to the rest of the molecule may be through either a heteroatom or a carbon in the heteroalkyl, heteroalkenyl, or heteroalkynyl chain. Unless stated otherwise specifically in the specification, a heteroalkyl, heteroalkenyl, or heteroalkynyl group is optionally substituted by one or more substituents such as those substituents described herein.

"Heteroalkylene", "heteroalkenylene" and "heteroalkynylene" refer to substituted or unsubstituted alkylene, alkenylene and alkynylene groups, respectively, in which one or more, such as 1, 2 or 3, of the carbon atoms are replaced with a heteroatom, such as O, N, P, Si, S, or combinations thereof. Any nitrogen, phosphorus, and sulfur heteroatoms present in the chain may optionally be oxidized, and any nitrogen heteroatoms may optionally be quaternized. If given, a numerical range refers to the chain length in total. For example, a 3- to 8-membered heteroalkylene group has a chain length of 3 to 8 atoms. The points of attachment of the heteroalkylene, heteroalkenylene or heteroalkynylene chain to the rest of the molecule can be through either one heteroatom or one carbon, or any two heteroatoms, any two carbons, or any one heteroatom and any one carbon in the heteroalkylene, heteroalkenylene or heteroalkynylene chain. Unless stated otherwise specifically in the specification, a heteroalkylene, heteroalkenylene, or heteroalkynylene group is optionally substituted by one or more substituents such as those substituents described herein.

"Carbocycle" refers to a saturated, unsaturated or aromatic ring in which each atom of the ring is a carbon atom. Carbocycle may include $C_{3-10}$ monocyclic rings, $C_{6-12}$ bicyclic rings, $C_{6-12}$ spirocyclic rings, and $C_{6-12}$ bridged rings. Each ring of a bicyclic carbocycle may be selected from saturated, unsaturated, and aromatic rings. In some embodiments, the carbocycle is a $C_{6-12}$ aryl group, such as $C_{6-10}$ aryl. In some embodiments, the carbocycle is a $C_{6-12}$ cycloalkyl group. In some embodiments, the carbocycle is a $C_{6-12}$ cycloalkenyl group. In an exemplary embodiment, an aromatic ring, e.g., phenyl, may be fused to a saturated or unsaturated ring, e.g., cyclohexane, cyclopentane, or cyclohexene. Any combination of saturated, unsaturated and aromatic bicyclic rings, as valence permits, are included in the definition of carbocycle. Exemplary carbocycles include cyclopentyl, cyclohexyl, cyclohexenyl, adamantly, phenyl, indanyl, and naphthyl. Unless state otherwise specifically in the specification, a carbocycle is optionally substituted by one or more substituents such as those substituents described herein.

"Heterocycle" refers to a saturated, unsaturated or aromatic ring comprising one or more heteroatoms, for example 1, 2 or 3 heteroatoms selected from O, S and N. Heterocycles include 3- to 10-membered monocyclic rings, 6- to 12-membered bicyclic rings, 6- to 12-membered spirocyclic rings, and 6- to 12-membered bridged rings. Each ring of a bicyclic heterocycle may be selected from saturated, unsaturated, and aromatic rings. The heterocycle may be attached to the rest of the molecule through any atom of the heterocycle, valence permitting, such as a carbon or nitrogen atom of the heterocycle. In some embodiments, the heterocycle is a 5- to 10-membered heteroaryl group, such as 5- or 6-membered heteroaryl. In some embodiments, the heterocycle is a 3- to 12-membered heterocycloalkyl group. In an exemplary embodiment, a heterocycle, e.g., pyridyl, may be fused to a saturated or unsaturated ring, e.g., cyclohexane, cyclopentane, or cyclohexene. Exemplary heterocycles include pyrrolidinyl, pyrrolyl, imidazolyl, pyrazolyl, triazolyl, piperidinyl, pyridinyl, pyrimidinyl, pyridazinyl, pyrazinyl, thiophenyl, oxazolyl, thiazolyl, morpholinyl, indazolyl, indolyl, and quinolinyl. Unless stated otherwise specifically in the specification, a heterocycle is optionally substituted by one or more substituents such as those substituents described herein.

"Heteroaryl" refers to a 5- to 12-membered aromatic ring that comprises at least one heteroatom, such as 1, 2 or 3 heteroatoms, selected from O, S and N. As used herein, the heteroaryl ring may be selected from monocyclic or bicyclic-including fused, spirocyclic and bridged ring systems—wherein at least one of the rings in the ring system is aromatic. The heteroatom(s) in the heteroaryl may optionally be oxidized. One or more nitrogen atoms, if present, are optionally quaternized. The heteroaryl may be attached to the rest of the molecule through any atom of the heteroaryl, valence permitting, such as a carbon or nitrogen atom of the heteroaryl. Examples of heteroaryl groups include, but are not limited to, azepinyl, benzimidazolyl, benzisothiazolyl, benzisoxazolyl, benzofuranyl, benzothiazolyl, benzothiophenyl, benzoxazolyl, furanyl, imidazolyl, indazolyl, indolyl, isoquinolinyl, isothiazolyl, isoxazolyl, oxadiazolyl, oxazolyl, purinyl, pyrazinyl, pyrazolidinyl, pyrazolyl, pyridazinyl, pyridazolyl, pyridyl, pyrimidinyl, pyrrolyl, quinazolinyl, quinolinyl, quinoxalinyl, tetrahydroquinolinyl, thiadiazolyl, thiazolyl, and thienyl groups. Unless stated otherwise specifically in the specification, a heteroaryl is optionally substituted by one or more substituents such as those substituents described herein.

Unless stated otherwise, hydrogen atoms are implied in structures depicted herein as necessary to satisfy the valence requirement.

A waved line "⌇" drawn across a bond or a dashed bond "---" are used interchangeably herein to denote where a bond disconnection or attachment occurs. For example, in the structure

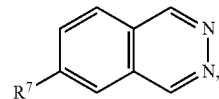

if $R^7$ is 1-cyclopropyl-1-carbonitrile as in

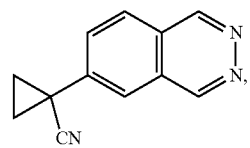 [SMILES: N#CC1(c2ccc3cnncc3c2)CC1]

then $R^7$ may be depicted as

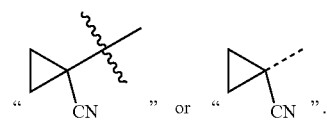

The term "substituted" refers to moieties having substituents replacing a hydrogen on one or more carbons or heteroatoms of the structure. It will be understood that "substitution" or "substituted with" includes the implicit proviso that such substitution is in accordance with permitted valence of the substituted atom and the substituent, and that the substitution results in a stable compound, e.g., which does not spontaneously undergo transformation such as by rearrangement, cyclization, elimination, etc. As used herein, the term "substituted" is contemplated to include all permissible substituents of organic compounds. In a broad aspect, the permissible substituents include acyclic and cyclic, branched and unbranched, carbocyclic and heterocyclic, aromatic and non-aromatic substituents of organic compounds. The permissible substituents can be one or more and the same or different for appropriate organic compounds. For purposes of this disclosure, heteroatoms such as nitrogen may have any permissible substituents of organic compounds described herein which satisfy the valences of the heteroatoms.

A compound disclosed herein, such as a compound of Formula (I), is optionally substituted by one or more, such as 1, 2 or 3 substituents selected from:

halogen, oxo, =NH, —CN, $C_{1-6}$ alkyl, $C_{2-6}$ alkenyl, $C_{2-6}$ alkynyl, $C_{3-10}$ carbocycle, —$CH_2$—($C_{3-10}$ carbocycle), 3- to 10-membered heterocycle, —$CH_2$-(3- to 10-membered heterocycle), —$OR^{21}$, —$SR^{21}$, —$N(R^{22})(R^{23})$, —$C(O)OR^{22}$, —$C(O)N(R^{22})(R^{23})$, —$C(O)C(O)N(R^{22})(R^{23})$, —$OC(O)N(R^{22})(R^{23})$, —$N(R^{22})C(O)N(R^{22})(R^{23})$, —$N(R^{24})C(O)OR^{25}$, —$N(R^{24})C(O)R^{25}$, —$N(R^{24})S(O)_2R^{25}$, —$C(O)R^{25}$, —$S(O)_2R^{25}$, —$S(O)_2N(R^{22})(R^{23})$, —$OCH_2C(O)OR^{22}$, and —$OC(O)R^{25}$, wherein $C_{1-6}$ alkyl, $C_{2-6}$ alkenyl, $C_{2-6}$ alkynyl, $C_{3-10}$ carbocycle, —$CH_2$—($C_{3-10}$ carbocycle), 3- to 10-membered heterocycle, and —$CH_2$-(3- to 10-membered heterocycle) are optionally substituted with one, two, or three groups independently selected from halogen, oxo, =NH, —CN, $C_{1-6}$ alkyl, $C_{1-6}$ haloalkyl, $C_{1-6}$ alkoxy, $C_{1-6}$ haloalkoxy, —$OR^{21}$, —$SR^{21}$, —$N(R^{22})(R^{23})$, —$C(O)OR^{22}$, —$C(O)N(R^{22})(R^{23})$, —$C(O)C(O)N(R^{22})(R^{23})$, —$OC(O)N(R^{22})(R^{23})$, —$N(R^{24})C(O)N(R^{22})(R^{23})$, —$N(R^{24})C(O)OR^{25}$, —$N(R^{24})C(O)R^{25}$, —$N(R^{22})S(O)_2R^{25}$, —$C(O)R^{25}$, —$S(O)_2R^{25}$, —$S(O)_2N(R^{22})(R^{23})$, and —$OC(O)R^{25}$;

$R^{21}$ is independently selected at each occurrence from H, $C_{1-6}$ alkyl, $C_{1-6}$ haloalkyl, $C_{2-6}$ alkenyl, $C_{2-6}$ alkynyl, $C_{3-10}$ carbocycle, and 3- to 10-membered heterocycle, wherein $C_{3-10}$ carbocycle and 3- to 10-membered heterocycle are optionally substituted with one, two, or three groups independently selected from halogen and $C_{1-6}$ alkyl;

$R^{22}$ is independently selected at each occurrence from H, $C_{1-6}$ alkyl, $C_{1-6}$ haloalkyl, $C_{2-6}$ alkenyl, $C_{2-6}$ alkynyl, $C_{3-10}$ carbocycle, and 3- to 10-membered heterocycle, wherein $C_{3-10}$ carbocycle and 3- to 10-membered heterocycle are optionally substituted with one, two, or three groups independently selected from halogen and $C_{1-6}$ alkyl;

$R^{23}$ is independently selected at each occurrence from H and $C_{1-6}$ alkyl;

$R^4$ is independently selected at each occurrence from H and $C_{1-6}$ alkyl; and $R^{25}$ is independently selected at each occurrence from $C_{1-6}$ alkyl, $C_{2-6}$ alkenyl, $C_{2-6}$ alkynyl, $C_{3-10}$ carbocycle, and 3- to 10-membered heterocycle, wherein $C_{1-6}$ alkyl, $C_{3-10}$ carbocycle, and 3- to 10-membered heterocycle are optionally substituted with one, two, or three groups independently selected from halogen, $C_{1-6}$ alkyl, $C_{1-6}$ haloalkyl, $C_{1-6}$ alkoxy, $C_{3-10}$ carbocycle, and 3- to 10-membered heterocycle.

In some embodiments, a compound disclosed herein, such as a compound of Formula (I), is optionally substituted by one or more, such as 1, 2 or 3 substituents selected from:

halogen, oxo, =NH, —CN, $C_{1-6}$ alkyl, $C_{2-6}$ alkenyl, $C_{2-6}$ alkynyl, $C_{3-10}$ carbocycle, —$CH_2$—($C_{3-10}$ carbocycle), 3- to 10-membered heterocycle, —$CH_2$-(3- to 10-membered heterocycle), —$OR^{21}$, —$SR^{21}$, —$N(R^{22})(R^{23})$, —$C(O)OR^{22}$, —$C(O)N(R^{22})(R^{23})$, —$C(O)C(O)N(R^{22})(R^{23})$, —$OC(O)N(R^{22})(R^{23})$, —$N(R^{22})C(O)N(R^{22})(R^{23})$, —$N(R^{24})C(O)OR^{25}$, —$N(R^{24})C(O)R^{25}$, —$N(R^{24})S(O)_2R^{25}$, —$C(O)R^{25}$, —$S(O)_2R^{25}$, —$S(O)_2N(R^{22})(R^{23})$, —$OCH_2C(O)OR^{22}$, and —$OC(O)R^{25}$, wherein $C_{1-6}$ alkyl, $C_{2-6}$ alkenyl, $C_{2-6}$ alkynyl, $C_{3-10}$ carbocycle, —$CH_2$—($C_{3-10}$ carbocycle), 3- to 10-membered heterocycle, and —$CH_2$-(3- to 10-membered heterocycle) are optionally substituted with one, two, or three groups independently selected from halogen, oxo, =NH, —CN, $C_{1-6}$ alkyl, $C_{1-6}$ haloalkyl, $C_{1-6}$ alkoxy, $C_{1-6}$ haloalkoxy, —$OR^{21}$, —$SR^{21}$, and —$N(R^{22})(R^{23})$;

$R^{21}$ is independently selected at each occurrence from H, $C_{1-6}$ alkyl, $C_{1-6}$ haloalkyl, $C_{2-6}$ alkenyl, $C_{2-6}$ alkynyl, $C_{3-10}$ carbocycle, and 3- to 10-membered heterocycle, wherein $C_{3-10}$ carbocycle and 3- to 10-membered heterocycle are optionally substituted with one, two, or three groups independently selected from halogen and $C_{1-6}$ alkyl;

$R^{22}$ is independently selected at each occurrence from H, $C_{1-6}$ alkyl, $C_{1-6}$ haloalkyl, $C_{2-6}$ alkenyl, $C_{2-6}$ alkynyl, $C_{3-10}$ carbocycle, and 3- to 10-membered heterocycle, wherein $C_{3-10}$ carbocycle and 3- to 10-membered heterocycle are optionally substituted with one, two, or three groups independently selected from halogen and $C_{1-6}$ alkyl;

$R^{23}$ is independently selected at each occurrence from H and $C_{1-6}$ alkyl;

$R^{24}$ is independently selected at each occurrence from H and $C_{1-6}$ alkyl; and $R^{25}$ is independently selected at each occurrence from $C_{1-6}$ alkyl, $C_{2-6}$ alkenyl, $C_{2-6}$ alkynyl, $C_{3-10}$ carbocycle, and 3- to 10-membered heterocycle, wherein $C_{1-6}$ alkyl, $C_{3-10}$ carbocycle, and 3- to 10-membered heterocycle are optionally substituted with one, two, or three groups independently selected from halogen, $C_{1-6}$ alkyl, $C_{1-6}$ haloalkyl, $C_{1-6}$ alkoxy, $C_{3-10}$ carbocycle, and 3- to 10-membered heterocycle.

In some embodiments, a compound disclosed herein, such as a compound of Formula (I), is optionally substituted by one or more, such as 1, 2 or 3 substituents selected from halogen, oxo, =NH, —CN, —$NO_2$, $C_{1-6}$ alkyl, $C_{2-6}$ alkenyl, $C_{2-6}$ alkynyl, $C_{3-10}$ carbocycle, —$CH_2$—($C_{3-10}$ carbocycle), 3- to 10-membered heterocycle, —$CH_2$-(3- to 10-membered heterocycle), —OH, —$OCH_3$, —$OCH_2CH_3$, —$NH_2$, —$NHCH_3$, and —$NHCH_2CH_3$, wherein $C_{1-6}$ alkyl, $C_{2-6}$ alkenyl, $C_{2-6}$ alkynyl, $C_{3-10}$ carbocycle, —$CH_2$—($C_{3-10}$ carbocycle), 3- to 10-membered heterocycle, and —$CH_2$-(3- to 10-membered heterocycle) are optionally substituted with one, two, or three groups independently selected from halogen, oxo, =NH, —CN, —$NO_2$, —$CH_3$, —$CH_2CH_3$, —$CH(CH_3)_2$, —$C(CH_3)_3$, —OH, —$OCH_3$, —$OCH_2CH_3$, —$NH_2$, —$NHCH_3$, and —$NHCH_2CH_3$.

It will be understood by those skilled in the art that substituents can themselves be substituted, if appropriate. Unless specifically stated as "unsubstituted", references to chemical moieties herein are understood to include substituted variants. For example, reference to a "heteroaryl" group or moiety implicitly includes both substituted and unsubstituted variants.

Where bivalent substituent groups are specified herein by their conventional chemical formulae, written from left to right, they are intended to encompass the isomer that would result from writing the structure from right to left, e.g., —$CH_2O$—is also intended to encompass —$OCH_2$—.

"Optional" or "optionally" means that the subsequently described event or circumstances may or may not occur, and that the description includes instances where the event or circumstance occurs and instances in which it does not. For example, an "optionally substituted" group may be either unsubstituted or substituted.

Compounds of the present disclosure also include crystalline and amorphous forms of those compounds, pharmaceutically acceptable salts, and active metabolites having the same type of activity, including, for example, polymorphs, pseudopolymorphs, solvates, hydrates, unsolvated polymorphs (including anhydrates), conformational polymorphs, amorphous forms of the compounds, and mixtures thereof.

The compounds described herein may exhibit their natural isotopic abundance, or one or more of the atoms may be artificially enriched in a particular isotope having the same atomic number, but an atomic mass or mass number different from the atomic mass or mass number predominantly found in nature. All isotopic variations of the compounds of the present disclosure, whether radioactive or not, are encompassed within the scope of the present disclosure. For example, hydrogen has three naturally occurring isotopes, denoted $^1H$ (protium), $^2H$ (deuterium), and $^3H$ (tritium). Protium is the most abundant isotope of hydrogen in nature. Enriching for deuterium may afford certain therapeutic advantages, such as increased in vivo half-life and/or exposure, or may provide a compound useful for investigating in vivo routes of drug elimination and metabolism. Examples of isotopes that may be incorporated into compounds of the present disclosure include, but are not limited to, $^2H$, $^3H$, $^{13}C$, $^{14}C$, $^{15}N$, $^{18}O$, $^{17}O$, $^{35}S$, $^{36}Cl$, and $^{18}F$. Of particular interest are compound of Formula (I) enriched in tritium or carbon-14, which can be used, for example, in tissue distribution studies; compounds of the disclosure enriched in deuterium—especially at a site of metabolism—resulting, for example, in compounds having greater metabolic stability; and compounds of Formula (I) enriched in a positron emitting isotope, such as $^{11}C$, $^{18}F$, $^{15}O$ and $^{13}N$, which can be used, for example, in Positron Emission Topography (PET) studies. Isotopically-enriched compounds may be prepared by conventional techniques well known to those skilled in the art.

As used herein, the phrase "of the formula", "having the formula" or "having the structure" is not intended to be limiting and is used in the same way that the term "comprising" is commonly used. For example, if one structure is depicted, it is understood that all stereoisomer and tautomer forms are encompassed, unless stated otherwise.

Certain compounds described herein contain one or more asymmetric centers and can thus give rise to enantiomers, diastereomers, and other stereoisomeric forms, the asymmetric centers of which can be defined, in terms of absolute stereochemistry, as (R)- or (S)-. In some embodiments, in order to optimize the therapeutic activity of the compounds of the disclosure, e.g., to treat fibrosis, it may be desirable that the carbon atoms have a particular configuration (e.g., (R,R), (S,S), (S,R), or (R,S)) or are enriched in a stereoisomeric form having such configuration. The compounds of the disclosure may be provided as racemic mixtures. Accordingly, the disclosure relates to racemic mixtures, pure stereoisomers (e.g., enantiomers and diastereomers), stereoisomer-enriched mixtures, and the like, unless otherwise indicated. When a chemical structure is depicted herein without any stereochemistry, it is understood that all possible stereoisomers are encompassed by such structure. Similarly, when a particular stereoisomer is shown or named herein, it will be understood by those skilled in the art that minor amounts of other stereoisomers may be present in the compositions of the disclosure unless otherwise indicated, provided that the utility of the composition as a whole is not eliminated by the presence of such other isomers. Individual stereoisomers may be obtained by numerous methods that are known in the art, including preparation using chiral synthons or chiral reagents, resolution using chiral chromatography using a suitable chiral stationary phase or support, or by chemically converting them into diastereomers, separating the diastereoisomers by conventional means such as chromatography or recrystallization, then regenerating the original stereoisomer.

Additionally, where applicable, all cis-trans or E/Z isomers (geometric isomers), tautomeric forms and topoisomeric forms of the compounds described herein are included with the scope of the disclosure unless otherwise specified.

The term "pharmaceutically acceptable" refers to a material that is not biologically or otherwise unacceptable when used in the subject compositions and methods. For example, the term "pharmaceutically acceptable carrier" refers to a material-such as an adjuvant, excipient, glidant, sweetening agent, diluent, preservative, dye, colorant, flavor enhancer, surfactant, wetting agent, dispersing agent, suspending agent, stabilizer, isotonic agent, solvent or emulsifier—that can be incorporated into a composition and administered to a patient without causing unacceptable biological effects or interacting in an unacceptable manner with other components of the composition. Such pharmaceutically acceptable materials typically have met the required standards of toxicological and manufacturing testing, and include those materials identified as suitable inactive ingredients by the U.S. Food and Drug Administration.

The terms "salt" and "pharmaceutically acceptable salt" refer to a salt prepared from a base or an acid. Pharmaceutically acceptable salts are suitable for administration to a patient, such as a mammal (for example, salts having acceptable mammalian safety for a given dosage regime). Salts can be formed from inorganic bases, organic bases, inorganic acids and organic acids. In addition, when a compound contains both a basic moiety, such as an amine, pyridine or imidazole, and an acidic moiety, such as a carboxylic acid or tetrazole, zwitterions may be formed and are included within the term "salt" as used herein. Preferred pharmaceutically acceptable salts of the compounds described herein are pharmaceutically acceptable acid addition salts and pharmaceutically acceptable base addition salts.

"Pharmaceutically acceptable acid addition salt" refers to those salts which retain the biological effectiveness and properties of the free bases, which are not biologically or otherwise undesirable, and which are formed with inorganic acids such as hydrochloric acid, hydrobromic acid, sulfuric acid, nitric acid, phosphoric acid, hydroiodic acid, hydrofluoric acid, phosphorous acid, and the like. Also included are salts that are formed with organic acids such as aliphatic mono- and dicarboxylic acids, phenyl-substituted alkanoic acids, hydroxy alkanoic acids, alkanedioic acids, aromatic acids, aliphatic and aromatic sulfonic acids, etc., and include, for example, acetic acid, trifluoroacetic acid, propionic acid, glycolic acid, pyruvic acid, oxalic acid, maleic acid, malonic acid, succinic acid, fumaric acid, tartaric acid, citric acid, benzoic acid, cinnamic acid, mandelic acid, methanesulfonic acid, ethanesulfonic acid, p-toluenesulfonic acid, salicylic acid, and the like. Exemplary salts thus include sulfates, pyrosulfates, bisulfates, sulfites, bisulfites, nitrates, phosphates, monohydrogenphosphates, dihydrogenphosphates, metaphosphates, pyrophosphates, chlorides, bromides, iodides, acetates, trifluoroacetates, propionates, caprylates, isobutyrates, oxalates, malonates, succinate suberates, sebacates, fumarates, maleates, mandelates, benzoates, chlorobenzoates, methylbenzoates, dinitrobenzoates, phthalates, benzenesulfonates, toluenesulfonates, phenylacetates, citrates, lactates, malates, tartrates, methanesulfonates, and the like. Also contemplated are salts of amino acids, such as arginates, gluconates, and galacturonates (see, for example, Berge S. M. et al., "Pharmaceutical Salts," Journal of Pharmaceutical Science, 66:1-19 (1997)). Acid addition salts of basic compounds are, in some embodiments, prepared by contacting the free base forms with a sufficient amount of the desired acid to produce the salt according to methods and techniques with which a skilled artisan is familiar.

"Pharmaceutically acceptable base addition salt" refers to those salts that retain the biological effectiveness and properties of the free acids, which are not biologically or otherwise undesirable. These salts are prepared from addition of an inorganic base or an organic base to the free acid. Pharmaceutically acceptable base addition salts are, in some embodiments, formed with metals or amines, such as alkali and alkaline earth metals or organic amines. Salts derived from inorganic bases include, but are not limited to, sodium, potassium, lithium, ammonium, calcium, magnesium, iron, zinc, copper, manganese, aluminum salts and the like. Salts derived from organic bases include, but are not limited to, salts of primary, secondary, and tertiary amines, substituted amines including naturally occurring substituted amines, cyclic amines and basic ion exchange resins, for example, isopropylamine, trimethylamine, diethylamine, triethylamine, tripropylamine, ethanolamine, diethanolamine, 2-dimethylaminoethanol, 2-diethylaminoethanol, dicyclohexylamine, lysine, arginine, histidine, caffeine, procaine, N,N-dibenzylethylenediamine, chloroprocaine, hydrabamine, choline, betaine, ethylenediamine, ethylenedianiline, N-methylglucamine, glucosamine, methylglucamine, theobromine, purines, piperazine, piperidine, N-ethylpiperidine, polyamine resins and the like. See Berge et al., supra.

The term "effective amount" or "therapeutically effective amount" refers to the amount of an agent that is sufficient to effect beneficial or desired results. The therapeutically effective amount may vary depending upon one or more of: the subject and disease condition being treated, the weight and age of the subject, the severity of the disease condition, the manner of administration and the like, which can readily be determined by one of ordinary skill in the art. An effective amount of an active agent may be administered in a single dose or in multiple doses. A component may be described herein as having at least an effective amount, or at least an amount effective, such as that associated with a particular goal or purpose, such as any described herein. The term "effective amount" also applies to a dose that will provide an image for detection by an appropriate imaging method. The specific dose may vary depending on one or more of: the particular agent chosen, the dosing regimen to be followed, whether it is administered in combination with other compounds, timing of administration, the tissue to be imaged, and the physical delivery system in which it is carried.

As used herein, "treating" or "treatment" refers to an approach for obtaining beneficial or desired results with respect to a disease, disorder, or medical condition (such as cancer) in a subject, including but not limited to the following: (a) preventing the disease or medical condition from occurring, e.g., preventing the reoccurrence of the disease or medical condition or prophylactic treatment of a subject that is pre-disposed to the disease or medical condition; (b) ameliorating the disease or medical condition, e.g., eliminating or causing regression of the disease or medical condition in a subject; (c) suppressing the disease or medical condition, e.g., slowing or arresting the development of the disease or medical condition in a subject; or (d) alleviating symptoms of the disease or medical condition in a subject. For example, "treating cancer" would include preventing cancer from occurring, ameliorating cancer, suppressing cancer, and alleviating the symptoms of cancer. Also, a therapeutic benefit is achieved with the eradication or amelioration of one or more of the physiological symptoms associated with the underlying disorder such that an improvement is observed in the subject, notwithstanding that the subject may still be afflicted with the underlying disorder.

A "therapeutic effect", as that term is used herein, encompasses a therapeutic benefit and/or prophylactic benefit as described above. A prophylactic effect includes delaying or eliminating the appearance of a disease or condition, delaying or eliminating the onset of symptoms of a disease or condition, slowing, halting, or reversing the progression of a disease or condition, or any combination thereof.

The terms "antagonist" and "inhibitor" are used interchangeably, and they refer to a compound having the ability to inhibit a biological function (e.g., activity, expression, binding, protein-protein interaction) of a target protein (e.g., SOS1). Accordingly, the terms "antagonist" and "inhibitor" are defined in the context of the biological role of the target protein. While preferred antagonists herein specifically interact with (e.g., bind to) the target, compounds that inhibit a biological activity of the target protein by interacting with other members of the signal transduction pathway of which the target protein is a member are also specifically included within this definition.

The term "selective inhibition" or "selectively inhibit" refers to the ability of a biologically active agent to preferentially reduce the target signaling activity as compared to off-target signaling activity, via direct or indirect interaction with the target.

The terms "subject" and "patient" refer to an animal, such as a mammal, for example a human. The methods described herein can be useful in both human therapeutics and veterinary applications. In some embodiments, the subject is a mammal, such as a human. "Mammal" includes humans and both domestic animals such as laboratory animals and household pets (e.g., cats, dogs, swine, cattle, sheep, goats, horses, rabbits), and non-domestic animals such as wildlife and the like.

The terms "therapeutic agent", "therapeutic capable agent" or "treatment agent" are used interchangeably and refer to a molecule or compound that confers some beneficial effect upon administration to a subject. The beneficial effect includes enablement of diagnostic determinations; amelioration of a disease, symptom, disorder, or pathological condition; reducing or preventing the onset of a disease, symptom, disorder or condition; and generally counteracting a disease, symptom, disorder or pathological condition.

The terms "polypeptide", "peptide" and "protein" are used interchangeably herein to refer to polymers of amino acids of any length. The polymer may be linear or branched, it may comprise modified amino acids, and it may be interrupted by non-amino acids. The terms also encompass an amino acid polymer that has been modified; for example, disulfide bond formation, glycosylation, lipidation, acetylation, phosphorylation, or any other manipulation, such as conjugation with a labeling component. As used herein the term "amino acid" refers to either natural and/or unnatural or synthetic amino acids, including glycine and both the D or L optical isomers, and amino acid analogs and peptidomimetics.

The terms "polynucleotide", "nucleotide", "nucleotide sequence", "nucleic acid" and "oligonucleotide" are used interchangeably. They refer to a polymeric form of nucleotides of any length, either deoxyribonucleotides or ribonucleotides, or analogs thereof. Polynucleotides may have any three-dimensional structure, and may perform any function, known or unknown. The following are non-limiting examples of polynucleotides: coding or non-coding regions of a gene or gene fragment, loci (locus) defined from linkage analysis, exons, introns, messenger RNA (mRNA), transfer RNA, ribosomal RNA, short interfering RNA (siRNA), short-hairpin RNA (shRNA), micro-RNA (miRNA), ribozymes, cDNA, recombinant polynucleotides, branched polynucleotides, plasmids, vectors, isolated DNA of any sequence, isolated RNA of any sequence, nucleic acid probes, and primers. A polynucleotide may comprise one or more modified nucleotides, such as methylated nucleotides and nucleotide analogs, such as peptide nucleic acid (PNA), morpholino and locked nucleic acid (LNA), glycol nucleic acid (GNA), threose nucleic acid (TNA), 2'-fluoro, 2'-OMe, and phosphorothiolated DNA. If present, modifications to the nucleotide structure may be imparted before or after assembly of the polymer. The sequence of nucleotides may be interrupted by non-nucleotide components. A polynucleotide may be further modified after polymerization, such as by conjugation with a labeling component or other conjugation target.

As used herein, "expression" refers to the process by which a polynucleotide is transcribed from a DNA template (such as into and mRNA or other RNA transcript) and/or the process by which a transcribed mRNA is subsequently translated into peptides, polypeptides, or proteins. Transcripts and encoded polypeptides may be collectively referred to as "gene product." If the polynucleotide is derived from genomic DNA, expression may include splicing of the mRNA in a eukaryotic cell.

An "antigen" is a moiety or molecule that contains an epitope, and, as such, also specifically binds to an antibody. An "antigen binding unit" may be whole or a fragment (or fragments) of a full-length antibody, a structural variant thereof, a functional variant thereof, or a combination thereof. A full-length antibody may be, for example, a monoclonal, recombinant, chimeric, deimmunized, humanized and human antibody. Examples of a fragment of a full-length antibody may include, but are not limited to, variable heavy (VH), variable light (VL), a heavy chain found in camelids, such as camels, llamas, and alpacas (VHH or $V_HH$), a heavy chain found in sharks (V-NAR domain), a single domain antibody (sdAb, e.g., "nanobody") that comprises a single antigen-binding domain, Fv, Fd, Fab, Fab', F(ab')2, and "r IgG" (or half antibody). Examples of modified fragments of antibodies may include, but are not limited to scFv, di-scFv or bi(s)-scFv, scFv-Fc, scFv-zipper, scFab, Fab2, Fab3, diabodies, single chain diabodies, tandem diabodies (Tandab's), tandem di-scFv, tandem tri-scFv, minibodies (e.g., (VH-VL-CH3)2, (scFv-CH3)2, ((scFv)2-CH3+CH3), ((scFv)2-$CH_3$) or (scFv-$CH_3$-scFv)2), and multibodies (e.g., triabodies or tetrabodies).

The term "antibody" and "antibodies" encompass any antigen binding units, including without limitation: monoclonal antibodies, human antibodies, humanized antibodies, camelised antibodies, chimeric antibodies, and any other epitope-binding fragments.

"Prodrug" is meant to indicate a compound that may be converted under physiological conditions or by solvolysis to a biologically active compound described herein (e.g., a compound of Formula (I)). Thus, the term "prodrug" refers to a precursor of a biologically active compound that is pharmaceutically acceptable. In some aspects, a prodrug is inactive when administered to a subject but is converted in vivo to an active compound, for example, by hydrolysis. The prodrug compound often offers advantages of solubility, tissue compatibility or delayed release in a mammalian organism (see, e.g., Bundgard, H., Design of Prodrugs (1985), pp. 7-9, 21-24 (Elsevier, Amsterdam); Higuchi, T., et al., "Pro-drugs as Novel Delivery Systems," (1987) A.C.S. Symposium Series, Vol. 14; and Bioreversible Carriers in Drug Design, ed. Edward B. Roche, American Pharmaceutical Association and Pergamon Press each of which is incorporated in full by reference herein). The term "prodrug" is also meant to include any covalently bonded carriers, which release the active compound in vivo when such prodrug is administered to a mammalian subject. Prodrugs of an active compound, as described herein, are typically prepared by modifying functional groups present in the active compound in such a way that the modifications are cleaved, either in routine manipulation or in vivo, to the parent active compound. Prodrugs include compounds wherein a hydroxy, amino or mercapto group is bonded to any group that, when the prodrug of the active compound is administered to a mammalian subject, cleaves to form a free hydroxy, free amino or free mercapto group, respectively. Examples of prodrugs include, but are not limited to, acetate, formate and benzoate derivatives of a hydroxy functional group, or acetamide, formamide and benzamide derivatives of an amine functional group in the active compound, and the like.

The term "in vivo" refers to an event that takes place in a subject's body. The term "ex vivo" refers to an event that first takes place outside of the subject's body for a subsequent in vivo application into a subject's body. For example, an ex vivo preparation may involve preparation of cells outside of a subject's body for the purpose of introduction of the prepared cells into the same or a different subject's body. The term "in vitro" refers to an event that takes place outside of a subject's body. For example, an in vitro assay encompasses any assay run outside of a subject's body. In vitro assays encompass cell-based assays in which cells alive or dead are employed. In vitro assays also encompass a cell-free assay in which no intact cells are employed.

The disclosure is also meant to encompass the in vivo metabolic products of the disclosed compounds. Such products may result from, for example, the oxidation, reduction, hydrolysis, amidation, esterification, and the like of the administered compound, primarily due to enzymatic processes. Accordingly, the disclosure includes compounds produced by a process comprising administering a compound disclosed herein to a mammal for a period of time sufficient to yield a metabolic product thereof. Such products are typically identified by administering a radiolabeled compound of the disclosure in a detectable dose to an animal, such as rat, mouse, guinea pig, monkey, or to a human, allowing sufficient time for metabolism to occur, and isolating its conversion products from the urine, blood or other biological samples.

The term "Ras" or "RAS" refers to a protein in the Rat sarcoma (Ras) superfamily of small GTPases, such as in the Ras subfamily. The Ras superfamily includes, but is not limited to, the Ras subfamily, Rho subfamily, Rab subfamily, Rap subfamily, Arf subfamily, Ran subfamily, Rheb subfamily, RGK subfamily, Rit subfamily, Miro subfamily, and Unclassified subfamily. In some embodiments, a Ras protein is selected from the group consisting of KRAS (K-Ras or K-ras or Kras), HRAS (or H-Ras), NRAS (or N-Ras), MRAS (or M-Ras), ERAS (or E-Ras), RRAS2 (or R-Ras2), RALA (or RalA), RALB (or RalB), RIT1, and any combination thereof, such as from KRAS, HRAS, NRAS, RALA, RALB, and any combination thereof.

The terms "Mutant Ras" and "Ras mutant", as used interchangeably herein, refer to a Ras protein with one or more amino acid mutations, such as with respect to a common reference sequence such as a wild-type (WT) sequence. In some embodiments, a mutant Ras is selected from a mutant KRAS, mutant HRAS, mutant NRAS, mutant MRAS, mutant ERAS, mutant RRAS2, mutant RALA, mutant RALB, mutant RIT1, and any combination thereof, such as from a mutant KRAS, mutant HRAS, mutant NRAS, mutant RALA, mutant RALB, and any combination thereof. In some embodiments, a mutation can be an introduced mutation, a naturally occurring mutation, or a non-naturally occurring mutation. In some embodiments, a mutation can be a substitution (e.g., a substituted amino acid), insertion (e.g., addition of one or more amino acids), or deletion (e.g., removal of one or more amino acids). In some embodiments, two or more mutations can be consecutive, non-consecutive, or a combination thereof. In some embodiments, a mutation can be present at any position of Ras. In some embodiments, a mutation can be present at position 12, 13, 62, 92, 95, or any combination thereof of Ras relative to SEQ ID No. 1 when optimally aligned. In some embodiments, a mutant Ras may comprise about or at least about 1, 2, 3, 4, 5, 6, 7, 8, 9, 10, 11, 12, 13, 14, 15, 16, 17, 18, 19, 20, 25, 30, 35, 40, 45, 50, or more than 50 mutations. In some embodiments, a mutant Ras may comprise up to about 1, 2, 3, 4, 5, 6, 7, 8, 9, 10, 11, 12, 13, 14, 15, 16, 17, 18, 19, 20, 25, 30, 35, 40, 45, or 50 mutations. In some embodiments, the mutant Ras is about or up to about 500, 400, 300, 250, 240, 233, 230, 220, 219, 210, 208, 206, 204, 200, 195, 190, 189, 188, 187, 186, 185, 180, 175, 174, 173, 172, 171, 170, 169, 168, 167, 166, 165, 160, 155, 150, 125, 100, 90, 80, 70, 60, 50, or fewer than 50 amino acids in length. In some embodiments, an amino acid of a mutation is a proteinogenic, natural, standard, non-standard, non-canonical, essential, non-essential, or non-natural amino acid. In some embodiments, an amino acid of a mutation has a positively charged side chain, a negatively charged side chain, a polar uncharged side chain, a non-polar side chain, a hydrophobic side chain, a hydrophilic side chain, an aliphatic side chain, an aromatic side chain, a cyclic side chain, an acyclic side chain, a basic side chain, or an acidic side chain. In some embodiments, a mutation comprises a reactive moiety. In some embodiments, a substituted amino acid comprises a reactive moiety. In some embodiments, a mutant Ras can be further modified, such as by conjugation with a detectable label. In some embodiments, a mutant Ras is a full-length or truncated polypeptide. For example, a mutant Ras can be a truncated polypeptide comprising residues 1-169 or residues 11-183 (e.g., residues 11-183 of a mutant RALA or mutant RALB).

Compounds

The compounds of Formula (I) disclosed herein-including the compounds of Formula (I-A), (I-B), (I-B1), (I-B2), (I-C), (I-C1), (I-C2), (I-C3), (I-D), (I-D1), (I-D2), (I-E), (I-E1), (II-B), (II-C), and (III)— or a pharmaceutically acceptable salt or solvate thereof, are SOS modulators and have a wide range of applications in therapeutics, diagnostics, and other biomedical research.

In certain aspects, the present disclosure provides a compound of Formula (I):

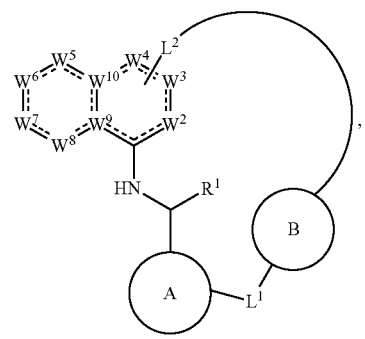

(I)

or a pharmaceutically acceptable salt or solvate thereof, wherein:

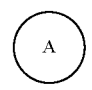

is selected from $C_{5-7}$ carbocycle and 5- to 7-membered heterocycle, each of which is optionally substituted with one or more $R^{11}$;

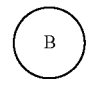

is absent or selected from $C_{3-8}$ carbocycle and 3- to 8-membered heterocycle, each of which is optionally substituted with one or more $R^{11a}$;

$L^1$ is selected from a bond, $C_{1-6}$ alkylene, and $C_{1-6}$ haloalkylene;

$L^2$ is selected from $C_{5-25}$ alkylene, $C_{5-25}$ alkenylene, $C_{5-25}$ alkynylene, 5- to 25-membered heteroalkylene, and 5- to 25-membered heteroalkenylene, each of which is optionally substituted with one or more $R^{11b}$, wherein $L^2$ is covalently bound to one of $W^3$, $W^4$, $W^5$, $W^6$, or $W^7$; or $L^2$ is $-L^3-D-L^4-$, wherein $L^4$ is covalently bound to one of $W^3$, $W^4$, $W^5$, $W^6$, or $W^7$;

$L^3$ is selected from $C_{1-10}$ alkylene, $C_{1-10}$ alkenylene, $C_{1-10}$ alkynylene, 2- to 10-membered heteroalkylene, and 2- to 10-membered heteroalkenylene, each of which is optionally substituted with one or more $R^{11b}$.

D is absent or selected from $C_{3-12}$ carbocycle and 3- to 12-membered heterocycle, each of which is optionally substituted with one or more $R^{11d}$;

$L^4$ is selected from $C_{1-10}$ alkylene, $C_{1-10}$ alkenylene, $C_{1-10}$ alkynylene, 2- to 10-membered heteroalkylene, and 2- to 10-membered heteroalkenylene, each of which is optionally substituted with one or more $R^{11b}$;

$W^2$ is selected from $N(R^{2b})$, N, $C(R^2)$, $C(R^2)(R^{2a})$, and $C(O)$;

$W^3$ is selected from $N(R^{3b})$, N, $C(R^3)$, $C(R^3)(R^{3a})$, and $C(O)$;

$W^4$ is selected from $N(R^{4b})$, N, $C(R^4)$, $C(R^4)(R^{4a})$, and $C(O)$;

$W^5$ is selected from $N(R^{5b})$, N, $C(R^5)$, $C(R^5)(R^{5a})$, and $C(O)$;

$W^6$ is selected from $N(R^{6b})$, N, $C(R^6)$, $C(R^6)(R^{6a})$, and $C(O)$;

$W^7$ is selected from $N(R^{7b})$, N, $C(R^7)$, $C(R^7)(R^{7a})$, and $C(O)$;

$W^8$ is selected from $N(R^{8b})$, N, $C(R^8)$, $C(R^8)(R^{8a})$, and $C(O)$;

$W^9$ is selected from N, $C(R^9)$, and C;

$W^{10}$ is selected from N, $C(R^{10})$, and C;

$R^1$ is $C_{1-3}$ alkyl optionally substituted with one or more $R^{11c}$;

$R^2$, $R^{2a}$, $R^{3a}$, $R^{4a}$, $R^{5a}$, $R^{6a}$, $R^{7a}$, $R^8$, and $R^{8a}$ are each independently selected from hydrogen, halogen, —CN, $C_{1-6}$ alkyl, $C_{2-6}$ alkenyl, $C_{2-6}$ alkynyl, $C_{3-10}$ carbocycle, 3- to 10-membered heterocycle, —$OR^{12}$, —$SR^{12}$, —$N(R^{12})(R^{13})$, —$C(O)OR^{12}$, —$OC(O)N(R^{12})(R^{13})$, —$N(R^{14})C(O)N(R^{12})(R^{13})$, —$N(R^{14})C(O)OR^{15}$, —$N(R^{14})S(O)_2R^{15}$, —$C(O)R^{15}$, —$S(O)R^{15}$, —$OC(O)R^{15}$, —$C(O)N(R^{12})(R^{13})$, —$C(O)C(O)N(R^{12})(R^{13})$, —$N(R^{14})C(O)R^{15}$, —$S(O)_2R^{15}$, —$S(O)_2N(R^{12})(R^{13})$, —$S(=O)(=NH)N(R^{12})(R^{13})$, —$CH_2C(O)N(R^{12})(R^{13})$, —$CH_2N(R^{14})C(O)R^{15}$, —$CH_2S(O)_2R^{15}$, and —$CH_2S(O)_2N(R^{12})(R^{13})$, wherein each $C_{1-6}$ alkyl, $C_{2-6}$ alkenyl, $C_{2-6}$ alkynyl, $C_{3-10}$ carbocycle, and 3- to 10-membered heterocycle is independently optionally substituted with one, two, or three $R^{20}$;

$R^3$, $R^4$, $R^5$, $R^6$, and $R^7$ are each independently selected from a bond to $L^2$, hydrogen, halogen, —CN, $C_{1-6}$ alkyl, $C_{2-6}$ alkenyl, $C_{2-6}$ alkynyl, $C_{3-10}$ carbocycle, 3- to 10-membered heterocycle, —$OR^{12}$, —$SR^{12}$, —$N(R^{12})(R^{13})$, —$C(O)OR^{12}$, —$OC(O)N(R^{12})(R^{13})$, —$N(R^{14})C(O)N(R^{12})(R^{13})$, —$N(R^{14})C(O)OR^{15}$, —$N(R^{14})S(O)_2R^{15}$, —$C(O)R^{15}$, —$S(O)R^{15}$, —$OC(O)R^{15}$, —$C(O)N(R^{12})(R^{13})$, —$C(O)C(O)N(R^{12})(R^{13})$, —$N(R^{14})C(O)R^{15}$, —$S(O)_2R^{15}$, —$S(O)_2N(R^{12})(R^{13})$, —$S(=O)(=NH)N(R^{12})(R^{13})$, —$CH_2C(O)N(R^{12})(R^{13})$, —$CH_2N(R^{14})C(O)R^{15}$, —$CH_2S(O)_2R^{15}$, and —$CH_2S(O)_2N(R^{12})(R^{13})$, wherein each $C_{1-6}$ alkyl, $C_{2-6}$ alkenyl, $C_{2-6}$ alkynyl, $C_{3-10}$ carbocycle, and 3- to 10-membered heterocycle is independently optionally substituted with one, two, or three $R^{20}$;

$R^{2b}$ and $R^{5b}$ are each independently selected from hydrogen, —CN, $C_{1-6}$ alkyl, $C_{2-6}$ alkenyl, $C_{2-6}$ alkynyl, $C_{3-10}$ carbocycle, 3- to 10-membered heterocycle, —$OR^{12}$, —$SR^{12}$, —$C(O)OR^{12}$, —$OC(O)N(R^{12})(R^{13})$, —$C(O)R^{15}$, —$S(O)R^{15}$, —$OC(O)R^{15}$, —$C(O)N(R^{12})(R^{13})$, —$C(O)C(O)N(R^{12})(R^{13})$, —$S(O)_2R^{15}$, —$S(O)_2N(R^{12})(R^{13})$, —$S(=O)(=NH)N(R^{12})(R^{13})$, —$CH_2C(O)N(R^{12})(R^{13})$, —$CH_2N(R^{14})C(O)R^{15}$, —$CH_2S(O)_2R^{15}$, and —$CH_2S(O)_2N(R^{12})(R^{13})$, wherein each $C_{1-6}$ alkyl, $C_{2-6}$ alkenyl, $C_{2-6}$ alkynyl, $C_{3-10}$ carbocycle and 3- to 10-membered heterocycle is independently optionally substituted with one, two, or three $R^{20}$;

$R^{3b}$, $R^{4b}$, $R^{5b}$, $R^{6b}$, and $R^{7b}$ are each independently selected from a bond to $L^2$, hydrogen, —CN, $C_{1-6}$ alkyl, $C_{2-6}$ alkenyl, $C_{2-6}$ alkynyl, $C_{3-10}$ carbocycle, 3- to 10-membered heterocycle, —$OR^{12}$, —$SR^{12}$, —$C(O)OR^{12}$, —$OC(O)N(R^{12})(R^{13})$, —$C(O)R^{15}$, —$S(O)R^{15}$, —$OC(O)R^{15}$, —$C(O)N(R^{12})(R^{13})$, —$C(O)C(O)N(R^{12})(R^{13})$, —$S(O)_2R^{15}$, —$S(O)_2N(R^{12})(R^{13})$, —$S(=O)(=NH)N(R^{12})(R^{13})$, —$CH_2C(O)N(R^{12})(R^{13})$, —$CH_2N(R^{14})C(O)R^{15}$, —$CH_2S(O)_2R^{15}$, and —$CH_2S(O)_2N(R^{12})(R^{13})$, wherein each $C_{1-6}$ alkyl, $C_{2-6}$ alkenyl, $C_{2-6}$ alkynyl, $C_{3-10}$ carbocycle and 3- to 10-membered heterocycle is independently optionally substituted with one, two, or three $R^{20}$;

$R^9$ and $R^{10}$ are each independently selected from hydrogen, $C_{1-6}$ alkyl, $C_{2-6}$ alkenyl, $C_{2-6}$ alkynyl, $C_{3-10}$ carbocycle, —$CH_2$—($C_{3-10}$ carbocycle), 3- to 10-membered heterocycle, and —$CH_2$-(3- to 10-membered heterocycle), wherein each $C_{1-6}$ alkyl, $C_{2-6}$ alkenyl, $C_{2-6}$ alkynyl, $C_{3-10}$ carbocycle, —$CH_2$—($C_{3-10}$ carbocycle), 3- to 10-membered heterocycle, and —$CH_2$-(3- to 10-membered heterocycle) is independently optionally substituted with one, two, or three $R^{20}$;

$R^{11}$, $R^{11a}$, and $R^{11d}$ are each independently selected at each occurrence from halogen, —CN, $C_{1-6}$ alkyl, $C_{2-6}$ alkenyl, $C_{2-6}$ alkynyl, $C_{3-10}$ carbocycle, 3- to 10-membered heterocycle, —$OR^{12}$, —$SR^{12}$, —$N(R^{12})(R^{13})$, —$C(O)OR^{12}$, —$OC(O)N(R^{12})(R^{13})$, —$N(R^{14})C(O)N(R^{12})(R^{13})$, —$N(R^{14})C(O)OR^{15}$, —$N(R^{14})S(O)_2R^{15}$, —$C(O)R^{15}$, —$S(O)R^{15}$, —$OC(O)R^{15}$, —$C(O)N(R^{12})(R^{13})$, —$C(O)C(O)N(R^{12})(R^{13})$, —$N(R^{14})C(O)R^{15}$, —$S(O)_2R^{15}$, —$S(O)_2N(R^{12})(R^{13})$, —$S(=O)(=NH)N(R^{12})(R^{13})$, —$CH_2C(O)N(R^{12})(R^{13})$, —$CH_2N(R^{14})C(O)R^{15}$, —$CH_2S(O)_2R^{15}$, —$CH_2S(O)_2N(R^{12})(R^{13})$, —$CH_2N(R^{12})S(O)_2(R^{13})$, and —$P(O)(R^{17})(R^{17a})$, wherein $C_{1-6}$ alkyl, $C_{2-6}$ alkenyl, $C_{2-6}$ alkynyl, $C_{3-10}$ carbocycle, and 3- to 10-membered heterocycle are optionally substituted with one, two, or three $R^{20}$;

$R^{11b}$ is independently selected at each occurrence from halogen, oxo, —CN, $C_{1-6}$ alkyl, $C_{2-6}$ alkenyl, $C_{2-6}$ alkynyl, $C_{3-10}$ carbocycle, 3- to 10-membered heterocycle, —$OR^{12}$, —$SR^{12}$, —$N(R^{12})(R^{13})$, —$C(O)OR^{12}$, —$OC(O)N(R^{12})(R^{13})$, —$N(R^{14})C(O)N(R^{12})(R^{13})$, —$N(R^{14})C(O)OR^{15}$, —$N(R^{14})S(O)_2R^{15}$, —$C(O)R^{15}$, —$S(O)R^{15}$, —$OC(O)R^{15}$, —$C(O)N(R^{12})(R^{13})$, —$C(O)C(O)N(R^{12})(R^{13})$, —$N(R^{14})C(O)R^{15}$, —$S(O)_2R^{15}$, —$S(O)_2N(R^{12})(R^{13})$, —$S(=O)(=NH)N(R^{12})(R^{13})$, —$CH_2C(O)N(R^{12})(R^{13})$, —$CH_2N(R^{14})C(O)R^{15}$, —$CH_2S(O)_2R^{15}$, —$CH_2S(O)_2N(R^{12})(R^{13})$, —$CH_2N(R^{12})S(O)_2(R^{13})$, and —$P(O)(R^{17})(R^{17a})$, wherein $C_{1-6}$ alkyl, $C_{2-6}$ alkenyl, $C_{2-6}$ alkynyl, $C_{3-10}$ carbocycle, and 3- to 10-membered heterocycle are optionally substituted with one, two, or three $R^{20}$;

$R^{11c}$ is independently selected at each occurrence from halogen, —$OR^{12}$, and —$N(R^{12})(R^{13})$;

$R^{12}$ is independently selected at each occurrence from hydrogen, $C_{1-6}$ alkyl, $C_{1-6}$ haloalkyl, $C_{2-6}$ alkenyl, $C_{2-6}$ alkynyl, $C_{3-10}$ carbocycle, and 3- to 10-membered heterocycle, wherein $C_{1-6}$ alkyl, $C_{2-6}$ alkenyl, $C_{2-6}$ alkynyl, $C_{3-10}$ carbocycle, and 3- to 10-membered heterocycle are optionally substituted with one, two, or three $R^{20}$;

$R^{13}$ is independently selected at each occurrence from hydrogen, $C_{1-6}$ alkyl, and $C_{1-6}$ haloalkyl; or $R^{12}$ and $R^{13}$, together with the nitrogen atom to which they are attached, form a 3- to 10-membered heterocycle optionally substituted with one, two, or three $R^{20}$;

$R^{14}$ is independently selected at each occurrence from hydrogen, $C_{1-6}$ alkyl, and $C_{1-6}$ haloalkyl;

$R^{15}$ is independently selected at each occurrence from $C_{1-6}$ alkyl, $C_{2-6}$ alkenyl, $C_{2-6}$ alkynyl, $C_{3-10}$ carbocycle, and 3- to 10-membered heterocycle, wherein $C_{1-6}$ alkyl, $C_{2-6}$ alkenyl, $C_{2-6}$ alkynyl, $C_{3-10}$ carbocycle, and 3- to 10-membered heterocycle are optionally substituted with one, two, or three $R^{20}$;

$R^{17}$ and $R^{17a}$ are each independently selected at each occurrence from $C_{1-6}$ alkyl and $C_{3-6}$ cycloalkyl, wherein $C_{1-6}$ alkyl and $C_{3-6}$ cycloalkyl are optionally substituted with one, two or three $R^{20}$; or $R^{17}$ and $R^{17a}$, together with the phosphorous atom to which they are attached, form a 3- to 10-membered heterocycle;

$R^{20}$ is independently selected at each occurrence from halogen, oxo, =NH, —CN, $C_{1-6}$ alkyl, $C_{2-6}$ alkenyl, $C_{2-6}$ alkynyl, $C_{3-10}$ carbocycle, —$CH_2$—($C_{3-10}$ carbocycle), 3- to 10-membered heterocycle, —$CH_2$-(3- to 10-membered heterocycle), —$OR^{21}$, —$SR^{21}$, —N(R$^{22}$)(R$^{23}$), —C(O)OR$^{22}$, —C(O)N(R$^{22}$)(R$^{23}$), —C(O)C(O)N(R$^{22}$)(R$^{23}$), —OC(O)N(R$^{22}$)(R$^{23}$), —N(R$^{22}$)C(O)N(R$^{22}$)(R$^{23}$), —N(R$^{24}$)C(O)OR$^{25}$, —N(R$^{24}$)C(O)R$^{25}$, —N(R$^{22}$)S(O)$_2$R$^{25}$, —C(O)R$^{25}$, —S(O)$_2$R$^{25}$, —S(O)$_2$N(R$^{22}$)(R$^{23}$), —OCH$_2$C(O)OR$^{22}$, and —OC(O)R$^{25}$, wherein C$_{1-6}$ alkyl, C$_{2-6}$ alkenyl, C$_{2-6}$ alkynyl, C$_{3-10}$ carbocycle, —CH$_2$—(C$_{3-10}$ carbocycle), 3- to 10-membered heterocycle, and —CH$_2$-(3- to 10-membered heterocycle) are optionally substituted with one, two, or three groups independently selected from halogen, oxo, =NH, —CN, C$_{1-6}$ alkyl, C$_{1-6}$ haloalkyl, C$_{1-6}$ alkoxy, C$_{1-6}$ haloalkoxy, —OR$^{21}$, —SR$^{21}$, —N(R$^{22}$)(R$^{23}$), —C(O)OR$^{22}$, —C(O)N(R$^{22}$)(R$^{23}$), —C(O)C(O)N(R$^{22}$)(R$^{23}$), —OC(O)N(R$^{22}$)(R$^{23}$), —N(R$^{24}$)C(O)N(R$^{22}$)(R$^{23}$), —N(R$^{24}$)C(O)OR$^{25}$, —N(R$^{24}$)C(O)R$^{25}$, —N(R$^{22}$)S(O)$_2$R$^{25}$, —C(O)R$^{25}$, —S(O)$_2$R$^{25}$, —S(O)$_2$N(R$^{22}$)(R$^{23}$), and —OC(O)R$^{25}$;

R$^{21}$ is independently selected at each occurrence from H, C$_{1-6}$ alkyl, C$_{1-6}$ haloalkyl, C$_{2-6}$ alkenyl, C$_{2-6}$ alkynyl, C$_{3-10}$ carbocycle, and 3- to 10-membered heterocycle, wherein C$_{3-10}$ carbocycle and 3- to 10-membered heterocycle are optionally substituted with one, two, or three groups independently selected from halogen and C$_{1-6}$ alkyl;

R$^{22}$ is independently selected at each occurrence from H, C$_{1-6}$ alkyl, C$_{1-6}$ haloalkyl, C$_{2-6}$ alkenyl, C$_{2-6}$ alkynyl, C$_{3-10}$ carbocycle, and 3- to 10-membered heterocycle, wherein C$_{3-10}$ carbocycle and 3- to 10-membered heterocycle are optionally substituted with one, two, or three groups independently selected from halogen and C$_{1-6}$ alkyl;

R$^{23}$ is independently selected at each occurrence from H and C$_{1-6}$ alkyl;

R$^{24}$ is independently selected at each occurrence from H and C$_{1-6}$ alkyl;

R$^{25}$ is independently selected at each occurrence from C$_{1-6}$ alkyl, C$_{2-6}$ alkenyl, C$_{2-6}$ alkynyl, C$_{3-10}$ carbocycle, and 3- to 10-membered heterocycle, wherein C$_{1-6}$ alkyl, C$_{3-10}$ carbocycle, and 3- to 10-membered heterocycle are optionally substituted with one, two, or three groups independently selected from halogen, C$_{1-6}$ alkyl, C$_{1-6}$ haloalkyl, C$_{1-6}$ alkoxy, C$_{3-10}$ carbocycle, and 3- to 10-membered heterocycle; and ------ indicates a single or double bond such that all valences are satisfied.

In certain aspects, the present disclosure provides a compound of Formula (I):

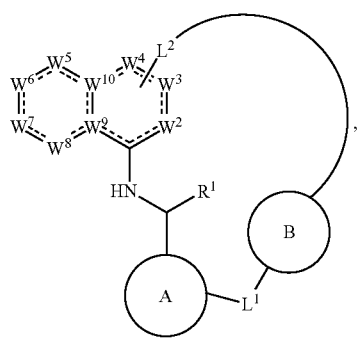

(I)

or a pharmaceutically acceptable salt or solvate thereof, wherein:

is selected from C$_{5-7}$ carbocycle and 5- to 7-membered heterocycle, each of which is optionally substituted with one or more R$^{11}$;

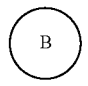

is absent or selected from C$_{3-8}$ carbocycle and 3- to 8-membered heterocycle, each of which is optionally substituted with one or more R$^{11a}$;

L$^1$ is selected from a bond, C$_{1-6}$ alkylene, and C$_{1-6}$ haloalkylene;

L$^2$ is selected from C$_{5-25}$ alkylene, C$_{5-25}$ alkenylene, C$_{5-25}$ alkynylene, 5- to 25-membered heteroalkylene, and 5- to 25-membered heteroalkenylene, each of which is optionally substituted with one or more R$^{11b}$, wherein L$^2$ is covalently bound to one of W$^3$, W$^4$, W$^5$, W$^6$, or W$^7$;

W$^2$ is selected from N(R$^{2b}$), N, C(R$^2$), C(R$^2$)(R$^{2a}$), and C(O);

W$^3$ is selected from N(R$^{3b}$), N, C(R$^3$), C(R$^3$)(R$^{3a}$), and C(O);

W$^4$ is selected from N(R$^{4b}$), N, C(R$^4$), C(R$^4$)(R$^{4a}$), and C(O);

W$^5$ is selected from N(R$^{5b}$), N, C(R$^5$), C(R$^5$)(R$^{5a}$), and C(O);

W$^6$ is selected from N(R$^{6b}$), N, C(R$^6$), C(R$^6$)(R$^{6a}$), and C(O);

W$^7$ is selected from N(R$^{7b}$), N, C(R$^7$), C(R$^7$)(R$^{7a}$), and C(O);

W$^8$ is selected from N(R$^{8b}$), N, C(R$^8$), C(R$^8$)(R$^{8a}$), and C(O);

W$^9$ is selected from N, C(R$^9$), and C;

W$^{10}$ is selected from N, C(R$^{10}$), and C;

R$^1$ is C$_{1-3}$ alkyl optionally substituted with one or more R$^{11}$;

R$^2$, R$^{2a}$, R$^{3a}$, R$^{4a}$, R$^{5a}$, R$^{6a}$, R$^{7a}$, R$^8$, and R$^{8a}$ are each independently selected from hydrogen, halogen, —CN, C$_{1-6}$ alkyl, C$_{2-6}$ alkenyl, C$_{2-6}$ alkynyl, C$_{3-10}$ carbocycle, 3- to 10-membered heterocycle, —OR$^{12}$, —SR$^{12}$, —N(R$^{12}$)(R$^{13}$), —C(O)OR$^{12}$, —OC(O)N(R$^{12}$)(R$^{13}$), —N(R$^{14}$)C(O)N(R$^{12}$)(R$^{13}$), —N(R$^{14}$)C(O)OR$^{15}$, —N(R$^{14}$)S(O)$_2$R$^{15}$, —C(O)R$^{15}$, —S(O)R$^{15}$, —OC(O)R$^{15}$, —C(O)N(R$^{12}$)(R$^{13}$), —C(O)C(O)N(R$^{12}$)(R$^{13}$), —N(R$^{14}$)C(O)R$^{15}$, —S(O)$_2$R$^{15}$, —S(O)$_2$N(R$^{12}$)(R$^{13}$), —S(=O)(=NH)N(R$^{12}$)(R$^{13}$), —CH$_2$C(O)N(R$^{12}$)(R$^{13}$), —CH$_2$N(R$^{14}$)C(O)R$^{15}$, —CH$_2$S(O)$_2$R$^{15}$, and —CH$_2$S(O)$_2$N(R$^{12}$)(R$^{13}$), wherein each C$_{1-6}$ alkyl, C$_{2-6}$ alkenyl, C$_{2-6}$ alkynyl, C$_{3-10}$ carbocycle, and 3- to 10-membered heterocycle is independently optionally substituted with one, two, or three R$^{20}$;

R$^3$, R$^4$, R$^5$, R$^6$, and R$^7$ are each independently selected from a bond to L$^2$, hydrogen, halogen, —CN, C$_{1-6}$ alkyl, C$_{2-6}$ alkenyl, C$_{2-6}$ alkynyl, C$_{3-10}$ carbocycle, 3- to 10-membered heterocycle, —OR$^{12}$, —SR$^{12}$, —N(R$^{12}$)(R$^{13}$), —C(O)OR$^{12}$, —OC(O)N(R$^{12}$)(R$^{13}$), —N(R$^{14}$)C(O)N(R$^{12}$)(R$^{13}$), —N(R$^{14}$)C(O)OR$^{15}$, —N(R$^{14}$)S(O)$_2$R$^{15}$, —C(O)R$^{15}$, —S(O)R$^{15}$, —OC(O)R$^{15}$, —C(O)N(R$^{12}$)(R$^{13}$), —C(O)C(O)N(R$^{12}$)(R$^{13}$), —N(R$^{14}$)C(O)

$R^{15}$, —S(O)$_2$R$^{15}$, —S(O)$_2$N(R$^{12}$)(R$^{13}$), —S(=O)(=NH)N(R$^{12}$)(R$^{13}$), —CH$_2$C(O)N(R$^{12}$)(R$^{13}$), —CH$_2$N(R$^{14}$)C(O)R$^{15}$, —CH$_2$S(O)$_2$R$^{15}$, and —CH$_2$S(O)$_2$N(R$^{12}$)(R$^{13}$), wherein each C$_{1-6}$ alkyl, C$_{2-6}$ alkenyl, C$_{2-6}$ alkynyl, C$_{3-10}$ carbocycle, and 3- to 10-membered heterocycle is independently optionally substituted with one, two, or three R$^{20}$;

$R^{2b}$ and $R^{8b}$ are each independently selected from hydrogen, —CN, C$_{1-6}$ alkyl, C$_{2-6}$ alkenyl, C$_{2-6}$ alkynyl, C$_{3-10}$ carbocycle, 3- to 10-membered heterocycle, —OR$^{12}$, —SR$^{12}$, —C(O)OR$^{12}$, —OC(O)N(R$^{12}$)(R$^{13}$), —C(O)R$^{15}$, —S(O)R$^{15}$, —OC(O)R$^{15}$, —C(O)N(R$^{12}$)(R$^{13}$), —C(O)C(O)N(R$^{12}$)(R$^{13}$), —S(O)$_2$R$^{15}$, —S(O)$_2$N(R$^{12}$)(R$^{13}$), —S(=O)(=NH)N(R$^{12}$)(R$^{13}$), —CH$_2$C(O)N(R$^{12}$)(R$^{13}$), —CH$_2$N(R$^{14}$)C(O)R$^{15}$, —CH$_2$S(O)$_2$R$^{15}$, and —CH$_2$S(O)$_2$N(R$^{12}$)(R$^{13}$), wherein each C$_{1-6}$ alkyl, C$_{2-6}$ alkenyl, C$_{2-6}$ alkynyl, C$_{3-10}$ carbocycle and 3- to 10-membered heterocycle is independently optionally substituted with one, two, or three R$^{20}$;

$R^{3b}$, $R^{4b}$, $R^{5b}$, $R^{6b}$, and $R^{7b}$ are each independently selected from a bond to L$^2$, hydrogen, —CN, C$_{1-6}$ alkyl, C$_{2-6}$ alkenyl, C$_{2-6}$ alkynyl, C$_{3-10}$ carbocycle, 3- to 10-membered heterocycle, —OR$^{12}$, —SR$^{12}$, —C(O)OR$^{12}$, —OC(O)N(R$^{12}$)(R$^{13}$), —C(O)R$^{15}$, —S(O)R$^{15}$, —OC(O)R$^{15}$, —C(O)N(R$^{12}$)(R$^{13}$), —C(O)C(O)N(R$^{12}$)(R$^{13}$), —S(O)$_2$R$^{15}$, —S(O)$_2$N(R$^{12}$)(R$^{13}$), —S(=O)(=NH)N(R$^{12}$)(R$^{13}$), —CH$_2$C(O)N(R$^{12}$)(R$^{13}$), —CH$_2$N(R$^{14}$)C(O)R$^{15}$, —CH$_2$S(O)$_2$R$^{15}$, and —CH$_2$S(O)$_2$N(R$^{12}$)(R$^{13}$), wherein each C$_{1-6}$ alkyl, C$_{2-6}$ alkenyl, C$_{2-6}$ alkynyl, C$_{3-10}$ carbocycle and 3- to 10-membered heterocycle is independently optionally substituted with one, two, or three R$^{20}$;

$R^9$ and $R^{10}$ are each independently selected from hydrogen, C$_{1-6}$ alkyl, C$_{2-6}$ alkenyl, C$_{2-6}$ alkynyl, C$_{3-10}$ carbocycle, —CH$_2$—(C$_{3-10}$ carbocycle), 3- to 10-membered heterocycle, and —CH$_2$-(3- to 10-membered heterocycle), wherein each C$_{1-6}$ alkyl, C$_{2-6}$ alkenyl, C$_{2-6}$ alkynyl, C$_{3-10}$ carbocycle, —CH$_2$—(C$_{3-10}$ carbocycle), 3- to 10-membered heterocycle, and —CH$_2$-(3- to 10-membered heterocycle) is independently optionally substituted with one, two, or three R$^{20}$;

$R^{11}$ and $R^{11a}$ are each independently selected at each occurrence from halogen, —CN, C$_{1-6}$ alkyl, C$_{2-6}$ alkenyl, C$_{2-6}$ alkynyl, C$_{3-10}$ carbocycle, 3- to 10-membered heterocycle, —OR$^{12}$, —SR$^{12}$, —N(R$^{12}$)(R$^{13}$), —C(O)OR$^{12}$, —OC(O)N(R$^{12}$)(R$^{13}$), —N(R$^{14}$)C(O)N(R$^{12}$)(R$^{13}$), —N(R$^{14}$)C(O)OR$^{15}$, —N(R$^{14}$)S(O)$_2$R$^{15}$, —C(O)R$^{15}$, —S(O)R$^{15}$, —OC(O)R$^{15}$, —C(O)N(R$^{12}$)(R$^{13}$), —C(O)C(O)N(R$^{12}$)(R$^{13}$), —N(R$^{14}$)C(O)R$^{15}$, —S(O)$_2$R$^{15}$, —S(O)$_2$N(R$^{12}$)(R$^{13}$), —S(=O)(=NH)N(R$^{12}$)(R$^{13}$), —CH$_2$C(O)N(R$^{12}$)(R$^{13}$), —CH$_2$N(R$^{14}$)C(O)R$^{15}$, —CH$_2$S(O)$_2$R$^{15}$, —CH$_2$S(O)$_2$N(R$^{12}$)(R$^{13}$), —CH$_2$N(R$^{12}$)S(O)$_2$(R$^{13}$), and —P(O)(R$^{17}$)(R$^{17a}$), wherein C$_{1-6}$ alkyl, C$_{2-6}$ alkenyl, C$_{2-6}$ alkynyl, C$_{3-10}$ carbocycle, and 3- to 10-membered heterocycle are optionally substituted with one, two, or three R$^{20}$;

$R^{11b}$ is independently selected at each occurrence from halogen, oxo, —CN, C$_{1-6}$ alkyl, C$_{2-6}$ alkenyl, C$_{2-6}$ alkynyl, C$_{3-10}$ carbocycle, 3- to 10-membered heterocycle, —OR$^{12}$, —SR$^{12}$, —N(R$^{12}$)(R$^{13}$), —C(O)OR$^{12}$, —OC(O)N(R$^{12}$)(R$^{13}$), —N(R$^{14}$)C(O)N(R$^{12}$)(R$^{13}$), —N(R$^{14}$)C(O)OR$^{15}$, —N(R$^{14}$)S(O)$_2$R$^{15}$, —C(O)R$^{15}$, —S(O)R$^{15}$, —OC(O)R$^{15}$, —C(O)N(R$^{12}$)(R$^{13}$), —C(O)C(O)N(R$^{12}$)(R$^{13}$), —N(R$^{14}$)C(O)R$^{15}$, —S(O)$_2$R$^{15}$, —S(O)$_2$N(R$^{12}$)(R$^{13}$), —S(=O)(=NH)N(R$^{12}$)(R$^{13}$), —CH$_2$C(O)N(R$^{12}$)(R$^{13}$), —CH$_2$N(R$^{14}$)C(O)R$^{15}$, —CH$_2$S(O)$_2$R$^{15}$, —CH$_2$S(O)$_2$N(R$^{12}$)(R$^{13}$), —CH$_2$N(R$^{12}$)S(O)$_2$(R$^{13}$), and —P(O)(R$^{17}$)(R$^{17a}$), wherein C$_{1-6}$ alkyl, C$_{2-6}$ alkenyl, C$_{2-6}$ alkynyl, C$_{3-10}$ carbocycle, and 3- to 10-membered heterocycle are optionally substituted with one, two, or three R$^{20}$;

$R^{11c}$ is independently selected at each occurrence from halogen, —OR$^{12}$, and —N(R$^{12}$)(R$^{13}$);

$R^{12}$ is independently selected at each occurrence from hydrogen, C$_{1-6}$ alkyl, C$_{1-6}$ haloalkyl, C$_{2-6}$ alkenyl, C$_{2-6}$ alkynyl, C$_{3-10}$ carbocycle, and 3- to 10-membered heterocycle, wherein C$_{1-6}$ alkyl, C$_{2-6}$ alkenyl, C$_{2-6}$ alkynyl, C$_{3-10}$ carbocycle, and 3- to 10-membered heterocycle are optionally substituted with one, two, or three R$^{20}$;

$R^{13}$ is independently selected at each occurrence from hydrogen, C$_{1-6}$ alkyl, and C$_{1-6}$ haloalkyl; or R$^{12}$ and R$^{13}$, together with the nitrogen atom to which they are attached, form a 3- to 10-membered heterocycle optionally substituted with one, two, or three R$^{20}$;

$R^{14}$ is independently selected at each occurrence from hydrogen, C$_{1-6}$ alkyl, and C$_{1-6}$ haloalkyl;

$R^{15}$ is independently selected at each occurrence from C$_{1-6}$ alkyl, C$_{2-6}$ alkenyl, C$_{2-6}$ alkynyl, C$_{3-10}$ carbocycle, and 3- to 10-membered heterocycle, wherein C$_{1-6}$ alkyl, C$_{2-6}$ alkenyl, C$_{2-6}$ alkynyl, C$_{3-10}$ carbocycle, and 3- to 10-membered heterocycle are optionally substituted with one, two, or three R$^{20}$;

$R^{17}$ and $R^{17a}$ are each independently selected at each occurrence from C$_{1-6}$ alkyl and C$_{3-6}$ cycloalkyl, wherein C$_{1-6}$ alkyl and C$_{3-6}$ cycloalkyl are optionally substituted with one, two or three R$^{20}$; or R$^{17}$ and R$^{17a}$, together with the phosphorous atom to which they are attached, form a 3- to 10-membered heterocycle;

$R^{20}$ is independently selected at each occurrence from halogen, oxo, =NH, —CN, C$_{1-6}$ alkyl, C$_{2-6}$ alkenyl, C$_{2-6}$ alkynyl, C$_{3-10}$ carbocycle, —CH$_2$—(C$_{3-10}$ carbocycle), 3- to 10-membered heterocycle, —CH$_2$-(3- to 10-membered heterocycle), —OR$^{21}$, —SR$^{21}$, —N(R$^{22}$)(R$^{23}$), —C(O)OR$^{22}$, —C(O)N(R$^{22}$)(R$^{23}$), —C(O)C(O)N(R$^{22}$)(R$^{23}$), —OC(O)N(R$^{22}$)(R$^{23}$), —N(R$^{22}$)C(O)N(R$^{22}$)(R$^{23}$), —N(R$^{24}$)C(O)OR$^{25}$, —N(R$^{24}$)C(O)R$^{25}$, —N(R$^{22}$)S(O)$_2$R$^{25}$, —C(O)R$^{25}$, —S(O)$_2$R$^{25}$, —S(O)$_2$N(R$^{22}$)(R$^{23}$), —OCH$_2$C(O)OR$^{22}$, and —OC(O)R$^{25}$, wherein C$_{1-6}$ alkyl, C$_{2-6}$ alkenyl, C$_{2-6}$ alkynyl, C$_{3-10}$ carbocycle, —CH$_2$—(C$_{3-10}$ carbocycle), 3- to 10-membered heterocycle, and —CH$_2$-(3- to 10-membered heterocycle) are optionally substituted with one, two, or three groups independently selected from halogen, oxo, =NH, —CN, C$_{1-6}$ alkyl, C$_{1-6}$ haloalkyl, C$_{1-6}$ alkoxy, C$_{1-6}$ haloalkoxy, —OR$^{21}$, —SR$^{21}$, —N(R$^{22}$)(R$^{23}$), —C(O)OR$^{22}$, —C(O)N(R$^{22}$)(R$^{23}$), —C(O)C(O)N(R$^{22}$)(R$^{23}$), —OC(O)N(R$^{22}$)(R$^{23}$), —N(R$^{24}$)C(O)N(R$^{22}$)(R$^{23}$), —N(R$^{24}$)C(O)OR$^{25}$, —N(R$^{24}$)C(O)R$^{25}$, —N(R$^{22}$)S(O)$_2$R$^{25}$, —C(O)R$^{25}$, —S(O)$_2$R$^{25}$, —S(O)$_2$N(R$^{22}$)(R$^{23}$), and —OC(O)R$^{25}$;

$R^{21}$ is independently selected at each occurrence from H, C$_{1-6}$ alkyl, C$_{1-6}$ haloalkyl, C$_{2-6}$ alkenyl, C$_{2-6}$ alkynyl, C$_{3-10}$ carbocycle, and 3- to 10-membered heterocycle, wherein C$_{3-10}$ carbocycle and 3- to 10-membered heterocycle are optionally substituted with one, two, or three groups independently selected from halogen and C$_{1-6}$alkyl;

$R^{22}$ is independently selected at each occurrence from H, C$_{1-6}$ alkyl, C$_{1-6}$ haloalkyl, C$_{2-6}$ alkenyl, C$_{2-6}$ alkynyl, C$_{3-10}$ carbocycle, and 3- to 10-membered heterocycle, wherein C$_{3-10}$ carbocycle and 3- to 10-membered heterocycle are optionally substituted with one, two, or three groups independently selected from halogen and $C_{1-6}$alkyl;

$R^{23}$ is independently selected at each occurrence from H and $C_{1-6}$ alkyl;

$R^{24}$ is independently selected at each occurrence from H and $C_{1-6}$ alkyl;

$R^{25}$ is independently selected at each occurrence from $C_{1-6}$ alkyl, $C_{2-6}$ alkenyl, $C_{2-6}$ alkynyl, $C_{3-10}$ carbocycle, and 3- to 10-membered heterocycle, wherein $C_{1-6}$ alkyl, $C_{3-10}$ carbocycle, and 3- to 10-membered heterocycle are optionally substituted with one, two, or three groups independently selected from halogen, $C_{1-6}$ alkyl, $C_{1-6}$ haloalkyl, $C_{1-6}$ alkoxy, $C_{3-10}$ carbocycle, and 3- to 10-membered heterocycle; and ----- indicates a single or double bond such that all valences are satisfied.

In some embodiments, the compound of Formula (I) is a compound of Formula (I-A):

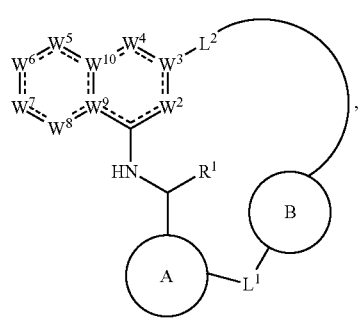

or a pharmaceutically acceptable salt or solvate thereof.

In some embodiments, the compound of Formula (I-A) is a compound selected from:

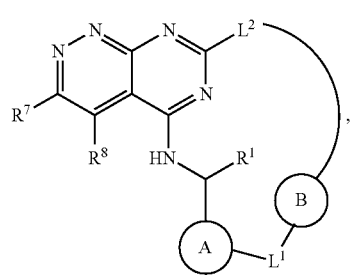

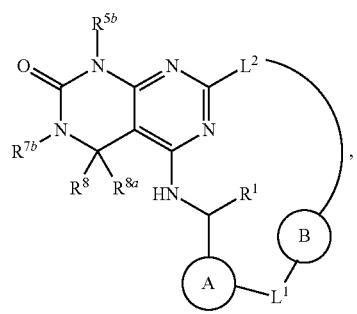

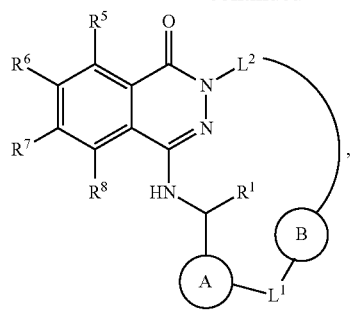

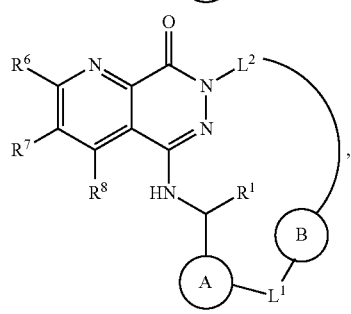

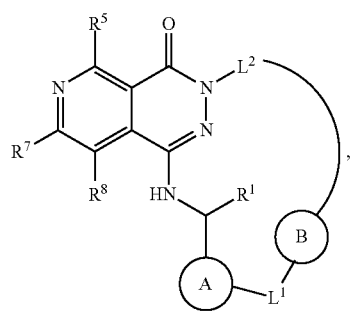

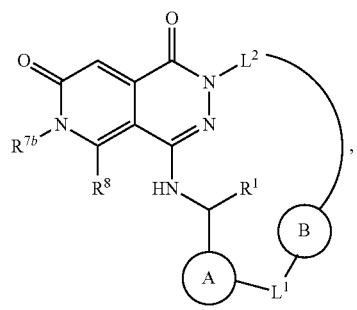

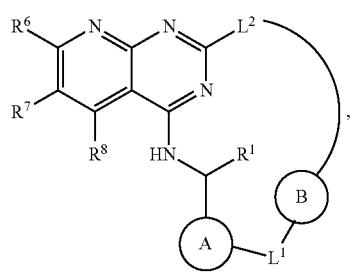

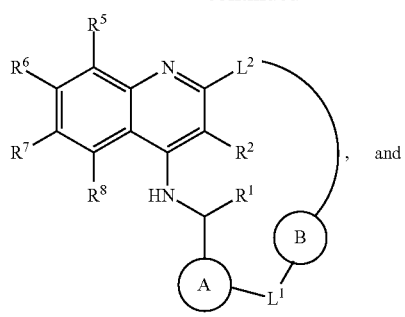
, and
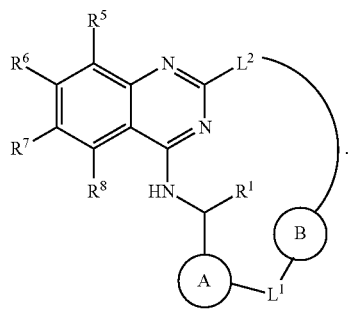
.
In some embodiments, the compound of Formula (I) is a compound of Formula (I-B), such as a compound of Formula (I-B1) or (I-B2):
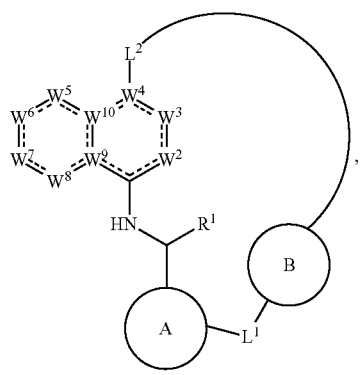
(I-B)
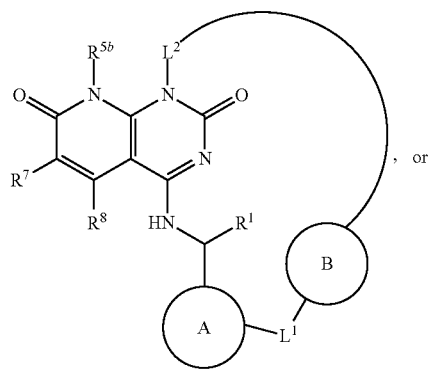
(I-B1)
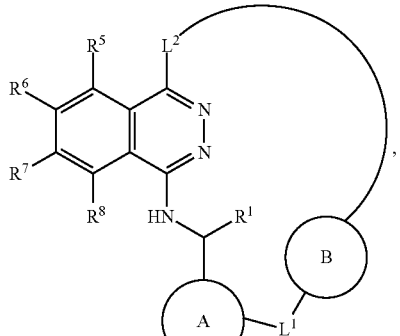
(I-B2)
or a pharmaceutically acceptable salt or solvate thereof.
In some embodiments, the compound of Formula (I-B) is a compound selected from:
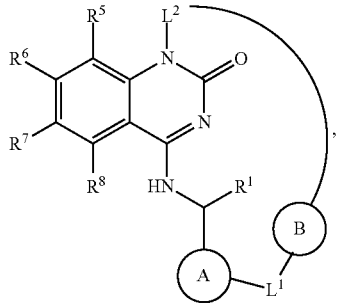
,
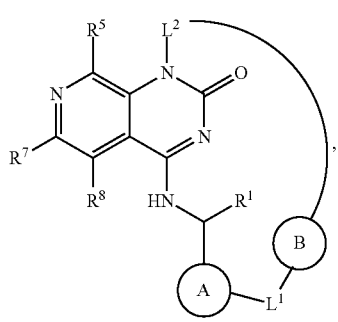
,
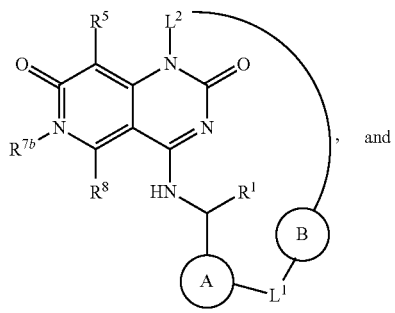
, and

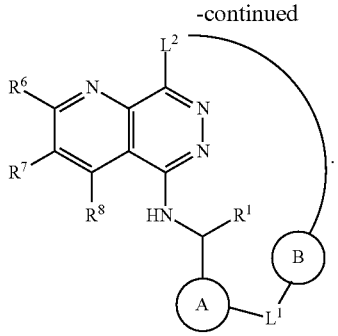
In some embodiments, the compound of Formula (I) is a compound of Formula (I-C), such as a compound of Formula (I-C1), (I-C2), or (I-C3):
(I-C)
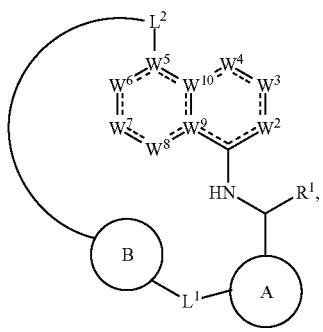
(I-C1)
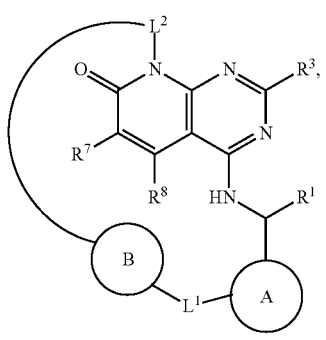
(I-C2)
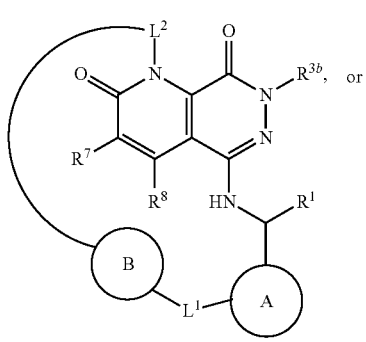
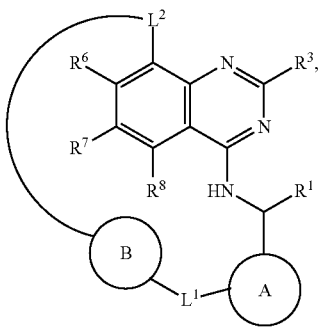
(I-C3)
or a pharmaceutically acceptable salt or solvate thereof.
In some embodiments, the compound of Formula (I-C) is a compound selected from:
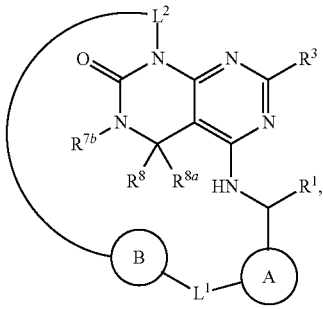
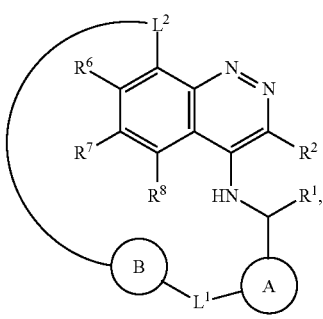
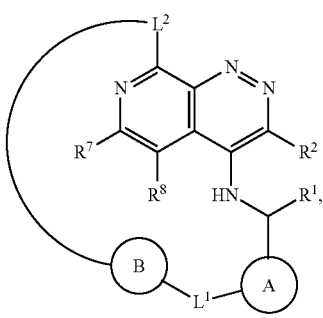

-continued
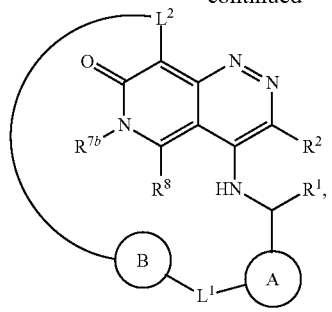
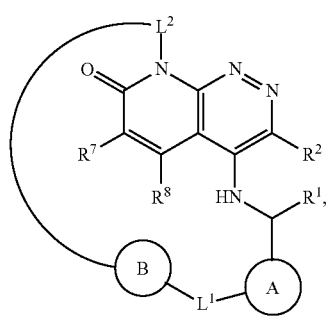
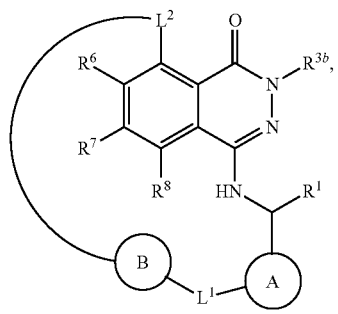
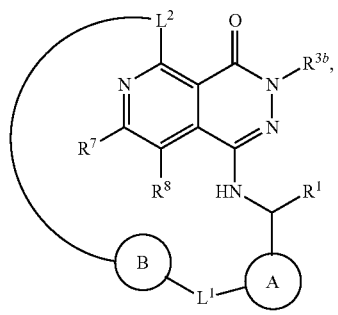
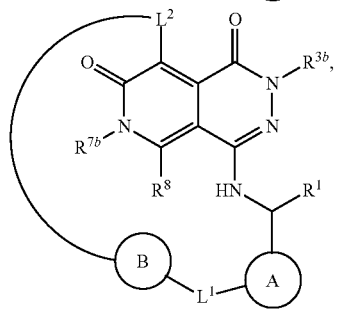
-continued
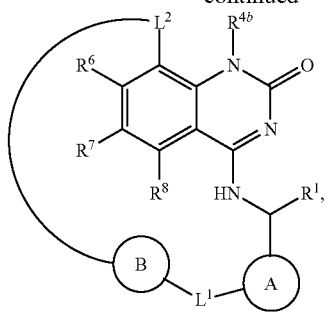
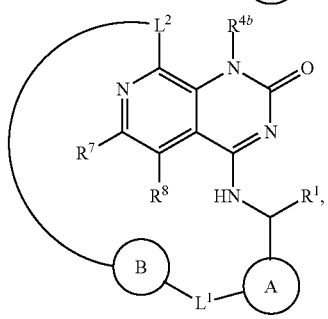
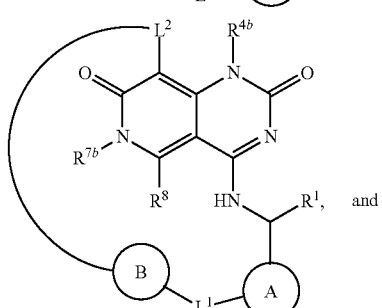
and
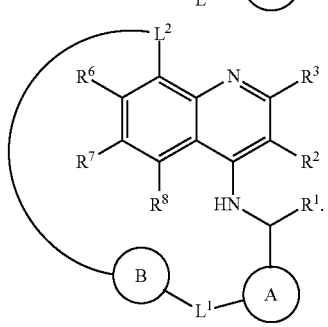
In some embodiments, the compound of Formula (I) is a compound of Formula (I-D), such as a compound of Formula (I-D1) or (I-D2):
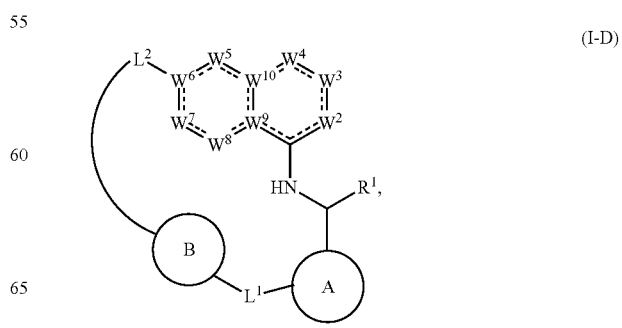
(I-D)

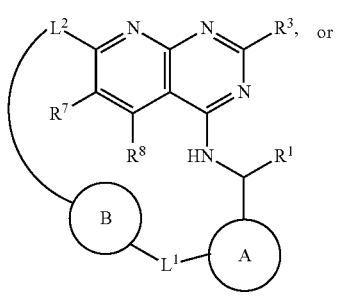
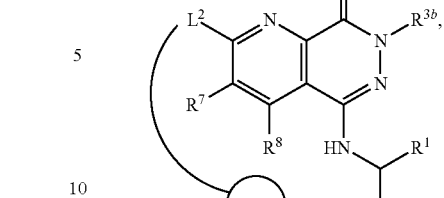 (I-D1)

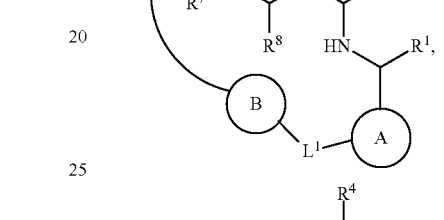
or a pharmaceutically acceptable salt or solvate thereof.
In some embodiments, the compound of Formula (I-D) is a compound selected from:
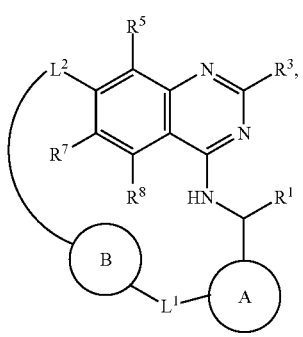 (I-D2)
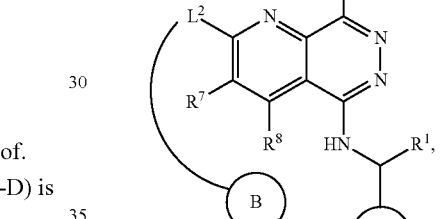
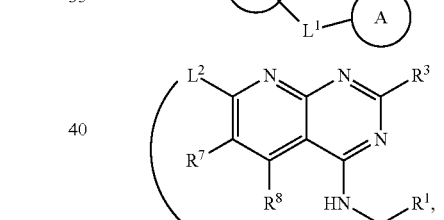
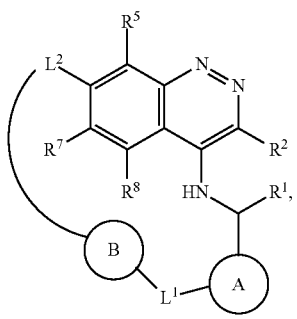
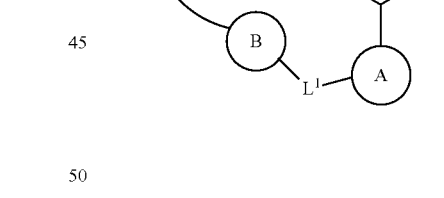 and
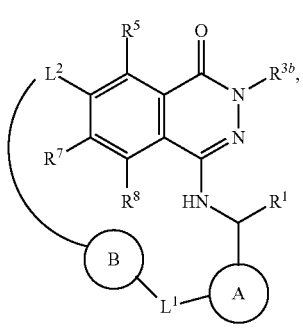
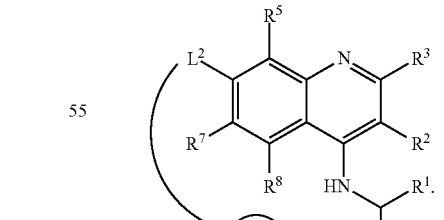
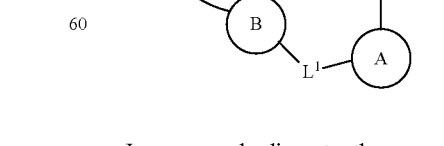
In some embodiments, the compound of Formula (I) is a compound of Formula (I-E), such as a compound of Formula (I-E1):

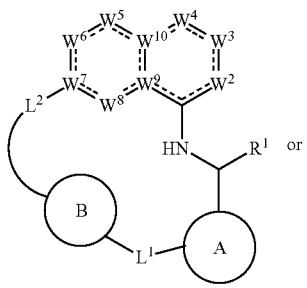
(I-E)
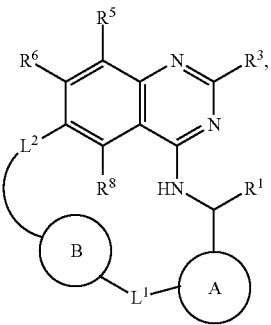
(I-E1)
or a pharmaceutically acceptable salt or solvate thereof.
In some embodiments, the compound of Formula (I-E) is a compound selected from:
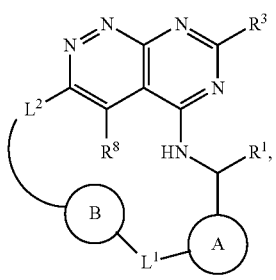
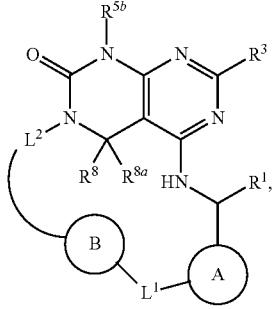
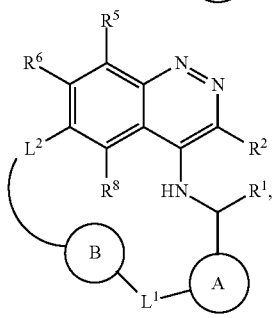
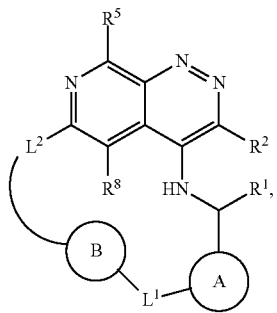
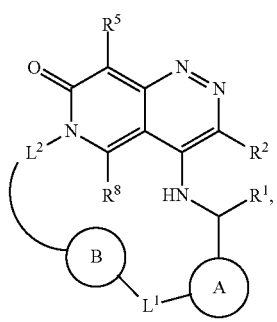
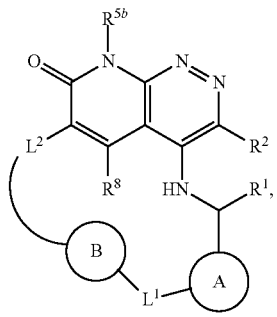
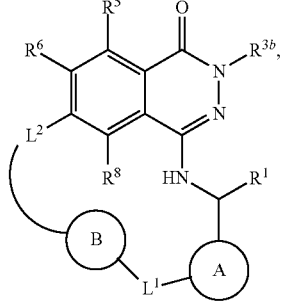
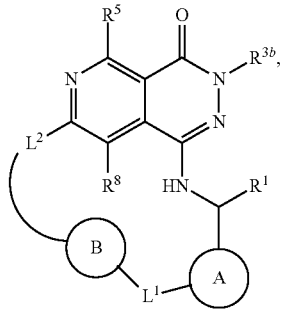

-continued

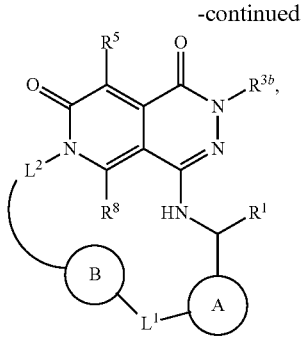

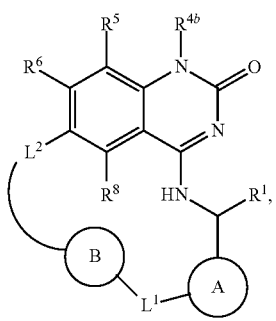

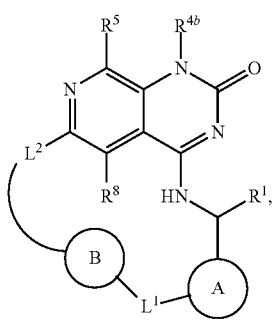

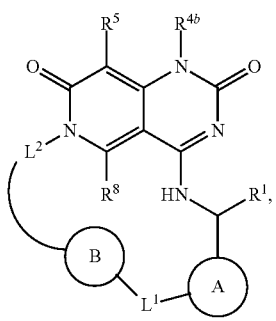

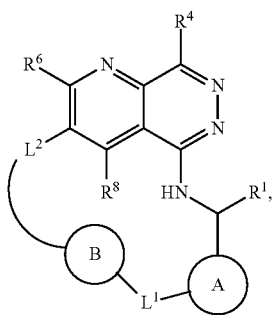

-continued

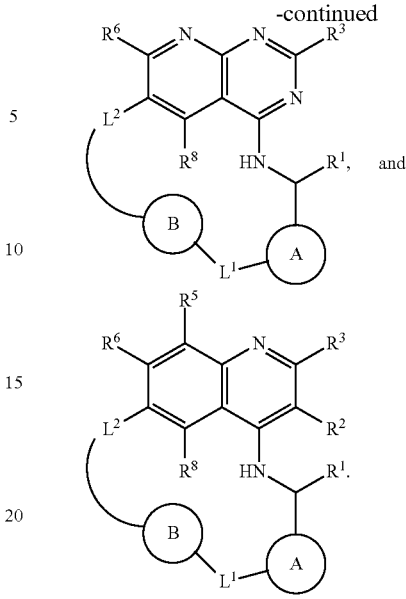

In some embodiments, for a compound of Formula (I), (I-A), (I-B), (I-C), (I-D), or (I-E), $W^2$ is N. In some embodiments, $W^3$ is selected from $N(R^{3b})$, N, $C(R^3)$, and C(O), such as $NCH_3$, N, CH, $CCH_3$, and C(O). In some embodiments, $W^3$ is selected from $C(R^3)$ and C(O), such as CH, $CCH_3$ and C(O). In some embodiments, $W^3$ is CH. In some embodiments, $W^3$ is $CCH_3$. In some embodiments, $W^4$ is selected from $N(R^{4b})$, N, $C(R^4)$, and C(O), such as $N(R^{4b})$, N, $C(R^4)$, and C(O), wherein $R^{4b}$ and $R^4$ are each independently a bond to $L^2$. In some embodiments, $W^4$ is selected from $N(R^{4b})$ and N, such as $N(R^{4b})$, wherein $R^{4b}$ is a bond to $L^2$. In some embodiments, $W^4$ is N. In some embodiments, $W^5$ is selected from $N(R^{5b})$, N, $C(R^5)$, and C(O), such as $N(R^{5b})$, $NCH_3$, N, CH, $C(R^5)$, and C(O), wherein $R^{5b}$ and $R^5$ are each independently a bond to $L^2$. In some embodiments, $W^5$ is selected from $N(R^{5b})$, N, and $C(R^5)$, such as $N(R^{5b})$, $NCH_3$, N, CH, and $C(R^5)$, wherein $R^{5b}$ and $R^5$ are each independently a bond to $L^2$. In some embodiments, $W^5$ is selected from $N(R^{5b})$ and $C(R^5)$, such as $N(R^{5b})$, $NCH_3$, and CH, wherein $R^{5b}$ is a bond to $L^2$. In some embodiments, $W^5$ is $N(R^{5b})$ In some embodiments, $W^6$ is selected from $C(R^6)$ and C(O), such as $COCH_3$, CH, $C(R^6)$, and C(O), wherein $R^6$ is a bond to $L^2$. In some embodiments, $W^6$ is C(O). In some embodiments, $W^7$ is $C(R^7)$, such as $W^7$ is $C(R^7)$ wherein $R^7$ is a bond to $L^2$. In some embodiments, $W^7$ is $C(R^7)$, wherein $R^7$ is not hydrogen, such as $R^7$ is selected from $C_{3-10}$ cycloalkyl, 3- to 10-membered heterocycloalkyl, and $—OR^{12}$, wherein $C_{3-10}$ cycloalkyl and 3- to 10-membered heterocycloalkyl are optionally substituted with one, two, or three $R^{20}$. In some embodiments, $W^8$ is $C(R^8)$, such as $W^8$ is CH. In some embodiments, $W^9$ is C. In some embodiments, $W^{10}$ is C.

In some embodiments, for a compound of Formula (I), (I-A), (I-C), (I-D), or (I-E), $W^2$ is N; $W^3$ is $N(R^{3b})$; $W^4$ is C(O); and $W^9$ and $W^{10}$ are each C, such as $W^2$ is N; $W^3$ is $NCH_3$; $W^4$ is C(O); and $W^9$ and $W^{10}$ are each C. In some embodiments, for a compound of Formula (I), (I-B), (I-C), (I-D), or (I-E), $W^2$ is N; $W^3$ is C(O); $W^4$ is $N(R^{4b})$; and $W^9$ and $W^{10}$ are each C, such as $W^2$ is N; $W^3$ is C(O); $W^4$ is $N(R^{4b})$, wherein $R^{4b}$ is a bond to $L^2$; and $W^9$ and $W^{10}$ are each C. In some embodiments, for a compound of Formula (I), (I-A), (I-C), (I-D), or (I-E), $W^2$ is N; $W^3$ is $C(R^3)$; $W^4$ is N; and $W^9$ and $W^{10}$ are each C, such as $W^2$ is N; $W^3$ is CH or CCH$_3$; $W^4$ is N; and $W^9$ and $W^{10}$ are each C. In some embodiments, for a compound of Formula (I), (I-A), (I-B), (I-C), (I-D), or (I-E), $W^5$ is C($R^5$); $W^6$ is C($R^6$); $W^7$ is C($R^7$); $W^8$ is C($R^8$); and $W^9$ and $W^{10}$ are each C, such as $W^5$ is CH or C($R^5$), wherein $R^5$ is a bond to $L^2$; $W^6$ is CH or C($R^6$), wherein $R^6$ is a bond to $L^2$; $W^7$ is C($R^7$); $W^8$ is CH; and $W^9$ and $W^{10}$ are each C. In some embodiments, for a compound of Formula (I), (I-A), (I-B), (I-C), or (I-E), $W^5$ is N($R^{5b}$); $W^6$ is C(O); $W^7$ is C($R^7$); $W^8$ is C($R^8$); and $W^9$ and $W^{10}$ are each C, such as $W^5$ is NCH$_3$ or N($R^{5b}$), wherein $R^{5b}$ is a bond to $L^2$; $W^6$ is C(O); $W^7$ is C($R^7$); $W^8$ is CH; and $W^9$ and $W^{10}$ are each C. In some embodiments, for a compound of Formula (I), (I-A), (I-B), (I-D), or (I-E), $W^5$ is N; $W^6$ is C($R^6$); $W^7$ is C($R^7$); $W^8$ is C($R^8$); and $W^9$ and $W^{10}$ are each C, such as $W^5$ is N; $W^6$ is COCH$_3$, CH, or C($R^6$), wherein $R^6$ is a bond to $L^2$; $W^7$ is C($R^7$); $W^8$ is CH; and $W^9$ and $W^{10}$ are each C. In some embodiments, for a compound of Formula (I), (I-A), (I-B), (I-C), (I-D), or (I-E), $W^2$ is N; $W^3$ is selected from N($R^{3b}$), N, C($R^3$), and C(O); $W^4$ is selected from N($R^{4b}$), N, C($R^4$), and C(O); $W^5$ is selected from N($R^{5b}$), N, and C($R^5$); $W^6$ is selected from C($R^6$) and C(O); $W^7$ is C($R^7$); $W^8$ is C($R^8$); and $W^9$ and $W^{10}$ are each C, such as $W^2$ is N; $W^3$ is selected from NCH$_3$, N, CH, CCH$_3$, and C(O); $W^4$ is selected from N($R^{4b}$), N, C($R^4$), and C(O), wherein $R^{4b}$ and $R^4$ are each independently a bond to $L^2$; $W^5$ is selected from N($R^{5b}$), NCH$_3$, N, CH, and C($R^5$), wherein $R^{5b}$ and $R^5$ are each independently a bond to $L^2$; $W^6$ is selected from COCH$_3$, CH, C($R^6$), and C(O), wherein $R^6$ is a bond to $L^2$; $W^7$ is C($R^7$); $W^8$ is CH; and $W^9$ and $W^{10}$ are each C. In some embodiments, for a compound of Formula (I), (I-A), (I-B), (I-C), (I-D), or (I-E), $W^2$ is N; $W^3$ is selected from C($R^3$) and C(O); $W^4$ is selected from N($R^{4b}$) and N; $W^5$ is selected from N($R^{5b}$) and C($R^5$); $W^6$ is selected from C($R^6$) and C(O); $W^7$ is C($R^7$); $W^8$ is CHI; and $W^9$ and $W^{10}$ are each C, such as $W^2$ is N; $W^3$ is selected from CHI, CCH$_3$, and C(O); $W^4$ is selected from N($W^{4b}$) and N, wherein $W^{4b}$ is a bond to $L^2$; $W^5$ is selected from N($R^{5b}$), NCH$_3$, CHI, and C($R^5$), wherein $R^{1b}$ and $R^5$ are each independently a bond to $L^2$; $W^6$ is selected from COCH$_3$, CHI, C($R^6$), and C(O), wherein $R^6$ is a bond to $L^2$; $W^7$ is C($R^7$); $W^8$ is CHI; and $W^9$ and $W^{10}$ are each C.

In some embodiments, for a compound of Formula (I),

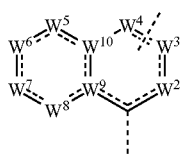

is selected from

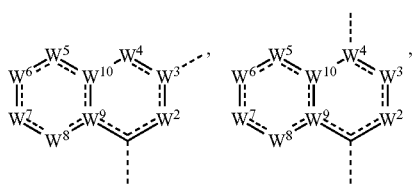

-continued

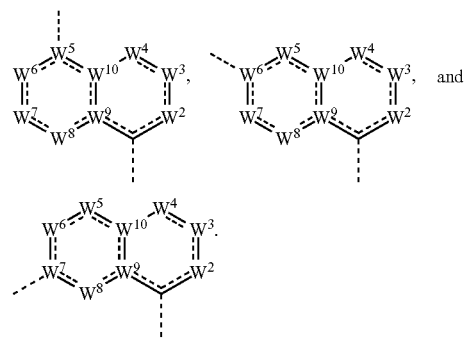

In some embodiments,

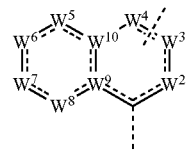

is selected from

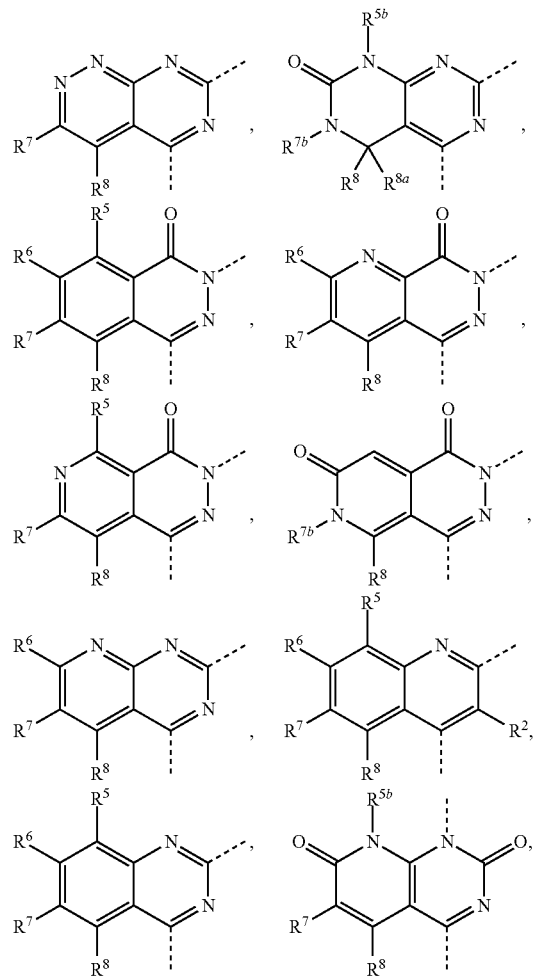

-continued
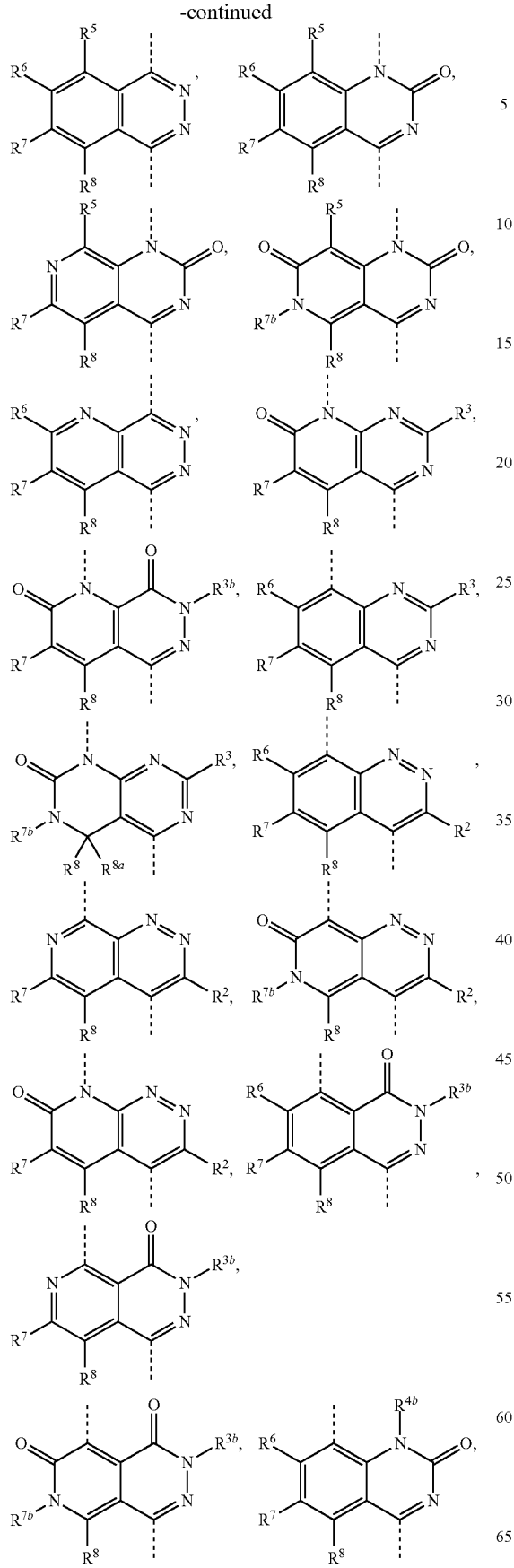
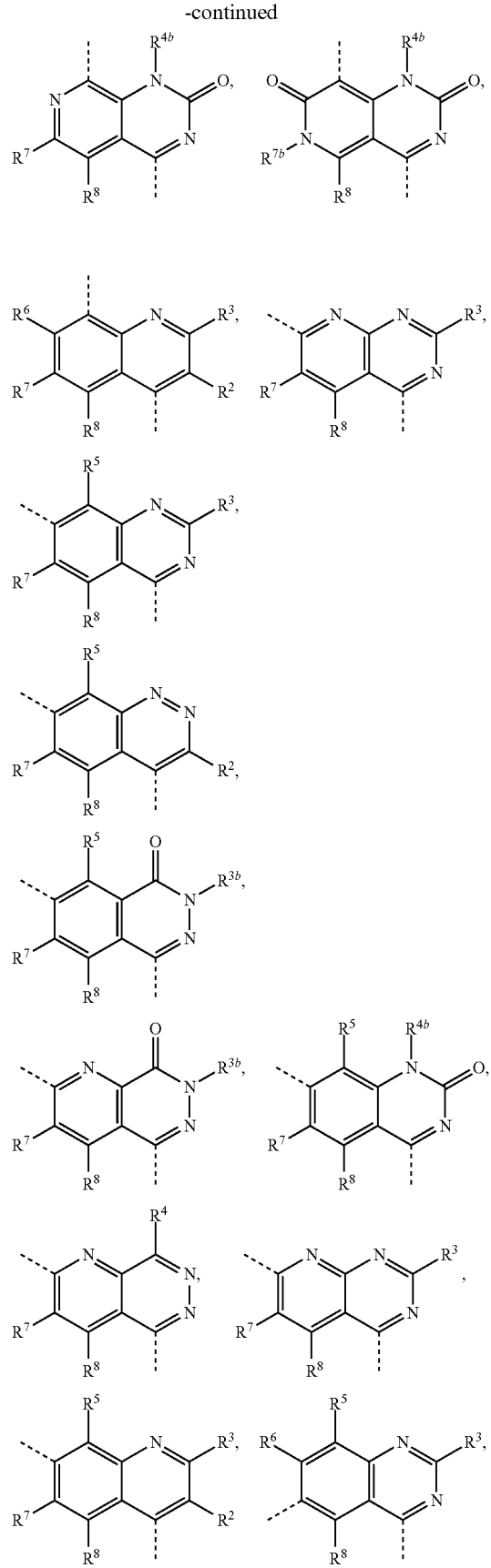

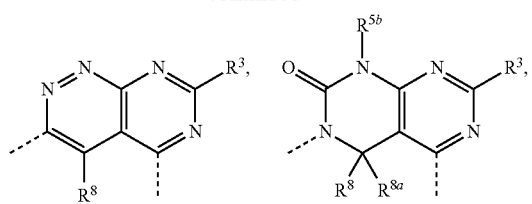
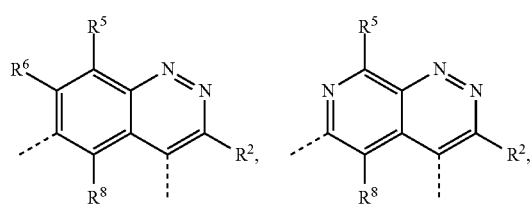
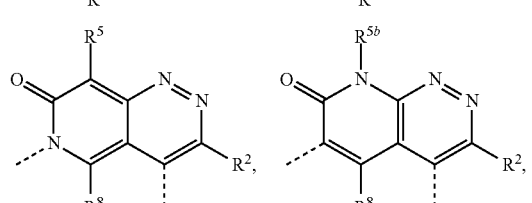
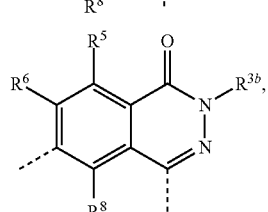
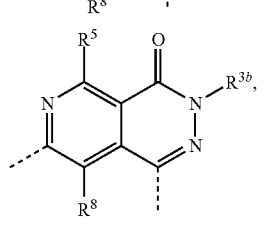
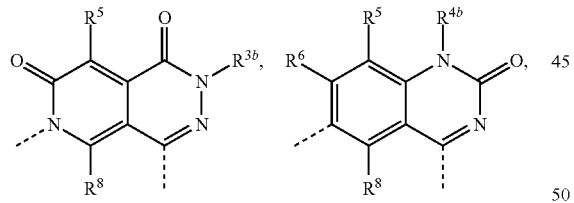
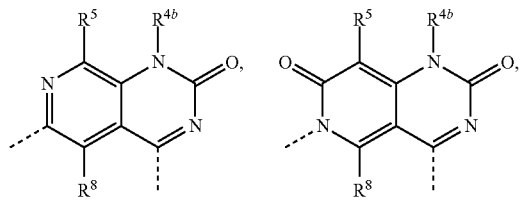
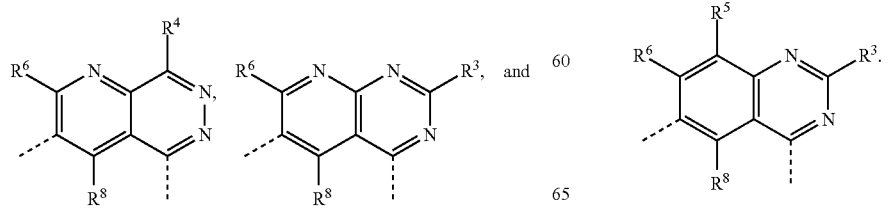
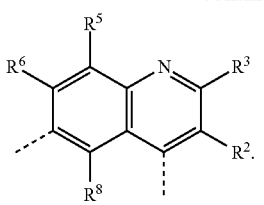
In some embodiments,
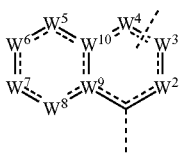
is selected from
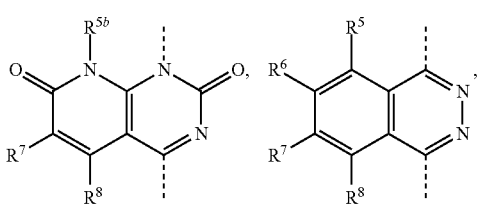
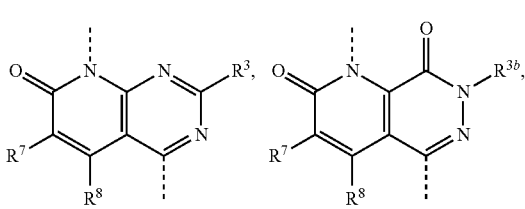
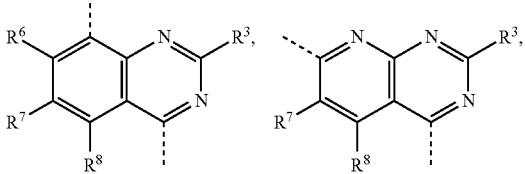
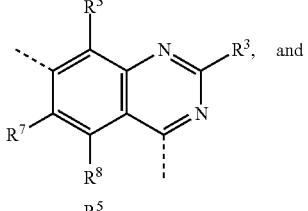
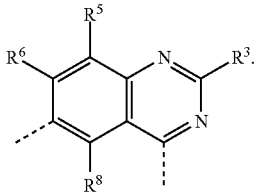

In some embodiments,
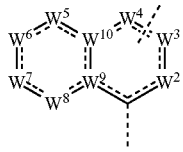
is selected from
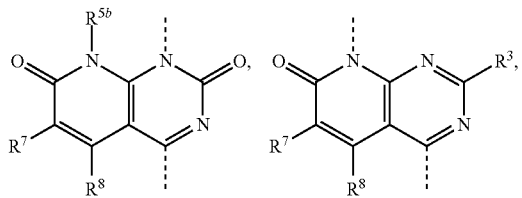
In some embodiments,
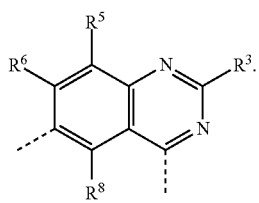
is
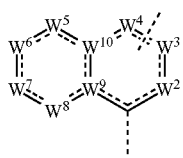
such as
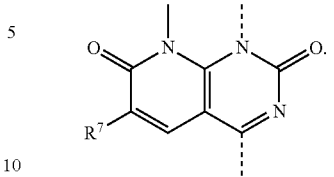
In some embodiments,
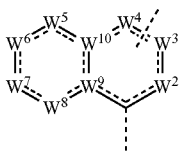
is
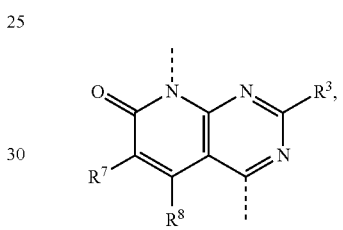
such as
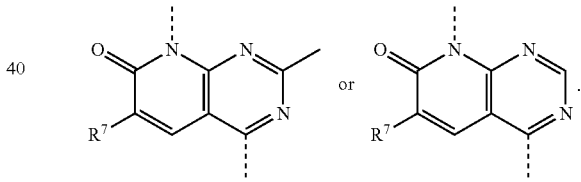
In some embodiments,
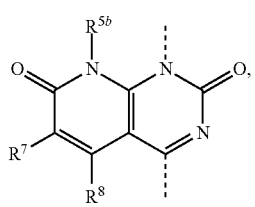
is
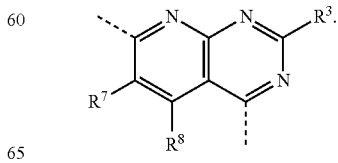

In some embodiments,
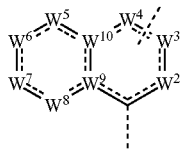
is
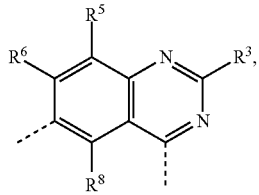
such as
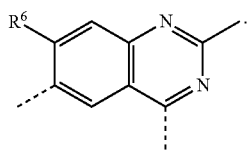
In some embodiments,
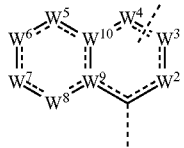
is selected from
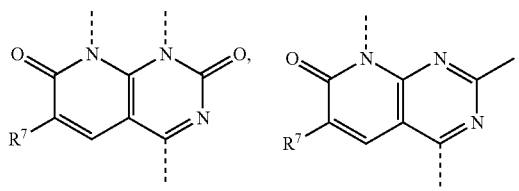
and 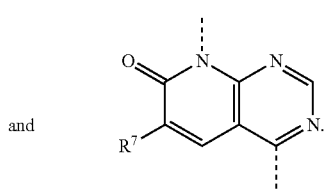
In some embodiments,
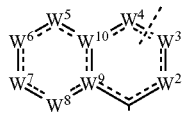
is
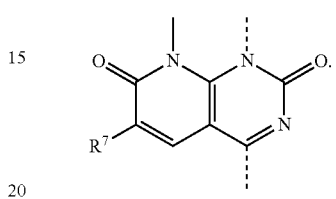
In some embodiments,
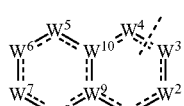
is
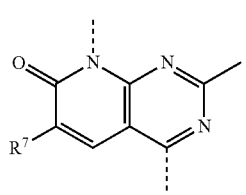
In some embodiments,
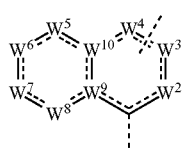
is
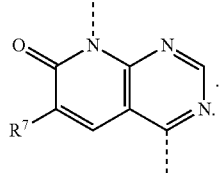
In some embodiments, for a compound of Formula (I), (I-A), (I-B), (I-C), (I-D), or (I-E), $R^2$, $R^{2a}$, $R^{3a}$, $R^{4a}$, $R^{5a}$, $R^{6a}$, $R^{7a}$, $R^8$, and $R^{8a}$ are each independently selected from hydrogen, halogen, —CN, $C_{1-3}$ alkyl, $C_{1-3}$ haloalkyl, —OH, —NH$_2$, —NHCH$_3$, and —N(CH$_3$)$_2$. In some embodiments, R$^2$, R$^{2}$, R$^{3a}$, R$^{4a}$, R$^{5a}$, R$^{6a}$, R$^{7a}$, R$^8$, and R$^{8a}$ are each independently selected from hydrogen and —CH$_3$, such as hydrogen.

In some embodiments, for a compound of Formula (I), (I-A), (I-B), (I-C), (I-D), or (I-E), R$^3$, R$^4$, R$^5$, and R$^6$ are each independently selected from a bond to L$^2$, hydrogen, halogen, —CN, C$_{1-6}$ alkyl, C$_{3-6}$ carbocycle, 3- to 6-membered heterocycle, —OR$^{12}$, —SR$^{12}$, —N(R$^{12}$)(R$^{13}$), —C(O)OR$^{12}$, —C(O)R$^{15}$, —S(O)R$^{15}$, —OC(O)R$^{15}$, —C(O)N(R$^{12}$)(R$^{13}$), —N(R$^{14}$)C(O)R$^{15}$, —S(O)$_2$R$^{15}$, and —S(O)$_2$N(R$^{12}$)(R$^{13}$), wherein each C$_{1-6}$ alkyl, C$_{3-6}$ carbocycle, and 3- to 6-membered heterocycle is independently optionally substituted with one, two, or three R$^{20}$; and R$^7$ is selected from a bond to L$^2$, C$_{1-6}$ alkyl, C$_{3-10}$ carbocycle, 3- to 10-membered heterocycle, —OR$^{12}$, —N(R$^{12}$)(R$^{13}$), —C(O)R$^{15}$, —C(O)N(R$^{12}$)(R$^{13}$), —S(O)$_2$R$^{15}$, and —SO$_2$N(R$^{12}$)(R$^{13}$), wherein C$_{1-6}$ alkyl, C$_{3-10}$ carbocycle, and 3- to 10-membered heterocycle are optionally substituted with one, two, or three R$^{20}$. In some embodiments, R$^3$, R$^4$, R$^5$, and R$^6$ are each independently selected from a bond to L$^2$, hydrogen, halogen, —CN, C$_{1-3}$ alkyl, C$_{1-3}$ haloalkyl, —OH, —OCH$_3$, —NH$_2$, —NHCH$_3$, —N(CH$_3$)$_2$; and R$^7$ is selected from a bond to L$^2$, C$_{1-6}$ alkyl, C$_{3-10}$ carbocycle, 3- to 10-membered heterocycle, —OR$^{12}$, —N(R$^{12}$)(R$^{13}$), —C(O)R$^{15}$, —C(O)N(R$^{12}$)(R$^{13}$), —S(O)$_2$R$^{15}$, and —SO$_2$N(R$^{12}$)(R$^{13}$), wherein C$_{1-6}$ alkyl, C$_{3-10}$ carbocycle, and 3- to 10-membered heterocycle are optionally substituted with one, two, or three R$^{20}$. In some embodiments, R$^3$, R$^4$, R, and R$^6$ are each independently selected from a bond to L$^2$, hydrogen, —CH$_3$, and —OCH$_3$; and R$^7$ is selected from a bond to L$^2$, C$_{1-6}$ alkyl, C$_{3-10}$ carbocycle, 3- to 10-membered heterocycle, —OR$^{12}$, —N(R$^{12}$)(R$^{13}$), —C(O)R$^{15}$, —C(O)N(R$^{12}$)(R$^{13}$), —S(O)$_2$R$^{15}$, and —SO$_2$N(R$^{12}$)(R$^{13}$), wherein C$_{1-6}$ alkyl, C$_{3-10}$ carbocycle, and 3- to 10-membered heterocycle are optionally substituted with one, two, or three R$^{20}$.

In some embodiments, for a compound of Formula (I), (I-A), (I-B), (I-C), (I-D), or (I-E), R$^{2b}$ and R$^{8b}$ are each independently selected from hydrogen and C$_{1-3}$ alkyl, such as hydrogen and —CH$_3$. In some embodiments, R$^{3b}$, R$^{4b}$, R$^{5b}$, R$^{61}$, and R$^{7b}$ are each independently selected from a bond to L$^2$, hydrogen, and C$_{1-3}$ alkyl, such as a bond to L$^2$, hydrogen, and —CH$_3$. In some embodiments, R$^{3b}$, R$^{4b}$, R$^{5b}$, R$^{6a}$, and R$^{7b}$ are each independently selected from a bond to L$^2$ and —CH$_3$. In some embodiments, R$^{3b}$, R$^{4b}$, R$^{5b}$, R$^{6b}$, and R$^{7b}$ are each independently selected from a bond to L$^2$. In some embodiments, R$^9$ and R$^{10}$ are each hydrogen.

For a compound of Formula (I) wherein L$^2$ is -L$^3$-D-L$^4$-, it is understood that the selection of "a bond to L$^2$" for one of R$^3$, R$^4$, R$^5$, R$^6$, R$^7$, R$^{3b}$, R$^{4b}$, R$^{5b}$, R$^{6b}$, or R$^{7b}$ inherently includes a bond to -L$^3$-D-L$^4$-, specifically to L$^4$. For the avoidance of doubt, any recitation of R$^3$, R$^4$, R$^5$, R$^6$, R$^7$, R$^{3b}$, R$^{4b}$, R$^{5b}$, R$^b$, and/or R$^{7b}$ that includes "a bond to L$^2$" also may be considered to include "a bond to L$^4$".

In some embodiments, for a compound of Formula (I), (I-A), (I-B), (I-B1), (I-B2), (I-C), (I-C1), (I-C2), (I-C3), (I-D), (I-D1), (I-D2), (I-E), or (I-E1), R$^1$ is selected from C$_{1-3}$ alkyl and C$_{1-3}$ haloalkyl, such as —CH$_3$, —CH$_2$CH$_3$, —CH(CH$_3$)$_2$, —CH$_2$F, —CF$_2$, —CF$_3$, —CH$_2$CH$_2$F, —CH$_2$CHF$_2$, and —CH$_2$CF$_3$. In some embodiments, R$^1$ is selected from C$_{1-3}$ alkyl, such as —CH$_3$ and —CH$_2$CH$_3$. In some embodiments, R$^1$ is —CH$_3$. In some embodiments, R$^1$ is (R)—CH$_3$. In some embodiments, R$^1$ is (S)—CH$_3$.

In some embodiments, for a compound of Formula (I), (I-B), (I-C), (I-C1), (I-C3), (I-D), (I-D1), (I-D2), (I-E), or (I-E1), R$^3$ is selected from hydrogen, halogen, —CN, C$_{1-6}$ alkyl, C$_{3-6}$ carbocycle, 3- to 6-membered heterocycle, —OR$^{12}$, —SR$^{12}$, —N(R$^{12}$)(R$^{13}$), —C(O)OR$^{12}$, —C(O)R$^{15}$, —S(O)R$^{15}$, —OC(O)R$^{15}$, —C(O)N(R$^{12}$)(R$^{13}$), —N(R$^{14}$)C(O)R$^{15}$, —S(O)$_2$R$^{15}$, and —S(O)$_2$N(R$^{12}$)(R$^{13}$), wherein each C$_{1-6}$ alkyl, C$_{3-6}$ carbocycle, and 3- to 6-membered heterocycle is independently optionally substituted with one, two, or three R$^{20}$. In some embodiments, R$^3$ is selected from hydrogen, halogen, —CN, C$_{1-3}$ alkyl, C$_{1-3}$ haloalkyl, —OH, —OCH$_3$, —NH$_2$, —NHCH$_3$, —N(CH$_3$)$_2$. In some embodiments, R$^3$ is selected from hydrogen, halogen, —CN, —OR$^{12}$, and C$_{1-6}$ alkyl optionally substituted with one, two, or three R$^{20}$. In some embodiments, R$^3$ is C$_{1-6}$ alkyl optionally substituted with one, two, or three R$^{20}$. In some embodiments, R$^3$ is hydrogen or —CH$_3$. In some embodiments, R$^3$ is hydrogen. In some embodiments, R$^3$ is —CH$_3$.

In some embodiments, for a compound of Formula (I), (I-B), (I-C), (I-C2), (I-D), or (I-E), R$^{3b}$ is selected from hydrogen and C$_{1-3}$ alkyl, such as hydrogen and —CH$_3$. In some embodiments, R$^{31}$ is —CH$_3$. In some embodiments, R$^{3b}$ is hydrogen.

In some embodiments, for a compound of Formula (I), (I-A), (I-B), (I-B2), (I-D), (I-D2), (I-E), or (I-E1), R$^5$ is selected from hydrogen, halogen, —CN, C$_{1-6}$ alkyl, C$_{3-6}$ carbocycle, 3- to 6-membered heterocycle, —OR$^{12}$, —SR$^{12}$, —N(R$^{12}$)(R$^{13}$), —C(O)OR$^{12}$, —C(O)R$^{15}$, —S(O)R$^{15}$, —OC(O)R$^{15}$, —C(O)N(R$^{12}$)(R$^{13}$), —N(R$^{14}$)C(O)R$^{15}$, —S(O)$_2$R$^{15}$, and —S(O)$_2$N(R$^{12}$)(R$^{13}$), wherein each C$_{1-6}$ alkyl, C$_{3-6}$ carbocycle, and 3- to 6-membered heterocycle is independently optionally substituted with one, two, or three R$^{20}$. In some embodiments, R$^5$ is selected from hydrogen, halogen, —CN, C$_{1-3}$ alkyl, C$_{1-3}$ haloalkyl, —OH, —OCH$_3$, —NH$_2$, —NHCH$_3$, —N(CH$_3$)$_2$. In some embodiments, R$^5$ is selected from hydrogen, —OR$^{12}$, and C$_{1-6}$ alkyl optionally substituted with one, two, or three R$^{20}$. In some embodiments, R$^5$ is hydrogen or —CH$_3$. In some embodiments, R$^5$ is hydrogen. In some embodiments, R$^5$ is —CH$_3$.

In some embodiments, for a compound of Formula (I), (I-A), (I-B), (I-B1), (I-D), or (I-E), R$^{5b}$ is selected from hydrogen and C$_{1-3}$ alkyl, such as hydrogen and —CH$_3$. In some embodiments, R$^{5b}$ is selected from hydrogen and C$_{1-6}$ alkyl optionally substituted with one, two, or three R$^{20}$. In some embodiments, R$^{5b}$ is —CH$_3$. In some embodiments, R$^{5b}$ is hydrogen. In some embodiments, R$^{5b}$ is a bond to L$^2$.

In some embodiments, for a compound of Formula (I), (I-A), (I-B), (I-B2), (I-C), (I-C3), (I-E), or (I-E1), R$^6$ is selected from hydrogen, halogen, —CN, C$_{1-6}$ alkyl, C$_{3-6}$ carbocycle, 3- to 6-membered heterocycle, —OR$^{12}$, —SR$^{12}$, —N(R$^{12}$)(R$^{13}$), —C(O)OR$^{12}$, —C(O)R$^{15}$, —S(O)R$^{15}$, —OC(O)R$^{15}$, —C(O)N(R$^{12}$)(R$^{13}$), —N(R$^{14}$)C(O)R$^{15}$, —S(O)$_2$R$^{15}$, and —S(O)$_2$N(R$^{12}$)(R$^{13}$), wherein each C$_{1-6}$ alkyl, C$_{3-6}$ carbocycle, and 3- to 6-membered heterocycle is independently optionally substituted with one, two, or three R$^{20}$. In some embodiments, R$^6$ is selected from hydrogen, halogen, —CN, C$_{1-3}$ alkyl, C$_{1-3}$ haloalkyl, —OH, —OCH$_3$, —NH$_2$, —NHCH$_3$, and —N(CH$_3$)$_2$. In some embodiments, R$^6$ is selected from hydrogen, —OR$^{12}$, and C$_{1-6}$ alkyl optionally substituted with one, two, or three R$^{20}$, and wherein R$^{12}$ is selected from C$_{1-6}$ alkyl. In some embodiments, R$^6$ is selected from hydrogen and —OCH$_3$. In some embodiments, R$^6$ is hydrogen. In some embodiments, R$^6$ is —OCH$_3$.

In some embodiments, for a compound of Formula (I), (I-A), (I-B), (I-B1), (I-B2), (I-C), (I-C1), (I-C2), (I-C3), (I-D), (I-D1), or (I-D2), R$^7$ is selected from C$_{1-6}$ alkyl, C$_{3-10}$ carbocycle, 3- to 10-membered heterocycle, —OR$^{12}$, —SR$^{12}$, —N(R$^{12}$)(R$^{13}$), —C(O)R$^{15}$, —C(O)N(R$^{12}$)(R$^{13}$), —N(R$^{14}$)C(O)R$^{15}$, —S(O)$_2$R$^{15}$, —S(O)$_2$N(R$^{12}$)(R$^{13}$), —CH$_2$C(O)N(R$^{12}$)(R$^{13}$), —CH$_2$N(R$^{14}$)C(O)R$^{15}$, —CH$_2$S $(O)_2R^{15}$, and —$CH_2S(O)_2N(R^{12})(R^{13})$, wherein each $C_{1-6}$ alkyl, $C_{3-10}$ carbocycle, and 3- to 10-membered heterocycle is independently optionally substituted with one, two, or three $R^{20}$. In some embodiments, $R^7$ is selected from $C_{1-6}$ alkyl, $C_{3-10}$ carbocycle, 3- to 10-membered heterocycle, —$OR^{12}$, —$N(R^{12})(R^{13})$, —$C(O)R^{15}$, —$C(O)N(R^{12})(R^{13})$, —$S(O)_2R^{15}$, and —$SO_2N(R^{12})(R^{13})$, wherein $C_{1-6}$ alkyl, $C_{3-10}$ carbocycle, and 3- to 10-membered heterocycle are optionally substituted with one, two, or three $R^{20}$. In some embodiments, $R^7$ is selected from $C_{1-6}$ alkyl, $C_{3-10}$ cycloalkyl, 3- to 10-membered heterocycloalkyl, and —$N(R^{12})(R^{13})$, wherein $C_{1-6}$ alkyl, $C_{3-10}$ cycloalkyl, and 3- to 10-membered heterocycloalkyl are optionally substituted with one, two, or three $R^{20}$. In some embodiments, $R^7$ is 3- to 10-membered heterocycloalkyl optionally substituted with one, two, or three $R^{20}$, such as $R^7$ is 4- to 6-membered heterocycloalkyl optionally substituted with one, two, or three $R^{20}$. In some embodiments, $R^7$ is 3- to 10-membered heterocycloalkyl optionally substituted with one, two, or three $R^{20}$, wherein the heterocycloalkyl comprises at least one O, N, or S, such as one O atom, one or two N atoms, or one S atom. In some embodiments, $R^7$ is 3- to 6-membered heterocycloalkyl optionally substituted with one, two, or three $R^{20}$, wherein the heterocycloalkyl comprises $S(O)_2$. In some embodiments, $R^7$ is $C_{3-10}$ cycloalkyl optionally substituted with one, two, or three $R^{20}$, such as $R^7$ is $C_{3-6}$ cycloalkyl optionally substituted with one, two, or three $R^{20}$. In some embodiments, $R^7$ is $C_{3-4}$ cycloalkyl optionally substituted with one $R^{20}$, optionally wherein $R^{20}$ is —CN. In some embodiments, $R^7$ is $C_{1-6}$ alkyl optionally substituted with one, two, or three $R^{20}$, such as $R^7$ is $C_{1-6}$ alkyl substituted with one or two $R^{20}$. In some embodiments, $R^7$ is —$N(R^{12})(R^{13})$. In some embodiments, $R^7$ is —$OR^{12}$, such as —O(3- to 6-membered heterocycloalkyl). In some embodiments, $R^7$ is substituted with at least one —CN. In some embodiments, $R^7$ is unsubstituted. In some embodiments, $R^7$ is selected from $C_{3-10}$ carbocycle and 3- to 10-membered heterocycle, each of which is optionally substituted with one, two, or three $R^{20}$. In some embodiments, $R^7$ is selected from $C_{3-10}$ carbocycle and 3- to 10-membered heterocycle, each of which is optionally substituted with one, two, or three substituents selected from oxo, —CN, and $C_{1-6}$ alkyl. In some embodiments, $R^7$ is 4- to 6-membered heterocycloalkyl substituted with one, two, or three substituents selected from oxo, —CN, and $C_{1-3}$ alkyl. In some embodiments, $R^7$ is $C_{3-4}$ cycloalkyl substituted with one, two, or three substituents selected from oxo, —CN, and $C_{1-3}$ alkyl.

In some embodiments, for a compound of Formula (I), (I-A), (I-B), (I-B1), (I-B2), (I-C), (I-C1), (I-C2), (I-C3), (I-D), (I-D1), or (I-D2), $R^7$ is selected from $C_{1-6}$ alkyl, $C_{3-10}$ carbocycle, 3- to 10-membered heterocycle, —$OR^{12}$, —$SR^{12}$, —$N(R^{12})(R^{13})$, —$C(O)R^{15}$, —$C(O)N(R^{12})(R^{13})$, —$N(R^{14})C(O)R^{15}$, —$S(O)_2R^{15}$, —$S(O)(NR^{12})R^{15}$, —$S(O)_2 N(R^{12})(R^{13})$, —$CH_2C(O)N(R^{12})(R^{13})$, —$CH_2N(R^{14})C(O)R^{15}$, —$CH_2S(O)_2R^{15}$, —$CH_2S(O)(NR^{12})R^{15}$, and —$CH_2S(O)_2N(R^{12})(R^{13})$, wherein each $C_{1-6}$ alkyl, $C_{3-10}$ carbocycle, and 3- to 10-membered heterocycle is independently optionally substituted with one, two, or three $R^{20}$. In some embodiments, $R^7$ is selected from $C_{1-6}$ alkyl, $C_{3-10}$ carbocycle, 3- to 10-membered heterocycle, —$OR^{12}$, —$N(R^{12})(R^{13})$, —$C(O)R^{15}$, —$C(O)N(R^{12})(R^{13})$, —$S(O)_2 R^{15}$, —$S(O)(NR^{12})R^{15}$, and —$SO_2N(R^{12})(R^{13})$, wherein $C_{1-6}$ alkyl, $C_{3-10}$ carbocycle, and 3- to 10-membered heterocycle are optionally substituted with one, two, or three $R^{20}$. In some embodiments, $R^7$ is 3- to 6-membered heterocycloalkyl optionally substituted with one, two, or three $R^{20}$, wherein the heterocycloalkyl comprises $S(O)(NR^{12})$.

In some embodiments, for a compound of Formula (I), (I-A), (I-B), (I-B1), (I-B2), (I-C), (I-C1), (I-C2), (I-C3), (I-D), (I-D1), or (I-D2), $R^7$ is

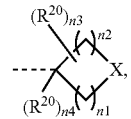

wherein:

n1 is an integer from 1 to 3;

n2 is an integer from 0 to 2;

n3 is an integer from 0 to 2;

n4 is 0 or 1; and

X is selected from —O—, —$S(O_2)$—, —$P(O)$—, —$CH_2$—, —$CH(OH)$—, —$CH(OR^{12})$—, —$CH(R^{20})$—, —$C(R^{20})_2$—, —$NR^{12}$—, —$CH(N(R^{12})(R^{13}))$—, —$CH(C(O)N(R^{12})(R^{13}))$—, and —$CH(S(O)_2 N(R^{12})(R^{13}))$—, wherein $R^{12}$, $R^{13}$, and $R^{20}$ are as defined elsewhere herein, and optionally wherein two $R^{20}$ groups, or $R^{20}$ and $R^{12}$, join together with the atom(s) to which they are attached to form a ring. For example, $R^7$ may be selected from

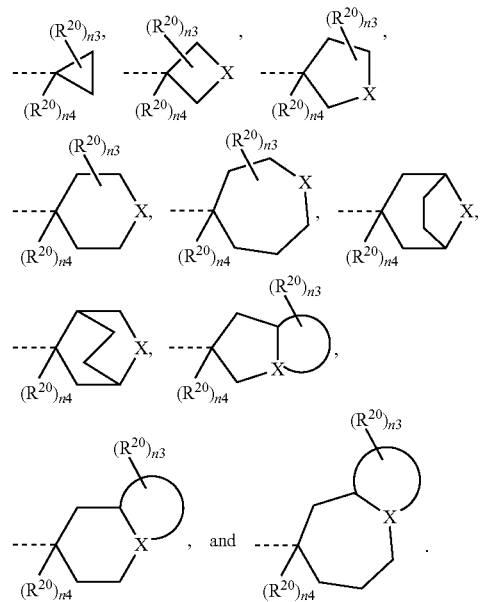

In some embodiments, X is selected from —O—, —$S(O)_2$—, —$S(O)(NR^{12})$—, —$P(O)$—, —$CH_2$—, —$CH(OH)$—, —$CH(OR^{12})$—, —$CH(R^{20})$—, —$C(R^{20})_2$—, —$NR^{12}$—, —$CH(N(R^{12})(R^{13}))$—, —$CH(C(O)N(R^{12})(R^{13}))$—, and —$CH(S(O)_2N(R^{12})(R^{13}))$—.

In some embodiments, for a compound of Formula (I), (I-A), (I-B), (I-B1), (I-B2), (I-C), (I-C1), (I-C2), (I-C3), (I-D), (I-D1), or (I-D2), $R^7$ is selected from

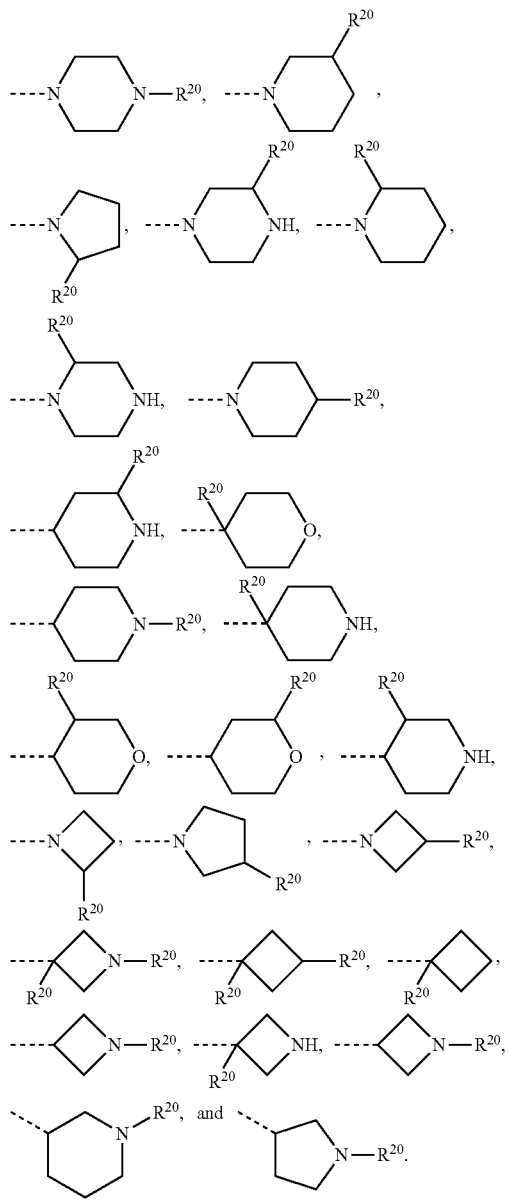
In some embodiments, R[7] is selected from
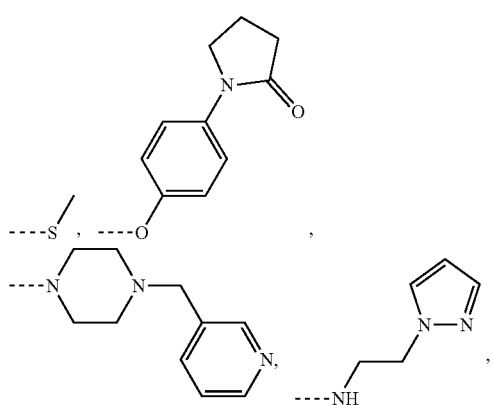
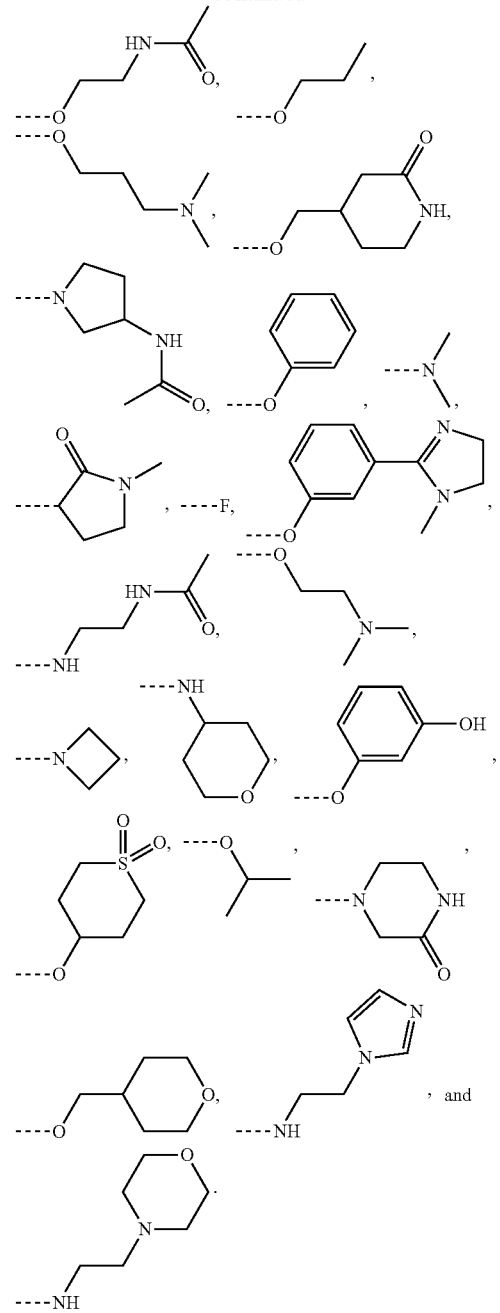
In some embodiments, R[7] is selected from
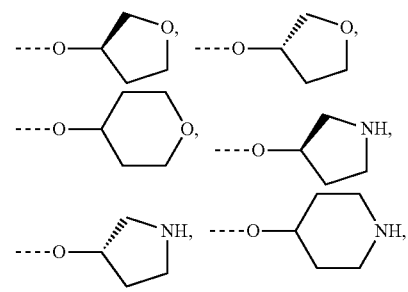

-continued
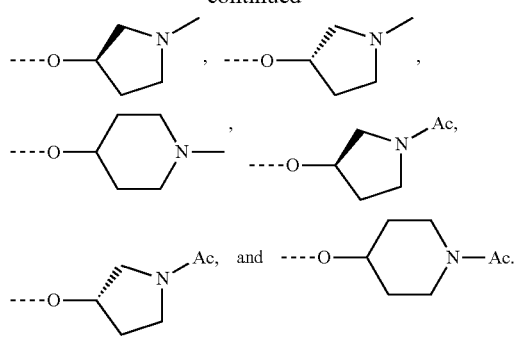
In some embodiments, $R^7$ is selected from
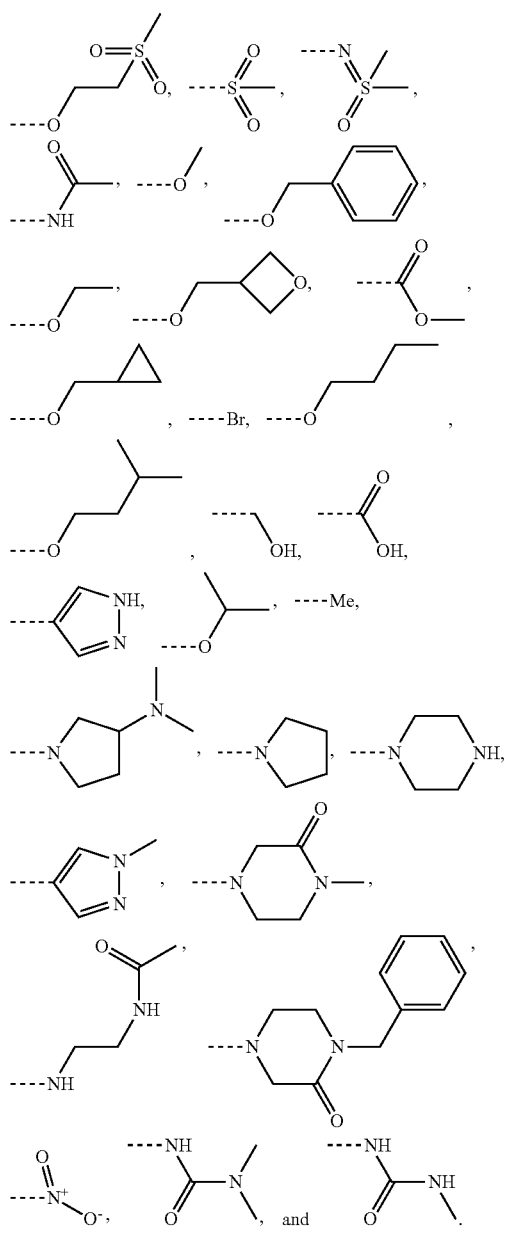
In some embodiments, $R^7$ is selected from
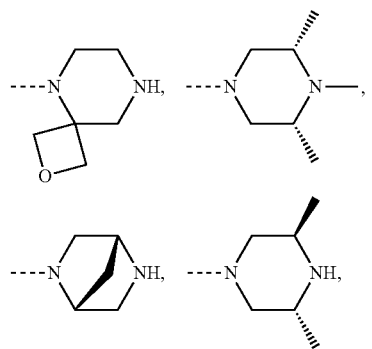
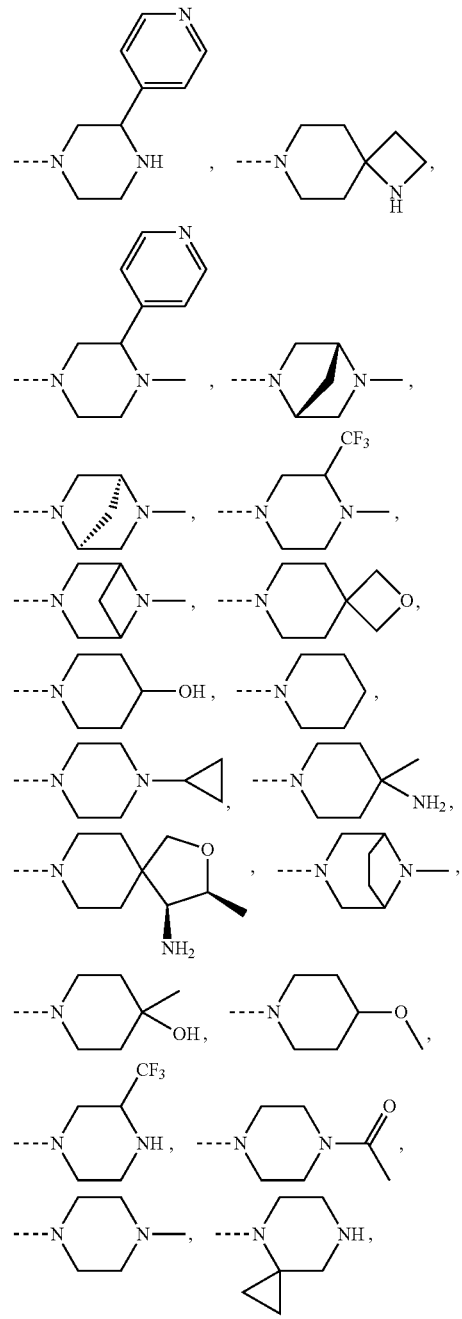

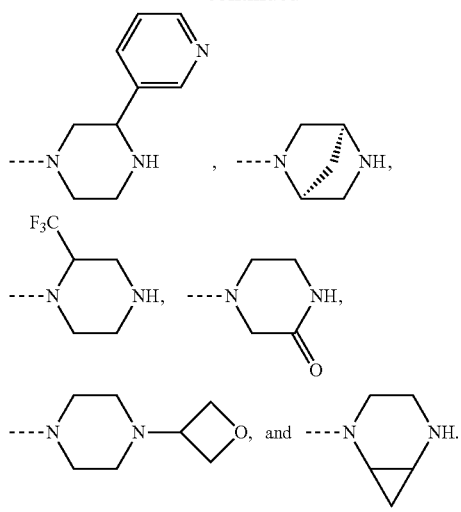
In some embodiments, R⁷ is selected from
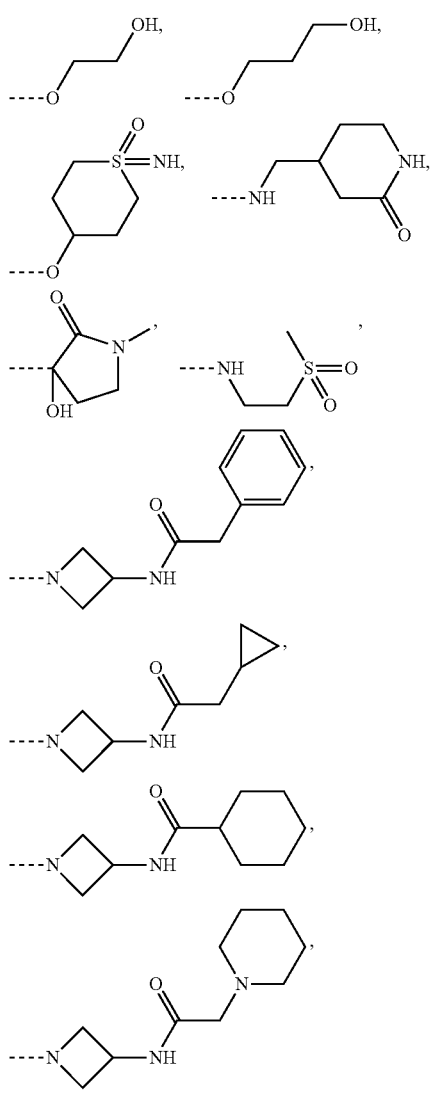
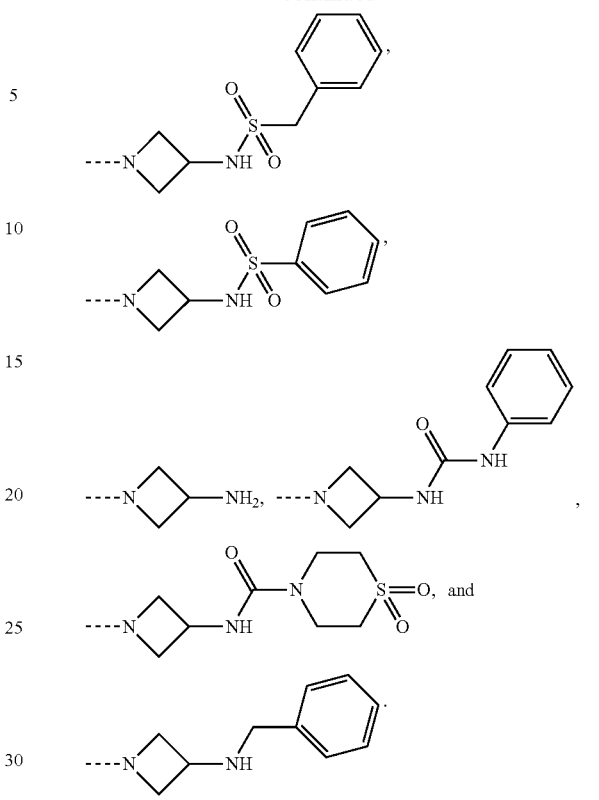
In some embodiments, R⁷ is selected from
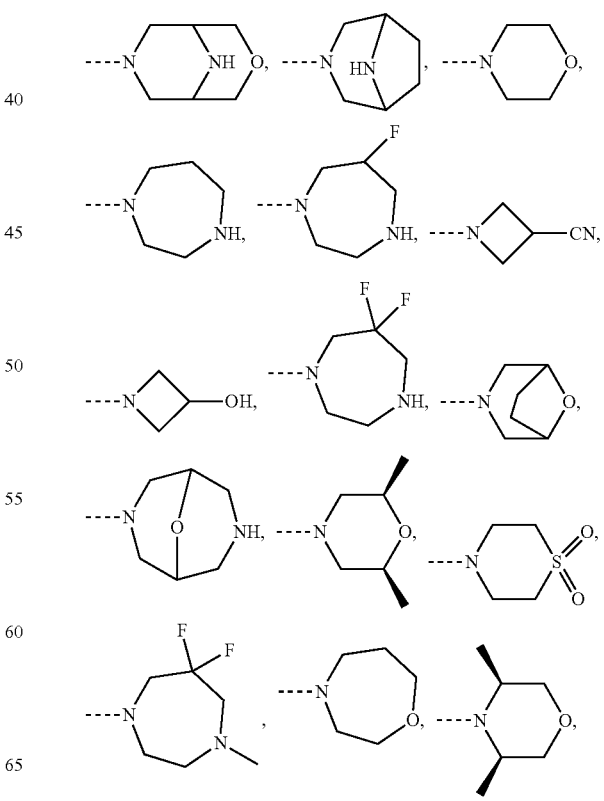

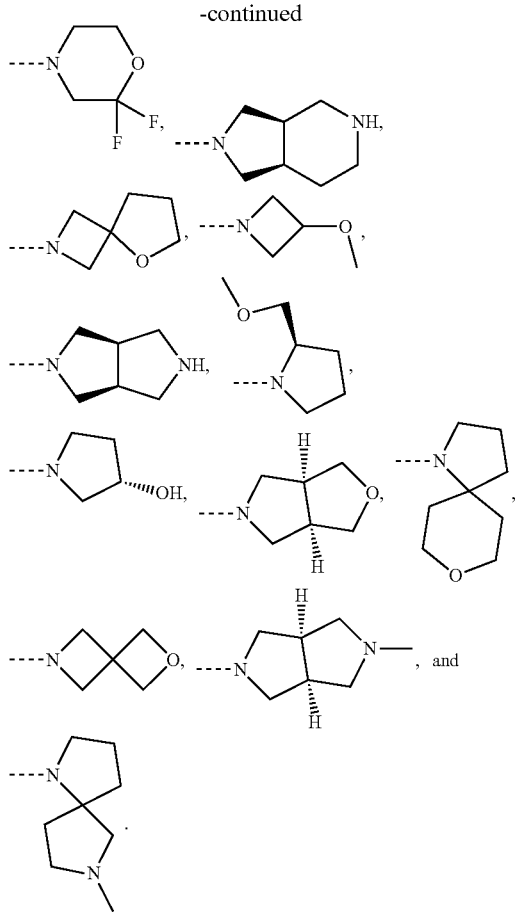
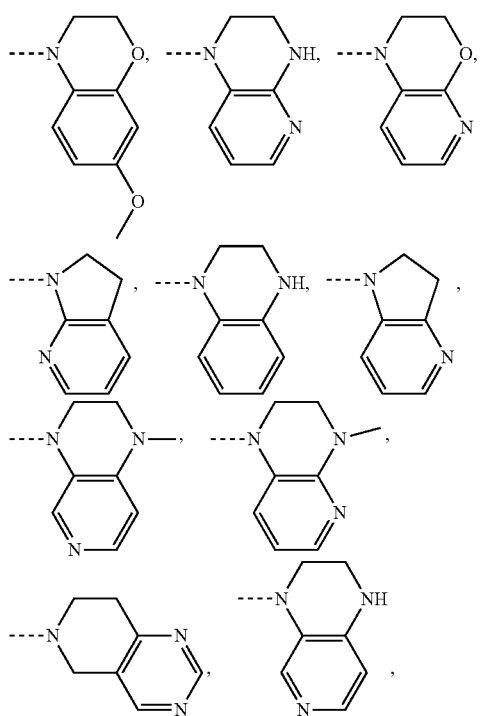
In some embodiments, R⁷ is selected from
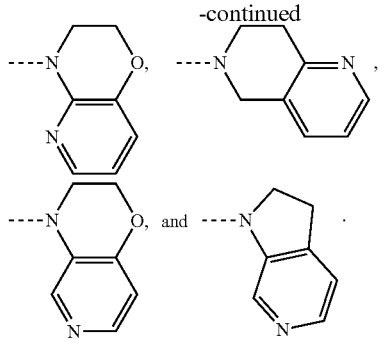
In some embodiments, R⁷ is selected from
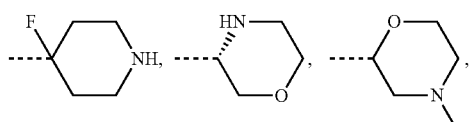
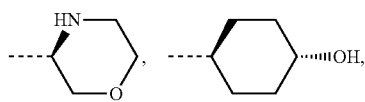
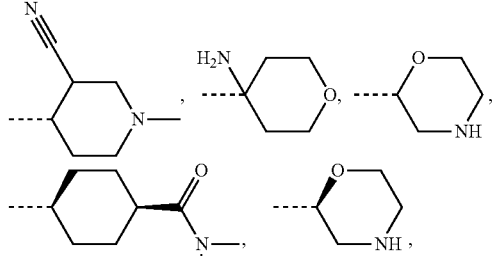
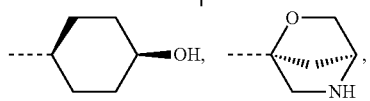
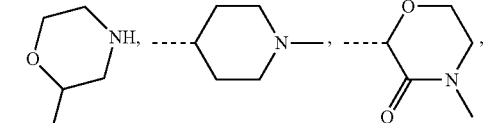
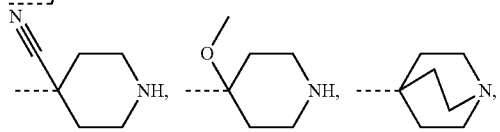
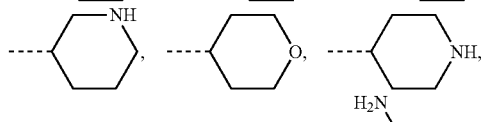
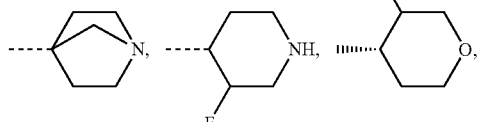
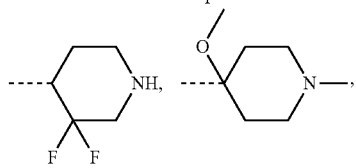

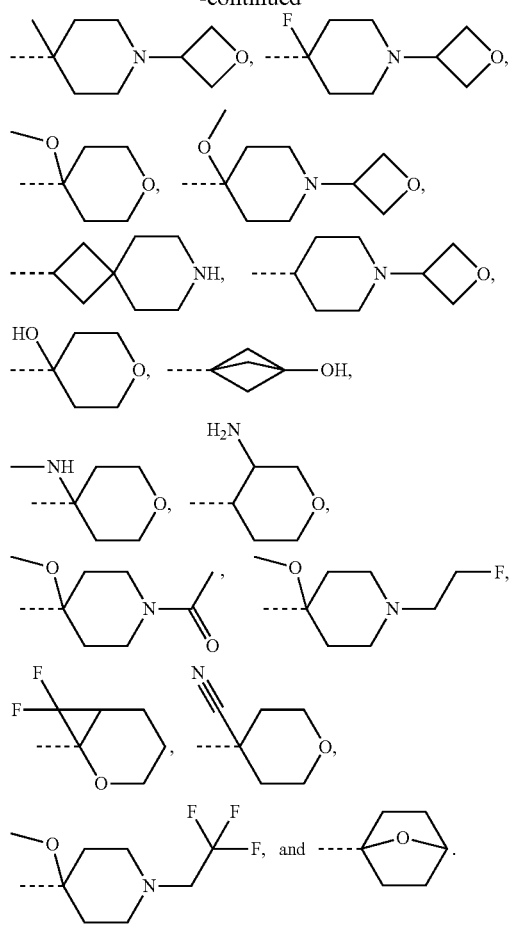
In some embodiments, R⁷ is selected from
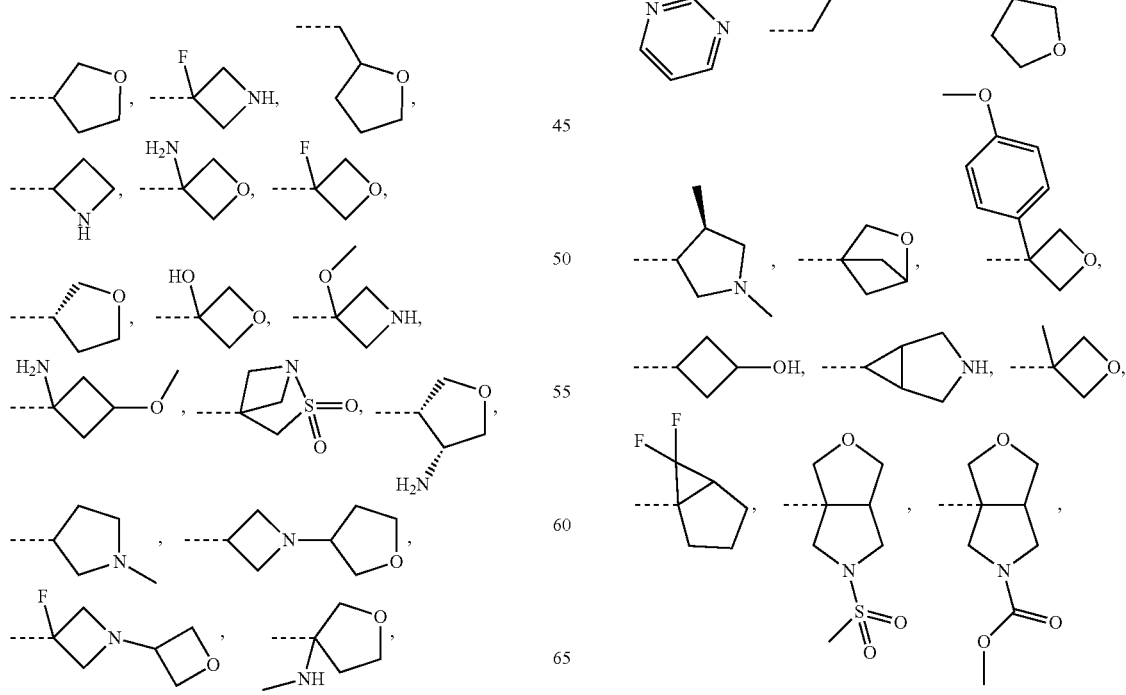
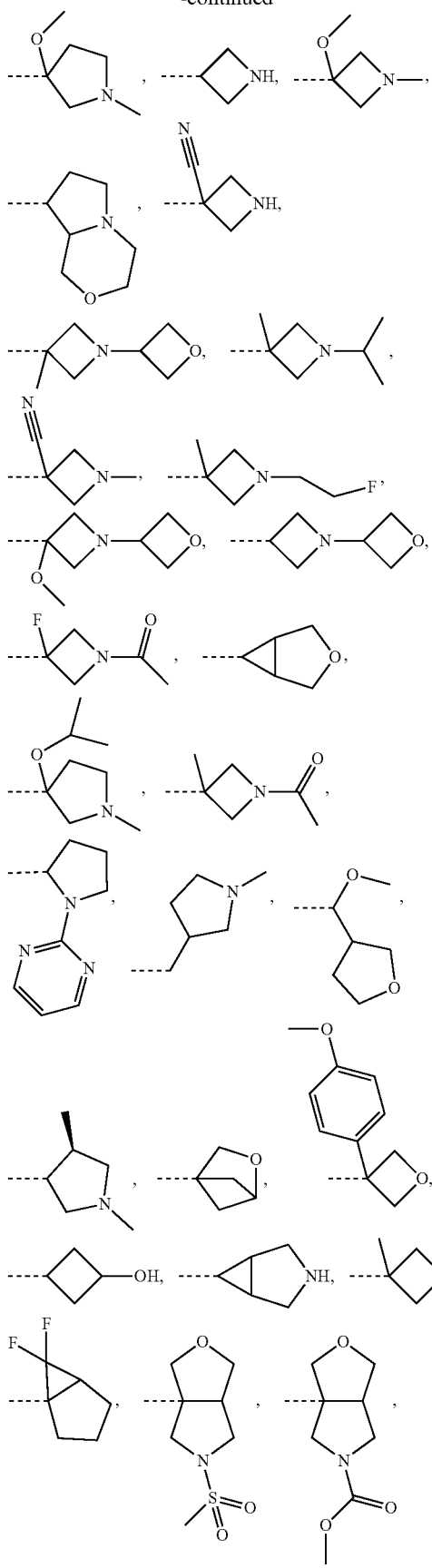

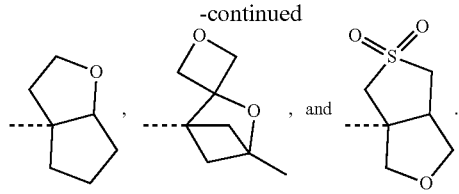
In some embodiments, $R^7$ is selected from
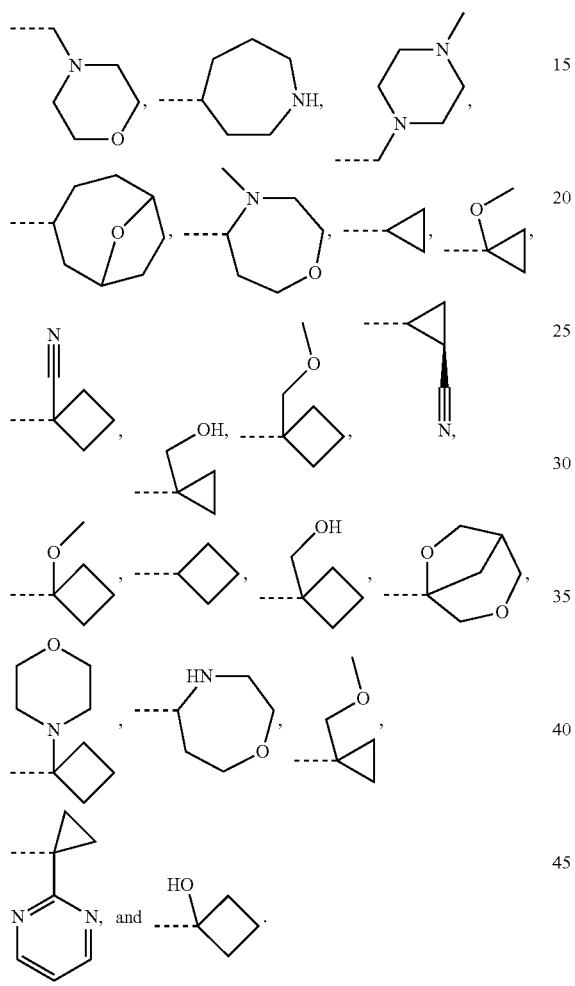
In some embodiments, $R^7$ is selected from
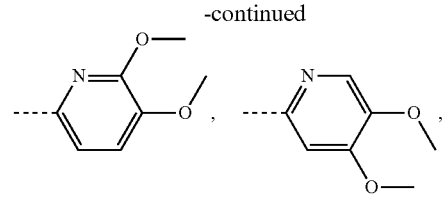
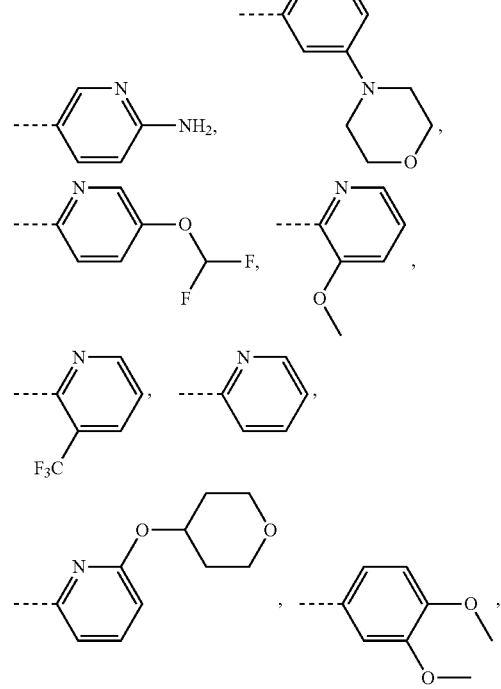
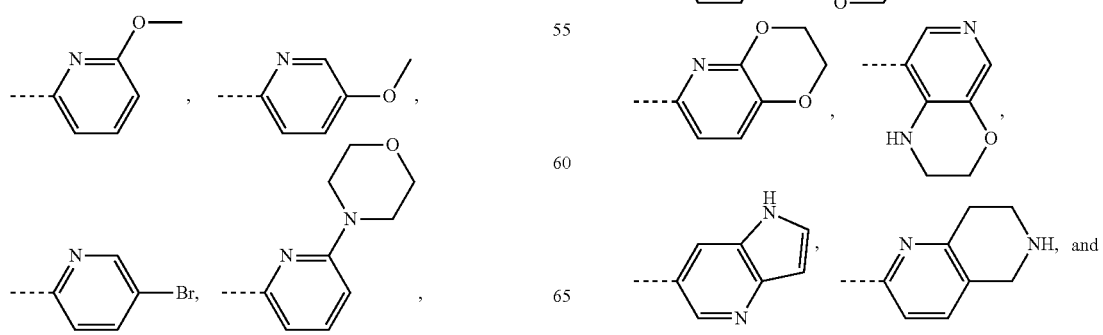

91
-continued
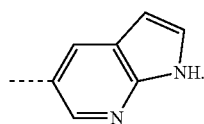
In some embodiments, $R^7$ is selected from
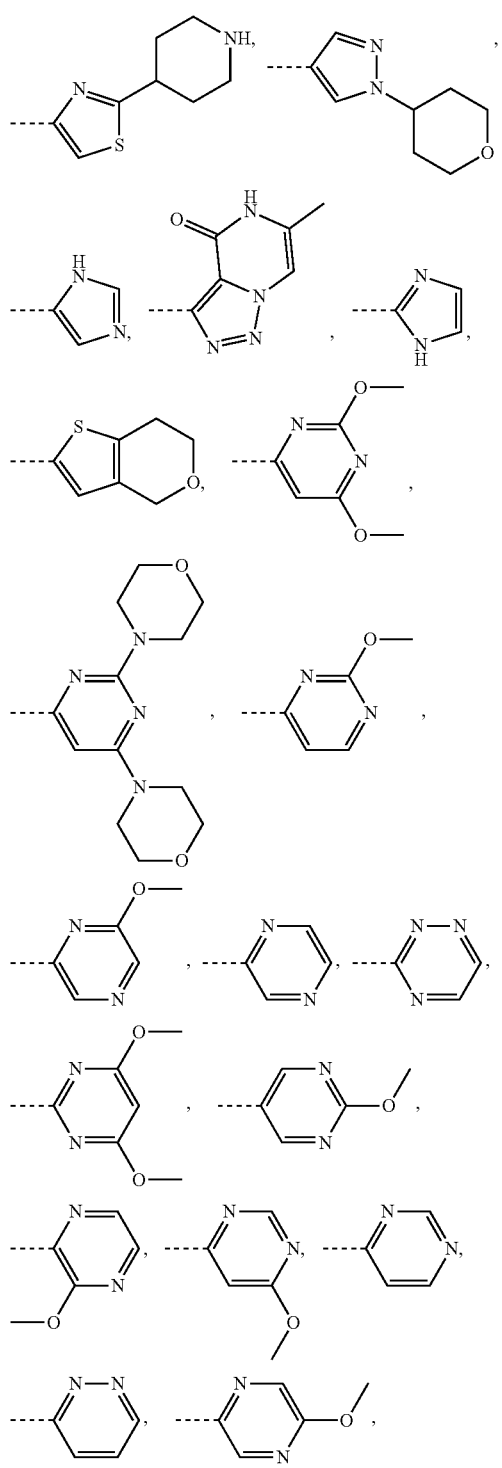
92
-continued
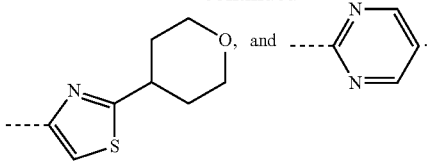
In some embodiments, $R^7$ is selected from
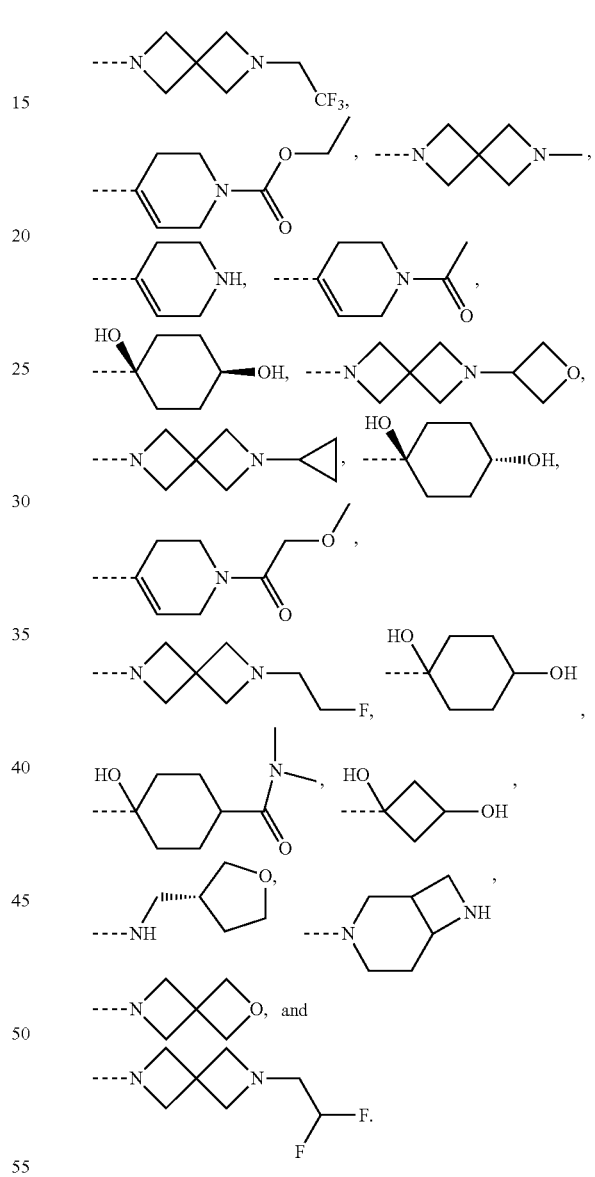
In some embodiments, $R^7$ is selected from
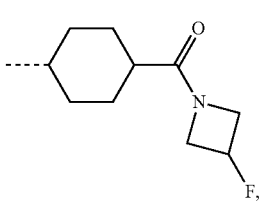

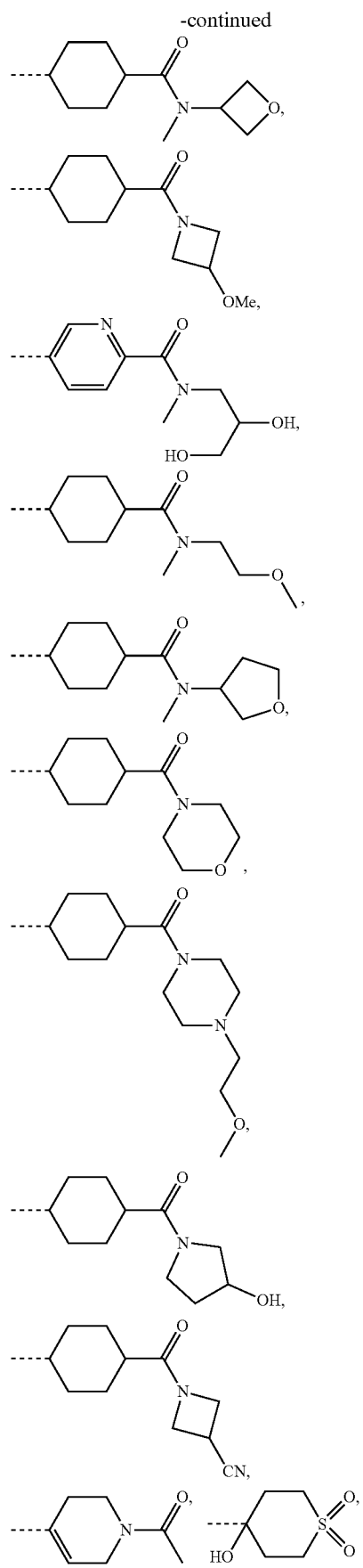
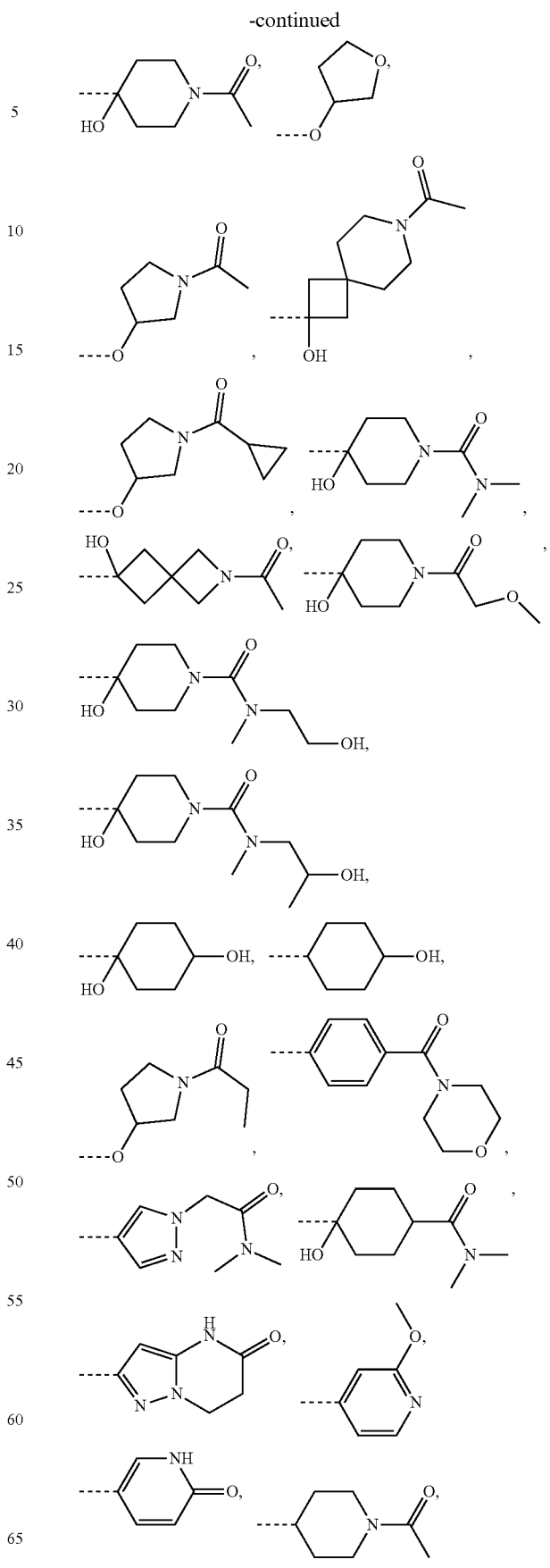

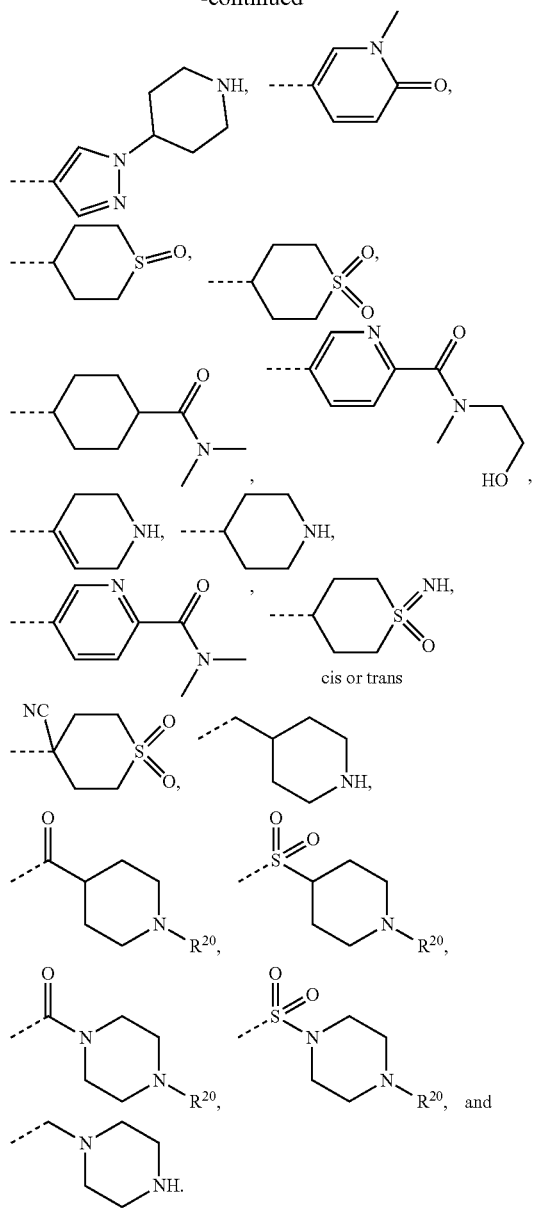
In some embodiments, R⁷ is selected from
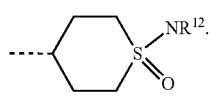
In some embodiments, R⁷ is selected from
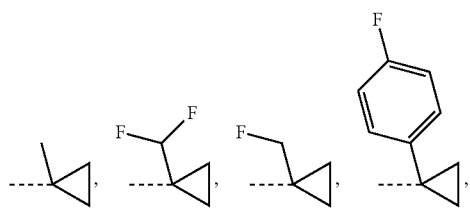
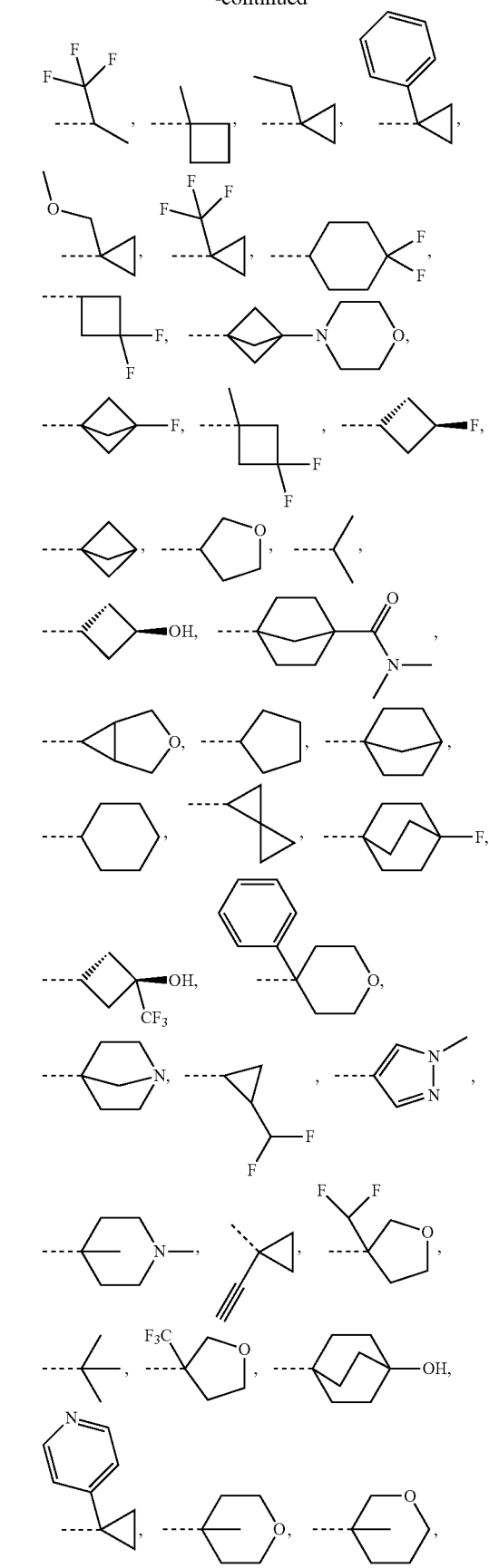

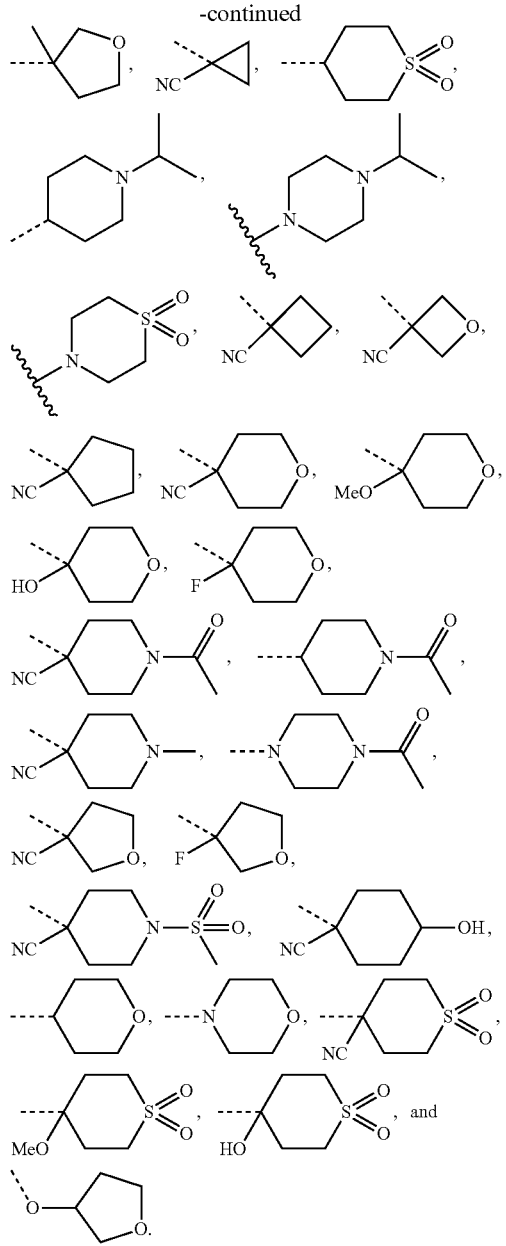
In some embodiments, R⁷ is selected from
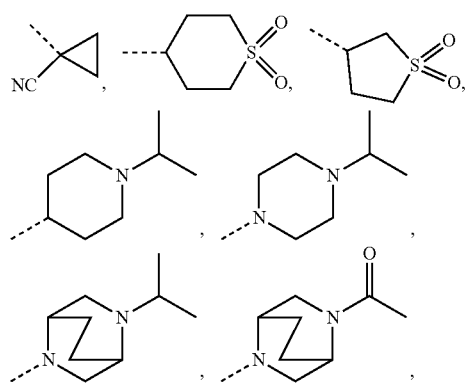
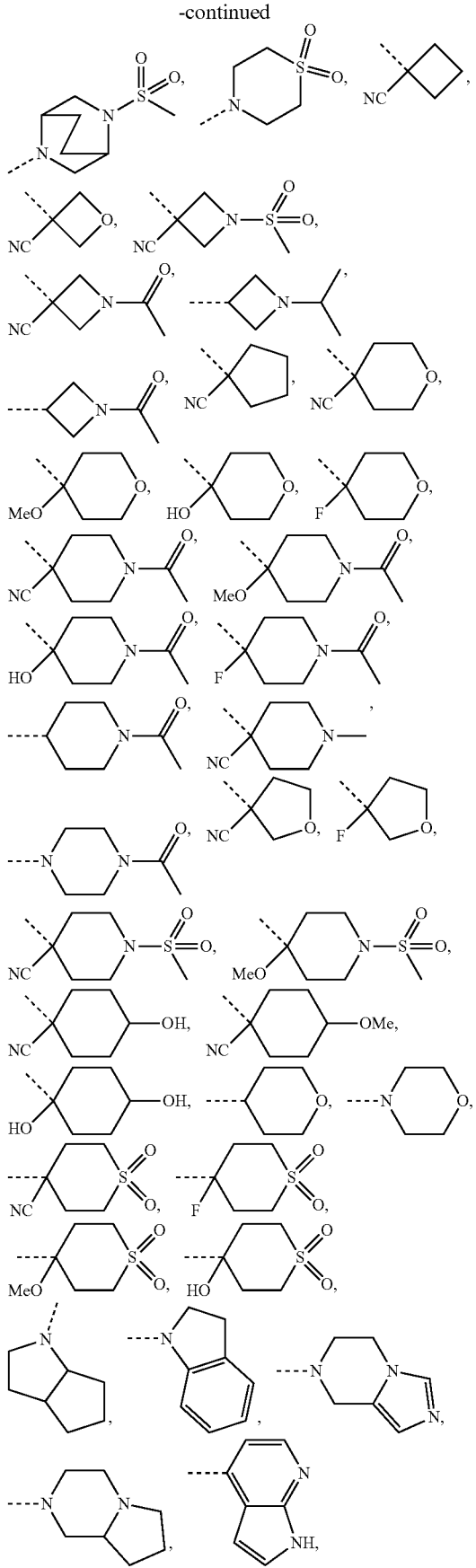

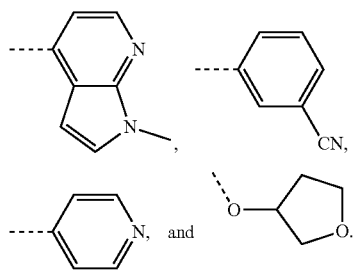
In some embodiments, R⁷ is selected from
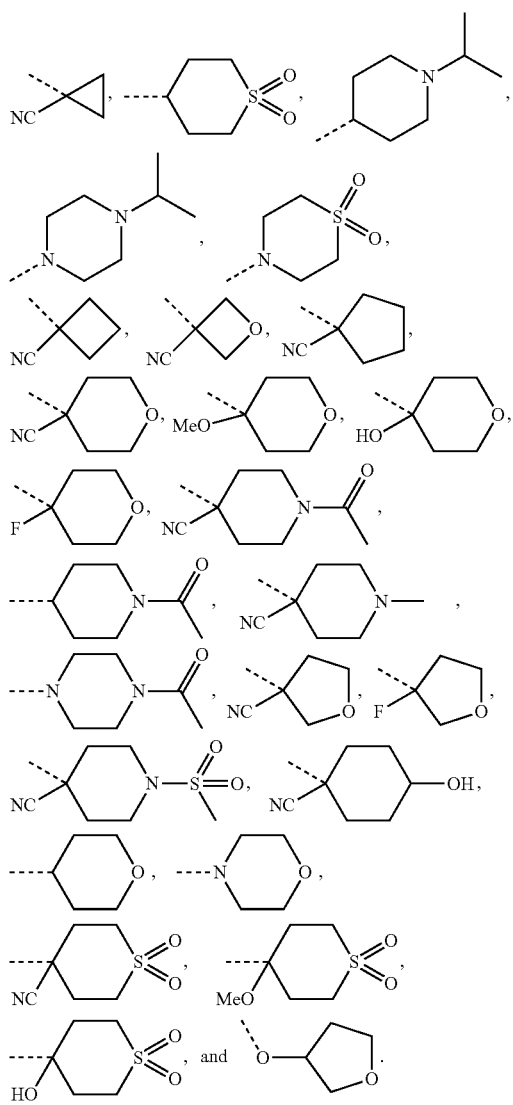
In some embodiments, R⁷ is selected from
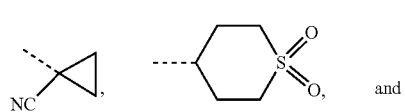
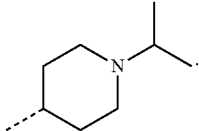
In some embodiments, R⁷ is
In some embodiments, R⁷ is
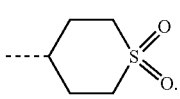
In some embodiments, R⁷ is
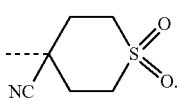
In some embodiments, R⁷ is
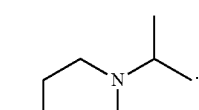
In some embodiments, R⁷ is
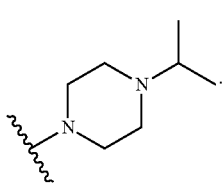 [SMILES: *N1CCN(C(C)C)CC1]
In some embodiments, R⁷ is
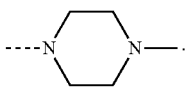
In some embodiments, R⁷ is
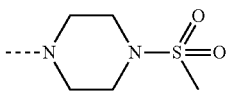

In some embodiments, R⁷ is

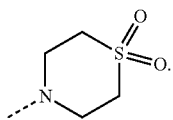

In some embodiments, R⁷ is

In some embodiments, R⁷ is

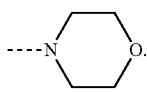

In some embodiments, for a compound of Formula (I), (I-A), (I-B), (I-B1), (I-B2), (I-C), (I-C1), (I-C2), (I-C3), (I-D), (I-D1), (I-D2), (I-E), or (I-E1), $R^8$ is selected from hydrogen, halogen, and $C_{1-6}$ alkyl optionally substituted with one, two, or three $R^{20}$. In some embodiments, $R^8$ is hydrogen.

In some embodiments, for a compound of Formula (I), (I-A), (I-B), (I-B1), (I-B2), (I-C), (I-C1), (I-C2), (I-C3), (I-D), (I-D1), (I-D2), (I-E), or (I-E1), (A)

is selected from $C_{3-10}$ carbocycle and 3- to 10-membered heterocycle, such as $C_{5-7}$ carbocycle and 5- to 7-membered heterocycle, each of which is optionally substituted with one or more $R^{11}$. In some embodiments, (A)

is selected from $C_{5-7}$ cycloalkyl, 5- to 7-membered heterocycloalkyl, 5- to 7-membered heteroaryl, and phenyl, each of which is optionally substituted with one or more $R^{11}$. In some embodiments, (A)

is selected from phenyl, pyridyl, and thiophenyl, each of which is optionally substituted with one or more $R^{11}$. In some embodiments, (A)

is selected from

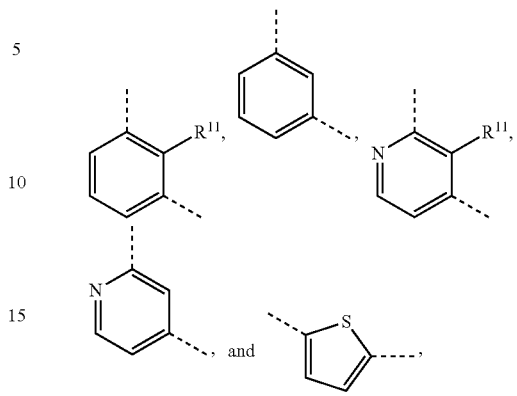

such as

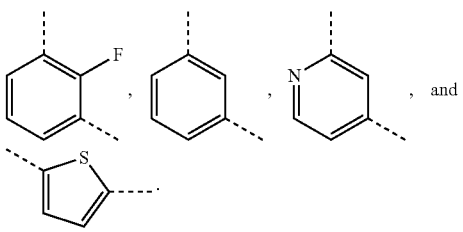

In some embodiments, $R^{11}$, when present, is independently selected at each occurrence from fluorine and —CH₃. In some embodiments, (A)

is selected from

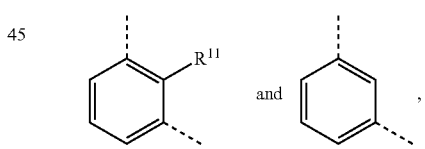

such as

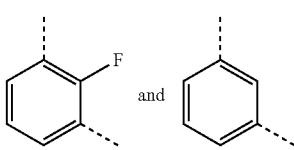

In some embodiments, (A)

is

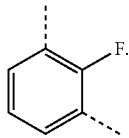

In some embodiments,

is

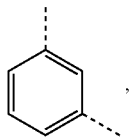

In some embodiments,

is

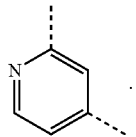

In some embodiments, for a compound of Formula (I), (I-A), (I-B), (I-B1), (I-B2), (I-C), (I-C1), (I-C2), (I-C3), (I-D), (I-D1), (I-D2), (I-E), or (I-E1), $L^1$ is selected from $C_{1-6}$ alkylene and $C_{1-6}$ haloalkylene, such as $C_{1-3}$ alkylene and $C_{1-3}$ haloalkylene. In some embodiments, $L^1$ is selected from a bond and $C_{1-3}$ haloalkylene. In some embodiments, $L^1$ is $C_{1-3}$ haloalkylene, such as $-CF_2-$, $-CF_2CH_2-$, or $-CF_2CH_2CH_2-$. In some embodiments, $L^1$ is $C_{1-2}$ haloalkylene, such as $-CF_2-$ or $-CF_2CH_2-$. In some embodiments, $L^1$ is $-CF_2-$. In some embodiments, $L^1$ is $-CF_2CH_2-$. In some embodiments, $L^1$ is $-CF_2CH_2CH_2-$. In some embodiments, $L^1$ is a bond. In some embodiments, $L^1$ is selected from a bond, $-O-$, $-NR^{12}-$, $-S-$, $C_{1-6}$ alkylene, $C_{1-6}$ haloalkylene, and 2- to 6-membered heteroalkylene, wherein $C_{1-6}$ alkylene, $C_{1-6}$ haloalkylene, and 2- to 6-membered heteroalkylene are optionally substituted with one or more $R^{11b}$. In some embodiments, $L^1$ is selected from $-O-$, $-NR^{12}-$, $-S-$, and 2- to 6-membered heteroalkylene, wherein 2- to 6-membered heteroalkylene is optionally substituted with one or more $R^{11b}$. In some embodiments, $L^1$ is $C_{1-6}$ alkylene optionally substituted with one or more $R^{11b}$, such as one, two, or three $R^{11b}$. In some embodiments, $L^1$ is selected from a bond, $-O-$, $-NR^{12}-$, $-S-$, $C_{1-3}$ alkylene, $C_{1-3}$ haloalkylene, and 2- to 3-membered heteroalkylene, wherein $C_{1-3}$ alkylene, $C_{1-3}$ haloalkylene, and 2- to 3-membered heteroalkylene are optionally substituted with one or more $R^{11b}$. In some embodiments, $L^1$ is selected from $-O-$, $-NR^{12}-$, $-S-$, and 2- to 3-membered heteroalkylene, wherein 2- to 3-membered heteroalkylene is optionally substituted with one or more $R^{11b}$. In some embodiments, $L^1$ is $C_{1-3}$ alkylene substituted with one or more $R^{11b}$, such as one, two, or three $R^{11b}$.

In some embodiments, for a compound of Formula (I), (I-A), (I-B), (I-B1), (I-B2), (I-C), (I-C1), (I-C2), (I-C3), (I-D), (I-D1), (I-D2), (I-E), or (I-E1),

is absent or selected from $C_{4-8}$ carbocycle and 4- to 8-membered heterocycle, each of which is optionally substituted with one or more $R^{11a}$. In some embodiments,

is absent or selected from phenyl and 4- to 8-membered heterocycle, each of which is optionally substituted with one or more $R^{11a}$. In some embodiments,

is selected from phenyl and 4- to 8-membered heterocycle, each of which is optionally substituted with one or more $R^{11a}$. In some embodiments,

is absent or selected from phenyl, azetidine, pyrrolidine, and piperidine, each of which is optionally substituted with one or more $R^{11a}$. In some embodiments,

is selected from phenyl, azetidine, pyrrolidine, and piperidine, each of which is optionally substituted with one or more $R^{11a}$. In some embodiments,

is selected from azetidine, pyrrolidine, and piperidine, each of which is optionally substituted with one or more $-CH_3$. In some embodiments,

is phenyl, optionally substituted with one or more $R^{11a}$. In some embodiments,

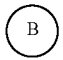

is

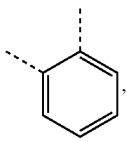, optionally substituted with one or more $R^{11a}$. In some embodiments,

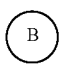

is

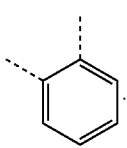.

In some embodiments,

is azetidine, optionally substituted with one or more $R^{11a}$. In some embodiments,

is

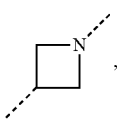, optionally substituted with one or more $R^{11a}$. In some embodiments,

is

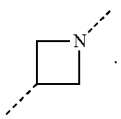.

In some embodiments,

is pyrrolidine, optionally substituted with one or more $R^{11a}$. In some embodiments,

is piperidine, optionally substituted with one or more $R^{11a}$. In some embodiments,

is

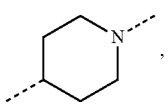, optionally substituted with one or more $R^{11a}$. In some embodiments,

is

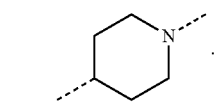.

In some embodiments,

is unsubstituted. In some embodiments,

is substituted with one or more $R^{11a}$, such as one, two or three $R^{11a}$. In some embodiments, $R^{11a}$ is independently selected at each occurrence from halogen, —CN, $C_{1-6}$ alkyl, $C_{3-6}$ carbocycle, 3- to 6-membered heterocycle, —$OR^{12}$, —$N(R^{12})(R^{13})$, —$N(R^{14})S(O)_2R^{15}$, —$C(O)N(R^{12})(R^{13})$, —$N(R^{14})C(O)R^{15}$, —$S(O)_2R^{15}$, and —$S(O)_2N(R^{12})(R^{13})$, wherein $C_{1-6}$ alkyl, $C_{3-6}$ carbocycle, and 3- to 6-membered heterocycle are optionally substituted with one, two, or three $R^{20}$. In some embodiments, $R^{11a}$ is independently selected at each occurrence from halogen, $C_{1-6}$ alkyl, and $C_{1-6}$ haloalkyl. In some embodiments, $R^{11a}$ is independently selected at each occurrence from $C_{1-6}$ alkyl. In some embodiments, $R^{11a}$ is —$CH_3$.

In some embodiments, for a compound of Formula (I), (I-A), (I-B), (I-B1), (I-B2), (I-C), (I-C1), (I-C2), (I-C3), (I-D), (I-D1), (I-D2), (I-E), or (I-E1), $L^2$ is selected from $C_{5-25}$ alkylene, $C_{5-25}$ alkenylene, $C_{5-25}$ alkynylene, 5- to 25-membered heteroalkenylene, and 5- to 25-membered heteroalkenylene, each of which is optionally substituted with one or more $R^{11b}$. In some embodiments, $L^2$ is selected from $C_{5-25}$ alkylene, $C_{5-25}$ alkenylene, 5- to 25-membered heteroalkenylene, and 5- to 25-membered heteroalkenylene, each of which is optionally substituted with one or more $R^{11b}$. In some embodiments, $L^2$, together with the atoms to which it is attached, forms a 16- to 36-membered macrocyclic ring, such as a 16- to 24-membered macrocyclic ring. In some embodiments, $L^2$ is selected from $C_{6-15}$ alkylene, $C_{6-15}$ alkenylene, $C_{6-15}$ alkynylene, 6- to 15-membered heteroalkylene, and 6- to 15-membered heteroalkenylene, each of which is optionally substituted with one or more $R^{11b}$. In some embodiments, $L^2$ is selected from $C_{5-10}$ alkylene, $C_{5-10}$ alkenylene, 5- to 10-membered heteroalkylene, and 5- to 10-membered heteroalkenylene, each of which is optionally substituted with one or more $R^{11b}$. In some embodiments, an alkenylene or heteroalkenylene of $L^2$ comprises one carbon-carbon double bond. In some embodiments, a heteroalkylene or heteroalkenylene of $L^2$ comprises at least one oxygen or nitrogen atom. In some embodiments, a heteroalkylene or heteroalkenylene of $L^2$ comprises at least one basic nitrogen. In some embodiments, $L^2$ is selected from $C_{5-9}$ alkylene, $C_{5-9}$ alkenylene, and 5- to 9-membered heteroalkylene, each of which is optionally substituted with one or more $R^{11b}$. In some embodiments, $L^2$ is selected from $C_{6-9}$ alkylene, $C_{6-9}$ alkenylene, and 6- to 9-membered heteroalkylene, each of which is optionally substituted with one or more $R^{11b}$. In some embodiments, $L^2$ is selected from $C_{5-8}$ alkylene, $C_{5-8}$ alkenylene, and 5- to 8-membered heteroalkylene, each of which is optionally substituted with one or more $R^{11b}$. In some embodiments, $L^2$ is selected from $C_{6-8}$ alkylene, $C_{6-8}$ alkenylene, and 6- to 8-membered heteroalkylene, each of which is optionally substituted with one or more $R^{11b}$. In some embodiments, $L^2$ is selected from $C_{6-8}$ alkylene and $C_{6-8}$ alkenylene, each of which is optionally substituted with one or more $R^{11b}$. In some embodiments, $L^2$ is selected from $C_6$ alkylene and $C_6$ alkenylene, each of which is optionally substituted with one or more $R^{11b}$. In some embodiments, $L^2$ is selected from $C_7$ alkylene and $C_7$ alkenylene, each of which is optionally substituted with one or more $R^{11b}$. In some embodiments, $L^2$ is selected from $C_8$ alkylene and $C_8$ alkenylene, each of which is optionally substituted with one or more $R^{11b}$. In some embodiments, $L^2$ is —$CH_2CHCH(CH_2)_4$—. In some embodiments, $L^2$ is 6- to 8-membered heteroalkylene, optionally substituted with one or more $R^{11b}$. In some embodiments, $L^2$ is 6-membered heteroalkylene, optionally substituted with one or more $R^{11b}$. In some embodiments, $L^2$ is 7-membered heteroalkylene, optionally substituted with one or more $R^{11b}$. In some embodiments, $L^2$ is 8-membered heteroalkylene, optionally substituted with one or more $R^{11b}$. In some embodiments, $L^2$ is 8-membered heteroalkylene, wherein the heteroalkylene comprises one oxygen atom. In some embodiments, $L^2$ is —$(CH_2)_{2-5}O(CH_2)_{0-5}$—, such as $L^2$ is —$(CH_2)_{2-5}O(CH_2)_{2-5}$—. In some embodiments, $L^2$ is —$(CH_2)_4O(CH_2)_3$—. In some embodiments, $R^{11b}$ is independently selected at each occurrence from halogen, oxo, $C_{1-6}$ alkyl, $C_{1-6}$ haloalkyl, $(C_{1-6}$ alkyl)-OH, and —OH. In some embodiments, $R^{11b}$ is independently selected at each occurrence from —F, =O, —$CH_3$, —$CH_2F$, —$CHF_2$, —$CF_3$, —$CH_2CH_2F$, —$CH_2CHF_2$, —$CH_2OH$, and —OH. In some embodiments, $R^{11b}$ is independently selected at each occurrence from —$CH_3$, —$CH_2OH$, —$CH_2F$, —$CHF_2$, and —$CF_3$, or two $R^{11b}$ join to form =O or $C_{3-6}$ cycloalkyl, such as cyclopropyl. In some embodiments, $R^{11b}$ is independently selected at each occurrence from —$CH_3$, —$CH_2OH$, —$CH_2F$, —$CHF_2$, and —$CF_3$, or two $R^{11b}$ join to form $C_{3-6}$ cycloalkyl, such as cyclopropyl. In some embodiments, $R^{11b}$ is independently selected at each occurrence from —$CH_3$, —F, —CN, and —OH. In some embodiments, $L^2$ comprises —C(O)N($R^{14}$)— or —N($R^{14}$)C(O)—. In some embodiments, $L^2$ comprises —O—. In some embodiments, $L^2$ is substituted with at least one —$CH_3$, —$CH_2OH$, —$CH_2F$, —$CHF_2$, or —$CF_3$, or two substituents join to form cyclopropyl. In some embodiments, $L^2$ is substituted with at least one —$CH_3$, —F, —CN, or —OH. In some embodiments, $L^2$ is unsubstituted.

In some embodiments, for a compound of Formula (I), (I-A), (I-B), (I-B1), (I-B2), (I-C), (I-C1), (I-C2), (I-C3), (I-D), (I-D1), (I-D2), (I-E), or (I-E1), $L^2$ is —$(C_{1-5}$ alkylene)-C(O)N($R^{14}$)—$(C_{1-5}$ alkylene)-, such as —$(C_{1-5}$ alkylene)-C(O)N($CH_3$)—$(C_{1-5}$ alkylene)- or —$(C_{1-5}$ alkylene)-C(O)NH—$(C_{1-5}$ alkylene)-, wherein $C_{1-5}$ alkylene is optionally substituted with one or more $R^{11b}$. In some embodiments, $L^2$ is —$(C_{1-2}$ alkylene)-C(O)N($R^{14}$)—$(C_{3-4}$ alkylene)-, such as —$(C_{1-2}$ alkylene)-C(O)N($CH_3$)—$(C_{3-4}$ alkylene)- or —$(C_{1-2}$ alkylene)-C(O)NH—$(C_{3-4}$ alkylene)-, wherein $C_{1-2}$ alkylene and $C_{3-4}$ alkylene are each independently optionally substituted with one or more $R^{11b}$. In some embodiments, $R^{11b}$ is independently selected at each occurrence from halogen, $C_{1-6}$ alkyl, $C_{1-6}$ haloalkyl, $(C_{1-6}$ alkyl)-OH, and —OH. In some embodiments, $R^{11b}$ is independently selected at each occurrence from —F, —$CH_3$, —$CH_2F$, —$CHF_2$, —$CF_3$, —$CH_2CH_2F$, —$CH_2CHF_2$, —$CH_2OH$, and —OH. In some embodiments, $R^{11b}$ is independently selected at each occurrence from —$CH_3$, —$CH_2OH$, —$CH_2F$, —$CHF_2$, and —$CF_3$, or two $R^{11b}$ join to form $C_{3-6}$ cycloalkyl, such as cyclopropyl. In some embodiments, $R^b$ is independently selected at each occurrence from —$CH_3$, —F, —CN, and —OH. In some embodiments, $L^2$ is substituted with at least one —$CH_3$, —F, —CN, or —OH.

In some embodiments, $L^2$ is selected from —$C(R^{11b})(R^{11b})$—$(C_{3-10}$ alkylene)-$C(R^{11b})(R^{11b})$—, —$CH(R^{11b})$—$(C_{3-10}$ alkylene)-$C(R^{11b})(R^{11b})$—, —$CH_2$—$(C_{3-10}$ alkylene)-$C(R^{11b})(R^{11b})$—, —$CH(R^{11b})$—$(C_{3-10}$ alkylene)-$CH(R^{11b})$—, —$CH_2$—$(C_{3-10}$ alkylene)-$CH(R^{11b})$—, —$C(R^{11b})(R^{11b})$—$(C_{3-10}$ alkenylene)-$C(R^{11b})(R^{11b})$—, —$CH(R^{11b})$—$(C_{3-10}$ alkenylene)-$C(R^{11b})(R^{11b})$—, —$CH_2$—$(C_{3-10}$ alkenylene)-$C(R^{11b})(R^{11b})$—, —CH $(R^{11b})$—$(C_{3-10}$ alkenylene)-CH$(R^{11b})$—, —CH$_2$—$(C_{3-10}$ alkenylene)-CH$(R^{11b})$—, —C$(R^{11b})(R^{11b})$-(3- to 10-membered heteroalkylene)-C$(R^{11b})(R^{11b})$—, —CH$(R^{11b})$-(3- to 10-membered heteroalkylene)-C$(R^{11b})(R^{11b})$—, —CH$_2$-(3- to 10-membered heteroalkylene)-C$(R^{11b})(R^{11b})$—, —CH$(R^{11b})$-(3- to 10-membered heteroalkylene)-CH$(R^{11b})$—, —CH$_2$-(3- to 10-membered heteroalkylene)-CH$(R^{11b})$—, —C$(R^{11b})(R^{11b})$-(3- to 10-membered heteroalkenylene)-C$(R^{11b})(R^{11b})$—, —CH$(R^{11b})$-(3- to 10-membered heteroalkenylene)-C$(R^{11b})(R^{11b})$—, —CH$_2$-(3- to 10-membered heteroalkenylene)-C$(R^{11b})(R^{11b})$—, —CH$(R^{11b})$-(3- to 10-membered heteroalkenylene)-CH$(R^{11b})$—, and —CH$_2$-(3- to 10-membered heteroalkenylene)-CH$(R^{11b})$—. In some embodiments, L$^2$ is selected from —C$(R^{11b})(R^{11b})$—$(C_{3-10}$ alkylene)-C$(R^{11b})(R^{11b})$—, —CH$(R^{11b})$—$(C_{3-10}$ alkylene)-C$(R^{11b})(R^{11b})$—, —CH$_2$—$(C_{3-10}$ alkylene)-C$(R^{11b})(R^{11b})$—, —CH$(R^{11b})$—$(C_{3-10}$ alkylene)-CH$(R^{11b})$—, and —CH$_2$—$(C_{3-10}$ alkylene)-CH$(R^{11b})$—. In some embodiments, L$^2$ is selected from —C$(R^{11b})(R^{11b})$—$(C_{3-10}$ alkenylene)-C$(R^{11b})(R^{11b})$—, —CH$(R^{11b})$—$(C_{3-10}$ alkenylene)-C$(R^{11b})(R^{11b})$—, —CH$_2$—$(C_{3-10}$ alkenylene)-C$(R^{11b})(R^{11b})$—, —CH$(R^{11b})$—$(C_{3-10}$ alkenylene)-CH$(R^{11b})$—, and —CH$_2$—$(C_{3-10}$ alkenylene)-CH$(R^{11b})$—. In some embodiments, L$^2$ is selected from —C$(R^{11b})(R^{11b})$-(3- to 10-membered heteroalkylene)-C$(R^{11b})(R^{11b})$—, —CH$(R^{11b})$-(3- to 10-membered heteroalkylene)-C$(R^{11b})(R^{11b})$—, —CH$_2$-(3- to 10-membered heteroalkylene)-C$(R^{11b})(R^{11b})$—, —CH$(R^{11b})$-(3- to 10-membered heteroalkylene)-CH$(R^{11b})$—, and —CH$_2$-(3- to 10-membered heteroalkylene)-CH$(R^{11b})$—. In some embodiments, L$^2$ is selected from —C$(R^{11b})(R^{11b})$-(3- to 10-membered heteroalkenylene)-C$(R^{11b})(R^{11b})$—, —CH$(R^{11b})$-(3- to 10-membered heteroalkenylene)-C$(R^{11b})(R^{11b})$—, —CH$_2$-(3- to 10-membered heteroalkenylene)-C$(R^{11b})(R^{11b})$—, —CH$(R^{11b})$-(3- to 10-membered heteroalkenylene)-CH$(R^{11b})$—, and —CH$_2$-(3- to 10-membered heteroalkenylene)-CH$(R^{11b})$—. Any $C_{3-10}$ alkylene, $C_{3-10}$ alkenylene, 3- to 10-membered heteroalkylene, or 3- to 10-membered heteroalkenylene in this paragraph may optionally be substituted with one or more $R^{11b}$. In some embodiments, $R^{11b}$ is independently selected at each occurrence from halogen, oxo, $C_{1-6}$ alkyl, $C_{1-6}$ haloalkyl, ($C_{1-6}$ alkyl)-OH, and —OH. In some embodiments, $R^{11b}$ is independently selected at each occurrence from —F, —CH$_3$, —CH$_2$F, —CHF$_2$, —CF$_3$, —CH$_2$CH$_2$F, —CH$_2$CHF$_2$, —CH$_2$OH, and —OH. In some embodiments, $R^{11b}$ is independently selected at each occurrence from —CH$_3$, —CH$_2$OH, —CH$_2$F, —CHF$_2$, and —CF$_3$, or two $R^{11b}$ join to form =O or $C_{3-6}$ cycloalkyl, such as cyclopropyl.

In some embodiments, for a compound of Formula (I), (I-A), (I-B), (I-B1), (I-B2), (I-C), (I-C1), (I-C2), (I-C3), (I-D), (I-D1), (I-D2), (I-E), or (I-E1), L$^2$ is -L$^3$-D-L$^4$-, wherein L$^3$ is selected from $C_{1-10}$ alkylene, $C_{1-10}$ alkenylene, $C_{1-10}$ alkynylene, 2- to 10-membered heteroalkylene, and 2- to 10-membered heteroalkenylene, each of which is optionally substituted with one or more $R^{11b}$; D is absent or selected from $C_{3-12}$ carbocycle and 3- to 12-membered heterocycle, each of which is optionally substituted with one or more $R^{11d}$; and L$^4$ is selected from $C_{1-10}$ alkylene, $C_{1-10}$ alkenylene, $C_{1-10}$ alkynylene, 2- to 10-membered heteroalkylene, and 2- to 10-membered heteroalkenylene, each of which is optionally substituted with one or more $R^{11d}$. As noted above, alkenylene and alkynylene groups comprise one or more carbon-carbon double or triple bonds, respectively (i.e., comprising two or more carbon atoms, for example as in $C_{2-10}$ alkenylene, $C_{2-10}$ alkynylene, $C_{2-8}$ alkenylene, $C_{2-8}$ alkynylene, $C_{5-25}$ alkenylene, $C_{5-25}$ alkynylene, $C_{6-15}$ alkenylene, $C_{6-15}$ alkynylene, $C_{5-10}$ alkenylene, and $C_{5-10}$ alkynylene). Similarly, a heteroalkenylene group comprises one or more carbon-carbon double bond (i.e., comprising two or more carbon atoms and one or more heteroatom, for example as in 3- to 10-membered heteroalkenylene, 3- to 8-membered heteroalkenylene, 5- to 25-membered heteroalkenylene, 6- to 15-membered heteroalkenylene, and 5- to 10-membered heteroalkenylene. In some embodiments, L$^2$ is -L$^3$-D-L$^4$-, wherein L$^3$ is selected from $C_{1-10}$ alkylene, $C_{1-10}$ alkenylene, $C_{1-10}$ alkynylene, 2- to 10-membered heteroalkylene, and 2- to 10-membered heteroalkenylene, each of which is optionally substituted with one or more $R^{11d}$; D is selected from $C_{3-12}$ carbocycle and 3- to 12-membered heterocycle, each of which is optionally substituted with one or more $R^{11d}$; and L$^4$ is absent. In some embodiments, L$^2$ is -L$^3$-D-L$^4$-, wherein L$^3$ is selected from $C_{1-8}$ alkylene, $C_{1-8}$ alkenylene, 2- to 8-membered heteroalkylene, and 2- to 8-membered heteroalkenylene, each of which is optionally substituted with one or more $R^{11b}$; D is absent or selected from $C_{3-10}$ carbocycle and 3- to 10-membered heterocycle, each of which is optionally substituted with one or more $R^{11d}$; and L$^4$ is selected from $C_{1-8}$ alkylene, $C_{1-8}$ alkenylene, 2- to 8-membered heteroalkylene, and 2- to 8-membered heteroalkenylene, each of which is optionally substituted with one or more $R^{11b}$. In some embodiments, L$^2$ is -L$^3$-D-L$^4$-, wherein L$^3$ is selected from $C_{1-8}$ alkylene, $C_{1-8}$ alkenylene, 2- to 8-membered heteroalkylene, and 2- to 8-membered heteroalkenylene, each of which is optionally substituted with one or more $R^{11b}$; D is selected from $C_{3-10}$ carbocycle and 3- to 10-membered heterocycle, each of which is optionally substituted with one or more $R^{11d}$; and L4 is selected from $C_{1-8}$ alkylene, $C_{1-8}$ alkenylene, 2- to 8-membered heteroalkylene, and 2- to 8-membered heteroalkenylene, each of which is optionally substituted with one or more $R^{11b}$. In some embodiments, $R^{11b}$ is independently selected at each occurrence from halogen, oxo, $C_{1-6}$ alkyl, $C_{1-6}$ haloalkyl, ($C_{1-6}$ alkyl)-OH, and —OH. In some embodiments, $R^{11b}$ is independently selected at each occurrence from —F, —CH$_3$, —CH$_2$F, —CHF$_2$, —CF$_3$, —CH$_2$CH$_2$F, —CH$_2$CHF$_2$, —CH$_2$OH, and —OH. In some embodiments, $R^{11b}$ is independently selected at each occurrence from —CH$_3$, —CH$_2$OH, —CH$_2$F, —CHF$_2$, and —CF$_3$, or two $R^{11b}$ join to form =O or $C_{3-6}$ cycloalkyl, such as cyclopropyl. In some embodiments, D is selected from phenyl and 5- to 8-membered heteroaryl, such as triazole and imidazole. In some embodiments, D is unsubstituted. In some embodiments, D is substituted with one or more $R^{11d}$, such as one, two, or three $R^{11d}$.

In some embodiments, for a compound of Formula (I), L$^2$ is covalently bound to one of W$^3$, W$^4$, W$^5$, W$^6$, or W$^7$; or L$^2$ is -L$^3$-D-L$^4$-, wherein L$^4$ is covalently bound to one of W$^3$, W$^4$, W$^5$, W$^6$, or W$^7$. For example, L$^2$ may be covalently bound to W$^3$—wherein R$^{3b}$ or R$^3$ is a bond to L$^2$—as depicted in Formula (I-A). In some embodiments, L$^2$ is covalently bound to W$^4$—wherein R$^{4b}$ or R$^4$ is a bond to L$^2$—as depicted in Formula (I-B). In some embodiments, L$^2$ is covalently bound to W$^5$—wherein R$^{5b}$ or R$^5$ is a bond to L$^2$—as depicted in Formula (I-C). In some embodiments, L$^2$ is covalently bound to W$^6$—wherein R$^{61'}$ or R$^6$ is a bond to L$^2$—as depicted in Formula (I-D). In some embodiments, L$^2$ is covalently bound to W$^7$—wherein R$^{7b}$ or R$^7$ is a bond to L$^2$—as depicted in Formula (I-E).

In some embodiments, for a compound of Formula (I), (I-A), (I-B), (I-B1), (I-B2), (I-C), (I-C1), (I-C2), (I-C3), (I-D), (I-D1), (I-D2), (I-E), or (I-E1):

$R^{20}$ is independently selected at each occurrence from halogen, oxo, =NH, —CN, $C_{1-6}$ alkyl, $C_{2-6}$ alkenyl, $C_{2-6}$ alkynyl, $C_{3-10}$ carbocycle, —CH$_2$—($C_{3-10}$ carbocycle), 3- to 10-membered heterocycle, —CH$_2$-(3- to 10-membered heterocycle), —OR$^{21}$, —SR$^{21}$, —N(R$^{22}$)(R$^{23}$), —C(O)OR$^{22}$, —C(O)N(R$^{22}$)(R$^{23}$), —C(O)C(O)N(R$^{22}$)(R$^{23}$), —OC(O)N(R$^{22}$)(R$^{23}$), —N(R$^{22}$)C(O)N(R$^{22}$)(R$^{23}$), —N(R$^{24}$)C(O)OR$^{25}$, —N(R$^{24}$)C(O)R$^{25}$, —N(R$^{24}$)S(O)$_2$R$^{25}$, —C(O)R$^{25}$, —S(O)$_2$R$^{25}$, —S(O)$_2$N(R$^{22}$)(R$^{23}$), —OCH$_2$C(O)OR$^{22}$, and —OC(O)R$^{25}$, wherein $C_{1-6}$ alkyl, $C_{2-6}$ alkenyl, $C_{2-6}$ alkynyl, $C_{3-10}$ carbocycle, —CH$_2$—($C_{3-10}$ carbocycle), 3- to 10-membered heterocycle, and —CH$_2$-(3- to 10-membered heterocycle) are optionally substituted with one, two, or three groups independently selected from halogen, oxo, =NH, —CN, $C_{1-6}$ alkyl, $C_{1-6}$ haloalkyl, $C_{1-6}$ alkoxy, $C_{1-6}$ haloalkoxy, —OR$^{21}$, —SR$^{21}$, and —N(R$^{22}$)(R$^{23}$);

$R^{21}$ is independently selected at each occurrence from H, $C_{1-6}$ alkyl, $C_{1-6}$ haloalkyl, $C_{2-6}$ alkenyl, $C_{2-6}$ alkynyl, $C_{3-10}$ carbocycle, and 3- to 10-membered heterocycle, wherein $C_{3-10}$ carbocycle and 3- to 10-membered heterocycle are optionally substituted with one, two, or three groups independently selected from halogen and $C_{1-6}$ alkyl;

$R^{22}$ is independently selected at each occurrence from H, $C_{1-6}$ alkyl, $C_{1-6}$ haloalkyl, $C_{2-6}$ alkenyl, $C_{2-6}$ alkynyl, $C_{3-10}$ carbocycle, and 3- to 10-membered heterocycle, wherein $C_{3-10}$ carbocycle and 3- to 10-membered heterocycle are optionally substituted with one, two, or three groups independently selected from halogen and $C_{1-6}$ alkyl;

$R^{23}$ is independently selected at each occurrence from H and $C_{1-6}$ alkyl;

$R^{24}$ is independently selected at each occurrence from H and $C_{1-6}$ alkyl; and $R^{25}$ is independently selected at each occurrence from $C_{1-6}$ alkyl, $C_{2-6}$ alkenyl, $C_{2-6}$ alkynyl, $C_{3-10}$ carbocycle, and 3- to 10-membered heterocycle, wherein $C_{1-6}$ alkyl, $C_{3-10}$ carbocycle, and 3- to 10-membered heterocycle are optionally substituted with one, two, or three groups independently selected from halogen, $C_{1-6}$ alkyl, $C_{1-6}$ haloalkyl, $C_{1-6}$ alkoxy, $C_{3-10}$ carbocycle, and 3- to 10-membered heterocycle.

In some embodiments, for a compound of Formula (I), (I-A), (I-B), (I-B1), (I-B2), (I-C), (I-C1), (I-C2), (I-C3), (I-D), (I-D1), (I-D2), (I-E), or (I-E1), $R^{20}$ is independently selected at each occurrence from halogen, oxo, =NR$^{22}$, —CN, $C_{1-6}$ alkyl, $C_{2-6}$ alkenyl, $C_{2-6}$ alkynyl, $C_{3-10}$ carbocycle, —CH$_2$—($C_{3-10}$ carbocycle), 3- to 10-membered heterocycle, —CH$_2$-(3- to 10-membered heterocycle), —OR$^{21}$, —SR$^{21}$, —N(R$^{22}$)(R$^{23}$), —C(O)OR$^{22}$, —C(O)N(R$^{22}$)(R$^{23}$), —C(O)C(O)N(R$^{22}$)(R$^{23}$), —OC(O)N(R$^{22}$)(R$^{23}$), —N(R$^{24}$)C(O)N(R$^{22}$)(R$^{23}$), —N(R$^{24}$)C(O)OR$^{25}$, —N(R$^{24}$)C(O)R$^{25}$, —N(R$^{24}$)S(O)$_2$R$^{25}$, —C(O)R$^{25}$, —S(O)$_2$R$^{25}$, —S(O)(NR$^{22}$)R$^{25}$, —S(O)$_2$N(R$^{22}$)(R$^{23}$), —OCH$_2$C(O)OR$^{22}$, and —OC(O)R$^{25}$, wherein $C_{1-6}$ alkyl, $C_{2-6}$ alkenyl, $C_{2-6}$ alkynyl, $C_{3-10}$ carbocycle, —CH$_2$—($C_{3-10}$ carbocycle), 3- to 10-membered heterocycle, and —CH$_2$-(3- to 10-membered heterocycle) are optionally substituted with one, two, or three groups independently selected from halogen, oxo, =NR$^{22}$, —CN, $C_{1-6}$ alkyl, $C_{1-6}$ haloalkyl, $C_{1-6}$ alkoxy, $C_{1-6}$ haloalkoxy, —OR$^{21}$, —SR$^{21}$, and —N(R$^{22}$)(R$^{23}$).

In some embodiments, for a compound of Formula (I), (I-A), (I-B), (I-B1), (I-B2), (I-C), (I-C1), (I-C2), (I-C3), (I-D), (I-D1), (I-D2), (I-E), or (I-E1), $R^{20}$ is independently selected at each occurrence from halogen, oxo, =NH, —CN, —NO$_2$, $C_{1-6}$ alkyl, $C_{2-6}$ alkenyl, $C_{2-6}$ alkynyl, $C_{3-10}$ carbocycle, —CH$_2$—($C_{3-10}$ carbocycle), 3- to 10-membered heterocycle, —CH$_2$-(3- to 10-membered heterocycle), —OH, —OCH$_3$, —OCH$_2$CH$_3$, —NH$_2$, —NHCH$_3$, and —NHCH$_2$CH$_3$, wherein $C_{1-6}$ alkyl, $C_{2-6}$ alkenyl, $C_{2-6}$ alkynyl, $C_{3-10}$ carbocycle, —CH$_2$—($C_{3-10}$ carbocycle), 3- to 10-membered heterocycle, and —CH$_2$-(3- to 10-membered heterocycle) are optionally substituted with one, two, or three groups independently selected from halogen, oxo, =NH, —CN, —NO$_2$, —CH$_3$, —CH$_2$CH$_3$, —CH(CH$_3$)$_2$, —C(CH$_3$)$_3$, —OH, —OCH$_3$, —OCH$_2$CH$_3$, —NH$_2$, —NHCH$_3$, and —NHCH$_2$CH$_3$.

In some embodiments, for a compound of Formula (I-B1), $R^{5l}$ is —CH$_3$; $R^7$ is selected from $C_{1-6}$ alkyl, $C_{3-10}$ carbocycle, 3- to 10-membered heterocycle, —N(R$^{12}$)(R$^{13}$), —C(O)R$^{15}$, —C(O)N(R$^{12}$)(R$^{13}$), —S(O)$_2$R$^{15}$, and —SO$_2$N(R$^{12}$)(R$^{13}$), wherein $C_{1-6}$ alkyl, $C_{3-10}$ carbocycle, and 3- to 10-membered heterocycle are optionally substituted with one, two, or three R$^{20}$; and R$^8$ is hydrogen. In some embodiments, for a compound of Formula (I-B2), R$^5$ is hydrogen; R$^6$ is selected from hydrogen and —OCH$_3$; R$^7$ is selected from $C_{1-6}$ alkyl, $C_{3-10}$ carbocycle, 3- to 10-membered heterocycle, —N(R$^{12}$)(R$^{13}$), —C(O)R$^{15}$, —C(O)N(R$^{12}$)(R$^{13}$), —S(O)$_2$R$^{15}$, and —SO$_2$N(R$^{12}$)(R$^{13}$), wherein $C_{1-6}$ alkyl, $C_{3-10}$ carbocycle, and 3- to 10-membered heterocycle are optionally substituted with one, two, or three R$^{20}$; and R$^8$ is hydrogen.

In some embodiments, for a compound of Formula (I-C1), R$^3$ is hydrogen or —CH$_3$; R$^7$ is selected from $C_{1-6}$ alkyl, $C_{3-10}$ carbocycle, 3- to 10-membered heterocycle, —N(R$^{12}$)(R$^{13}$), —C(O)R$^{15}$, —C(O)N(R$^{12}$)(R$^{13}$), —S(O)$_2$R$^{15}$, and —SO$_2$N(R$^{12}$)(R$^{13}$), wherein $C_{1-6}$ alkyl, $C_{3-10}$ carbocycle, and 3- to 10-membered heterocycle are optionally substituted with one, two, or three R$^{20}$; and R$^8$ is hydrogen. In some embodiments, for a compound of Formula (I-C2), R$^{3b}$ is —CH$_3$; R$^7$ is selected from $C_{1-6}$ alkyl, $C_{3-10}$ carbocycle, 3- to 10-membered heterocycle, —N(R$^{12}$)(R$^{13}$), —C(O)R$^{15}$, —C(O)N(R$^{12}$)(R$^{13}$), —S(O)$_2$R$^{15}$, and —SO$_2$N(R$^{12}$)(R$^{13}$), wherein $C_{1-6}$ alkyl, $C_{3-10}$ carbocycle, and 3- to 10-membered heterocycle are optionally substituted with one, two, or three R$^{20}$; and R$^8$ is hydrogen. In some embodiments, for a compound of Formula (I-C3), R$^3$ is hydrogen or —CH$_3$; R$^6$ is selected from hydrogen and —OCH$_3$; R$^7$ is selected from $C_{1-6}$ alkyl, $C_{3-10}$ carbocycle, 3- to 10-membered heterocycle, —N(R$^{12}$)(R$^{13}$), —C(O)R$^{15}$, —C(O)N(R$^{12}$)(R$^{13}$), —S(O)$_2$R$^{15}$, and —SO$_2$N(R$^{12}$)(R$^{13}$), wherein $C_{1-6}$ alkyl, $C_{3-10}$ carbocycle, and 3- to 10-membered heterocycle are optionally substituted with one, two, or three R$^{20}$; and R$^8$ is hydrogen.

In some embodiments, for a compound of Formula (I), (I-A), (I-B), (I-B1), (I-B2), (I-C), (I-C1), (I-C2), (I-C3), (I-D), (I-D1), (I-D2), (I-E), or (I-E1): R$^1$ is —CH$_3$;

Ⓐ is selected from phenyl and 5- to 7-membered heteroaryl, each of which is optionally substituted with one or more R$^{11}$; L$^1$ is selected from a bond and $C_{1-3}$ haloalkylene;

Ⓑ is selected from absent, phenyl, and 4- to 8-membered heterocycle, wherein the phenyl and 4- to 8-membered heterocycle are optionally substituted with one or more $R^{11a}$; and $L^2$ is selected from $C_{5-10}$ alkylene, $C_{5-10}$ alkenylene, 5- to 10-membered heteroalkylene, and 5- to 10-membered heteroalkenylene, each of which is optionally substituted with one or more $R^{11b}$. In some embodiments, $R^{11}$, when present, is fluorine; $R^{11a}$, when present, is —$CH_3$; and $R^{11b}$, when present, is selected from halogen, oxo, $C_{1-6}$ alkyl, $C_{1-6}$ haloalkyl, ($C_{1-6}$ alkyl)-OH, and —OH.

In some embodiments, for a compound of Formula (I), (I-A), (I-B), (I-B1), (I-B2), (I-C), (I-C1), (I-C2), (I-C3), (I-D), (I-D1), (I-D2), (I-E), or (I-E1): $R^1$ is —$CH_3$;

Ⓐ is selected from

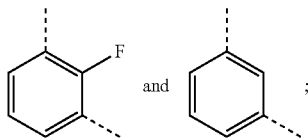

$L^1$ is $C_{1-2}$ haloalkylene;

Ⓑ is

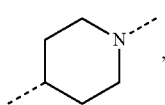

optionally substituted with one or more $R^{11a}$; and $L^2$ is selected from $C_{6-8}$ alkylene, $C_{6-8}$ alkenylene, and 6- to 8-membered heteroalkylene, each of which is optionally substituted with one or more $R^{11b}$. In some embodiments, $R^1$ is —$CH_3$;

Ⓐ is

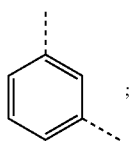

$L^1$ is $C_{1-2}$ haloalkylene;

Ⓑ is

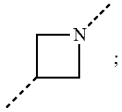

and $L^2$ is 6- to 8-membered heteroalkylene, optionally substituted with one or more $R^{11b}$. In some embodiments, $R^1$ is —$CH_3$;

Ⓐ is selected from

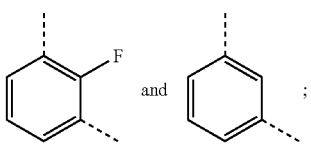

$L^1$ is $C_{1-2}$ haloalkylene;

Ⓑ is

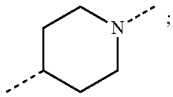

optionally substituted with one or more $R^{11a}$; and $L^2$ is selected from $C_{6-8}$ alkylene and $C_{6-8}$ alkenylene, each of which is optionally substituted with one or more $R^{11b}$. In some embodiments, $R^1$ is —$CH_3$;

Ⓐ is

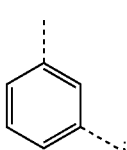

$L^1$ is $C_{1-2}$ haloalkylene;

is

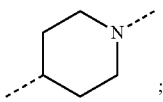

and $L^2$ is $C_{6-8}$ alkenylene, optionally substituted with one or more $R^{11b}$. In some embodiments, $R^1$ is —$CH_3$;

is selected from

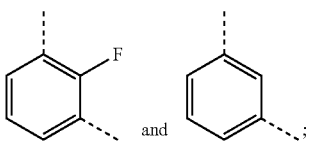

$L^1$ is $C_{1-2}$ haloalkylene;

is

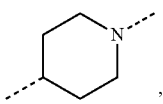

optionally substituted with one or more $R^{11a}$; and $L^2$ is —($C_{1-2}$ alkylene)-C(O)N($CH_3$)—($C_{3-4}$ alkylene)- or —($C_{1-2}$ alkylene)-C(O)NH—($C_{3-4}$ alkylene)-, wherein $C_{1-2}$ alkylene and $C_{3-4}$ alkylene are each independently optionally substituted with one or more $R^{11b}$. In some embodiments, $R^{11a}$, when present, is —$CH_3$; and $R^{11b}$, when present, is selected from halogen, —CN, oxo, $C_{1-3}$ alkyl, $C_{1-3}$ haloalkyl, ($C_{1-3}$ alkyl)-OH, and —OH.

In some embodiments, for a compound of Formula) (I-A), (I-B), (I-B1), (I-B2), (I-C), (I-C1), (I-C2), (I-C3), (I-D), (I-D1) (I-D2), (I-E), or (I-E1): $R^1$ is —$CH_3$;

is selected from

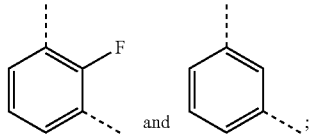

$L^1$ is $C_{1-2}$ haloalkylene;

is

and $L^2$ is selected from $C_{6-8}$ alkylene, $C_{6-8}$ alkenylene, and 6- to 8-membered heteroalkylene, each of which is optionally substituted with one or more $R^{11b}$. In some embodiments, $R^1$ is —$CH_3$;

is selected from

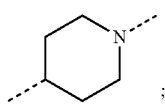

$L^1$ is $C_{1-2}$ haloalkylene;

is (piperidine structure)

and $L^2$ is selected from $C_{6-8}$ alkylene and $C_{6-8}$ alkenylene, each of which is optionally substituted with one or more $R^{11b}$. In some embodiments, $R^1$ is —$CH_3$;

is selected from

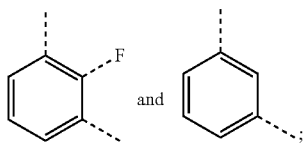

$L^1$ is $C_{1-2}$ haloalkylene;

B is

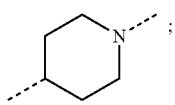

and $L^2$ is —($C_{1-2}$ alkylene)-C(O)N(CH$_3$)—($C_{3-4}$ alkylene)- or —($C_{1-2}$ alkylene)-C(O)NH—($C_{3-4}$ alkylene)-, wherein $C_{1-2}$ alkylene and $C_{3-4}$ alkylene are each independently optionally substituted with one or more $R^{11b}$. In some embodiments, $R^{11b}$, when present, is selected from halogen, —CN, oxo, $C_{1-3}$ alkyl, $C_{1-3}$ haloalkyl, ($C_{1-3}$ alkyl)-OH, and —OH.

In some embodiments, a compound of Formula (I) is a compound of the formula:

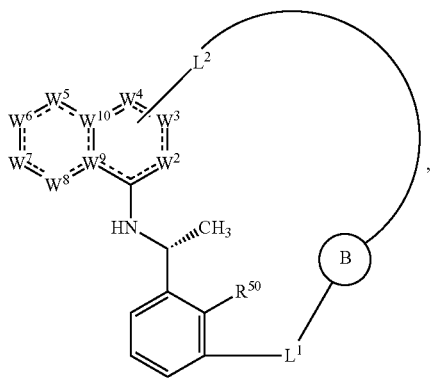

such as

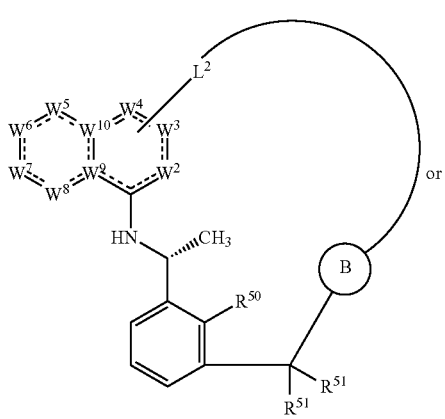

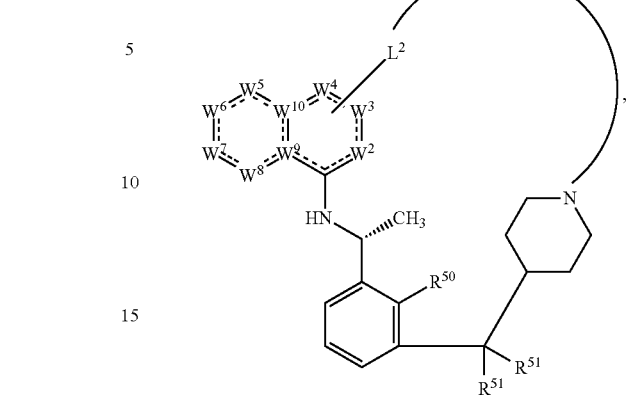

wherein $R^{50}$ is hydrogen or $R^{11}$ and $R^{51}$ is hydrogen or halogen.

In some embodiments, a compound of Formula (I) is a compound of the formula:

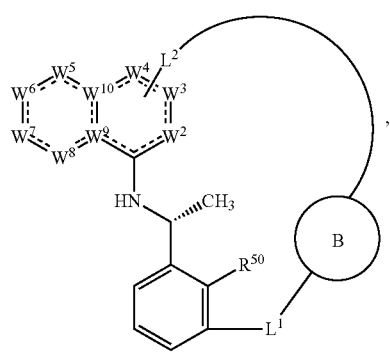

such as

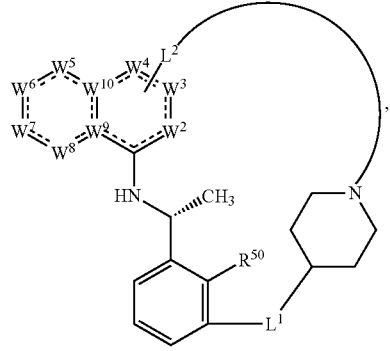

-continued
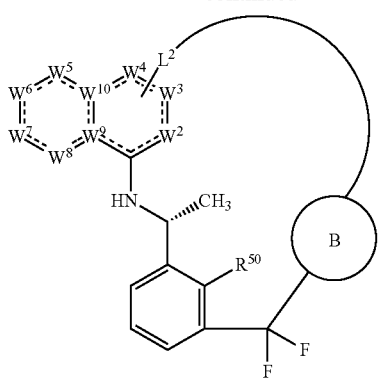
or
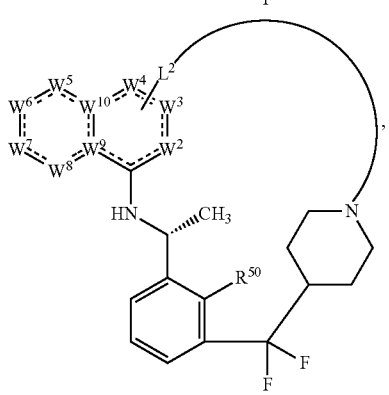
wherein R[50] is hydrogen or fluoro. In some embodiments, a compound of Formula (I-A) is a compound of the formula:
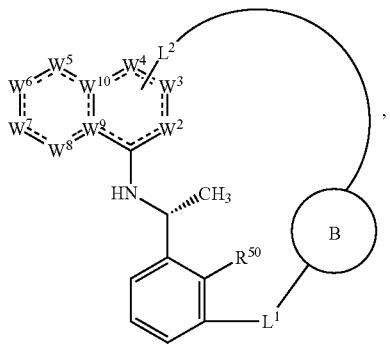
such as
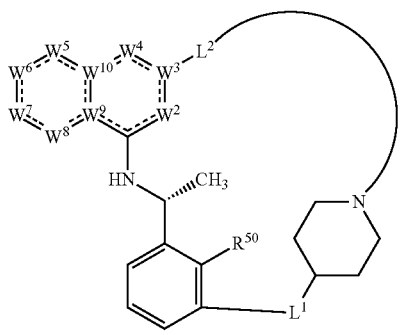
-continued
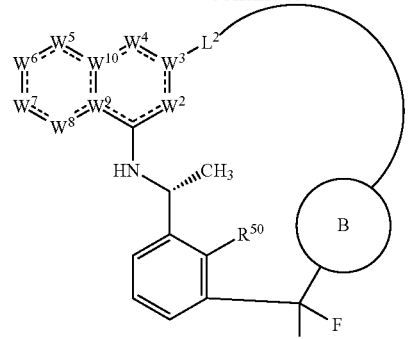
or
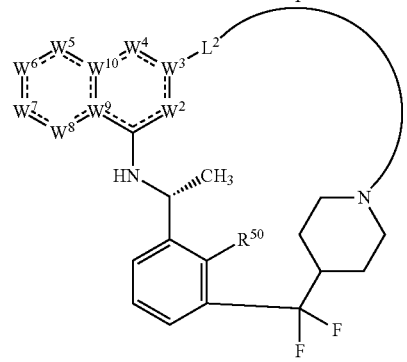
wherein R[50] is hydrogen or fluoro. In some embodiments, a compound of Formula (I-B) is a compound of the formula:
,
such as
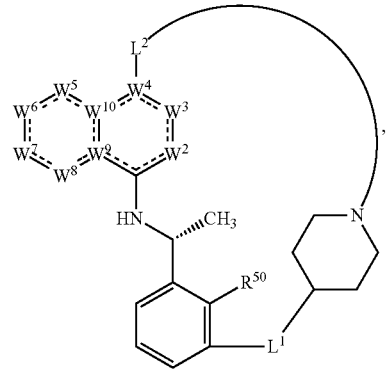
, -continued
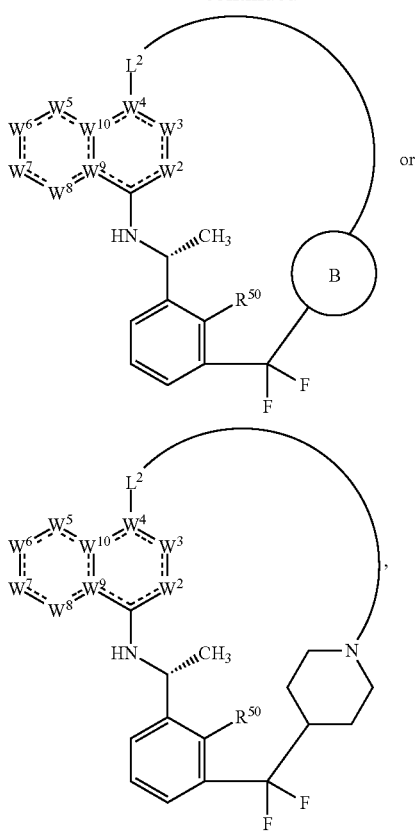
or
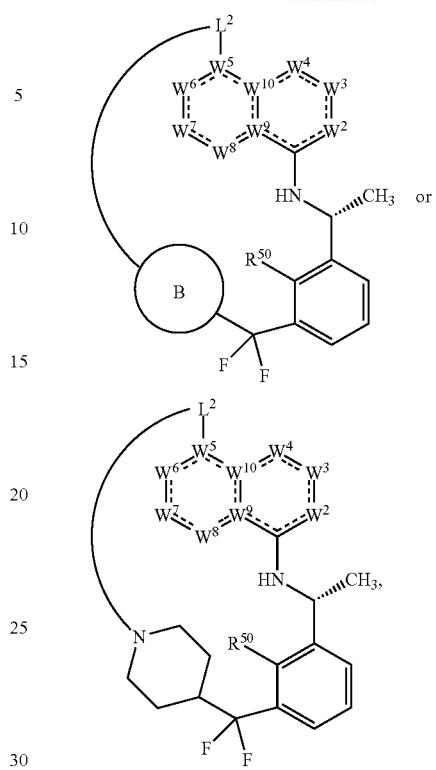
or
wherein R⁵⁰ is hydrogen or fluoro. In some embodiments, a compound of Formula (I-C) is a compound of the formula:
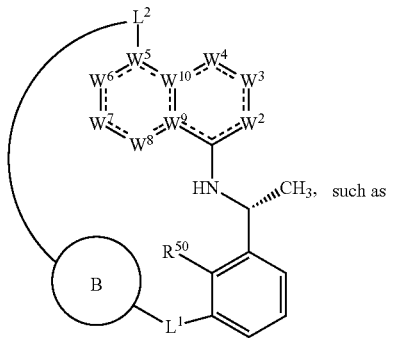 such as
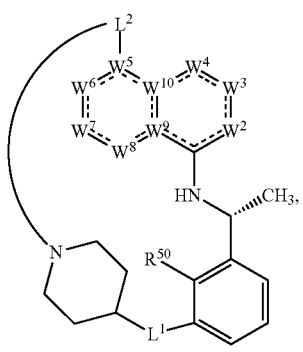
wherein R⁵⁰ is hydrogen or fluoro. In some embodiments, a compound of Formula (I-C) is a compound of the formula,
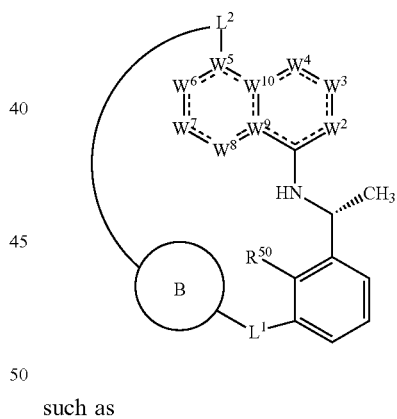
such as
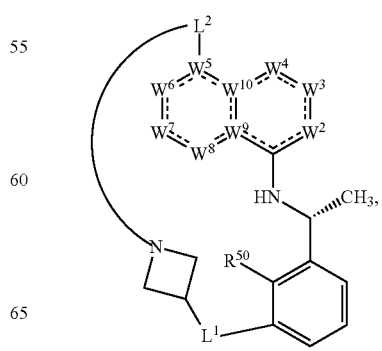

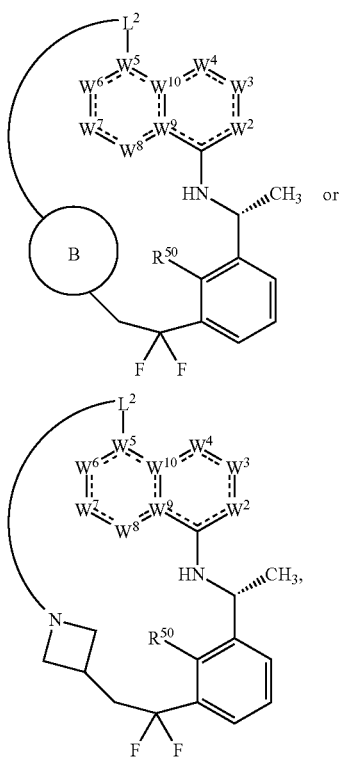
wherein R$^{50}$ is hydrogen or fluoro. In some embodiments, a compound of Formula (I-D) is a compound of the formula:
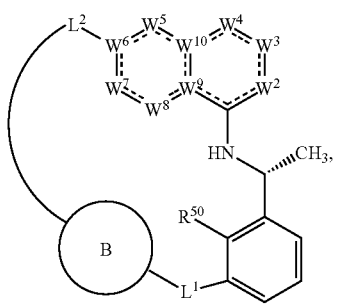
such as
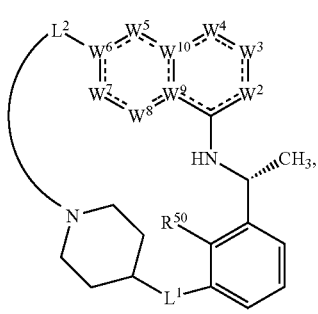
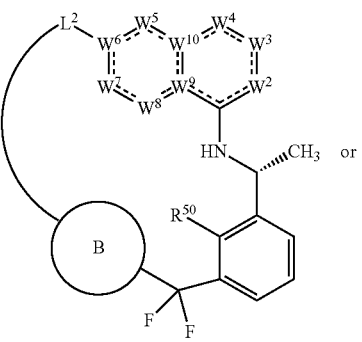
wherein R$^{10}$ is hydrogen or fluoro. In some embodiments, a compound of Formula (I-E) is a compound of the formula:
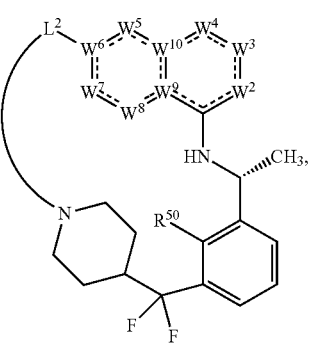
such as
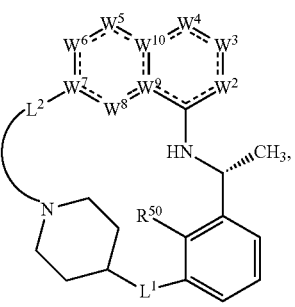

-continued

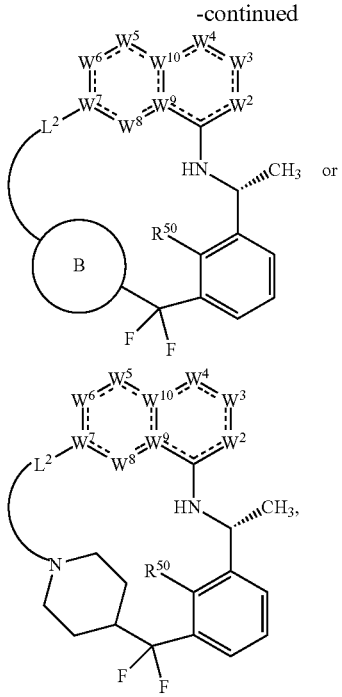

wherein $R^{50}$ is hydrogen or fluoro. In some embodiments, $L^1$ is $C_{1-3}$ haloalkylene, such as $C_{1-2}$ haloalkylene or $C_{1-2}$ fluoroalkylene. In some embodiments, $L^2$ is selected from $C_{6-8}$ alkylene, $C_{6-8}$ alkenylene, and 6- to 8-membered heteroalkylene, each of which is optionally substituted with one or more $R^{11b}$. In some embodiments, $L^2$ is selected from $C_{6-8}$ alkylene and $C_{6-8}$ alkenylene, each of which is optionally substituted with one or more $R^{11b}$. In some embodiments, $L^2$ is —($C_{1-2}$ alkylene)-C(O)N(CH$_3$)—($C_{3-4}$ alkylene)- or —($C_{1-2}$ alkylene)-C(O)NH—($C_{3-4}$ alkylene)-, wherein $C_{1-2}$ alkylene and $C_{3-4}$ alkylene are each independently optionally substituted with one or more $R^{11b}$. In some embodiments, $R^{11b}$, when present, is selected from halogen, —CN, $C_{1-3}$ alkyl, $C_{1-3}$ haloalkyl, ($C_{1-3}$ alkyl)-OH, and —OH. In some embodiments, $R^{10}$ is hydrogen. In some embodiments, $R^{10}$ is fluoro.

In certain aspects, the present disclosure provides a compound of Formula (I-C1):

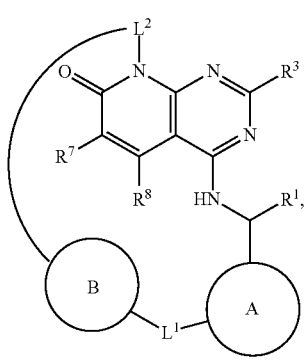

(I-C1)

or a pharmaceutically acceptable salt or solvate thereof, wherein:

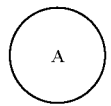

is selected from

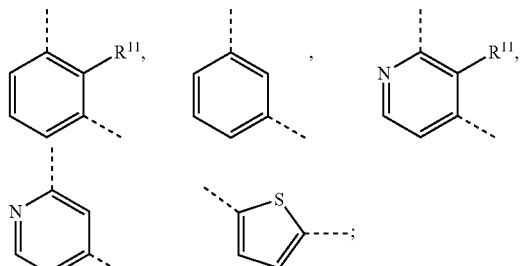

is selected from azetidine, pyrrolidine, and piperidine, each of which is optionally substituted with one or more —CH$_3$;
$L^1$ is $C_{1-3}$ haloalkylene;
$L^2$ is selected from $C_{5-10}$ alkylene, $C_{5-10}$ alkenylene, 5- to 10-membered heteroalkylene, and 5- to 10-membered heteroalkenylene, each of which is optionally substituted with one or more $R^{11b}$;
$R^1$ is —CH$_3$;
$R^3$ is hydrogen or —CH$_3$;
$R^7$ is selected from

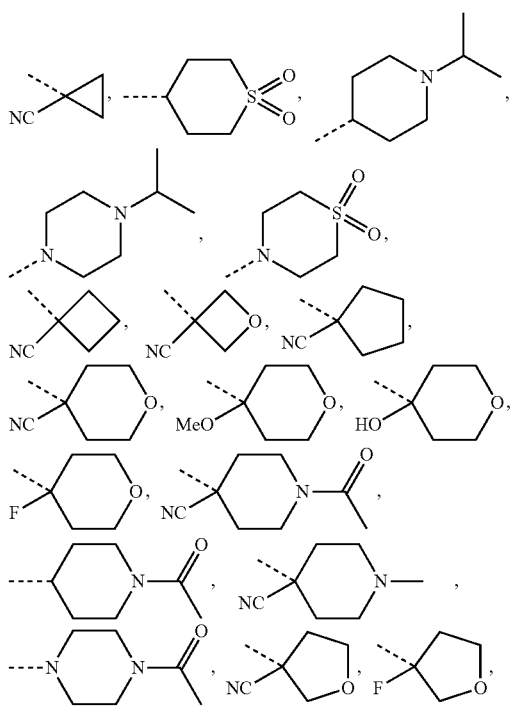

-continued

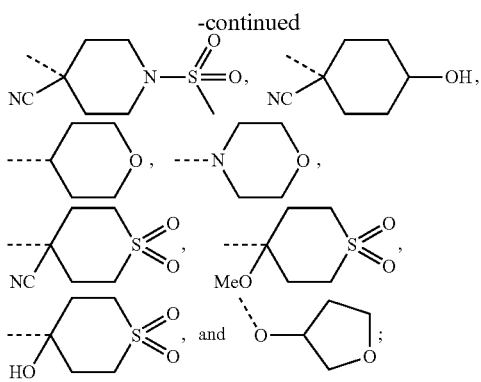

R[8] is hydrogen;
R[11] is selected from fluorine and —CH₃; and
R[11b] is selected from halogen, oxo, $C_{1-6}$ alkyl, $C_{1-6}$ haloalkyl, ($C_{1-6}$ alkyl)-OH, and —OH.

In certain aspects, the present disclosure provides a compound of Formula (I-C1):

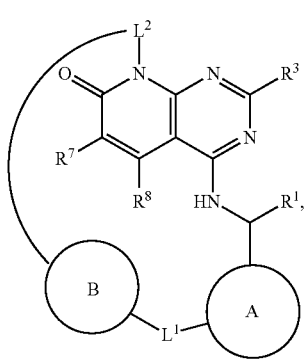

(I-C1)

or a pharmaceutically acceptable salt or solvate thereof, wherein:

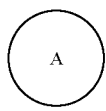

is selected from

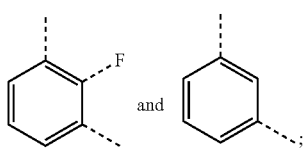

is selected from azetidine, pyrrolidine, and piperidine;
$L^1$ is selected from —CF₂—, —CF₂CH₂—, and —CF₂CH₂CH₂—;
$L^2$ is selected from $C_{5-10}$ alkylene, $C_{5-10}$ alkenylene, 5- to 10-membered heteroalkylene, and 5- to 10-membered heteroalkenylene;
$R^1$ is —CH₃;
$R^3$ is hydrogen or —CH₃;
$R^7$ is selected from

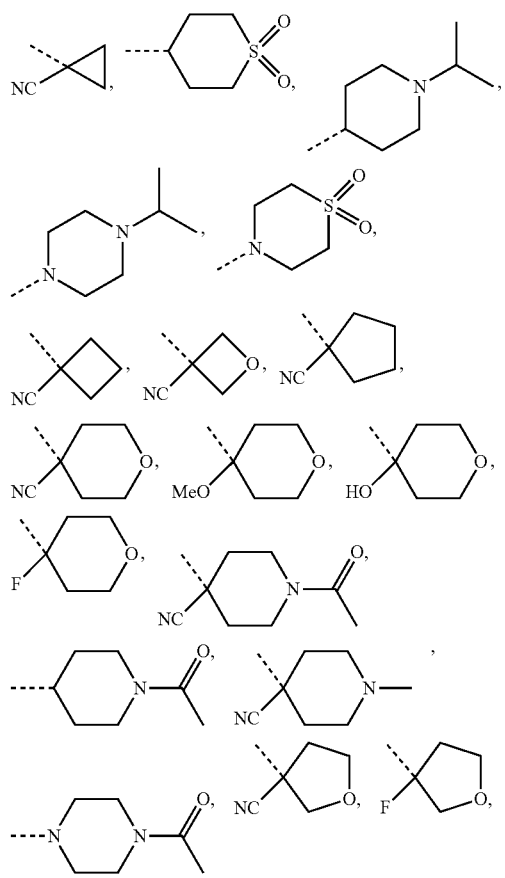

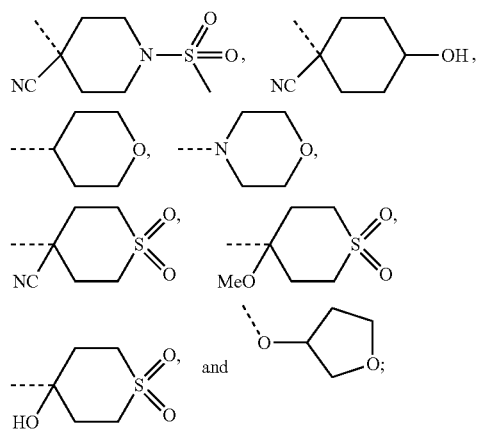

and
$R^8$ is hydrogen.

In certain aspects, the present disclosure provides a compound of Formula (I-C1):

(I-C1)

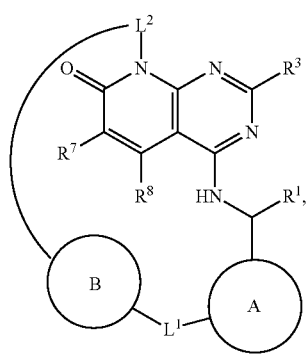

or a pharmaceutically acceptable salt or solvate thereof, wherein:

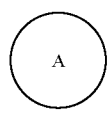

is selected from

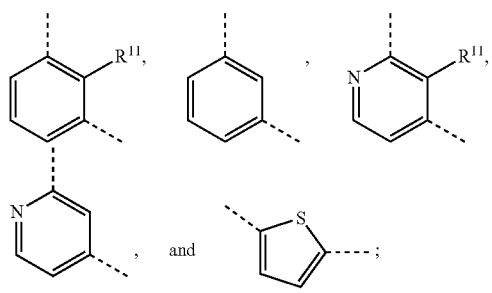

is selected from azetidine, pyrrolidine, and piperidine, each of which is optionally substituted with one or more —CH$_3$;
L$^1$ is C$_{1-3}$ haloalkylene;
L$^2$ is C$_{5-10}$ alkenylene optionally substituted with one or more R$^{11b}$;
R$^1$ is —CH$_3$;
R$^3$ is —CH$_3$;
R$^7$ is selected from

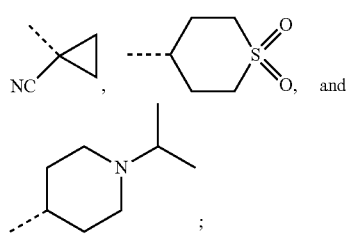

R$^8$ is hydrogen;
R$^{11}$ is selected from fluorine and —CH$_3$; and
R$^{11b}$ is selected from halogen, oxo, C$_{1-6}$ alkyl, C$_{1-6}$ haloalkyl, (C$_{1-6}$ alkyl)-OH, and —OH.

In certain aspects, the present disclosure provides a compound of Formula (I-C1):

(I-C1)

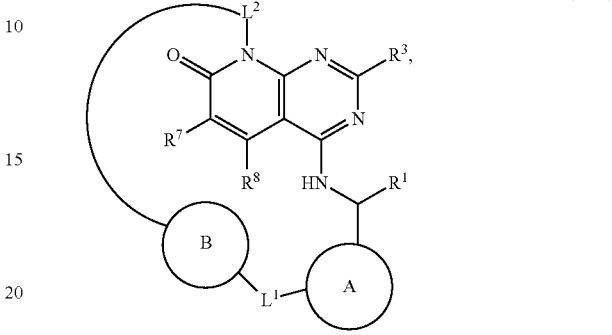

or a pharmaceutically acceptable salt or solvate thereof, wherein:

is selected from

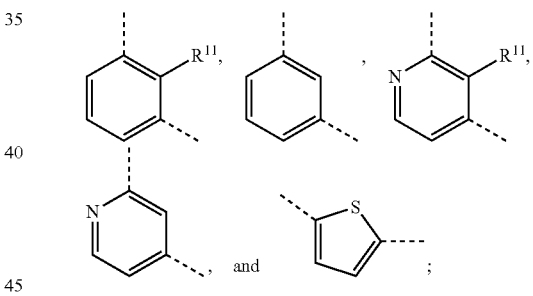

is selected from azetidine, pyrrolidine, and piperidine, each of which is optionally substituted with one or more —CH$_3$;
L$^1$ is C$_{1-3}$ haloalkylene;
L$^2$ is selected from 5- to 10-membered heteroalkylene optionally substituted with one or more R$^{11b}$;
R$^1$ is —CH$_3$;
R$^3$ is hydrogen or —CH$_3$;
R$^7$ is selected from

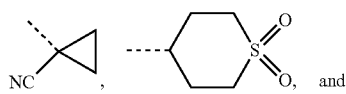

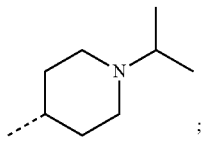

R[8] is hydrogen;
R[11] is selected from fluorine and —CH$_3$; and
R[11b] is selected from halogen, oxo, C$_{1-6}$ alkyl, C$_{1-6}$ haloalkyl, (C$_{1-6}$ alkyl)-OH, and —OH.

In certain aspects, the present disclosure provides a compound of Formula (I):

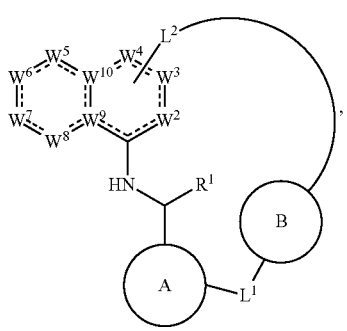

(I)

or a pharmaceutically acceptable salt or solvate thereof, wherein:

is selected from phenyl and 5- to 7-membered heteroaryl, each of which is optionally substituted with one or more R[11];

is absent or selected from phenyl and 4- to 8-membered heterocycle, each of which is optionally substituted with one or more R[11a];

L$^1$ is selected from a bond and C$_{1-3}$ haloalkylene;
L$^2$ is selected from C$_{5-10}$ alkylene, C$_{5-10}$ alkenylene, 5- to 10-membered heteroalkylene, and 5- to 10-membered heteroalkenylene, each of which is optionally substituted with one or more R[11b], wherein L$^2$ is covalently bound to one of W$^3$, W$^4$, W$^5$, W$^6$, or W$^7$; or L$^2$ is -L$^3$-D-L$^4$-, wherein L$^4$ is covalently bound to one of W$^3$, W$^4$, W$^5$, W$^6$, or W$^7$;
L$^3$ is selected from C$_1$s alkylene, C$_1$s alkenylene, 2- to 8-membered heteroalkylene, and 2- to 8-membered heteroalkenylene, each of which is optionally substituted with one or more R[11b];
D is selected from C$_{3-10}$ carbocycle and 3- to 10-membered heterocycle, each of which is optionally substituted with one or more R[11d];
L$^4$ is selected from C$_{1-8}$ alkylene, C$_{1-8}$ alkenylene, 2- to 8-membered heteroalkylene, and 2- to 8-membered heteroalkenylene, each of which is optionally substituted with one or more R[11b]

W$^2$ is N;
W$^3$ is selected from N(R[3b]), N, C(R$^3$), and C(O);
W$^4$ is selected from N(R[4b]), N, C(R$^4$), and C(O);
W$^5$ is selected from N(R[5b]), N, and C(R$^5$);
W$^6$ is selected from C(R$^6$) and C(O);
W$^7$ is C(R$^7$);
W$^8$ is C(R$^8$);
W$^9$ and W$^{10}$ are each C;
R$^1$ is —CH$_3$;
R$^2$, R[2a], R[3a], R[4a], R[5a], R[6a], R[7a], R$^8$, and R[8a] are each independently selected from hydrogen and —CH$_3$;
R$^3$, R$^4$, R$^5$, and R$^6$ are each independently selected from a bond to L$^2$, hydrogen, halogen, —CN, C$_{1-3}$ alkyl, C$_{1-3}$ haloalkyl, —OH, —OCH$_3$, —NH$_2$, —NHCH$_3$, —N(CH$_3$)$_2$;
R$^7$ is selected from a bond to L$^2$, C$_{1-6}$ alkyl, C$_{3-10}$ carbocycle, 3- to 10-membered heterocycle, —OR$^{12}$, —N(R$^{12}$)(R$^{13}$), —C(O)R$^{15}$, —C(O)N(R$^{12}$)(R$^{13}$), —S(O)$_2$R$^{15}$, and —SO$_2$N(R$^{12}$)(R$^{13}$), wherein C$_{1-6}$ alkyl, C$_{3-10}$ carbocycle, and 3- to 10-membered heterocycle are optionally substituted with one, two, or three R$^{20}$;
R[3b], R[4b], and R[5b] are each independently selected from a bond to L$^2$, hydrogen, and C$_{1-3}$ alkyl;
R[11], R[11a], and R[11d] are each independently selected at each occurrence from halogen, —CN, C$_{1-6}$ alkyl, C$_{2-6}$ alkenyl, C$_{2-6}$ alkynyl, C$_{3-10}$ carbocycle, 3- to 10-membered heterocycle, —OR$^{12}$, —SR$^{12}$, —N(R$^{12}$)(R$^{13}$), —C(O)OR$^{12}$, —OC(O)N(R$^{12}$)(R$^{13}$), —N(R$^{14}$)C(O)N(R$^{12}$)(R$^{13}$), —N(R$^{14}$)C(O)OR$^{15}$, —N(R$^{14}$)S(O)$_2$R$^{15}$, —C(O)R$^{15}$, —S(O)R$^{15}$, —OC(O)R$^{15}$, —C(O)N(R$^{12}$)(R$^{13}$), —C(O)C(O)N(R$^{12}$)(R$^{13}$), —N(R$^{14}$)C(O)R$^{15}$, —S(O)$_2$R$^{15}$, —S(O)$_2$N(R$^{12}$)(R$^{13}$), —S(=O)(=NH)N(R$^{12}$)(R$^{13}$), —CH$_2$C(O)N(R$^{12}$)(R$^{13}$), —CH$_2$N(R$^{14}$)C(O)R$^{15}$, —CH$_2$S(O)$_2$R$^{15}$, —CH$_2$S(O)$_2$N(R$^{12}$)(R$^{13}$), —CH$_2$N(R$^{12}$)S(O)$_2$(R$^{13}$), and —P(O)(R$^{17}$)(R[17a]), wherein C$_{1-6}$ alkyl, C$_{2-6}$ alkenyl, C$_{2-6}$ alkynyl, C$_{3-10}$ carbocycle, and 3- to 10-membered heterocycle are optionally substituted with one, two, or three R$^{20}$;
R[11b] is independently selected at each occurrence from halogen, oxo, —CN, C$_{1-6}$ alkyl, C$_{2-6}$ alkenyl, C$_{2-6}$ alkynyl, C$_{3-10}$ carbocycle, 3- to 10-membered heterocycle, —OR$^{12}$, —SR$^{12}$, —N(R$^{12}$)(R$^{13}$), —C(O)OR$^{12}$, —OC(O)N(R$^{12}$)(R$^{13}$), —N(R$^{14}$)C(O)N(R$^{12}$)(R$^{13}$), —N(R$^{14}$)C(O)OR$^{15}$, —N(R$^{14}$)S(O)$_2$R$^{15}$, —C(O)R$^{15}$, —S(O)R$^{15}$, —OC(O)R$^{15}$, —C(O)N(R$^{12}$)(R$^{13}$), —C(O)C(O)N(R$^{12}$)(R$^{13}$), —N(R$^{14}$)C(O)R$^{15}$, —S(O)$_2$R$^{15}$, —S(O)$_2$N(R$^{12}$)(R$^{13}$), —S(=O)(=Ni)N(R$^{12}$)(R$^{13}$), —CH$_2$C(O)N(R$^{12}$)(R$^{13}$), —CH$_2$N(R$^{14}$)C(O)R$^{15}$, —CH$_2$S(O)$_2$R$^{15}$, —CH$_2$S(O)$_2$N(R$^{12}$)(R$^{13}$), —CH$_2$N(R$^{12}$)S(O)$_2$(R$^{13}$), and —P(O)(R$^{17}$)(R[17a]), wherein C$_{1-6}$ alkyl, C$_{2-6}$ alkenyl, C$_{2-6}$ alkynyl, C$_{3-10}$ carbocycle, and 3- to 10-membered heterocycle are optionally substituted with one, two, or three R$^{20}$;
R$^{12}$ is independently selected at each occurrence from hydrogen, C$_{1-6}$ alkyl, C$_{1-6}$ haloalkyl, C$_{2-6}$ alkenyl, C$_{2-6}$ alkynyl, C$_{3-10}$ carbocycle, and 3- to 10-membered heterocycle, wherein C$_{1-6}$ alkyl, C$_{2-6}$ alkenyl, C$_{2-6}$ alkynyl, C$_{3-10}$ carbocycle, and 3- to 10-membered heterocycle are optionally substituted with one, two, or three R$^{20}$;
R$^{13}$ is independently selected at each occurrence from hydrogen, C$_{1-6}$ alkyl, and C$_{1-6}$ haloalkyl; or R$^{12}$ and R$^{13}$, together with the nitrogen atom to which they are attached, form a 3- to 10-membered heterocycle optionally substituted with one, two, or three R$^{20}$;

R¹⁴ is independently selected at each occurrence from hydrogen, $C_{1-6}$ alkyl, and $C_{1-6}$ haloalkyl;

R¹⁵ is independently selected at each occurrence from $C_{1-6}$ alkyl, $C_{2-6}$ alkenyl, $C_{2-6}$ alkynyl, $C_{3-10}$ carbocycle, and 3- to 10-membered heterocycle, wherein $C_{1-6}$ alkyl, $C_{2-6}$ alkenyl, $C_{2-6}$ alkynyl, $C_{3-10}$ carbocycle, and 3- to 10-membered heterocycle are optionally substituted with one, two, or three $R^{20}$;

R¹⁷ and R¹⁷ᵃ are each independently selected at each occurrence from $C_{1-6}$ alkyl and $C_{3-6}$ cycloalkyl, wherein $C_{1-6}$ alkyl and $C_{3-6}$ cycloalkyl are optionally substituted with one, two or three $R^{20}$; or $R^{17}$ and $R^{17a}$, together with the phosphorous atom to which they are attached, form a 3- to 10-membered heterocycle;

R²⁰ is independently selected at each occurrence from halogen, oxo, =NH, —CN, $C_{1-6}$ alkyl, $C_{2-6}$ alkenyl, $C_{2-6}$ alkynyl, $C_{3-10}$ carbocycle, —CH₂—($C_{3-10}$ carbocycle), 3- to 10-membered heterocycle, —CH₂-(3- to 10-membered heterocycle), —OR²¹, —SR²¹, —N(R²²)(R²³), —C(O)OR²², —C(O)N(R²²)(R²³), —C(O)C(O)N(R²²)(R²³), —OC(O)N(R²²)(R²³), —N(R²²)C(O)N(R²²)(R²³), —N(R²⁴)C(O)OR²⁵, —N(R²⁴)C(O)R²⁵, —N(R²²)S(O)₂R²⁵, —C(O)R²⁵, —S(O)₂R²⁵, —S(O)₂N(R²²)(R²³), —OCH₂C(O)OR²², and —OC(O)R²⁵, wherein $C_{1-6}$ alkyl, $C_{2-6}$ alkenyl, $C_{2-6}$ alkynyl, $C_{3-10}$ carbocycle, —CH₂—($C_{3-10}$ carbocycle), 3- to 10-membered heterocycle, and —CH₂-(3- to 10-membered heterocycle) are optionally substituted with one, two, or three groups independently selected from halogen, oxo, =NH, —CN, $C_{1-6}$ alkyl, $C_{1-6}$ haloalkyl, $C_{1-6}$ alkoxy, $C_{1-6}$ haloalkoxy, —OR²¹, —SR²¹, —N(R²²)(R²³), —C(O)OR²², —C(O)N(R²²)(R²³), —C(O)C(O)N(R²²)(R²³), —OC(O)N(R²²)(R²³), —N(R²⁴)C(O)N(R²²)(R²³), —N(R²⁴)C(O)OR²⁵, —N(R²⁴)C(O)R²⁵, —N(R²²)S(O)₂R²⁵, —C(O)R²⁵, —S(O)₂R²⁵, —S(O)₂N(R²²)(R²³), and —OC(O)R²⁵;

R²¹ is independently selected at each occurrence from H, $C_{1-6}$ alkyl, $C_{1-6}$ haloalkyl, $C_{2-6}$ alkenyl, $C_{2-6}$ alkynyl, $C_{3-10}$ carbocycle, and 3- to 10-membered heterocycle, wherein $C_{3-10}$ carbocycle and 3- to 10-membered heterocycle are optionally substituted with one, two, or three groups independently selected from halogen and $C_{1-6}$ alkyl;

R²² is independently selected at each occurrence from H, $C_{1-6}$ alkyl, $C_{1-6}$ haloalkyl, $C_{2-6}$ alkenyl, $C_{2-6}$ alkynyl, $C_{3-10}$ carbocycle, and 3- to 10-membered heterocycle, wherein $C_{3-10}$ carbocycle and 3- to 10-membered heterocycle are optionally substituted with one, two, or three groups independently selected from halogen and $C_{1-6}$ alkyl;

R²³ is independently selected at each occurrence from H and $C_{1-6}$ alkyl;

R²⁴ is independently selected at each occurrence from H and $C_{1-6}$ alkyl;

R²⁵ is independently selected at each occurrence from $C_{1-6}$ alkyl, $C_{2-6}$ alkenyl, $C_{2-6}$ alkynyl, $C_{3-10}$ carbocycle, and 3- to 10-membered heterocycle, wherein $C_{1-6}$ alkyl, $C_{3-10}$ carbocycle, and 3- to 10-membered heterocycle are optionally substituted with one, two, or three groups independently selected from halogen, $C_{1-6}$ alkyl, $C_{1-6}$ haloalkyl, $C_{1-6}$ alkoxy, $C_{3-10}$ carbocycle, and 3- to 10-membered heterocycle; and ----- indicates a single or double bond such that all valences are satisfied.

In certain aspects, the present disclosure provides a compound of Formula (III):

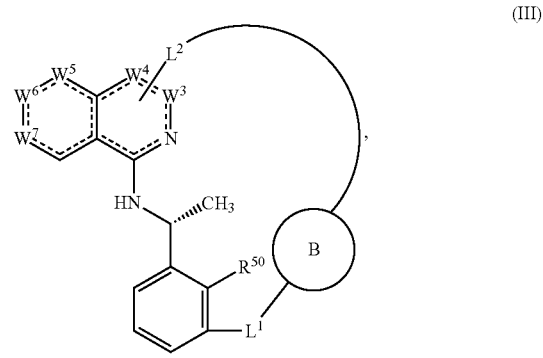

(III)

or a pharmaceutically acceptable salt or solvate thereof, wherein:

is selected from 3- to 8-membered heterocycle, optionally substituted with one or more $R^{11a}$;

$L^1$ is selected from a bond, $C_{1-6}$ alkylene, and $C_{1-6}$ haloalkylene;

$L^2$ is selected from $C_{5-25}$ alkylene, $C_{5-25}$ alkenylene, $C_{5-25}$ alkynylene, 5- to 25-membered heteroalkylene, and 5- to 25-membered heteroalkenylene, each of which is optionally substituted with one or more $R^{11b}$, wherein $L^2$ is covalently bound to one of $W^3$, $W^4$, $W^5$, $W^6$, or $W^7$; or $L^2$ is -$L^3$-D-$L^4$-, wherein $L^4$ is covalently bound to one of $W^3$, $W^4$, $W^5$, $W^6$, or $W^7$;

$L^3$ is selected from $C_{1-10}$ alkylene, $C_{1-10}$ alkenylene, $C_{1-10}$ alkynylene, 2- to 10-membered heteroalkylene, and 2- to 10-membered heteroalkenylene, each of which is optionally substituted with one or more $R^{11b}$; D is absent or selected from $C_{3-12}$ carbocycle and 3- to 12-membered heterocycle, each of which is optionally substituted with one or more $R^{11d}$;

$L^4$ is selected from $C_{1-10}$ alkylene, $C_{1-10}$ alkenylene, $C_{1-10}$ alkynylene, 2- to 10-membered heteroalkylene, and 2- to 10-membered heteroalkenylene, each of which is optionally substituted with one or more $R^{11b}$;

$W^3$ is selected from N(R³ᵇ) and N and $W^4$ is selected from C(R⁴) and C(O); or $W^3$ is selected from C(R³) and C(O), and $W^4$ is selected from N(R⁴ᵇ) and N;

$W^5$ is selected from N(R⁵ᵇ), N, and C(R⁵);

$W^6$ is selected from N, C(R⁶), and C(O);

$W^7$ is selected from N, C(R⁷), and C(O);

$R^{50}$ is hydrogen or halogen;

$R^3$, $R^4$, $R^5$, $R^6$, and $R^7$ are each independently selected from a bond to $L^2$, hydrogen, halogen, —CN, $C_{1-6}$ alkyl, $C_{2-6}$ alkenyl, $C_{2-6}$ alkynyl, $C_{3-10}$ carbocycle, 3- to 10-membered heterocycle, —OR¹², —SR¹², —N(R¹²)(R¹³), —C(O)OR¹², —OC(O)N(R¹²)(R¹³), —N(R¹⁴)C(O)N(R¹²)(R¹³), —N(R¹⁴)C(O)OR¹⁵, —N(R¹⁴)S(O)₂R¹⁵, —C(O)R¹⁵, —S(O)R¹⁵, —OC(O)R¹⁵, —C(O)N(R¹²)(R¹³), —C(O)C(O)N(R¹²)(R¹³), —N(R¹⁴)C(O)R¹⁵, —S(O)₂R¹⁵, —S(O)₂N(R¹²)(R¹³), —S(=O)(=NH)N(R¹²)(R¹³), —CH₂C(O)N(R¹²)(R¹³), —CH₂N(R¹⁴)C(O)R¹⁵, —CH₂S(O)₂R¹⁵, and —CH₂S(O)₂N(R¹²)(R¹³), wherein each $C_{1-6}$ alkyl, $C_{2-6}$ alkenyl, $C_{2-6}$ alkynyl, $C_{3-10}$ carbocycle, and 3- to 10-membered heterocycle is independently optionally substituted with one, two, or three $R^{20}$;

$R^{3b}$, $R^{4b}$, and $R^{5b}$ are each independently selected from a bond to $L^2$, hydrogen, —CN, $C_{1-6}$ alkyl, $C_{2-6}$ alkenyl, $C_{2-6}$ alkynyl, $C_{3-10}$ carbocycle, 3- to 10-membered heterocycle, —$OR^{12}$, —$SR^{12}$, —$C(O)OR^{12}$, —$OC(O)N(R^{12})(R^{13})$, —$C(O)R^{15}$, —$S(O)R^{15}$, —$OC(O)R^{15}$, —$C(O)N(R^{12})(R^{13})$, —$C(O)C(O)N(R^{12})(R^{13})$, —$S(O)_2R^{15}$, —$S(O)_2N(R^{12})(R^{13})$, —$S(=O)(=NH)N(R^{12})(R^{13})$, —$CH_2C(O)N(R^{12})(R^{13})$, —$CH_2N(R^{14})C(O)R^{15}$, —$CH_2S(O)_2R^{15}$, and —$CH_2S(O)_2N(R^{12})(R^{13})$, wherein each $C_{1-6}$ alkyl, $C_{2-6}$ alkenyl, $C_{2-6}$ alkynyl, $C_{3-10}$ carbocycle and 3- to 10-membered heterocycle is independently optionally substituted with one, two, or three $R^{20}$;

$R^{11a}$ and $R^{11d}$ are each independently selected at each occurrence from halogen, —CN, $C_{1-6}$ alkyl, $C_{2-6}$ alkenyl, $C_{2-6}$ alkynyl, $C_{3-10}$ carbocycle, 3- to 10-membered heterocycle, —$OR^{12}$, —$SR^{12}$, —$N(R^{12})(R^{13})$, —$C(O)OR^{12}$, —$OC(O)N(R^{12})(R^{13})$, —$N(R^{14})C(O)N(R^{12})(R^{13})$, —$N(R^{14})C(O)OR^{15}$, —$N(R^{14})S(O)_2R^{15}$, —$C(O)R^{15}$, —$S(O)R^{15}$, —$OC(O)R^{15}$, —$C(O)N(R^{12})(R^{13})$, —$C(O)C(O)N(R^{12})(R^{13})$, —$N(R^{14})C(O)R^{15}$, —$S(O)_2R^{15}$, —$S(O)_2N(R^{12})(R^{13})$, —$S(=O)(=NH)N(R^{12})(R^{13})$, —$CH_2C(O)N(R^{12})(R^{13})$, —$CH_2N(R^{14})C(O)R^{15}$, —$CH_2S(O)_2R^{15}$, —$CH_2S(O)_2N(R^{12})(R^{13})$, —$CH_2N(R^{12})S(O)_2(R^{13})$, and —$P(O)(R^{17})(R^{17a})$, wherein $C_{1-6}$ alkyl, $C_{2-6}$ alkenyl, $C_{2-6}$ alkynyl, $C_{3-10}$ carbocycle, and 3- to 10-membered heterocycle are optionally substituted with one, two, or three $R^{20}$;

$R^{11b}$ is independently selected at each occurrence from halogen, oxo, —CN, $C_{1-6}$ alkyl, $C_{2-6}$ alkenyl, $C_{2-6}$ alkynyl, $C_{3-10}$ carbocycle, 3- to 10-membered heterocycle, —$OR^{12}$, —$SR^{12}$, —$N(R^{12})(R^{13})$, —$C(O)OR^{12}$, —$OC(O)N(R^{12})(R^{13})$, —$N(R^{14})C(O)N(R^{12})(R^{13})$, —$N(R^{14})C(O)OR^{15}$, —$N(R^{14})S(O)_2R^{15}$, —$C(O)R^{15}$, —$S(O)R^{15}$, —$OC(O)R^{15}$, —$C(O)N(R^{12})(R^{13})$, —$C(O)C(O)N(R^{12})(R^{13})$, —$N(R^{14})C(O)R^{15}$, —$S(O)_2R^{15}$, —$S(O)_2N(R^{12})(R^{13})$, —$S(=O)(=NH)N(R^{12})(R^{13})$, —$CH_2C(O)N(R^{12})(R^{13})$, —$CH_2N(R^{14})C(O)R^{15}$, —$CH_2S(O)_2R^{15}$, —$CH_2S(O)_2N(R^{12})(R^{13})$, —$CH_2N(R^{12})S(O)_2(R^{13})$, and —$P(O)(R^{17})(R^{17a})$, wherein $C_{1-6}$ alkyl, $C_{2-6}$ alkenyl, $C_{2-6}$ alkynyl, $C_{3-10}$ carbocycle, and 3- to 10-membered heterocycle are optionally substituted with one, two, or three $R^{20}$;

$R^{12}$ is independently selected at each occurrence from hydrogen, $C_{1-6}$ alkyl, $C_{1-6}$ haloalkyl, $C_{2-6}$ alkenyl, $C_{2-6}$ alkynyl, $C_{3-10}$ carbocycle, and 3- to 10-membered heterocycle, wherein $C_{1-6}$ alkyl, $C_{2-6}$ alkenyl, $C_{2-6}$ alkynyl, $C_{3-10}$ carbocycle, and 3- to 10-membered heterocycle are optionally substituted with one, two, or three $R^{20}$;

$R^{13}$ is independently selected at each occurrence from hydrogen, $C_{1-6}$ alkyl, and $C_{1-6}$ haloalkyl; or $R^{12}$ and $R^{13}$, together with the nitrogen atom to which they are attached, form a 3- to 10-membered heterocycle optionally substituted with one, two, or three $R^{20}$;

$R^{14}$ is independently selected at each occurrence from hydrogen, $C_{1-6}$ alkyl, and $C_{1-6}$ haloalkyl;

$R^{15}$ is independently selected at each occurrence from $C_{1-6}$ alkyl, $C_{2-6}$ alkenyl, $C_{2-6}$ alkynyl, $C_{3-10}$ carbocycle, and 3- to 10-membered heterocycle, wherein $C_{1-6}$ alkyl, $C_{2-6}$ alkenyl, $C_{2-6}$ alkynyl, $C_{3-10}$ carbocycle, and 3- to 10-membered heterocycle are optionally substituted with one, two, or three $R^{20}$;

$R^{17}$ and $R^{17a}$ are each independently selected at each occurrence from $C_{1-6}$ alkyl and $C_{3-6}$ cycloalkyl, wherein $C_{1-6}$ alkyl and $C_{3-6}$ cycloalkyl are optionally substituted with one, two or three $R^{20}$; or $R^{17}$ and $R^{17a}$, together with the phosphorous atom to which they are attached, form a 3- to 10-membered heterocycle;

$R^{20}$ is independently selected at each occurrence from halogen, oxo, =NH, —CN, $C_{1-6}$ alkyl, $C_{2-6}$ alkenyl, $C_{2-6}$ alkynyl, $C_{3-10}$ carbocycle, —$CH_2$—$(C_{3-10}$ carbocycle), 3- to 10-membered heterocycle, —$CH_2$-(3- to 10-membered heterocycle), —$OR^{21}$, —$SR^{21}$, —$N(R^{22})(R^{23})$, —$C(O)OR^{22}$, —$C(O)N(R^{22})(R^{23})$, —$C(O)C(O)N(R^{22})(R^{23})$, —$OC(O)N(R^{22})(R^{23})$, —$N(R^{22})C(O)N(R^{22})(R^{23})$, —$N(R^{24})C(O)OR^{25}$, —$N(R^{24})C(O)R^{25}$, —$N(R^{22})S(O)_2R^{25}$, —$C(O)R^{25}$, —$S(O)_2R^{25}$, —$S(O)_2N(R^{22})(R^{23})$, —$OCH_2C(O)OR^{22}$, and —$OC(O)R^{25}$, wherein $C_{1-6}$ alkyl, $C_{2-6}$ alkenyl, $C_{2-6}$ alkynyl, $C_{3-10}$ carbocycle, —$CH_2$—$(C_{3-10}$ carbocycle), 3- to 10-membered heterocycle, and —$CH_2$-(3- to 10-membered heterocycle) are optionally substituted with one, two, or three groups independently selected from halogen, oxo, =NH, —CN, $C_{1-6}$ alkyl, $C_{1-6}$ haloalkyl, $C_{1-6}$ alkoxy, $C_{1-6}$ haloalkoxy, —$OR^{21}$, —$SR^{21}$, —$N(R^{22})(R^{23})$, —$C(O)OR^{22}$, —$C(O)N(R^{22})(R^{23})$, —$C(O)C(O)N(R^{22})(R^{23})$, —$OC(O)N(R^{22})(R^{23})$, —$N(R^{22})C(O)N(R^{22})(R^{23})$, —$N(R^{24})C(O)OR^{25}$, —$N(R^{24})C(O)R^{25}$, —$N(R^{22})S(O)_2R^{25}$, —$C(O)R^{25}$, —$S(O)_2R^{25}$, —$S(O)_2N(R^{22})(R^{23})$, and —$OC(O)R^{25}$;

$R^{21}$ is independently selected at each occurrence from H, $C_{1-6}$ alkyl, $C_{1-6}$ haloalkyl, $C_{2-6}$ alkenyl, $C_{2-6}$ alkynyl, $C_{3-10}$ carbocycle, and 3- to 10-membered heterocycle, wherein $C_{3-10}$ carbocycle and 3- to 10-membered heterocycle are optionally substituted with one, two, or three groups independently selected from halogen and $C_{1-6}$ alkyl;

$R^{22}$ is independently selected at each occurrence from H, $C_{1-6}$ alkyl, $C_{1-6}$ haloalkyl, $C_{2-6}$ alkenyl, $C_{2-6}$ alkynyl, $C_{3-10}$ carbocycle, and 3- to 10-membered heterocycle, wherein $C_{3-10}$ carbocycle and 3- to 10-membered heterocycle are optionally substituted with one, two, or three groups independently selected from halogen and $C_{1-6}$ alkyl;

$R^{23}$ is independently selected at each occurrence from H and $C_{1-6}$ alkyl;

$R^{24}$ is independently selected at each occurrence from H and $C_{1-6}$ alkyl;

$R^{25}$ is independently selected at each occurrence from $C_{1-6}$ alkyl, $C_{2-6}$ alkenyl, $C_{2-6}$ alkynyl, $C_{3-10}$ carbocycle, and 3- to 10-membered heterocycle, wherein $C_{1-6}$ alkyl, $C_{3-10}$ carbocycle, and 3- to 10-membered heterocycle are optionally substituted with one, two, or three groups independently selected from halogen, $C_{1-6}$ alkyl, $C_{1-6}$ haloalkyl, $C_{1-6}$ alkoxy, $C_{3-10}$ carbocycle, and 3- to 10-membered heterocycle; and ----- indicates a single or double bond such that all valences are satisfied.

In certain aspects, the present disclosure provides a compound of Formula (III):

(III)

[Structure diagram showing a bicyclic heteroaromatic system with W3-W7 positions, connected to an HN-CH(CH3) group attached to a phenyl ring bearing R50 and L1, with L2 linker to ring B]

or a pharmaceutically acceptable salt or solvate thereof, wherein:

[Ring B diagram]

is selected from 3- to 8-membered heterocycle, optionally substituted with one or more $R^{11a}$;

- $L^1$ is selected from a bond, $C_{1-6}$ alkylene, and $C_{1-6}$ haloalkylene;
- $L^2$ is selected from $C_{5-25}$ alkylene, $C_{5-25}$ alkenylene, $C_{5-25}$ alkynylene, 5- to 25-membered heteroalkylene, and 5- to 25-membered heteroalkenylene, each of which is optionally substituted with one or more $R^{11b}$, wherein $L^2$ is covalently bound to one of $W^3$, $W^4$, $W^5$, $W^6$, or $W^7$.
- $W^3$ is selected from $N(R^{3b})$ and N and $W^4$ is selected from $C(R^4)$ and $C(O)$; or $W^3$ is selected from $C(R^3)$ and $C(O)$, and $W^4$ is selected from $N(R^{4b})$ and N;
- $W^5$ is selected from $N(R^{5b})$, N, and $C(R^5)$;
- $W^6$ is selected from N, $C(R^6)$, and $C(O)$;
- $W^7$ is selected from N, $C(R^7)$, and $C(O)$;
- $R^{50}$ is hydrogen or halogen;
- $R^3$, $R^4$, $R^5$, $R^6$, and $R^7$ are each independently selected from a bond to $L^2$, hydrogen, halogen, —CN, $C_{1-6}$ alkyl, $C_{2-6}$ alkenyl, $C_{2-6}$ alkynyl, $C_{3-10}$ carbocycle, 3- to 10-membered heterocycle, —$OR^{12}$, —$SR^{12}$, —$N(R^{12})(R^{13})$, —$C(O)OR^{12}$, —$OC(O)N(R^{12})(R^{13})$, —$N(R^{14})C(O)N(R^{12})(R^{13})$, —$N(R^{14})C(O)OR^{15}$, —$N(R^{14})S(O)_2R^{15}$, —$C(O)R^{15}$, —$S(O)R^{15}$, —$OC(O)R^{15}$, —$C(O)N(R^{12})(R^{13})$, —$C(O)C(O)N(R^{12})(R^{13})$, —$N(R^{14})C(O)R^{15}$, —$S(O)_2R^{15}$, —$S(O)_2N(R^{12})(R^{13})$, —$S(=O)(=NH)N(R^{12})(R^{13})$, —$CH_2C(O)N(R^{12})(R^{13})$, —$CH_2N(R^{14})C(O)R^{15}$, —$CH_2S(O)_2R^{15}$, and —$CH_2S(O)_2N(R^{12})(R^{13})$, wherein each $C_{1-6}$ alkyl, $C_{2-6}$ alkenyl, $C_{2-6}$ alkynyl, $C_{3-10}$ carbocycle, and 3- to 10-membered heterocycle is independently optionally substituted with one, two, or three $R^{20}$;
- $R^{3b}$, $R^{4b}$, and $R^{5b}$ are each independently selected from a bond to $L^2$, hydrogen, —CN, $C_{1-6}$ alkyl, $C_{2-6}$ alkenyl, $C_{2-6}$ alkynyl, $C_{3-10}$ carbocycle, 3- to 10-membered heterocycle, —$OR^{12}$, —$SR^{12}$, —$C(O)OR^{12}$, —$OC(O)N(R^{12})(R^{13})$, —$C(O)R^{15}$, —$S(O)R^{15}$, —$OC(O)R^{15}$, —$C(O)N(R^{12})(R^{13})$, —$C(O)C(O)N(R^{12})(R^{13})$, —$S(O)_2R^{15}$, —$S(O)_2N(R^{12})(R^{13})$, —$S(=O)(=NH)N(R^{12})(R^{13})$, —$CH_2C(O)N(R^{12})(R^{13})$, —$CH_2N(R^{14})C(O)R^{15}$, —$CH_2S(O)_2R^{15}$, and —$CH_2S(O)_2N(R^{12})(R^{13})$, wherein each $C_{1-6}$ alkyl, $C_{2-6}$ alkenyl, $C_{2-6}$ alkynyl, $C_{3-10}$ carbocycle and 3- to 10-membered heterocycle is independently optionally substituted with one, two, or three $R^{20}$;
- $R^{11a}$ is independently selected at each occurrence from halogen, —CN, $C_{1-6}$ alkyl, $C_{2-6}$ alkenyl, $C_{2-6}$ alkynyl, $C_{3-10}$ carbocycle, 3- to 10-membered heterocycle, —$OR^{12}$, —$SR^{12}$, —$N(R^{12})(R^{13})$, —$C(O)OR^{12}$, —$OC(O)N(R^{12})(R^{13})$, —$N(R^{14})C(O)N(R^{12})(R^{13})$, —$N(R^{14})C(O)OR^{15}$, —$N(R^{14})S(O)_2R^{15}$, —$C(O)R^{15}$, —$S(O)R^{15}$, —$OC(O)R^{15}$, —$C(O)N(R^{12})(R^{13})$, —$C(O)C(O)N(R^{12})(R^{13})$, —$N(R^{14})C(O)R^{15}$, —$S(O)_2R^{15}$, —$S(O)_2N(R^{12})(R^{13})$, —$S(=O)(=NH)N(R^{12})(R^{13})$, —$CH_2C(O)N(R^{12})(R^{13})$, —$CH_2N(R^{14})C(O)R^{15}$, —$CH_2S(O)_2R^{15}$, —$CH_2S(O)_2N(R^{12})(R^{13})$, —$CH_2N(R^{12})S(O)_2(R^{13})$, and —$P(O)(R^{17})(R^{17a})$, wherein $C_{1-6}$ alkyl, $C_{2-6}$ alkenyl, $C_{2-6}$ alkynyl, $C_{3-10}$ carbocycle, and 3- to 10-membered heterocycle are optionally substituted with one, two, or three $R^{20}$;
- $R^{11b}$ is independently selected at each occurrence from halogen, oxo, —CN, $C_{1-6}$ alkyl, $C_{2-6}$ alkenyl, $C_{2-6}$ alkynyl, $C_{3-10}$ carbocycle, 3- to 10-membered heterocycle, —$OR^{12}$, —$SR^{12}$, —$N(R^{12})(R^{13})$, —$C(O)OR^{12}$, —$OC(O)N(R^{12})(R^{13})$, —$N(R^{14})C(O)N(R^{12})(R^{13})$, —$N(R^{14})C(O)OR^{15}$, —$N(R^{14})S(O)_2R^{15}$, —$C(O)R^{15}$, —$S(O)R^{15}$, —$OC(O)R^{15}$, —$C(O)N(R^{12})(R^{13})$, —$C(O)C(O)N(R^{12})(R^{13})$, —$N(R^{14})C(O)R^{15}$, —$S(O)_2R^{15}$, —$S(O)_2N(R^{12})(R^{13})$, —$S(=O)(=NH)N(R^{12})(R^{13})$, —$CH_2C(O)N(R^{12})(R^{13})$, —$CH_2N(R^{14})C(O)R^{15}$, —$CH_2S(O)_2R^{15}$, —$CH_2S(O)_2N(R^{12})(R^{13})$, —$CH_2N(R^{12})S(O)_2(R^{13})$, and —$P(O)(R^{17})(R^{17a})$, wherein $C_{1-6}$ alkyl, $C_{2-6}$ alkenyl, $C_{2-6}$ alkynyl, $C_{3-10}$ carbocycle, and 3- to 10-membered heterocycle are optionally substituted with one, two, or three $R^{20}$;
- $R^{12}$ is independently selected at each occurrence from hydrogen, $C_{1-6}$ alkyl, $C_{1-6}$ haloalkyl, $C_{2-6}$ alkenyl, $C_{2-6}$ alkynyl, $C_{3-10}$ carbocycle, and 3- to 10-membered heterocycle, wherein $C_{1-6}$ alkyl, $C_{2-6}$ alkenyl, $C_{2-6}$ alkynyl, $C_{3-10}$ carbocycle, and 3- to 10-membered heterocycle are optionally substituted with one, two, or three $R^{20}$;
- $R^{13}$ is independently selected at each occurrence from hydrogen, $C_{1-6}$ alkyl, and $C_{1-6}$ haloalkyl; or $R^{12}$ and $R^{13}$, together with the nitrogen atom to which they are attached, form a 3- to 10-membered heterocycle optionally substituted with one, two, or three $R^{20}$;
- $R^{14}$ is independently selected at each occurrence from hydrogen, $C_{1-6}$ alkyl, and $C_{1-6}$ haloalkyl;
- $R^{15}$ is independently selected at each occurrence from $C_{1-6}$ alkyl, $C_{2-6}$ alkenyl, $C_{2-6}$ alkynyl, $C_{3-10}$ carbocycle, and 3- to 10-membered heterocycle, wherein $C_{1-6}$ alkyl, $C_{2-6}$ alkenyl, $C_{2-6}$ alkynyl, $C_{3-10}$ carbocycle, and 3- to 10-membered heterocycle are optionally substituted with one, two, or three $R^{20}$;
- $R^{17}$ and $R^{17a}$ are each independently selected at each occurrence from $C_{1-6}$ alkyl and $C_{3-6}$ cycloalkyl, wherein $C_{1-6}$ alkyl and $C_{3-6}$ cycloalkyl are optionally substituted with one, two or three $R^{20}$; or $R^{17}$ and $R^{17a}$, together with the phosphorous atom to which they are attached, form a 3- to 10-membered heterocycle;
- $R^{20}$ is independently selected at each occurrence from halogen, oxo, =NH, —CN, $C_{1-6}$ alkyl, $C_{2-6}$ alkenyl, $C_{2-6}$ alkynyl, $C_{3-10}$ carbocycle, —$CH_2$—($C_{3-10}$ carbocycle), 3- to 10-membered heterocycle, —$CH_2$-(3- to 10-membered heterocycle), —$OR^{21}$, —$SR^{21}$, —$N(R^{22})(R^{23})$, —$C(O)OR^{22}$, —$C(O)N(R^{22})(R^{23})$, —$C(O)C(O)N(R^{22})(R^{23})$, —$OC(O)N(R^{22})(R^{23})$, —$N(R^{22})C(O)N(R^{22})(R^{23})$, —$N(R^{24})C(O)OR^{25}$, —$N(R^{24})C(O)R^{25}$, —$N(R^{22})S(O)_2R^{25}$, —$C(O)R^{25}$, —S(O)$_2$R$^{25}$, —S(O)$_2$N(R$^{22}$)(R$^{23}$), —OCH$_2$C(O)OR$^{22}$, and —OC(O)R$^{25}$, wherein C$_{1-6}$ alkyl, C$_{2-6}$ alkenyl, C$_{2-6}$ alkynyl, C$_{3-10}$ carbocycle, —CH$_2$—(C$_{3-10}$ carbocycle), 3- to 10-membered heterocycle, and —CH$_2$-(3- to 10-membered heterocycle) are optionally substituted with one, two, or three groups independently selected from halogen, oxo, =NH, —CN, C$_{1-6}$ alkyl, C$_{1-6}$ haloalkyl, C$_{1-6}$ alkoxy, C$_{1-6}$ haloalkoxy, —OR$^{21}$, —SR$^{21}$, —N(R$^{22}$)(R$^{23}$), —C(O)OR$^{22}$, —C(O)N(R$^{22}$)(R$^{23}$), —C(O)C(O)N(R$^{22}$)(R$^{23}$), —OC(O)N(R$^{22}$)(R$^{23}$), —N(R$^{24}$)C(O)N(R$^{22}$)(R$^{23}$), —N(R$^{24}$)C(O)OR$^{25}$, —N(R$^{24}$)C(O)R$^{25}$, —N(R$^{22}$)S(O)$_2$R$^{25}$, —C(O)R$^{25}$, —S(O)$_2$R$^{25}$, —S(O)$_2$N(R$^{22}$)(R$^{23}$), and —OC(O)R$^{25}$;

R$^{21}$ is independently selected at each occurrence from H, C$_{1-6}$ alkyl, C$_{1-6}$ haloalkyl, C$_{2-6}$ alkenyl, C$_{2-6}$ alkynyl, C$_{3-10}$ carbocycle, and 3- to 10-membered heterocycle, wherein C$_{3-10}$ carbocycle and 3- to 10-membered heterocycle are optionally substituted with one, two, or three groups independently selected from halogen and C$_{1-6}$ alkyl;

R$^{22}$ is independently selected at each occurrence from H, C$_{1-6}$ alkyl, C$_{1-6}$ haloalkyl, C$_{2-6}$ alkenyl, C$_{2-6}$ alkynyl, C$_{3-10}$ carbocycle, and 3- to 10-membered heterocycle, wherein C$_{3-10}$ carbocycle and 3- to 10-membered heterocycle are optionally substituted with one, two, or three groups independently selected from halogen and C$_{1-6}$ alkyl;

R$^{23}$ is independently selected at each occurrence from H and C$_{1-6}$ alkyl;

R$^{24}$ is independently selected at each occurrence from H and C$_{1-6}$ alkyl;

R$^{25}$ is independently selected at each occurrence from C$_{1-6}$ alkyl, C$_{2-6}$ alkenyl, C$_{2-6}$ alkynyl, C$_{3-10}$ carbocycle, and 3- to 10-membered heterocycle, wherein C$_{1-6}$ alkyl, C$_{3-10}$ carbocycle, and 3- to 10-membered heterocycle are optionally substituted with one, two, or three groups independently selected from halogen, C$_{1-6}$ alkyl, C$_{1-6}$ haloalkyl, C$_{1-6}$ alkoxy, C$_{3-10}$ carbocycle, and 3- to 10-membered heterocycle; and ----- indicates a single or double bond such that all valences are satisfied.

In some embodiments, a compound of Formula (III) is a compound of the formula:

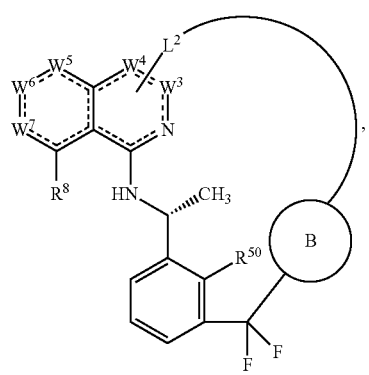

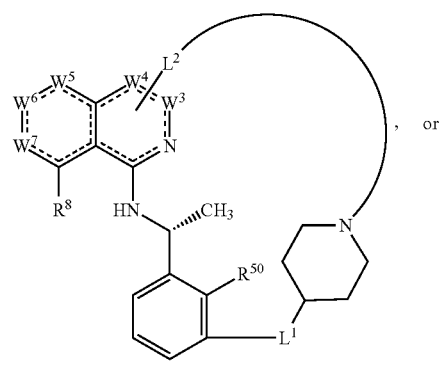

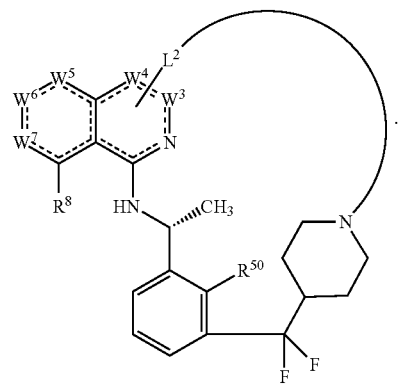

In some embodiments, a compound of Formula (III) is a compound of the formula:

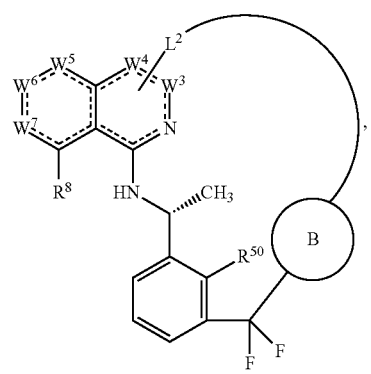

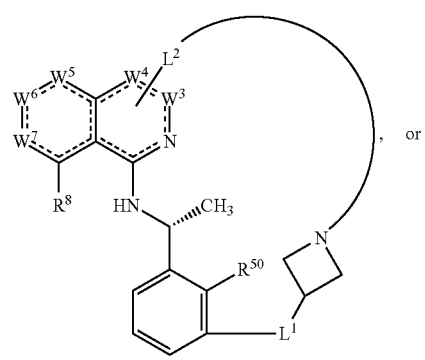

141

-continued

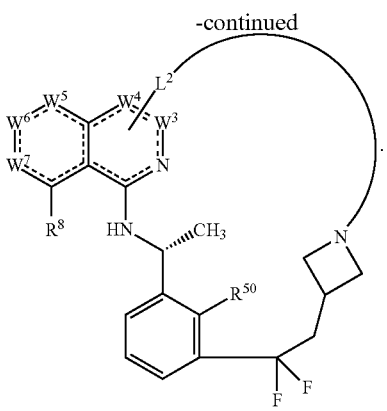

In some embodiments, for a compound of Formula (III),

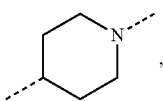

is selected from azetidine, pyrrolidine, and piperidine, each of which is optionally substituted with one or more $R^{11a}$. In some embodiments,

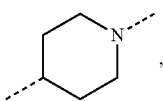

is

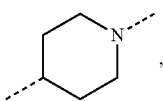

each of which is optionally substituted with one or more $R^{11a}$. In some embodiments,

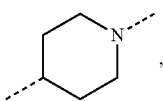

is

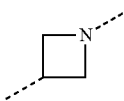

optionally substituted with one or more $R^{11a}$. In some embodiments, $L^1$ is $C_{1-3}$ haloalkylene. In some embodiments, $L^2$ is selected from $C_{5-10}$ alkylene, $C_{5-10}$ alkenylene, 5- to 10-membered heteroalkylene, and 5- to 10-membered heteroalkenylene, each of which is optionally substituted with one or more $R^{11b}$, wherein $L^2$ is covalently bound to one of $W^3$, $W^4$, $W^5$, $W^6$, or $W^7$; or $L^2$ is $-L^3-D-L^4-$, wherein $L^4$ is covalently bound to one of $W^3$, $W^4$, $W^5$, $W^6$, or $W^7$; $L^3$ is selected from $C_{1-8}$ alkylene, $C_{1-8}$ alkenylene, 2- to 8-membered heteroalkylene, and 2- to 8-membered heteroalkenylene, each of which is optionally substituted with one or more $R^{11b}$; D is selected from $C_{3-10}$ carbocycle and 3- to 10-membered heterocycle, each of which is optionally substituted with one or more $R^{11d}$; and $L^4$ is selected from $C_{1-8}$ alkylene, $C_{1-8}$ alkenylene, 2- to 8-membered heteroalkylene, and 2- to 8-membered heteroalkenylene, each of which is optionally substituted with one or more $R^{11b}$.

In certain aspects, the present disclosure provides a compound of the formula:

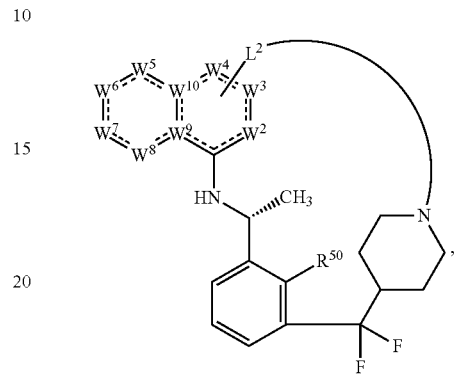

or a pharmaceutically acceptable salt or solvate thereof, wherein:
$L^2$ is selected from $C_{5-10}$ alkylene, $C_{5-10}$ alkenylene, 5- to 10-membered heteroalkylene, and 5- to 10-membered heteroalkenylene, each of which is optionally substituted with one or more $R^{11b}$, wherein $L^2$ is covalently bound to one of $W^3$, $W^4$, $W^5$, $W^6$, or $W^7$; or $L^2$ is $-L^3-D-L^4-$, wherein $L^4$ is covalently bound to one of $W^3$, $W^4$, $W^5$, $W^6$, or $W^7$;
$L^3$ is selected from $C_{1-8}$ alkylene, $C_{1-8}$ alkenylene, 2- to 8-membered heteroalkylene, and 2- to 8-membered heteroalkenylene, each of which is optionally substituted with one or more $R^{11b}$.
D is selected from $C_{3-10}$ carbocycle and 3- to 10-membered heterocycle, each of which is optionally substituted with one or more $R^{11d}$;
$L^4$ is selected from $C_{1-8}$ alkylene, $C_{1-8}$ alkenylene, 2- to 8-membered heteroalkylene, and 2- to 8-membered heteroalkenylene, each of which is optionally substituted with one or more $R^{11b}$;
$W^2$ is selected from $N(R^{2b})$, N, $C(R^2)$, $C(R^2)(R^{2a})$, and $C(O)$;
$W^3$ is selected from $N(R^{3b})$, N, $C(R^3)$, $C(R^3)(R^{3a})$, and $C(O)$;
$W^4$ is selected from $N(R^{4b})$, N, $C(R^4)$, $C(R^4)(R^{4a})$, and $C(O)$;
$W^5$ is selected from $N(R^{5b})$, N, $C(R^5)$, $C(R^5)(R^{5a})$, and $C(O)$;
$W^6$ is selected from $N(R^{6b})$, N, $C(R^6)$, $C(R^6)(R^{6a})$, and $C(O)$;
$W^7$ is selected from $N(R^{7b})$, N, $C(R^7)$, $C(R^7)(R^{7a})$, and $C(O)$;
$W^8$ is selected from $N(R^{8b})$, N, $C(R^8)$, $C(R^8)(R^{8a})$, and $C(O)$;
$W^9$ is selected from N, $C(R^9)$, and C;
$W^{10}$ is selected from N, $C(R^{10})$, and C;
$R^2$, $R^{2a}$, $R^{3a}$, $R^{4a}$, $R^{5a}$, $R^{6a}$, $R^{7a}$, $R^8$, and $R^{8a}$ are each independently selected from hydrogen, halogen, —CN, $C_{1-6}$ alkyl, $C_{2-6}$ alkenyl, $C_{2-6}$ alkynyl, $C_{3-10}$ carbocycle, 3- to 10-membered heterocycle, —$OR^{12}$, —$SR^{12}$, —$N(R^{12})(R^{13})$, —$C(O)OR^{12}$, —$OC(O)N(R^{12})(R^{13})$, —$N(R^{14})C(O)N(R^{12})(R^{13})$, —$N(R^{14})C(O)OR^{15}$, —N($R^{14}$)S(O)$_2$$R^{15}$, —C(O)$R^{15}$, —S(O)$R^{15}$, —OC(O)$R^{15}$, —C(O)N($R^{12}$)($R^{13}$), —C(O)C(O)N($R^{12}$)($R^{13}$), —N($R^{14}$)C(O)$R^{15}$, —S(O)$_2$$R^{15}$, —S(O)$_2$N($R^{12}$)($R^{13}$), —S(=O)(=NH)N($R^{12}$)($R^{13}$), —CH$_2$C(O)N($R^{12}$)($R^{13}$), —CH$_2$N($R^{14}$)C(O)$R^{15}$, —CH$_2$S(O)$_2$$R^{15}$, and —CH$_2$S(O)$_2$N($R^{12}$)($R^{13}$), wherein each C$_{1-6}$ alkyl, C$_{2-6}$ alkenyl, C$_{2-6}$ alkynyl, C$_{3-10}$ carbocycle, and 3- to 10-membered heterocycle is independently optionally substituted with one, two, or three $R^{20}$;

$R^3$, $R^4$, $R^5$, $R^6$, and $R^7$ are each independently selected from a bond to $L^2$, hydrogen, halogen, —CN, C$_{1-6}$ alkyl, C$_{2-6}$ alkenyl, C$_{2-6}$ alkynyl, C$_{3-10}$ carbocycle, 3- to 10-membered heterocycle, —O$R^{12}$, —S$R^{12}$, —N($R^{12}$)($R^{13}$), —C(O)O$R^{12}$, —OC(O)N($R^{12}$)($R^{13}$), —N($R^{14}$)C(O)N($R^{12}$)($R^{13}$), —N($R^{14}$)C(O)O$R^{15}$, —N($R^{14}$)S(O)$_2$$R^{15}$, —C(O)$R^{15}$, —S(O)$R^{15}$, —OC(O)$R^{15}$, —C(O)N($R^{12}$)($R^{13}$), —C(O)C(O)N($R^{12}$)($R^{13}$), —N($R^{14}$)C(O)$R^{15}$, —S(O)$_2$$R^{15}$, —S(O)$_2$N($R^{12}$)($R^{13}$), —S(=O)(=NH)N($R^{12}$)($R^{13}$), —CH$_2$C(O)N($R^{12}$)($R^{13}$), —CH$_2$N($R^{14}$)C(O)$R^{15}$, —CH$_2$S(O)$_2$$R^{15}$, and —CH$_2$S(O)$_2$N($R^{12}$)($R^{13}$), wherein each C$_{1-6}$ alkyl, C$_{2-6}$ alkenyl, C$_{2-6}$ alkynyl, C$_{3-10}$ carbocycle, and 3- to 10-membered heterocycle is independently optionally substituted with one, two, or three $R^{20}$;

$R^{2b}$ and $R^{8b}$ are each independently selected from hydrogen, —CN, C$_{1-6}$ alkyl, C$_{2-6}$ alkenyl, C$_{2-6}$ alkynyl, C$_{3-10}$ carbocycle, 3- to 10-membered heterocycle, —O$R^{12}$, —S$R^{12}$, —C(O)O$R^{12}$, —OC(O)N($R^{12}$)($R^{13}$), —C(O)$R^{15}$, —S(O)$R^{15}$, —OC(O)$R^{15}$, —C(O)N($R^{12}$)($R^{13}$), —C(O)C(O)N($R^{12}$)($R^{13}$), —S(O)$_2$$R^{15}$, —S(O)$_2$N($R^{12}$)($R^{13}$), —S(=O)(=NH)N($R^{12}$)($R^{13}$), —CH$_2$C(O)N($R^{12}$)($R^{13}$), —CH$_2$N($R^{14}$)C(O)$R^{15}$, —CH$_2$S(O)$_2$$R^{15}$, and —CH$_2$S(O)$_2$N($R^{12}$)($R^{13}$), wherein each C$_{1-6}$ alkyl, C$_{2-6}$ alkenyl, C$_{2-6}$ alkynyl, C$_{3-10}$ carbocycle and 3- to 10-membered heterocycle is independently optionally substituted with one, two, or three $R^{20}$;

$R^{3b}$, $R^{4b}$, $R^{5b}$, $R^{6b}$, and $R^{7b}$ are each independently selected from a bond to $L^2$, hydrogen, —CN, C$_{1-6}$ alkyl, C$_{2-6}$ alkenyl, C$_{2-6}$ alkynyl, C$_{3-10}$ carbocycle, 3- to 10-membered heterocycle, —O$R^{12}$, —S$R^{12}$, —C(O)O$R^{12}$, —OC(O)N($R^{12}$)($R^{13}$), —C(O)$R^{15}$, —S(O)$R^{15}$, —OC(O)$R^{15}$, —C(O)N($R^{12}$)($R^{13}$), —C(O)C(O)N($R^{12}$)($R^{13}$), —S(O)$_2$$R^{15}$, —S(O)$_2$N($R^{12}$)($R^{13}$), —S(=O)(=NH)N($R^{12}$)($R^{13}$), —CH$_2$C(O)N($R^{12}$)($R^{13}$), —CH$_2$N($R^{14}$)C(O)$R^{15}$, —CH$_2$S(O)$_2$$R^{15}$, and —CH$_2$S(O)$_2$N($R^{12}$)($R^{13}$), wherein each C$_{1-6}$ alkyl, C$_{2-6}$ alkenyl, C$_{2-6}$ alkynyl, C$_{3-10}$ carbocycle and 3- to 10-membered heterocycle is independently optionally substituted with one, two, or three $R^{20}$;

$R^9$ and $R^{10}$ are each independently selected from hydrogen, C$_{1-6}$ alkyl, C$_{2-6}$ alkenyl, C$_{2-6}$ alkynyl, C$_{3-10}$ carbocycle, —CH$_2$—(C$_{3-10}$ carbocycle), 3- to 10-membered heterocycle, and —CH$_2$-(3- to 10-membered heterocycle), wherein each C$_{1-6}$ alkyl, C$_{2-6}$ alkenyl, C$_{2-6}$ alkynyl, C$_{3-10}$ carbocycle, —CH$_2$—(C$_{3-10}$ carbocycle), 3- to 10-membered heterocycle, and —CH$_2$-(3- to 10-membered heterocycle) is independently optionally substituted with one, two, or three $R^{20}$;

$R^{11d}$ is independently selected at each occurrence from halogen, —CN, C$_{1-6}$ alkyl, C$_{2-6}$ alkenyl, C$_{2-6}$ alkynyl, C$_{3-10}$ carbocycle, 3- to 10-membered heterocycle, —O$R^{12}$, —S$R^{12}$, —N($R^{12}$)($R^{13}$), —C(O)O$R^{12}$, —OC(O)N($R^{12}$)($R^{13}$), —N($R^{14}$)C(O)N($R^{12}$)($R^{13}$), —N($R^{14}$)C(O)O$R^{15}$, —N($R^{14}$)S(O)$_2$$R^{15}$, —C(O)$R^{15}$, —S(O)$R^{15}$, —OC(O)$R^{15}$, —C(O)N($R^{12}$)($R^{13}$), —C(O)C(O)N($R^{12}$)($R^{13}$), —N($R^{14}$)C(O)$R^{15}$, —S(O)$_2$$R^{15}$, —S(O)$_2$N($R^{12}$)($R^{13}$), —S(=O)(=Ni)N($R^{12}$)($R^{13}$), —CH$_2$C(O)N($R^{12}$)($R^{13}$), —CH$_2$N($R^{14}$)C(O)$R^{15}$, —CH$_2$S(O)$_2$$R^{15}$, —CH$_2$S(O)$_2$N($R^{12}$)($R^{13}$), —CH$_2$N($R^{12}$)S(O)$_2$($R^{13}$), and —P(O)($R^{17}$)($R^{17a}$), wherein C$_{1-6}$ alkyl, C$_{2-6}$ alkenyl, C$_{2-6}$ alkynyl, C$_{3-10}$ carbocycle, and 3- to 10-membered heterocycle are optionally substituted with one, two, or three $R^{20}$;

$R^{11b}$ is independently selected at each occurrence from halogen, oxo, —CN, C$_{1-6}$ alkyl, C$_{2-6}$ alkenyl, C$_{2-6}$ alkynyl, C$_{3-10}$ carbocycle, 3- to 10-membered heterocycle, —O$R^{12}$, —S$R^{12}$, —N($R^{12}$)($R^{13}$), —C(O)O$R^{12}$, —OC(O)N($R^{12}$)($R^{13}$), —N($R^{14}$)C(O)N($R^{12}$)($R^{13}$), —N($R^{14}$)C(O)O$R^{15}$, —N($R^{14}$)S(O)$_2$$R^{15}$, —C(O)$R^{15}$, —S(O)$R^{15}$, —OC(O)$R^{15}$, —C(O)N($R^{12}$)($R^{13}$), —C(O)C(O)N($R^{12}$)($R^{13}$), —N($R^{14}$)C(O)$R^{15}$, —S(O)$_2$$R^{15}$, —S(O)$_2$N($R^{12}$)($R^{13}$), —S(=O)(=NH)N($R^{12}$)($R^{13}$), —CH$_2$C(O)N($R^{12}$)($R^{13}$), —CH$_2$N($R^{14}$)C(O)$R^{15}$, —CH$_2$S(O)$_2$$R^{15}$, —CH$_2$S(O)$_2$N($R^{12}$)($R^{13}$), —CH$_2$N($R^{12}$)S(O)$_2$($R^{13}$), and —P(O)($R^{17}$)($R^{17a}$), wherein C$_{1-6}$ alkyl, C$_{2-6}$ alkenyl, C$_{2-6}$ alkynyl, C$_{3-10}$ carbocycle, and 3- to 10-membered heterocycle are optionally substituted with one, two, or three $R^{20}$;

$R^{12}$ is independently selected at each occurrence from hydrogen, C$_{1-6}$ alkyl, C$_{1-6}$ haloalkyl, C$_{2-6}$ alkenyl, C$_{2-6}$ alkynyl, C$_{3-10}$ carbocycle, and 3- to 10-membered heterocycle, wherein C$_{1-6}$ alkyl, C$_{2-6}$ alkenyl, C$_{2-6}$ alkynyl, C$_{3-10}$ carbocycle, and 3- to 10-membered heterocycle are optionally substituted with one, two, or three $R^{20}$;

$R^{13}$ is independently selected at each occurrence from hydrogen, C$_{1-6}$ alkyl, and C$_{1-6}$ haloalkyl; or $R^{12}$ and $R^{13}$, together with the nitrogen atom to which they are attached, form a 3- to 10-membered heterocycle optionally substituted with one, two, or three $R^{20}$;

$R^{14}$ is independently selected at each occurrence from hydrogen, C$_{1-6}$ alkyl, and C$_{1-6}$ haloalkyl;

$R^{15}$ is independently selected at each occurrence from C$_{1-6}$ alkyl, C$_{2-6}$ alkenyl, C$_{2-6}$ alkynyl, C$_{3-10}$ carbocycle, and 3- to 10-membered heterocycle, wherein C$_{1-6}$ alkyl, C$_{2-6}$ alkenyl, C$_{2-6}$ alkynyl, C$_{3-10}$ carbocycle, and 3- to 10-membered heterocycle are optionally substituted with one, two, or three $R^{20}$;

$R^{17}$ and $R^{17a}$ are each independently selected at each occurrence from C$_{1-6}$ alkyl and C$_{3-6}$ cycloalkyl, wherein C$_{1-6}$ alkyl and C$_{3-6}$ cycloalkyl are optionally substituted with one, two or three $R^{20}$; or $R^{17}$ and $R^{17a}$, together with the phosphorous atom to which they are attached, form a 3- to 10-membered heterocycle;

$R^{20}$ is independently selected at each occurrence from halogen, oxo, =NH, —CN, C$_{1-6}$ alkyl, C$_{2-6}$ alkenyl, C$_{2-6}$ alkynyl, C$_{3-10}$ carbocycle, —CH$_2$—(C$_{3-10}$ carbocycle), 3- to 10-membered heterocycle, —CH$_2$-(3- to 10-membered heterocycle), —O$R^{21}$, —S$R^{21}$, —N($R^{22}$)($R^{23}$), —C(O)O$R^{22}$, —C(O)N($R^{22}$)($R^{23}$), —C(O)C(O)N($R^{22}$)($R^{23}$), —OC(O)N($R^{22}$)($R^{23}$), —N($R^{22}$)C(O)N($R^{22}$)($R^{23}$), —N($R^{24}$)C(O)O$R^{25}$, —N($R^{24}$)C(O)$R^{25}$, —N($R^{22}$)S(O)$_2$$R^{25}$, —C(O)$R^{25}$, —S(O)$_2$$R^{25}$, —S(O)$_2$N($R^{22}$)($R^{23}$), —OCH$_2$C(O)O$R^{22}$, and —OC(O)$R^{25}$, wherein C$_{1-6}$ alkyl, C$_{2-6}$ alkenyl, C$_{2-6}$ alkynyl, C$_{3-10}$ carbocycle, —CH$_2$—(C$_{3-10}$ carbocycle), 3- to 10-membered heterocycle, and —CH$_2$-(3- to 10-membered heterocycle) are optionally substituted with one, two, or three groups independently selected from halogen, oxo, =NH, —CN, C$_{1-6}$ alkyl, C$_{1-6}$ haloalkyl, C$_{1-6}$ alkoxy, C$_{1-6}$ haloalkoxy, —O$R^{21}$, —S$R^{21}$, —N($R^{22}$)($R^{23}$), —C(O)O$R^{22}$, —C(O)N($R^{22}$)($R^{23}$), —C(O)C(O)N($R^{22}$)($R^{23}$), —OC(O)N($R^{22}$)($R^{23}$), —N($R^{24}$)C(O)N($R^{22}$)($R^{23}$), —N($R^{24}$)C(O)

OR$^{25}$, —N(R$^{24}$)C(O)R$^{25}$, —N(R$^{22}$)S(O)$_2$R$^{25}$, —C(O)R$^{25}$, —S(O)$_2$R$^{25}$, —S(O)$_2$N(R$^{22}$)(R$^{23}$), and —OC(O)R$^{25}$;

R$^{21}$ is independently selected at each occurrence from H, C$_{1-6}$ alkyl, C$_{1-6}$ haloalkyl, C$_{2-6}$ alkenyl, C$_{2-6}$ alkynyl, C$_{3-10}$ carbocycle, and 3- to 10-membered heterocycle, wherein C$_{3-10}$ carbocycle and 3- to 10-membered heterocycle are optionally substituted with one, two, or three groups independently selected from halogen and C$_{1-6}$ alkyl;

R$^{22}$ is independently selected at each occurrence from H, C$_{1-6}$ alkyl, C$_{1-6}$ haloalkyl, C$_{2-6}$ alkenyl, C$_{2-6}$ alkynyl, C$_{3-10}$ carbocycle, and 3- to 10-membered heterocycle, wherein C$_{3-10}$ carbocycle and 3- to 10-membered heterocycle are optionally substituted with one, two, or three groups independently selected from halogen and C$_{1-6}$ alkyl;

R$^{23}$ is independently selected at each occurrence from H and C$_{1-6}$ alkyl;

R$^{24}$ is independently selected at each occurrence from H and C$_{1-6}$ alkyl;

R$^{25}$ is independently selected at each occurrence from C$_{1-6}$ alkyl, C$_{2-6}$ alkenyl, C$_{2-6}$ alkynyl, C$_{3-10}$ carbocycle, and 3- to 10-membered heterocycle, wherein C$_{1-6}$ alkyl, C$_{3-10}$ carbocycle, and 3- to 10-membered heterocycle are optionally substituted with one, two, or three groups independently selected from halogen, C$_{1-6}$ alkyl, C$_{1-6}$ haloalkyl, C$_{1-6}$ alkoxy, C$_{3-10}$ carbocycle, and 3- to 10-membered heterocycle; and ----- indicates a single or double bond such that all valences are satisfied.

In certain aspects, the present disclosure provides a compound of Formula (II-B) or (II-C):

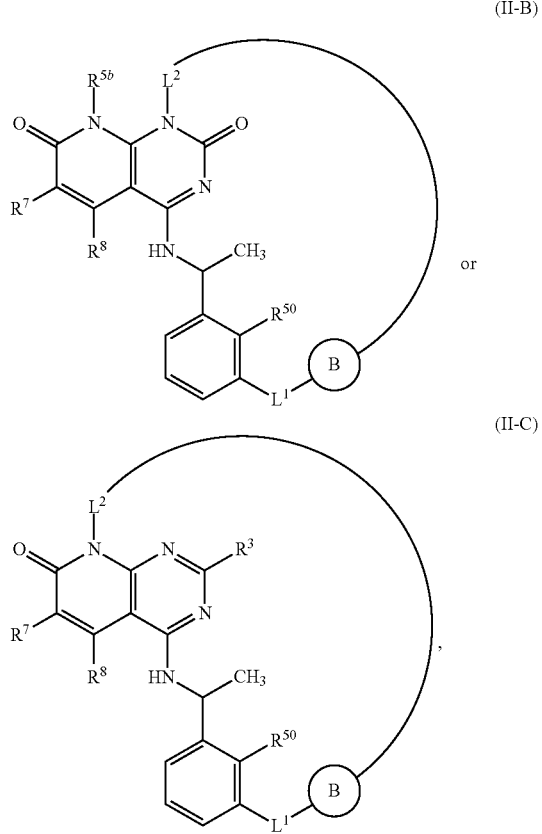

or a pharmaceutically acceptable salt or solvate thereof, wherein:

is absent or 4- to 8-membered heterocycle optionally substituted with one or more R$^{11a}$;

L$^1$ is C$_{1-3}$ haloalkylene;

L$^2$ is selected from C$_{5-10}$ alkylene, C$_{5-10}$ alkenylene, 5- to 10-membered heteroalkylene, and 5- to 10-membered heteroalkenylene, each of which is optionally substituted with one or more R$^{11b}$; or L$^2$ is -L$^3$-D-L$^4$-;

L$^3$ is selected from C$_{1-8}$ alkylene, C$_{1-8}$ alkenylene, 2- to 8-membered heteroalkylene, and 2- to 8-membered heteroalkenylene, each of which is optionally substituted with one or more R$^{11b}$;

D is selected from C$_{3-10}$ carbocycle and 3- to 10-membered heterocycle, each of which is optionally substituted with one or more R$^{11d}$;

L$^4$ is selected from C$_{1-8}$ alkylene, C$_{1-8}$ alkenylene, 2- to 8-membered heteroalkylene, and 2- to 8-membered heteroalkenylene, each of which is optionally substituted with one or more R$^{11b}$;

R$^3$ and R$^8$ are each independently selected from hydrogen and —CH$_3$;

R$^7$ is selected from C$_{3-8}$ carbocycle and 3- to 8-membered heterocycle, each of which is optionally substituted with one, two, or three R$^{20}$;

R$^{5b}$ is selected from hydrogen and C$_{1-3}$ alkyl;

R$^{50}$ is selected from hydrogen and halogen;

R$^{11a}$ and R$^{11d}$ are each independently selected at each occurrence from halogen, —CN, C$_{1-6}$ alkyl, C$_{2-6}$ alkenyl, C$_{2-6}$ alkynyl, C$_{3-10}$ carbocycle, 3- to 10-membered heterocycle, —OR$^{12}$, —SR$^{12}$, —N(R$^{12}$)(R$^{13}$), —C(O)OR$^{12}$, —OC(O)N(R$^{12}$)(R$^{13}$), —N(R$^{14}$)C(O)N(R$^{12}$)(R$^{13}$), —N(R$^{14}$)C(O)OR$^{15}$, —N(R$^{14}$)S(O)$_2$R$^{15}$, —C(O)R$^{15}$, —S(O)R$^{15}$, —OC(O)R$^{15}$, —C(O)N(R$^{12}$)(R$^{13}$), —C(O)C(O)N(R$^{12}$)(R$^{13}$), —N(R$^{14}$)C(O)R$^{15}$, —S(O)$_2$R$^{15}$, —S(O)$_2$N(R$^{12}$)(R$^{13}$), —S(=O)(=NH)N(R$^{12}$)(R$^{13}$), —CH$_2$C(O)N(R$^{12}$)(R$^{13}$), —CH$_2$N(R$^{14}$)C(O)R$^{15}$, —CH$_2$S(O)$_2$R$^{15}$, —CH$_2$S(O)$_2$N(R$^{12}$)(R$^{13}$), —CH$_2$N(R$^{12}$)S(O)$_2$(R$^{13}$), and —P(O)(R$^{17}$)(R$^{17a}$), wherein C$_{1-6}$ alkyl, C$_{2-6}$ alkenyl, C$_{2-6}$ alkynyl, C$_{3-10}$ carbocycle, and 3- to 10-membered heterocycle are optionally substituted with one, two, or three R$^{20}$;

R$^{11b}$ is independently selected at each occurrence from halogen, oxo, —CN, C$_{1-6}$ alkyl, C$_{2-6}$ alkenyl, C$_{2-6}$ alkynyl, C$_{3-10}$ carbocycle, 3- to 10-membered heterocycle, —OR$^{12}$, —SR$^{12}$, —N(R$^{12}$)(R$^{13}$), —C(O)OR$^{12}$, —OC(O)N(R$^{12}$)(R$^{13}$), —N(R$^{14}$)C(O)N(R$^{12}$)(R$^{13}$), —N(R$^{14}$)C(O)OR$^{15}$, —N(R$^{14}$)S(O)$_2$R$^{15}$, —C(O)R$^{15}$, —S(O)R$^{15}$, —OC(O)R$^{15}$, —C(O)N(R$^{12}$)(R$^{13}$), —C(O)C(O)N(R$^{12}$)(R$^{13}$), —N(R$^{14}$)C(O)R$^{15}$, —S(O)$_2$R$^{15}$, —S(O)$_2$N(R$^{12}$)(R$^{13}$), —S(=O)(=NH)N(R$^{12}$)(R$^{13}$), —CH$_2$C(O)N(R$^{12}$)(R$^{13}$), —CH$_2$N(R$^{14}$)C(O)R$^{15}$, —CH$_2$S(O)$_2$R$^{15}$, —CH$_2$S(O)$_2$N(R$^{12}$)(R$^{13}$), —CH$_2$N(R$^{12}$)S(O)$_2$(R$^{13}$), and —P(O)(R$^{17}$)(R$^{17a}$), wherein C$_{1-6}$ alkyl, C$_{2-6}$ alkenyl, C$_{2-6}$ alkynyl, C$_{3-10}$ carbocycle, and 3- to 10-membered heterocycle are optionally substituted with one, two, or three R$^{20}$;

R$^{12}$ is independently selected at each occurrence from hydrogen, C$_{1-6}$ alkyl, C$_{1-6}$ haloalkyl, C$_{2-6}$ alkenyl, C$_{2-6}$ alkynyl, C$_{3-10}$ carbocycle, and 3- to 10-membered heterocycle, wherein C$_{1-6}$ alkyl, C$_{2-6}$ alkenyl, C$_{2-6}$ alkynyl, $C_{3-10}$ carbocycle, and 3- to 10-membered heterocycle are optionally substituted with one, two, or three $R^{20}$;

$R^{13}$ is independently selected at each occurrence from hydrogen, $C_{1-6}$ alkyl, and $C_{1-6}$ haloalkyl; or $R^{12}$ and $R^{13}$, together with the nitrogen atom to which they are attached, form a 3- to 10-membered heterocycle optionally substituted with one, two, or three $R^{20}$;

$R^{14}$ is independently selected at each occurrence from hydrogen, $C_{1-6}$ alkyl, and $C_{1-6}$ haloalkyl;

$R^{15}$ is independently selected at each occurrence from $C_{1-6}$ alkyl, $C_{2-6}$ alkenyl, $C_{2-6}$ alkynyl, $C_{3-10}$ carbocycle, and 3- to 10-membered heterocycle, wherein $C_{1-6}$ alkyl, $C_{2-6}$ alkenyl, $C_{2-6}$ alkynyl, $C_{3-10}$ carbocycle, and 3- to 10-membered heterocycle are optionally substituted with one, two, or three $R^{20}$;

$R^{17}$ and $R^{17a}$ are each independently selected at each occurrence from $C_{1-6}$ alkyl and $C_{3-6}$ cycloalkyl, wherein $C_{1-6}$ alkyl and $C_{3-6}$ cycloalkyl are optionally substituted with one, two or three $R^{20}$; or $R^{17}$ and $R^{17a}$, together with the phosphorous atom to which they are attached, form a 3- to 10-membered heterocycle;

$R^{20}$ is independently selected at each occurrence from halogen, oxo, =NH, —CN, $C_{1-6}$ alkyl, $C_{2-6}$ alkenyl, $C_{2-6}$ alkynyl, $C_{3-10}$ carbocycle, —CH$_2$—($C_{3-10}$ carbocycle), 3- to 10-membered heterocycle, —CH$_2$-(3- to 10-membered heterocycle), —OR$^{21}$, —SR$^{21}$, —N(R$^{22}$)(R$^{23}$), —C(O)OR$^{22}$, —C(O)N(R$^{22}$)(R$^{23}$), —C(O)C(O)N(R$^{22}$)(R$^{23}$), —OC(O)N(R$^{22}$)(R$^{23}$), —N(R$^{22}$)C(O)N(R$^{22}$)(R$^{23}$), —N(R$^{24}$)C(O)OR$^{25}$, —N(R$^{24}$)C(O)R$^{25}$, —N(R$^{22}$)S(O)$_2$R$^{25}$, —C(O)R$^{25}$, —S(O)$_2$R$^{25}$, —S(O)$_2$N(R$^{22}$)(R$^{23}$), —OCH$_2$C(O)OR$^{22}$, and —OC(O)R$^{25}$, wherein $C_{1-6}$ alkyl, $C_{2-6}$ alkenyl, $C_{2-6}$ alkynyl, $C_{3-10}$ carbocycle, —CH$_2$—($C_{3-10}$ carbocycle), 3- to 10-membered heterocycle, and —CH$_2$-(3- to 10-membered heterocycle) are optionally substituted with one, two, or three groups independently selected from halogen, oxo, =NH, —CN, $C_{1-6}$ alkyl, $C_{1-6}$ haloalkyl, $C_{1-6}$ alkoxy, $C_{1-6}$ haloalkoxy, —OR$^{21}$, —SR$^{21}$, —N(R$^{22}$)(R$^{23}$), —C(O)OR$^{22}$, —C(O)N(R$^{22}$)(R$^{23}$), —C(O)C(O)N(R$^{22}$)(R$^{23}$), —OC(O)N(R$^{22}$)(R$^{23}$), —N(R$^{24}$)C(O)N(R$^{22}$)(R$^{23}$), —N(R$^{24}$)C(O)OR$^{25}$, —N(R$^{24}$)C(O)R$^{25}$, —N(R$^{22}$)S(O)$_2$R$^{25}$, —C(O)R$^{25}$, —S(O)$_2$R$^{25}$, —S(O)$_2$N(R$^{22}$)(R$^{23}$), and —OC(O)R$^{25}$;

$R^{21}$ is independently selected at each occurrence from hydrogen, $C_{1-6}$ alkyl, $C_{1-6}$ haloalkyl, $C_{2-6}$ alkenyl, $C_{2-6}$ alkynyl, $C_{3-10}$ carbocycle, and 3- to 10-membered heterocycle, wherein $C_{3-10}$ carbocycle and 3- to 10-membered heterocycle are optionally substituted with one, two, or three groups independently selected from halogen and $C_{1-6}$ alkyl;

$R^{22}$ is independently selected at each occurrence from hydrogen, $C_{1-6}$ alkyl, $C_{1-6}$ haloalkyl, $C_{2-6}$ alkenyl, $C_{2-6}$ alkynyl, $C_{3-10}$ carbocycle, and 3- to 10-membered heterocycle, wherein $C_{3-10}$ carbocycle and 3- to 10-membered heterocycle are optionally substituted with one, two, or three groups independently selected from halogen and $C_{1-6}$ alkyl;

$R^{23}$ is independently selected at each occurrence from hydrogen and $C_{1-6}$ alkyl;

$R^{24}$ is independently selected at each occurrence from hydrogen and $C_{1-6}$ alkyl; and $R^{25}$ is independently selected at each occurrence from $C_{1-6}$ alkyl, $C_{2-6}$ alkenyl, $C_{2-6}$ alkynyl, $C_{3-10}$ carbocycle, and 3- to 10-membered heterocycle, wherein $C_{1-6}$ alkyl, $C_{3-10}$ carbocycle, and 3- to 10-membered heterocycle are optionally substituted with one, two, or three groups independently selected from halogen, $C_{1-6}$ alkyl, $C_{1-6}$ haloalkyl, $C_{1-6}$ alkoxy, $C_{3-10}$ carbocycle, and 3- to 10-membered heterocycle.

In some embodiments, the present disclosure provides a compound of Formula (II-B) or (II-C):

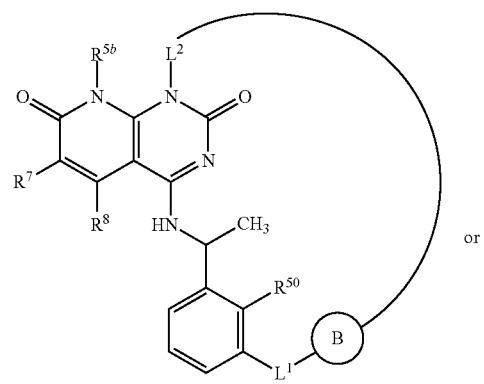

(II-B)

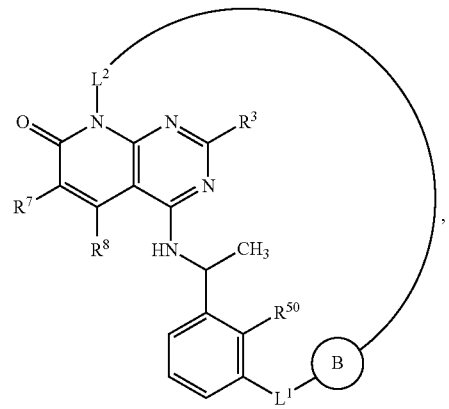

(II-C)

or a pharmaceutically acceptable salt or solvate thereof, wherein:

B is absent or 4- to 8-membered heterocycle optionally substituted with one or more $R^{11a}$;

$L^1$ is $C_{1-3}$ haloalkylene;

$L^2$ is selected from $C_{5-10}$ alkylene, $C_{5-10}$ alkenylene, 5- to 10-membered heteroalkylene, and 5- to 10-membered heteroalkenylene, each of which is optionally substituted with one or more $R^{11b}$;

$R^3$, $R^{5b}$, and $R^8$ are each independently selected from hydrogen and —CH$_3$;

$R^7$ is selected from $C_{3-8}$ carbocycle and 3- to 8-membered heterocycle, each of which is optionally substituted with one, two, or three $R^{20}$;

$R^{50}$ is selected from hydrogen and halogen;

$R^{11a}$ is independently selected at each occurrence from halogen, $C_{1-3}$ alkyl, and $C_{1-3}$ haloalkyl;

$R^{11b}$ is independently selected at each occurrence from halogen, oxo, —CN, $C_{1-3}$ alkyl, and —OH; and $R^{20}$ is independently selected at each occurrence from halogen, oxo, —CN, and $C_{1-6}$ alkyl.

In some embodiments, the present disclosure provides a compound of Formula (II-C):

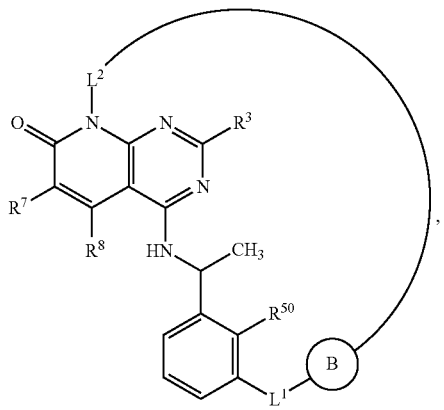

(II-C)

or a pharmaceutically acceptable salt or solvate thereof, wherein:

is absent or 4- to 8-membered heterocycle optionally substituted with one or more $R^{11a}$;

$L^1$ is $C_{1-3}$ haloalkylene;

$L^2$ is selected from $C_{5-10}$ alkylene, $C_{5-10}$ alkenylene, 5- to 10-membered heteroalkylene, and 5- to 10-membered heteroalkenylene, each of which is optionally substituted with one or more $R^{11b}$;

$R^3$ is hydrogen;

$R^8$ is selected from hydrogen and —CH$_3$;

$R^7$ is selected from

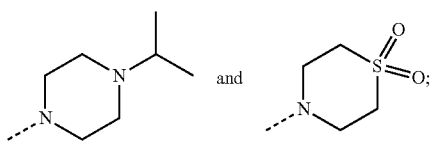

$R^{50}$ is selected from hydrogen and halogen;

$R^{11a}$ is independently selected at each occurrence from halogen, $C_{1-3}$ alkyl, and $C_{1-3}$ haloalkyl;

$R^{11b}$ is independently selected at each occurrence from halogen, oxo, —CN, $C_{1-3}$ alkyl, and —OH; and $R^{20}$ is independently selected at each occurrence from halogen, oxo, —CN, and $C_{1-6}$ alkyl.

In some embodiments, the present disclosure provides a compound of Formula (II-C):

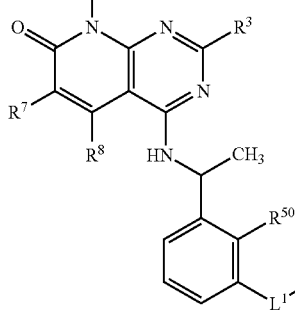

(II-C)

or a pharmaceutically acceptable salt or solvate thereof, wherein:

is 4- to 8-membered heterocycle optionally substituted with one or more $R^{11a}$;

$L^1$ is $C_{1-3}$ haloalkylene;

$L^2$ is selected from $C_{5-10}$ alkylene, $C_{5-10}$ alkenylene, 5- to 10-membered heteroalkylene, and 5- to 10-membered heteroalkenylene, each of which is optionally substituted with one or more $R^{11b}$.

$R^3$ is selected from hydrogen and —CH$_3$;

$R^8$ is selected from hydrogen and —CH$_3$;

$R^7$ is selected from

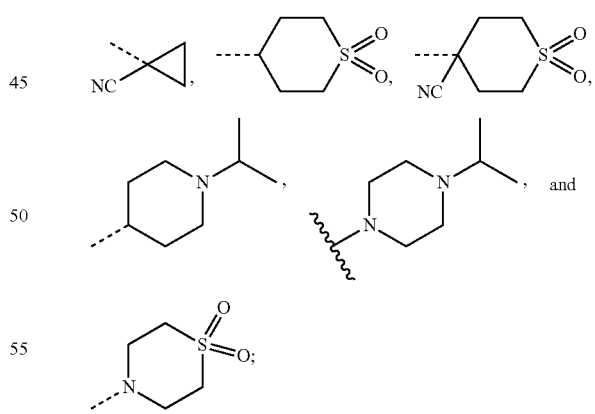

$R^{50}$ is selected from hydrogen and halogen;

$R^{11a}$ is independently selected at each occurrence from halogen, $C_{1-3}$ alkyl, and $C_{1-3}$ haloalkyl; and $R^{11b}$ is independently selected at each occurrence from halogen, oxo, —CN, $C_{1-3}$ alkyl, and —OH.

In some embodiments, the present disclosure provides a compound of Formula (II-C):

(II-C)

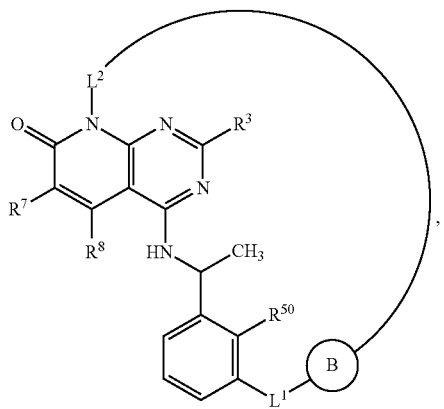

or a pharmaceutically acceptable salt or solvate thereof, wherein:

is 4- to 6-membered heterocycle;
$L^1$ is $C_{1-3}$ haloalkylene;
$L^2$ is selected from $C_{5-10}$ alkylene, $C_{5-10}$ alkenylene, and 5- to 10-membered heteroalkylene;
$R^3$ is selected from hydrogen and —$CH_3$;
$R^8$ is hydrogen;
$R^7$ is selected from

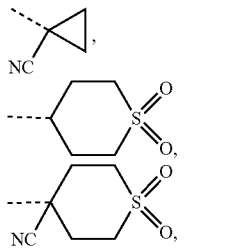

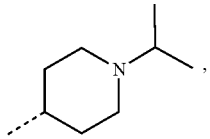

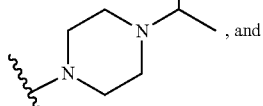

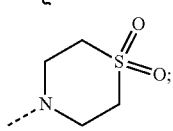

and
$R^{50}$ is selected from hydrogen and halogen.

In some embodiments, the present disclosure provides a compound of Formula (II-C):

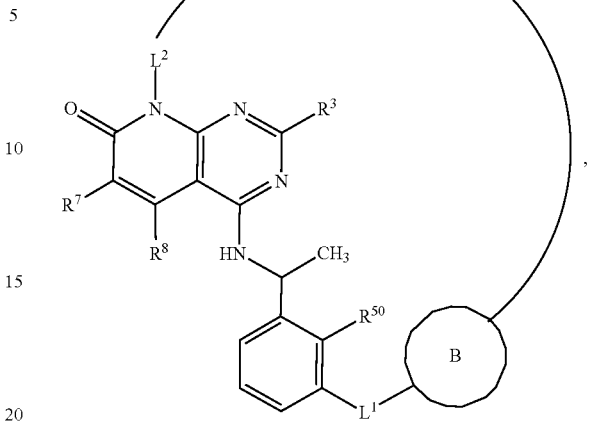

or a pharmaceutically acceptable salt or solvate thereof, wherein:

is

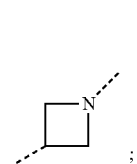

;

$L^1$ is —$CF_2CH_2$—;
$L^2$ is 5- to 10-membered heteroalkylene, wherein the heteroalkylene comprises one oxygen atom;
$R^3$ is selected from hydrogen and —$CH_3$;
$R^8$ is hydrogen;
$R^7$ is selected from

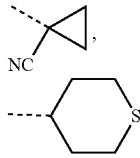

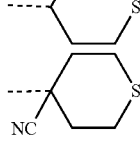

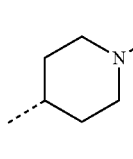

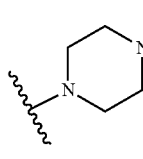

, and

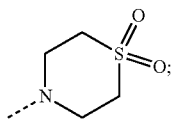

and

R⁵⁰ is selected from hydrogen and halogen.

In some embodiments, the present disclosure provides a compound of Formula (II-C):

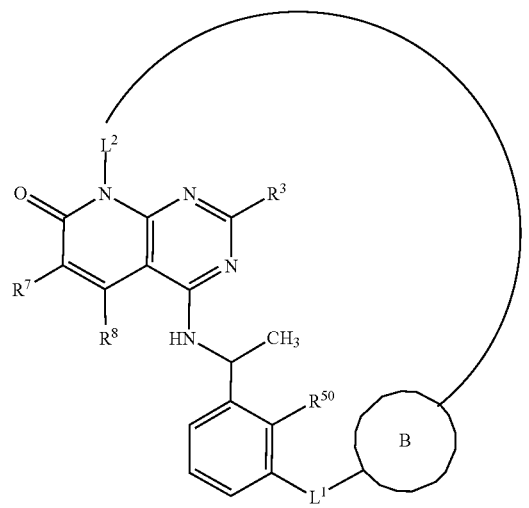

(II-C)

or a pharmaceutically acceptable salt or solvate thereof, wherein:

is

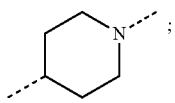

L¹ is —CF₂—;
L² is selected from $C_{5-10}$ alkenylene;
R³ is selected from hydrogen and —CH₃;
R⁸ is hydrogen;
R⁷ is selected from

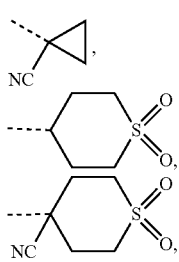

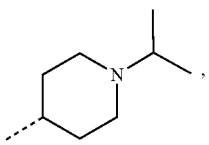

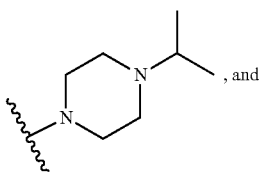

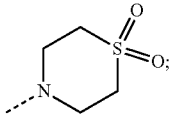

and

R⁵⁰ is selected from hydrogen and halogen.

In some embodiments, a compound of Formula (II-B) is a compound of the formula:

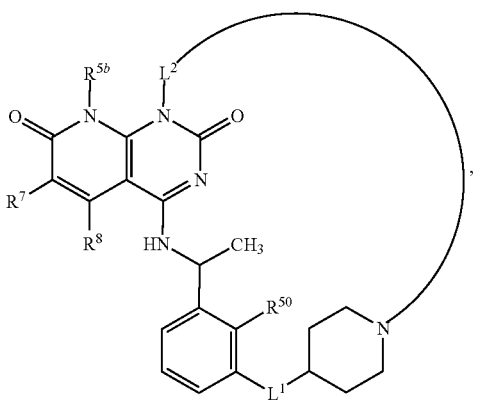

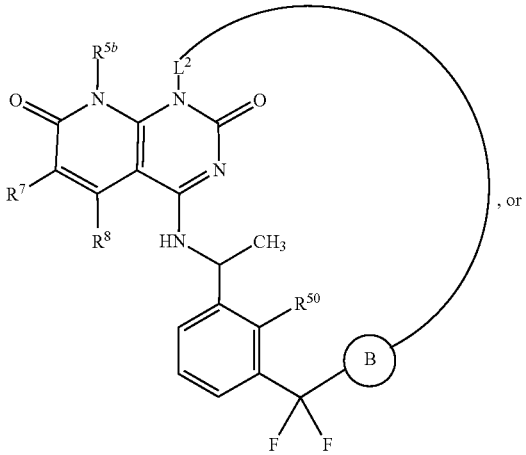

-continued

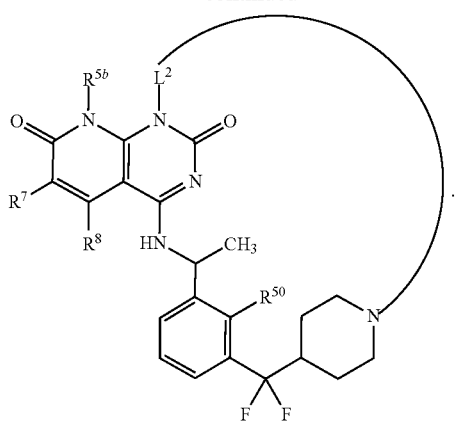

In some embodiments, $R^{5b}$ is —CH$_3$; $R^8$ is hydrogen; and $R^{50}$ is selected from hydrogen and fluoro. In some embodiments, $R^{5b}$ is —CH$_3$; $R^8$ is hydrogen; and $R^{50}$ is hydrogen. In some embodiments, $R^{5b}$ is —CH$_3$; $R^8$ is hydrogen; and $R^{50}$ is fluoro. In some embodiments, $R^7$ is selected from

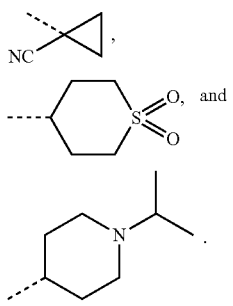

In some embodiments, $R^{5b}$ is —CH$_3$; $R^8$ is hydrogen; $R^{50}$ is hydrogen; and $R^7$ is selected from

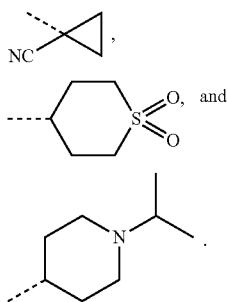

In some embodiments, $R^{5b}$ is —CH$_3$; $R^8$ is hydrogen; $R^{50}$ is fluoro; and $R^7$ is selected from

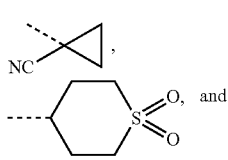

-continued

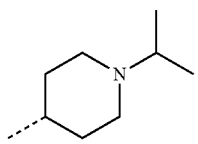

In some embodiments, $R^{5b}$ is —CH$_3$; $R^8$ is hydrogen; $R^{50}$ is selected from hydrogen and fluoro; and $R^7$ is

In some embodiments, $R^{5b}$ is —CH$_3$; $R^8$ is hydrogen; $R^{50}$ is selected from hydrogen and fluoro; and $R^7$ is

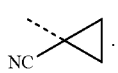

In some embodiments, $R^{5b}$ is —CH$_3$; $R^8$ is hydrogen; $R^{50}$ is selected from hydrogen and fluoro; and $R^7$ is

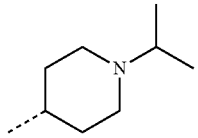

In some embodiments, a compound of Formula (II-C) is a compound of the formula:

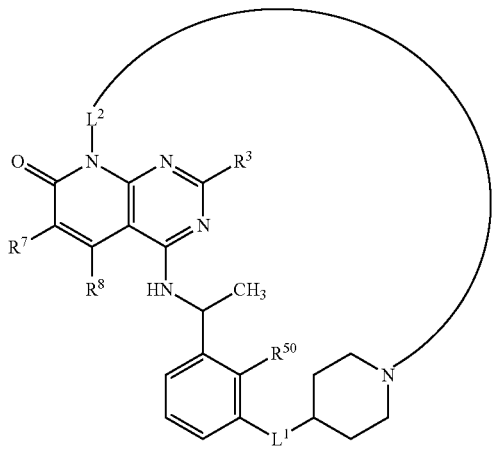

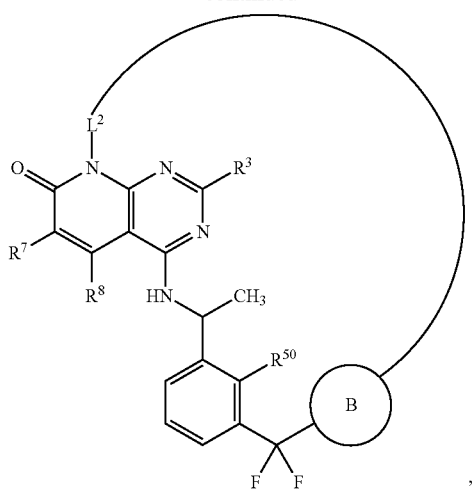

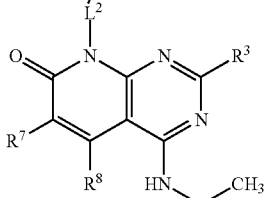, or

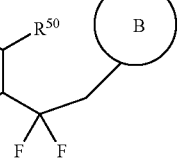

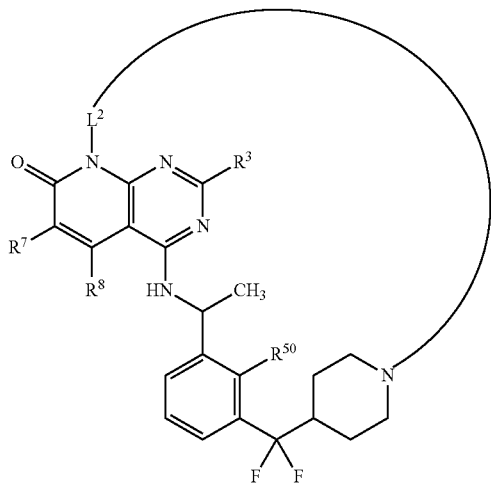

In some embodiments, a compound of Formula (II-C) is a compound of the formula:

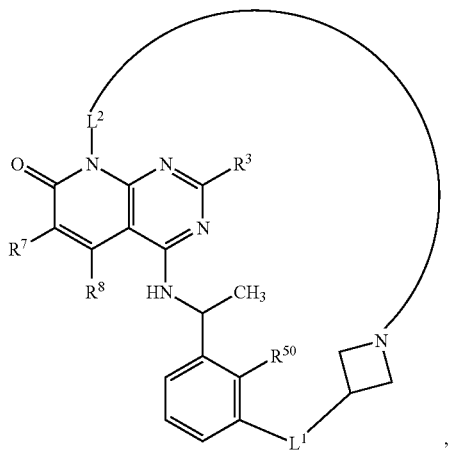

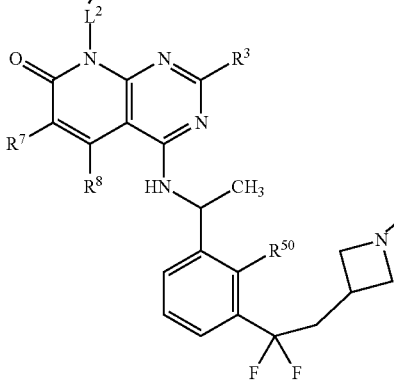, or

In some embodiments, $R^3$ is selected from hydrogen and —CH$_3$; $R^8$ is hydrogen; and $R^{50}$ is selected from hydrogen and fluoro. In some embodiments, $R^3$ is selected from hydrogen and —CH$_3$; $R^8$ is hydrogen; and $R^{50}$ is hydrogen. In some embodiments, $R^3$ is selected from hydrogen and —CH$_3$; $R^8$ is hydrogen; and $R^{50}$ is fluoro. In some embodiments, $R^3$ is hydrogen; $R^8$ is hydrogen; and $R^{50}$ is hydrogen. In some embodiments, $R^3$ is hydrogen; $R^8$ is hydrogen; and $R^{50}$ is fluoro. In some embodiments, $R^3$ is —CH$_3$; $R^8$ is hydrogen; and $R^{50}$ is hydrogen. In some embodiments, $R^3$ is —CH$_3$; $R^1$ is hydrogen; and $R^{50}$ is fluoro. In some embodiments, $R^7$ is selected from

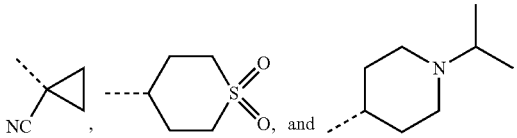

In some embodiments, $R^3$ is selected from hydrogen and —CH$_3$; $R^8$ is hydrogen; $R^{50}$ is hydrogen; and $R^7$ is selected from

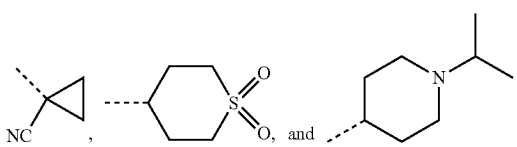

In some embodiments, R³ is selected from hydrogen and —CH₃; R⁸ is hydrogen; R⁵⁰ is fluoro; and R⁷ is selected from

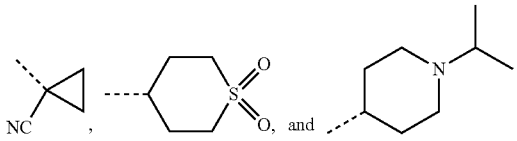

In some embodiments, R³ is hydrogen; R⁸ is hydrogen; R⁵⁰ is selected from hydrogen and fluoro; and R⁷ is selected from

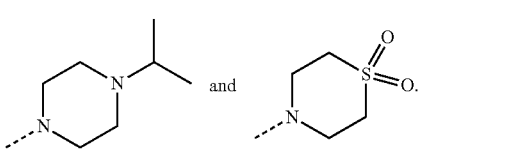

In some embodiments, R³ is hydrogen; R⁸ is hydrogen; R⁵⁰ is hydrogen; and R⁷ is selected from

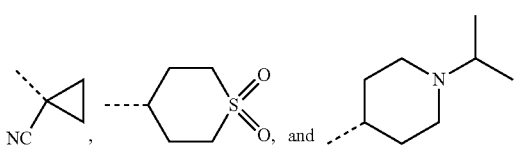

In some embodiments, R³ is hydrogen; R⁸ is hydrogen; R⁵⁰ is fluoro; and R⁷ is selected from

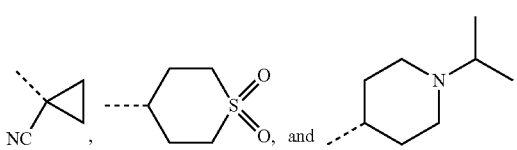

In some embodiments, R³ is —CH₃; R⁸ is hydrogen; R⁵⁰ is hydrogen; and R⁷ is selected from

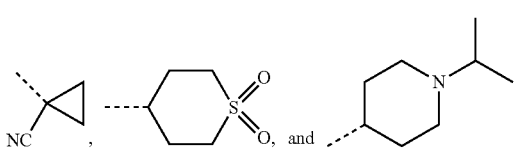

In some embodiments, R³ is —CH₃; R⁸ is hydrogen; R⁵⁰ is fluoro; and R⁷ is selected from

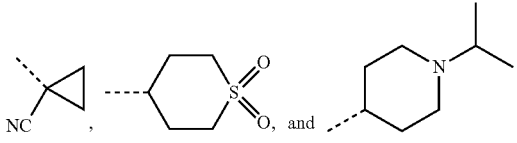

In some embodiments, R³ is selected from hydrogen and —CH₃; R⁸ is hydrogen; R⁵⁰ is selected from hydrogen and fluoro; and R⁷ is

In some embodiments, R³ is selected from hydrogen and —CH₃; R⁸ is hydrogen; R⁵⁰ is selected from hydrogen and fluoro; and R⁷ is

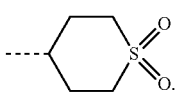

In some embodiments, R³ is selected from hydrogen and —CH₃; R⁸ is hydrogen; R⁵⁰ is selected from hydrogen and fluoro; and R⁷ is

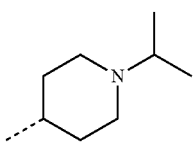

Embodiments disclosed herein that refer to a compound of Formula (I), (I-A), (I-B), (I-B1), (I-B2), (I-C), (I-C1), (I-C2), (I-C3), (I-D), (I-D1), (I-D2), (I-E), and/or (I-E1) are also intended to apply to a compound of Formula (II-B), (II-C), and (III) unless the context of the embodiment clearly dictates otherwise (e.g., the embodiment refers solely to a variable not present in the compound of Formula (II-B), (II-C), or (III), such as R¹).

Also provided is a compound selected from:

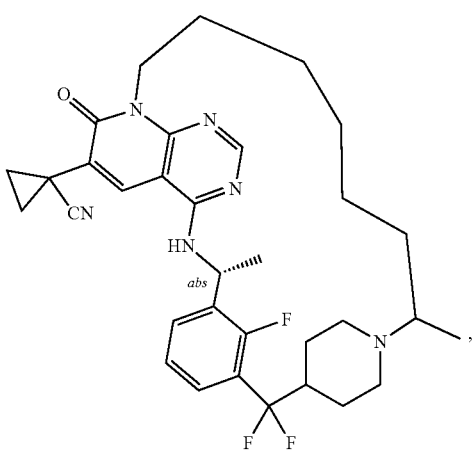

161
-continued
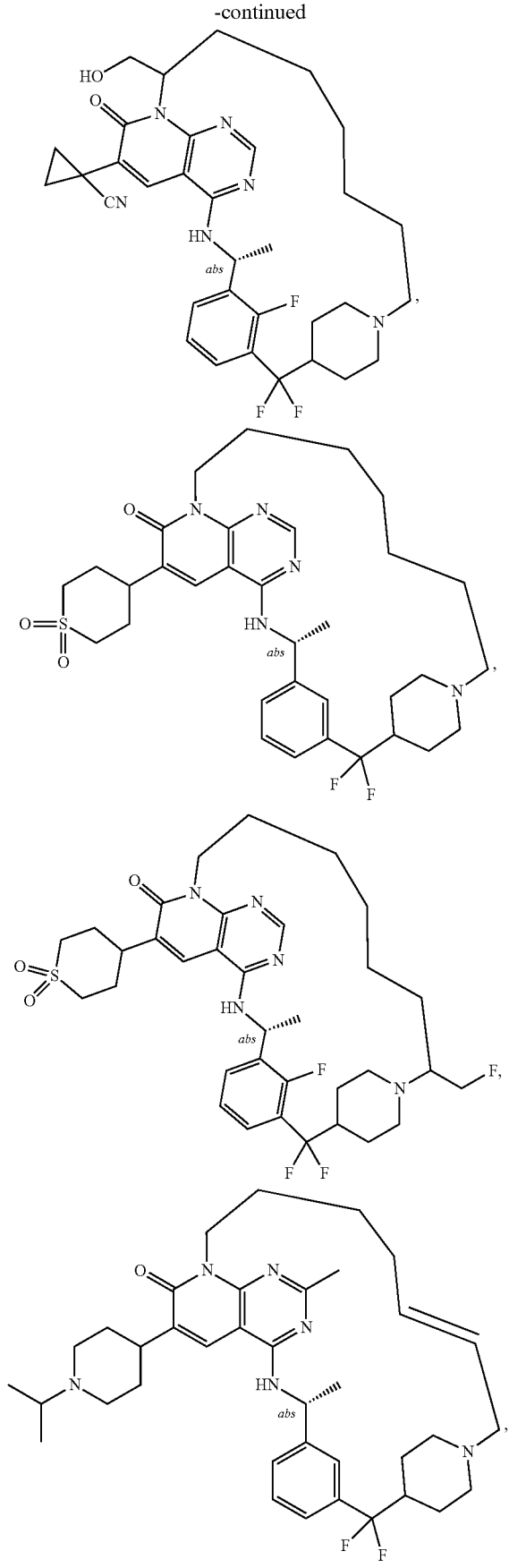
162
-continued
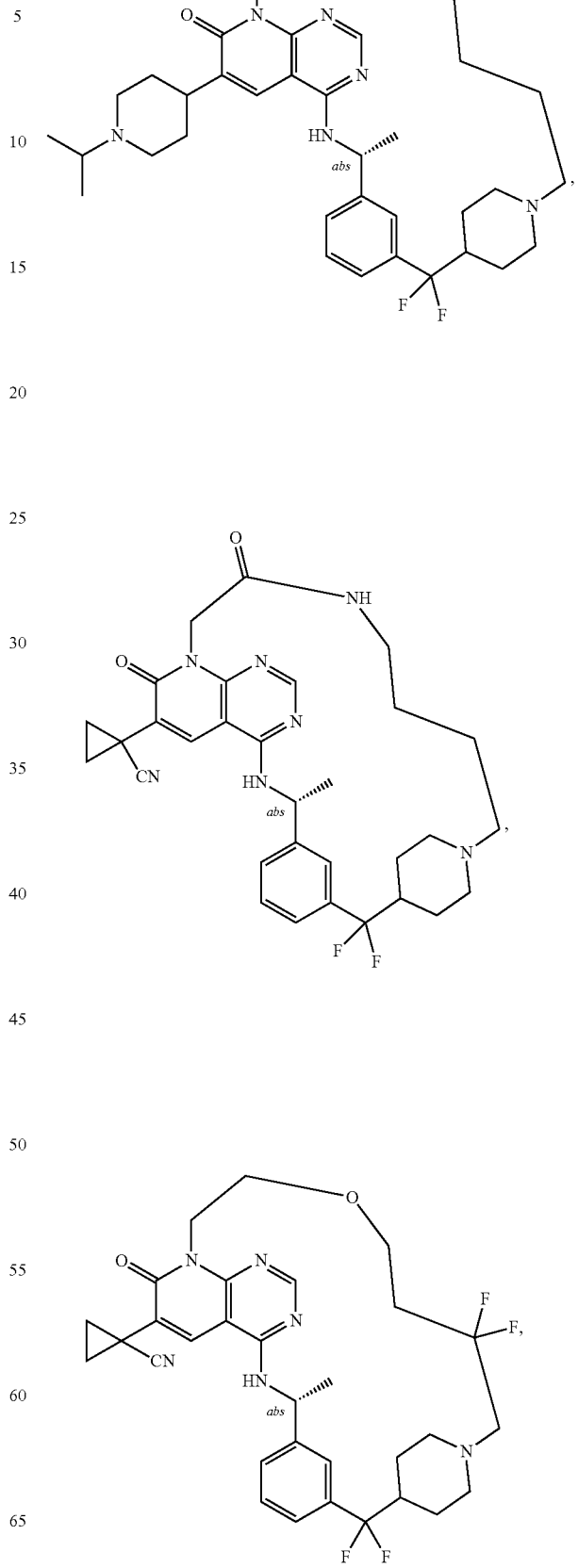

163
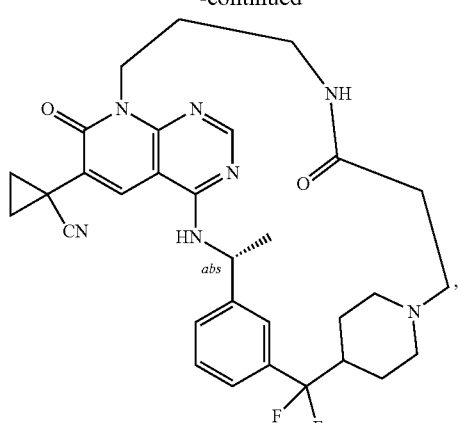
164
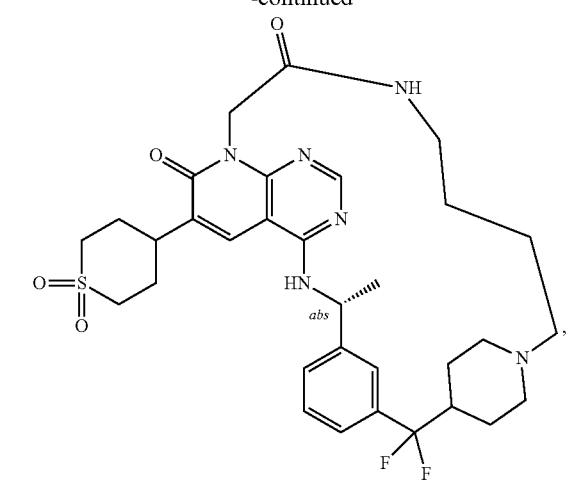
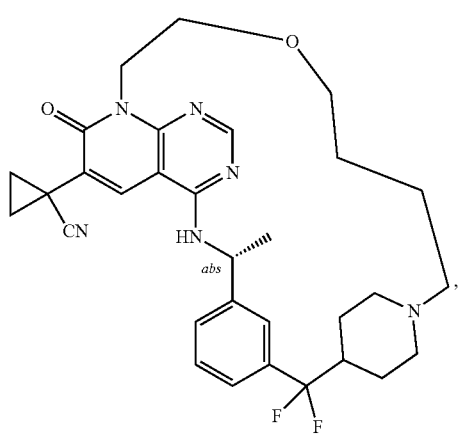
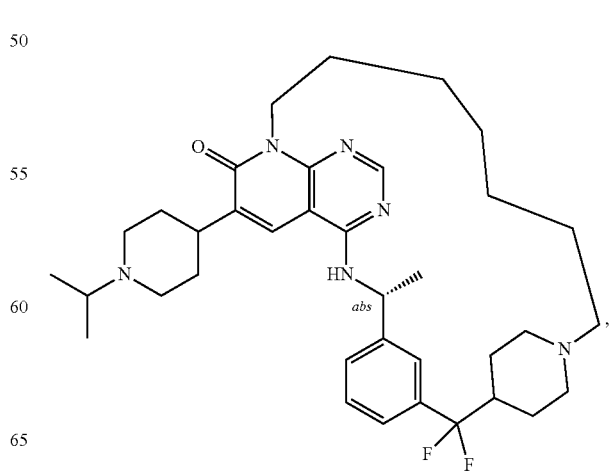
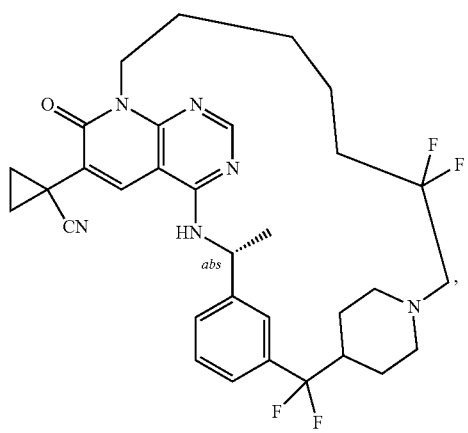

165
-continued
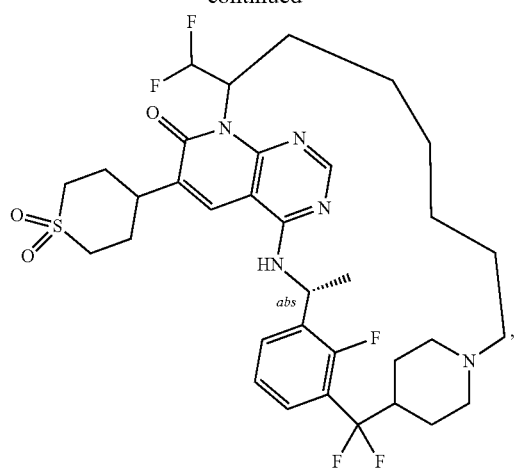
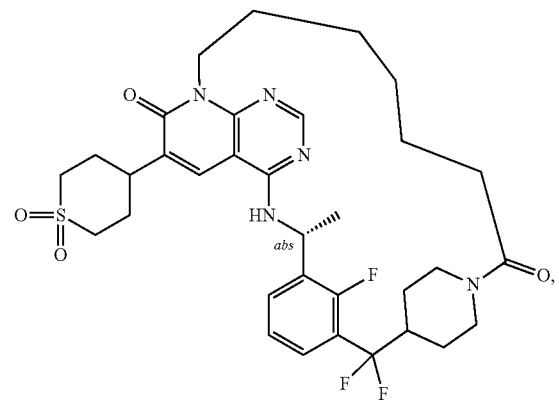
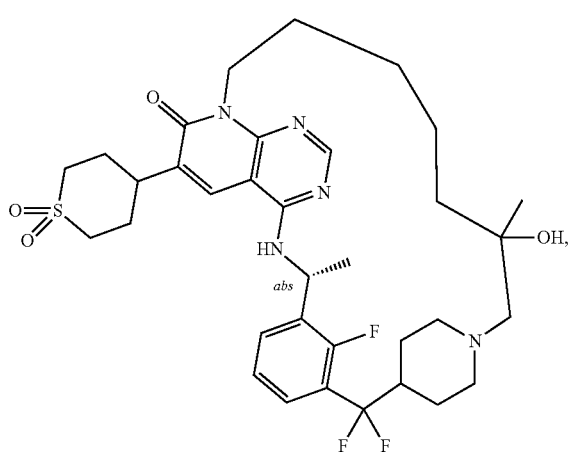
166
-continued
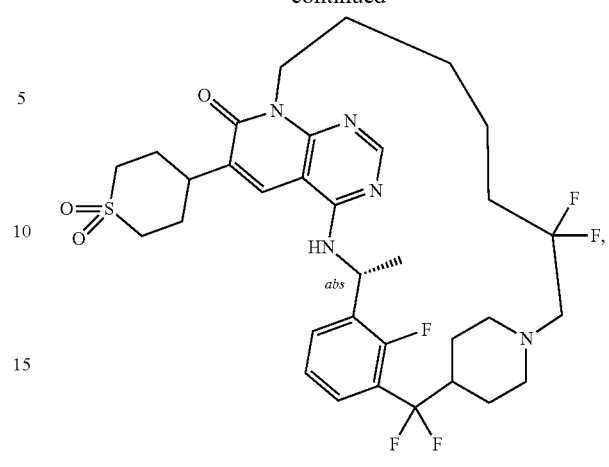
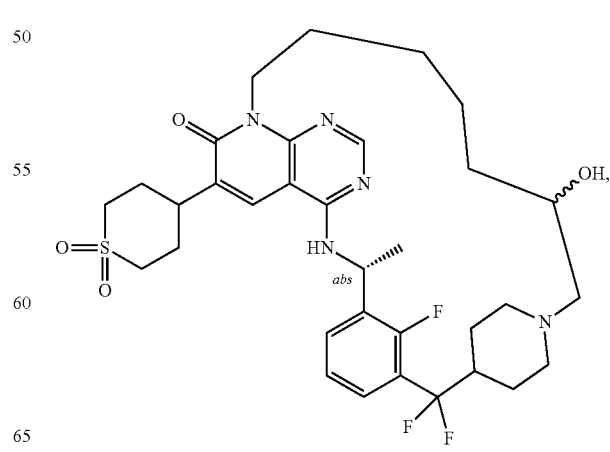

167
-continued
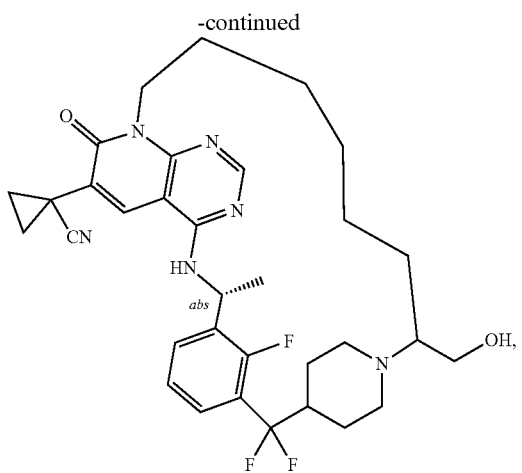
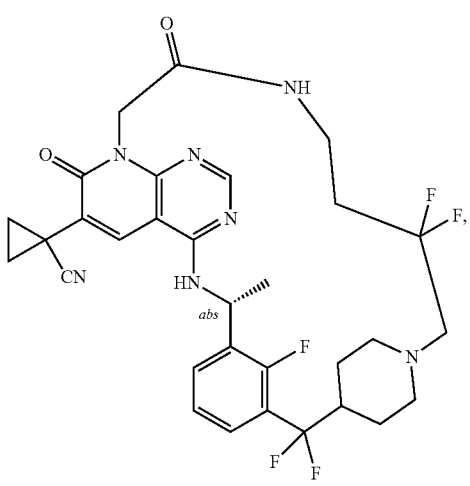
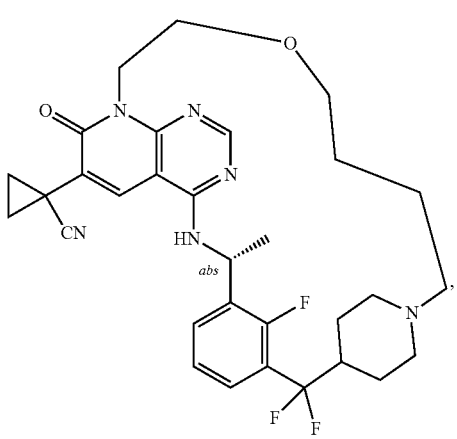
168
-continued
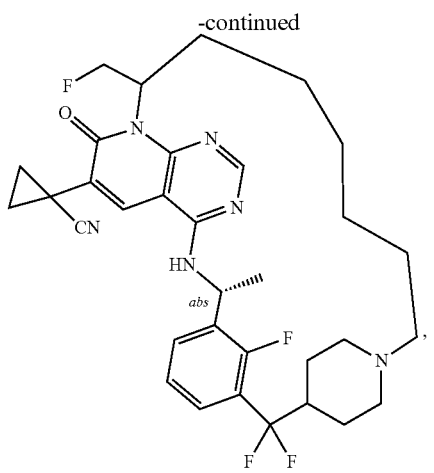
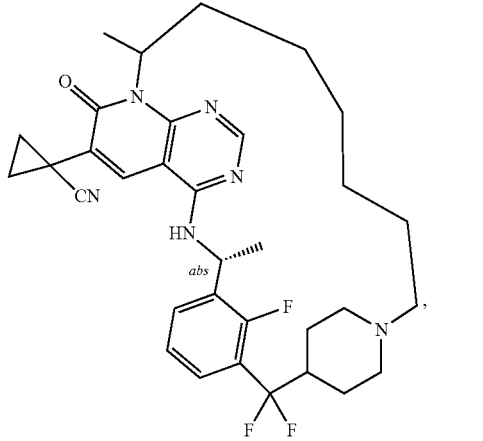
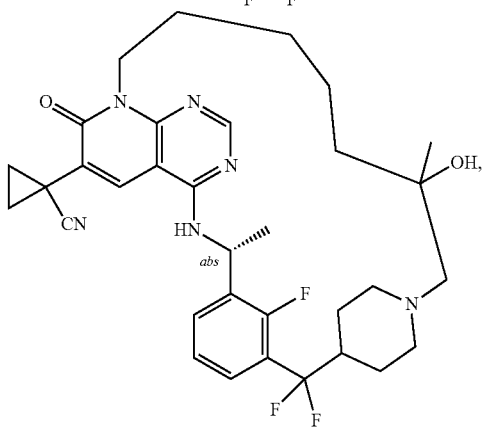
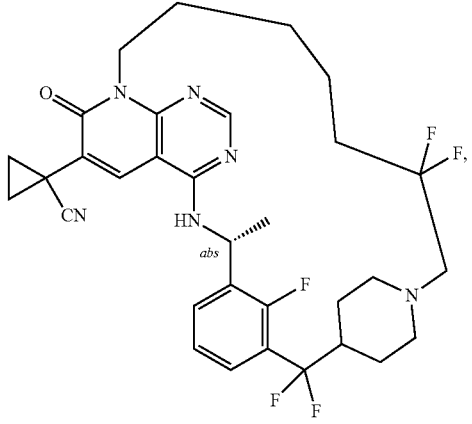

169
-continued
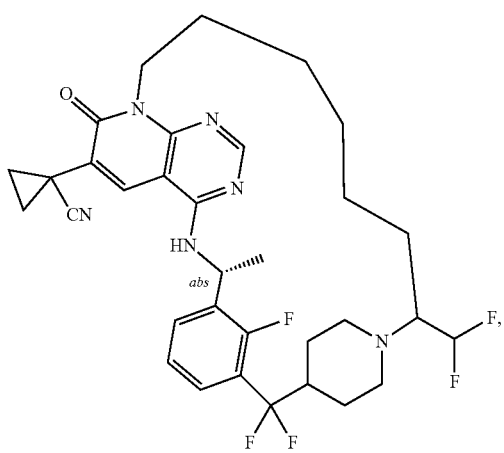
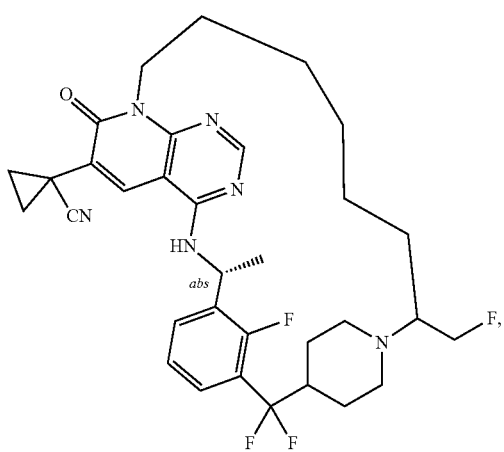
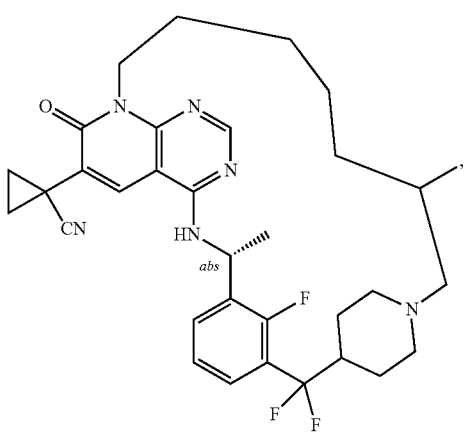
170
-continued
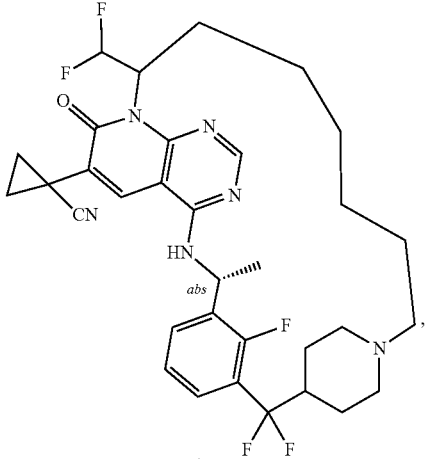
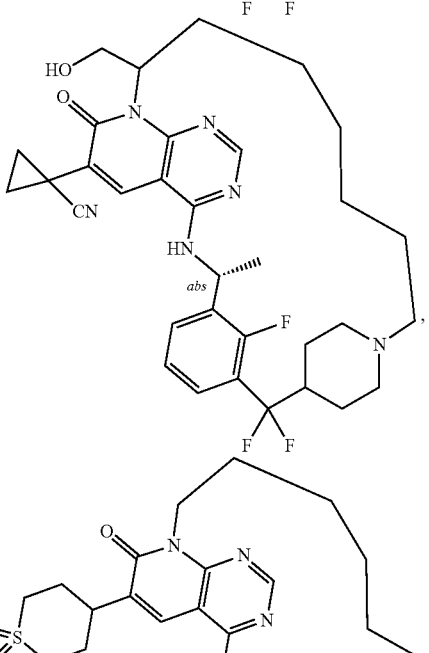
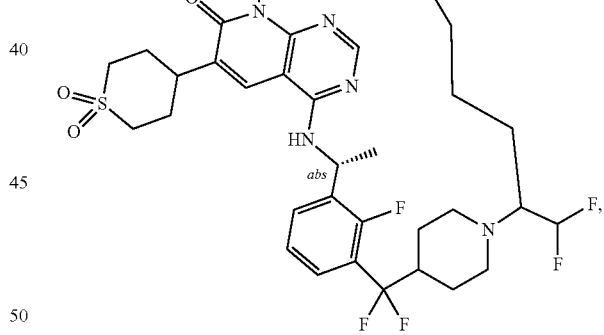
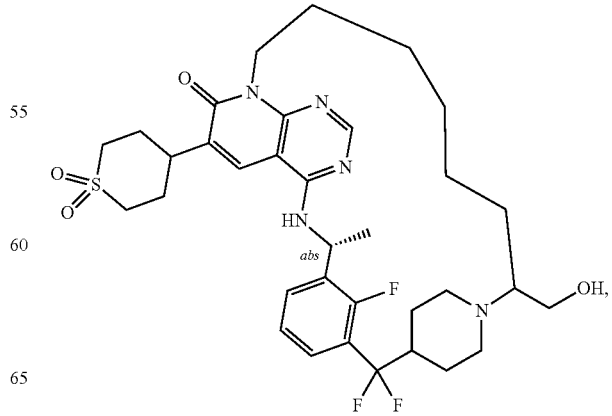

171
-continued
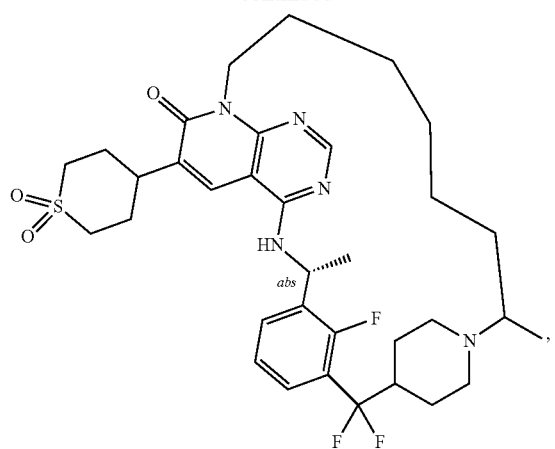
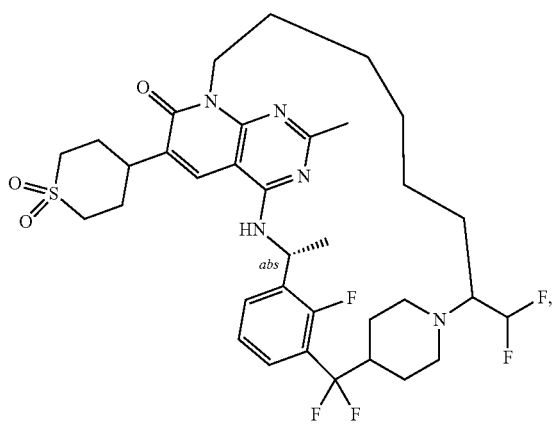
172
-continued
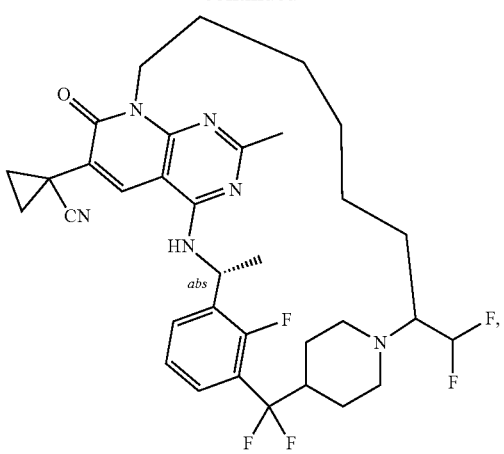
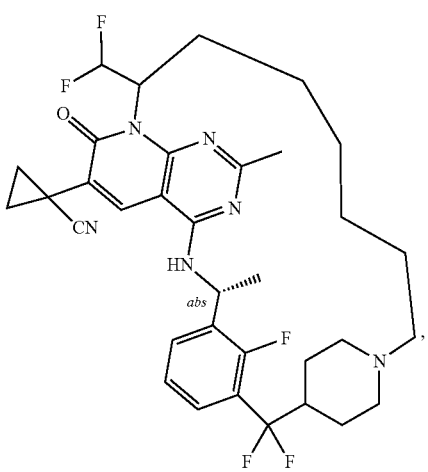

173
-continued
174
-continued
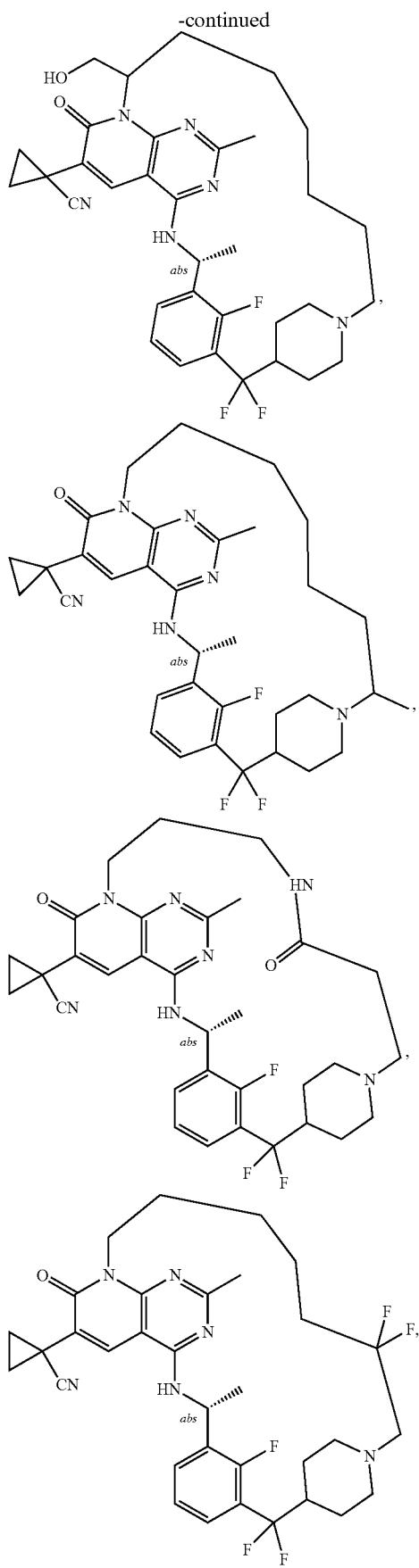
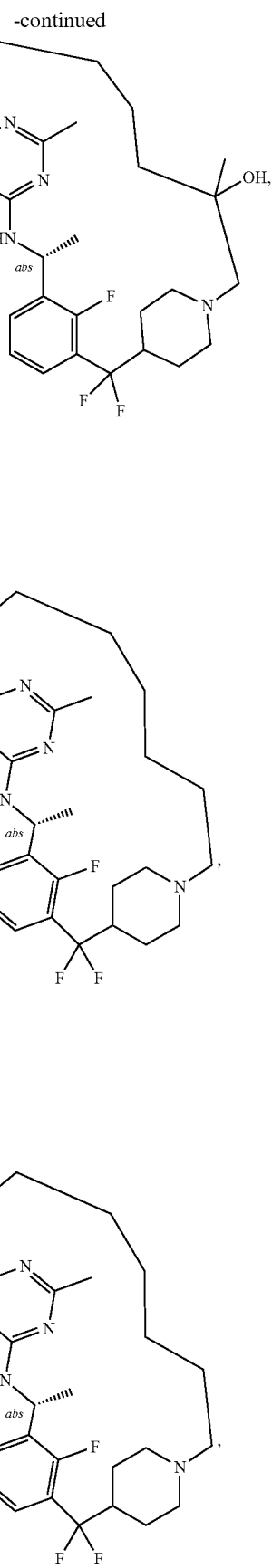

175
-continued
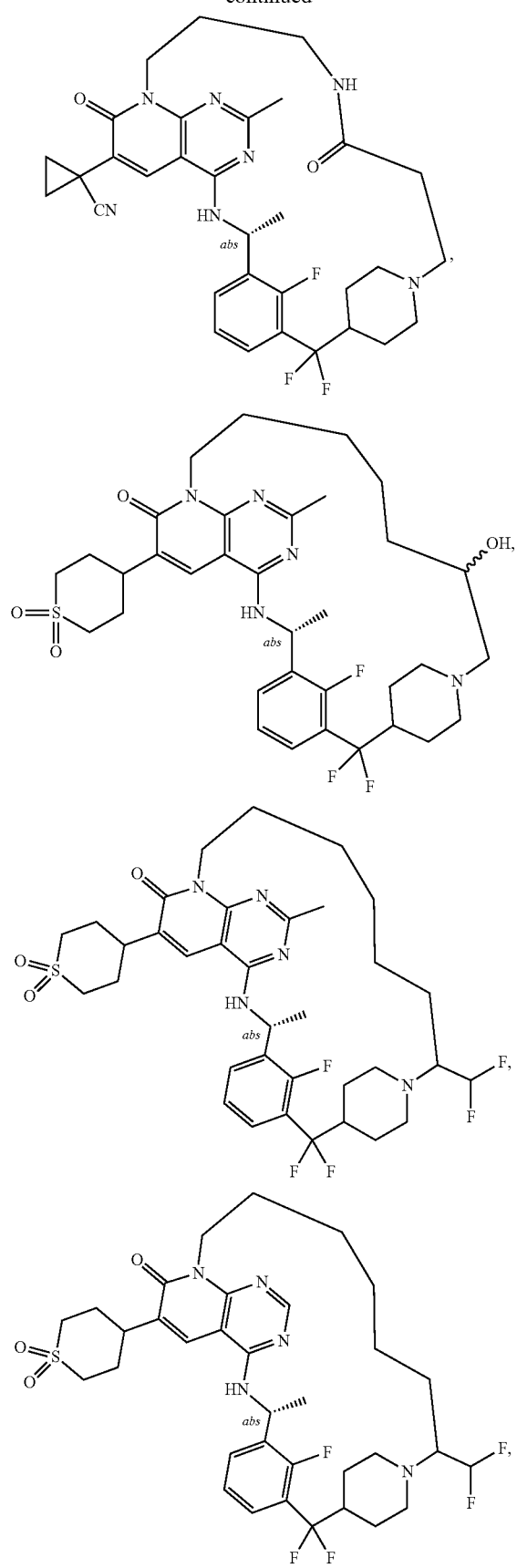
176
-continued
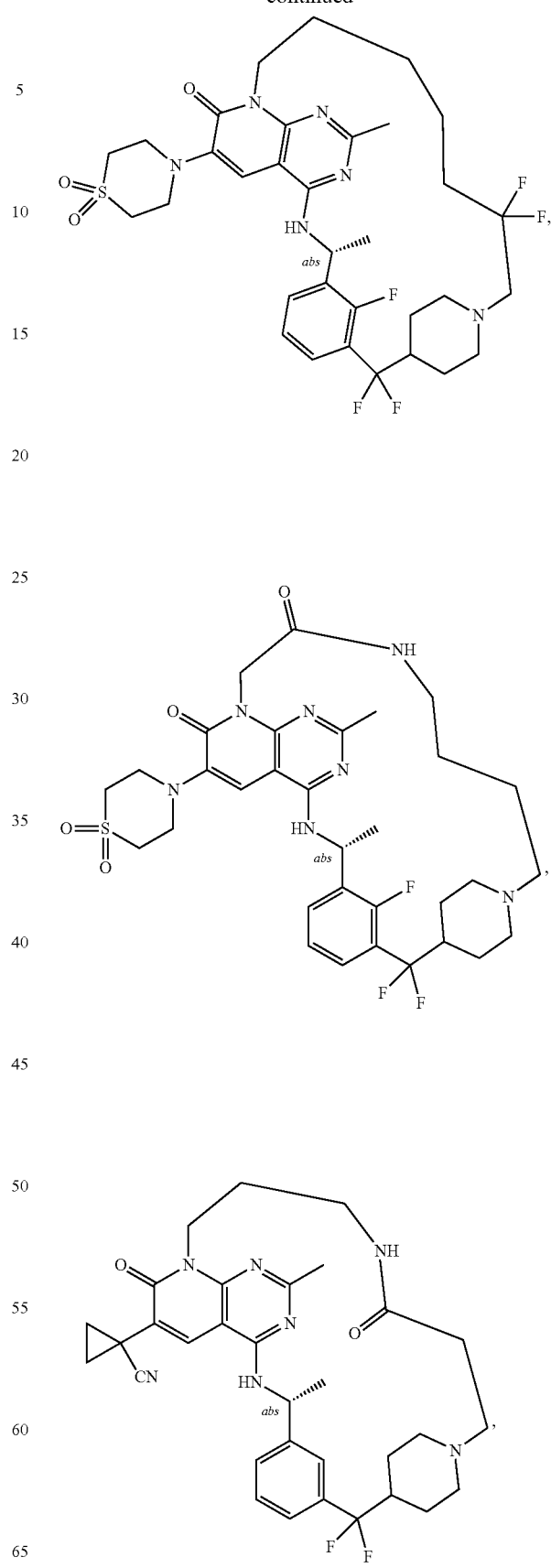

177
-continued
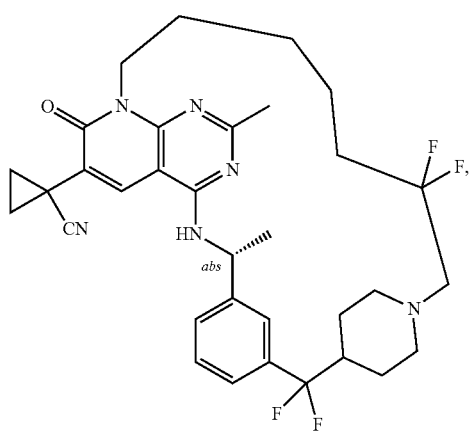
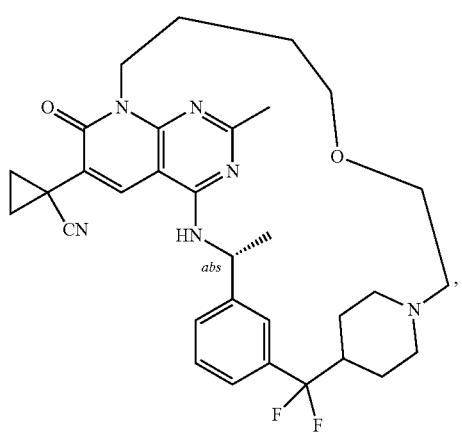
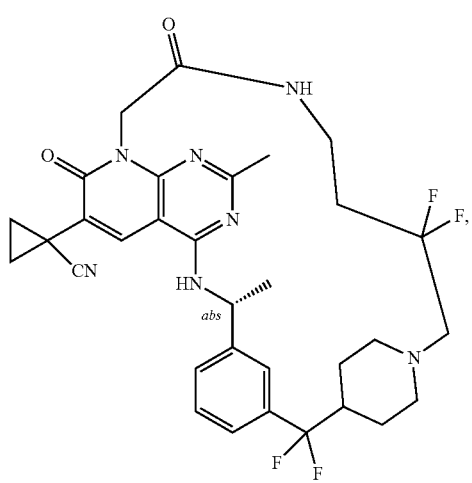
178
-continued
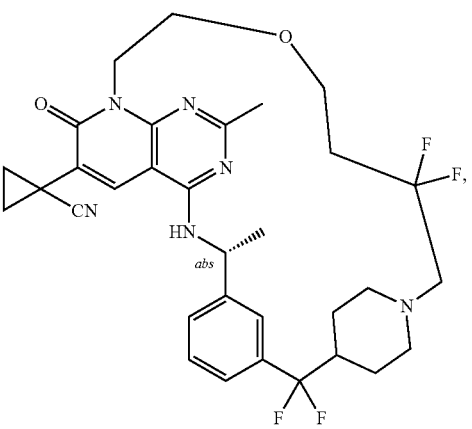
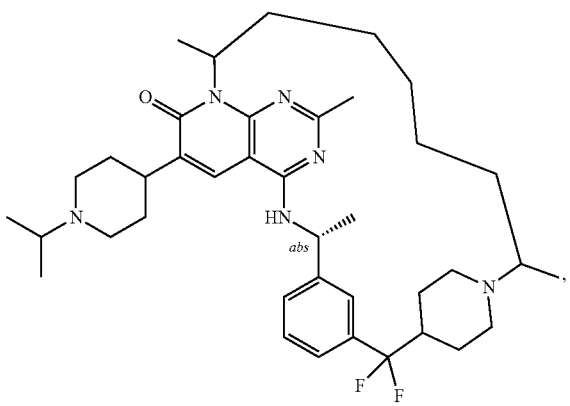
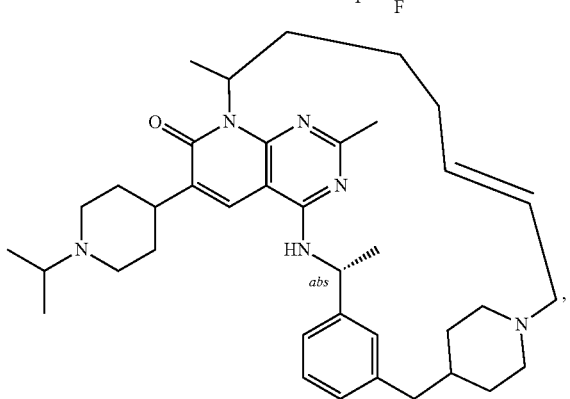
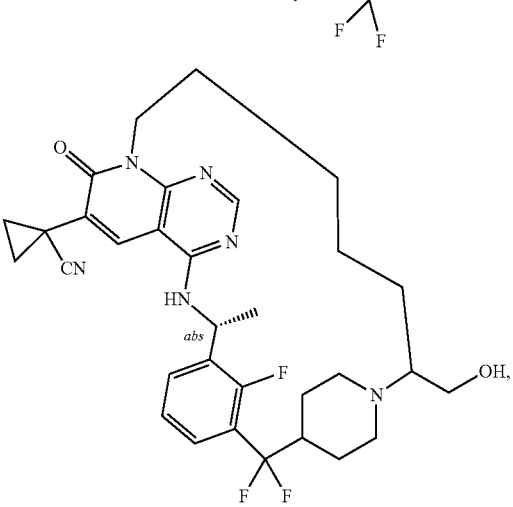

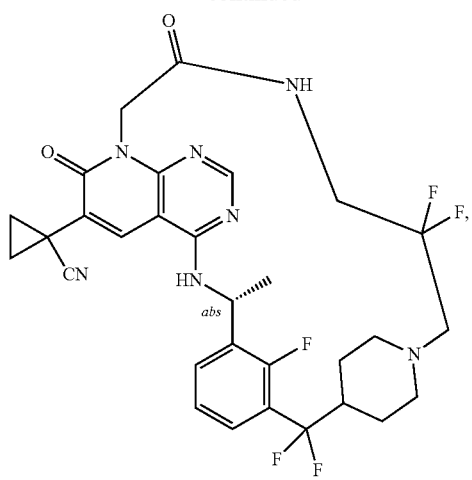
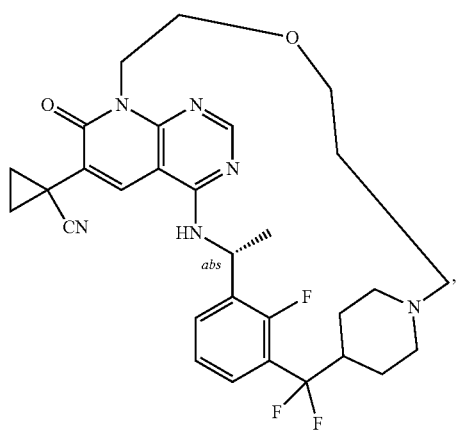
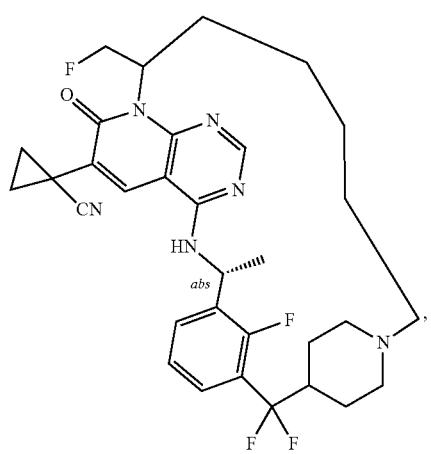
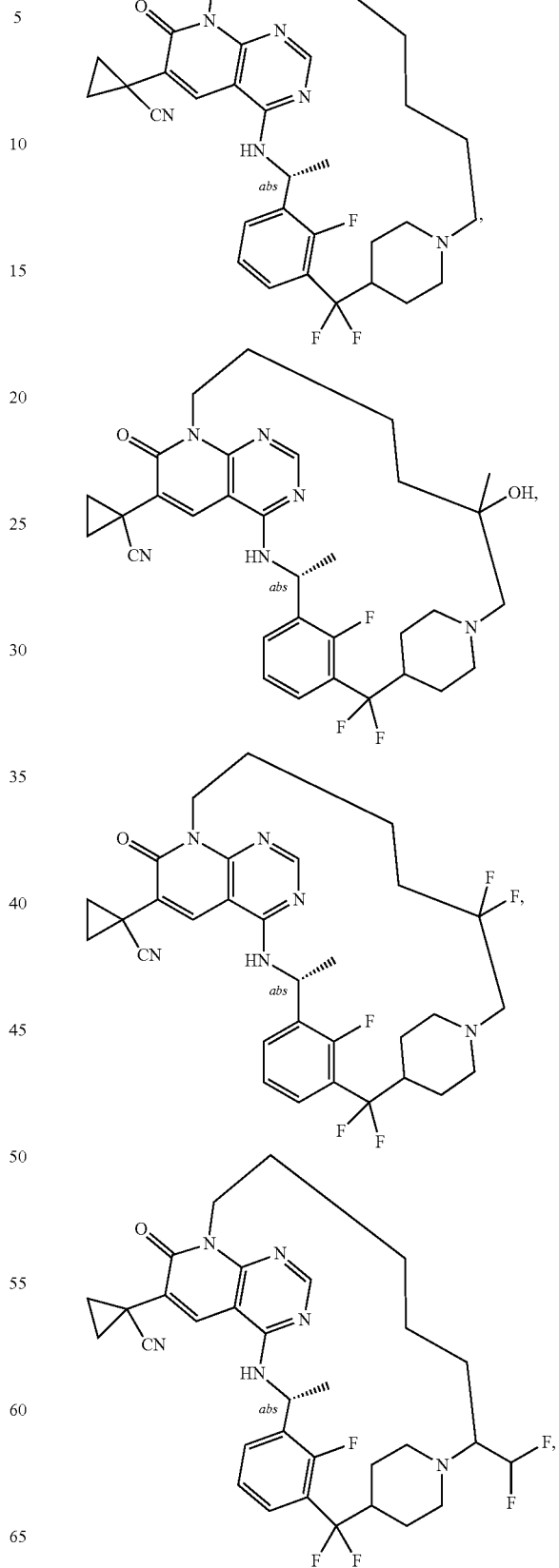

181
-continued
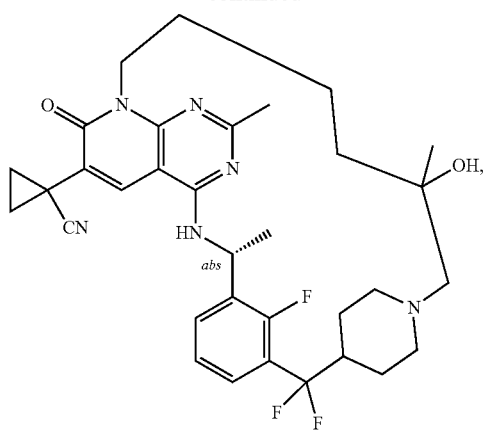
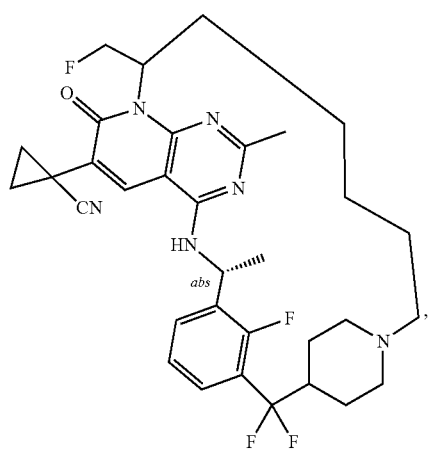
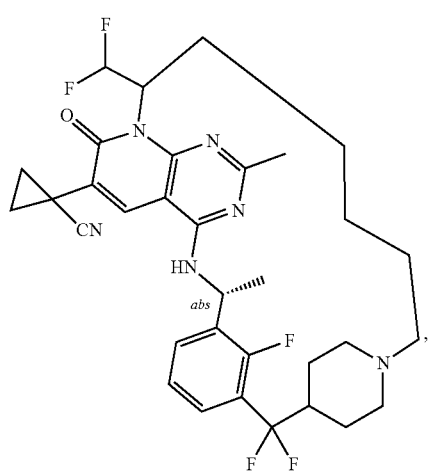
182
-continued
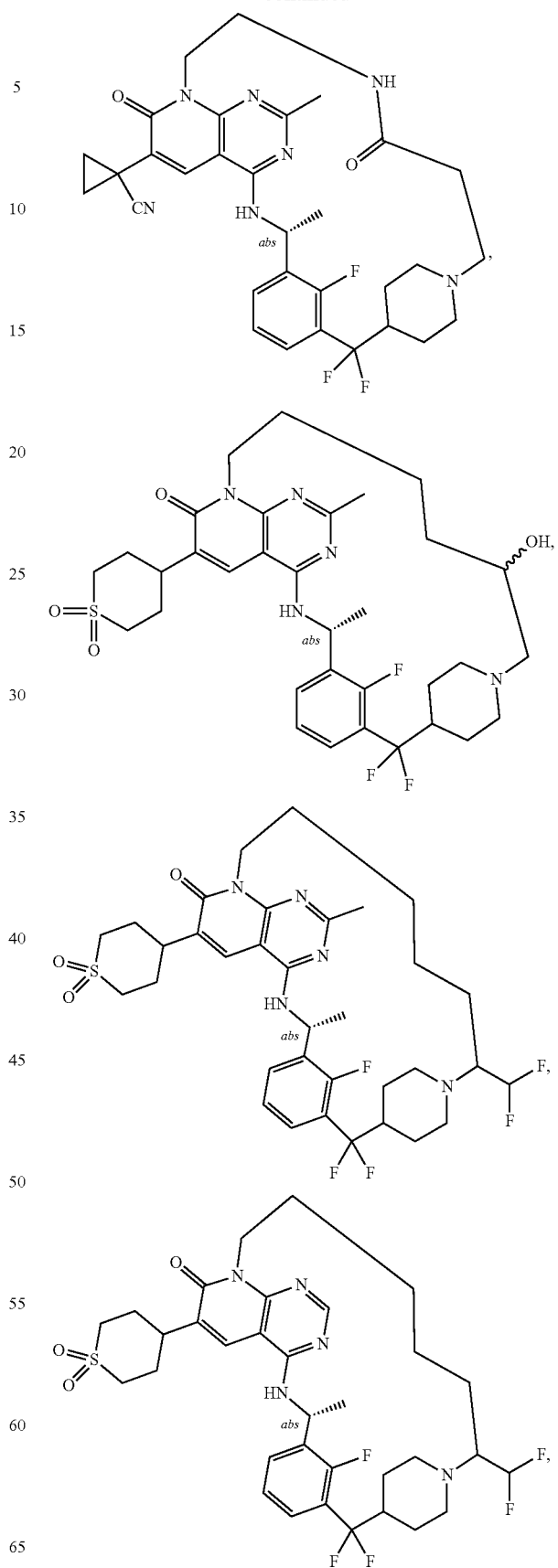

183
-continued
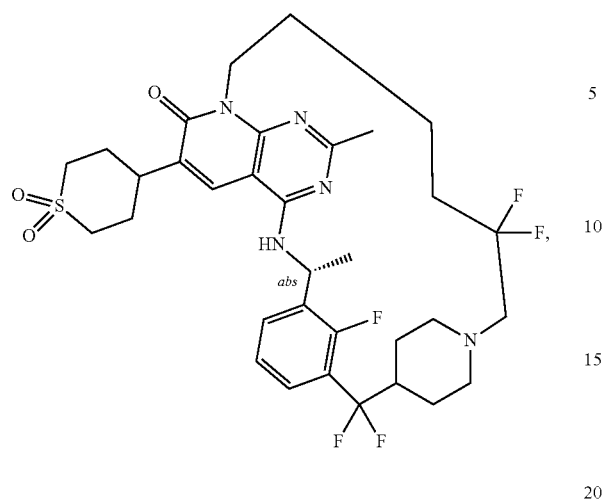
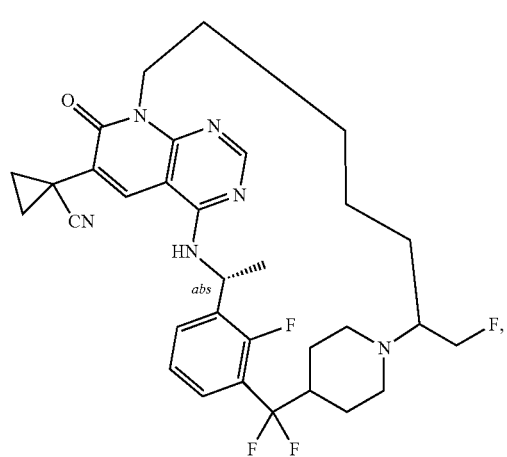
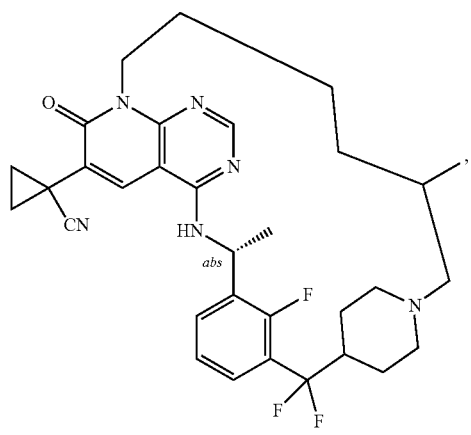
184
-continued
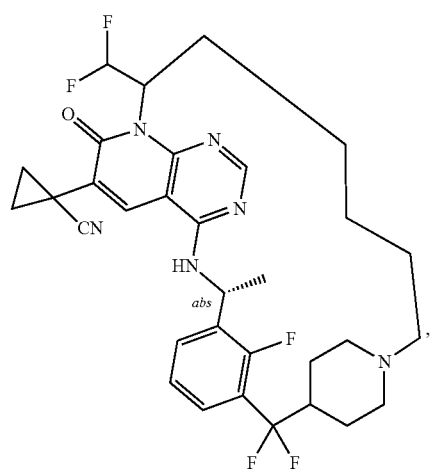
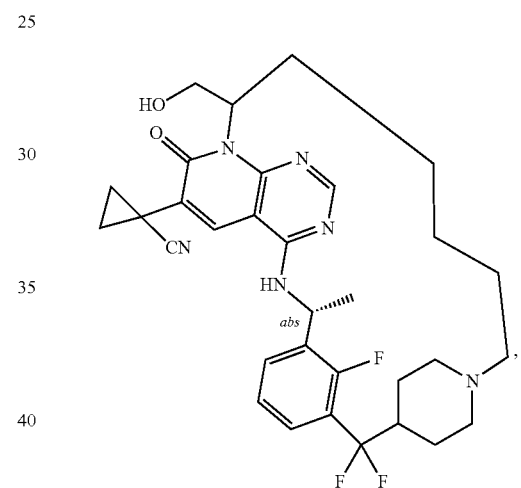
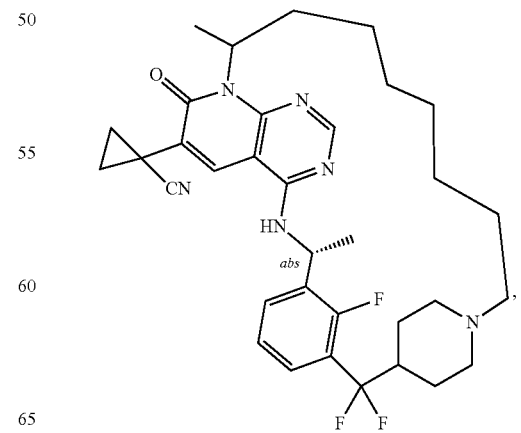

185
-continued
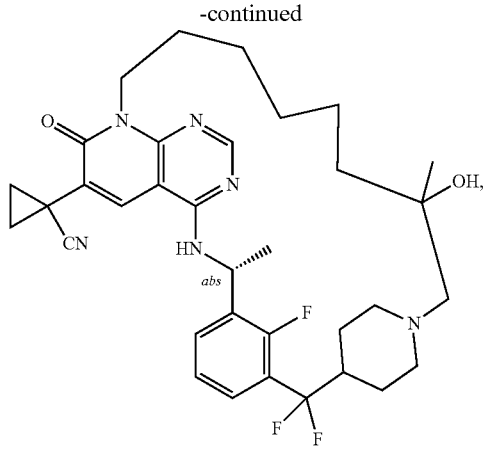
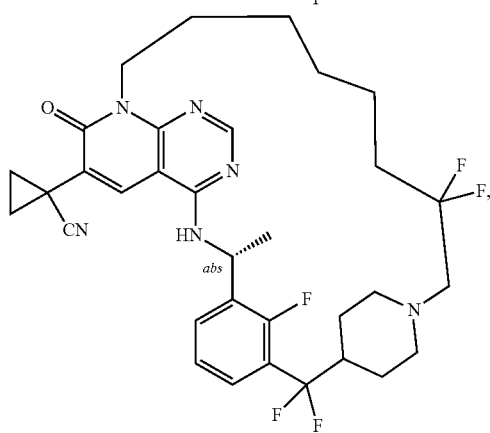
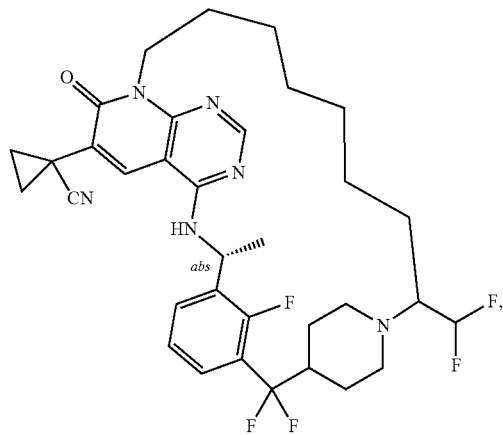
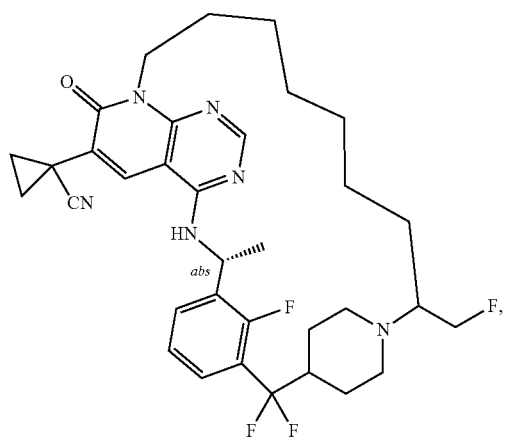
186
-continued
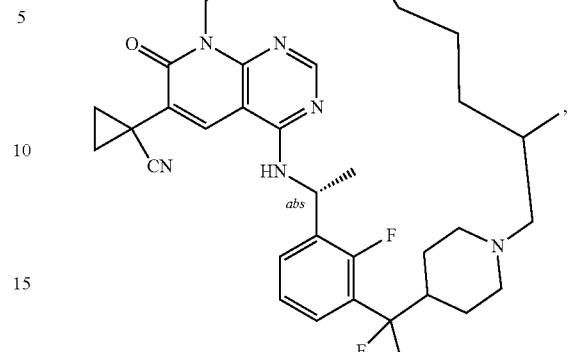
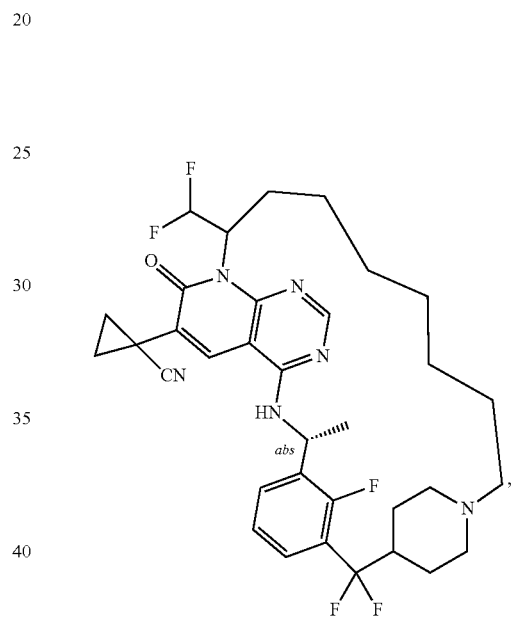
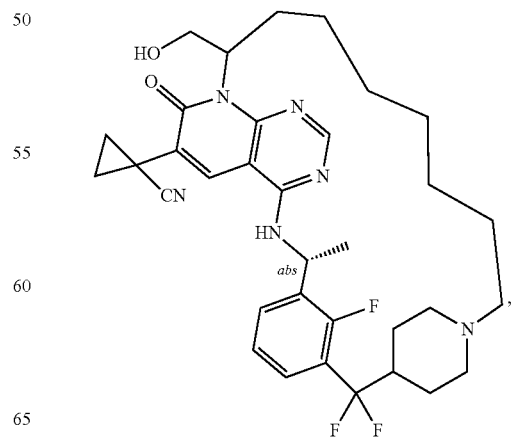

187
-continued
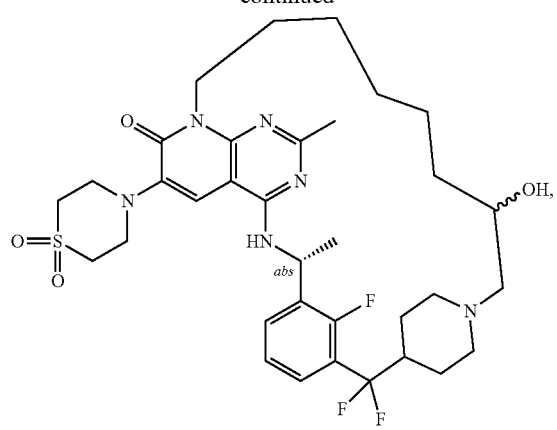
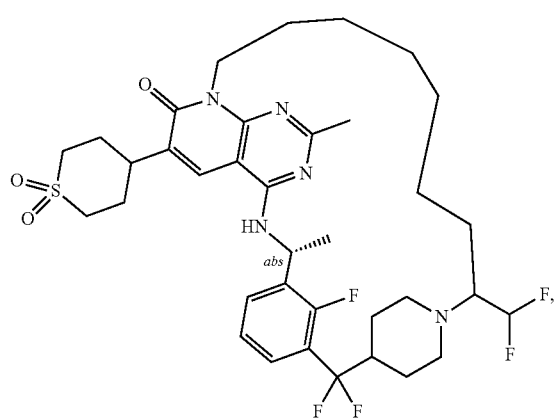
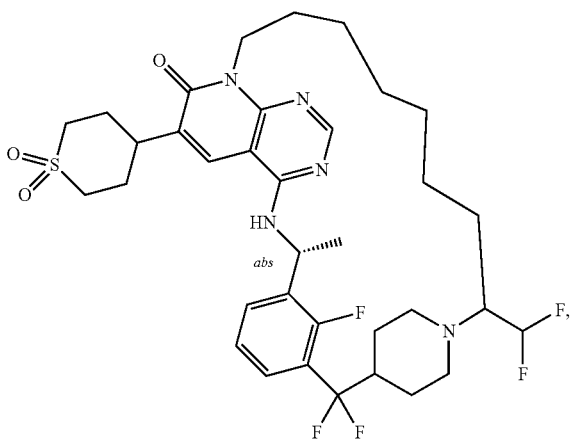
188
-continued
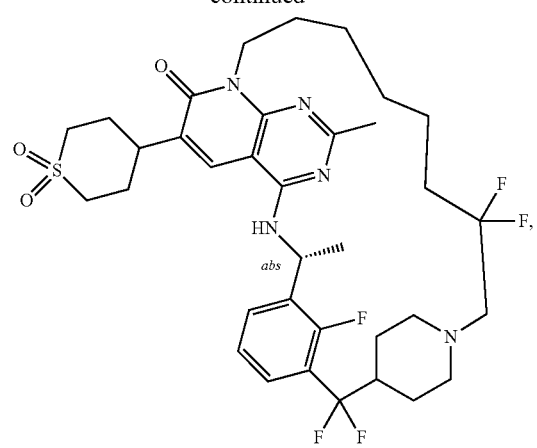
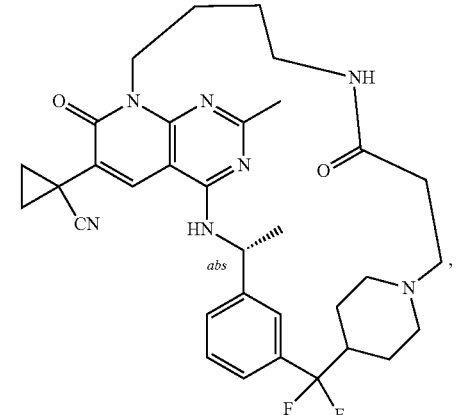

189
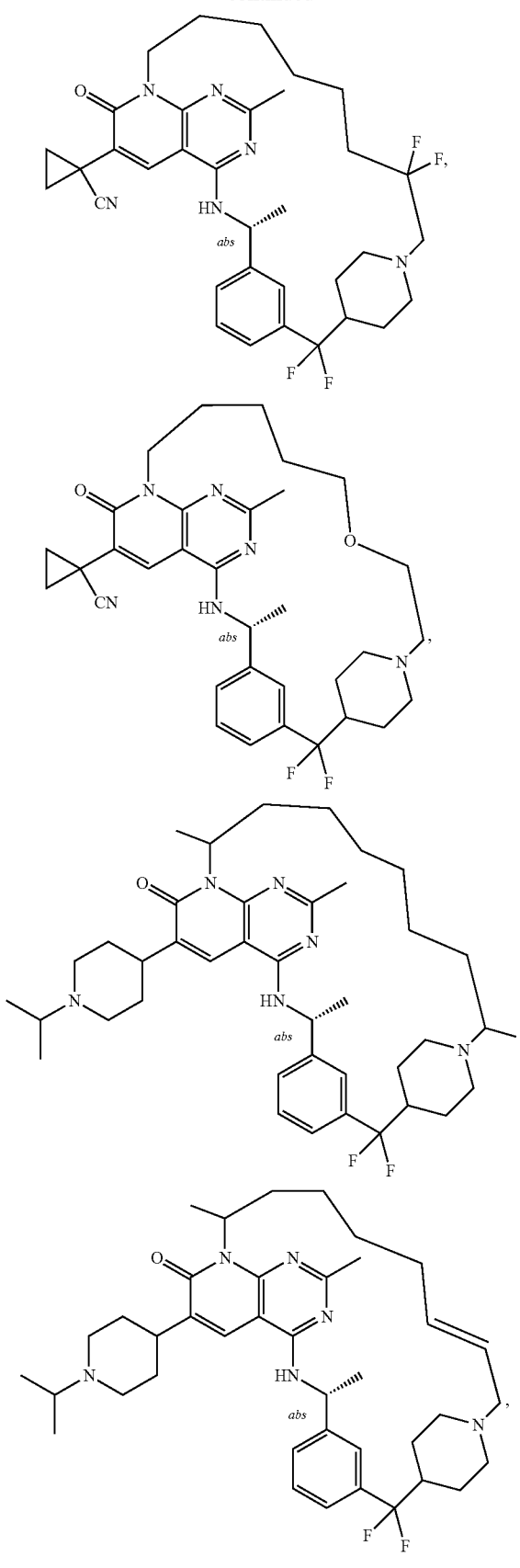
190
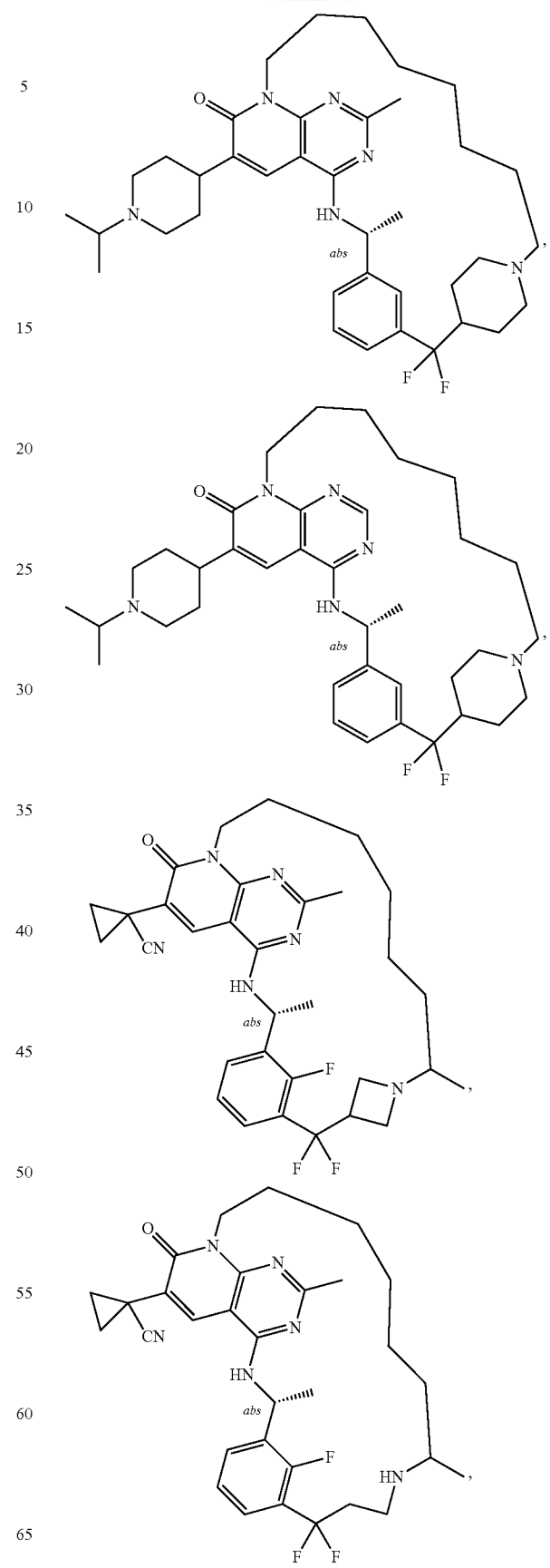

191
-continued
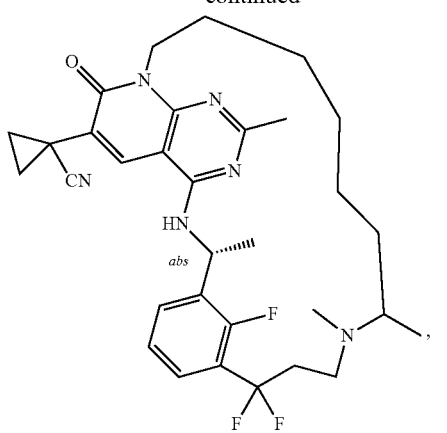
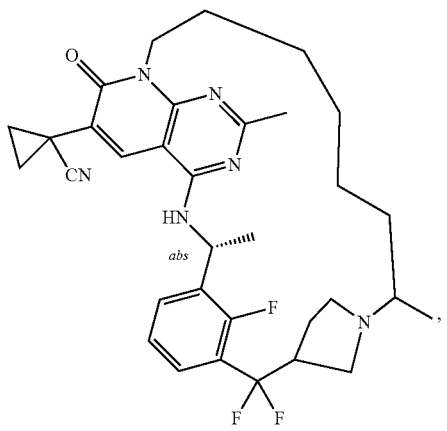
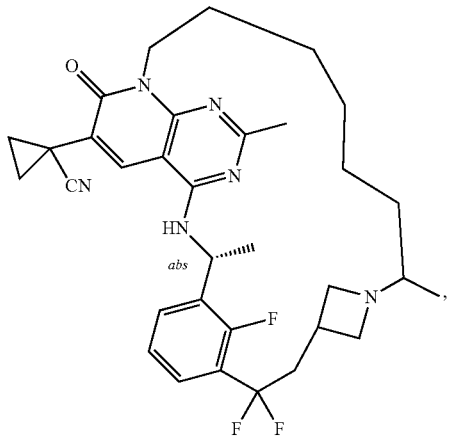
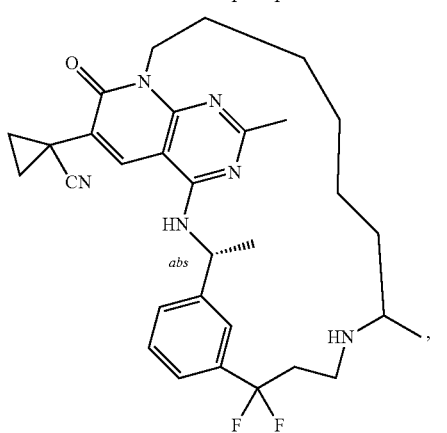
192
-continued
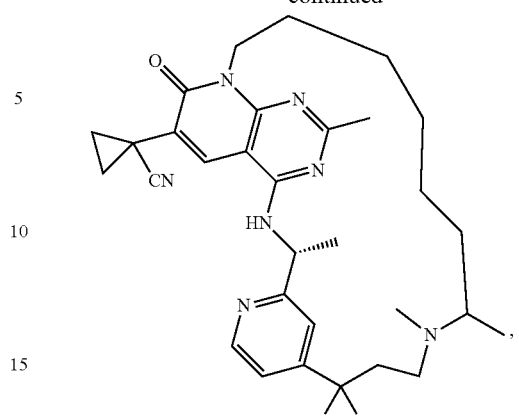
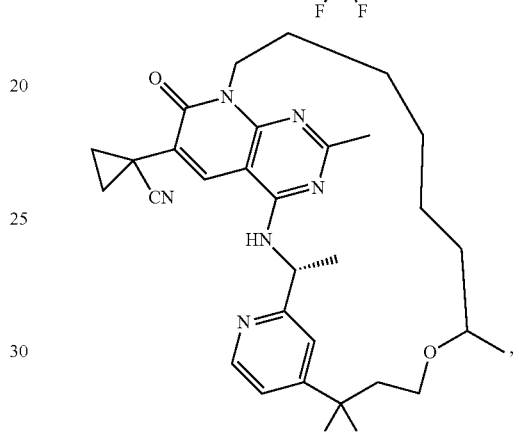
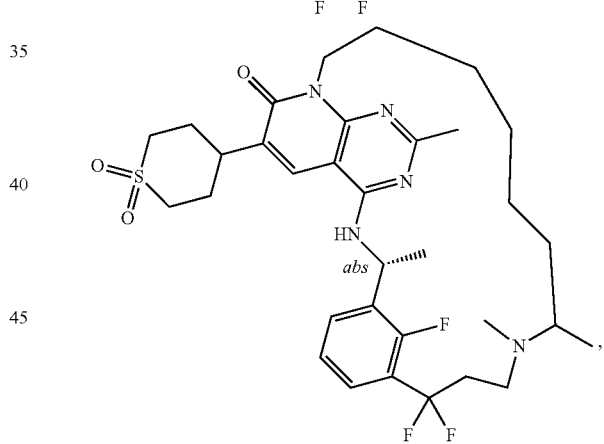
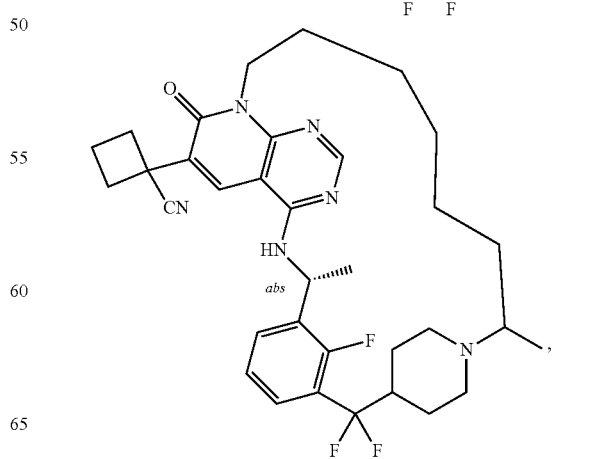

193
-continued
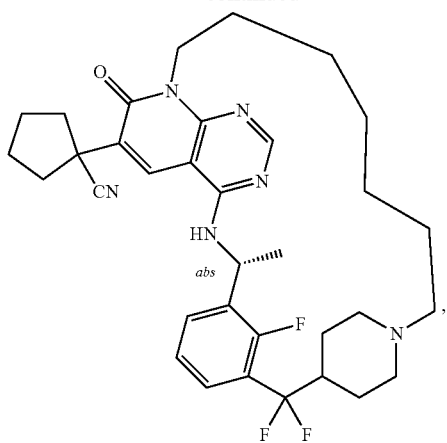
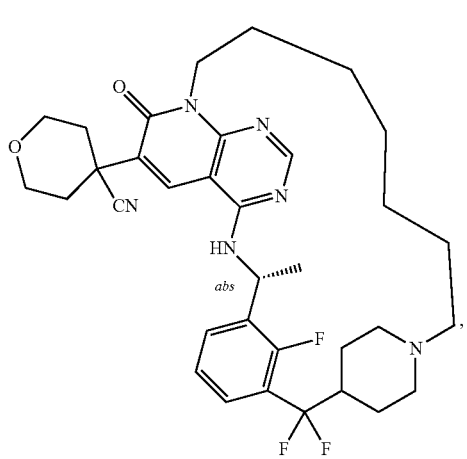
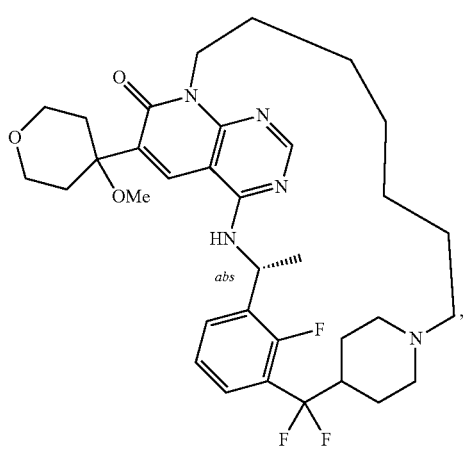
194
-continued
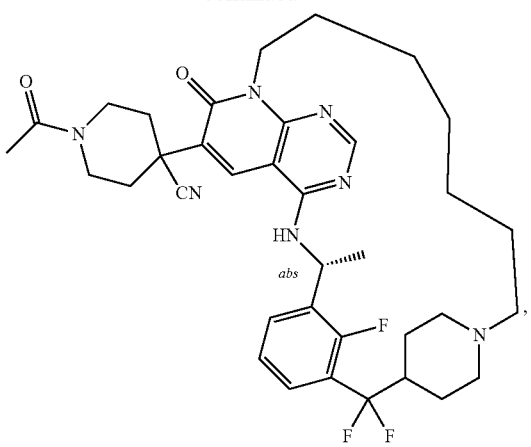
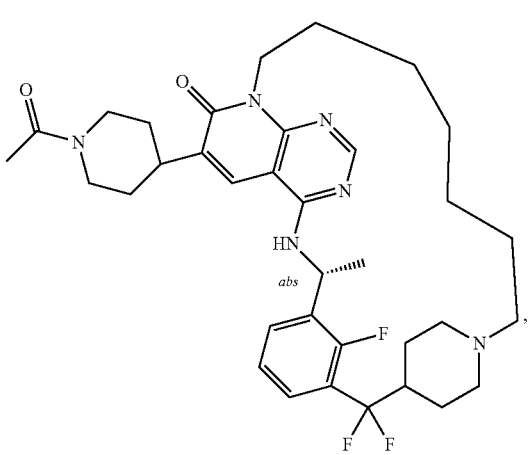
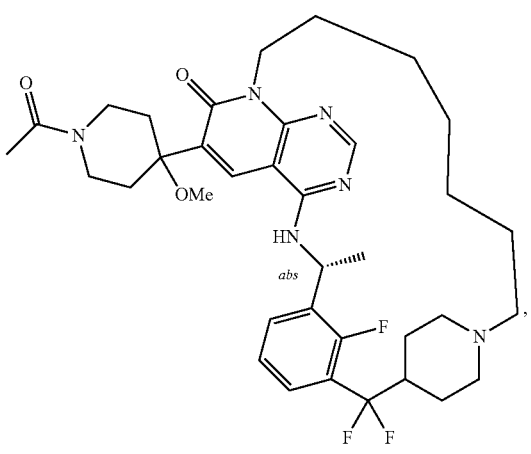

195
-continued
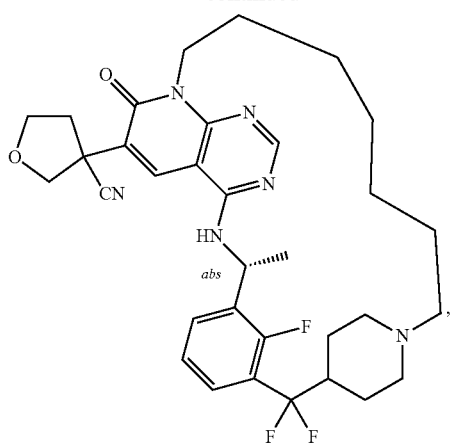
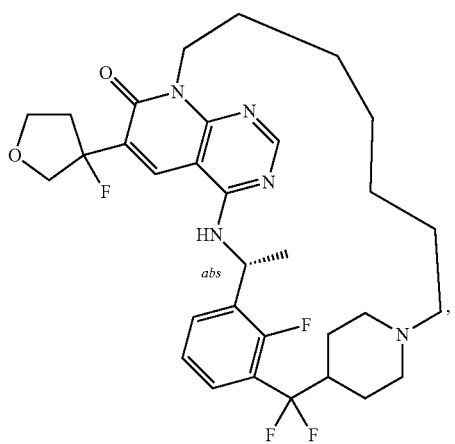
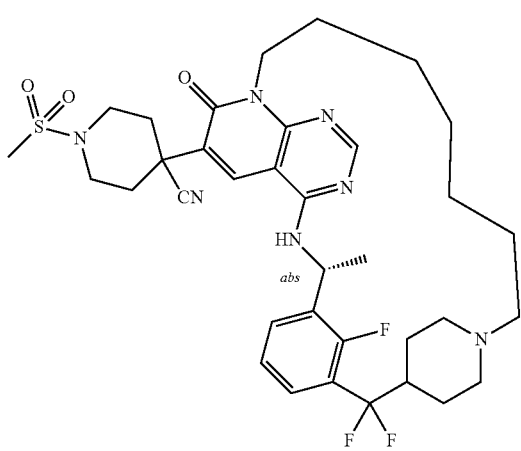
196
-continued
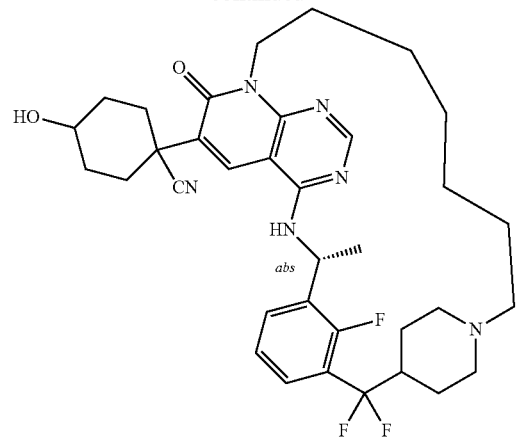
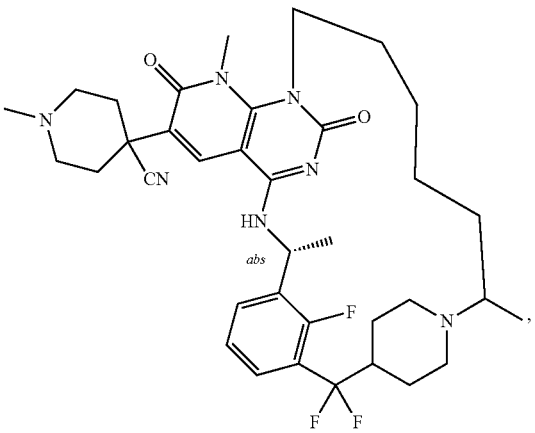
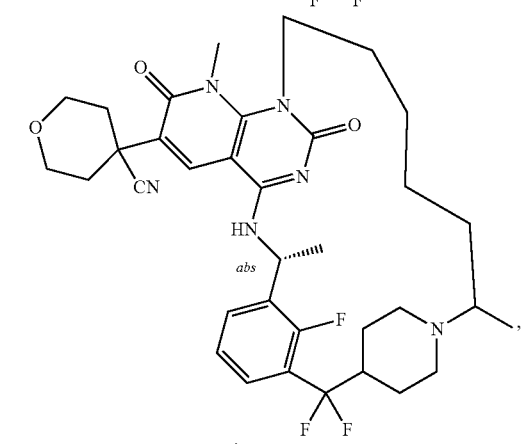
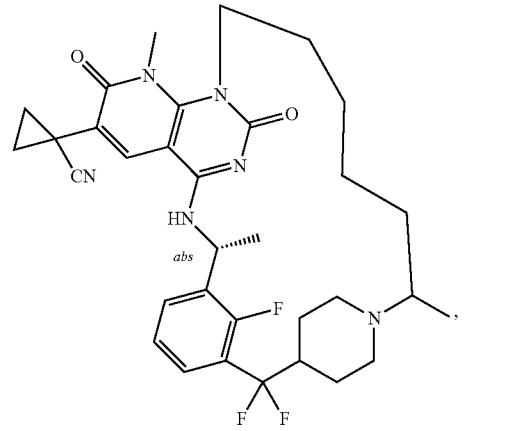

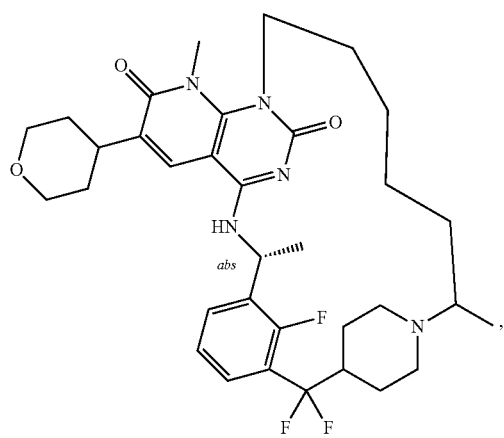
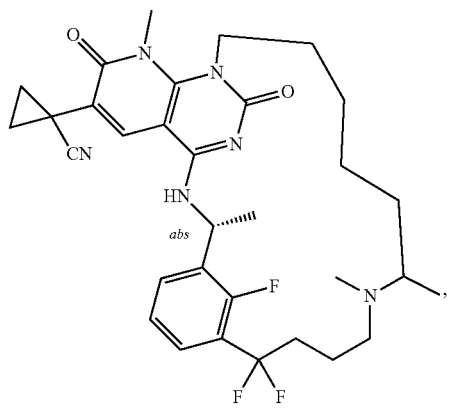
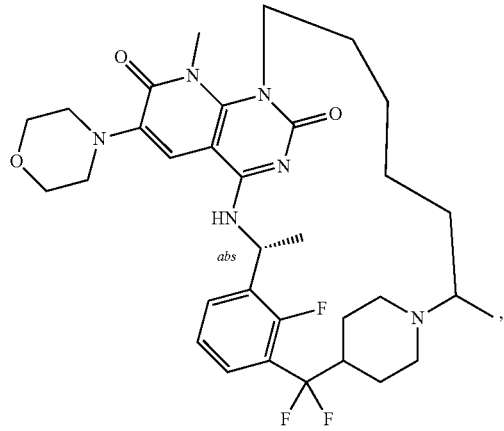
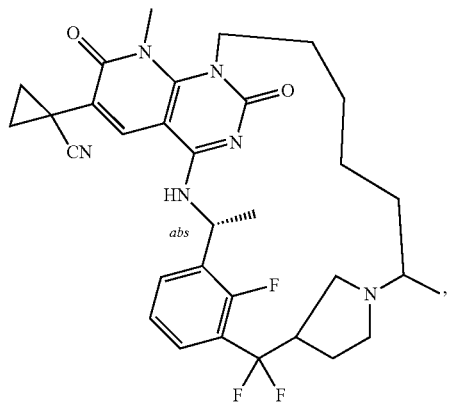
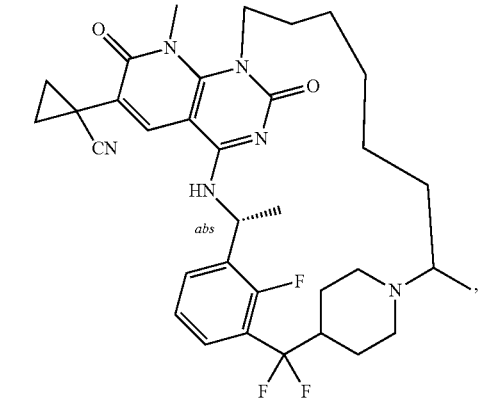
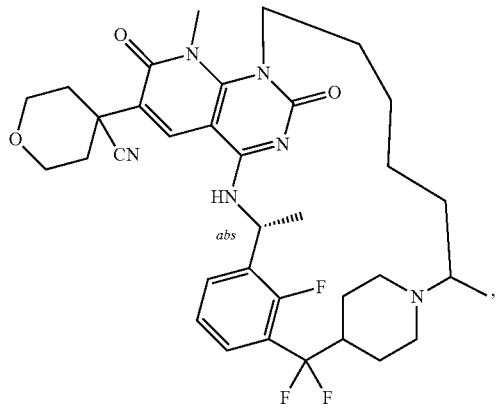
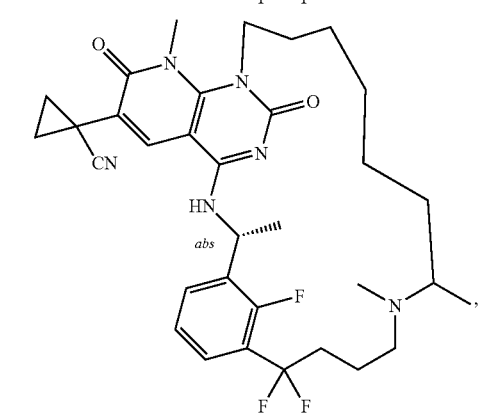
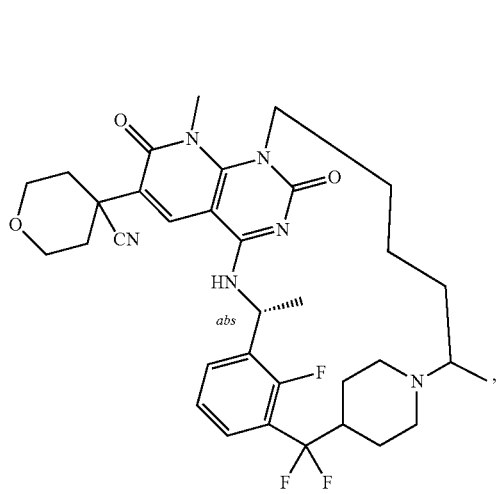

199
-continued
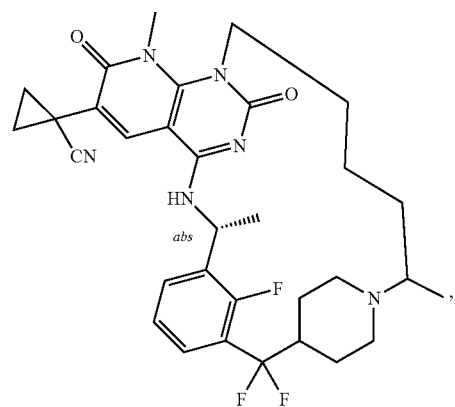
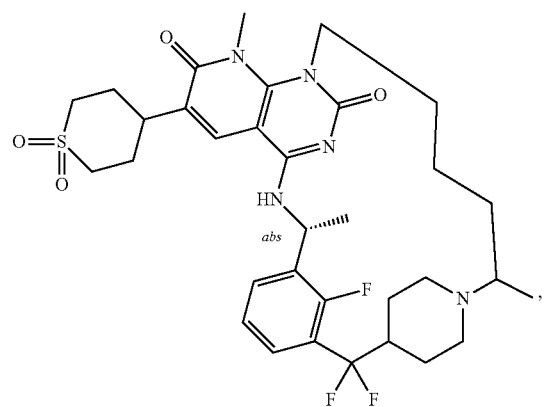
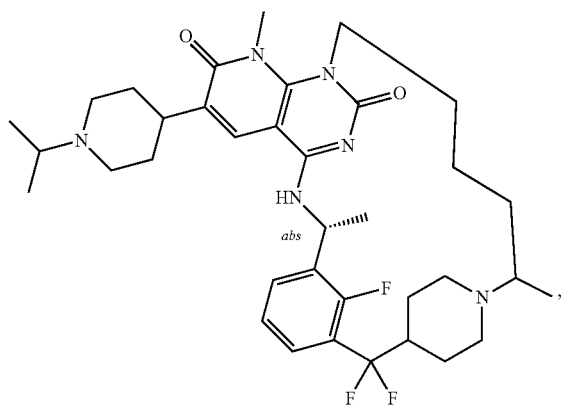
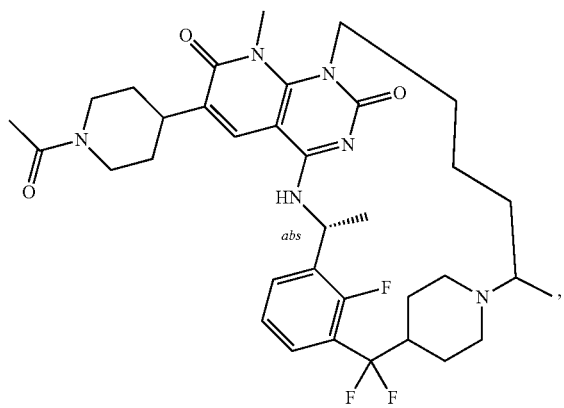
200
-continued
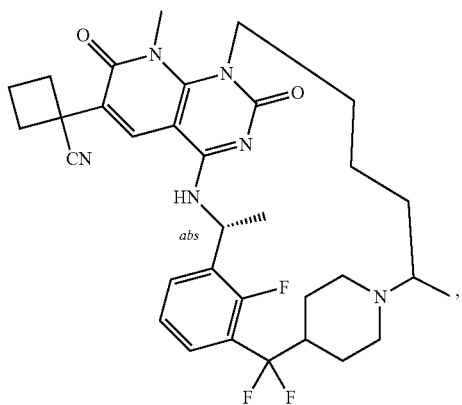
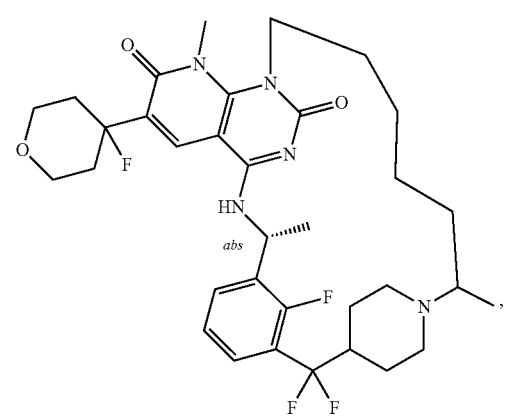
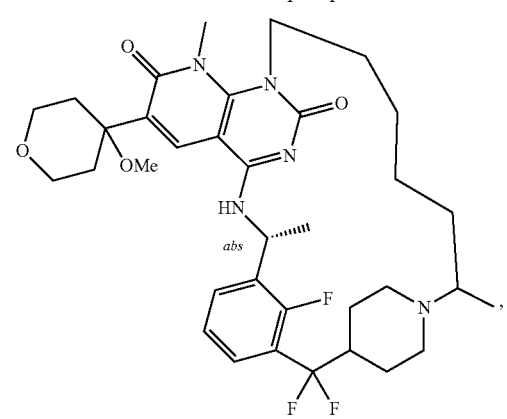
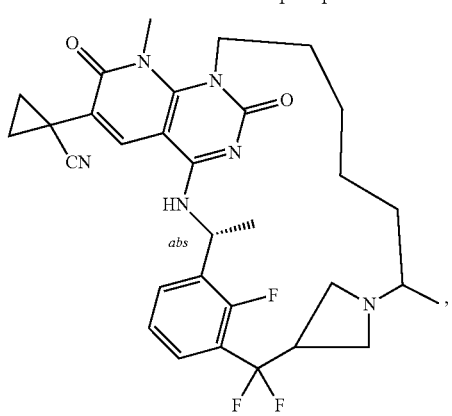

201
-continued
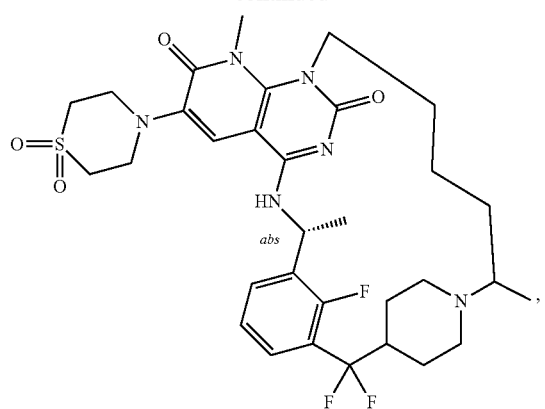
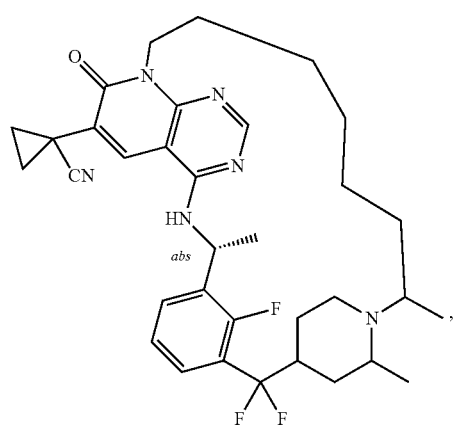
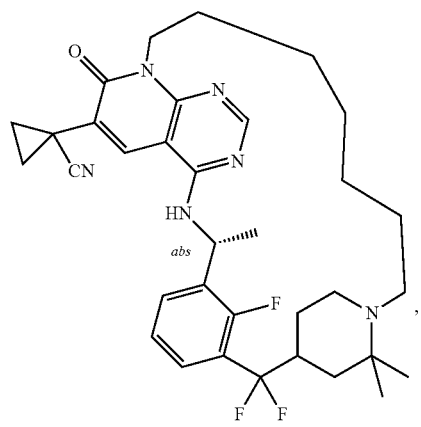
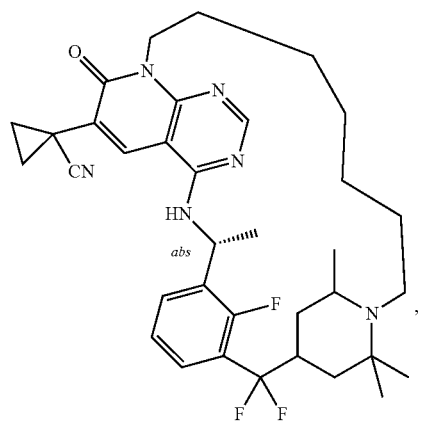
202
-continued
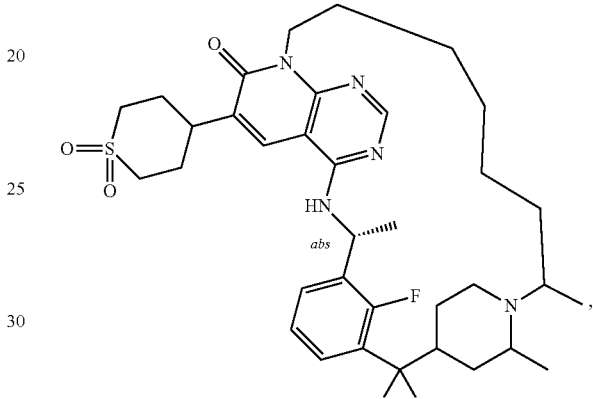
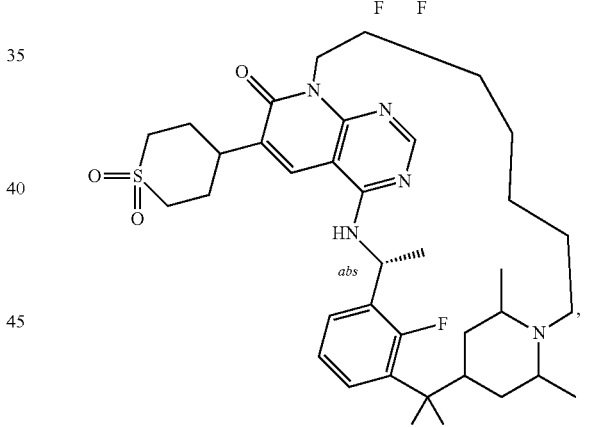
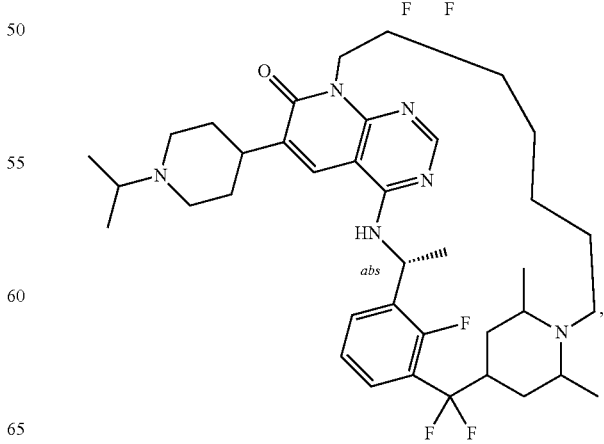
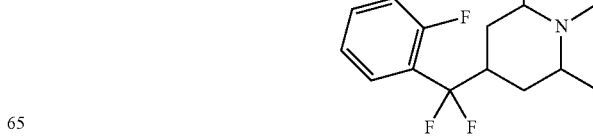

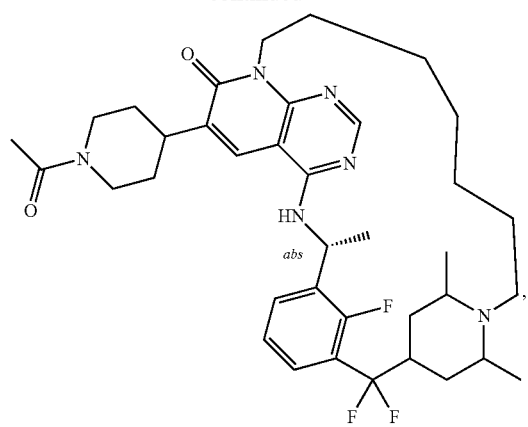
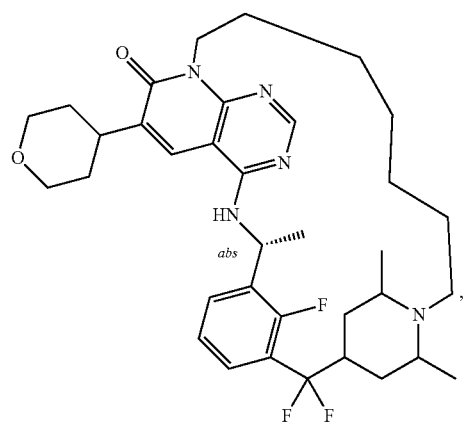
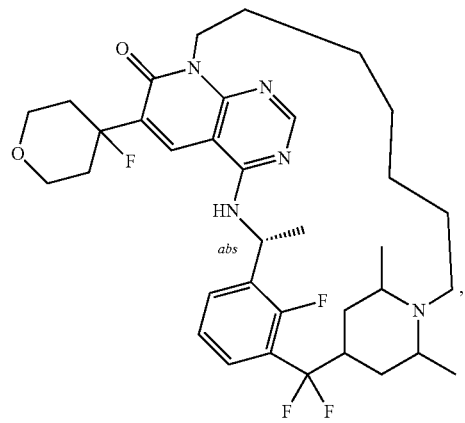
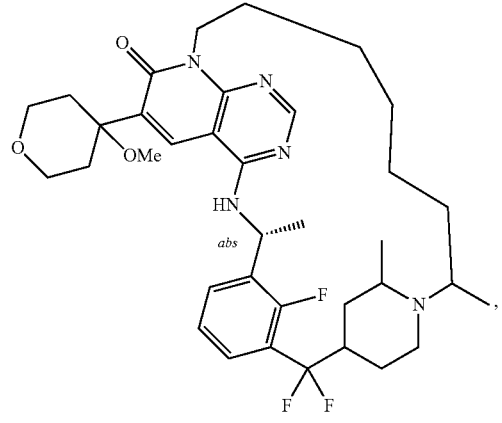
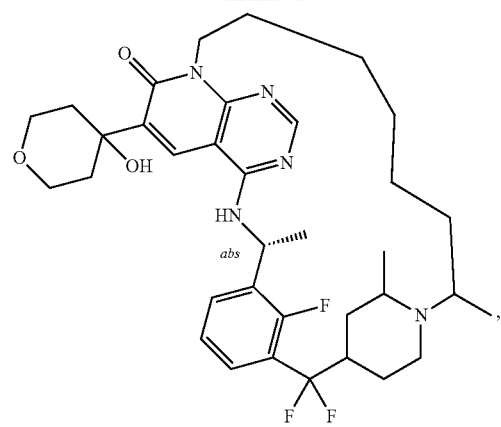
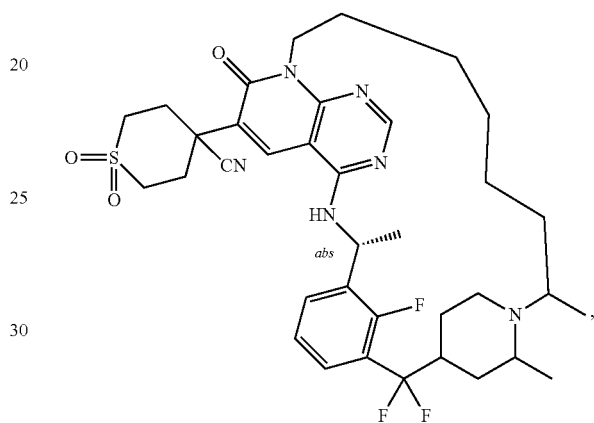

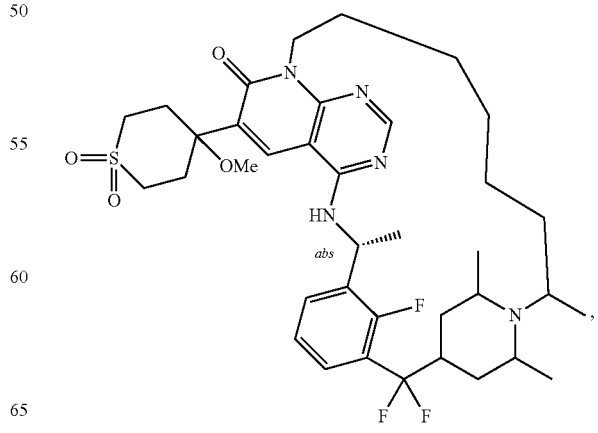

205
-continued
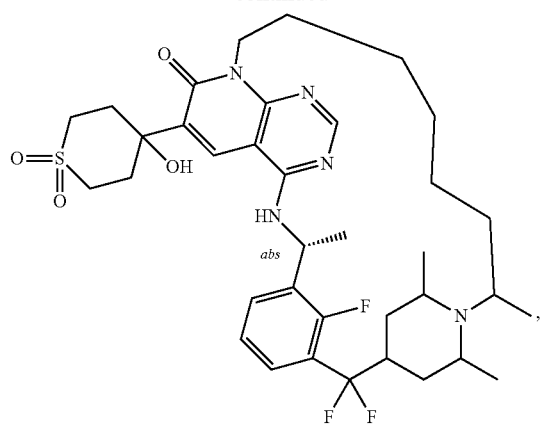
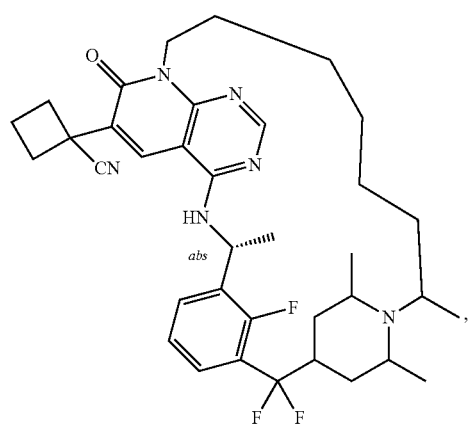
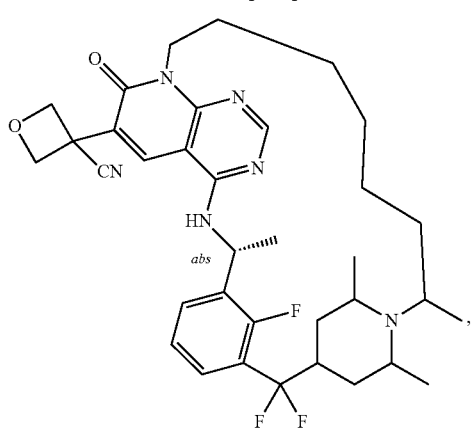
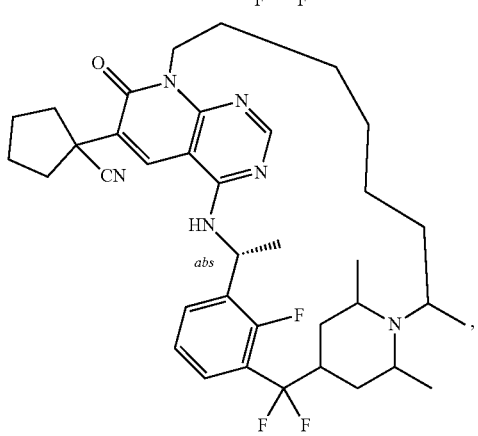
206
-continued
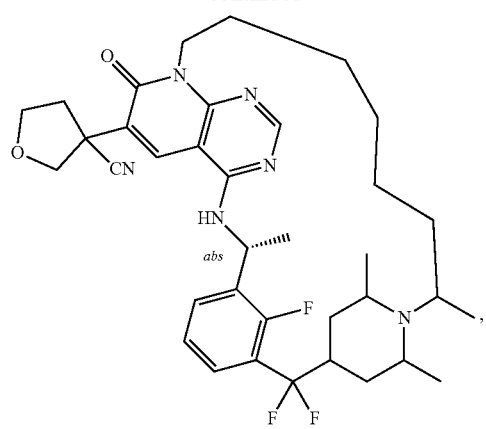
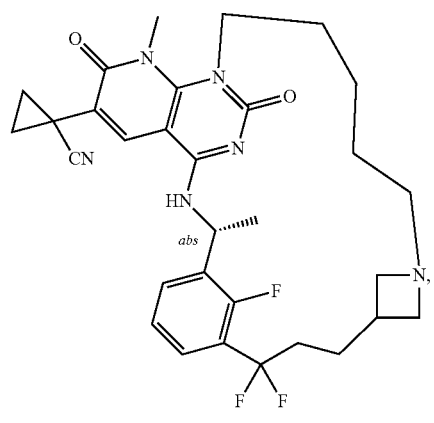
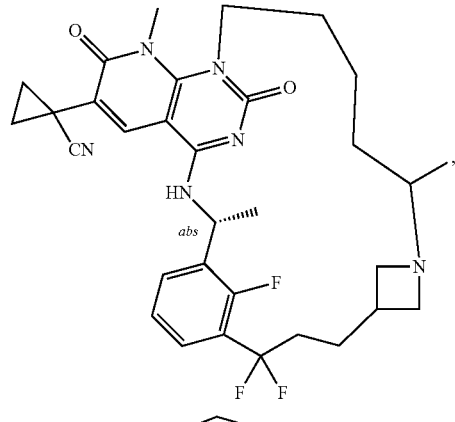
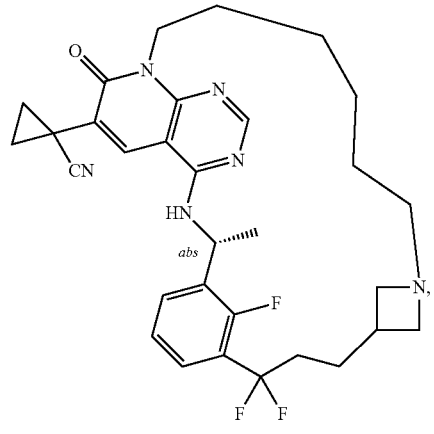

207
-continued
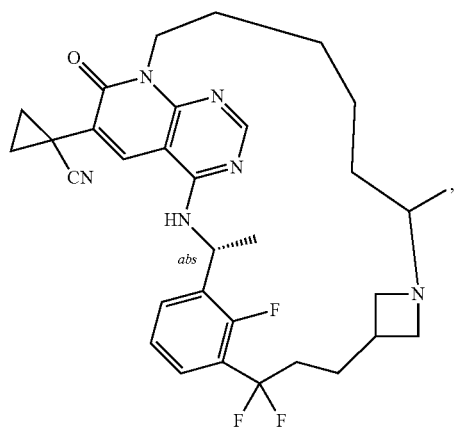
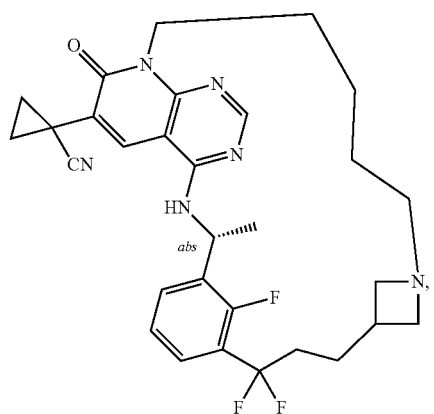
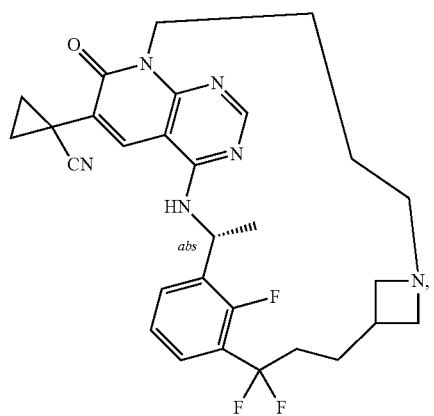
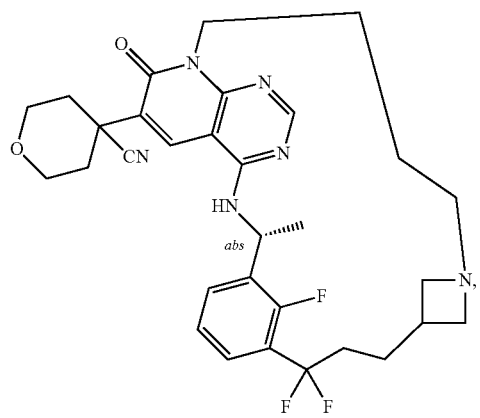
208
-continued
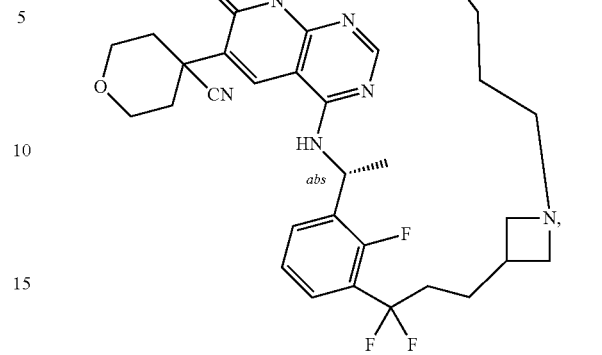
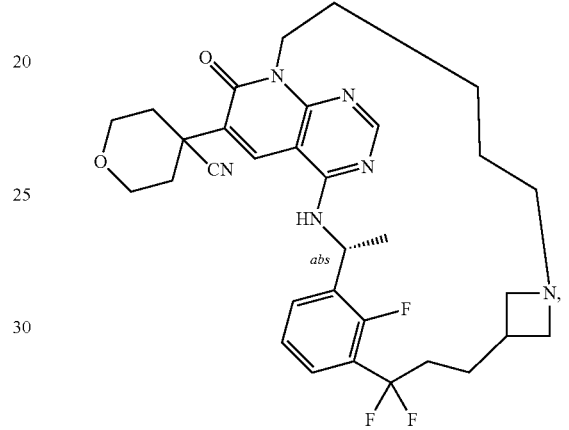
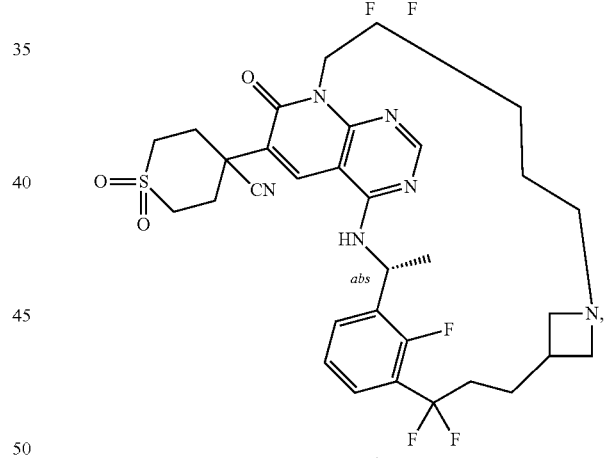
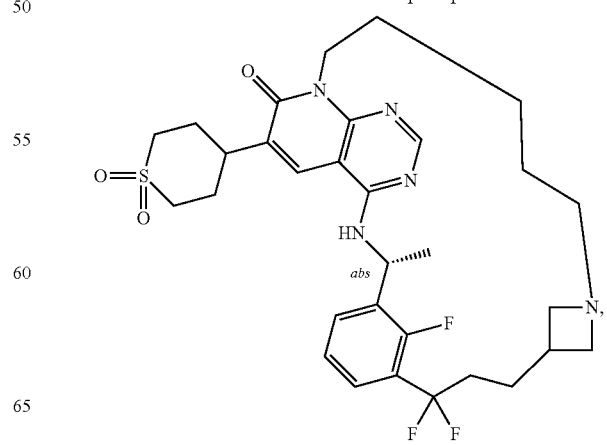

209
-continued
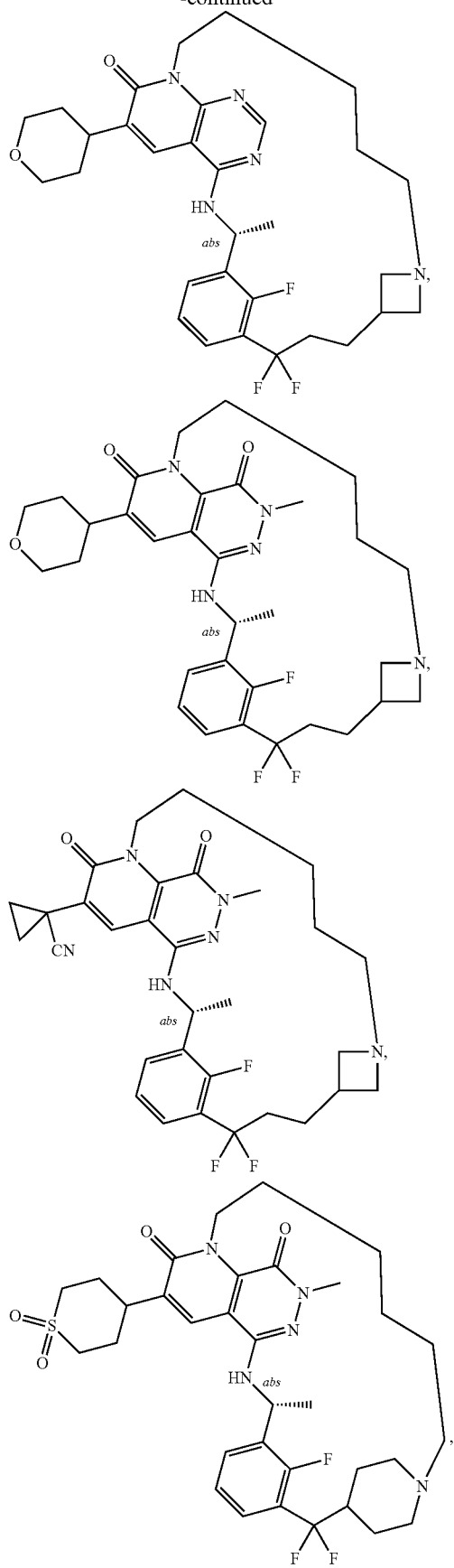
210
-continued
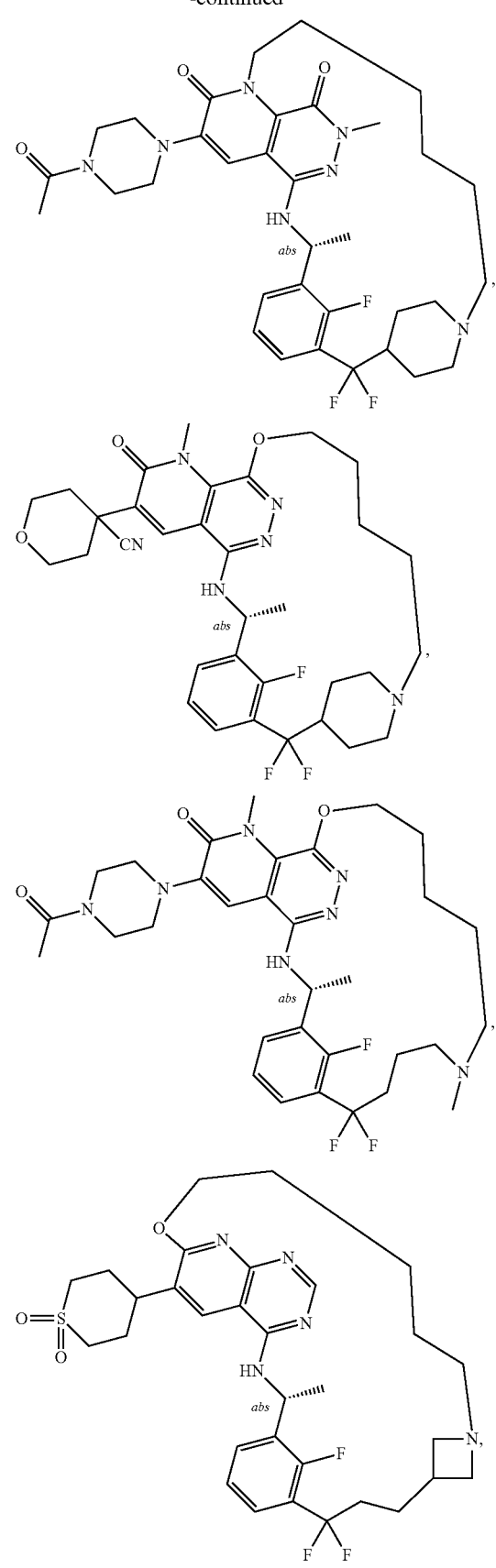

211
-continued
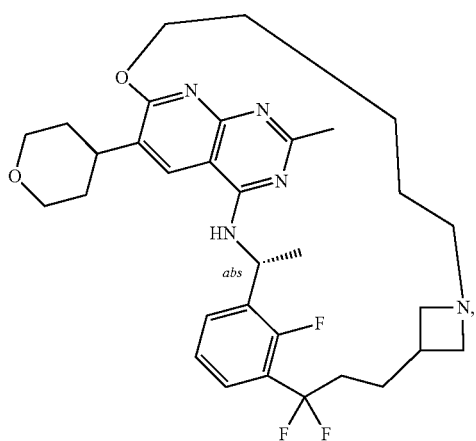
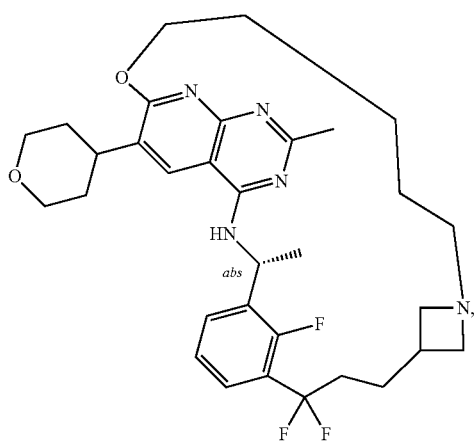
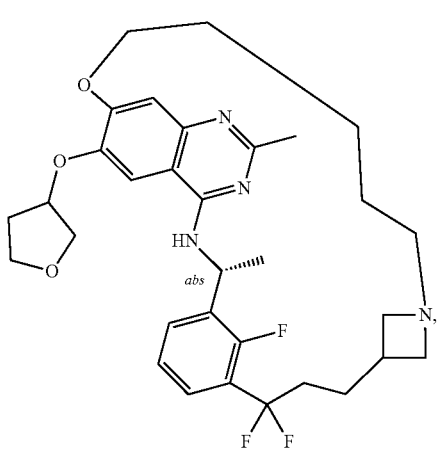
212
-continued
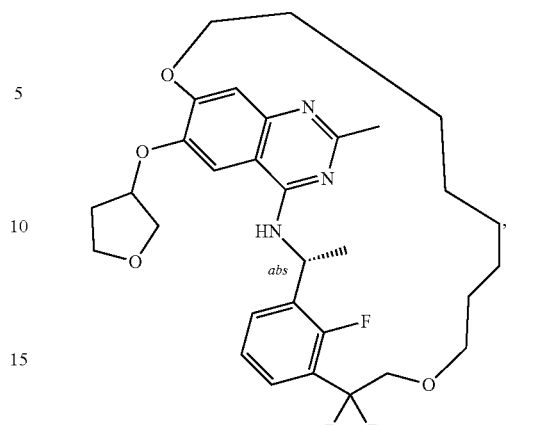
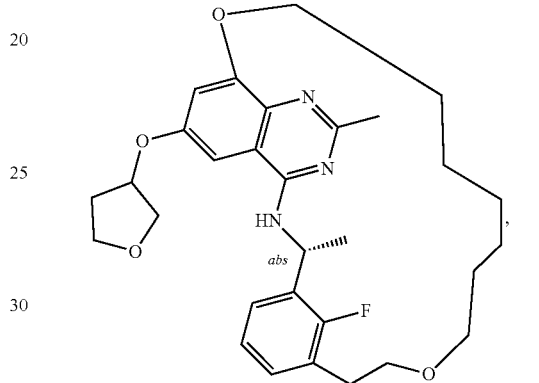
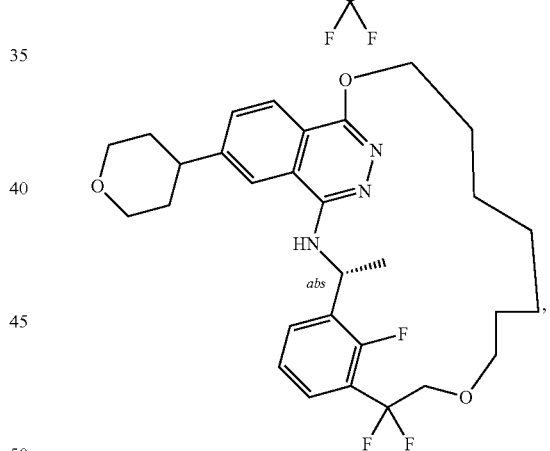
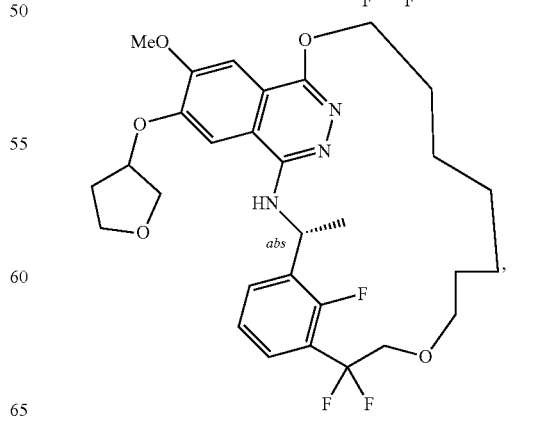

213
-continued
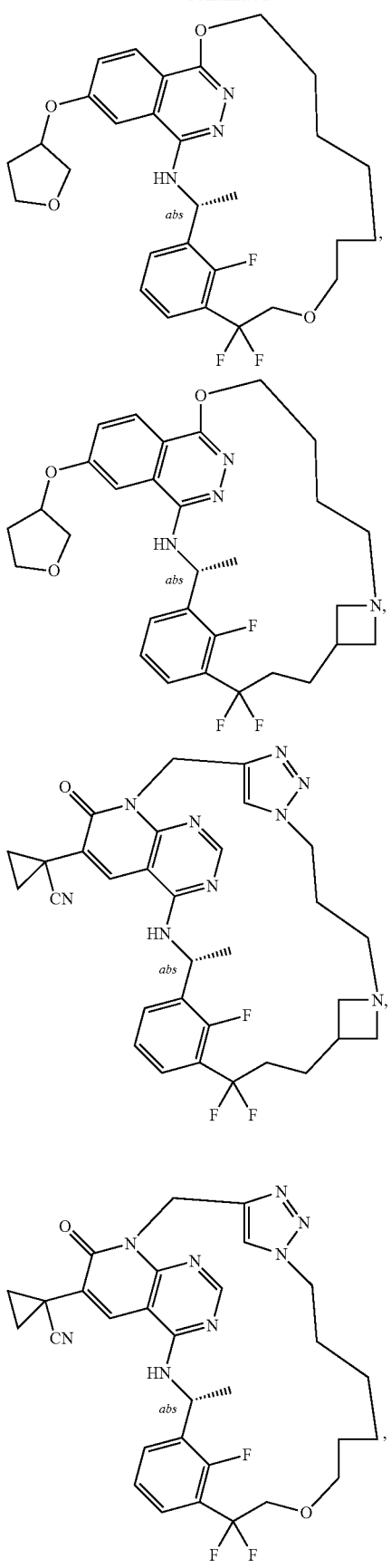
214
-continued
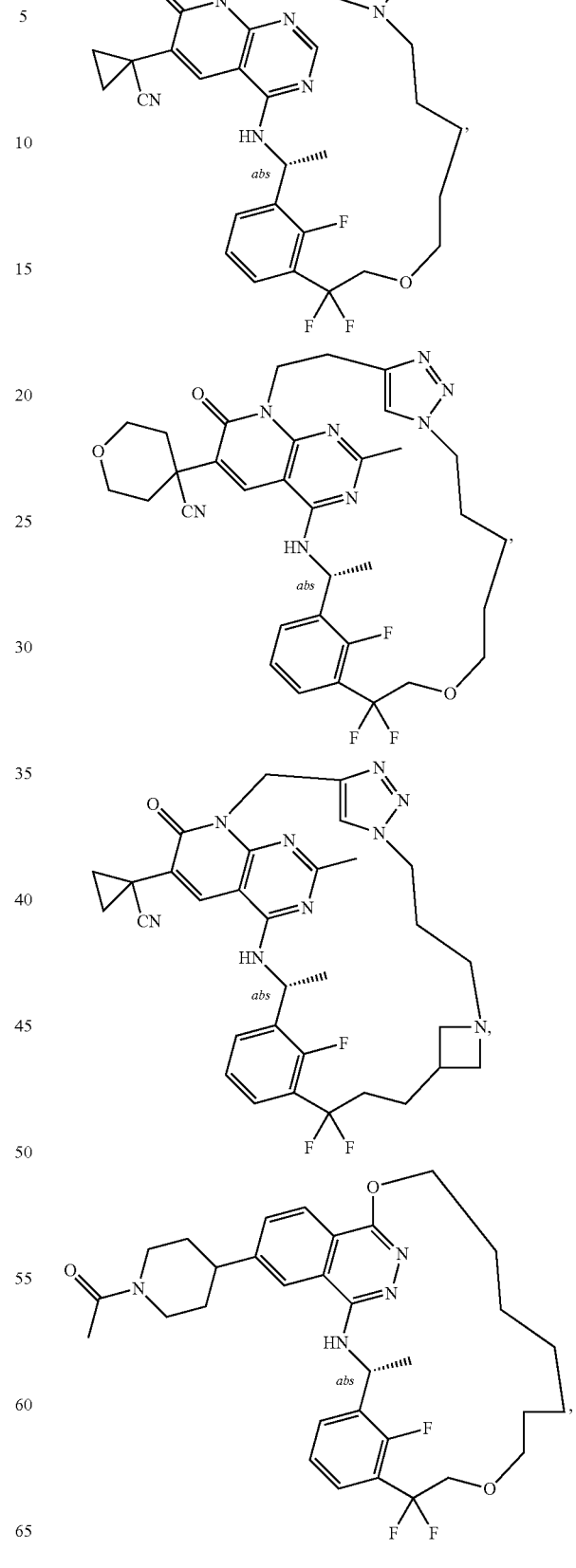

-continued
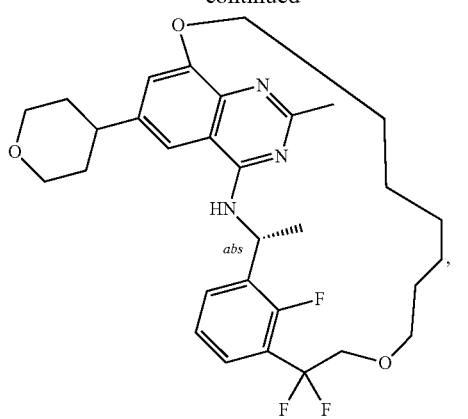
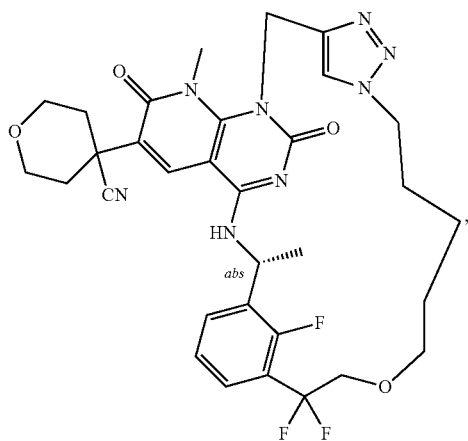
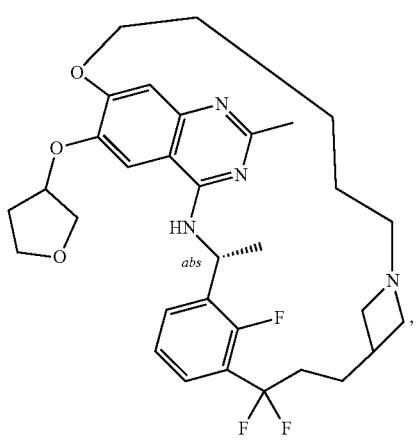
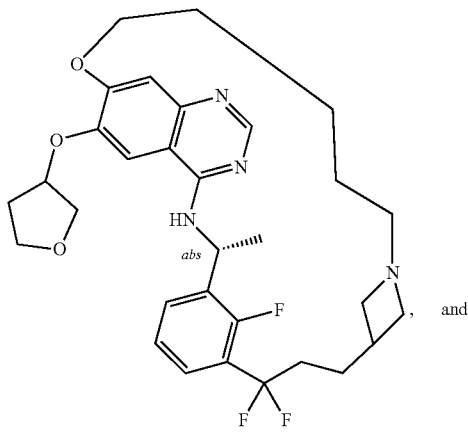
and
-continued
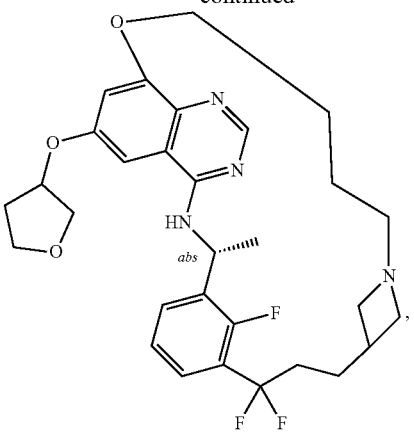
or a pharmaceutically acceptable salt or solvate thereof.
Also provided is a compound selected from:
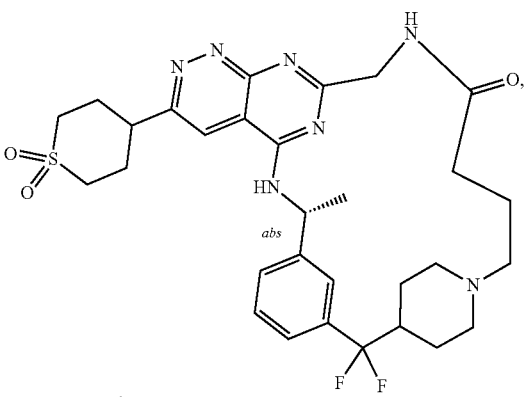
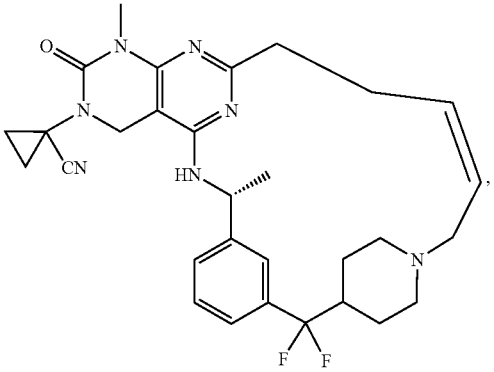
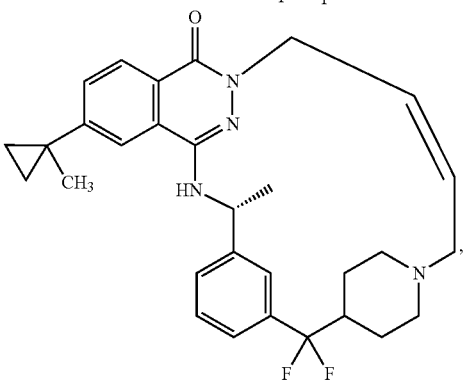

217
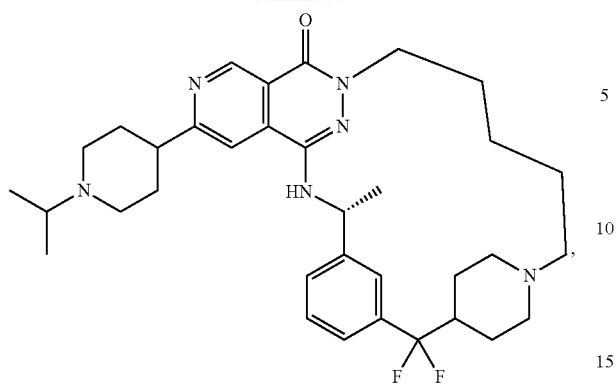
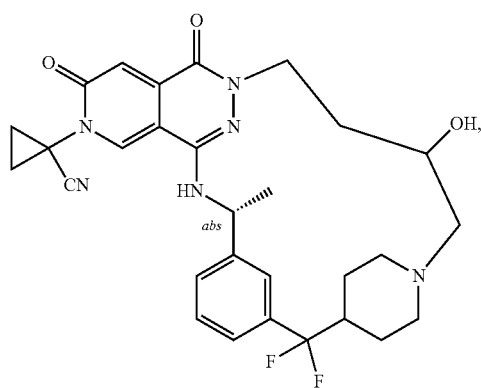
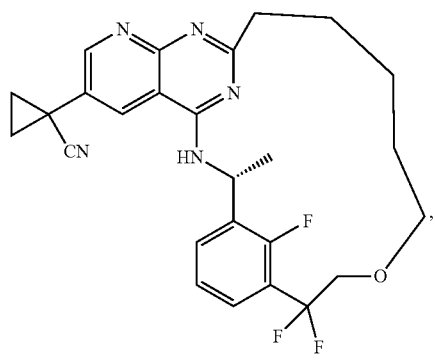
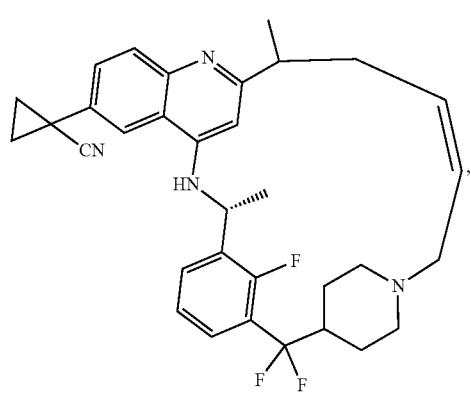
218
-continued
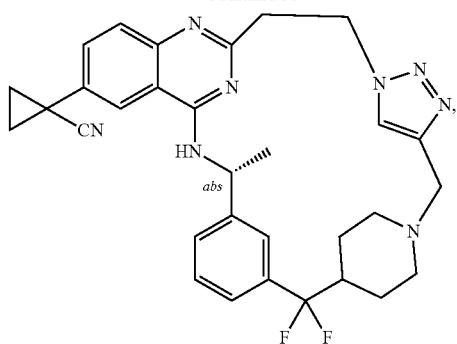
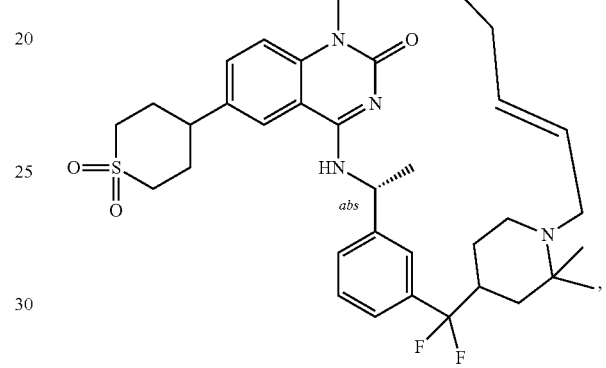
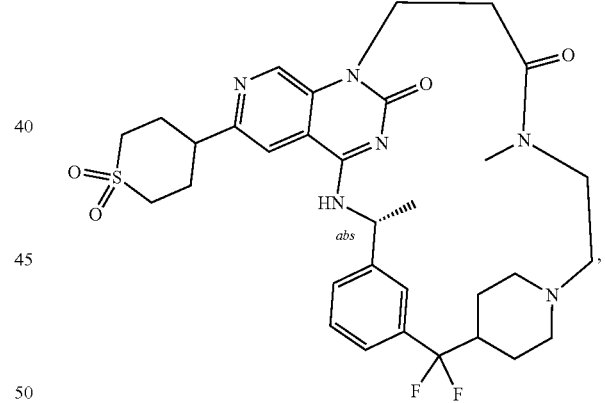
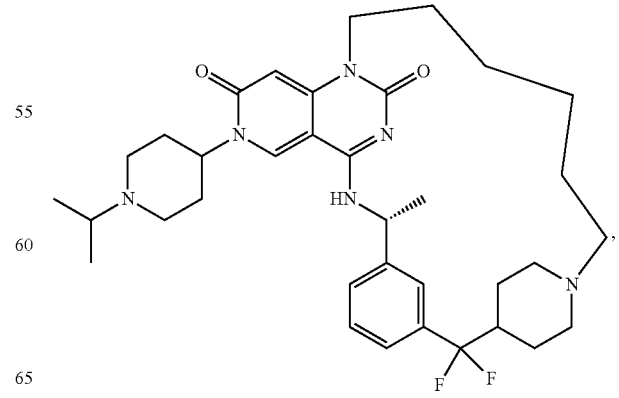

219
-continued
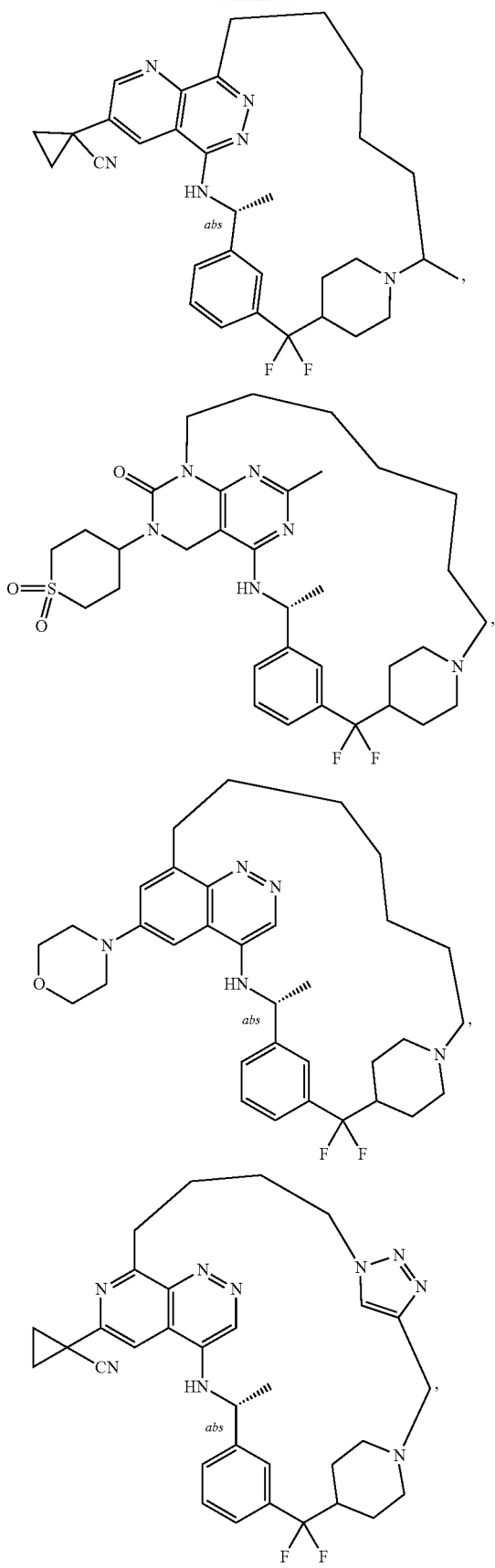
220
-continued
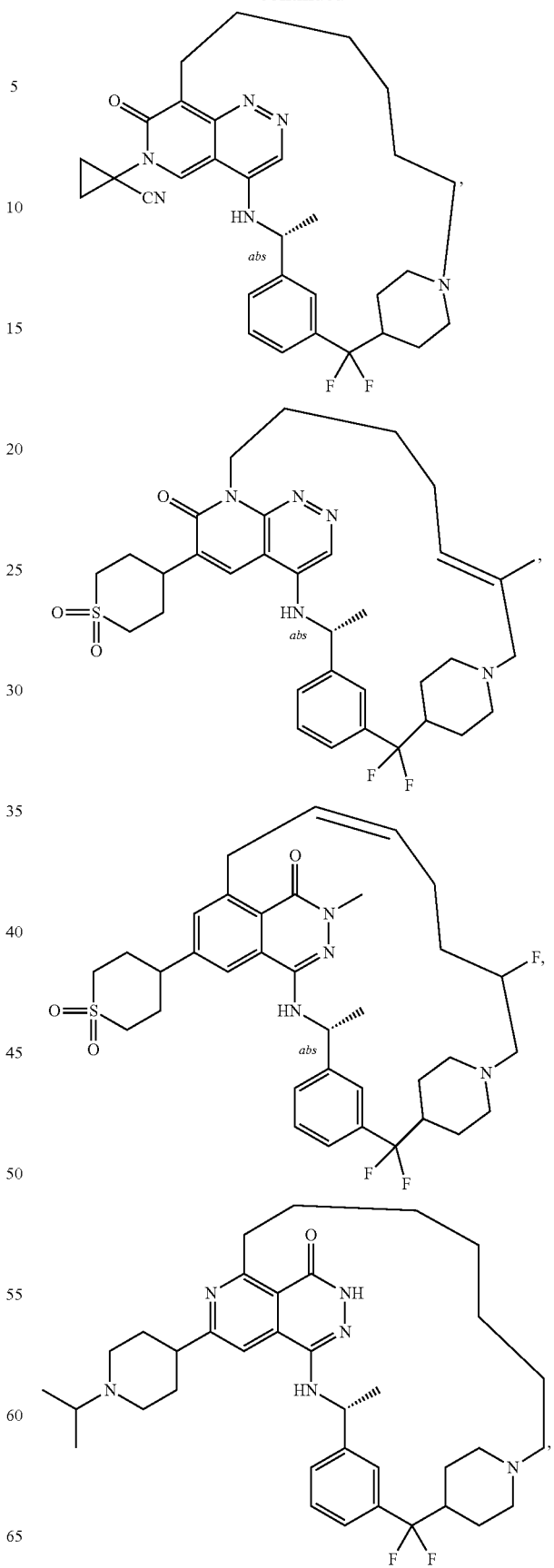

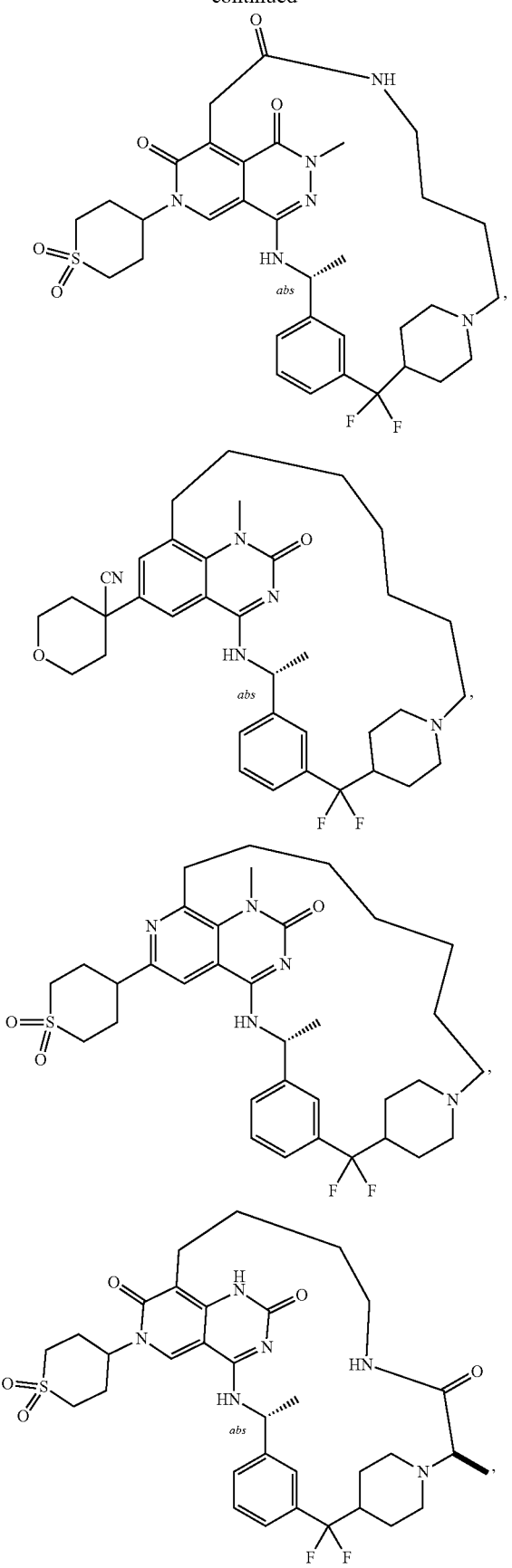
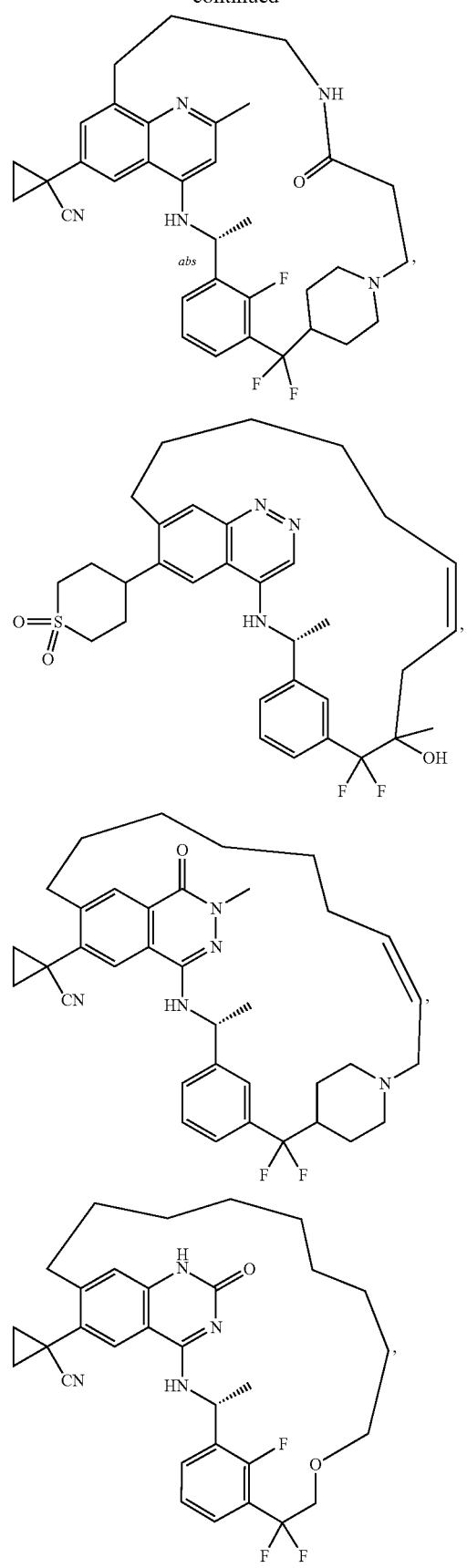

223
-continued
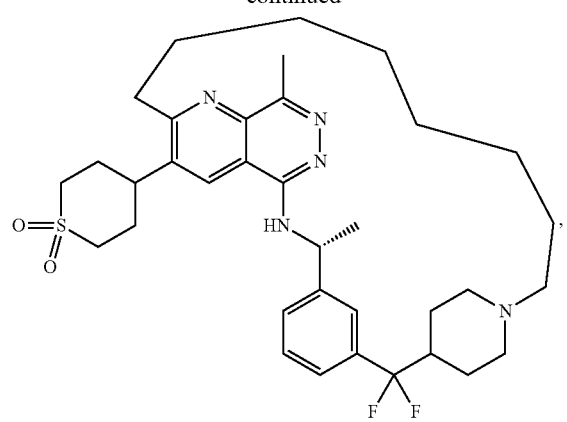
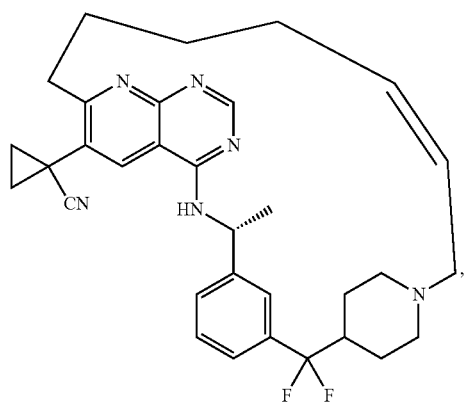
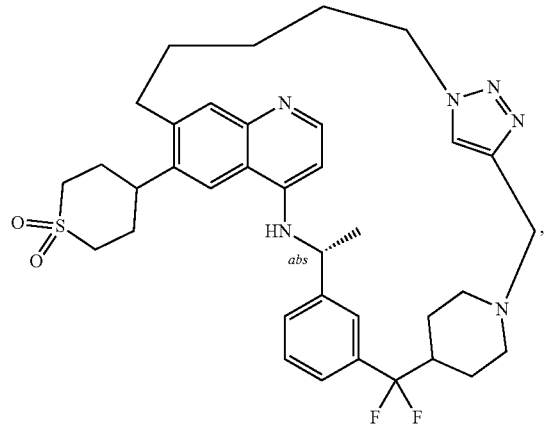
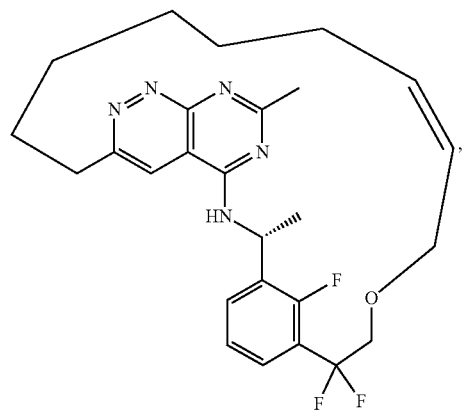
224
-continued
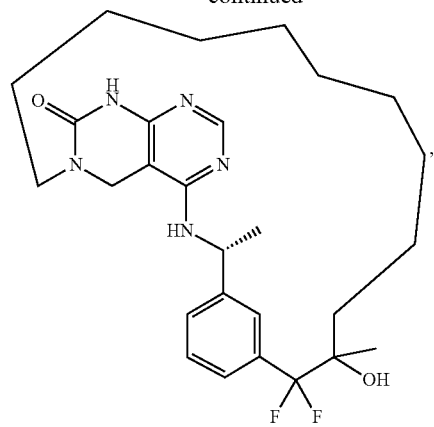
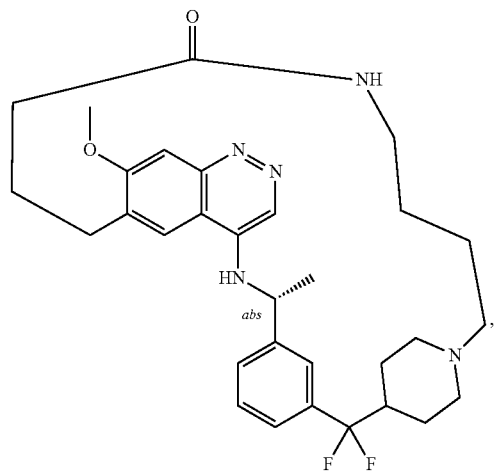
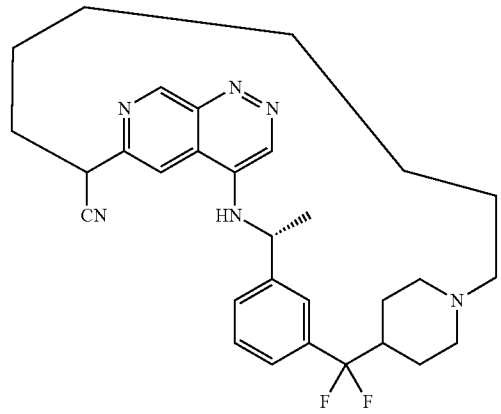
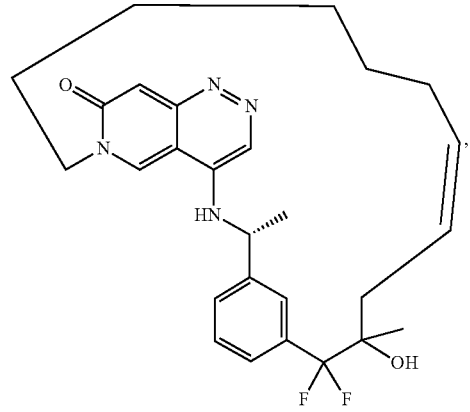

225
-continued
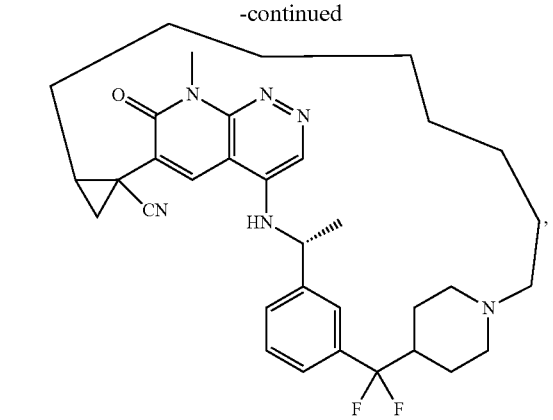
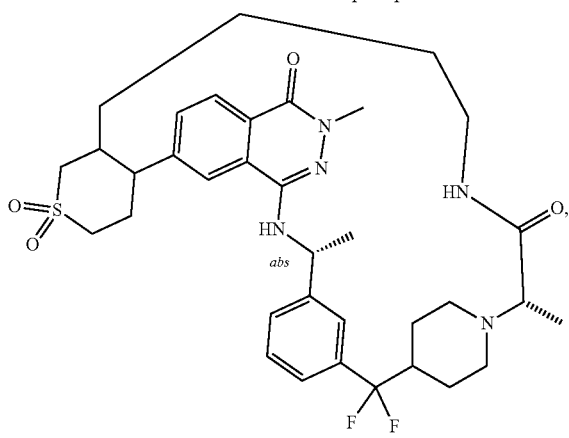
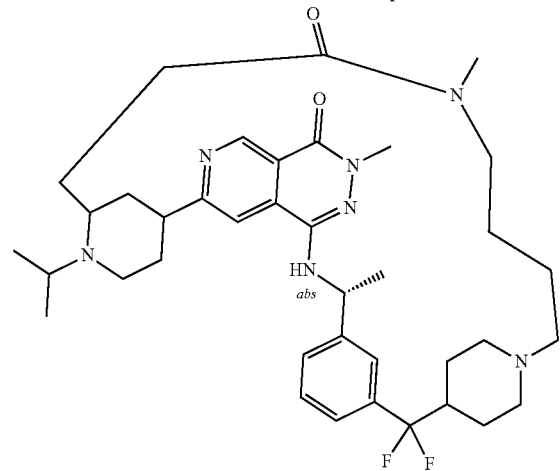
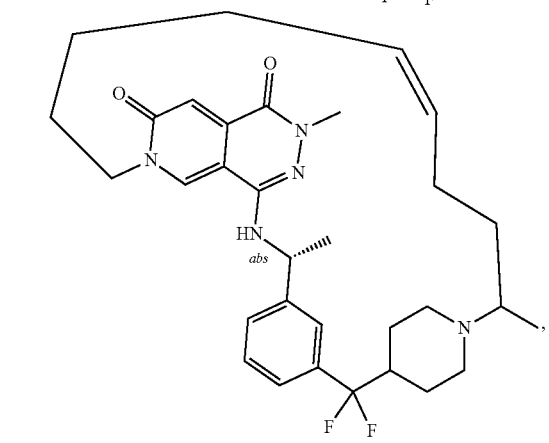
226
-continued
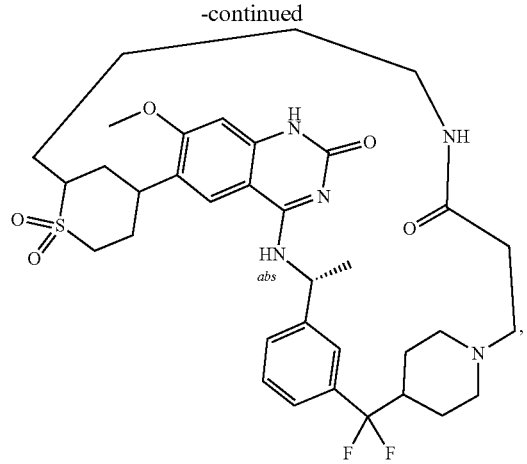
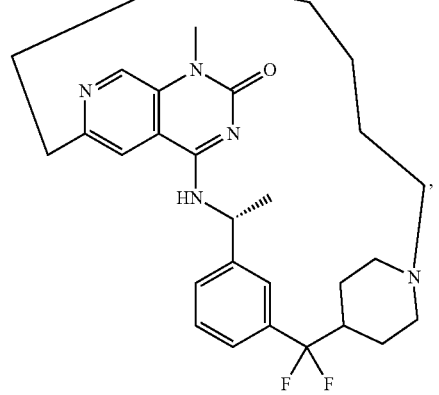
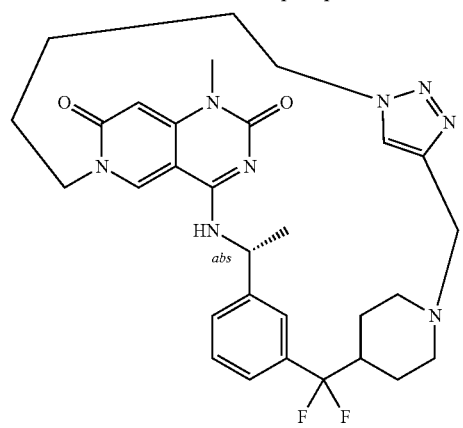
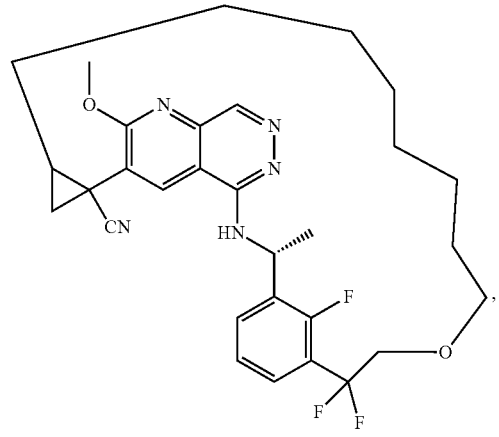

227
-continued
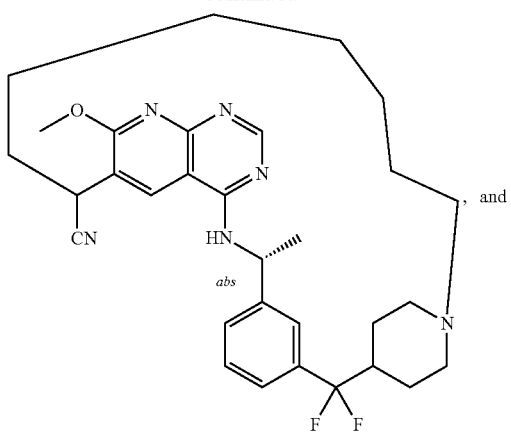
, and
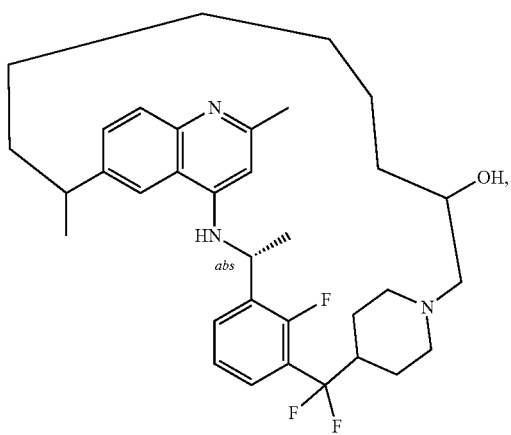 [SMILES: Cc1cc2c3cc(ccc3n1)C(C)CCCCCCC(O)CN1CCC(CC1)C(F)(F)c1cccc(c1F)[C@@H](C)N2]
or a pharmaceutically acceptable salt or solvate thereof.
In some embodiments, the present disclosure provides a compound selected from
228
-continued
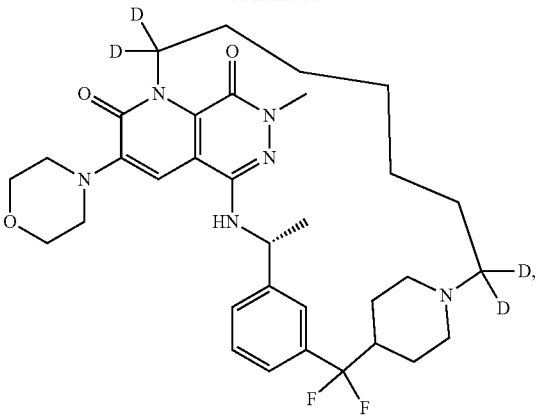
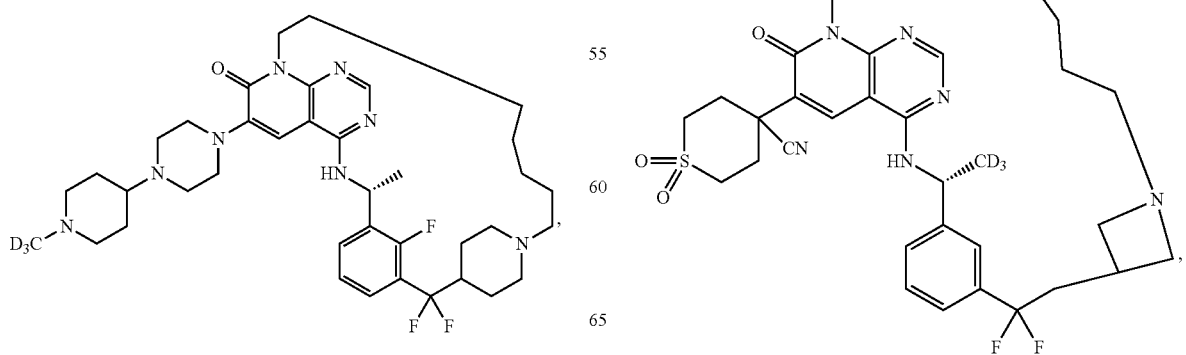

229
-continued
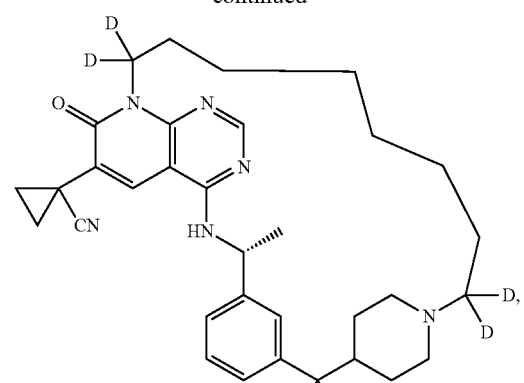
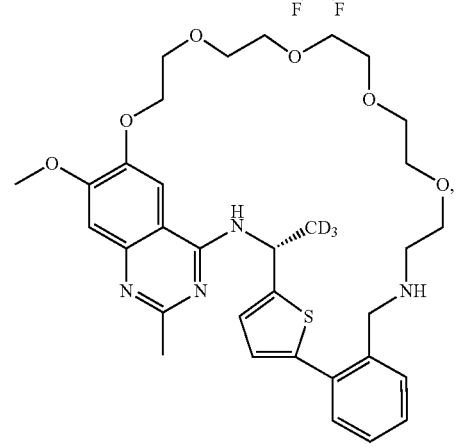
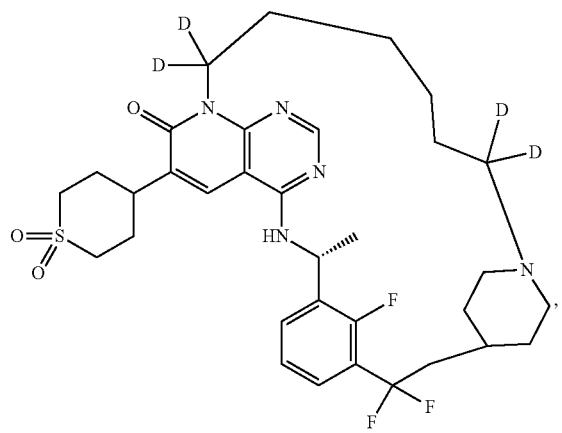
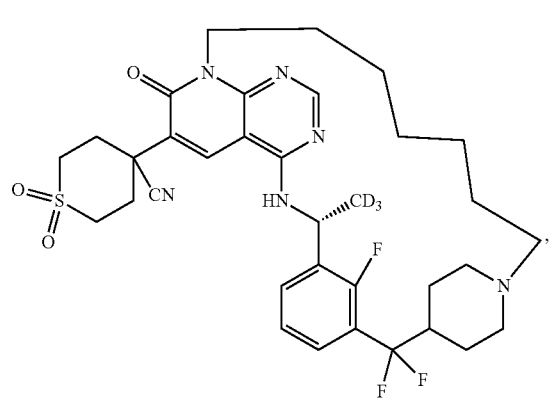
230
-continued
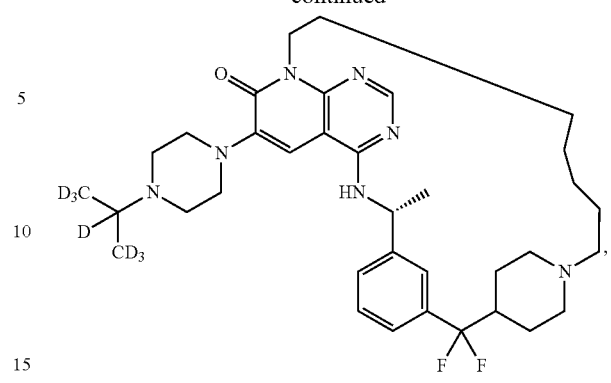
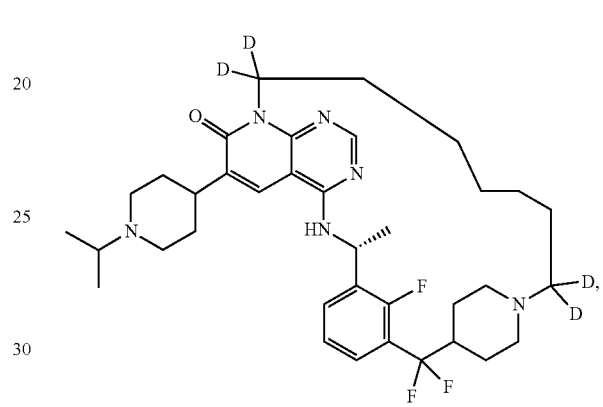
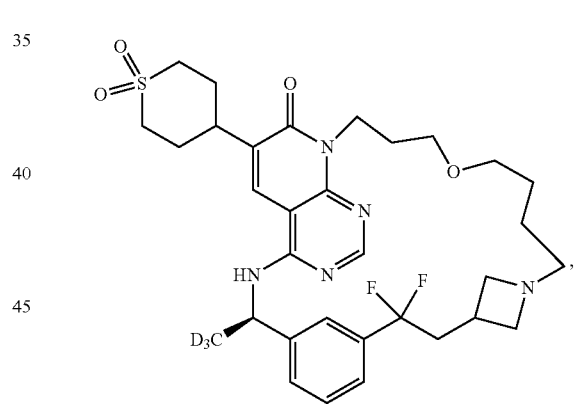
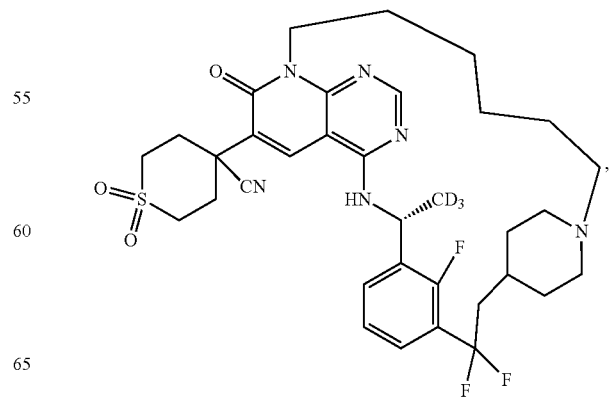

231
-continued
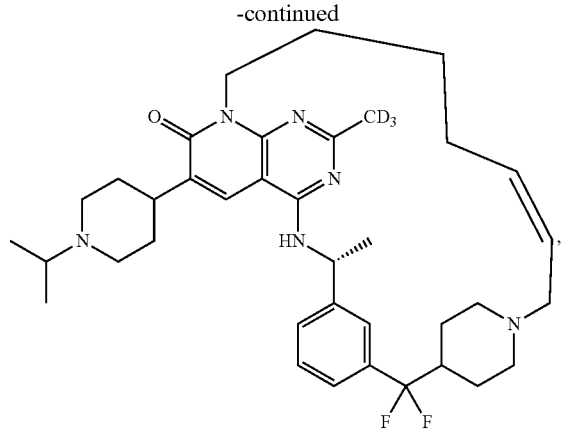
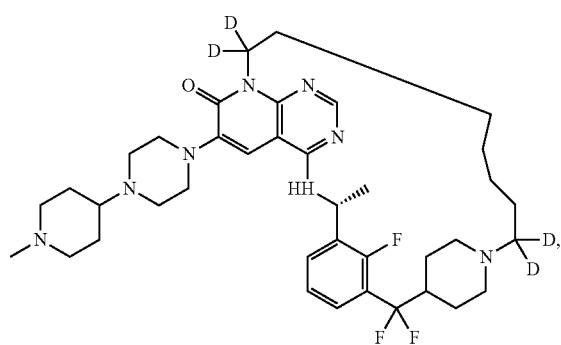
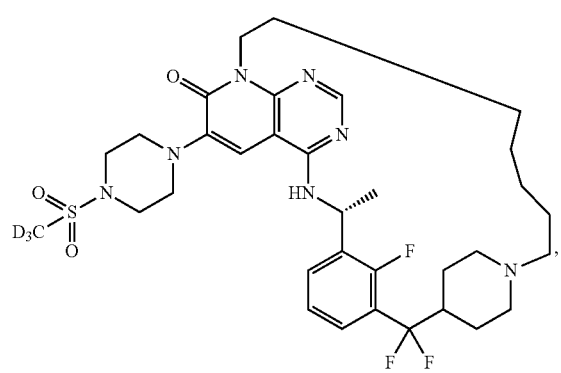
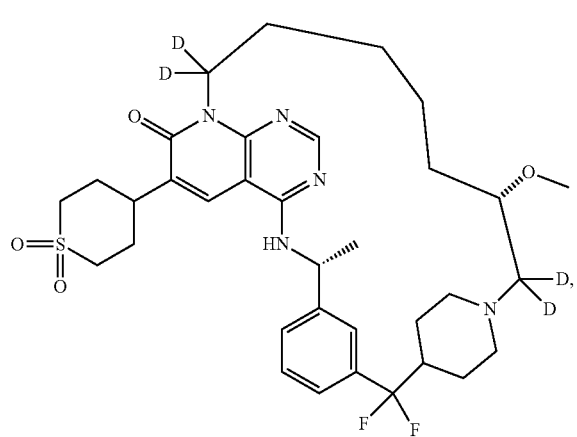
232
-continued
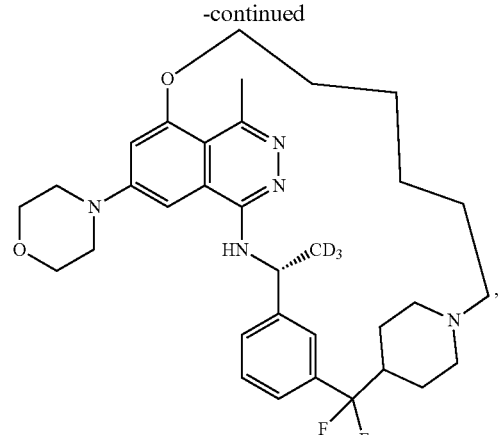
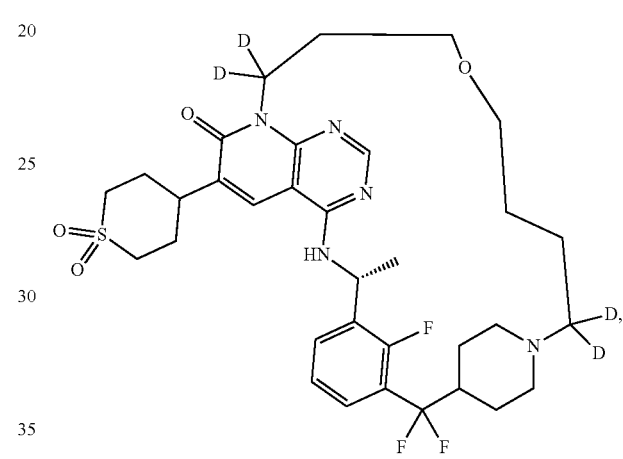
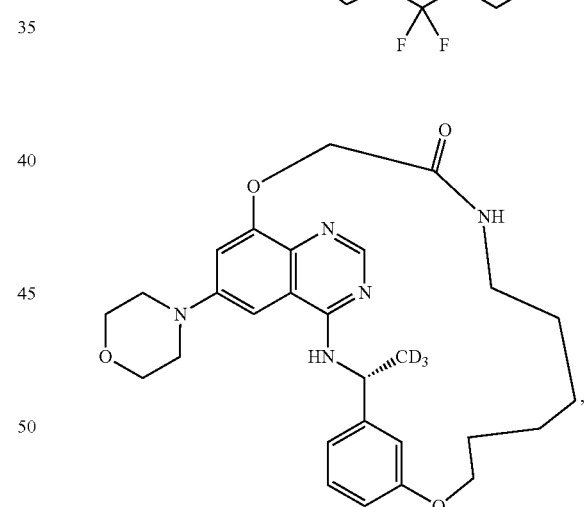
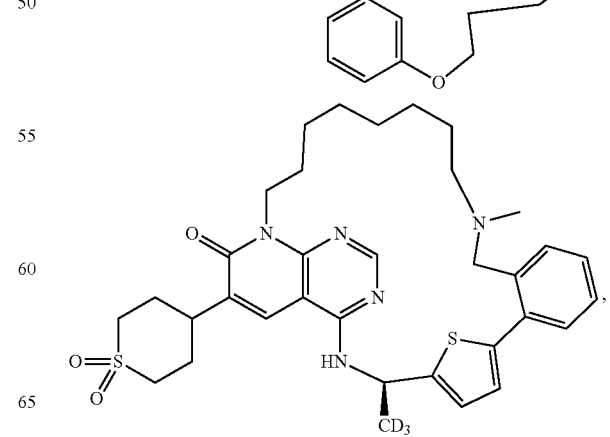

233
-continued
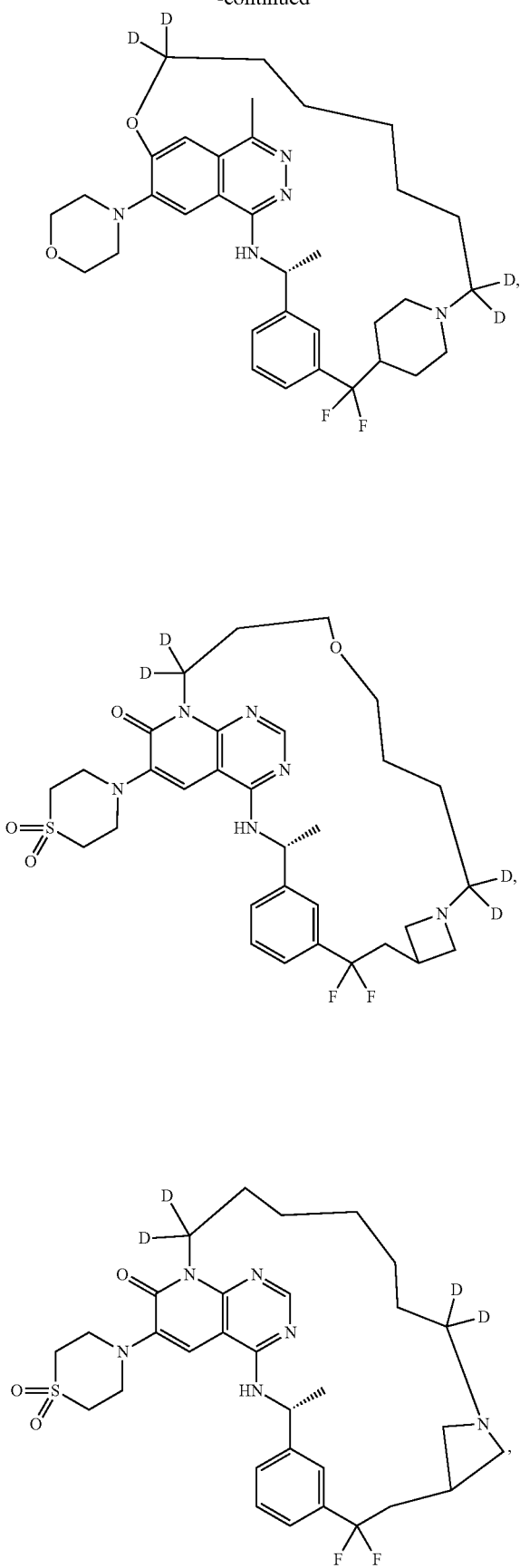
234
-continued
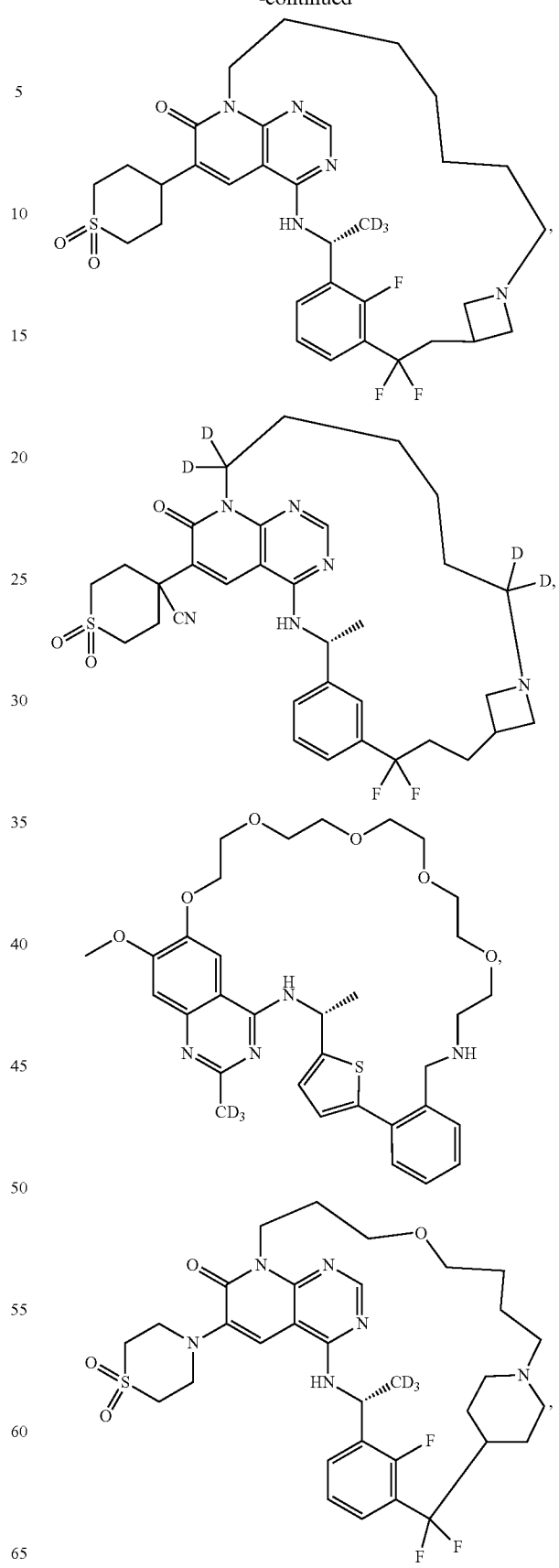

235
-continued
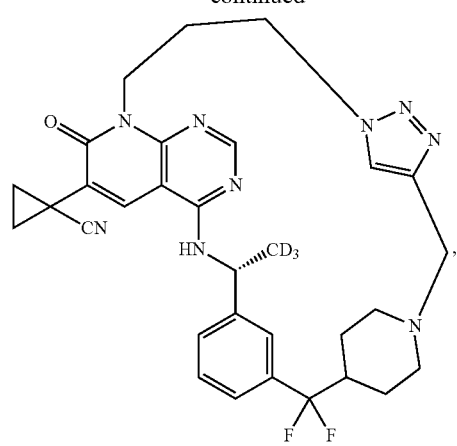
236
-continued
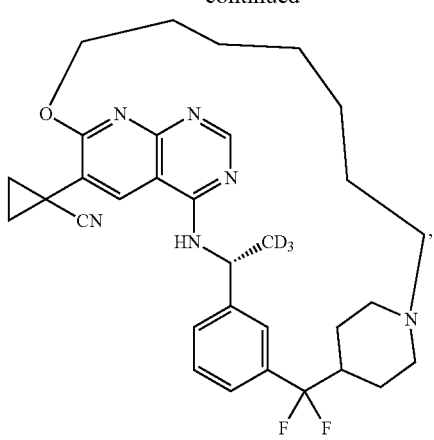
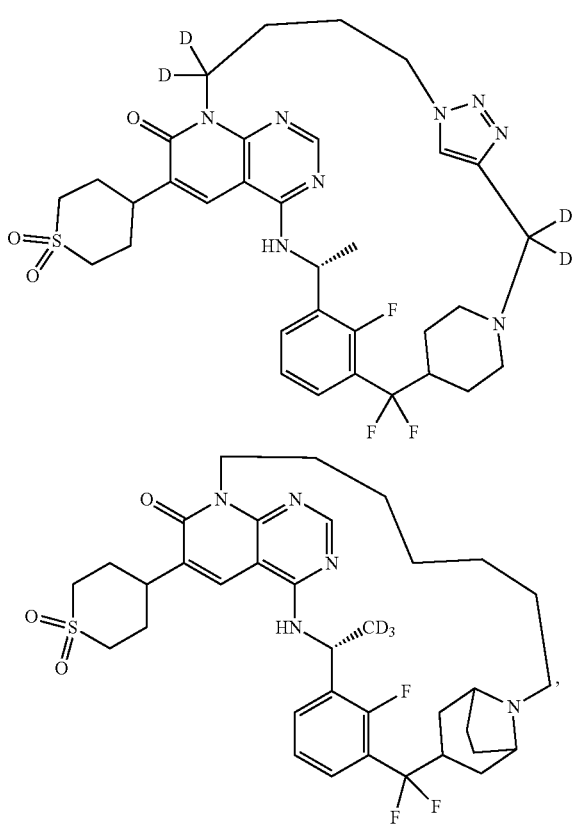
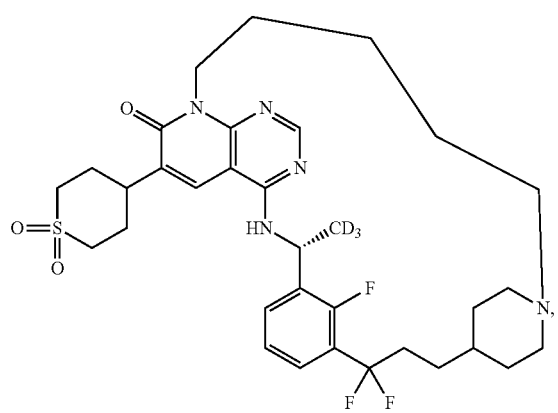
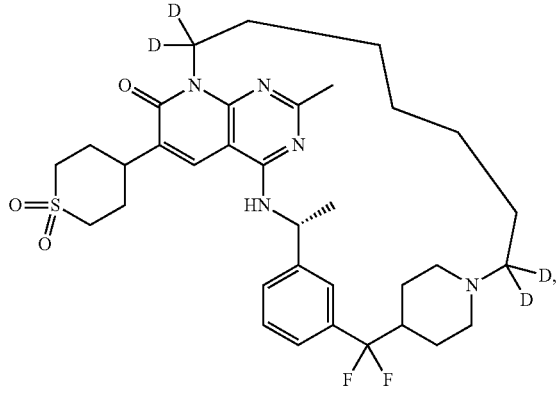
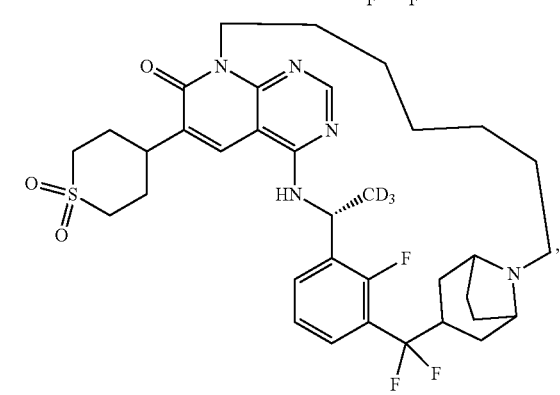
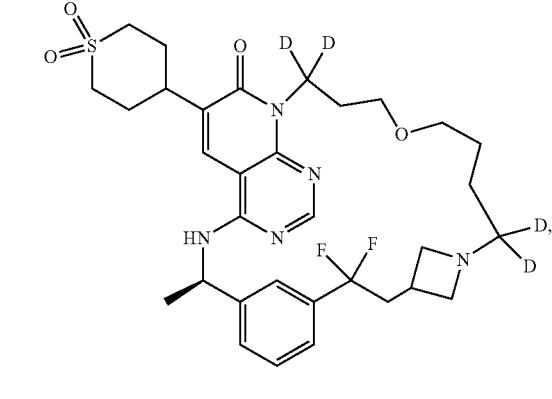
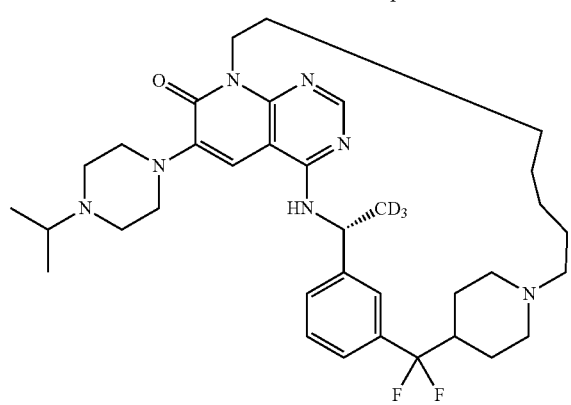

237
-continued
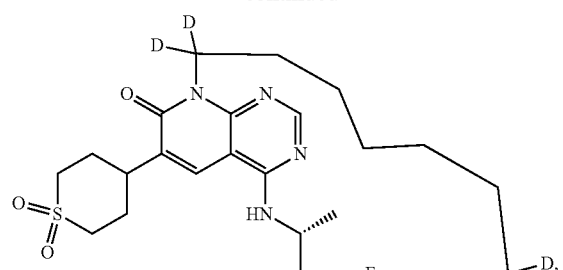
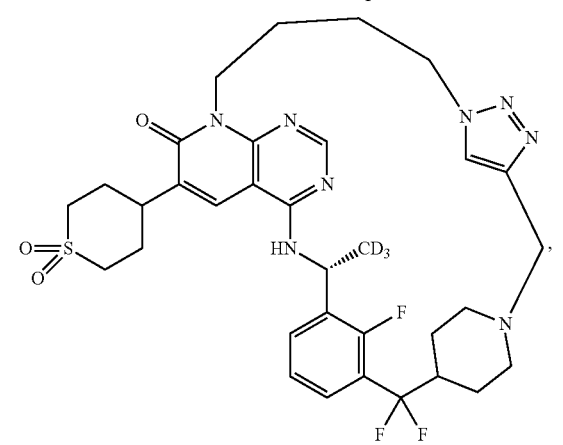
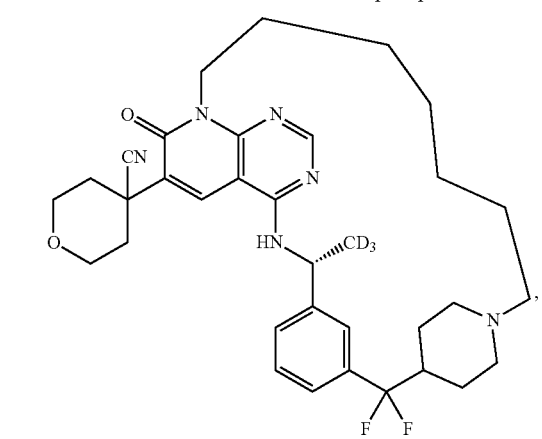
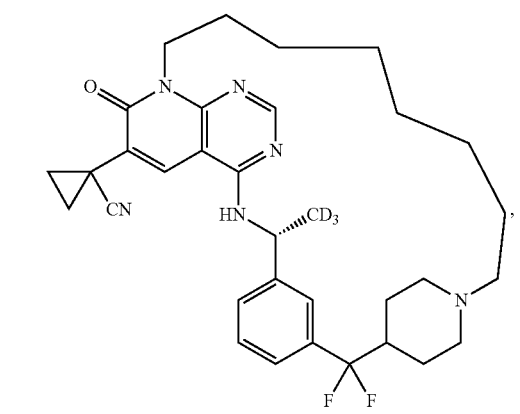
238
-continued
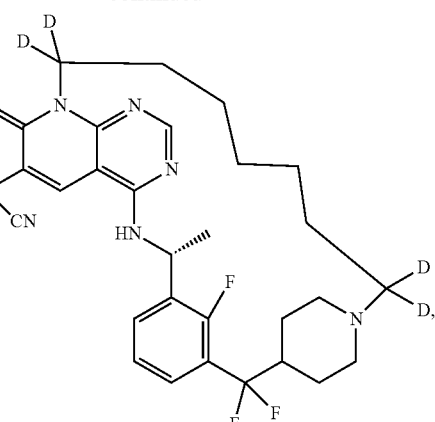
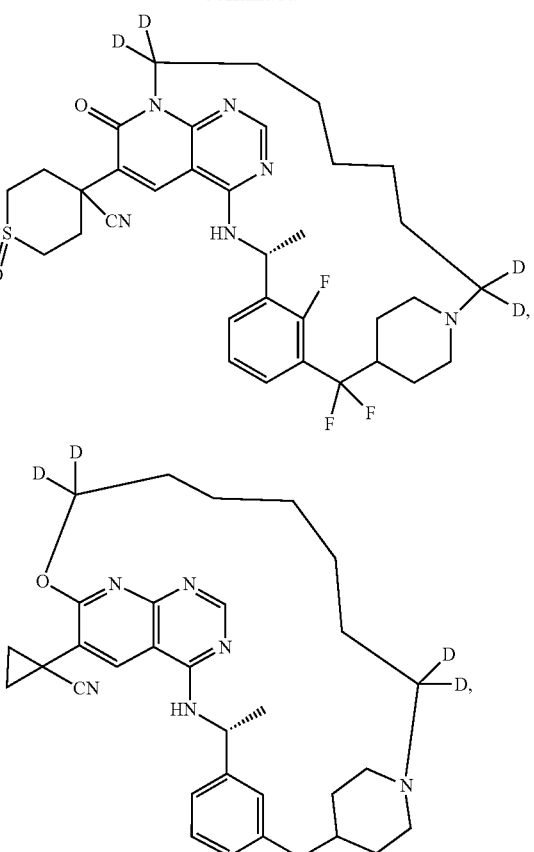
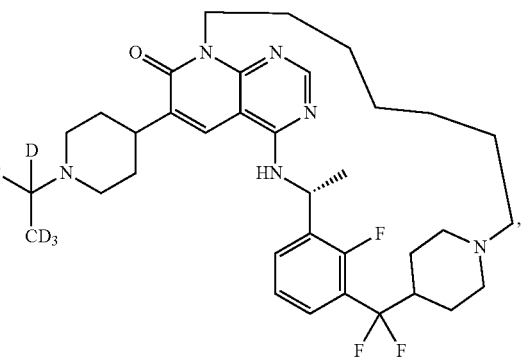
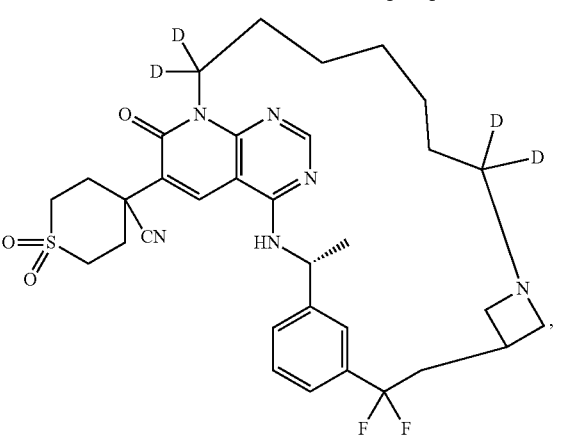

239
-continued
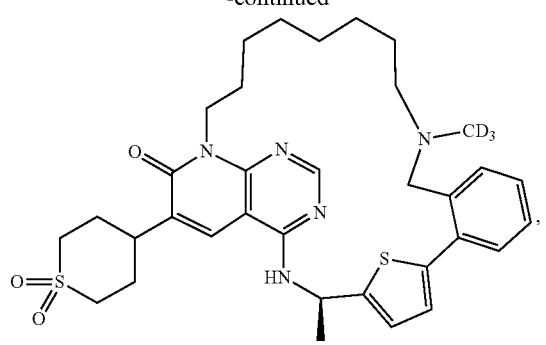
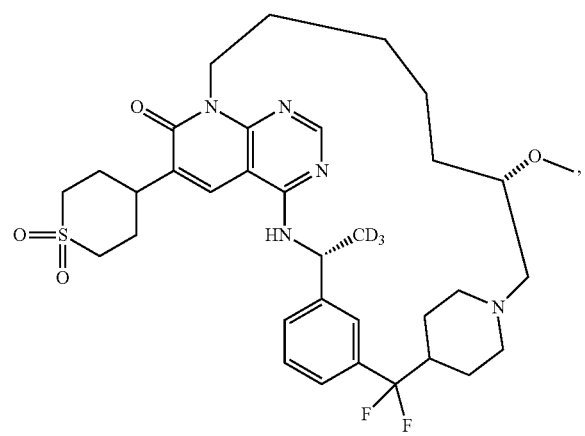
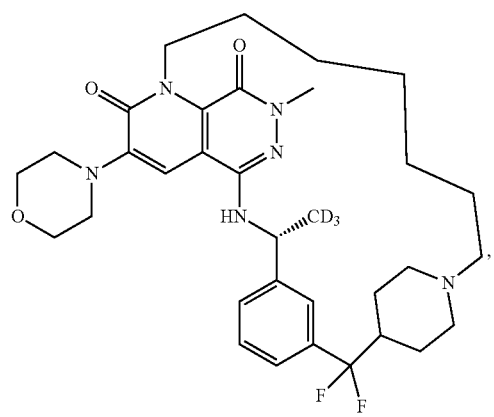
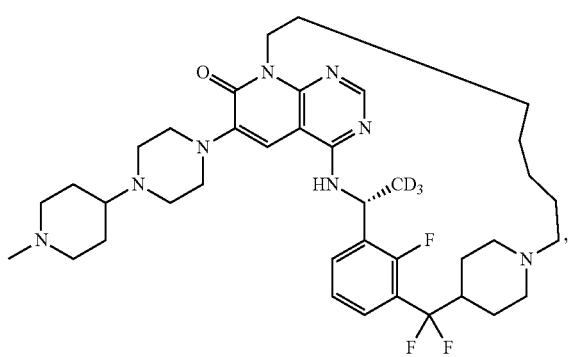
240
-continued
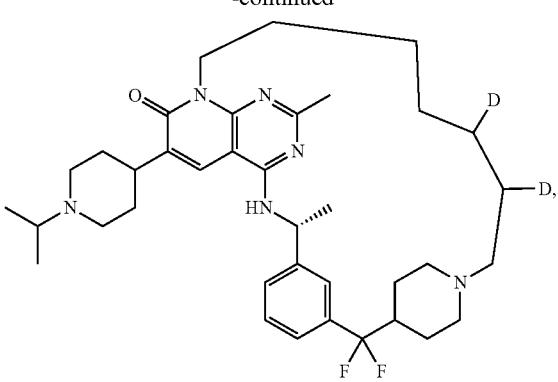
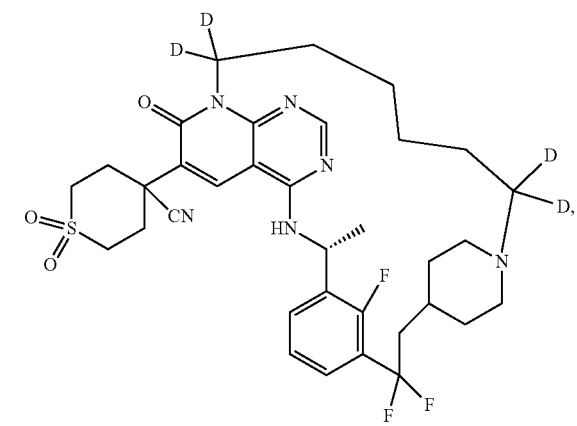
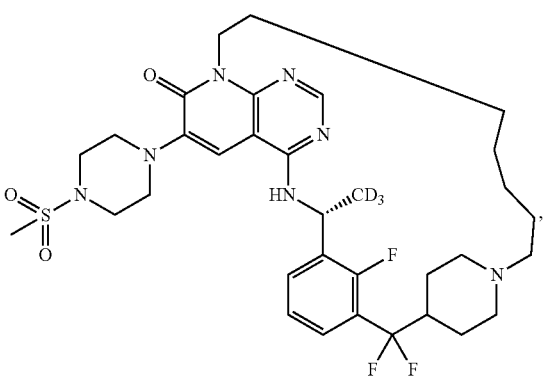

-continued
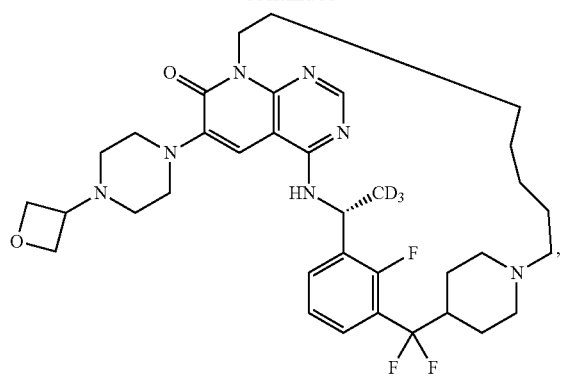
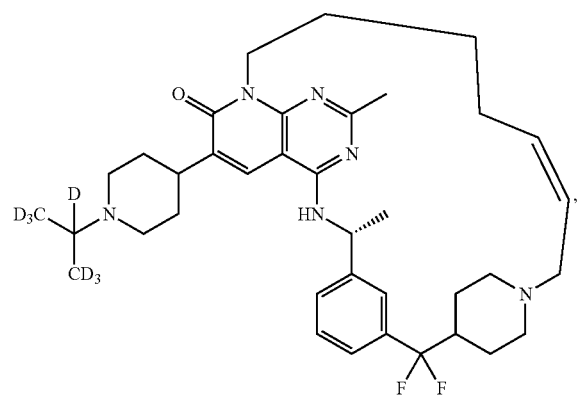
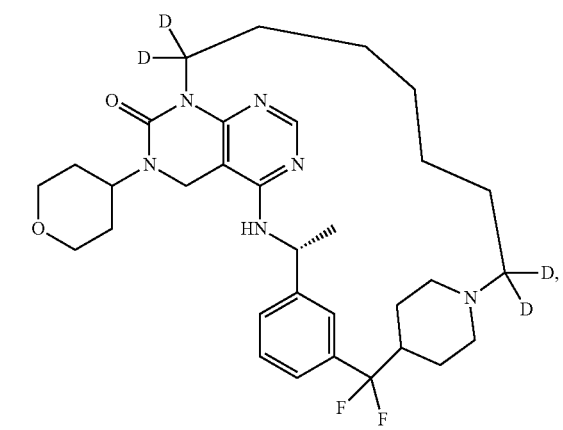
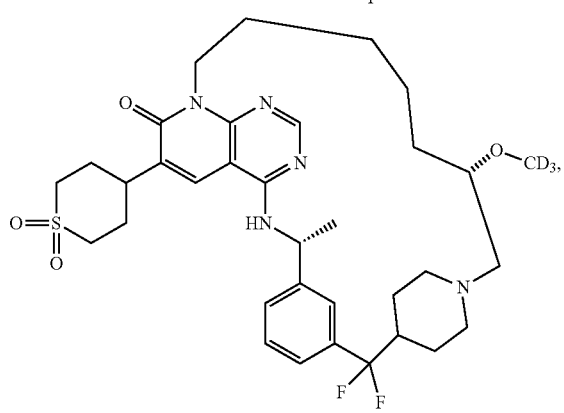
-continued
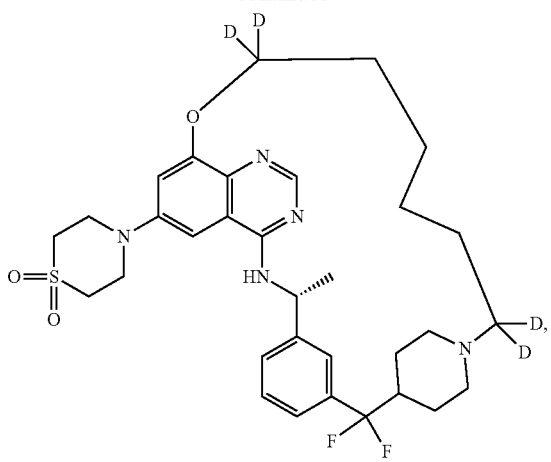
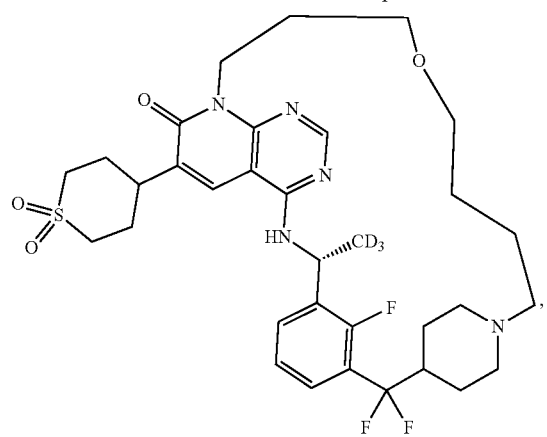
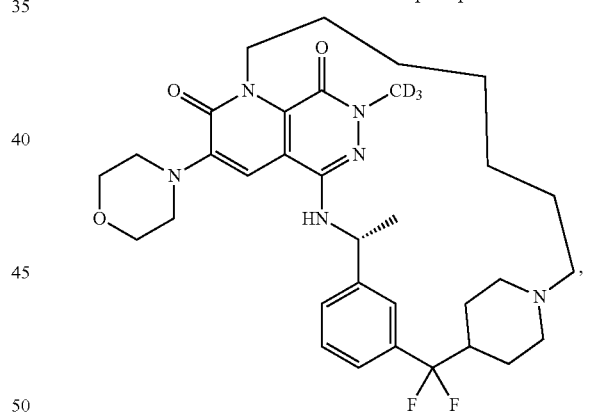
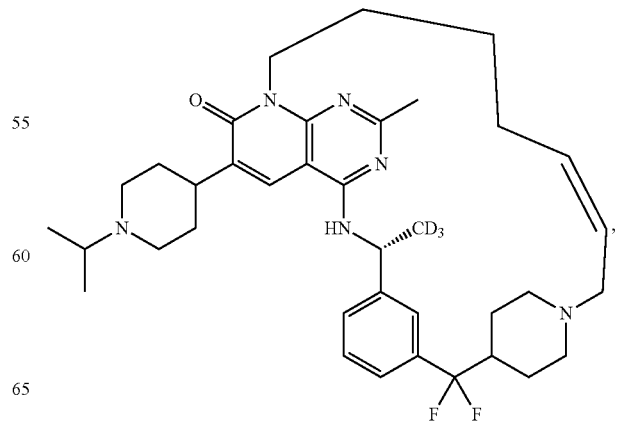

243
-continued
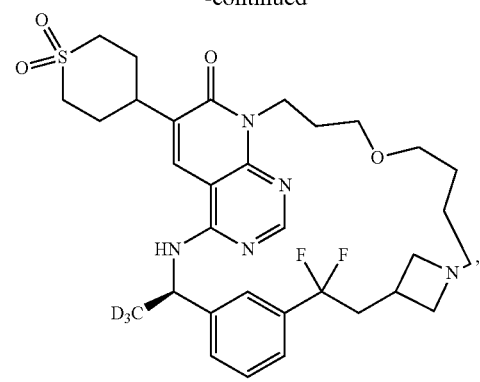
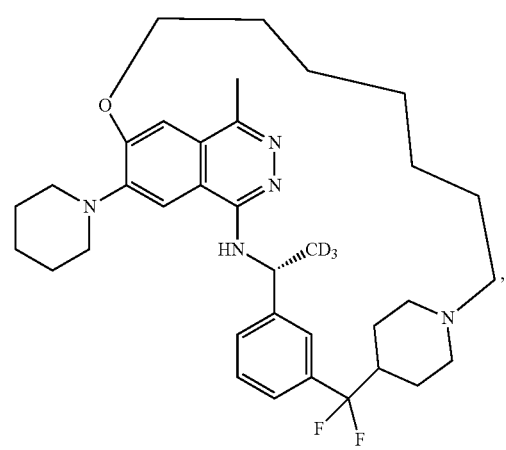
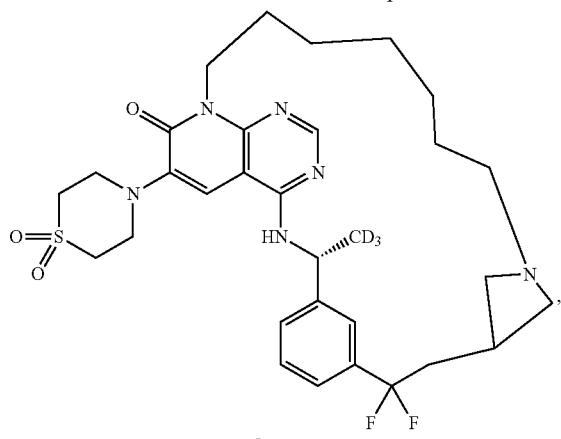
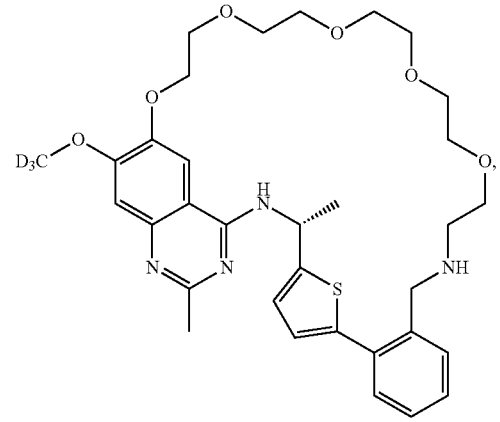
244
-continued
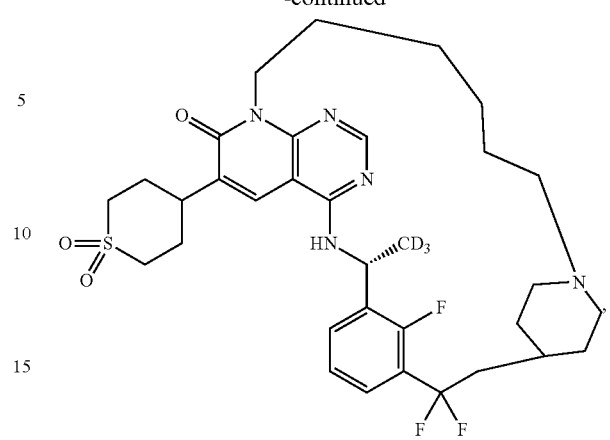
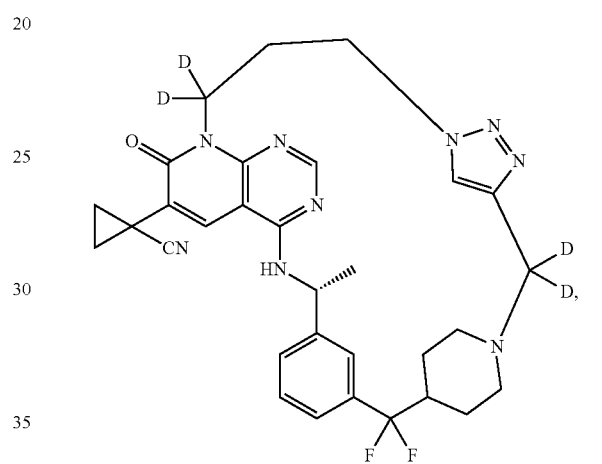
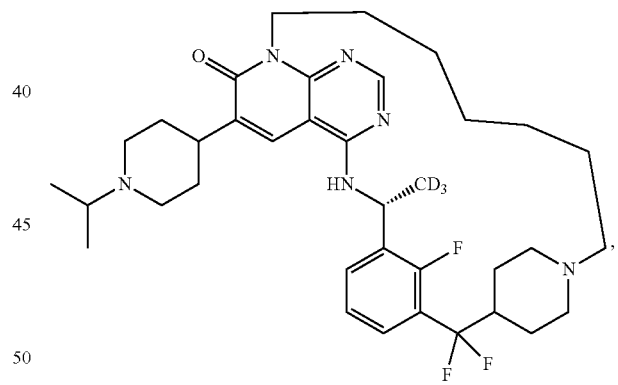
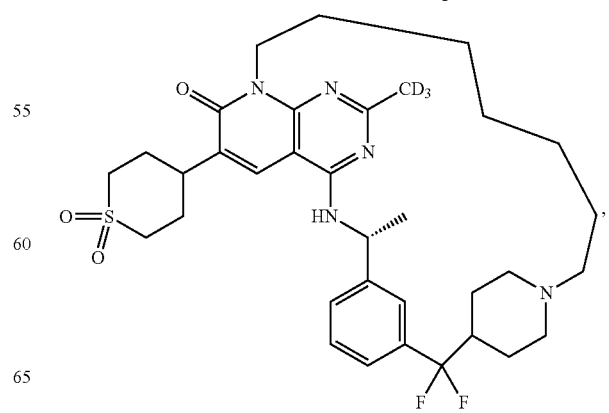

245
-continued
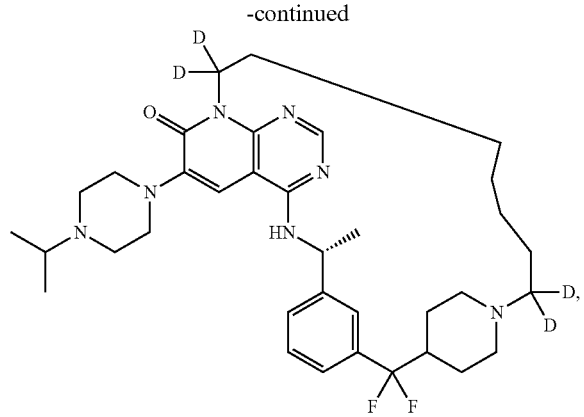
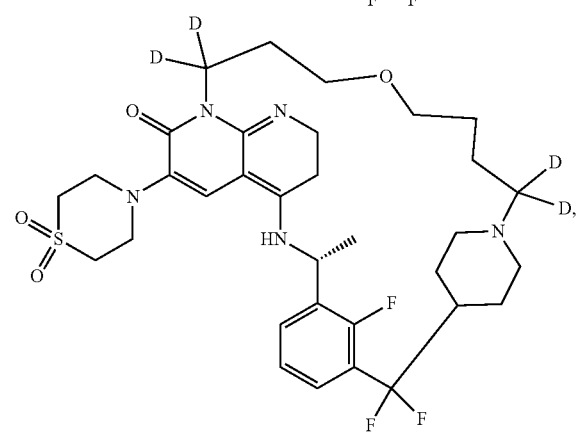
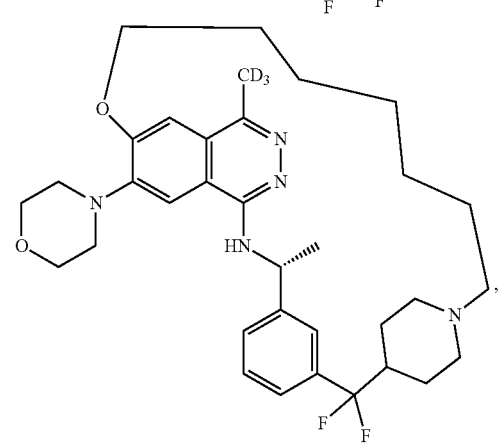
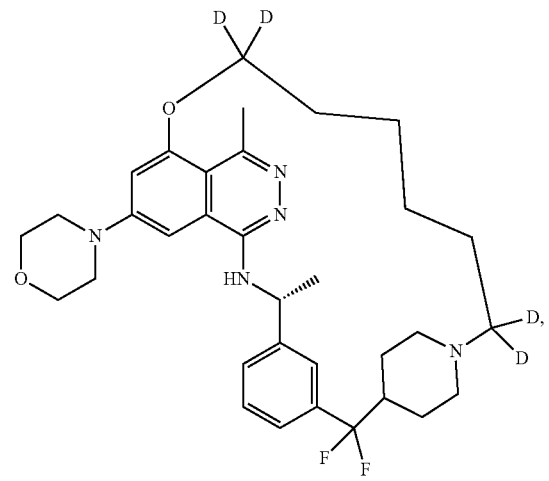
246
-continued
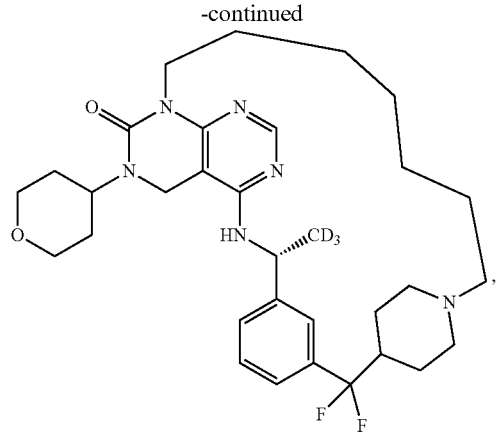
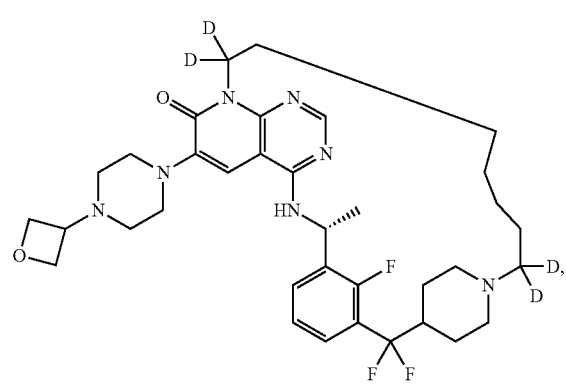
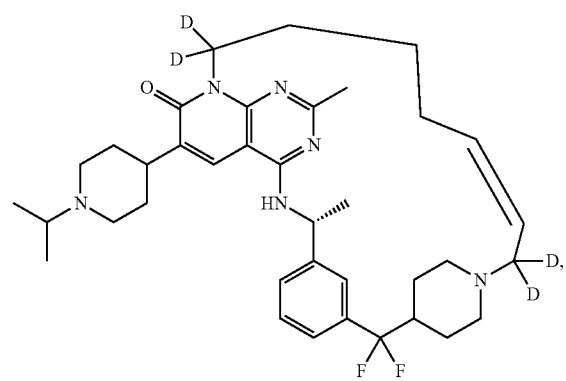
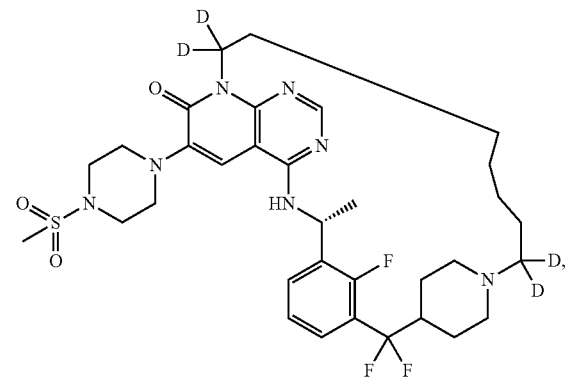

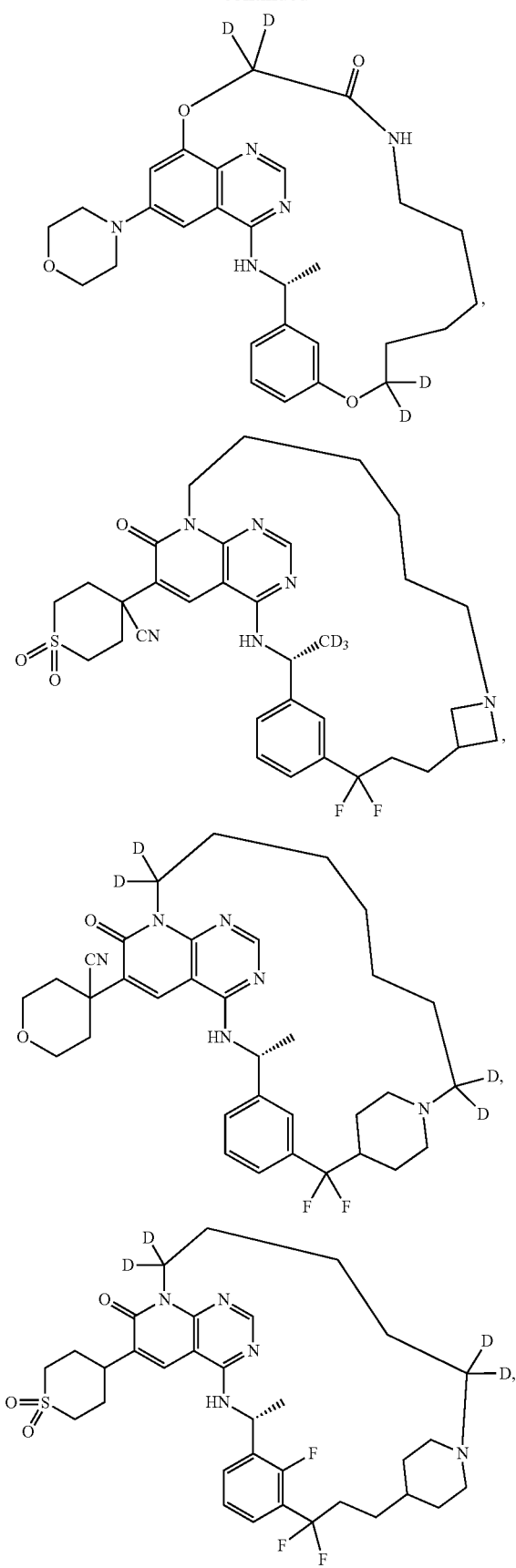
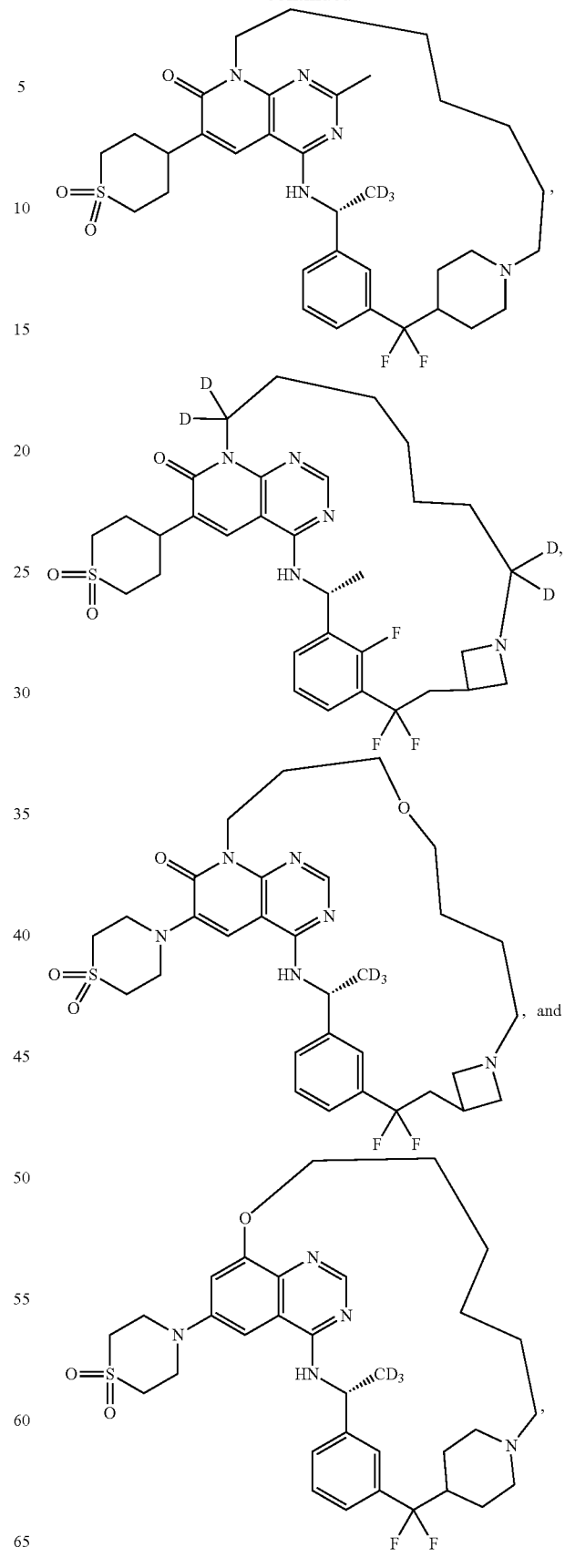

249
or a pharmaceutically acceptable salt or solvate thereof.
In some embodiments, the present disclosure provides a compound selected from
250
-continued
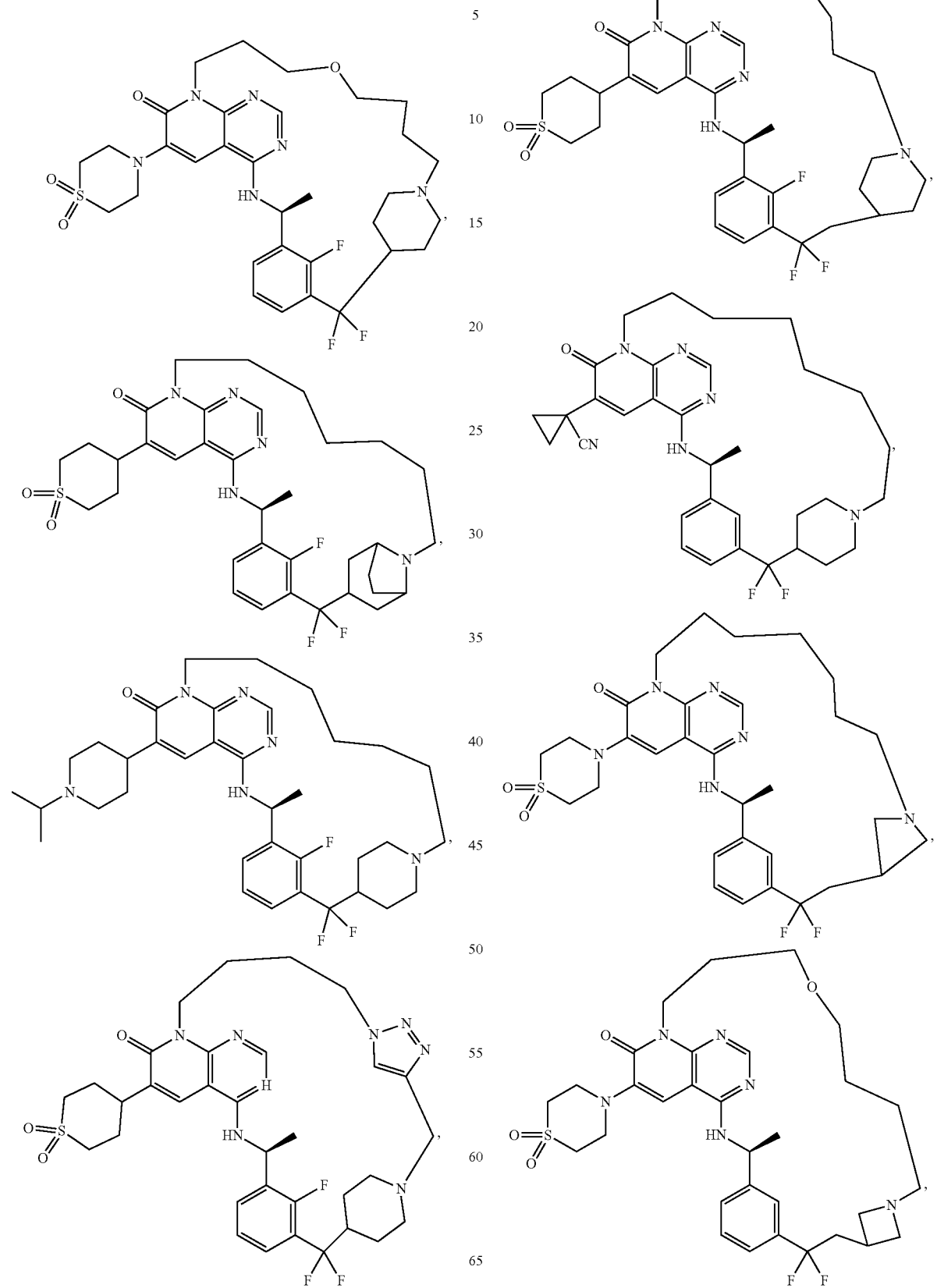

251
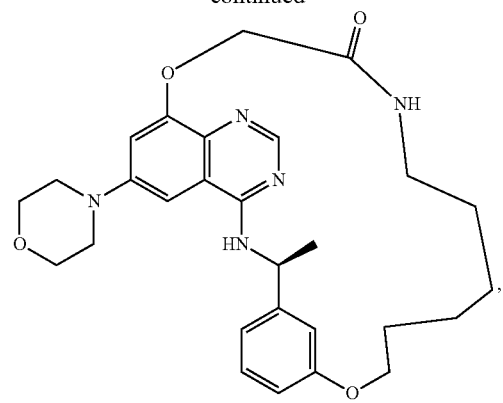
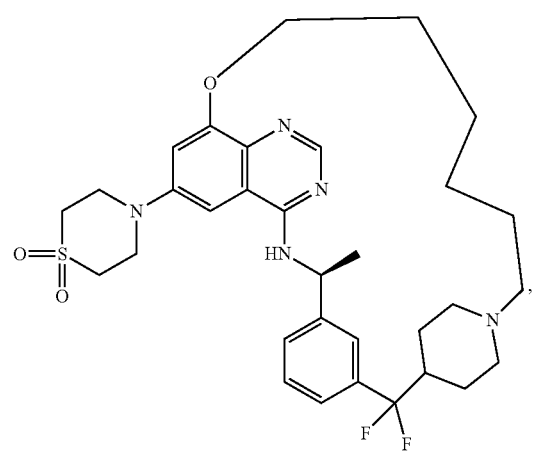
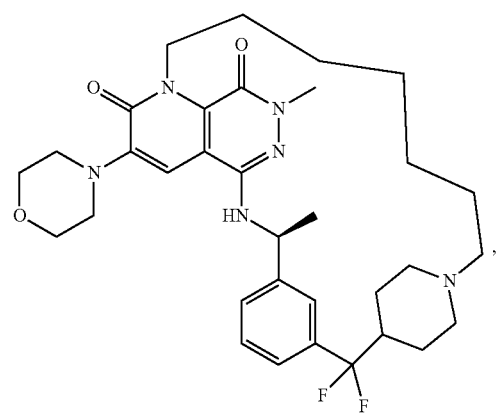
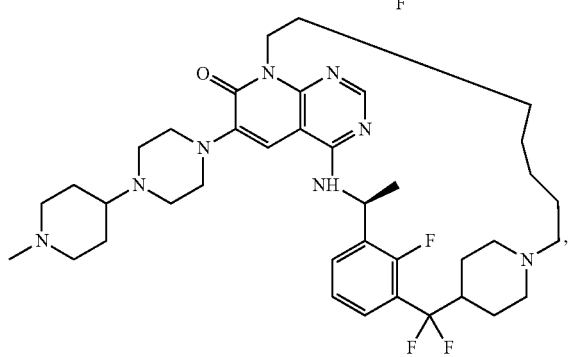
252
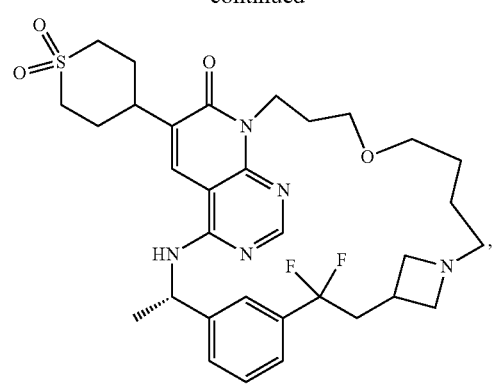
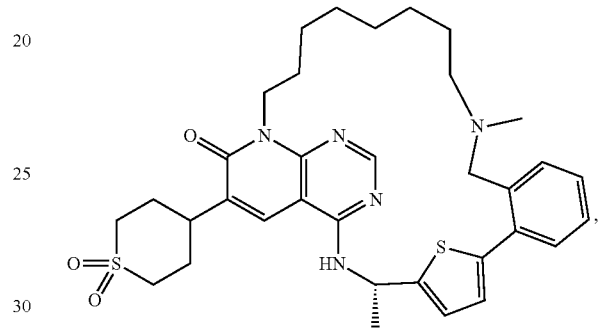
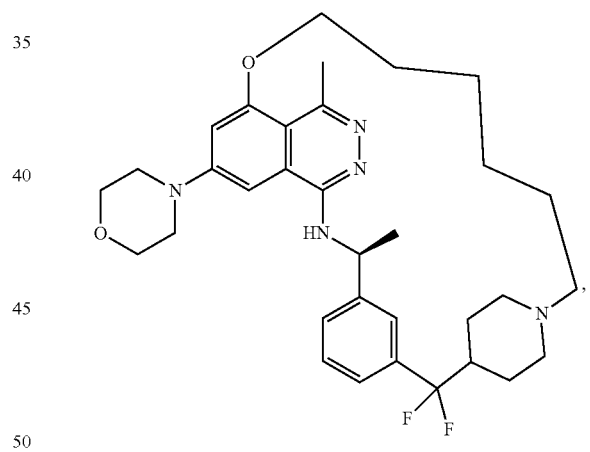
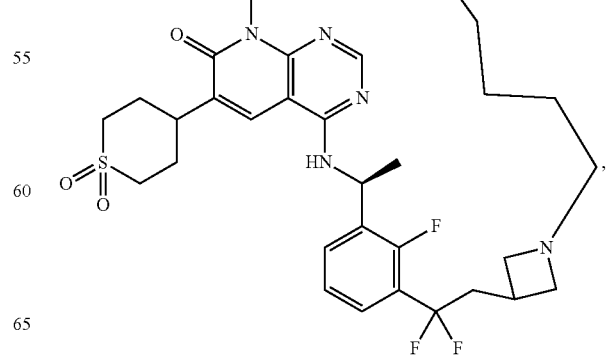

253
-continued
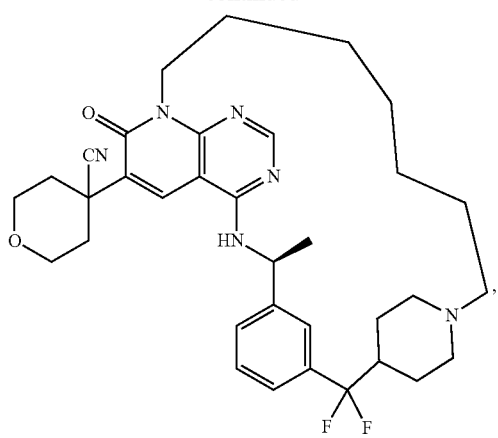
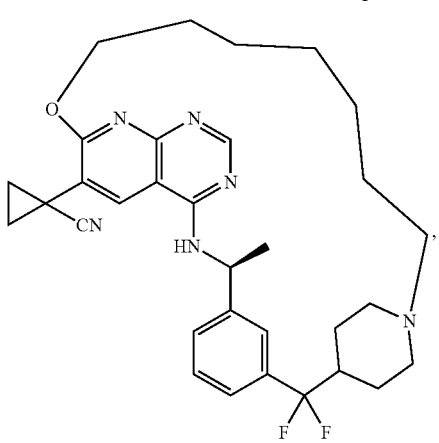
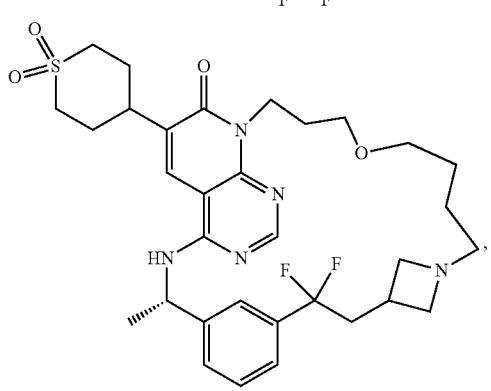
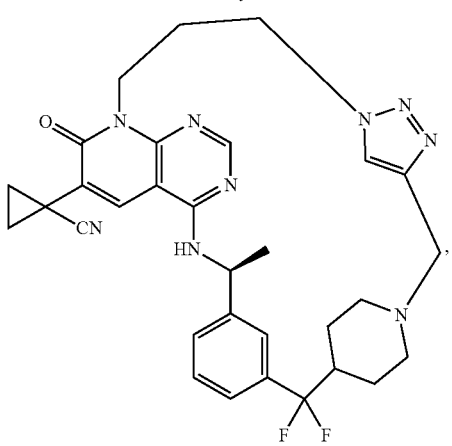
254
-continued
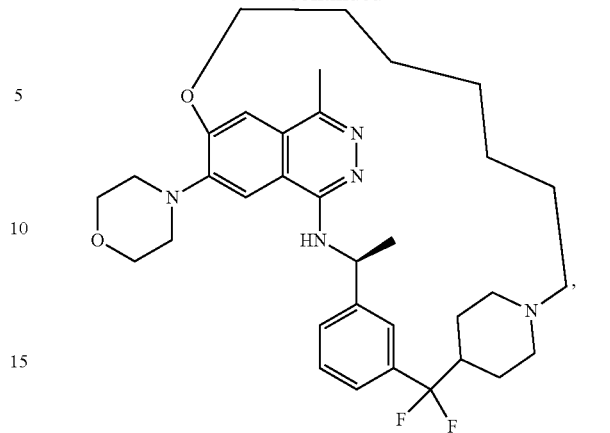
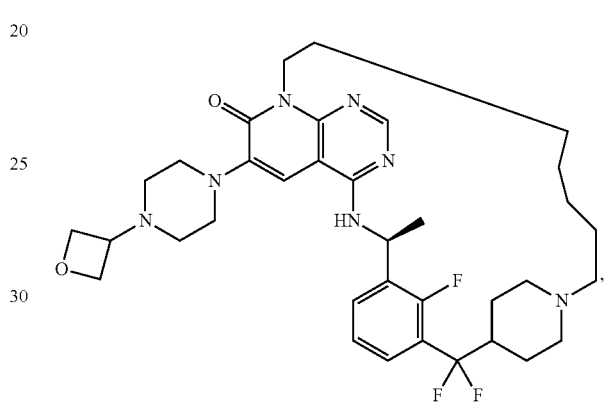
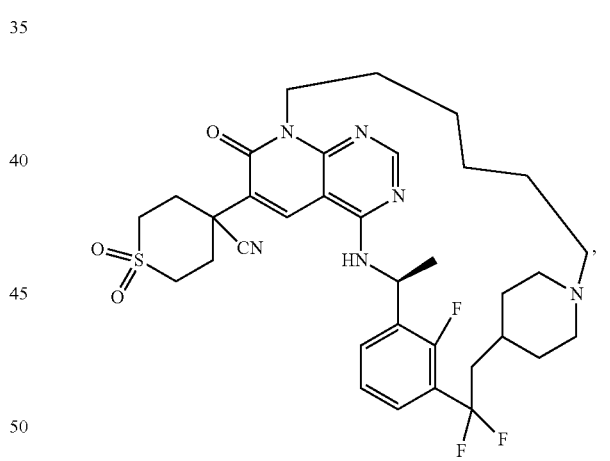
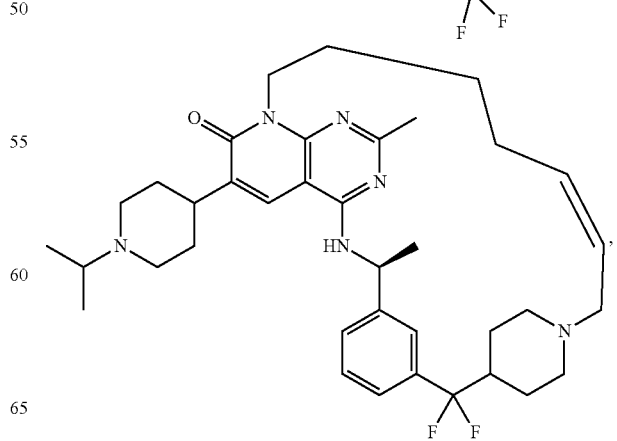

255
-continued
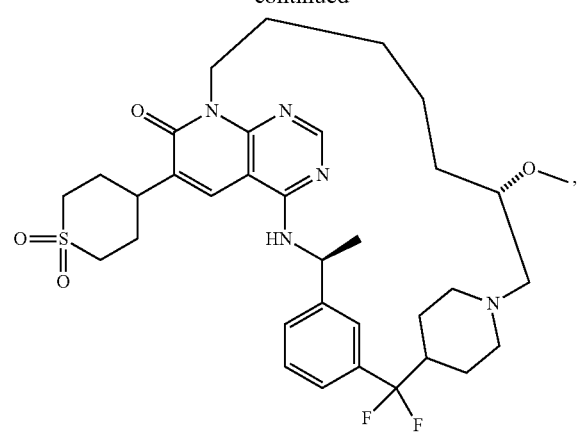
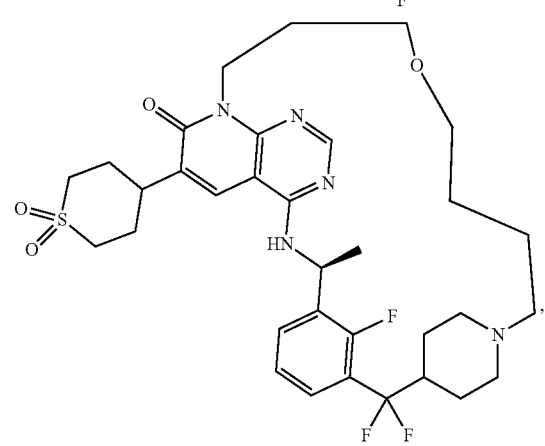
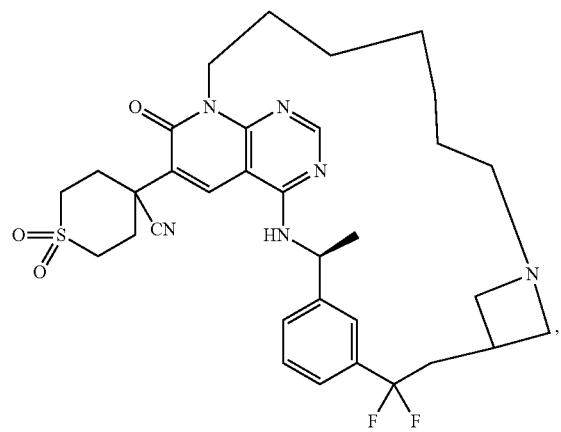
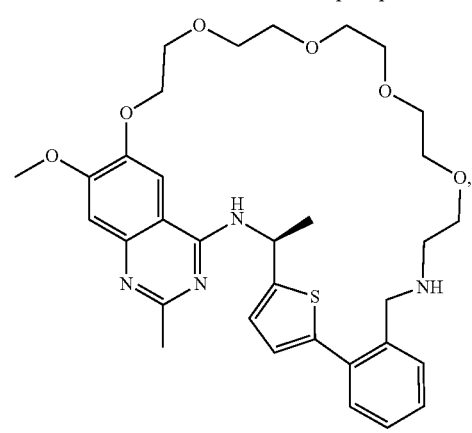
256
-continued
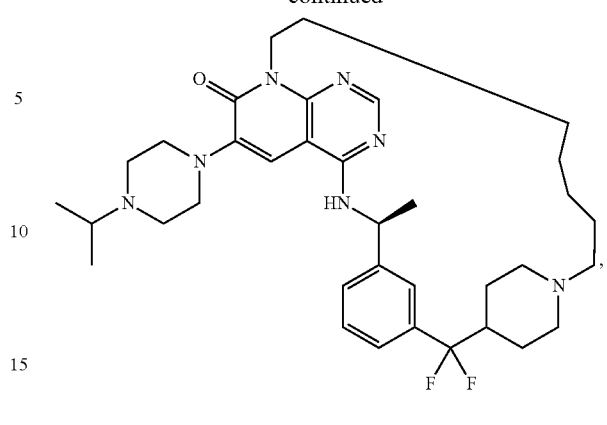
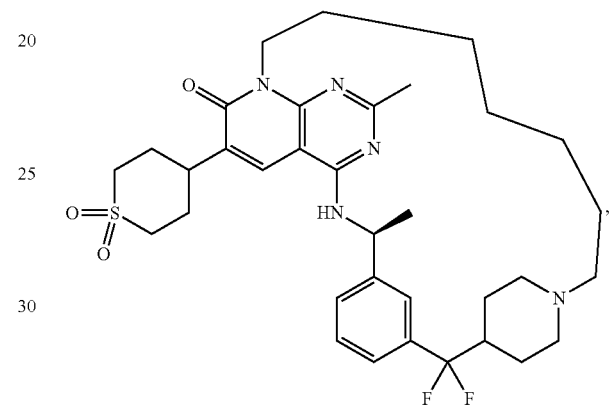
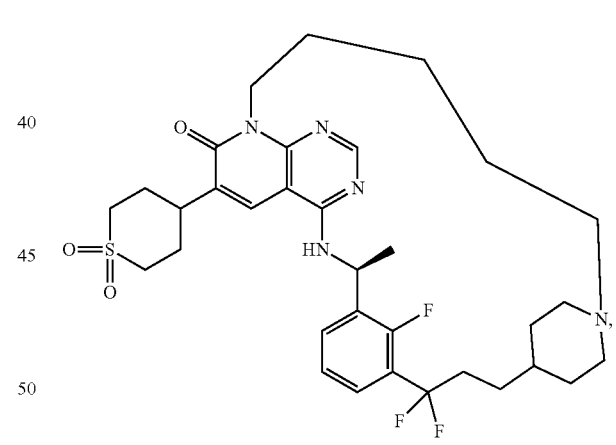
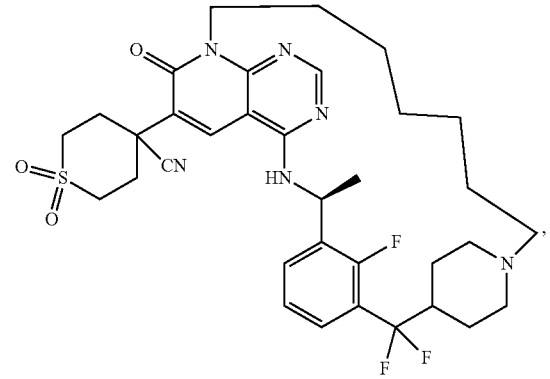

257
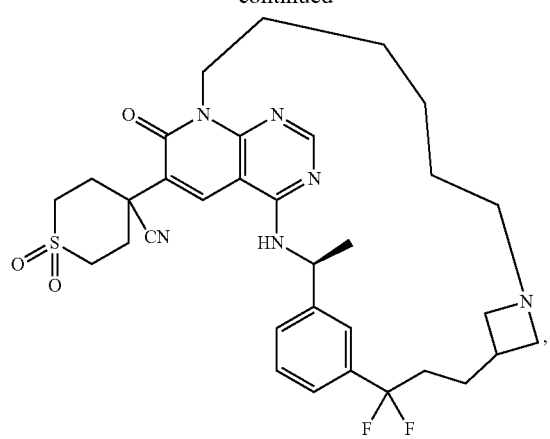
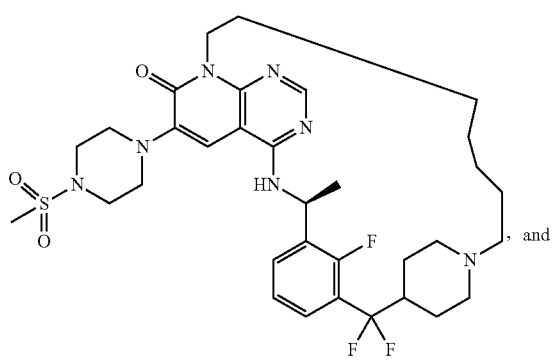
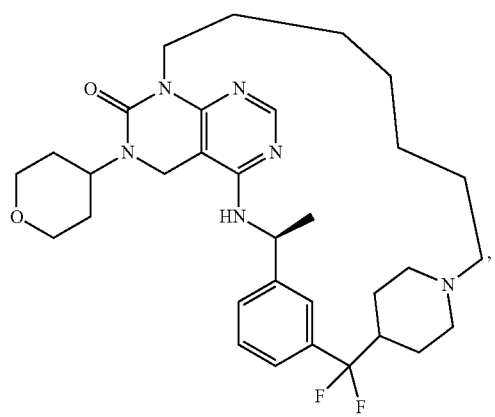
or a pharmaceutically acceptable salt or solvate thereof.
In some embodiments, the present disclosure provides a compound selected from
258
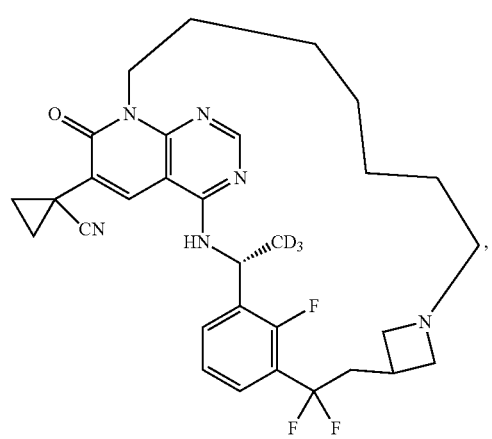
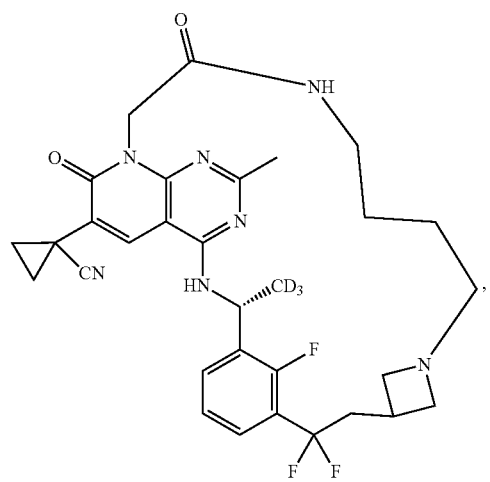
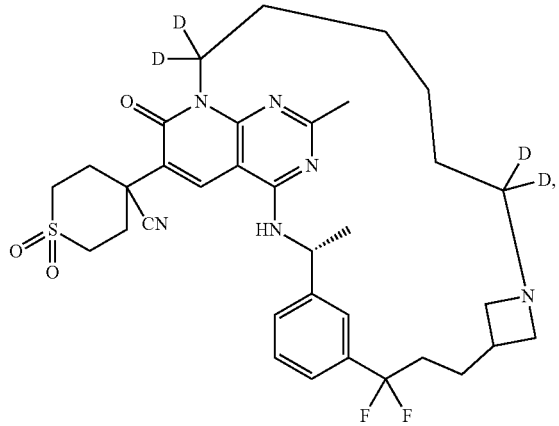

259
-continued
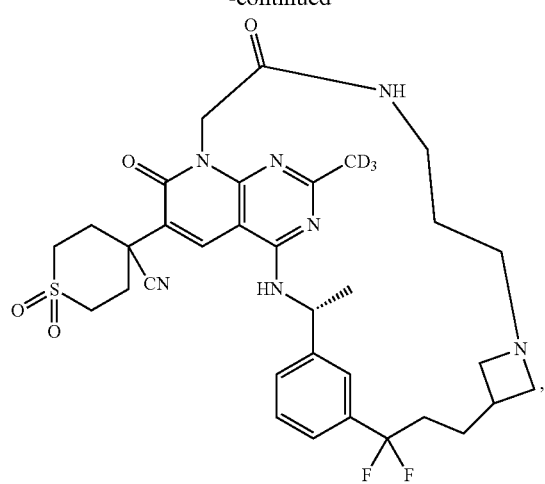
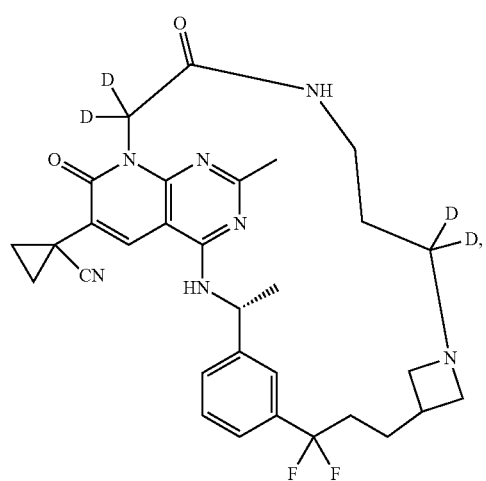
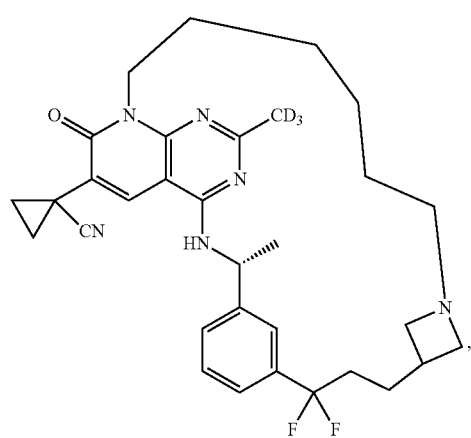
260
-continued
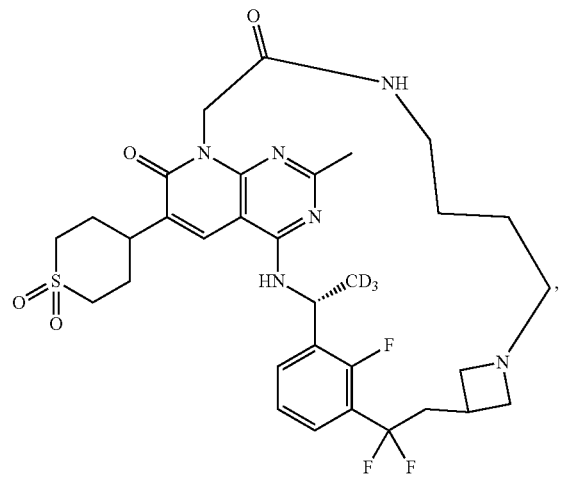
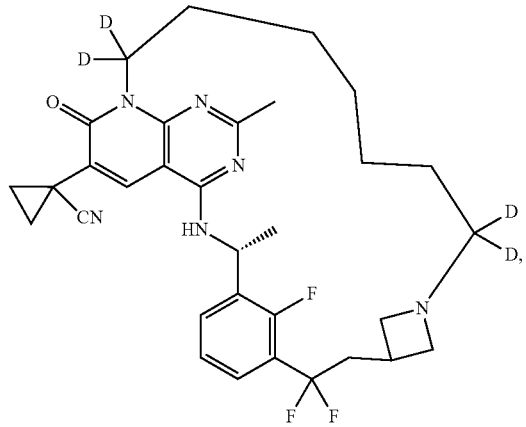

261
-continued
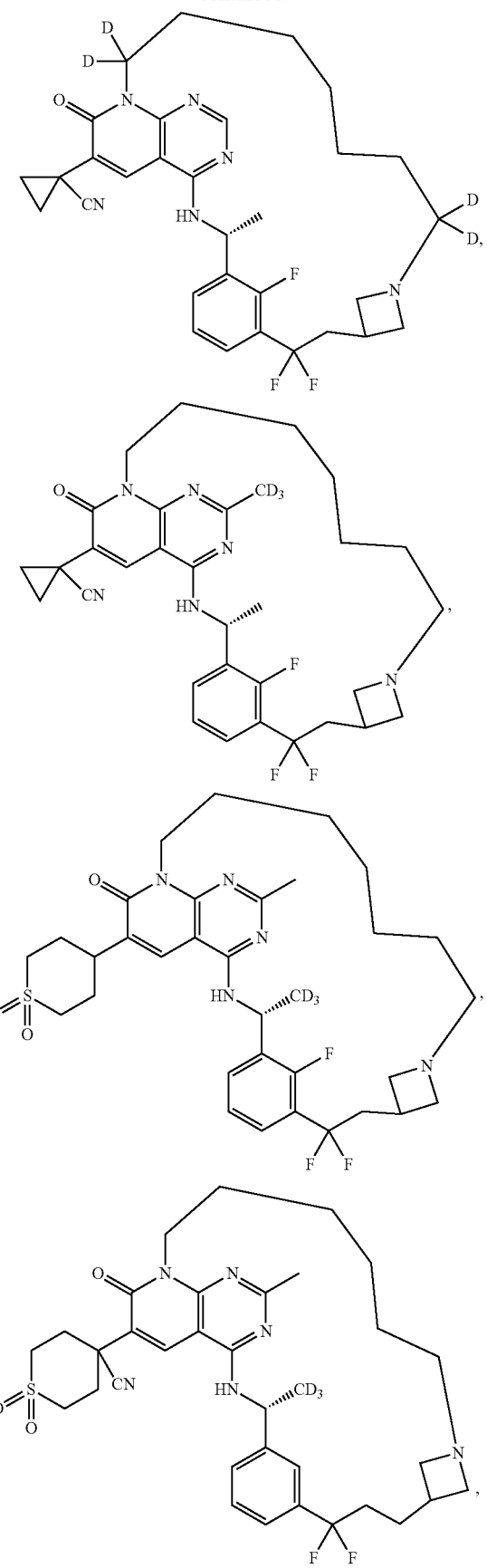
262
-continued
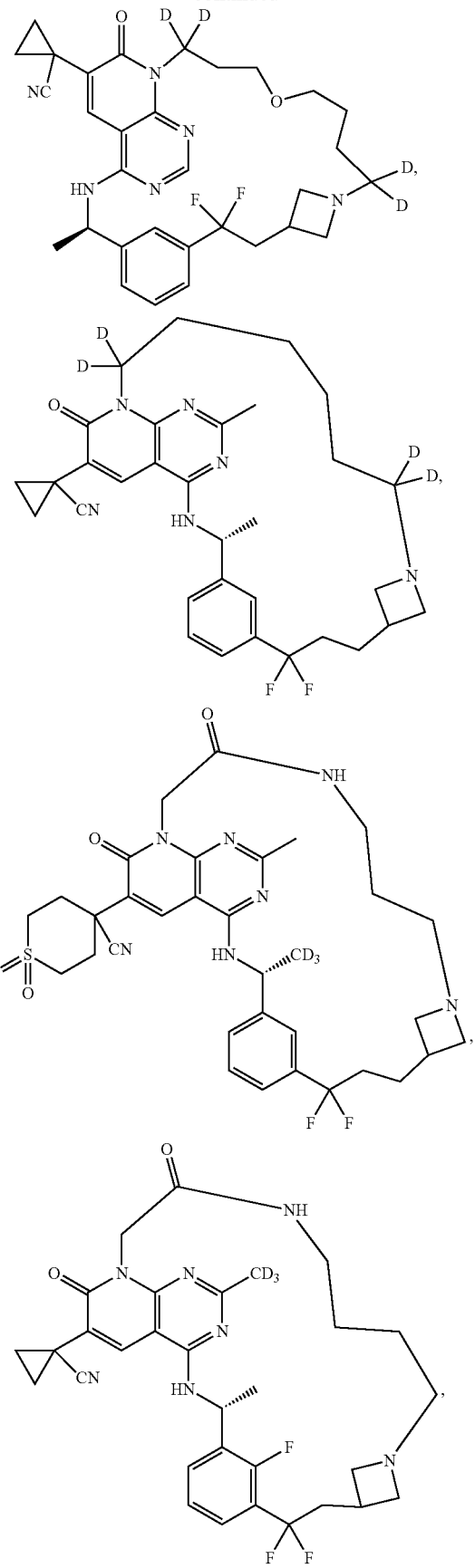

263
-continued
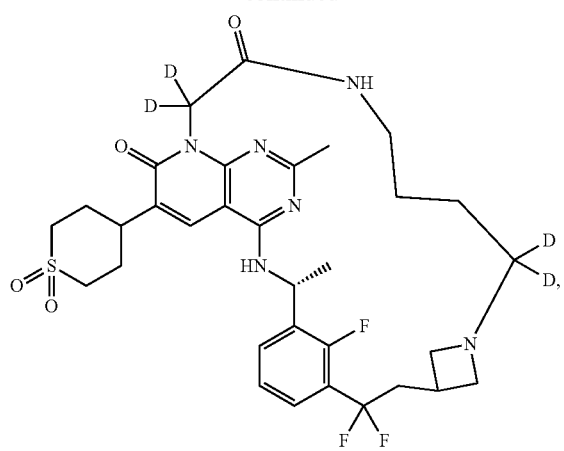
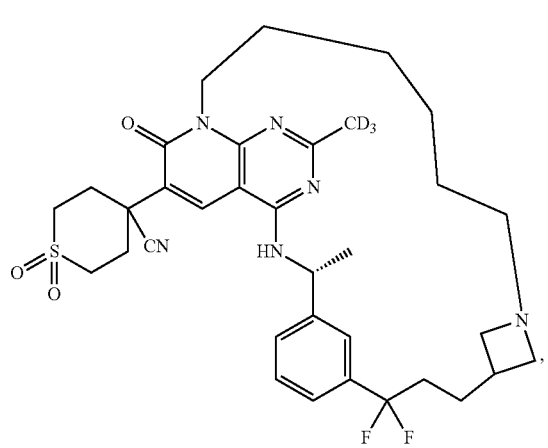
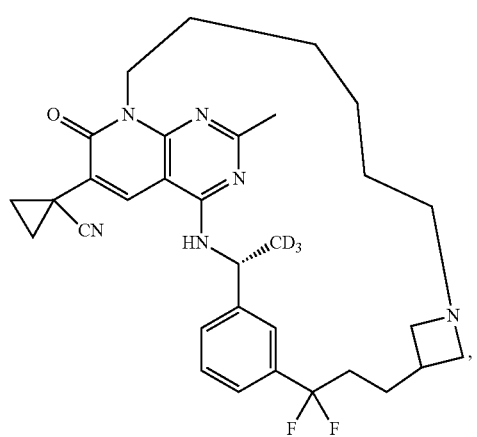
264
-continued
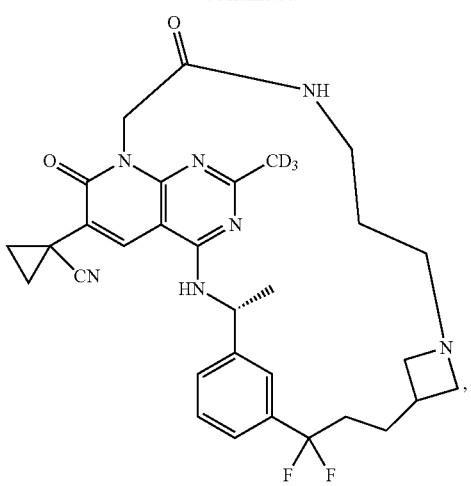
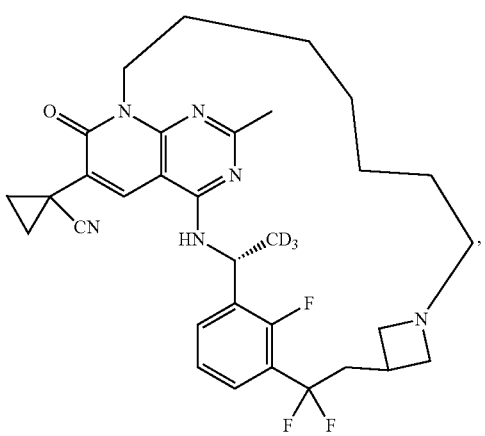
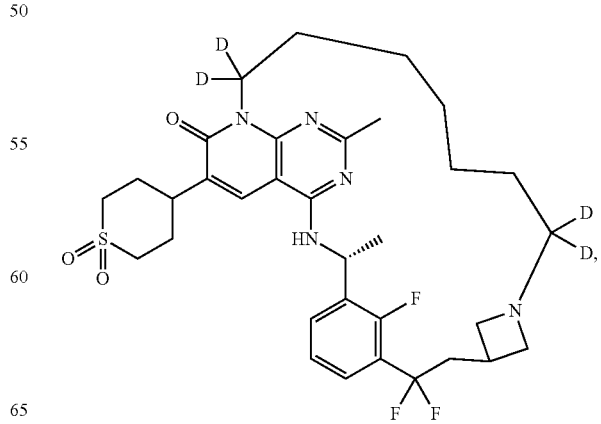

265
-continued
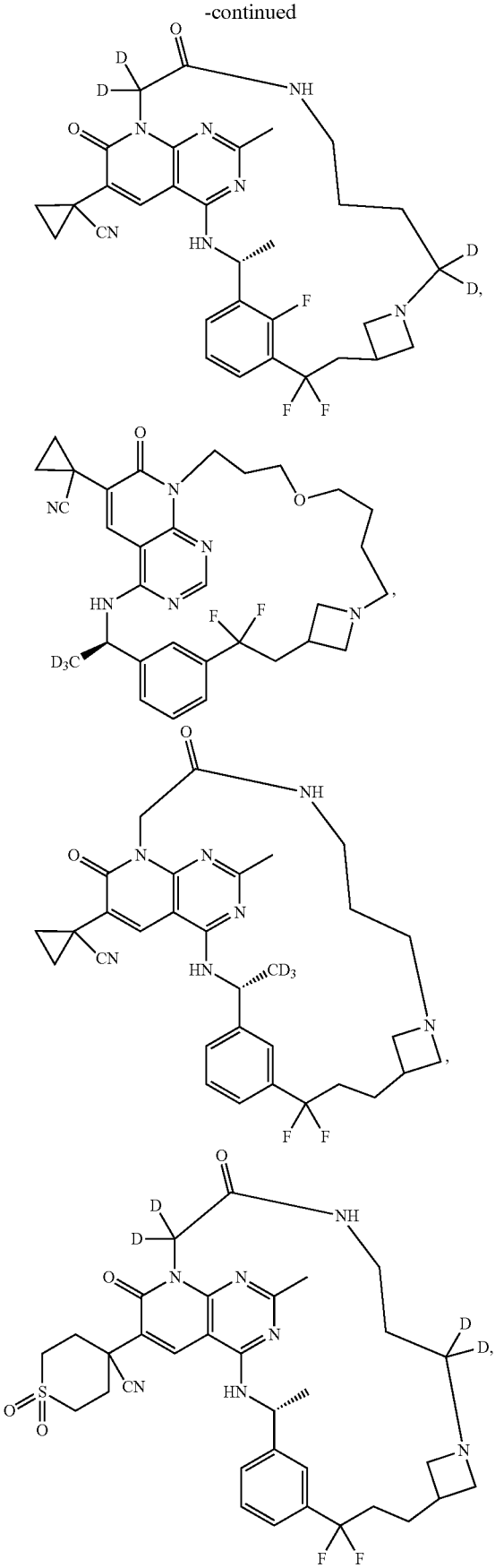
266
-continued
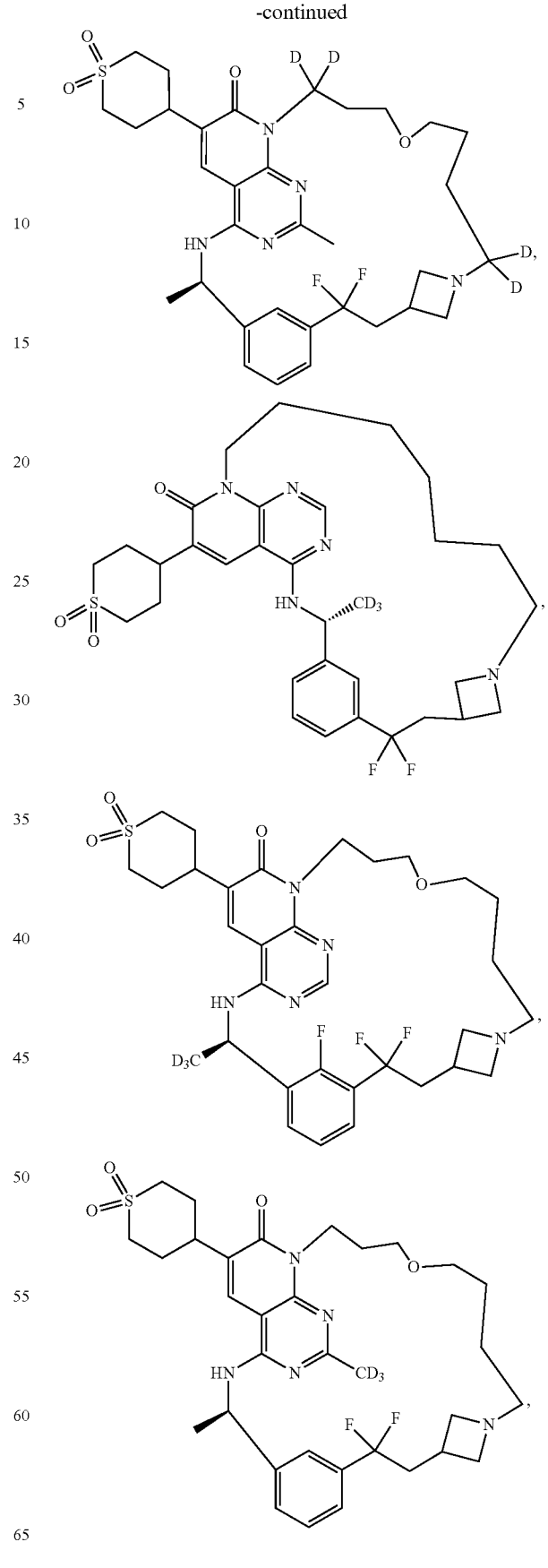

267
-continued
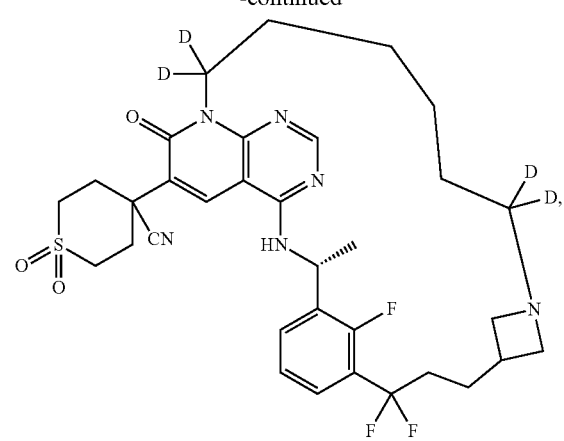
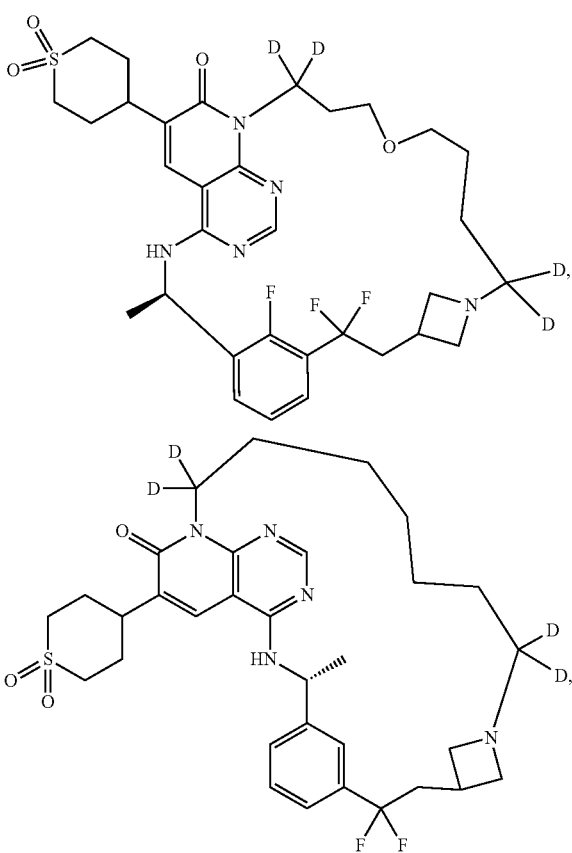
268
-continued
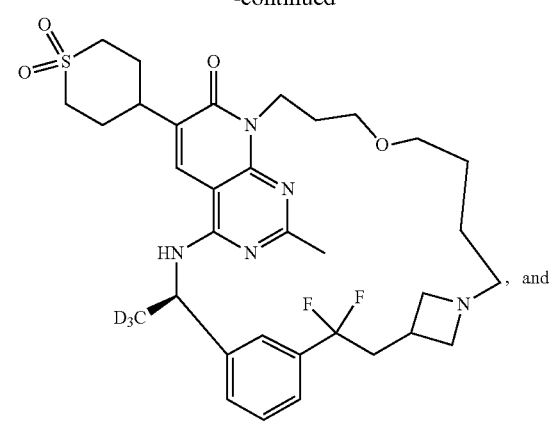
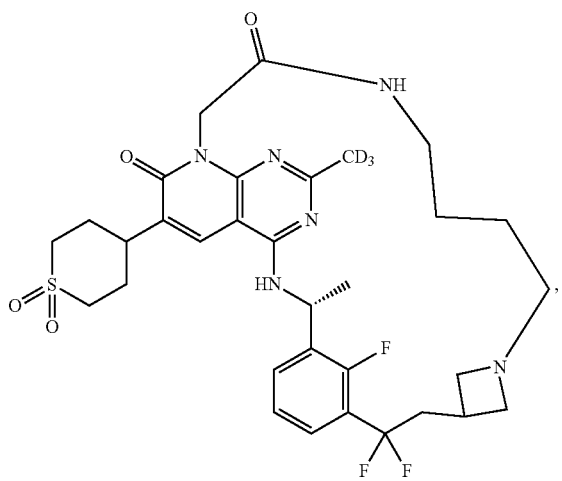 [SMILES: [2H]C([2H])([2H])c1nc2c3cc(C4CCS(=O)(=O)CC4)c(=O)n(c3n1)CC(=O)NCCCCN1CC(C1)CC(F)(F)c1cccc(c1F)[C@@H](C)N2]
or a pharmaceutically acceptable salt or solvate thereof.
In some embodiments, the present disclosure provides a compound selected from
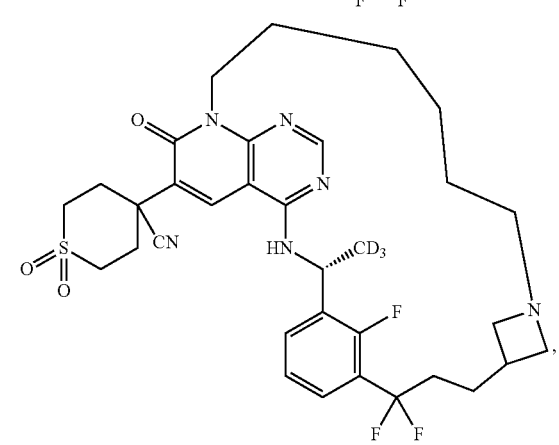
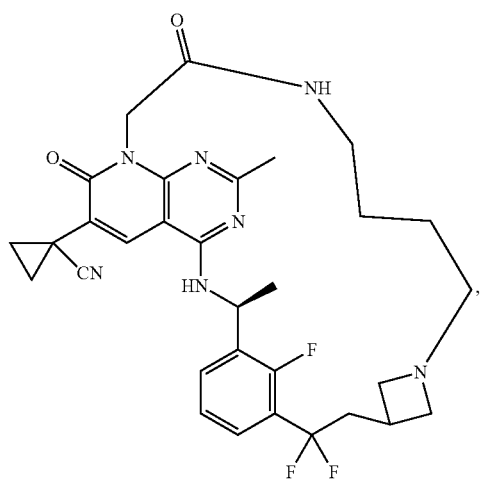

269
-continued
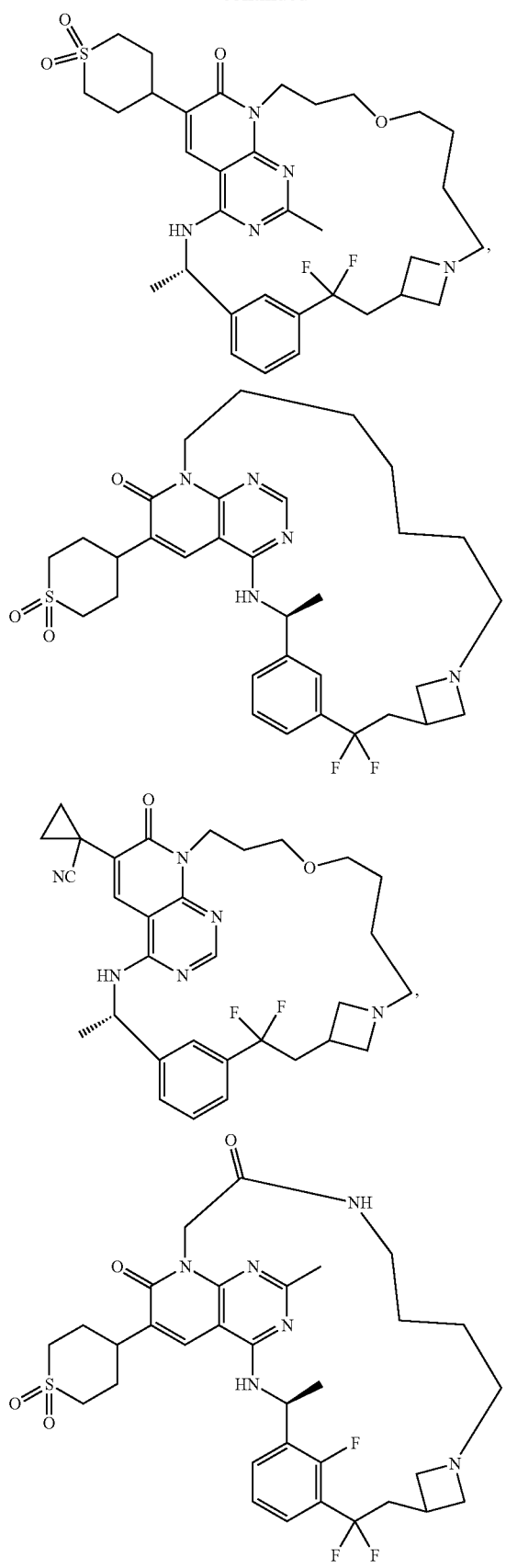
270
-continued
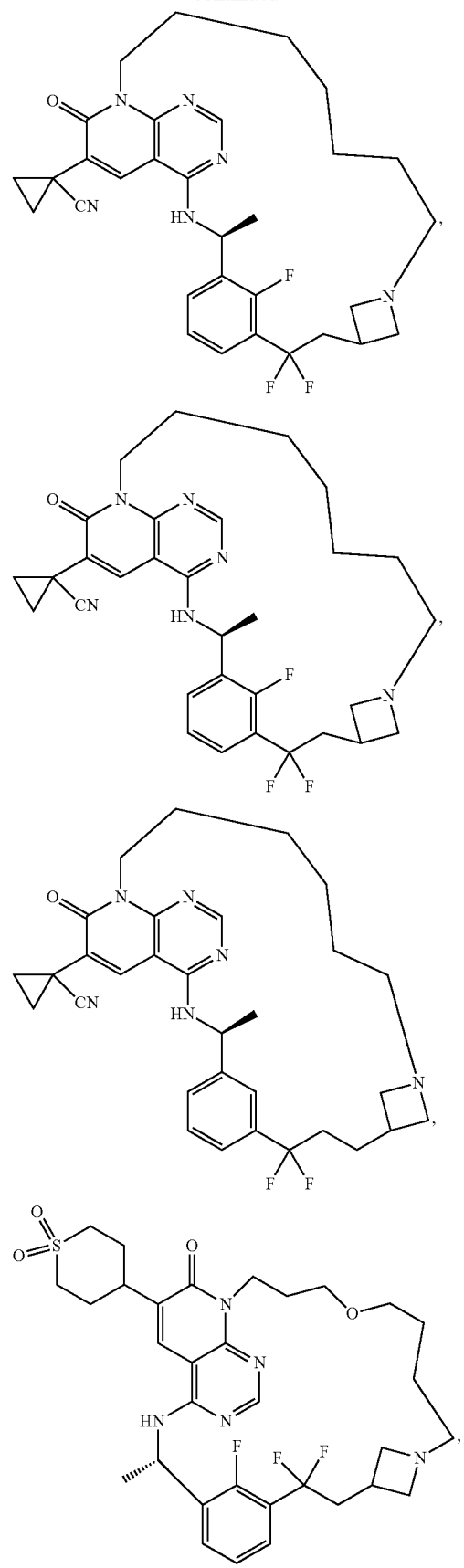

271
-continued
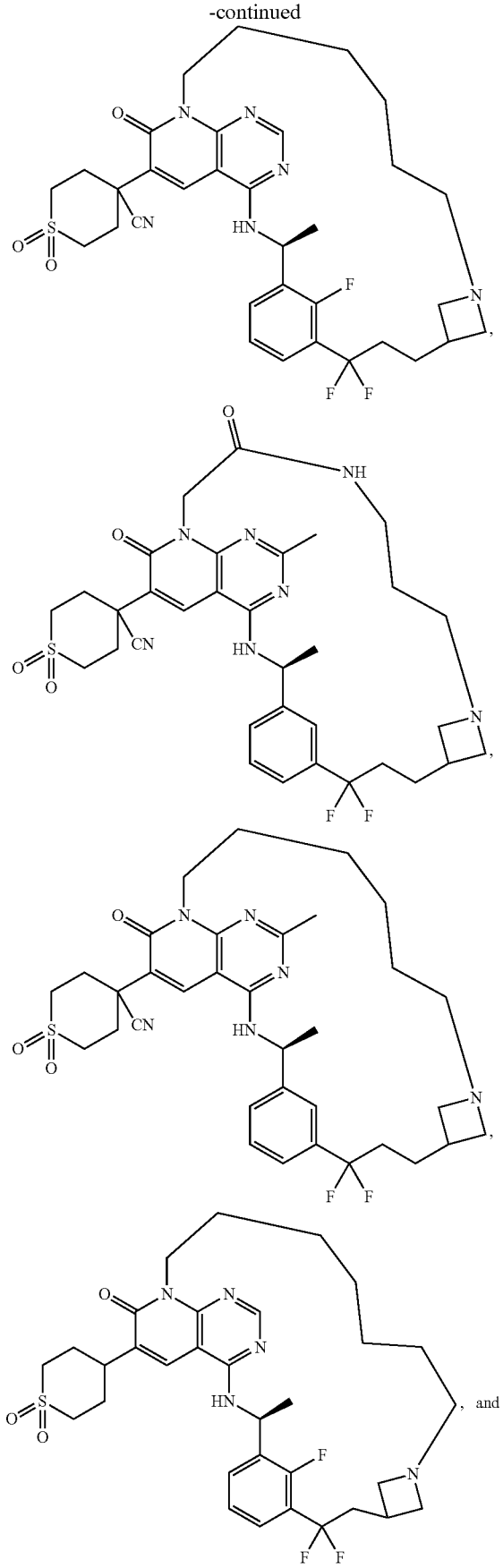
272
-continued
or a pharmaceutically acceptable salt or solvate thereof.
In some embodiments, the present disclosure provides a compound selected from 273
-continued
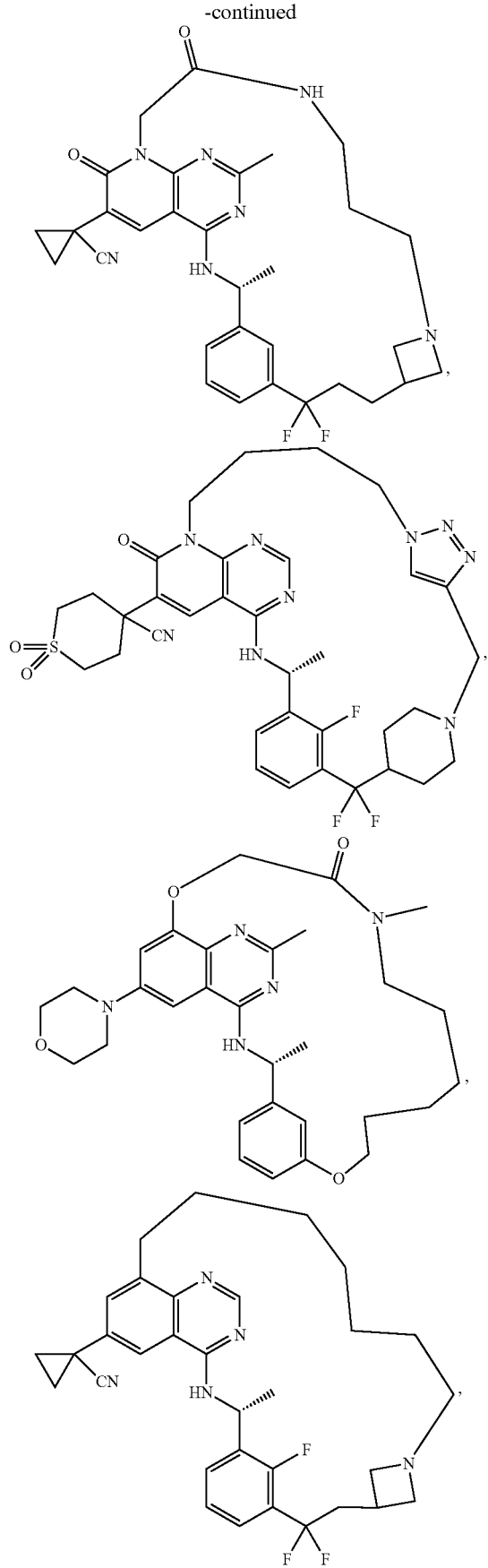
274
-continued
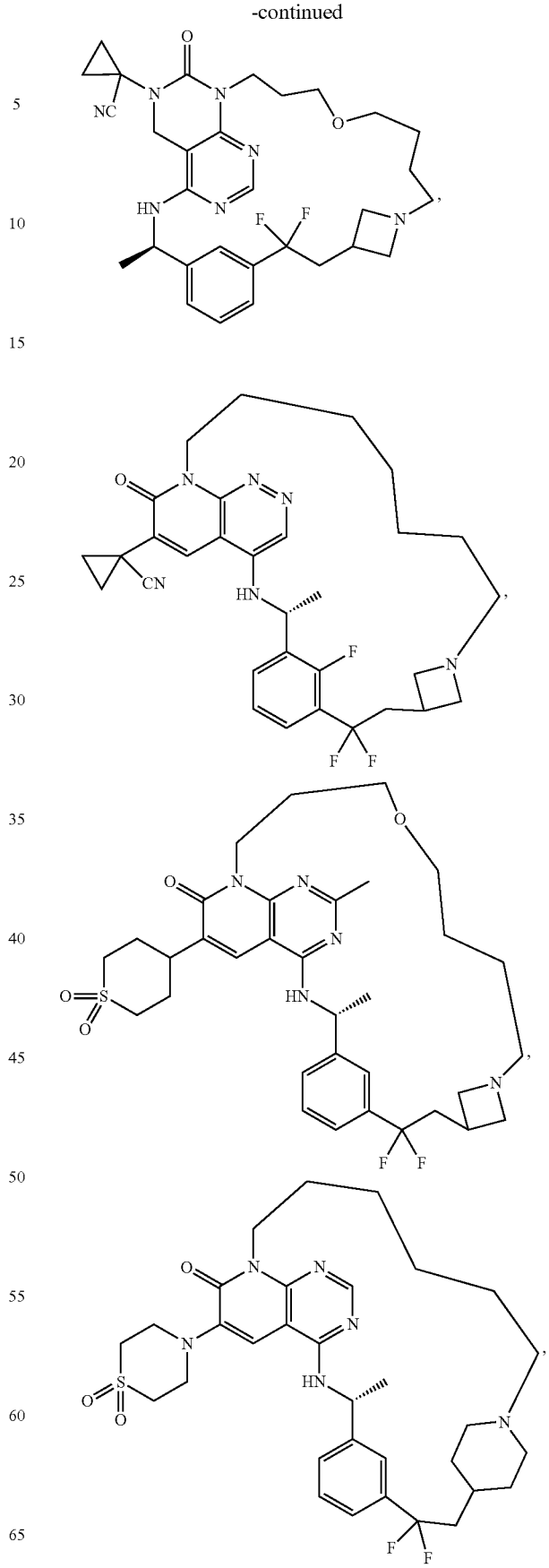

275
-continued
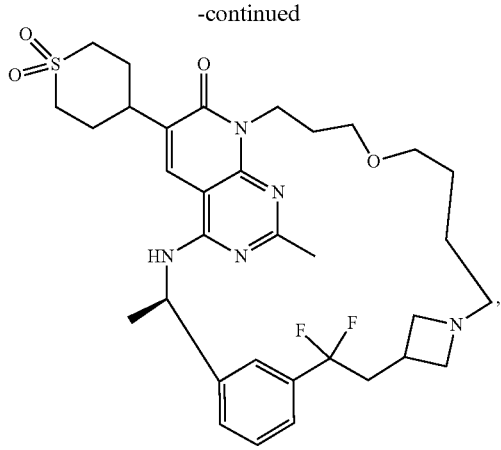
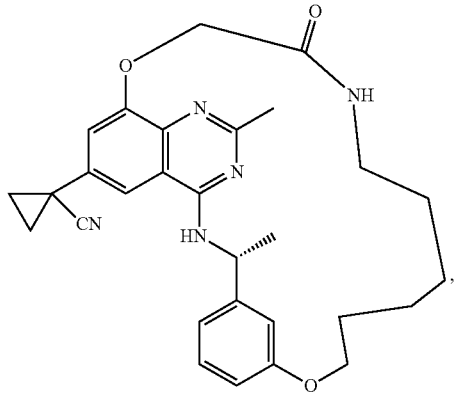
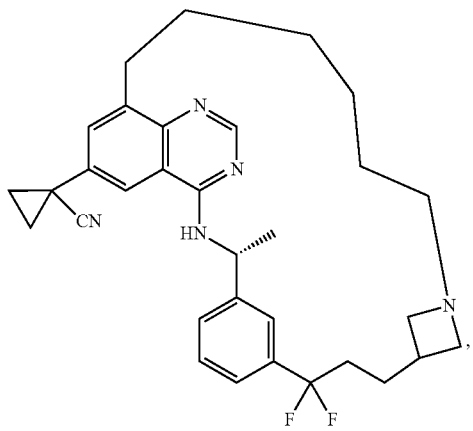
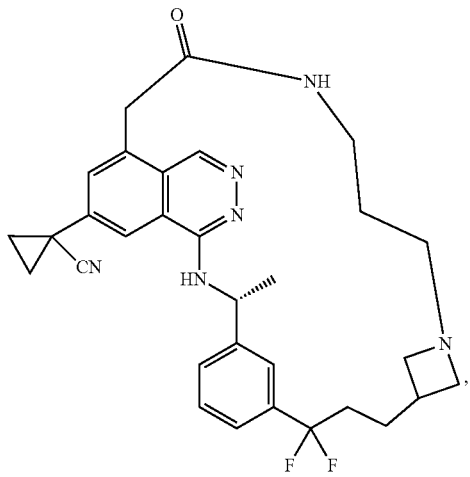
276
-continued
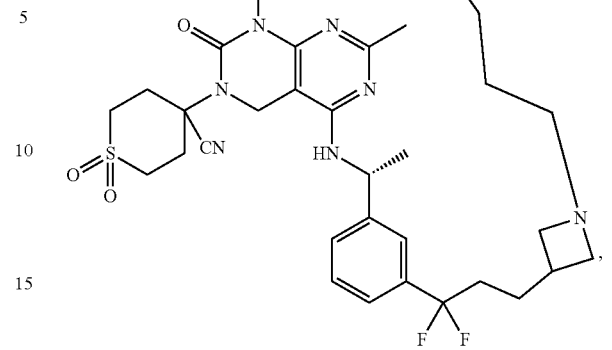
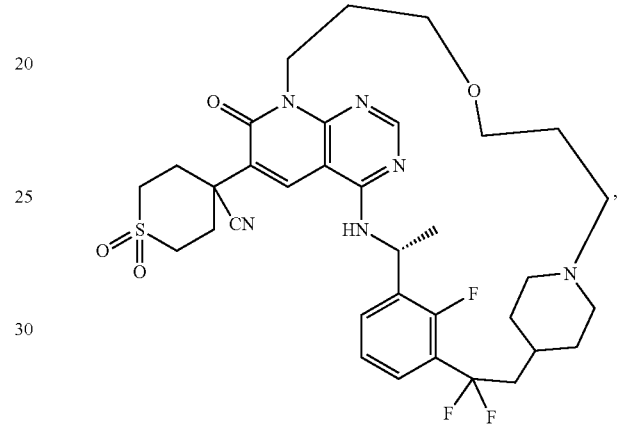
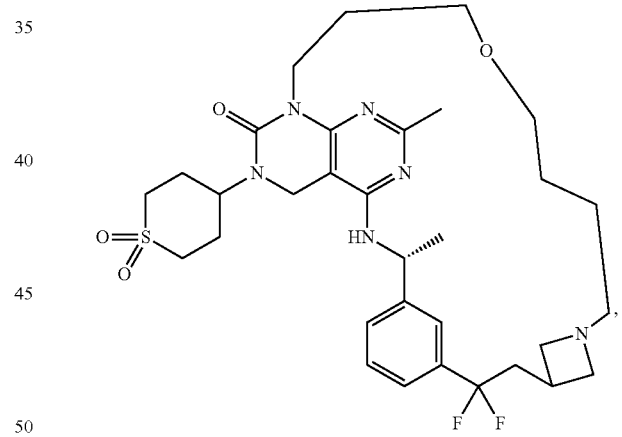
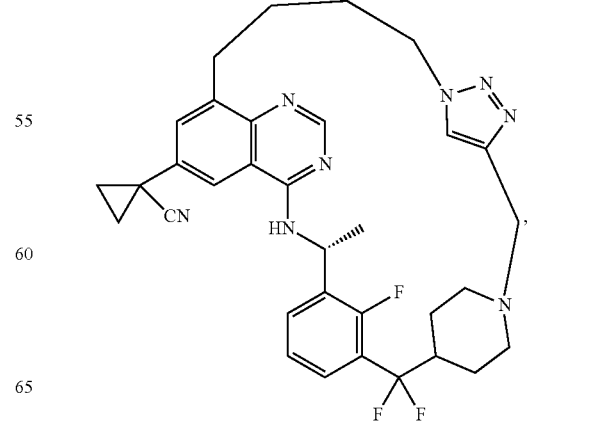

277
-continued
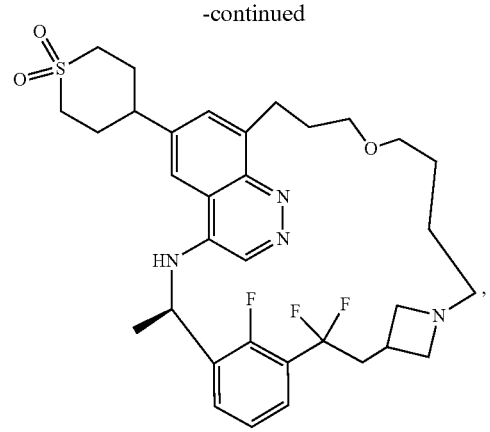
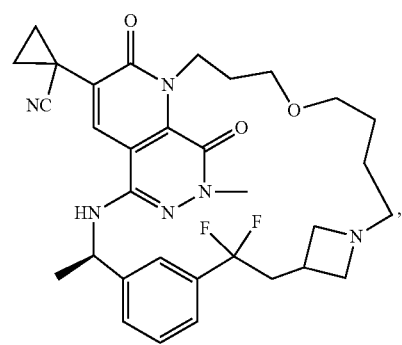
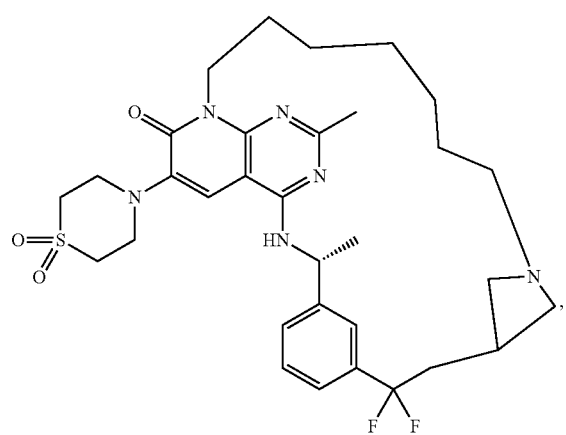
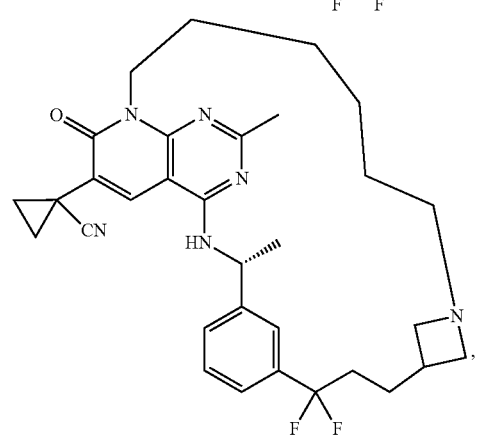
278
-continued
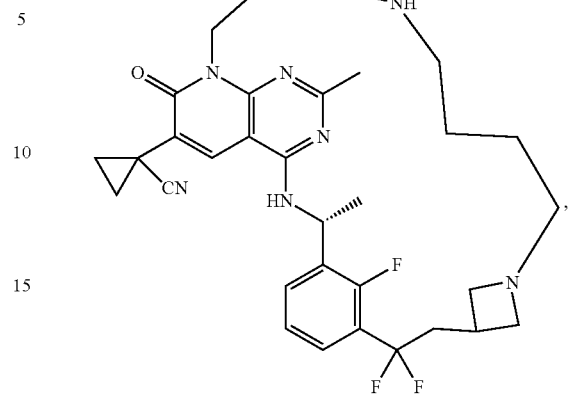
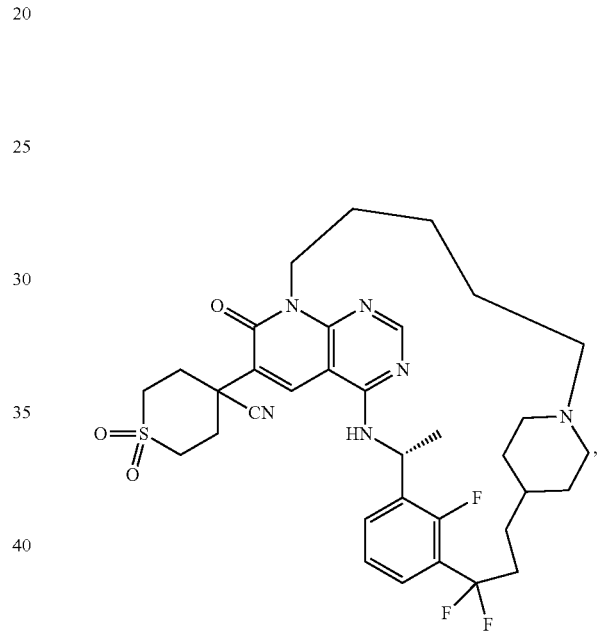
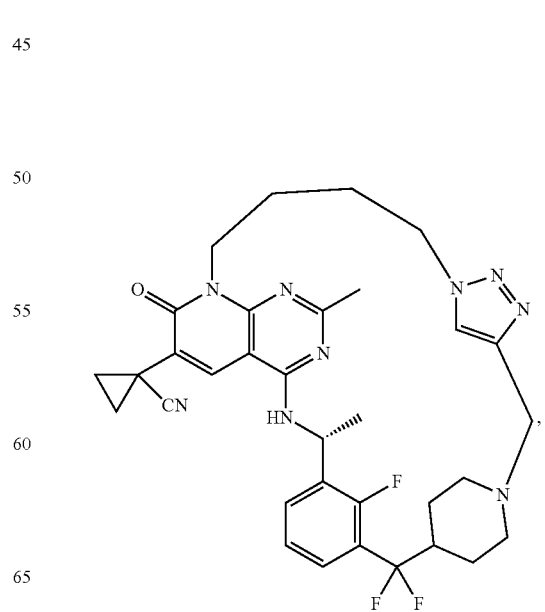

-continued
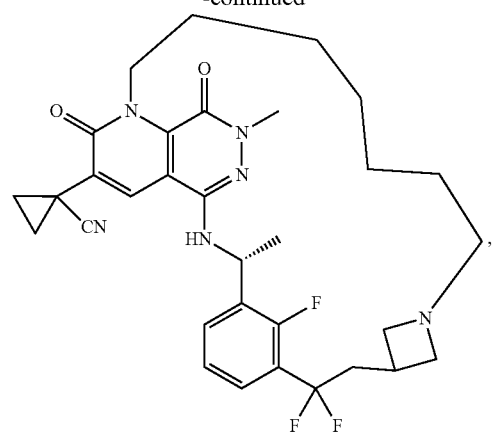
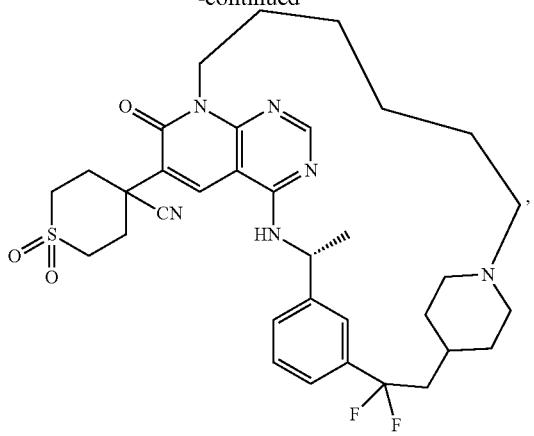

281
-continued
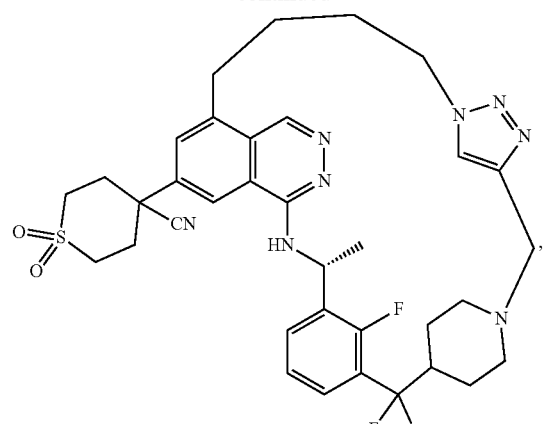
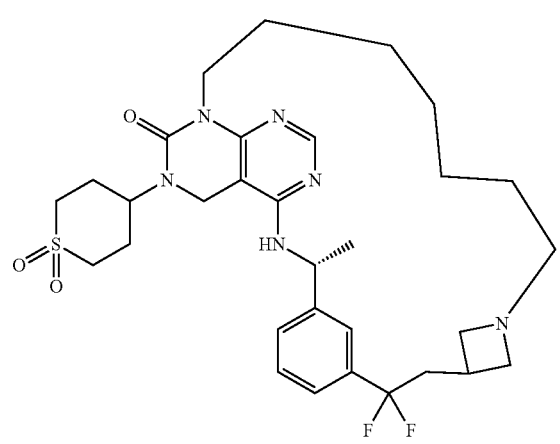
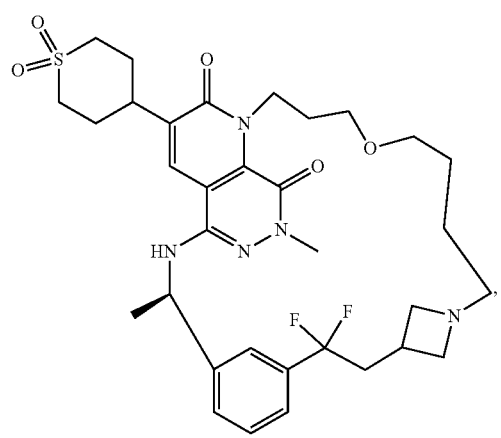
282
-continued
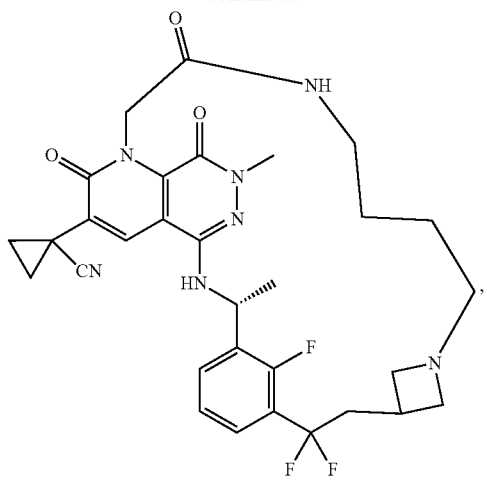
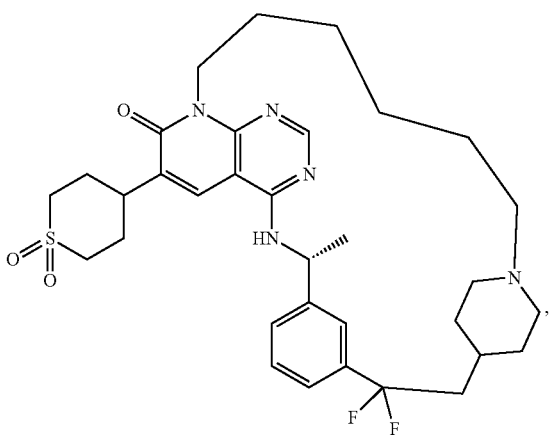
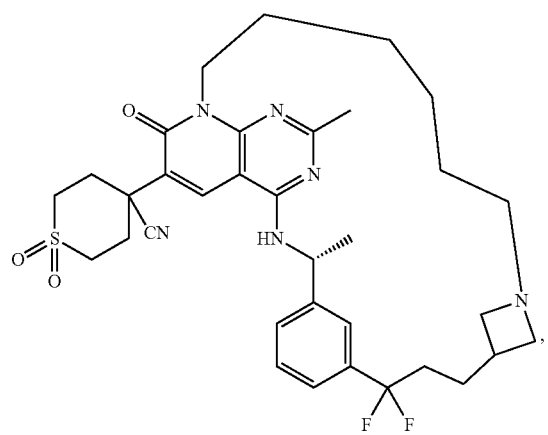

283
-continued
284
-continued
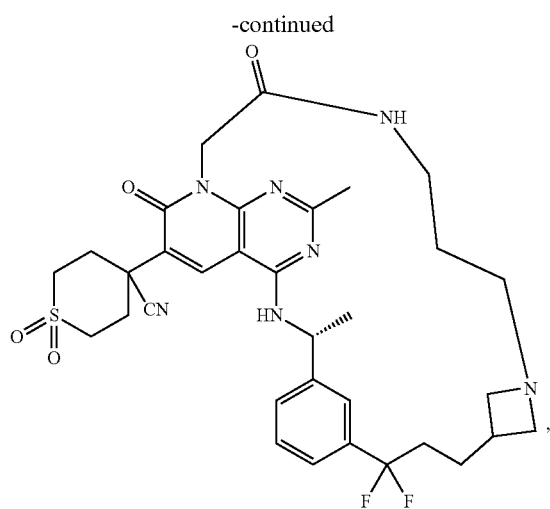
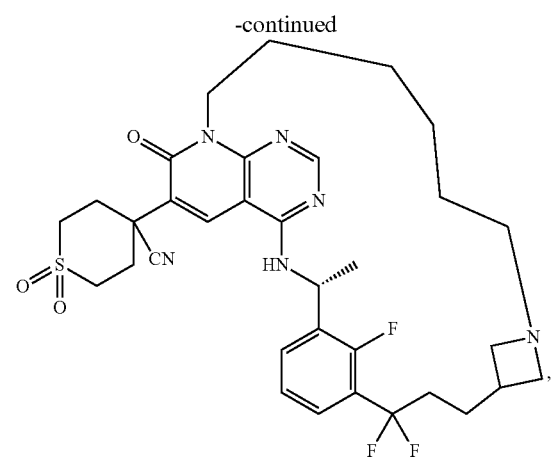
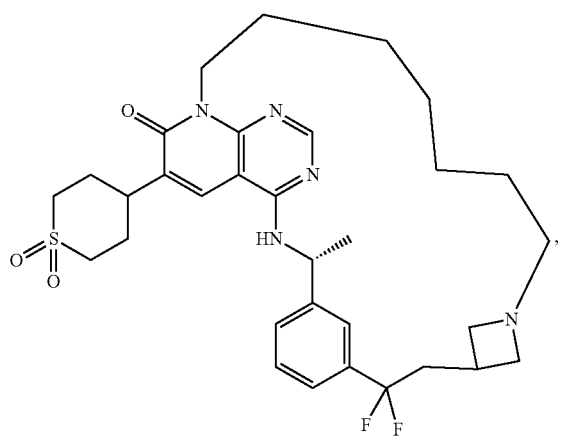
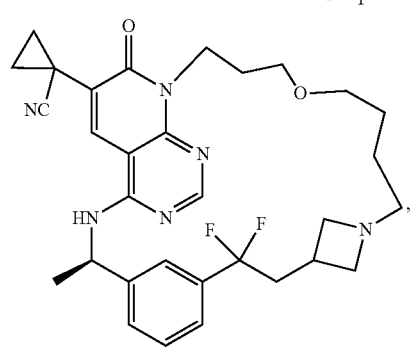
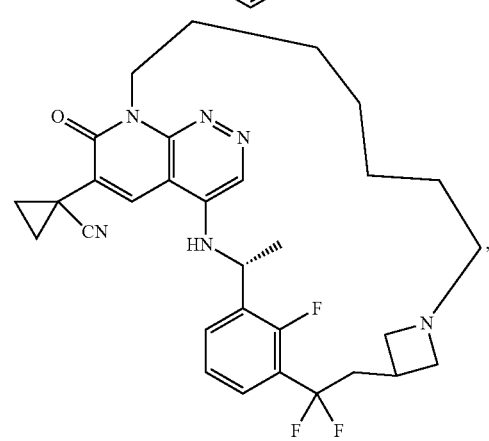

285
-continued
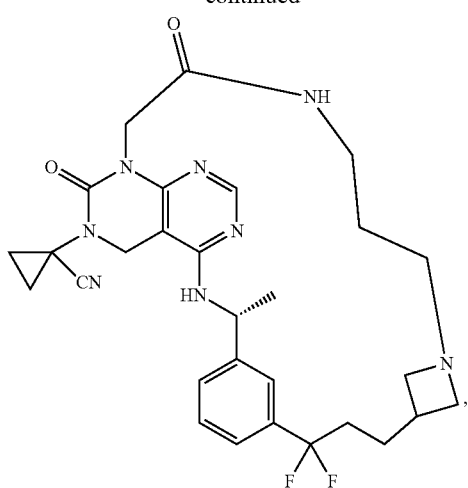
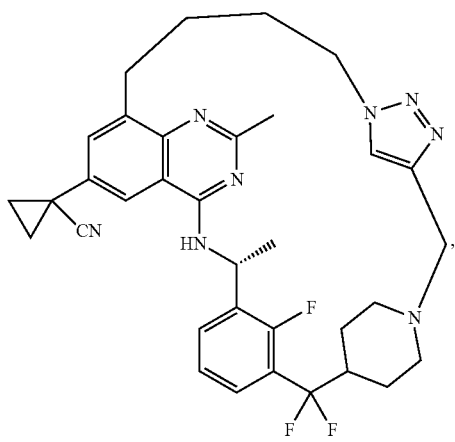
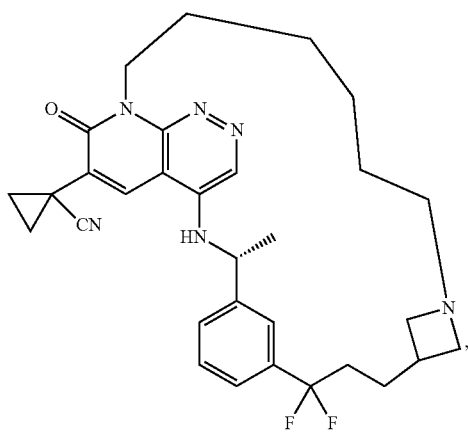
286
-continued
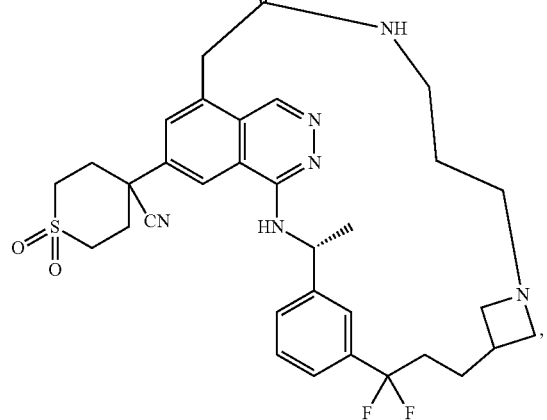
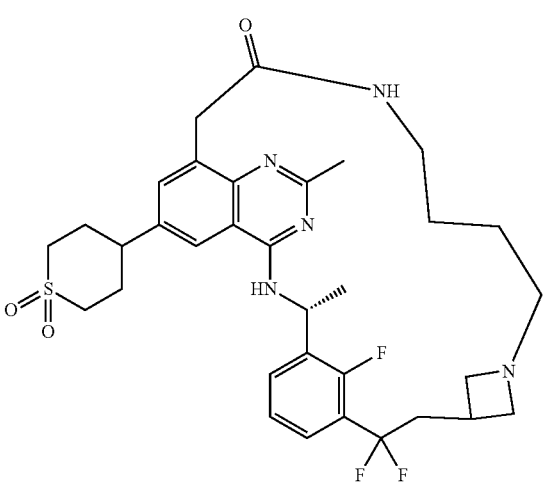
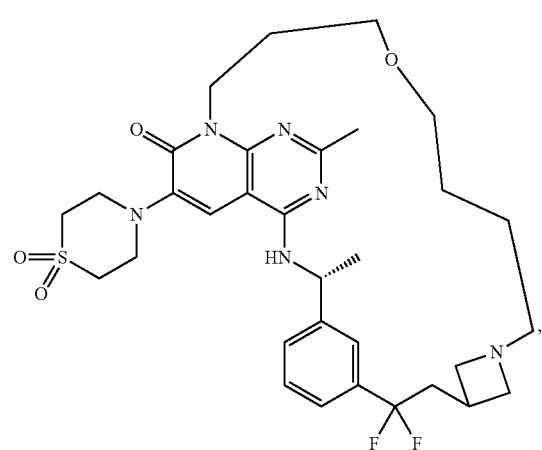

287
-continued
288
-continued
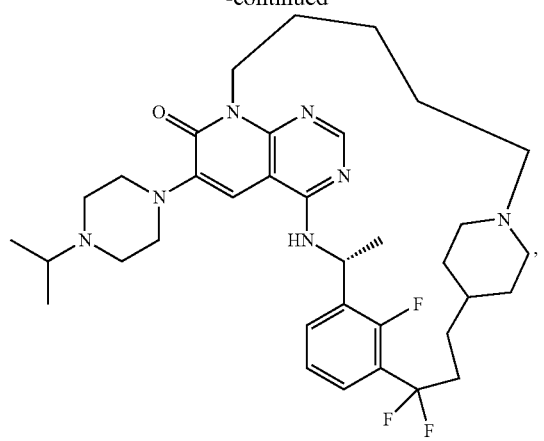
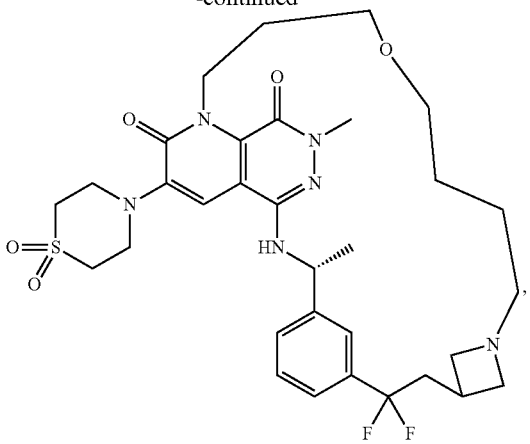

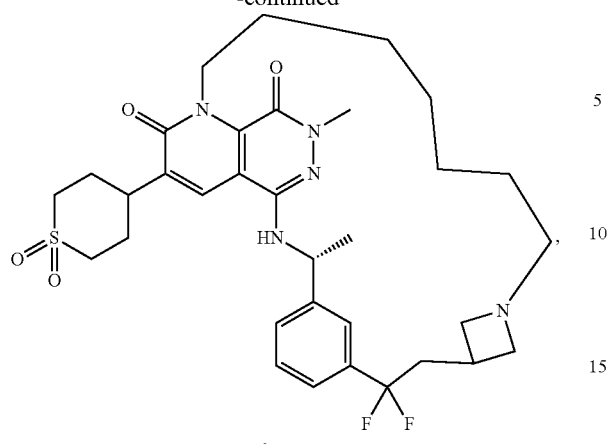
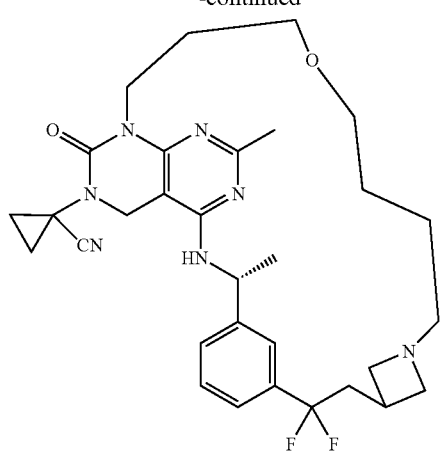
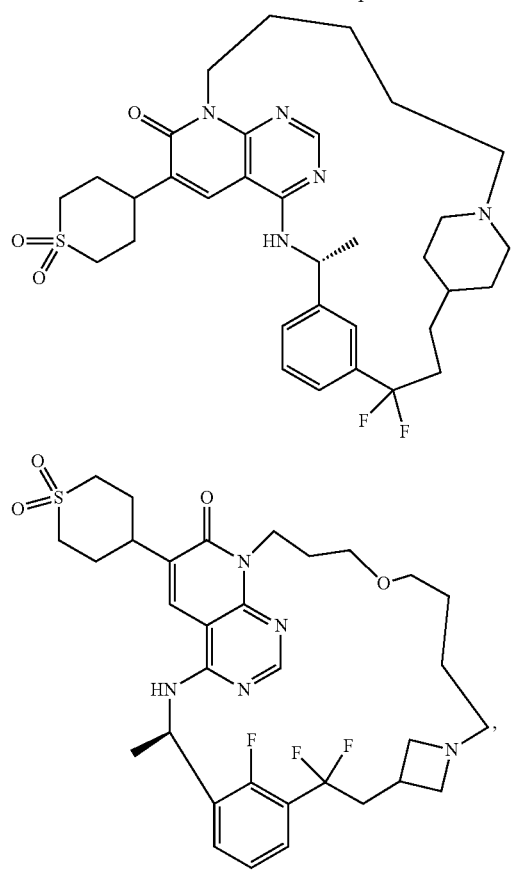
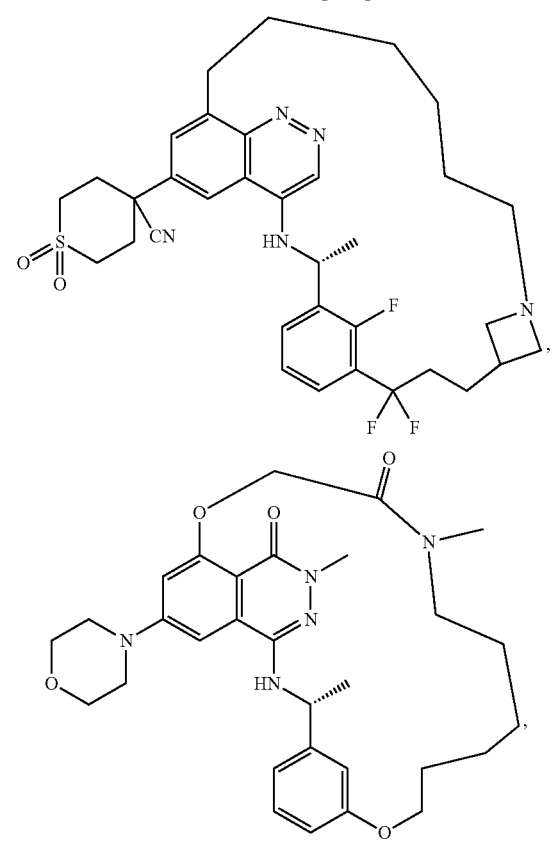

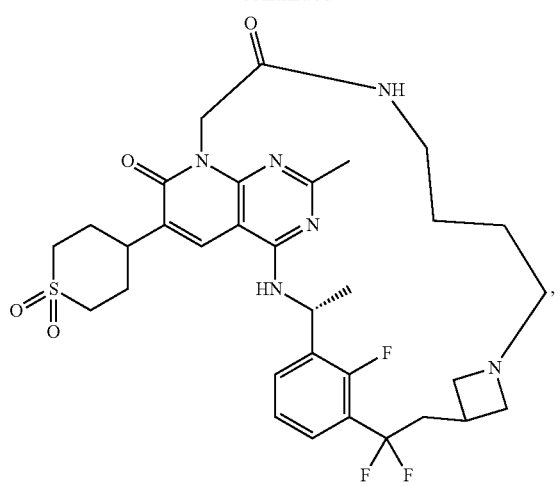
or a pharmaceutically acceptable salt or solvate thereof.
In some embodiments, a compound of Formula (I) is a compound of the formula:
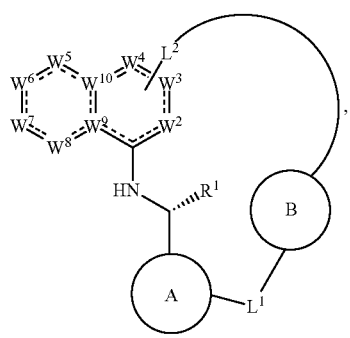
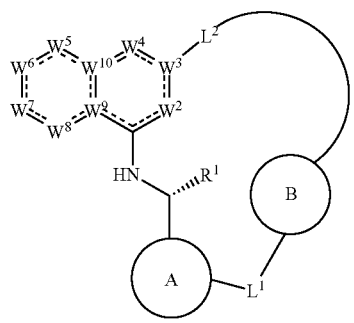
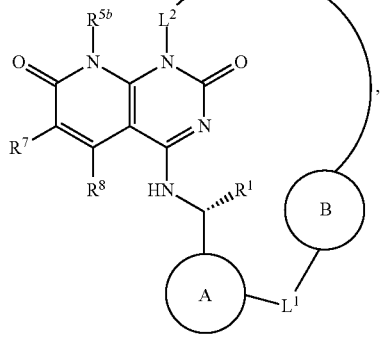
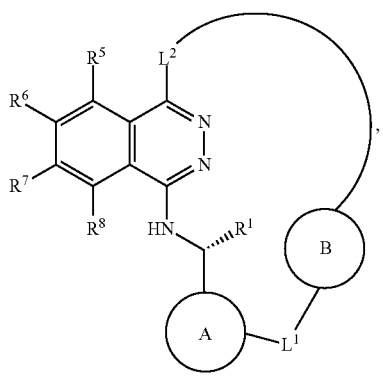
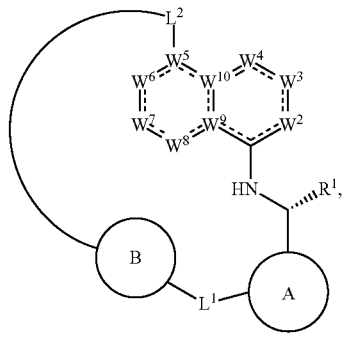
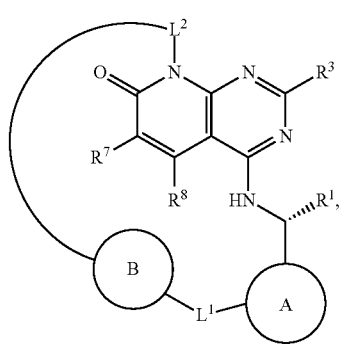

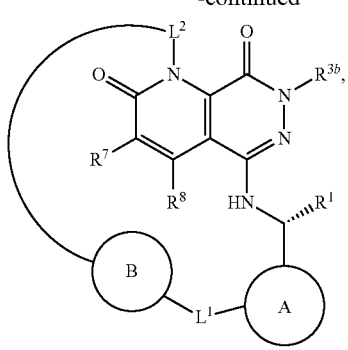

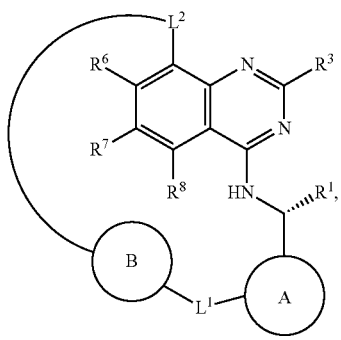

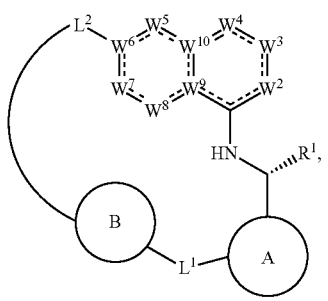

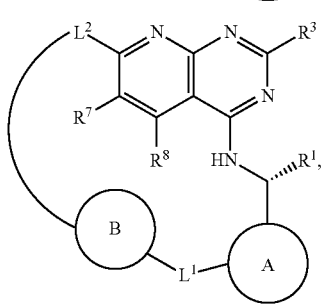

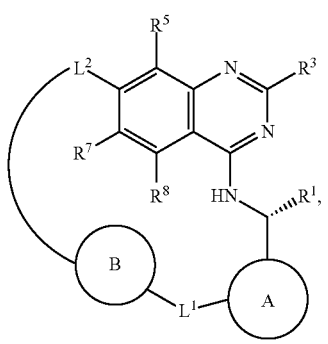

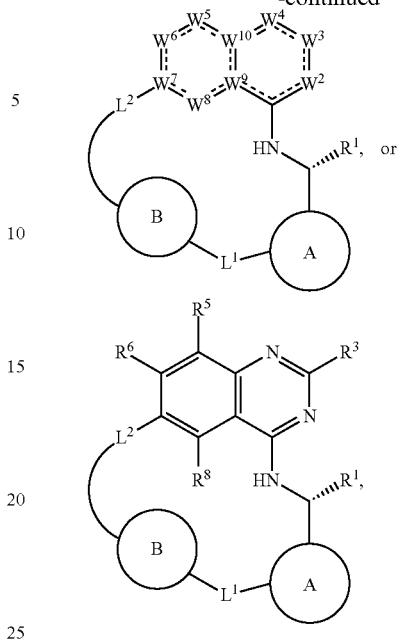

or a salt or solvate thereof.

In some embodiments, a compound of Formula (I), such as a compound of Formula (I-A), (I-B), (I-B1), (I-B2), (I-C), (I-C1), (I-C2), (I-C3), (I-D), (I-D1), (I-D2), (I-E), (I-E1), (II-B), (II-C), or (III), is provided as a substantially pure stereoisomer. In some embodiments, the stereoisomer is provided in at least 80% enantiomeric excess, such as at least 85%, at least 90%, at least 95%, at least 96%, at least 97%, at least 98%, at least 99%, or at least 99.9% enantiomeric excess.

In some embodiments, the compounds described herein exist as their pharmaceutically acceptable salts. In some embodiments, the methods disclosed herein include methods of treating diseases by administering such pharmaceutically acceptable salts. In some embodiments, the methods disclosed herein include methods of treating diseases by administering such pharmaceutically acceptable salts as pharmaceutical compositions.

In some embodiments, the compounds described herein possess acidic or basic groups and therefore react with any of a number of inorganic or organic bases or inorganic or organic acids to form a pharmaceutically acceptable salt. In some embodiments, such salts are prepared in situ during the final isolation and purification of the compounds described herein, or by separately reacting a purified compound in its free form with a suitable acid or base, and isolating the salt thus formed.

In some embodiments, the compounds described herein exist as solvates. In some embodiments are methods of treating diseases by administering such solvates. Further described herein are methods of treating diseases by administering such solvates as pharmaceutical compositions.

Solvates contain either stoichiometric or non-stoichiometric amounts of a solvent, and, in some embodiments, are formed during the process of crystallization with pharmaceutically acceptable solvents such as water, ethanol, and the like. Hydrates are formed when the solvent is water, or alcoholates are formed when the solvent is alcohol. Solvates of the compounds described herein are conveniently prepared or formed during the processes described herein. By way of example only, hydrates of the compounds described herein are conveniently prepared by recrystallization from an aqueous/organic solvent mixture, using organic solvents including, but not limited to, dioxane, tetrahydrofuran, or MeOH. In addition, the compounds provided herein exist in unsolvated as well as solvated forms. In general, the solvated forms are considered equivalent to the unsolvated forms for the purposes of the compounds and methods provided herein.

In certain aspects, the present disclosure provides a compound of the formula A-L$^{AB}$-B wherein:

A is a monovalent form of a compound described herein;
L$^{AB}$ is a covalent linker bonded to A and B; and
B is a monovalent form of a degradation enhancer.

A "degradation enhancer" is a compound capable of binding a ubiquitin ligase protein (e.g., E3 ubiquitin ligase protein) or a compound capable of binding a protein that is capable of binding to a ubiquitin ligase protein to form a protein complex capable of conjugating a ubiquitin protein to a target protein. In some embodiments, the degradation enhancer is capable of binding to an E3 ubiquitin ligase protein or a protein complex comprising an E3 ubiquitin ligase protein. In some embodiments, the degradation enhancer is capable of binding to an E2 ubiquitin-conjugating enzyme. In some embodiments, the degradation enhancer is capable of binding to a protein complex comprising an E2 ubiquitin-conjugating enzyme and an E3 ubiquitin ligase protein.

In some embodiments, the degradation enhancer is capable of binding a protein selected from E3A, mdm2, APC, EDD1, SOCS/BC-box/eloBC/CUL5/RING, LNXp80, CBX4, CBLL1, HACE1, HECTD1, HECTD2, HECTD3, HECTD4, HECW1, HECW2, HERC1, HERC2, HERC3, HERC4, HER5, HERC6, HUWE1, ITCH, NEDD4, NEDD4L, PPIL2, PRPF19, PIAS1, PIAS2, PIAS3, PIAS4, RANBP2, RNF4, RBX1, SMURF1, SMURF2, STUB1, TOPORS, TRIP12, UBE3A, UBE3B, UBE3C, UBE3D, UBE4A, UBE4B, UBOX5, UBR5, VHL (von-Hippel-Lindau ubiquitin ligase), WWP1, WWP2, Parkin, MKRN1, CMA (chaperon-mediated autophagy), SCFb-TRCP (Skip-Cullin-F box (Beta-TRCP) ubiquitin complex), b-TRCP (b-transducing repeat-containing protein), cIAP1 (cellular inhibitor of apoptosis protein 1), APC/C (anaphase-promoting complex/cyclosome), CRBN (cereblon), CUL4-RBX1-DDB1-CRBN (CRL4$^{CRBN}$) ubiquitin ligase, XIAP, IAP, KEAP1, DCAF15, RNF114, DCAF16, AhR, SOCS2, KLHL12, UBR2, SPOP, KLHL3, KLHL20, KLHDC2, SPSB1, SPSB2, SPSB4, SOCS6, FBXO4, FBXO31, BTRC, FBW7, CDC20, PML, TRIM21, TRIM24, TRIM33, GID4, avadomide, iberdomide, and CC-885. In some embodiments, the degradation enhancer is capable of binding a protein selected from UBE2A, UBE2B, UBE2C, UBE2D1, UBE2D2, UBE2D3, UBE2DR, UBE2E1, UBE2E2, UBE2E3, UBE2F, UBE2G1, UBE2G2, UBE2H, UBE2I, UBE2J1, UBE2J2, UBE2K, UBE2L3, UBE2L6, UBE2L1, UBE2L2, UBE2L4, UBE2M, UBE2N, UBE2O, UBE2Q1, UBE2Q2, UBE2R$^1$, UBE2R$^2$, UBE2S, UBE2T, UBE2U, UBE2V1, UBE2V2, UBE2W, UBE2Z, ATG3, BIRC6, and UFC1. In some embodiments, the degradation enhancer is a compound described in Ishida and Ciulli, SLAS Discovery 2021, Vol. 25(4) 484-502, which is incorporated by reference in its entirety for any purpose, for example VH032, VH101, VH298, thalidomide, bestatin, methyl bestatin, nutlin, idasanutlin, bardoxolone, bardoxolone methyl, indisulam (E7070), E7820, chloroquinoxaline sulfonamide (CQS), nimbolide, KB02, ASTX660, lenalidomide, or pomalidomide.

In some embodiments, the degradation enhancer is a compound described in US20180050021, WO2016146985, WO2018189554, WO2018119441, WO2018140809, WO2018119448, WO2018119357, WO2018118598, WO2018102067, WO201898280, WO201889736, WO201881530, WO201871606, WO201864589, WO201852949, WO2017223452, WO2017204445, WO2017197055, WO2017197046, WO2017180417, WO2017176958, WO201711371, WO2018226542, WO2018223909, WO2018189554, WO2016169989, WO2016146985, CN105085620B, CN106543185B, U.S. Pat. Nos. 10,040,804, 9,938,302, 10,144,745, 10,145,848, 9,938,264, 9,632,089, 9,821,068, 9,758,522, 9,500,653, 9,765,019, 8,507,488, 8,299,057, US20180298027, US20180215731, US20170065719, US20170037004, US20160272639, US20150291562, or US20140356322, each of which is incorporated by reference in its entirety for any purpose.

In some embodiments L$^{AB}$ is -L$^{AB1}$-L$^{AB2}$-L$^{AB3}$-L$^{AB4}$-L$^{AB5}$-;

L$^{AB1}$, L$^{AB2}$, L$^{AB3}$, L$^{AB4}$, and L$^{AB5}$ are each independently selected from a bond, —O—, —N(R$^{100}$)—, —C(O)—, —N(R$^{100}$)C(O)—, —C(O)N(R$^{100}$)—, —S—, —S(O)$_2$—, —S(O)—, —S(O)$_2$N(R$^{100}$)—, —S(O)N(R$^{100}$)—, —N(R$^{100}$)S(O)—, —N(R$^{100}$)S(O)$_2$—, C$_{1-6}$ alkylene, —(O—C$_{1-6}$alkyl)$_x$-, —(C$_{1-6}$ alkyl-), C$_{2-6}$ alkenylene, C$_{2-6}$ alkynylene, C$_{1-6}$ haloalkylene, C$_{3-12}$ carbocyclene, and 3- to 10-membered heterocyclene, wherein C$_{1-6}$ alkylene, C$_{2-6}$ alkenylene, C$_{2-6}$ alkynylene, C$_{1-6}$ haloalkylene, C$_{3-12}$ carbocyclene, and 3- to 10-membered heterocyclene are optionally substituted with one, two, or three R$^{20}$; and wherein each C$_{1-6}$ alkyl of —(O—C$_{1-6}$ alkyl)$_2$- and —(C$_{1-6}$ alkyl-O)$_2$— is optionally substituted with one, two, or three R$^{20}$;

each z is independently an integer from 0 to 10;

R$^{100}$ is independently selected at each occurrence from hydrogen, C$_{1-6}$ alkyl, C$_{2-6}$ alkenyl, C$_{2-6}$ alkynyl, C$_{3-10}$ carbocycle, —CH$_2$—(C$_{3-10}$ carbocycle), 3- to 10-membered heterocycle, and —CH$_2$-(3- to 10-membered heterocycle), wherein C$_{1-6}$ alkyl, C$_{2-6}$ alkenyl, C$_{2-6}$ alkynyl, C$_{3-10}$ carbocycle, —CH$_2$—(C$_{3-10}$ carbocycle), 3- to 10-membered heterocycle, and —CH$_2$-(3- to 10-membered heterocycle) are optionally substituted with one, two, or three R$^{20}$;

R$^{20}$ is independently selected at each occurrence from halogen, oxo, =NH, —CN, C$_{1-6}$ alkyl, C$_{2-6}$ alkenyl, C$_{2-6}$ alkynyl, C$_{3-10}$ carbocycle, —CH$_2$—(C$_{3-10}$ carbocycle), 3- to 10-membered heterocycle, —CH$_2$-(3- to 10-membered heterocycle), —OR$^{21}$, —SR$^{21}$, —N(R$^{22}$)(R$^{23}$), —C(O)OR$^{22}$, —C(O)N(R$^{22}$)(R$^{23}$), —C(O)C(O)N(R$^{22}$)(R$^{23}$), —OC(O)N(R$^{22}$)(R$^{23}$), —N(R$^{22}$)C(O)N(R$^{22}$)(R$^{23}$), —N(R$^{24}$)C(O)OR$^{25}$, —N(R$^{24}$)C(O)R$^{25}$, —N(R$^{22}$)S(O)$_2$R$^{25}$, —C(O)R$^{25}$, —S(O)$_2$R$^{25}$, —S(O)$_2$N(R$^{22}$)(R$^{23}$), —OCH$_2$C(O)OR$^{22}$, and —OC(O)R$^{25}$, wherein C$_{1-6}$ alkyl, C$_{2-6}$ alkenyl, C$_{2-6}$ alkynyl, C$_{3-10}$ carbocycle, —CH$_2$—(C$_{3-10}$ carbocycle), 3- to 10-membered heterocycle, and —CH$_2$-(3- to 10-membered heterocycle) are optionally substituted with one, two, or three groups independently selected from halogen, oxo, =NH, —CN, C$_{1-6}$ alkyl, C$_{1-6}$ haloalkyl, C$_{1-6}$ alkoxy, C$_{1-6}$ haloalkoxy, —OR$^{21}$, —SR$^{21}$, —N(R$^{22}$)(R$^{23}$), —C(O)OR$^{22}$, —C(O)N(R$^{22}$)(R$^{23}$), —C(O)C(O)N(R$^{22}$)(R$^{23}$), —OC(O)N(R$^{22}$)(R$^{23}$), —N(R$^{22}$)C(O)N(R$^{22}$)(R$^{23}$), —N(R$^{24}$)C(O)OR$^{25}$, —N(R$^{24}$)C(O)R$^{25}$, —N(R$^{22}$)S(O)$_2$R$^{25}$, —C(O)R$^{25}$, —S(O)$_2$R$^{25}$, —S(O)$_2$N(R$^{22}$)(R$^{23}$), and —OC(O)R$^{25}$;

$R^{21}$ is independently selected at each occurrence from H, $C_{1-6}$ alkyl, $C_{1-6}$ haloalkyl, $C_{2-6}$ alkenyl, $C_{2-6}$ alkynyl, $C_{3-10}$ carbocycle, and 3- to 10-membered heterocycle, wherein $C_{3-10}$ carbocycle and 3- to 10-membered heterocycle are optionally substituted with one, two, or three groups independently selected from halogen and $C_{1-6}$ alkyl;

$R^{22}$ is independently selected at each occurrence from H, $C_{1-6}$ alkyl, $C_{1-6}$ haloalkyl, $C_{2-6}$ alkenyl, $C_{2-6}$ alkynyl, $C_{3-10}$ carbocycle, and 3- to 10-membered heterocycle, wherein $C_{3-10}$ carbocycle and 3- to 10-membered heterocycle are optionally substituted with one, two, or three groups independently selected from halogen and $C_{1-6}$ alkyl;

$R^{23}$ is independently selected at each occurrence from H and $C_{1-6}$ alkyl;

$R^{24}$ is independently selected at each occurrence from H and $C_{1-6}$ alkyl; and $R^{25}$ is independently selected at each occurrence from $C_{1-6}$ alkyl, $C_{2-6}$ alkenyl, $C_{2-6}$ alkynyl, $C_{3-10}$ carbocycle, and 3- to 10-membered heterocycle, wherein $C_{1-6}$ alkyl, $C_{3-10}$ carbocycle, and 3- to 10-membered heterocycle are optionally substituted with one, two, or three groups independently selected from halogen, $C_{1-6}$ alkyl, $C_{1-6}$ haloalkyl, $C_{1-6}$ alkoxy, $C_{3-10}$ carbocycle, and 3- to 10-membered heterocycle.

In some embodiments, $L^{AB}$ is —$(O-C_2$ alkyl$)_z$- and z is an integer from 1 to 10. In some embodiments, $L^A$ is —$(C_2$ alkyl-O—$)_z$— and z is an integer from 1 to 10. In some embodiments, $L^{AB}$ is —$(CH_2)_{xx1}L^{12}(CH_2O)_{xx2}$—, wherein $L^{AB2}$ is a bond, a 5- or 6-membered heterocyclene, phenylene, —$C_{2-4}$ alkynylene, —$SO_2$— or —NH—; and zz1 and zz2 are independently an integer from 0 to 10. In some embodiments, $L^{AB}$ is —$(CH_2)_{zz1}(CH_2O)_{xx2}$—, wherein zz1 and zz2 are each independently an integer from 0 to 10. In some embodiments, $L^{AB}$ is a PEG linker (e.g., divalent linker of 1 to 10 ethylene glycol subunits). In some embodiments, B is a monovalent form of a compound selected from

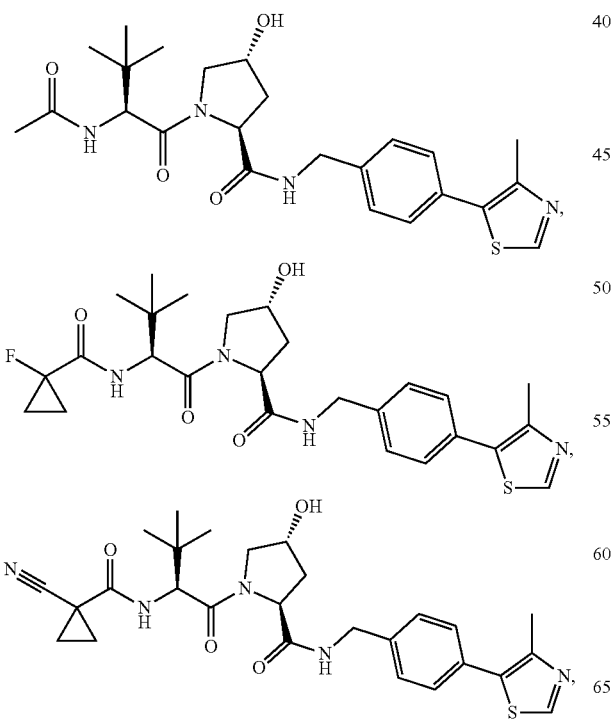

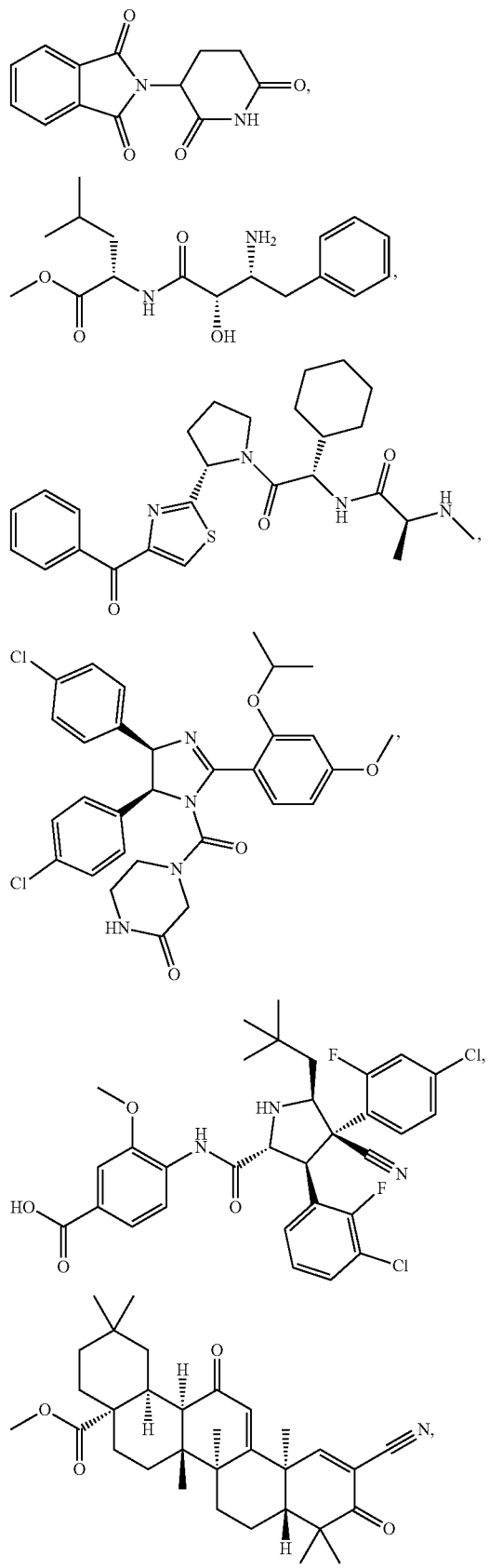

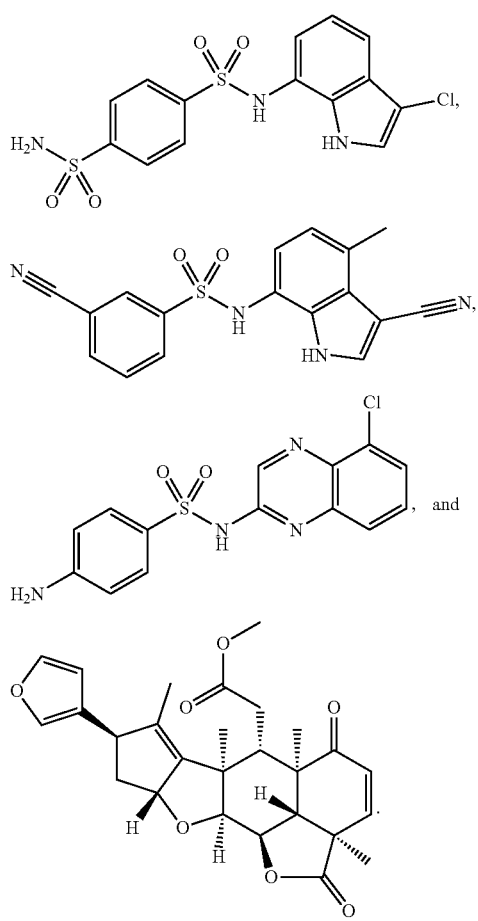
In some embodiments B is a monovalent form
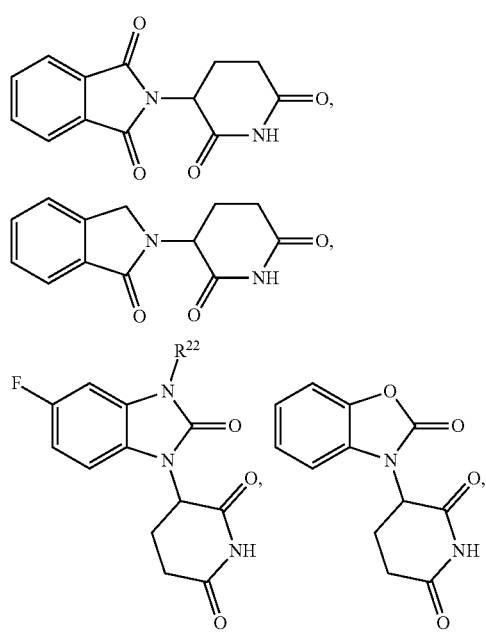
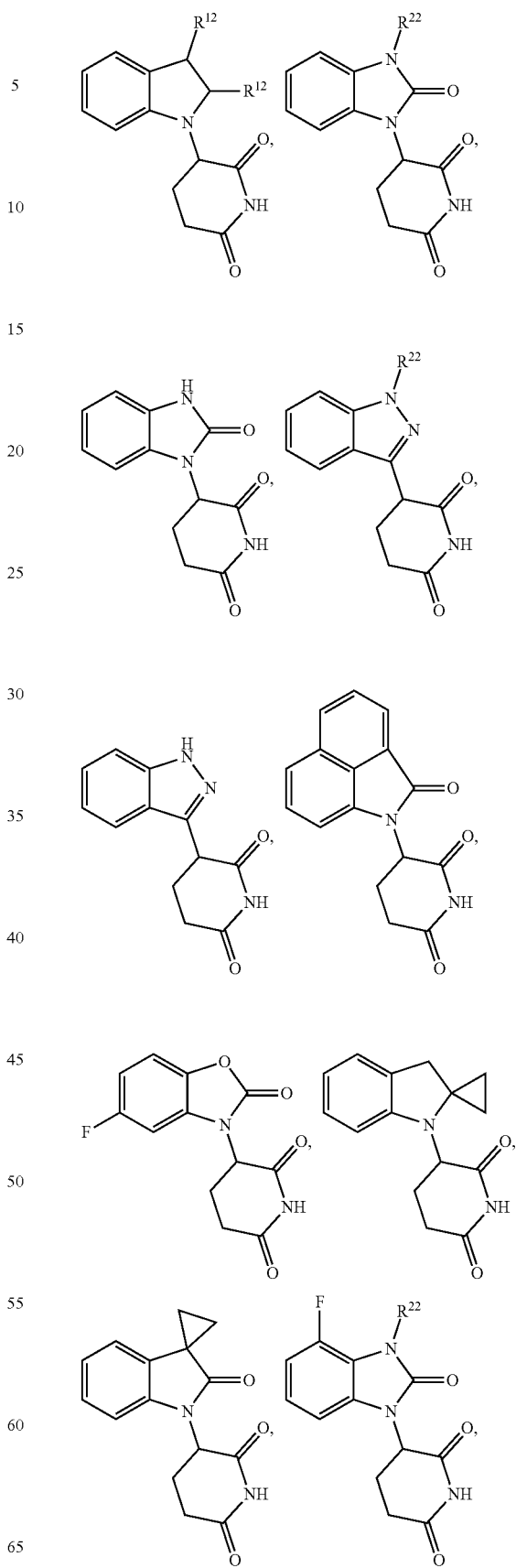

301
-continued
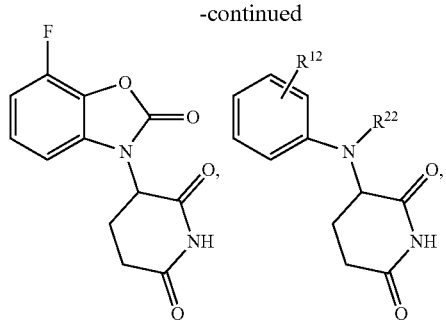
302
-continued
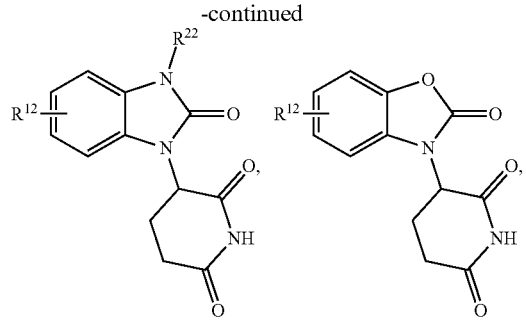
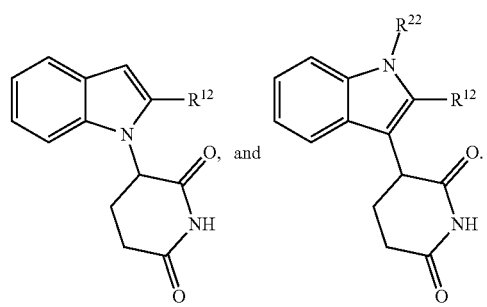
Also provided is a compound selected from
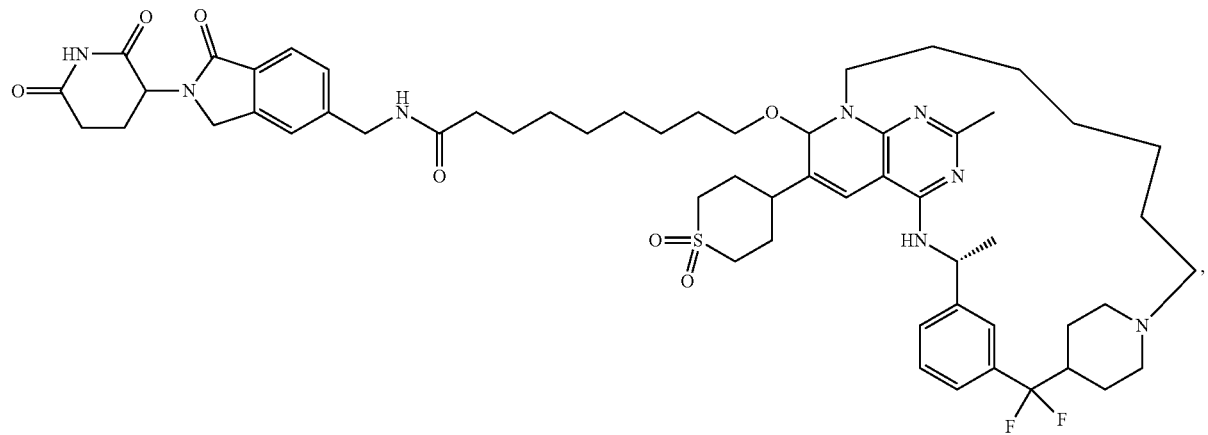

-continued
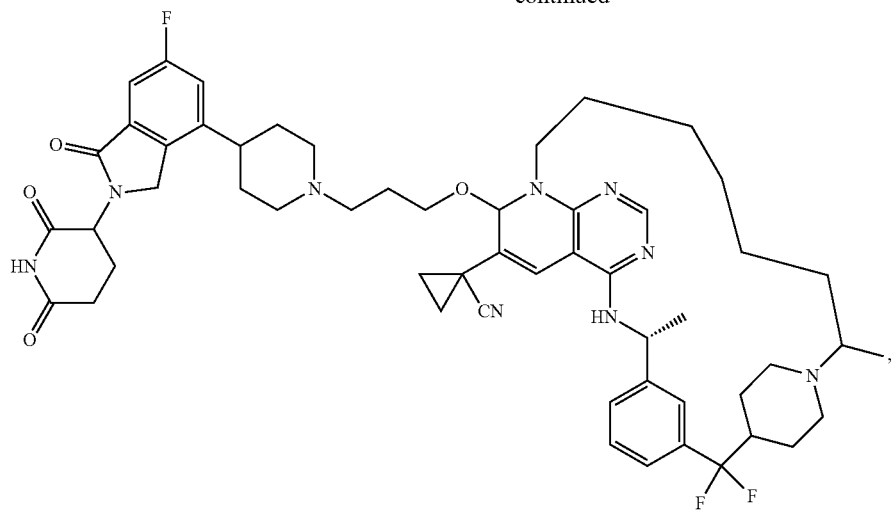
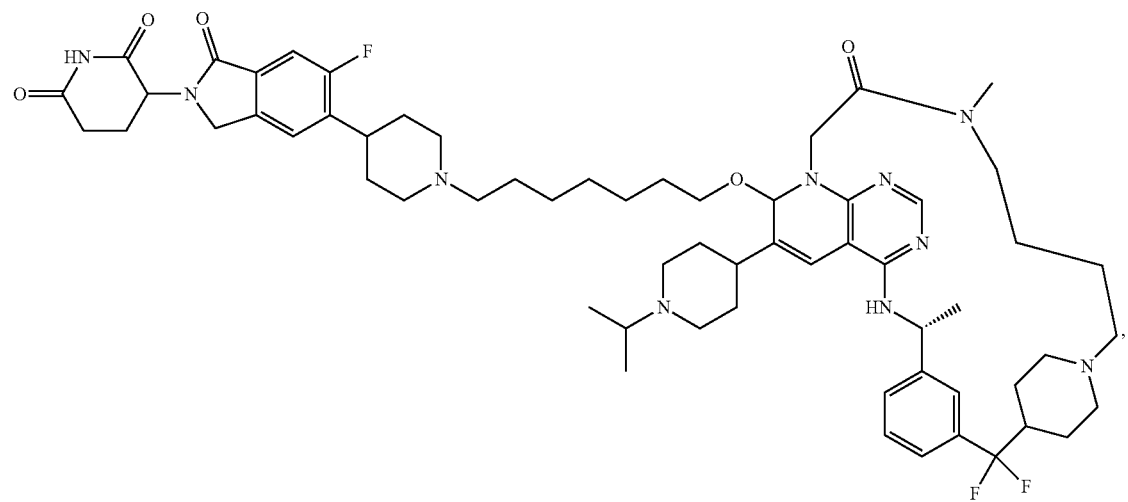
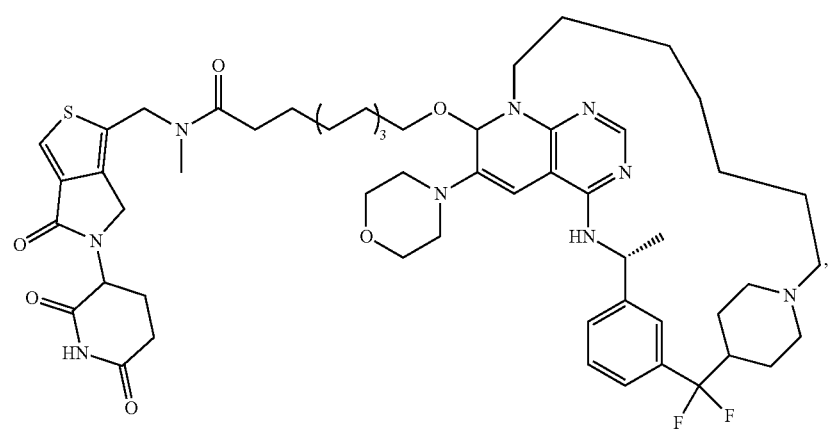

-continued
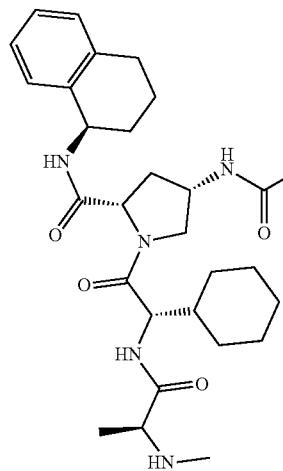
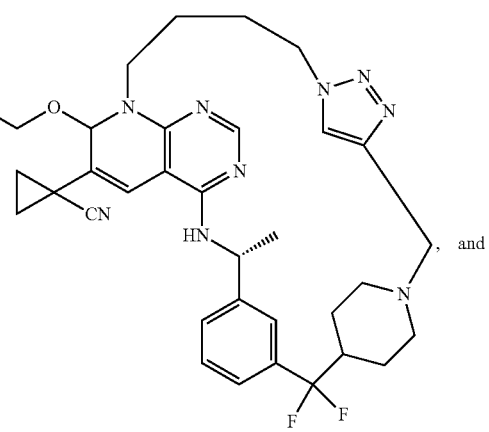
, and
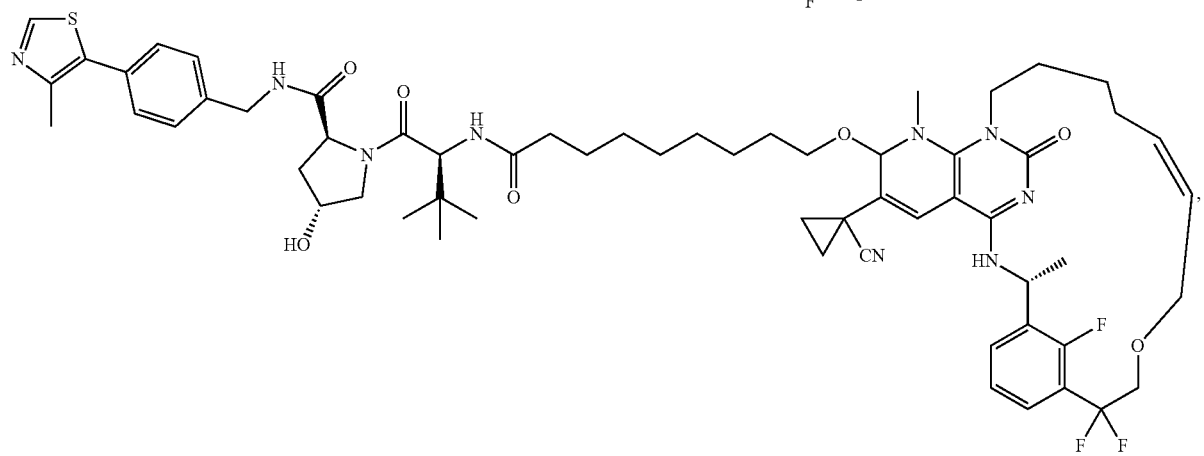
or a pharmaceutically acceptable salt or solvate thereof. In some embodiments, provided herein is a compound selected from,
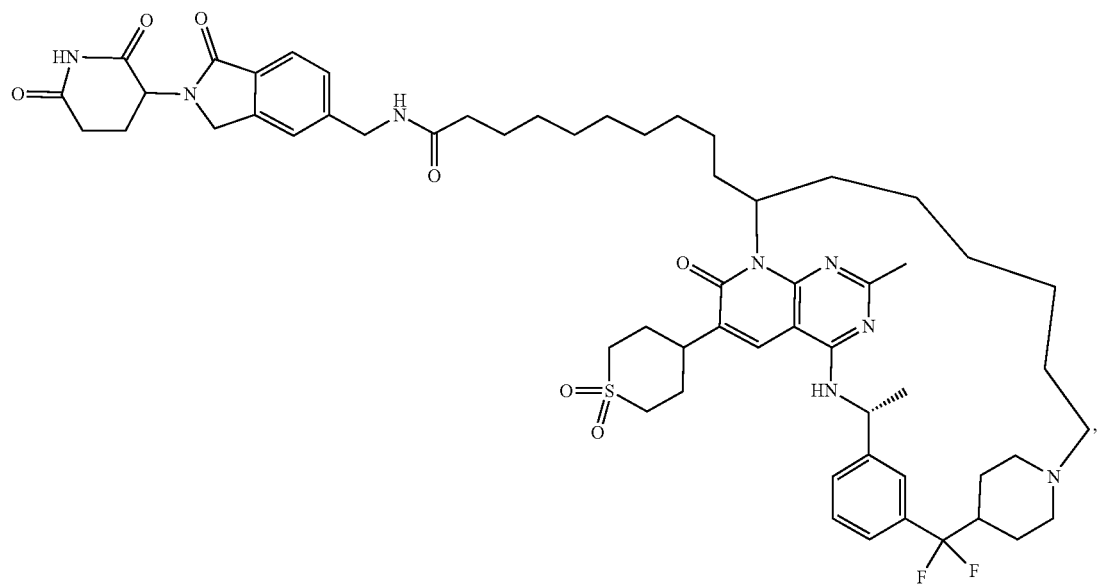

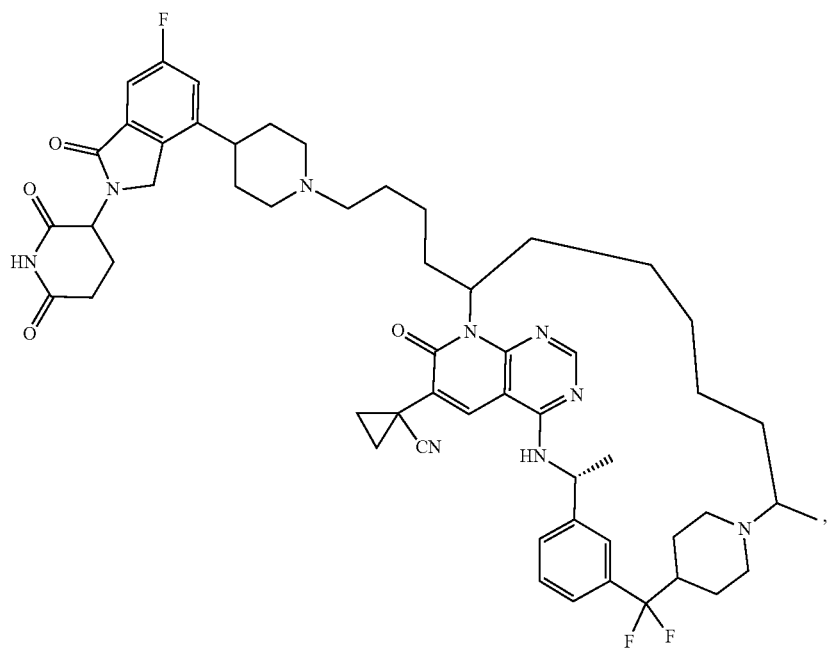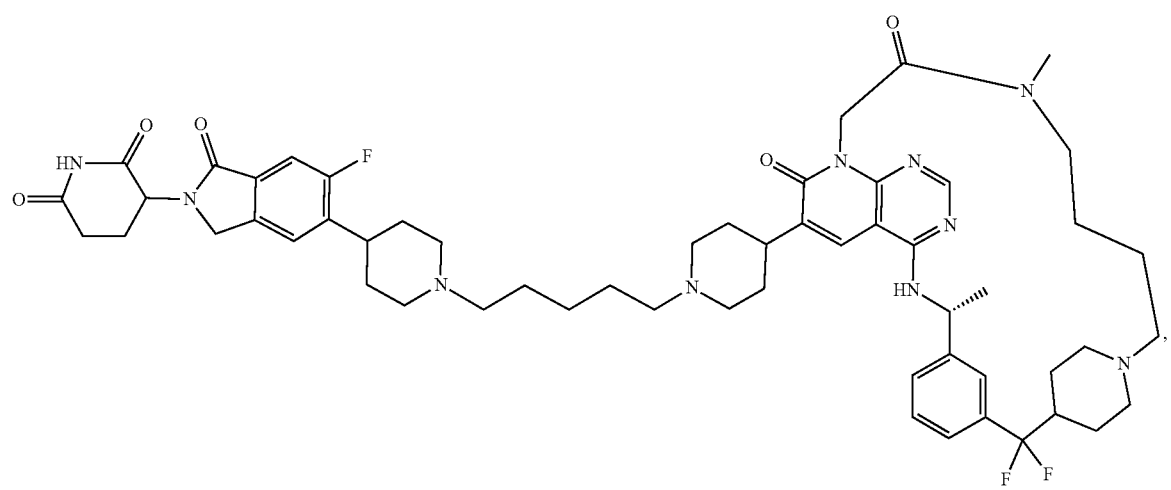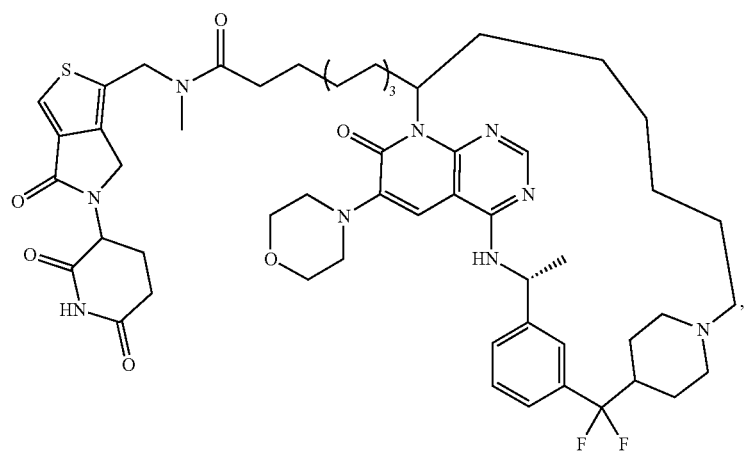

309
310
-continued
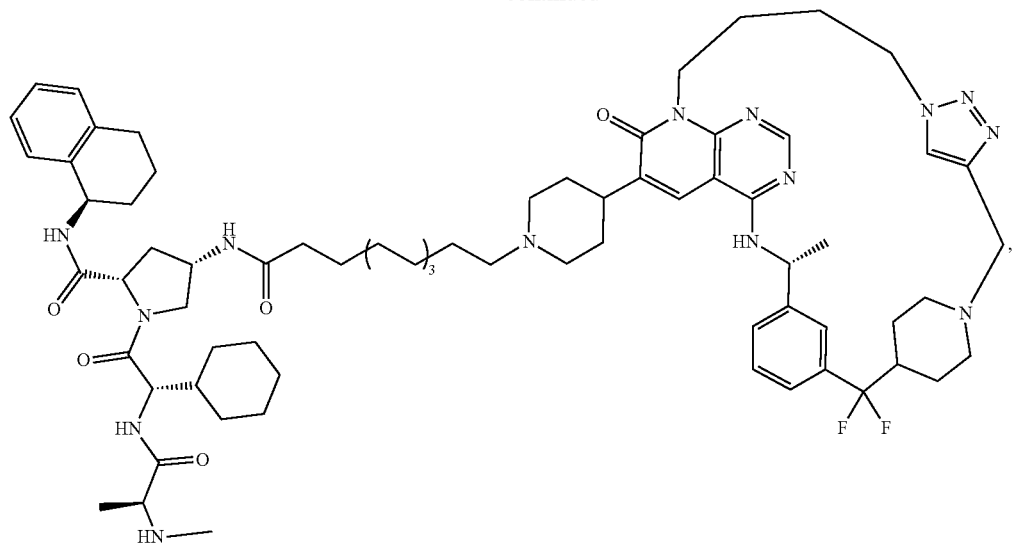
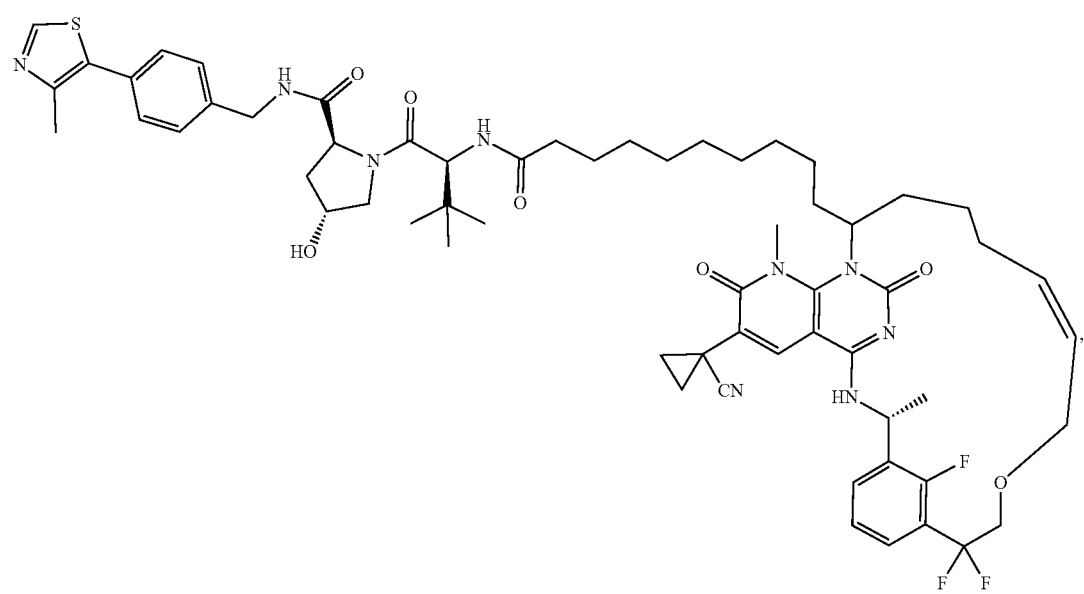
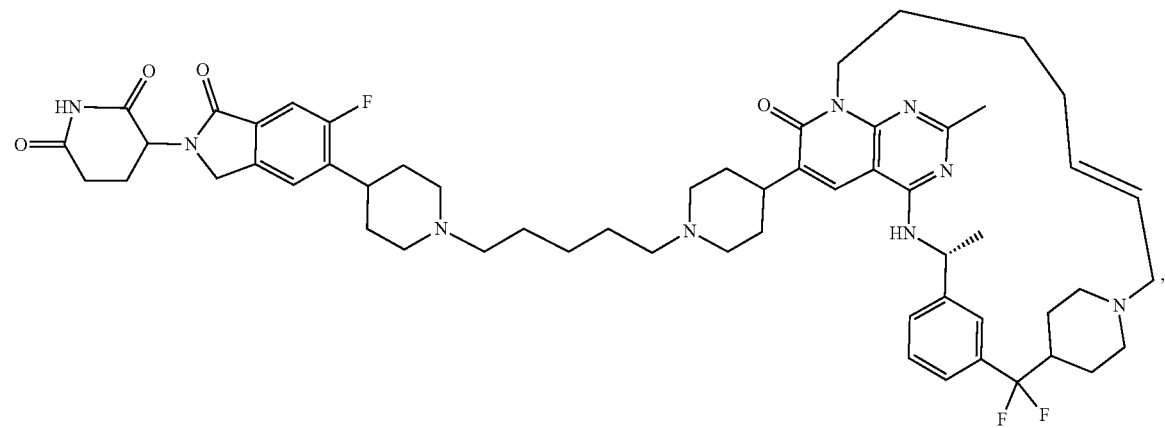

-continued
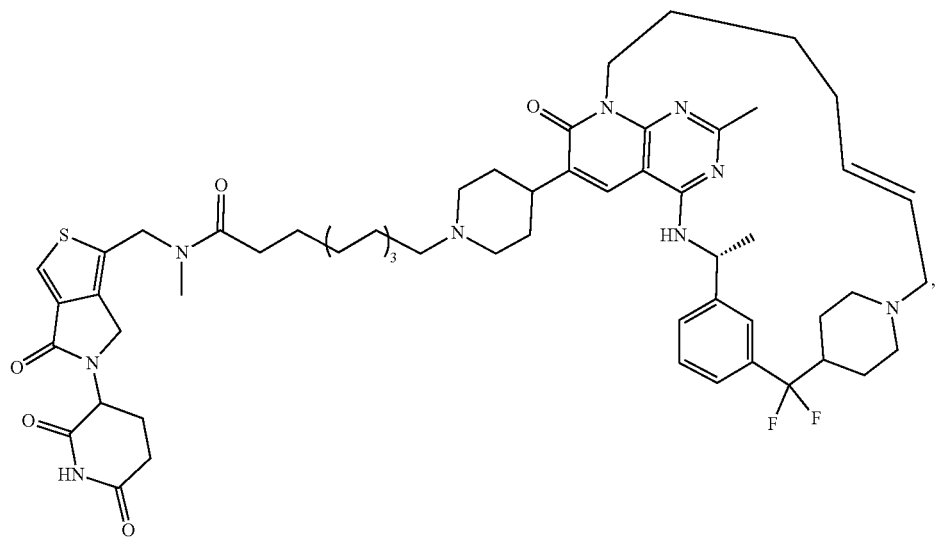
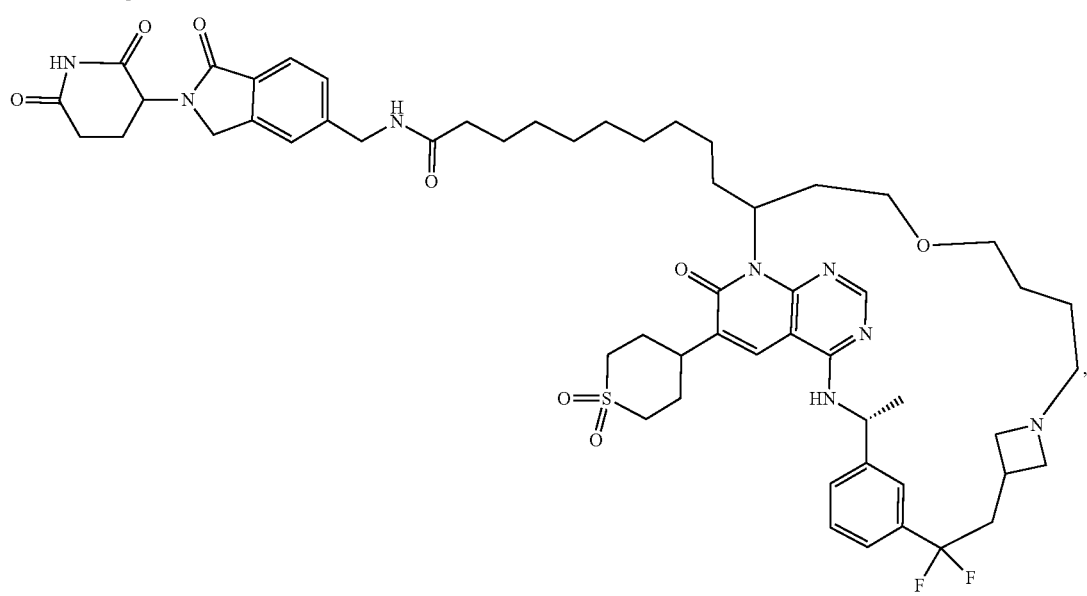
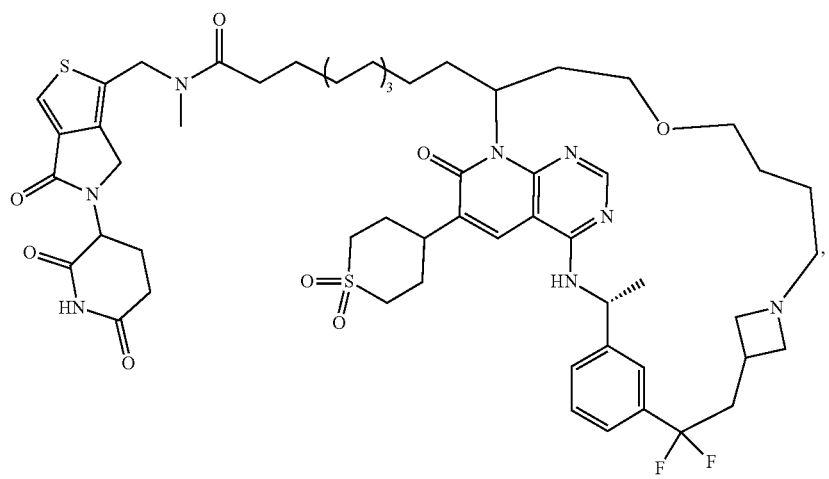

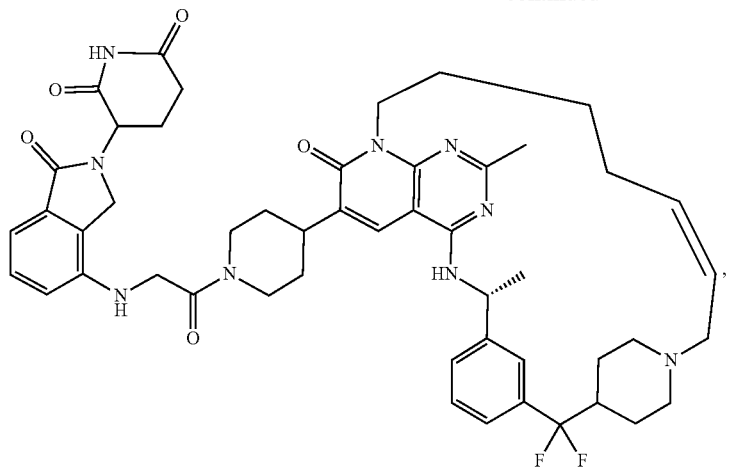
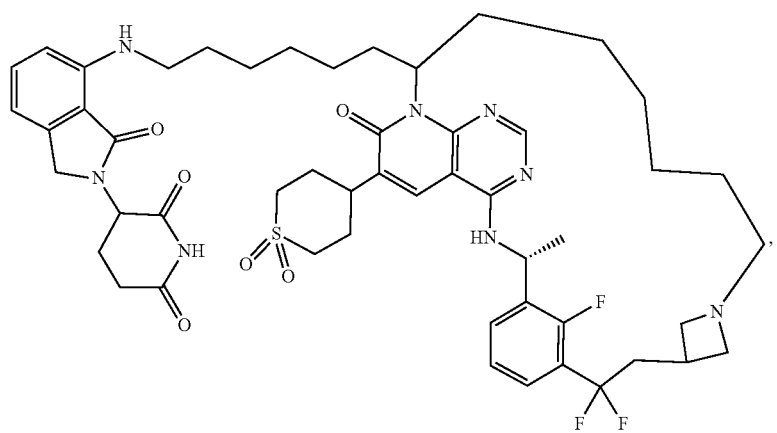
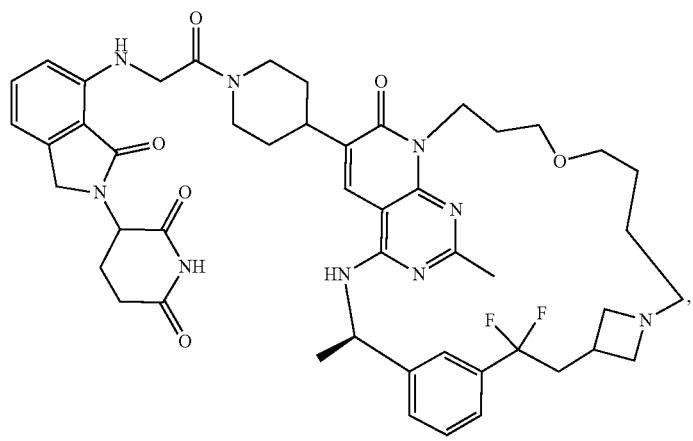

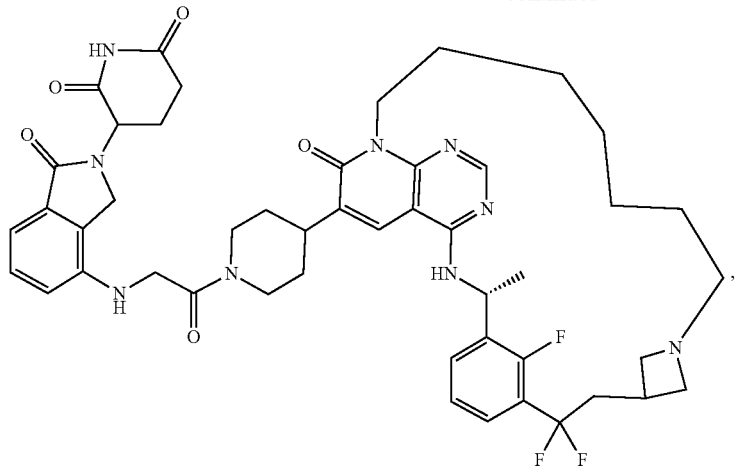
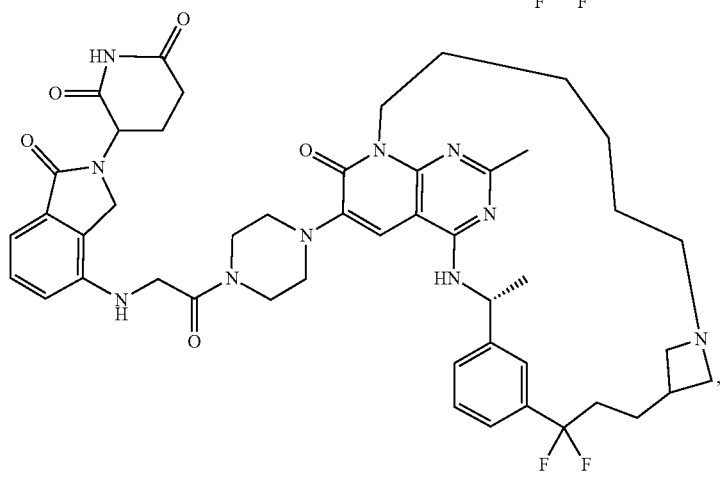
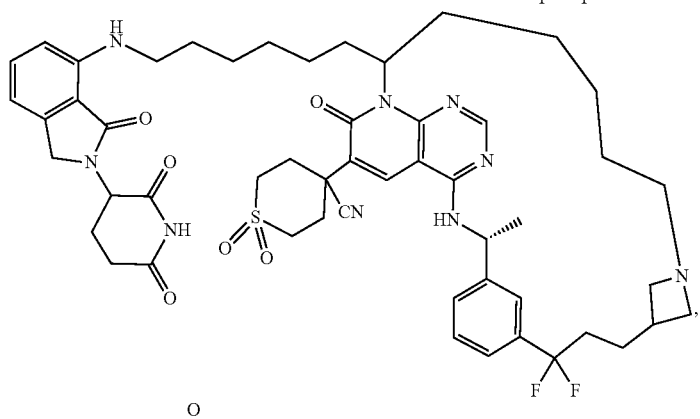
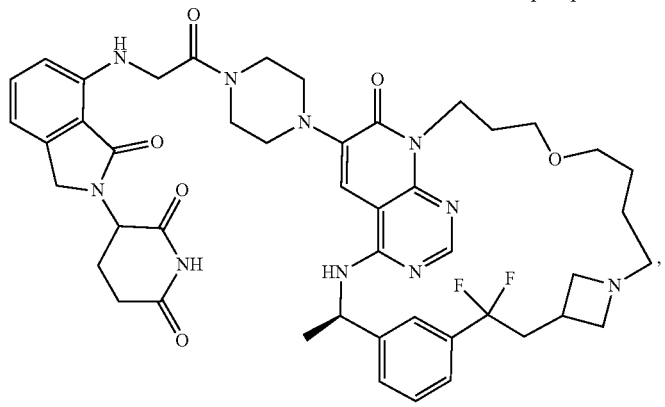

-continued
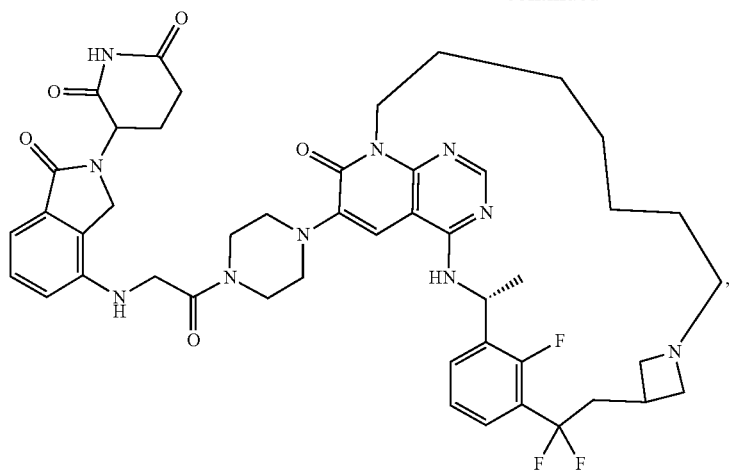
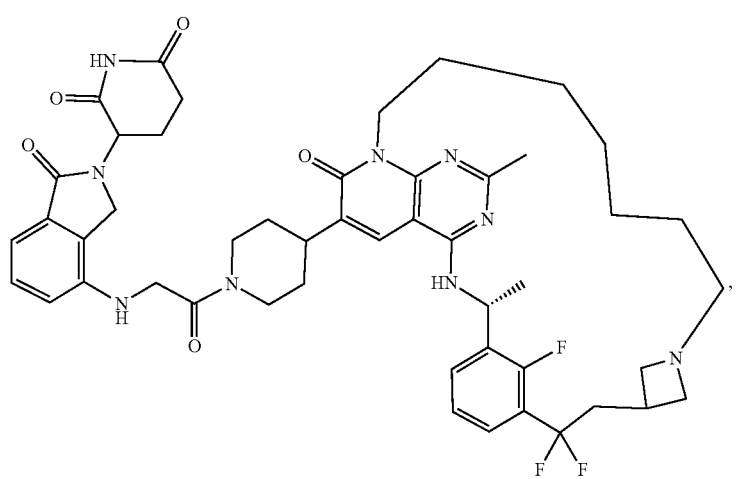
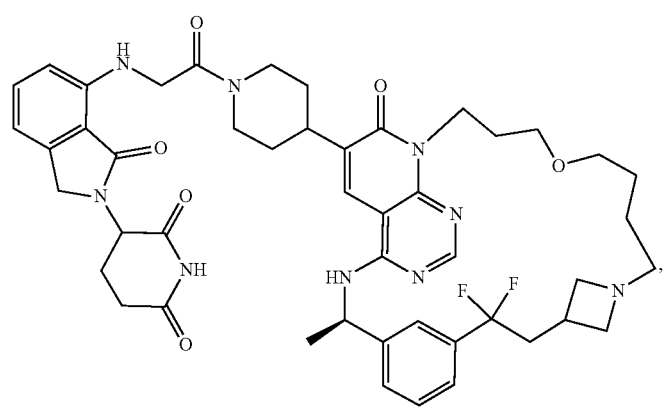

-continued
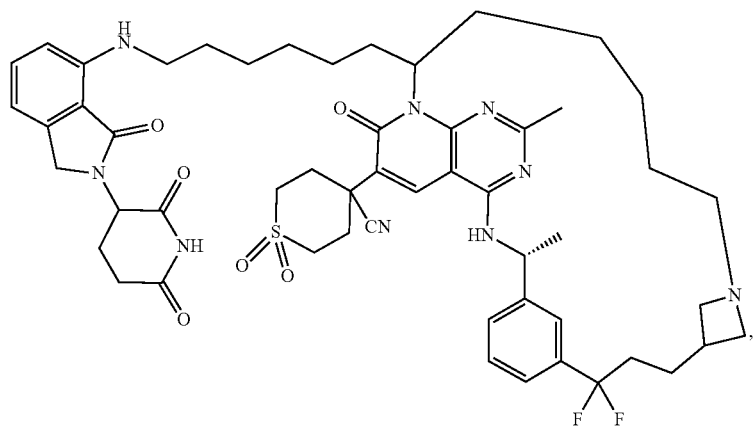
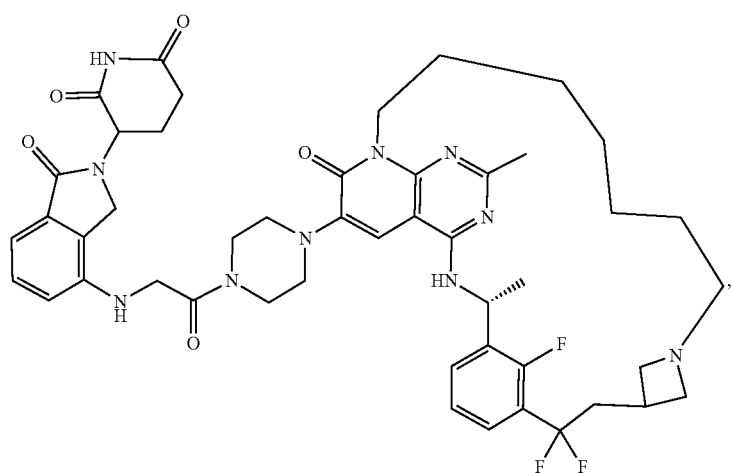
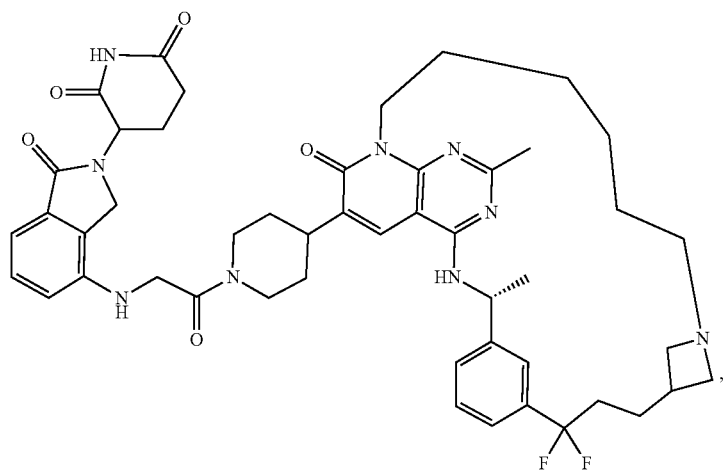

-continued
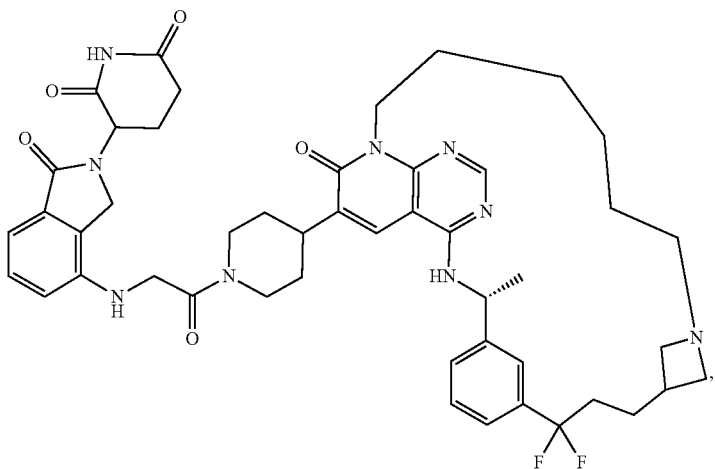
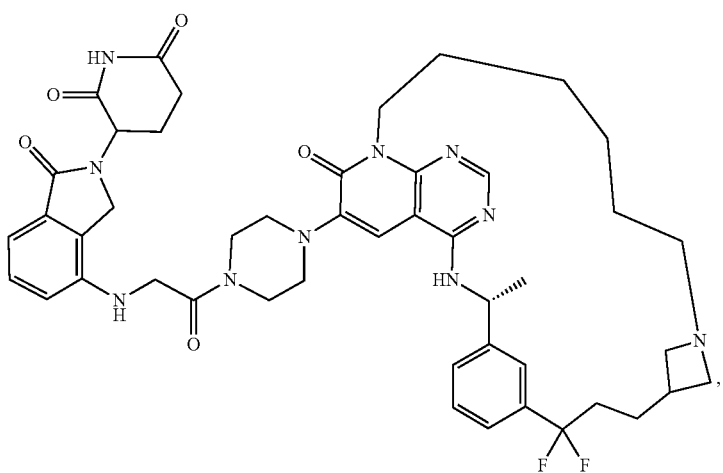
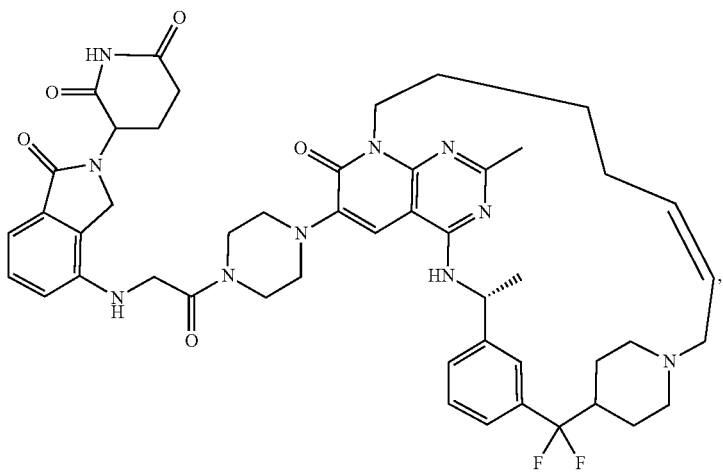

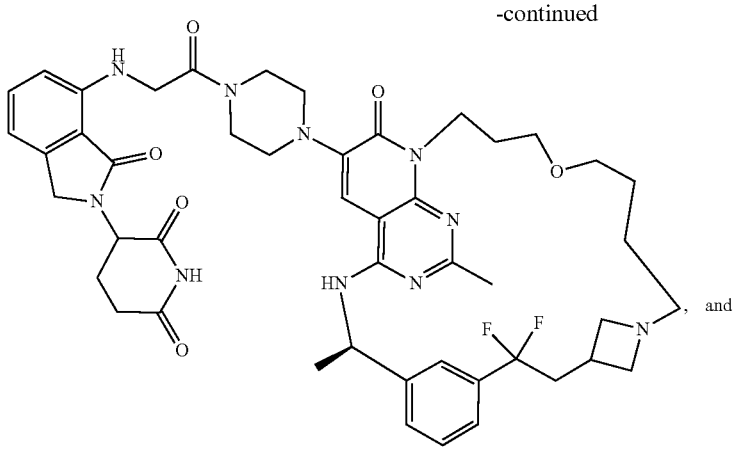

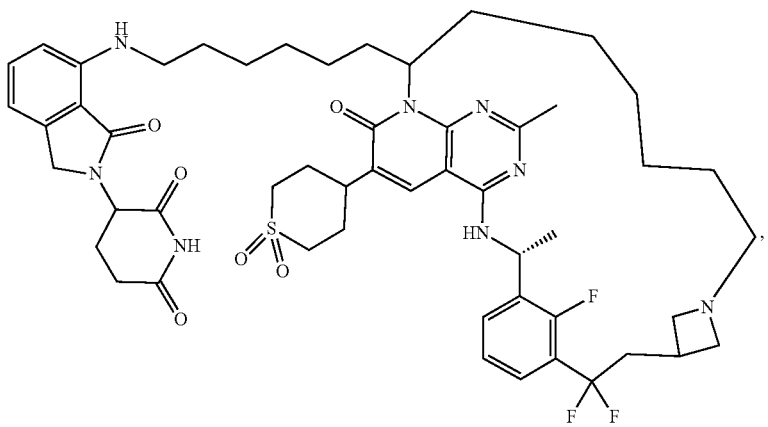

or a pharmaceutically acceptable salt or solvate thereof.

The chemical entities described herein can be synthesized according to one or more illustrative schemes herein and/or techniques known in the art. Materials used herein are either commercially available or prepared by synthetic methods generally known in the art. These schemes are not limited to the compounds listed in the examples or by any particular substituents, which are employed for illustrative purposes. Although various steps are described and depicted in Schemes 1-8 and Examples 1-36, the steps in some cases may be performed in a different order than the order shown in Schemes 1-8 and Examples 1-36. Various modifications to these synthetic reaction schemes may be made and will be suggested to one skilled in the art having referred to the present disclosure. Numberings or R groups in each scheme typically have the same meanings as those defined elsewhere herein unless otherwise indicated.

Unless specified to the contrary, the reactions described herein take place at atmospheric pressure, generally within a temperature range from −10° C. to 200° C. Further, except as otherwise specified, reaction times and conditions are intended to be approximate, e.g., taking place at about atmospheric pressure within a temperature range of about −10° C. to about 110° C. over a period of about 1 to about 24 hours; reactions left to run overnight average a period of about 16 hours.

In general, compounds of the disclosure may be prepared by the following reaction schemes:

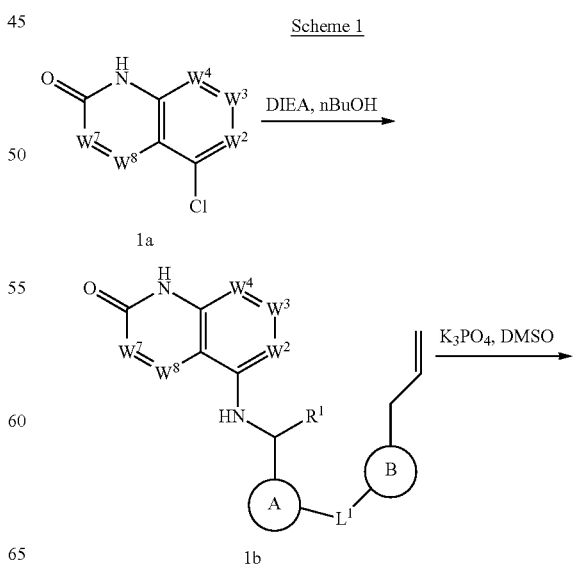

Scheme 1

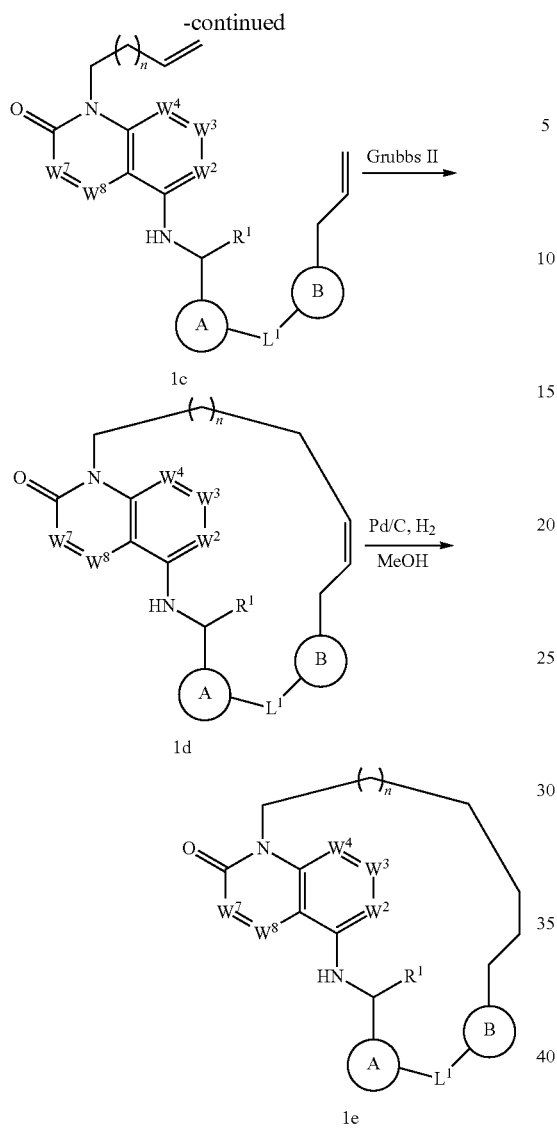

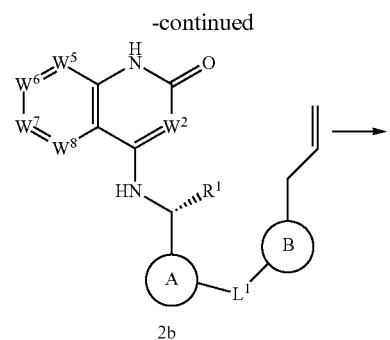

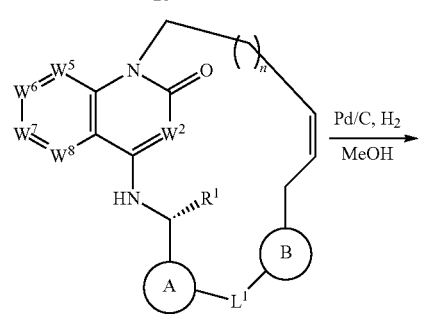

In some embodiments, a compound of Formula 1e may be prepared according to Scheme 1. For example, heteroaryl amine 1b can be formed from chloride 1a via a nucleophilic aromatic substitution reaction. Substitution of the lactam can proceed under basic conditions to give diene 1c, which can undergo a cross metathesis reaction—such as Grubbs cross metathesis reaction—to form macrocycle 1d. Optionally, 1d may be subjected to one or more subsequent reactions, such as a hydrogenation reaction, to provide a compound of Formula 1e.

Scheme 2

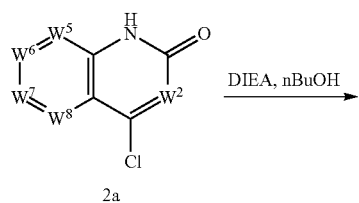

Similarly, in some embodiments, a compound of Formula 2e may be prepared according to Scheme 2. For example, heteroaryl amine 2b can be formed from chloride 2a via a nucleophilic aromatic substitution reaction. Substitution of the lactam can proceed under basic conditions to give diene 2c, which can undergo a cross metathesis reaction—such as Grubbs cross metathesis reaction—to form macrocycle 2d. Optionally, 2d may be subjected to one or more subsequent reactions, such as a hydrogenation reaction, to provide a compound of Formula 2e.

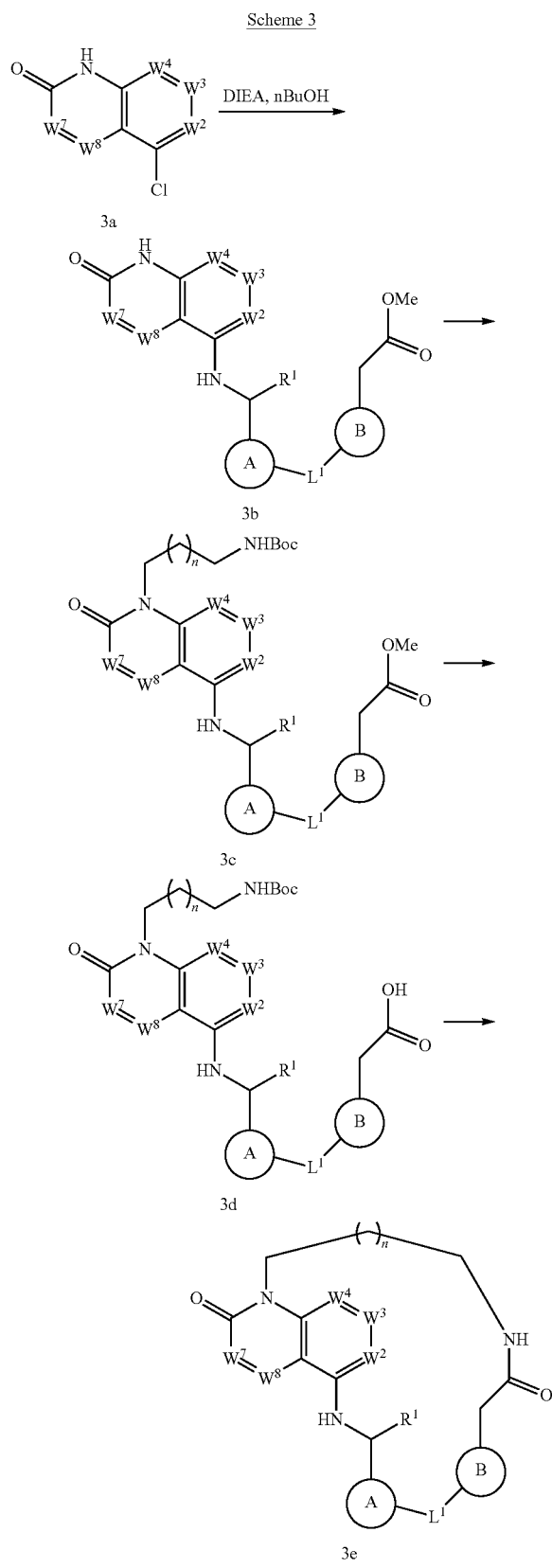

Scheme 3 amine 3b can be formed from chloride 3a via a substitution reaction. Substitution of the lactam can give protected amine 3c. Hydrolysis of the ester can form carboxylic acid 3d, which can undergo deprotection and peptide coupling reactions to afford macrocycle of Formula 3e.

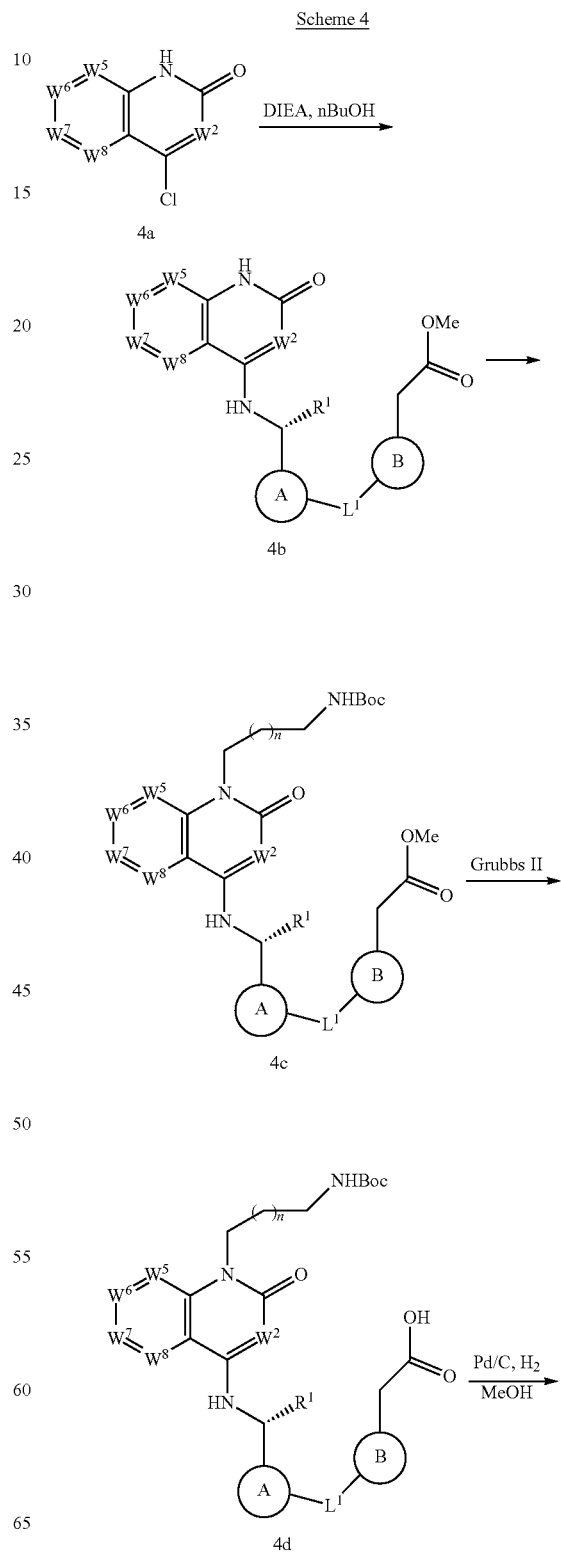

Scheme 4

In some embodiments, a compound of Formula 3e may be prepared according to Scheme 3. For example, heteroaryl -continued

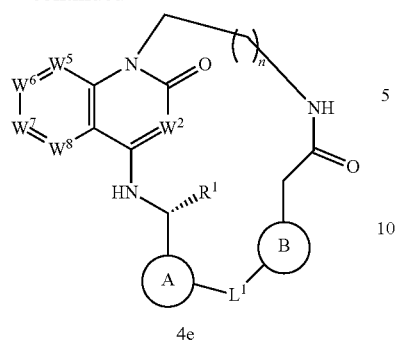

4e

Similarly, in some embodiments, a compound of Formula 4e may be prepared according to Scheme 4. For example, heteroaryl amine 4b can be formed from chloride 4a via a substitution reaction. Substitution of the lactam can give protected amine 4c. Hydrolysis of the ester can form carboxylic acid 4d, which can undergo deprotection and peptide coupling reactions to afford a macrocycle of Formula 4e.

Scheme 5

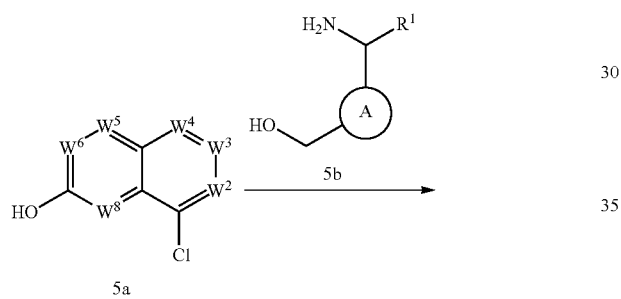

5a

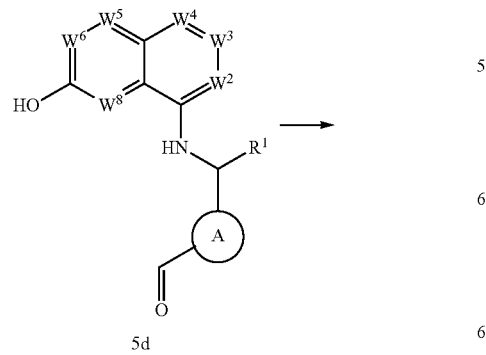

-continued

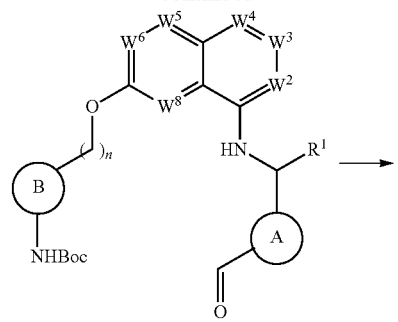

5e

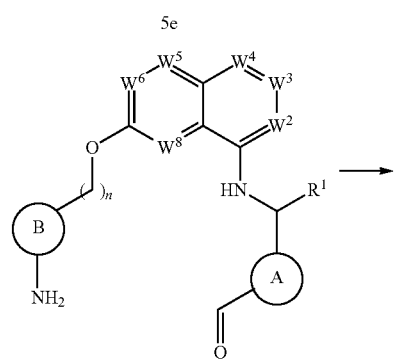

5f

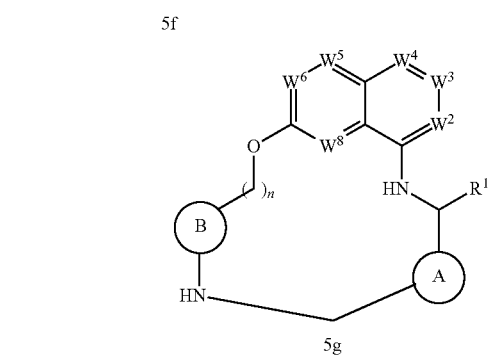

5g

In some embodiments, a compound of Formula 5g may be prepared according to Scheme 5. For example, heteroaryl amine 3c can be formed by coupling chloride 5a with amine 5b. Oxidation of the alcohol can give aldehyde 5d, which can be followed with substitution of the phenol to give 5e. Removal of the amine protecting group can afford 5f, which can undergo a reductive amination to form a macrocycle of Formula 5g.

Scheme 6

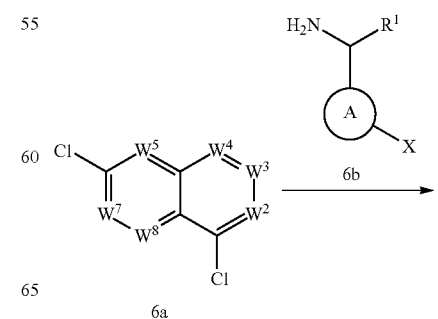

6a

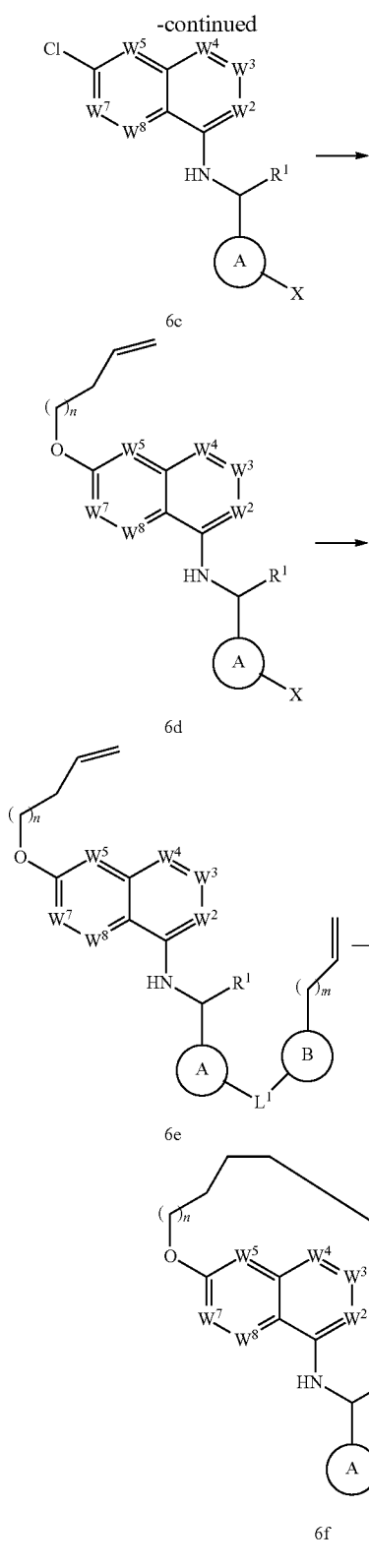

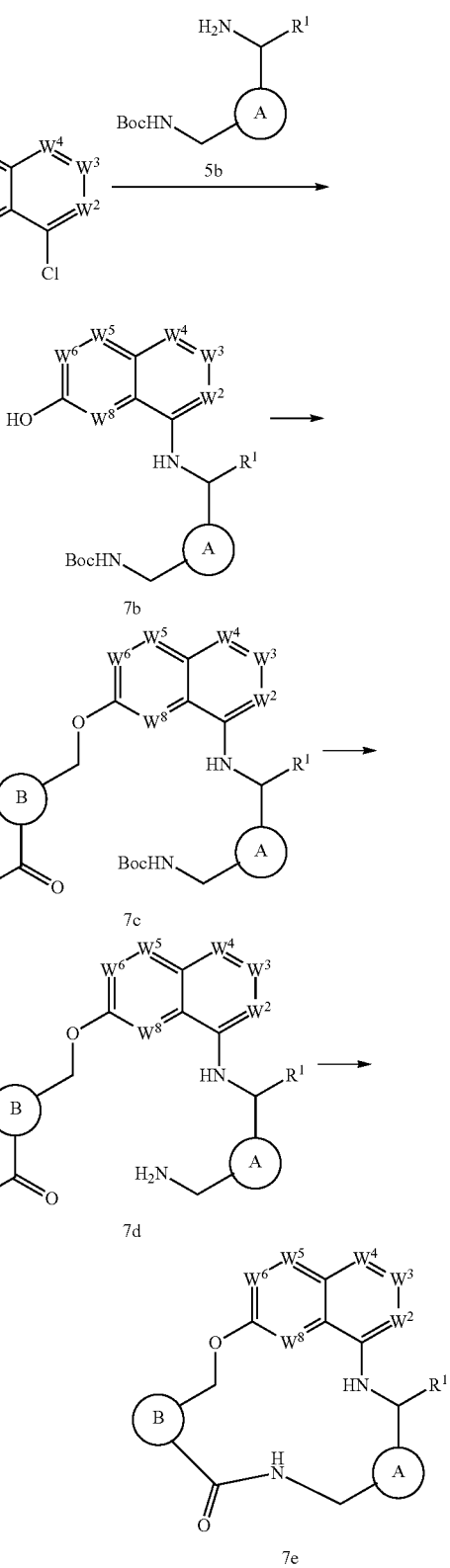

tion—can be followed by hydrogenation of the resulting double bond to provide a macrocycle of Formula 6f.

In some embodiments, a compound of Formula 6f may be prepared according to Scheme 6. For example, heteroaryl amine 6c can be formed by coupling chloride 1a with amine 6b. Substitution of the phenol to olefin 6d can be followed by installation of a second olefin to give diene 6e. A cross metathesis reaction-such as Grubbs cross metathesis reac- In some embodiments, a compound of Formula 7e may be prepared according to Scheme 7. For example, heteroaryl amine 7b can be formed by coupling chloride 7a with amine 5b. Substitution of the phenol can give 7c. Ester hydrolysis and deprotection of the amine can give 7d, which can be cyclized to form a macrocycle of Formula 7e via a peptide coupling reaction.

Scheme 8

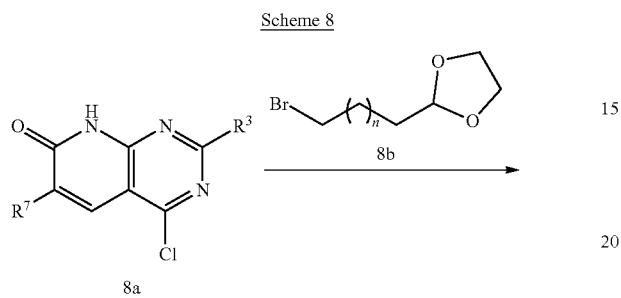

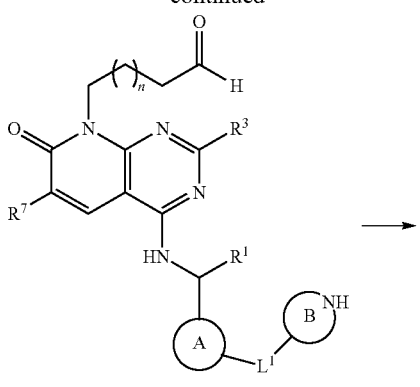

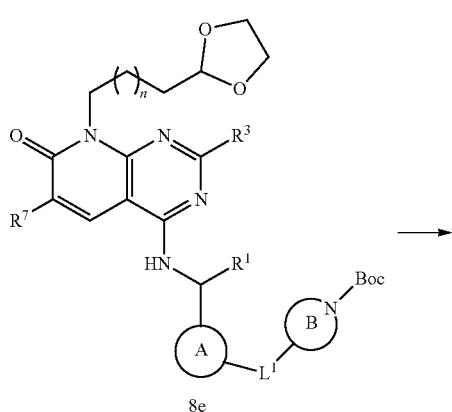

In some embodiments, a compound of Formula 8g may be prepared according to Scheme 8. For example, substitution of lactam 8a with a suitable bromo dioxolane (8b) can give acetal 8c. Nucleophilic aromatic substitution with amine 8d can provide heteroaryl amine 8e, which can be treated with a suitable acid, such as HCl, to remove the Boc protecting group and reveal the aldehyde. Finally, cyclization of 8f can proceed via reductive amination conditions to give a macrocycle of Formula 8g.

In some embodiments, a compound of the 4 present disclosure, for example, a compound of a formula given in Table 1, was synthesized according to one of the general routes outlined in Schemes 1-8, Examples 1-36, or by methods generally known in the art. In some embodiments, exemplary compounds may include, but are not limited to, a compound selected from Table 1, or a salt or solvate thereof.

TABLE 1

| No. | Structure | Chemical Name | [M + H]$^+$ |
|---|---|---|---|
| 1 | 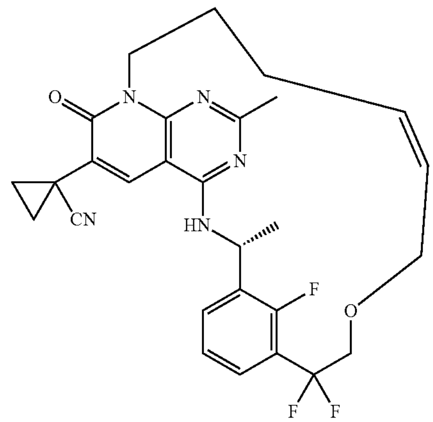 [SMILES: Cc1nc2c3cc(C4(C#N)CC4)c(=O)n(c3n1)CCC/C=C\COCC(F)(F)c1cccc(c1F)[C@@H](C)N2] | 1-((3R,Z)-4$^2$,5,5-trifluoro-1$^2$,3-dimethyl-1$^7$-oxo-1$^7$,1$^8$-dihydro-7-oxa-2-aza-1(4,8)-pyrido[2,3-d]pyrimidina-4(1,3)-benzenacyclotridecaphan-9-en-1$^6$-yl)cyclopropane-1-carbonitrile | 524.4 |
| 2 | 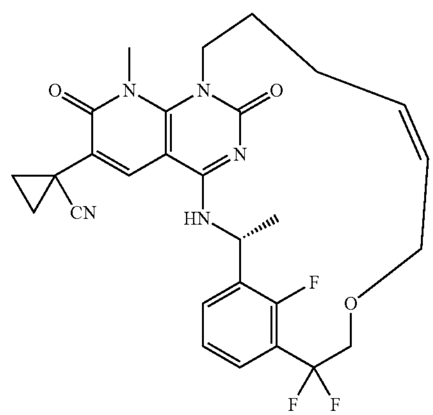 [SMILES: C[C@H]1Nc2nc(=O)n(c3c2cc(C2(C#N)CC2)c(=O)n3C)CCC/C=C\COCC(F)(F)c2cccc1c2F] | 1-((1$^3$E,3R,9Z)-4$^2$,5,5-trifluoro-1$^8$,3-dimethyl-1$^2$,1$^7$-dioxo-1$^1$,1$^2$,1$^7$,1$^8$-tetrahydro-7-oxa-2-aza-1(4,1)-pyrido[2,3-d]pyrimidina-4(1,3)-benzenacyclotridecaphan-9-en-1$^6$-yl)cyclopropane-1-carbonitrile | 540.4 |
| 3 | 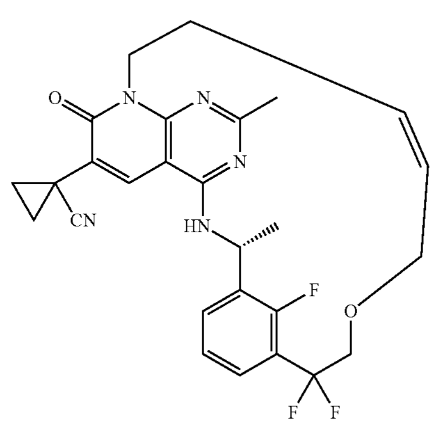 [SMILES: Cc1nc2c3cc(C4(C#N)CC4)c(=O)n(c3n1)CC/C=C\COCC(F)(F)c1cccc(c1F)[C@@H](C)N2] | 1-((3R,Z)-4$^2$,5,5-trifluoro-1$^2$,3-dimethyl-1$^7$-oxo-1$^7$,1$^8$-dihydro-7-oxa-2-aza-1(4,8)-pyrido[2,3-d]pyrimidina-4(1,3)-benzenacyclododecaphan-9-en-1$^6$-yl)cyclopropane-1-carbonitrile | 510.4 |

TABLE 1-continued

| No. | Structure | Chemical Name | [M + H]⁺ |
|---|---|---|---|
| 4 | 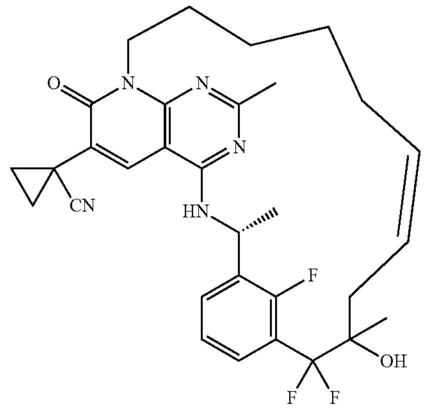 [SMILES: Cc1nc2c3cc(C4(C#N)CC4)c(=O)n(c3n1)CCCCC/C=C\CC(C)(O)C(F)(F)c1cccc(c1F)[C@@H](C)N2] | 1-((3R,Z)-5,5-difluoro-6-hydroxy-1²,3,6-trimethyl-1⁷-oxo-1⁷,1⁸-dihydro-2-aza-1(4,8)-pyrido[2,3-d]pyrimidina-4(1,3)-benzenacyclotetradecaphan-8-en-1⁶-yl)cyclopropane-1-carbonitrile | 548.3 |
| 5 | 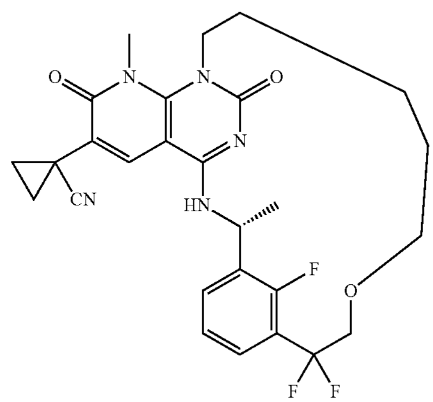 [SMILES: C[C@H]1Nc2nc(=O)n(c3c2cc(C2(C#N)CC2)c(=O)n3C)CCCCCOCC(F)(F)c2cccc1c2F] | 1-((3R,E)-4²,5,5-trifluoro-1⁸,3-dimethyl-1²,1⁷-dioxo-1¹,1²,1⁷,1⁸-tetrahydro-7-oxa-2-aza-1(4,1)-pyrido[2,3-d]pyrimidina-4(1,3)-benzenacyclododecaphane-1⁶-yl)cyclopropane-1-carbonitrile | 528.4 |
| 6 | 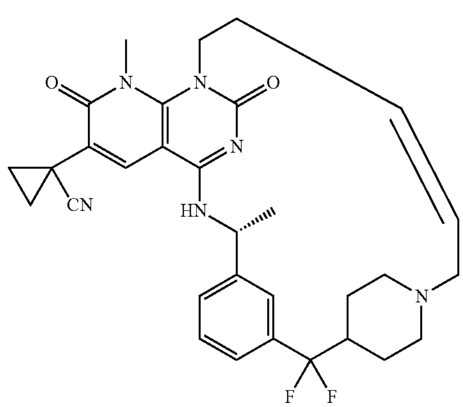 [SMILES: C[C@H]1Nc2nc(=O)n(c3c2cc(C2(C#N)CC2)c(=O)n3C)CC/C=C\CN2CCC(CC2)C(F)(F)c2cccc1c2] | 1-((6³E,4R,9Z)-2,2-difluoro-6⁸,4-dimethyl-6²,6⁷-dioxo-6¹,6²,6⁷,6⁸-tetrahydro-5-aza-6(4,1)-pyrido[2,3-d]pyrimidina-1(4,1)-piperidina-3(1,3)-benzenacycloundecaphan-9-en-6⁶-yl)cyclopropane-1-carbonitrile | 561.4 |

TABLE 1-continued

| No. | Structure | Chemical Name | [M + H]⁺ |
|---|---|---|---|
| 7 | 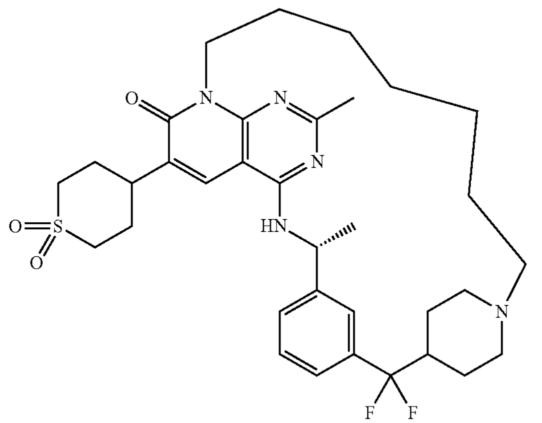 [SMILES: Cc1nc2c3cc(C4CCS(=O)(=O)CC4)c(=O)n(c3n1)CCCCCCCN1CCC(CC1)C(F)(F)c1cccc(c1)[C@@H](C)N2] | (4R)-6⁶-(1,1-dioxidotetrahydro-2H-thiopyran-4-yl)-2,2-difluoro-6²,4-dimethyl-6⁷,6⁸-dihydro-5-aza-6(4,8)-pyrido[2,3-d]pyrimidina-1(4,1)-piperidina-3(1,3)-benzenacyclotridecaphan-6⁷-one | 644.5 |
| 8 | 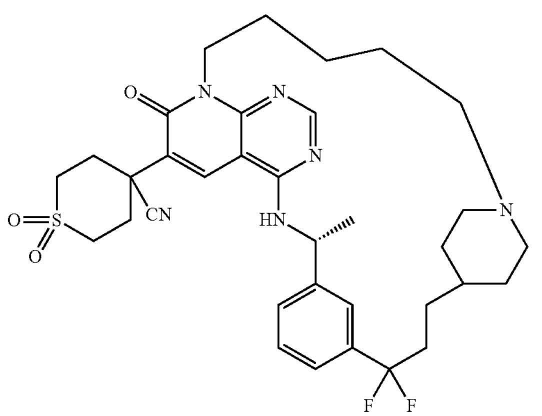 [SMILES: C[C@H]1Nc2ncnc3c2cc(C2(C#N)CCS(=O)(=O)CC2)c(=O)n3CCCCCN2CCC(CC2)CCC(F)(F)c2cccc1c2] | 4-((3R)-5,5-difluoro-3-methyl-1⁷-oxo-1⁷,1⁸-dihydro-2-aza-1(4,8)-pyrido[2,3-d]pyrimidina-8(4,1)-piperidina-4(1,3)-benzenacyclotridecaphane-1⁶-yl)tetrahydro-2H-thiopyran-4-carbonitrile 1,1-dioxide | 653.3 |
| 9 | 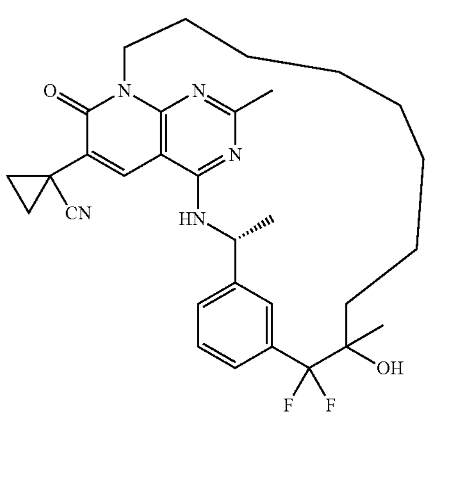 [SMILES: Cc1nc2c3cc(C4(C#N)CC4)c(=O)n(c3n1)CCCCCCCCC(C)(O)C(F)(F)c1cccc(c1)[C@@H](C)N2] | 1-((3R)-5,5-difluoro-6-hydroxy-1²,3,6-trimethyl-1⁷-oxo-1⁷,1⁸-dihydro-2-aza-1(4,8)-pyrido[2,3-d]pyrimidina-4(1,3)-benzenacyclotetradecaphane-1⁶-yl)cyclopropane-1-carbonitrile | 550.4 |

TABLE 1-continued

| No. | Structure | Chemical Name | [M + H]+ |
|---|---|---|---|
| 10 | 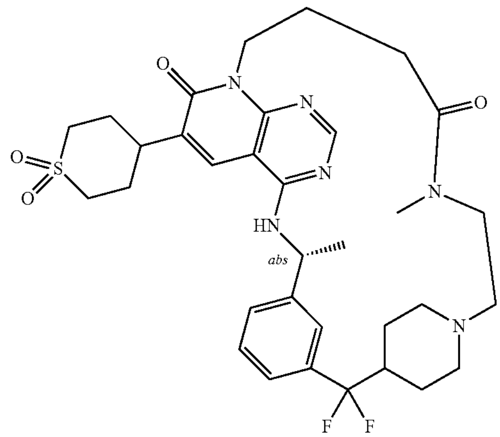 [SMILES: C[C@H]1Nc2ncnc3c2cc(C2CCS(=O)(=O)CC2)c(=O)n3CCCC(=O)N(C)CCN2CCC(CC2)C(F)(F)c2cccc1c2] | (4R)-6⁶-(1,1-dioxidotetrahydro-2H-thiopyran-4-yl)-2,2-difluoro-4,11-dimethyl-6⁷,6⁸-dihydro-5,11-diaza-6(4,8)-pyrido[2,3-d]pyrimidina-1(4,1)-piperidina-3(1,3)-benzenacyclotridecaphane-6⁷,10-dione | 657.4 |
| 11 | 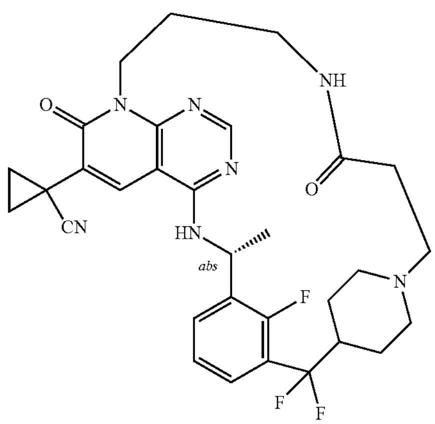 [SMILES: C[C@H]1Nc2ncnc3c2cc(C2(C#N)CC2)c(=O)n3CCCNC(=O)CCN2CCC(CC2)C(F)(F)c2cccc1c2F] | 1-((4R)-3²,2,2-trifluoro-4-methyl-6⁷,11-dioxo-6⁷,6⁸-dihydro-5,10-diaza-6(4,8)-pyrido[2,3-d]pyrimidina-1(4,1)-piperidina-3(1,3)-benzenacyclotridecaphane-6⁶-yl)cyclopropane-1-carbonitrile | 594.5 |
| 12 | 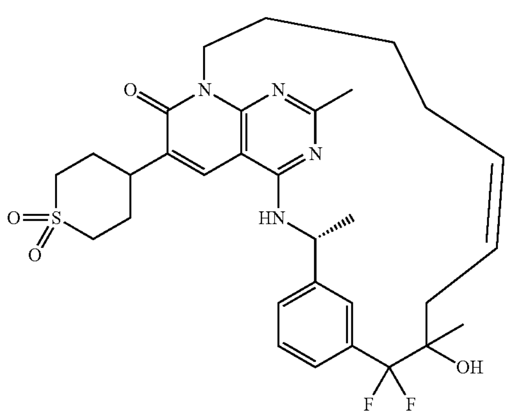 [SMILES: Cc1nc2c3cc(C4CCS(=O)(=O)CC4)c(=O)n(c3n1)CCCC/C=C\CC(C)(O)C(F)(F)c1cccc(c1)[C@@H](C)N2] | (3R,Z)-1⁶-(1,1-dioxidotetrahydro-2H-thiopyran-4-yl)-5,5-difluoro-6-hydroxy-1²,3,6-trimethyl-1⁷,1⁸-dihydro-2-aza-1(4,8)-pyrido[2,3-d]pyrimidina-4(1,3)-benzenacyclotridecaphan-8-en-1⁷-one | 601.4 |

TABLE 1-continued

| No. | Structure | Chemical Name | [M + H]+ |
|---|---|---|---|
| 13 | 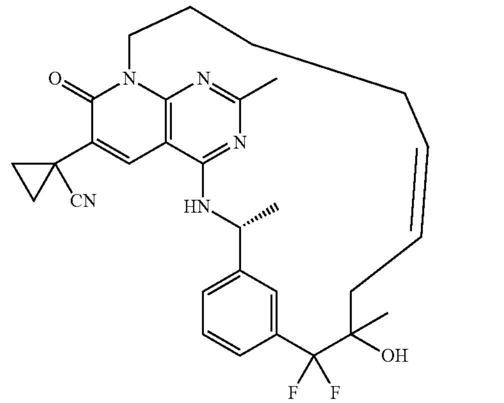 [SMILES: Cc1nc2c3cc(C4(C#N)CC4)c(=O)n(c3n1)CCCC/C=C\CC(C)(O)C(F)(F)c1cccc(c1)[C@@H](C)N2] | 1-((3R,Z)-5,5-difluoro-6-hydroxy-1$^2$,3,6-trimethyl-1$^7$-oxo-1$^7$,1$^8$-dihydro-2-aza-1(4,8)-pyrido[2,3-d]pyrimidina-4(1,3)-benzenacyclotridecaphan-8-en-1$^6$-yl)cyclopropane-1-carbonitrile | 534.4 |
| 14 | 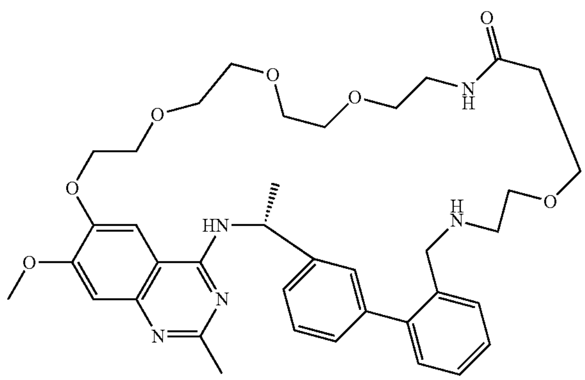 [SMILES: COc1cc2nc(C)nc3c2cc1OCCOCCOCCOCCNC(=O)CCOCCNCc1ccccc1-c1cccc(c1)[C@@H](C)N3] | (R)-5$^7$-methoxy-5$^2$,3-dimethyl-6,9,12,15,22-pentaoxa-4,18,25-triaza-5(4,6)-quinazolina-1(1,2),2(1,3)-dibenzenacyclohexacosaphan-19-one | 688.4 |
| 15 | 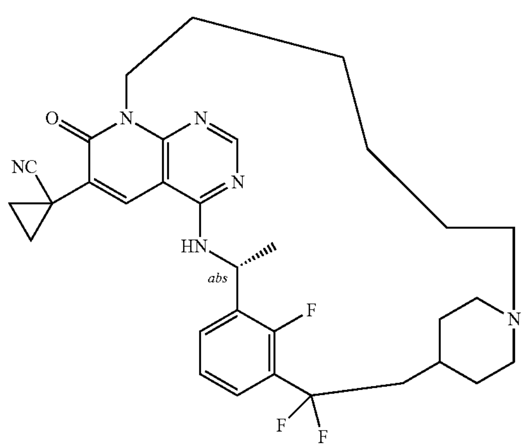 [SMILES: C[C@H]1Nc2ncnc3c2cc(C2(C#N)CC2)c(=O)n3CCCCCCN2CCC(CC2)CC(F)(F)c2cccc1c2F] | 1-((3R)-4$^2$,5,5-trifluoro-3-methyl-1$^7$-oxo-1$^7$,1$^8$-dihydro-2-aza-1(4,8)-pyrido[2,3-d]pyrimidina-7(4,1)-piperidina-4(1,3)-benzenacyclotridecaphane-1$^6$-yl)cyclopropane-1-carbonitrile | 579.4 |

TABLE 1-continued

| No. | Structure | Chemical Name | [M + H]+ |
|---|---|---|---|
| 16 | 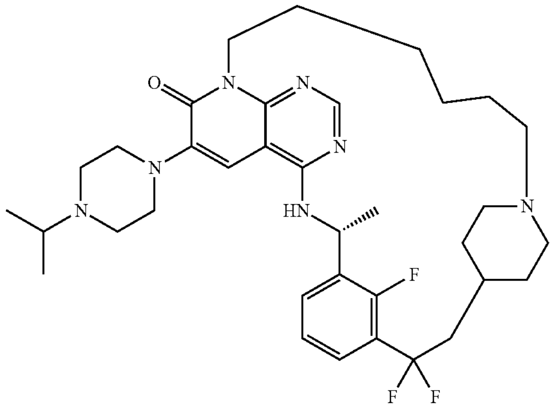 [SMILES: CC(C)N1CCN(c2cc3c4ncnc3n(c2=O)CCCCCCN2CCC(CC2)CC(F)(F)c2cccc(c2F)[C@@H](C)N4)CC1] | (3R)-4$^2$,5,5-trifluoro-1$^6$-(4-isopropylpiperazin-1-yl)-3-methyl-1$^7$,1$^8$-dihydro-2-aza-1(4,8)-pyrido[2,3-d]pyrimidina-7(4,1)-piperidina-4(1,3)-benzenacyclotridecaphan-1$^7$-one | 640.8 |
| 17 | 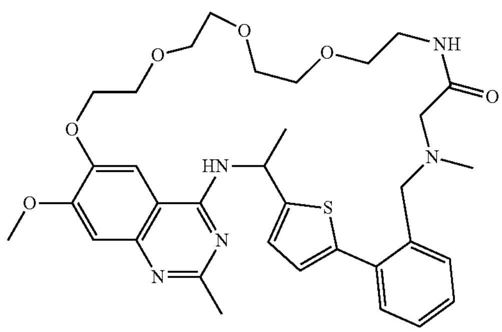 [SMILES: COc1cc2nc(C)nc3c2cc1OCCOCCOCCOCCNC(=O)CN(C)Cc1ccccc1C1=CC=C(S1)C(C)N3] | 5$^7$-methoxy-5$^2$,3,21-trimethyl-6,9,12,15-tetraoxa-4,18,21-triaza-5(4,6)-quinazolina-2(2,5)-thiophena-1(1,2)-benzenacyclodocosaphan-19-one | 650.3 |
| 18 | 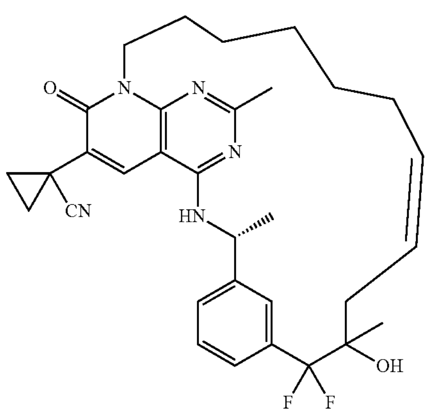 [SMILES: Cc1nc2c3cc(C4(C#N)CC4)c(=O)n(c3n1)CCCCCC/C=C\CC(C)(O)C(F)(F)c1cccc(c1)[C@@H](C)N2] | 1-((3R,Z)-5,5-difluoro-6-hydroxy-1$^2$,3,6-trimethyl-1$^7$-oxo-1$^7$,1$^8$-dihydro-2-aza-1(4,8)-pyrido[2,3-d]pyrimidina-4(1,3)-benzenacyclopentadecaphan-8-en-1$^6$-yl)cyclopropane-1-carbonitrile | 562.4 |
| 19 | 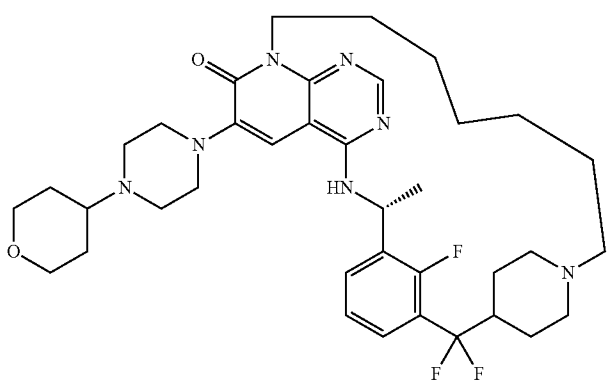 [SMILES: C[C@H]1Nc2ncnc3c2cc(N2CCN(C4CCOCC4)CC2)c(=O)n3CCCCCCCN2CCC(CC2)C(F)(F)c2cccc1c2F] | (4R)-3$^2$,2,2-trifluoro-4-methyl-6$^6$-(4-(tetrahydro-2H-pyran-4-yl)piperazin-1-yl)-6$^7$,68-dihydro-5-aza-6(4,8)-pyrido[2,3-d]pyrimidina-1(4,1)-piperidina-3(1,3)-benzenacyclotridecaphan-6$^7$-one | 682.5 |

TABLE 1-continued

| No. | Structure | Chemical Name | [M + H]+ |
|---|---|---|---|
| 20 | 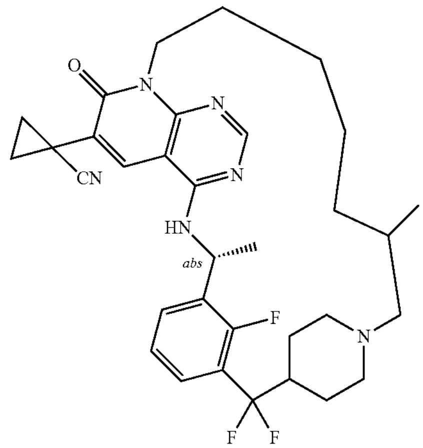 [SMILES: CC1CCCCCn2c(=O)c(C3(C#N)CC3)cc3c(ncnc32)N[C@H](C)c2cccc(c2F)C(F)(F)C2CCN(CC2)C1] | 1-((4R)-3²,2,2-trifluoro-4,12-dimethyl-6⁷-oxo-6⁷,6⁸-dihydro-5-aza-6(4,8)-pyrido[2,3-d]pyrimidina-1(4,1)-piperidina-3(1,3)-benzenacyclotridecaphane-6⁶-yl)cyclopropane-1-carbonitrile | 593.4 |
| 21 | 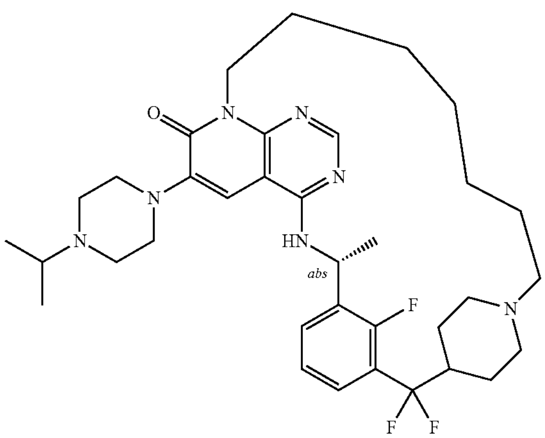 [SMILES: CC(C)N1CCN(c2cc3c4ncnc3n(c2=O)CCCCCCCN2CCC(CC2)C(F)(F)c2cccc(c2F)[C@@H](C)N4)CC1] | (4R)-3²,2,2-trifluoro-6⁶-(4-isopropylpiperazin-1-yl)-4-methyl-6⁷,6⁸-dihydro-5-aza-6(4,8)-pyrido[2,3-d]pyrimidina-1(4,1)-piperidina-3(1,3)-benzenacyclotridecaphan-6⁷-one | 640.3 |
| 22 | 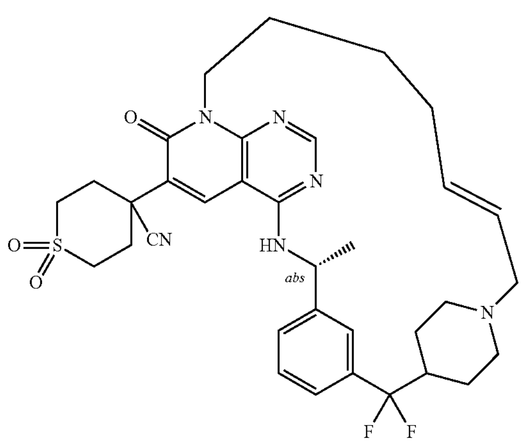 [SMILES: C[C@H]1Nc2ncnc3c2cc(C2(C#N)CCS(=O)(=O)CC2)c(=O)n3CCCC/C=C/CN2CCC(CC2)C(F)(F)c2cccc1c2] | 4-((4R,E)-2,2-difluoro-4-methyl-6⁷-oxo-6⁷,6⁸-dihydro-5-aza-6(4,8)-pyrido[2,3-d]pyrimidina-1(4,1)-piperidina-3(1,3)-benzenacyclotridecaphan-11-en-6⁶-yl)tetrahydro-2H-thiopyran-4-carbonitrile 1,1-dioxide | 651.3 |

TABLE 1-continued

| No. | Structure | Chemical Name | [M + H]+ |
|---|---|---|---|
| 23 | 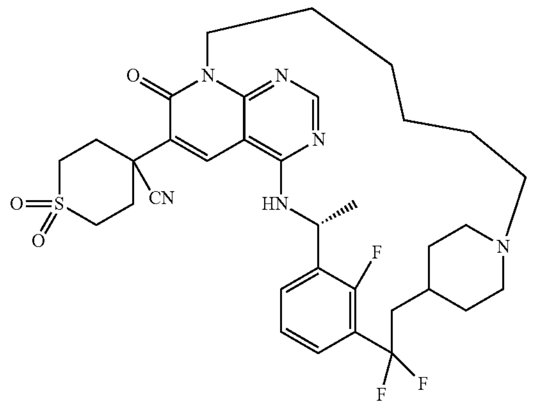 [SMILES: C[C@H]1Nc2ncnc3c2cc(C2(C#N)CCS(=O)(=O)CC2)c(=O)n3CCCCCCN2CCC(CC2)CC(F)(F)c2cccc1c2F] | 4-((3R)-4$^2$,5,5-trifluoro-3-methyl-1$^7$-oxo-1$^7$,1$^8$-dihydro-2-aza-1(4,8)-pyrido[2,3-d]pyrimidina-7(4,1)-piperidina-4(1,3)-benzenacyclotridecaphane-1$^6$-yl)tetrahydro-2H-thiopyran-4-carbonitrile 1,1-dioxide | 671.3 |
| 24 | 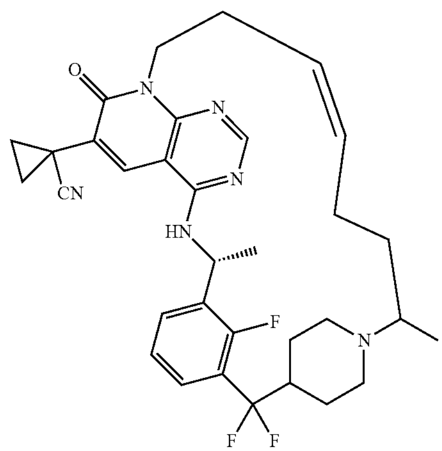 [SMILES: CC1CC/C=C\CCn2c(=O)c(C3(C#N)CC3)cc3c(ncnc32)N[C@H](C)c2cccc(c2F)C(F)(F)C2CCN1CC2] | 1-((4R,Z)-3$^2$,2,2-trifluoro-4,13-dimethyl-6$^7$-oxo-6$^7$,6$^8$-dihydro-5-aza-6(4,8)-pyrido[2,3-d]pyrimidina-1(4,1)-piperidina-3(1,3)-benzenacyclotridecaphan-9-en-6$^6$-yl)cyclopropane-1-carbonitrile | 591.5 |
| 25 | 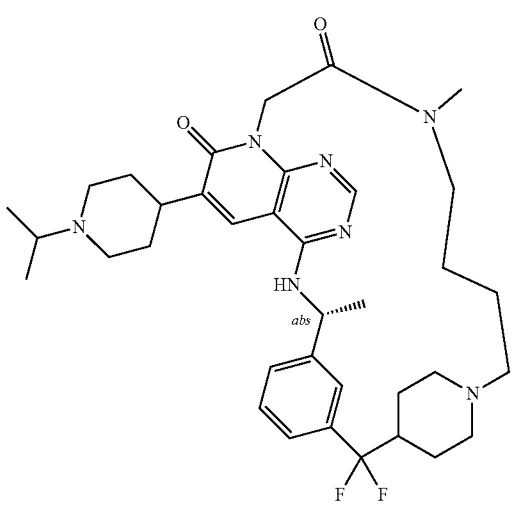 [SMILES: CC(C)N1CCC(c2cc3c4ncnc3n(c2=O)CC(=O)N(C)CCCCN2CCC(CC2)C(F)(F)c2cccc(c2)[C@@H](C)N4)CC1] | (4R)-2,2-difluoro-6$^6$-(1-isopropylpiperidin-4-yl)-4,9-dimethyl-6$^7$,6$^8$-dihydro-5,9-diaza-6(4,8)-pyrido[2,3-d]pyrimidina-1(4,1)-piperidina-3(1,3).benzenacyclotridecaphane-6$^7$,8-dione | 650.3 |

TABLE 1-continued

| No. | Structure | Chemical Name | [M + H]⁺ |
|---|---|---|---|
| 26 | 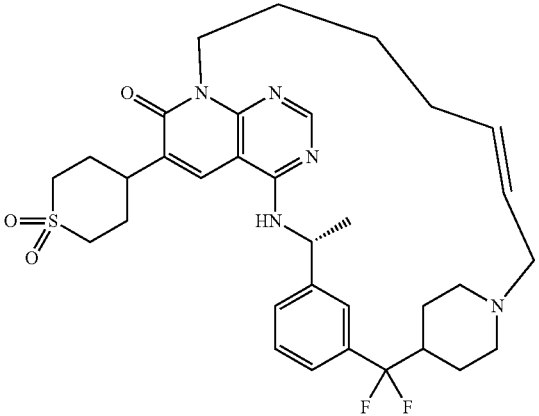 [SMILES: C[C@H]1Nc2ncnc3c2cc(C2CCS(=O)(=O)CC2)c(=O)n3CCCC/C=C/CN2CCC(CC2)C(F)(F)c2cccc1c2] | (4R,E)-6⁶-(1,1-dioxidotetrahydro-2H-thiopyran-4-yl)-2,2-difluoro-4-methyl-6⁷,6⁸-dihydro-5-aza-6(4,8)-pyrido[2,3-d]pyrimidina-1(4,1)-piperidina-3(1,3)-benzenacyclotridecaphan-11-en-6⁷-one | 626.4 |
| 27 | 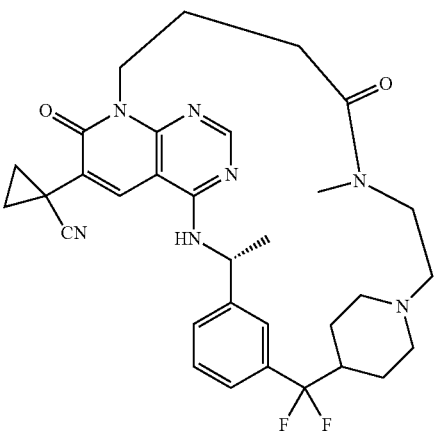 [SMILES: C[C@H]1Nc2ncnc3c2cc(C2(C#N)CC2)c(=O)n3CCCC(=O)N(C)CCN2CCC(CC2)C(F)(F)c2cccc1c2] | 1-((4R)-2,2-difluoro-4,11-dimethyl-6⁷,10-dioxo-6⁷,6⁸-dihydro-5,11-diaza-6(4,8)-pyrido[2,3-d]pyrimidina-1(4,1)-piperidina-3(1,3)-benzenacyclotridecaphane-6⁶-yl)cyclopropane-1-carbonitrile | 590.3 |
| 28 | 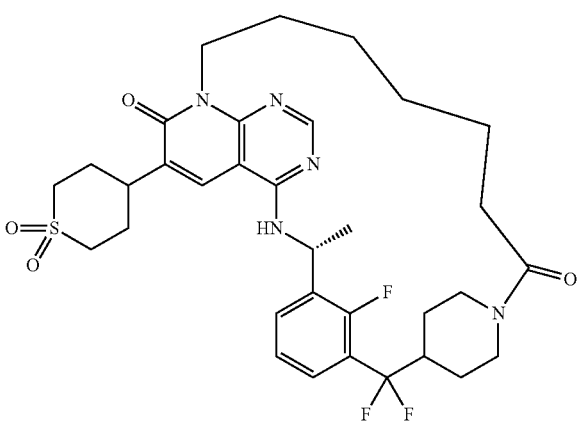 [SMILES: C[C@H]1Nc2ncnc3c2cc(C2CCS(=O)(=O)CC2)c(=O)n3CCCCCCC(=O)N2CCC(CC2)C(F)(F)c2cccc1c2F] | (4R)-6⁶-(1,1-dioxidotetrahydro-2H-thiopyran-4-yl)-3²,2,2-trifluoro-4-methyl-6⁷,6⁸-dihydro-5-aza-6(4,8)-pyrido[2,3-d]pyrimidina-1(4,1)-piperidina-3(1,3)-benzenacyclotridecaphane-6⁷,13-dione | 660.2 |

TABLE 1-continued

| No. | Structure | Chemical Name | [M + H]+ |
|---|---|---|---|
| 29 | 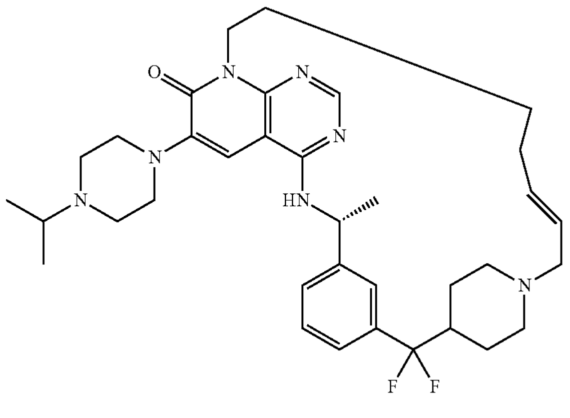 [SMILES: CC(C)N1CCN(c2cc3c4ncnc3n(c2=O)CCCC/C=C/CN2CCC(CC2)C(F)(F)c2cccc(c2)[C@@H](C)N4)CC1] | (4R,E)-2,2-difluoro-6⁶-(4-isopropylpiperazin-1-yl)-4-methyl-6⁷,6⁸-dihydro-5-aza-6(4,8)-pyrido[2,3-d]pyrimidina-1(4,1)-piperidina-3(1,3)-benzenacyclotridecaphan-11-en-6⁷-one | 620.3 |
| 30 | 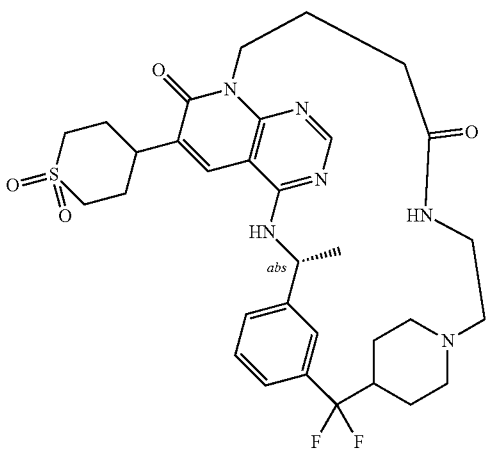 [SMILES: C[C@H]1Nc2ncnc3c2cc(C2CCS(=O)(=O)CC2)c(=O)n3CCCC(=O)NCCN2CCC(CC2)C(F)(F)c2cccc1c2] | (4R)-6⁶-(1,1-dioxidotetrahydro-2H-thiopyran-4-yl)-2,2-difluoro-4-methyl-6⁷,6⁸-dihydro-5,11-diaza-6(4,8)-pyrido[2,3-d]pyrimidina-1(4,1)-piperidina-3(1,3)-benzenacyclotridecaphane-6⁷,10-dione | 643.4 |
| 31 | 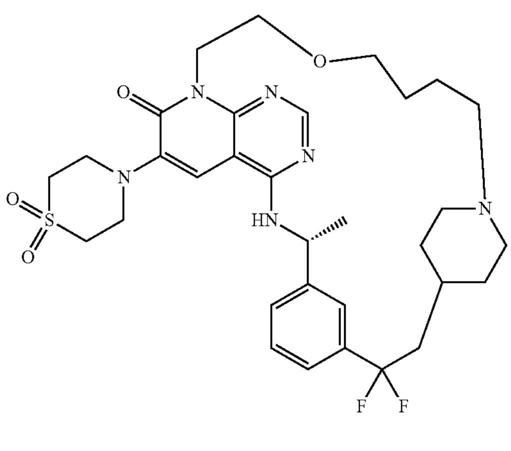 [SMILES: C[C@H]1Nc2ncnc3c2cc(N2CCS(=O)(=O)CC2)c(=O)n3CCOCCCCN2CCC(CC2)CC(F)(F)c2cccc1c2] | (3R)-1⁶-(1,1-dioxidotetrahydro-2H-thiopyran-4-yl)-5,5-difluoro-3-methyl-1⁷,1⁸-dihydro-12-oxa-2-aza-1(4,8)-pyrido[2,3-d]pyrimidina-7(4,1)-piperidina-4(1,3)-benzenacyclotetradecaphan-1⁷-one | 664.5 |

TABLE 1-continued

| No. | Structure | Chemical Name | [M + H]+ |
|---|---|---|---|
| 32 | 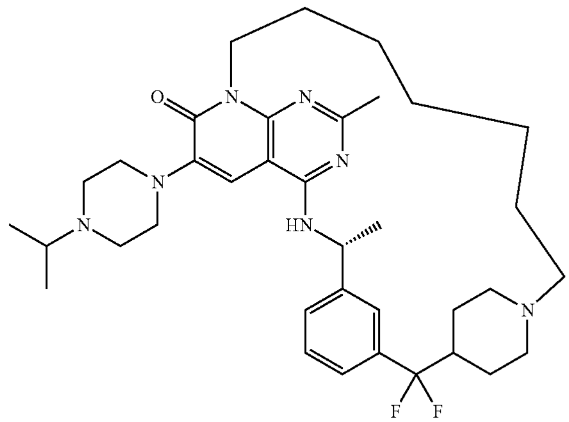 [SMILES: Cc1nc2c3cc(N4CCN(C(C)C)CC4)c(=O)n(c3n1)CCCCCCCN1CCC(CC1)C(F)(F)c1cccc(c1)[C@@H](C)N2] | (4R)-2,2-difluoro-6⁶-(1-isopropylpiperidin-4-yl)-6²,4-dimethyl-6⁷,6⁸-dihydro-5-aza-6(4,8)-pyrido[2,3-d]pyrimidina-1(4,1)-piperidina-3(1,3)-benzenacyclotridecaphan-6⁷-one | 635.6 |
| 33 | 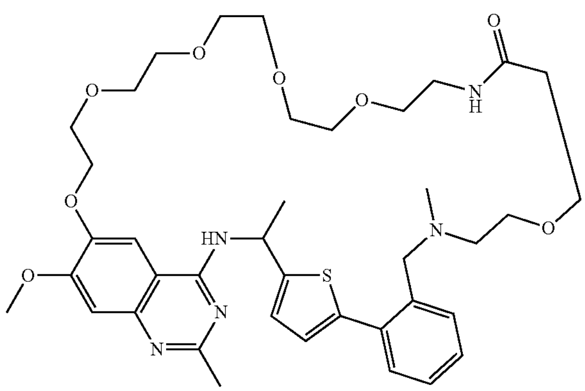 [SMILES: COc1cc2nc(C)nc3c2cc1OCCOCCOCCOCCOCCNC(=O)CCOCCN(C)Cc1ccccc1-c1ccc(s1)C(C)N3] | 5⁷-methoxy-5²,3,28-trimethyl-6,9,12,15,18,25-hexaoxa-4,21,28-triaza-5(4,6)-quinazolina-2(2,5)-thiophena-1(1,2)-benzenacyclononacosaphan-22-one | 752.4 |
| 34 | 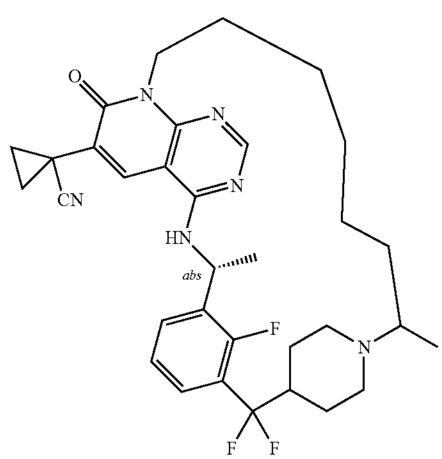 [SMILES: CC1CCCCCCn2c(=O)c(C3(C#N)CC3)cc3c(ncnc32)N[C@H](C)c2cccc(c2F)C(F)(F)C2CCN1CC2] | 1-((4R)-3²,2,2-trifluoro-4,13-dimethyl-6⁷-oxo-6⁷,6⁸-dihydro-5-aza-6(4,8)-pyrido[2,3-d]pyrimidina-1(4,1)-piperidina-3(1,3)-benzenacyclotridecaphane-6⁶-yl)cyclopropane-1-carbonitrile | 593.4 |

TABLE 1-continued

| No. | Structure | Chemical Name | [M + H]+ |
| --- | --- | --- | --- |
| 35 | 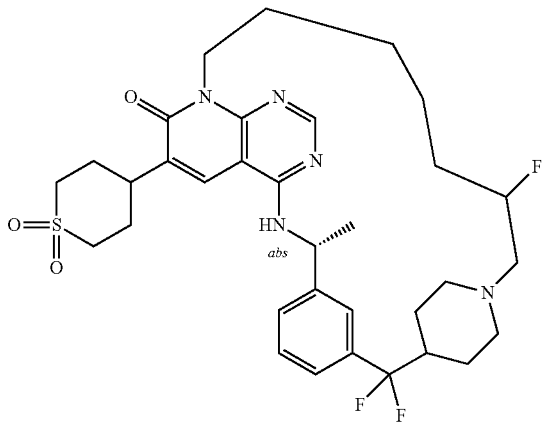 [SMILES: C[C@H]1Nc2ncnc3c2cc(C2CCS(=O)(=O)CC2)c(=O)n3CCCCCC(F)CN2CCC(CC2)C(F)(F)c2cccc1c2] | (4R)-6⁶-(1,1-dioxidotetrahydro-2H-thiopyran-4-yl)-2,2,12-trifluoro-4-methyl-6⁷,6⁸-dihydro-5-aza-6(4,8)-pyrido[2,3-d]pyrimidina-1(4,1)-piperidina-3(1,3)-benzenacyclotridecaphan-6⁷-one | 646.4 |
| 36 | 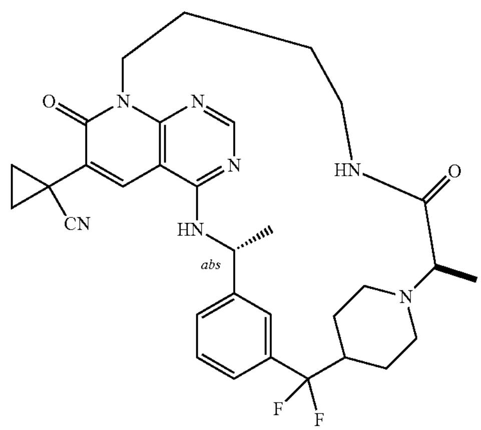 [SMILES: C[C@@H]1C(=O)NCCCCn2c(=O)c(C3(C#N)CC3)cc3c(ncnc32)N[C@H](C)c2cccc(c2)C(F)(F)C2CCN1CC2] | 1-((4R,13R)-2,2-difluoro-4,13-dimethyl-6⁷,12-dioxo-6⁷,6⁸-dihydro-5,11-diaza-6(4,8)-pyrido[2,3-d]pyrimidina-1(4,1)-piperidina-3(1,3)-benzenacyclotridecaphane-6⁶-yl)cyclopropane-1-carbonitrile | 590.3 |
| 37 | 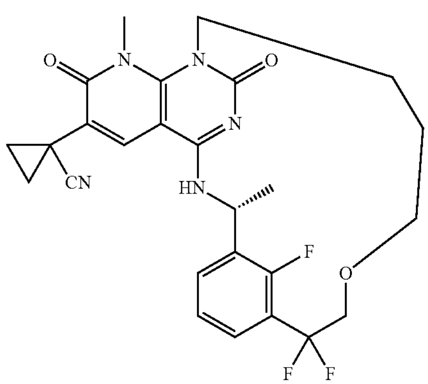 [SMILES: C[C@H]1Nc2nc(=O)n(c3c2cc(C2(C#N)CC2)c(=O)n3C)CCCCOCC(F)(F)c2cccc1c2F] | 1-((3R,E)-4²,5,5-trifluoro-1⁸,3-dimethyl-1²,1⁷-dioxo-1¹,1²,1⁷,1⁸-tetrahydro-7-oxa-2-aza-1(4,1)-pyrido[2,3-d]pyrimidina-4(1,3)-benzenacycloundecaphane-1⁶-yl)cyclopropane-1-carbonitrile | 514.3 |

TABLE 1-continued

| No. | Structure | Chemical Name | [M + H]+ |
|---|---|---|---|
| 38 | 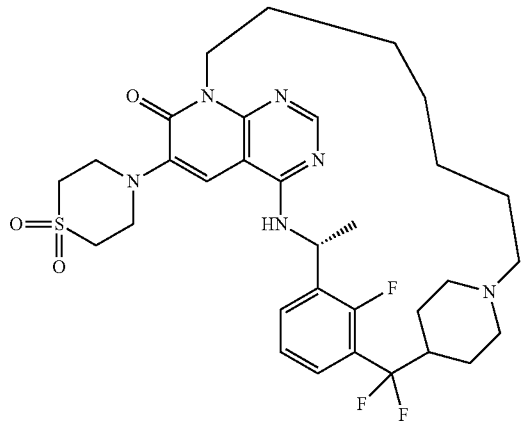 [SMILES: C[C@H]1Nc2ncnc3c2cc(N2CCS(=O)(=O)CC2)c(=O)n3CCCCCCCN2CCC(CC2)C(F)(F)c2cccc1c2F] | (4R)-6⁶-(1,1-dioxidothiomorpholino)-3²,2,2-trifluoro-4-methyl-6⁷,6⁸-dihydro-5-aza-6(4,8)-pyrido[2,3-d]pyrimidina-1(4,1)-piperidina-3(1,3)-benzenacyclotridecaphan-6⁷-one | 647.6 |
| 39 | 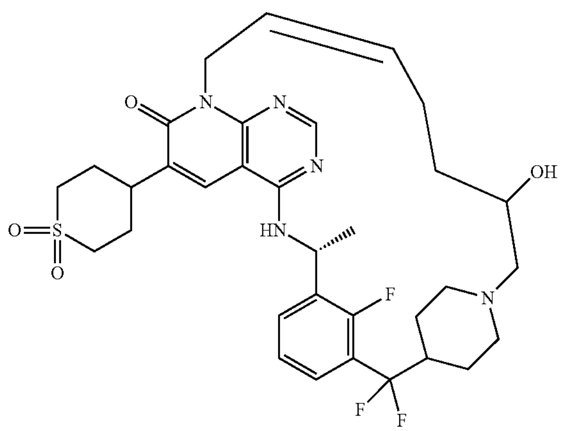 [SMILES: C[C@H]1Nc2ncnc3c2cc(C2CCS(=O)(=O)CC2)c(=O)n3C/C=C\CCC(O)CN2CCC(CC2)C(F)(F)c2cccc1c2F] | (4R,Z)-6⁶-(1,1-dioxidotetrahydro-2H-thiopyran-4-yl)-3²,2,2-trifluoro-12-hydroxy-4-methyl-6⁷,6⁸-dihydro-5-aza-6(4,8)-pyrido[2,3-d]pyrimidina-1(4,1)-piperidina-3(1,3)-benzenacyclotridecaphan-8-en-6⁷-one | 660.4 |
| 40 | 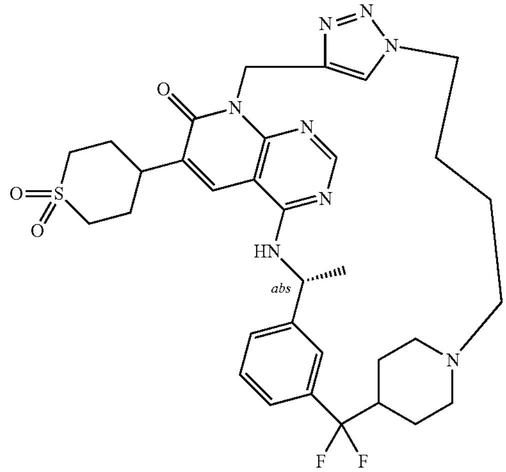 [SMILES: C[C@H]1Nc2ncnc3c2cc(C2CCS(=O)(=O)CC2)c(=O)n3Cc2cn(nn2)CCCCN2CCC(CC2)C(F)(F)c2cccc1c2] | (5R,Z)-3⁶-(1,1-dioxidotetrahydro-2H-thiopyran-4-yl)-7,7-difluoro-5-methyl-3⁷,3⁸-dihydro-1¹H-4-aza-3(8,4)-pyrido[2,3-d]pyrimidina-8(4,1)-piperidina-1(4,1)-triazola-6(1,3)-benzenacyclododecaphan-3⁷-one | 667.3 |

TABLE 1-continued

| No. | Structure | Chemical Name | [M + H]+ |
|---|---|---|---|
| 41 | 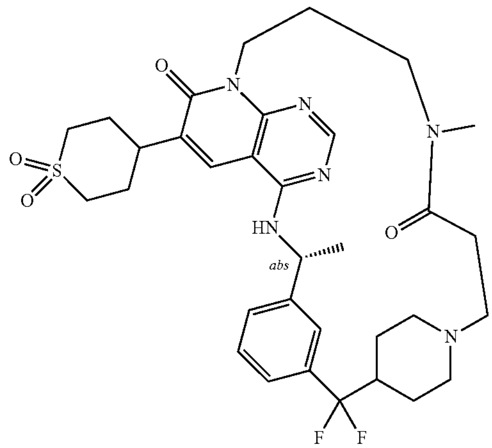 [SMILES: C[C@H]1Nc2ncnc3c2cc(C2CCS(=O)(=O)CC2)c(=O)n3CCCN(C)C(=O)CCN2CCC(CC2)C(F)(F)c2cccc1c2] | (4R)-6⁶-(1,1-dioxidotetrahydro-2H-thiopyran-4-yl)-2,2-difluoro-4,10-dimethyl-6⁷,6⁸-dihydro-5,10-diaza-6(4,8)-pyrido[2,3-d]pyrimidina-1(4,1)-piperidina-3(1,3)-benzenacyclotridecaphane-6⁷,11-dione | 657.4 |
| 42 | 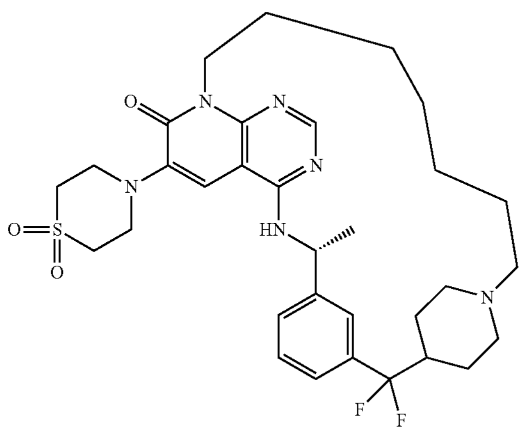 [SMILES: C[C@H]1Nc2ncnc3c2cc(N2CCS(=O)(=O)CC2)c(=O)n3CCCCCCCN2CCC(CC2)C(F)(F)c2cccc1c2] | (4R)-6⁶-(1,1-dioxidothiomorpholino)-2,2-difluoro-4-methyl-6⁷,6⁸-dihydro-5-aza-6(4,8)-pyrido[2,3-d]pyrimidina-1(4,1)-piperidina-3(1,3)-benzenacyclotridecaphan-6⁷-one | 629.3 |
| 43 | 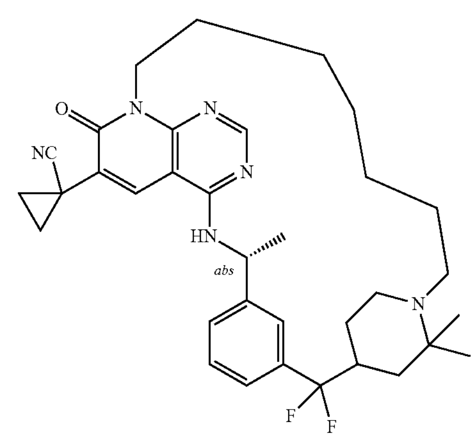 [SMILES: C[C@H]1Nc2ncnc3c2cc(C2(C#N)CC2)c(=O)n3CCCCCCCN2CCC(CC2(C)C)C(F)(F)c2cccc1c2] | 1-((4R)-2,2-difluoro-1²,1²,4-trimethyl-6⁷-oxo-6⁷,6⁸-dihydro-5-aza-6(4,8)-pyrido[2,3-d]pyrimidina-1(4,1)-piperidina-3(1,3)-benzenacyclotridecaphane-6⁶-yl)cyclopropane-1-carbonitrile | 589.3 |

TABLE 1-continued

| No. | Structure | Chemical Name | [M + H]+ |
|---|---|---|---|
| 44 | 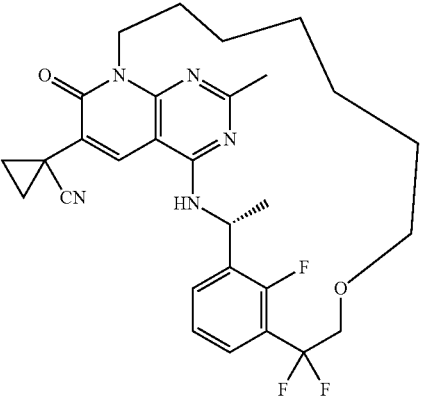 [SMILES: Cc1nc2c3cc(C4(C#N)CC4)c(=O)n(c3n1)CCCCCCCOCC(F)(F)c1cccc(c1F)[C@@H](C)N2] | 1-((3R)-4²,5,5-trifluoro-1²,3-dimethyl-1⁷-oxo-1⁷,1⁸-dihydro-7-oxa-2-aza-1(4,8)-pyrido[2,3-d]pyrimidina-4(1,3)-benzenacyclotetradecaphane-1⁶-yl)cyclopropane-1-carbonitrile | 540.4 |
| 45 | 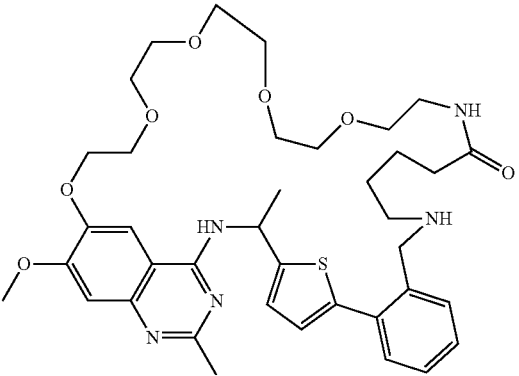 [SMILES: COc1cc2nc(C)nc3c2cc1OCCOCCOCCOCCOCCNC(=O)CCCCNCc1ccccc1-c1ccc(s1)C(C)N3] | 5⁷-methoxy-5²,3-dimethyl-6,9,12,15,18-pentaoxa-4,21,27-triaza-5(4,6)-quinazolina-2(2,5)-thiophena-1(1,2)-benzenacyclooctacosaphan-22-one | 722.4 |
| 46 | 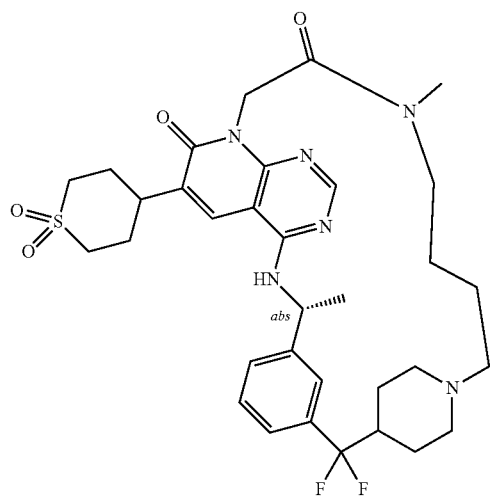 [SMILES: C[C@H]1Nc2ncnc3c2cc(C2CCS(=O)(=O)CC2)c(=O)n3CC(=O)N(C)CCCCN2CCC(CC2)C(F)(F)c2cccc1c2] | (4R)-6⁶-(1,1-dioxidotetrahydro-2H-thiopyran-4-yl)-2,2-difluoro-4,9-dimethyl-6⁷,6⁸-dihydro-5,9-diaza-6(4,8)-pyrido[2,3-d]pyrimidina-1(4,1)-piperidina-3(1,3)-benzenacyclotridecaphane-6⁷,8-dione | 657.3 |

TABLE 1-continued

| No. | Structure | Chemical Name | [M + H]$^+$ |
|---|---|---|---|
| 47 | 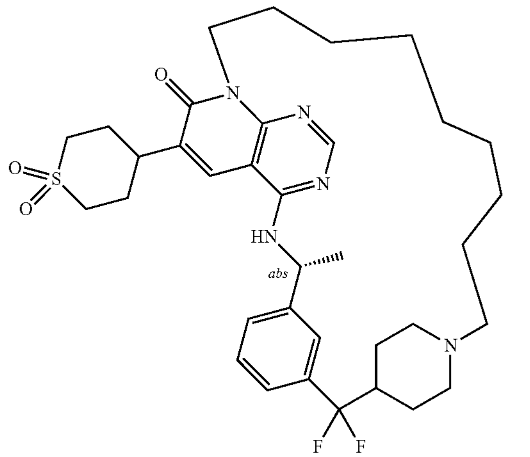 [SMILES: C[C@H]1Nc2ncnc3c2cc(C2CCS(=O)(=O)CC2)c(=O)n3CCCCCCCCCN2CCC(CC2)C(F)(F)c2cccc1c2] | (4R)-6$^6$-(1,1-dioxidotetrahydro-2H-thiopyran-4-yl)-2,2-difluoro-4-methyl-6$^7$,6$^8$-dihydro-5-aza-6(4,8)-pyrido[2,3-d]pyrimidina-1(4,1)-piperidina-3(1,3)-benzenacyclopentadecaphan-6$^7$-one | 656.3 |
| 48 | 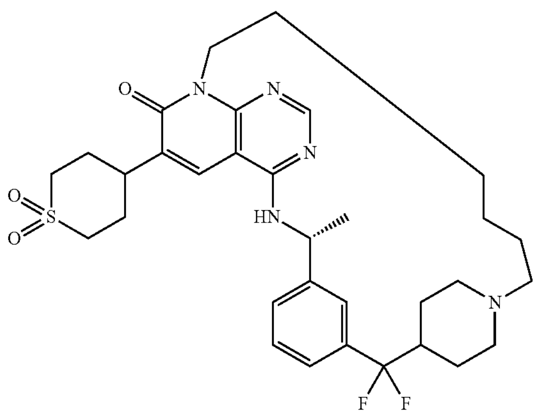 [SMILES: C[C@H]1Nc2ncnc3c2cc(C2CCS(=O)(=O)CC2)c(=O)n3CCCCCCN2CCC(CC2)C(F)(F)c2cccc1c2] | (4R)-6$^6$-(1,1-dioxidotetrahydro-2H-thiopyran-4-yl)-2,2-difluoro-4-methyl-6$^7$,6$^8$-dihydro-5-aza-6(4,8)-pyrido[2,3-d]pyrimidina-1(4,1)-piperidina-3(1,3)-benzenacyclododecaphan-6$^7$-one | 614.4 |
| 49 | 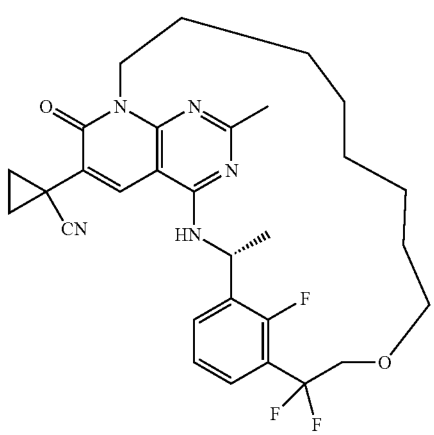 [SMILES: Cc1nc2c3cc(C4(C#N)CC4)c(=O)n(c3n1)CCCCCCCCOCC(F)(F)c1cccc(c1F)[C@@H](C)N2] | 1-((3R)-4$^2$,5,5-trifluoro-1$^2$,3-dimethyl-1$^7$-oxo-1$^7$,1$^8$-dihydro-7-oxa-2-aza-1(4,8)-pyrido[2,3-d]pyrimidina-4(1,3)-benzenacyclopentadecaphane-1$^6$-yl)cyclopropane-1-carbonitrile | 554.3 |

TABLE 1-continued

| No. | Structure | Chemical Name | [M + H]+ |
|---|---|---|---|
| 50 | 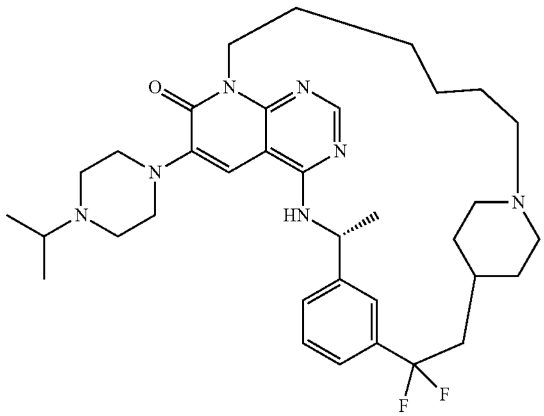 [SMILES: CC(C)N1CCN(c2cc3c4ncnc3n(c2=O)CCCCCCN2CCC(CC2)CC(F)(F)c2cccc(c2)[C@@H](C)N4)CC1] | (3R)-5,5-difluoro-1⁶-(4-isopropylpiperazin-1-yl)-3-methyl-1⁷,1⁸-dihydro-2-aza-1(4,8)-pyrido[2,3-d]pyrimidina-7(4,1)-piperidina-4(1,3)-benzenacyclotridecaphan-1⁷-one | 622.4 |
| 51 | 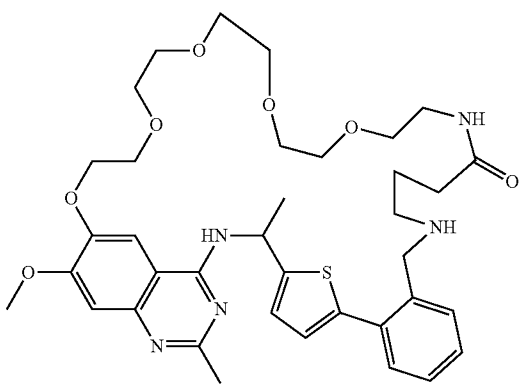 [SMILES: COc1cc2nc(C)nc3c2cc1OCCOCCOCCOCCOCCNC(=O)CCCNCc1ccccc1-c1ccc(s1)C(C)N3] | 5⁷-methoxy-5²,3-dimethyl-6,9,12,15,18-pentaoxa-4,21,26-triaza-5(4,6)-quinazolina-2(2,5)-thiophena-1(1,2)-benzenacycloheptacosaphan-22-one | 708.3 |
| 52 | 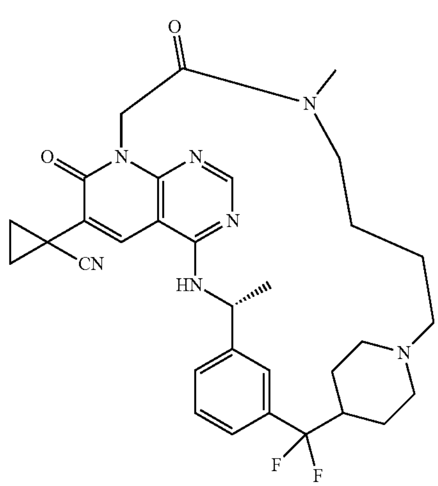 [SMILES: C[C@H]1Nc2ncnc3c2cc(C2(C#N)CC2)c(=O)n3CC(=O)N(C)CCCCN2CCC(CC2)C(F)(F)c2cccc1c2] | 1-((4R)-2,2-difluoro-4,9-dimethyl-6⁷,8-dioxo-6⁷,6⁸-dihydro-5,9-diaza-6(4,8)-pyrido[2,3-d]pyrimidina-1(4,1)-piperidina-3(1,3)-benzenacyclotridecaphane-6⁶-yl)cyclopropane-1-carbonitrile | 590.3 |

TABLE 1-continued

| No. | Structure | Chemical Name | [M + H]+ |
|---|---|---|---|
| 53 | 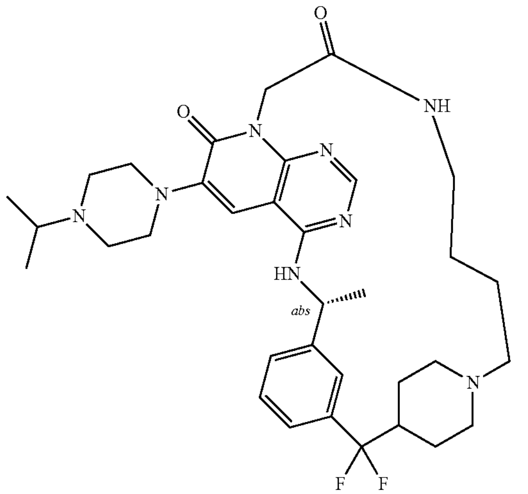 [SMILES: CC(C)N1CCN(c2cc3c4ncnc3n(c2=O)CC(=O)NCCCCN2CCC(CC2)C(F)(F)c2cccc(c2)[C@@H](C)N4)CC1] | (4R)-2,2-difluoro-6⁶-(4-isopropylpiperazin-1-yl)-4-methyl-6⁷,6⁸-dihydro-5,9-diaza-6(4,8)-pyrido[2,3-d]pyrimidina-1(4,1)-piperidina-3(1,3)-benzenacyclotridecaphane-6⁷,8-dione | 637.2 |
| 54 | 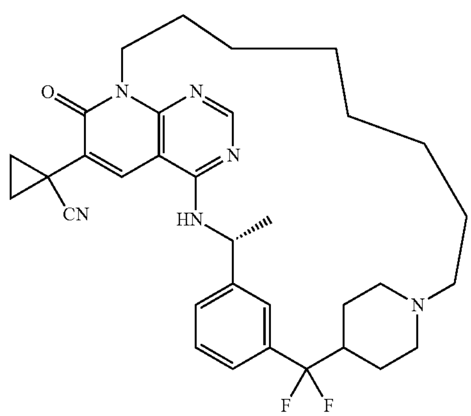 [SMILES: C[C@H]1Nc2ncnc3c2cc(C2(C#N)CC2)c(=O)n3CCCCCCCCN2CCC(CC2)C(F)(F)c2cccc1c2] | 1-((4R)-2,2-difluoro-4-methyl-6⁷-oxo-6⁷,6⁸-dihydro-5-aza-6(4,8)-pyrido[2,3-d]pyrimidina-1(4,1)-piperidina-3(1,3)-benzenacyclotetradecaphane-6⁶-yl)cyclopropane-1-carbonitrile | 575.4 |
| 55 | 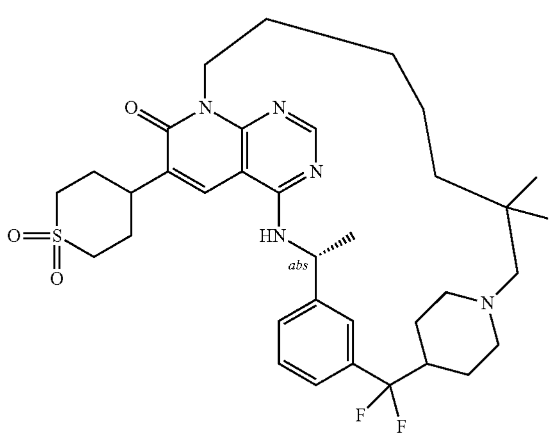 [SMILES: C[C@H]1Nc2ncnc3c2cc(C2CCS(=O)(=O)CC2)c(=O)n3CCCCCC(C)(C)CN2CCC(CC2)C(F)(F)c2cccc1c2] | (4R)-6⁶-(1,1-dioxidotetrahydro-2H-thiopyran-4-yl)-2,2-difluoro-4,12,12-trimethyl-6⁷,6⁸-dihydro-5-aza-6(4,8)-pyrido[2,3-d]pyrimidina-1(4,1)-piperidina-3(1,3)-benzenacyclotridecaphan-6⁷-one | 656.6 |

TABLE 1-continued

| No. | Structure | Chemical Name | [M + H]⁺ |
|---|---|---|---|
| 56 | 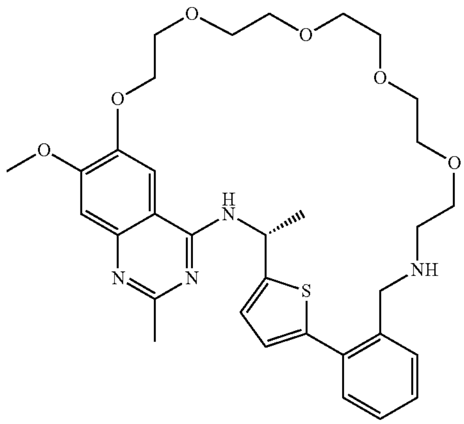 [SMILES: COc1cc2nc(C)nc3c2cc1OCCOCCOCCOCCOCCNCc1ccccc1C1=CC=C(S1)[C@@H](C)N3] | (R)-5⁷-methoxy-5²,3-dimethyl-6,9,12,15,18-pentaoxa-4,21-diaza-5(4,6)-quinazolina-2(2,5)-thiophena-1(1,2)-benzenacyclodocosaphane | 623.2 |
| 57 | 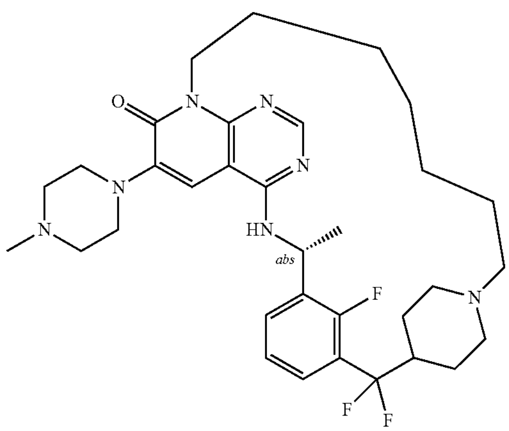 [SMILES: C[C@H]1Nc2ncnc3c2cc(N2CCN(C)CC2)c(=O)n3CCCCCCCN2CCC(CC2)C(F)(F)c2cccc1c2F] | (4R)-3²,2,2-trifluoro-4-methyl-6⁶-(4-methylpiperazin-1-yl)-6⁷,6⁸-dihydro-5-aza-6(4,8)-pyrido[2,3-d]pyrimidina-1(4,1)-piperidina-3(1,3)-benzenacyclotridecaphan-6⁷-one | 612.3 |
| 58 | 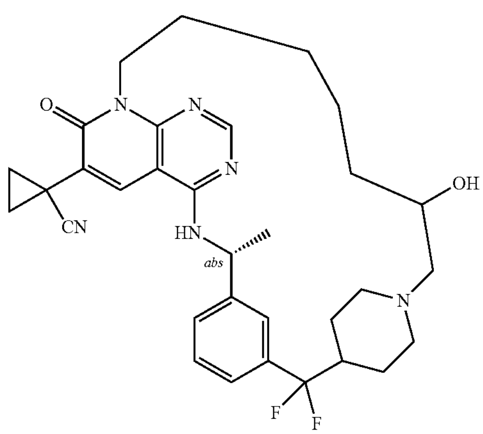 [SMILES: C[C@H]1Nc2ncnc3c2cc(C2(C#N)CC2)c(=O)n3CCCCCC(O)CN2CCC(CC2)C(F)(F)c2cccc1c2] | 1-((4R)-2,2-difluoro-12-hydroxy-4-methyl-6⁷-oxo-6⁷,6⁸-dihydro-5-aza-6(4,8)-pyrido[2,3-d]pyrimidina-1(4,1)-piperidina-3(1,3)-benzenacyclotridecaphane-6⁶-yl)cyclopropane-1-carbonitrile | 577.3 |
| 59 | 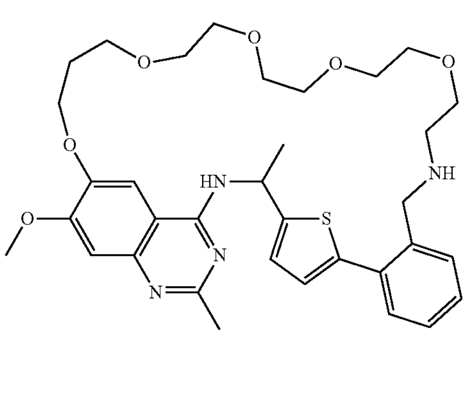 [SMILES: COc1cc2nc(C)nc3c2cc1OCCCOCCOCCOCCOCCNCc1ccccc1-c1ccc(s1)C(C)N3] | 5⁷-methoxy-5²,3-dimethyl-6,10,13,16,19-pentaoxa-4,22-diaza-5(4,6)-quinazolina-2(2,5)-thiophena-1(1,2)-benzenacyclotricosaphane | 637.3 |

TABLE 1-continued

| No. | Structure | Chemical Name | [M + H]+ |
|---|---|---|---|
| 60 | 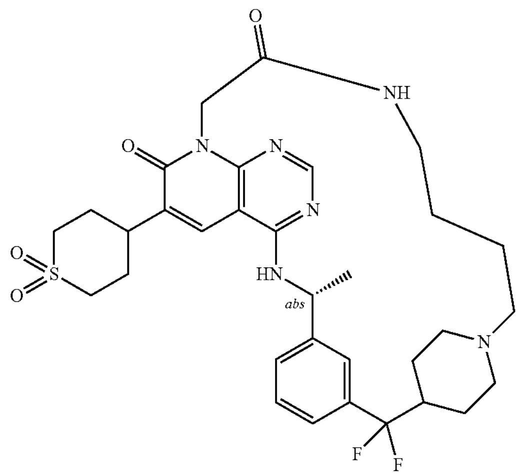 [SMILES: C[C@H]1Nc2ncnc3c2cc(C2CCS(=O)(=O)CC2)c(=O)n3CC(=O)NCCCCN2CCC(CC2)C(F)(F)c2cccc1c2] | (4R)-6⁶-(1,1-dioxidotetrahydro-2H-thiopyran-4-yl)-2,2-difluoro-4-methyl-6⁷,6⁸-dihydro-5,9-diaza-6(4,8)-pyrido[2,3-d]pyrimidina-1(4,1)-piperidina-3(1,3)-benzenacyclotridecaphane-6⁷,8-dione | 643.3 |
| 61 | 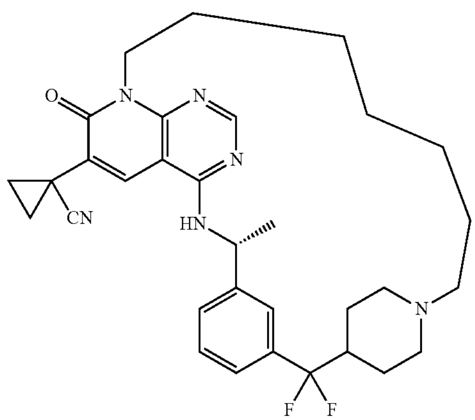 [SMILES: C[C@H]1Nc2ncnc3c2cc(C2(C#N)CC2)c(=O)n3CCCCCCCN2CCC(CC2)C(F)(F)c2cccc1c2] | 1-((4R)-2,2-difluoro-4-methyl-6⁷-oxo-6⁷,6⁸-dihydro-5-aza-6(4,8)-pyrido[2,3-d]pyrimidina-1(4,1)-piperidina-3(1,3)-benzenacyclotridecaphane-6⁶-yl)cyclopropane-1-carbonitrile | 561.5 |
| 62 | 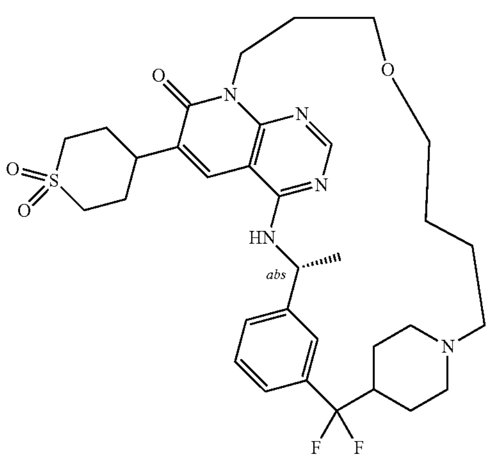 [SMILES: C[C@H]1Nc2ncnc3c2cc(C2CCS(=O)(=O)CC2)c(=O)n3CCCOCCCCN2CCC(CC2)C(F)(F)c2cccc1c2] | (4R)-66-(1,1-dioxidotetrahydro-2H-thiopyran-4-yl)-2,2-difluoro-4-methyl-67,68-dihydro-10-oxa-5-aza-6(4,8)-pyrido[2,3-d]pyrimidina-1(4,1)-piperidina-3(1,3)-benzenacyclotetradecaphan-6⁷-one | 644.5 |

TABLE 1-continued

| No. | Structure | Chemical Name | [M + H]+ |
|---|---|---|---|
| 63 | 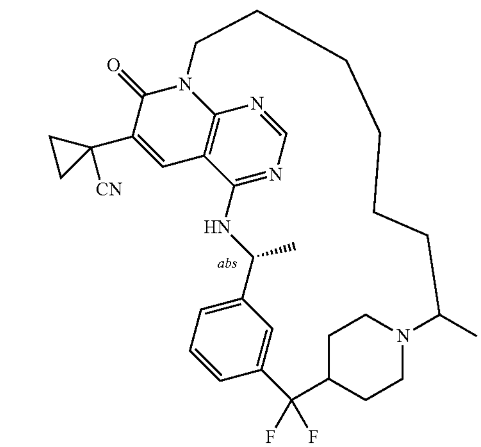 [SMILES: CC1CCCCCCn2c(=O)c(C3(C#N)CC3)cc3c(ncnc32)N[C@H](C)c2cccc(c2)C(F)(F)C2CCN1CC2] | 1-((4R)-2,2-difluoro-4,13-dimethyl-6$^7$-oxo-6$^7$,6$^8$-dihydro-5-aza-6(4,8)-pyrido[2,3-d]pyrimidina-1(4,1)-piperidina-3(1,3)-benzenacyclotridecaphane-6$^6$-yl)cyclopropane-1-carbonitrile | 575.3 |
| 64 | 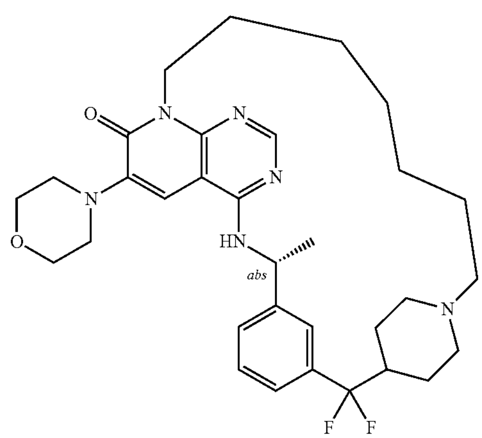 [SMILES: C[C@H]1Nc2ncnc3c2cc(N2CCOCC2)c(=O)n3CCCCCCCN2CCC(CC2)C(F)(F)c2cccc1c2] | (4R)-2,2-difluoro-4-methyl-6$^6$-morpholino-6$^7$,6$^8$-dihydro-5-aza-6(4,8)-pyrido[2,3-d]pyrimidina-1(4,1)-piperidina-3(1,3)-benzenacyclotridecaphan-6$^7$-one | 581.3 |
| 65 | 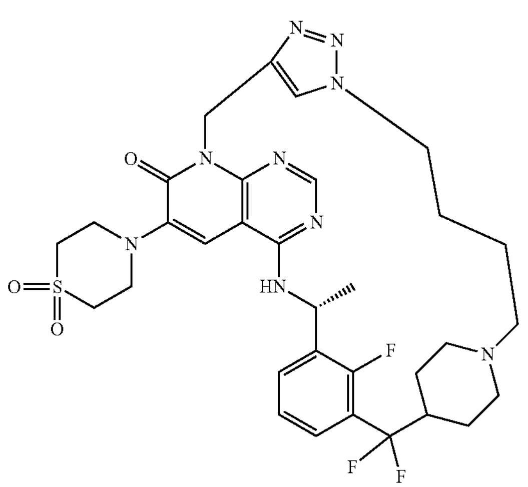 [SMILES: C[C@H]1Nc2ncnc3c2cc(N2CCS(=O)(=O)CC2)c(=O)n3Cc2cn(nn2)CCCCN2CCC(CC2)C(F)(F)c2cccc1c2F] | (5R,Z)-3$^6$-(1,1-dioxidothiomorpholino)-6$^2$,7,7-trifluoro-5-methyl-3$^7$,3$^8$-dihydro-1$^1$H-4-aza-3(8,4)-pyrido[2,3-d]pyrimidina-8(4,1)-piperidina-1(4,1)-triazola-6(1,3)-benzenacyclododecaphan-3$^7$-one | 686.2 |

| No. | Structure | Chemical Name | [M + H]+ |
|---|---|---|---|
| 66 | 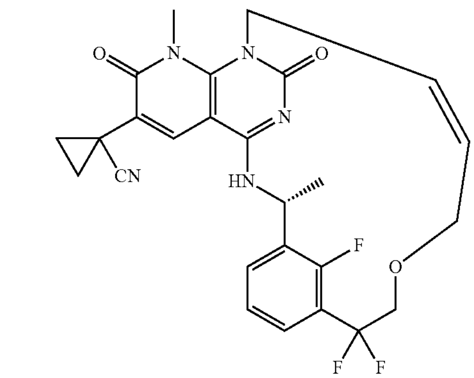 [SMILES: C[C@H]1Nc2nc(=O)n(c3c2cc(C2(C#N)CC2)c(=O)n3C)C/C=C\COCC(F)(F)c2cccc1c2F] | 1-((1³E,3R,9Z)-4²,5,5-trifluoro-1⁸,3-dimethyl-1²,1⁷-dioxo-1¹,1²,1⁷,1⁸-tetrahydro-7-oxa-2-aza-1(4,1)-pyrido[2,3-d]pyrimidina-4(1,3)-benzenacycloundecaphan-9-en-1⁶-yl)cyclopropane-1-carbonitrile | 512.3 |
| 67 | 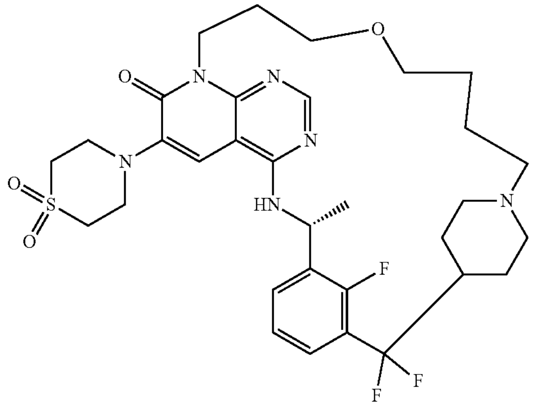 [SMILES: C[C@H]1Nc2ncnc3c2cc(N2CCS(=O)(=O)CC2)c(=O)n3CCCOCCCCN2CCC(CC2)C(F)(F)c2cccc1c2F] | (4R)-6⁶-(4-acetylpiperazin-1-yl)-3²,2,2-trifluoro-4-methyl-6⁷,6⁸-dihydro-5-aza-6(4,8)-pyrido[2,3-d]pyrimidina-1(4,1)-piperidina-3(1,3)-benzenacyclotridecaphan-6⁷-one | 640.4 |
| 68 | 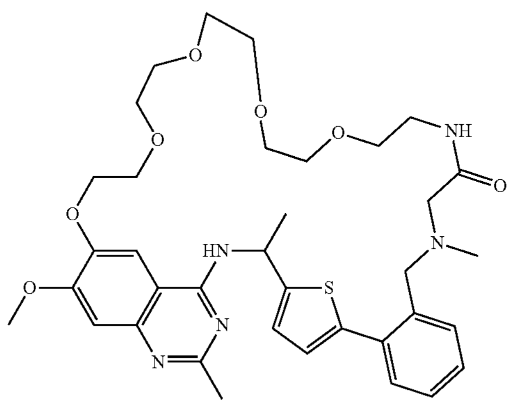 [SMILES: COc1cc2nc(C)nc3c2cc1OCCOCCOCCOCCOCCNC(=O)CN(C)Cc1ccccc1C1=CC=C(S1)C(C)N3] | 5⁷-methoxy-5²,3,24-trimethyl-6,9,12,15,18-pentaoxa-4,21,24-triaza-5(4,6)-quinazolina-2(2,5)-thiophena-1(1,2)-benzenacyclopentacosaphan-22-one | 694.3 |
| 69 | 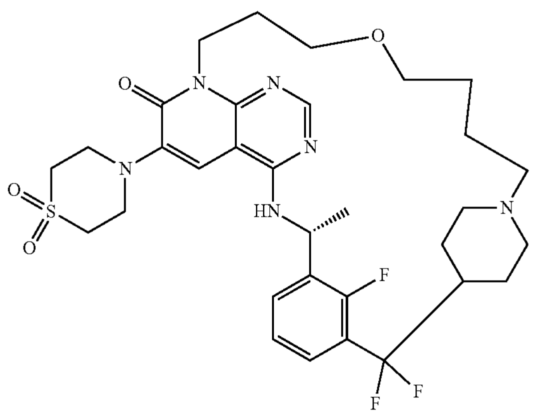 [SMILES: C[C@H]1Nc2ncnc3c2cc(N2CCS(=O)(=O)CC2)c(=O)n3CCCOCCCCN2CCC(CC2)C(F)(F)c2cccc1c2F] | (4R)-6⁶-(1,1-dioxidothiomorpholino)-3²,2,2-trifluoro-4-methyl-6⁷,6⁸-dihydro-10-oxa-5-aza-6(4,8)-pyrido[2,3-d]pyrimidina-1(4,1)-piperidina-3(1,3)-benzenacyclotetradecaphan-6⁷-one | 663.3 |

| No. | Structure | Chemical Name | [M + H]+ |
|---|---|---|---|
| 70 | 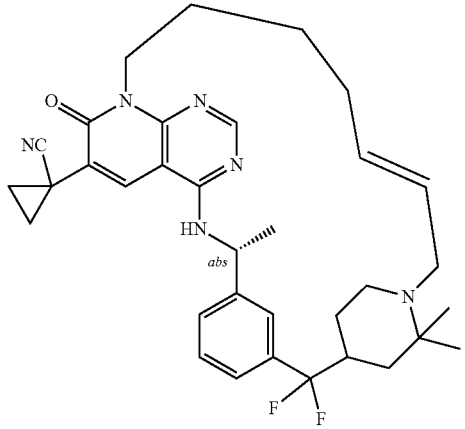 [SMILES: C[C@H]1Nc2ncnc3c2cc(C2(C#N)CC2)c(=O)n3CCCC/C=C/CN2CCC(CC2(C)C)C(F)(F)c2cccc1c2] | 1-((4R,E)-2,2-difluoro-1$^2$,1$^2$,4-trimethyl-6$^7$-oxo-6$^7$,6$^8$-dihydro-5-aza-6(4,8)-pyrido[2,3-d]pyrimidina-1(4,1)-piperidina-3(1,3)-benzenacyclotridecaphan-11-en-6$^6$-yl)cyclopropane-1-carbonitrile | 587.4 |
| 71 | 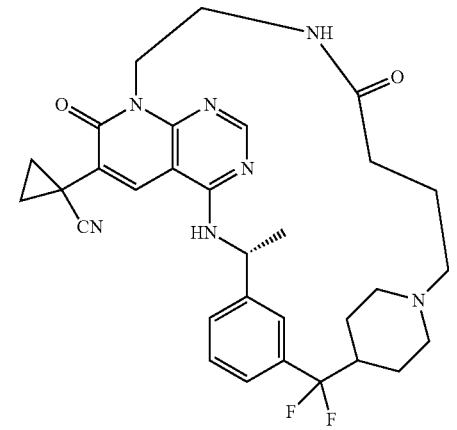 [SMILES: C[C@H]1Nc2ncnc3c2cc(C2(C#N)CC2)c(=O)n3CCNC(=O)CCCN2CCC(CC2)C(F)(F)c2cccc1c2] | 1-((4R)-2,2-difluoro-4-methyl-6$^7$,10-dioxo-6$^7$,6$^8$-dihydro-5,9-diaza-6(4,8)-pyrido[2,3-d]pyrimidina-1(4,1)-piperidina-3(1,3)-benzenacyclotridecaphane-6$^6$-yl)cyclopropane-1-carbonitrile | 576.3 |
| 72 | 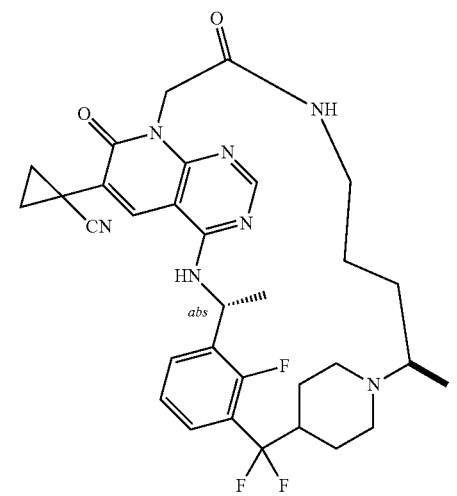 [SMILES: C[C@@H]1CCCNC(=O)Cn2c(=O)c(C3(C#N)CC3)cc3c(ncnc32)N[C@H](C)c2cccc(c2F)C(F)(F)C2CCN1CC2] | 1-((4R,13R)-3$^2$,2,2-trifluoro-4,13-dimethyl-6$^7$,8-dioxo-6$^7$,6$^8$-dihydro-5,9-diaza-6(4,8)-pyrido[2,3-d]pyrimidina-1(4,1)-piperidina-3(1,3)-benzenacyclotridecaphane-6$^6$-yl)cyclopropane-1-carbonitrile | 608.3 |

TABLE 1-continued

| No. | Structure | Chemical Name | [M + H]⁺ |
|---|---|---|---|
| 73 | 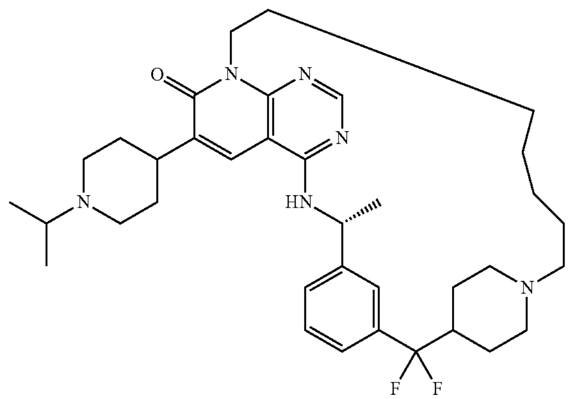 [SMILES: CC(C)N1CCC(c2cc3c4ncnc3n(c2=O)CCCCCCCN2CCC(CC2)C(F)(F)c2cccc(c2)[C@@H](C)N4)CC1] | (4R)-2,2-difluoro-6⁶-(1-isopropylpiperidin-4-yl)-4-methyl-6⁷,6⁸-dihydro-5-aza-6(4,8)-pyrido[2,3-d]pyrimidina-1(4,1)-piperidina-3(1,3)-benzenacyclotridecaphan-6⁷-one | 621.6 |
| 74 | 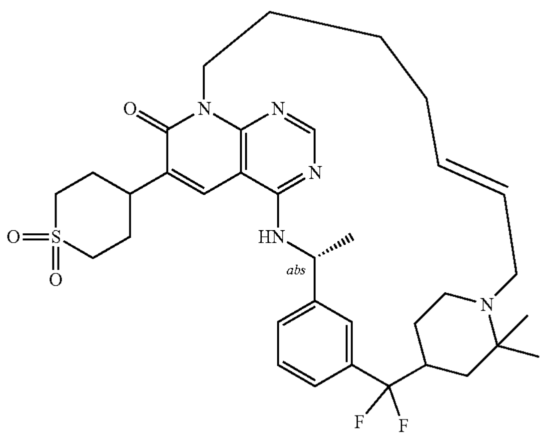 [SMILES: C[C@H]1Nc2ncnc3c2cc(C2CCS(=O)(=O)CC2)c(=O)n3CCCC/C=C/CN2CCC(CC2(C)C)C(F)(F)c2cccc1c2] | (4R,E)-6⁶-(1,1-dioxidotetrahydro-2H-thiopyran-4-yl)-2,2-difluoro-1²,1²,4-trimethyl-6⁷,6⁸-dihydro-5-aza-6(4,8)-pyrido[2,3-d]pyrimidina-1(4,1)-piperidina-3(1,3)-benzenacyclotridecaphan-11-en-6⁷-one | 654.3 |
| 75 | 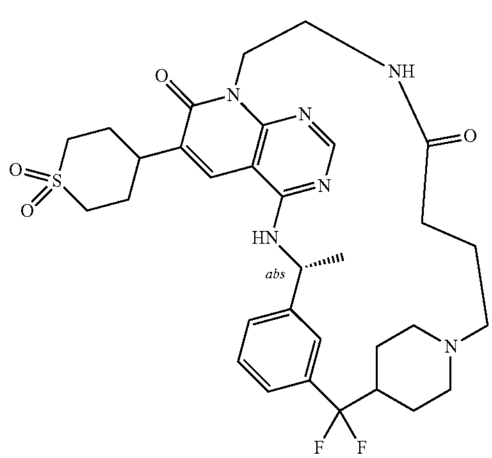 [SMILES: C[C@H]1Nc2ncnc3c2cc(C2CCS(=O)(=O)CC2)c(=O)n3CCNC(=O)CCCN2CCC(CC2)C(F)(F)c2cccc1c2] | (4R)-6⁶-(1,1-dioxidotetrahydro-2H-thiopyran-4-yl)-2,2-difluoro-4-methyl-6⁷,6⁸-dihydro-5,9-diaza-6(4,8)-pyrido[2,3-d]pyrimidina-1(4,1)-piperidina-3(1,3)-benzenacyclotridecaphane-6⁷,10-dione | 643.2 |

TABLE 1-continued

| No. | Structure | Chemical Name | [M + H]+ |
|---|---|---|---|
| 76 | 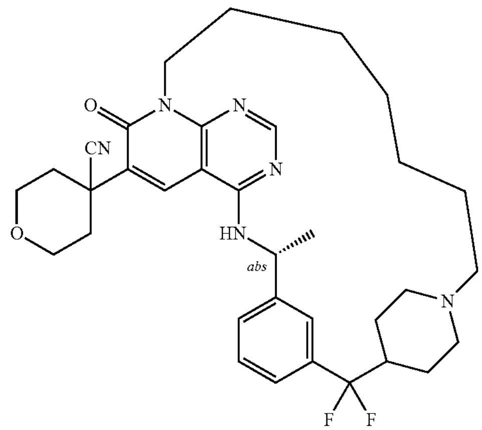 [SMILES: C[C@H]1Nc2ncnc3c2cc(C2(C#N)CCOCC2)c(=O)n3CCCCCCCN2CCC(CC2)C(F)(F)c2cccc1c2] | 4-((4R)-2,2-difluoro-4-methyl-6$^7$-oxo-6$^7$,6$^8$-dihydro-5-aza-6(4,8)-pyrido[2,3-d]pyrimidina-1(4,1)-piperidina-3(1,3)-benzenacyclotridecaphane-6$^6$-yl)tetrahydro-2H-pyran-4-carbonitrile | 605.2 |
| 77 | 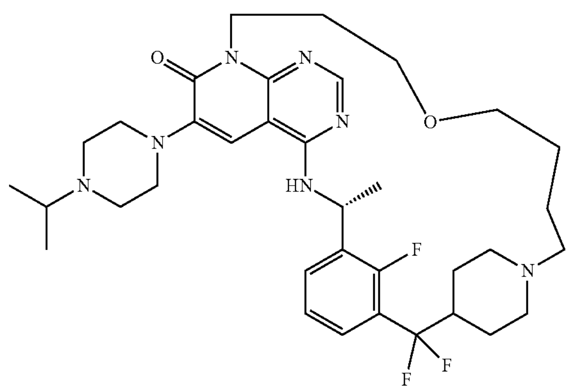 [SMILES: CC(C)N1CCN(c2cc3c4ncnc3n(c2=O)CCCOCCCCN2CCC(CC2)C(F)(F)c2cccc(c2F)[C@@H](C)N4)CC1] | (4R)-3$^2$,2,2-trifluoro-6$^6$-(4-isopropylpiperazin-1-yl)-4-methyl-6$^7$,6$^8$-dihydro-10-oxa-5-aza-6(4,8)-pyrido[2,3-d]pyrimidina-1(4,1)-piperidina-3(1,3)-benzenacyclotetradecaphan-6$^7$-one | 656.6 |
| 78 | 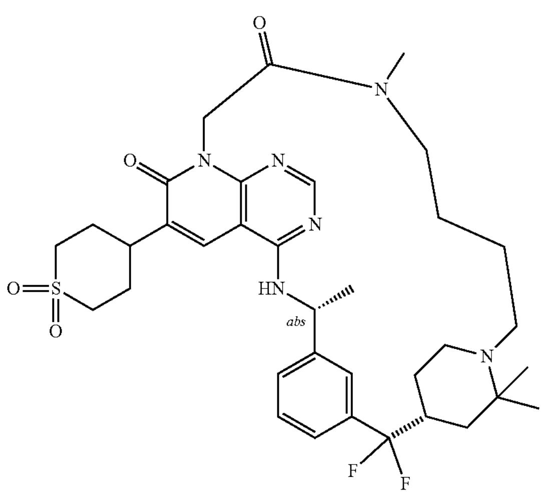 | (1$^4$R,4R)-6$^6$-(1,1-dioxidotetrahydro-2H-thiopyran-4-yl)-2,2-difluoro-1$^2$,1$^2$,4,9-tetramethyl-6$^7$,6$^8$-dihydro-5,9-diaza-6(4,8)-pyrido[2,3-d]pyrimidina-1(4,1)-piperidina-3(1,3)-benzenacyclotridecaphane-6$^7$,8-dione | 685.3 |

TABLE 1-continued

| No. | Structure | Chemical Name | [M + H]+ |
|---|---|---|---|
| 79 | 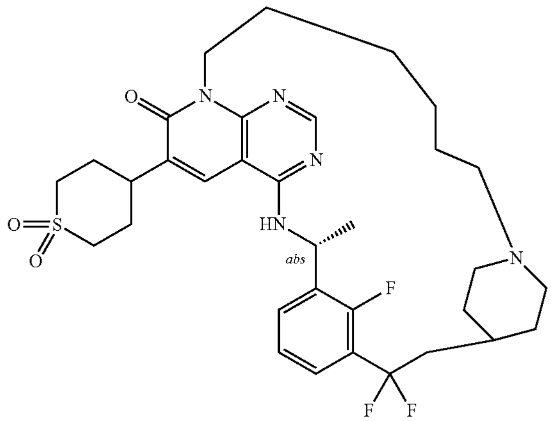 [SMILES: C[C@H]1Nc2ncnc3c2cc(C2CCS(=O)(=O)CC2)c(=O)n3CCCCCCN2CCC(CC2)CC(F)(F)c2cccc1c2F] | (3R)-1⁶-(1,1-dioxidotetrahydro-2H-thiopyran-4-yl)-4²,5,5-trifluoro-3-methyl-1⁷,1⁸-dihydro-2-aza-1(4,8)-pyrido[2,3-d]pyrimidina-7(4,1)-piperidina-4(1,3)-benzenacyclotridecaphan-1⁷-one | 646.1 |
| 80 | 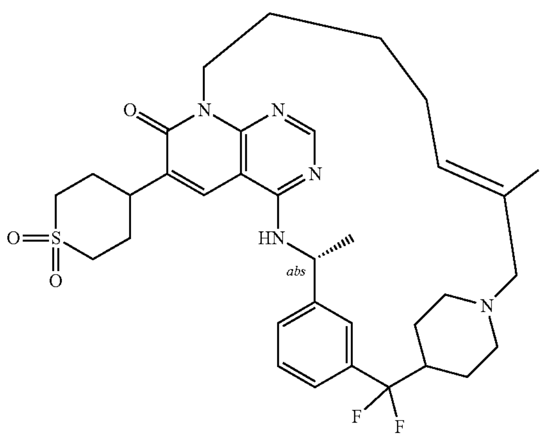 [SMILES: C/C1=C\CCCCn2c(=O)c(C3CCS(=O)(=O)CC3)cc3c(ncnc32)N[C@H](C)c2cccc(c2)C(F)(F)C2CCN(CC2)C1] | (4R,E)-6⁶-(1,1-dioxidotetrahydro-2H-thiopyran-4-yl)-2,2-difluoro-4,12-dimethyl-6⁷,6⁸-dihydro-5-aza-6(4,8)-pyrido[2,3-d]pyrimidina-1(4,1)-piperidina-3(1,3)-benzenacyclotridecaphan-11-en-6⁷-one | 640.3 |
| 81 | 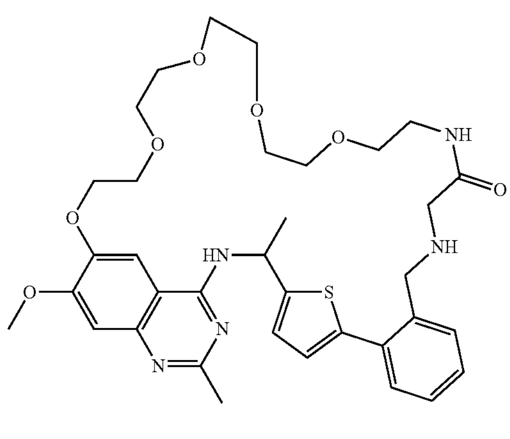 [SMILES: COc1cc2nc(C)nc3c2cc1OCCOCCOCCOCCOCCNC(=O)CNCc1ccccc1C1=CC=C(S1)C(C)N3] | 5⁷-methoxy-5²,3-dimethyl-6,9,12,15,18-pentaoxa-4,21,24-triaza-5(4,6)-quinazolina-2(2,5)-thiophena-1(1,2)-benzenacyclopentacosaphan-22-one | 680.3 |

TABLE 1-continued

| No. | Structure | Chemical Name | [M + H]+ |
|---|---|---|---|
| 82 | 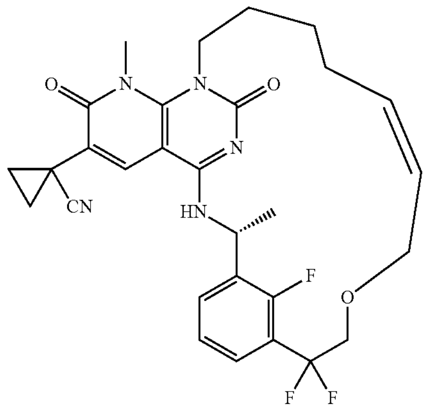 [SMILES: C[C@H]1Nc2nc(=O)n(c3c2cc(C2(C#N)CC2)c(=O)n3C)CCCC/C=C\COCC(F)(F)c2cccc1c2F] | 1-((1³E,3R,9Z)-4²,5,5-trifluoro-1⁸,3-dimethyl-1²,1⁷-dioxo-1¹,1²,1⁷,1⁸-tetrahydro-7-oxa-2-aza-1(4,1)-pyrido[2,3-d]pyrimidina-4(1,3)-benzenacyclotetradecaphan-9-en-1⁶-yl)cyclopropane-1-carbonitrile | 554.4 |
| 83 | 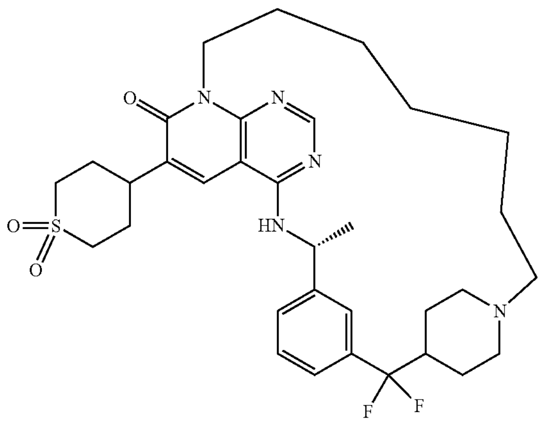 [SMILES: C[C@H]1Nc2ncnc3c2cc(C2CCS(=O)(=O)CC2)c(=O)n3CCCCCCCN2CCC(CC2)C(F)(F)c2cccc1c2] | (4R)-6⁶-(1,1-dioxidotetrahydro-2H-thiopyran-4-yl)-2,2-difluoro-4-methyl-6⁷,6⁸-dihydro-5-aza-6(4,8)-pyrido[2,3-d]pyrimidina-1(4,1)-piperidina-3(1,3)-benzenacyclotridecaphan-6⁷-one | 628.3 |
| 84 | 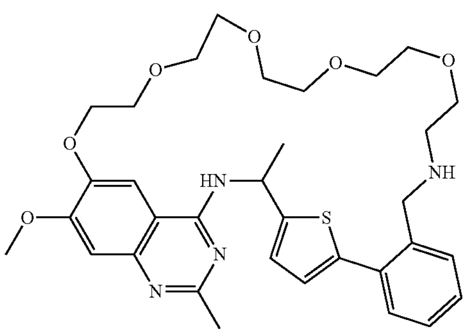 [SMILES: COc1cc2nc(C)nc3c2cc1OCCOCCOCCOCCOCCNCc1ccccc1C1=CC=C(S1)C(C)N3] | 5⁷-methoxy-5²,3-dimethyl-6,9,12,15,18-pentaoxa-4,21-diaza-5(4,6)-quinazolina-2(2,5)-thiophena-1(1,2)-benzenacyclodocosaphane | 623.3 |
| 85 | 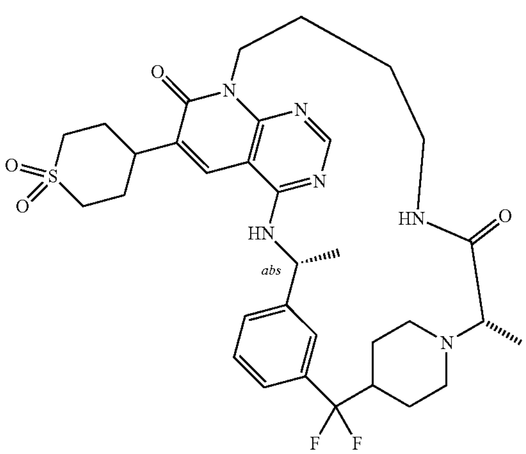 [SMILES: C[C@H]1Nc2ncnc3c2cc(C2CCS(=O)(=O)CC2)c(=O)n3CCCCNC(=O)[C@H](C)N2CCC(CC2)C(F)(F)c2cccc1c2] | (4R,13S)-6⁶-(1,1-dioxidotetrahydro-2H-thiopyran-4-yl)-2,2-difluoro-4,13-dimethyl-6⁷,6⁸-dihydro-5,11-diaza-6(4,8)-pyrido[2,3-d]pyrimidina-1(4,1)-piperidina-3(1,3)-benzenacyclotridecaphane-6⁷,12-dione | 657.3 |

TABLE 1-continued

| No. | Structure | Chemical Name | [M + H]⁺ |
|---|---|---|---|
| 86 | 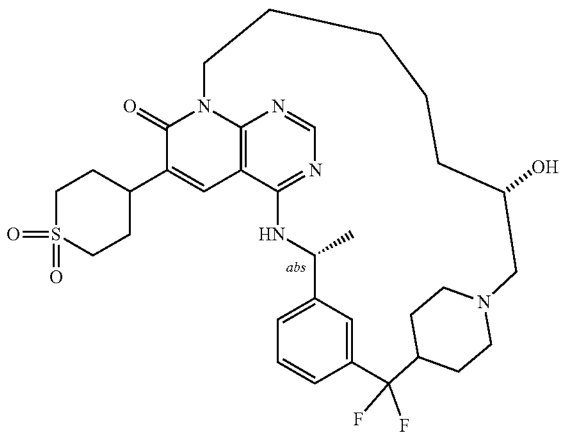 [SMILES: C[C@H]1Nc2ncnc3c2cc(C2CCS(=O)(=O)CC2)c(=O)n3CCCCC[C@H](O)CN2CCC(CC2)C(F)(F)c2cccc1c2] | (4R,12S)-6⁶-(1,1-dioxidotetrahydro-2H-thiopyran-4-yl)-2,2-difluoro-12-hydroxy-4-methyl-6⁷,6⁸-dihydro-5-aza-6(4,8)-pyrido[2,3-d]pyrimidina-1(4,1)-piperidina-3(1,3)-benzenacyclotridecaphan-6⁷-one | 644.3 |
| 87 | 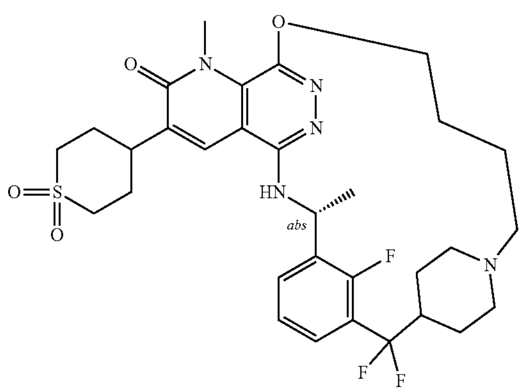 [SMILES: C[C@H]1Nc2nnc(c3c2cc(C2CCS(=O)(=O)CC2)c(=O)n3C)OCCCCN2CCC(CC2)C(F)(F)c2cccc1c2F] | (R)-6³-(1,1-dioxidotetrahydro-2H-thiopyran-4-yl)-3²,2,2-trifluoro-6¹,4-dimethyl-6¹,6²-dihydro-7-oxa-5-aza-6(5,8)-pyrido[2,3-d]pyridazina-1(4,1)-piperidina-3(1,3)-benzenacycloundecaphan-6²-one | 634.2 |
| 88 | 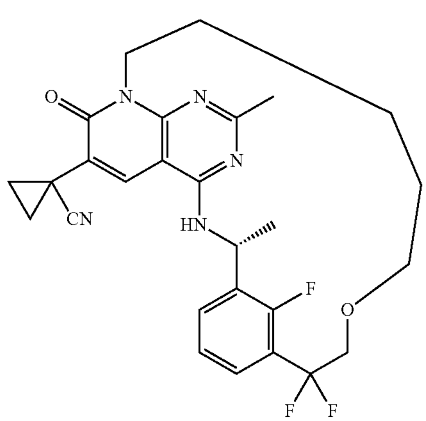 [SMILES: Cc1nc2c3cc(C4(C#N)CC4)c(=O)n(c3n1)CCCCCOCC(F)(F)c1cccc(c1F)[C@@H](C)N2] | 1-((3R)-4²,5,5-trifluoro-1²,3-dimethyl-1⁷-oxo-1⁷,1⁸-dihydro-7-oxa-2-aza-1(4,8)-pyrido[2,3-d]pyrimidina-4(1,3)-benzenacyclododecaphane-1⁶-yl)cyclopropane-1-carbonitrile | 512.4 |

TABLE 1-continued

| No. | Structure | Chemical Name | [M + H]+ |
|---|---|---|---|
| 89 | 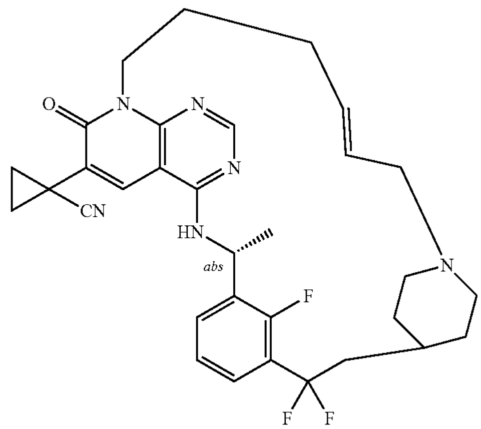 [SMILES: C[C@H]1Nc2ncnc3c2cc(C2(C#N)CC2)c(=O)n3CCC/C=C/CN2CCC(CC2)CC(F)(F)c2cccc1c2F] | 1-((3R,E)-4$^2$,5,5-trifluoro-3-methyl-1$^7$-oxo-1$^7$,1$^8$-dihydro-2-aza-1(4,8)-pyrido[2,3-d]pyrimidina-7(4,1)-piperidina-4(1,3)-benzenacyclotridecaphan-9-en-1$^6$-yl)cyclopropane-1-carbonitrile | 577.2 |
| 90 | 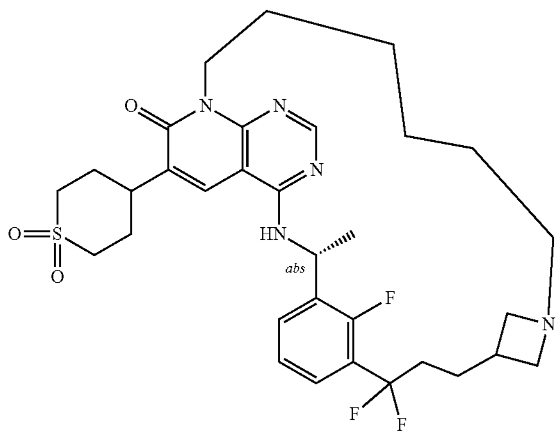 [SMILES: C[C@H]1Nc2ncnc3c2cc(C2CCS(=O)(=O)CC2)c(=O)n3CCCCCCN2CC(CCC(F)(F)c3cccc1c3F)C2] | (3R)-1$^6$-(1,1-dioxidotetrahydro-2H-thiopyran-4-yl)-4$^2$,5,5-trifluoro-3-methyl-1$^7$,1$^8$-dihydro-2-aza-1(4,8)-pyrido[2,3-d]pyrimidina-8(3,1)-azetidina-4(1,3)-benzenacyclotetradecaphan-1$^7$-one | 632.2 |
| 91 | 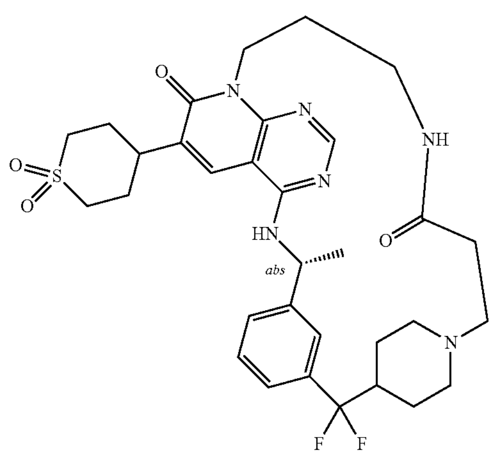 [SMILES: C[C@H]1Nc2ncnc3c2cc(C2CCS(=O)(=O)CC2)c(=O)n3CCCNC(=O)CCN2CCC(CC2)C(F)(F)c2cccc1c2] | (4R)-6$^6$-(1,1-dioxidotetrahydro-2H-thiopyran-4-yl)-2,2-difluoro-4-methyl-6$^7$,6$^8$-dihydro-5,10-diaza-6(4,8)-pyrido[2,3-d]pyrimidina-1(4,1)-piperidina-3(1,3)-benzenacyclotridecaphane-6$^7$,11-dione | 643.2 |

TABLE 1-continued

| No. | Structure | Chemical Name | [M + H]⁺ |
|---|---|---|---|
| 92 | 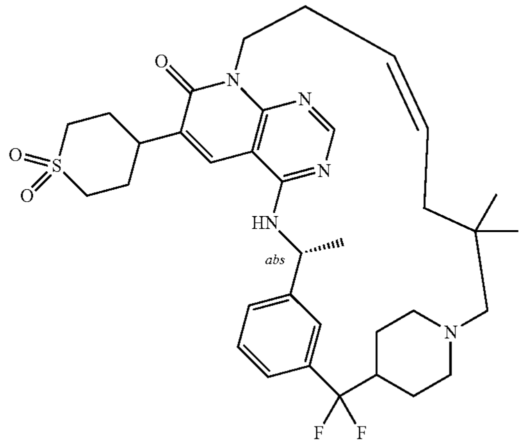 [SMILES: C[C@H]1Nc2ncnc3c2cc(C2CCS(=O)(=O)CC2)c(=O)n3CC/C=C\CC(C)(C)CN2CCC(CC2)C(F)(F)c2cccc1c2] | (4R,Z)-6⁶-(1,1-dioxidotetrahydro-2H-thiopyran-4-yl)-2,2-difluoro-4,12,12-trimethyl-6⁷,6⁸-dihydro-5-aza-6(4,8)-pyrido[2,3-d]pyrimidina-1(4,1)-piperidina-3(1,3)-benzenacyclotridecaphan-9-en-6⁷-one | 654.4 |
| 93 | 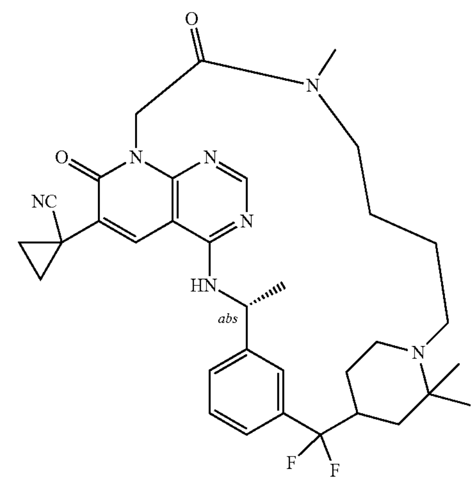 [SMILES: C[C@H]1Nc2ncnc3c2cc(C2(C#N)CC2)c(=O)n3CC(=O)N(C)CCCCN2CCC(CC2(C)C)C(F)(F)c2cccc1c2] | 1-((4R)-2,2-difluoro-1²,1²,4,9-tetramethyl-6⁷,8-dioxo-6⁷,6⁸-dihydro-5,9-diaza-6(4,8)-pyrido[2,3-d]pyrimidina-1(4,1)-piperidina-3(1,3)-benzenacyclotridecaphane-6⁶-yl)cyclopropane-1-carbonitrile | 618.3 |
| 94 | 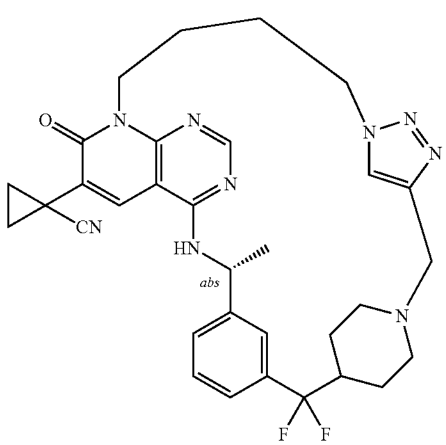 [SMILES: C[C@H]1Nc2ncnc3c2cc(C2(C#N)CC2)c(=O)n3CCCCn2cc(nn2)CN2CCC(CC2)C(F)(F)c2cccc1c2] | 1-((6R,Z)-4,4-difluoro-6-methyl-8⁷-oxo-8⁷,8⁸-dihydro-1¹H-7-aza-8(4,8)-pyrido[2,3-d]pyrimidina-3(1,4)-piperidina-1(4,1)-triazola-5(1,3)-benzenacyclododecaphane-8⁶-yl)cyclopropane-1-carbonitrile | 600.3 |

TABLE 1-continued

| No. | Structure | Chemical Name | [M + H]⁺ |
|---|---|---|---|
| 95 | 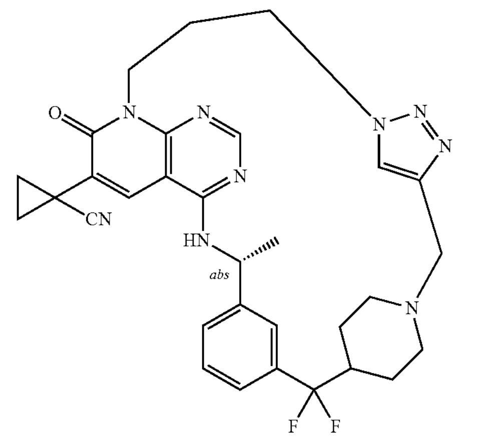 [SMILES: C[C@H]1Nc2ncnc3c2cc(C2(C#N)CC2)c(=O)n3CCCn2cc(nn2)CN2CCC(CC2)C(F)(F)c2cccc1c2] | 1-((6R,Z)-4,4-difluoro-6-methyl-8⁷-oxo-8⁷,8⁸-dihydro-1¹H-7-aza-8(4,8)-pyrido[2,3-d]pyrimidina-3(1,4)-piperidina-1(4,1)-triazola-5(1,3)-benzenacycloundecaphane-8⁶-yl)cyclopropane-1-carbonitrile | 586.4 |
| 96 | 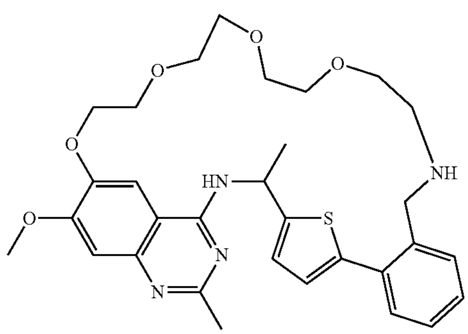 [SMILES: COc1cc2nc(C)nc3c2cc1OCCOCCOCCOCCNCc1ccccc1C1=CC=C(S1)C(C)N3] | 5⁷-methoxy-5²,3-dimethyl-6,9,12,15-tetraoxa-4,18-diaza-5(4,6)-quinazolina-2(2,5)-thiophena-1(1,2)-benzenacyclononadecaphane | 579.3 |
| 97 | 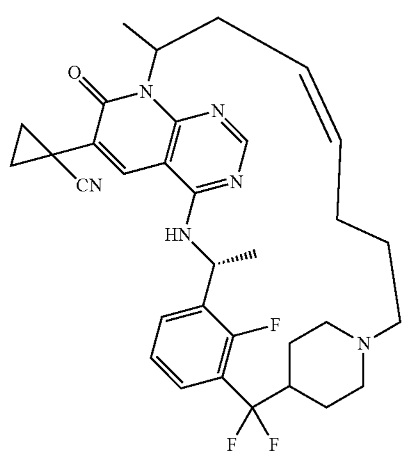 [SMILES: CC1C/C=C\CCCN2CCC(CC2)C(F)(F)c2cccc(c2F)[C@@H](C)Nc2ncnc3c2cc(C2(C#N)CC2)c(=O)n31] | 1-((4R,Z)-3²,2,2-trifluoro-4,7-dimethyl-6⁷-oxo-6⁷,6⁸-dihydro-5-aza-6(4,8)-pyrido[2,3-d]pyrimidina-1(4,1)-piperidina-3(1,3)-benzenacyclotridecaphan-9-en-6⁶-yl)cyclopropane-1-carbonitrile | 591.5 |

TABLE 1-continued

| No. | Structure | Chemical Name | [M + H]+ |
|---|---|---|---|
| 98 | 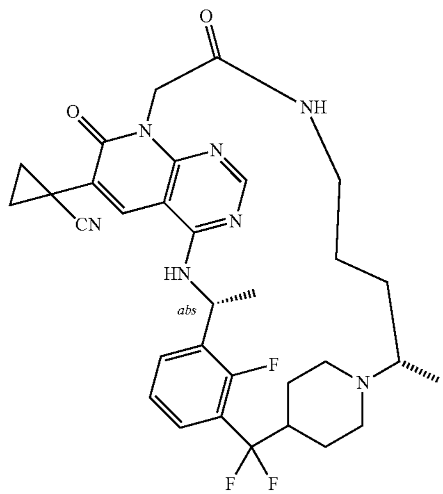 [SMILES: C[C@H]1Nc2ncnc3c2cc(C2(C#N)CC2)c(=O)n3CC(=O)NCCC[C@H](C)N2CCC(CC2)C(F)(F)c2cccc1c2F] | 1-((4R,13S)-3$^2$,2,2-trifluoro-4,13-dimethyl-6$^7$,8-dioxo-6$^7$,6$^8$-dihydro-5,9-diaza-6(4,8)-pyrido[2,3-d]pyrimidina-1(4,1)-piperidina-3(1,3)-benzenacyclotridecaphane-6$^6$-yl)cyclopropane-1-carbonitrile | 608.3 |
| 99 | 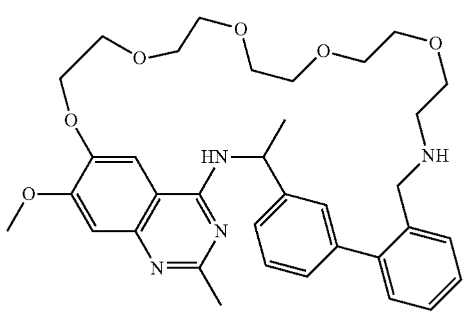 [SMILES: COc1cc2nc(C)nc3c2cc1OCCOCCOCCOCCOCCNCc1ccccc1-c1cccc(c1)C(C)N3] | 5$^7$-methoxy-5$^2$,3-dimethyl-6,9,12,15,18-pentaoxa-4,21-diaza-5(4,6)-quinazolina-1(1,2),2(1,3)-dibenzenacyclodocosaphane | 617.4 |
| 100 | 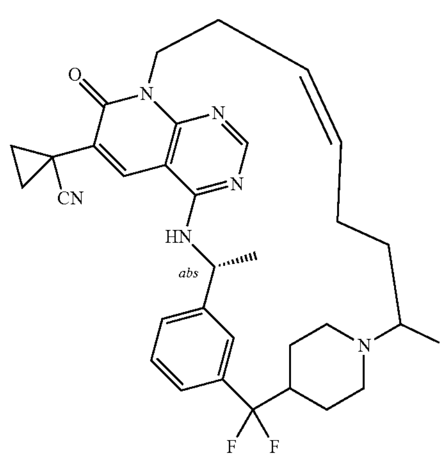 [SMILES: CC1CC/C=C\CCn2c(=O)c(C3(C#N)CC3)cc3c(ncnc32)N[C@H](C)c2cccc(c2)C(F)(F)C2CCN1CC2] | 1-((4R,Z)-2,2-difluoro-4,13-dimethyl-6$^7$-oxo-6$^7$,6$^8$-dihydro-5-aza-6(4,8)-pyrido[2,3-d]pyrimidina-1(4,1)-piperidina-3(1,3)-benzenacyclotridecaphan-9-en-6$^6$-yl)cyclopropane-1-carbonitrile | 573.3 |

TABLE 1-continued

| No. | Structure | Chemical Name | [M + H]+ |
|---|---|---|---|
| 101 | 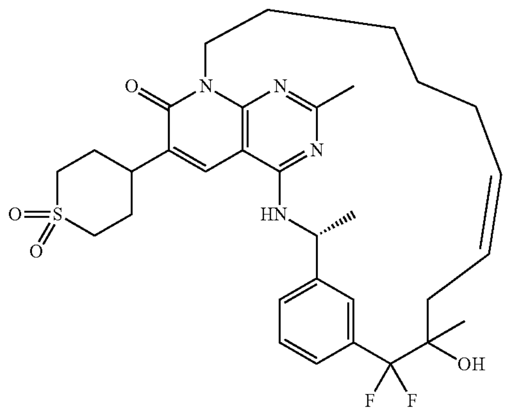 [SMILES: Cc1nc2c3cc(C4CCS(=O)(=O)CC4)c(=O)n(c3n1)CCCCC/C=C\CC(C)(O)C(F)(F)c1cccc(c1)[C@@H](C)N2] | (3R,Z)-1$^6$-(1,1-dioxidotetrahydro-2H-thiopyran-4-yl)-5,5-difluoro-6-hydroxy-1$^2$,3,6-trimethyl-1$^7$,1$^8$-dihydro-2-aza-1(4,8)-pyrido[2,3-d]pyrimidina-4(1,3)-benzenacyclotetradecaphan-8-en-1$^7$-one | 615.4 |
| 102 | 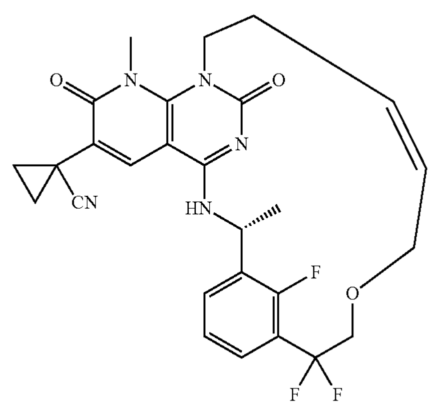 [SMILES: C[C@H]1Nc2nc(=O)n(c3c2cc(C2(C#N)CC2)c(=O)n3C)CC/C=C\COCC(F)(F)c2cccc1c2F] | 1-((1$^3$E,3R,9Z)-4$^2$,5,5-trifluoro-1$^8$,3-dimethyl-1$^2$,1$^7$-dioxo-1$^1$,1$^2$,1$^7$,1$^8$-tetrahydro-7-oxa-2-aza-1(4,1)-pyrido[2,3-d]pyrimidina-4(1,3)-benzenacyclododecaphan-9-en-1$^6$-yl)cyclopropane-1-carbonitrile | 526.4 |
| 103 | 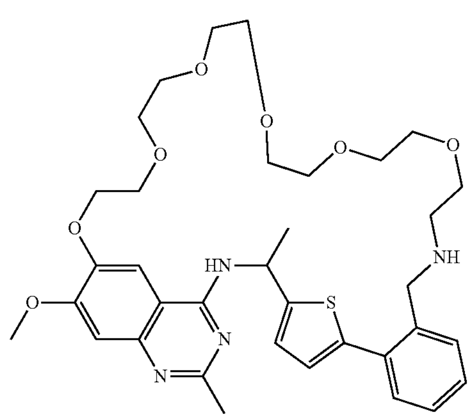 [SMILES: COc1cc2nc(C)nc3c2cc1OCCOCCOCCOCCOCCOCCNCc1ccccc1C1=CC=C(S1)C(C)N3] | 5$^7$-methoxy-5$^2$,3-dimethyl-6,9,12,15,18,21-hexaoxa-4,24-diaza-5(4,6)-quinazolina-2(2,5)-thiophena-1(1,2)-benzenacyclopentacosaphane | 667.3 |

TABLE 1-continued

| No. | Structure | Chemical Name | [M + H]$^+$ |
|---|---|---|---|
| 104 | 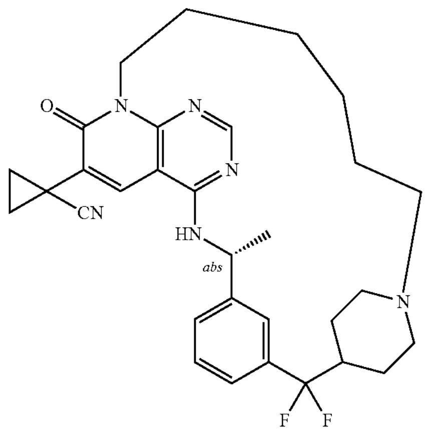 [SMILES: C[C@H]1Nc2ncnc3c2cc(C2(C#N)CC2)c(=O)n3CCCCCCN2CCC(CC2)C(F)(F)c2cccc1c2] | 1-((4R)-2,2-difluoro-4-methyl-6$^7$-oxo-6$^7$,6$^8$-dihydro-5-aza-6(4,8)-pyrido[2,3-d]pyrimidina-1(4,1)-piperidina-3(1,3)-benzenacyclododecaphane-6$^6$-yl)cyclopropane-1-carbonitrile | 547.3 |
| 105 | 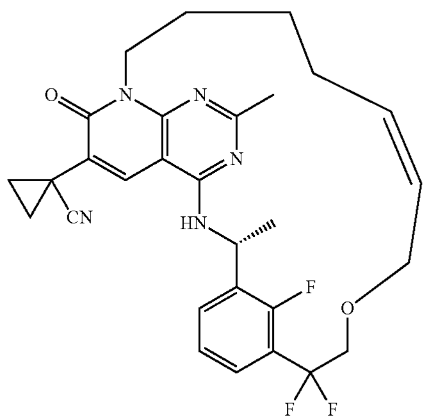 [SMILES: Cc1nc2c3cc(C4(C#N)CC4)c(=O)n(c3n1)CCCC/C=C\COCC(F)(F)c1cccc(c1F)[C@@H](C)N2] | 1-((3R,Z)-4$^2$,5,5-trifluoro-1$^2$,3-dimethyl-1$^7$-oxo-1$^7$,1$^8$-dihydro-7-oxa-2-aza-1(4,8)-pyrido[2,3-d]pyrimidina-4(1,3)-benzenacyclotetradecaphan-9-en-1$^6$-yl)cyclopropane-1-carbonitrile | 538.4 |
| 106 | 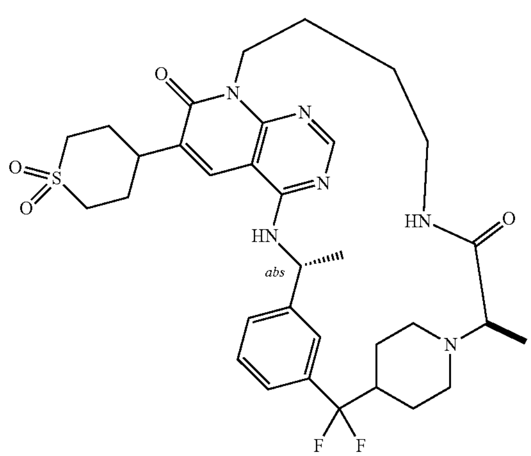 [SMILES: C[C@@H]1C(=O)NCCCCn2c(=O)c(C3CCS(=O)(=O)CC3)cc3c(ncnc32)N[C@H](C)c2cccc(c2)C(F)(F)C2CCN1CC2] | (4R,13R)-6$^6$-(1,1-dioxidotetrahydro-2H-thiopyran-4-yl)-2,2-difluoro-4,13-dimethyl-6$^7$,6$^8$-dihydro-5,11-diaza-6(4,8)-pyrido[2,3-d]pyrimidina-1(4,1)-piperidina-3(1,3)-benzenacyclotridecaphane-6$^7$,12-dione | 657.3 |

TABLE 1-continued

| No. | Structure | Chemical Name | [M + H]+ |
|---|---|---|---|
| 107 | 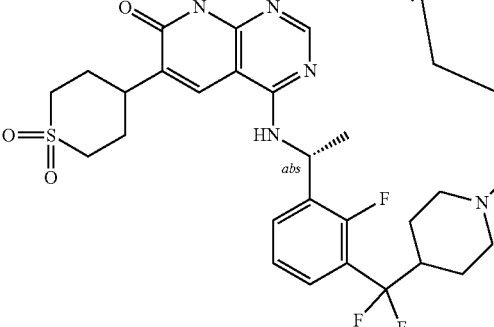 | (4R,Z)-6⁶-(1,1-dioxidotetrahydro-2H-thiopyran-4-yl)-3²,2,2-trifluoro-4,12-dimethyl-6⁷,6⁸-dihydro-5-aza-6(4,8)-pyrido[2,3-d]pyrimidina-1(4,1)-piperidina-3(1,3)-benzenacyclotridecaphan-9-en-6⁷-one | 658.2 |
| 108 | 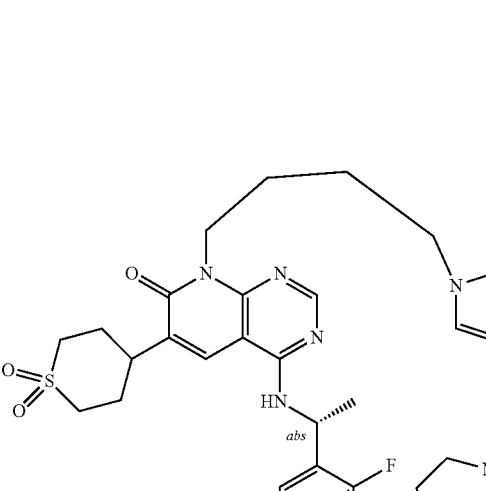 | (6R,Z)-8⁶-(1,1-dioxidotetrahydro-2H-thiopyran-4-yl)-5²,4,4-trifluoro-6-methyl-8⁷,8⁸-dihydro-1¹H-7-aza-8(4,8)-pyrido[2,3-d]pyrimidina-3(1,4)-piperidina-1(4,1)-triazola-5(1,3)-benzenacyclododecaphan-8⁷-one | 685.2 |
| 109 | 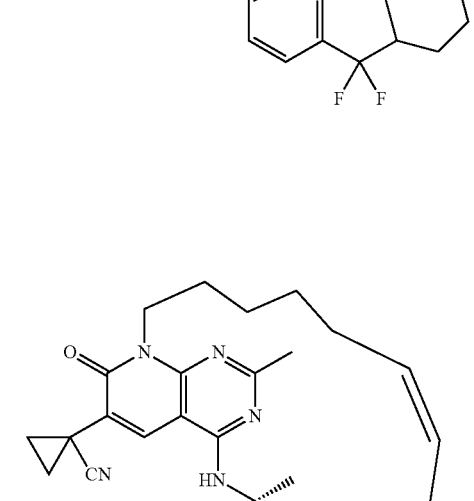 | 1-((3R,Z)-4²,5,5-trifluoro-1²,3-dimethyl-1⁷-oxo-1⁷,1⁸-dihydro-7-oxa-2-aza-1(4,8)-pyrido[2,3-d]pyrimidina-4(1,3)-benzenacyclopentadecaphan-9-en-1⁶-yl)cyclopropane-1-carbonitrile | 552.4 |

TABLE 1-continued

| No. | Structure | Chemical Name | [M + H]+ |
|---|---|---|---|
| 110 | 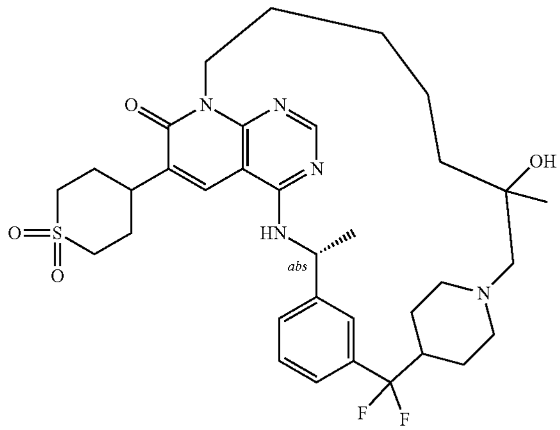 [SMILES: C[C@H]1Nc2ncnc3c2cc(C2CCS(=O)(=O)CC2)c(=O)n3CCCCCC(C)(O)CN2CCC(CC2)C(F)(F)c2cccc1c2] | (4R)-6⁶-(1,1-dioxidotetrahydro-2H-thiopyran-4-yl)-2,2-difluoro-12-hydroxy-4,12-dimethyl-6⁷,6⁸-dihydro-5-aza-6(4,8)-pyrido[2,3-d]pyrimidina-1(4,1)-piperidina-3(1,3)-benzenacyclotridecaphan-6⁷-one | 658.3 |
| 111 | 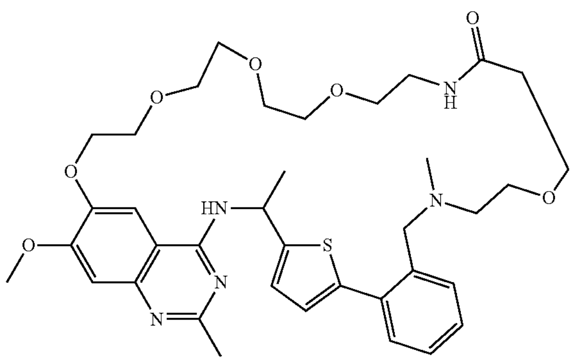 | 5⁷-methoxy-5²,3,25-trimethyl-6,9,12,15,22-pentaoxa-4,18,25-triaza-5(4,6)-quinazolina-2(2,5)-thiophena-1(1,2)-benzenacyclohexacosaphan-19-one | 708.3 |
| 112 | 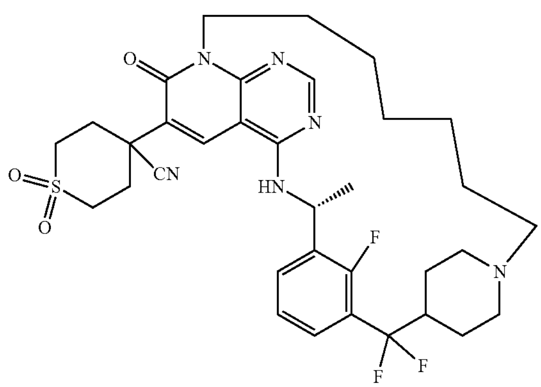 [SMILES: C[C@H]1Nc2ncnc3c2cc(C2(C#N)CCS(=O)(=O)CC2)c(=O)n3CCCCCCCN2CCC(CC2)C(F)(F)c2cccc1c2F] | 4-((4R)-3²,2,2-trifluoro-4-methyl-6⁷-oxo-6⁷,6⁸-dihydro-5-aza-6(4,8)-pyrido[2,3-d]pyrimidina-1(4,1)-piperidina-3(1,3)-benzenacyclotridecaphane-6⁶-yl)tetrahydro-2H-thiopyran-4-carbonitrile 1,1-dioxide | 671.5 |
| 113 | 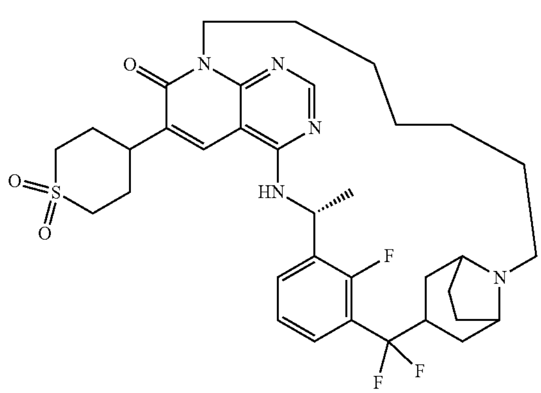 [SMILES: C[C@H]1Nc2ncnc3c2cc(C2CCS(=O)(=O)CC2)c(=O)n3CCCCCCCN2C3CCC2CC(C3)C(F)(F)c2cccc1c2F] | (1¹S,1⁵R,4R)-6⁶-(1,1-dioxidotetrahydro-2H-thiopyran-4-yl)-3²,2,2-trifluoro-4-methyl-6⁷,6⁸-dihydro-1⁸,5-diaza-6(4,8)-pyrido[2,3-d]pyrimidina-1(3,8)-bicyclo[3.2.1]octana-3(1,3)-benzenacyclotridecaphan-6⁷-one | 672.3 |

TABLE 1-continued

| No. | Structure | Chemical Name | [M + H]+ |
|---|---|---|---|
| 114 | 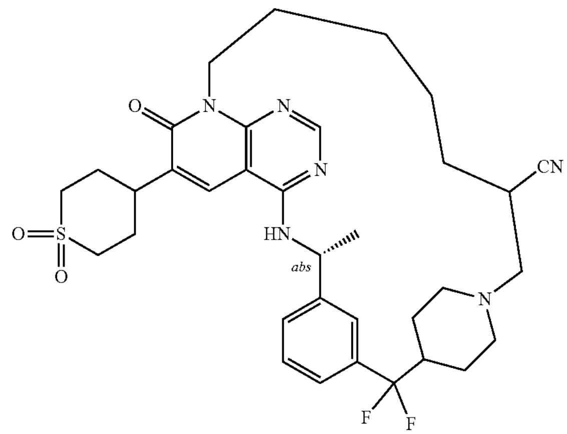 [SMILES: C[C@H]1Nc2ncnc3c2cc(C2CCS(=O)(=O)CC2)c(=O)n3CCCCCC(C#N)CN2CCC(CC2)C(F)(F)c2cccc1c2] | (4R)-6$^6$-(1,1-dioxidotetrahydro-2H-thiopyran-4-yl)-2,2-difluoro-4-methyl-6$^7$-oxo-6$^7$,6$^8$-dihydro-5-aza-6(4,8)-pyrido[2,3-d]pyrimidina-1(4,1)-piperidina-3(1,3)-benzenacyclotridecaphane-12-carbonitrile | 653.2 |
| 115 | 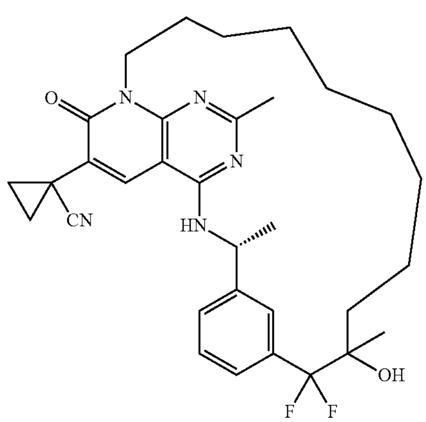 [SMILES: Cc1nc2c3cc(C4(C#N)CC4)c(=O)n(c3n1)CCCCCCCCCC(C)(O)C(F)(F)c1cccc(c1)[C@@H](C)N2] | 1-((3R)-5,5-difluoro-6-hydroxy-1$^2$,3,6-trimethyl-1$^7$-oxo-1$^7$,1$^8$-dihydro-2-aza-1(4,8)-pyrido[2,3-d]pyrimidina-4(1,3)-benzenacyclopentadecaphane-1$^6$-yl)cyclopropane-1-carbonitrile | 564.4 |
| 116 | 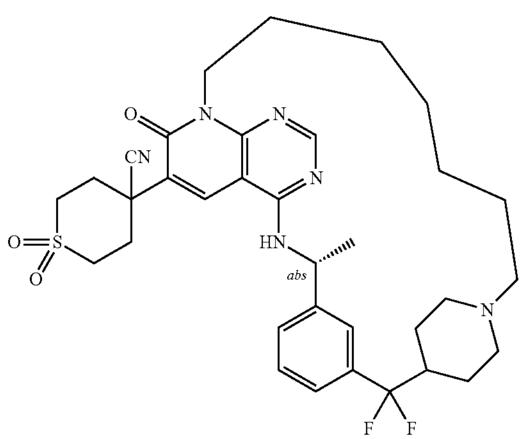 [SMILES: C[C@H]1Nc2ncnc3c2cc(C2(C#N)CCS(=O)(=O)CC2)c(=O)n3CCCCCCCN2CCC(CC2)C(F)(F)c2cccc1c2] | 4-((4R)-2,2-difluoro-4-methyl-6$^7$-oxo-6$^7$,6$^8$-dihydro-5-aza-6(4,8)-pyrido[2,3-d]pyrimidina-1(4,1)-piperidina-3(1,3)-benzenacyclotridecaphane-6$^6$-yl)tetrahydro-2H-thiopyran-4-carbonitrile 1,1-dioxide | 653.4 |

TABLE 1-continued

| No. | Structure | Chemical Name | [M + H]+ |
|---|---|---|---|
| 117 | 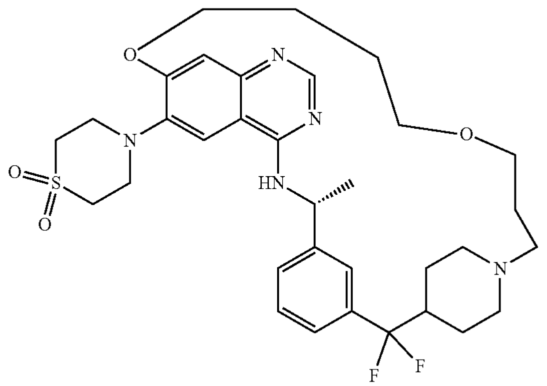 [SMILES: C[C@H]1Nc2ncnc3cc(c(N4CCS(=O)(=O)CC4)cc23)OCCCCOCCCN2CCC(CC2)C(F)(F)c2cccc1c2] | (R)-4-(2,2-difluoro-4-methyl-7,12-dioxa-5-aza-6(4,7)-quinazolina-1(4,1)-piperidina-3(1,3)-benzenacyclopentadecaphane-6⁶-yl)thiomorpholine 1,1-dioxide | 644.4 |
| 118 | 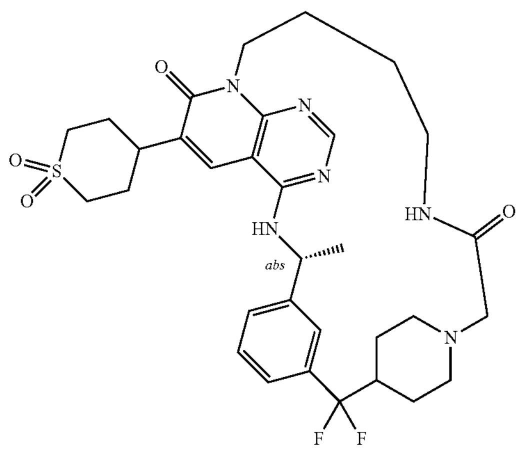 [SMILES: C[C@H]1Nc2ncnc3c2cc(C2CCS(=O)(=O)CC2)c(=O)n3CCCCNC(=O)CN2CCC(CC2)C(F)(F)c2cccc1c2] | (4R)-6⁶-(1,1-dioxidotetrahydro-2H-thiopyran-4-yl)-2,2-difluoro-4-methyl-6⁷,6⁸-dihydro-5,11-diaza-6(4,8)-pyrido[2,3-d]pyrimidina-1(4,1)-piperidina-3(1,3)-benzenacyclotridecaphane-6⁷,12-dione | 643.3 |
| 119 | 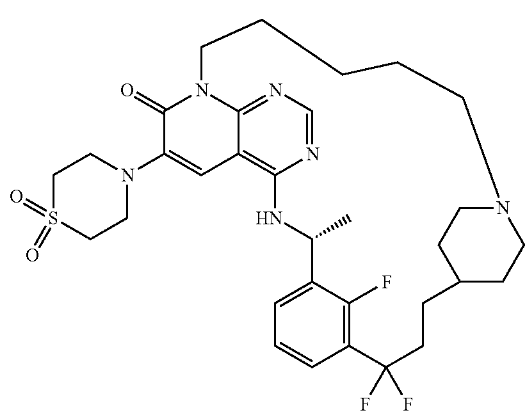 [SMILES: C[C@H]1Nc2ncnc3c2cc(N2CCS(=O)(=O)CC2)c(=O)n3CCCCCN2CCC(CC2)CCC(F)(F)c2cccc1c2F] | (3R)-1⁶-(1,1-dioxidothiomorpholino)-4²,5,5-trifluoro-3-methyl-1⁷,1⁸-dihydro-2-aza-1(4,8)-pyrido[2,3-d]pyrimidina-8(4,1)-piperidina-4(1,3)-benzenacyclotridecaphan-1⁷-one | 647.3 |

TABLE 1-continued

| No. | Structure | Chemical Name | [M + H]⁺ |
|---|---|---|---|
| 120 | 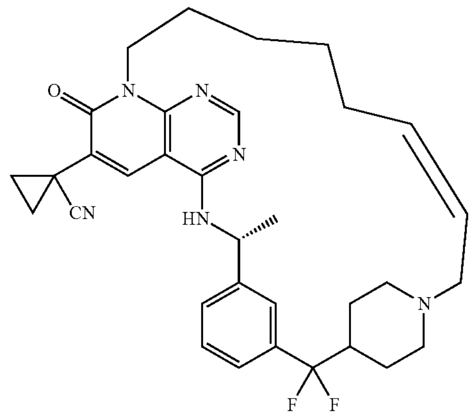 [SMILES: C[C@H]1Nc2ncnc3c2cc(C2(C#N)CC2)c(=O)n3CCCCC/C=C\CN2CCC(CC2)C(F)(F)c2cccc1c2] | 1-((4R,Z)-2,2-difluoro-4-methyl-6⁷-oxo-6⁷,6⁸-dihydro-5-aza-6(4,8)-pyrido[2,3-d]pyrimidina-1(4,1)-piperidina-3(1,3)-benzenacyclotetradecaphan-12-en-6⁶-yl)cyclopropane-1-carbonitrile | 573.4 |
| 121 | 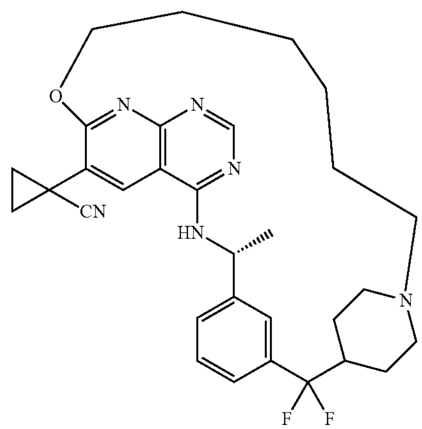 [SMILES: C[C@H]1Nc2ncnc3nc(c(C4(C#N)CC4)cc23)OCCCCCCN2CCC(CC2)C(F)(F)c2cccc1c2] | (R)-1-(2,2-difluoro-4-methyl-7-oxa-5-aza-6(4,7)-pyrido[2,3-d]pyrimidina-1(4,1)-piperidina-3(1,3)-benzenacyclotridecaphane-6⁶-yl)cyclopropane-1-carbonitrile | 547.3 |
| 122 | 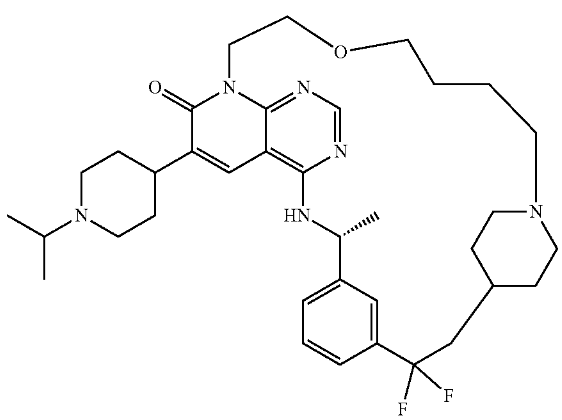 [SMILES: CC(C)N1CCC(c2cc3c4ncnc3n(c2=O)CCOCCCCN2CCC(CC2)CC(F)(F)c2cccc(c2)[C@@H](C)N4)CC1] | (3R)-5,5-difluoro-1⁶-(1-isopropylpiperidin-4-yl)-3-methyl-1⁷,1⁸-dihydro-12-oxa-2-aza-1(4,8)-pyrido[2,3-d]pyrimidina-7(4,1)-piperidina-4(1,3)-benzenacyclotetradecaphan-1⁷-one | 637.5 |

| No. | Structure | Chemical Name | [M + H]⁺ |
|---|---|---|---|
| 123 | 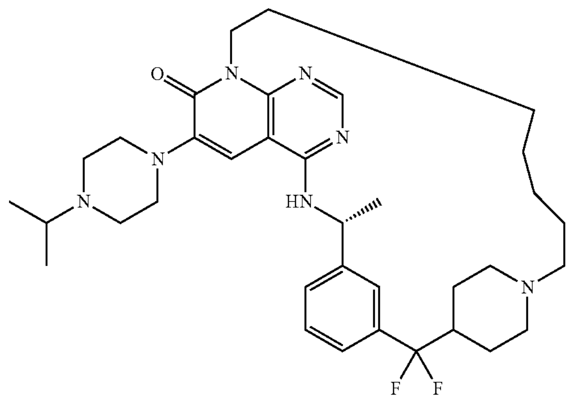 [SMILES: CC(C)N1CCN(c2cc3c4ncnc3n(c2=O)CCCCCCCN2CCC(CC2)C(F)(F)c2cccc(c2)[C@@H](C)N4)CC1] | (4R)-2,2-difluoro-6⁶-(4-isopropylpiperazin-1-yl)-4-methyl-6⁷,6⁸-dihydro-5-aza-6(4,8)-pyrido[2,3-d]pyrimidina-1(4,1)-piperidina-3(1,3)-benzenacyclotridecaphan-6⁷-one | 622.3 |
| 124 | 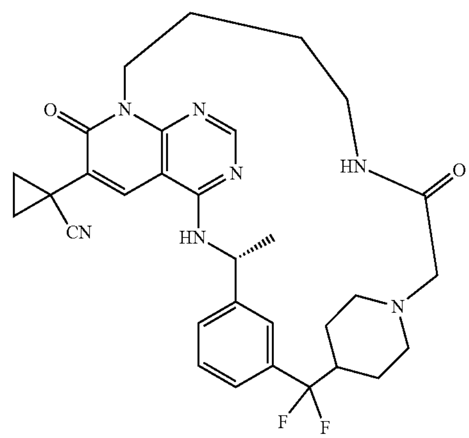 [SMILES: C[C@H]1Nc2ncnc3c2cc(C2(C#N)CC2)c(=O)n3CCCCNC(=O)CN2CCC(CC2)C(F)(F)c2cccc1c2] | 1-((4R)-2,2-difluoro-4-methyl-6⁷,12-dioxo-6⁷,6⁸-dihydro-5,11-diaza-6(4,8)-pyrido[2,3-d]pyrimidina-1(4,1)-piperidina-3(1,3)-benzenacyclotridecaphane-6⁶-yl)cyclopropane-1-carbonitrile | 576.3 |
| 125 | 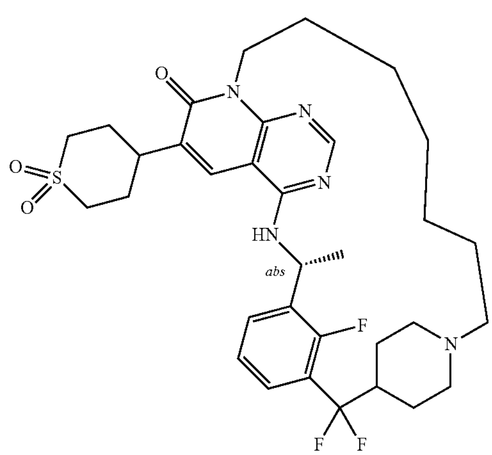 [SMILES: C[C@H]1Nc2ncnc3c2cc(C2CCS(=O)(=O)CC2)c(=O)n3CCCCCCCN2CCC(CC2)C(F)(F)c2cccc1c2F] | (4R)-6⁶-(1,1-dioxidotetrahydro-2H-thiopyran-4-yl)-3²,2,2-trifluoro-4-methyl-6⁷,6⁸-dihydro-5-aza-6(4,8)-pyrido[2,3-d]pyrimidina-1(4,1)-piperidina-3(1,3)-benzenacyclotridecaphan-6⁷-one | 646.3 |

TABLE 1-continued

| No. | Structure | Chemical Name | [M + H]+ |
|---|---|---|---|
| 126 | 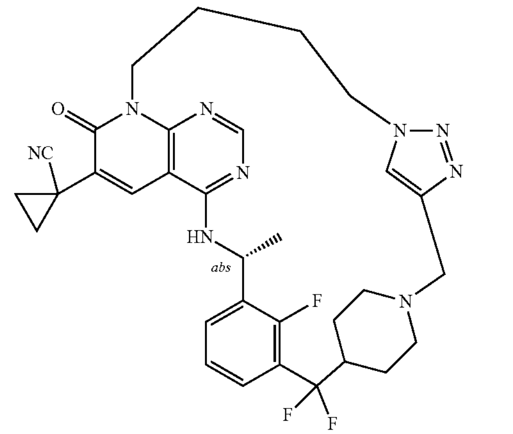 [SMILES: C[C@H]1Nc2ncnc3c2cc(C2(C#N)CC2)c(=O)n3CCCCn2cc(nn2)CN2CCC(CC2)C(F)(F)c2cccc1c2F] | 1-((6R,Z)-5$^2$,4,4-trifluoro-6-methyl-8$^7$-oxo-8$^7$,8$^8$-dihydro-1$^1$H-7-aza-8(4,8)-pyrido[2,3-d]pyrimidina-3(1,4)-piperidina-1(4,1)-triazola-5(1,3)-benzenacyclododecaphane-8$^6$-yl)cyclopropane-1-carbonitrile | 618.4 |
| 127 | 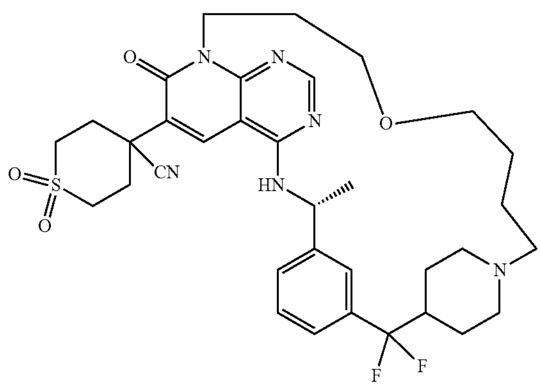 [SMILES: C[C@H]1Nc2ncnc3c2cc(C2(C#N)CCS(=O)(=O)CC2)c(=O)n3CCCOCCCCN2CCC(CC2)C(F)(F)c2cccc1c2] | 4-((4R)-2,2-difluoro-4-methyl-6$^7$-oxo-6$^7$,6$^8$-dihydro-10-oxa-5-aza-6(4,8)-pyrido[2,3-d]pyrimidina-1(4,1)-piperidina-3(1,3)-benzenacyclotetradecaphane-6$^6$-yl)tetrahydro-2H-thiopyran-4-carbonitrile 1,1-dioxide | 669.3 |
| 128 | 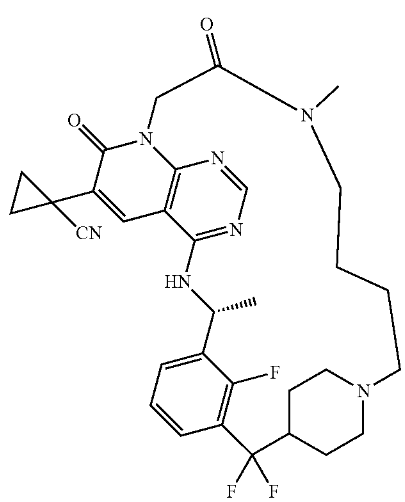 [SMILES: C[C@H]1Nc2ncnc3c2cc(C2(C#N)CC2)c(=O)n3CC(=O)N(C)CCCCN2CCC(CC2)C(F)(F)c2cccc1c2F] | 1-((4R)-3$^2$,2,2-trifluoro-4,9-dimethyl-6$^7$,8-dioxo-6$^7$,6$^8$-dihydro-5,9-diaza-6(4,8)-pyrido[2,3-d]pyrimidina-1(4,1)-piperidina-3(1,3)-benzenacyclotridecaphane-6$^6$-yl)cyclopropane-1-carbonitrile | 608.4 |

TABLE 1-continued

| No. | Structure | Chemical Name | [M + H]⁺ |
|---|---|---|---|
| 129 | 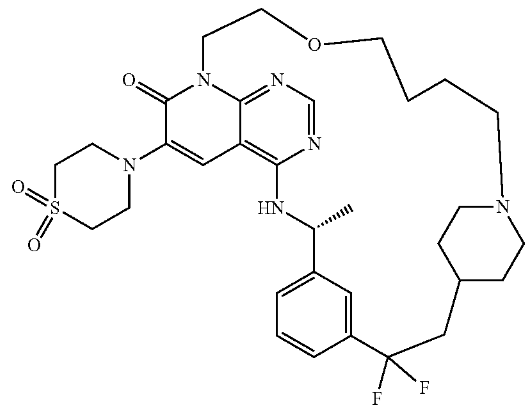 [SMILES: C[C@H]1Nc2ncnc3c2cc(N2CCS(=O)(=O)CC2)c(=O)n3CCOCCCCN2CCC(CC2)CC(F)(F)c2cccc1c2] | (3R)-1⁶-(1,1-dioxidothiomorpholino)-5,5-difluoro-3-methyl-1⁷,1⁸-dihydro-12-oxa-2-aza-1(4,8)-pyrido[2,3-d]pyrimidina-7(4,1)-piperidina-4(1,3)-benzenacyclotetradecaphan-1⁷-one | 645.4 |
| 130 | 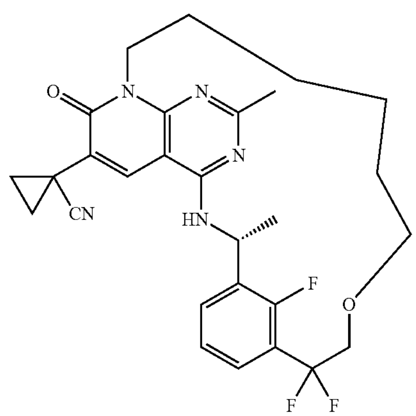 [SMILES: Cc1nc2c3cc(C4(C#N)CC4)c(=O)n(c3n1)CCCCCCOCC(F)(F)c1cccc(c1F)[C@@H](C)N2] | 1-((3R)-4²,5,5-trifluoro-1²,3-dimethyl-1⁷-oxo-1⁷,1⁸-dihydro-7-oxa-2-aza-1(4,8)-pyrido[2,3-d]pyrimidina-4(1,3)-benzenacyclotridecaphane-1⁶-yl)cyclopropane-1-carbonitrile | 526.4 |
| 131 | 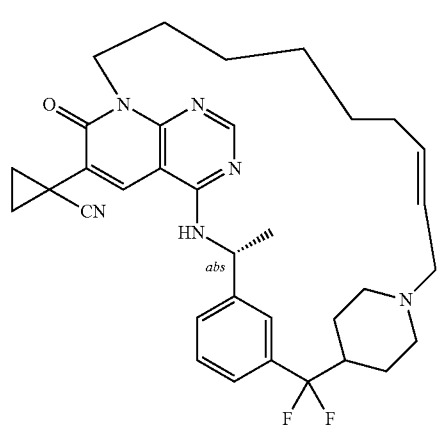 [SMILES: C[C@H]1Nc2ncnc3c2cc(C2(C#N)CC2)c(=O)n3CCCCCC/C=C/CN2CCC(CC2)C(F)(F)c2cccc1c2] | 1-((4R,E)-2,2-difluoro-4-methyl-6⁷-oxo-6⁷,6⁸-dihydro-5-aza-6(4,8)-pyrido[2,3-d]pyrimidina-1(4,1)-piperidina-3(1,3)-benzenacyclopentadecaphan-13-en-6⁶-yl)cyclopropane-1-carbonitrile | 587.3 |

TABLE 1-continued

| No. | Structure | Chemical Name | [M + H]+ |
| --- | --- | --- | --- |
| 132 | 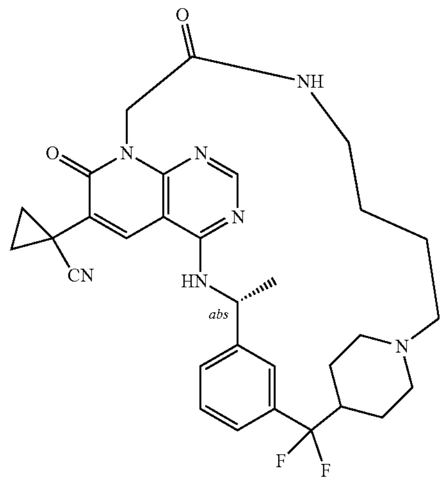 [SMILES: C[C@H]1Nc2ncnc3c2cc(C2(C#N)CC2)c(=O)n3CC(=O)NCCCCN2CCC(CC2)C(F)(F)c2cccc1c2] | 1-((4R)-2,2-difluoro-4-methyl-6⁷,8-dioxo-6⁷,6⁸-dihydro-5,9-diaza-6(4,8)-pyrido[2,3-d]pyrimidina-1(4,1)-piperidina-3(1,3)-benzenacyclotridecaphane-6⁶-yl)cyclopropane-1-carbonitrile | 576.7 |
| 133 | 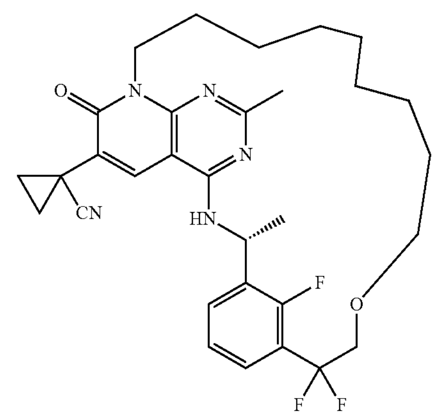 [SMILES: Cc1nc2c3cc(C4(C#N)CC4)c(=O)n(c3n1)CCCCCCCCCOCC(F)(F)c1cccc(c1F)[C@@H](C)N2] | 1-((3R)-4²,5,5-trifluoro-1²,3-dimethyl-1⁷-oxo-1⁷,1⁸-dihydro-7-oxa-2-aza-1(4,8)-pyrido[2,3-d]pyrimidina-4(1,3)-benzenacyclohexadecaphane-1⁶-yl)cyclopropane-1-carbonitrile | 568.5 |
| 134 | 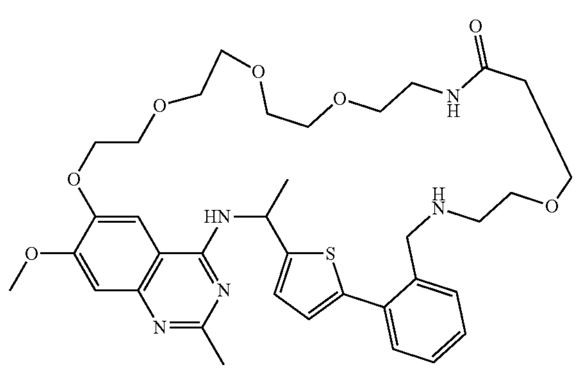 [SMILES: COc1cc2nc(C)nc3c2cc1OCCOCCOCCOCCNC(=O)CCOCCNCc1ccccc1C1=CC=C(S1)C(C)N3] | 5⁷-methoxy-5²,3-dimethyl-6,9,12,15,22-pentaoxa-4,18,25-triaza-5(4,6)-quinazolina-2(2,5)-thiophena-1(1,2)-benzenacyclohexacosaphan-19-one | 694.3 |

TABLE 1-continued

| No. | Structure | Chemical Name | [M + H]⁺ |
|---|---|---|---|
| 135 | 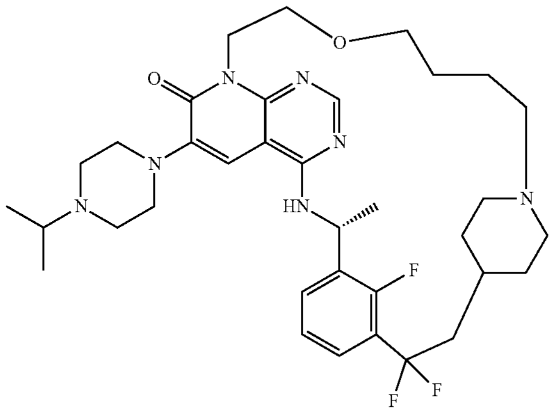 [SMILES: CC(C)N1CCN(c2cc3c4ncnc3n(c2=O)CCOCCCCN2CCC(CC2)CC(F)(F)c2cccc(c2F)[C@@H](C)N4)CC1] | (3R)-4²,5,5-trifluoro-1⁶-(4-isopropylpiperazin-1-yl)-3-methyl-1⁷,1⁸-dihydro-12-oxa-2-aza-1(4,8)-pyrido[2,3-d]pyrimidina-7(4,1)-piperidina-4(1,3)-benzenacyclotetradecaphan-1⁷-one | 656.7 |
| 136 | 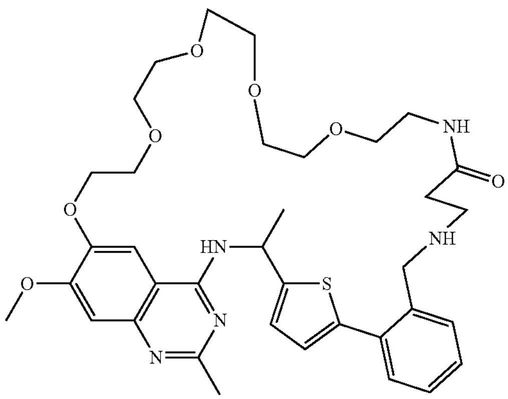 [SMILES: COc1cc2nc(C)nc3c2cc1OCCOCCOCCOCCOCCNC(=O)CCNCc1ccccc1C1=CC=C(S1)C(C)N3] | 5⁷-methoxy-5²,3-dimethyl-6,9,12,15,18-pentaoxa-4,21,25-triaza-5(4,6)-quinazolina-2(2,5)-thiophena-1(1,2)-benzenacyclohexacosaphan-22-one | 694.3 |
| 137 | 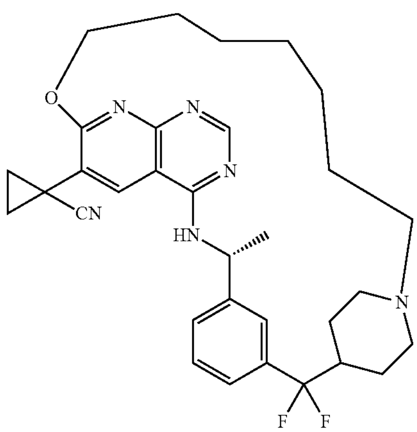 [SMILES: C[C@H]1Nc2ncnc3nc(c(C4(C#N)CC4)cc23)OCCCCCCCN2CCC(CC2)C(F)(F)c2cccc1c2] | (R)-1-(2,2-difluoro-4-methyl-7-oxa-5-aza-6(4,7)-pyrido[2,3-d]pyrimidina-1(4,1)-piperidina-3(1,3)-benzenacyclotetradecaphane-6⁶-yl)cyclopropane-1-carbonitrile | 561.4 |
| 138 | 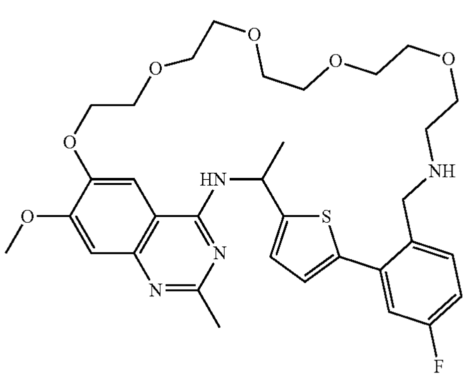 [SMILES: COc1cc2nc(C)nc3c2cc1OCCOCCOCCOCCOCCNCc1ccc(F)cc1C1=CC=C(S1)C(C)N3] | 1⁵-fluoro-5⁷-methoxy-5²,3-dimethyl-6,9,12,15,18-pentaoxa-4,21-diaza-5(4,6)-quinazolina-2(2,5)-thiophena-1(1,2)-benzenacyclodocosaphane | 641.3 |

TABLE 1-continued

| No. | Structure | Chemical Name | [M + H]+ |
|---|---|---|---|
| 139 | 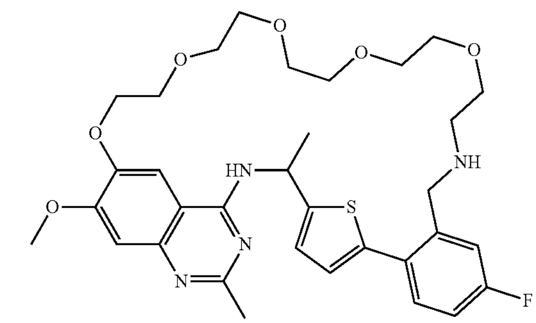 [SMILES: COc1cc2nc(C)nc3c2cc1OCCOCCOCCOCCOCCNCc1cc(F)ccc1C1=CC=C(S1)C(C)N3] | 1⁴-fluoro-5⁷-methoxy-5²,3-dimethyl-6,9,12,15,18-pentaoxa-4,21-diaza-5(4,6)-quinazolina-2(2,5)-thiophena-1(1,2)-benzenacyclodocosaphane | 641.3 |
| 140 | 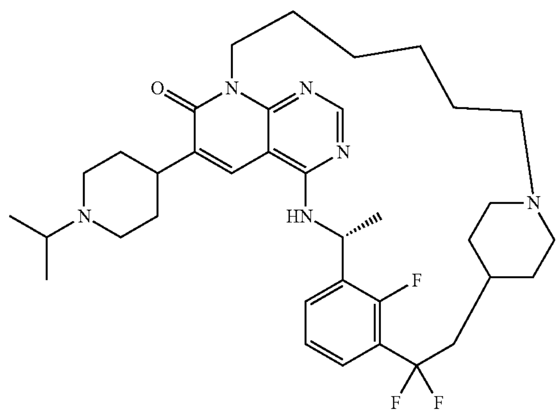 [SMILES: CC(C)N1CCC(c2cc3c4ncnc3n(c2=O)CCCCCCN2CCC(CC2)CC(F)(F)c2cccc(c2F)[C@@H](C)N4)CC1] | (3R)-4²,5,5-trifluoro-1⁶-(1-isopropylpiperidin-4-yl)-3-methyl-1⁷,1⁸-dihydro-2-aza-1(4,8)-pyrido[2,3-d]pyrimidina-7(4,1)-piperidina-4(1,3)-benzenacyclotridecaphan-1⁷-one | 639.3 |
| 141 | 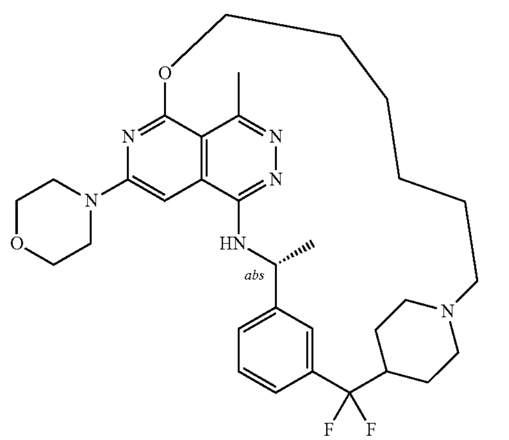 [SMILES: Cc1nnc2c3cc(N4CCOCC4)nc(c13)OCCCCCCN1CCC(CC1)C(F)(F)c1cccc(c1)[C@@H](C)N2] | (R)-2,2-difluoro-6⁴,4-dimethyl-6⁷-morpholino-7-oxa-5-aza-6(1,5)-pyrido[3,4-d]pyridazina-1(4,1)-piperidina-3(1,3)-benzenacyclotridecaphane | 581.2 |
| 142 | 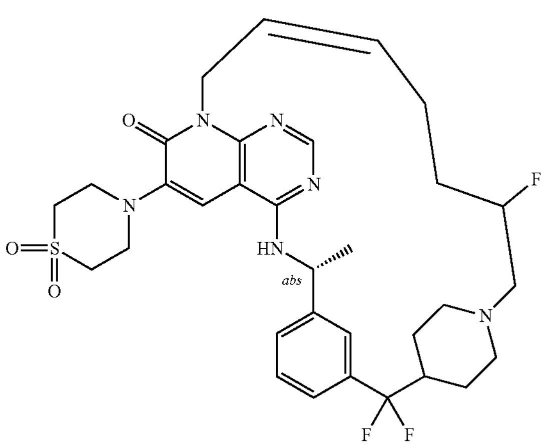 [SMILES: C[C@H]1Nc2ncnc3c2cc(N2CCS(=O)(=O)CC2)c(=O)n3C/C=C\CCC(F)CN2CCC(CC2)C(F)(F)c2cccc1c2] | (4R,Z)-6⁶-(1,1-dioxidotetrahydro-2H-thiopyran-4-yl)-2,2,1²-trifluoro-4-methyl-6⁷,6⁸-dihydro-5-aza-6(4,8)-pyrido[2,3-d]pyrimidina-1(4,1)-piperidina-3(1,3)-benzenacyclotridecaphan-8-en-6⁷-one | 644.2 |

TABLE 1-continued

| No. | Structure | Chemical Name | [M + H]+ |
|---|---|---|---|
| 143 | 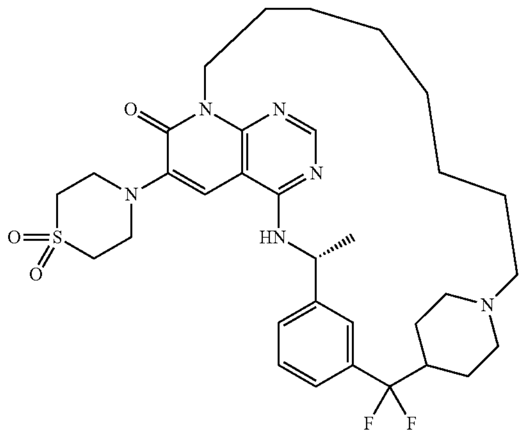 [SMILES: C[C@H]1Nc2ncnc3c2cc(N2CCS(=O)(=O)CC2)c(=O)n3CCCCCCCCN2CCC(CC2)C(F)(F)c2cccc1c2] | (4R)-6⁶-(1,1-dioxidotetrahydro-2H-thiopyran-4-yl])-2,2-difluoro-4-methyl-6⁷,6⁸-dihydro-5-aza-6(4,8)-pyrido[2,3-d]pyrimidina-1(4,1)-piperidina-3(1,3)-benzenacyclotetradecaphan-6⁷-one | 642.4 |
| 144 | 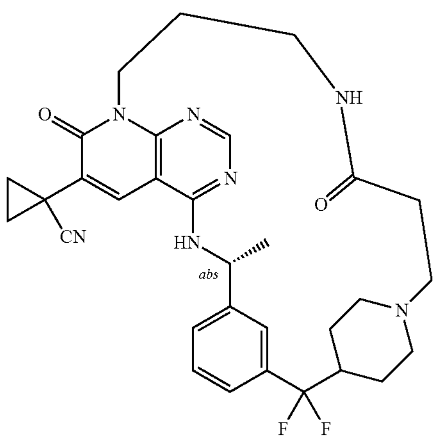 [SMILES: C[C@H]1Nc2ncnc3c2cc(C2(C#N)CC2)c(=O)n3CCCNC(=O)CCN2CCC(CC2)C(F)(F)c2cccc1c2] | 1-((4R)-2,2-difluoro-4-methyl-6⁷,11-dioxo-6⁷,6⁸-dihydro-5,10-diaza-6(4,8)-pyrido[2,3-d]pyrimidina-1(4,1)-piperidina-3(1,3)-benzenacyclotridecaphane-6⁶-yl)cyclopropane-1-carbonitrile | 576.3 |
| 145 | 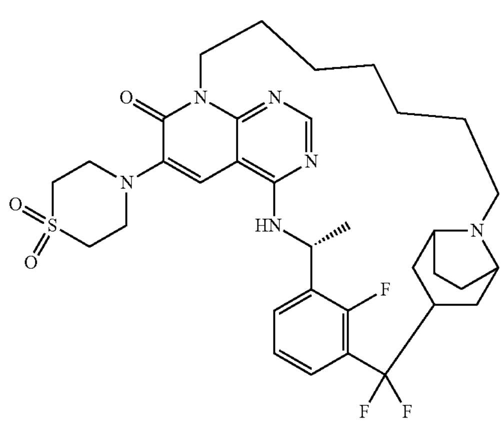 [SMILES: C[C@H]1Nc2ncnc3c2cc(N2CCS(=O)(=O)CC2)c(=O)n3CCCCCCCN2C3CCC2CC(C3)C(F)(F)c2cccc1c2F] | (1¹S,1⁵R,4R)-6⁶-(1,1-dioxidotetrahydro-2H-thiopyran-4-yl)-3²,2,2-trifluoro-4-methyl-6⁷,6⁸-dihydro-1⁸,5-diaza-6(4,8)-pyrido[2,3-d]pyrimidina-1(3,8)-bicyclo[3.2.1]octana-3(1,3)-benzenacyclotridecaphan-6⁷-one | 672.3 |

TABLE 1-continued

| No. | Structure | Chemical Name | [M + H]+ |
|---|---|---|---|
| 146 | 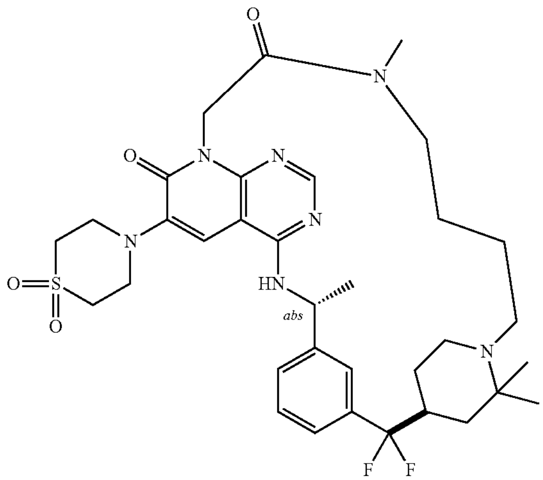 | (1⁴S,4R)-6⁶-(1,1-dioxidotetrahydro-2H-thiopyran-4-yl)-2,2-difluoro-1²,1²,4,9-tetramethyl-6⁷,6⁸-dihydro-5,9-diaza-6(4,8)-pyrido[2,3-d]pyrimidina-1(4,1)-piperidina-3(1,3)-benzenacyclotridecaphane-6⁷,8-dione | 685.3 |
| 147 | 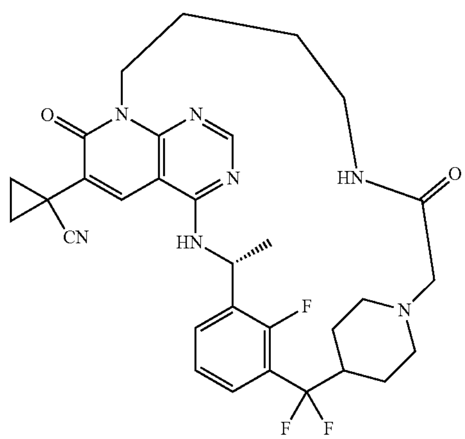 [SMILES: C[C@H]1Nc2ncnc3c2cc(C2(C#N)CC2)c(=O)n3CCCCNC(=O)CN2CCC(CC2)C(F)(F)c2cccc1c2F] | 1-((4R)-3²,2,2-trifluoro-4-methyl-6⁷,12-dioxo-6⁷,6⁸-dihydro-5,11-diaza-6(4,8)-pyrido[2,3-d]pyrimidina-1(4,1)-piperidina-3(1,3)-benzenacyclotridecaphane-6⁶-yl)cyclopropane-1-carbonitrile | 594.3 |
| 148 | 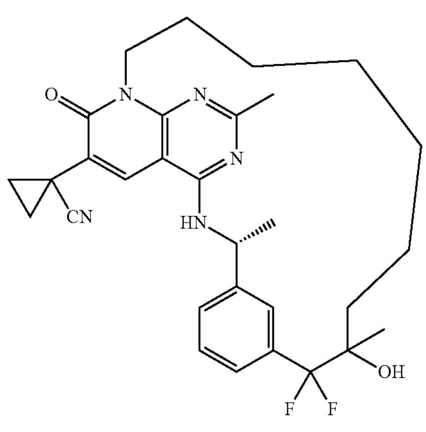 [SMILES: Cc1nc2c3cc(C4(C#N)CC4)c(=O)n(c3n1)CCCCCCCC(C)(O)C(F)(F)c1cccc(c1)[C@@H](C)N2] | 1-((3R)-5,5-difluoro-6-hydroxy-1²,3,6-trimethyl-1⁷-oxo-1⁷,1⁸-dihydro-2-aza-1(4,8)-pyrido[2,3-d]pyrimidina-4(1,3)-benzenacyclotridecaphane-1⁶-yl)cyclopropane-1-carbonitrile | 536.4 |

TABLE 1-continued

| No. | Structure | Chemical Name | [M + H]⁺ |
|---|---|---|---|
| 149 | 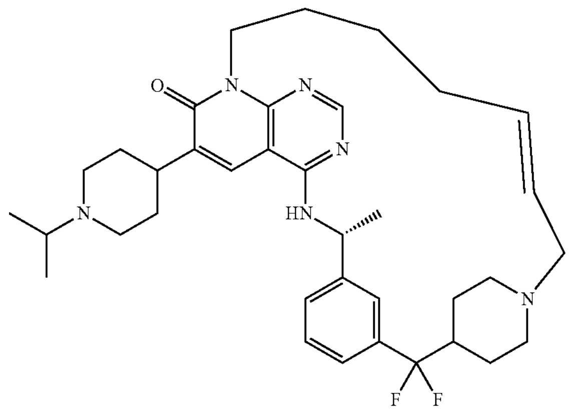 [SMILES: CC(C)N1CCC(c2cc3c4ncnc3n(c2=O)CCCC/C=C/CN2CCC(CC2)C(F)(F)c2cccc(c2)[C@@H](C)N4)CC1] | (4R,E)-2,2-difluoro-6⁶-(1-isopropylpiperidin-4-yl)-4-methyl-6⁷,6⁸-dihydro-5-aza-6(4,8)-pyrido[2,3-d]pyrimidina-1(4,1)-piperidina-3(1,3)-benzenacyclotridecaphan-11-en-6⁷-one | 619.4 |
| 150 | 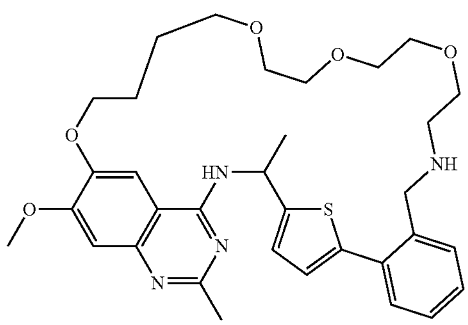 [SMILES: COc1cc2nc(C)nc3c2cc1OCCCCOCCOCCOCCNCc1ccccc1C1=CC=C(S1)C(C)N3] | 5⁷-methoxy-5²,3-dimethyl-6,11,14,17-tetraoxa-4,20-diaza-5(4,6)-quinazolina-2(2,5)-thiophena-1(1,2)-benzenacyclohenicosaphane | 607.3 |
| 151 | 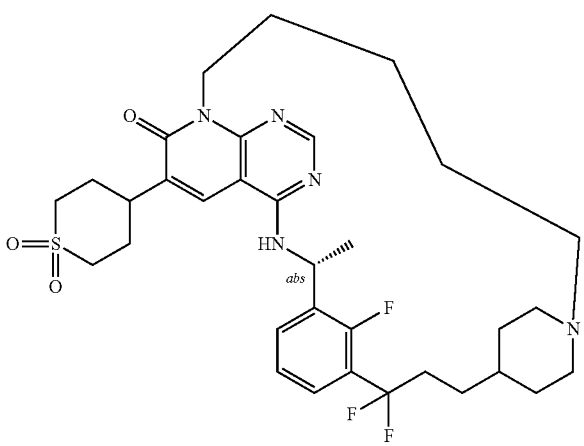 [SMILES: C[C@H]1Nc2ncnc3c2cc(C2CCS(=O)(=O)CC2)c(=O)n3CCCCCN2CCC(CC2)CCC(F)(F)c2cccc1c2F] | (3R)-1⁶-(1,1-dioxidotetrahydro-2H-thiopyran-4-yl)-4²,5,5-trifluoro-3-methyl-1⁷,1⁸-dihydro-2-aza-1(4,8)-pyrido[2,3-d]pyrimidina-8(4,1)-piperidina-4(1,3)-benzenacyclotridecaphan-1⁷-one | 646.2 |
| 152 | 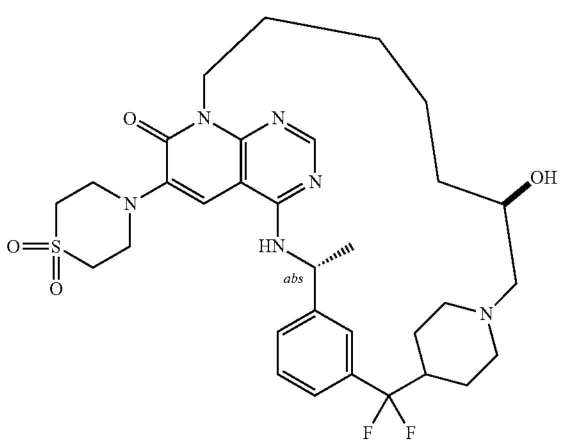 [SMILES: C[C@H]1Nc2ncnc3c2cc(N2CCS(=O)(=O)CC2)c(=O)n3CCCCC[C@@H](O)CN2CCC(CC2)C(F)(F)c2cccc1c2] | (4R,12R)-6⁶-(1,1-dioxidotetrahydro-2H-thiopyran-4-yl)-2,2-difluoro-12-hydroxy-4-methyl-6⁷,6⁸-dihydro-5-aza-6(4,8)-pyrido[2,3-d]pyrimidina-1(4,1)-piperidina-3(1,3)-benzenacyclotridecaphan-6⁷-one | 644.2 |

TABLE 1-continued

| No. | Structure | Chemical Name | [M + H]⁺ |
|---|---|---|---|
| 153 | 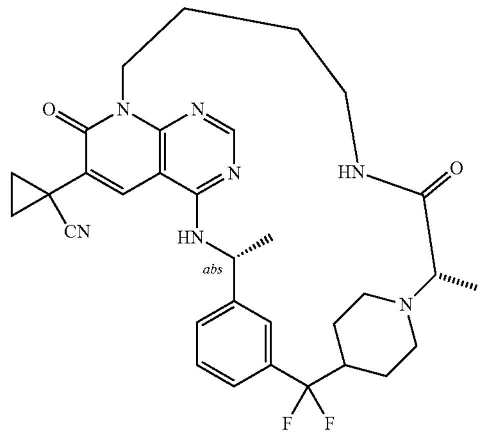 [SMILES: C[C@H]1Nc2ncnc3c2cc(C2(C#N)CC2)c(=O)n3CCCCNC(=O)[C@H](C)N2CCC(CC2)C(F)(F)c2cccc1c2] | 1-((4R,13S)-2,2-difluoro-4,13-dimethyl-6$^7$,12-dioxo-6$^7$,6$^8$-dihydro-5,11-diaza-6(4,8)-pyrido[2,3-d]pyrimidina-1(4,1)-piperidina-3(1,3)-benzenacyclotridecaphane-6$^6$-yl)cyclopropane-1-carbonitrile | 590.3 |
| 154 | 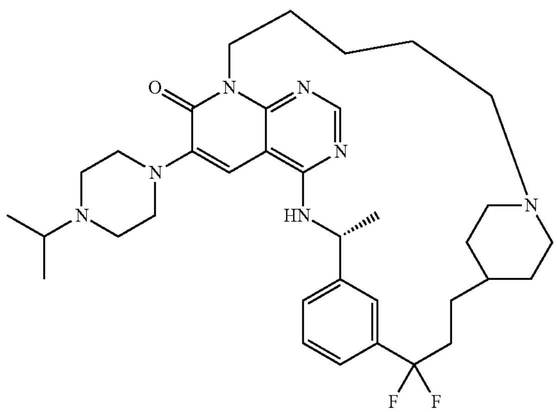 [SMILES: CC(C)N1CCN(c2cc3c4ncnc3n(c2=O)CCCCCN2CCC(CC2)CCC(F)(F)c2cccc(c2)[C@@H](C)N4)CC1] | (3R)-5,5-difluoro-1$^6$-(4-isopropylpiperazin-1-yl)-3-methyl-1$^7$,1$^8$-dihydro-2-aza-1(4,8)-pyrido[2,3-d]pyrimidina-8(4,1)-piperidina-4(1,3)-benzenacyclotridecaphan-1$^7$-one | 622.4 |
| 155 | 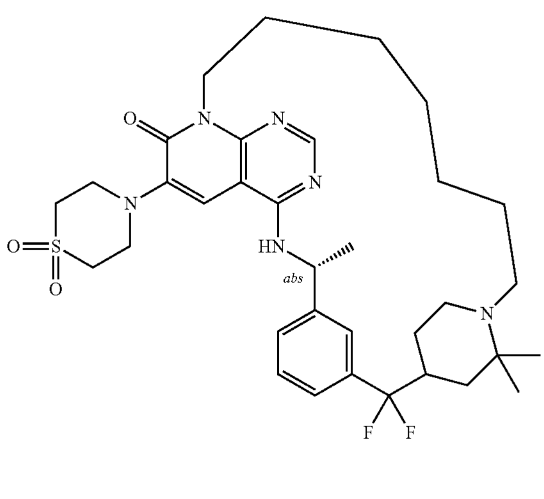 [SMILES: C[C@H]1Nc2ncnc3c2cc(N2CCS(=O)(=O)CC2)c(=O)n3CCCCCCCN2CCC(CC2(C)C)C(F)(F)c2cccc1c2] | (4R)-6$^6$-(1,1-dioxidotetrahydro-2H-thiopyran-4-yl)-2,2-difluoro-1$^2$,1$^2$,4-trimethyl-6$^7$,6$^8$-dihydro-5-aza-6(4,8)-pyrido[2,3-d]pyrimidina-1(4,1)-piperidina-3(1,3)-benzenacyclotridecaphan-6$^7$-one | 656.3 |

TABLE 1-continued

| No. | Structure | Chemical Name | [M + H]+ |
|---|---|---|---|
| 156 | 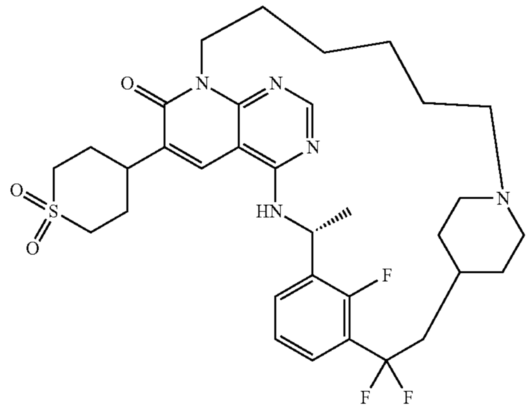 [SMILES: C[C@H]1Nc2ncnc3c2cc(C2CCS(=O)(=O)CC2)c(=O)n3CCCCCCN2CCC(CC2)CC(F)(F)c2cccc1c2F] | (3R)-1⁶-(1,1-dioxidothiomorpholino)-4²,5,5-trifluoro-3-methyl-1⁷,1⁸-dihydro-2-aza-1(4,8)-pyrido[2,3-d]pyrimidina-7(4,1)-piperidina-4(1,3)-benzenacyclotridecaphan-1⁷-one | 646.8 |
| 157 | 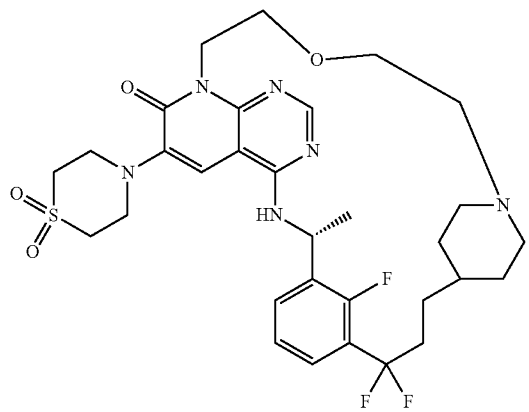 [SMILES: C[C@H]1Nc2ncnc3c2cc(N2CCS(=O)(=O)CC2)c(=O)n3CCOCCN2CCC(CC2)CCC(F)(F)c2cccc1c2F] | (3R)-1⁶-(1,1-dioxidotetrahydro-2H-thiopyran-4-yl)-4²,5,5-trifluoro-3-methyl-1⁷,1⁸-dihydro-11-oxa-2-aza-1(4,8)-pyrido[2,3-d]pyrimidina-8(4,1)-piperidina-4(1,3)-benzenacyclotridecaphan-1⁷-one | 648.6 |
| 158 | 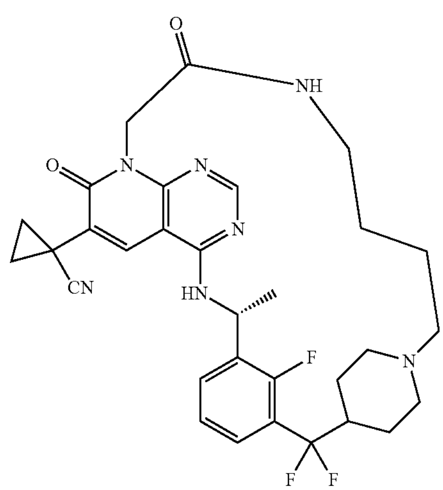 [SMILES: C[C@H]1Nc2ncnc3c2cc(C2(C#N)CC2)c(=O)n3CC(=O)NCCCCN2CCC(CC2)C(F)(F)c2cccc1c2F] | 1-((4R)-3²,2,2-trifluoro-4-methyl-6⁷,8-dioxo-6⁷,6⁸-dihydro-5,9-diaza-6(4,8)-pyrido[2,3-d]pyrimidina-1(4,1)-piperidina-3(1,3)-benzenacyclotridecaphane-6⁶-yl)cyclopropane-1-carbonitrile | 594.7 |

TABLE 1-continued

| No. | Structure | Chemical Name | [M + H]+ |
|---|---|---|---|
| 159 | 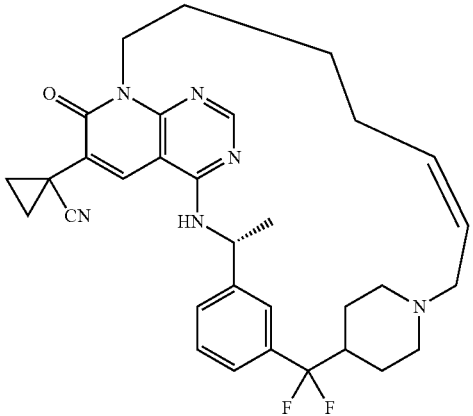 [SMILES: C[C@H]1Nc2ncnc3c2cc(C2(C#N)CC2)c(=O)n3CCCC/C=C\CN2CCC(CC2)C(F)(F)c2cccc1c2] | 1-((4R,Z)-2,2-difluoro-4-methyl-6$^7$-oxo-6$^7$,6$^8$-dihydro-5-aza-6(4,8)-pyrido[2,3-d]pyrimidina-1(4,1)-piperidina-3(1,3)-benzenacyclotridecaphan-11-en-6$^6$-yl)cyclopropane-1-carbonitrile | 559.4 |
| 160 | 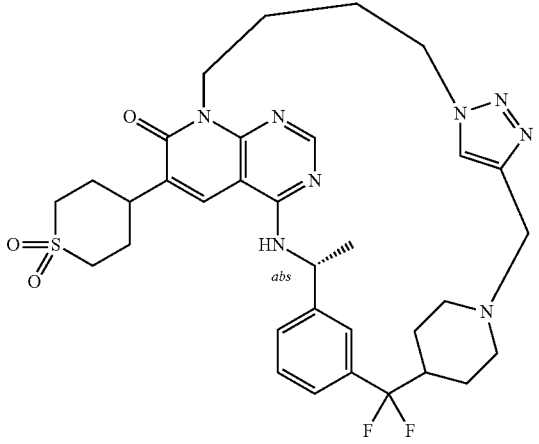 [SMILES: C[C@H]1Nc2ncnc3c2cc(C2CCS(=O)(=O)CC2)c(=O)n3CCCCn2cc(nn2)CN2CCC(CC2)C(F)(F)c2cccc1c2] | (6R,Z)-8$^6$-(1,1-dioxidotetrahydro-2H-thiopyran-4-yl)-4,4-difluoro-6-methyl-8$^7$,8$^8$-dihydro-1$^1$H-7-aza-8(4,8)-pyrido[2,3-d]pyrimidina-3(1,4)-piperidina-1(4,1)-triazola-5(1,3)-benzenacyclododecaphan-8$^7$-one | 667.3 |
| 161 | 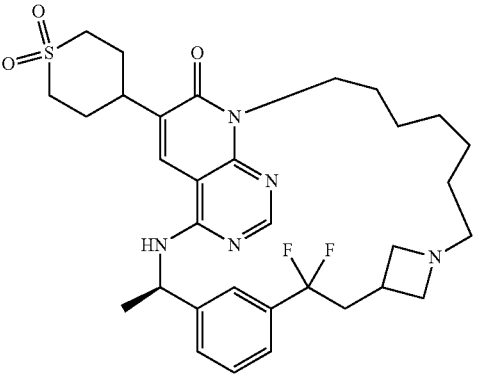 [SMILES: C[C@H]1Nc2ncnc3c2cc(C2CCS(=O)(=O)CC2)c(=O)n3CCCCCCCN2CC(C2)CC(F)(F)c2cccc1c2] | (3R)-1$^6$-(1,1-dioxidotetrahydro-2H-thiopyran-4-yl)-5,5-difluoro-3-methyl-1$^7$,1$^8$-dihydro-2-aza-1(4,8)-pyrido[2,3-d]pyrimidina-7(3,1)-azetidina-4(1,3)-benzenacyclotetradecaphan-1$^7$-one | 614.3 |

TABLE 1-continued

| No. | Chemical Name | [M + H]⁺ |
|---|---|---|
| 162 | (4R)-3²,2,2-trifluoro-6⁶-(1-isopropylpiperidin-4-yl)-4-methyl-6⁷,6⁸-dihydro-5-aza-6(4,8)-pyrido[2,3-d]pyrimidina-1(4,1)-piperidina-3(1,3)-benzenacyclotridecaphan-6⁷-one | 639.7 |
| 163 | (4R)-2,2-difluoro-6⁶-(4-isopropylpiperazin-1-yl)-4,9-dimethyl-6⁷,6⁸-dihydro-5,9-diaza-6(4,8)-pyrido[2,3-d]pyrimidina-1(4,1)-piperidina-3(1,3)-benzenacyclotridecaphane-6⁷,8-dione | 651.3 |
| 164 | (4R)-6⁶-(1,1-dioxidotetrahydro-2H-thiopyran-4-yl)-3²,2,2-trifluoro-12-hydroxy-4-methyl-6⁷,6⁸-dihydro-5-aza-6(4,8)-pyrido[2,3-d]pyrimidina-1(4,1)-piperidina-3(1,3)-benzenacyclotridecaphan-6⁷-one | 662.4 |

TABLE 1-continued

| No. | Structure | Chemical Name | [M + H]+ |
|---|---|---|---|
| 165 | 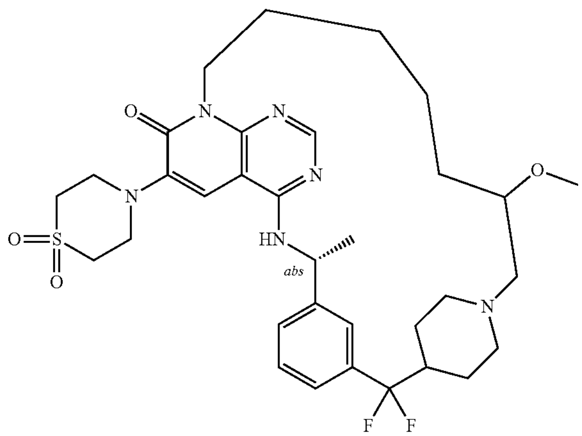 | (4R)-6⁶-(1,1-dioxidotetrahydro-2H-thiopyran-4-yl)-2,2-difluoro-12-methoxy-4-methyl-6⁷,6⁸-dihydro-5-aza-6(4,8)-pyrido[2,3-d]pyrimidina-1(4,1)-piperidina-3(1,3)-benzenacyclotridecaphan-6⁷-one | 658.3 |
| 166 | 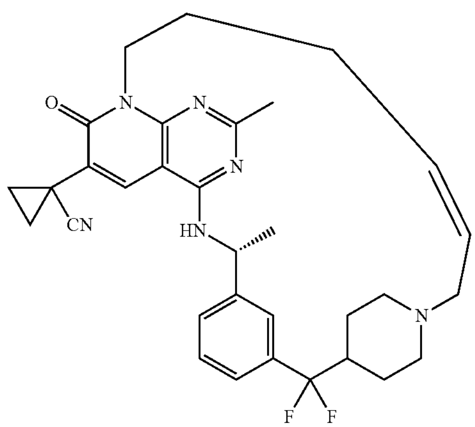 [SMILES: Cc1nc2c3cc(C4(C#N)CC4)c(=O)n(c3n1)CCC/C=C\CN1CCC(CC1)C(F)(F)c1cccc(c1)[C@@H](C)N2] | 1-((4R,Z)-2,2-difluoro-6²,4-dimethyl-6⁷-oxo-6⁷,6⁸-dihydro-5-aza-6(4,8)-pyrido[2,3-d]pyrimidina-1(4,1)-piperidina-3(1,3)-benzenacyclododecaphan-10-en-6⁶-yl)cyclopropane-1-carbonitrile | 559.5 |
| 167 | 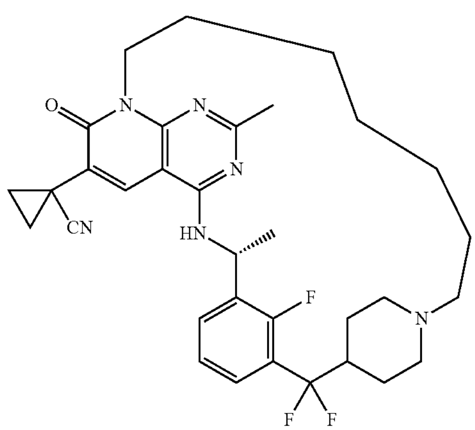 [SMILES: Cc1nc2c3cc(C4(C#N)CC4)c(=O)n(c3n1)CCCCCCCN1CCC(CC1)C(F)(F)c1cccc(c1F)[C@@H](C)N2] | 1-((4R)-3²,2,2-trifluoro-6²,4-dimethyl-6⁷-oxo-6⁷,6⁸-dihydro-5-aza-6(4,8)-pyrido[2,3-d]pyrimidina-1(4,1)-piperidina-3(1,3)-benzenacyclotridecaphane-6⁶-yl)cyclopropane-1-carbonitrile | 593.5 |

TABLE 1-continued

| No. | Structure | Chemical Name | [M + H]+ |
|---|---|---|---|
| 168 | 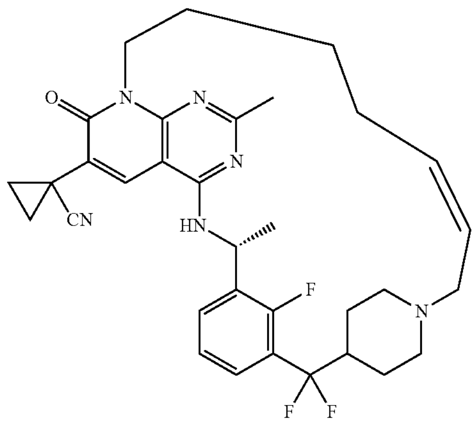 [SMILES: Cc1nc2c3cc(C4(C#N)CC4)c(=O)n(c3n1)CCCC/C=C\CN1CCC(CC1)C(F)(F)c1cccc(c1F)[C@@H](C)N2] | 1-((4R,Z)-3$^2$,2,2-trifluoro-6$^2$,4-dimethyl-6$^7$-oxo-6$^7$,6$^8$-dihydro-5-aza-6(4,8)-pyrido[2,3-d]pyrimidina-1(4,1)-piperidina-3(1,3)-benzenacyclotridecaphan-11-en-6$^6$-yl)cyclopropane-1-carbonitrile | 591.5 |
| 169 | 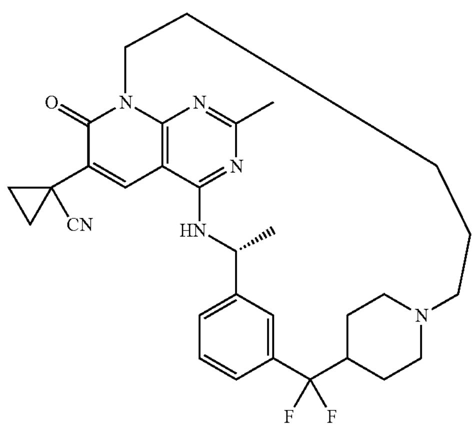 [SMILES: Cc1nc2c3cc(C4(C#N)CC4)c(=O)n(c3n1)CCCCCN1CCC(CC1)C(F)(F)c1cccc(c1)[C@@H](C)N2] | 1-((4R)-2,2-difluoro-6$^2$,4-dimethyl-6$^7$-oxo-6$^7$,6$^8$-dihydro-5-aza-6(4,8)-pyrido[2,3-d]pyrimidina-1(4,1)-piperidina-3(1,3)-benzenacycloundecaphane-6$^6$-yl)cyclopropane-1-carbonitrile | 547.4 |
| 170 | 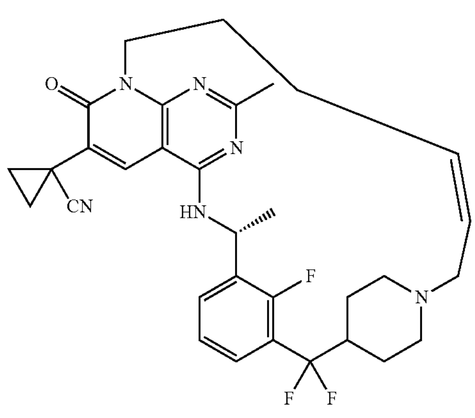 [SMILES: Cc1nc2c3cc(C4(C#N)CC4)c(=O)n(c3n1)CCC/C=C\CN1CCC(CC1)C(F)(F)c1cccc(c1F)[C@@H](C)N2] | 1-((4R,Z)-3$^2$,2,2-trifluoro-6$^2$,4-dimethyl-6$^7$-oxo-6$^7$,6$^8$-dihydro-5-aza-6(4,8)-pyrido[2,3-d]pyrimidina-1(4,1)-piperidina-3(1,3)-benzenacyclododecaphan-10-en-6$^6$-yl)cyclopropane-1-carbonitrile | 577.5 |

TABLE 1-continued

| No. | Structure | Chemical Name | [M + H]+ |
|---|---|---|---|
| 171 | 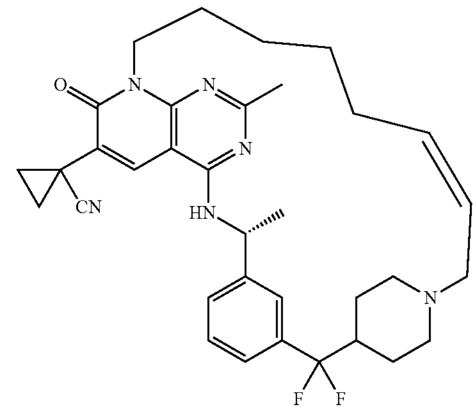 [SMILES: Cc1nc2c3cc(C4(C#N)CC4)c(=O)n(c3n1)CCCCC/C=C\CN1CCC(CC1)C(F)(F)c1cccc(c1)[C@@H](C)N2] | 1-((4R,Z)-2,2-difluoro-6$^2$,4-dimethyl-6$^7$-oxo-6$^7$,6$^8$-dihydro-5-aza-6(4,8)-pyrido[2,3-d]pyrimidina-1(4,1)-piperidina-3(1,3)-benzenacyclotetradecaphan-12-en-6$^6$-yl)cyclopropane-1-carbonitrile | 587.5 |
| 172 | 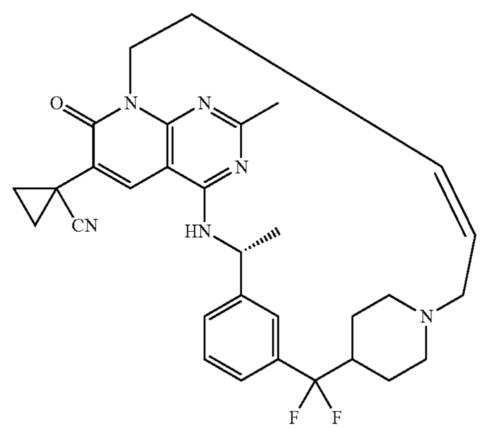 [SMILES: Cc1nc2c3cc(C4(C#N)CC4)c(=O)n(c3n1)CC/C=C\CN1CCC(CC1)C(F)(F)c1cccc(c1)[C@@H](C)N2] | 1-((4R,Z)-2,2-difluoro-6$^2$,4-dimethyl-6$^7$-oxo-6$^7$,6$^8$-dihydro-5-aza-6(4,8)-pyrido[2,3-d]pyrimidina-1(4,1)-piperidina-3(1,3)-benzenacycloundecaphan-9-en-6$^6$-yl)cyclopropane-1-carbonitrile | 545.4 |
| 173 | 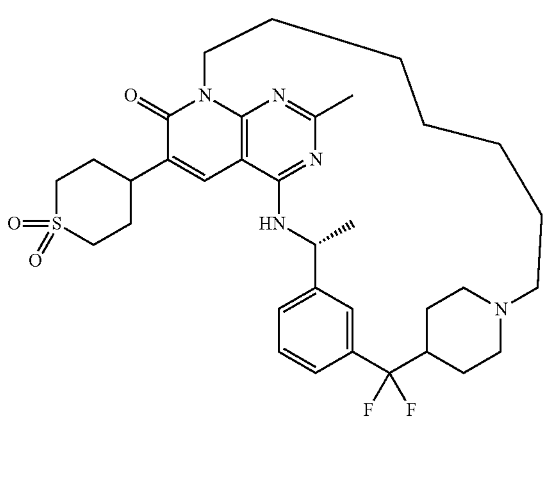 [SMILES: Cc1nc2c3cc(C4CCS(=O)(=O)CC4)c(=O)n(c3n1)CCCCCCCN1CCC(CC1)C(F)(F)c1cccc(c1)[C@@H](C)N2] | (4R)-6$^6$-(1,1-dioxidotetrahydro-2H-thiopyran-4-yl)-2,2-difluoro-6$^2$,4-dimethyl-6$^7$,6$^8$-dihydro-5-aza-6(4,8)-pyrido[2,3-d]pyrimidina-1(4,1)-piperidina-3(1,3)-benzenacyclotridecaphan-6$^7$-one | 642.5 |

TABLE 1-continued

| No. | Structure | Chemical Name | [M + H]+ |
|---|---|---|---|
| 174 | 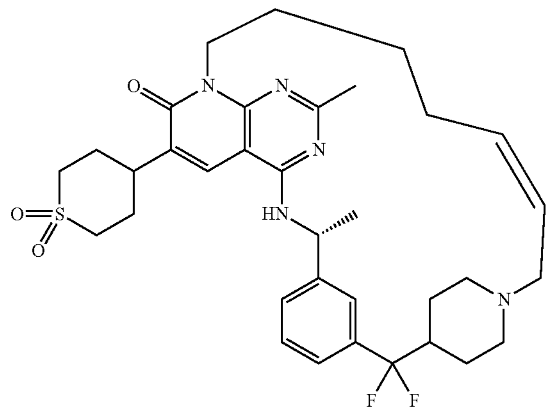 [SMILES: Cc1nc2c3cc(C4CCS(=O)(=O)CC4)c(=O)n(c3n1)CCCC/C=C\CN1CCC(CC1)C(F)(F)c1cccc(c1)[C@@H](C)N2] | (4R,Z)-6⁶-(1,1-dioxidotetrahydro-2H-thiopyran-4-yl)-2,2-difluoro-6²,4-dimethyl-6⁷,6⁸-dihydro-5-aza-6(4,8)-pyrido[2,3-d]pyrimidina-1(4,1)-piperidina-3(1,3)-benzenacyclotridecaphan-11-en-6⁷-one | 640.5 |
| 175 | 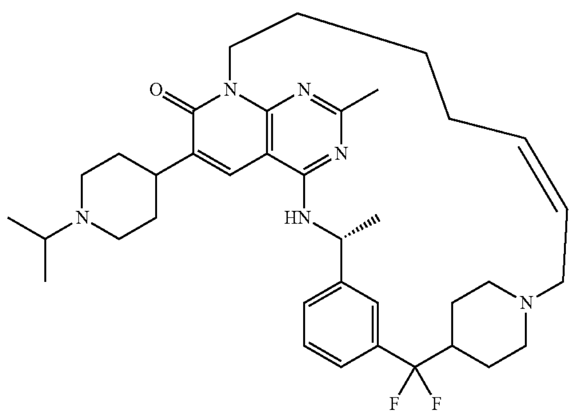 [SMILES: Cc1nc2c3cc(C4CCN(C(C)C)CC4)c(=O)n(c3n1)CCCC/C=C\CN1CCC(CC1)C(F)(F)c1cccc(c1)[C@@H](C)N2] | (4R,Z)-2,2-difluoro-6⁶-(1-isopropylpiperidin-4-yl)-6²,4-dimethyl-6⁷,6⁸-dihydro-5-aza-6(4,8)-pyrido[2,3-d]pyrimidina-1(4,1)-piperidina-3(1,3)-benzenacyclotridecaphan-11-en-6⁷-one | 633.5 |
| 176 | 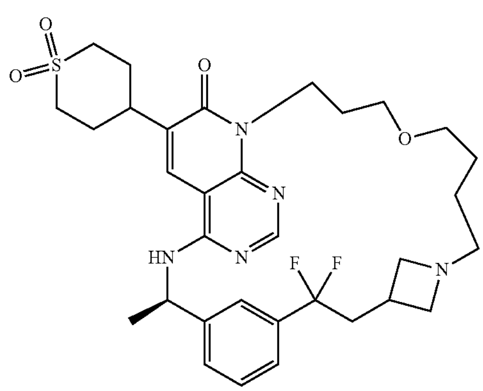 [SMILES: C[C@H]1Nc2ncnc3c2cc(C2CCS(=O)(=O)CC2)c(=O)n3CCCOCCCCN2CC(C2)CC(F)(F)c2cccc1c2] | (3R)-1⁶-(1,1-dioxidotetrahydro-2H-thiopyran-4-yl)-5,5-difluoro-3-methyl-1⁷,1⁸-dihydro-12-oxa-2-aza-1(4,8)-pyrido[2,3-d]pyrimidina-7(3,1)-azetidina-4(1,3)-benzenacyclopentadecaphan-1⁷-one | 630.4 |

TABLE 1-continued

| No. | Structure | Chemical Name | [M + H]+ |
|---|---|---|---|
| 177 | 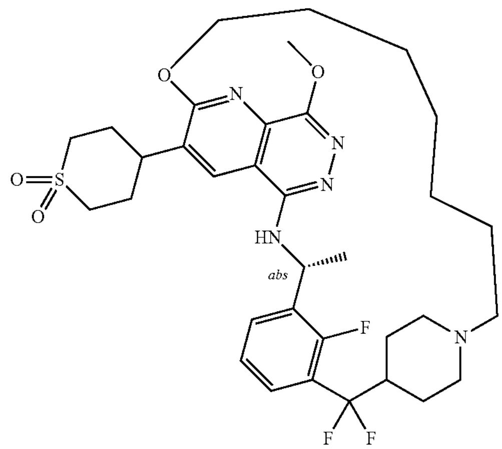 [SMILES: COc1nnc2c3cc(C4CCS(=O)(=O)CC4)c(nc13)OCCCCCCCN1CCC(CC1)C(F)(F)c1cccc(c1F)[C@@H](C)N2] | (R)-4-(3²,2,2-trifluoro-6⁸-methoxy-4-methyl-7-oxa-5-aza-6(5,2)-pyrido[2,3-d]pyridazina-1(4,1)-piperidina-3(1,3)-benzenacyclotetradecaphane-6³-yl)tetrahydro-2H-thiopyran 1,1-dioxide | 676.3 |
| 178 | 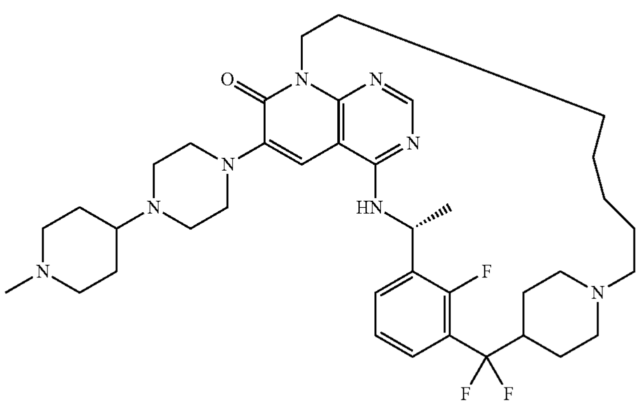 [SMILES: C[C@H]1Nc2ncnc3c2cc(N2CCN(C4CCN(C)CC4)CC2)c(=O)n3CCCCCCCN2CCC(CC2)C(F)(F)c2cccc1c2F] | (4R)-3₂,2,2-trifluoro-4-methyl-6₆-(4-(1-methylpiperidin-4-yl)piperazin-1-yl)-6₇,6₈-dihydro-5-aza-6(4,8)-pyrido[2,3-d]pyrimidina-1(4,1)-piperidina-3(1,3)-benzenacyclotridecaphan-6⁷-one | 695.5 |
| 179 | 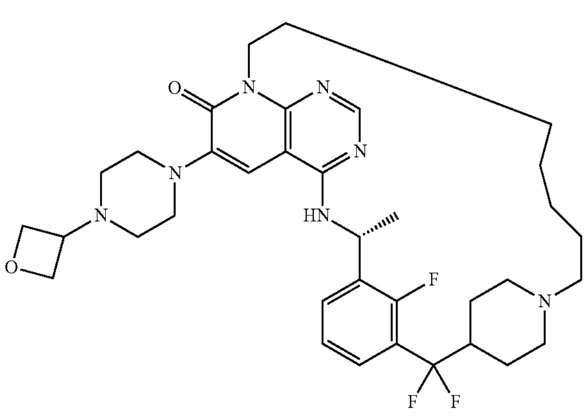 [SMILES: C[C@H]1Nc2ncnc3c2cc(N2CCN(C4COC4)CC2)c(=O)n3CCCCCCCN2CCC(CC2)C(F)(F)c2cccc1c2F] | (4R)-3²,2,2-trifluoro-4-methyl-6⁶-(4-(oxetan-3-yl)piperazin-1-yl)-6⁷,6⁸-dihydro-5-aza-6(4,8)-pyrido[2,3-d]pyrimidina-1(4,1)-piperidina-3(1,3)-benzenacyclotridecaphan-6⁷-one | 654.3 |

TABLE 1-continued

| No. | Structure | Chemical Name | [M + H]+ |
| --- | --- | --- | --- |
| 180 | 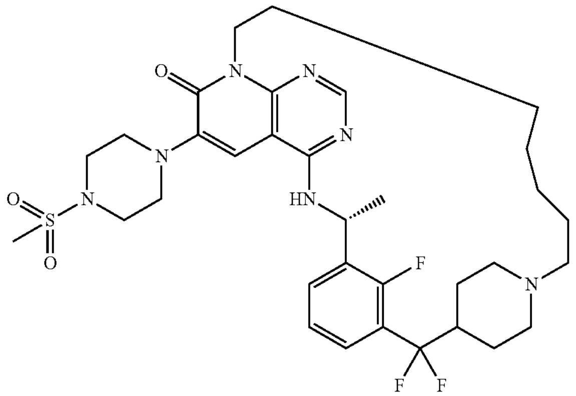 [SMILES: C[C@H]1Nc2ncnc3c2cc(N2CCN(S(C)(=O)=O)CC2)c(=O)n3CCCCCCCN2CCC(CC2)C(F)(F)c2cccc1c2F] | (4R)-3$^2$,2,2-trifluoro-4-methyl-6$^6$-(4-(methylsulfonyl)piperazin-1-yl)-6$^7$,6$^8$-dihydro-5-aza-6(4,8)-pyrido[2,3-d]pyrimidina-1(4,1)-piperidina-3(1,3)-benzenacyclotridecaphan-6$^7$-one | 676.4 |
| 181 | 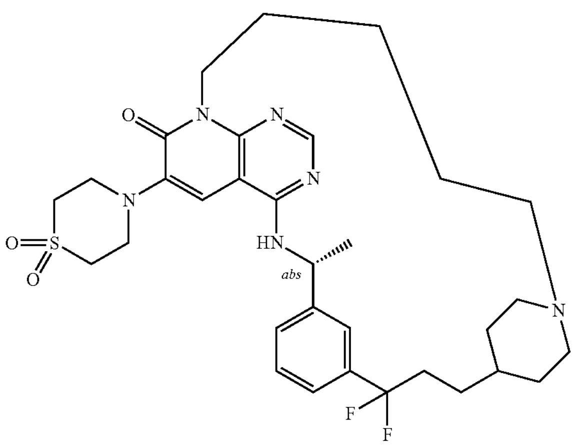 [SMILES: C[C@H]1Nc2ncnc3c2cc(N2CCS(=O)(=O)CC2)c(=O)n3CCCCCN2CCC(CC2)CCC(F)(F)c2cccc1c2] | (3R)-1$^6$-(1,1-dioxidothiomorpholino)-5,5-difluoro-3-methyl-1$^7$,1$^8$-dihydro-2-aza-1(4,8)-pyrido[2,3-d]pyrimidina-8(4,1)-piperidina-4(1,3)-benzenacyclotridecaphan-1$^7$-one | 629.3 |
| 182 | 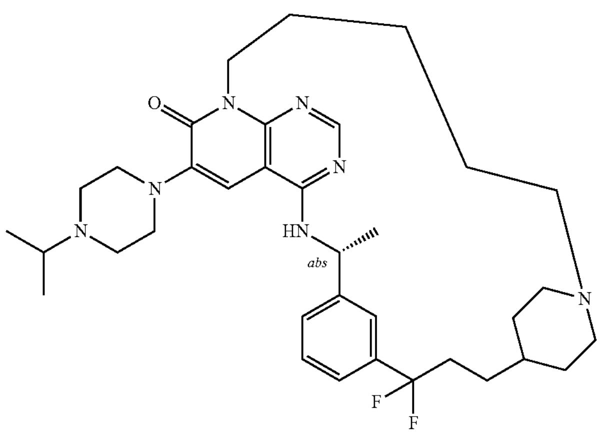 [SMILES: CC(C)N1CCN(c2cc3c4ncnc3n(c2=O)CCCCCN2CCC(CC2)CCC(F)(F)c2cccc(c2)[C@@H](C)N4)CC1] | (3R)-5,5-difluoro-1$^6$-(1-isopropylpiperidin-4-yl)-3-methyl-1$^7$,1$^8$-dihydro-2-aza-1(4,8)-pyrido[2,3-d]pyrimidina-8(4,1)-piperidina-4(1,3)-benzenacyclotridecaphan-1$^7$-one | 621.4 |

TABLE 1-continued

| No. | Structure | Chemical Name | [M + H]+ |
|---|---|---|---|
| 183 | 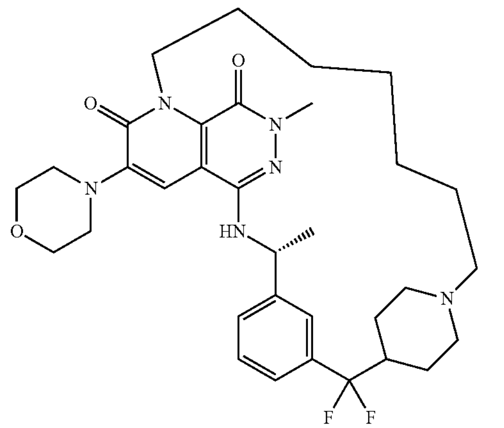 [SMILES: C[C@H]1Nc2nn(C)c(=O)c3c2cc(N2CCOCC2)c(=O)n3CCCCCCCN2CCC(CC2)C(F)(F)c2cccc1c2] | (4R,E)-2,2-difluoro-6⁷,4-dimethyl-6³-morpholino-6¹,6²,6⁷,6⁸-tetrahydro-5-aza-6(5,1)-pyrido[2,3-d]pyridazina-1(4,1)-piperidina-3(1,3)-benzenacyclotridecaphane-6²,6⁸-dione | 611.5 |
| 184 | 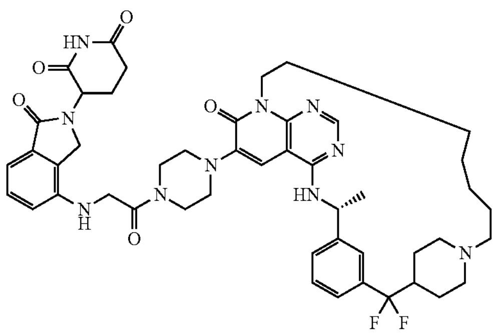 [SMILES: C[C@H]1Nc2ncnc3c2cc(N2CCN(C(=O)CNc4cccc5c4CN(C4CCC(=O)NC4=O)C5=O)CC2)c(=O)n3CCCCCCCN2CCC(CC2)C(F)(F)c2cccc1c2] | 3-(4-((2-(4-((4R)-2,2-difluoro-4-methyl-6⁷-oxo-6⁷,6⁸-dihydro-5-aza-6(4,8)-pyrido[2,3-d]pyrimidina-1(4,1)-piperidina-3(1,3)-benzenacyclotridecaphane-6⁶-yl)piperazin-1-yl)-2-oxoethyl)amino)-1-oxoisoindolin-2-yl)piperidine-2,6-dione | 879.7 |
| 185 | 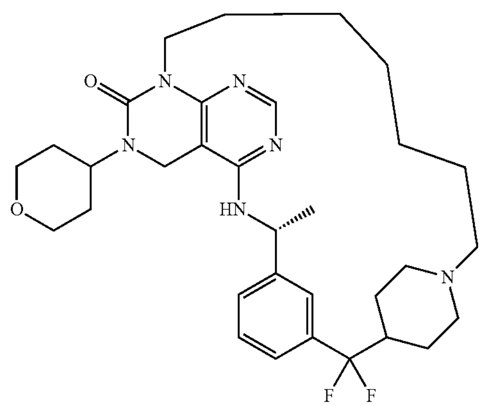 [SMILES: C[C@H]1Nc2ncnc3c2CN(C2CCOCC2)C(=O)N3CCCCCCCN2CCC(CC2)C(F)(F)c2cccc1c2] | (4R)-2,2-difluoro-4-methyl-6³-(tetrahydro-2H-pyran-4-yl)-6¹,6²,6³,6⁴-tetrahydro-5-aza-6(5,1)-pyrimido[4,5-d]pyrimidina-1(4,1)-piperidina-3(1,3)-benzenacyclotridecaphan-6²-one | 583.5 |
| 186 | 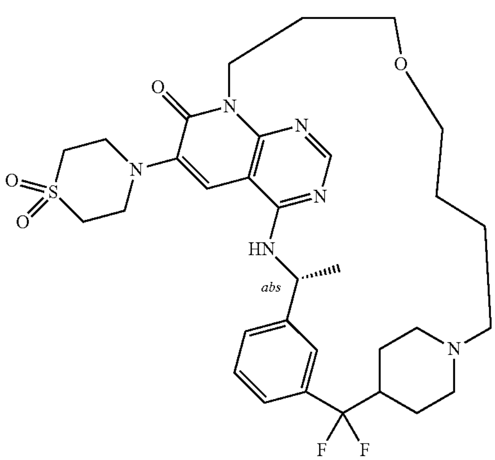 [SMILES: C[C@H]1Nc2ncnc3c2cc(N2CCS(=O)(=O)CC2)c(=O)n3CCCOCCCCN2CCC(CC2)C(F)(F)c2cccc1c2] | (4R)-6⁶-(1,1-dioxidothiomorpholino)-2,2-difluoro-4-methyl-6⁷,6⁸-dihydro-10-oxa-5-aza-6(4,8)-pyrido[2,3-d]pyrimidina-1(4,1)-piperidina-3(1,3)-benzenacyclotetradecaphan-6⁷-one | 645.3 |

TABLE 1-continued

| No. | Structure | Chemical Name | [M + H]+ |
|---|---|---|---|
| 187 | 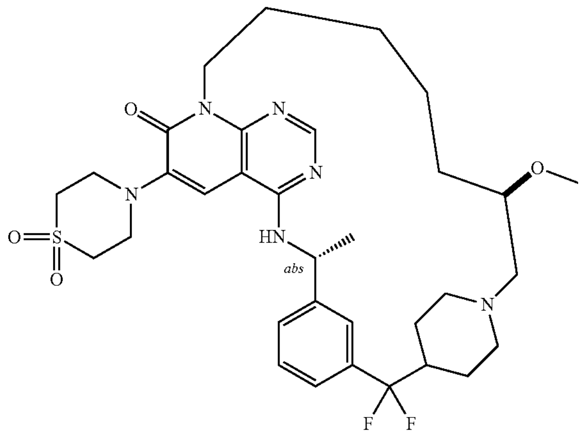 [SMILES: CO[C@@H]1CCCCCn2c(=O)c(N3CCS(=O)(=O)CC3)cc3c(ncnc32)N[C@H](C)c2cccc(c2)C(F)(F)C2CCN(CC2)C1] | (4R,12R)-6⁶-(1,1-dioxidotetrahydro-2H-thiopyran-4-yl)-2,2-difluoro-12-methoxy-4-methyl-6⁷,6⁸-dihydro-5-aza-6(4,8)-pyrido[2,3-d]pyrimidina-1(4,1)-piperidina-3(1,3)-benzenacyclotridecaphan-6⁷-one | 658.3 |
| 188 | 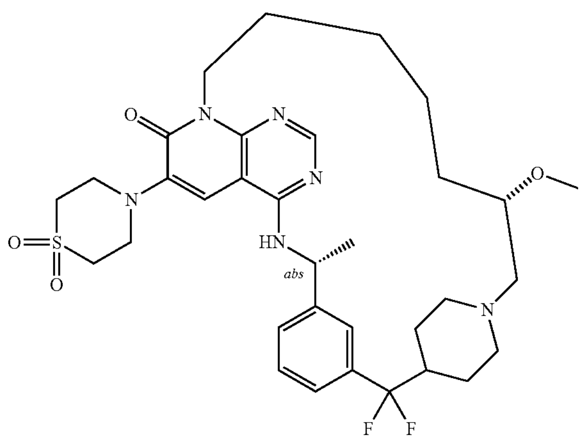 [SMILES: CO[C@H]1CCCCCn2c(=O)c(N3CCS(=O)(=O)CC3)cc3c(ncnc32)N[C@H](C)c2cccc(c2)C(F)(F)C2CCN(CC2)C1] | (4R,12S)-6⁶-(1,1-dioxidotetrahydro-2H-thiopyran-4-yl)-2,2-difluoro-12-methoxy-4-methyl-6⁷,6⁸-dihydro-5-aza-6(4,8)-pyrido[2,3-d]pyrimidina-1(4,1)-piperidina-3(1,3)-benzenacyclotridecaphan-6⁷-one | 658.6 |
| 189 | 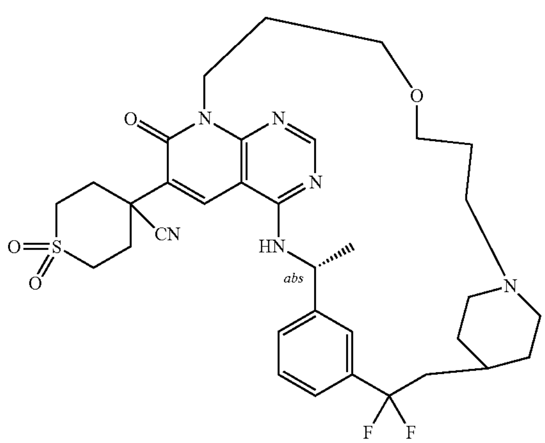 [SMILES: C[C@H]1Nc2ncnc3c2cc(C2(C#N)CCS(=O)(=O)CC2)c(=O)n3CCCOCCCN2CCC(CC2)CC(F)(F)c2cccc1c2] | 4-((3R)-5,5-difluoro-3-methyl-1⁷-oxo-1⁷,1⁸-dihydro-11-oxa-2-aza-1(4,8)-pyrido[2,3-d]pyrimidina-7(4,1)-piperidina-4(1,3)-benzenacyclotetradecaphane-1⁶-yl)tetrahydro-2H-thiopyran-4-carbonitrile 1,1-dioxide | 669.3 |

TABLE 1-continued

| No. | Structure | Chemical Name | [M + H]+ |
|---|---|---|---|
| 190 | 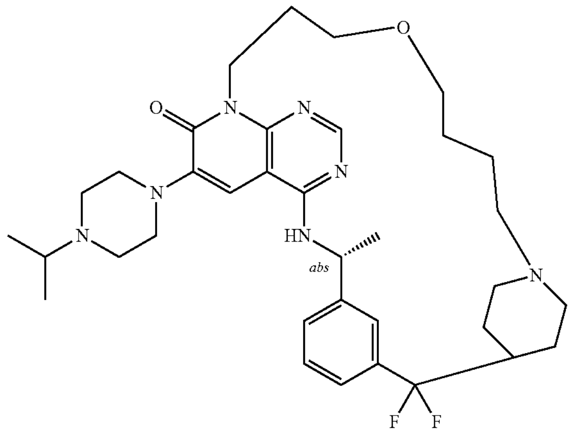 [SMILES: CC(C)N1CCN(c2cc3c4ncnc3n(c2=O)CCCOCCCCN2CCC(CC2)C(F)(F)c2cccc(c2)[C@@H](C)N4)CC1] | (4R)-2,2-difluoro-6⁶-(4-isopropylpiperazin-1-yl)-4-methyl-6⁷,6⁸-dihydro-10-oxa-5-aza-6(4,8)-pyrido[2,3-d]pyrimidina-1(4,1)-piperidina-3(1,3)-benzenacyclotetradecaphan-6⁷-one | 638.4 |
| 191 | 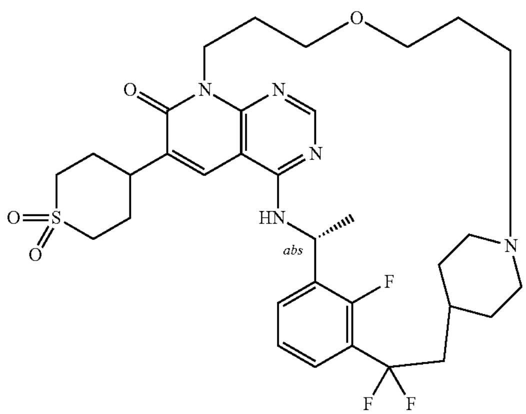 [SMILES: C[C@H]1Nc2ncnc3c2cc(C2CCS(=O)(=O)CC2)c(=O)n3CCCOCCCN2CCC(CC2)CC(F)(F)c2cccc1c2F] | (3R)-1⁶-(1,1-dioxidotetrahydro-2H-thiopyran-4-yl)-4²,5,5-trifluoro-3-methyl-1⁷,1⁸-dihydro-11-oxa-2-aza-1(4,8)-pyrido[2,3-d]pyrimidina-7(4,1)-piperidina-4(1,3)-benzenacyclotetradecaphan-1⁷-one | 662.3 |
| 192 | 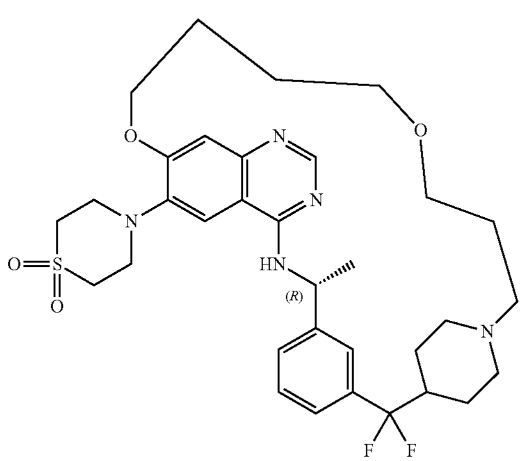 | (R)-4-(2,2-difluoro-4-methyl-7,12-dioxa-5-aza-6(4,7)-quinazolina-1(4,1)-piperidina-3(1,3)-benzenacyclopentadecaphane-6⁶-yl)thiomorpholine 1,1-dioxide | 644.4 |

TABLE 1-continued

| No. | Structure | Chemical Name | [M + H]+ |
|---|---|---|---|
| 193 | 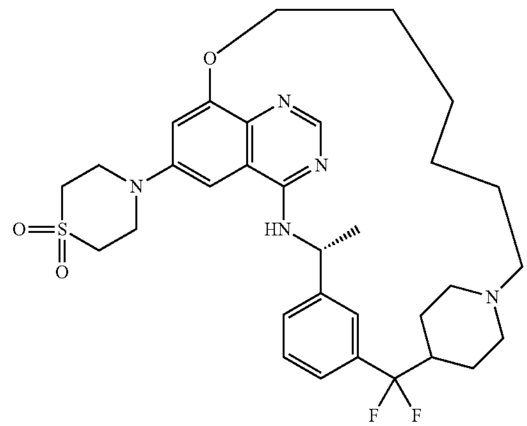 [SMILES: C[C@H]1Nc2ncnc3c(cc(N4CCS(=O)(=O)CC4)cc23)OCCCCCCN2CCC(CC2)C(F)(F)c2cccc1c2] | (R)-4-(2,2-difluoro-4-methyl-7-oxa-5-aza-6(4,8)-quinazolina-1(4,1)-piperidina-3(1,3)-benzenacyclotridecaphane-6⁶-yl)thiomorpholine 1,1-dioxide | 614.6 |
| 194 | 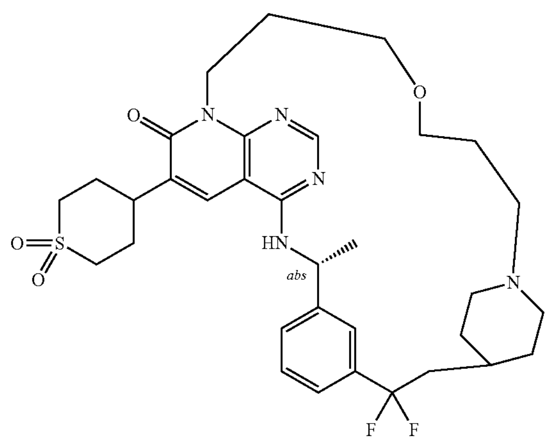 [SMILES: C[C@H]1Nc2ncnc3c2cc(C2CCS(=O)(=O)CC2)c(=O)n3CCCOCCCN2CCC(CC2)CC(F)(F)c2cccc1c2] | (3R)-1⁶-(1,1-dioxidotetrahydro-2H-thiopyran-4-yl)-5,5-difluoro-3-methyl-1⁷,1⁸-dihydro-11-oxa-2-aza-1(4,8)-pyrido[2,3-d]pyrimidina-7(4,1)-piperidina-4(1,3)-benzenacyclotetradecaphan-1⁷-one | 644.3 |
| 195 | 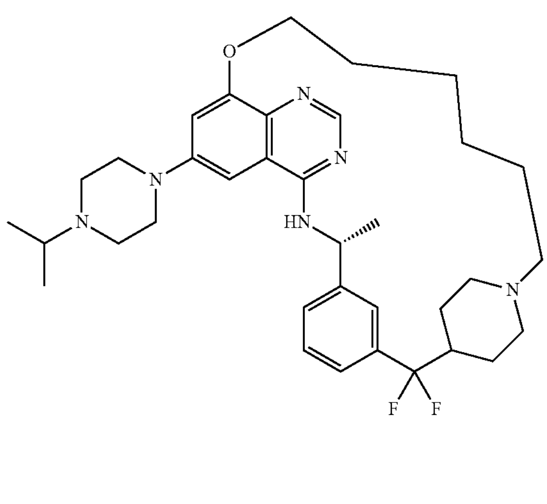 [SMILES: CC(C)N1CCN(c2cc3c4ncnc(c4c2)N[C@H](C)c2cccc(c2)C(F)(F)C2CCN(CCCCCCO3)CC2)CC1] | (R)-2,2-difluoro-6⁶-(4-isopropylpiperazin-1-yl)-4-methyl-7-oxa-5-aza-6(4,8)-quinazolina-1(4,1)-piperidina-3(1,3)-benzenacyclotridecaphane | 607.5 |

TABLE 1-continued

| No. | Structure | Chemical Name | [M + H]⁺ |
|---|---|---|---|
| 196 | 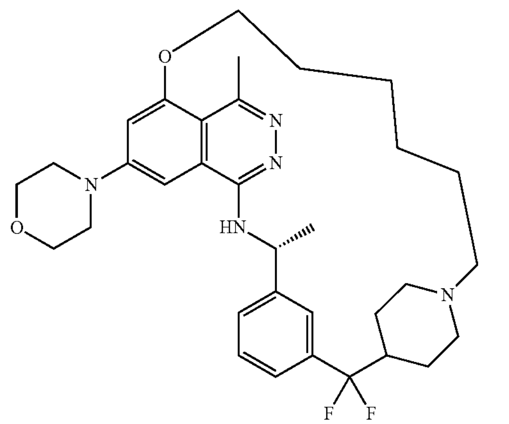 [SMILES: Cc1nnc2c3cc(N4CCOCC4)cc(c13)OCCCCCCN1CCC(CC1)C(F)(F)c1cccc(c1)[C@@H](C)N2] | (R)-2,2-difluoro-6⁴,4-dimethyl-6⁷-morpholino-7-oxa-5-aza-6(1,5)-phthalazina-1(4,1)-piperidina-3(1,3)-benzenacyclotridecaphane | 580.5 |
| 197 | 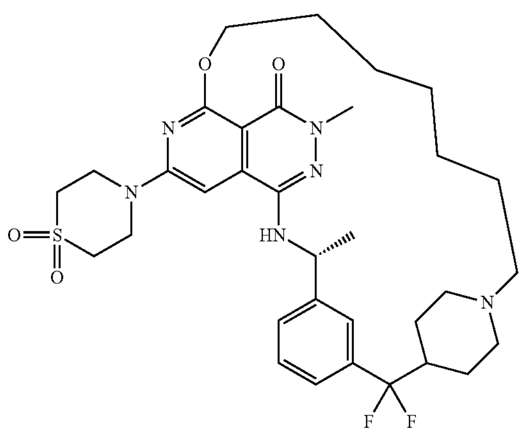 [SMILES: C[C@H]1Nc2nn(C)c(=O)c3c(nc(N4CCS(=O)(=O)CC4)cc23)OCCCCCCCN2CCC(CC2)C(F)(F)c2cccc1c2] | (R)-6⁷-(1,1-dioxidothiomorpholino)-2,2-difluoro-6³,4-dimethyl-6³,6⁴-dihydro-7-oxa-5-aza-6(1,5)-pyrido[3,4-d]pyridazina-1(4,1)-piperidina-3(1,3)-benzenacyclotetradecaphan-6⁴-one | 659.3 |
| 198 | 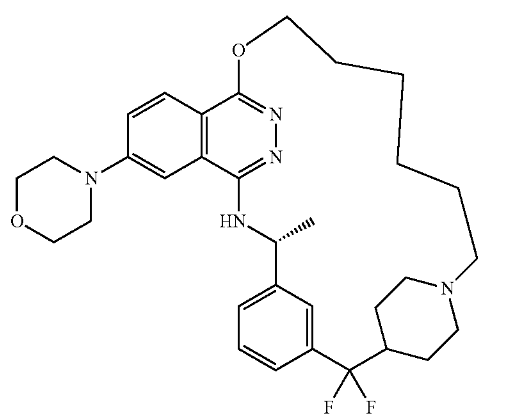 [SMILES: C[C@H]1Nc2nnc(c3ccc(N4CCOCC4)cc23)OCCCCCCN2CCC(CC2)C(F)(F)c2cccc1c2] | (R)-2,2-difluoro-4-methyl-6⁷-morpholino-7-oxa-5-aza-6(1,4)-phthalazina-1(4,1)-piperidina-3(1,3)-benzenacyclotridecaphane | |

TABLE 1-continued

| No. | Chemical Name | [M + H]+ |
|---|---|---|
| 200 | (R)-2,2-difluoro-4-methyl-6⁶-morpholino-7-oxa-5-aza-6(1,4)-phthalazina-1(4,1)-piperidina-3(1,3)-benzenacyclotridecaphane | |
| 201 | (R)-6⁷-(1,1-dioxidothiomorpholino)-3²,2,2-trifluoro-6³,4-dimethyl-6³,6⁴-dihydro-7-oxa-5-aza-6(1,5)-pyrido[3,4-d]pyridazina-1(4,1)-piperidina-3(1,3)-benzenacyclotetradecaphan-6⁴-one | |
| 202 | 4-((4R)-3²,2,2-trifluoro-4-methyl-6⁷-oxo-6⁷,6⁸-dihydro-10-oxa-5-aza-6(4,8)-pyrido[2,3-d]pyrimidina-1(4,1)-piperidina-3(1,3)-benzenacyclotetradecaphane-6⁶-yl)tetrahydro-2H-thiopyran-4-carbonitrile 1,1-dioxide | 687.3 |

TABLE 1-continued

| No. | Structure | Chemical Name | [M + H]+ |
|---|---|---|---|
| 203 | 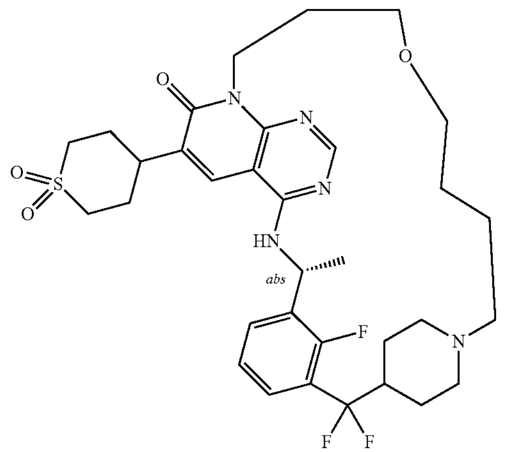 [SMILES: C[C@H]1Nc2ncnc3c2cc(C2CCS(=O)(=O)CC2)c(=O)n3CCCOCCCCN2CCC(CC2)C(F)(F)c2cccc1c2F] | (4R)-6⁶-(1,1-dioxidotetrahydro-2H-thiopyran-4-yl)-3²,2,2-trifluoro-4-methyl-6⁷,6⁸-dihydro-10-oxa-5-aza-6(4,8)-pyrido[2,3-d]pyrimidina-1(4,1)-piperidina-3(1,3)-benzenacyclotetradecaphan-6⁷-one | 662.3 |
| 204 | 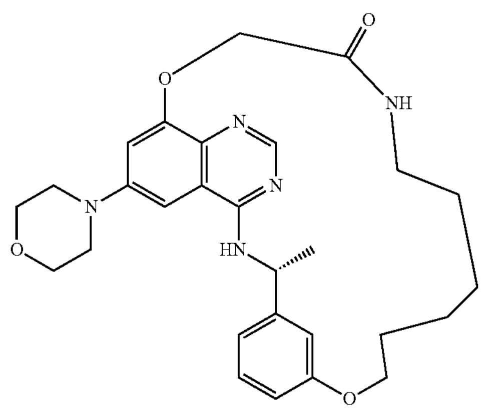 [SMILES: C[C@H]1Nc2ncnc3c(cc(N4CCOCC4)cc23)OCC(=O)NCCCCCCOc2cccc1c2] | (R)-3-methyl-1⁶-morpholino-5,15-dioxa-2,12-diaza-1(4,8)-quinazolina-4(1,3)-benzenacyclopentadecaphan-13-one | 506.4 |
| 205 | 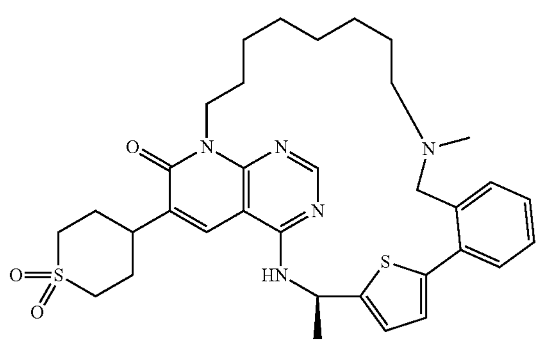 [SMILES: C[C@H]1Nc2ncnc3c2cc(C2CCS(=O)(=O)CC2)c(=O)n3CCCCCCCCN(C)Cc2ccccc2C2=CC=C1S2] | (3R)-5⁶-(1,1-dioxidotetrahydro-2H-thiopyran-4-yl)-3,14-dimethyl-5⁷,5⁸-dihydro-4,14-diaza-5(4,8)-pyrido[2,3-d]pyrimidina-2(2,5)-thiophena-1(1,2)-benzenacyclopentadecaphan-5⁷-one | 634.5 |
| 206 | 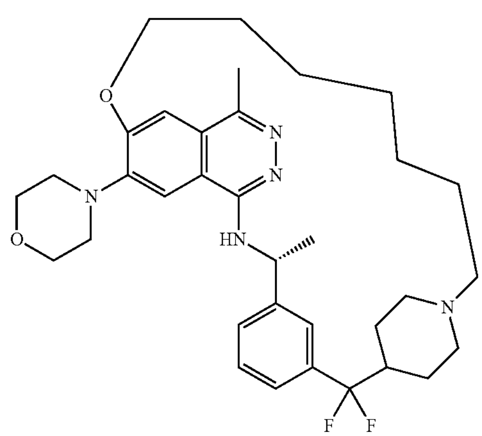 [SMILES: Cc1nnc2c3cc(N4CCOCC4)c(cc13)OCCCCCCCN1CCC(CC1)C(F)(F)c1cccc(c1)[C@@H](C)N2] | (R)-2,2-difluoro-6⁴,4-dimethyl-6⁷-morpholino-7-oxa-5-aza-6(1,6)-phthalazina-1(4,1)-piperidina-3(1,3)-benzenacyclotetradecaphane | 594.5 |

TABLE 1-continued

| No. | Structure | Chemical Name | [M + H]+ |
|---|---|---|---|
| 207 | 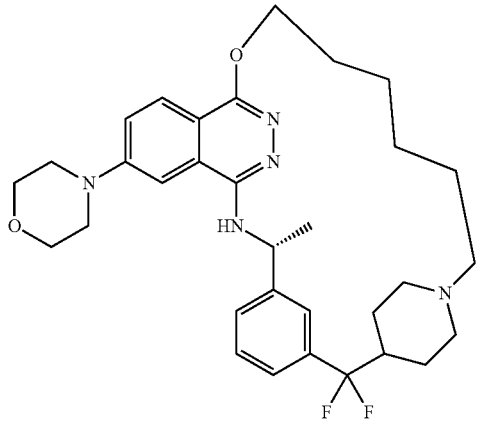 [SMILES: C[C@H]1Nc2nnc(c3ccc(N4CCOCC4)cc23)OCCCCCCN2CCC(CC2)C(F)(F)c2cccc1c2] | (R)-2,2-difluoro-4-methyl-$6^7$-morpholino-7-oxa-5-aza-6(1,4)-phthalazina-1(4,1)-piperidina-3(1,3)-benzenacyclotridecaphane and (R)-2,2-difluoro-4-methyl-$6^6$-morpholino-7-oxa-5-aza-6(1,4)-phthalazina-1(4,1)-piperidina-3(1,3)-benzenacyclotridecaphane (mixture of regioisomers) | 566.2 |
| 208 | 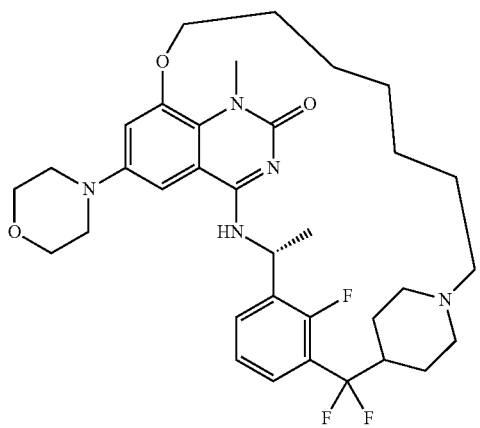 [SMILES: C[C@H]1Nc2nc(=O)n(C)c3c(cc(N4CCOCC4)cc23)OCCCCCCCN2CCC(CC2)C(F)(F)c2cccc1c2F] | (R)-$3^2$,2,2-trifluoro-$6^1$,4-dimethyl-$6^6$-morpholino-$6^1$,$6^2$-dihydro-7-oxa-5-aza-6(4,8)-quinazolina-1(4,1)-piperidina-3(1,3)-benzenacyclotetradecaphan-$6^2$-one | 628.4 |
| 209 | 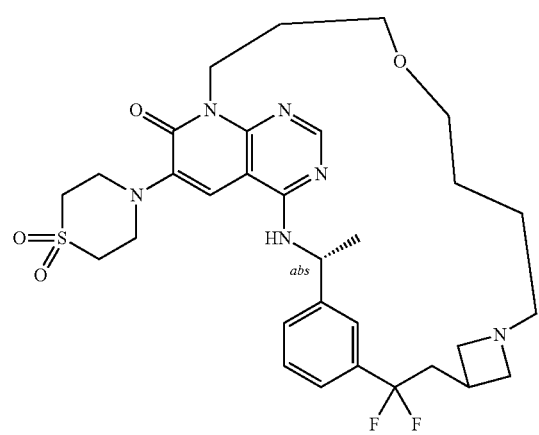 [SMILES: C[C@H]1Nc2ncnc3c2cc(N2CCS(=O)(=O)CC2)c(=O)n3CCCOCCCCN2CC(C2)CC(F)(F)c2cccc1c2] | (3R)-$1^6$-(1,1-dioxidothiomorpholino)-5,5-difluoro-3-methyl-$1^7$,$1^8$-dihydro-12-oxa-2-aza-1(4,8)-pyrido[2,3-d]pyrimidina-7(3,1)-azetidina-4(1,3)-benzenacyclopentadecaphan-$1^7$-one | 631.6 |

TABLE 1-continued

| No. | Structure | Chemical Name | [M + H]+ |
|---|---|---|---|
| 210 | 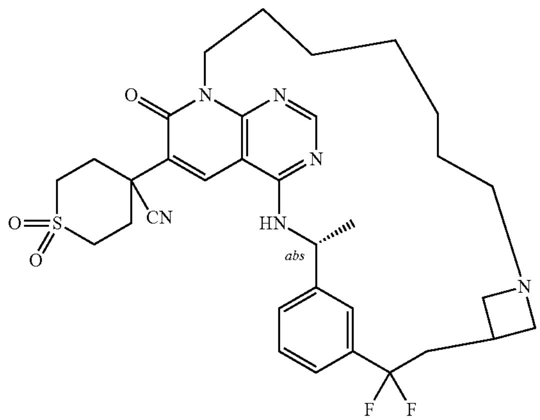 [SMILES: C[C@H]1Nc2ncnc3c2cc(C2(C#N)CCS(=O)(=O)CC2)c(=O)n3CCCCCCCN2CC(C2)CC(F)(F)c2cccc1c2] | 4-((3R)-5,5-difluoro-3-methyl-1⁷-oxo-1⁷,1⁸-dihydro-2-aza-1(4,8)-pyrido[2,3-d]pyrimidina-7(3,1)-azetidina-4(1,3)-benzenacyclotetradecaphane-1⁶-yl)tetrahydro-2H-thiopyran-4-carbonitrile 1,1-dioxide | 639.5 |
| 211 | 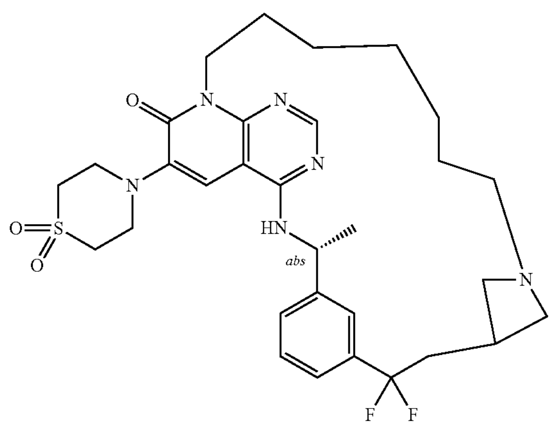 [SMILES: C[C@H]1Nc2ncnc3c2cc(N2CCS(=O)(=O)CC2)c(=O)n3CCCCCCCN2CC(C2)CC(F)(F)c2cccc1c2] | (3R)-1⁶-(1,1-dioxidothiomorpholino)-5,5-difluoro-3-methyl-1⁷,1⁸-dihydro-2-aza-1(4,8)-pyrido[2,3-d]pyrimidina-7(3,1)-azetidina-4(1,3)-benzenacyclotetradecaphan-1⁷-one | 615.3 |
| 212 | 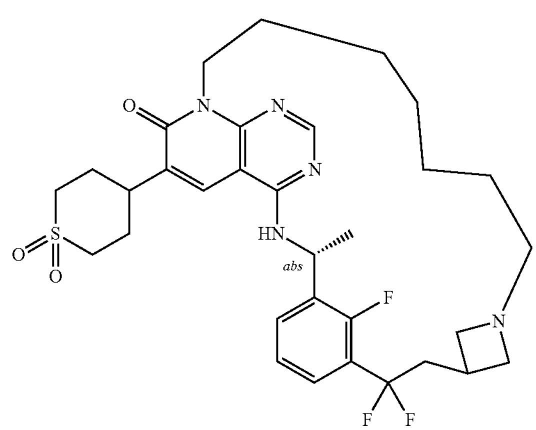 [SMILES: C[C@H]1Nc2ncnc3c2cc(C2CCS(=O)(=O)CC2)c(=O)n3CCCCCCCN2CC(C2)CC(F)(F)c2cccc1c2F] | (3R)-1⁶-(1,1-dioxidotetrahydro-2H-thiopyran-4-yl)-4²,5,5-trifluoro-3-methyl-1⁷,1⁸-dihydro-2-aza-1(4,8)-pyrido[2,3-d]pyrimidina-7(3,1)-azetidina-4(1,3)-benzenacyclotetradecaphan-1⁷-one | 632.0 |

TABLE 1-continued

| No. | Structure | Chemical Name | [M + H]+ |
|---|---|---|---|
| 213 | 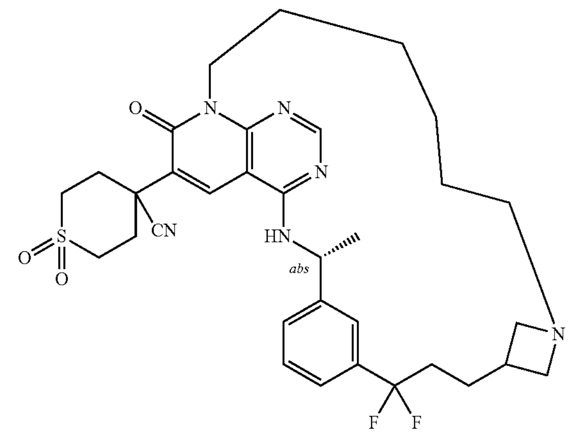 [SMILES: C[C@H]1Nc2ncnc3c2cc(C2(C#N)CCS(=O)(=O)CC2)c(=O)n3CCCCCCN2CC(CCC(F)(F)c3cccc1c3)C2] | 4-((3R)-5,5-difluoro-3-methyl-1⁷-oxo-1⁷,1⁸-dihydro-2-aza-1(4,8)-pyrido[2,3-d]pyrimidina-8(3,1)-azetidina-4(1,3)-benzenacyclotetradecaphane-1⁶-yl)tetrahydro-2H-thiopyran-4-carbonitrile 1,1-dioxide | 639.2 |

In some embodiments, the compounds of the present disclosure exhibit one or more functional characteristics described herein. For example, a subject compound is capable of reducing Ras signaling output. In some instances, a subject compound is capable of disrupting a Ras-SOS interaction, including disrupting interaction or binding between a mutant Kras (e.g., Kras G12C) and SOS1, or between a wildtype Kras and SOS1, thereby reducing Ras signaling output. In some embodiments, a subject compound binds specifically to a SOS protein, including SOS1. In some embodiments, the IC50 of a subject compound (including those shown in Table 1) for a SOS protein is less than about 5 μM, less than about 1 μM, less than about 50 nM, less than about 10 nM, less than about 1 nM, less than about 0.5 nM, less than about 100 μM, or less than about 50 pM, as measured in an in vitro assay known in the art or exemplified herein.

A reduction in Ras signaling output can be evidenced by one or more members of the following: (i) an increase in steady state level of GDP-bound Ras protein; (ii) a reduction in steady state level of GTP-bound Ras protein; (iii) a reduction of phosphorylated AKTs473, (iv) a reduction of phosphorylated ERLKT202/y204, (v) a reduction of phosphorylated S6S235/236, (vi) reduction (e.g., inhibition) of cell growth of Ras-driven tumor cells (e.g., those derived from a tumor cell line disclosed herein), and (vii) an interference or disruption of the interaction or binding between a SOS protein (e.g., SOS1) with a Ras protein such as a wildtype or a mutant Ras. In some cases, the reduction in Ras signaling output can be evidenced by two, three, four, five, six, or all of (i)-(vii) above.

It shall be understood that different aspects of the invention can be appreciated individually, collectively, or in combination with each other. Various aspects of the invention described herein may be applied to any of the particular applications disclosed herein. The compositions of matter including compounds of any formulae disclosed herein in the compounds section of the present disclosure may be utilized in the methods section including methods of use and production disclosed herein, or vice versa.

Methods

In certain aspects, the present disclosure provides a method of treating cancer in a subject in need thereof, comprising administering to the subject a therapeutically effective amount of a compound described herein, or a pharmaceutically acceptable salt or solvate thereof. In some embodiments, the cancer is a solid tumor or a hematological cancer. In some embodiments, the subject is administered an additional agent or therapy.

In certain aspects, the present disclosure provides a method of reducing Ras signaling output, comprising contacting a SOS1 protein with an effective amount of a compound described herein, or a pharmaceutically acceptable salt or solvate thereof, thereby reducing the Ras signaling output. In some embodiments, the compound disrupts interaction between a Ras protein and SOS1. In some embodiments, the Ras protein is a wildtype K-Ras or a mutant K-Ras.

In certain aspects, the present disclosure provides a method of inhibiting cell growth, comprising administering to a cell expressing SOS1 an effective amount of a compound described herein, or a pharmaceutically acceptable salt or solvate thereof, thereby inhibiting growth of said cells.

In certain aspects, the present disclosure provides a method of reducing Ras signaling output of a cell, comprising contacting the cell with an effective amount of a compound Formula (I), or a pharmaceutically acceptable salt or solvate thereof, in combination with an additional agent, wherein the additional agent is a chemotherapeutic agent, a radioactive agent, an immune modulator, or an inhibitor against one or more targets selected from the group of: MEK, epidermal growth factor receptor (EGFR), FGFR1, FGFR2, FGFR3, FGFR4, mitotic kinase, topoisomerase, ALK, c-MET, ErbB2, AXL, NTRK1, RET, A-Raf, B-Raf, C-Raf, ERK, MDM2, mTOR, BET, IGF1/2, IGF1-R, CDK9, SHC, GAB, GRB, PI3-kinase, MAPK, SHIP1, SHIP2, SHP1, SHP2, SRC, JAK, PARP, BTK, FLT3, HDAC, VEGFR, PDGFR, LCK, Bcr-Abl, AKT, wildtype KRas, KRas mutant (e.g., KrasG12C, KRas G12D, KRas G12S, KRas G12V, KRas G13D, KRas G13C, or KRas G13V), ROS1, CDK4/6, and a mutant of the one or more target thereof, wherein the compound of Formula (I) has the structure:

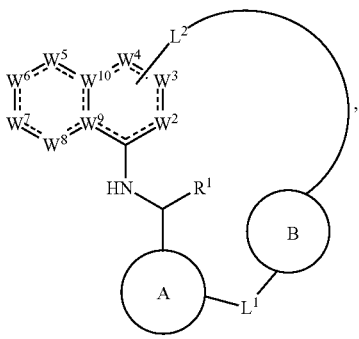

(I)

wherein:

is selected from $C_{5-7}$ carbocycle and 5- to 7-membered heterocycle, each of which is optionally substituted with one or more $R^{11a}$;

is absent or selected from $C_{3-8}$ carbocycle and 3- to 8-membered heterocycle, each of which is optionally substituted with one or more $R^{11a}$;

- $L^1$ is selected from a bond, $C_{1-6}$ alkylene, and $C_{1-6}$ haloalkylene;
- $L^2$ is selected from $C_{5-25}$ alkylene, $C_{5-25}$ alkenylene, $C_{5-25}$ alkynylene, 5- to 25-membered heteroalkylene, and 5- to 25-membered heteroalkenylene, each of which is optionally substituted with one or more $R^{11b}$, wherein $L^2$ is covalently bound to one of $W^3$, $W^4$, $W^5$, $W^6$, or $W^7$; or $L^2$ is -$L^3$-D-$L^4$-, wherein $L^4$ is covalently bound to one of $W^3$, $W^4$, $W^5$, $W^6$, or $W^7$;
- $L^3$ is selected from $C_{1-10}$ alkylene, $C_{1-10}$ alkenylene, $C_{1-10}$ alkynylene, 2- to 10-membered heteroalkylene, and 2- to 10-membered heteroalkenylene, each of which is optionally substituted with one or more $R^{11b}$;
- D is absent or selected from $C_{3-12}$ carbocycle and 3- to 12-membered heterocycle, each of which is optionally substituted with one or more $R^{11d}$;
- $L^4$ is selected from $C_{1-10}$ alkylene, $C_{1-10}$ alkenylene, $C_{1-10}$ alkynylene, 2- to 10-membered heteroalkylene, and 2- to 10-membered heteroalkenylene, each of which is optionally substituted with one or more $R^{11b}$;
- $W^2$ is selected from $N(R^{2b})$, N, $C(R^2)$, $C(R^2)(R^{2a})$, and $C(O)$;
- $W^3$ is selected from $N(R^{3b})$, N, $C(R^3)$, $C(R^3)(R^{3a})$, and $C(O)$;
- $W^4$ is selected from $N(R^{4b})$, N, $C(R^4)$, $C(R^4)(R^{4a})$, and $C(O)$;
- $W^5$ is selected from $N(R^{5b})$, N, $C(R^5)$, $C(R^5)(R^{5a})$, and $C(O)$;
- $W^6$ is selected from $N(R^{6b})$, N, $C(R^6)$, $C(R^6)(R^{6a})$, and $C(O)$;
- $W^7$ is selected from $N(R^{7b})$, N, $C(R^7)$, $C(R^7)(R^{7a})$, and $C(O)$;
- $W^8$ is selected from $N(R^{11b})$, N, $C(R^8)$, $C(R^8)(R^{8a})$, and $C(O)$;
- $W^9$ is selected from N, $C(R^9)$, and C;
- $W^{10}$ is selected from N, $C(R^{10})$, and C;
- $R^1$ is $C_{1-3}$ alkyl optionally substituted with one or more $R^{11c}$;
- $R^2$, $R^{2a}$, $R^{3a}$, $R^{4a}$, $R^{5a}$, $R^{6a}$, $R^{7a}$, $R^8$, and $R^{8a}$ are each independently selected from hydrogen, halogen, —CN, $C_{1-6}$ alkyl, $C_{2-6}$ alkenyl, $C_{2-6}$ alkynyl, $C_{3-10}$ carbocycle, 3- to 10-membered heterocycle, —$OR^{12}$, —$SR^{12}$, —$N(R^{12})(R^{13})$, —$C(O)OR^{12}$, —$OC(O)N(R^{12})(R^{13})$, —$N(R^{14})C(O)N(R^{12})(R^{13})$, —$N(R^{14})C(O)OR^{15}$, —$N(R^{14})S(O)_2R^{15}$, —$C(O)R^{15}$, —$S(O)R^{15}$, —$OC(O)R^{15}$, —$C(O)N(R^{12})(R^{13})$, —$C(O)C(O)N(R^{12})(R^{13})$, —$N(R^{14})C(O)R^{15}$, —$S(O)_2R^{15}$, —$S(O)_2N(R^{12})(R^{13})$, —$S(=O)(=NH)N(R^{12})(R^{13})$, —$CH_2C(O)N(R^{12})(R^{13})$, —$CH_2N(R^{14})C(O)R^{15}$, —$CH_2S(O)_2R^{15}$, and —$CH_2S(O)_2N(R^{12})(R^{13})$, wherein each $C_{1-6}$ alkyl, $C_{2-6}$ alkenyl, $C_{2-6}$ alkynyl, $C_{3-10}$ carbocycle, and 3- to 10-membered heterocycle is independently optionally substituted with one, two, or three $R^{20}$;
- $R^3$, $R^4$, $R^5$, $R^6$, and $R^7$ are each independently selected from a bond to $L^2$, hydrogen, halogen, —CN, $C_{1-6}$ alkyl, $C_{2-6}$ alkenyl, $C_{2-6}$ alkynyl, $C_{3-10}$ carbocycle, 3- to 10-membered heterocycle, —$OR^{12}$, —$SR^{12}$, —$N(R^{12})(R^{13})$, —$C(O)OR^{12}$, —$OC(O)N(R^{12})(R^{13})$, —$N(R^{14})C(O)N(R^{12})(R^{13})$, —$N(R^{14})C(O)OR^{15}$, —$N(R^{14})S(O)_2R^{15}$, —$C(O)R^{15}$, —$S(O)R^{15}$, —$OC(O)R^{15}$, —$C(O)N(R^{12})(R^{13})$, —$C(O)C(O)N(R^{12})(R^{13})$, —$N(R^{14})C(O)R^{15}$, —$S(O)_2R^{15}$, —$S(O)_2N(R^{12})(R^{13})$, —$S(=O)(=NH)N(R^{12})(R^{13})$, —$CH_2C(O)N(R^{12})(R^{13})$, —$CH_2N(R^{14})C(O)R^{15}$, —$CH_2S(O)_2R^{15}$, and —$CH_2S(O)_2N(R^{12})(R^{13})$, wherein each $C_{1-6}$ alkyl, $C_{2-6}$ alkenyl, $C_{2-6}$ alkynyl, $C_{3-10}$ carbocycle, and 3- to 10-membered heterocycle is independently optionally substituted with one, two, or three $R^{20}$;
- $R^{2b}$ and $R^{8b}$ are each independently selected from hydrogen, —CN, $C_{1-6}$ alkyl, $C_{2-6}$ alkenyl, $C_{2-6}$ alkynyl, $C_{3-10}$ carbocycle, 3- to 10-membered heterocycle, —$OR^{12}$, —$SR^{12}$, —$C(O)OR^{12}$, —$OC(O)N(R^{12})(R^{13})$, —$C(O)R^{15}$, —$S(O)R^{15}$, —$OC(O)R^{15}$, —$C(O)N(R^{12})(R^{13})$, —$C(O)C(O)N(R^{12})(R^{13})$, —$S(O)_2R^{15}$, —$S(O)_2N(R^{12})(R^{13})$, —$S(=O)(=NH)N(R^{12})(R^{13})$, —$CH_2C(O)N(R^{12})(R^{13})$, —$CH_2N(R^{14})C(O)R^{15}$, —$CH_2S(O)_2R^{15}$, and —$CH_2S(O)_2N(R^{12})(R^{13})$, wherein each $C_{1-6}$ alkyl, $C_{2-6}$ alkenyl, $C_{2-6}$ alkynyl, $C_{3-10}$ carbocycle and 3- to 10-membered heterocycle is independently optionally substituted with one, two, or three $R^{20}$;
- $R^{3b}$, $R^{4b}$, $R^{5b}$, $R^{6b}$, and $R^{7b}$ are each independently selected from a bond to $L^2$, hydrogen, —CN, $C_{1-6}$ alkyl, $C_{2-6}$ alkenyl, $C_{2-6}$ alkynyl, $C_{3-10}$ carbocycle, 3- to 10-membered heterocycle, —$OR^{12}$, —$SR^{12}$, —$C(O)OR^{12}$, —$OC(O)N(R^{12})(R^{13})$, —$C(O)R^{15}$, —$S(O)R^{15}$, —$OC(O)R^{15}$, —$C(O)N(R^{12})(R^{13})$, —$C(O)C(O)N(R^{12})(R^{13})$, —$S(O)_2R^{15}$, —$S(O)_2N(R^{12})(R^{13})$, —$S(=O)(=NH)N(R^{12})(R^{13})$, —$CH_2C(O)N(R^{12})(R^{13})$, —$CH_2N(R^{14})C(O)R^{15}$, —$CH_2S(O)_2R^{15}$, and —$CH_2S(O)_2N(R^{12})(R^{13})$, wherein each $C_{1-6}$ alkyl, $C_{2-6}$ alkenyl, $C_{2-6}$ alkynyl, $C_{3-10}$ carbocycle and 3- to 10-membered heterocycle is independently optionally substituted with one, two, or three $R^{20}$;
- $R^9$ and $R^{10}$ are each independently selected from hydrogen, $C_{1-6}$ alkyl, $C_{2-6}$ alkenyl, $C_{2-6}$ alkynyl, $C_{3-10}$ carbocycle, —$CH_2$—($C_{3-10}$ carbocycle), 3- to 10-membered heterocycle, and —$CH_2$-(3- to 10-membered heterocycle), wherein each $C_{1-6}$ alkyl, $C_{2-6}$ alkenyl, $C_{2-6}$ alkynyl, $C_{3-10}$ carbocycle, —$CH_2$—($C_{3-10}$ carbocycle), 3- to 10-membered heterocycle, and —CH$_2$-(3- to 10-membered heterocycle) is independently optionally substituted with one, two, or three R$^{20}$;

R$^{11}$, R$^{11a}$, and R$^{11d}$ are each independently selected at each occurrence from halogen, —CN, C$_{1-6}$ alkyl, C$_{2-6}$ alkenyl, C$_{2-6}$ alkynyl, C$_{3-10}$ carbocycle, 3- to 10-membered heterocycle, —OR$^{12}$, —SR$^{12}$, —N(R$^{12}$)(R$^{13}$), —C(O)OR$^{12}$, —OC(O)N(R$^{12}$)(R$^{13}$), —N(R$^{14}$)C(O)N(R$^{12}$)(R$^{13}$), —N(R$^{14}$)C(O)OR$^{15}$, —N(R$^{14}$)S(O)$_2$R$^{15}$, —C(O)R$^{15}$, —S(O)R$^{15}$, —OC(O)R$^{15}$, —C(O)N(R$^{12}$)(R$^{13}$), —C(O)C(O)N(R$^{12}$)(R$^{13}$), —N(R$^{14}$)C(O)R$^{15}$, —S(O)$_2$R$^{15}$, —S(O)$_2$N(R$^{12}$)(R$^{13}$), —S(=O)(=NH)N(R$^{12}$)(R$^{13}$), —CH$_2$C(O)N(R$^{12}$)(R$^{13}$), —CH$_2$N(R$^{14}$)C(O)R$^{15}$, —CH$_2$S(O)$_2$R$^{15}$, —CH$_2$S(O)$_2$N(R$^{12}$)(R$^{13}$), —CH$_2$N(R$^{12}$)S(O)$_2$(R$^{13}$), and —P(O)(R$^{17}$)(R$^{17a}$), wherein C$_{1-6}$ alkyl, C$_{2-6}$ alkenyl, C$_{2-6}$ alkynyl, C$_{3-10}$ carbocycle, and 3- to 10-membered heterocycle are optionally substituted with one, two, or three R$^{20}$;

R$^{11b}$ is independently selected at each occurrence from halogen, oxo, —CN, C$_{1-6}$ alkyl, C$_{2-6}$ alkenyl, C$_{2-6}$ alkynyl, C$_{3-10}$ carbocycle, 3- to 10-membered heterocycle, —OR$^{12}$, —SR$^{12}$, —N(R$^{12}$)(R$^{13}$), —C(O)OR$^{12}$, —OC(O)N(R$^{12}$)(R$^{13}$), —N(R$^{14}$)C(O)N(R$^{12}$)(R$^{13}$), —N(R$^{14}$)C(O)OR$^{15}$, —N(R$^{14}$)S(O)$_2$R$^{15}$, —C(O)R$^{15}$, —S(O)R$^{15}$, —OC(O)R$^{15}$, —C(O)N(R$^{12}$)(R$^{13}$), —C(O)C(O)N(R$^{12}$)(R$^{13}$), —N(R$^{14}$)C(O)R$^{15}$, —S(O)$_2$R$^{15}$, —S(O)$_2$N(R$^{12}$)(R$^{13}$), —S(=O)(=NH)N(R$^{12}$)(R$^{13}$), —CH$_2$C(O)N(R$^{12}$)(R$^{13}$), —CH$_2$N(R$^{14}$)C(O)R$^{15}$, —CH$_2$S(O)$_2$R$^{15}$, —CH$_2$S(O)$_2$N(R$^{12}$)(R$^{13}$), —CH$_2$N(R$^{12}$)S(O)$_2$(R$^{13}$), and —P(O)(R$^{17}$)(R$^{17a}$), wherein C$_{1-6}$ alkyl, C$_{2-6}$ alkenyl, C$_{2-6}$ alkynyl, C$_{3-10}$ carbocycle, and 3- to 10-membered heterocycle are optionally substituted with one, two, or three R$^{20}$;

R$^{11'}$ is independently selected at each occurrence from halogen, —OR$^{12}$, and —N(R$^{12}$)(R$^{13}$);

R$^{12}$ is independently selected at each occurrence from hydrogen, C$_{1-6}$ alkyl, C$_{1-6}$ haloalkyl, C$_{2-6}$ alkenyl, C$_{2-6}$ alkynyl, C$_{3-10}$ carbocycle, and 3- to 10-membered heterocycle, wherein C$_{1-6}$ alkyl, C$_{2-6}$ alkenyl, C$_{2-6}$ alkynyl, C$_{3-10}$ carbocycle, and 3- to 10-membered heterocycle are optionally substituted with one, two, or three R$^{20}$;

R$^{13}$ is independently selected at each occurrence from hydrogen, C$_{1-6}$ alkyl, and C$_{1-6}$ haloalkyl; or R$^{12}$ and R$^{13}$, together with the nitrogen atom to which they are attached, form a 3- to 10-membered heterocycle optionally substituted with one, two, or three R$^{20}$;

R$^{14}$ is independently selected at each occurrence from hydrogen, C$_{1-6}$ alkyl, and C$_{1-6}$ haloalkyl;

R$^{15}$ is independently selected at each occurrence from C$_{1-6}$ alkyl, C$_{2-6}$ alkenyl, C$_{2-6}$ alkynyl, C$_{3-10}$ carbocycle, and 3- to 10-membered heterocycle, wherein C$_{1-6}$ alkyl, C$_{2-6}$ alkenyl, C$_{2-6}$ alkynyl, C$_{3-10}$ carbocycle, and 3- to 10-membered heterocycle are optionally substituted with one, two, or three R$^{20}$;

R$^{17}$ and R$^{17a}$ are each independently selected at each occurrence from C$_{1-6}$ alkyl and C$_{3-6}$ cycloalkyl, wherein C$_{1-6}$ alkyl and C$_{3-6}$ cycloalkyl are optionally substituted with one, two or three R$^{20}$; or R$^{17}$ and R$^{17a}$, together with the phosphorous atom to which they are attached, form a 3- to 10-membered heterocycle;

R$^{20}$ is independently selected at each occurrence from halogen, oxo, =NH, —CN, C$_{1-6}$ alkyl, C$_{2-6}$ alkenyl, C$_{2-6}$ alkynyl, C$_{3-10}$ carbocycle, —CH$_2$—(C$_{3-10}$ carbocycle), 3- to 10-membered heterocycle, —CH$_2$-(3- to 10-membered heterocycle), —OR$^{21}$, —SR$^{21}$, —N(R$^{22}$)(R$^{23}$), —C(O)OR$^{22}$, —C(O)N(R$^{22}$)(R$^{23}$), —C(O)C(O)N(R$^{22}$)(R$^{23}$), —OC(O)N(R$^{22}$)(R$^{23}$), —N(R$^{22}$)C(O)N(R$^{22}$)(R$^{23}$), —N(R$^{24}$)C(O)OR$^{25}$, —N(R$^{24}$)C(O)R$^{25}$, —N(R$^{22}$)S(O)$_2$R$^{25}$, —C(O)R$^{25}$, —S(O)$_2$R$^{25}$, —S(O)$_2$N(R$^{22}$)(R$^{23}$), —OCH$_2$C(O)OR$^{22}$, and —OC(O)R$^{25}$, wherein C$_{1-6}$ alkyl, C$_{2-6}$ alkenyl, C$_{2-6}$ alkynyl, C$_{3-10}$ carbocycle, —CH$_2$—(C$_{3-10}$ carbocycle), 3- to 10-membered heterocycle, and —CH$_2$-(3- to 10-membered heterocycle) are optionally substituted with one, two, or three groups independently selected from halogen, oxo, =NH, —CN, C$_{1-6}$ alkyl, C$_{1-6}$ haloalkyl, C$_{1-6}$ alkoxy, C$_{1-6}$ haloalkoxy, —OR$^{21}$, —SR$^{21}$, —N(R$^{22}$)(R$^{23}$), —C(O)OR$^{22}$, —C(O)N(R$^{22}$)(R$^{23}$), —C(O)C(O)N(R$^{22}$)(R$^{23}$), —OC(O)N(R$^{22}$)(R$^{23}$), —N(R$^{24}$)C(O)N(R$^{22}$)(R$^{23}$), —N(R$^{24}$)C(O)OR$^{25}$, —N(R$^{24}$)C(O)R$^{25}$, —N(Ru)S(O)$_2$R$^{25}$, —C(O)R$^{25}$, —S(O)$_2$R$^{25}$, —S(O)$_2$N(R$^{22}$)(R$^{23}$), and —OC(O)R$^{25}$;

R$^{21}$ is independently selected at each occurrence from H, C$_{1-6}$ alkyl, C$_{1-6}$ haloalkyl, C$_{2-6}$ alkenyl, C$_{2-6}$ alkynyl, C$_{3-10}$ carbocycle, and 3- to 10-membered heterocycle, wherein C$_{3-10}$ carbocycle and 3- to 10-membered heterocycle are optionally substituted with one, two, or three groups independently selected from halogen and C$_{1-6}$ alkyl;

R$^{22}$ is independently selected at each occurrence from H, C$_{1-6}$ alkyl, C$_{1-6}$ haloalkyl, C$_{2-6}$ alkenyl, C$_{2-6}$ alkynyl, C$_{3-10}$ carbocycle, and 3- to 10-membered heterocycle, wherein C$_{3-10}$ carbocycle and 3- to 10-membered heterocycle are optionally substituted with one, two, or three groups independently selected from halogen and C$_{1-6}$ alkyl;

R$^{23}$ is independently selected at each occurrence from H and C$_{1-6}$ alkyl;

R$^{24}$ is independently selected at each occurrence from H and C$_{1-6}$ alkyl;

R$^{25}$ is independently selected at each occurrence from C$_{1-6}$ alkyl, C$_{2-6}$ alkenyl, C$_{2-6}$ alkynyl, C$_{3-10}$ carbocycle, and 3- to 10-membered heterocycle, wherein C$_{1-6}$ alkyl, C$_{3-10}$ carbocycle, and 3- to 10-membered heterocycle are optionally substituted with one, two, or three groups independently selected from halogen, C$_{1-6}$ alkyl, C$_{1-6}$ haloalkyl, C$_{1-6}$ alkoxy, C$_{3-10}$ carbocycle, and 3- to 10-membered heterocycle; and ------ indicates a single or double bond such that all valences are satisfied.

In some embodiments, the additional agent is an inhibitor against one or more targets selected from MEK, epidermal growth factor receptor (EGFR), A-Raf, B-Raf, C-Raf, ErbB2 (Her2), SHP2, wildtype KRas, a KRas mutant, and CDK4/6. In some embodiments, the additional agent is a chemotherapeutic agent, a radioactive agent, or an immune modulator.

In certain aspects, the present disclosure provides a SOS1 protein bound by a compound described herein, or a pharmaceutically acceptable salt or solvate thereof, wherein interaction of the SOS1 protein with a Ras protein is reduced as compared to a SOS1 protein unbound to said compound.

In certain aspects, the present disclosure provides a method of treating cancer in a subject in need thereof, comprising administering to the subject a therapeutically effective amount of a compound of Formula (I), (I-A), (I-B), (I-B1), (I-B2), (I-C), (I-C1), (I-C2), (I-C3), (I-D), (I-D1), (I-D2), (I-E), (I-E1), (II-B), (II-C), or (III), or a pharmaceutically acceptable salt or solvate thereof. In some embodiments, the cancer is a solid tumor or a hematological cancer, such as a solid tumor. In some embodiments, the cancer is selected from prostate cancer, brain cancer, colon cancer, rectal cancer, renal-cell carcinoma, liver cancer, lung cancer, non-small cell carcinoma of the lung, cancer of the small intestine, cancer of the esophagus, melanoma, bone cancer, pancreatic cancer, skin cancer, cancer of the head or neck, cutaneous or intraocular malignant melanoma, uterine cancer, ovarian cancer, rectal cancer, cancer of the anal region, stomach cancer, testicular cancer, uterine cancer, carcinoma of the fallopian tubes, carcinoma of the endometrium, carcinoma of the cervix, carcinoma of the vagina, carcinoma of the vulva, Hodgkin's Disease, non-Hodgkin's lymphoma, cancer of the endocrine system, cancer of the thyroid gland, cancer of the parathyroid gland, cancer of the adrenal gland, sarcoma of soft tissue, cancer of the urethra, cancer of the penis, solid tumors of childhood, cancer of the bladder, cancer of the kidney or ureter, carcinoma of the renal pelvis, neoplasm of the central nervous system (CNS), primary CNS lymphoma, tumor angiogenesis, spinal axis tumor, brain stem glioma, pituitary adenoma, Kaposi's sarcoma, epidermoid cancer, squamous cell cancer, T-cell lymphoma, environmentally induced cancers, combinations of said cancers, and metastatic lesions of said cancers. In some embodiments, the cancer is a hematological cancer, such as chronic lymphocytic leukemia (CLL), acute leukemia, acute lymphoid leukemia (ALL), B-cell acute lymphoid leukemia (B-ALL), T-cell acute lymphoid leukemia (T-ALL), chronic myelogenous leukemia (CML), B cell prolymphocytic leukemia, blastic plasmacytoid dendritic cell neoplasm, Burkitt's lymphoma, diffuse large B cell lymphoma, follicular lymphoma, hairy cell leukemia, small cell- or a large cell-follicular lymphoma, malignant lymphoproliferative conditions, MALT lymphoma, mantle cell lymphoma, marginal zone lymphoma, multiple myeloma, myelodysplasia and myelodysplastic syndrome, non-Hodgkin's lymphoma, Hodgkin's lymphoma, plasmablastic lymphoma, plasmacytoid dendritic cell neoplasm, Waldenstrom macroglobulinemia, or pre-leukemia. In some embodiments, the cancer is one or more cancers selected from chronic lymphocytic leukemia (CLL), acute myeloid leukemia (AML), T-cell acute lymphoblastic leukemia (T-ALL), B cell acute lymphoblastic leukemia (B-ALL), and acute lymphoblastic leukemia (ALL).

Any of the treatment methods disclosed herein can be administered alone or in combination or in conjunction with another therapy or another agent. By "combination" it is meant to include (a) formulating a subject composition containing a subject compound together with another agent, and (b) using a subject composition separate from another agent as an overall treatment regimen. By "conjunction" it is meant that another therapy or agent is administered either simultaneously, concurrently, or sequentially with a subject composition comprising a compound disclosed herein, with no specific time limits, wherein such conjunctive administration provides a therapeutic effect.

In some embodiments, a subject treatment method is combined with surgery, cellular therapy, chemotherapy, radiation, and/or immunosuppressive agents. Additionally, compositions of the present disclosure can be combined with other therapeutic agents, such as other anti-cancer agents, anti-allergic agents, anti-nausea agents (or anti-emetics), pain relievers, cytoprotective agents, immunostimulants, and combinations thereof. In some embodiments, a subject treatment method is combined with a chemotherapeutic agent.

Exemplary chemotherapeutic agents include an anthracycline (e.g., doxorubicin (e.g., liposomal doxorubicin)), a vinca alkaloid (e.g., vinblastine, vincristine, vindesine, vinorelbine), an alkylating agent (e.g., cyclophosphamide, decarbazine, melphalan, ifosfamide, temozolomide), an immune cell antibody (e.g., alemtuzamab, gemtuzumab, rituximab, ofatumumab, tositumomab, brentuximab), an antimetabolite (including, e.g., folic acid antagonists, pyrimidine analogs, purine analogs and adenosine deaminase inhibitors (e.g., fludarabine)), a TNFR glucocorticoid induced TNFR related protein (GITR) agonist, a proteasome inhibitor (e.g., aclacinomycin A, gliotoxin or bortezomib), an immunomodulator such as thalidomide or a thalidomide derivative (e.g., lenalidomide). Additional chemotherapeutic agents contemplated for use in combination include busulfan (Myleran®), busulfan injection (Busulfex®), cladribine (Leustatin®), cyclophosphamide (Cytoxan® or Neosar®), cytarabine, cytosine arabinoside (Cytosar-U®), cytarabine liposome injection (DepoCyt®), daunorubicin hydrochloride (Cerubidine®), daunorubicin citrate liposome injection (DaunoXome®), dexamethasone, doxorubicin hydrochloride (Adriamycin®, Rubex®), etoposide (Vepesid®), fludarabine phosphate (Fludara®), hydroxyurea (Hydrea®), Idarubicin (Idamycin®), mitoxantrone (Novantrone®), Gemtuzumab Ozogamicin (Mylotarg®), anastrozole (Arimidex®), bicalutamide (Casodex®), bleomycin sulfate (Blenoxane®), busulfan injection (Busulfex®), capecitabine (Xeloda®), N4-pentoxycarbonyl-5-deoxy-5-fluorocytidine, carboplatin (Paraplatin®), carmustine (BiCNU®), chlorambucil (Leukeran®), cisplatin (Platinol®), dacarbazine (DTIC-Dome®), dactinomycin (Actinomycin D, Cosmegan), dexamethasone, docetaxel (Taxotere®), 5-fluorouracil (Adrucil®, Efudex®), flutamide (Eulexin®), tezacitibine, Gemcitabine (difluorodeoxycitidine), ifosfamide (IFEX®), irinotecan (Camptosar®), L-asparaginase (ELSPAR®), leucovorin calcium, melphalan (Alkeran®), 6-mercaptopurine (Purinethol®), methotrexate (Folex®), mitoxantrone (Novantrone®), mylotarg, paclitaxel (Taxol®), phoenix (Yttrium90/M4X-DTPA), pentostatin, polifeprosan 20 with carmustine implant (Gliadel®), tamoxifen citrate (Nolvadex®), teniposide (Vumon®), 6-thioguanine, thiotepa, tirapazamine (Tirazone®), topotecan hydrochloride for injection (Hycamptin®), vinblastine (Velban®), vincristine (Oncovin®), and vinorelbine (Navelbine®).

Anti-cancer agents of particular interest for combinations with a compound of the present disclosure include: anthracyclines; alkylating agents; antimetabolites; drugs that inhibit either the calcium dependent phosphatase calcineurin or the p70S6 kinase FK506 or inhibit the p70S6 kinase; mTOR inhibitors; immunomodulators; vinca alkaloids; proteosome inhibitors; GITR agonists; protein tyrosine phosphatase inhibitors; a CDK4 kinase inhibitor; a BTK inhibitor; a MKN kinase inhibitor; a DGK kinase inhibitor; or an oncolytic virus.

Exemplary antimetabolites include, without limitation, pyrimidine analogs, purine analogs and adenosine deaminase inhibitors): methotrexate (Rheumatrex®, Trexall®), 5-fluorouracil (Adrucil®, Efudex®, Fluoroplex®), floxuridine (FUDF®), cytarabine (Cytosar-U®, Tarabine PFS), 6-mercaptopurine (Puri-Nethol®)), 6-thioguanine (Thioguanine Tabloid®), fludarabine phosphate (Fludara®), pentostatin (Nipent®), pemetrexed (Alimta®), raltitrexed (Tomudex®), cladribine (Leustatin®), clofarabine (Clofarex®, Clolar®), azacitidine (Vidaza®), decitabine and gemcitabine (Gemzar®). Preferred antimetabolites include, cytarabine, clofarabine and fludarabine.

Exemplary alkylating agents include, without limitation, nitrogen mustards, ethylenimine derivatives, alkyl sulfonates, nitrosoureas and triazenes): uracil mustard (Aminouracil Mustard®, Chlorethaminacil®, Demethyldopan®, Desmethyldopan®, Haemanthamine®, Nordopan®, Uracil nitrogen Mustard®, Uracillost®, Uracilmostaza®, Uramustin®, Uramustine®), chlormethine (Mustargen®), cyclophosphamide (Cytoxan®, Neosar®, Clafen®, Endoxan®, Procytox®, Revimmune™), ifosfamide (Mitoxana®), melphalan (Alkeran®), Chlorambucil (Leukeran®), pipobroman (Amedel®, Vercyte®), triethylenemelamine (Hemel®, Hexalen®, Hexastat®), triethylenethiophosphoramine, Temozolomide (Temodar®), thiotepa (Thioplex®), busulfan (Busilvex®, Myleran®), carmustine (BiCNU®), lomustine (CeeNU®), streptozocin (Zanosar®), and Dacarbazine (DTIC-Dome®). Additional exemplary alkylating agents include, without limitation, Oxaliplatin (Eloxatin®); Temozolomide (Temodar® and Temodal®); Dactinomycin (also known as actinomycin-D, Cosmegen®); Melphalan (also known as L-PAM, L-sarcolysin, and phenylalanine mustard, Alkeran®); Altretamine (also known as hexamethylmelamine (HMM), Hexalen®); Carmustine (BiCNU®); Bendamustine (Treanda®); Busulfan (Busulfex® and Myleran®); Carboplatin (Paraplatin®); Lomustine (also known as CCNU, CeeNU®); Cisplatin (also known as CDDP, Platinol® and Platinol®-AQ); Chlorambucil (Leukeran®); Cyclophosphamide (Cytoxan® and Neosar®); Dacarbazine (also known as DTIC, DIC and imidazole carboxamide, DTIC-Dome®); Altretamine (also known as hexamethylmelamine (HMM), Hexalen®); Ifosfamide (Ifex®); Prednumustine; Procarbazine (Matulane®); Mechlorethamine (also known as nitrogen mustard, mustine and mechloroethamine hydrochloride, Mustargen®); Streptozocin (Zanosar®); Thiotepa (also known as thiophosphoamide, TESPA and TSPA, Thioplex®); Cyclophosphamide (Endoxan®, Cytoxan®, Neosar®, Procytox®, Revimmune®); and Bendamustine HCl (Treanda®).

In some embodiments, compositions provided herein can be administered in combination with radiotherapy, such as radiation. Whole body radiation may be administered at 12 Gy. A radiation dose may comprise a cumulative dose of 12 Gy to the whole body, including healthy tissues. A radiation dose may comprise from 5 Gy to 20 Gy. A radiation dose may be 5 Gy, 6 Gy, 7 Gy, 8 Gy, 9 Gy, 10 Gy, 11 Gy, 12, Gy, 13 Gy, 14 Gy, 15 Gy, 16 Gy, 17 Gy, 18 Gy, 19 Gy, or up to 20 Gy. Radiation may be whole body radiation or partial body radiation. In the case that radiation is whole body radiation it may be uniform or not uniform. For example, when radiation may not be uniform, narrower regions of a body such as the neck may receive a higher dose than broader regions such as the hips.

Where desirable, an immunosuppressive agent can be used in conjunction with a subject treatment method. Exemplary immunosuppressive agents include but are not limited to cyclosporin, azathioprine, methotrexate, mycophenolate, and FK506, antibodies, or other immunoablative agents such as CAMPATH, anti-CD3 antibodies (e.g., muromonab, otelixizumab) or other antibody therapies, cytoxin, fludarabine, cyclosporin, FK506, rapamycin, mycophenolic acid, steroids, FR901228, cytokines, and irradiation, peptide vaccine, and any combination thereof. In accordance with the presently disclosed subject matter, the above-described various methods can comprise administering at least one immunomodulatory agent. In certain embodiments, the at least one immunomodulatory agent is selected from the group consisting of immunostimulatory agents, checkpoint immune blockade agents (e.g., blockade agents or inhibitors of immune checkpoint genes, such as, for example, PD-1, PD-L1, CTLA-4, IDO, TIM3, LAG3, TIGIT, BTLA, VISTA, ICOS, KIRs and CD39), radiation therapy agents, chemotherapy agents, and combinations thereof. In some embodiments, the immunostimulatory agents are selected from the group consisting of IL-12, an agonist costimulatory monoclonal antibody, and combinations thereof. In one embodiment, the immunostimulatory agent is IL-12. In some embodiments, the agonist costimulatory monoclonal antibody is selected from the group consisting of an anti-4-1BB antibody (e.g., urelumab, PF-05082566), an anti-OX40 antibody (pogalizumab, tavolixizumab, PF-04518600), an anti-ICOS antibody (BMS986226, MEDI-570, GSK3359609, JTX-2011), and combinations thereof. In one embodiment, the agonist costimulatory monoclonal antibody is an anti-4-1 BB antibody. In some embodiments, the checkpoint immune blockade agents are selected from the group consisting of anti-PD-L1 antibodies (atezolizumab, avelumab, durvalumab, BMS-936559), anti-CTLA-4 antibodies (e.g., tremelimumab, ipilimumab), anti-PD-1 antibodies (e.g., pembrolizumab, nivolumab), anti-LAG3 antibodies (e.g., C9B7W, 410C9), anti-B7-113 antibodies (e.g., DS-5573a), anti-TIM3 antibodies (e.g., F38-2E2), and combinations thereof. In one embodiment, the checkpoint immune blockade agent is an anti-PD-L1 antibody. In some cases, a compound of the present disclosure can be administered to a subject in conjunction with (e.g., before, simultaneously or following) bone marrow transplantation, T cell ablative therapy using either chemotherapy agents such as, fludarabine, external-beam radiation therapy (XRT), cyclophosphamide, or antibodies such as OKT3 or CAMPATH. In some cases, expanded cells can be administered before or following surgery. Alternatively, compositions comprising a compound described herein can be administered with immunostimulants. Immunostimulants can be vaccines, colony stimulating agents, interferons, interleukins, viruses, antigens, co-stimulatory agents, immunogenicity agents, immunomodulators, or immunotherapeutic agents. An immunostimulant can be a cytokine such as an interleukin. One or more cytokines can be introduced with modified cells provided herein. Cytokines can be utilized to boost function of modified T lymphocytes (including adoptively transferred tumor-specific cytotoxic T lymphocytes) to expand within a tumor microenvironment. In some cases, IL-2 can be used to facilitate expansion of the modified cells described herein. Cytokines such as IL-15 can also be employed. Other relevant cytokines in the field of immunotherapy can also be utilized, such as IL-2, IL-7, IL-12, IL-15, IL-21, or any combination thereof. An interleukin can be IL-2, or aldesleukin. Aldesleukin can be administered in low dose or high dose. A high dose aldesleukin regimen can involve administering aldesleukin intravenously every 8 hours, as tolerated, for up to about 14 doses at about 0.037 mg/kg (600,000 IU/kg). An immunostimulant (e.g., aldesleukin) can be administered within 24 hours after a cellular administration. An immunostimulant (e.g., aldesleukin) can be administered in as an infusion over about 15 minutes about every 8 hours for up to about 4 days after a cellular infusion. An immunostimulant (e.g., aldesleukin) can be administered at a dose from about 100,000 IU/kg, 200,000 IU/kg, 300,000 IU/kg, 400,000 IU/kg, 500,000 IU/kg, 600,000 IU/kg, 700,000 IU/kg, 800,000 IU/kg, 900,000 IU/kg, or up to about 1,000,000 IU/kg. In some cases, aldesleukin can be administered at a dose from about 100,000 IU/kg to 300,000 IU/kg, from 300,000 IU/kg to 500,000 IU/kg, from 500,000 IU/kg to 700,000 IU/kg, from 700,000 IU/kg to about 1,000,000 IU/kg.

In some embodiments, a compound disclosed herein capable of modulating a SOS protein (e.g., SOS1) to reduce Ras signaling output may be administered in combination or in conjunction with one or more pharmacologically active agents including but not limited to: (1) an inhibitor of MEK (e.g., MEK1, MEK2) or of mutants thereof (e.g., trametinib, cobimetinib, binimetinib, selumetinib, refametinib, AZD6244); (2) an inhibitor of epidermal growth factor receptor (EGFR) and/or of mutants thereof (e.g., afatinib, erlotinib, gefitinib, lapatinib, cetuximab panitumumab, osimertinib, olmutinib, EGF-816); (3) an immunotherapeutic agent (e.g., checkpoint immune blockade agents, as disclosed herein); (4) a taxane (e.g., paclitaxel, docetaxel); (5) an anti-metabolite (e.g. antifolates such as methotrexate, raltitrexed, pyrimidine analogues such as 5-fluorouracil (5-FU), ribonucleoside and deoxyribonucleoside analogues, capecitabine and gemcitabine, purine and adenosine analogues such as mercaptopurine, thioguanine, cladribine and pentostatin, cytarabine (ara C), fludarabine); (6) an inhibitor of FGFR1 and/or FGFR2 and/or FGFR3 and/or of mutants thereof (e.g., nintedanib); (7) a mitotic kinase inhibitor (e.g., a CDK4/6 inhibitor, such as, for example, palbociclib, ribociclib, abemaciclib); (8) an anti-angiogenic drug (e.g., an anti-VEGF antibody, such as, for example, bevacizumab); (9) a topoisomerase inhibitor (e.g. epipodophyllotoxins such as for example etoposide and etopophos, teniposide, amsacrin, topotecan, irinotecan, mitoxantrone); (10) a platinum-containing compound (e.g. cisplatin, oxaliplatin, carboplatin); (11) an inhibitor of ALK and/or of mutants thereof (e.g. crizotinib, alectinib, entrectinib, brigatinib); (12) an inhibitor of c-MET and/or of mutants thereof (e.g., K252a, SU11274, PHA665752, PF2341066); (13) an inhibitor of BCR-ABL and/or of mutants thereof (e.g., imatinib, dasatinib, nilotinib); (14) an inhibitor of ErbB2 (Her2) and/or of mutants thereof (e.g., afatinib, lapatinib, trastuzumab, pertuzumab); (15) an inhibitor of AXL and/or of mutants thereof (e.g., R428, amuvatinib, XL-880); (16) an inhibitor of NTRK1 and/or of mutants thereof (e.g., Merestinib); (17) an inhibitor of RET and/or of mutants thereof (e.g., BLU-667, Lenvatinib); (18) an inhibitor of A-Raf, B-Raf (e.g., Sorafenib, Vemurafenib, Debrafenib, Encorafenib) and/or C-Raf and/or of mutants thereof (RAF-709, LY-3009120); (19) an inhibitor of ERK and/or of mutants thereof (e.g., ulixertinib); (20) an MDM2 inhibitor (e.g., HDM-201, NVP-CGM097, RG-71 12, MK-8242, RG-7388, SAR405838, AMG-232, DS-3032, RG-7775, APG-115); (21) an inhibitor of mTOR (e.g., rapamycin, temsirolimus, everolimus, ridaforolimus); (22) an inhibitor of BET (e.g., I-BET 151, I-BET 762, OTX-015, TEN-010, CPI-203, CPI-0610, olionon, RVX-208, ABBC-744, LY294002, AZD5153, MT-1, MS645); (23) an inhibitor of IGF1/2 and/or of IGF1-R (e.g., xentuzumab, MEDI-573); (24) an inhibitor of CDK9 (e.g., DRB, flavopiridol, CR8, AZD 5438, purvalanol B, AT7519, dinaciclib, SNS-032); (25) an inhibitor of farnesyl transferase (e.g., tipifarnib); (26) an inhibitor of SHIP pathway including SHIP2 inhibitor (e.g., 6-(4-amino-4-methylpiperidin-1-yl)-3-(2,3-dichlorophenyl)pyrazin-2-amine), as well as SHIP1 inhibitors; (27) an inhibitor of SRC (e.g., dasatinib); (28) an inhibitor of JAK (e.g., tofacitinib); (29) a PARP inhibitor (e.g. Olaparib, Rucaparib, Niraparib, Talazoparib), (30) a BTK inhibitor (e.g. Ibrutinib, Acalabrutinib, Zanubrutinib), (31) a ROS1 inhibitor (e.g., entrectinib), (32) an inhibitor of FLT3, HDAC, VEGFR, PDGFR, LCK, Bcr-Abl or AKT, (33) an inhibitor of Kras12C mutant (e.g., including but not limited to AMG510, MRTX849, and any covalent inhibitors binding to the cysteine residue 12 of Kras, the structures of these compounds are publicly known) (e.g., an inhibitor of Ras G12C as described in US20180334454, US20190144444, US20150239900, U.S. Ser. No. 10/246,424, US20180086753, WO2018143315, WO2018206539, WO20191107519, WO2019141250, WO2019150305, U.S. Pat. No. 9,862,701, US20170197945, US20180086753, U.S. Ser. No. 10/144,724, US20190055211, US20190092767, US20180127396, US20180273523, U.S. Ser. No. 10/280,172, US20180319775, US20180273515, US20180282307, US20180282308, WO2019051291, WO2019213526, WO2019213516, WO2019217691, WO2019241157, WO2019217307, WO2020047192, WO2017087528, WO2018218070, WO2018218069, WO2018218071, WO2020027083, WO2020027084, WO2019215203, WO2019155399, WO2020035031, WO2014160200, WO2018195349, WO2018112240, WO2019204442, WO2019204449, WO2019104505, WO2016179558, WO2016176338, or related patents and applications, each of which is incorporated by reference in its entirety), (34) a SHC inhibitor (e.g., PP2, AID371185), (35) a GAB inhibitor (e.g., GAB-0001), (36) a GRB inhibitor, (37) a PI-3 kinase inhibitor (e.g., Idelalisib, Copanlisib, Duvelisib, Alpelisib, Taselisib, Perifosine, Buparlisib, Umbralisib, NVP-BEZ235-AN), (38) a MARPK inhibitor, (39) CDK4/6 (e.g., palbociclib, ribociclib, abemaciclib), (40) a MAPK inhibitor (e.g., VX-745, VX-702, RO-4402257, SCIO-469, BIRB-796, SD-0006, PH-797804, AMG-548, LY2228820, SB-681323, GW-856553, RWJ67657, BCT-197), (41) an inhibitor of SHP pathway including SHP2 inhibitor (e.g., 6-(4-amino-4-methylpiperidin-1-yl)-3-(2,3-dichlorophenyl)pyrazin-2-amine, RMC-4630, ERAS-601,

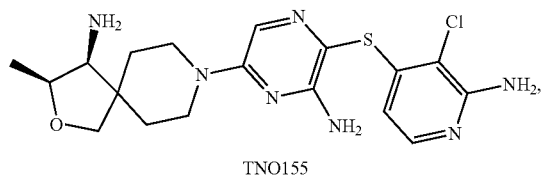

TNO155

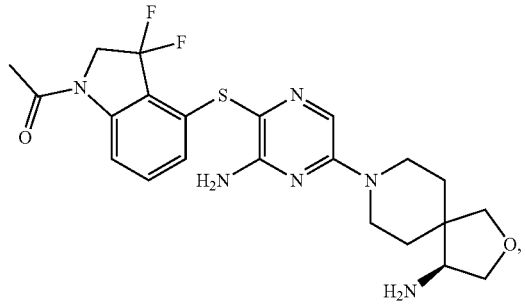

JAB-3068

-continued
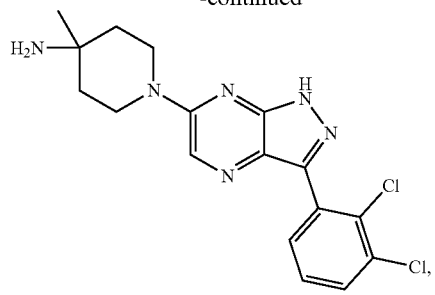
IACS-13909/BBP-398
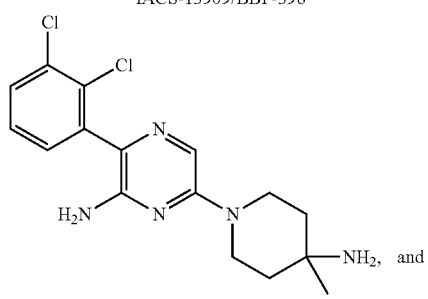
SHP099
-continued
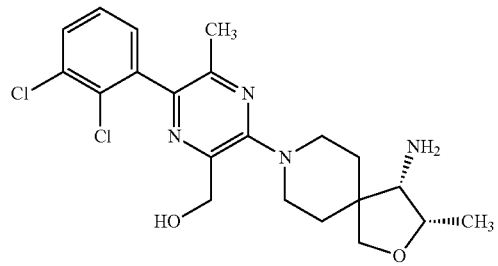
RMC-4550
as well as SHP1 inhibitors; or (42) an inhibitor of a wildtype KRas or a Kras mutant (e.g., Kras G12D including a compound described in WO2021041671, KRas G12C, KRas G12D, KRas G12S, KRas G12V, KRas G13D, KRas G13C, or KRas G13V), such as LY3537982, JAB-21822, BBO-8520, D-1553, BI-1823911, RMC-9805,
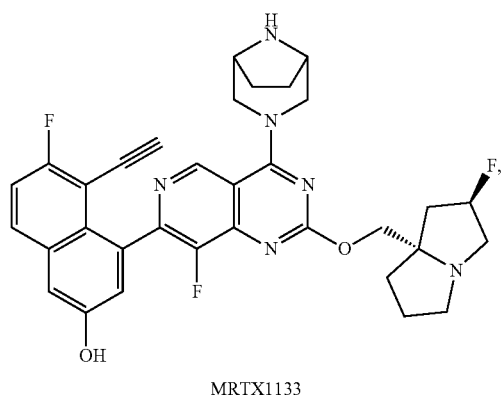
MRTX1133
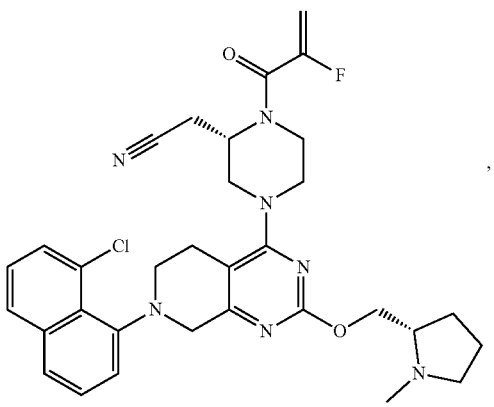
MRTX849
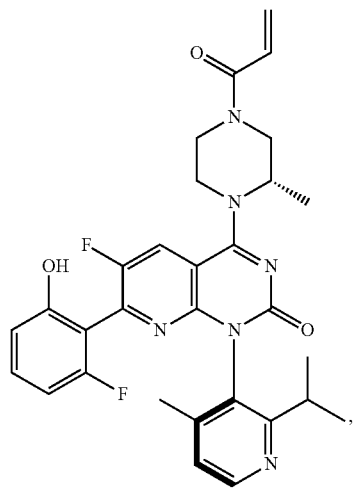
AMG510
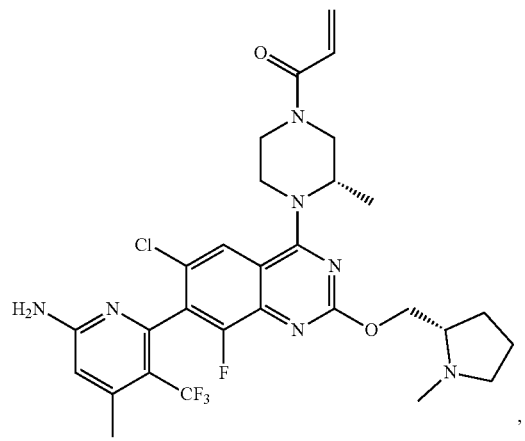
GDC-6036

-continued

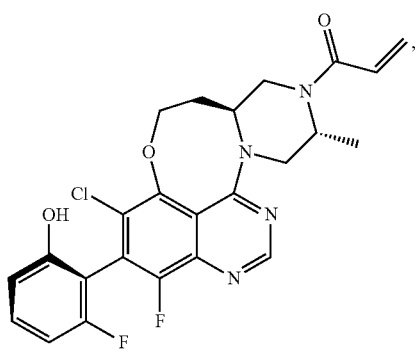
AZD4625

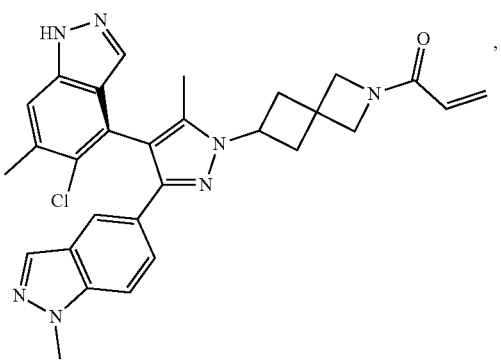
JDQ443

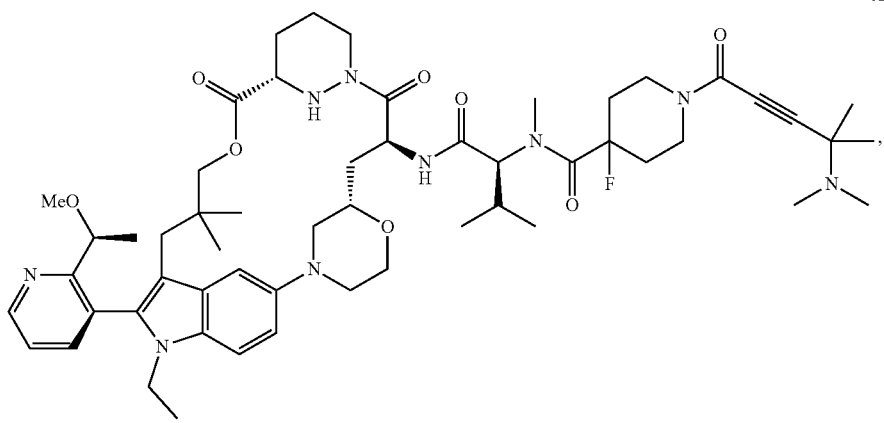
RMC-6291

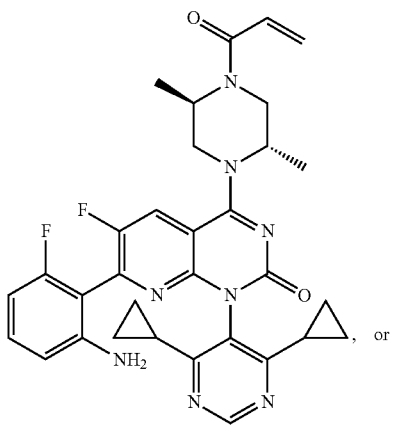, or

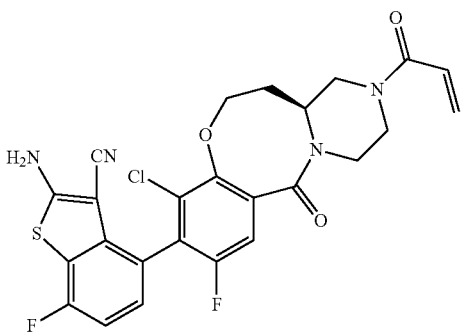.

In some embodiments, the KRAS or mutant KRAS inhibitor is a compound disclosed in WO2021041671, WO2023004102, WO2022223037, WO2023041059, WO2021118877, WO2020233592, WO2021091967, WO2021091982, WO2021091956, WO2022060836, or related patents and applications, each of which is incorporated by reference in its entirety. Inhibitors of any of the exemplary targets are applicable to the corresponding mutant targets having one or more mutations therein. In some embodiments, a compound disclosed herein capable of inhibiting a SOS protein (e.g., SOS1) to reduce Ras signaling output may be administered in combination or in conjunction with one or more checkpoint immune blockade agents (e.g., anti-PD-1 and/or anti-PD-L1 antibody, anti-CLTA-4 antibody).

In combination therapy, a compound provided herein and other anti-cancer agent(s) may be administered either simultaneously, concurrently or sequentially with no specific time limits, wherein such administration provides therapeutically effective levels of the two compounds in the body of the patient. In some embodiments, a compound of the present disclosure and another anti-cancer agent(s) are generally administered sequentially in any order by infusion or orally. The dosing regimen may vary depending upon the stage of the disease, physical fitness of the patient, safety profiles of the individual drugs, and tolerance of the individual drugs, as well as other criteria known to the attending physician and medical practitioner(s) administering the combination. The compound of the present invention and other anti-cancer agent(s) may be administered within minutes of each other, hours, days, or even weeks apart depending upon the particular cycle being used for treatment. In addition, the cycle could include administration of one drug more often than the other during the treatment cycle and at different doses per administration of the drug.

An antibiotic can be administered to a subject as part of a therapeutic regime. An antibiotic can be administered at a therapeutically effective dose. An antibiotic can kill or inhibit growth of bacteria. An antibiotic can be a broad spectrum antibiotic that can target a wide range of bacteria. Broad spectrum antibiotics, either a $3^{rd}$ or $4^{th}$ generation, can be cephalosporin or a quinolone. An antibiotic can also be a narrow spectrum antibiotic that can target specific types of bacteria. An antibiotic can target a bacterial cell wall such as penicillins and cephalosporins. An antibiotic can target a cellular membrane such as polymyxins. An antibiotic can interfere with essential bacterial enzymes such as antibiotics: rifamycins, lipiarmycins, quinolones, and sulfonamides. An antibiotic can also be a protein synthesis inhibitor such as macrolides, lincosamides, and tetracyclines. An antibiotic can also be a cyclic lipopeptide such as daptomycin, glycylcyclines such as tigecycline, oxazolidiones such as linezolid, and lipiarmycins such as fidaxomicin. In some cases, an antibiotic can be $1^{st}$ generation, $2^{nd}$ generation, $3^{rd}$ generation, 4th generation, or $5^{th}$ generation. A first-generation antibiotic can have a narrow spectrum. Examples of $1^{st}$ generation antibiotics can be penicillins (Penicillin G or Penicillin V), Cephalosporins (Cephazolin, Cephalothin, Cephapirin, Cephalethin, Cephradin, or Cephadroxin). In some cases, an antibiotic can be $2^{nd}$ generation. $2^{nd}$ generation antibiotics can be a penicillin (Amoxicillin or Ampicillin), Cephalosporin (Cefuroxime, Cephamandole, Cephoxitin, Cephaclor, Cephrozil, Loracarbef). In some cases, an antibiotic can be $3^{rd}$ generation. A $3^{rd}$ generation antibiotic can be penicillin (carbenicillin and ticarcillin) or cephalosporin (Cephixime, Cephtriaxone, Cephotaxime, Cephtizoxime, and Cephtazidime). An antibiotic can also be a $4^{th}$ generation antibiotic. A $4^{th}$ generation antibiotic can be Cephipime. An antibiotic can also be $5^{th}$ generation. $5^{th}$ generation antibiotics can be Cephtaroline or Cephtobiprole.

In some cases, an anti-viral agent may be administered as part of a treatment regime. In some cases, a herpes virus prophylaxis can be administered to a subject as part of a treatment regime. A herpes virus prophylaxis can be valacyclovir (Valtrex). Valtrex can be used orally to prevent the occurrence of herpes virus infections in subjects with positive HSV serology. It can be supplied in 500 mg tablets. Valacyclovir can be administered at a therapeutically effective amount.

In some cases, a treatment regime may be dosed according to a body weight of a subject. In subjects who are determined obese (BMI>35) a practical weight may need to be utilized. BMI is calculated by: BMI=weight (kg)/[height (m)]$^2$. Body weight may be calculated for men as 50 kg+2.3*(number of inches over 60 inches) or for women 45.5 kg+2.3*(number of inches over 60 inches). An adjusted body weight may be calculated for subjects who are more than 20% of their ideal body weight. An adjusted body weight may be the sum of an ideal body weight+(0.4×(actual body weight−ideal body weight)). In some cases, a body surface area may be utilized to calculate a dosage. A body surface area (BSA) may be calculated by: BSA (m2) =√Height (cm)*Weight (kg)/3600.

In some embodiments, the present disclosure provides a method of reducing Ras signaling output, comprising contacting a SOS protein (e.g., SOS1) with an effective amount of a compound of Formula (I), (I-A), (I-B), (I-B1), (I-B2), (I-C), (I-C1), (I-C2), (I-C3), (I-D), (I-D1), (I-D2), (I-E), (I-E1), (II-B), (II-C), or (III), or a pharmaceutically acceptable salt or solvate thereof, thereby reducing the Ras signaling output. In some embodiments, the compound inhibits the SOS1 protein activity or disrupts interaction or binding between a SOS1 protein and a Ras protein. In some embodiments, a compound of Formula (I), (I-A), (I-B), (I-B1), (I-B2), (I-C), (I-C1), (I-C2), (I-C3), (I-D), (I-D1), (I-D2), (I-E), (I-E1), (II-B), (II-C), or (III) inhibits SOS1 or disrupts interaction or binding between SOS1 and one or more of the following: a K-Ras protein including wildtype and any mutant thereof, such as a K-Ras G12D mutant or K-Ras G12V mutant.

In some embodiments, the present disclosure provides a method of reducing Ras signaling output in a cell by contacting the cell with a compound of the present disclosure. A reduction in Ras signaling can be evidenced by one or more of the following: (i) an increase in steady state level of GDP-bound Ras protein; (ii) a reduction in steady state level of GTP-bound Ras protein; (iii) a reduction of phosphorylated AKTs473, (iv) a reduction of phosphorylated ERKT202/y204, (v) a reduction of phosphorylated S6S235/236, (vi) reduction (e.g., inhibition) of cell growth of Ras-driven tumor cells (e.g., those derived from a tumor cell line disclosed herein), and (vii) an interference or disruption of the interaction or binding between a SOS protein (e.g., SOS1) with a Ras protein such as a wildtype or a mutant Ras. In some cases, the reduction in Ras signaling output can be evidenced by two, three, four, five, six or all of (i)-(vii) above. In some embodiments, the reduction of any one or more of (i)-(vii) can be 0.1-fold, 0.2-fold, 0.3-fold, 0.4-fold, 0.5-fold, 0.6-fold, 0.7-fold, 0.8-fold, 0.9-fold, 1-fold, 2-fold, 3-fold, 4-fold, 5-fold, 6-fold, 7-fold, 8-fold, 9-fold, 10-fold, 20-fold, 30-fold, 40-fold, 50-fold, 60-fold, 70-fold, 80-fold, 90-fold, 100-fold, 200-fold, 300-fold, 400-fold, 500-fold, 600-fold, 700-fold, 800-fold, 900-fold, 1000-fold, 2000-fold, 3000-fold, 4000-fold, 5000-fold, or more as compared to a control untreated with a subject compound. A reduction in cell growth can be demonstrated with the use of tumor cells or cell lines. A tumor cell line can be derived from a tumor in one or more tissues, e.g., pancreas, lung, ovary, biliary tract, intestine (e.g., small intestine, large intestine, colon), endometrium, stomach, hematopoietic tissue (e.g., lymphoid tissue), etc. Examples of a tumor cell line with a K-Ras mutation may include, but are not limited to, A549 (e.g., K-Ras G12S), AGS (e.g., K-Ras G12D), ASPC1 (e.g., K-Ras G12D), Calu-6 (e.g., K-Ras Q61K), CFPAC-1 (e.g., K-Ras G12V), CL40 (e.g., K-Ras G12D), COLO678 (e.g., K-Ras G12D), COR-L23 (e.g., K-Ras G12V), DAN-G (e.g., K-Ras G12V), GP2D (e.g., K-Ras G12D), GSU (e.g., K-Ras G12F), HCT116 (e.g., K-Ras G13D), HEC1A (e.g., K-Ras G12D), HEC1B (e.g., K-Ras G12F), HEC50B (e.g., K-Ras G12F), HEYA8 (e.g., K-Ras G12D or G13D), HPAC (e.g., K-Ras G12D), HPAFII (e.g., K-Ras G12D), HUCCT1 (e.g., K-Ras G12D), KARPAS620 (e.g., K-Ras G13D), KOPN8 (e.g., K-Ras G13D), KP-3 (e.g., K-Ras G12V), KP-4 (e.g., K-Ras G12D), L3.3 (e.g., K-Ras G12D), LoVo (e.g., K-Ras G13D), LS180 (e.g., K-Ras G12D), LS513 (e.g., K-Ras G12D), MCAS (e.g., K-Ras G12D), NB4 (e.g., K-Ras A18D), NCI-H1355 (e.g., K-Ras G13C), NCI-H1573 (e.g., K-Ras G12A), NCI-H1944 (e.g., K-Ras G13D), NCI-H2009 (e.g., K-Ras G12A), NCI-H441 (e.g., K-Ras G12V), NCI-H747 (e.g., K-Ras G13D), NOMO-1 (e.g., K-Ras G12D), OV7 (e.g., K-Ras G12D), PANC0203 (e.g., K-Ras G12D), PANC0403 (e.g., K-Ras G12D), PANC0504 (e.g., K-Ras G12D), PANC0813 (e.g., K-Ras G12D), PANC1 (e.g., K-Ras G12D), Panc-10.05 (e.g., K-Ras G12D), PaTu-8902 (e.g., K-Ras G12V), PK1 (e.g., K-Ras G12D), PK45H (e.g., K-Ras G12D), PK59 (e.g., K-Ras G12D), SK-CO-1 (e.g., K-Ras G12V), SKLU1 (e.g., K-Ras G12D), SKM-1 (e.g., K-Ras K117N), SNU1 (e.g., K-Ras G12D), SNU1033 (e.g., K-Ras G12D), SNU1197 (e.g., K-Ras G12D), SNU407 (e.g., K-Ras G12D), SNU410 (e.g., K-Ras G12D), SNU601 (e.g., K-Ras G12D), SNU61 (e.g., K-Ras G12D), SNU8 (e.g., K-Ras G12D), SNU869 (e.g., K-Ras G12D), SNU-C2A (e.g., K-Ras G12D), SU.86.86 (e.g., K-Ras G12D), SUIT2 (e.g., K-Ras G12D), SW1990 (e.g., K-Ras G12D), SW403 (e.g., K-Ras G12V), SW480 (e.g., K-Ras G12V), SW620 (e.g., K-Ras G12V), SW948 (e.g., K-Ras Q61L), T3M10 (e.g., K-Ras G12D), TCC-PAN2 (e.g., K-Ras G12R), TGBC11TKB (e.g., K-Ras G12D), and MIA Pa-Ca (e.g., MIA Pa-Ca 2 (e.g., K-Ras G12C)).

In some embodiments, the present disclosure provides a SOS protein (e.g., SOS1) bound by a compound of Formula (I), (I-A), (I-B), (I-B1), (I-B2), (I-C), (I-C1), (I-C2), (I-C3), (I-D), (I-D1), (I-D2), (I-E), (I-E1), (II-B), (II-C), or (III), or a pharmaceutically acceptable salt or solvate thereof, wherein interaction of the SOS1 protein with a Ras protein is reduced as compared to a SOS1 protein unbound to said compound.

Pharmaceutical Compositions and Methods of Administration

In certain aspects, the present disclosure provides a pharmaceutical composition comprising a compound described herein, or a pharmaceutically acceptable salt or solvate thereof, and a pharmaceutically acceptable excipient.

A compound of Formula (I), (I-A), (I-B), (I-B1), (I-B2), (I-C), (I-C1), (I-C2), (I-C3), (I-D), (I-D1), (I-D2), (I-E), (I-E1), (II-B), (II-C), or (III), or a pharmaceutically acceptable salt or solvate thereof, may be administered to a subject in a biologically compatible form suitable for administration to treat or prevent a disease, disorder or condition. A compound described herein may be administered in any pharmacological form including a therapeutically effective amount of a compound of Formula (I), (I-A), (I-B), (I-B1), (I-B2), (I-C), (I-C1), (I-C2), (I-C3), (I-D), (I-D1), (I-D2), (I-E), (I-E1), (II-B), (II-C), or (III), or a pharmaceutically acceptable salt or solvate thereof, alone or in combination with a pharmaceutically acceptable carrier. In some embodiments, the present disclosure provides a pharmaceutical composition comprising a pharmaceutically acceptable excipient and a compound of Formula (I), (I-A), (I-B), (I-B31), (I-B32), (I-C), (I-C1), (I-C2), (I-C3), (I-D), (I-D1), (I-D2), (I-E), (I-E1), (II-B), (II-C), or (III), or a pharmaceutically acceptable salt or solvate thereof.

In some embodiments, a compound described herein is administered as a pure chemical. In some embodiments, a compound described herein is combined with a pharmaceutically suitable or acceptable carrier (also referred to herein as a pharmaceutically suitable (or acceptable) excipient, physiologically suitable (or acceptable) excipient, or physiologically suitable (or acceptable) carrier) selected on the basis of a chosen route of administration and standard pharmaceutical practice as described, for example, in Remington: The Science and Practice of Pharmacy (Gennaro, 21st Ed. Mack Pub. Co., Easton, PA (2005)).

Accordingly, provided herein is a pharmaceutical composition comprising at least one compound described herein, or a pharmaceutically acceptable salt, together with one or more pharmaceutically acceptable excipients. The excipient(s) (or carrier(s)) is acceptable or suitable if the excipient is compatible with the other ingredients of the composition and not deleterious to the recipient of the composition.

In practicing any of the subject methods, the compounds described herein may be administered either alone or in combination with pharmaceutically acceptable carriers, excipients or diluents, in a pharmaceutical composition. Administration of the compounds and compositions described herein can be affected by any method that enables delivery of the compounds to the site of action. These methods include, though are not limited to delivery via enteral routes (including oral, gastric or duodenal feeding tube, rectal suppository and rectal enema), parenteral routes (injection or infusion, including intraarterial, intracardiac, intradermal, intraduodenal, intramedullary, intramuscular, intraosseous, intraperitoneal, intrathecal, intravascular, intravenous, intravitreal, epidural and subcutaneous), inhalational, transdermal, transmucosal, sublingual, buccal and topical (including epicutaneous, dermal, enema, eye drops, ear drops, intranasal, vaginal) administration, although the most suitable route may depend upon, for example, the condition and disorder of the recipient. By way of example only, a compound described herein can be administered locally to the area in need of treatment, by for example, local infusion during surgery, topical application such as creams or ointments, injection, catheter, or implant. The administration can also be by direct injection at the site of a diseased tissue or organ. In some embodiments, a compound described herein is administered orally.

In practicing any of the subject methods, a pharmaceutical composition suitable for oral administration may be presented as a discrete unit such as a capsule, cachet or tablet, each containing a predetermined amount of the active ingredient; as a powder or granules; as a solution or a suspension in an aqueous liquid or a non-aqueous liquid; or as an oil-in-water liquid emulsion or a water-in-oil liquid emulsion. In some embodiments, the active ingredient is presented as a bolus, electuary or paste.

Pharmaceutical compositions which can be used orally include tablets, push-fit capsules made of gelatin, as well as soft, sealed capsules made of gelatin and a plasticizer, such as glycerol or sorbitol. Tablets may be made by compression or molding, optionally with one or more accessory ingredients. Compressed tablets may be prepared by compressing in a suitable machine the active ingredient in a free-flowing form such as a powder or granules, optionally mixed with binders, inert diluents, or lubricating, surface active or dispersing agents. Molded tablets may be made by molding in a suitable machine a mixture of the powdered compound moistened with an inert liquid diluent. In some embodiments, the tablets are coated or scored and are formulated so as to provide slow or controlled release of the active ingredient therein. All formulations for oral administration should be in dosages suitable for such administration. The push-fit capsules can contain the active ingredients in admixture with filler such as lactose, binders such as starches, and/or lubricants such as talc or magnesium stearate and, optionally, stabilizers. In soft capsules, the active compounds may be dissolved or suspended in suitable liquids, such as fatty oils, liquid paraffin, or liquid polyethylene glycols. In some embodiments, stabilizers are added. Dragee cores are provided with suitable coatings. For this purpose, concentrated sugar solutions may be used, which may optionally contain gum arabic, talc, polyvinyl pyrrolidone, carbopol gel, polyethylene glycol, and/or titanium dioxide, lacquer solutions, and suitable organic solvents or solvent mixtures. Dyestuffs or pigments may be added to the tablets or Dragee coatings for identification or to characterize different combinations of active compound doses.

In some embodiments, a pharmaceutical composition is formulated for parenteral administration by injection, e.g., by bolus injection or continuous infusion. Formulations for injection may be presented in unit dosage form, e.g., in ampoules or in multi-dose containers, with an added preservative. The compositions may take such forms as suspensions, solutions or emulsions in oily or aqueous vehicles, and may contain formulatory agents such as suspending, stabilizing and/or dispersing agents. The compositions may be presented in unit-dose or multi-dose containers, for example sealed ampoules and vials, and may be stored in powder form or in a freeze-dried (lyophilized) condition requiring only the addition of the sterile liquid carrier, for example, saline or sterile pyrogen-free water, immediately prior to use. Extemporaneous injection solutions and suspensions may be prepared from sterile powders, granules and tablets of the kind previously described.

Pharmaceutical compositions for parenteral administration include aqueous and non-aqueous (oily) sterile injection solutions of the active compounds which may contain antioxidants, buffers, bacteriostats and solutes which render the formulation isotonic with the blood of the intended recipient; and aqueous and non-aqueous sterile suspensions which may include suspending agents and thickening agents. Suitable lipophilic solvents or vehicles include fatty oils such as sesame oil, or synthetic fatty acid esters, such as ethyl oleate or triglycerides, or liposomes. Aqueous injection suspensions may contain substances which increase the viscosity of the suspension, such as sodium carboxymethyl cellulose, sorbitol, or dextran. Optionally, the suspension may also contain suitable stabilizers or agents which increase the solubility of the compounds to allow for the preparation of highly concentrated solutions.

Pharmaceutical compositions may also be formulated as a depot preparation. Such long-acting formulations may be administered by implantation (for example subcutaneously or intramuscularly) or by intramuscular injection. Thus, for example, the compounds may be formulated with suitable polymeric or hydrophobic materials (for example, as an emulsion in an acceptable oil) or ion exchange resins, or as sparingly soluble derivatives, for example, as a sparingly soluble salt.

EXAMPLES

The following examples are provided for illustrative purposes only and not to limit the scope of the claims provided herein.

As used herein, the following abbreviations, unless otherwise indicated, shall be understood to have the following meanings:

ACN or MeCN acetonitrile
AcOH acetic acid
Ac acetyl
BINAP 2,2'-bis(diphenylphosphino)-1,1'-binaphthalene
Bn benzyl
BOC or Boc tert-butyl carbamate
i-Bu iso-butyl
t-Bu tert-butyl
DCM dichloromethane ($CH_2Cl_2$)
DIBAL-H diisobutylaluminum hydride
DIPEA or DIEA diisopropylethylamine
DMAP 4-(N,N-dimethylamino)pyridine
DME 1,2-dimethoxyethane
DMF N,N-dimethylformamide
DMA N,N-dimethylacetamide
DMSO dimethylsulfoxide
Dppf or dppf 1,1'-bis(diphenylphosphino)ferrocene
EDC or EDCI N-(3-dimethylaminopropyl)-N'-ethylcarbodiimide hydrochloride
eq equivalent(s)
Et ethyl
$Et_2O$ diethyl ether
EtOH ethanol
EtOAc ethyl acetate
HPLC high performance liquid chromatography
KHMDS potassium bis(trimethylsilyl)amide
NaHMDS sodium bis(trimethylsilyl)amide
LiHMDS lithium bis(trimethylsilyl)amide
LAH lithium aluminum anhydride
LCMS liquid chromatography mass spectrometry
Me methyl
MeOH methanol
MS mass spectroscopy
Ms mesyl
NMR nuclear magnetic resonance
Ph phenyl
iPr/i-Pr iso-propyl
RP-HPLC reverse-phase high-pressure liquid chromatography
rt room temperature
TBS tert-butyldimethylsilyl
TEA triethylamine
TFA trifluoroacetic acid
THF tetrahydrofuran
TLC thin layer chromatography
TMS trimethylsilyl
TsOH/p-TsOH p-toluenesulfonic acid Unless noted otherwise, all materials, such as reagents, starting materials and solvents, were purchased from commercial suppliers, such as Sigma-Aldrich, VWR, and the like, and were used without further purification. Reactions were run under nitrogen atmosphere, unless noted otherwise. The progress of reactions was monitored by thin layer chromatography (TLC), analytical high performance liquid chromatography (anal. HPLC), and mass spectrometry, the details of which may be provided in specific examples.

Reactions were worked up as described specifically in each preparation; commonly, reaction mixtures were purified by extraction and other purification methods such as temperature- and solvent-dependent crystallization, and precipitation. In addition, reaction mixtures were routinely purified by preparative HPLC, for example, using Microsorb C18 or Microsorb BDS column packings and conventional eluents. Progress of reactions was typically monitored by liquid chromatography mass spectrometry (LCMS). Characterization of isomers was typically done by Nuclear Overhauser effect spectroscopy (NOE). Characterization of reaction products was routinely carried out by mass spectrometry and/or $^1$H-NMR spectroscopy. For NMR measurement, samples were dissolved in deuterated solvent ($CD_3OD$, $CDCl_3$, or DMSO-$d_6$).

Example 1: Synthesis of 1-((4R)-2,2-difluoro-4-methyl-6$^7$-oxo-6$^7$,6$^8$-dihydro-5-aza-6(4,8)-pyrido[2,3-d]pyrimidina-1(4,1)- piperidina-3(1,3)-benzenacyclotetradecaphane-6$^6$-yl)cyclopropane-1-carbonitrile (54)

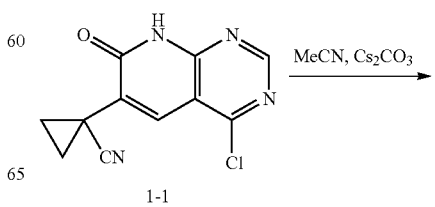

1-1

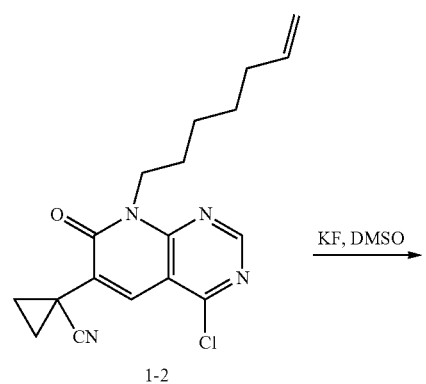

1-2

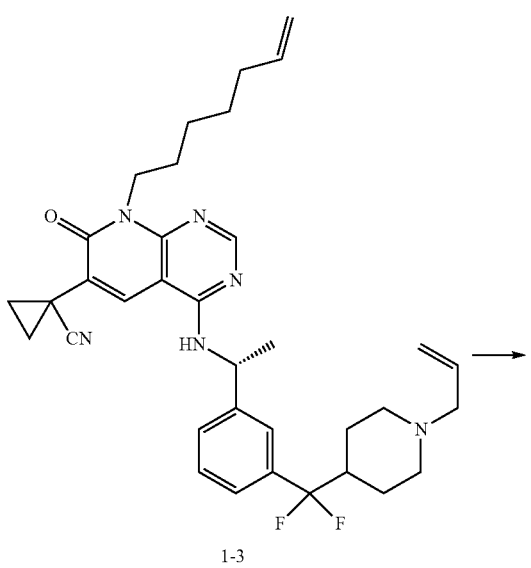

1-3

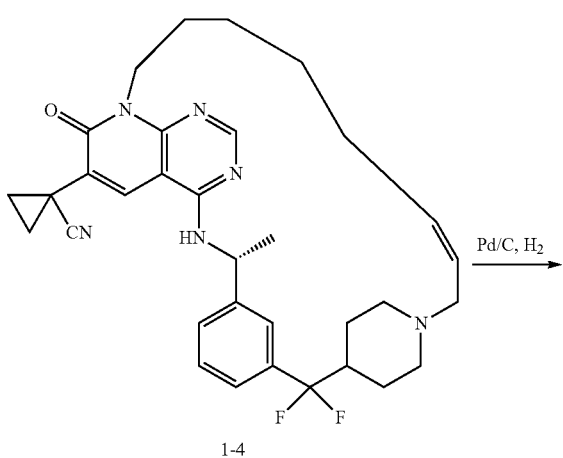

1-4

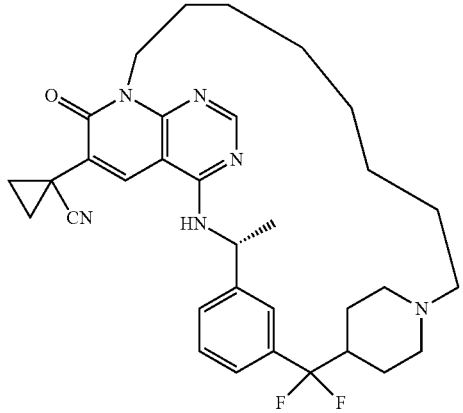

54

Step A: Preparation of 1-(4-chloro-8-(hept-6-en-1-yl)-7-oxo-7,8-dihydropyrido[2,3-d]pyrimidin-6-yl)cyclopropane-1-carbonitrile (1-2). To a stirred solution of 1-(4-chloro-7-oxo-7,8-dihydropyrido[2,3-d]pyrimidin-6-yl)cyclopropane-1-carbonitrile (300 mg) in MeCN (20 mL) was added $Cs_2CO_3$ (300 mg) and 7-bromo-hept-1-ene (240 mg). The mixture was stirred for 2 hours at 70° C. It was cooled down to room temperature and the solvent was removed under reduced pressure. The mixture was extracted by ethyl acetate and water. Organics were separated and combined, washed with brine, dried over $Na_2SO_4$, filtered and concentrated to give a residue. The residue was purified by flash chromatography to afford 1-2 (250 mg). ESI-MS m/z: $[M+H]^+=343.1$.

Step B: Preparation of (R)-1-(4-((1-(3-((1-allylpiperidin-4-yl)difluoromethyl)phenyl)ethyl)amino)-8-(hept-6-en-1-yl)-7-oxo-7,8-dihydropyrido[2,3-d]pyrimidin-6-yl)cyclopropane-1-carbonitrile (1-3). To a stirred solution of 1-2 (250 mg) in DMSO (20 mL) was added 1-(3-((1-allylpiperidin-4-yl)difluoromethyl)phenyl)ethan-1-amine (180 mg) and KF (200 mg). The mixture was stirred for 2 hours at 100° C. It was cooled to room temperature, water was added, and the mixture was extracted by ethyl acetate. Organics were combined, washed with brine, dried over $Na_2SO_4$, filtered and concentrated to give a residue. The residue was purified by flash chromatography to afford 1-3 (170 mg). ESI-MS m/z: $[M+H]^+=601.2$.

Step C: Preparation of 1-((4R,Z)-2,2-difluoro-4-methyl-$6^7$-oxo-$6^7,6^8$-dihydro-5-aza-6(4,8)-pyrido[2,3-d]pyrimidina-1(4,1)-piperidina-3(1,3)-benzenacyclotetradecaphan-12-en-$6^6$-yl)cyclopropane-1-carbonitrile (1-4). To a stirred solution of 1-3 (170 mg) in DCM (200 mL) was added Grubbs II catalyst (40 mg). The mixture was stirred overnight at 40° C. It was cooled to room temperature and solvent was removed to give a residue. The residue was purified by flash chromatography to afford 1-4 (30 mg). ESI-MS m/z: $[M+H]^+=573.2$.

Step D: Preparation of 1-((4R)-2,2-difluoro-4-methyl-$6^7$-oxo-$6^7,6^8$-dihydro-5-aza-6(4,8)-pyrido[2,3-d]pyrimidina-1(4,1)-piperidina-3(1,3)-benzenacyclotetradecaphane-$6^6$-yl)cyclopropane-1-carbonitrile (54). To a stirred solution of 1-4 (20 mg) in MeOH (10 mL) was added Pd/C (5 mg). It was evacuated and back filled with hydrogen. This was repeated 3 times. The mixture was stirred for 3 hours under $H_2$. It was filtered through celite and washed with ethyl acetate. Organics were combined and the solvent was removed to provide a crude residue. The residue was purified by flash chromatography to afford the title compound (10 mg). ESI-MS m/z: [M+H]$^+$=575.2. $^1$HNMR (400 MHz, CD$_3$OD) 8.40 (s, 1H), 8.36 (s, 1H), 7.62-7.60 (m, 1H), 7.51-7.47 (m, 2H), 7.31-7.29 (m, 1H), 5.5-5.4 (m, 1H), 4.6-4.5 (m, 1H), 4.38-4.3 (m, 1H), 3.09-3.07 (m, 2H), 2.62-2.60 (m, 2H), 2.43-2.38 (m, 2H), 2.25-2.22 (m, 2H), 1.82-1.74 (m, 4H), 1.71-1.68 (m, 5H), 1.60-1.49 (m, 4H), 1.40-1.30 (m, 6H), 1.25-1.12 (m, 4H).

Example 2: Synthesis of (4R)-6$^6$-(1,1-dioxidotetrahydro-2H-thiopyran-4-yl)-2,2-difluoro-6$^2$,4-dimethyl-6$^7$,6$^8$-dihydro-5-aza-6(4,8)-pyrido[2,3-d]pyrimidina-1(4,1)-piperidina-3(1,3)-benzenacyclotridecaphan-6$^7$-one (173)

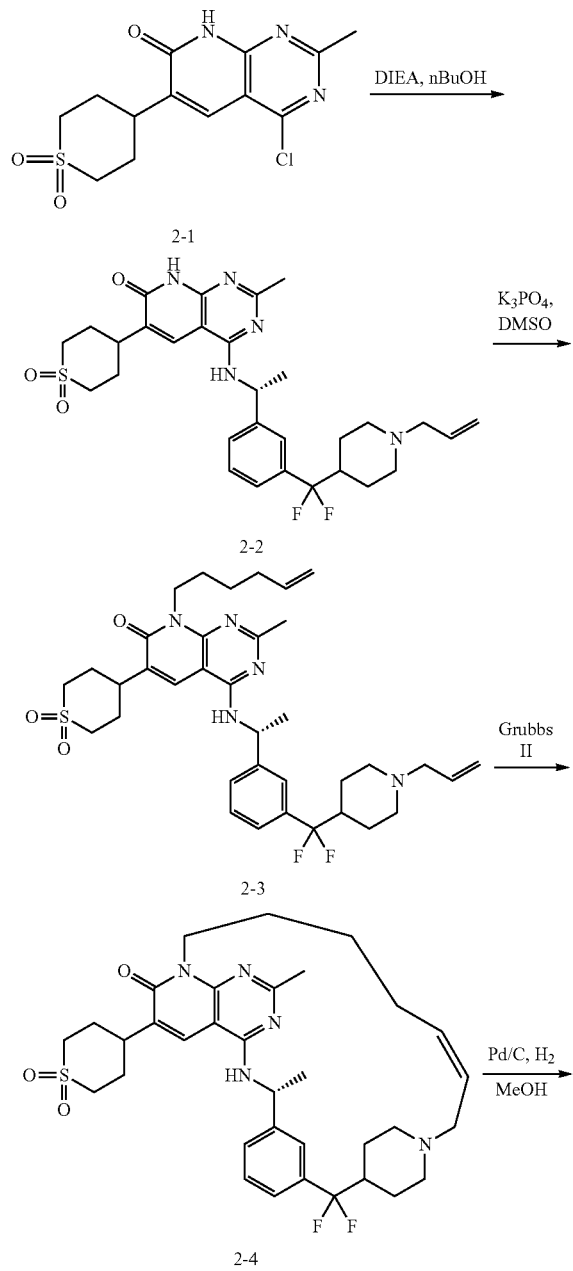

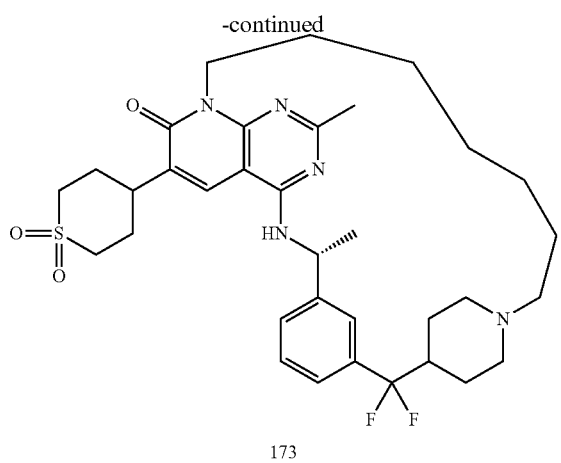

Step A: Preparation of (R)-4-((1-(3-((1-allylpiperidin-4-yl)difluoromethyl)phenyl)ethyl)amino)-6-(1,1-dioxidotetrahydro-2H-thiopyran-4-yl)-2-methylpyrido[2,3-d]pyrimidin-7(8H)-one (2-2). To a solution of 4-chloro-6-(1,1-dioxidotetrahydro-2H-thiopyran-4-yl)-2-methylpyrido[2,3-d]pyrimidin-7(8H)-one (2-1) (400 mg, 1.23 mmol) in n-BuOH (15 mL) was added (R)-1-(3-((1-allylpiperidin-4-yl)difluoromethyl)phenyl)ethan-1-amine (396 mg, 1.35 mmol) and DIEA (789 mg, 6.12 mmol). The resulting mixture was stirred overnight at 120° C. under argon. The resulting mixture was cooled to room temperature and water was added (30 mL), then the mixture was extracted with ethyl acetate (20 mL×2). The organics were combined, washed with brine, dried over Na$_2$SO$_4$, filtered and solvent was removed under reduced pressure to give a crude residue. The crude was purified by flash chromatography on silica gel (dichloromethane:methyl alcohol=30:1) to afford desired product 2-2 (650 mg) as a solid. ESI-MS m/z: [M+H]$^+$=586.

Step B: Preparation of (R)-4-((1-(3-((1-allylpiperidin-4-yl)difluoromethyl)phenyl)ethyl)amino)-6-(1,1-dioxidotetrahydro-2H-thiopyran-4-yl)-8-(hex-5-en-1-yl)-2-methylpyrido[2,3-d]pyrimidin-7(8H)-one (2-3). To a solution of 2-2 (400 mg, 0.69 mmol) in DMSO (15 mL) was added 6-bromohex-1-ene (167 mg, 1.03 mmol) and K$_3$PO$_4$ (435 mg, 2.06 mmol). The resulting mixture was stirred overnight at 55° C. under argon. The resulting mixture was cooled to room temperature, water was added (30 ml), and the mixture was extracted with ethyl acetate (20 mL×2). The organics were washed with brine, dried over Na$_2$SO$_4$, filtered and concentrated under reduced pressure to give a crude residue. The crude residue was purified by flash chromatography on silica gel (dichloromethane:methyl alcohol=30:1) to afford the desired product (370 mg) as a solid. ESI-MS m/z: [M+H]$^+$=668.

Step C: Preparation of (4R,Z)-6$^6$-(1,1-dioxidotetrahydro-2H-thiopyran-4-yl)-2,2-difluoro-6$^2$,4-dimethyl-6$^7$,6$^8$-dihydro-5-aza-6(4,8)-pyrido[2,3-d]pyrimidina-1(4,1)-piperidina-3(1,3)-benzenacyclotridecaphan-11-en-6$^7$-one (2-4). To a solution 2-3 (370 mg, 0.56 mmol) in DCM (125 mL) was added Grubbs II catalyst (165 mg, 0.20 mmol). The resulting mixture was stirred overnight at RT under argon. Water (30 mL) was added. The organics were combined, washed with brine, dried over Na$_2$SO$_4$, filtered and solvent was removed under reduced pressure to give a crude residue. The crude residue was purified by flash chromatography on silica gel (dichloromethane:methyl alcohol=25:1) to afford the desired product (230 mg) as a solid. ESI-MS m/z: [M+H]$^+$=640.

Step D: Preparation of (4R)-6⁶-(1,1-dioxidotetrahydro-2H-thiopyran-4-yl)-2,2-difluoro-6²,4-dimethyl-6⁷,6⁸-dihydro-5-aza-6(4,8)-pyrido[2,3-d]pyrimidina-1(4,1)-piperidina-3(1,3)-benzenacyclotridecaphan-6⁷-one (173). To a solution of 2-4 (50 mg, 0.08 mmol) in MeOH (20 mL) was added Pd/C (10%) (9 mg, 0.01 mmol). The resulting mixture was stirred for 2 hours at room temperature under hydrogen. It was filtered and solvent was removed under reduced pressure to give a crude residue. The crude residue was purified by prep-TLC (dichloromethane:methyl alcohol=25:1) to afford the title compound (12 mg) as a white solid. ESI-MS m/z: [M+H]⁺=642. ¹H NMR (400 MHz, DMSO) δ: 8.11 (s, 1H), 7.47-7.46 (d, 1H, J=7.6 Hz), 7.39-7.35 (t, 1H, J=7.6 Hz), 7.19 (s, 1H), 7.16 (d, 1H, J=7.6 Hz), 5.35-5.30 (m, 1H), 4.70-4.64 (m, 1H), 4.12-4.05 (m, 1H), 3.30-3.20 (m, 2H), 3.20-3.03 (m, 4H), 2.87-2.81 (m, 2H), 2.55-2.52 (m, 2H), 2.47-2.40 (m, 2H), 2.20-2.17 (m, 8H), 1.92-1.92 (m, 2H), 1.71-1.67 (d, 3H, J=7.2 Hz), 1.61-1.37 (m, 4H), 1.28-1.18 (m, 8H).

Example 3: Synthesis of (R)-5⁷-methoxy-5²,3-dimethyl-6,9,12,15,18-pentaoxa-4,21-diaza-5(4,6)-quinazolina-2(2,5)-thiophena-1(1,2)-benzenacyclodocosaphane (56)

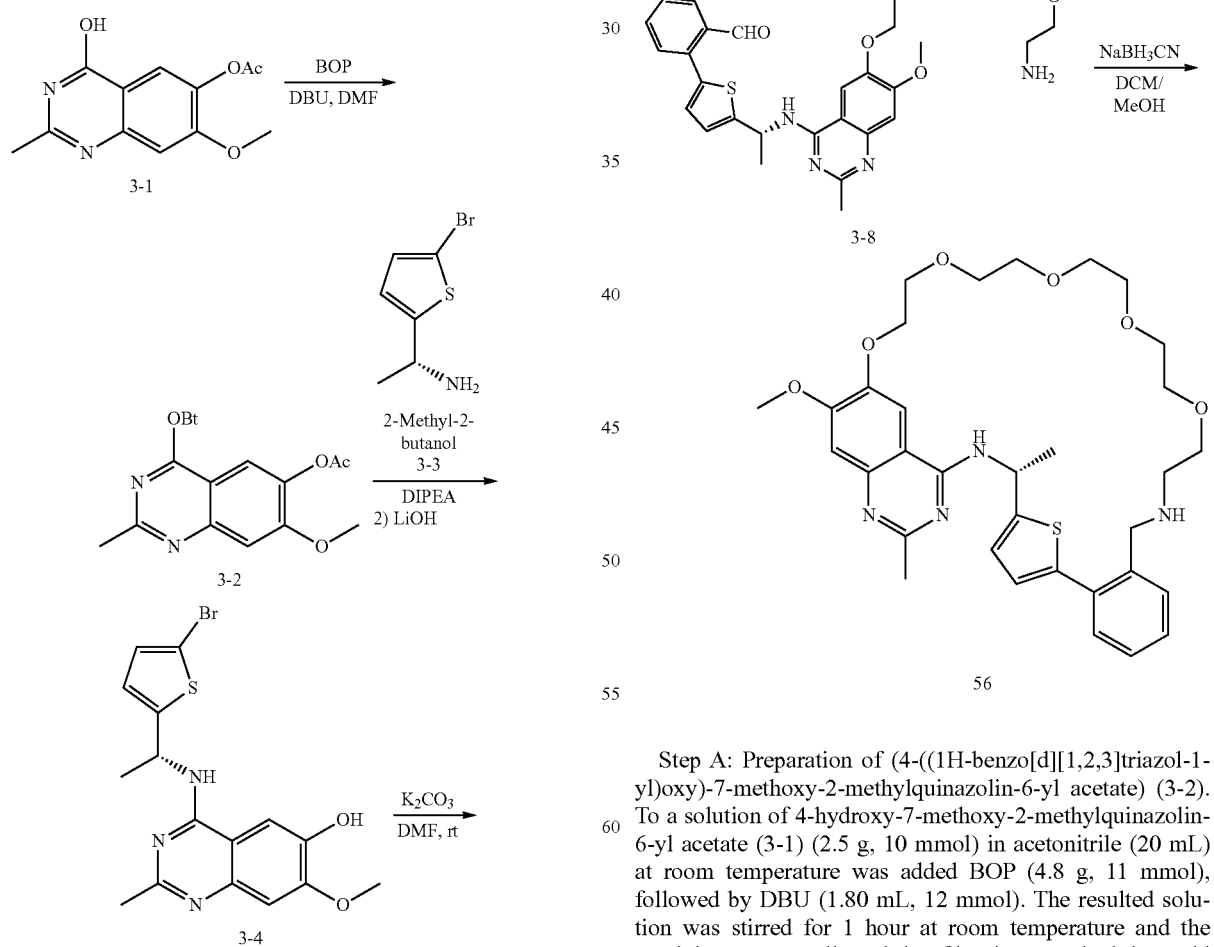

Step A: Preparation of (4-((1H-benzo[d][1,2,3]triazol-1-yl)oxy)-7-methoxy-2-methylquinazolin-6-yl acetate) (3-2). To a solution of 4-hydroxy-7-methoxy-2-methylquinazolin-6-yl acetate (3-1) (2.5 g, 10 mmol) in acetonitrile (20 mL) at room temperature was added BOP (4.8 g, 11 mmol), followed by DBU (1.80 mL, 12 mmol). The resulted solution was stirred for 1 hour at room temperature and the precipitate was collected by filtration, washed by cold acetonitrile (10 mL), dried and used in the next step directly without further purification.

Step B: Preparation of (R)-4-((1-(5-bromothiophen-2-yl)ethyl)amino)-7-methoxy-2-methylquinazolin-6-ol (3-4). 3-2 (365 mg, 1 mmol) was mixed with (R)-1-(5-bromothiophen-2-yl)ethan-1-amine (3-3) (410 mg, 2.0 mmol) in 2-methyl-2-butanol (5 mL), then DIEA (0.42 mL, 3 mmol) was added. The mixture was stirred at 105° C. overnight. The reaction mixture was cooled down to room temperature. The resulting solution was concentrated and redissolved into 1M lithium hydroxide (5 mL). After the completion of de-acetylation, the reaction was neutralized by 1M HCl and the resulting solution concentrated and purified by reverse phase liquid chromatography (HPLC) using an Isco CombiFlash liquid chromatograph eluted with 5% to 95% acetonitrile/water with 0.1% TFA as the modifier, which yielded 610 mg of the desired product. ESI-MS m/z: $(M+H)^+=394.2$.

Step C: Preparation of tert-butyl (R)-(14-((4-((1-(5-bromothiophen-2-yl)ethyl)amino)-7-methoxy-2-methylquinazolin-6-yl)oxy)-3,6,9,12-tetraoxatetradecyl)carbamate (3-5). 3-4 (40 mg, 0.1 mmol) and tert-butyl (14-bromo-3,6,9,12-tetraoxatetradecyl)carbamate (40 mg, 0.11 mmol) were mixed into DMF (2 mL), then potassium carbonate (28 mg, 0.2 mmol) was added. The mixture was stirred overnight at room temperature. The resulting solution was purified by reverse phase liquid chromatography (HPLC) using an Isco CombiFlash liquid chromatograph eluted with 5% to 95% acetonitrile/water with 0.1% TFA as the modifier, which yielded 61 mg of desired product. ESI-MS m/z: $(M+H)^+=713.2$.

Step D: Preparation of (R)-2-(5-(1-((6-((14-amino-3,6,9,12-tetraoxatetradecyl)oxy)-7-methoxy-2-methylquinazolin-4-yl)amino)ethyl)thiophen-2-yl)benzaldehyde (3-7). 3-5 (50 mg, 0.07 mmol), (2-formylphenyl)boronic acid (3-6) (30 mg, 0.2 mmol) and Pd(TPP) (10 mg, 0.01 mmol) were added into dioxane (3 mL) and 2M $K_2CO_3$ (1 mL). The resulting mixture was degassed with nitrogen for 10 min. then heated to 100° C. for 30 min and cooled down. The reaction solution was partitioned between dichloromethane (50 mL) and brine (10 mL). The organic layer was separated and dried over sodium sulfate, filtered and concentrated. The resulting crude residue was purified by normal phase liquid chromatography (HPLC) using an Isco CombiFlash liquid chromatograph eluted with dichloromethane and methanol (0% to 20%), which yielded 42 mg of desired product, ESI-MS m/z: $(M+H)^+=739.3$.

Step E: Preparation of (R)-$5^7$-methoxy-$5^2$,3-dimethyl-6,9,12,15,18-pentaoxa-4,21-diaza-5(4,6)-quinazolina-2(2,5)-thiophena-1(1,2)-benzenacyclodocosaphane (56). 3-7 was dissolved into 20% trifluoroacetic acid in dichloromethane (2 mL), and the solution was stirred for 2 hours at room temperature using LCMS to monitor the progress of deprotection. The resulting solution was concentrated and used directly in the next step without further purification.

The crude residue was redissolved into 20% methanol in dichloromethane (2 mL), then a drop of acetic acid was added to the solution followed by sodium cyanoborohydride (20 mg, 0.3 mmol). The resulting solution was stirred overnight at room temperature. It was concentrated and purified by reverse phase liquid chromatography (HPLC) using an Isco CombiFlash liquid chromatograph eluted with 5% to 95% acetonitrile/water with 0.1% TFA as the modifier, which yielded 21 mg of the title compound: ESI-MS m/z: $(M+H)^+=623.2$. $^1$HNMR(CD$_3$OD): 7.91 (11H, s), 7.62 (11H, d, J=8 Hz), 7.52 (3H, m), 7.26 (11H, d, J=4 Hz), 7.08 (11H, s), 7.05 (11H, d, 4 Hz), 6.26 (1H, m), 4.43 (1H, m), 4.27 (1H, m), 4.04 (3H, s), 3.90 (2H, m), 3.37-3.45 (16H, m), 3.17 (1H, m), 3.05 (3H, m), 2.72 (3H, s), 1.89 (3H, d, J=8 Hz).

Example 4: Synthesis of (R)-1-(2,2-difluoro-4-methyl-7-oxa-5-aza-6(4,7)-pyrido[2,3-d]pyrimidina-1(4,1)-piperidina-3(1,3)- benzenacyclotetradecaphane-$6^6$-yl)cyclopropane-1-carbonitrile (137)

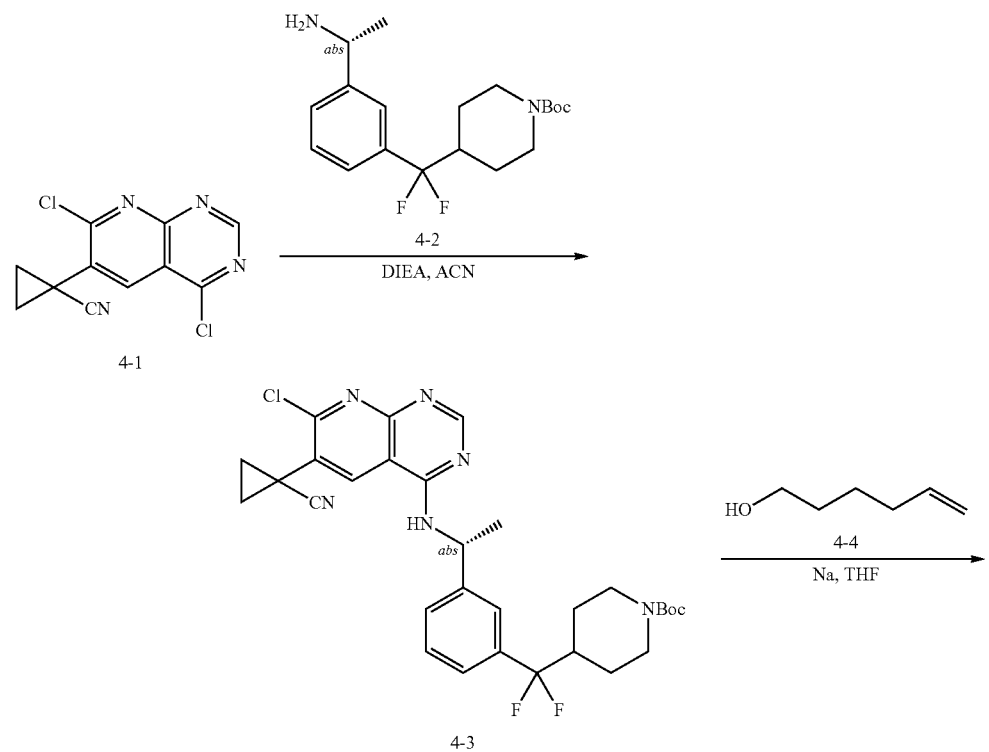

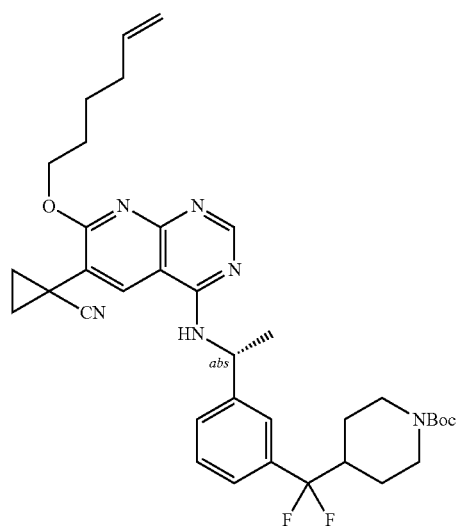
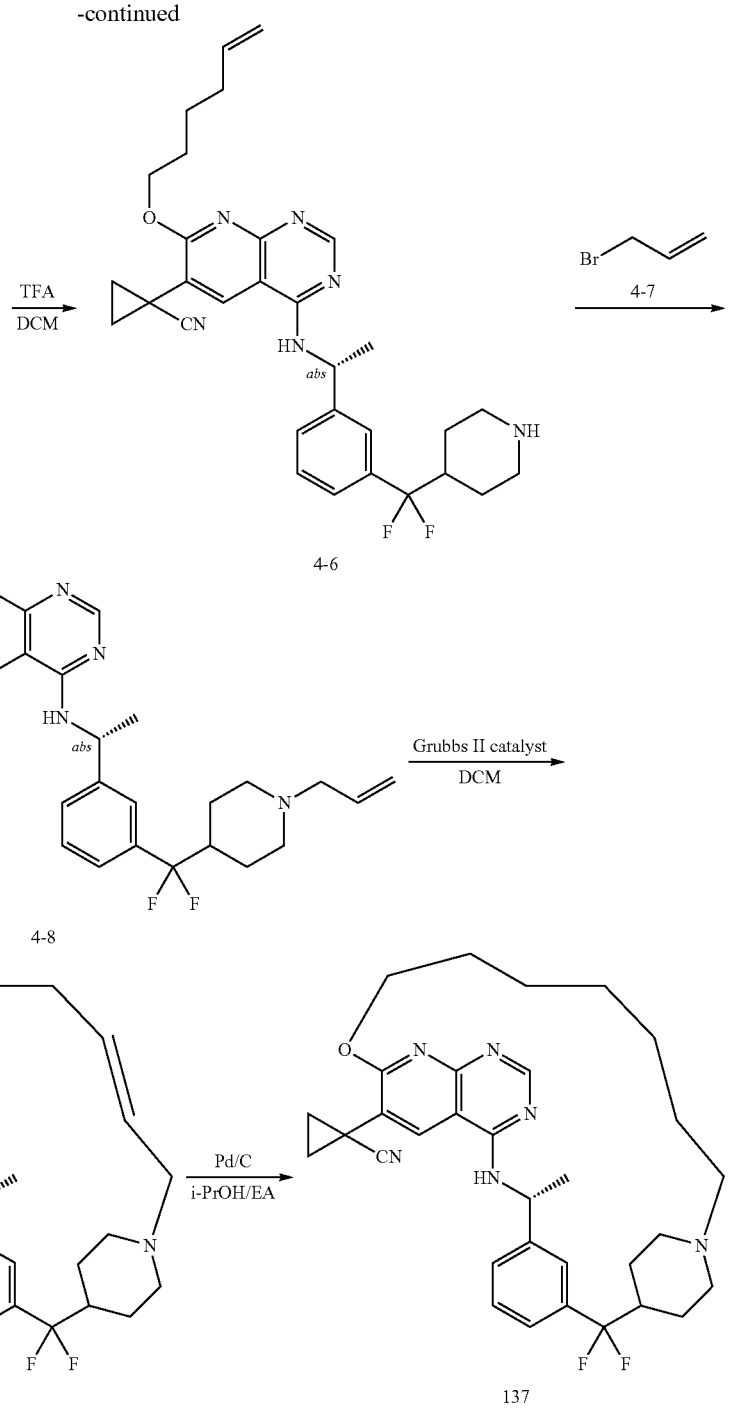

Step A: Preparation of tert-butyl (R)-4-((3-(1-((7-chloro-6-(1-cyanocyclopropyl)pyrido[2,3-d]pyrimidin-4-yl)amino)ethyl)phenyl)difluoromethyl)piperidine-1-carboxylate (4-3). To a solution of 1-(4,7-dichloropyrido[2,3-d]pyrimidin-6-yl)cyclopropane-1-carbonitrile (4-1) (500 mg, 1.9 mmol) and tert-butyl (R)-4-((3-(1-aminoethyl)phenyl)difluoromethyl)piperidine-1-carboxylate (4-2) (525 mg, 1.48 mmol) in acetonitrile (15 mL) was added DIEA (725 mg, 5.62 mmol). The mixture was stirred at room temperature overnight. After removal of most of the acetonitrile, water (150 mL) was added and the mixture was extracted with ethyl acetate (150 mL×3), then the combined organic layers were washed with brine, dried over anhydrous $Na_2SO_4$, filtrated and concentrated to give a residue. The residue was purified by flash chromatography (petroleum ether/ethyl acetate=2/1) to afford the desired product as a light-yellow solid. ESI-MS m/z: $(M+H)^+$=583.2.

Step B: Preparation of tert-butyl (R)-4-((3-(1-((6-(1-cyanocyclopropyl)-7-(hex-5-en-1-yloxy)pyrido[2,3-d]pyrimidin-4-yl)amino)ethyl)phenyl)difluoromethyl)piperidine-1-carboxylate (4-5). To a solution of hex-5-en-1-ol (4-4) (1 g, 9.98 mmol) in THF (25 mL) were added flakes of sodium (1 g, 43.48 mmol). The mixture was stirred at room temperature overnight, then a solution of 4-3 (300 mg, 0.51 mmol) in THF (10 mL) was added and the resulting mixture was stirred at room temperature for 24 hours. The mixture was poured into water (50 mL) and extracted with ethyl acetate (50 mL×3), then the combined organic layers were washed with brine, dried over anhydrous $Na_2SO_4$, filtered and the solvent removed under reduced pressure to give a crude residue. The crude residue was purified by flash chromatography (petroleum ether/ethyl acetate=1/1) to afford the desired product as a light-yellow solid. ESI-MS m/z: $(M+H)^+$=647.3.

Step C: Preparation of (R)-1-(4-((1-(3-(difluoro(piperidin-4-yl)methyl)phenyl)ethyl)amino)-7-(hex-5-en-1-yloxy)pyrido[2,3-d]pyrimidin-6-yl)cyclopropane-1-carbonitrile (4-6). To a stirring solution of 4-5 (200 mg, 0.31 mmol) in dry DCM (10 mL) in a round bottom flask was added TFA (2 mL, DCM/TFA: 5/1). The reaction mixture was stirred at room temperature for 2 hours, then concentrated to afford the desired product as a light-yellow solid, which was used in next step without further purification. ESI-MS m/z: $(M+H)^+$=547.4.

Step D: Preparation of (R)-1-(4-((1-(3-((1-allylpiperidin-4-yl)difluoromethyl)phenyl)ethyl)amino)-7-(hex-5-en-1-yloxy)pyrido[2,3-d]pyrimidin-6-yl)cyclopropane-1-carbonitrile (4-8). To a solution of 4-6 (120 mg, 0.22 mmol) in THF (10 mL) was added 3-bromoprop-1-ene (4-7) (40 mg, 0.33 mmol) and TEA (66.67 mg, 0.66 mmol) at −10° C. The mixture was warmed to room temperature for 16 hours with stirring. Water (100 mL) was added and the mixture was extracted with ethyl acetate (100 mL×3). The combined organic layers were washed with brine, dried over anhydrous $Na_2SO_4$, filtrated and concentrated to give a residue. The residue was purified by flash chromatography (petroleum ether/ethyl acetate=1/1) to afford the desired product as a light yellow solid. ESI-MS m/z: $(M+H)^+$=587.2.

Step E: Preparation of (R,E)-1-(2,2-difluoro-4-methyl-7-oxa-5-aza-6(4,7)-pyrido[2,3-d]pyrimidina-1(4,1)-piperidina-3(1,3)-benzenacyclotetradecaphan-12-en-$6^6$-yl)cyclopropane-1-carbonitrile (4-9). 4-8 (125 mg, 0.21 mmol) in 250 mL of dry DCM was degassed under vacuum and purged with argon for several minutes. Then, Grubbs II catalyst (66.12 mg, 0.080 mmol) was added to the mixture and the mixture was degassed several times then back filled with argon. The reaction mixture was stirred at 40° C. overnight under argon, then cooled to room temperature and most of the DCM removed under reduced pressure. The mixture was diluted with water (20 mL) and DCM (20 mL), then filtered through a celite pad and the pad rinsed with DCM. The filtrate was extracted with DCM (30 mL×3). The combined organics were combined, washed with brine (60 mL×1), and dried with $Na_2SO_4$, then filtered and solvent removed under reduced pressure to give a residue. The residue was purified by prep-TLC (DCM/MeOH=12/1) to afford the desired product as a light-yellow solid. ESI-MS m/z: $(M+H)^+$=559.3.

Step F: Preparation of (R)-1-(2,2-difluoro-4-methyl-7-oxa-5-aza-6(4,7)-pyrido[2,3-d]pyrimidina-1(4,1)-piperidina-3(1,3)-benzenacyclotetradecaphane-$6^6$-yl)cyclopropane-1-carbonitrile (137). To a solution of 4-9 (30 mg, 0.054 mmol) in 5 mL of iPrOH/ethyl acetate (5/1) was added Pd/C (10%, 15 mg). The suspension was degassed under vacuum and purged with hydrogen several times, then stirred at room temperature overnight under hydrogen atmosphere. The suspension was filtered through a pad of celite and the filter cake was washed with MeOH (10 mL×5). The combined filtrates were concentrated and the crude product was purified by column chromatography, then by prep-HPLC to afford the desired product as a white solid. ESI-MS m/z: $(M+H)^+$=561.4. $^1$H NMR (400 MHz, DMSO) δ 8.82 (s, 1H), 8.47 (d, J=7.3 Hz, 1H), 8.35 (s, 1H), 7.55 (d, J=7.3 Hz, 1H), 7.43 (t, J=7.6 Hz, 1H), 7.32 (s, 1H), 7.20 (d, J=8.0 Hz, 1H), 5.50-5.43 (m, 1H), 5.36 (t, J=9.1 Hz, 1H), 4.15-4.08 (m, 1H), 2.17 (d, J=10.2 Hz, 1H), 1.99 (d, J=27.4 Hz, 3H), 1.78 (s, 2H), 1.65 (d, J=7.1 Hz, 5H), 1.51 (t, J=12.7 Hz, 4H), 1.38 (d, J=9.6 Hz, 3H), 1.29-1.19 (m, 4H), 1.06 (s, 4H), 0.93-0.84 (m, 1H), 0.67 (d, J=11.9 Hz, 1H), 0.39 (d, J=9.1 Hz, 1H).

Example 5: Synthesis of 4-((4R)-2,2-difluoro-4-methyl-$6^7$-oxo-$6^7$,$6^8$-dihydro-5-aza-6(4,8)-pyrido[2,3-d]pyrimidina-1(4,1)-piperidina-3(1,3)-benzenacyclotridecaphane-$6^6$-yl)tetrahydro-2H-pyran-4-carbonitrile (76)

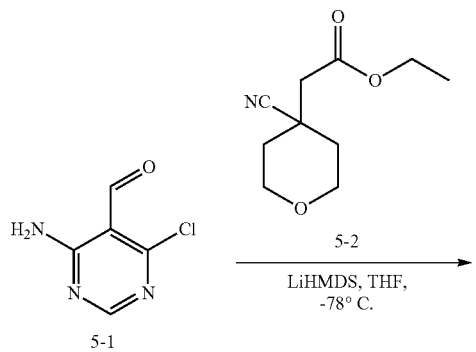

-continued
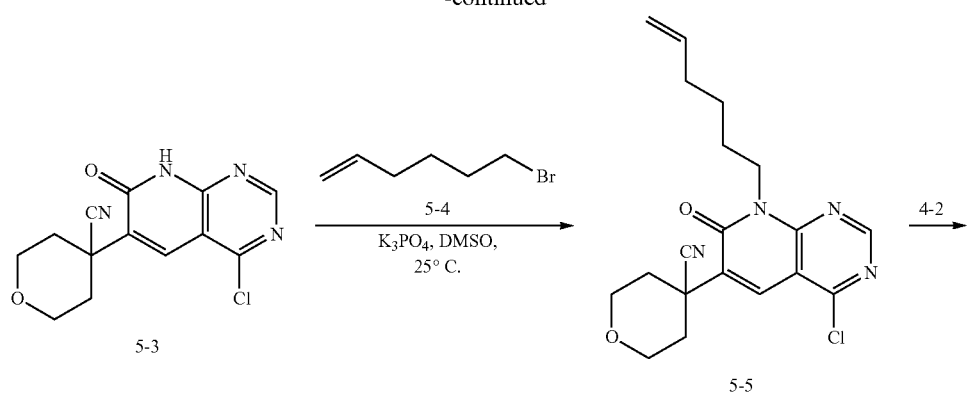
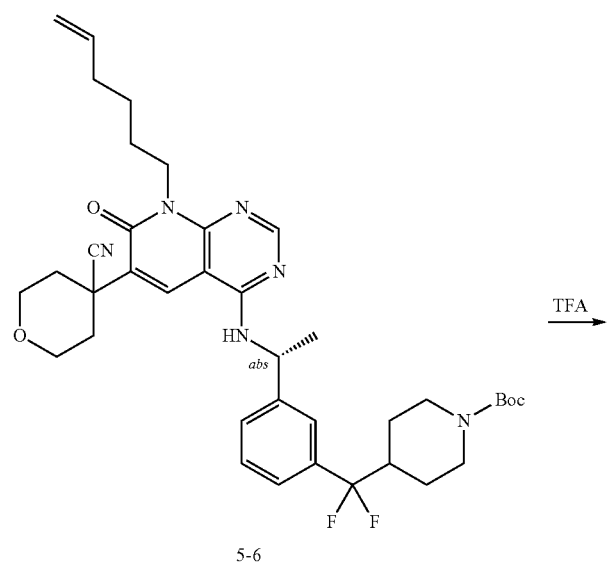
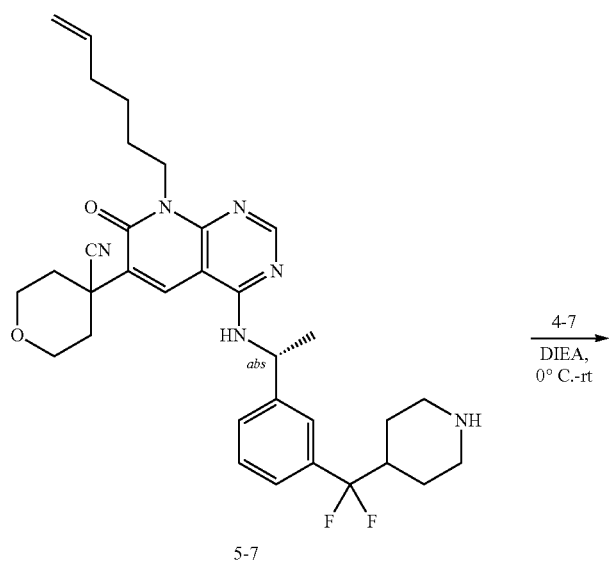

-continued

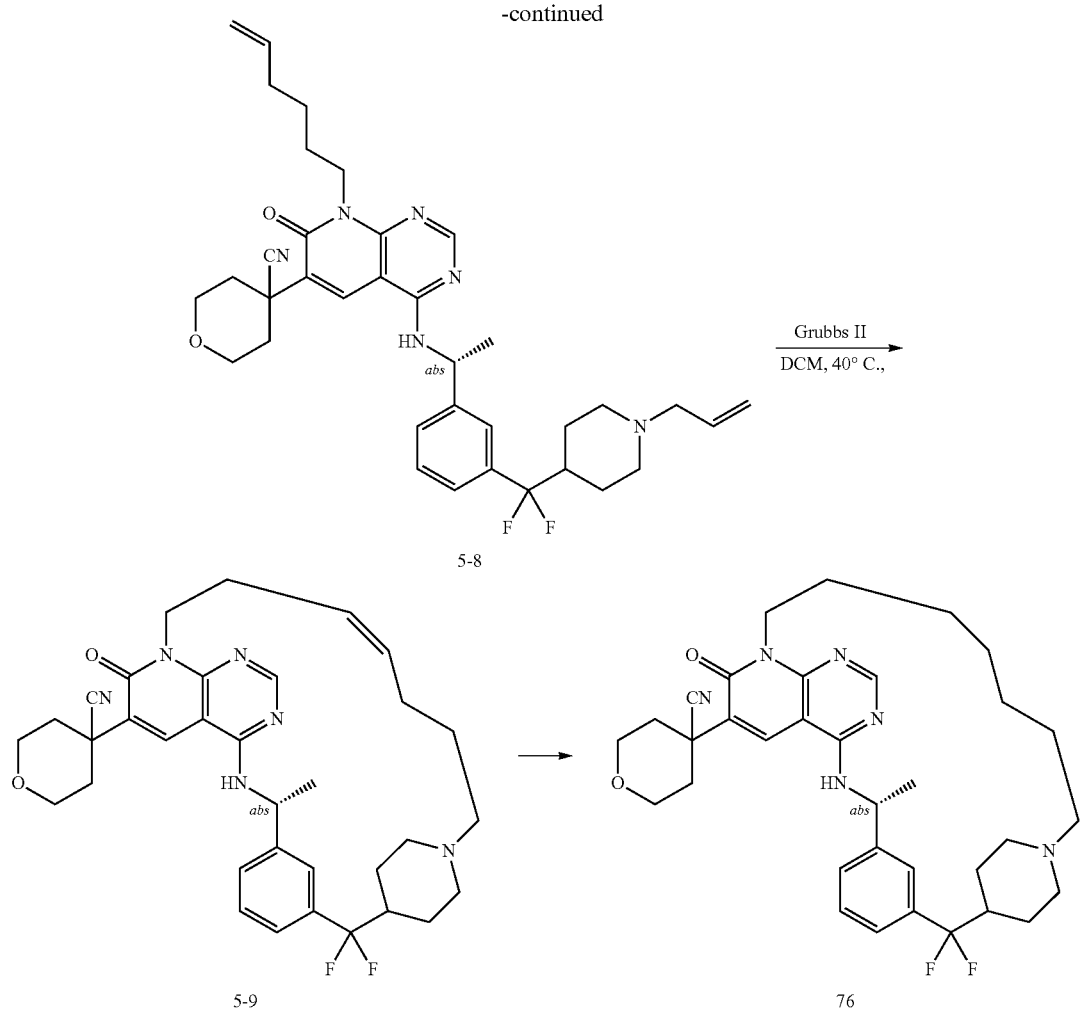

Step A: Preparation of 4-(4-chloro-7-oxo-7,8-dihydropyrido[2,3-d]pyrimidin-6-yl)tetrahydro-2H-pyran-4-carbonitrile (5-3). To a solution of ethyl 2-(4-cyanotetrahydro-2H-pyran-4-yl)acetate (5-2) (752 mg, 3.82 mmol, 1.2 eq) in THF (10 mL) was added LiHMDS (1.0 M, 38.2 mL, 38.2 mmol) at −78° C. under nitrogen. The mixture was stirred at −78° C. for 1 hour, then 4-amino-6-chloropyrimidine-5-carbaldehyde (5-1) (500 mg, 3.18 mmol, 1 eq) was added. The reaction mixture was stirred an additional 2 hours at −78° C., then quenched with NH$_4$Cl solution and extracted with ethyl acetate (50 mL×3). The combined organics were washed with brine (150 mL), dried over Na$_2$SO$_4$, filtrated, and solvent removed under reduced pressure to give a residue. The residue was purified by silica gel column chromatography to afford the desired product as a white solid. ESI-MS m/z: (M+H)$^+$=291.1.

Step B: Preparation of 4-(4-chloro-8-(hex-5-en-1-yl)-7-oxo-7,8-dihydropyrido[2,3-d]pyrimidin-6-yl)tetrahydro-2H-pyran-4-carbonitrile (5-5). To a solution of 5-3 (180 mg, 0.62 mmol, 1.0 eq) in DMSO (5 mL) was added 6-bromohex-1-ene (5-4) (120.6 mg, 0.74 mmol, 1.2 eq) and K$_3$PO$_4$ (40.9 mg, 1.86 mmol, 3.0 eq) at 25° C. The mixture was stirred for 1 hour at room temperature, then poured into water and extracted with ethyl acetate (10 mL×3). The combined organics were washed with brine (15 mL), dried over Na$_2$SO$_4$, filtered and solvent removed under reduced pressure to give a crude residue. The crude residue was purified by silica gel column chromatography to afford the desired product as a white solid. ESI-MS m/z: (M+H)$^+$=373.2.

Step C: Preparation of tert-butyl (R)-4-((3-(1-((6-(4-cyanotetrahydro-2H-pyran-4-yl)-8-(hex-5-en-1-yl)-7-oxo-7,8-dihydropyrido[2,3-d]pyrimidin-4-yl)amino)ethyl)phenyl)difluoromethyl)piperidine-1-carboxylate (5-6). To a solution of 5-5 (180 mg, 0.48 mmol, 1.0 eq) in DMSO (5 mL) was added 4-2 (169.9 mg, 0.48 mmol, 1.0 eq) and KF (83.5 mg, 1.44 mmol, 3.0 eq) at 25° C. under nitrogen. The mixture was stirred for 1 hour at 100° C., then poured into water and extracted with ethyl acetate (10 mL×3). The combined organic layer was washed with brine (15 mL) and dried over Na$_2$SO$_4$, then filtered and solvent removed under reduced pressure to give a residue. The residue was purified by silica gel column chromatography to afford the desired product (280 mg, 84% yield) as a white solid. ESI-MS m/z: (M+H)$^+$=691.2.

Step D: Preparation of (R)-4-(4-((1-(3-(difluoro(piperidin-4-yl)methyl)phenyl)ethyl)amino)-8-(hex-5-en-1-yl)-7-oxo-7,8-dihydropyrido[2,3-d]pyrimidin-6-yl)tetrahydro-2H-pyran-4-carbonitrile (5-7). To a solution of 5-6 (280 mg, 0.4 mmol, 1.0 eq) in DCM (5 mL) was added TFA (1 mL) at 25° C. The mixture was stirred for 1 hour at 25° C., then concentrated under reduced pressure to give the desired product as a brown solid, used in the next step without further purification. ESI-MS m/z: (M+H)⁺=591.1.

Step E: Preparation of (R)-4-(4-((1-(3-((1-allylpiperidin-4-yl)difluoromethyl)phenyl)ethyl)amino)-8-(hex-5-en-1-yl)-7-oxo-7,8-dihydropyrido[2,3-d]pyrimidin-6-yl)tetrahydro-2H-pyran-4-carbonitrile (5-8). To a solution of 5-7 (200 mg, 0.33 mmol, 1.0 eq) in DCM (5 mL) was added DIEA (127.7 mg, 0.99 mmol, 3.0 eq) and 4-7 (39.6 mg, 0.33 mmol, 1.0 eq) at 25° C. The mixture was stirred for 16 hours at 25° C., then poured into water and extracted with ethyl acetate (10 mL×3). The combined organics were washed with brine (15 mL) and dried over Na₂SO₄, then filtered and solvent removed under reduced pressure to give a crude residue. The crude residue was purified by silica gel column chromatography to afford the desired product as a white solid. ESI-MS m/z: (M+H)⁺=631.4.

Step F: Preparation of 4-((4R,Z)-2,2-difluoro-4-methyl-6⁷-oxo-6⁷,6⁸-dihydro-5-aza-6(4,8)-pyrido[2,3-d]pyrimidina-1(4,1)-piperidina-3(1,3)-benzenacyclotridecaphan-9-en-6⁶-yl)tetrahydro-2H-pyran-4-carbonitrile (5-9). To a solution of 5-8 (130 mg, 0.20 mmol, 1.0 eq) in DCM (200 mL) was added Grubbs II catalyst (50.9 mg, 0.06 mmol, 0.3 eq) at 25° C. under nitrogen. The mixture was stirred for 16 hours at 40° C., then concentrated under reduced pressure to give a residue, which was purified by prep-TLC (EA:MeOH=20:1) to give the desired product as white solid. ESI-MS m/z: (M+H)⁺=603.2.

Step G: Preparation of 4-((4R)-2,2-difluoro-4-methyl-6⁷-oxo-6⁷,6⁸-dihydro-5-aza-6(4,8)-pyrido[2,3-d]pyrimidina-1(4,1)-piperidina-3(1,3)-benzenacyclotridecaphane-6⁶-yl)tetrahydro-2H-pyran-4-carbonitrile (76). To a solution of 5-9 (50 mg, 0.08 mmol, 1.0 eq) in THF (10 mL) was added Pd/C (50 mg) at 25° C. under hydrogen. The mixture was stirred for 30 min at 25° C., then filtered and concentrated under reduced pressure to give a residue. The residue was purified by prep-HPLC to afford the desired product as a white solid. ESI-MS m/z: (M+H)⁺=605.2. ¹H NMR (400 MHz, MeOD) δ 8.28 (d, J=1.6 Hz, 2H), 7.55 (d, J=7.9 Hz, 1H), 7.45 (t, J=7.8 Hz, 1H), 7.39 (s, 1H), 7.26 (d, J=7.9 Hz, 1H), 5.40-5.30 (m, 1H), 4.73 (dd, J=14.2, 8.2 Hz, 1H), 4.24 (dd, J=11.0, 6.0 Hz, 1H), 4.13-4.04 (m, 2H), 3.92 (dd, J=20.0, 8.5 Hz, 2H), 3.05 (d, J=8.8 Hz, 1H), 2.88 (d, J=15.2 Hz, 1H), 2.63-2.37 (m, 4H), 2.32-2.17 (m, 1H), 2.06 (dd, J=13.7, 9.2 Hz, 3H), 1.83-1.76 (m, 1H), 1.72 (d, J=7.2 Hz, 3H), 1.61 (dd, J=21.5, 11.6 Hz, 5H), 1.34 (s, 7H), 1.12 (d, J=7.9 Hz, 1H), 1.05-0.94 (m, 1H).

Example 6: Synthesis of 1-((6R,Z)-4,4-difluoro-6-methyl-8⁷-oxo-8⁷,8⁸-dihydro-11H-7-aza-8(4,8)-pyrido[2,3-d]pyrimidina-3(1,4)-piperidina-1(4,1)-triazola-5(1,3)-benzenacycloundecaphane-8⁶-yl)cyclopropane-1-carbonitrile (95)

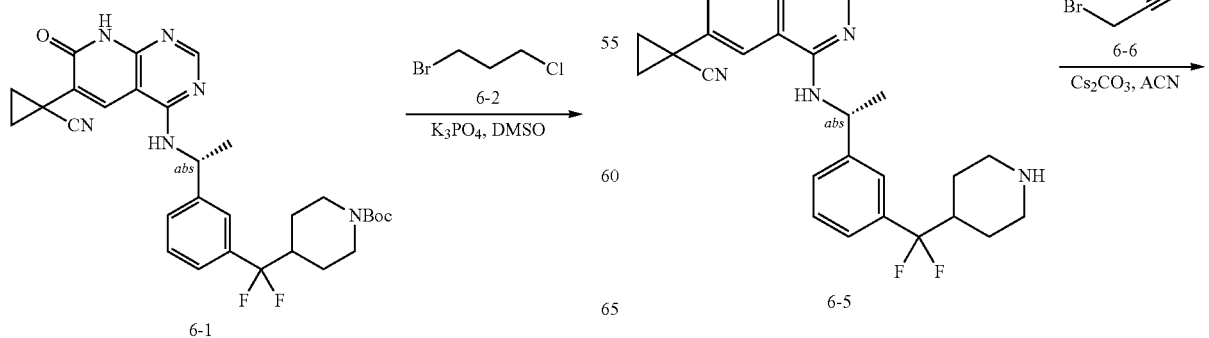

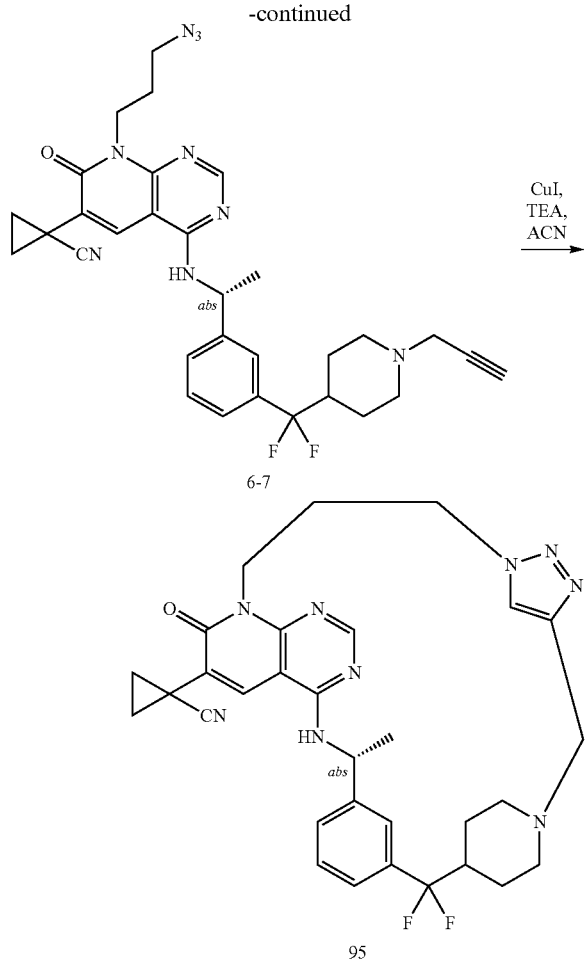

Step A: Preparation of tert-butyl (R)-4-((3-(1-((8-(3-chloropropyl)-6-(1-cyanocyclopropyl)-7-oxo-7,8-dihydropyrido[2,3-d]pyrimidin-4-yl)amino)ethyl)phenyl)difluoromethyl)piperidine-1-carboxylate (6-3). To a 25 mL round bottom flask was added tert-butyl (R)-4-((3-(1-((6-(1-cyanocyclopropyl)-7-oxo-7,8-dihydropyrido[2,3-d]pyrimidin-4-yl)amino)ethyl)phenyl)difluoromethyl) piperidine-1-carboxylate (6-1) (400 mg, 0.70 mmol), 1-bromo-3-chloropropane (6-2) (134 mg, 0.84 mmol) and $K_3PO_4$ (290 mg, 2.12 mmol) in dry DMSO (10 mL). The mixture was stirred at room temperature for 2 hours, then diluted with water (50 mL) and extracted with ethyl acetate (50 mL×3). The organics were combined, dried over sodium sulfate, filtered and concentrated under reduced pressure to give a residue. The residue was purified on silica gel column eluting with petroleum ether:ethyl acetate (1:1) to give the desired product as a yellow oil. ESI-MS m/z: $(M+H)^+=641.2$.

Step B: Preparation of tert-butyl (R)-4-((3-(1-((8-(3-azidopropyl)-6-(1-cyanocyclopropyl)-7-oxo-7,8-dihydropyrido[2,3-d]pyrimidin-4-yl)amino)ethyl)phenyl)difluoromethyl)piperidine-1-carboxylate (6-4). To a 50 mL round bottom flask was added 6-3 (300 mg, 0.47 mmol) and $NaN_3$ (61 mg, 0.94 mmol) in DMSO (10 mL). The mixture was stirred at 100° C. for 2 h under nitrogen, then cooled to room temperature and diluted with water (50 mL). The mixture was extracted with ethyl acetate (50 mL×3). The organics were combined, washed with brine and dried over sodium sulfate, then filtered and concentrated under reduced pressure to give a residue. The residue was purified on silica gel column eluting with petroleum ether:ethyl acetate=1:1 to give the desired product as a white solid. ESI-MS m/z: $(M+H)^+=648.3$.

Step C: Preparation of (R)-1-(8-(3-azidopropyl)-4-((1-(3-(difluoro(piperidin-4-yl)methyl)phenyl)ethyl)amino)-7-oxo-7,8-dihydropyrido[2,3-d]pyrimidin-6-yl)cyclopropane-1-carbonitrile (6-5). To a 50 mL round bottom flask was added 6-4 (50 mg, 0.077 mmol) and TFA (1 mL) in DCM (5 mL). The resulting mixture was stirred at room temperature for 2 hours, then adjusted to pH ~7 with $NaHCO_3$(aq.) and the product extracted in DCM (30 mL×3). The organics were combined, washed with brine and dried over sodium sulfate, then filtered and concentrated under reduced pressure to give desired product as a white solid, which was used in the next step directly without further purification. ESI-MS m/z: $(M+H)^+=548.2$.

Step D: Preparation of (R)-1-(8-(3-azidopropyl)-4-((1-(3-(difluoro(1-(prop-2-yn-1-yl)piperidin-4-yl)methyl)phenyl)ethyl)amino)-7-oxo-7,8-dihydropyrido[2,3-d]pyrimidin-6-yl)cyclopropane-1-carbonitrile (6-7). To a 25 mL round bottom flask was added 6-5 (40 mg, 0.072 mmol) and $Cs_2CO_3$ (24 mg, 0.072 mmol) in acetonitrile (10 mL). Then, 3-bromoprop-1-yne (6-6) (10.8 mg, 0.072 mmol) was added at 0° C. The mixture was stirred at room temperature overnight, then diluted with water (30 mL) and the solution extracted with ethyl acetate (30 mL×3). The organic layers were combined, washed with brine, dried over sodium sulfate, filtered and concentrated under reduced pressure to give a residue. The residue was purified by silica gel chromatography eluting with petroleum ether:ethyl acetate=1:1 to give the desired product as a white solid. ESI-MS m/z: $(M+H)^+=586.3$.

Step E: Preparation of 1-((6R,Z)-4,4-difluoro-6-methyl-$8^7$-oxo-$8^7$,$8^8$-dihydro-11H-7-aza-8(4,8)-pyrido[2,3-d]pyrimidina-3(1,4)-piperidina-1(4,1)-triazola-5(1,3)-benzenacycloundecaphane-$8^6$-yl)cyclopropane-1-carbonitrile (95). To a 50 mL round bottom flask was added 6-7 (15 mg, 0.026 mmol), CuI (10 mg, 0.052 mmol) and triethylamine (7.8 mg, 0.078 mmol) in acetonitrile (20 mL). The mixture was stirred at 80° C. for 16 hours, then cooled to room temperature, diluted with water (20 mL) and extracted with ethyl acetate (30 mL×3). The organics were combined, washed with brine, dried over sodium sulfate, filtered and concentrated under reduced pressure to give a residue. The residue was purified by prep-HPLC (acetonitrile with 0.1% of FA in water, 5% to 95%) to give the desired product as a white solid. ESI-MS m/z: $(M+H)^+=586.4$. $^1$H NMR (400 MHz, DMSO) δ 8.35-8.25 (m, 2H), 8.03 (s, 1H), 7.63 (s, 1H), 7.54-7.39 (m, 3H), 7.19 (d, J=6.2 Hz, 1H), 5.25 (s, 1H), 4.65 (s, 1H), 4.42-4.25 (m, 2H), 4.12-3.98 (m, 1H), 2.73-2.60 (m, 3H), 2.02-1.70 (m, 5H), 1.68-1.51 (m, 7H), 1.40-1.19 (m, 3H), 0.88-0.74 (m, 2H).

Example 7: Synthesis of (6R,Z)-8⁶-(1,1-dioxidotetrahydro-2H-thiopyran-4-yl)-5²,4,4-trifluoro-6-methyl-8⁷,8⁸-dihydro-11H-7-aza-8(4,8)-pyrido[2,3-d]pyrimidina-3(1,4)-piperidina-1(4,1)-triazola-5(1,3)-benzenacyclododecaphan-8⁷-one (108)

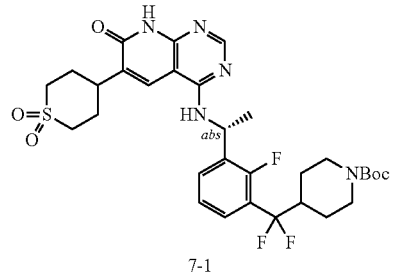

7-1

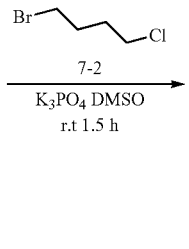

7-2

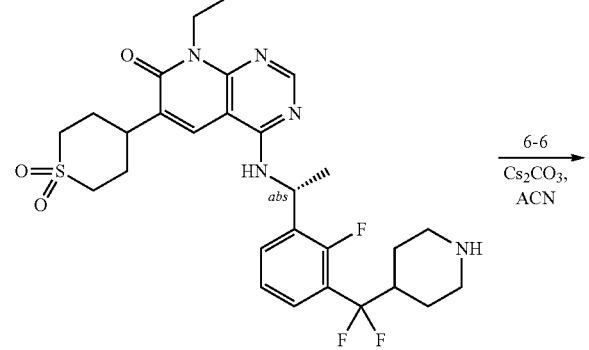

7-5

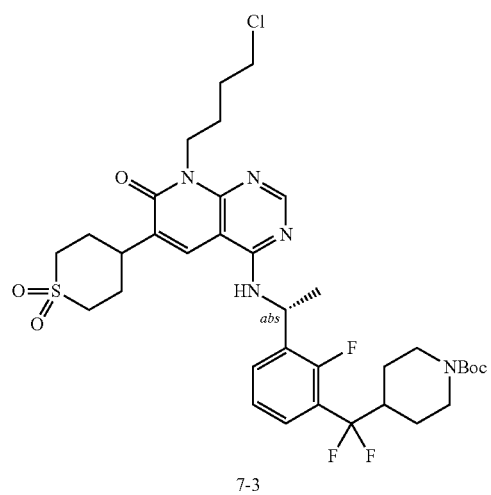

7-3

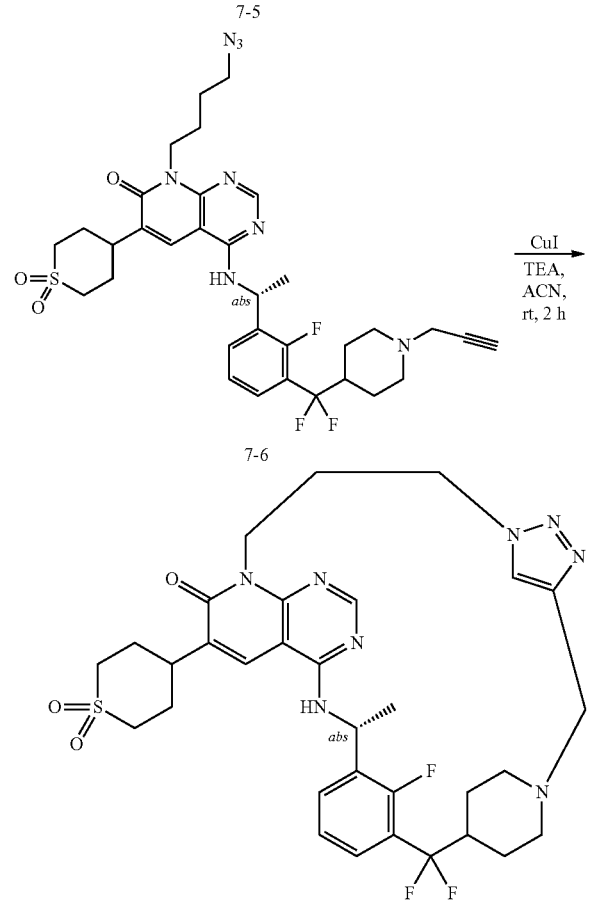

7-6

108

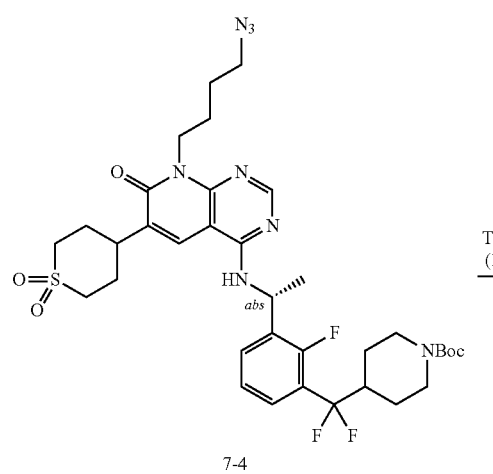

7-4

Step A: Preparation of tert-butyl (R)-4-((3-(1-((8-(4-chlorobutyl)-6-(1,1-dioxidotetrahydro-2H-thiopyran-4-yl)-7-oxo-7,8-dihydropyrido[2,3-d]pyrimidin-4-yl)amino)ethyl)-2-fluorophenyl)difluoromethyl)piperidine-1-carboxylate (7-3). To a stirring solution of tert-butyl (R)-4-((3-(1-((6-(1,1-dioxidotetrahydro-2H-thiopyran-4-yl)-7-oxo-7,8-dihydropyrido[2,3-d]pyrimidin-4-yl)amino)ethyl)-2-fluorophenyl)difluoromethyl)piperidine-1-carboxylate (7-1) (130 mg, 0.2 mmol) in DMSO (3 mL) in a round bottom flask was added 1-bromo-4-chlorobutane (7-2) (52 mg, 0.3 mmol) and $K_3PO_4$ (128 mg, 0.6 mmol). The resulting mixture was stirred at room temperature for 1.5 hours. Ethyl acetate (10 mL) and water (30 mL) were added. The resulting mixture was extracted with ethyl acetate (2×20 mL). The organics were combined and washed with brine (30 mL), dried over sodium sulfate, then filtered and solvent removed under reduced pressure to give a residue, which was purified by silica gel column (0%-70% ethyl acetate in petroleum ether) to give the desired product as a white solid. ESI-MS m/z: (M+H)$^+$=684.1.

Step B: Preparation of tert-butyl (R)-4-((3-(1-((8-(4-azidobutyl)-6-(1,1-dioxidotetrahydro-2H-thiopyran-4-yl)-7-oxo-7,8-dihydropyrido[2,3-d]pyrimidin-4-yl)amino)ethyl)-2-fluorophenyl)difluoromethyl)piperidine-1-carboxylate (7-4). A mixture of 7-3 (136 mg, 0.184 mmol) and NaN$_3$ (24 mg, 0.367 mmol) in DMSO (3 mL) was heated to 100° C. for 2 hours. The mixture was cooled to room temperature and diluted with ethyl acetate/water (30 mL/30 mL), then extracted with ethyl acetate (20 mL×2). The extracts were combined, washed with brine (30 mL), dried over sodium sulfate, filtered and solvent removed under reduced pressure to give a residue, which was purified by silica gel column (petroleum ether:ethyl acetate=1:1) to give the desired product as a white solid. ESI-MS m/z: (M+H)$^+$=747.3.

Step C: Preparation of (R)-8-(4-azidobutyl)-4-((1-(3-(difluoro(piperidin-4-yl)methyl)-2-fluorophenyl)ethyl)amino)-6-(1,1-dioxidotetrahydro-2H-thiopyran-4-yl)pyrido[2,3-d]pyrimidin-7(8H)-one (7-5). To a solution of 7-4 (110 mg, 0.147 mmol) in DCM (5 mL) was added TFA (2 mL) and the mixture was stirred at room temperature for 0.5 hours. The pH was adjusted to ~9 by aqueous sat. NaHCO$_3$, then extracted with DCM (10 mL×2). The combined organics were washed with brine, dried over anhydrous Na$_2$SO$_4$, filtered, and concentrated to give a residue. The residue was purified by flash chromatography (DCM/MeOH=10/1) to afford the desired product as a light-yellow solid. ESI-MS m/z: (M+H)$^+$=647.3.

Step D: Preparation of (R)-8-(4-azidobutyl)-4-((1-(3-(difluoro(1-(prop-2-yn-1-yl)piperidin-4-yl)methyl)-2-fluorophenyl)ethyl)amino)-6-(1,1-dioxidotetrahydro-2H-thiopyran-4-yl)pyrido[2,3-d]pyrimidin-7(8H)-one (7-6). To a solution of 7-5 (70 mg, 0.108 mmol) and Cs$_2$CO$_3$ (106 mg, 0.324 mmol) in acetonitrile (10 mL) was added 6-6 (10 mg, 0.0864 mmol, 80% purity) at 0° C. and the mixture was stirred at room temperature for 2 hours. Water (20 mL) was added and mixture was extracted with ethyl acetate (20 mL×2). The combined organic layers were washed with brine, dried over anhydrous Na$_2$SO$_4$, filtered and concentrated to give a residue. The residue was purified by flash chromatography (petroleum ether/ethyl acetate=1/1) to afford the desired product as a yellow solid. ESI-MS m/z: (M+H)$^+$=685.2.

Step E: Preparation of (6R,Z)-8$^6$-(1,1-dioxidotetrahydro-2H-thiopyran-4-yl)-5$^2$,4,4-trifluoro-6-methyl-8$^7$,8$^8$-dihydro-11H-7-aza-8(4,8)-pyrido[2,3-d]pyrimidina-3(1,4)-piperidina-1(4,1)-triazola-5(1,3)-benzenacyclododecaphan-8$^7$-one (108). To a solution of 7-6 (62 mg, 0.091 mmol) in acetonitrile (99.2 mL, 0.001 mmol/mL) was added triethylamine (28 mg, 0.272 mmol) and CuI (35 mg, 0.181 mmol). The mixture was stirred at room temperature for 2 hours under nitrogen, then concentrated under reduced pressure to give a residue, which was purified by prep-HPLC to give the product as a white solid. ESI-MS m/z: (M+H)$^+$=685.2. $^1$H NMR (400 MHz, DMSO) δ 8.48-8.39 (m, 1H), 8.13 (d, J=4.3 Hz, 2H), 8.00-7.82 (m, 1H), 7.71-7.61 (m, 1H), 7.36-7.19 (m, 2H), 5.65-5.49 (m, 1H), 4.62-4.49 (m, 1H), 4.42-4.07 (m, 4H), 3.43-3.26 (m, 3H), 3.17 (s, 4H), 3.04-2.71 (m, 2H), 2.13 (s, 5H), 1.96-1.71 (m, 4H), 1.66 (d, J=7.1 Hz, 3H), 1.49-0.75 (m, 5H).

Example 8: Synthesis of (4R)-2,2-difluoro-6$^6$-(4-isopropylpiperazin-1-yl)-4-methyl-6$^7$,6$^8$-dihydro-5-aza-6(4,8)-pyrido[2,3-d]pyrimidina-1(4,1)-piperidina-3(1,3)-benzenacyclotridecaphan-6$^7$-one (123)

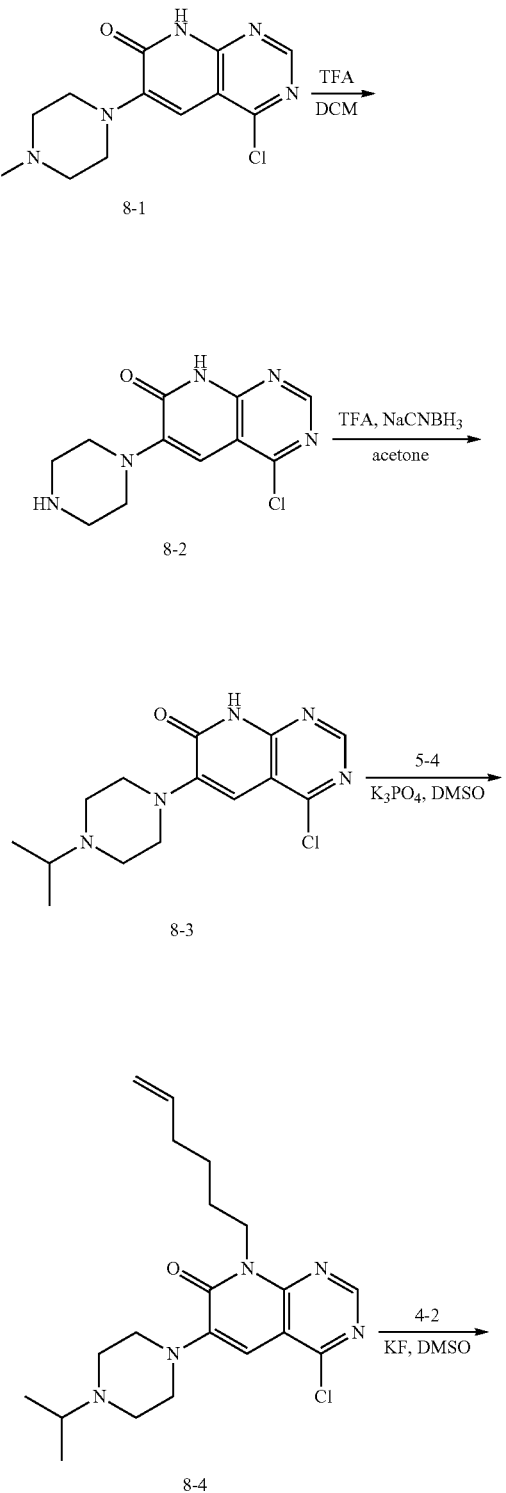

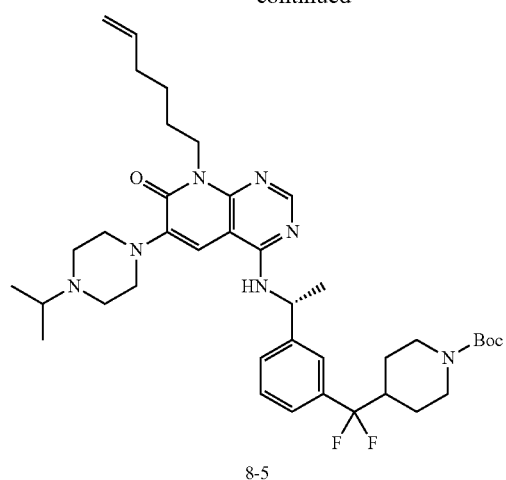

8-5

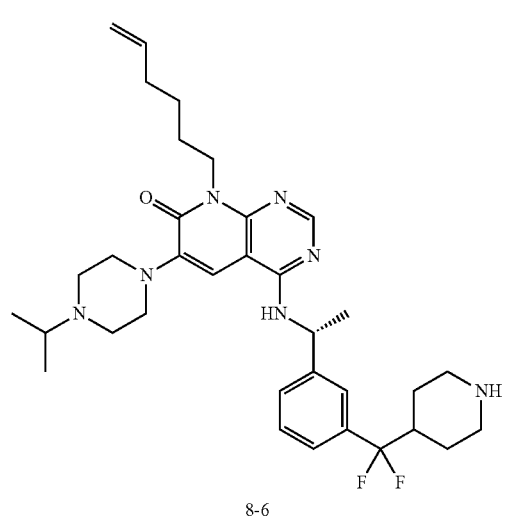

8-6

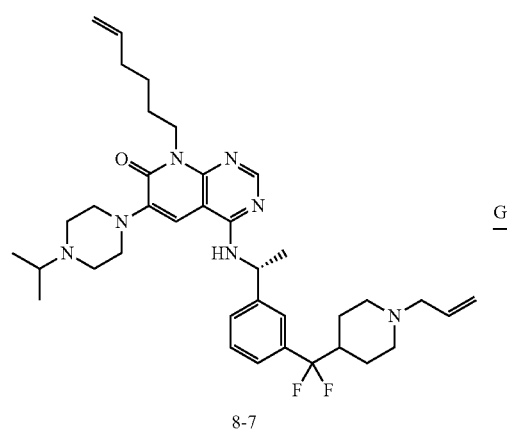

8-7

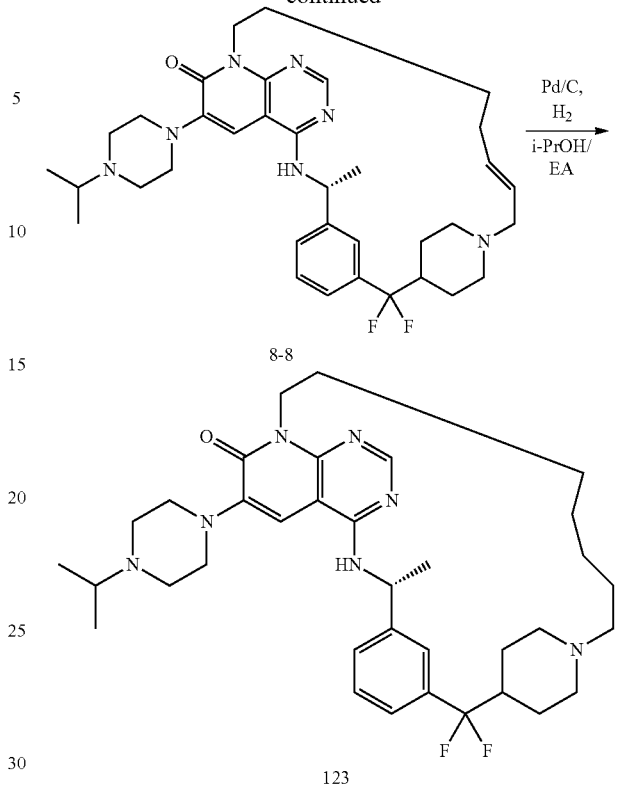

8-8

123

Step A: Preparation of 4-chloro-6-(piperazin-1-yl)pyrido[2,3-d]pyrimidin-7(8H)-one (8-2). To a stirring solution of tert-butyl 4-(4-chloro-7-oxo-7,8-dihydropyrido[2,3-d]pyrimidin-6-yl)piperazine-1-carboxylate (8-1) (1 g) in dry DCM (15 mL) in a round bottom flask was added TFA (3 mL, DCM/TFA: 5/1). The resulting mixture was stirred at room temperature for 2 hours, then concentrated to afford the crude product as a white solid, which was used in next step without further purification. ESI-MS m/z: (M+H)⁺= 266.1.

Step B: Preparation of 4-chloro-6-(4-isopropylpiperazin-1-yl)pyrido[2,3-d]pyrimidin-7(8H)-one (8-3). To a solution of 8-2 (800 mg crude) in acetone (15 mL) was added NaCNBH₃ (472.48 mg, 7.52 mmol), followed by triethyl amine to make the system alkaline (pH-9-10) at room temperature. The mixture was stirred at room temperature overnight. After removal of most of the acetone, the mixture was poured into water (50 mL) and extracted with ethyl acetate (50 mL×3), then the combined organics were washed with brine, dried over anhydrous Na₂SO₄, filtered and solvent removed under reduced pressure to give a residue. The residue was purified by flash chromatography (DCM/MeOH=8/1) to afford the desired product as a light yellow solid. ESI-MS m/z: (M+H)⁺=308.1.

Step C: Preparation of 4-chloro-8-(hex-5-en-1-yl)-6-(4-isopropylpiperazin-1-yl)pyrido[2,3-d]pyrimidin-7(8H)-one (8-4). To a mixture of 8-3 in DMSO (15 mL) was added K₃PO₄ (466 mg, 2.20 mmol), followed by 5-4 (286 mg, 1.76 mmol). The mixture was stirred at room temperature for 1 hour. Water (150 mL) was added, and the mixture was extracted with ethyl acetate (150 mL×3). The combined organics were washed with brine, dried over anhydrous Na₂SO₄, filtrated and concentrated to give a residue. The residue was purified by flash chromatography (petroleum ether/ethyl acetate=1/1) to afford the desired product as a light-yellow solid. ESI-MS m/z: (M+H)⁺=390.1.

Step D: Preparation of tert-butyl (R)-4-(difluoro(3-(1-((8-(hex-5-en-1-yl)-6-(4-isopropylpiperazin-1-yl)-7-oxo-7,8-dihydropyrido[2,3-d]pyrimidin-4-yl)amino)ethyl)phenyl) methyl)piperidine-1-carboxylate (8-5). To a solution of 8-4 (460 mg, 1.18 mmol) and 4-2 (419 mg, 1.18 mmol) in dry DMSO (10 mL) was added KF (410 mg, 7.08 mmol). The mixture was stirred at 60° C. overnight, then cooled to room temperature. Water (150 mL) was added, and the mixture was extracted with ethyl acetate (150 mL×3). The combined organics were washed with brine, dried over anhydrous Na₂SO₄, filtrated and concentrated to give a residue. The residue was purified by flash chromatography (petroleum ether/ethyl acetate=2/1) to afford the desired product as a light-yellow solid. ESI-MS m/z: (M+H)⁺=708.1.

Step E: Preparation of (R)-4-((1-(3-(difluoro(piperidin-4-yl)methyl)phenyl)ethyl)amino)-8-(hex-5-en-1-yl)-6-(4-isopropylpiperazin-1-yl)pyrido[2,3-d]pyrimidin-7(8H)-one (8-6). To a stirring solution of 8-5 (486 mg, 0.69 mmol) in dry DCM (10 mL) in a round bottom flask was added TFA (2 ml, DCM/TFA=5/1). The reaction mixture was stirred at room temperature for 2 hours, then concentrated to afford the crude desired product as a white solid, which was used in next step without further purification.

Step F: Preparation of (R)-4-((1-(3-((1-allylpiperidin-4-yl)difluoromethyl)phenyl)ethyl)amino)-8-(hex-5-en-1-yl)-6-(4-isopropylpiperazin-1-yl)pyrido[2,3-d]pyrimidin-7 (8H)-one (8-7). To a solution of 8-6 (390 mg, 0.65 mmol) in 10 mL of THF was added 4-7 (78 mg, 0.65 mmol) and TEA (200 mg, 1.95 mmol) at −10° C. The resulting solution was warmed to room temperature and stirred overnight. Water (100 mL) was added and the mixture was extracted with ethyl acetate (100 mL×3). The combined organics were washed with brine, dried over anhydrous Na₂SO₄, filtrated and solvent was removed under reduced pressure to give a residue. The residue was purified by flash chromatography (petroleum ether/ethyl acetate=1/1) to afford the desired product as a light-yellow solid. ESI-MS m/z: (M+H)⁺= 648.4.

Step G: Preparation of (4R,E)-2,2-difluoro-6⁶-(4-isopropylpiperazin-1-yl)-4-methyl-6⁷,6⁸-dihydro-5-aza-6(4,8)-pyrido[2,3-d]pyrimidina-1(4,1)-piperidina-3(1,3)-benzenacyclotridecaphan-11-en-6⁷-one (8-8). A solution of 8-7 (260 mg, 0.40 mmol) in 200 mL of dry DCM was degassed under vacuum and back filled with argon. This process was repeated 3 times. Grubbs II catalyst (66.12 mg, 0.080 mmol) was added, and the degas process above was repeated. The reaction mixture was stirred at 40° C. overnight under argon, then cooled to room temperature and most of the DCM removed. The mixture was diluted with water (20 mL) and ethyl acetate (20 mL), then filtered through a celite pad and the pad rinsed with ethyl acetate. The mixture was then extracted with ethyl acetate (30 mL×3) and the combined organics were washed with brine (60 mL), dried with Na₂SO₄, filtered and solvent removed under reduced pressure to give a residue. The residue was purified by prep-TLC (DCM/MeOH=12/1) to afford the desired product as a light-yellow solid. ESI-MS m/z: (M+H)⁺=620.2.

Step H: Preparation of (4R)-2,2-difluoro-6⁶-(4-isopropylpiperazin-1-yl)-4-methyl-6⁷,6⁸-dihydro-5-aza-6(4,8)-pyrido[2,3-d]pyrimidina-1(4,1)-piperidina-3(1,3)-benzenacyclotridecaphan-6⁷-one (123). To a solution of 8-8 (130 mg, 0.21 mmol) in 10 mL of i-PrOH/ethyl acetate (5/1) was added Pd/C (10%, 65 mg). The suspension was degassed under vacuum and back-filled with hydrogen. This process was repeated several times. The resulting reaction mixture was stirred at room temperature overnight under hydrogen atmosphere. The suspension was filtered through a pad of Celite, and the filter cake was washed with MeOH (10 mL×5). The combined filtrates were concentrated, and the crude product was purified by column chromatography and then by prep-HPLC to afford the desired product as a white solid. ESI-MS m/z: (M+H)⁺=622.3. ¹H NMR (400 MHz, DMSO) δ 8.23 (s, 1H), 8.08 (d, J=10.6 Hz, 2H), 7.55 (d, J=7.8 Hz, 1H), 7.49-7.41 (m, 2H), 7.19 (d, J=6.4 Hz, 2H), 5.30-5.20 (m, 1H), 4.66-4.56 (m, 1H), 4.13-4.06 (m, 1H), 3.18 (d, J=25.0 Hz, 4H), 2.82-2.66 (m, 3H), 2.62 (s, 5H), 2.18 (t, J=10.6 Hz, 1H), 2.06 (d, J=12.1 Hz, 1H), 1.85-1.74 (m, 2H), 1.66 (d, J=7.1 Hz, 4H), 1.45 (dd, J=29.6, 19.9 Hz, 5H), 1.20 (d, J=12.2 Hz, 4H), 1.00 (dd, J=22.1, 10.9 Hz, 9H), 0.65 (d, J=9.0 Hz, 1H).

Example 9: Synthesis of (3R)-1⁶-(1,1-dioxidotetrahydro-2H-thiopyran-4-yl)-4²,5,5-trifluoro-3-methyl-1⁷,1⁸-dihydro-2-aza-1(4,8)-pyrido[2,3-d]pyrimidina-7(4,1)-piperidina-4(1,3)-benzenacyclotridecaphan-1⁷-one (79)

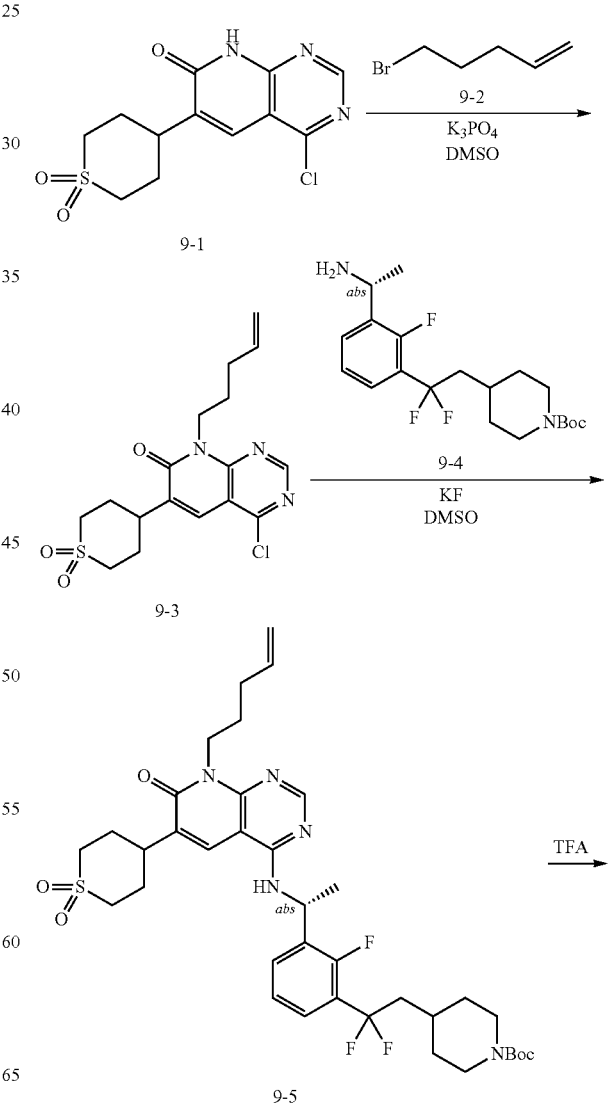

-continued

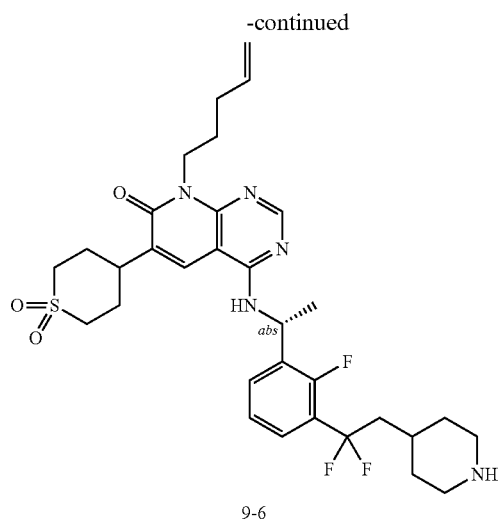

9-6

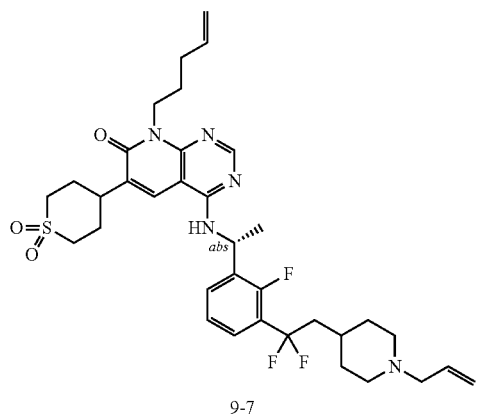

9-7

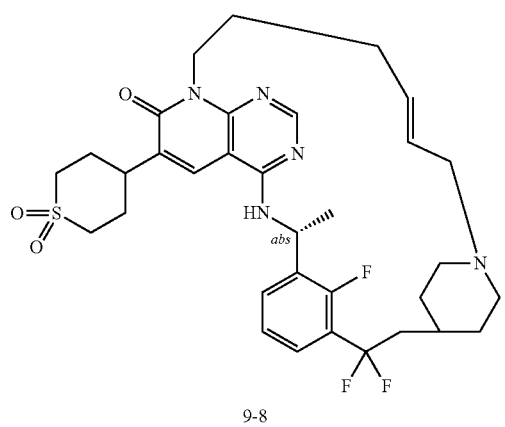

9-8

→ Grubbs II
DCM, 40° C.

→ Pd/C, H₂
THF

-continued

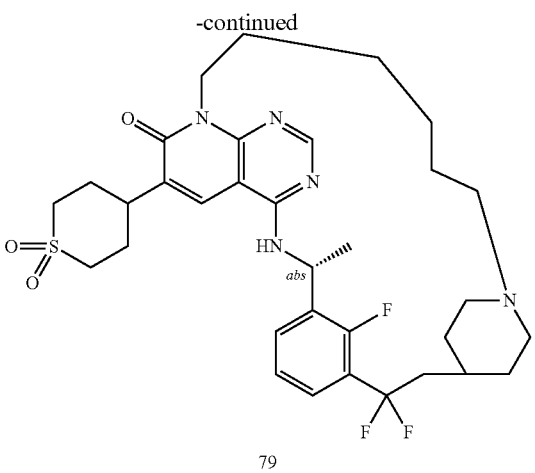

79

→ 4-7
DIEA
DCM

Step A: Preparation of 4-chloro-6-(1,1-dioxidotetrahydro-2H-thiopyran-4-yl)-8-(pent-4-en-1-yl)pyrido[2,3-d]pyrimidin-7(8H)-one (9-3). To a solution of 4-chloro-6-(1,1-dioxidotetrahydro-2H-thiopyran-4-yl)pyrido[2,3-d]pyrimidin-7(8H)-one (9-1) (1 g, 3.19 mmol, 1.0 eq) in DMSO (10 mL) was added 5-bromopent-1-ene (9-2) (567.4 mg, 3.8 mmol, 1.2 eq) and K₃PO₄ (2.0 g, 9.57 mmol, 3.0 eq) at 25° C. The mixture was stirred for 1 hour at room temperature, then poured into water and extracted with ethyl acetate (20 mL×3). The combined organics were washed with brine (30 mL), dried over Na₂SO₄, filtered and solvent removed under reduced pressure to give a residue. The residue was purified by silica gel column chromatography to afford the desired product as a white solid. ESI-MS m/z: (M+H)⁺=382.2.

Step B: Preparation of tert-butyl (R)-4-(2-(3-(1-((6-(1,1-dioxidotetrahydro-2H-thiopyran-4-yl)-7-oxo-8-(pent-4-en-1-yl)-7,8-dihydropyrido[2,3-d]pyrimidin-4-yl)amino)ethyl)-2-fluorophenyl)-2,2-difluoroethyl)piperidine-1-carboxylate (9-5). To a solution of 9-3 (300 mg, 0.78 mmol, 1.0 eq) in DMSO (5 mL) was added tert-butyl (R)-4-(2-(3-(1-aminoethyl)-2-fluorophenyl)-2,2-difluoroethyl)piperidine-1-carboxylate (9-4) (303.9 mg, 0.78 mmol, 1.0 eq) and KF (135.7 mg, 2.34 mmol, 3.0 eq) at 25° C. under nitrogen. The mixture was stirred for 1 hour at 100° C., then cooled to room temperature. The reaction mixture was poured into water and extracted with ethyl acetate (10 mL×3). The combined organics was washed with brine (15 mL) and dried over Na₂SO₄, then filtered and solvent removed under reduced pressure to give a residue. The residue was purified by silica gel column chromatography to afford the desired product as a white solid. ESI-MS m/z: (M+H)⁺=732.2.

Step C: Preparation of (R)-4-((1-(3-(1,1-difluoro-2-(piperidin-4-yl)ethyl)-2-fluorophenyl)ethyl)amino)-6-(1,1-dioxidotetrahydro-2H-thiopyran-4-yl)-8-(pent-4-en-1-yl)pyrido[2,3-d]pyrimidin-7(8H)-one (9-6). To a solution of 9-5 (400 mg, 0.54 mmol, 1.0 eq) in DCM (5 mL) was added TFA (1 mL) at 25° C. The mixture was stirred for 1 hour at 25° C., then concentrated under reduced pressure to give the desired product as a brown solid, which was used in the next step without further purification. ESI-MS m/z: (M+H)⁺=632.3.

Step D: Preparation of (R)-4-((1-(3-(2-(1-allylpiperidin-4-yl)-1,1-difluoroethyl)-2-fluorophenyl)ethyl)amino)-6-(1,1-dioxidotetrahydro-2H-thiopyran-4-yl)-8-(pent-4-en-1-yl)pyrido[2,3-d]pyrimidin-7(8H)-one (9-7). To a solution of 9-6 (300 mg, 0.47 mmol, 1.0 eq) in DCM (5 mL) was added DIEA (183.9 mg, 1.42 mmol, 3.0 eq) and 4-7 (56.4 mg, 0.47 mmol, 1.0 eq) at 25° C. The mixture was stirred for 16 hours at 25° C., then poured into water and extracted with ethyl acetate (10 mL×3). The combined organics were washed with brine (15 mL) and dried over Na₂SO₄, then filtered and solvent removed under reduced pressure to give a residue. The residue was purified by silica gel column chromatography to afford the desired product as a white solid. ESI-MS m/z: (M+H)⁺=672.2.

Step E: Preparation of (3R,E)-1⁶-(1,1-dioxidotetrahydro-2H-thiopyran-4-yl)-4²,5,5-trifluoro-3-methyl-1⁷,1⁸-dihydro-2-aza-1(4,8)-pyrido[2,3-d]pyrimidina-7(4,1)-piperidina-4(1,3)-benzenacyclotridecaphan-9-en-17-one (9-8). To a solution of 9-7 (200 mg, 0.29 mmol, 1.0 eq) in DCM (300 mL) was added Grubbs II catalyst (76.3 mg, 0.09 mmol, 0.3 eq) at 25° C. under nitrogen. The mixture was stirred for 16 hours at 40° C., then cooled to room temperature and concentrated under reduced pressure to give a residue. The residue was purified by prep-TLC (EA: MeOH=20:1) to give the desired product as a white solid. ESI-MS m/z: (M+H)⁺=644.2.

Step F: Preparation of (3R)-1⁶-(1,1-dioxidotetrahydro-2H-thiopyran-4-yl)-4²,5,5-trifluoro-3-methyl-1⁷,1⁸-dihydro-2-aza-1(4,8)-pyrido[2,3-d]pyrimidina-7(4,1)-piperidina-4(1,3)-benzenacyclotridecaphan-17-one (79). To a solution of 9-8 (28 mg, 0.04 mmol, 1.0 eq) in THF (10 mL) was added Pd/C (28 mg) at 25° C. under hydrogen. The mixture was stirred for 30 min at 25° C., then filtered and the filtrate concentrated under reduced pressure to give a residue. The residue was purified by prep-HPLC to afford the desired product as a white solid. ESI-MS m/z: (M+H)⁺=646.1. ¹H NMR (400 MHz, MeOD) δ 8.39 (s, 1H), 8.30 (s, 1H), 8.22 (d, J=6.8 Hz, 1H), 7.69 (t, J=6.6 Hz, 1H), 7.41 (t, J=6.7 Hz, 1H), 7.25 (t, J=7.8 Hz, 1H), 5.76 (d, J=7.0 Hz, 1H), 5.34 (s, 1H), 4.71 (dd, J=12.6, 6.2 Hz, 2H), 4.34 (dd, J=12.2, 6.5 Hz, 1H), 3.15 (d, J=13.9 Hz, 2H), 2.77 (s, 3H), 2.47-2.09 (m, 9H), 2.03 (s, 1H), 1.86 (dd, J=13.3, 6.9 Hz, 1H), 1.77-1.58 (m, 5H), 1.51 (s, 1H), 1.39-1.32 (m, 6H), 1.24-1.10 (m, 4H), 0.89 (d, J=7.0 Hz, 1H).

Example 10: Synthesis of (3R)-1⁶-(1,1-dioxidotetrahydro-2H-thiopyran-4-yl)-4²,5,5-trifluoro-3-methyl-1⁷,1⁸-dihydro-2-aza-1(4,8)-pyrido[2,3-d]pyrimidina-8(4,1)-piperidina-4(1,3)-benzenacyclotridecaphan-1⁷-one (151)

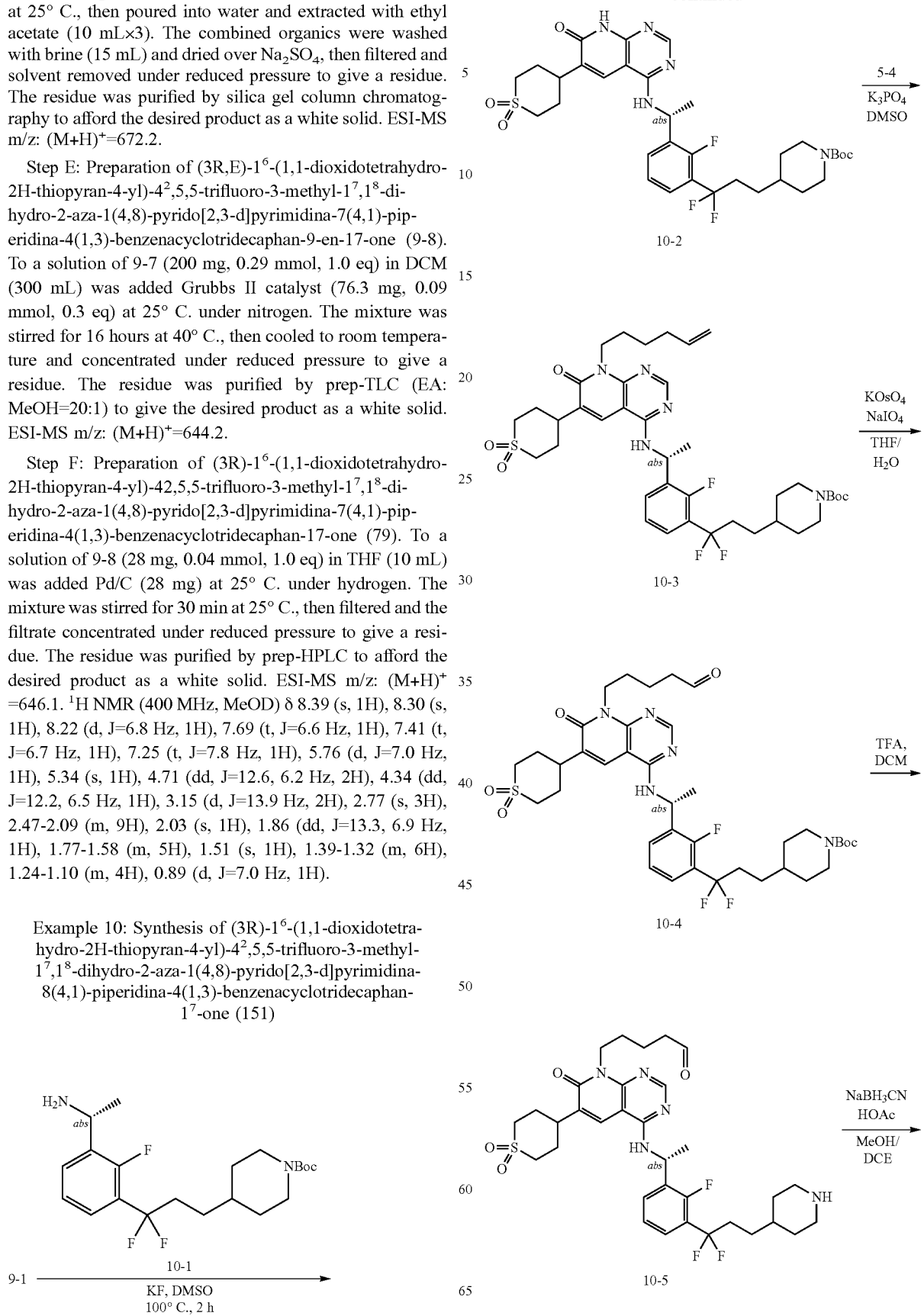

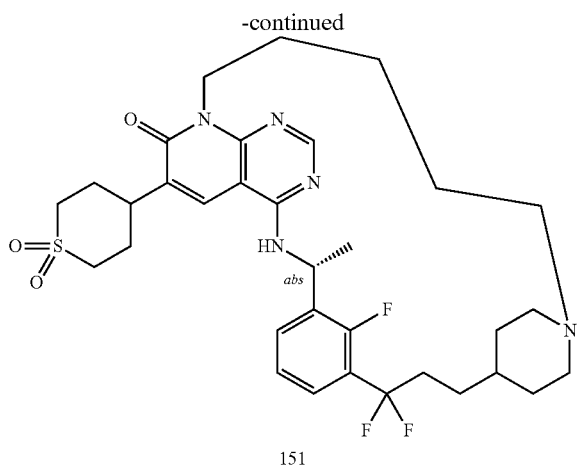

151

Step A: Preparation of tert-butyl (R)-4-(3-(3-(1-((6-(1,1-dioxidotetrahydro-2H-thiopyran-4-yl)-7-oxo-7,8-dihydro-pyrido[2,3-d]pyrimidin-4-yl)amino)ethyl)-2-fluorophenyl)-3,3-difluoropropyl)piperidine-1-carboxylate (10-2). To a stirred solution of 9-1 (300 mg, 0.958 mmol) and tert-butyl (R)-4-(3-(3-(1-aminoethyl)-2-fluorophenyl)-3,3-difluoro-propyl)piperidine-1-carboxylate (10-1) (319 mg, 0.798 mmol) in dry DMSO (20 mL) was added KF (334 mg, 5.748 mmol) and the resultant solution was heated to 100° C. for 2 hours under nitrogen. The reaction mixture was cooled to room temperature and diluted with ethyl acetate (50 mL) and water (200 mL), then extracted with ethyl acetate (3×50 mL). The combined organics were washed with brine, dried over Na$_2$SO$_4$, filtered and concentrated under reduced pressure to give a residue, which was purified by flash chromatography (DCM:MeOH=10:1) to obtain the desired product as a yellow solid. ESI-MS m/z: (M+H)$^+$=678.2.

Step B: Preparation of tert-butyl (R)-4-(3-(3-(1-((6-(1,1-dioxidotetrahydro-2H-thiopyran-4-yl)-8-(hex-5-en-1-yl)-7-oxo-7,8-dihydropyrido[2,3-d]pyrimidin-4-yl)amino)ethyl)-2-fluorophenyl)-3,3-difluoropropyl)piperidine-1-carboxylate (10-3). To a stirred solution of 10-2 (300 mg, 0.44 mmol) and 5-4 (108 mg, 0.66 mmol) in DMSO (5 mL) was added K$_3$PO$_4$ (282 mg, 0.66 mmol), and the resultant solution was stirred at room temperature for 1 hour. The mixture was poured into water and extracted with ethyl acetate (40 mL×3). The combined organics were washed with brine, dried over Na$_2$SO$_4$, filtered and concentrated under reduced pressure to give a residue, which was purified by com-flash chromatography on a silica gel column (0%~60% ethyl acetate in petroleum ether) to give the desired product as a white foamed solid. ESI-MS m/z: (M+Na)$^+$=782.2.

Step C: Preparation of tert-butyl (R)-4-(3-(3-(1-((6-(1,1-dioxidotetrahydro-2H-thiopyran-4-yl)-7-oxo-8-(5-oxopentyl)-7,8-dihydropyrido[2,3-d]pyrimidin-4-yl)amino)ethyl)-2-fluorophenyl)-3,3-difluoropropyl)piperidine-1-carboxylate (10-4). To a stirred solution of 10-3 (250 mg, 0.329 mmol) in THF (30 mL) and water (20 mL) was added K$_2$OsO$_4$·2H$_2$O (10 mg, 0.0329 mmol) and NaIO$_4$(211 mg, 0.987 mmol) at 0° C. The resultant solution was allowed to warm to room temperature and stirred for 4 hours, then diluted with ethyl acetate (50 mL) and water (30 mL). The organic phase was separated, and the aqueous phase was extracted with ethyl acetate (30 mL) twice. The combined organics were combined, washed with brine, dried over Na$_2$SO$_4$, filtered and concentrated under reduced pressure to give the desired product as a brown oil, which was used in the next step without further purification. ESI-MS m/z: (M+H)$^+$=762.5.

Step D: Preparation of (R)-5-(4-((1-(3-(1,1-difluoro-3-(piperidin-4-yl)propyl)-2-fluorophenyl)ethyl)amino)-6-(1,1-dioxidotetrahydro-2H-thiopyran-4-yl)-7-oxopyrido[2,3-d]pyrimidin-8(7H)-yl)pentanal (10-5). To a stirred solution of 10-4 (250 mg crude) in DCM (10 mL) was added TFA (2 mL) and the resulting solution was stirred at room temperature for 30 minutes. The mixture was diluted with DCM (30 mL) and adjusted to PH-8 with aqueous sat. NaHCO$_3$. The aqueous phase was extracted with DCM (30 mL) twice. The combined organic layers were dried over Na$_2$SO$_4$, filtered and concentrated under reduced pressure to give the desired product as a light-yellow oil, which was used in the next step without further purification.

Step E: Preparation of (3R)-16-(1,1-dioxidotetrahydro-2H-thiopyran-4-yl)-4$^2$,5,5-trifluoro-3-methyl-1$^7$,1$^8$-dihydro-2-aza-1(4,8)-pyrido[2,3-d]pyrimidina-8(4,1)-piperidina-4(1,3)-benzenacyclotridecaphan-1$^7$-one (151). To a stirred solution of 10-5 (250 mg crude, ~0.33 mmol) in MeOH/dichloroethane (220 mL/110 mL, 0.001M) was added HOAc (2 drops) and the resulting solution was stirred at room temperature for 30 minutes. NaBH$_3$CN (52 mg, 0.83 mmol) was added to the mixture and the resulting solution was stirred at room temperature for 1 hour. The mixture was concentrated under reduced pressure to give a residue, which was purified by com-flash chromatography on a silica gel column (0%~10% MeOH in DCM) and prep-HPLC to give the desired product as a white solid. ESI-MS m/z: (M+H)$^+$= 646.2. $^1$H NMR (400 MHz, DMSO-D2O) δ 8.35 (s, 1H), 8.19 (s, 1H), 7.79 (d, J=7.0 Hz, 1H), 7.45-7.23 (m, 2H), 5.87 (q, J=6.8 Hz, 1H), 4.79 (t, J=9.9 Hz, 1H), 4.03 (dd, J=8.2, 4.6 Hz, 1H), 3.44-3.29 (m, 2H), 3.18 (dd, J=22.1, 8.6 Hz, 3H), 2.87 (d, J=10.7 Hz, 1H), 2.48-1.52 (m, 18H), 1.41-0.91 (m, 6H), 0.73 (d, J=11.4 Hz, 1H), 0.56-0.40 (m, 1H), 0.36-0.19 (m, 1H).

Example 11: Synthesis of (4R)-3$^2$,2,2-trifluoro-6$^6$-(1-isopropylpiperidin-4-yl)-4-methyl-6$^7$,6$^8$-dihydro-5-aza-6(4,8)-pyrido[2,3-d]pyrimidina-1(4,1)-piperidina-3(1,3)-benzenacyclotridecaphan-6$^7$-one (162)

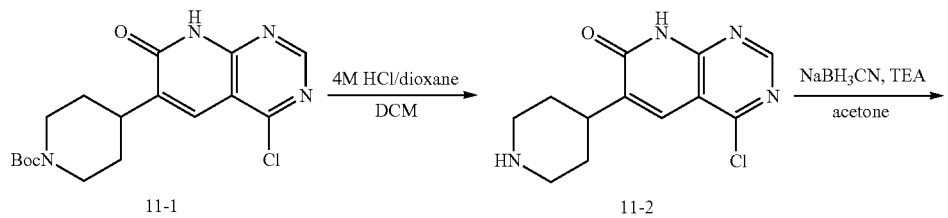

-continued
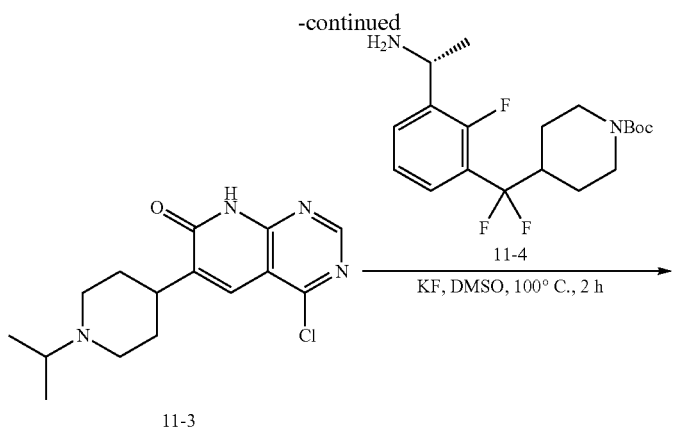
11-3 + 11-4 →(KF, DMSO, 100° C., 2 h)
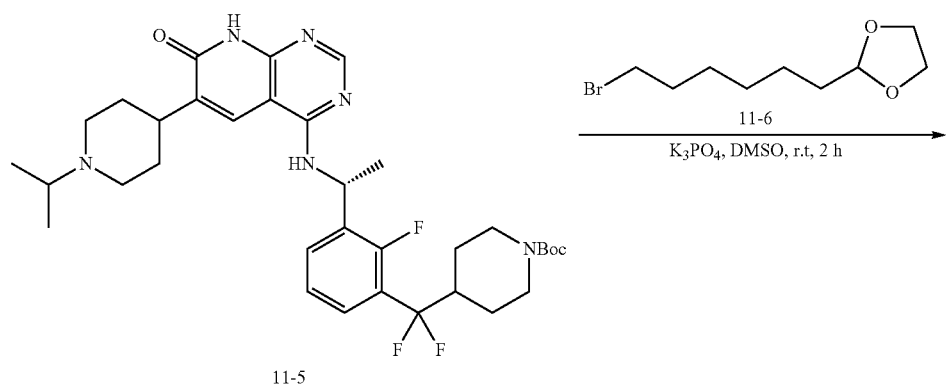
11-5
→(K₃PO₄, DMSO, r.t, 2 h) with 11-6
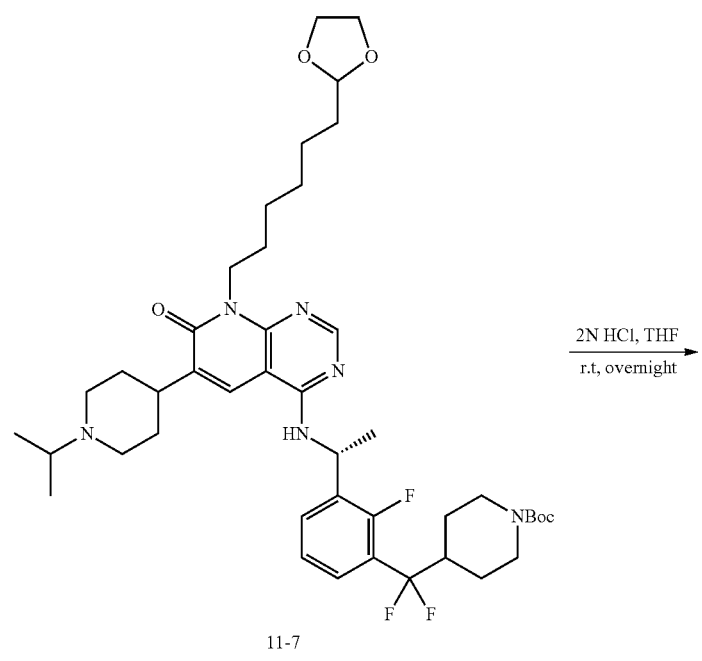
11-7
→ 2N HCl, THF, r.t, overnight

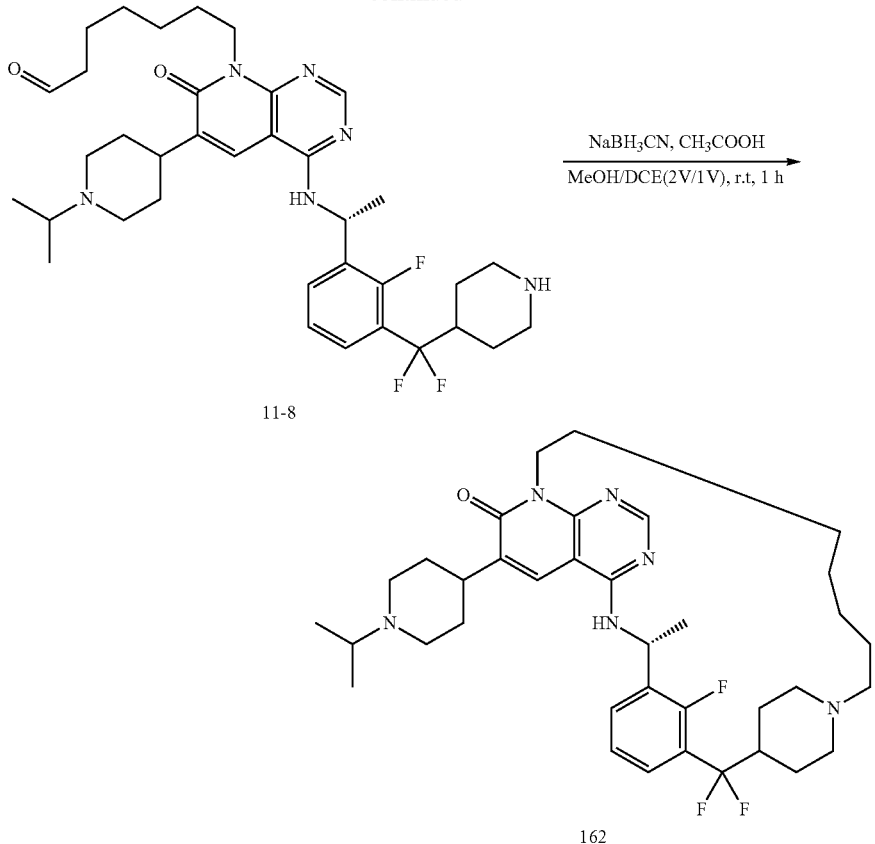

11-8

162

Step A: Preparation of 4-chloro-6-(piperidin-4-yl)pyrido[2,3-d]pyrimidin-7(8H)-one (11-2). To a solution of tert-butyl 4-(4-chloro-7-oxo-7,8-dihydropyrido[2,3-d]pyrimidin-6-yl)piperidine-1-carboxylate (11-1) (4.5 g, 1.0 eq., 12.36 mmol) in dioxane (200 mL) was added HCl (4M in dioxane, 200 mL). The mixture was stirred at room temperature for 1 hour, then concentrated in vacuo to provide the desired product as a yellow solid which was used directly in the next step without further purification. ESI-MS m/z: (M+H)$^+$=265.0.

Step B: Preparation of 4-chloro-6-(1-isopropylpiperidin-4-yl)pyrido[2,3-d]pyrimidin-7(8H)-one (11-3). To a suspension of 11-2 (4 g, 1.0 eq., 12.36 mmol) in acetone (100 mL) was added triethylamine to adjust the pH to 7-8, then NaBH$_3$CN (1.9 g, 2.5 eq., 30.90 mmol) was added and the reaction mixture was stirred at room temperature overnight. The reaction mixture was concentrated in vacuo and the residue was purified by silica gel column chromatography to provide the desired product as a white solid. ESI-MS m/z: (M+H)$^+$=307.2.

Step C: Preparation of tert-butyl (R)-4-(difluoro(2-fluoro-3-(1-(((6-(1-isopropylpiperidin-4-yl)-7-oxo-7,8-dihydropyrido[2,3-d]pyrimidin-4-yl)amino)ethyl)phenyl)methyl)piperidine-1-carboxylate (11-5). 11-3 (310 mg, 1.0 eq., 1.01 mmol), tert-butyl (R)-4-((3-(1-aminoethyl)-2-fluorophenyl)difluoromethyl)piperidine-1-carboxylate (11-4) (376 mg, 1.2 eq., 1.21 mmol) and KF (352 mg, 6.0 eq., 6.07 mmol) were dissolved in dry DMSO (5 mL). The resulting mixture was stirred at 100° C. for 2 hours under nitrogen, then cooled and solvent removed under reduced pressure to give a residue. The residue was treated with water and extracted with ethyl acetate (3×30 mL). The combined organics were washed with brine, dried over Na$_2$SO$_4$, filtered and concentrated under reduced pressure to give a residue, which was purified on a silica gel column (0%-5% MeOH in DCM) to give the desired product as a yellow oil. ESI-MS m/z: (M+H)$^+$=643.5.

Step D: Preparation of tert-butyl (R)-4-((3-(1-((8-(6-(1,3-dioxolan-2-yl)hexyl)-6-(1-isopropylpiperidin-4-yl)-7-oxo-7,8-dihydropyrido[2,3-d]pyrimidin-4-yl)amino)ethyl)-2-fluorophenyl)difluoromethyl)piperidine-1-carboxylate (11-7). To a stirred solution of 11-5 (515 mg, 1.0 eq., 0.80 mmol) and 2-(6-bromohexyl)-1,3-dioxolane (11-6) (283 mg, 1.5 eq., 1.20 mmol) in DMSO (5 mL) was added K$_3$PO$_4$ (510 mg, 3.0 eq., 2.40 mmol) and the resulting mixture was stirred at room temperature for 2 hours. The mixture was diluted with ethyl acetate and water (20 mL/30 mL) and extracted with ethyl acetate (3×30 mL). The combined organic layer was washed with brine, dried over Na$_2$SO$_4$, filtered and concentrated to give a residue. The residue was purified on a silica gel column (0%-7% MeOH in DCM) to give the desired product as light-yellow solid. ESI-MS m/z: (M+H)$^+$=799.4.

Step E: Preparation of (R)-7-(4-((1-(3-(difluoro(piperidin-4-yl)methyl)-2-fluorophenyl)ethyl)amino)-6-(1-isopropylpiperidin-4-yl)-7-oxopyrido[2,3-d]pyrimidin-8(7H)-yl)heptanal (11-8). To a solution of 11-7 (359 mg, 1.0 eq., 0.45 mmol) in THF (36 mL) was added HCl (72 mL, 2 M in water) at room temperature and the resulting solution was stirred at room temperature for 16 hours. The mixture was treated with saturated NaHCO$_3$ solution and extracted with ethyl acetate (3×50 mL). The combined organic layer was washed with brine, dried over Na₂SO₄, filtered and concentrated to give the desired product which was used directly in the next step without further purification. ESI-MS m/z: (M+H)⁺=655.

Step F: Preparation of (4R)-3²,2,2-trifluoro-6⁶-(1-isopropylpiperidin-4-yl)-4-methyl-6⁷,6⁸-dihydro-5-aza-6(4,8)-pyrido[2,3-d]pyrimidina-1(4,1)-piperidina-3(1,3)-benzenacyclotridecaphan-6⁷-one (162). 11-8 (294 mg, 1.0 eq., 0.45 mmol) was dissolved in MeOH and 1,2-dichloroethane (MeOH:1,2-dichloroethane=300 mL:150 mL) and 1 drop of acetic acid was added. The mixture was stirred for 0.5 hours at room temperature, then NaBH₃CN (70 mg, 2.5 eq., 1.12 mmol) was added and the mixture stirred at room temperature for an additional 0.5 hours. The reaction mixture was concentrated to provide a residue which was purified by prep-HPLC to give the desired product. ESI-MS m/z: (M+H)⁺=639.7. ¹H NMR (400 MHz, DMSO-D₂O) δ 8.42 (brs. 1H), 8.17 (s, 1H), 8.14 (s, 11H), 7.66 (m, 11H), 7.27 (t, J=7.5 Hz, 11H), 7.19 (t, J=6.5 Hz, 11H), 5.54 (q, J=7.2 Hz, 11H), 4.71-4.59 (m, 11H), 4.09-3.99 (m, 1H), 3.5-2.79 (m, 5H), 2.61-2.52 (m, 2H), 2.44-2.35 (m, 1H), 2.19-2.08 (m, 3H), 1.96-1.79 (m, 4H), 1.73-1.61 (m, 8H), 1.43 (m, 3H), 1.20-1.13 (m, 2H), 1.21-0.99 (m, 8H), 0.76-0.58 (m, 4H).

Example 12: Synthesis of 4-((4R)-3²,2,2-trifluoro-4-methyl-6⁷-oxo-6⁷,6⁸-dihydro-5-aza-6(4,8)-pyrido[2,3-d]pyrimidina-1(4,1)-piperidina-3(1,3)-benzenacyclotridecaphane-6⁶-yl)tetrahydro-2H-thiopyran-4-carbonitrile 1,1-dioxide (112)

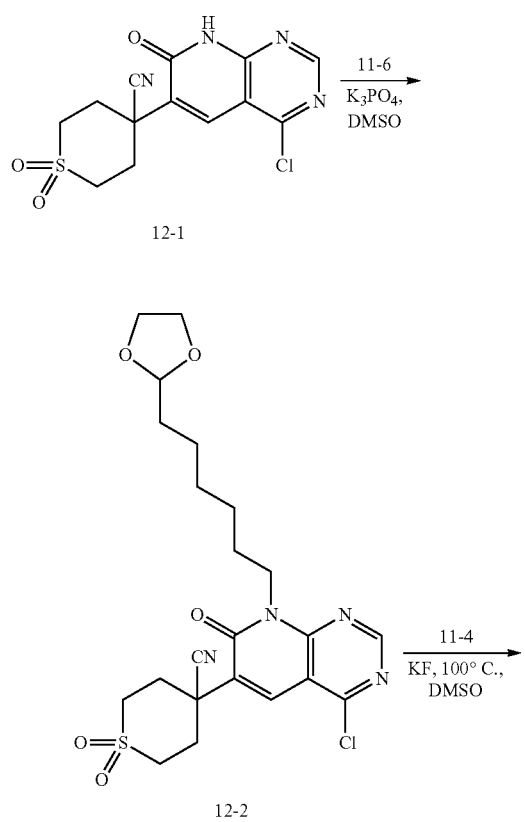

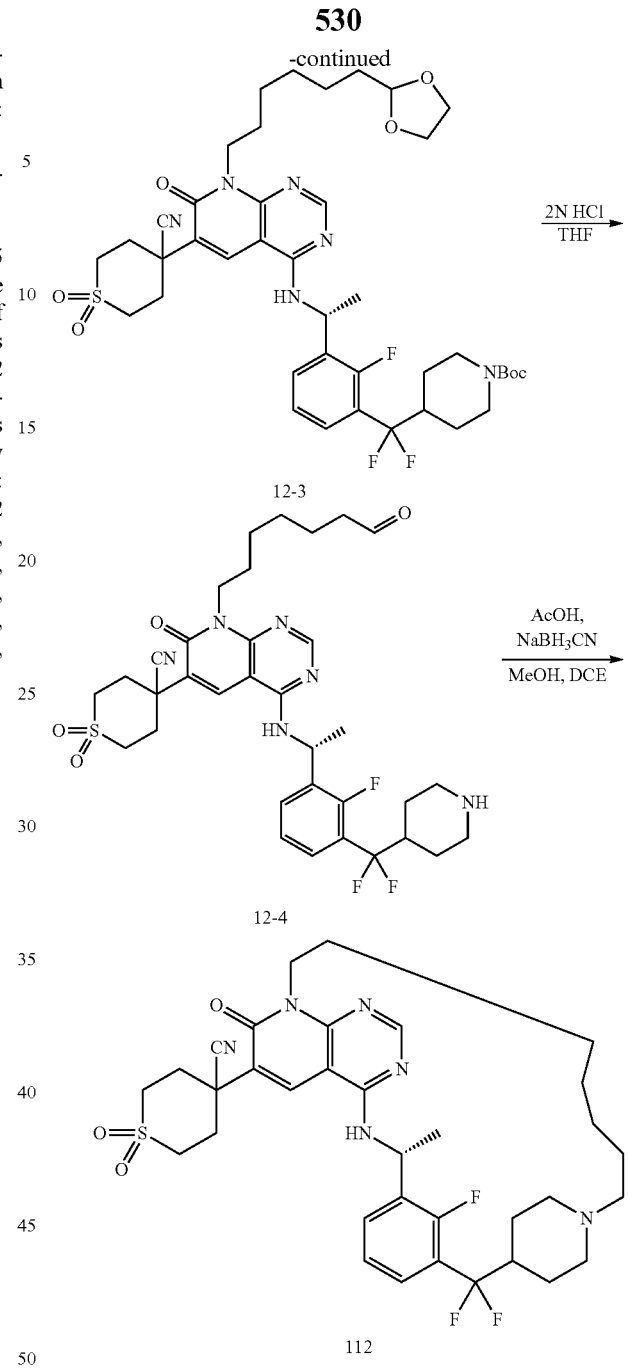

Step A: Preparation of 4-(8-(6-(1,3-dioxolan-2-yl)hexyl)-4-chloro-7-oxo-7,8-dihydropyrido[2,3-d]pyrimidin-6-yl)tetrahydro-2H-thiopyran-4-carbonitrile 1,1-dioxide (12-2). To a solution of 4-(4-chloro-7-oxo-7,8-dihydropyrido[2,3-d]pyrimidin-6-yl)tetrahydro-2H-thiopyran-4-carbonitrile 1,1-dioxide (12-1) (300 mg, 1 eq, 0.88 mmol) in DMSO (10 mL) at 25° C. were added 11-6 (314.2 g, 1.5 eq., 1.33 mmol) and K₃PO₄ (559 mg, 3.0 eq., 2.64 mmol). The mixture was stirred at 25° C. for 2 hours, then cooled, poured into water, and extracted with DCM (3×20 mL). The combined organics were washed with brine, dried over Na₂SO₄, filtered and concentrated under reduced pressure to give a residue, which was purified by silica gel column chromatography to afford the desired product. ESI-MS m/z: (M+H)⁺=495.0.

Step B: Preparation of tert-butyl (R)-4-((3-(1-((8-(6-(1,3-dioxolan-2-yl)hexyl)-6-(4-cyano-1,1-dioxidotetrahydro- 2H-thiopyran-4-yl)-7-oxo-7,8-dihydropyrido[2,3-d]pyrimidin-4-yl)amino)ethyl)-2-fluorophenyl)difluoromethyl)piperidine-1-carboxylate (12-3). To a solution of 12-2 (220 mg, 1 eq, 0.44 mmol) in DMSO (10 mL) at 25° C. were added 11-4 (165 mg, 1.0 eq., 0.44 mmol) and KF (76 mg, 3.0 eq., 1.32 mmol). The mixture was stirred at 100° C. for 2 hours, then cooled to room temperature, poured into water, and extracted with ethyl acetate (3×20 mL). The combined organics were washed with brine, dried over Na$_2$SO$_4$, filtered and concentrated under reduced pressure to give a residue, which was purified by silica gel column chromatography to afford the desired product. ESI-MS m/z: (M+H)$^+$=831.4.

Step C: Preparation of (R)-4-(4-((1-(3-(difluoro(piperidin-4-yl)methyl)-2-fluorophenyl)ethyl)amino)-7-oxo-8-(7-oxoheptyl)-7,8-dihydropyrido[2,3-d]pyrimidin-6-yl)tetrahydro-2H-thiopyran-4-carbonitrile 1,1-dioxide (12-4). To a solution of 12-3 (280 mg, 1 eq, 0.34 mmol) in THF (10 mL) at 25° C. was added HCl (2N, 30 ml). The resulting mixture was stirred at 25° C. for 1 hour and carefully added to ice-water (30 mL) with stirring. The pH of the mixture was adjusted to 8 with NaHCO$_3$, then the mixture was extracted with ethyl acetate (3×30 mL). The combined organics were washed with brine, dried over Na$_2$SO$_4$, filtered and concentrated under reduced pressure to give a residue, which was purified by silica gel column chromatography to afford the desired product (100.0 mg). ESI-MS m/z: (M+H)$^+$=687.4.

Step D: Preparation of 4-((4R)-3$^2$,2,2-trifluoro-4-methyl-6$^7$-oxo-6$^7$,6$^8$-dihydro-5-aza-6(4,8)-pyrido[2,3-d]pyrimidina-1(4,1)- piperidina-3(1,3)-benzenacyclotridecaphane-6$^6$-yl)tetrahydro-2H-thiopyran-4-carbonitrile 1,1-dioxide (112). To a solution of 12-4 (100 mg, 1 eq, 0.15 mmol) in MeOH (125 mL) and dichloroethane (75 mL) at 25° C. was added acetic acid (0.1 mL). The mixture was stirred at 25° C. for 30 minutes, then NaBH$_3$CN (27.5 mg, 0.44 mmol) was added and the resulting mixture stirred at 25° C. for 16 hours. The solvent was removed under reduced pressure to give a residue. The residue was extracted with DCM (3×20 mL), then the combined organic extracts were washed with NaHCO$_3$ solution and brine, dried over Na$_2$SO$_4$, filtered, and concentrated under reduced pressure to give a residue. The residue was purified by silica gel column chromatography to afford the desired product (27.51 mg). ESI-MS m/z: (M+H)$^+$=671.5. $^1$H NMR (400 MHz, DMSO) δ 8.73 (d, J=6.2 Hz, 1H), 8.33 (s, 1H), 8.24 (s, 1H), 7.66 (t, J=6.5 Hz, 11H), 7.28 (t, J=7.7 Hz, 11H), 7.20 (t, J=6.5 Hz, 11H), 5.61-5.50 (m, 11H), 4.69 (m, 11H), 4.12-4.04 (m, 11H), 3.53-3.44 (m, 3H), 2.99 (d, J=10.9 Hz, 1H), 2.83 (t, J=12.7 Hz, 2H), 2.58 (m, 2H), 2.45 (m, 1H), 2.22-2.10 (m, 3H), 1.95-1.83 (m, 2H), 1.72- 1.58 (m, 6H), 1.53-1.31 (m, 3H), 1.21-1.02 (m, 5H), 0.91-0.63 (m, 4H).

Example 13: Synthesis of 4-((3R)-4$^2$,5,5-trifluoro-3-methyl-1$^7$-oxo-1$^7$,1$^8$-dihydro-2-aza-1(4,8)-pyrido[2,3-d]pyrimidina-7(4,1)-piperidina-4(1,3)-benzenacyclotridecaphane-1$^6$-yl)tetrahydro-2H-thiopyran-4-carbonitrile 1,1-dioxide (23)

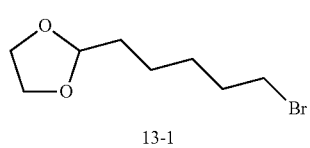

12-1 ⟶ 13-1 ⟶

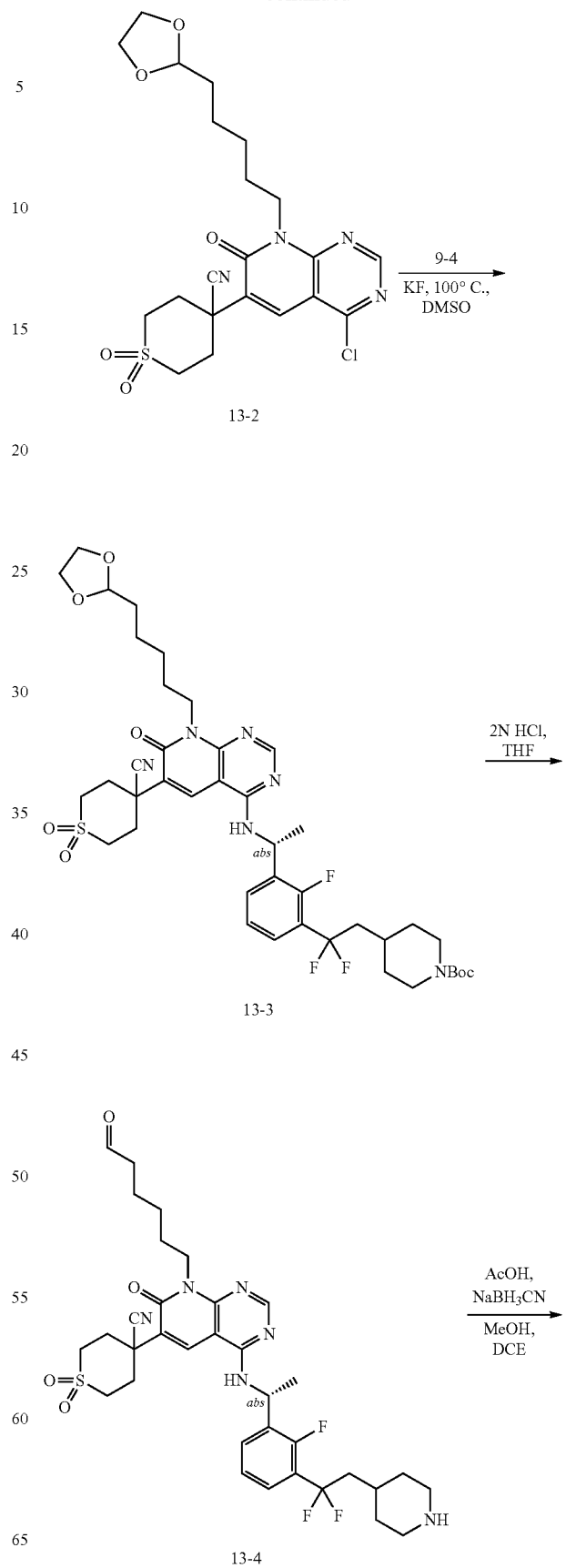

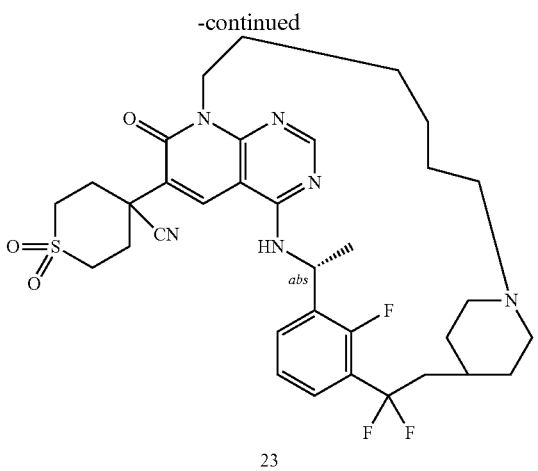

23

Step A: Preparation of 4-(8-(5-(1,3-dioxolan-2-yl)pentyl)-4-chloro-7-oxo-7,8-dihydropyrido[2,3-d]pyrimidin-6-yl)tetrahydro-2H-thiopyran-4-carbonitrile 1,1-dioxide (13-2). To a solution of 12-1 (200 mg, 1 eq, 0.59 mmol) in DMSO (3 mL) at 25° C. were added 2-(5-bromopentyl)-1,3-dioxolane (13-1) (0.21 g, 1.5 eq., 0.94 mmol) and $K_3PO_4$ (376 mg, 3.0 eq., 1.77 mmol). The mixture was stirred at 25° C. for 2 hours, then cooled to room temperature, poured into water, and extracted with DCM (3×5 mL). The combined organics were washed with brine, dried over $Na_2SO_4$, filtered and concentrated under reduced pressure to give a residue, which was purified by silica gel column chromatography to afford the desired product. ESI-MS m/z: $(M+H)^+$=481.0.

Step B: Preparation of tert-butyl (R)-4-(2-(3-(1-((8-(5-(1,3-dioxolan-2-yl)pentyl)-6-(4-cyano-1,1-dioxidotetrahydro-2H-thiopyran-4-yl)-7-oxo-7,8-dihydropyrido[2,3-d]pyrimidin-4-yl)amino)ethyl)-2-fluorophenyl)-2,2-difluoroethyl)piperidine-1l-carboxylate (13-3). To a solution of 13-2 (210 mg, 1 eq, 0.44 mmol) in DMSO (3 mL) at 25° C. were added 9-4 (168 mg, 1.0 eq., 0.437 mmol) and KF (76 mg, 3.0 eq., 1.31 mmol). The mixture was stirred at 100° C. for 2 hours, then cooled to room temperature, poured into water, and extracted with ethyl acetate (3×5 mL). The combined organics were washed with brine, dried over $Na_2SO_4$, filtered and concentrated under reduced pressure to give a residue, which was purified by silica gel column chromatography to afford the desired product. ESI-MS m/z: $(M+H)^+$=831.03.

Step C: Preparation of (R)-4-(4-((1-(3-(1,1-difluoro-2-(piperidin-4-yl)ethyl)-2-fluorophenyl)ethyl)amino)-7-oxo-8-(6-oxohexyl)-7,8-dihydropyrido[2,3-d]pyrimidin-6-yl)tetrahydro-2H-thiopyran-4-carbonitrile 1,1-dioxide (13-4). To a solution of 13-3 (260 mg, 1 eq, 0.31 mmol) in THF (3 mL) at 25° C. was added HCl (2N, 1 mL, 0.2 mmol). The resulting reaction mixture was stirred at 25° C. for 1 hour, then slowly added to ice-water (5 mL) with stirring. The resulting mixture was treated with saturated $NaHCO_3$ solution to adjust the pH to ~8, then extracted with ethyl acetate (3×10 mL). The combined organics were washed with brine, dried over $Na_2SO_4$, filtered and concentrated under reduced pressure to give a residue, which was purified by silica gel column chromatography to afford the desired product. ESI-MS m/z: $(M+H)^+$=687.4.

Step D: Preparation of 4-((3R)-42,5,5-trifluoro-3-methyl-$1^7$-oxo-$1^7$,$1^8$-dihydro-2-aza-1(4,8)-pyrido[2,3-d]pyrimidina-7(4,1)-piperidina-4(1,3)-benzenacyclotridecaphane-$1^6$-yl)tetrahydro-2H-thiopyran-4-carbonitrile 1,1-dioxide (23). To a solution of 13-4 (230 mg, 1 eq, 0.33 mmol) in methanol (250 mL) at 25° C. were added dichloroethane (125 mL) and acetic acid (0.1 mL). The resulting mixture was stirred at 25° C. for 30 minutes, then $NaBH_3CN$ (36 mg, 0.56 mmol) was added. The reaction mixture was stirred at 25° C. for 16 hours, then concentrated in vacuo and the residue extracted with DCM (3×10 mL). The organic extracts were combined, washed with $NaHCO_3$ solution and brine, dried over $Na_2SO_4$, filtered, and concentrated under reduced pressure to give a residue. The residue was purified by silica gel column chromatography to afford the desired product. ESI-MS m/z: $(M+H)^+$=671.4. $^1H$ NMR (400 MHz, DMSO) δ 8.48 (s, 1H), 8.37 (s, 1H), 7.79 (m, 1H), 7.47 (m, 1H), 7.28 (m, 1H), 5.64 (m, 1H), 4.51 (m, 1H), 4.24 (m, 1H), 3.51-3.30 (m, 7H), 2.76 (m, 3H), 2.54-2.48 (m, 1H), 2.50 (m, 1H), 2.27 (m, 1H), 2.21 (m, 1H), 2.23-2.02 (m, 3H), 1.76-1.70 (m, 1H), 1.64 (m, 2H), 1.51-1.45 (m, 2H), 1.40-1.34 (m, 1H), 1.25 (m, 1H), 1.15-0.98 (m, 5H), 0.96-0.71 (m, 4H).

Example 14: Synthesis of (4R)-$6^6$-(1,1-dioxidothiomorpholino)-$3^2$,2,2-trifluoro-4-methyl-$6^7$,$6^8$-dihydro-10-oxa-5-aza-6(4,8)-pyrido[2,3-d]pyrimidina-1(4,1)-piperidina-3(1,3)-benzenacyclotetradecaphan-$6^7$-one (69)

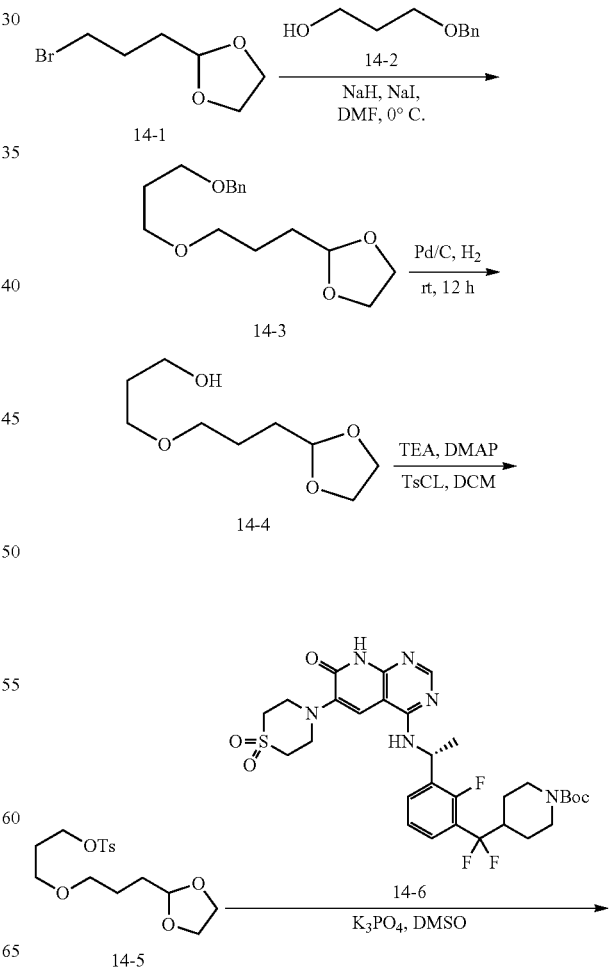

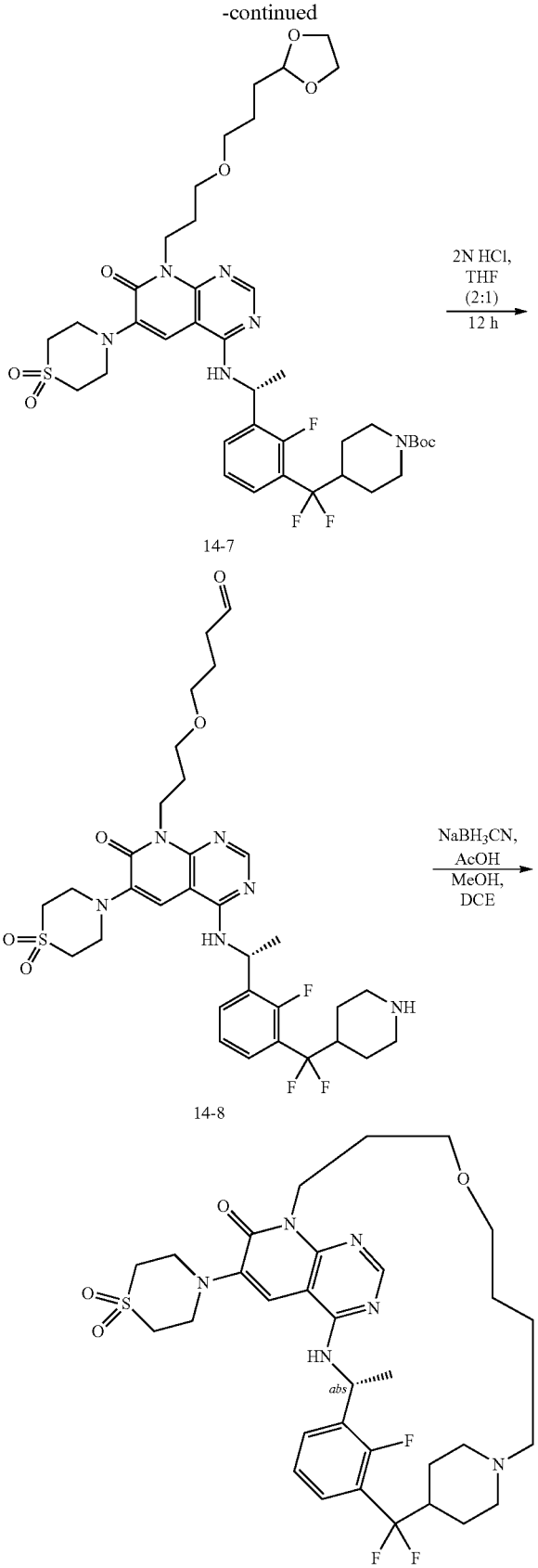

Step A: Preparation of 2-(3-(3-(benzyloxy)propoxy)propyl)-1,3-dioxolane (14-3). To a solution of 3-(benzyloxy)propan-1-ol (14-2) (9.2 g, 1.2 eq., 55.4 mmol) in DMF (40 mL) was added NaH (60% dispersed in mineral oil) (5.54 g, 5 eq., 231 mmol) at 0° C. under nitrogen atmosphere. The resulting mixture was stirred for 1 hour at 0° C., then 2-(3-bromopropyl)-1,3-dioxolane (14-1) (9 g, 1 eq., 46.2 mmol) and NaI (693 mg, 0.1 eq., 4.62 mmol) in DMF (10 mL) were added dropwise at 0° C. The mixture was stirred for 2 hours at room temperature, then quenched by addition of water (200 mL) at 0° C. The resulting mixture was extracted with ethyl acetate (3×300 mL) and the combined organic layers were washed with brine (3×900 mL), dried over $Na_2SO_4$, filtered and solvent removed in vacuo to give a residue which was purified by silica gel column chromatography (0%-15% ethyl acetate in petroleum ether) to afford the desired product as a colorless oil. $^1$H NMR (400 MHz, $CDCl_3$) δ 7.37-7.25 (m, 5H), 4.88 (t, J=4.4 Hz, 1H), 4.50 (s, 2H), 4.02-3.78 (m, 4H), 3.59-3.39 (m, 6H), 1.93-1.83 (m, 2H), 1.76-1.67 (m, 4H).

Step B: Preparation of 3-(3-(1,3-dioxolan-2-yl)propoxy)propan-1-ol (14-4). To a solution of 14-3 (4 g, 1 eq., 14.29 mmol) in EtOH (50 mL) was added Pd/C (10% on carbon) (2.4 g). The mixture was stirred for 12 hours at room temperature under hydrogen atmosphere. The resulting mixture was filtered through celite and the filtrate was concentrated in vacuo to give a residue. The residue was purified by silica gel column chromatography (0%-30% ethyl acetate in petroleum ether) to afford the desired product as a colorless oil.

Step C: Preparation of 3-(3-(1,3-dioxolan-2-yl)propoxy)propyl 4-methylbenzenesulfonate (14-5). To a solution of 14-4 (2.7 g, 1 eq., 14.2 mmol) in DCM (20 mL) were added DMAP (346 mg, 0.2 eq., 2.84 mmol), TsCl (4.1 g, 1.5 eq., 21.5 mmol) and triethylamine (4.3 g, 3 eq., 42.6 mmol) at room temperature under nitrogen atmosphere. The mixture was stirred at room temperature for 2 hours, then quenched by adding water (120 mL). The organic layer was collected and the aqueous phase was extracted with DCM (3×100 mL). The combined organics were washed with brine, dried over $Na_2SO_4$, filtered and concentrated under reduced pressure to give a residue, which was purified by silica gel column chromatography (0%-50% ethyl acetate in petroleum ether) to afford the desired product as a colorless oil. $^1$H NMR (400 MHz, $CDCl_3$) δ 7.79 (d, J=8.2 Hz, 2H), 7.35 (d, J=8.1 Hz, 2H), 4.85 (t, J=4.2 Hz, 1H), 4.10-3.80 (m, 4H), 3.58-3.02 (m, 4H), 2.45 (s, 3H), 2.09-1.79 (m, 2H), 1.86-1.53 (m, 4H), 1.46-1.07 (m, 2H).

Step D: Preparation of tert-butyl (R)-4-((3-(1-((8-(3-(3-(1,3-dioxolan-2-yl)propoxy)propyl)-6-(1,1-dioxidothiomorpholino)-7-oxo-7,8-dihydropyrido[2,3-d]pyrimidin-4-yl)amino)ethyl)-2-fluorophenyl)difluoromethyl)piperidine-1-carboxylate (14-7). To a solution of tert-butyl (R)-4-((3-(1-((6-(1,1-dioxidothiomorpholino)-7-oxo-7,8-dihydropyrido[2,3-d]pyrimidin-4-yl)amino)ethyl)-2-fluorophenyl)difluoromethyl)piperidine-1-carboxylate (14-6) (300 mg, 1 eq., 0.46 mmol) in DMSO (5 mL) were added 14-5 (238 mg, 1.5 eq., 0.7 mmol) and $K_3PO_4$ (293 mg, 3 eq., 1.38 mmol) at room temperature. The reaction mixture was stirred for 4 hours at room temperature, then poured into water (60 mL) and extracted with ethyl acetate (3×70 mL). The combined organics were washed with brine, dried over $Na_2SO_4$, filtered and concentrated under reduced pressure to give a residue, which was purified by silica gel column chromatography (0%-10% MeOH in DCM) to afford the desired product as a white solid. ESI-MS m/z: (M+H)$^+$=823.

Step E: Preparation of (R)-4-(3-(4-((1-(3-(difluoro(piperidin-4-yl)methyl)-2-fluorophenyl)ethyl)amino)-6-(1,1-dioxidothiomorpholino)-7-oxopyrido[2,3-d]pyrimidin-8(7H)-yl)propoxy)butanal (14-8). To a solution of 14-7 (240 mg, 1 eq., 0.29 mmol) in THF (3 mL) was added HCl (2 N aqueous, 6 mL). The resulting mixture was stirred for 16 hours at room temperature, then the pH was adjusted to 7-8 with the saturated NaHCO$_3$ solution and extracted with DCM (3×40 mL). The combined organics were washed with brine, dried over Na$_2$SO$_4$, filtered and concentrated under reduced pressure to give the desired product, which was used directly in the next step without further purification. ESI-MS m/z: (M+H)$^+$=679.

Step F: Preparation of (4R)-6$^6$-(1,1-dioxidothiomorpholino)-3$^2$,2,2-trifluoro-4-methyl-6$^7$,6$^8$-dihydro-10-oxa-5-aza-6(4,8)-pyrido[2,3-d]pyrimidina-1(4,1)-piperidina-3(1,3)-benzenacyclotetradecaphan-6$^7$-one (69). To a solution of 14-8 (200 mg, 1 eq., 0.30 mmol) in 1,2-dichloroethane (100 mL) and MeOH (200 mL) was added acetic acid (10 drops). The mixture was stirred at room temperature for 0.5 hours, then NaBH$_3$CN (46 mg, 2.5 eq., 0.75 mmol) was added and the reaction mixture stirred an additional 1 hour at room temperature. The reaction mixture was concentrated in vacuo to give a residue, which was dissolved in DCM (30 mL) and treated with sat. NaHCO$_3$ (80 mL) at room temperature for 2 hours. The organic layer was collected and the aqueous layer was extracted with DCM (3×50 mL). The combined organics were dried over Na$_2$SO$_4$, filtered and concentrated under reduced pressure to give a residue, which was purified by silica gel column chromatography (MeOH in DCM 0-13%) to afford the desired product as a white solid. ESI-MS m/z: (M+H)$^+$=663.3. $^1$H NMR (400 MHz, DMSO) δ 8.26-8.16 (m, 2H), 7.58 (d, J=13.7 Hz, 2H), 7.20 (s, 2H), 5.47 (brs, 1H), 4.68-4.51 (m, 1H), 4.25-4.09 (m, 1H), 3.65 (brs, 4H), 3.28-3.21 (m, 9H), 2.94 (m, 1H), 2.68 (m, 1H), 2.15 (m, 3H), 1.84 (m, 3H), 1.66 (m, 4H), 1.50-1.30 (m, 6H), 0.66 (s, 1H).

Example 15: Synthesis of (1$^1$S, 1$^5$R,4R)-6$^6$-(1,1-dioxidotetrahydro-2H-thiopyran-4-yl)-3$^2$,2,2-trifluoro-4-methyl-6$^7$,6$^8$-dihydro-1$^8$,5-diaza-6(4,8)-pyrido[2,3-d]pyrimidina-1(3,8)-bicyclo[3.2.1]octana-3(1,3)-benzenacyclotridecaphan-6$^7$-one (145 and 113)

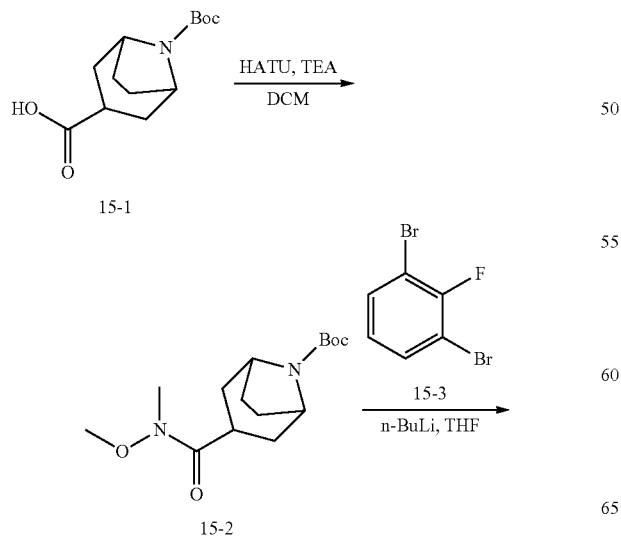

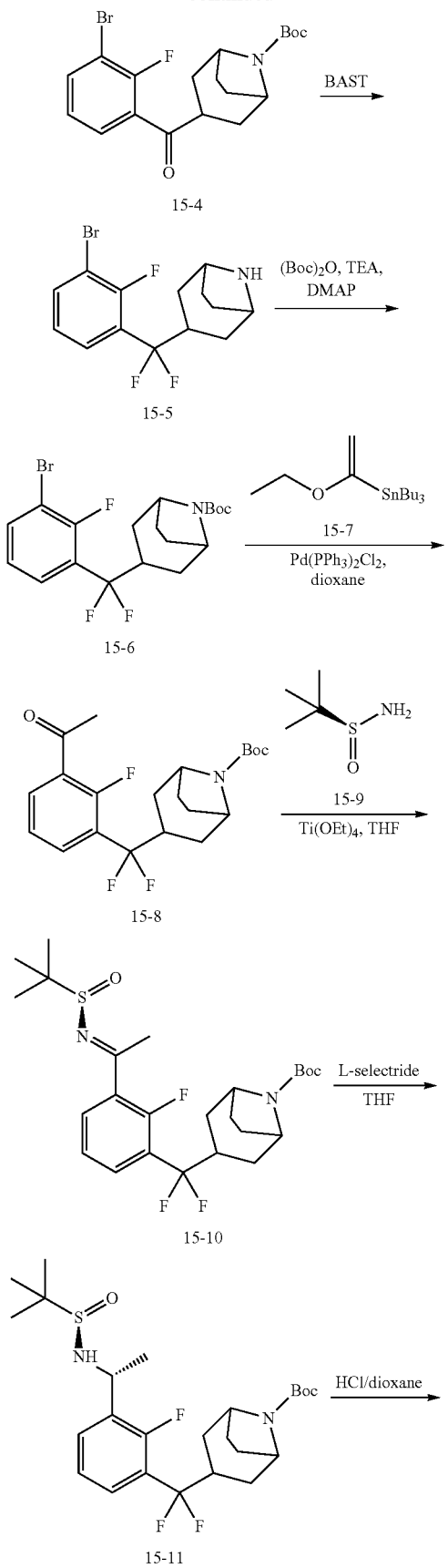

-continued

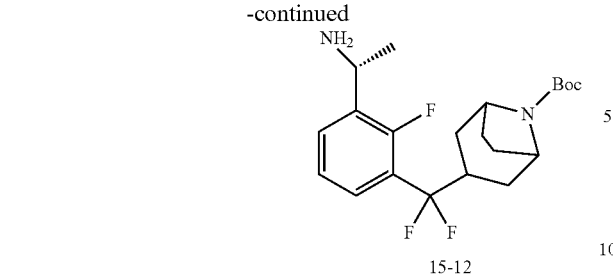

15-12

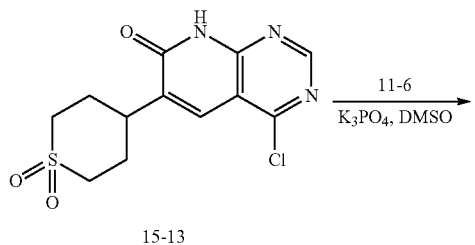

15-13

11-6
———————→
K₃PO₄, DMSO

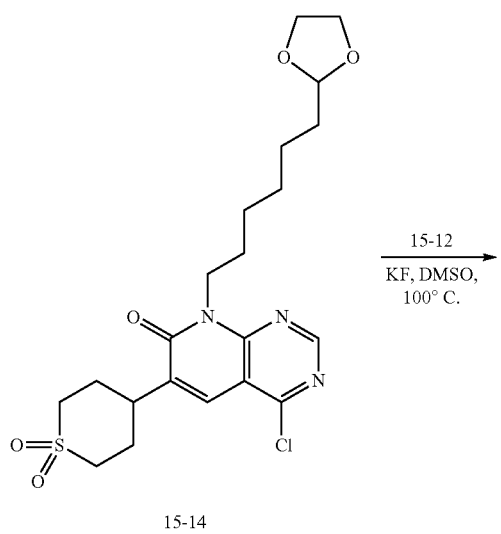

15-14

15-12
———————→
KF, DMSO,
100° C.

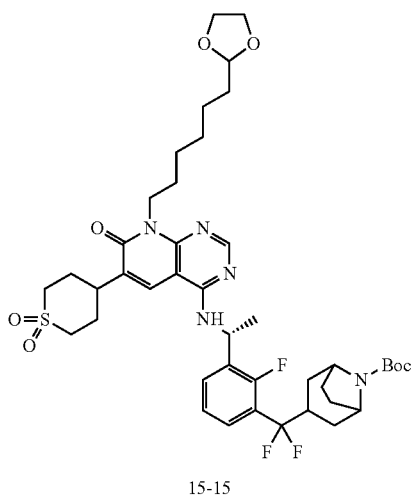

15-15

1. 2N HCl, THF
2. NaBH₃CN
———————→

-continued

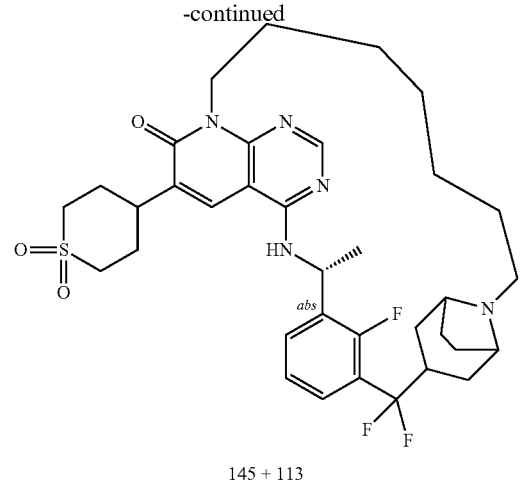

145 + 113

Step A: Preparation of tert-butyl 3-(methoxy(methyl)carbamoyl)-8-azabicyclo[3.2.1]octane-8-carboxylate (15-2). To a stirring solution of 8-(tert-butoxycarbonyl)-8-azabicyclo[3.2.1]octane-3-carboxylic acid (15-1) (5 g, 1.0 eq., 19.61 mmol) in 100 mL DCM were added HATU (11.2 g, 1.5 eq., 29.41 mmol) and triethylamine (6 g, 3.0 eq., 58.02 mmol). The reaction mixture was stirred for 2 hours at room temperature, then quenched with water and extracted with DCM (3×100 mL). The combined organics were dried over Na₂SO₄, filtered and concentrated under reduced pressure to give a residue, which was purified by silica gel column chromatography to give the desired product. ESI-MS m/z: (M+H)⁺=299.3.

Step B: Preparation of tert-butyl 3-(3-bromo-2-fluorobenzoyl)-8-azabicyclo[3.2.1]octane-8-carboxylate (15-4). To a stirring solution of 1,3-dibromo-2-fluorobenzene (15-3) (2.9 g, 1.1 eq., 11.07 mmol) in THF (80 mL) was added n-BuLi (2.5 M in hexane, 4.8 mL, 1.2 eq., 1.21 mmol) dropwise at −78° C. The reaction mixture was stirred for 1 hour at −78° C. under nitrogen, then a solution of 15-2 (3 g, 1.0 eq., 1.68 mmol) in THF (20 mL) was added. The resulting mixture was stirred for 1 hour at −78° C. under nitrogen, then quenched with saturated NH₄Cl solution. The mixture was extracted with DCM (3×100 mL). The combined organics were washed with brine, dried over Na₂SO₄, filtered and concentrated under reduced pressure to give a residue, which was purified by silica gel column chromatography to afford the desired product. ESI-MS m/z: (M+H)⁺=412.

Step C: Preparation of 3-((3-bromo-2-fluorophenyl)difluoromethyl)-8-azabicyclo[3.2.1]octane (15-5). A solution of 15-4 (1.6 g, 1.0 eq., 3.89 mmol) in BAST (20 mL) was stirred at 35° C. for 16 hours. The solution was cooled to room temperature, quenched with saturated NaHCO₃ solution at 0° C., and extracted with ethyl acetate (3×100 mL). The combined organics were washed with brine, dried over Na₂SO₄, filtered and concentrated under reduced pressure to give the desired product, which was used directly in the next step without further purification. ESI-MS m/z: (M+H)⁺= 334.8.

Step D: Preparation of tert-butyl 3-((3-bromo-2-fluorophenyl)difluoromethyl)-8-azabicyclo[3.2.1]octane-8-carboxylate (15-6). To a stirred solution of 15-5 (600 mg, 1.0 eq., 1.80 mmol) in DCM (20 mL) were added (Boc)₂O (590 mg, 1.5 eq., 2.70 mmol), triethyl amine (546 mg, 3.0 eq., 5.41 mmol) and DMAP (22 mg, 0.1 eq., 0.18 mmol). The reaction mixture was stirred for 1 hour at room temperature, then quenched by adding water and extracted with DCM (3×100 mL). The combined organics were washed with brine, dried over Na$_2$SO$_4$, filtered and concentrated under reduced pressure to give a residue, which was purified by silica gel column chromatography to give the desired product. ESI-MS m/z: (M+H)$^+$=434.8.

Step E: Preparation of tert-butyl 3-((3-acetyl-2-fluorophenyl)difluoromethyl)-8-azabicyclo[3.2.1]octane-8-carboxylate (15-8). To a stirred solution of 15-6 (460 mg, 1.0 eq., 0.12 mmol) in dioxane (20 mL) were added tributyl (1-ethoxyvinyl)stannane (15-7) (767 mg, 1.5 eq., 2.13 mmol) and Pd(PPh$_3$)$_2$Cl$_2$ (75 mg, 0.1 eq., 0.11 mmol). The reaction mixture was stirred for 16 hours at 80° C. under nitrogen, then was quenched with KF solution and extracted with ethyl acetate (3×100 mL). The combined organics were washed with brine, dried over Na$_2$SO$_4$, filtered and concentrated under reduced pressure to give a residue, which was dissolved in THF (1 mL) and treated with HCl (1N aq. 1 mL). The resulting mixture was stirred for 1 hour at room temperature, then quenched with saturated NaHCO$_3$ solution and extracted with DCM (3×30 mL). The combined organics were washed with brine, dried over Na$_2$SO$_4$, filtered and concentrated under reduced pressure to give a residue, which was purified by silica gel column chromatography to give the desired product. ESI-MS m/z: (M−C$_4$H$_8$+H)$^+$=342.1.

Step F: Preparation of tert-butyl 3-((3-((E)-1-(((R)-tert-butylsulfinyl)imino)ethyl)-2-fluorophenyl)difluoromethyl)-8-azabicyclo[3.2.1]-octane-8-carboxylate (15-10). To a stirred solution of 15-8 (140 mg, 1.0 eq., 0.35 mmol) in DCM (5 mL) was added (S)-2-methylpropane-2-sulfinamide (15-9) (64 mg, 1.5 eq., 0.53 mmol) and Ti(OEt)$_4$ (241 mg, 3.0 eq., 1.06 mmol). The reaction mixture was stirred for 16 hours at 80° C. under nitrogen, then cooled to room temperature, quenched with water, and extracted with ethyl acetate (3×30 mL). The combined organics were washed with brine, dried over Na$_2$SO$_4$, filtered and concentrated under reduced pressure to give a residue, which was purified by silica gel column chromatography to give the desired product. ESI-MS m/z: (M+H)$^+$=501.3.

Step G: Preparation of tert-butyl 3-((3-((R)-1-(((R)-tert-butylsulfinyl)amino)ethyl)-2-fluorophenyl)difluoromethyl)-8-azabicyclo[3.2.1]octane-8-carboxylate (15-11). To a stirring solution of 15-10 (100 mg, 1.0 eq., 0.2 mmol) in THF (5 mL) was added L-selectride (1M, 0.4 ml, 2.0 eq., 0.4 mmol) dropwise at −78° C. The reaction mixture was stirred for 1 hour at −78° C. under nitrogen, then quenched with saturated NH$_4$Cl solution and extracted with DCM (3×10 mL). The combined organics were washed with brine, dried over Na$_2$SO$_4$, filtered and concentrated under reduced pressure to give a residue, which was purified by silica gel column chromatography to give the desired product. ESI-MS m/z: (M+H)$^+$=503.2.

Step H: Preparation of tert-butyl 3-((3-((R)-1-aminoethyl)-2-fluorophenyl)difluoromethyl)-8-azabicyclo[3.2.1]octane-8-carboxylate (15-12). To a stirred solution of 15-11 (60 mg, 1.0 eq., 0.12 mmol) in MeOH (0.96 mL) was added HCl (1 N, 0.24 mL). The resulting mixture was stirred for 1 hour at room temperature, then treated with sat. aqueous NaHCO$_3$ and extracted with DCM (3×10 mL). The combined organics were washed with brine, dried over Na$_2$SO$_4$, filtered and concentrated under reduced pressure to give a residue, which was purified by silica gel column chromatography to give the desired product. ESI-MS m/z: (M+H)$^+$=399.2.

Step I: Preparation of 8-(6-(1,3-dioxolan-2-yl)hexyl)-4-chloro-6-(1,1-dioxidotetrahydro-2H-thiopyran-4-yl)pyrido[2,3-d]pyrimidin-7(8H)-one (15-14). To a stirred solution of 4-chloro-6-(1,1-dioxidotetrahydro-2H-thiopyran-4-yl)pyrido[2,3-d]pyrimidin-7(8H)-one (15-13) (200 mg, 0.64 mmol) and 11-6 (181 mg, 0.77 mmol) in DMSO (5 mL) was added K$_3$PO$_4$(407 mg, 1.92 mmol) and the resulting mixture was stirred at room temperature for 2 hours. The mixture was then poured into water and extracted with ethyl acetate (3×50 mL). The combined organics were washed with brine, dried over Na$_2$SO$_4$, filtered and concentrated under reduced pressure to give a residue, which was purified by silica gel column to give the desired product. ESI-MS m/z: (M+H)$^+$=470.

Step J: Preparation of tert-butyl 3-((3-((R)-1-((8-(6-(1,3-dioxolan-2-yl)hexyl)-6-(1,1-dioxidotetrahydro-2H-thiopyran-4-yl)-7-oxo-7,8-dihydropyrido[2,3-d]pyrimidin-4-yl)amino)ethyl)-2-fluorophenyl)difluoromethyl)-8-azabicyclo[3.2.1]octane-8-carboxylate (15-15). To a stirred solution of 15-14 (65 mg, 0.14 mmol) and 15-12 (50 mg, 0.13 mmol) in dry DMSO (5 mL) was added KF (22 mg, 0.38 mmol) and the resulting mixture was stirred at 100° C. for 2 hours under nitrogen. The reaction mixture was cooled to room temperature and poured into water (20 mL), then extracted with ethyl acetate (3×20 mL). The combined organics were washed with brine, dried over Na$_2$SO$_4$, filtered and concentrated under reduced pressure to give a residue, which was purified by silica gel column to obtain the desired product. ESI-MS m/z: (M+Na)$^+$=853.8.

Step K: Preparation of (11S,15R,4R)-6$^6$-(1,1-dioxidotetrahydro-2H-thiopyran-4-yl)-3$2$,2,2-trifluoro-4-methyl-6$^7$,6$^8$-dihydro-1$^8$,5-diaza-6(4,8)-pyrido[2,3-d]pyrimidina-1(3,8)-bicyclo[3.2.1]octana-3(1,3)-benzenacyclotridecaphan-6$^7$-one (5 and 113). To a stirred solution of 15-15 (65 mg) in THF (2 mL) was added HCl (2N, 4 mL) and the resulting mixture was stirred at room temperature for 20 hours. The mixture was diluted with THF (5 mL) and treated with aqueous sat. NaHCO$_3$, then extracted with DCM (3×20 mL). The combined organics were washed with brine, dried over Na$_2$SO$_4$, filtered and concentrated under reduced pressure to give the desired product, which was used directly in next step without further purification.

To a stirred solution of 7-(4-(((1R)-1-(3-((8-azabicyclo[3.2.1]octan-3-yl)difluoromethyl)-2-fluorophenyl)ethyl)amino)-6-(1,1-dioxidotetrahydro-2H-thiopyran-4-yl)-7-oxopyrido[2,3-d]pyrimidin-8(7H)-yl)heptanal (30 mg, 0.044 mmol) in MeOH and dichloroethane (methanol:dichloroethane=24 mL:12 mL) was added acetic acid (2 drops). The resulting mixture was stirred at room temperature for 30 min, then NaBH$_3$CN (8.3 mg, 0.13 mmol) was added and the resulting mixture was stirred at room temperature for 1 hour. The mixture was concentrated under reduced pressure to give a residue, which was purified by prep-TLC to give two products. 145 (less polar) ESI-MS m/z: (M+H)$^+$=672.3. $^1$H NMR (400 MHz, DMSO) δ 8.28 (brs, 1H); 8.19 (s, 1H); 8.06 (s, 1H); 7.74 (brs, 1H); 7.31 (brs, 1H); 7.20 (brs, 1H); 5.68 (brs, 1H); 5.33 (brs, 1H); 4.75 (brs, 1H); 4.04 (d, J=11.3 Hz, 1H); 3.35 (m, 4H); 3.16 (m, 4H); 2.13 (m, 4H); 1.82 (m, 3H); 1.65 (m, 5H); 1.49 (m, 4H); 1.35 (m, 4H); 1.09 (m, 2H); 0.85 (m, 4H); and 113 (polar) ESI-MS m/z: (M+H)$^+$=672.3. $^1$H NMR (400 MHz, DMSO) δ 8.26 (s, 1H), 8.19 (s, 1H), 8.06 (s, 1H), 7.68 (m, 1H); 7.29 (m, 1H), 7.19 (m, 1H), 5.68-5.51 (m, 1H), 4.75 (m, 1H), 4.12-3.95 (m, 1H), 3.37 (m, 4H), 3.17 (m, 4H), 2.15 (m, 5H), 1.88-1.78 (m, 3H), 1.64 (m, 4H), 1.54-1.42 (m, 6H), 1.36-1.33 (m, 2H), 1.03 (s, 2H), 0.89-0.80 (m, 5H).

Example 16: Synthesis of (3R)-1⁶-(1,1-dioxidotetrahydro-2H-thiopyran-4-yl)-5,5-difluoro-3-methyl-1⁷,1⁸-dihydro-12-oxa-2-aza-1(4,8)-pyrido[2,3-d]pyrimidina-7(3,1)-azetidina-4(1,3)-benzenacyclopentadecaphan-1⁷-one (176)
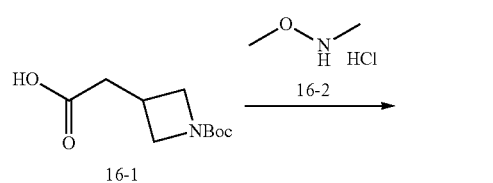
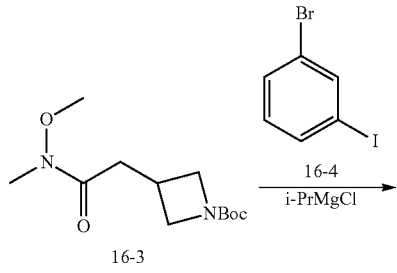
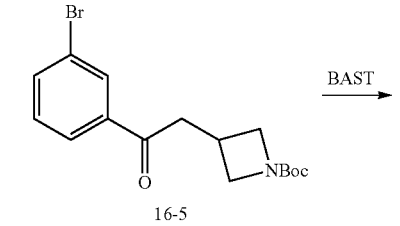
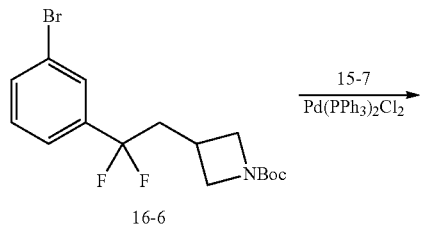
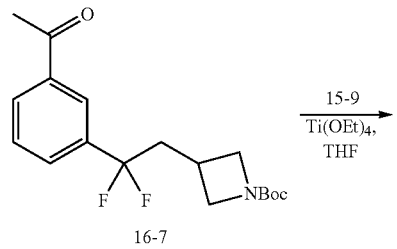
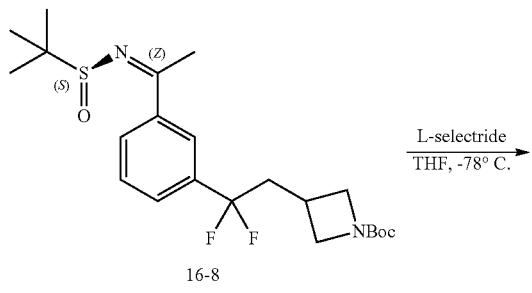
-continued
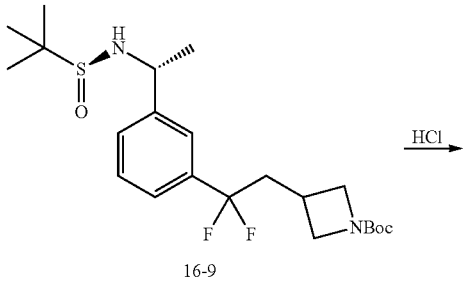
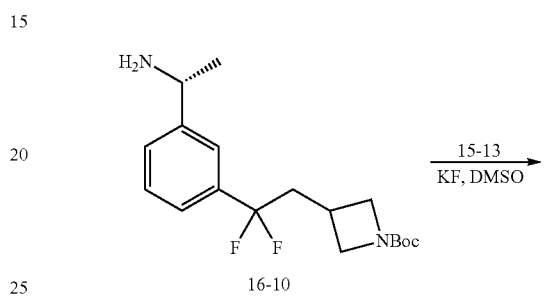
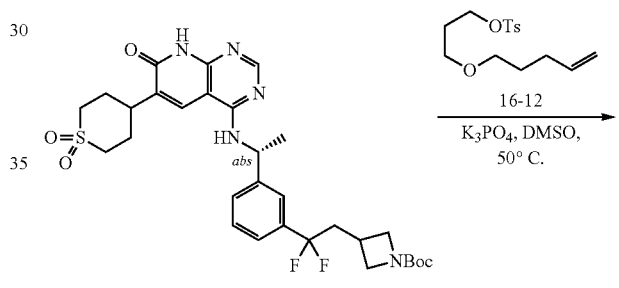
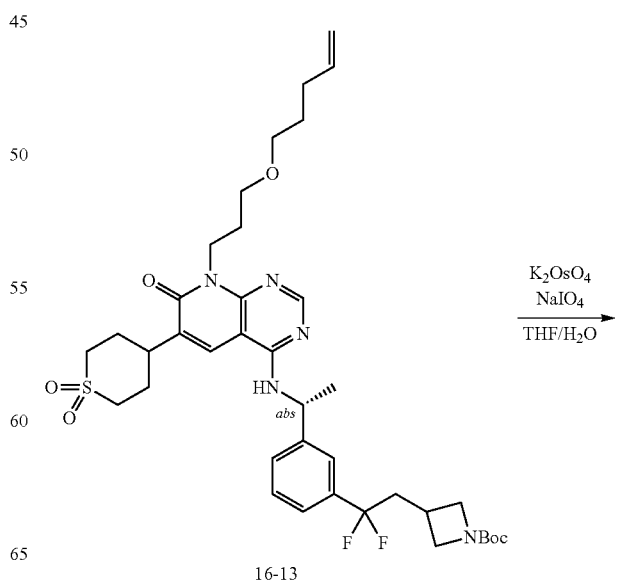

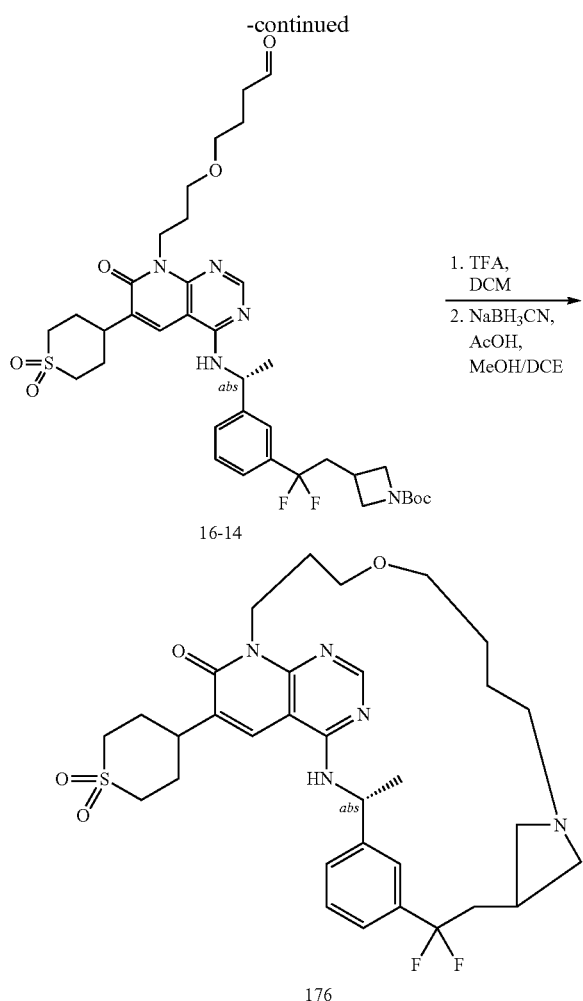

Step A: Preparation of tert-butyl 3-(2-(methoxy(methyl)amino)-2-oxoethyl)azetidine-1-carboxylate (16-3). To a solution of 2-(1-(tert-butoxycarbonyl)azetidin-3-yl)acetic acid (16-1) (10 g, 1.0 eq., 46.5 mmol), N,O-dimethylhydroxylamine hydrochloride (16-2) (5.47 g, 1.2 eq., 55.8 mmol) and DIEA (18.0 g, 3.0 eq., 139.5 mmol) in DCM (100 mL) was added drop-wise T$_3$P (35.5 g, 1.2 eq., 55.8 mmol, 50% in ethyl acetate) at 0° C., and the resulting solution was stirred at room temperature for 12 hours. The reaction mixture was quenched by addition water, the organic phase was separated, and the aqueous phase was extracted with DCM (2×200 mL). The combined organics were washed with brine, dried over Na$_2$SO$_4$, filtered and concentrated under reduced pressure to give a residue, which was purified by silica gel chromatography (petroleum ether/ethyl acetate=3/1) to provide the desired product as a colorless oil. $^1$H NMR (400 MHz, DMSO) δ 3.92 (s, 2H), 3.66 (s, 3H), 3.50 (s, 2H), 3.07 (s, 3H), 2.81-2.66 (m, 3H), 1.37 (s, 9H).

Step B: Preparation of tert-butyl 3-(2-(3-bromophenyl)-2-oxoethyl)azetidine-1-carboxylate (16-5). To a solution of 1-bromo-3-iodobenzene (16-4) (11.52 g, 1.05 eq., 40.7 mmol) in dry THF (120 mL) was added drop-wise i-PrMgCl (40.7 mL, 1.05 eq., 40.7 mmol, 2M) at −78° C. under nitrogen atmosphere. The reaction mixture was allowed to warm to 0° C. and stirred for 2 hours, then cooled to −78° C. and 16-3 (10 g, 1.0 eq., 38.76 mmol) in dry THF (50 mL) at −78° C. added drop-wise while maintaining the reaction temperature below −55° C. The reaction mixture was allowed to warm to room temperature and stirred for 12 hours. The reaction was quenched with saturated aqueous NH$_4$Cl and extracted with ethyl acetate (3×80 mL). The combined organics were washed with brine, dried over Na$_2$SO$_4$, filtered and concentrated under reduced pressure to give a residue, which was purified by flash silica gel column chromatography (petroleum ether:ethyl acetate=10:1) to give the desired product as a yellow oil. ESI-MS m/z: (M+Na)$^+$=376.0. $^1$H NMR (400 MHz, DMSO) δ 8.09 (t, J=1.7 Hz, 1H), 8.03-7.90 (m, 1H), 7.89-7.78 (m, 1H), 7.58-7.43 (m, 1H), 4.08-3.91 (m, 2H), 3.61-3.50 (m, 2H), 3.45 (d, J=7.4 Hz, 2H), 2.97-2.85 (m, 1H), 1.37 (s, 9H).

Step C: Preparation of tert-butyl 3-(2-(3-bromophenyl)-2,2-difluoroethyl)azetidine-1-carboxylate (16-6). A solution of 16-5 (3.8 g, 1.0 eq., 10.76 mmol) in bis(2-methoxyethyl)aminosulfurtrifluoride (11.89 g, 5.0 eq., 53.8 mmol) was stirred at 50° C. for 56 hours under nitrogen atmosphere, then cooled to room temperature and quenched with saturated aqueous NaHCO$_3$ (80 mL) at 0° C. The mixture was extracted with ethyl acetate (3×50 mL) and the combined organics were washed with brine, dried over Na$_2$SO$_4$, filtered and concentrated under reduced pressure to give a residue, which was purified by flash silica gel column chromatography (petroleum ether:ethyl acetate=10:1) to give the desired product as a yellow oil. ESI-MS m/z: (M+H−tBu)$^+$=320.0. $^1$H NMR (400 MHz, DMSO) δ 7.88-7.66 (m, 2H), 7.59-7.39 (m, 2H), 3.84 (s, 2H), 3.51 (s, 2H), 2.80-2.64 (m, 1H), 2.64-2.53 (m, 2H), 1.36 (s, 9H).

Step D: Preparation of tert-butyl 3-(2-(3-acetylphenyl)-2,2-difluoroethyl)azetidine-1-carboxylate (16-7). A solution of 16-6 (2.6 g, 1.0 eq., 6.93 mmol), 15-7 (3.8 g, 1.5 eq., 10.4 mmol) and Pd(PPh$_3$)$_2$Cl$_2$ (487 mg, 0.1 eq., 0.693 mmol) in 1,4-dioxane (30 mL) was stirred at 100° C. for 12 hours under nitrogen atmosphere. The mixture was cooled to room temperature and quenched with saturated aqueous KF (80 mL). The resulting solution was stirred for 1 hour, then filtered and the filter cake washed with ethyl acetate. The filtrate was extracted with ethyl acetate (3×50 mL). The combined organic phase was concentrated to afford a residue, which was dissolved in THF (50 mL) and HCl (1M). The resulting mixture was stirred at room temperature for 1 hour, then treated with saturated aqueous NaHCO$_3$. The mixture was extracted with ethyl acetate (3×50 mL) and the combined organic layers were dried over Na$_2$SO$_4$, filtered, and concentrated to give a residue, which was purified by flash silica gel column chromatography (0%-20% ethyl acetate in petroleum ether) to afford the desired product as a light-yellow oil. ESI-MS m/z: (M+Na)$^+$=362.2. 1H NMR (400 MHz, DMSO) δ 8.10 (d, J=7.7 Hz, 1H), 8.02 (s, 1H), 7.78 (d, J=7.8 Hz, 1H), 7.66 (t, J=7.7 Hz, 1H), 3.84 (s, 2H), 3.52 (s, 2H), 2.82-2.67 (m, 1H), 2.64 (s, 3H), 2.62-2.52 (m, 2H), 1.35 (s, 9H).

Step E: Preparation of tert-butyl (S,Z)-3-(2-(3-(1-((tert-butylsulfinyl)imino)ethyl)phenyl)-2,2-difluoroethyl)azetidine-1-carboxylate (16-8). A solution of 16-7 (2.2 g, 1.0 eq., 6.49 mmol), 15-9 (1.02 g, 1.3 eq., 8.44 mmol) and tetraethyl titanate (4.44 g, 3.0 eq. 19.47 mmol) in THF (20 mL) was stirred at 80° C. for 16 hours under nitrogen. The resulting mixture was cooled to room temperature and diluted with ethyl acetate (50 mL) and water (100 mL). The resulting solution was stirred for 1 hour and filtered through celite. The filter cake was washed with ethyl acetate and the aqueous phase was extracted with ethyl acetate (3×50 mL). The combined organics were washed with brine, dried over Na$_2$SO$_4$, filtered and concentrated under reduced pressure to give a residue, which was purified by com-flash column (0%~40% ethyl acetate in petroleum ether) to give the desired product as a yellow oil. ESI-MS m/z: (M+H)+=443.3. ¹H NMR (400 MHz, DMSO) δ 8.03 (d, J=7.7 Hz, 1H), 7.97 (s, 1H), 7.70 (d, J=7.8 Hz, 1H), 7.63 (t, J=7.7 Hz, 1H), 3.84 (s, 2H), 3.51 (s, 2H), 2.77 (s, 3H), 2.75-2.67 (m, 1H), 2.58 (td, J=16.8, 7.3 Hz, 2H), 1.35 (s, 9H), 1.23 (s, 9H).

Step F: Preparation of tert-butyl 3-(2-(3-((R)-1-(((S)-tert-butylsulfinyl)amino)ethyl)phenyl)-2,2-difluoroethyl)azetidine-1-carboxylate (16-9). To a solution of 16-8 (2.28 g, 1.0 eq., 5.16 mmol) in dry THF (20 mL) was added dropwise L-selectride (10.32 mL, 2.0 eq., 10.32 mmol, 1M) at −78° C. under nitrogen atmosphere. The resulting solution was stirred for 1 hour, then quenched by addition of saturated aqueous NH₄Cl and extracted with ethyl acetate (3×50 mL). The combined organics were washed with brine, dried over Na₂SO₄, filtered and concentrated under reduced pressure to give a residue, which was purified by flash silica gel column chromatography (0-50% ethyl acetate in petroleum ether) to give the desired product as a light-yellow oil. ESI-MS m/z: (M+H)+=445.4. ¹H NMR (400 MHz, DMSO) δ 7.59-7.40 (m, 3H), 7.36 (d, J=7.3 Hz, 1H), 5.43 (d, J=5.1 Hz, 1H), 4.57-4.37 (m, 1H), 3.79 (s, 2H), 3.44 (s, 2H), 2.72-2.60 (m, 1H), 2.58-2.51 (m, 2H), 1.46 (d, J=6.7 Hz, 3H), 1.34 (s, 9H), 1.11 (s, 9H).

Step G: Preparation of tert-butyl (R)-3-(2-(3-(1-aminoethyl)phenyl)-2,2-difluoroethyl)azetidine-1-carboxylate (16-10). To a stirred solution of 16-9 (1.88 g, 4.23 mmol) in MeOH (32 mL) was added HCl/dioxane (8 mL, 1.9 eq., 8.037 mmol, 1M) at 0° C. The resulting mixture was stirred for 2 hours, then treated with sat. aqueous NaHCO₃ and extracted with ethyl acetate (3×50 mL). The combined organics were washed with brine, dried over Na₂SO₄, filtered and concentrated under reduced pressure to give the desired product as a yellow oil, which was used in the next step without further purification. ESI-MS m/z: (M+H)+=341.3.

Step H: Preparation of tert-butyl (R)-3-(2-(3-(1-((6-(1,1-dioxidotetrahydro-2H-thiopyran-4-yl)-7-oxo-7,8-dihydropyrido[2,3-d]pyrimidin-4-yl)amino)ethyl)phenyl)-2,2-difluoroethyl)azetidine-1-carboxylate (16-11). To a solution of 15-13 (300 mg, 1 eq., 0.95 mmol) in DMSO (10 mL) at 25° C. were added 16-10 (358 mg, 1.1 eq., 1.05 mmol) and KF (444.6 mg, 6.0 eq., 5.70 mmol). The mixture was stirred at 100° C. for 2 hours, then cooled to room temperature, poured into water and extracted with ethyl acetate (3×50 mL). The combined organics were washed with brine, dried over Na₂SO₄, filtered and concentrated under reduced pressure to give a residue, which was purified by silica gel column chromatography to afford the desired product. ESI-MS m/z: (M+H)+=618.3.

Step I: Preparation of tert-butyl (R)-3-(2-(3-(1-((6-(1,1-dioxidotetrahydro-2H-thiopyran-4-yl)-7-oxo-8-(3-(pent-4-en-1-yloxy)propyl)-7,8-dihydropyrido[2,3-d]pyrimidin-4-yl)amino)ethyl)phenyl)-2,2-difluoroethyl)azetidine-1-carboxylate (16-13). To a stirring solution of 16-11 (450 mg, 0.73 mmol) in DMSO (20 mL) were added 3-(pent-4-en-1-yloxy)propyl 4-methylbenzenesulfonate (16-12) (260 mg, 0.87 mmol) and K₃PO₄ (462 mg, 2.18 mmol). The resulting mixture was stirred at 30° C. for 2 hours, then cooled to room temperature, quenched with water, and extracted with ethyl acetate (20 mL×3). The combined organics were washed with brine, dried over Na₂SO₄, filtered and concentrated under reduced pressure to give a residue, which was purified by com-flash chromatography on a silica gel column to give the desired product. ESI-MS m/z: (M+H)+=744.8.

Step J: Preparation of tert-butyl (R)-3-(2-(3-(1-((6-(1,1-dioxidotetrahydro-2H-thiopyran-4-yl)-7-oxo-8-(3-(4-oxobutoxy)propyl)-7,8-dihydropyrido[2,3-d]pyrimidin-4-yl)amino)ethyl)phenyl)-2,2-difluoroethyl)azetidine-1-carboxylate (16-14). To a stirred solution of 16-13 (310 mg, 0.42 mmol) in THF and H₂O (40 mL) was added K₂OsO₄ (3.07 mg, 0.0083 mmol) at 0° C. The resulting mixture was stirred for 5 minutes, then NaIO₄ (451 mg, 2.09 mmol) was added and the reaction stirred at 25° C. for 2 hours. The reaction mixture was treated with Na₂S₂O₃ solution and extracted with ethyl acetate (20 ml×3). The combined organics were washed with brine, dried over Na₂SO₄, filtered and concentrated under reduced pressure to give a residue, which was purified by com-flash chromatography on a silica gel column to give the desired product. ESI-MS m/z: (M+H)+=746.8.

Step K: Preparation of (3R)-1⁶-(1,1-dioxidotetrahydro-2H-thiopyran-4-yl)-5,5-difluoro-3-methyl-1⁷,1⁸-dihydro-12-oxa-2-aza-1(4,8)-pyrido[2,3-d]pyrimidina-7(3,1)-azetidina-4(1,3)-benzenacyclopentadecaphan-1⁷-one (176). To a stirred solution of 16-14 (240 mg, 0.32 mmol) in DCM (20 mL) was added TFA (5 mL). The resulting mixture was stirred at 25° C. for 2 hours, then concentrated in vacuo to give the free amine, which was used in next step directly without further purification. ESI-MS m/z: (M+H)+=646.8.

To a stirred solution of (R)-4-(3-(4-((1-(3-(2-(azetidin-3-yl)-1,1-difluoroethyl)phenyl)ethyl)amino)-6-(1,1-dioxidotetrahydro-2H-thiopyran-4-yl)-7-oxopyrido[2,3-d]pyrimidin-8(7H)-yl)propoxy)butanal (165 mg, 0.26 mmol) in methanol and dichloroethane (150 mL) was added AcOH (2 drops) and NaBH₃CN (48.4 mg, 0.77 mmol). The resulting mixture was stirred at 25° C. for 2 hours, then treated with water and extracted with DCM (150 ml×3). The combined organics were washed with brine, dried over Na₂SO₄, filtered and concentrated under reduced pressure to give a residue, which was purified by com-flash chromatography on a silica gel column to give the desired product. ESI-MS m/z: (M+H)+=630.4. ¹H NMR (400 MHz, DMSO) δ 8.36 (s, 1H), 8.17 (s, 1H), 7.58 (d, J=6.7 Hz, 2H), 7.45 (t, J=7.9 Hz, 1H), 7.33 (d, J=7.7 Hz, 1H), 5.49 (q, J=6.9 Hz, 1H), 4.71 (dd, J=12.8, 6.7 Hz, 1H), 4.28-4.09 (m, 1H), 3.37 (m, 3H), 3.30-3.23 (m, 1H), 3.22-3.11 (m, 3H), 2.97 (t, J=6.0 Hz, 2H), 2.89 (brs, 1H), 2.80 (brs, 1H), 2.46-2.30 (m, 3H), 2.28-2.09 (m, 6H), 2.03 (t, J=10.9 Hz, 2H), 1.93 (m, 2H), 1.61 (d, J=7.1 Hz, 3H), 1.23 (s, 1H), 1.13-0.93 (m, 2H), 0.74-0.67 (m, 2H).

Example 17: Synthesis of (4R)-3²,2,2-trifluoro-4-methyl-6⁶-(4-(methylsulfonyl)piperazin-1-yl)-6⁷,6⁸-dihydro-5-aza-6(4,8)-pyrido[2,3-d]pyrimidina-1(4,1)-piperidina-3(1,3)-benzenacyclotride-caphan-6⁷-one (180)

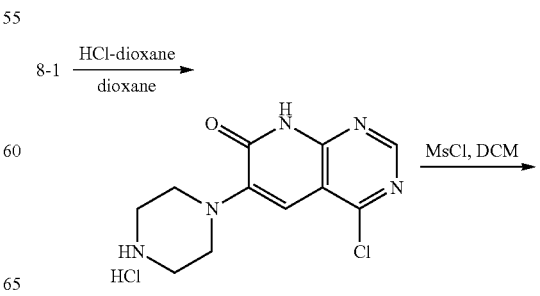

17-1

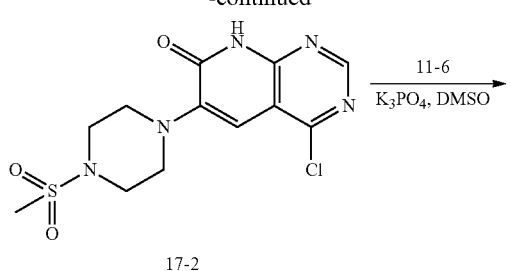

17-2

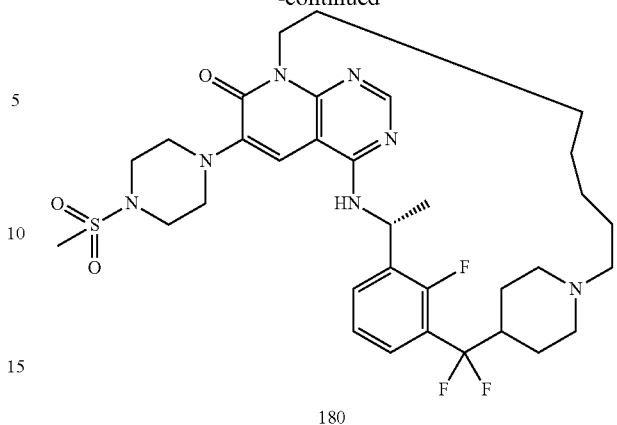

180

Step A: Preparation of 4-chloro-6-(piperazin-1-yl)pyrido[2,3-d]pyrimidin-7(8H)-one (17-1). To a solution of 8-1 (1 g, 1.0 eq., 2.73 mmol) in dioxane (10 mL) was added HCl (4N in dioxane, 10 mL). The mixture was stirred for 2 hours at room temperature, then concentrated in vacuo to obtain the desired product as a hydrogen chloride salt (726 mg, crude yellow solid) which was used directly in the next step without further purification. ESI-MS m/z: (M+H)$^+$=266.1.

Step B: Preparation of 4-chloro-6-(4-(methylsulfonyl)piperazin-1-yl)pyrido[2,3-d]pyrimidin-7(8H)-one (17-2). To a stirred solution of 17-1 (726 mg, 1.0 eq., 2.73 mmol) and triethylamine (831 mg, 3.0 eq., 8.22 mmol) in DCM (8 mL) was added methanesulfonyl chloride (345 mg, 1.1 eq., 3.01 mmol) at 0'° C. The mixture was stirred for 5 hours at room temperature, then diluted with DCM (100 mL) and water (100 mL). The organic layer was separated and the aqueous layer was extracted with DCM (100 mL×2). The combined organics were washed with brine, dried over Na$_2$SO$_4$, filtered and concentrated under reduced pressure to give a residue, which was purified by silica gel column chromatography (0%-10% MeOH in DCM) to obtain the desired product as a yellow solid. ESI-MS m/z: (M+H)$^+$=344.0.

Step C: Preparation of 8-(6-(1,3-dioxolan-2-yl)hexyl)-4-chloro-6-(4-(methylsulfonyl)piperazin-1-yl)pyrido[2,3-d]pyrimidin-7(8H)-one (17-3). To a solution of 17-2 (450 mg, 1.0 eq., 1.31 mmol) in DMSO (5 mL) was added 11-6 (372 mg, 1.2 eq., 1.57 mmol) and K$_3$PO$_4$ (827 mg, 3 eq., 3.90 mmol). The mixture was stirred for 4 hours at room temperature, then poured into water (100 mL) and extracted with ethyl acetate (80 mL×3). The combined organics were washed with brine, dried over Na$_2$SO$_4$, filtered and concentrated under reduced pressure to give a residue, which was purified by silica gel column chromatography (0%-50% ethyl acetate in petroleum ether) to obtain the desired product as a white solid. ESI-MS m/z: (M+Na)$^+$=522.1.

Step D: Preparation of tert-butyl (R)-4-((3-(1-((8-(6-(1,3-dioxolan-2-yl)hexyl)-6-(4-(methylsulfonyl)piperazin-1-yl)-7-oxo-7,8-dihydropyrido[2,3-d]pyrimidin-4-yl)amino)ethyl)-2-fluorophenyl)difluoromethyl)piperidine-1-carboxylate (17-4). To a solution of 17-3 (350 mg, 1.2 eq., 0.70 mmol) in DMSO (4 mL) was added 11-4 (216 mg, 1.0 eq., 0.58 mmol) and KF (204 mg, 6 eq., 3.51 mmol). The mixture was stirred for 4 hours at 100° C. under an argon atmosphere, then cooled to room temperature, poured into water (60 mL), and extracted with ethyl acetate (50 mL×3). The combined organics were washed with brine, dried over Na$_2$SO$_4$, filtered and concentrated under reduced pressure to give a residue, which was purified by silica gel column chromatography (0%-50% ethyl acetate in petroleum ether) to obtain the desired product as a yellow solid. ESI-MS m/z: (M+H)$^+$=836.3.

Step E: Preparation of (R)-7-(4-((1-(3-(difluoro(piperidin-4-yl)methyl)-2-fluorophenyl)ethyl)amino)-6-(4-(methylsulfonyl)piperazin-1-yl)-7-oxopyrido[2,3-d]pyrimidin-8(7H)-yl)heptanal (17-5). To a solution of 17-4 (400 mg, 1.0 eq., 0.48 mmol) in THF (5 mL) was added HCl (2N aqueous, 10 mL). The mixture was stirred for 16 hours at room temperature, then cooled to 0° C. and sat. NaHCO$_3$ solution added to adjust the pH to 7~8. The mixture was extracted with DCM (150 mL×5) and the combined organics were washed with brine, dried over Na$_2$SO$_4$, filtered and concentrated under reduced pressure to obtain the desired product, which was used directly in the next step without further purification. ESI-MS m/z: (M+H)$^+$=692.3.

Step F: Preparation of (4R)-32,2,2-trifluoro-4-methyl-66-(4-(methylsulfonyl)piperazin-1-yl)-67,68-dihydro-5-aza-6(4,8)-pyrido[2,3-d]pyrimidina-1(4,1)-piperidina-3(1,3)-benzenacyclotride-caphan-67-one (180). To a solution of 17-5 (300 mg) in 1,2-dichloroethane (160 mL) and MeOH (320 mL) was added HOAc (20 drops). The mixture was stirred at room temperature for 0.5 hours followed by the addition of NaBH$_3$CN (80 mg, 2.5 eq., 1.07 mmol). The resulting mixture was stirred for 0.5 hours at room temperature and concentrated in vacuo to give a residue. The residue was purified by prep-HPLC to obtain the desired product as a white solid. ESI-MS m/z: (M+H)$^+$=676.4. $^1$H NMR (400 MHz, DMSO) δ 8.11 (s, 1H), 7.68 (t, J=6.4 Hz, 1H), 7.50 (s, 1H), 7.28 (t, J=7.7 Hz, 1H), 7.20 (t, J=6.6 Hz, 1H), 5.54-5.53 (m, 1H), 4.78-4.65 (m, 1H), 4.15-4.02 (m, 1H), 3.35-3.17 (m, 8H), 2.99- 2.93 (m, 4H), 2.19-2.09 (m, 3H), 1.96-1.79 (m, 2H), 1.72-1.62 (m, 7H), 1.52-1.35 (m, 2H), 1.24-1.07 (m, 5H), 0.85-0.69 (m, 3H).

Example 18: Synthesis of (4R)-6$^6$-(1,1-dioxidotetrahydro-2H-thiopyran-4-yl)-2,2-difluoro-12-methoxy-4-methyl-6$^7$,6$^8$-dihydro-5-aza-6(4,8)-pyrido[2,3-d]pyrimidina-1(4,1)-piperidina-3(1,3)-benzenacyclotridecaphan-6$^7$-one (188)

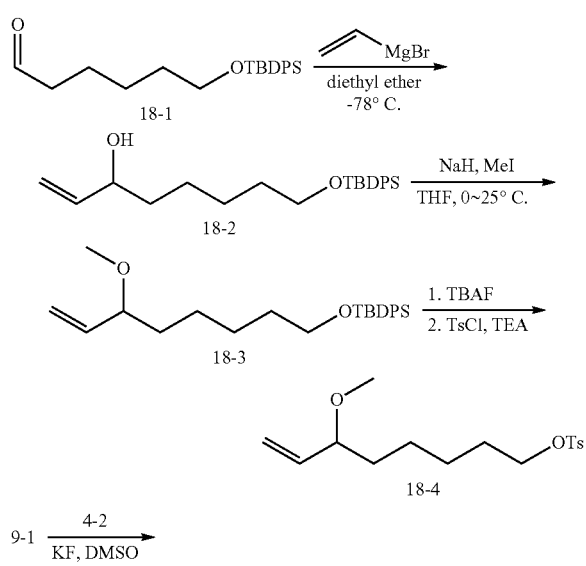

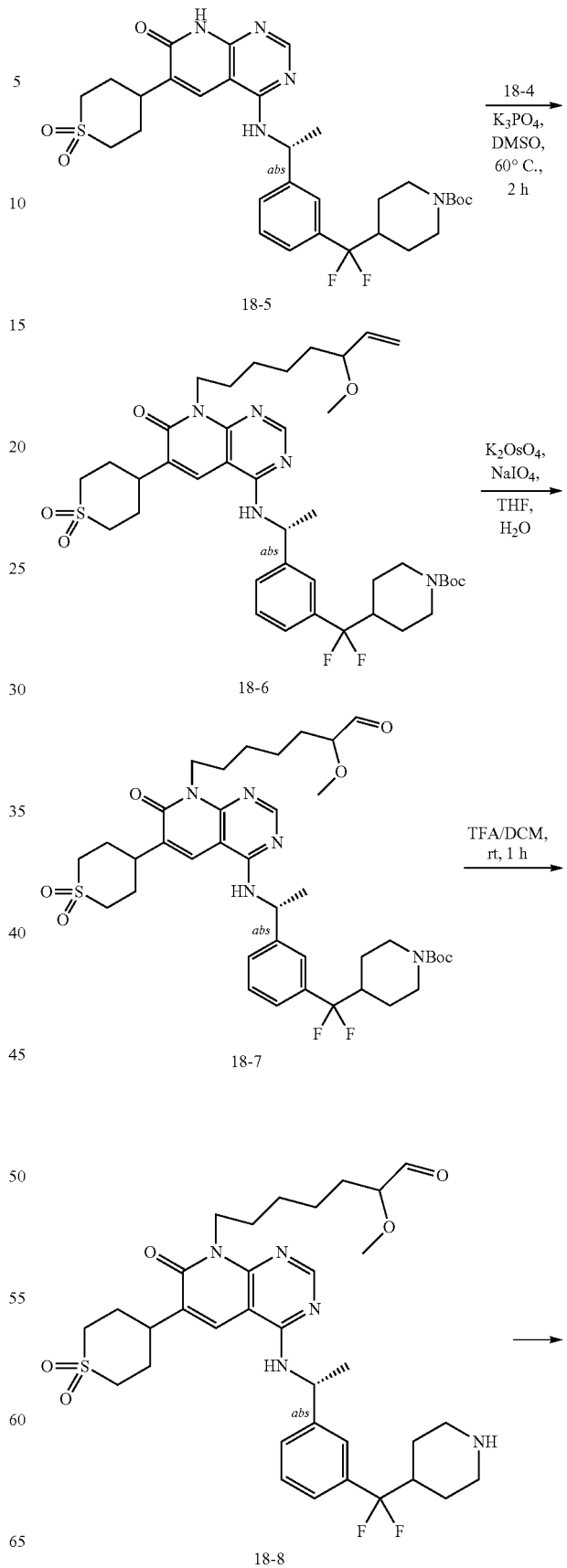

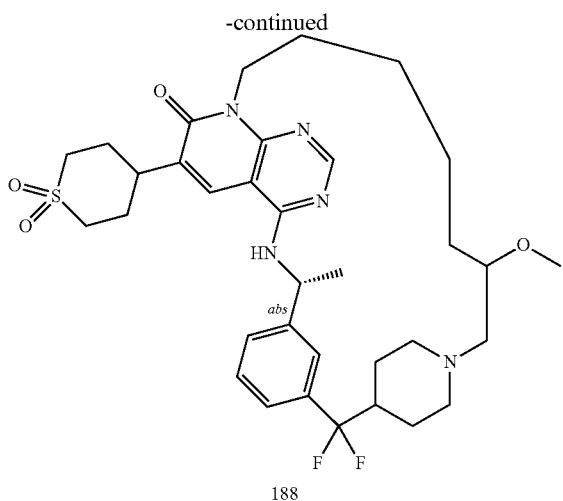

188

Step A: Preparation of 8-((tert-butyldiphenylsilyl)oxy) oct-1-en-3-ol (18-2). To a solution of 6-((tert-butyldiphenylsilyl)oxy)hexanal (18-1, 28 g, 1 eq., 79.09 mmol) in ether (100 mL) at −78° C., vinylmagnesium bromide (1M, 79.09 mL, 79.09 mmol) was added slowly over 30 minutes. The mixture was stirred for two hours and was partitioned between ether (100 mL) and saturated NH$_4$Cl solution (50 mL). The organic layer was separated and the aqueous phase was extracted with ether (2×100 mL). The combined organics were washed with brine, dried over Na$_2$SO$_4$, filtered and concentrated under reduced pressure to give a residue, which was purified by silica gel column chromatography (0%-40% ethyl acetate in petroleum ether) to afford the desired product as a yellow oil. $^1$H NMR (400 MHz, CDCl3) δ 7.72-7.59 (m, 4H), 7.48-7.31 (m, 6H), 5.90-5.80 (m, 1H), 5.20-5.10 (m, 2H), 3.65 (t, J=6.4 Hz, 2H), 1.61-1.46 (m, 5H), 1.43-1.32 (m, 3H), 1.04 (s, 9H).

Step B: Preparation of tert-butyl((6-methoxyoct-7-en-1-yl)oxy)diphenylsilane (18-3). To a solution of 18-2 (15 g, 1 eq., 39.26 mmol) in THF (100 mL) at 0° C. was added NaH (60% dispersed in mineral oil, 1.57 g, 1.0 eq., 39.26 mmol). The mixture was stirred for 0.5 hours at 0° C., then methyl iodide (6.69 g, 1.2 eq., 47.11 mmol) was added and the resulting mixture was warmed up and stirred at 25° C. for 2 hours. The reaction mixture was quenched with NH$_4$Cl (aq., 40 mL), then the organic layer was collected and the aqueous phase was extracted with ethyl acetate (2×100 mL). The combined organics were washed with brine, dried over Na$_2$SO$_4$, filtered and concentrated under reduced pressure to give a residue, which was purified by silica gel column chromatography (0%-40% ethyl acetate in petroleum ether) to obtain the desired product as a yellow oil.

Step C: Preparation of 6-methoxyoct-7-en-1-ol. To a solution of 18-3 (14 g, 1 eq., 35.35 mmol) in THF (50 mL) at 25° C. was added tetra-n-butylammonium fluoride (1M in THF, 70.70 mL, 2.0 eq., 70.70 mmol). The mixture was stirred for 2 hours at 25° C., poured into water, and extracted with ethyl acetate (3×100 mL). The combined organics were washed with brine, dried over Na$_2$SO$_4$, filtered and concentrated under reduced pressure to give a residue, which was purified by silica gel column chromatography (0%-40% ethyl acetate in petroleum ether) to afford the desired product as a yellow oil. $^1$H NMR (400 MHz, CDCl3) δ 5.64 (ddd, J=16.9, 10.6, 7.8 Hz, 1H), 5.25-5.07 (m, 2H), 3.64 (t, J=6.6 Hz, 2H), 3.50 (dd, J=13.7, 6.7 Hz, 1H), 3.27 (s, 3H), 1.65-1.52 (m, 3H), 1.42-1.32 (m, 5H).

Step D: Preparation of 6-methoxyoct-7-en-1-yl 4-methylbenzenesulfonate (18-4). To a solution of 6-methoxyoct-7-en-1-ol (4.9 g, 1 eq., 31.01 mmol) in DCM (50 mL) at 25° C. was added p-toluenesulfonyl chloride (8.84 g, 1.5 eq., 46.52 mmol) and triethylamine (9.40 g, 3.0 eq., 93.03 mmol). The mixture was stirred for 16 hours at 25° C., then poured into water and extracted with DCM (3×100 mL). The combined organics were washed with brine, dried over Na$_2$SO$_4$, filtered and concentrated under reduced pressure to give a residue, which was purified by silica gel column chromatography (0%-30% ethyl acetate in petroleum ether) to afford the desired product (9.6 g) as a yellow oil. $^1$H NMR (400 MHz, CDCl$_3$) δ 7.79 (d, J=8.0 Hz, 2H), 7.34 (d, J=8.0 Hz, 2H), 5.68-5.58 (m, 1H), 5.25-5.07 (m, 2H), 4.01 (t, J=6.6 Hz, 2H), 3.50 (dd, J=13.7, 6.7 Hz, 1H), 3.27 (s, 3H), 2.44 (s, 3H), 1.65-1.52 (m, 3H), 1.42-1.32 (m, 5H).

Step E: Preparation of tert-butyl (R)-4-((3-(1-((6-(1,1-dioxidotetrahydro-2H-thiopyran-4-yl)-7-oxo-7,8-dihydropyrido[2,3-d]pyrimidin-4-yl)amino)ethyl)phenyl)difluoromethyl)piperidine-1-carboxylate (18-5). To a solution of 9-1 (2100 mg, 1.2 eq., 6.69 mmol) in DMSO (30 mL) were added 4-2 (2000 mg, 1 eq., 5.64 mmol) and KF (1900 mg, 6 eq., 33.84 mmol) at room temperature. The mixture was stirred at 100° C. under an argon atmosphere for 2 hours, then poured into water (300 mL) and extracted with ethyl acetate (100 mL×3). The combined organics were washed with brine, dried over Na$_2$SO$_4$, filtered and concentrated under reduced pressure to give a residue, which was purified by silica gel column chromatography (0%-50% ethyl acetate in petroleum ether) to obtain the desired product as a yellow solid. ESI-MS m/z: (M+H)$^+$=632.2.

Step F: Preparation tert-butyl 4-((3-((1R)-1-((6-(1,1-dioxidotetrahydro-2H-thiopyran-4-yl)-8-(6-methoxyoct-7-en-1-yl)-7-oxo-7,8-dihydropyrido[2,3-d]pyrimidin-4-yl)amino)ethyl)phenyl)-difluoromethyl)piperidine-1-carboxylate (18-6). To a solution of 18-5 (632 mg, 1 eq., 1.00 mmol) in DMSO (6 mL) was added 18-4 (469 mg, 1.5 eq., 1.50 mmol) and K$_3$PO$_4$ (636 mg, 3 eq., 3.00 mmol) at room temperature. The mixture was stirred at 60° C. under an argon atmosphere for 2 hours, then cooled, poured into 160 mL of water, and extracted with ethyl acetate (100 mL×3). The combined organics were washed with brine, dried over Na$_2$SO$_4$, filtered and concentrated under reduced pressure to give a residue, which was purified by silica gel column chromatography (0%-55% ethyl acetate in petroleum ether) to obtain the desired product as a white film. ESI-MS m/z: (M+H)$^+$=772.4.

Step G: Preparation of tert-butyl 4-((3-((1R)-1-((6-(1,1-dioxidotetrahydro-2H-thiopyran-4-yl)-8-(6-methoxy-7-oxo-heptyl)-7-oxo-7,8-dihydropyrido[2,3-d]pyrimidin-4-yl)amino)ethyl)phenyl)-difluoromethyl)piperidine-1-carboxylate (18-7). To a solution of 18-6 (473 mg, 1 eq., 0.61 mmol) in THF (21 mL) and water (14 mL) was added K$_2$OsO$_4$ (33 mg, 0.1 eq., 0.061 mmol) at 0° C. The resulting mixture was stirred for 10 min, after which NaIO$_4$ (397 mg, 3 eq., 1.84 mmol) was added. The mixture was stirred at room temperature under an argon atmosphere for 16 hours, then diluted with water (60 mL) and extracted with ethyl acetate (80 mL×3). The combined organics were washed with brine, dried over Na$_2$SO$_4$, filtered and concentrated under reduced pressure to obtain the desired product which was used directly in the next step without further purification. ESI-MS m/z: (M+1)$^+$=774.3.

Step H: Preparation of 7-(4-(((R)-1-(3-(difluoro(piperidin-4-yl)methyl)phenyl)ethyl)amino)-6-(1,1-dioxidotetrahydro-2H-thiopyran-4-yl)-7-oxopyrido[2,3-d]pyrimidin-8(7H)-yl)-2-methoxyheptanal (18-8). To a solution of 18-7

(500 mg, 1 eq., 0.61 mmol) in DCM (7.5 mL) was added trifluoroacetic acid (1.5 mL) at room temperature. The resulting mixture was stirred at room temperature for 1 hour, then cooled to 0° C., treated with sat. NaHCO$_3$ (50 mL), and stirred for 20 minutes. The mixture was extracted with DCM (50 mL×6) and the combined organics were washed with brine, dried over Na$_2$SO$_4$, filtered and concentrated under reduced pressure to obtain the desired product, which was used directly in the next step without further purification. ESI-MS m/z: (M+H)$^+$=674.3.

Step I: Preparation of (4R)-6$^6$-(1,1-dioxidotetrahydro-2H-thiopyran-4-yl)-2,2-difluoro-12-methoxy-4-methyl-6$^7$,6$^8$-dihydro-5-aza-6(4,8)-pyrido[2,3-d]pyrimidina-1(4,1)-piperidina-3(1,3)-benzenacyclotridecaphan-6$^7$-one (188). To the solution of 18-8 (500 mg, 1 eq., 0.61 mmol) in MeOH (408 mL) and 1,2-dichloroethane (204 mL), HOAc (23 drops) was added at room temperature. The mixture was stirred at room temperature for 0.5 hours followed by the addition of NaBH$_3$CN (96 mg, 2.5 eq., 1.53 mmol). It was stirred at room temperature for 0.5 hour, concentrated and the residue was dissolved into 40 mL of DCM:MeOH (10:1). Sat. NaHCO$_3$ (60 mL) was then added and the mixture was stirred at room temperature for 1 hour. The organic layer was collected and the aqueous phase was extracted with DCM (40 mL×2). The combined organics were washed with brine, dried over Na$_2$SO$_4$, filtered and concentrated under reduced pressure to give a residue, which was purified by silica gel column chromatography (0%-5% MeOH in DCM) followed by chiral-HPLC to obtain the desired product as a white solid. ESI-MS m/z: (M+H)$^+$= 658.6; 1H NMR (400 MHz, DMSO) δ 8.44 (d, J=6.9 Hz, 1H), 8.24 (s, 1H), 8.23 (s, 1H), 7.55 (d, J=7.5 Hz, 1H), 7.45 (t, J=7.6 Hz, 1H), 7.35 (s, 1H), 7.20 (d, J=7.6 Hz, 1H), 5.47-5.17 (m, 1H), 4.6-4.39 (m, 1H), 4.32-4.08 (m, 1H), 3.39-3.34 (m, 2H), 3.28-3.09 (m, 6H), 3.00-2.92 (m, 1H), 2.69-2.56 (m, 2H), 2.27-2.01 (m, 6H), 1.96-1.61 (m, 7H), 1.58-1.56 (m, 2H), 1.43-1.02 (m, 6H), 1.01-0.72 (m, 3H).

Example 19: Synthesis of (4R)-3$^2$,2,2-trifluoro-4-methyl-6$^6$-(4-(oxetan-3-yl)piperazin-1-yl)-6$^7$,6$^8$-dihydro-5-aza-6(4,8)-pyrido[2,3-d]pyrimidina-1(4,1)-piperidina-3(1,3)-benzenacyclo-tridecaphan-6$^7$-one (179)

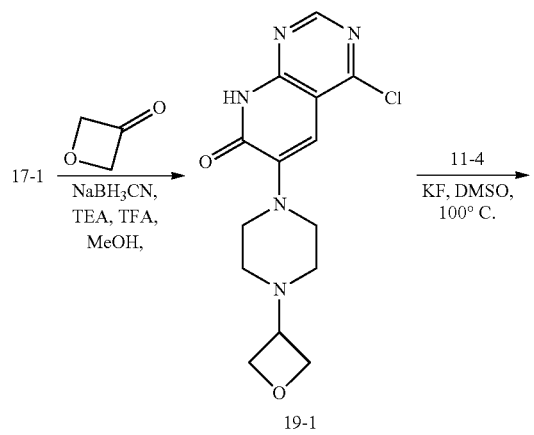

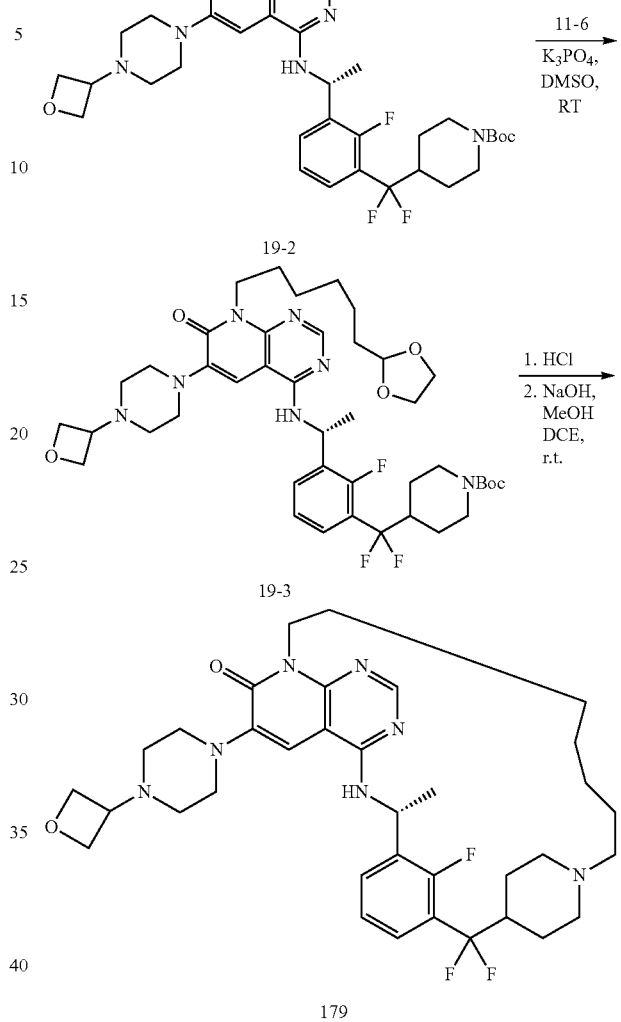

Step A: Preparation of 4-chloro-6-(4-(oxetan-3-yl)piperazin-1-yl)pyrido[2,3-d]pyrimidin-7(8H)-one (19-1). To a stirred solution of 17-1 (6.17 g, 1.0 eq., 23.29 mmol), triethylamine (7.05 g, 3.0 eq., 69.87 mmol), oxetan-3-one (10.1 g, 6.0 eq., 139.74 mmol) in methanol (60 mL) was added NaBH$_3$CN (3.66 g, 2.5 eq., 58.23 mmol) followed by acetic acid (6 drops). The mixture was stirred for 16 hours at room temperature and concentrated in vacuo to give a residue. The residue was purified by silica gel column chromatography (0%-5% MeOH in DCM) to obtain the desired product as a yellow solid. ESI-MS m/z: (M+H)$^+$= 322.0.

Step B: Preparation of tert-butyl (R)-4-(difluoro(2-fluoro-3-(1-((6-(4-(oxetan-3-yl)piperazin-1-yl)-7-oxo-7,8-dihydropyrido[2,3-d]pyrimidin-4-yl)amino)ethyl)phenyl)methyl)piperidine-1-carboxylate (19-2). To a solution of 19-1 (5.85 g, 1.2 eq., 18.23 mmol) in DMSO (50 mL) was added 11-4 (5.65 g, 1 eq., 15.19 mmol) and KF (5.04 g, 5.7 eq., 86.58 mmol). The mixture was stirred at 100° C. for 4 hours under nitrogen, then cooled to room temperature, poured into water (500 mL), and extracted with ethyl acetate (4×300 mL). The combined organics were washed with brine, dried over Na$_2$SO$_4$, filtered and concentrated under reduced pressure to give a residue, which was purified by silica gel column chromatography (0%-4% MeOH in DCM) to obtain the desired product as a yellow solid. ESI-MS m/z: (M+H)$^+$ =658.3.

Step C: Preparation of tert-butyl (R)-4-((3-(1-((8-(6-(1,3-dioxolan-2-yl)hexyl)-6-(4-(oxetan-3-yl)piperazin-1-yl)-7-oxo-7,8-dihydropyrido[2,3-d]pyrimidin-4-yl)amino)ethyl)-2-fluorophenyl)difluoromethyl)piperidine-1-carboxylate (19-3). To a solution of 19-2 (6.02 g, 1 eq., 9.12 mmol) in DMSO (60 mL) was added 11-6 (2.60 g, 1.2 eq., 10.96 mmol) and $K_3PO_4$ (5.91 g, 3 eq., 27.41 mmol). The mixture was stirred at room temperature for 4 hours, then poured into water (600 mL) and extracted with ethyl acetate (3×200 mL). The combined organics were washed with brine, dried over $Na_2SO_4$, filtered and concentrated under reduced pressure to give a residue, which was purified by silica gel column chromatography (0%-5% MeOH in DCM) to obtain the desired product as a yellow solid. ESI-MS m/z: (M+H)$^+$= 814.2.

Step D: Preparation of (R)-7-(4-((1-(3-(difluoro(piperidin-4-yl)methyl)-2-fluorophenyl)ethyl)amino)-6-(4-(oxetan-3-yl)piperazin-1-yl)-7-oxopyrido[2,3-d]pyrimidin-8(7H)-yl)heptanal. To a solution of 19-3 (4.50 g, 1 eq., 5.53 mmol) in THF (45 mL) was added HCl (2N aqueous, 90 mL). The mixture was stirred for 16 hours at room temperature, then the pH was adjusted to 7-8 with saturated $NaHCO_3$ and the resulting mixture extracted with DCM (3×100 mL). The combined organic layer was dried over $Na_2SO_4$, filtered, and concentrated under reduced pressure to afford the desired product, which was used directly in the next step without further purification. ESI-MS m/z: (M+H)$^+$= 670.2.

Step E: Preparation of (4R)-3$^2$,2,2-trifluoro-4-methyl-6$^6$-(4-(oxetan-3-yl)piperazin-1-yl)-6$^7$,6$^8$-dihydro-5-aza-6(4,8)-pyrido[2,3-d]pyrimidina-1(4,1)-piperidina-3(1,3)-benzenacyclo-tridecaphan-6$^7$-one (179). To a solution of (R)-7-(4-((1-(3-(difluoro(piperidin-4-yl)methyl)-2-fluorophenyl) ethyl)amino)-6-(4-(oxetan-3-yl)piperazin-1-yl)-7-oxopyrido[2,3-d]pyrimidin-8(7H)-yl)heptanal (4.50 g, 1 eq., 5.53 mmol) in 1,2-dichloroethane (1844 mL) and methanol (3688 mL) was added acetic acid (50 drops). The mixture was stirred at room temperature for 0.5 hours followed by the addition of $NaBH_3CN$ (870.01 mg, 2.5 eq., 13.84 mmol) and stirred for 16 hours at the same temperature. The reaction mixture was concentrated, diluted with DCM (150 mL) and treated with saturated $NaHCO_3$ (150 mL). The organic layers were combined and the aqueous layer was extracted with ethyl acetate (200 mL×3). The combined organics were washed with brine, dried over $Na_2SO_4$, filtered and concentrated under reduced pressure to give a residue, which was purified by silica gel column chromatography (0%-10% MeOH in DCM) to afford the desired product as a white solid. ESI-MS m/z: (M+H)$^+$=654.3; $^1$H NMR (400 MHz, DMSO) δ 8.20 (d, J=6.7 Hz, 1H), 8.09 (s, 1H), 7.67 (t, J=6.8 Hz, 1H), 7.38 (s, 1H), 7.27 (t, J=7.8 Hz, 1H), 7.18 (t, J=6.5 Hz, 1H), 5.63-5.45 (m, 1H), 4.74-4.46 (m, 5H), 4.10-3.99 (m, 1H), 3.54-3.47 (m, 1H), 3.27-3.14 (m, 4H), 3.01-2.96 (m, 1H), 2.60-2.56 (m, 1H), 2.468-2.42 (m, 3H), 2.18-2.06 (m, 3H), 1.96-1.84 (m, 2H), 1.75-1.60 (m, 7H), 1.50-1.35 (m, 2H), 1.25-1.05 (m, 5H), 0.83-0.63 (m, 3H).

Example 20: Synthesis of (4R)-6$^6$-(1,1-dioxidotetrahydro-2H-thiopyran-4-yl)-3$^2$,2,2-trifluoro-4-methyl-6$^7$,6$^8$-dihydro-10-oxa-5-aza-6(4,8)-pyrido[2,3-d]pyrimidina-1(4,1)-piperidina-3(1,3)-benzenacyclotetradecaphan-6$^7$-one (203)

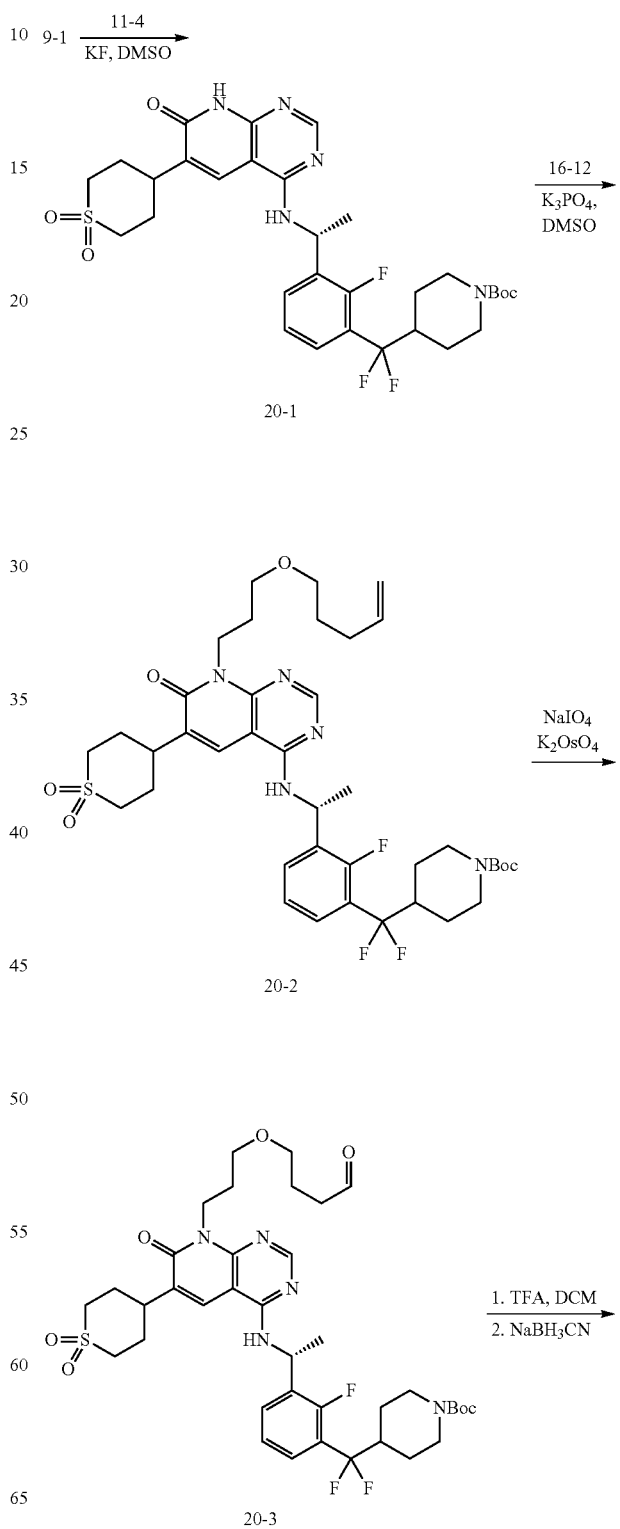

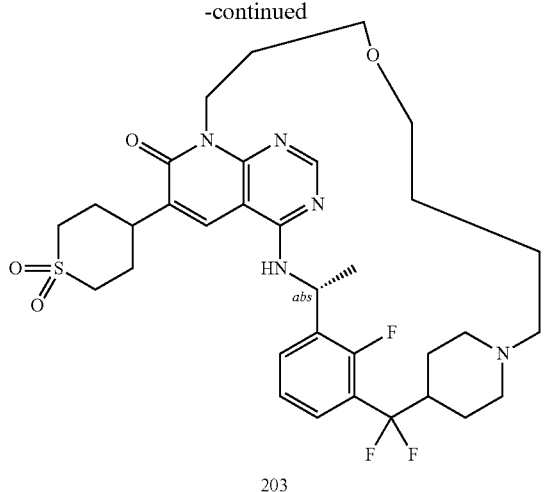

203

Step A: Preparation of tert-butyl (R)-4-((3-(1-((6-(1,1-dioxidotetrahydro-2H-thiopyran-4-yl)-7-oxo-7,8-dihydropyrido[2,3-d]pyrimidin-4-yl)amino)ethyl)-2-fluorophenyl)difluoromethyl)-piperidine-1-carboxylate (20-1). A solution of 11-4 (300 mg, 1.0 eq., 0.96 mmol), 9-1 (428 mg, 1.2 eq., 1.15 mmol) and KF (334 mg, 6.0 eq., 5.75 mmol) in anhydrous dimethyl sulfoxide (5 mL, 0.2M) was stirred at 100° C. for 2 hours under nitrogen. The mixture was cooled to room temperature, then diluted with ethyl acetate (20 mL) and water (40 mL) and extracted with ethyl acetate (20 mL×3). The combined organics were washed with brine, dried over $Na_2SO_4$, filtered and concentrated under reduced pressure to give a residue, which was purified by com-flash chromatography on a silica gel column (0%-10% methanol in dichloromethane) to afford the desired product as a yellow solid. ESI-MS m/z: (M+H)$^+$=650.3.

Step B: Preparation of tert-butyl (R)-4-((3-(1-((6-(1,1-dioxidotetrahydro-2H-thiopyran-4-yl)-7-oxo-8-(3-(pent-4-en-1-yloxy)propyl)-7,8-dihydropyrido[2,3-d]pyrimidin-4-yl)amino)ethyl)-2-fluorophenyl)difluoromethyl)piperidine-1-carboxylate (20-2). To a stirred solution of 20-1 (550 mg, 1.0 eq., 0.85 mmol) in dimethyl sulfoxide (6 mL) were added 16-12 (380 mg, 1.5 eq., 1.27 mmol) and $K_3PO_4$ (539 mg, 3.0 eq., 2.54 mmol), and the resulting mixture was stirred at room temperature for 2 hours. The mixture was diluted with ethyl acetate (20 mL) and water (40 mL), then extracted with ethyl acetate (20 mL×3). The combined organics were washed with brine, dried over $Na_2SO_4$, filtered and concentrated under reduced pressure to give a residue, which was purified by com-flash chromatography on a silica gel column (0%~10% methanol in dichloromethane) to afford the desired product as a yellow solid. ESI-MS m/z: (M+H)$^+$=776.3.

Step C: Preparation of tert-butyl (R)-4-((3-(1-((6-(1,1-dioxidotetrahydro-2H-thiopyran-4-yl)-7-oxo-8-(3-(4-oxobutoxy)propyl)-7,8-dihydropyrido[2,3-d]pyrimidin-4-yl)amino)ethyl)-2-fluorophenyl)difluoromethyl)piperidine-1-carboxylate (20-3). To a solution of 20-2 (600 mg, 1.0 eq., 0.77 mmol) in THF (54 mL) and water (36 mL) was added $NaIO_4$ (992 mg, 6.0 eq., 4.64 mmol), followed by $K_2OsO_4 \cdot 2H_2O$ (50 mg) at 0° C. The reaction mixture was allowed to warm to room temperature and stirred for 3 hours. Organic solvent was mostly removed, then ethyl acetate (40 mL) was added. The mixture was extracted with ethyl acetate (2×40 mL) and the combined organics were washed with brine, dried over $Na_2SO_4$, filtered and concentrated under reduced pressure to give the desired product as a light-yellow oil, which was used directly in the next step without further purification. ESI-MS m/z: (M+H)$^+$=778.3.

Step D: Preparation of (R)-4-(3-(4-((1-(3-(difluoro(piperidin-4-yl)methyl)-2-fluorophenyl)ethyl)amino)-6-(1,1-dioxidotetrahydro-2H-thiopyran-4-yl)-7-oxopyrido[2,3-d]pyrimidin-8(7H)-yl)propoxy)butanal. To a stirred solution of 20-3 (600 mg, crude) in DCM (10 mL) was added trifluoroacetic acid (2 mL) drop-wise at room temperature. The resulting mixture was stirred at room temperature for 2 hours, then concentrated to give the desired product as a light-yellow oil which was used directly in next step without further purification. ESI-MS m/z: (M+H)$^+$=678.3.

Step E: Preparation of (4R)-6$^6$-(1,1-dioxidotetrahydro-2H-thiopyran-4-yl)-3$^2$,2,2-trifluoro-4-methyl-6$^7$,6$^8$-dihydro-10-oxa-5-aza-6(4,8)-pyrido[2,3-d]pyrimidina-1(4,1)-piperidina-3(1,3)-benzenacyclotetradecaphan-6$^7$-one (203). To a solution of (R)-4-(3-(4-((1-(3-(difluoro(piperidin-4-yl)methyl)-2-fluorophenyl)ethyl)amino)-6-(1,1-dioxidotetrahydro-2H-thiopyran-4-yl)-7-oxopyrido[2,3-d]pyrimidin-8(7H)-yl)propoxy)butanal (600 mg, crude) in methanol/1,2-dichloroethane (500 mL/200 mL) was added acetic acid (10 drops) and the resulting mixture was stirred for 30 minutes at room temperature. Then, sodium cyanoborohydride (140 mg, 2.5 eq., 2.22 mmol) was added and the resulting mixture was stirred at room temperature for 1 hour, then concentrated under reduced pressure to give a residue which was purified by prep-HPLC (formic acid condition) to give the desired product as a light-yellow solid. ESI-MS m/z: (M+H)$^+$=662.3. $^1$H NMR (400 MHz, DMSO-D2O) δ 8.28 (s, 1H), 8.17 (s, 1H), 7.58 (d, J=7.1 Hz, 1H), 7.28-7.16 (m, 2H), 5.47 (q, J=7.3 Hz, 11H), 4.63-4.46 (m, 11H), 4.25-4.10 (m, 11H), 3.44-3.27 (m, 5H), 3.25-3.11 (m, 4H), 2.89 (d, J=10.0 Hz, 11H), 2.67 (d, J=11.3 Hz, 1H), 2.23-2.06 (m, 7H), 1.92-1.78 (m, 3H), 1.76-1.61 (m, 5H), 1.60-1.50 (m, 1H), 1.50-1.29 (m, 5H), 0.75-0.60 (m, 1H).

Example 21: Synthesis of (4R)-3$^2$,2,2-trifluoro-4-methyl-6$^6$-(4-(1-methylpiperidin-4-yl)piperazin-1-yl)-6$^7$,6$^8$-dihydro-5-aza-6(4,8)-pyrido[2,3-d]pyrimidina-1(4,1)-piperidina-3(1,3)-benzenacyclotridecaphan-6$^7$-one (178)

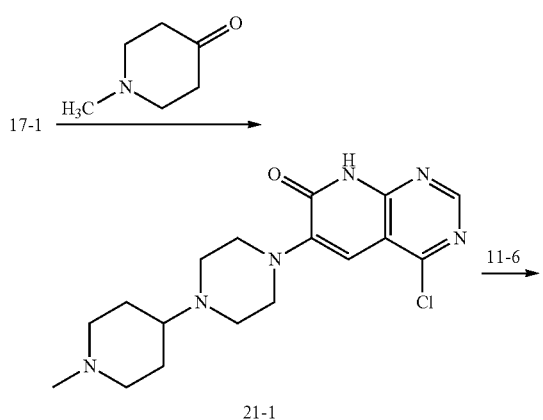

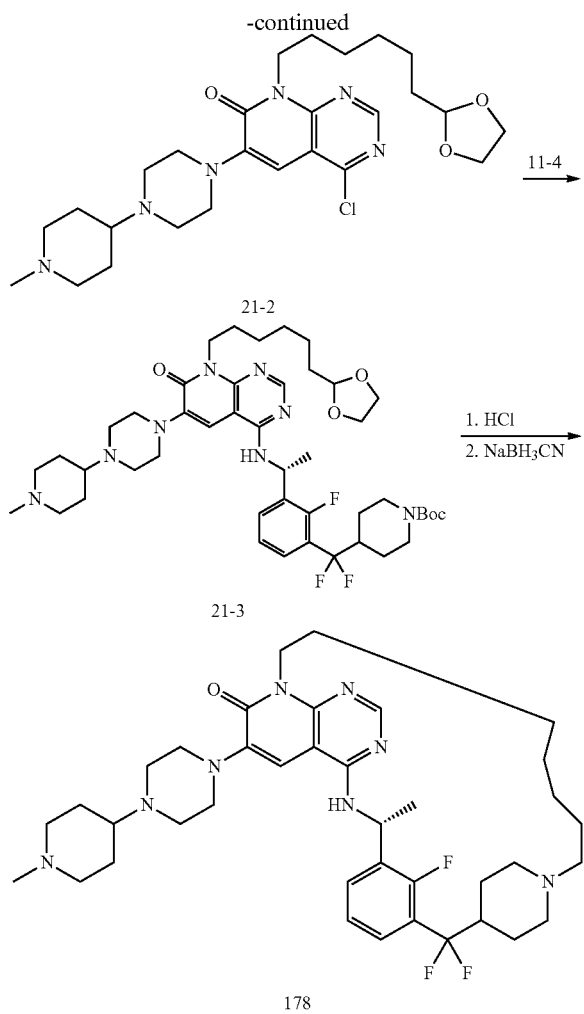

Step A: Preparation of 4-chloro-6-(4-(1-methylpiperidin-4-yl)piperazin-1-yl)pyrido[2,3-d]pyrimidin-7(8H)-one (21-1). To a stirred solution of 17-1 (726 mg, 2.73 mmol, 1 eq.), triethylamine (836 mg, 3 eq., 8.19 mmol) and 1-methylpiperidin-4-one (1.86 g, 6 eq., 16.43 mmol) in methanol (8 mL) was added NaBH$_3$CN (428 mg, 3 eq., 6.80 mmol) followed by acetic acid (6 drops). The mixture was stirred for 16 hours at room temperature, concentrated in vacuo, then diluted with ethyl acetate (50 mL) and water (50 mL) and extracted with ethyl acetate (2×50 mL). The combined organics were washed with brine, dried over Na$_2$SO$_4$, filtered and concentrated under reduced pressure to give a residue, which was purified by silica gel column chromatography (MeOH in DCM 0~12%) to afford the desired product as a yellow solid. ESI-MS m/z: (M+H)$^+$=363.2.

Step B: Preparation of 8-(6-(1,3-dioxolan-2-yl)hexyl)-4-chloro-6-(4-(1-methylpiperidin-4-yl)piperazin-1-yl)pyrido[2,3-d]pyrimidin-7(8H)-one (21-2). To a solution of 21-1 (500 mg, 1.38 mmol, 1 eq.) in DMSO (10 mL) were added 11-6 (392 mg, 1.65 mmol, 1.2 eq.) and K$_3$PO$_4$ (876 mg, 4.13 mmol, 3 eq.). The mixture was stirred for 4 hours at room temperature, then diluted with ethyl acetate (150 mL) and water (150 mL) and extracted with ethyl acetate (2×150 mL). The combined organics were washed with brine, dried over Na$_2$SO$_4$, filtered and concentrated under reduced pressure to give a residue, which was purified by silica gel column chromatography (MeOH in DCM 0~10%) to afford the desired product as a yellow solid. ESI-MS m/z: (M+H)$^+$= 519.3.

Step C: Preparation of tert-butyl (R)-4-((3-(1-((8-(6-(1,3-dioxolan-2-yl)hexyl)-6-(4-(1-methylpiperidin-4-yl)piperazin-1-yl)-7-oxo-7,8-dihydropyrido[2,3-d]pyrimidin-4-yl)amino)ethyl)-2-fluorophenyl)difluoromethyl)piperidine-1-carboxylate (21-3). To a solution of 21-2 (330 mg, 0.64 mmol, 1.2 eq.) in DMSO (4 mL) were added 11-4 (197 mg, 0.53 mmol, 1 eq.) and KF (185 mg, 3.18 mmol, 6 eq.). The mixture was stirred for 4 hours at 100° C. and cooled to room temperature, then diluted with ethyl acetate (40 mL) and water (50 mL) and extracted with ethyl acetate (2×50 mL). The combined organics were washed with brine, dried over Na$_2$SO$_4$, filtered and concentrated under reduced pressure to give a residue, which was purified by silica gel column chromatography (ethyl acetate in petroleum ether 0-10%) to afford the desired product as a yellow solid. ESI-MS m/z: (M+H)$^+$=855.5.

Step D: Preparation of (R)-7-(4-((1-(3-(difluoro(piperidin-4-yl)methyl)-2-fluorophenyl)ethyl)amino)-6-(4-(1-methylpiperidin-4-yl)piperazin-1-yl)-7-oxopyrido[2,3-d]pyrimidin-8(7H)-yl)heptanal. To a solution of 21-3 (420 mg, 0.49 mmol, 1 eq.) in THF (5 mL) was added HCl (aq. 2N, 10 mL). The mixture was stirred for 16 hours at room temperature, then the pH was adjusted to 7-8 with saturated NaHCO$_3$ solution and the mixture extracted with DCM (3×50 mL). The combined organics were washed with brine, dried over Na$_2$SO$_4$, filtered and concentrated under reduced pressure to afford the desired product as a yellow foam, which was used directly in the next step without further purification. ESI-MS m/z: (M+H)$^+$=711.4.

Step E: Preparation of (4R)-3$^2$,2,2-trifluoro-4-methyl-6$^6$-(4-(1-methylpiperidin-4-yl)piperazin-1-yl)-6$^7$,6$^8$-dihydro-5-aza-6(4,8)-pyrido[2,3-d]pyrimidina-1(4,1)-piperidina-3(1,3)-benzenacyclotridecaphan-6$^7$-one (178). To a solution of (R)-7-(4-((1-(3-(difluoro(piperidin-4-yl)methyl)-2-fluorophenyl)ethyl)amino)-6-(4-(1-methylpiperidin-4-yl)piperazin-1-yl)-7-oxopyrido[2,3-d]pyrimidin-8(7H)-yl)heptanal (300 mg, 0.43 mmol, 1 eq.) in 1,2-dichloroethane (160 mL) and methanol (330 mL) was added acetic acid (20 drops). The mixture was stirred at room temperature for 0.5 hours followed by the addition of NaBH$_3$CN (67 mg, 1.08 mmol, 2.5 eq). The reaction mixture was stirred for 16 hours at room temperature and concentrated to give a residue. The residue was treated with DCM (60 mL) and saturated NaHCO$_3$ (60 mL), stirred at room temperature for 1 hour and extracted with DCM (3×60 mL). The combined organics were washed with brine, dried over Na$_2$SO$_4$, filtered and concentrated under reduced pressure to give a residue, which was purified by silica gel column chromatography (MeOH in DCM 0%-10%) to afford the desired product as a white solid. ESI-MS m/z: (M+H)$^+$=695.5; $^1$H NMR (400 MHz, DMSO): δ 8.19 (d, J=6.7 Hz, 1H), 8.09 (s, 1H), 7.67 (t, J=6.2 Hz, 1H), 7.37 (s, 1H), 7.29-7.25 (m, 1H), 7.20-7.16 (m, 1H), 5.59-5.50 (m, 1H), 4.75-4.63 (m, 1H), 4.09-4.00 (m, 1H), 3.18-3.13 (m, 4H), 3.00-2.96 (m, 1H), 2.87-2.82 (m, 2H), 2.68-2.63 (m, 4H), 2.26-2.08 (m, 7H), 1.98-1.75 (m, 6H), 1.69-1.60 (m, 6H), 1.52-1.35 (m, 5H), 1.25-1.04 (m, 6H), 0.80-0.67 (m, 3H).

Example 22: Synthesis of (R)-3-methyl-1⁶-morpholino-5,15-dioxa-2,12-diaza-1(4,8)-quinazolina-4(1,3)-benzenacyclopentadecaphan-13-one (204)

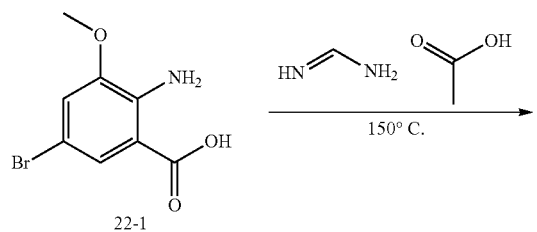

22-1

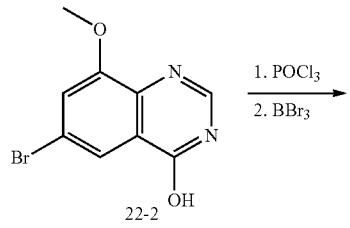

22-2

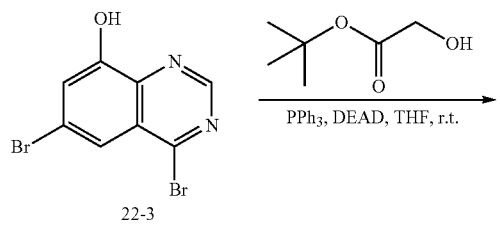

22-3

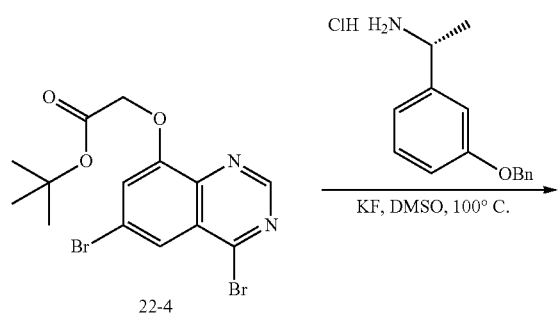

22-4

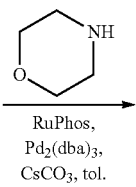

22-5

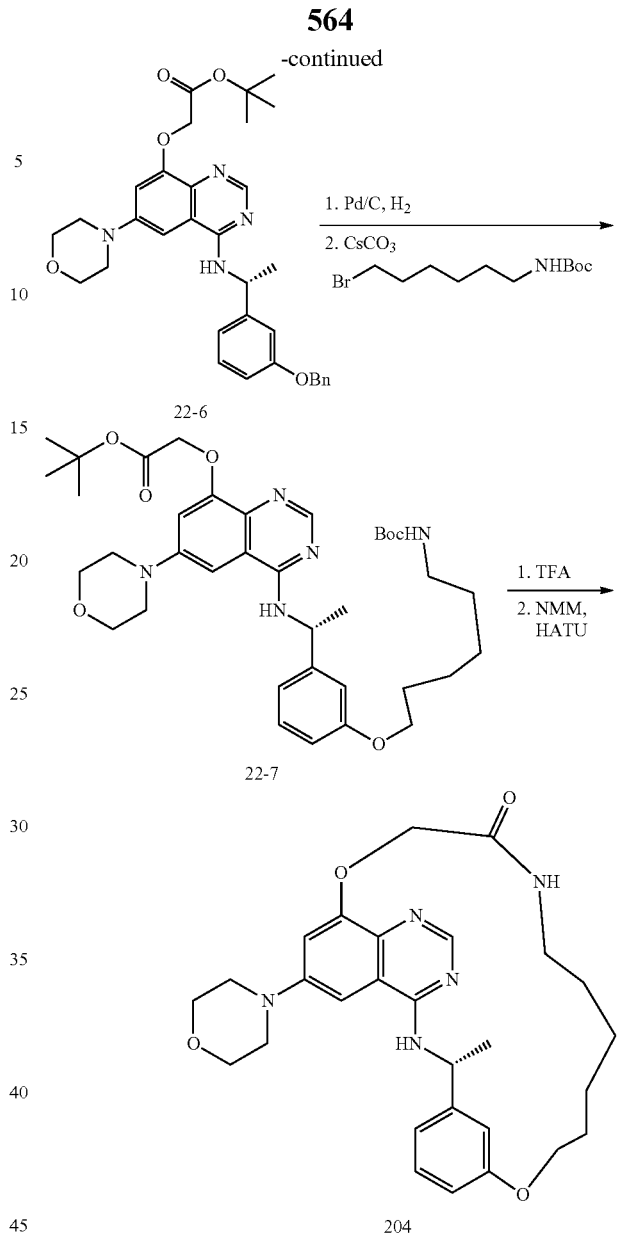

22-6

22-7

204

Step A: Preparation of 6-bromo-8-methoxyquinazolin-4-ol (22-2). To a solution of 2-amino-5-bromo-3-methoxybenzoic acid (22-1, 8 g, 1 eq., 32.52 mmol) was added formamidine acetate (34 g, 10.0 eq., 325.2 mmol) in a round bottomed flask. The mixture was stirred at 150° C. for 3 hours and cooled to room temperature, then added to ice water and filtered. The filter cake was washed with water and dried to obtain the desired product as a grey solid. ESI-MS m/z: (M+H)⁺=254.8. $^1$H NMR (400 MHz, DMSO) δ 12.44 (s, 1H), 8.07 (d, J=3.4 Hz, 1H), 7.74 (d, J=2.1 Hz, 1H), 7.49 (d, J=2.1 Hz, 1H), 3.92 (s, 3H).

Step B: Preparation of 6-bromo-4-chloro-8-methoxyquinazoline. 22-2 (4 g, 1 eq., 15.75 mmol) in POCl₃ (40 mL) was stirred at 110° C. for 16 hours. The reaction mixture was cooled and concentrated, and the resulting residue was diluted with ethyl acetate and added dropwise to ice water. The mixture was treated with sat. aqueous NaHCO₃ and extracted with ethyl acetate (50 mL×3). The combined organics were washed with brine, dried over Na₂SO₄, filtered and concentrated under reduced pressure to give a residue, which was purified by silica gel column chromatography (0%-50% ethyl acetate in petroleum ether) to afford the desired product as a yellow solid. ESI-MS m/z: (M+H)$^+$=273.8. $^1$H NMR (400 MHz, DMSO) δ 8.15 (s, 1H), 7.76 (d, J=2.1 Hz, 1H), 7.52 (d, J=2.1 Hz, 1H), 3.94 (s, 3H).

Step C: Preparation of 4,6-dibromoquinazolin-8-ol (22-3). To a solution of 6-bromo-4-chloro-8-methoxyquinazoline (2 g, 1 eq., 7.35 mmol) in DCM (15 mL) was added BBr$_3$ (44.1 mL, 6.0 eq., 44.1 mmol, 1 M) dropwise at 0° C. The resulting mixture was stirred at room temperature for 16 hours, then poured into ice water and extracted with DCM (50 mL×3). The combined organics were washed with brine, dried over Na$_2$SO$_4$, filtered and concentrated under reduced pressure to give a residue, which was purified by silica gel column chromatography (0%-50% ethyl acetate in petroleum ether) to afford the desired product as a yellow solid. ESI-MS m/z: (M+H)$^+$=302.8. $^1$H NMR (400 MHz, DMSO) δ 11.30 (s, 1H), 9.01 (s, 1H), 7.73 (d, J=2.0 Hz, 1H), 7.53 (d, J=2.0 Hz, 1H).

Step D: Preparation of tert-butyl 2-((4,6-dibromoquinazolin-8-yl)oxy)acetate (22-4). To a solution of 22-3 (350 mg, 1 eq., 1.16 mmol) in THF (7 mL) was added tert-butyl 2-hydroxyacetate (230 mg, 1.5 eq., 1.74 mmol) and PPh$_3$ (607 mg, 2 eq., 2.32 mmol). Then, diethyl azodicarboxylate (404 mg, 2 eq., 2.32 mmol) was added at 0° C. under nitrogen and the mixture was stirred at room temperature for 16 hours. The reaction was quenched by addition of water (30 mL) and extracted with ethyl acetate (3×30 mL). The combined organics were washed with brine, dried over Na$_2$SO$_4$, filtered and concentrated under reduced pressure to give a residue, which was purified by silica gel column chromatography (0%-50% ethyl acetate in petroleum ether) to afford the desired product as a white solid. ESI-MS m/z: (M+H)$^+$=418.9.

Step E: Preparation of tert-butyl (R)-2-((4-((1-(3-(benzyloxy)phenyl)ethyl)amino)-6-bromoquinazolin-8-yl)oxy)acetate (22-5). To a solution of 22-4 (210 mg, 1 eq., 0.50 mmol) in DMSO (10 mL) was added (R)-1-(3-(benzyloxy)phenyl)ethan-1-amine hydrochloride (145 mg, 1.1 eq., 0.55 mmol) and KF (175 mg, 6.0 eq., 3.02 mmol). The mixture was stirred at 100° C. for 2 hours under nitrogen, then cooled to room temperature, poured into water, and extracted with ethyl acetate (3×30 mL). The combined organics were washed with brine, dried over Na$_2$SO$_4$, filtered and concentrated under reduced pressure to give a residue, which was purified by silica gel column chromatography (0%~10% methanol in dichloromethane) to afford the desired product as a yellow solid. ESI-MS m/z: (M+H)$^+$=564.1.

Step F: Preparation of tert-butyl (R)-2-((4-((1-(3-(benzyloxy)phenyl)ethyl)amino)-6-morpholinoquinazolin-8-yl)oxy)acetate (22-6). To a mixture of 22-5 (100 mg, 0.2 eq., 0.177 mmol), morpholine (31 mg, 2 eq., 0.356 mmol) and Cs$_2$CO$_3$ (173 mg, 3 eq., 0.531 mmol) in toluene (10 mL) were added tris(dibenzylideneacetone)dipalladium (16 mg, 0.1 eq., 0.0178 mmol) and 2-dicyclohexylphosphino-2',6'-di-1-propoxy-1,1'-biphenyl (16 mg, 0.2 eq., 0.0356 mmol). The resulting mixture was stirred at 100° C. for 16 hours under nitrogen and cooled to room temperature. The mixture was diluted with ethyl acetate (20 mL) and water (20 mL), then the organic layer was collected and the aqueous layer was extracted with ethyl acetate (3×20 mL). The combined organics were washed with brine, dried over Na$_2$SO$_4$, filtered and concentrated under reduced pressure to give a residue, which was purified by silica gel column chromatography (0%~10% methanol in dichloromethane) to afford the desired product as a yellow solid. ESI-MS m/z: (M+H)$^+$= 571.2.

Step G: Preparation of tert-butyl (R)-2-((4-((1-(3-hydroxyphenyl)ethyl)amino)-6-morpholinoquinazolin-8-yl)oxy)acetate. A mixture of 22-6 (93 mg) and Pd/C (90 mg) in methanol (30 mL) was stirred at room temperature for 16 hours under hydrogen atmosphere. The reaction mixture was filtered and the filtrate was concentrated in vacuo to give a residue, which was purified by flash silica gel column chromatography (0%~10% methanol in dichloromethane) to afford the desired product as a white solid. ESI-MS m/z: (M+H)$^+$=481.1.

Step H: Preparation of tert-butyl (R)-2-((4-((1-(3-((6-((tert-butoxycarbonyl)amino)hexyl)oxy)phenyl)ethyl)amino)-6-morpholinoquinazolin-8-yl)oxy)acetate (22-7). To a solution of tert-butyl (R)-2-((4-((1-(3-hydroxyphenyl)ethyl)amino)-6-morpholinoquinazolin-8-yl)oxy)acetate (28 mg, 1 eq., 0.058 mmol) in acetonitrile (4 mL) was added tert-butyl (6-bromohexyl)carbamate (18 mg, 1.1 eq., 0.064 mmol) and Cs$_2$CO$_3$ (57 mg, 3.0 eq., 0.174 mmol). The mixture was stirred at 70° C. for 4 hours under nitrogen and cooled to room temperature. The reaction mixture was concentrated, and the residue was dissolved into ethyl acetate (10 mL) and washed with water (20 mL). The organic layer was collected, and the aqueous layer was extracted with ethyl acetate (3×20 mL). The combined organics were washed with brine, dried over Na$_2$SO$_4$, filtered and concentrated under reduced pressure to give a residue, which was purified by silica gel column chromatography (0%-100% ethyl acetate in petroleum ether) to afford the desired product as a yellow solid. ESI-MS m/z: (M+H)$^+$=680.6.

Step I: Preparation of (R)-2-((4-((1-(3-((6-aminohexyl)oxy)phenyl)ethyl)amino)-6-morpholinoquinazolin-8-yl)oxy)acetic acid. A solution of 22-7 (32 mg, 0.047 mmol) in TFA (1 mL) and DCM (5 mL) was stirred at room temperature for 16 hours, then concentrated and purified by reverse phase chromatography to afford the desired product as a yellow solid. ESI-MS m/z: (M+H)$^+$=524.3.

Step J: Preparation of (R)-3-methyl-1$^6$-morpholino-5,15-dioxa-2,12-diaza-1(4,8)-quinazolina-4(1,3)-benzenacyclopentadecaphan-13-one (204). To a solution of (R)-2-((4-((1-(3-((6-aminohexyl)oxy)phenyl)ethyl)amino)-6-morpholinoquinazolin-8-yl)oxy)acetic acid (23 mg, 1 eq., 0.044 mmol) in dry DMF (8.8 mL, 0.005 M) was added 4-methylmorpholine (24 mg, 5.0 eq., 0.22 mmol) and the resulting mixture was stirred at room temperature for 1 hour. Then, 2-(7-azabenzotriazol-1-yl)-N,N,N',N'-tetramethyluronium hexafluorophosphate (26 mg, 1.5 eq., 0.066 mmol) was added and the mixture was stirred at room temperature for 1 hour. The reaction mixture was poured into water and extracted with ethyl acetate (3×15 mL). The combined organics were washed with brine, dried over Na$_2$SO$_4$, filtered and concentrated under reduced pressure to give a residue, which was purified by prep-TLC (methanol:dichloromethane 1:15) to afford the desired product as a yellow solid. ESI-MS m/z: (M+H)$^+$=506.5. $^1$H NMR (400 MHz, DMSO) δ 8.39 (s, 1H), 7.35-7.21 (m, 3H), 7.02 (d, J=7.7 Hz, 1H), 6.93 (s, 1H), 6.68 (dd, J=8.1, 2.1 Hz, 1H), 5.72-5.65 (m, 1H), 4.87-4.72 (m, 2H), 3.87-3.78 (m, 6H), 3.45-3.38 (m, 1H), 3.27-3.23 (m, 4H), 2.72-2.67 (m, 1H), 2.22-1.97 (m, 2H), 1.68 (d, J=7.1 Hz, 3H), 1.49-1.45 (m, 2H), 1.19-1.05 (m, 3H), 0.97-0.87 (m, 2H), 0.59-0.43 (m, 2H).

Example 23: Synthesis of (4R)-2,2-difluoro-4-methyl-6³-(tetrahydro-2H-pyran-4-yl)-6¹,6²,6³,6⁴-tetrahydro-5-aza-6(5,1)-pyrimido[4,5-d]pyrimidina-1(4,1)-piperidina-3(1,3)-benzenacyclotridecaphan-6²-one (185)

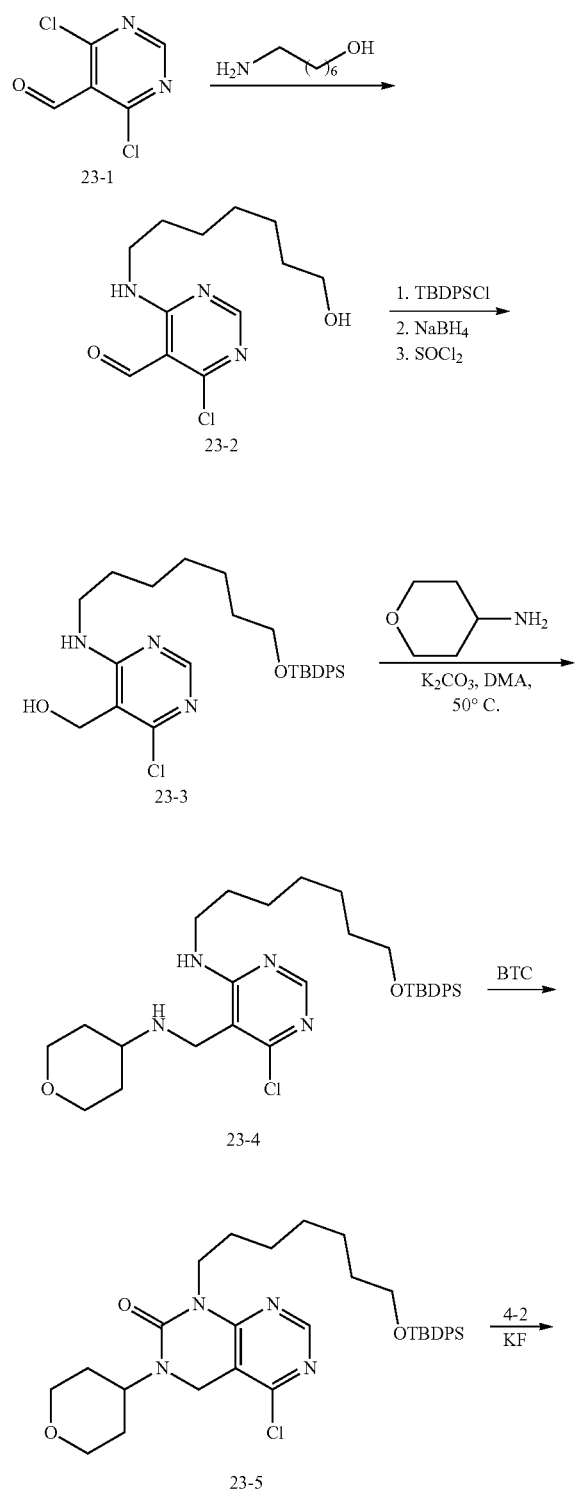

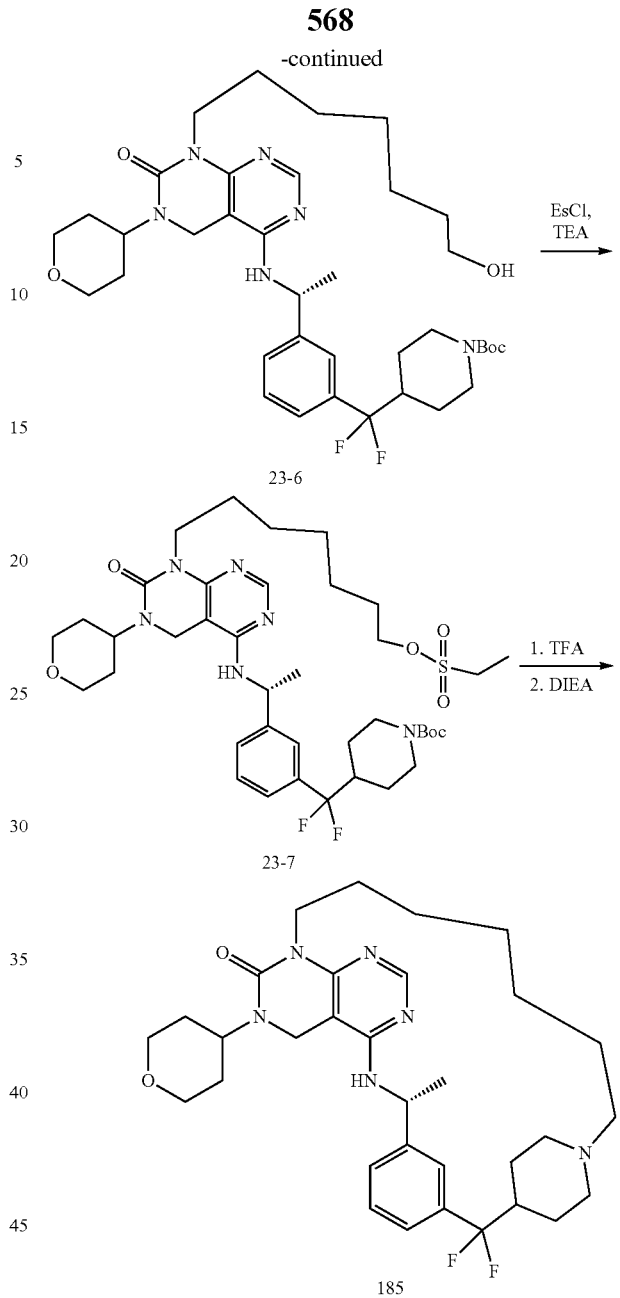

Step A: Preparation of 4-chloro-6-((7-hydroxyheptyl)amino)pyrimidine-5-carbaldehyde (23-2). To a solution of 4,6-dichloropyrimidine-5-carbaldehyde (23-1, 5 g, 1.0 eq., 28.25 mmol) in chloroform (40 mL) were added triethylamine (4.28 g, 1.5 eq., 42.37 mmol) and 7-aminoheptan-1-ol (2.48 g, 0.67 eq., 18.93 mmol) at 0° C. The reaction mixture was stirred at room temperature for 5 hours, quenched with a saturated ammonium chloride solution (50 mL), and extracted with chloroform (50 mL×3). The combined organics were washed with brine, dried over $Na_2SO_4$, filtered and concentrated under reduced pressure to give a residue, which was purified by silica gel column chromatography (silica gel, 0-10% methanol in dichloromethane) to give the desired product. ESI-MS m/z: $(M+H)^+$=272.0.

Step B: Preparation of 4-((7-((tert-butyldiphenylsilyl)oxy)heptyl)amino)-6-chloropyrimidine-5-carbaldehyde. To a solution of 23-2 (2.82 g, 1.0 eq., 10.37 mmol) in DCM (40 mL) were added TBDPSCl (3.71 g, 1.3 eq., 13.48 mmol) and imidazole (1.20 g, 1.7 eq., 17.62 mmol). The mixture was stirred at room temperature for 16 hours, diluted with water (50 mL), and extracted with DCM (50 mL×3). The combined organics were washed with brine, dried over Na$_2$SO$_4$, filtered and concentrated under reduced pressure to give a residue, which was purified by silica gel column chromatography (silica gel, 0-10% ethyl acetate in petroleum ether) to give the desired product as a yellow oil. ESI-MS m/z: (M+H)$^+$=510.0.

Step C: Preparation of (4-((7-((tert-butyldiphenylsilyl) oxy)heptyl)amino)-6-chloropyrimidin-5-yl)methanol. To a solution of 4-((7-((tert-butyldiphenylsilyl)oxy)heptyl) amino)-6-chloropyrimidine-5-carbaldehyde (2.54 g, 1.0 eq, 4.98 mmol) in MeOH (22.5 mL) and DCM (7.5 ml) was added NaBH$_4$ (227 mg, 1.2 eq., 5.98 mmol) at room temperature. The mixture was stirred at room temperature for 5 hours, quenched with water (50 mL), and extracted with DCM (50 mL×3). The combined organics were washed with brine, dried over Na$_2$SO$_4$, filtered and concentrated under reduced pressure to give a residue, which was purified by silica gel column chromatography (silica gel, 0-25% ethyl acetate in petroleum ether) to afford the desired product as a yellow oil. ESI-MS m/z: (M+H)$^+$=512.0.

Step D: Preparation of N-(7-((tert-butyldiphenylsilyl) oxy)heptyl)-6-chloro-5-(chloromethyl)pyrimidin-4-amine (23-3). To a solution of (4-((7-((tert-butyldiphenylsilyl)oxy) heptyl)amino)-6-chloropyrimidin-5-yl)methanol (3.12 g, 1.0 eq., 6.10 mmol) in dichloromethane (30 mL) was added SOCl$_2$ (762 mg, 1.05 eq., 6.41 mmol) at 0° C. The mixture was stirred at room temperature overnight, poured into sat. NaHCO$_3$ (30 mL), and extracted with DCM (30 mL×3). The combined organics were washed with brine, dried over Na$_2$SO$_4$, filtered and concentrated under reduced pressure to give a residue, which was purified by silica gel column chromatography (0-10% methanol in dichloromethane) to give the desired product as a yellow oil. ESI-MS m/z: (M+H)$^+$=530.2.

Step E: Preparation of N-(7-((tert-butyldiphenylsilyl)oxy) heptyl)-6-chloro-5-(((tetrahydro-2H-pyran-4-yl)amino) methyl)pyrimidin-4-amine (23-4). To a solution of 23-3 (1.0 g, 1.0 eq., 1.89 mmol) in DMA (25 mL) were added K$_2$CO$_3$ (574 mg, 2.2 eq., 4.16 mmol) and tetrahydro-2H-pyran-4-amine (200 mg, 1.05 eq., 1.98 mmol) at room temperature. The mixture was stirred at 50° C. for 3 hours and cooled to room temperature, then diluted with water (250 mL) and extracted with ethyl acetate (100 mL×3). The combined organics were washed with brine, dried over Na$_2$SO$_4$, filtered and concentrated under reduced pressure to give a residue, which was purified by silica gel column chromatography (0%-30% ethyl acetate in petroleum ether (containing 10% TEA)) to give the desired product as a yellow oil. ESI-MS m/z: (M+H)$^+$=595.0.

Step F: Preparation of 1-(7-((tert-butyldiphenylsilyl)oxy) heptyl)-5-chloro-3-(tetrahydro-2H-pyran-4-yl)-3,4-dihydropyrimido[4,5-d]pyrimidin-2(1H)-one (23-5). To a solution of 23-4 (660 mg, 1.0 eq., 1.11 mmol) and triethylamine (785 mg, 7.0 eq., 7.77 mmol) in dichloromethane (20 mL) was added triphosgene (330 mg, 1.0 eq., 1.11 mmol) at 0° C. The resulting mixture was stirred for 30 min, then warmed and stirred at 40° C. for 24 hours. The mixture was cooled to room temperature, then treated with aq. NaHCO$_3$ (50 mL) and extracted with dichloromethane (50 mL×3). The combined organics were washed with brine, dried over Na$_2$SO$_4$, filtered and concentrated under reduced pressure to give a residue, which was purified by silica gel column chromatography (silica gel, 0-10% methanol in dichloromethane) to give the desired product. ESI-MS m/z: (M+H)$^+$=621.0.

Step G: Preparation of tert-butyl (R)-4-(difluoro(3-(1-((8-(7-hydroxyheptyl)-7-oxo-6-(tetrahydro-2H-pyran-4-yl)-5,6,7,8-tetrahydropyrimido[4,5-d]pyrimidin-4-yl)amino)ethyl) phenyl)methyl)-piperidine-1-carboxylate (23-6). A mixture of 23-5 (200 mg, 1.0 eq., 0.323 mmol), 4-2 (126 mg, 1.1 eq., 0.355 mmol) and KF (243 mg, 13.0 eq., 4.19 mmol) in dry DMSO (5 mL) was stirred at 100° C. overnight under nitrogen. The reaction mixture was then cooled, poured into water (50 mL), and extracted with ethyl acetate (40 mL×3). The combined organics were washed with brine, dried over Na$_2$SO$_4$, filtered and concentrated under reduced pressure to give a residue, which was purified by silica gel column chromatography (silica gel, 0-10% methanol in dichloromethane) to afford the desired product. ESI-MS m/z: (M+H)$^+$=701.0.

Step H: Preparation of tert-butyl (R)-4-((3-(1-((8-(7-((ethylsulfonyl)oxy)heptyl)-7-oxo-6-(tetrahydro-2H-pyran-4-yl)-5,6,7,8-tetrahydropyrimido[4,5-d]pyrimidin-4-yl) amino)ethyl)-phenyl)difluoromethyl)piperidine-1-carboxylate (23-7). To a solution of 23-6 (220 mg, 1.0 eq., 0.314 mmol) and triethylamine (159 mg, 5.0 eq., 1.571 mmol) in dichloromethane (22 mL) was added ethanesulfonyl chloride (162 mg, 4.0 eq., 1.257 mmol) dropwise at 0° C. The mixture was stirred at the same temperature for 10 min, diluted with water (20 mL), and extracted with DCM (20 mL×3). The combined organics were washed with brine, dried over Na$_2$SO$_4$, filtered and concentrated under pressure to give a residue, which was purified by silica gel column chromatography (0-5% methanol in dichloromethane) to give the desired product as a white solid. ESI-MS m/z: (M+H)$^+$=793.2.

Step I: Preparation of (R)-7-(5-((1-(3-(difluoro(piperidin-4-yl)methyl)phenyl)ethyl)amino)-2-oxo-3-(tetrahydro-2H-pyran-4-yl)-3,4-dihydropyrimido[4,5-d]pyrimidin-1(2H)-yl)heptyl ethanesulfonate. To a solution of 23-7 (165 mg, 1.0 eq., 0.208 mmol) in dichloromethane (4.25 mL) was added TFA (0.85 mL) at room temperature. The mixture was stirred for 30 minutes and concentrated to give the desired product (180 mg crude) as light-yellow oil, which was used in next step directly without further purification. ESI-MS m/z: (M+H)$^+$=693.1.

Step J: Preparation of (4R)-2,2-difluoro-4-methyl-6$^3$-(tetrahydro-2H-pyran-4-yl)-6$^1$,6$^2$,6$^3$,6$^4$-tetrahydro-5-aza-6(5,1)-pyrimido[4,5-d]pyrimidina-1(4,1)-piperidina-3(1,3)-benzenacyclotridecaphan-6$^2$-one (185). To a solution of (R)-7-(5-(((1-(3-(difluoro(piperidin-4-yl)methyl)phenyl)ethyl) amino)-2-oxo-3-(tetrahydro-2H-pyran-4-yl)-3,4-dihydropyrimido[4,5-d]pyrimidin-1(2H)-yl)heptyl ethanesulfonate (180 mg crude, 0.208 mmol) in acetonitrile (52 mL, 0.005 M) was added N,N-diisopropylethylamine (335 mg, 2.601 mmol) at room temperature. The mixture was stirred at 70° C. for 16 hours under nitrogen, then cooled to room temperature and concentrated under reduced pressure to give a residue, which was diluted with dichloromethane (80 mL). The mixture was treated with sat. aqueous NaHCO$_3$ (80 mL) and stirred for 2 hours. The organic layer was collected, and the aqueous layer was extracted with DCM (50 mL×3). The combined organics were washed with brine, dried over Na$_2$SO$_4$, filtered and concentrated under reduced pressure to give a residue, which was purified by silica gel column chromatography (0-5% methanol in dichloromethane) to give the desired product as a white solid. ESI-MS m/z: (M+H)$^+$=583.3. $^1$H NMR (400 MHz, DMSO) δ 7.98 (s, 1H), 7.56-7.42 (m, 2H), 7.20 (d, J=6.6 Hz, 2H), 7.04 (d, J=6.3 Hz, 1H), 5.21-5.08 (m, 1H), 4.55-4.40 (m, 1H), 4.28-4.17 (m, 2H), 4.14-4.04 (m, 1H), 4.00-3.97 (m, 2H), 3.78-3.70 (m, 1H), 3.45-3.39 (m, 2H), 2.80-2.65

(m, 2H), 2.30-2.18 (m, 1H), 2.15-1.68 (m, 3H), 1.90-1.68 (m, 3H), 1.61-1.55 (m, 4H), 1.55-1.26 (m, 8H), 1.20-0.75 (m, 7H).

Example 24: Synthesis of (R)-2,2-difluoro-6⁴,4-dimethyl-6⁷-morpholino-7-oxa-5-aza-6(1,6)-phthalazina-1(4,1)-piperidina-3(1,3)-benzenacyclotetradecaphane (206)

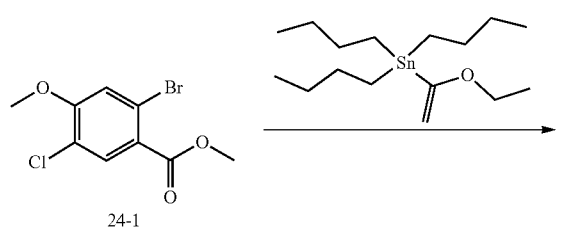

24-1

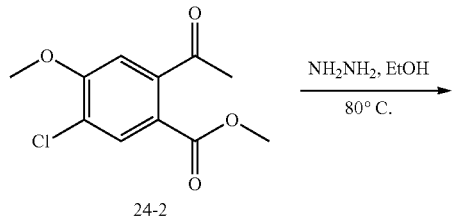

24-2

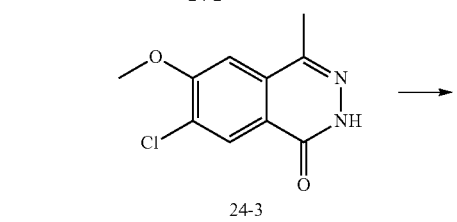

24-3

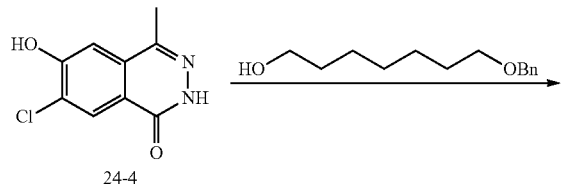

24-4

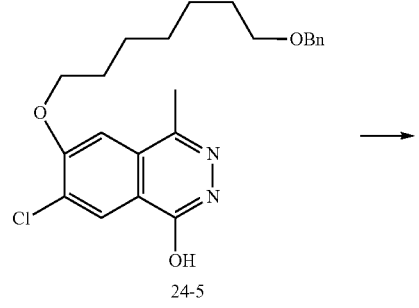

24-5

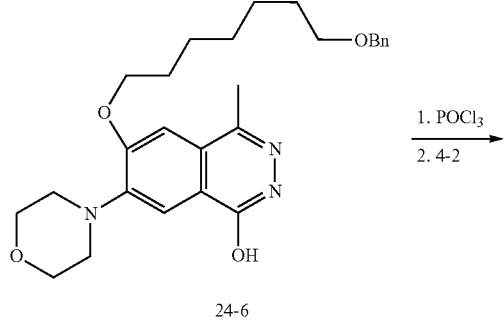

24-6

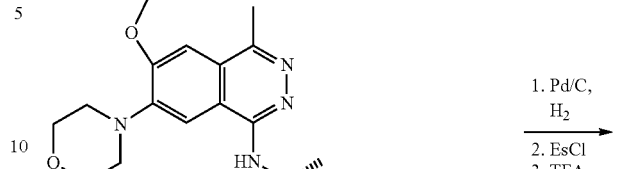

24-7

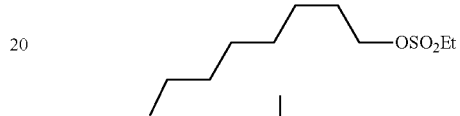

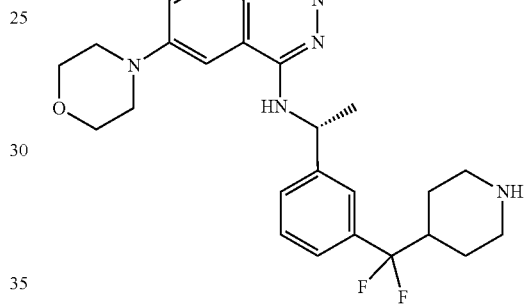

24-8

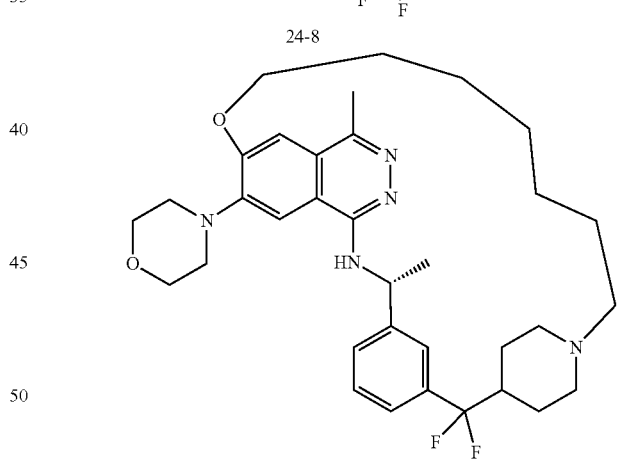

206

Step A: Preparation of methyl 2-acetyl-5-chloro-4-methoxybenzoate (24-2). A solution of methyl 2-bromo-5-chloro-4-methoxybenzoate (24-1) (1.4 g, 1.0 eq., 5.04 mmol), tributyl(1-ethoxyvinyl)stannane (2.73 g, 1.5 eq., 7.54 mmol) and bis(triphenylphosphine)palladium(II) chloride (353 mg, 0.1 eq., 0.50 mmol) in dry 1,4-dioxane (50 mL) was stirred at 100° C. for 16 hours under nitrogen atmosphere. The reaction mixture was cooled to room temperature, diluted with sat. aqueous KF (aq., 50 mL) and stirred for 1 hour, then filtered and the filtrate extracted with ethyl acetate (3×50 mL). The combined organics were washed with brine, dried over Na₂SO₄, filtered and concentrated under reduced pressure to give a residue, which was dissolved into THF (20 mL) and HCl (20 mL, 3 M in water). The mixture was stirred at room temperature for 1 hour, then extracted with ethyl acetate (3×80 mL). The combined organics were washed with brine, dried over $Na_2SO_4$, filtered and concentrated under reduced pressure to give a residue, which was purified by silica gel column chromatograph (0-100% dichloromethane in petroleum ether) to afford the desired product as a white solid. ESI-MS m/z: $(M+H)^+$=242.9. $^1H$ NMR (400 MHz, DMSO): δ 7.87 (s, 1H), 7.28 (s, 1H), 3.97 (s, 3H), 3.79 (s, 3H), 3.30 (s, 3H), 2.48 (s, 3H).

Step B: Preparation of 7-chloro-6-methoxy-4-methylphthalazin-1(2H)-one (24-3). A solution of 24-2 (1.1 g, 1.0 eq., 4.55 mmol) and hydrazine hydrate (296 mg, 1.3 eq., 5.91 mmol) in ethanol (40 mL) was stirred at 80° C. for 16 hours. The reaction mixture was cooled to room temperature and concentrated under reduced pressure to give a residue, which was triturated in ethanol (10 mL) and filtered to afford the desired product as a white solid. ESI-MS m/z: $(M+H)^+$= 225.0. $^1H$ NMR (400 MHz, DMSO): δ 12.44 (s, 1H), 8.19 (s, 1H), 7.39 (s, 1H), 4.08 (s, 3H), 2.54 (s, 3H).

Step C: Preparation of 7-chloro-6-hydroxy-4-methylphthalazin-1(2H)-one (24-4). To a solution of 24-3 (500 mg, 1.0 eq., 2.23 mmol) in dry 1,2-dichloroethane (12 mL) was added $BBr_3$ (1.68 g, 3.0 eq., 6.69 mmol). The mixture was stirred at 80° C. for 16 hours, then cooled to room temperature, quenched with methyl alcohol (20 mL) and concentrated to afford the desired product as a light yellow solid, which was used directly in the next step without further purification. ESI-MS m/z: $(M+H)^+$=210.9. $^1H$ NMR (400 MHz, DMSO) δ 12.31 (s, 1H), 8.13 (s, 1H), 7.28 (s, 1H), 2.42 (s, 3H).

Step D: Preparation of 6-((7-(benzyloxy)heptyl)oxy)-7-chloro-4-methylphthalazin-1-ol (24-5). To a solution of 24-4 (500 mg, 2.38 mmol) and 7-(benzyloxy)heptan-1-ol (1.06 g, 2.0 eq., 4.76 mmol) in toluene (50 mL), was added (cyanomethylene)tributylphosphorane (1.15 g, 2.0 eq., 4.76 mmol) at room temperature. The mixture was stirred for 2 hours at 80° C., then cooled to room temperature, diluted with water (50 mL) and extracted with ethyl acetate (3×50 mL). The combined organics were washed with brine, dried over $Na_2SO_4$, filtered and concentrated under reduced pressure to give a residue, which was purified by silica gel column chromatography (0%~50% ethyl acetate in petroleum ether) to afford the desired product as a white solid. ESI-MS m/z: $(M+H)^+$=415.2.

Step E: Preparation of 6-((7-(benzyloxy)heptyl)oxy)-4-methyl-7-morpholinophthalazin-1-ol (24-6). To a mixture of 24-5 (370 mg, 1.0 eq., 0.90 mmol), morpholine (117 mg, 1.5 eq., 1.34 mmol), tris(dibenzylideneacetone)dipalladium (41 mg, 0.05 eq., 0.05 mmol), and Ru-Phos (42 mg, 0.1 eq., 0.09 mmol) in dry 1,4-dioxane (30 mL) was added t-BuOK (1.8 mL, 2.0 eq., 1.80 mmol, 1M in THF). The mixture was stirred at 110° C. for 20 hours under nitrogen, then cooled to room temperature, diluted with water (50 mL) and extracted with ethyl acetate (50 mL×3). The combined organics were washed with brine, dried over $Na_2SO_4$, filtered and concentrated under reduced pressure to give a residue, which was purified by silica gel column chromatograph (0%~5% dichloromethane in ethyl acetate) to give the desired product as a light-yellow solid. ESI-MS m/z: $(M+H)^+$=466.2.

Step F: Preparation of 4-(7-((7-(benzyloxy)heptyl)oxy)-4-chloro-1-methylphthalazin-6-yl)morpholine. To a solution of 24-6 (230 mg, 1.0 eq., 0.50 mmol) in phosphorus oxychloride (10 mL) was added N-ethyl-N-(1-methylethyl)-2-propanamine (193 mg, 3.0 eq., 1.47 mmol) dropwise at room temperature. The mixture was stirred at 90° C. for 30 minutes under nitrogen, then cooled to room temperature and concentrated under reduced pressure to give a residue which was dissolved in ethyl acetate (50 mL) and washed with sat. aqueous $NaHCO_3$ (50 mL×1). The organic layer was washed with brine, dried over $Na_2SO_4$, filtered and concentrated under reduced pressure to give a residue, which was purified by silica gel column chromatography (0%-100% ethyl acetate in petroleum ether) to obtain the desired product as a yellow solid. ESI-MS m/z: $(M+H)^+$=484.2.

Step G: Preparation of tert-butyl (R)-4-((3-(1-((6-((7-(benzyloxy)heptyl)oxy)-4-methyl-7-morpholinophthalazin-1-yl)amino)ethyl)phenyl)difluoromethyl)piperidine-1-carboxylate (24-7). A mixture of 4-(7-((7-(benzyloxy)heptyl)oxy)-4-chloro-1-methylphthalazin-6-yl)morpholine (200 mg, 1.0 eq., 0.52 mmol), 4-2 (184 mg, 1.0 eq., 0.52 mmol), tris(dibenzylideneacetone)dipalladium (48 mg, 0.1 eq., 0.052 mmol), BINAP (65 mg, 0.2 eq., 0.11 mmol) and $Cs_2CO_3$ (423 mg, 2.5 eq., 1.3 mmol) in dry 1,4-dioxane (40 mL) was stirred at 110° C. for 16 hours under nitrogen. The reaction mixture was then cooled to room temperature, poured into water (40 mL), and extracted with ethyl acetate (50 mL×2). The combined organics were washed with brine, dried over $Na_2SO_4$, filtered and concentrated under reduced pressure to give a residue, which was purified by silica gel column chromatography (0%~100% ethyl acetate in petroleum ether) to afford the desired product as a yellow solid. ESI-MS m/z: $(M+H)^+$=801.1.

Step H: Preparation of tert-butyl (R)-4-(difluoro(3-(1-((6-((7-hydroxyheptyl)oxy)-4-methyl-7-morpholinophthalazin-1-yl)amino)ethyl)phenyl)methyl)piperidine-1-carboxylate. To a solution of 24-7 (200 mg, 1.0 eq., 0.25 mmol) in methanol (40 mL) was added Pd/C (200 mg). The mixture was stirred at 50° C. for 12 hours under hydrogen, then cooled to room temperature, filtered and the filtrate concentrated to give a residue. The residue was purified by prep-TLC (methanol:dichloromethane=1:15) to give the desired product as a yellow oil. ESI-MS m/z: $(M+H)^+$=712.0.

Step I: Preparation of tert-butyl (R)-4-((3-(1-((6-((7-((ethylsulfonyl)oxy)heptyl)oxy)-4-methyl-7-morpholinophthalazin-1-yl)amino)ethyl)phenyl)difluoromethyl)piperidine-1-carboxylate. To a solution of tert-butyl (R)-4-(difluoro(3-(1-((6-((7-hydroxyheptyl)oxy)-4-methyl-7-morpholinophthalazin-1-yl)amino)ethyl)phenyl) methyl) piperidine-1-carboxylate (100 mg, 1.0 eq., 0.14 mmol) and triethylamine (72 mg, 5.0 eq., 0.71 mmol) in dichloromethane (20 mL) was added ethanesulfonyl chloride (73 mg, 4.0 eq., 0.56 mmol) dropwise at 0° C. The solution was stirred for 10 minutes, then diluted with water (40 mL) and dichloromethane (40 mL). The organic layer was collected and the aqueous layer was extracted with dichloromethane (2×40 mL). The combined organics were washed with brine, dried over $Na_2SO_4$, filtered and concentrated under reduced pressure to give a residue, which was purified by silica gel column chromatography ((0%~100% ethyl acetate in petroleum ether)) to afford the desired product as a brown oil. ESI-MS m/z: $(M+H)^+$=804.

Step J: Preparation of (R)-7-((1-((1-(3-(difluoro(piperidin-4-yl)methyl)phenyl)ethyl)amino)-4-methyl-7-morpholinophthalazin-6-yl)oxy)heptyl ethanesulfonate (24-8). To a stirred solution of tert-butyl (R)-4-((3-(1-((6-((7-((ethylsulfonyl)oxy)heptyl)oxy)-4-methyl-7-morpholinophthalazin-1-yl)amino)ethyl)phenyl)difluoromethyl) piperidine-1-carboxylate (100 mg, 1.0 eq., 0.14 mmol) in dichloromethane (5 mL) was added TFA (1 mL) at room temperature. The mixture was stirred at room temperature for 30 minutes and concentrated to give the desired product as a yellow oil, which was used in the next step without further purification. ESI-MS m/z: (M+H)+=704.

Step K: Preparation of (R)-2,2-difluoro-6⁴,4-dimethyl-6⁷-morpholino-7-oxa-5-aza-6(1,6)-phthalazina-1(4,1)-piperidina-3(1,3)-benzenacyclotetradecaphane (206). To a solution of 24-8 (87 mg crude, 1.0 eq., 0.14 mmol) in acetonitrile (24 mL, 0.005 M) was added N,N-diisoproylethylamine (161.14 mg, 10 eq., 1.25 mmol) at room temperature. The solution was stirred at 70° C. for 40 hours, then cooled to room temperature and concentrated under reduced pressure to give a residue. The residue was suspended in dichloromethane (80 mL) and treated with sat. NaHCO₃ (80 mL). The resulting mixture was stirred for 2 hours. The organic layer was collected, and the aqueous layer was extracted with dichloromethane (2×50 mL). The combined organics were washed with brine, dried over Na₂SO₄, filtered and concentrated under reduced pressure to give a residue, which was purified by silica gel column chromatography (0%-100% (methanol:dichloromethane=1:15) in DCM)) to afford the desired product as a light-yellow solid. ESI-MS m/z: (M+H)+=594.5. ¹H NMR (400 MHz, DMSO) δ 7.77 (s, 1H), 7.52 (d, J=7.8 Hz, 1H), 7.41-7.39 (m, 2H), 7.25 (s, 1H), 7.18 (d, J=7.1 Hz, 1H), 5.55-5.45 (m, 1H), 4.36-4.34 (m, 1H), 4.29-4.21 (m, 1H), 3.86-3.80 (m, 4H), 3.32-3.19 (m, 4H), 2.56 (s, 3H), 2.22-2.01 (m, 3H), 1.93-1.85 (m, 1H), 1.72-1.35 (m, 12H), 1.21-1.03 (m, 5H), 0.72-0.46 (m, 2H).

Example 25: Synthesis of (3R)-5⁶-(1,1-dioxidotetrahydro-2H-thiopyran-4-yl)-3,14-dimethyl-5⁷,5⁸-dihydro-4,14-diaza-5(4,8)-pyrido[2,3-d]pyrimidina-2(2,5)-thiophena-1(1,2)-benzenacyclopentadecaphan-5⁷-one (205)

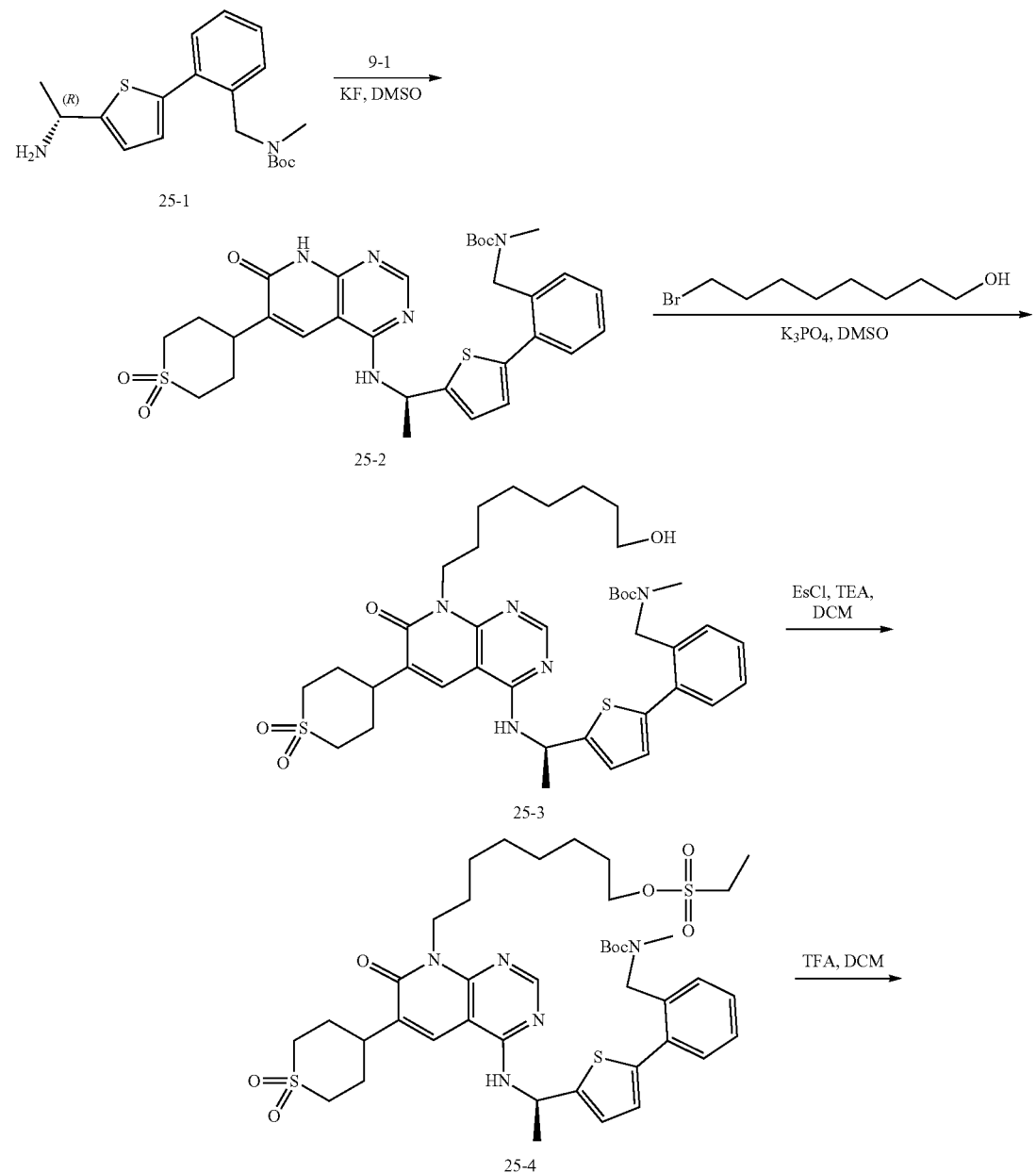

577 578

-continued

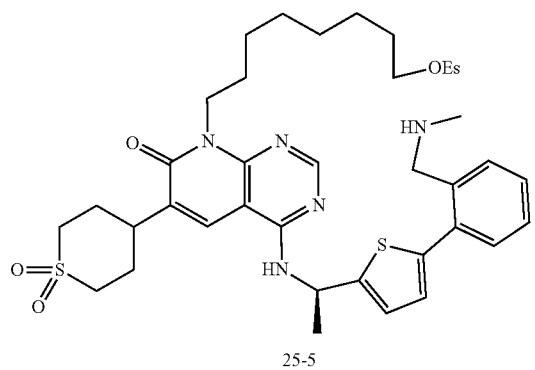

25-5

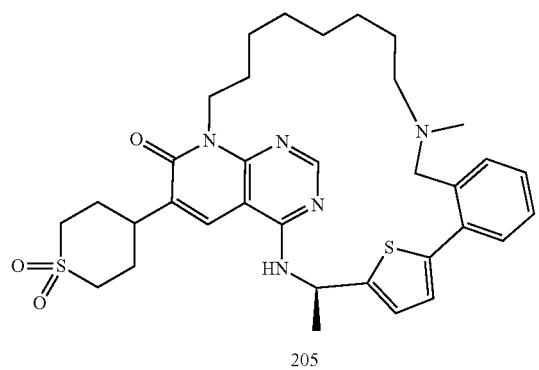

205

Step A: Preparation of tert-butyl (R)-(2-(5-(1-(((6-(1,1-dioxidotetrahydro-2H-thiopyran-4-yl)-7-oxo-7,8-dihydro-pyrido[2,3-d]pyrimidin-4-yl)amino)ethyl)thiophen-2-yl)benzyl)(methyl)-carbamate (25-2). To a solution of tert-butyl (R)-(2-(5-(1-aminoethyl)thiophen-2-yl)benzyl)(methyl)carbamate (25-1, 110 mg, 1.0 eq., 0.32 mmol) in anhydrous DMSO (2 mL) were added 9-1 (119 mg, 1.2 eq., 0.38 mmol) and potassium fluoride (111 mg, 6.0 eq., 1.90 mmol). The reaction mixture was stirred for 2 hours at 100° C. under nitrogen, then cooled to room temperature, poured into water, and extracted with ethyl acetate (3×10 mL). The combined organics were washed with brine, dried over $Na_2SO_4$, filtered and concentrated under reduced pressure to give a residue, which was purified by silica gel column chromatography (85-95% ethyl acetate in petroleum ether) to provide the desired product as a white solid. ESI-MS m/z: $(M+H)^+=624$.

Step B: Preparation of tert-butyl (R)-(2-(5-(1-(((6-(1,1-dioxidotetrahydro-2H-thiopyran-4-yl)-8-(8-hydroxyoctyl)-7-oxo-7,8-dihydropyrido[2,3-d]pyrimidin-4-yl)amino)ethyl)thiophen-2-yl)benzyl)(methyl)carbamate (25-3). To a solution of 25-2 (120 mg, 1.0 eq., 0.19 mmol) in DMSO (2 mL) were added 8-bromooctan-1-ol (61 mg, 1.5 eq., 0.29 mmol) and potassium phosphate tribasic (123 mg, 3.0 eq., 0.58 mmol). The reaction mixture was stirred for 2 hours at room temperature, then poured into water and extracted with ethyl acetate (3×10 mL). The combined organics were washed with brine, dried over $Na_2SO_4$, filtered and concentrated under reduced pressure to give a residue, which was purified by silica gel column chromatography (85-95% ethyl acetate in petroleum ether) to afford the desired product as a white solid. ESI-MS m/z: $(M+H)^+=752$.

Step C: Preparation of (R)-8-(4-((1-(5-(2-(((tert-butoxycarbonyl)(methyl)amino)methyl)-phenyl)thiophen-2-yl)ethyl)amino)-6-(1,1-dioxidotetrahydro-2H-thiopyran-4-yl)-7-oxopyrido-[2,3-d]pyrimidin-8(7H)-yl)octyl ethanesulfonate (25-4). To a solution of 25-3 (110 mg, 1.0 eq., 0.15 mmol) and triethylamine (74 mg, 5.0 eq., 0.73 mmol) in DCM (2 mL) was added ethanesulfonyl chloride (76 mg, 4.0 eq., 0.59 mmol) dropwise at 0° C. The mixture was then stirred for 10 minutes at room temperature and concentrated. The residue was purified by silica gel column chromatography (70-80% ethyl acetate in petroleum ether) to provide the desired product as a white solid. ESI-MS m/z: $(M+H)^+=844$.

Step D: Preparation of (R)-8-(6-(1,1-dioxidotetrahydro-2H-thiopyran-4-yl)-4-((1-(5-(2-((methylamino)methyl)phenyl)thiophen-2-yl)ethyl)amino)-7-oxopyrido[2,3-d]pyrimidin-8(7H)-yl)octyl ethanesulfonate (25-5). To a solution of 25-4 (100 mg, 1.0 eq., 0.12 mmol) in DCM (5 mL) was added trifluoroacetic acid (1 mL) at 0° C. The mixture was stirred for 2 hours at room temperature and concentrated to provide the desired product (110 mg crude) as a white solid, which was used directly in the next step without further purification. ESI-MS m/z: $(M+H)^+=744$.

Step E: Preparation of (3R)-5[6]-(1,1-dioxidotetrahydro-2H-thiopyran-4-yl)-3,14-dimethyl-5[7],5[8]-dihydro-4,14-di-aza-5(4,8)-pyrido[2,3-d]pyrimidina-2(2,5)-thiophena-1(1,2)-benzenacyclopentadecaphan-5[7]-one (205). To a solution of 25-5 (110 mg, 1.0 eq., 0.15 mmol) in acetonitrile (28 mL) was added N,N-diisopropylethylamine (1.91 g, 100.0 eq., 14.8 mmol) and the resulting mixture was stirred for 36 hours at 70° C. The reaction mixture was cooled to room temperature, then concentrated to give a residue. The residue was purified by silica gel column chromatography (85-95% ethyl acetate in petroleum ether), then purified with prep-HPLC (formic acid) to afford the desired product. ESI-MS m/z: $(M+H)^+=634$. $^1$H NMR (400 MHz, DMSO-D2O) δ 8.41 (s, 1H), 8.20 (s, 1H), 7.45-7.35 (m, 1H), 7.35-7.25 (m, 3H), 7.04 (d, J=3.6 Hz, 1H), 6.99 (d, J=3.6 Hz, 1H), 5.88 (d, J=6.9 Hz, 1H), 4.64 (s, 1H), 4.43-4.21 (m, 1H), 3.48-3.08 (m, 8H), 2.20-1.94 (m, 8H), 1.80-1.63 (m, 5H), 1.16-0.96 (m, 5H), 0.93-0.81 (m, 3H), 0.76-0.55 (m, 2H).

Example 26: Synthesis of (4R,E)-2,2-difluoro-6[7],4-dimethyl-6[3]-morpholino-6[1],6[2],6[7],6[8]-tetrahydro-5-aza-6(5,1)-pyrido[2,3-d]pyridazina-1(4,1)-piperidina-3(1,3)-benzenacyclotridecaphane-6[2],6[8]-dione (183)

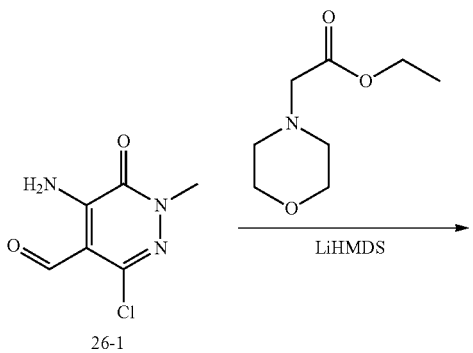

26-1

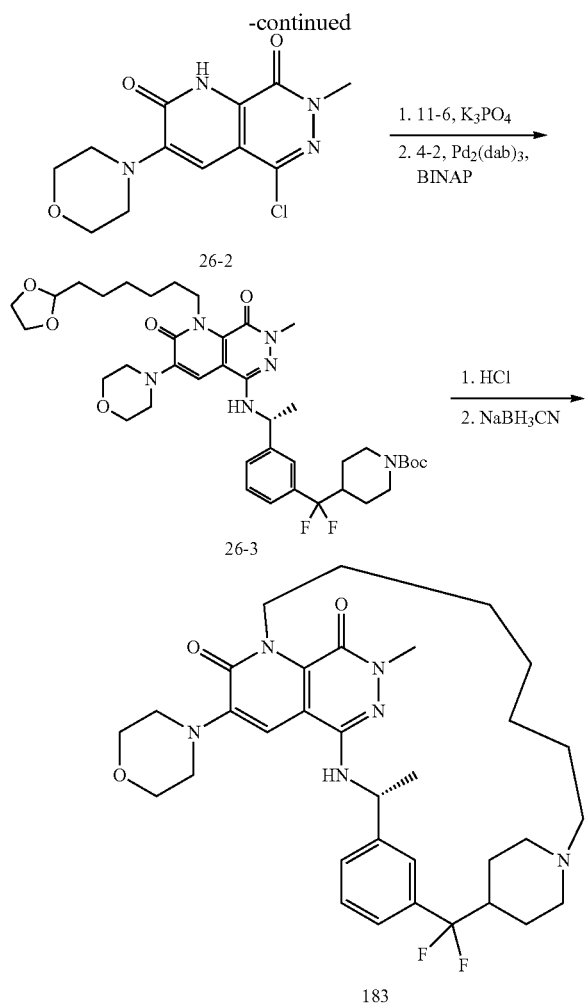

Step A: Preparation of 5-chloro-7-methyl-3-morpholino-1,7-dihydropyrido[2,3-d]pyridazine-2,8-dione (26-2). To a stirred solution of 5-amino-3-chloro-1-methyl-6-oxo-1,6-dihydropyridazine-4-carbaldehyde (26-1, 1.0 g, 1.0 eq., 5.35 mmol) and ethyl 2-morpholinoacetate (1.85 g, 2.0 eq., 10.7 mmol) in dry THF (50 mL) was added lithium bis(trimethylsilyl)amide (32.1 mL, 6.0 eq., 32.1 mmol, 1M) dropwise at −78° C. under nitrogen. The resulting mixture was allowed to warm to room temperature and stirred for 1 hour, then quenched with sat. aqueous NH₄Cl and adjusted to pH ~3 with HCl (3N, aq.). The resulting solution was extracted with DCM/MeOH (V/V=10:1, 50 mL×6). The combined organics were washed with brine, dried over Na₂SO₄, filtered and concentrated under reduced pressure to give a residue, which was purified by com-flash silica gel column (0%-5% MeOH in DCM) to afford the desired product as a light-yellow solid. ESI-MS m/z: (M+H)⁺=297.0.

Step B: Preparation of 1-(6-(1,3-dioxolan-2-yl)hexyl)-5-chloro-7-methyl-3-morpholino-1,7-dihydropyrido[2,3-d]pyridazine-2,8-dione. To a solution of 26-2 (1.0 g, 1.0 eq., 3.38 mmol) in DMSO (20 mL) was added 11-6 (798 mg, 1.0 eq., 3.38 mmol) and K₃PO₄ (2.15 mg, 3.0 eq., 10.14 mmol). The resulting mixture was stirred at room temperature for 3 days, then heated to 100° C. for 4 hours. The reaction mixture was cooled to room temperature and diluted with ethyl acetate/water (50 mL/200 mL). The organic phase was separated and the aqueous phase was extracted with ethyl acetate (60 mL×3). The combined organics were washed with brine, dried over Na₂SO₄, filtered and concentrated under reduced pressure to give a residue, which was purified by com-flash silica gel column (0%-50% ethyl acetate/DCM (V/V=1/1) in PE) to provide the desired product as a light yellow solid. ESI-MS m/z: (M+H)⁺=453.2.

Step C: Preparation of tert-butyl (R)-4-((3-(1-((1-(6-(1,3-dioxolan-2-yl)hexyl)-7-methyl-3-morpholino-2,8-dioxo-1,2,7,8-tetrahydropyrido[2,3-d]pyridazin-5-yl)amino)ethyl)phenyl)-difluoromethyl)piperidine-1-carboxylate (26-3). A mixture of 1-(6-(1,3-dioxolan-2-yl)hexyl)-5-chloro-7-methyl-3-morpholino-1,7-dihydropyrido[2,3-d]pyridazine-2,8-dione (250 mg, 1.0 eq., 0.553 mmol), 4-2 (196 mg, 1.0 eq., 0.553 mmol), Pd₂(dba)₃ (51 mg, 0.1 eq., 0.0553 mmol), BINAP (70 mg, 0.2 eq., 0.111 mmol) and cesium carbonate (449 mg, 2.5 eq., 1.38 mmol) in dry 1,4-dioxane (25 mL) was heated at 110° C. with stirring for 16 hours under nitrogen. The reaction mixture was cooled down to room temperature, then diluted with water (50 mL) and ethyl acetate (40 mL). The organic phase was separated, and the aqueous phase was extracted with ethyl acetate (50 mL×2). The combined organics were washed with brine, dried over Na₂SO₄, filtered and concentrated under reduced pressure to give a residue, which was purified by com-flash column (0%~50% ethyl acetate in petroleum ether) to afford the desired product as a light yellow foamed solid. ESI-MS m/z: (M+H)⁺=771.3.

Step D: Preparation of (R)-7-(5-((1-(3-(difluoro(piperidin-4-yl)methyl)phenyl)ethyl)amino)-7-methyl-3-morpholino-2,8-dioxo-7,8-dihydropyrido[2,3-d]pyridazin-1(2H)-yl)heptanal. To a stirred solution of 26-3 (150 mg, 1.0 eq., 0.195 mmol) in THF (5 mL) was added HCl (10 mL, 20 mmol, 2N) dropwise and the resulting mixture was stirred at room temperature for 72 hours. The reaction mixture was diluted with ethyl acetate (15 mL), cooled to 0° C., adjusted to pH ~8 with sat. NaHCO₃, then extracted with ethyl acetate/THF (V/V=3:1, 50 mL×3). The combined organics were washed with brine, dried over Na₂SO₄, filtered and concentrated under reduced pressure to give the desired product as light-yellow oil, which was used directly in the next step without further purification. ESI-MS m/z: (M+H)⁺= 627.3.

Step E: Preparation of (4R,E)-2,2-difluoro-6⁷,4-dimethyl-6³-morpholino-6¹,6²,6⁷,6⁸-tetrahydro-5-aza-6(5,1)-pyrido[2,3-d]pyridazina-1(4,1)-piperidina-3(1,3)-benzenacyclotridecaphane-6²,6⁸-dione (183). To a stirred solution of (R)-7-(5-((1-(3-(difluoro(piperidin-4-yl)methyl)phenyl)ethyl)amino)-7-methyl-3-morpholino-2,8-dioxo-7,8-dihydropyrido[2,3-d]pyridazin-1(2H)-yl)heptanal (160 mg crude, 1.0 eq., ~0.195 mmol) in MeOH/1,2-dichloroethane (130 mL/65 mL, 0.001 M) was added acetic acid (2 drops) and the result solution was stirred at room temperature for 30 minutes. Sodium cyanoborohydride (31 mg, 2.5 eq., 0.488 mmol) was added and the resulting mixture was stirred at room temperature for 1 hour. The reaction mixture was concentrated under reduced pressure to give a residue, which was diluted with DCM/sat. NaHCO₃ and extracted with DCM (50 mL×3). The combined organics were washed with brine, dried over Na₂SO₄, filtered and concentrated under reduced pressure to give a residue, which was purified by com-flash silica gel column (0%~5% MeOH in DCM) and prep-HPLC (formic acid) to provide the desired product as a yellow solid. ESI-MS m/z: (M+H)⁺=611.5. ¹H NMR (400 MHz, DMSO-D2O) 7.53-7.39 (m, 2H), 7.30-7.17 (m, 2H), 7.00 (s, 1H), 5.62-5.50 (m, 1H), 4.80 (q, J=6.8 Hz, 1H), 4.42-4.33 (m, 1H), 3.83-3.75 (m, 4H), 3.48-3.43 (m, 2H), 3.33-3.26 (m, 2H), 3.12 (s, 3H), 2.81-2.71 (m, 2H), 2.32-

2.23 (m, 1H), 2.19-2.09 (m, 1H), 1.96-1.68 (m, 4H), 1.57 (d, J=7.0 Hz, 3H), 1.49-1.26 (m, 9H), 1.12-0.93 (m, 2H), 0.78-0.51 (m, 2H).
Example 27: Synthesis of (R)-2,2-difluoro-6[4],4-dimethyl-6[7]-morpholino-7-oxa-5-aza-6(1,5)-phthalazina-1(4,1)-piperidina-3(1,3)-benzenacyclotridecaphane (196)
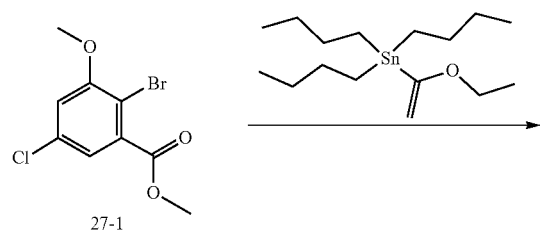
27-1
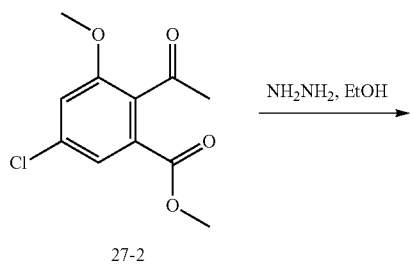
27-2
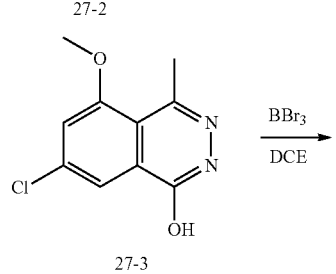
27-3
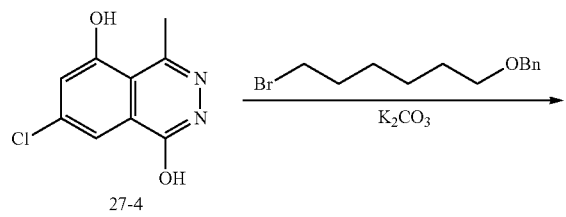
27-4
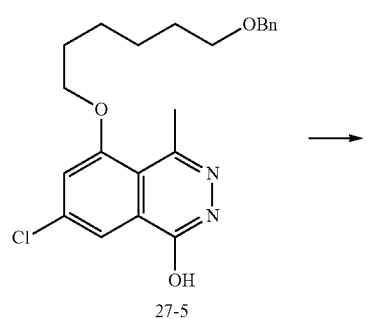
27-5
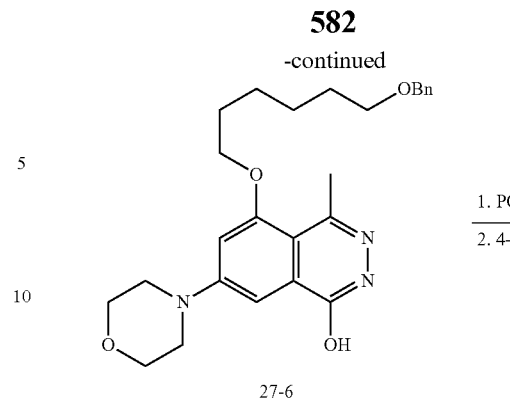
27-6
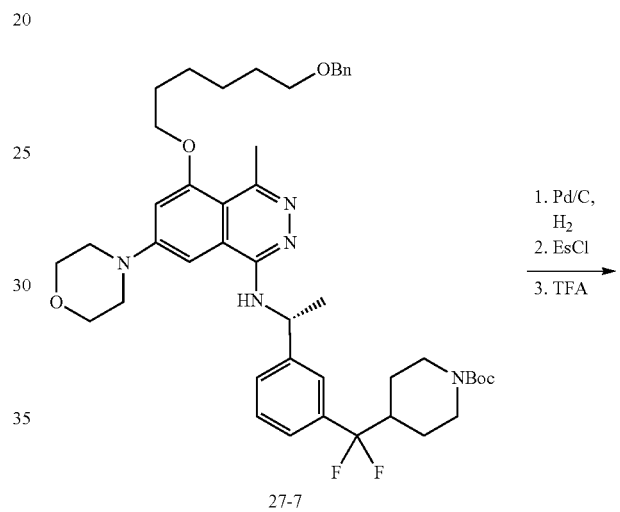
27-7
27-8

-continued

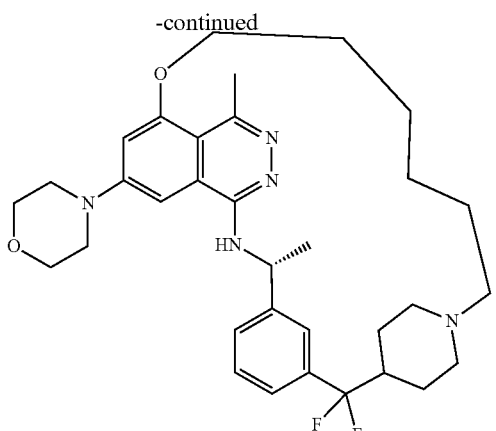

196

Step A: Preparation of methyl 2-acetyl-5-chloro-3-methoxybenzoate (27-2). A mixture of methyl 2-bromo-5-chloro-3-methoxybenzoate (27-1, 2.0 g, 1.0 eq., 7.2 mmol), tributyl(1-ethoxyvinyl)stannane (3.90 g, 1.5 eq., 10.8 mmol) and Pd(PPh$_3$)$_2$Cl$_2$ (510 mg, 0.1 eq., 0.72 mmol) in dry 1,4-dioxane (30 mL) was stirred at 100° C. for 16 hours under nitrogen atmosphere. The mixture was cooled to room temperature and quenched with sat. aqueous KF, then stirred for 1 hour. This mixture was filtered and the filtrate was extracted with ethyl acetate (3×50 mL). The combined organic phase was concentrated, diluted with THF (20 mL), treated with HCl (20 mL, 3 M in H$_2$O) and the resulting mixture was stirred at room temperature for 1 hour. The mixture was then extracted with ethyl acetate (3×80 mL) and the combined organics were washed with brine, dried over Na$_2$SO$_4$, filtered and concentrated under reduced pressure to give a residue, which was purified by com-flash column (0%-10% ethyl acetate in petroleum ether) to provide the desired product as a white solid. ESI-MS m/z: (M+H)$^+$= 243.0.

Step B: Preparation of 7-chloro-5-methoxy-4-methylphthalazin-1-ol (27-3). A mixture of 27-2 (1.4 g, 1.0 eq., 5.78 mmol) and hydrazine hydrate (3.1 g, 10.0 eq., 57.8 mmol) in ethanol (40 mL) and THF (6 mL) was stirred at 80° C. for 16 hours, then cooled and concentrated under reduced pressure to give a residue. The residue was triturated in ethanol (10 mL) to afford the desired product as an off-white solid. ESI-MS m/z: (M+H)$^+$=224.9. $^1$H NMR (400 MHz, DMSO) δ 12.57 (s, 1H), 7.75 (s, 1H), 7.53 (s, 1H), 3.98 (s, 3H), 2.57 (s, 3H).

Step C: Preparation of 7-chloro-4-methylphthalazine-1,5-diol (27-4). 27-3 (500 mg, 1.0 eq., 2.23 mmol) was suspended in dry 1,2-dichloroethane (12 mL), then BBr$_3$ (1.68 g, 3.0 eq., 6.69 mmol) was added at room temperature. The resulting mixture was irradiated in a microwave reactor for 2 hours at 80° C., then cooled to room temperature and quenched with methanol. The mixture was concentrated to give the desired product as a light-yellow solid, which was used directly in the next step without further purification. ESI-MS m/z: (M+H)$^+$=210.9.

Step D: Preparation of 5-((6-(benzyloxy)hexyl)oxy)-7-chloro-4-methylphthalazin-1-ol (27-5). To a solution of 27-4 (600 mg, 2.23 mmol) in DMF (15 mL) was added and K$_2$CO$_3$ (1.85 g, 6.0 eq., 13.38 mmol) and (((6-bromohexyl)oxy)methyl)benzene (604 mg, 1.0 eq., 2.23 mmol) at room temperature and the resulting mixture was stirred at 30° C. for 5 days. The reaction mixture was cooled to room temperature and water (100 mL) was added with stirring. A solid precipitated and the mixture was filtered and the filter cake washed with water (50 mL) and methanol (10 mL) to afford the desired product. ESI-MS m/z: (M+H)$^+$=401.1. $^1$H NMR (400 MHz, DMSO) δ 12.56 (s, 1H), 7.73 (d, J=1.8 Hz, 1H), 7.48 (d, J=1.8 Hz, 1H), 7.39-7.19 (m, 5H), 4.44 (s, 2H), 4.15 (t, J=6.2 Hz, 2H), 3.44 (t, J=6.4 Hz, 2H), 2.58 (s, 3H), 1.92-1.76 (m, 2H), 1.65-1.34 (m, 6H).

Step E: Preparation of 5-((6-(benzyloxy)hexyl)oxy)-4-methyl-7-morpholinophthalazin-1-ol (27-6). To a mixture of 27-5 (670 mg, 1.0 eq., 1.675 mmol) and morpholine (219 mg, 1.5 eq., 2.51 mmol), Pd$_2$(dba)$_3$ (77 mg, 0.05 eq., 0.08375 mmol), Ru-Phos (79 mg, 0.1 eq., 0.1675 mmol) in dry 1,4-dioxane (40 mL) was added t-BuOK (3.4 mL, 2.0 eq., 3.35 mmol, 1M in THF). The resulting mixture was heated to 110° C. with stirring for 20 hours under nitrogen, then cooled to room temperature, diluted with ethyl acetate (50 mL)/water (50 mL) and extracted with ethyl acetate (50 mL×3). The combined organics were washed with brine, dried over Na$_2$SO$_4$, filtered and concentrated under reduced pressure to give a residue, which was purified by com-flash chromatography on a silica gel column (0%-5% MeOH in DCM) to afford the desired product as a light-yellow solid. ESI-MS m/z: (M+H)$^+$=452.3.

Step F: Preparation of 4-(8-((6-(benzyloxy)hexyl)oxy)-4-chloro-1-methylphthalazin-6-yl)morpholine. To a stirred solution of 27-6 (300 mg, 1.0 eq., 0.67 mmol) in phosphorus oxychloride (10 mL) was added drop-wise DIEA (257 mg, 3.0 eq., 2.01 mmol) at room temperature, then the resulting mixture was heated to 90° C. and stirred for 1.5 hours under nitrogen. The mixture was concentrated under reduced pressure to give a residue, which was diluted with ethyl acetate (20 mL) and added to a cold mixture of water (20 mL) and ethyl acetate (20 mL) dropwise while stirring. It was then treated with sat. aqueous NaHCO$_3$ to adjust the pH to 8. The organic phase was separated, and the aqueous phase was extracted with ethyl acetate (30 mL×2). The combined organics were washed with brine, dried over Na$_2$SO$_4$, filtered and concentrated under reduced pressure to give a residue, which was purified by com-flash column chromatography (0%~100% ethyl acetate in petroleum ether) to afford the desired product as a light-yellow solid. ESI-MS m/z: (M+H)$^+$=470.2.

Step G: Preparation of tert-butyl (R)-4-((3-(1-((5-((6-(benzyloxy)hexyl)oxy)-4-methyl-7-morpholinophthalazin-1-yl)amino)ethyl)phenyl)difluoromethyl)piperidine-1-carboxylate (27-7). A mixture of 4-(8-((6-(benzyloxy)hexyl)oxy)-4-chloro-1-methylphthalazin-6-yl)morpholine (277 mg, 1.0 eq., 0.59 mmol), 4-2 (220 mg, 1.05 eq., 0.62 mmol), Pd$_2$(dba)$_3$ (54 mg, 0.1 eq., 0.059 mmol), BINAP (74 mg, 0.2 eq., 0.118 mmol) and Cs$_2$CO$_3$ (480 mg, 2.5 eq., 1.475 mmol) in dry 1,4-dioxane (45 mL) was heated to 110° C. with stirring for 16 hours under nitrogen. The mixture was cooled to room temperature, then diluted with water (50 mL) and ethyl acetate (40 mL). The organic phase was separated and the aqueous phase was extracted with ethyl acetate (50 mL×2). The combined organics were washed with brine, dried over Na$_2$SO$_4$, filtered and concentrated under reduced pressure to give a residue, which was purified by com-flash column chromatography (0%~100% ethyl acetate in petroleum ether) and by prep-TLC (ethyl acetate:petroleum ether=1:0) to afford the desired product as a light foamed yellow solid. ESI-MS m/z: (M+H)$^+$=788.4.

Step H: Preparation of tert-butyl (R)-4-(difluoro(3-(1-((5-((6-hydroxyhexyl)oxy)-4-methyl-7-morpholinophthalazin-1-yl)amino)ethyl)phenyl)methyl)piperidine-1-carboxylate. To a stirred solution of 27-7 (268 mg, 1.0 eq., 0.34 mmol)

in MeOH (20 mL) was added Pd(OH)$_2$/C (50 mg) and Pd/C (50 mg) and the resulting mixture was stirred at 50° C. for 60 hours under hydrogen. The mixture was cooled to room temperature, filtered and the filtrate was concentrated to give a residue. The residue was purified by prep-TLC (MeOH: DCM=1:15) to afford the desired product as a yellow oil. ESI-MS m/z: (M+H)$^+$=698.4.

Step I: Preparation of tert-butyl (R)-4-((3-(1-((5-((6-((ethylsulfonyl)oxy)hexyl)oxy)-4-methyl-7-morpholinophthalazin-1-yl)amino)ethyl)phenyl)difluoromethyl)piperidine-1-carboxylate. To a stirred solution of tert-butyl (R)-4-(difluoro(3-(1-((5-((6-hydroxyhexyl)oxy)-4-methyl-7-morpholinophthalazin-1-yl)amino)ethyl)phenyl)methyl)-piperidine-1-carboxylate (168 mg, 1.0 eq., 0.24 mmol) and triethylamine (122 mg, 5.0 eq., 1.20 mmol) in DCM (20 mL) was added ethanesulfonyl chloride (123 mg, 4.0 eq., 0.96 mmol) at 0° C. dropwise. The resulting solution was stirred for 10 minutes, then diluted with DCM/water and extracted with DCM (20 mL×3). The combined organics were washed with brine, dried over Na$_2$SO$_4$, filtered and concentrated under reduced pressure to give a residue, which was purified by com-flash chromatography on a silica gel column (0%-100% ethyl acetate in petroleum ether) to afford the desired product as a brown oil. ESI-MS m/z: (M+H)$^+$=790.3.

Step J: Preparation of (R)-6-((1-((1-(3-(difluoro(piperidin-4-yl)methyl)phenyl)ethyl)amino)-4-methyl-7-morpholinophthalazin-5-yl)oxy)hexyl ethanesulfonate (27-8). To a stirred solution of tert-butyl (R)-4-((3-(1-((5-((6-((ethylsulfonyl)oxy)hexyl)oxy)-4-methyl-7-morpholinophthalazin-1-yl)amino)ethyl)phenyl)difluoromethyl) piperidine-1-carboxylate (110 mg, 1.0 eq., 0.139 mmol) in DCM (6 mL) was added TFA (1 mL) dropwise at room temperature and the resulting solution was stirred at room temperature for 30 minutes. The mixture was concentrated to afford the desired product as light-yellow oil, which was used directly in the next step without further purification. ESI-MS m/z: (M+H)$^+$=690.5.

Step K: Preparation of (R)-2,2-difluoro-6$^4$,4-dimethyl-6$^7$-morpholino-7-oxa-5-aza-6(1,5)-phthalazina-1(4,1)-piperidina-3(1,3)-benzenacyclotridecaphane (196). To a stirred solution of 27-8 (150 mg crude, 0.139 mmol) in acetonitrile (28 mL, 0.005M) was added N,N-diisopropylethylamine (179 mg, 1.39 mmol) at room temperature and the resulting solution was heated to 70° C. for 40 hours with stirring. The mixture was cooled to room temperature, then concentrated under reduced pressure to give a residue which was diluted with DCM (30 mL)/sat. aqueous NaHCO$_3$ (80 mL). The resulting mixture was stirred for 2 hours, then the aqueous phase was extracted with DCM (30 mL×3). The combined organics were washed with brine, dried over Na$_2$SO$_4$, filtered and concentrated under reduced pressure to give a residue, which was purified by com-flash chromatography on a silica gel column (0%-100% (MeOH:DCM=1:12) in DCM) and prep-HPLC(FA) to afford the desired product as a light yellow solid. ESI-MS m/z: (M+1)$^+$=580.3. 1H NMR (400 MHz, DMSO-D$_2$O) 7.55 (d, J=7.7 Hz, 1H), 7.47 (t, J=7.6 Hz, 1H), 7.29 (s, 1H), 7.19 (d, J=7.5 Hz, 1H), 7.03 (s, 1H), 6.94 (s, 1H), 5.30 (q, J=7.0 Hz, 1H), 4.45-4.34 (m, 1H), 4.29-4.18 (m, 1H), 3.90-3.80 (m, 4H), 3.64-3.53 (m, 4H), 2.87 (d, J=11.2 Hz, 1H), 2.69 (s, 3H), 2.43-2.32 (m, 2H), 2.15-1.04 (m, 17H), 0.40-0.17 (m, 2H).

Example 28: Synthesis of R)-4-(2,2-difluoro-4-methyl-7-oxa-5-aza-6(4,8)-quinazolina-1(4,1)-piperidina-3(1,3)-benzenacyclotridecaphane-6$^6$-yl)thiomorpholine 1,1-dioxide (193)

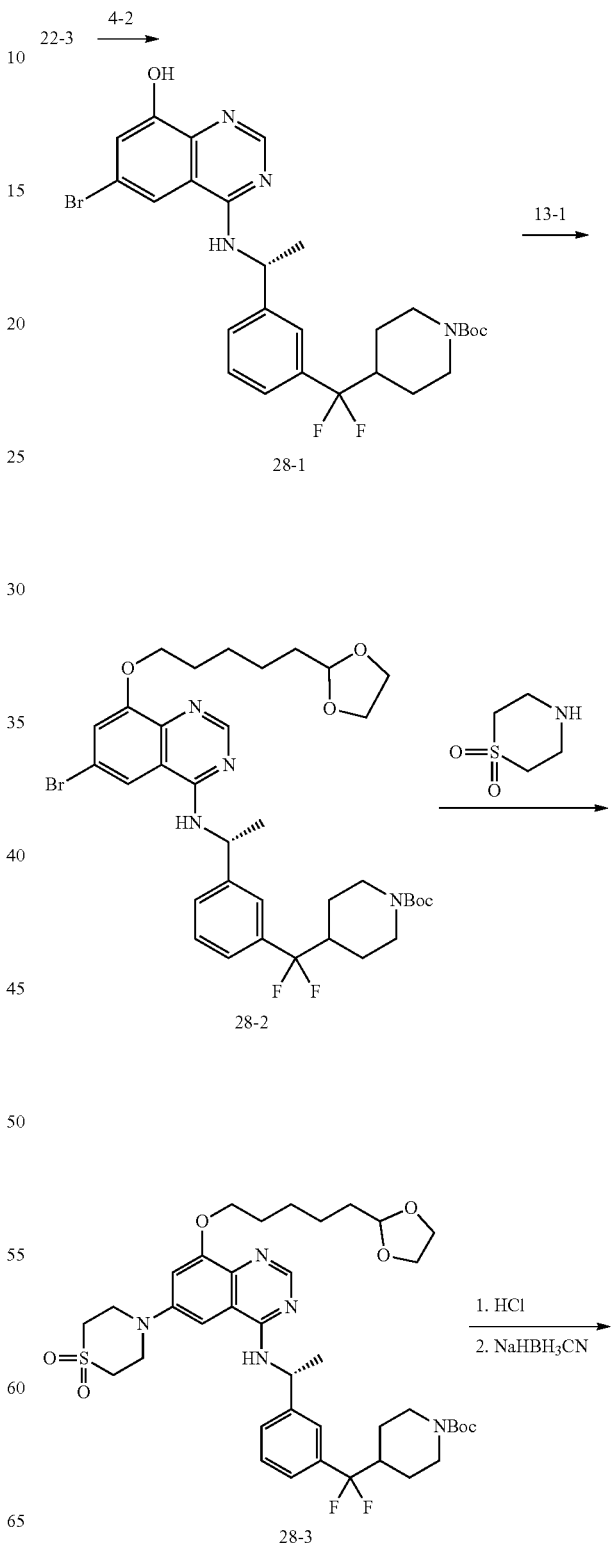

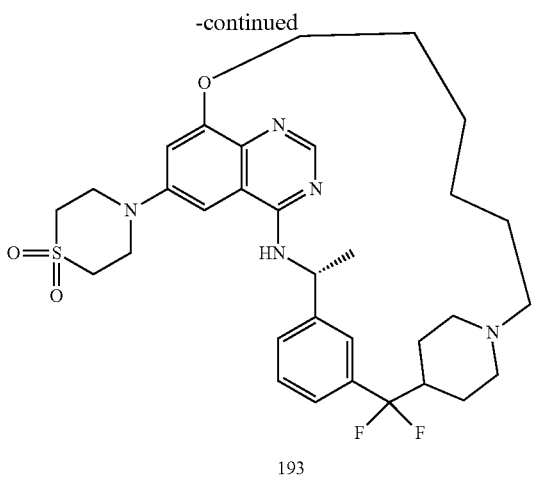

193

Step A: Preparation of tert-butyl (R)-4-((3-(1-((6-bromo-8-hydroxyquinazolin-4-yl)amino)ethyl)phenyl)difluoromethyl)piperidine-1-carboxylate (28-1). To the solution of 22-3 (300 mg, 1 eq., 0.99 mmol) in DMSO (8 mL) were added 4-2 (350 mg, 1.0 eq., 0.99 mmol) and N,N-diisopropylethylamine (383 mg, 3.0 eq., 2.97 mmol). The mixture was stirred at room temperature for 2 hours, poured into water, and extracted with ethyl acetate (3×50 mL). The combined organics were dried over $Na_2SO_4$, filtered and concentrated under reduced pressure to give a residue, which was purified by reverse phase chromatography to afford the desired product as a yellow solid. ESI-MS m/z: $(M+H)^+$=577.1.

Step B: Preparation of tert-butyl (R)-4-((3-(1-((8-((5-(1,3-dioxolan-2-yl)pentyl)oxy)-6-bromoquinazolin-4-yl)amino)ethyl)phenyl)difluoromethyl)piperidine-1-carboxylate (28-2). To the solution of 28-1 (100 mg, 1 eq., 0.17 mmol) in MeCN (4 mL) and DMF (1 mL) were added 13-1 (49 mg, 1.3 eq., 0.22 mmol) and $K_2CO_3$ (70 mg, 3.0 eq., 0.51 mmol). The resulting mixture was stirred at 70° C. for 16 hours, then cooled to room temperature, added to water, and extracted with ethyl acetate (3×50 mL). The combined organics were washed with brine, dried over $Na_2SO_4$, filtered and concentrated under reduced pressure to give a residue, which was purified by silica gel column chromatography (0%-10% MeOH in DCM) to afford the desired product as a yellow solid. ESI-MS m/z: $(M+H)^+$=719.1.

Step C: Preparation of tert-butyl (R)-4-((3-(1-((8-((5-(1,3-dioxolan-2-yl)pentyl)oxy)-6-(1,1-dioxidothiomorpholino)quinazolin-4-yl)amino)ethyl)phenyl)difluoromethyl)piperidine-1-carboxylate (28-3). To a solution of 28-2 (60 mg, 1 eq., 0.08 mmol) in toluene (1.5 mL) were added thiomorpholine 1,1-dioxide (13 mg, 1.2 eq., 0.096 mmol), tris(dibenzylideneacetone)dipalladium (7 mg, 0.1 eq., 0.008 mmol), BINAP (10 mg, 0.2 eq., 0.016 mmol) and $Cs_2CO_3$ (156 mg, 6.0 eq., 0.48 mmol). The mixture was stirred at 100° C. for 16 hours under nitrogen, then cooled to room temperature, poured into water and extracted with ethyl acetate (3×50 mL). The combined organics were washed with brine, dried over $Na_2SO_4$, filtered and concentrated under reduced pressure to give a residue, which was purified by prep-TLC (MeOH:DCM=1:12) to afford the desired product as a yellow solid. ESI-MS m/z: $(M+H)^+$=774.2.

Step D: Preparation of (R)-6-((4-((1-(3-(difluoro(piperidin-4-yl)methyl)phenyl)ethyl)amino)-6-(1,1-dioxidothiomorpholino)quinazolin-8-yl)oxy)hexanal. To a solution of 28-3 (40 mg, 1 eq., 0.05 mmol) in THF (2 mL) was added HCl (4 mL, 2N (aqueous)) at room temperature. The resulting mixture was stirred at room temperature for 32 hours, then cooled to 0° C. and treated with sat. aqueous $NaHCO_3$ to adjust the pH to 7-8. The mixture was extracted with DCM (30 mL×7). The combined organics were washed with brine, dried over $Na_2SO_4$, filtered and concentrated under reduced pressure to give the desired product as a light-yellow foam, which was used directly in the next step without further purification. ESI-MS m/z: $(M+H)^+$=630.2.

Step E: Preparation of (R)-4-(2,2-difluoro-4-methyl-7-oxa-5-aza-6(4,8)-quinazolina-1(4,1)-piperidina-3(1,3)-benzenacyclotridecaphane-$6^6$-yl)thiomorpholine 1,1-dioxide (193). To a solution of (R)-6-((4-((1-(3-(difluoro(piperidin-4-yl)methyl)phenyl)ethyl)amino)-6-(1,1-dioxidothiomorpholino)quinazolin-8-yl)oxy)hexanal (30 mg, 1 eq., 0.05 mmol) in MeOH/1,2-dichloroethane (33 mL/17 mL, 0.001 M) was added acetic acid (3 drops). The resulting mixture was stirred at room temperature for 0.5 hours, then sodium cyanoborohydride (8 mg, 2.5 eq., 0.125 mmol) was added and the mixture stirred at room temperature for 1 hour. The mixture was then concentrated and the residue dissolved in 10 mL DCM:MeOH (10:1) and treated with sat. aqueous $NaHCO_3$. The mixture was stirred at room temperature for 1 hour. The organic layer was separated and the aqueous layer was extracted with DCM (20 mL×3). The combined organics were washed with brine, dried over $Na_2SO_4$, filtered and concentrated under reduced pressure to give a residue, which was purified by prep-HPLC to provide the desired product as a yellow solid. ESI-MS m/z: $(M+H)^+$=614.6. $^1$H NMR (400 MHz, DMSO-D2O) δ 8.11 (s, 1H), 7.59 (d, J=7.8 Hz, 1H), 7.49 (t, J=7.6 Hz, 1H), 7.35-7.32 (m, 1H), 7.22-7.16 (m, 2H), 7.04 (s, 1H), 5.50-5.42 (m, 1H), 4.33-4.27 (m, 1H), 4.23-4.16 (m, 1H), 4.02-3.97 (m, 4H), 3.32-3.26 (m, 4H), 2.28-2.19 (m, 1H), 2.11-2.03 (m, 1H), 1.95-1.85 (m, 1H), 1.79-1.57 (m, 9H), 1.42-1.25 (m, 6H), 1.11-0.99 (m, 2H), 0.53-0.45 (m, 1H), 0.19-0.10 (m, 1H).

Example 29: Synthesis of (R)-2,2-difluoro-4-methyl-$6^7$-morpholino-7-oxa-5-aza-6(1,4)-phthalazina-1(4,1)-piperidina-3(1,3)-benzenacyclotridecaphane and (R)-2,2-difluoro-4-methyl-$6^6$-morpholino-7-oxa-5-aza-6(1,4)-phthalazina-1(4,1)-piperidina-3(1,3)-benzenacyclotridecaphane (198 and 200)

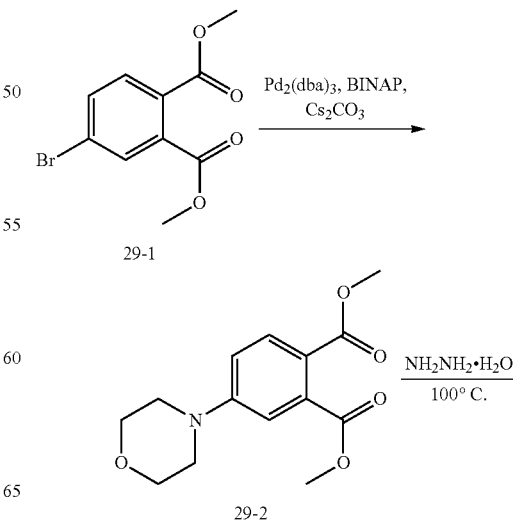

589
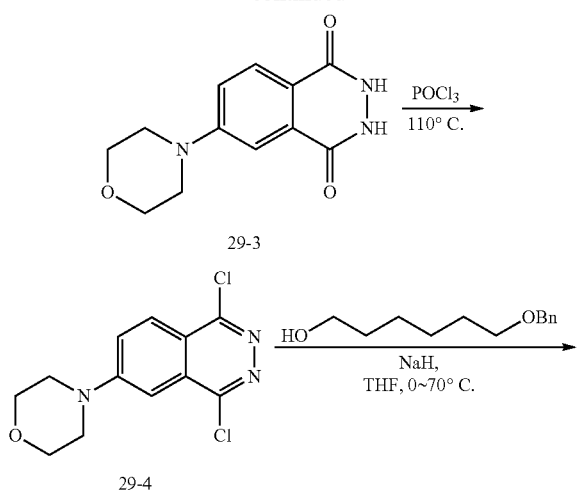
29-3
29-4
29-5a: R²⁹ᵃ = H, R²⁹ᵇ = morpholino
29-5b: R²⁹ᵃ = morpholino, R²⁹ᵇ = H
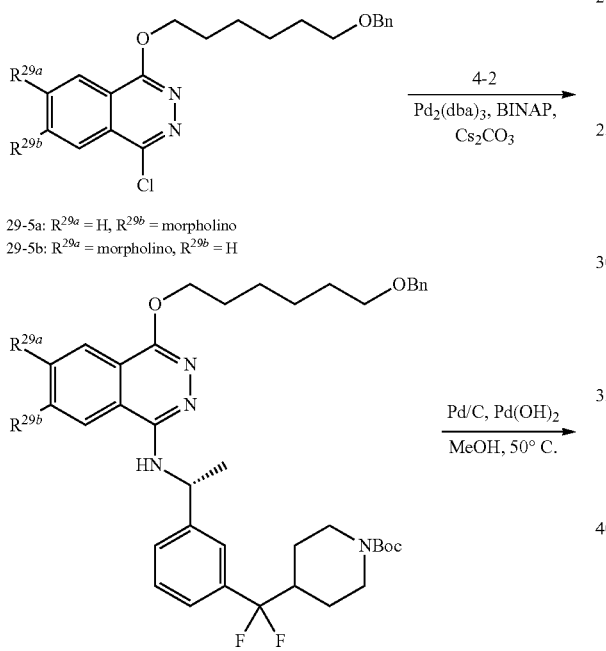
29-6a: R²⁹ᵃ = H, R²⁹ᵇ = morpholino
29-6b: R²⁹ᵃ = morpholino, R²⁹ᵇ = H
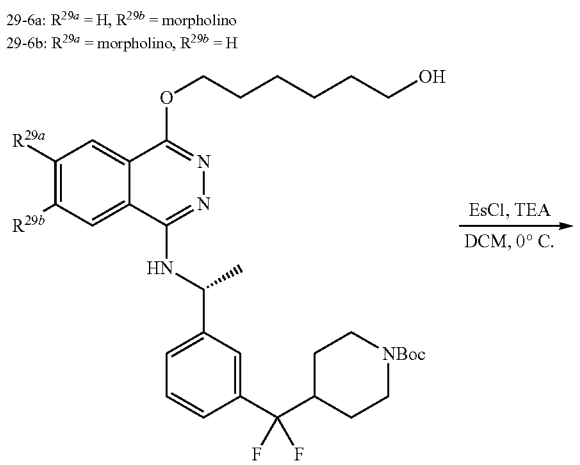
29-7a: R²⁹ᵃ = H, R²⁹ᵇ = morpholino
29-7b: R²⁹ᵃ = morpholino, R²⁹ᵇ = H
590
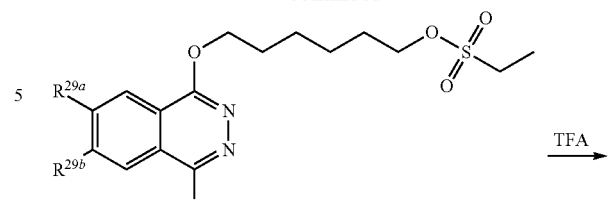
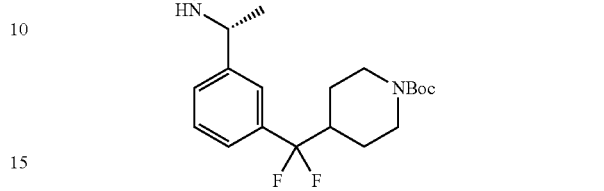
29-8a: R²⁹ᵃ = H, R²⁹ᵇ = morpholino
29-8b: R²⁹ᵃ = morpholino, R²⁹ᵇ = H
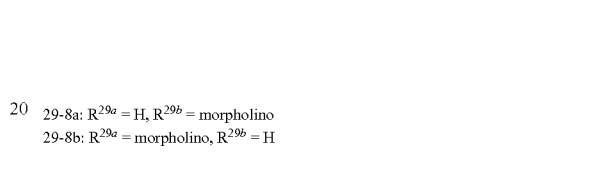
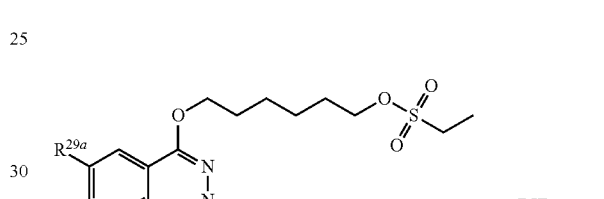
29-9a: R²⁹ᵃ = H, R²⁹ᵇ = morpholino
29-9b: R²⁹ᵃ = morpholino, R²⁹ᵇ = H
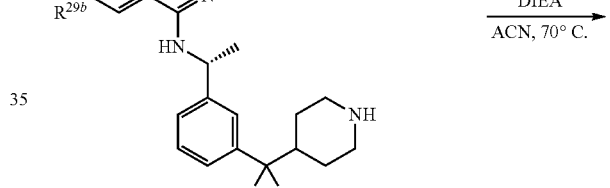
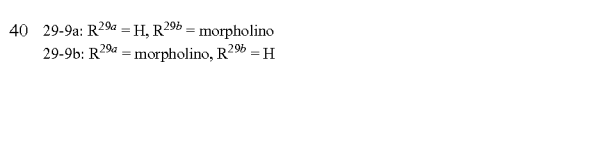
198

Step A: Preparation of dimethyl 4-morpholinophthalate (29-2). A mixture of dimethyl 4-bromophthalate (29-1) (11.00 g, 1.0 eq., 40.44 mmol), morpholine (5.28 g, 1.5 eq., 60.66 mmol), Pd$_2$(dba)$_3$ (3.71 g, 0.1 eq., 4.05 mmol), BINAP (5.04 g, 0.2 eq., 8.09 mmol) and cesium carbonate (13.19 g, 1.0 eq., 40.44 mmol) in anhydrous 1,4-dioxane (550 mL) was heated to 110° C. and stirred for 16 hours under nitrogen. The mixture was cooled to room temperature and diluted with water (200 mL) and ethyl acetate (200 mL), then extracted with ethyl acetate (3×200 mL). The combined organics were washed with brine, dried over Na$_2$SO$_4$, filtered and concentrated under reduced pressure to give a residue, which was purified by com-flash chromatography on a silica gel column (0%~50% ethyl acetate in petroleum ether) to give the desired product as a yellow solid. ESI-MS m/z: (M+H)$^+$=280.1. $^1$H NMR (400 MHz, DMSO) δ 7.72 (d, J=8.8 Hz, 1H), 7.07 (s, 1H), 7.02 (d, J=2.6 Hz, 1H), 3.78 (s, 3H), 3.75 (s, 3H), 3.74-3.69 (m, 4H), 3.32-3.26 (m, 4H).

Step B: Preparation of 6-morpholino-2,3-dihydrophthalazine-1,4-dione (29-3). A solution of 29-2 (3.50 g, 1.0 eq., 12.55 mmol) in hydrazine hydrate (20 mL) was heated to 100° C. and stirred for 16 hours. The mixture was cooled to room temperature and concentrated to give a residue, which triturated with water (50 mL) and filtered. The filter cake was washed with water (100 mL) and methanol (100 mL) to give the desired product as a white solid. ESI-MS m/z: (M+H)$^+$=248.0.

Step C: Preparation of 4-(1,4-dichlorophthalazin-6-yl)morpholine (29-4). A solution of 29-3 (3.00 g, 1.0 eq., 12.15 mmol) in phosphorus oxychloride (30 mL) was heated to 110° C. and stirred for 16 hours under nitrogen. The mixture was cooled to room temperature and concentrated to give a residue, which was diluted with dichloromethane (20 mL) and slowly added to ice water. The mixture was treated with saturated sodium bicarbonate solution slowly to adjust the pH to ~8. The resulting mixture was extracted with dichloromethane (3×50 mL). The combined organics were washed with brine, dried over Na$_2$SO$_4$, filtered and concentrated under reduced pressure to give a residue, which was purified by com-flash chromatography on a silica gel column (0%~50% ethyl acetate in petroleum ether) to give the desired product as a yellow solid. ESI-MS m/z: (M+H)$^+$=284.0. $^1$H NMR (400 MHz, DMSO) δ 8.10 (d, J=9.3 Hz, 1H), 7.94 (d, J=9.2 Hz, 1H), 7.26 (s, 1H), 3.84-3.76 (m, 4H), 3.58-3.50 (m, 4H).

Step D: Preparation of 4-(1-((6-(benzyloxy)hexyl)oxy)-4-chlorophthalazin-6-yl)morpholine (29-5a) and 4-(4-((6-(benzyloxy)hexyl)oxy)-1-chlorophthalazin-6-yl)morpholine (29-5b). To a solution of 6-(benzyloxy)hexan-1-ol (1.69 g, 1.2 eq., 8.11 mmol) in anhydrous tetrahydrofuran (50 mL) was added sodium hydride (542 mg, 2.0 eq., 13.52 mmol) at 0° C. under nitrogen. After 1 hour of stirring at 0° C. under nitrogen, 29-4 (1.95 g, 1.0 eq., 6.76 mmol) was slowly added at 0° C. and the resulting mixture stirred for 3 hours at 70° C. under nitrogen. The mixture was then cooled to room temperature and slowly added to ice water, then extracted with ethyl acetate (3×30 mL). The combined organics were washed with brine, dried over Na$_2$SO$_4$, filtered and concentrated under reduced pressure to give a residue, which was purified by com-flash chromatography on a silica gel column (0%-10% ethyl acetate in dichloromethane) to give a mixture of 29-5a (ESI-MS m/z: (M+H)$^+$=456.2) and 29-5b (ESI-MS m/z: (M+H)$^+$=456.2) as a yellow solid.

Step E: Preparation of tert-butyl (R)-4-((3-(1-((4-((6-(benzyloxy)hexyl)oxy)-7-morpholinophthalazin-1-yl)amino)ethyl)phenyl)difluoromethyl)piperidine-1-carboxylate (29-6a) and tert-butyl (R)-4-((3-(1-((4-((6-(benzyloxy)hexyl)oxy)-6-morpholinophthalazin-1-yl)amino)ethyl)phenyl)difluoromethyl)piperidine-1-carboxylate (29-6b). A mixture of 29-5a and 29-5b (500 mg, 1.0 eq., 1.10 mmol), 4-2 (389 mg, 1.0 eq., 1.10 mmol), Pd$_2$(dba)$_3$ (101 mg, 0.1 eq., 0.11 mmol), BINAP (137 mg, 0.2 eq., 0.22 mmol) and cesium carbonate (896 mg, 2.5 eq., 2.75 mmol) in anhydrous 1,4-dioxane (20 mL) was heated to 110° C. and stirred for 16 hours under nitrogen. The reaction mixture was cooled to room temperature and diluted with water (10 mL) and ethyl acetate (10 mL), then extracted with ethyl acetate (3×30 mL). The combined organics were washed with brine, dried over Na$_2$SO$_4$, filtered and concentrated under reduced pressure to give a residue, which was purified by com-flash chromatography on a silica gel column (0~50% ethyl acetate in petroleum ether) to give a mixture of 29-6a (ESI-MS m/z: (M+H)$^+$=774.7) and 29-6b (ESI-MS m/z: (M+H)$^+$=774.7) as a yellow solid.

Step F: Preparation of tert-butyl (R)-4-(difluoro(3-(1-((4-((6-hydroxyhexyl)oxy)-7-morpholinophthalazin-1-yl)amino)ethyl)phenyl)methyl)piperidine-1-carboxylate (29-7a) and tert-butyl (R)-4-(difluoro(3-(1-((4-((6-hydroxyhexyl)oxy)-6-morpholinophthalazin-1-yl)amino)ethyl)phenyl)methyl)piperidine-1-carboxylate (29-7b). A mixture of 29-6a and 29-6b (610 mg, 1.0 eq., 0.79 mmol), Pd/C (153 mg) and Pd(OH)$_2$/C (153 mg) in methanol (20 mL) was stirred for 24 hours at 50° C. under hydrogen. The reaction mixture was cooled to room temperature, filtered, and the filter cake was washed with methanol (60 mL). The filtrate was concentrated to give the title mixture of compounds as a yellow solid, which was used directly in the next step without further purification. ESI-MS m/z: (M+H)$^+$=684.6.

Step G: Preparation of tert-butyl (R)-4-((3-(1-((4-((6-((ethylsulfonyl)oxy)hexyl)oxy)-7-morpholinophthalazin-1-yl)amino)ethyl)phenyl)difluoromethyl)piperidine-1-carboxylate (29-8a) and tert-butyl (R)-4-((3-(1-((4-((6-((ethylsulfonyl)oxy)hexyl)oxy)-6-morpholinophthalazin-1-yl)amino)ethyl)phenyl)difluoromethyl) piperidine-1-carboxylate (29-8b). To a stirred solution of 29-7a and 29-7b (420 mg, 1.0 eq., 0.62 mmol) and triethylamine (248 mg, 4.0 eq., 2.46 mmol) in dichloromethane (10 mL) was added drop-wise ethanesulfonyl chloride (397 mg, 5.0 eq., 3.08 mmol) at 0° C. The resulting solution was stirred for 30 minutes, then diluted with water and extracted with dichloromethane (3×20 mL). The combined organics were washed with brine, dried over Na$_2$SO$_4$, filtered and concentrated under reduced pressure to give a residue, which was purified by com-flash chromatography on a silica gel column (0%-50% ethyl acetate in petroleum ether) to give the title mixture of compounds, which was used directly in the next step. ESI-MS m/z: (M+H)$^+$=776.6.

Step H: Preparation of (R)-6-((4-((1-(3-(difluoro(piperidin-4-yl)methyl)phenyl)ethyl)amino)-7-morpholinophthalazin-1-yl)oxy)hexyl ethanesulfonate (29-9a) and (R)-6-((4-((1-(3-(difluoro(piperidin-4-yl)methyl)phenyl)ethyl)amino)-6-morpholinophthalazin-1-yl)oxy)hexyl ethanesulfonate (29-9b). To a stirred solution of 29-8a and 29-8b (385 mg, 1.0 eq., 0.50 mmol) in dichloromethane (10 mL) was added drop-wise trifluoroacetic acid (2 mL) at room temperature and the resulting mixture was stirred at room temperature for 1 hour. The mixture was concentrated to provide the title mixture of compounds, which was used directly in the next step. ESI-MS m/z: (M+H)$^+$=676.5.

Step I: Preparation of (R)-2,2-difluoro-4-methyl-6$^7$-morpholino-7-oxa-5-aza-6(1,4)-phthalazina-1(4,1)-piperidina-3(1,3)-benzenacyclotridecaphane (198) and (R)-2,2-difluoro-4-methyl-6$^6$-morpholino-7-oxa-5-aza-6(1,4)-phthalazina-1(4,1)-piperidina-3(1,3)-benzenacyclotridecaphane (200). A mixture of 29-9a and 29-9b (335 mg, 1.0 eq., 0.50 mmol) was dissolved in acetonitrile (100 mL), then N,N-diisopropylethylamine (1.92 g, 30.0 eq., 14.88 mmol) was added at room temperature. The resulting solution was heated to 70° C. for 16 hours under nitrogen, then acetonitrile was removed to provide a residue. The residue was diluted with dichloromethane (40 mL)/sat. aqueous sodium bicarbonate (40 mL) and the resulting solution was stirred for 1 h. The aqueous phase was extracted with dichloromethane (3×50 mL) and the combined organics were washed with brine, dried over Na$_2$SO$_4$, filtered and concentrated under reduced pressure to give a residue, which was purified by com-flash chromatography on a silica gel column (0%~50% ethyl acetate in petroleum ether) to give a crude product which was purified by chiral separation to give the two desired products, each as a white solid. Peak 1: ESI-MS m/z: (M+H)$^+$=566.5. $^1$H NMR (400 MHz, DMSO) δ 7.85 (d, J=9.0 Hz, 1H), 7.65 (s, 1H), 7.59-7.49 (m, 2H), 7.41 (t, J=7.6 Hz, 1H), 7.19 (s, 1H), 7.16-6.95 (m, 2H), 5.35-5.25 (m, 1H), 4.64 (t, J=10.2 Hz, 1H), 3.98-3.88 (m, 1H), 3.88-3.77 (m, 4H), 3.48-3.36 (m, 4H), 2.73-2.63 (m, 1H), 2.17-1.70 (m, 5H), 1.69-1.47 (m, 7H), 1.43-1.18 (m, 4H), 1.18-1.04 (m, 1H), 1.02-0.88 (m, 1H), 0.87-0.77 (m, 1H), 0.76-0.61 (m, 1H), 0.16-0.00 (m, 1H). Peak 2: ESI-MS m/z: (M+H)$^+$=566.5. $^1$H NMR (400 MHz, DMSO) δ 8.40 (d, J=9.2 Hz, 1H), 7.72-7.64 (m, 1H), 7.52 (d, J=7.8 Hz, 1H), 7.40 (t, J=7.7 Hz, 1H), 7.24-7.15 (m, 2H), 7.15-7.01 (m, 2H), 5.40-5.19 (m, 1H), 4.62 (t, J=10.0 Hz, 1H), 4.05-3.91 (m, 1H), 3.88-3.72 (m, 4H), 3.32-3.24 (m, 4H), 2.73-2.60 (m, 1H), 2.16-1.87 (m, 4H), 1.85-1.71 (m, 1H), 1.69-1.47 (m, 7H), 1.46-1.22 (m, 4H), 1.17-1.05 (m, 1H), 1.02-0.87 (m, 1H), 0.84-0.73 (m, 1H), 0.75-0.57 (m, 1H), 0.09-0.00 (m, 1H).

Example 30: Synthesis of (R)-6$^7$-(1,1-dioxidothiomorpholino)-3$^2$,2,2-trifluoro-6$^3$,4-dimethyl-6$^3$,6$^4$-dihydro-7-oxa-5-aza-6(1,5)-pyrido[3,4-d]pyridazina-1(4,1)-piperidina-3(1,3)-benzenacyclotetradecaphan-6$^4$-one (201)

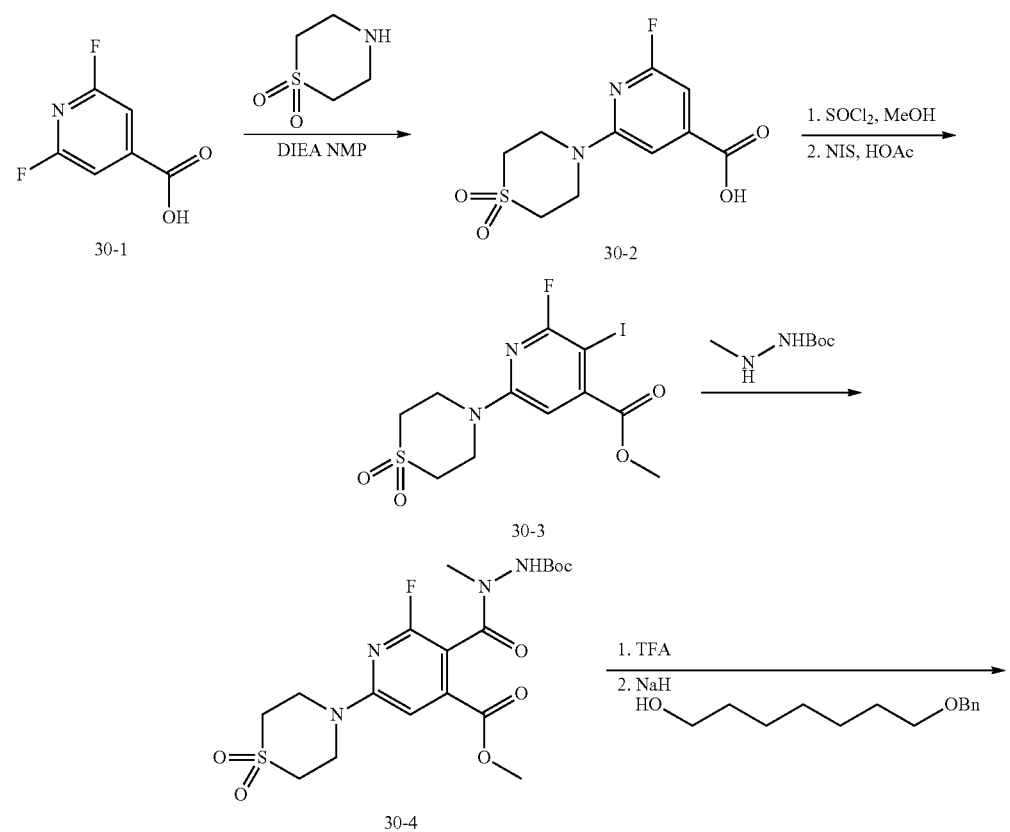

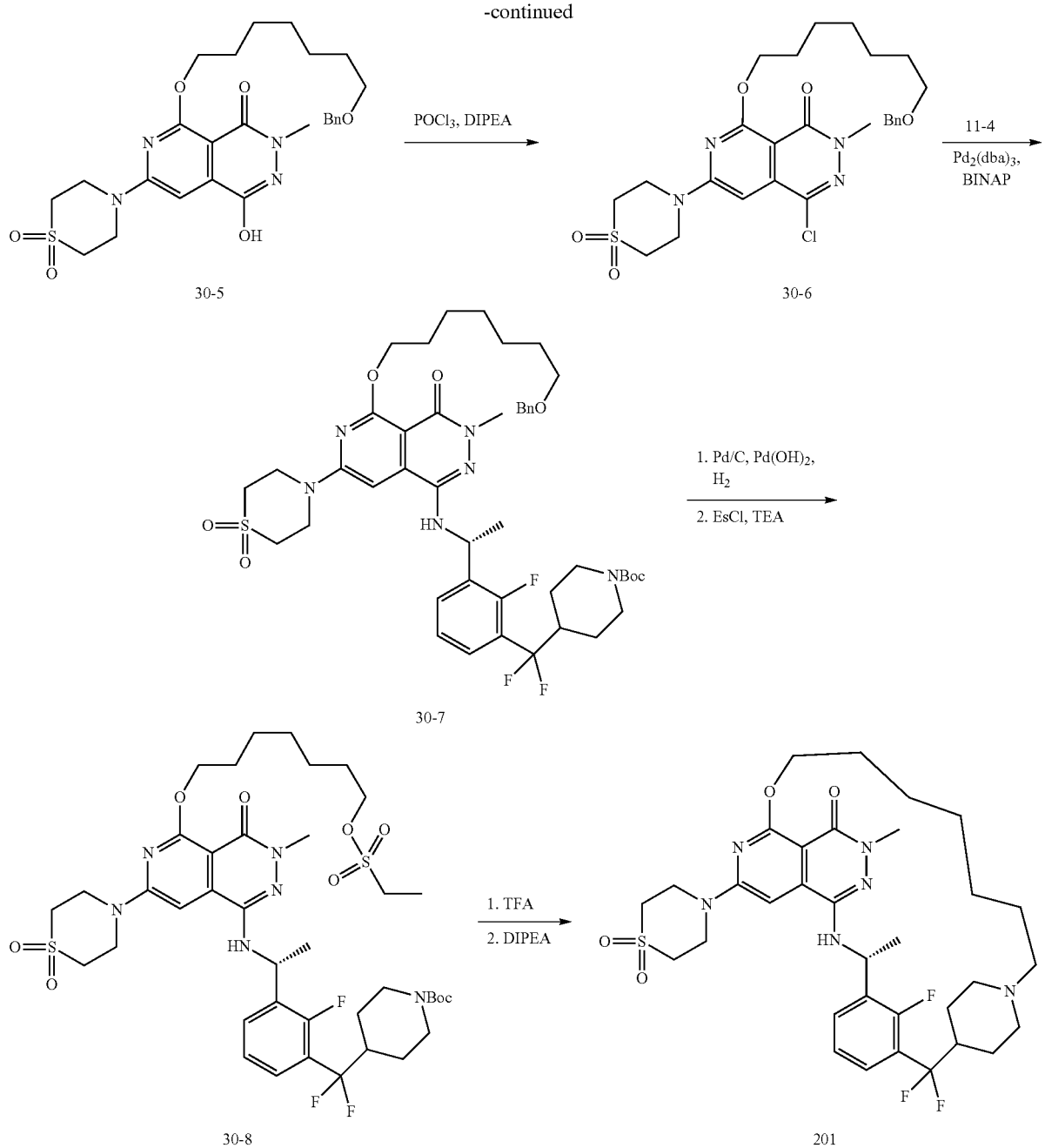

Step A: Preparation of 2-(1,1-dioxidothiomorpholino)-6-fluoroisonicotinic acid (30-2). To a solution of 2,6-difluoroisonicotinic acid (30-1, 10020 mg, 1.0 eq., 62.98 mmol) and N,N-diisopropylethylamine (8140 mg, 1.0 eq., 63.10 mmol) in 1-methyl-2-pyrrolidinone (100 mL) was added thiomorpholine 1,1-dioxide (9365 mg, 1.1 eq., 69.28 mmol) at room temperature. The mixture was stirred at 100° C. for 72 hours, then cooled to room temperature, diluted with water (1000 mL) and treated with 2N HCl to adjust the pH to ~3-4. The mixture was extracted with ethyl acetate (500 mL×3). The combined organics were washed with brine, dried over $Na_2SO_4$, filtered and concentrated under reduced pressure to give the desired product as a white solid. ESI-MS m/z: $(M+H)^+$=275.0.

Step B: Preparation of methyl 2-(1,1-dioxidothiomorpholino)-6-fluoroisonicotinate. To a solution of 30-2 (15 g, 1.0 eq., crude) in methanol (1 L) and added thionyl chloride (100 mL) dropwise at 0° C. The reaction mixture was stirred at room temperature overnight and concentrated in vacuo. The residue thus obtained was dissolved into dichloromethane (300 mL) and cooled to 0° C. The mixture was adjusted to pH 7 with sat. $NaHCO_3$. The organic layer was collected and the aqueous layer was extracted with dichloromethane (3×200 mL). The combined organics were washed with brine, dried over $Na_2SO_4$, filtered and concentrated under reduced pressure to give a residue, which was purified by silica gel column chromatography (0%~40% ethyl acetate in petroleum ether) to provide the desired product as a yellow solid. ESI-MS m/z: $(M+H)^+$=289.0.

Step C: Preparation of methyl 6-(1,1-dioxidothiomorpholino)-2-fluoro-3-iodoisonicotinate (30-3). To a solution of methyl 2-(1,1-dioxidothiomorpholino)-6-fluoroisonicotinate (6.0 g, 1.0 eq., 20.8 mmol) in acetic acid (100 mL) was added N-iodosuccinimide (5.2 g, 1.1 eq., 22.9 mmol). The reaction mixture was stirred at room temperature overnight under nitrogen atmosphere and concentrated in vacuo to give a residue. The residue was diluted with dichloromethane (80 mL) and water (80 mL), then the organic layer was collected and the aqueous layer was extracted with dichloromethane (3×50 mL). The combined organics were washed with brine, dried over $Na_2SO_4$, filtered and concentrated under reduced pressure to give a residue, which was purified by silica gel column chromatography (0~5% ethyl acetate in dichloromethane) to give the desired product as a white solid. ESI-MS m/z: $(M+H)^+$=414.9.

Step D: Preparation of methyl 3-(2-(tert-butoxycarbonyl)-1-methylhydrazine-1-carbonyl)-6-(1,1-dioxidothiomorpholino)-2-fluoroisonicotinate (30-4). To a solution of 30-3 (4700 mg, 1.0 eq., 11.35 mmol), tert-butyl 2-methylhydrazine-1-carboxylate (2654 mg, 1.6 eq., 18.16 mmol), $Pd_2(dba)_3$ (1038 mg, 0.1 eq, 1.13 mmol), tri-tert-butylphosphine tetrafluoroborate (658 mg, 0.2 eq., 2.27 mmol) and molybdenumhexacarbonyl (3594 mg, 1.2 eq., 13.62 mmol) in N,N-dimethylformamide (80 mL) was added N,N-diisopropylethylamine (4708 mg, 5.0 eq., 36.22 mmol) at room temperature. The mixture was stirred at 100° C. overnight, then cooled to room temperature, poured into 800 mL water, and extracted with ethyl acetate (3×300 mL). The combined organics were washed with brine, dried over $Na_2SO_4$, filtered and concentrated under reduced pressure to give a residue, which was purified by silica gel column chromatography (0%-50% ethyl acetate in dichloromethane) to give the desired product as a white solid. ESI-MS m/z: $(M+Na)^+$= 483.1.

Step E: Preparation of 7-(1,1-dioxidothiomorpholino)-5-fluoro-3-methyl-2,3-dihydropyrido[3,4-d]pyridazine-1,4-dione. To a solution of 30-4 (1240 mg, 1.0 eq., 2.69 mmol) in dichloromethane (20 mL) was added trifluoroacetic acid (4 mL) at room temperature. The mixture was stirred at room temperature overnight, then concentrated to give a residue. The residue was treated with ethyl acetate (10 mL) and the resulting mixture was stirred at room temperature for 1 hour. The mixture was filtered and the filter cake was dried to obtain the desired product as a yellow solid. ESI-MS m/z: $(M+H)^+$=329.0.

Step F: Preparation of 5-((7-(benzyloxy)heptyl)oxy)-7-(1,1-dioxidothiomorpholino)-1-hydroxy-3-methylpyrido[3,4-d]pyridazin-4(3H)-one (30-5). To the solution of 7-(benzyloxy)heptan-1-ol (1479 mg, 5.0 eq., 6.66 mmol) in N,N-dimethylformamide (12 mL) was added NaH (60% dispersed in mineral oil) (267 mg, 5.25 eq., 6.99 mmol) at 0° C. The mixture was stirred at 0° C. for 1 hour, then a solution of 7-(1,1-dioxidothiomorpholino)-5-fluoro-3-methyl-2,3-dihydropyrido[3,4-d]pyridazine-1,4-dione (437 mg, 1.0 eq., 1.33 mmol) in N,N-dimethylformamide (4 mL) was added. The resulting mixture was stirred at 60° C. for 1 hour, then cooled to room temperature, quenched with water (100 mL), and extracted with ethyl acetate (3×80 mL). The combined organics were washed with brine, dried over $Na_2SO_4$, filtered and concentrated under reduced pressure to give a residue, which was purified by silica gel column chromatography (0%-70% ethyl acetate in petroleum ether, then 0~15% methanol in dichloromethane) to give the desired product as a white solid. ESI-MS m/z: $(M+H)^+$= 531.2.

Step G: Preparation of 5-((7-(benzyloxy)heptyl)oxy)-1-chloro-7-(1,1-dioxidothiomorpholino)-3-methylpyrido[3,4-d]pyridazin-4(3H)-one (30-6). To a solution of 30-5 (100 mg, 1.0 eq., 0.19 mmol) in phosphorus oxychloride (5 mL) was added N,N-diisopropylethylamine (98 mg, 4.0 eq., 0.75 mmol) at room temperature. The resulting mixture was stirred at 90° C. overnight, then cooled to room temperature, concentrated, and the resulting residue diluted with ethyl acetate (40 mL). The mixture was treated with sat. $NaHCO_3$ (40 mL) slowly at 0° C. The organic layer was collected and the aqueous layer was extracted with ethyl acetate (3×40 mL). The combined organic layer was concentrated to give a residue, which was purified by silica gel column chromatography (0%~8% methanol in dichloromethane) to provide the desired product as a light-yellow solid. ESI-MS m/z: $(M+H)^+$=549.2.

Step H: Preparation of tert-butyl (R)-4-((3-(1-((5-((7-(benzyloxy)heptyl)oxy)-7-(1,1-dioxidothiomorpholino)-3-methyl-4-oxo-3,4-dihydropyrido[3,4-d]pyridazin-1-yl)amino)ethyl)-2-fluorophenyl)difluoromethyl)piperidine-1-carboxylate (30-7). To a mixture of 30-6 (80 mg, 1.0 eq., 0.15 mmol), 11-4 (81 mg, 1.0 eq., 0.22 mmol) and $Cs_2CO_3$ (238 mg, 5.0 eq., 0.73 mmol) in toluene (5 mL) were added $Pd_2(dba)_3$ (13 mg, 0.1 eq., 0.015 mmol) and BINAP (18 mg, 0.2 eq., 0.029 mmol) at room temperature. The mixture was stirred at 110° C. overnight, then cooled to room temperature and concentrated to give a residue. The residue was diluted with water (30 mL) and ethyl acetate (30 mL). The organic layer was collected and the aqueous layer was extracted with ethyl acetate (2×30 mL). The combined organic layer was concentrated to give a residue. The residue was purified by silica gel column chromatography (0%~8% methanol in dichloromethane) to obtain the crude product, which was further purified by prep-TLC (dichloromethane: ethyl acetate 1:1) to provide the desired product as a yellow solid. ESI-MS m/z: $(M+H)^+$=885.2.

Step I: Preparation of tert-butyl (R)-4-((3-(1-((7-(1,1-dioxidothiomorpholino)-5-((7-hydroxyheptyl)oxy)-3-methyl-4-oxo-3,4-dihydropyrido[3,4-d]pyridazin-1-yl)amino)ethyl)-2-fluorophenyl)difluoromethyl)piperidine-1-carboxylate. To a mixture of 30-7 (110 mg, 1.0 eq., 0.12 mmol) in methanol (50 mL) was added Pd/C (39 mg) and Pd $(011)_2$ (39 mg) at room temperature. The mixture was stirred at 50° C. for 40 hours under hydrogen atmosphere, then cooled to room temperature, filtered, and the filtrate concentrated to give a residue. The residue was purified by prep-TLC (dichloromethane:methanol 25:1) to obtain the desired product as a light-yellow foam. ESI-MS m/z: $(M+H)^+$=795.2.

Step J: Preparation of tert-butyl (R)-4-((3-(1-((7-(1,1-dioxidothiomorpholino)-5-((7-((ethylsulfonyl)oxy)heptyl)oxy)-3-methyl-4-oxo-3,4-dihydropyrido[3,4-d]pyridazin-1-yl)amino)ethyl)-2-fluorophenyl)difluoromethyl)piperidine-1-carboxylate (30-8). To a solution of tert-butyl (R)-4-((3-(1-((7-(1,1-dioxidothiomorpholino)-5-((7-hydroxyheptyl)oxy)-3-methyl-4-oxo-3,4-dihydropyrido[3,4-d]pyridazin-1-yl)amino)ethyl)-2-fluorophenyl)difluoromethyl)piperidine-1-carboxylate (75 mg, 1.0 eq., 0.094 mmol) and triethylamine (47 mg, 5.0 eq., 0.47 mmol) in dichloromethane (4 mL) was added ethanesulfonyl chloride (48 mg, 4.0 eq., 0.38 mmol) dropwise at 0° C. The mixture was stirred at 0° C. under argon atmosphere for 5 minutes, then poured into 40 mL water and extracted with dichloromethane (3×30 mL). The combined organics were washed with brine, dried over $Na_2SO_4$, filtered and concentrated under reduced pressure to give a residue, which was purified by prep-TLC (methanol:dichloromethane=1:20) to give the desired product as a yellow oil. ESI-MS m/z: (M+H)+=887.2.

Step K: Preparation of (R)-7-((1-((1-(3-(difluoro(piperidin-4-yl)methyl)-2-fluorophenyl)ethyl)amino)-7-(1,1-dioxidothiomorpholino)-3-methyl-4-oxo-3,4-dihydropyrido[3,4-d]pyridazin-5-yl)oxy)heptyl ethanesulfonate. To a solution of 30-8 (75 mg, 1.0 eq., 0.085 mmol) in dichloromethane (7.5 mL) was added trifluoroacetic acid (1.5 mL) at room temperature. The mixture was stirred at room temperature for 1 hour, then concentrated to give the desired product which was used directly in next step without further purification. ESI-MS m/z: (M+H)+=787.2.

Step L: Preparation of (R)-6⁷-(1,1-dioxidothiomorpholino)-3²,2,2-trifluoro-6³,4-dimethyl-6³,6⁴-dihydro-7-oxa-5-aza-6(1,5)-pyrido[3,4-d]pyridazina-1(4,1)-piperidina-3(1,3)-benzenacyclotetradecaphan-6⁴-one (201). To a solution of (R)-7-((1-((1-(3-(difluoro(piperidin-4-yl)methyl)-2-fluorophenyl)ethyl)amino)-7-(1,1-dioxidothiomorpholino)-3-methyl-4-oxo-3,4-dihydropyrido[3,4-d]pyridazin-5-yl)oxy)heptyl ethanesulfonate (60 mg, 1.0 eq., 0.085 mmol) in acetonitrile (20 mL) was added N,N-diisopropylethylamine (109 mg, 0.85 mmol) at room temperature. The mixture was stirred at 70° C. for 40 hours, then cooled to room temperature, concentrated, and the residue dissolved into DCM (30 mL). The residue was treated with sat. NaHCO₃ (150 mL) and stirred at room temperature for 1.5 hours. The organic layer was collected and the aqueous layer was extracted with DCM (30 mL×4). The combined organics were washed with brine, dried over Na₂SO₄, filtered and concentrated under reduced pressure to give a residue, which was purified by prep-TLC (methanol:dichloromethane=1:10) to afford the desired product as a white solid. ESI-MS m/z: (M+H)+=677.5. ¹H NMR (400 MHz, DMSO) δ 7.71-7.59 m, 1H), 7.30-7.20 (m, 2H), 6.92 (s, 1H), 6.55 (d, J=7.3 Hz, 1H), 5.07-4.84 (m, 1H), 4.67-4.62 (m, 1H), 4.35-4.04 (m, 5H), 3.27-3.18 (m, 4H), 3.11 (s, 3H), 2.70-2.63 (m, 1H), 2.20-2.08 (m, 1H), 1.96-1.48 (m, 1H), 1.43-1.28 (m, 2H), 1.23-1.00 (m, 7H), 0.94-0.76 (m, 2H).

Example 31: Synthesis of (R)-3²,2,2-trifluoro-6¹,4-dimethyl-66-morpholino-6¹,6²-dihydro-7-oxa-5-aza-6(4,8)-quinazolina-1(4,1)-piperidina-3(1,3)-benzenacyclotetradecaphan-6²-one (208)

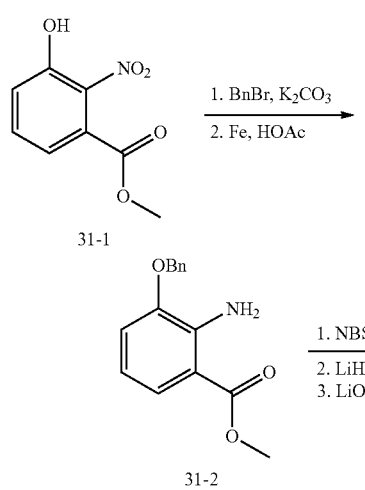

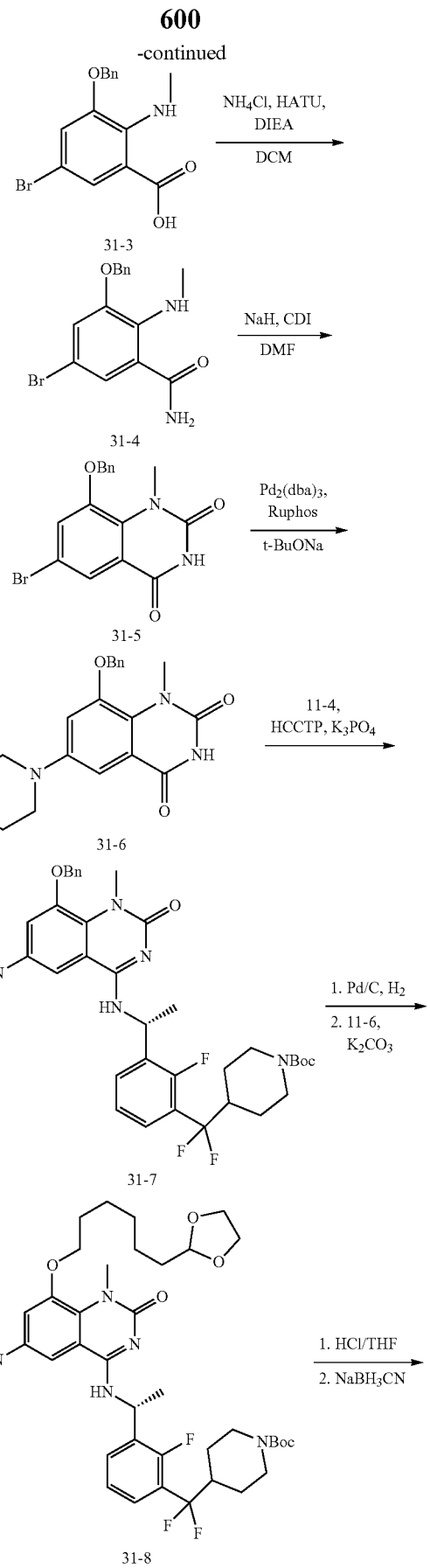

-continued

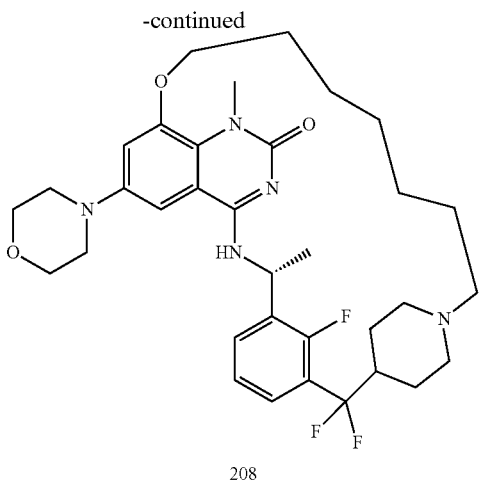

208

Step A: Preparation of methyl 3-(benzyloxy)-2-nitrobenzoate. To a solution of methyl 3-hydroxy-2-nitrobenzoate (31-1, 15 g, 1.0 eq., 76.13 mmol) in methanol (100 mL) and dichloromethane (100 mL) were added (bromomethyl)benzene (60.88 g, 4.7 eq., 304.52 mmol) and $K_2CO_3$ (8.4 g, 5.0 eq., 60.5 mmol). The mixture was stirred at 50° C. for 16 hours, then cooled to room temperature, diluted with water (150 mL) and extracted with dichloromethane (3×150 mL). The combined organics were washed with brine, dried over $Na_2SO_4$, filtered and concentrated under reduced pressure to give a residue, which was purified by silica gel column chromatography (ethyl acetate in petroleum ether 0-25%) to obtain the desired product as a white solid. $^1$H NMR (400 MHz, DMSO-d6): δ 7.78-7.62 (m, 2H), 7.59 (d, J=7.6 Hz, 1H), 7.48-7.28 (m, 5H), 5.34 (s, 2H), 3.84 (s, 3H).

Step B: Preparation of methyl 2-amino-3-(benzyloxy) benzoate (31-2). To a solution of methyl 3-(benzyloxy)-2-nitrobenzoate (20 g, 1.0 eq., 69.67 mmol) in acetic acid (120 mL) was added iron powder (39.02 g, 10.0 eq., 696.7 mmol). The mixture was stirred for 4 hours at 70° C. and cooled to room temperature, then filtered and the filter cake washed with ethyl acetate (3×100 mL). The filtrate was diluted with water (300 mL) and extracted with ethyl acetate (3×300 mL). The combined organics were washed with brine, dried over $Na_2SO_4$, filtered and concentrated under reduced pressure to give a residue, which was purified by silica gel column chromatography (ethyl acetate in dichloromethane 0-70%) to provide the desired product as a white solid. ESI-MS m/z: $(M+H)^+$=258.1.

Step C: Preparation of methyl 2-amino-3-(benzyloxy)-5-bromobenzoate. To a solution of 31-2 (17.3 g, 1.0 eq., 67.05 mmol) in dimethylformamide (50 mL) was added N-bromosuccinimide (11.93 g, 1.0 eq., 67.05 mmol) at 0° C. The mixture was stirred for 2 hours at room temperature, diluted with water (200 mL) and extracted with ethyl acetate (3×200 mL). The combined organics were washed with brine, dried over $Na_2SO_4$, filtered and concentrated under reduced pressure to give a residue, which was purified by silica gel column chromatography (ethyl acetate in petroleum ether 0-50%) to give the desired product as a white solid. ESI-MS m/z: $(M+H)^+$=336.0.

Step D: Preparation of methyl 3-(benzyloxy)-5-bromo-2-(methylamino)benzoate. To a solution of methyl 2-amino-3-(benzyloxy)-5-bromobenzoate (6 g, 1.0 eq., 17.86 mmol) and iodomethane (3.80 g, 1.5 eq., 26.79 mmol) in tetrahydrofuran (60 mL) was added lithium bis(trimethylsilyl)amide (1M, 23.2 mL, 1.3 eq., 7.8 mmol) at 0° C. The mixture was stirred for 4 hours at room temperature, then ammonium chloride (aq., 40 mL) was added to quench the reaction. The organic layer was collected and the aqueous layer was extracted with ethyl acetate (2×100 mL). The combined organics were washed with brine, dried over $Na_2SO_4$, filtered and concentrated under reduced pressure to give a residue, which was purified by silica gel column chromatography (ethyl acetate in petroleum ether 0~50%) to afford the desired product as a white solid. ESI-MS m/z: $(M+H)^+$=350.0.

Step E: Preparation of 3-(benzyloxy)-5-bromo-2-(methylamino)benzoic acid (31-3). To a solution of methyl 3-(benzyloxy)-5-bromo-2-(methylamino)benzoate (1.4 g, 1.0 eq., 4.00 mmol) in THF (14 mL), water (3.5 mL) and methanol (3.5 mL) was added LiOH—$H_2O$ (839 mg, 5.0 eq., 20.0 mmol). The mixture was stirred for 16 hours at 30° C. and solvents were removed under reduced pressure. The residue was dissolved in water (25 mL), acidified to pH ~4 with HCl (2 N aqueous), and extracted with ethyl acetate (3×50 mL). The combined organics were washed with brine, dried over $Na_2SO_4$, filtered and concentrated under reduced pressure to give the desired product as a yellow solid. ESI-MS m/z: $(M+H)^+$=336.5.

Step F: Preparation of 3-(benzyloxy)-5-bromo-2-(methylamino)benzamide (31-4). To a mixture of 31-3 (1.38 g, 1.0 eq., 4.10 mmol), ammonium chloride (1.33 g, 6.0 eq., 24.6 mmol), and N,N-diisopropylethylamine (2.12 g, 4.0 eq., 16.4 mmol) in dichloromethane (20 mL) was added HATU (3.12 g, 2 eq., 8.2 mmol). The mixture was stirred for 2 hours at 25° C. under argon atmosphere, poured into water (60 mL), and extracted with dichloromethane (3×70 mL). The combined organics were washed with brine, dried over $Na_2SO_4$, filtered and concentrated under reduced pressure to give a residue, which was purified by silica gel column chromatography (ethyl acetate in petroleum ether 0~60%) to provide the desired product as a yellow solid. ESI-MS m/z: $(M+H)^+$=334.9.

Step G: Preparation of 8-(benzyloxy)-6-bromo-1-methylquinazoline-2,4(1H,3H)-dione (31-5). To a solution of 31-4 (890 mg, 1.0 eq., 2.66 mmol) in dimethylformamide (8 mL) was added NaH (60% dispersed in mineral oil) (372.4 mg, 3.5 eq., 9.31 mmol) at room temperature. The mixture was stirred at room temperature for 1 hour, then 1,1'-carbonyldiimidazole (1.08 g, 2.5 eq., 6.65 mmol) was added slowly and stirred at room temperature overnight. The reaction mixture was poured into water (80 mL) and extracted with ethyl acetate (4×80 mL). The combined organics were washed with brine, dried over $Na_2SO_4$, filtered and concentrated under reduced pressure to give a residue, which was purified by silica gel column chromatography (methanol in dichloromethane 0-10%) to afford the desired product as a light-yellow solid. ESI-MS m/z: $(M+H)^+$=360.9.

Step H: Preparation of 8-(benzyloxy)-1-methyl-6-morpholinoquinazoline-2,4(1H,3H)-dione (31-6). To a mixture of 31-5 (920 mg, 1.0 eq., 2.56 mmol), morpholine (1.12 g, 5.0 eq., 12.8 mmol), Ruphos (238 mg, 0.2 eq., 0.51 mmol) and sodium tert-butoxide (738 mg, 3.0 eq., 7.68 mmol) in toluene (20 mL) was added $Pd_2(dba)_3$ (467 mg, 0.2 eq., 0.51 mmol). The mixture was stirred at 100° C. for 6 hours under argon atmosphere, cooled to room temperature, then concentrated to give a residue. The residue was diluted with water (100 mL) and extracted with ethyl acetate (4×120 mL). The combined organics were washed with brine, dried over $Na_2SO_4$, filtered and concentrated under reduced pressure to give a residue, which was purified by silica gel column chromatography (ethyl acetate in dichloromethane 0~50%) to give the desired product as a light-yellow solid. ESI-MS m/z: (M+H)⁺=368.2.

Step I: Preparation of tert-butyl (R)-4-((3-(1-((8-(benzyloxy)-1-methyl-6-morpholino-2-oxo-1,2-dihydroquinazolin-4-yl)amino)ethyl)-2-fluorophenyl)difluoromethyl)piperidine-1-carboxylate (31-7). To a solution of 31-6 (160 mg, 1.0 eq., 0.44 mmol) in acetonitrile (3 mL) were added phosphonitrilic chloride trimer (306 mg, 2.0 eq., 0.88 mmol) and K₃PO₄ (373 mg, 4.0 eq., 1.76 mmol). The mixture was stirred at 40° C. for 4 hours under argon atmosphere, then 11-4 (246 mg, 1.5 eq., 0.66 mmol) was added. The reaction mixture was stirred at 40° C. overnight, then cooled to room temperature, diluted with water (50 mL) and extracted with ethyl acetate (6×60 mL). The combined organics were washed with brine, dried over Na₂SO₄, filtered and concentrated under reduced pressure to give a residue, which was purified by C-18 column chromatography (FA condition, acetonitrile in water 5-95%) to afford the desired product as a yellow solid. ESI-MS m/z: (M+H)⁺=722.3.

Step J: Preparation of tert-butyl (R)-4-(difluoro(2-fluoro-3-(1-((8-hydroxy-1-methyl-6-morpholino-2-oxo-1,2-dihydroquinazolin-4-yl)amino)ethyl)phenyl)methyl)piperidine-1-carboxylate. To a solution of 31-7 (150 mg, 1.0 eq., 0.21 mmol) in methanol (9 mL) and ethyl acetate (3 mL) was added Pd/C (75 mg) (10%). The mixture was stirred for 2 hours at room temperature under hydrogen atmosphere, then filtered and the filter cake was washed with methanol (2×40 mL) and ethyl acetate (2×40 mL). The filtrate was concentrated under reduced pressure to give a residue. The residue was purified by silica gel column chromatography (methanol in dichloromethane 0~10%) to afford the desired product as a light-yellow solid. ESI-MS m/z: (M+H)⁺=632.7.

Step K: Preparation of tert-butyl (R)-4-((3-(1-((8-((6-(1,3-dioxolan-2-yl)hexyl)oxy)-1-methyl-6-morpholino-2-oxo-1,2-dihydroquinazolin-4-yl)amino)ethyl)-2-fluorophenyl)difluoromethyl)piperidine-1-carboxylate (31-8). To a solution of tert-butyl (R)-4-(difluoro(2-fluoro-3-(1-((8-hydroxy-1-methyl-6-morpholino-2-oxo-1,2-dihydroquinazolin-4-yl)amino)ethyl)phenyl)methyl)piperidine-1-carboxylate (130 mg, 1.0 eq., 0.21 mmol) in acetonitrile (5 mL) were added 11-6 (149 mg, 3.0 eq., 0.63 mmol) and K₂CO₃ (116 mg, 4.0 eq., 0.84 mmol). The mixture was stirred for 16 hours at 70° C. under argon atmosphere, cooled to room temperature, and poured into water (40 mL), then extracted with ethyl acetate (3×40 mL). The combined organics were washed with brine, dried over Na₂SO₄, filtered and concentrated under reduced pressure to give a residue, which was purified by silica gel column chromatography (methanol in dichloromethane 0~-55%) to afford the desired product as a light-yellow solid. ESI-MS m/z: (M+H)⁺=788.4.

Step L: Preparation of (R)-7-((4-((1-(3-(difluoro(piperidin-4-yl)methyl)-2-fluorophenyl)ethyl)amino)-1-methyl-6-morpholino-2-oxo-1,2-dihydroquinazolin-8-yl)oxy)heptanal. To a solution of 31-8 (50 mg, 1.0 eq., 0.06 mmol) in THF (2 mL) was added HCl (2.5 N aqueous, 3 mL). The mixture was stirred for 16 hours at room temperature and adjusted to pH-8 with the saturated aqueous NaHCO₃, then extracted with dichloromethane (3×40 mL). The combined organic layer was dried over Na₂SO₄, filtered, and concentrated in vacuo to provide the desired product, which was used directly in the next step without further purification. ESI-MS m/z: (M+H)⁺=644.3.

Step M: Preparation of (R)-3²,2,2-trifluoro-6¹,4-dimethyl-6⁶-morpholino-6¹,6²-dihydro-7-oxa-5-aza-6(4,8)-quinazolina-1(4,1)-piperidina-3(1,3)-benzenacyclotetradecaphan-6²-one (208). To a solution of (R)-7-((4-((1-(3-(difluoro(piperidin-4-yl)methyl)-2-fluorophenyl)ethyl) amino)-1-methyl-6-morpholino-2-oxo-1,2-dihydroquinazolin-8-yl)oxy)heptanal (50 mg, 1.0 eq., 0.08 mmol) in methanol (40 mL) and 1,2-dichloroethane (20 mL) was added AcOH (6 drops). The mixture was stirred at room temperature for 0.5 hours, then NaBH₃CN (13 mg, 2.5 eq., 0.2 mmol) was added and the mixture was stirred at room temperature overnight. The reaction mixture was concentrated and diluted with dichloromethane (20 mL), then washed with the saturated aqueous NaHCO₃(20 mL) and the aqueous layer extracted with dichloromethane (3×40 mL). The combined organics were dried over Na₂SO₄, filtered and concentrated under reduced pressure to give a residue, which was purified by silica gel column chromatography (methanol in dichloromethane 0~55%) to afford the desired product as a yellow solid. ESI-MS m/z: (M+H)⁺=628.5. ¹H NMR (400 MHz, DMSO) δ 8.15 (s, 1H), 7.70-7.63 (m, 1H), 7.29-7.17 (m, 2H), 7.12 (s, 1H), 6.95 (s, 1H), 5.53-5.43 (m, 1H), 4.25-4.05 (m, 2H), 3.81-3.77 (m, 4H), 3.56 (s, 3H), 3.21-3.14 (m, 5H), 2.69-2.65 (m, 1H), 2.46-2.39 (m, 1H), 2.10-1.95 (m, 2H), 1.94-1.83 (m, 2H), 1.79-1.72 (m, 2H), 1.68 (d, J=7.2 Hz, 3H), 1.58-1.45 (m, 3H), 1.35-1.26 (m, 5H), 1.17-1.12 (m, 2H), 1.03-0.92 (m, 1H), 0.81-0.71 (m, 1H).

Example 32: Synthesis of (3R)-1⁶-(1,1-dioxidothiomorpholino)-5,5-difluoro-3-methyl-1⁷,1⁸-dihydro-12-oxa-2-aza-1(4,8)-pyrido[2,3-d]pyrimidina-7(3,1)-azetidina-4(1,3)-benzenacyclopentade-caphan-1⁷-one (209)

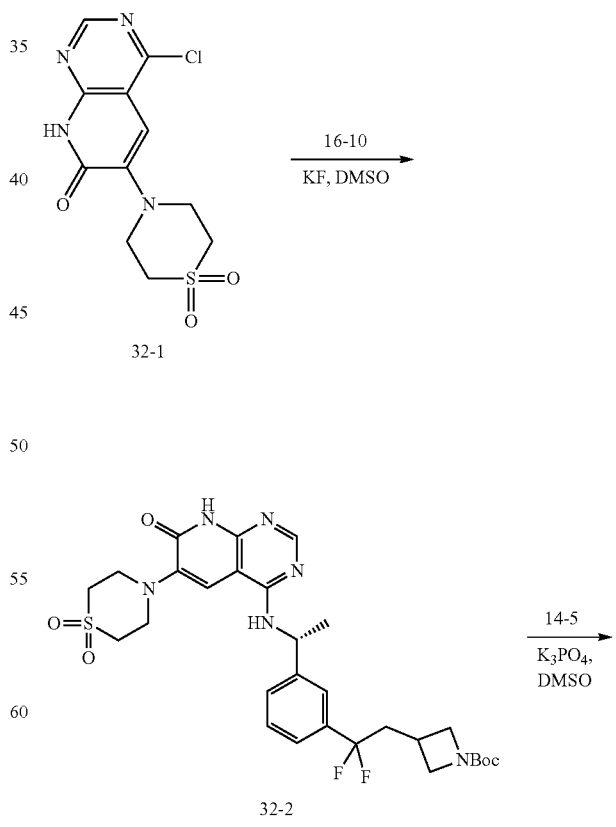

-continued

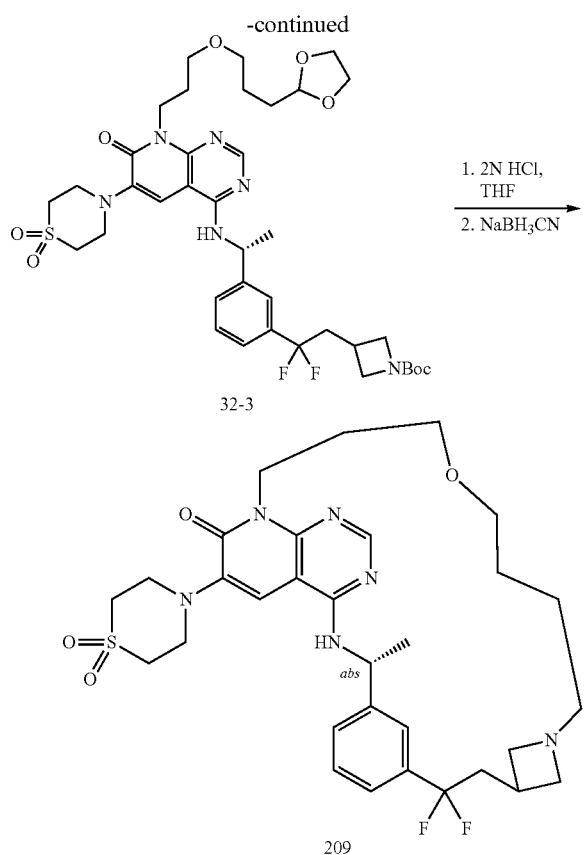

32-3

1. 2N HCl, THF
2. NaBH₃CN

209

Step A: Preparation of tert-butyl (R)-3-(2-(3-(1-((6-(1,1-dioxidothiomorpholino)-7-oxo-7,8-dihydropyrido[2,3-d]pyrimidin-4-yl)amino)ethyl)phenyl)-2,2-difluoroethyl)azetidine-1-carboxylate (32-2). A solution of 16-10 (200 mg, 1.0 eq., 0.59 mmol), 4-chloro-6-(1,1-dioxidothiomorpholino)pyrido[2,3-d]pyrimidin-7(8H)-one (32-1, 204 mg, 1.1 eq., 0.65 mmol) and KF (205 mg, 6.0 eq., 3.53 mmol) in anhydrous dimethyl sulfoxide (3 mL, 0.2 M) was stirred at 100° C. for 2 hours under nitrogen. The mixture was cooled to room temperature and diluted with ethyl acetate (20 mL) and water (40 mL), then extracted with ethyl acetate (20 mL×3). The combined organics were dried over Na₂SO₄, filtered and concentrated under reduced pressure to give a residue, which was purified by com-flash chromatography on a silica gel column (0%~10% methanol in dichloromethane) to give the desired product as a yellow solid. ESI-MS m/z: (M+H)⁺=619.3.

Step B: Preparation of tert-butyl (R)-3-(2-(3-(1-((8-(3-(3-(1,3-dioxolan-2-yl)propoxy)propyl)-6-(1,1-dioxidothiomorpholino)-7-oxo-7,8-dihydropyrido[2,3-d]pyrimidin-4-yl)amino)ethyl)phenyl)-2,2-difluoroethyl)azetidine-1-carboxylate (32-3). To a stirred solution of 32-2 (210 mg, 1.0 eq., 0.34 mmol) in dimethyl sulfoxide (5 mL, 0.07 M) was added 14-5 (175 mg, 1.5 eq., 0.51 mmol), K₃PO₄ (216 mg, 3.0 eq., 1.02 mmol) and the resulting solution was stirred at room temperature for 2 hours. The reaction mixture was diluted with ethyl acetate (20 mL) and water (40 mL), then extracted with ethyl acetate (20 mL×3). The combined organics were dried over Na₂SO₄, filtered and concentrated under reduced pressure to give a residue, which was purified by com-flash chromatography on a silica gel column (0%~85% ethyl acetate in petroleum ether) to give the desired product as a yellow solid. ESI-MS m/z: (M+H)⁺=791.4.

Step C: Preparation of (R)-4-(3-(4-((1-(3-(2-(azetidin-3-yl)-1,1-difluoroethyl)phenyl)ethyl)amino)-6-(1,1-dioxidothiomorpholino)-7-oxopyrido[2,3-d]pyrimidin-8(7H)-yl)propoxy)butanal. To a stirred solution of 32-3 (200 mg, 1.0 eq., 0.25 mmol) in tetrahydrofuran (10 mL) was added drop-wise hydrochloric acid (20 mL, 2N) at room temperature and the resulting mixture was stirred at room temperature overnight. The reaction mixture was diluted with aq. NaHCO₃ and extracted with DCM (3×50 mL). The combined organics were dried over Na₂SO₄, filtered and concentrated under reduced pressure to give the desired product as light yellow oil, which was used in the next step without further purification. ESI-MS m/z: (M+H)⁺=647.4.

Step D: Preparation of (3R)-1⁶-(1,1-dioxidothiomorpholino)-5,5-difluoro-3-methyl-1⁷,1⁸-dihydro-12-oxa-2-aza-1(4,8)-pyrido[2,3-d]pyrimidina-7(3,1)-azetidina-4(1,3)-benzenacyclopentade-caphan-1⁷-one (209). To a solution of (R)-4-(3-(4-((1-(3-(2-(azetidin-3-yl)-1,1-difluoroethyl)phenyl)ethyl)amino)-6-(1,1-dioxidothiomorpholino)-7-oxopyrido[2,3-d]pyrimidin-8(7H)-yl)propoxy)butanal (200 mg, crude) in MeOH/1,2-dichloroethane (150 mL/60 mL) was added acetic acid (1 drop) and the mixture was stirred for 30 minute at room temperature. Then, sodium cyanoborohydride (44 mg, 2.5 eq., 0.69 mmol) was added and the resulting mixture was stirred at room temperature for 1 hour. The mixture was concentrated to give a residue, which was purified by prep-HPLC (formic acid condition) to give the desired product as a light yellow solid. ESI-MS m/z: (M+H)⁺=631.6. 1H NMR (400 MHz, DMSO-D2O) δ 8.30 (s, 1H), 7.64 (s, 1H), 7.59 (s, 1H), 7.55 (d, J=7.5 Hz, 1H), 7.42 (t, J=7.7 Hz, 1H), 7.31 (d, J=7.9 Hz, 1H), 5.57 (q, J=6.7 Hz, 1H), 4.82-4.61 (m, 1H), 4.31-4.14 (m, 1H), 3.80-3.66 (m, 4H), 3.43-3.36 (m, 1H), 3.35-3.26 (m, 5H), 3.02-2.77 (m, 4H), 2.43-2.21 (m, 3H), 2.19-2.10 (m, 1H), 2.05-1.84 (m, 5H), 1.60 (d, J=7.1 Hz, 3H), 1.07-0.97 (m, 2H), 0.76-0.52 (m, 2H).

Example 33: Synthesis of 4-((3R)-5,5-difluoro-3-methyl-1⁷-oxo-1⁷,1⁸-dihydro-2-aza-1(4,8)-pyrido[2,3-d]pyrimidina-7(3,1)- azetidina-4(1,3)-benzenacyclotetradecaphane-1⁶-yl)tetrahydro-2H-thiopyran-4-carbonitrile 1,1-dioxide (210)

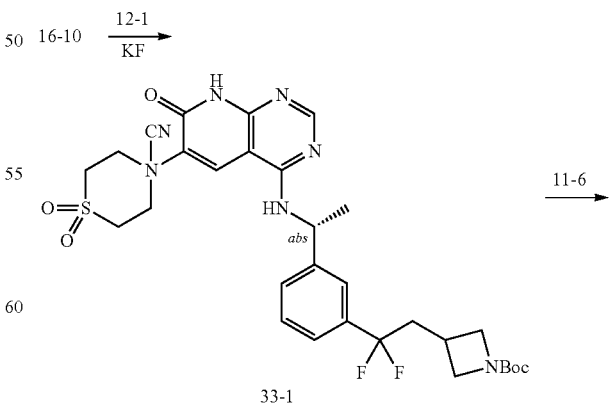

33-1

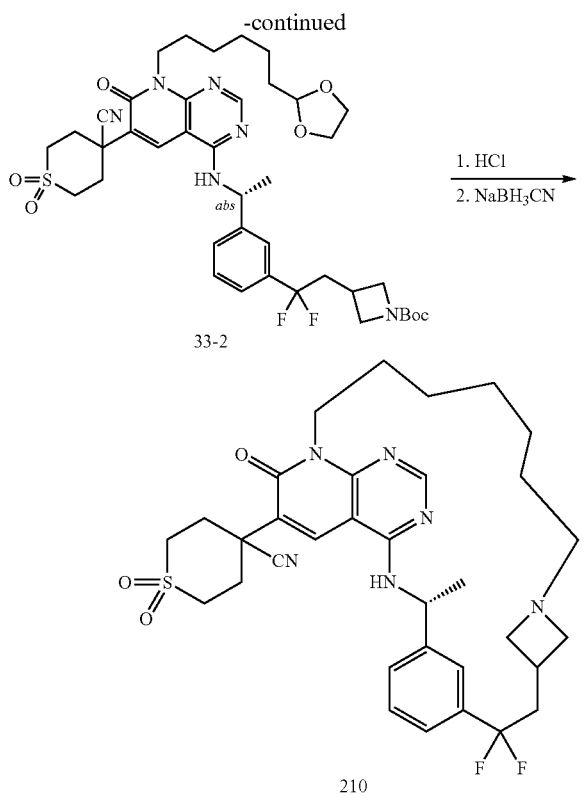

Step A: Preparation of tert-butyl (R)-3-(2-(3-(1-((6-(4-cyano-1,1-dioxidotetrahydro-2H-thiopyran-4-yl)-7-oxo-7,8-dihydropyrido[2,3-d]pyrimidin-4-yl)amino)ethyl)phenyl)-2,2-difluoroethyl)azetidine-1-carboxylate (33-1). To a stirred solution of 16-10 (200 mg, 1.0 eq., 0.592 mmol) and 12-1 (261 mg, 1.0 eq., 0.592 mmol) in DMSO (6 mL) was added KF (206 mg, 6.0 eq., 3.552 mmol), and the resulting mixture was heated to 100° C. for 2 hours under nitrogen with stirring. The reaction mixture was cooled to room temperature, diluted with water and extracted with ethyl acetate (50 mL×3). The combined organics were washed with brine, dried over Na$_2$SO$_4$, filtered and concentrated under reduced pressure to give a residue, which was purified by flash chromatography on a silica gel column (0%~5% MeOH in DCM) to afford the desired product as a light yellow foamed solid. ESI-MS m/z: (M+H)$^+$=643.3.

Step B: Preparation of tert-butyl (R)-3-(2-(3-(1-((8-(6-(1,3-dioxolan-2-yl)hexyl)-6-(4-cyano-1,1-dioxidotetrahydro-2H-thiopyran-4-yl)-7-oxo-7,8-dihydropyrido[2,3-d]pyrimidin-4-yl)amino)ethyl)phenyl)-2,2-difluoroethyl)azetidine-1-carboxylate (33-2). To a stirred solution of 33-1 (200 mg, 1.0 eq., 0.31 mmol) and 11-6 (110 mg, 1.5 eq., 0.465 mmol) in DMSO (6 mL) was added K$_3$PO$_4$ (198 mg, 3.0 eq., 0.93 mmol) and the resulting mixture was stirred at room temperature for 1 hour. The reaction mixture was diluted with ethyl acetate/water (20 mL/60 mL) and extracted with ethyl acetate (50 ml×3). The combined organics were washed with brine, dried over Na$_2$SO$_4$, filtered and concentrated under reduced pressure to give a residue, which was purified by flash chromatography on a silica gel column (0%~50% ethyl acetate in petroleum ether) to give the desired product as a white foam solid. ESI-MS m/z: (M+H)$^+$=799.4.

Step C: Preparation of (R)-4-(4-((1-(3-(2-(azetidin-3-yl)-1,1-difluoroethyl)phenyl)ethyl)amino)-7-oxo-8-(7-oxoheptyl)-7,8-dihydropyrido[2,3-d]pyrimidin-6-yl)tetrahydro-2H-thiopyran-4-carbonitrile 1,1-dioxide. To a stirred solution of 33-2 (178 mg, 1.0 eq., 0.22 mmol) in THF (5 mL) was added HCl (10 mL, 2N) dropwise and the resulting mixture was stirred at room temperature for 16 hours. The reaction mixture was diluted with DCM (30 mL) and the pH adjusted to ~8 with sat. aqueous NaHCO$_3$. The mixture was extracted with DCM (100 mL×3) and the combined organics were washed with brine, dried over Na$_2$SO$_4$, filtered and concentrated under reduced pressure to give the desired product as a light yellow solid, which was used directly in the next step without further purification. ESI-MS m/z: (M+H)$^+$=655.4.

Step D: Preparation of 4-((3R)-5,5-difluoro-3-methyl-1$^7$-oxo-1$^7$,1$^8$-dihydro-2-aza-1(4,8)-pyrido[2,3-d]pyrimidina-7(3,1)-azetidina-4(1,3)-benzenacyclotetradecaphane-1$^6$-yl)tetrahydro-2H-thiopyran-4-carbonitrile 1,1-dioxide (210). To a stirred solution of (R)-4-(4-((1-(3-(2-(azetidin-3-yl)-1,1-difluoroethyl)phenyl)ethyl)amino)-7-oxo-8-(7-oxoheptyl)-7,8-dihydropyrido[2,3-d]pyrimidin-6-yl)tetrahydro-2H-thiopyran-4-carbonitrile 1,1-dioxide (170 mg crude, 1.0 eq., ~0.22 mmol) in methanol/1,2-dichloroethane (167 mL/83 mL) was added acetic acid (2 drops) and the resulting solution was stirred at room temperature for 30 minutes. Sodium cyanoborohydride (40 mg, 2.5 eq., 0.625 mmol) was added and the resulting mixture was stirred at room temperature for 1 hour. The reaction mixture was concentrated, treated with DCM and sat. aqueous NaHCO$_3$ solution and extracted with DCM (50 mL×3). The combined organics were washed with brine, dried over Na$_2$SO$_4$, filtered and concentrated under reduced pressure to give a residue, which was purified by flash chromatography (0%-100% (MeOH:DCM=1:15) in DCM) to give the desired product as a white solid. ESI-MS m/z: (M+H)$^+$=639.5. $^1$H NMR (400 MHz, DMSO-D2O) δ 8.40 (s, 2H), 7.63 (d, J=7.6 Hz, 1H), 7.54-7.45 (m, 2H), 7.33 (d, J=7.7 Hz, 1H), 5.40 (q, J=6.9 Hz, 1H), 4.69 (t, J=9.4 Hz, 1H), 4.20-4.13 (m, 1H), 3.51-3.36 (m, 4H), 3.22 (s, 1H), 3.08 (s, 1H), 2.95-2.75 (m, 3H), 2.67-2.61 (m, 1H), 2.53-2.43 (m, 4H), 2.36-2.25 (m, 1H), 1.85-1.26 (m, 7H), 1.26-0.72 (m, 8H).

Example 34: Synthesis of (3R)-1$^6$-(1,1-dioxidothiomorpholino)-5,5-difluoro-3-methyl-1$^7$,1$^8$-dihydro-2-aza-1(4,8)-pyrido[2,3-d]pyrimidina-7(3,1)-azetidina-4(1,3)-benzenacyclotetradecaphan-1$^7$-one (211)

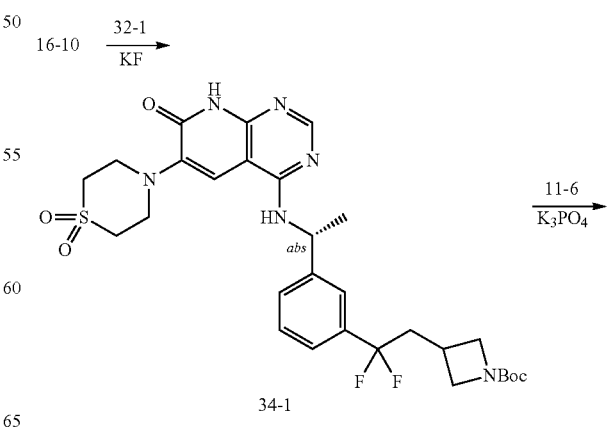

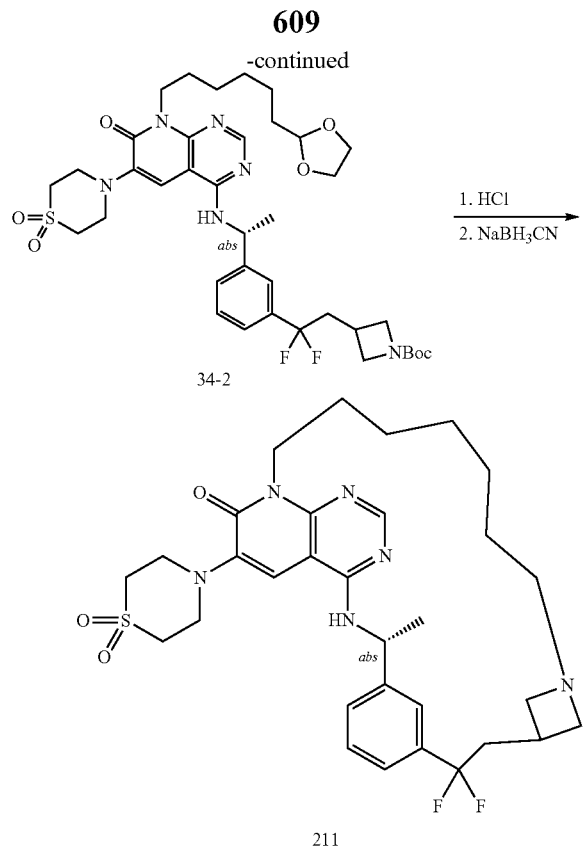

Step A: Preparation of tert-butyl (R)-3-(2-(3-(1-((6-(1,1-dioxidothiomorpholino)-7-oxo-7,8-dihydropyrido[2,3-d]pyrimidin-4-yl)amino)ethyl)phenyl)-2,2-difluoroethyl)azetidine-1-carboxylate (34-1). A mixture of 16-10 (200 mg, 1.0 eq., 0.588 mmol), 32-1 (184.61 mg, 1.0 eq., 0.588 mmol) and KF (204 mg, 6.0 eq., 3.527 mmol) in dry DMSO (4 mL) was stirred at 100° C. for 2 hours under nitrogen. The reaction mixture was then cooled and concentrated, poured into water, and extracted with ethyl acetate (3×30 mL). The combined organics were washed with brine, dried over Na$_2$SO$_4$, filtered and concentrated under reduced pressure to give a residue, which was purified by com-flash chromatography on a silica gel column (0%-80% ethyl acetate in petroleum ether) to give the desired product as a light-yellow oil. ESI-MS m/z: (M+H)$^+$=619.2.

Step B: Preparation of tert-butyl (R)-3-(2-(3-(1-((8-(6-(1,3-dioxolan-2-yl)hexyl)-6-(1,1-dioxidothiomorpholino)-7-oxo-7,8-dihydropyrido[2,3-d]pyrimidin-4-yl)amino)ethyl)phenyl)-2,2-difluoroethyl)azetidine-1-carboxylate (34-2). To a stirred solution of 34-1 (182 mg, 1.0 eq., 0.294 mmol) and 11-6 (104 mg, 1.5 eq., 0.442 mmol) in DMSO (5 mL) was added K$_3$PO$_4$ (187 mg, 3.0 eq., 0.883 mmol) and the resulting solution was stirred at room temperature for 2 hours. The reaction mixture was diluted with ethyl acetate/water (40 mL/30 mL) and extracted with ethyl acetate (3×30 mL). The combined organics were washed with brine, dried over Na$_2$SO$_4$, filtered and concentrated under reduced pressure to give a residue, which was purified by com-flash chromatography on a silica gel column (0%-80% ethyl acetate in petroleum ether) to give the desired product. ESI-MS m/z: (M+H)$^+$=775.4.

Step C: Preparation of (R)-7-(4-((1-(3-(2-(azetidin-3-yl)-1,1-difluoroethyl)phenyl)ethyl)amino)-6-(1,1-dioxidothiomorpholino)-7-oxopyrido[2,3-d]pyrimidin-8(7H)-yl)heptanal. To a solution of 34-2 (191 mg, 1.0 eq., 0.247 mmol) in THF (19.1 mL) was added HCl (38.2 mL, 2 M in water) and the resulting solution was stirred at room temperature for 16 hours. The reaction mixture was treated with NaHCO$_3$ and extracted with ethyl acetate (3×50 mL). The combined organics were washed with brine, dried over Na$_2$SO$_4$, filtered and concentrated under reduced pressure to give the desired product, which was used directly in the next step without further purification. ESI-MS m/z: (M+H)$^+$=631.3.

Step D: Preparation of (3R)-1$^6$-(1,1-dioxidothiomorpholino)-5,5-difluoro-3-methyl-1$^7$,1$^8$-dihydro-2-aza-1(4,8)-pyrido[2,3-d]pyrimidina-7(3,1)-azetidina-4(1,3)-benzenacyclotetradecaphan-1$^7$-one (211). To a solution of (R)-7-(4-((1-(3-(2-(azetidin-3-yl)-1,1-difluoroethyl)phenyl)ethyl)amino)-6-(1,1-dioxidothiomorpholino)-7-oxopyrido[2,3-d]pyrimidin-8(7H)-yl)heptanal (172 mg crude, 1.0 eq., 0.273 mmol) in MeOH/1,2-dichloroethane (180 mL/90 mL, c=0.001M) was added 1 drop of acetic acid and the resulting mixture was stirred for 0.5 hours at room temperature. NaBH$_3$CN (42 mg, 2.5 eq., 0.682 mmol) was added followed by stirring at room temperature for an additional 0.5 hours. The reaction mixture was concentrated to provide a residue which was purified by prep-HPLC to obtain the desired product. ESI-MS m/z: (M+H)$^+$=775.4. $^1$H NMR (400 MHz, DMSO-D2O) δ 8.27 (s, 1H), 7.72 (s, 1H), 7.62 (d, J=7.8 Hz, 1H), 7.52-7.44 (m, 2H), 7.30 (d, J=7.6 Hz, 1H), 5.39 (q, J=6.6 Hz, 1H), 4.76-4.64 (m, 1H), 4.18-4.06 (m, 1H), 3.31 (s, 4H), 3.23-2.96 (m, 2H), 2.83-2.69 (m, 1H), 2.51-2.22 (m, 5H), 2.08-1.90 (m, 1H), 1.76-1.65 (m, 1H), 1.64-1.52 (m, 4H), 1.41 (t, J=22.0 Hz, 2H), 1.33-1.24 (m, 2H), 1.18-1.00 (m, 4H), 0.95-0.78 (m, 4H).

Example 35: Synthesis of (3R)-16-(1,1-dioxidotetrahydro-2H-thiopyran-4-yl)-42,5,5-trifluoro-3-methyl-17,18-dihydro-2-aza-1(4,8)-pyrido[2,3-d]pyrimidina-7(3,1)-azetidina-4(1,3)-benzenacyclotetradecaphan-17-one (212)

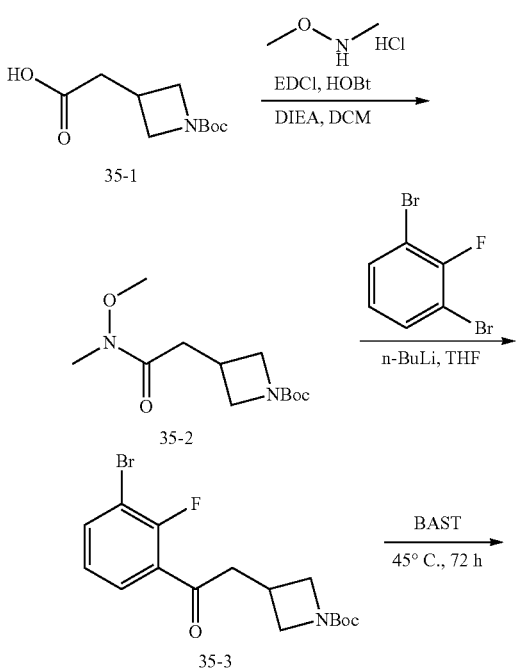

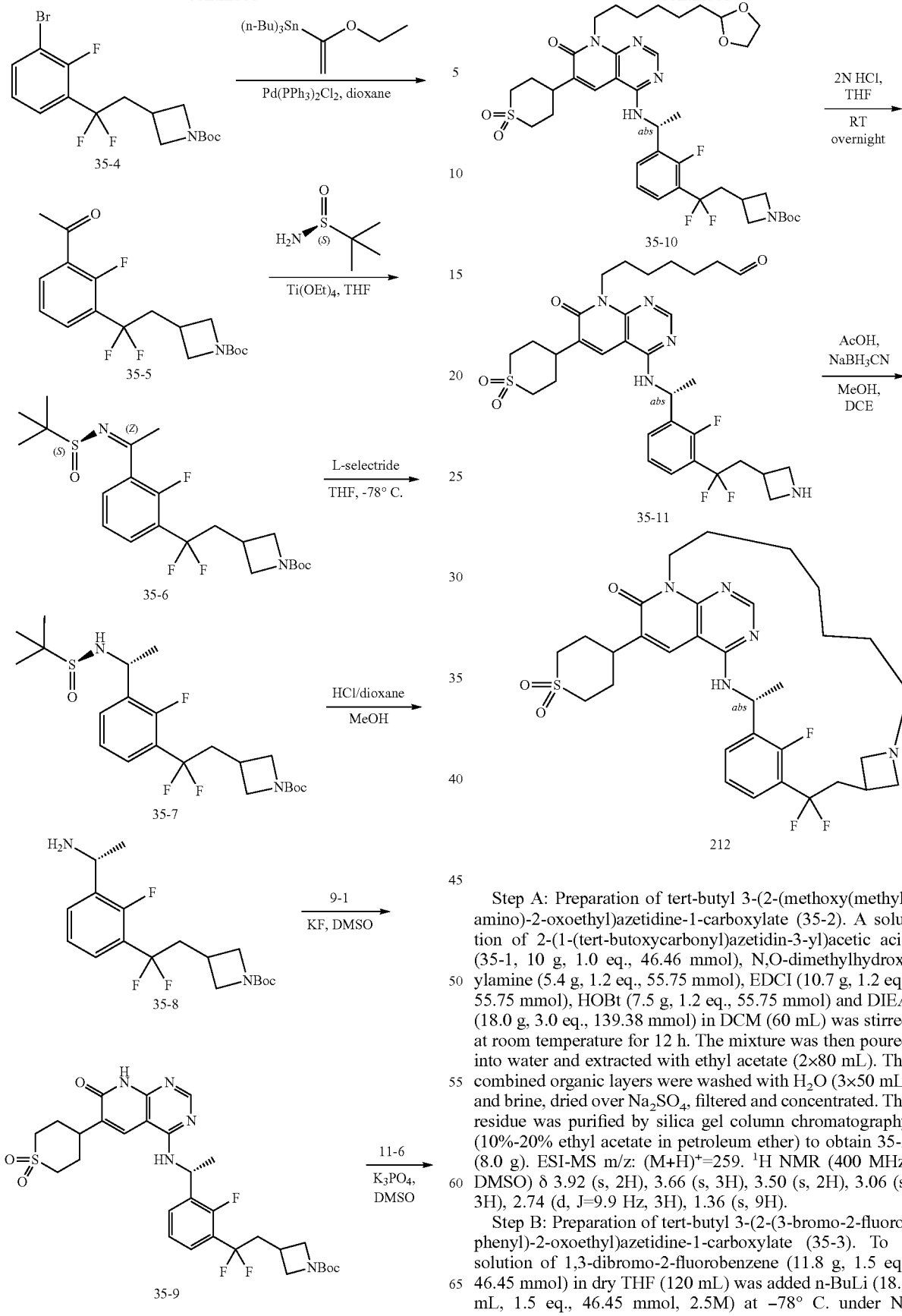

Step A: Preparation of tert-butyl 3-(2-(methoxy(methyl)amino)-2-oxoethyl)azetidine-1-carboxylate (35-2). A solution of 2-(1-(tert-butoxycarbonyl)azetidin-3-yl)acetic acid (35-1, 10 g, 1.0 eq., 46.46 mmol), N,O-dimethylhydroxylamine (5.4 g, 1.2 eq., 55.75 mmol), EDCI (10.7 g, 1.2 eq., 55.75 mmol), HOBt (7.5 g, 1.2 eq., 55.75 mmol) and DIEA (18.0 g, 3.0 eq., 139.38 mmol) in DCM (60 mL) was stirred at room temperature for 12 h. The mixture was then poured into water and extracted with ethyl acetate (2×80 mL). The combined organic layers were washed with $H_2O$ (3×50 mL) and brine, dried over $Na_2SO_4$, filtered and concentrated. The residue was purified by silica gel column chromatography (10%-20% ethyl acetate in petroleum ether) to obtain 35-2 (8.0 g). ESI-MS m/z: $(M+H)^+=259$. $^1H$ NMR (400 MHz, DMSO) δ 3.92 (s, 2H), 3.66 (s, 3H), 3.50 (s, 2H), 3.06 (s, 3H), 2.74 (d, J=9.9 Hz, 3H), 1.36 (s, 9H).

Step B: Preparation of tert-butyl 3-(2-(3-bromo-2-fluorophenyl)-2-oxoethyl)azetidine-1-carboxylate (35-3). To a solution of 1,3-dibromo-2-fluorobenzene (11.8 g, 1.5 eq., 46.45 mmol) in dry THF (120 mL) was added n-BuLi (18.6 mL, 1.5 eq., 46.45 mmol, 2.5M) at −78° C. under $N_2$ atmosphere and the mixture was stirred at −78° C. for 1 h.

Then, a solution of 35-2 (8.0 g, 1.0 eq., 30.97 mmol) in dry THF (20 mL) was added into the above solution at −78° C. The mixture was allowed to warm to room temperature and stirred for 2 h, then quenched with sat. aqueous NH$_4$Cl (100 mL) and extracted with ethyl acetate (2×100 mL). The combined organic layers were dried over Na$_2$SO$_4$, filtered, and concentrated. The residue was purified by silica gel column chromatography (20-30% ethyl acetate in petroleum ether) to obtain 35-3 (2.95 g). ESI-MS m/z: (M+H)$^+$=372.

Step C: Preparation of tert-butyl 3-(2-(3-bromo-2-fluorophenyl)-2,2-difluoroethyl)azetidine-1-carboxylate (35-4). 35-3 (4.95 g, 1 eq., 13.29 mmol) in bis(2-methoxyethyl)aminosulfurtrifluoride (20 mL) was stirred for 72 h at 50° C. The mixture was poured into ice water slowly and the solution was extracted with ethyl acetate (3×50 mL). The combined organic layers were washed with brine, dried over Na$_2$SO$_4$ and concentrated. The residue was purified by silica gel column chromatography (0%-30% ethyl acetate in petroleum ether) to obtain 35-4 (3.05 g). ESI-MS m/z: (M+H)$^+$=395.

Step D: Preparation of tert-butyl 3-(2-(3-acetyl-2-fluorophenyl)-2,2-difluoroethyl)azetidine-1-carboxylate (35-5). A solution of 35-4 (3.05 g, 1.0 eq., 7.74 mmol), tributyl(1-ethoxyvinyl)stannane (4.2 g, 1.5 eq., 11.60 mmol) and Pd(PPh$_3$)$_2$Cl$_2$ (1.1 g, 0.2 eq., 1.55 mmol) in dioxane (35 mL) was heated to 100° C. for 16 h under nitrogen. The mixture was cooled to room temperature and quenched with sat. aqueous KF (50 mL). The resulting solution was stirred for 1 h and filtered. The filter cake was washed with ethyl acetate and the filtrate was extracted with ethyl acetate (3×40 mL). The combined organic phase was concentrated to afford a residue, which was dissolved in THF (30 mL) and HCl (3M in water). The resulting solution was stirred at room temperature for 1 h and the mixture was basified with sat. aqueous NaHCO$_3$. The mixture was extracted with ethyl acetate (3×200 mL) and the combined organic layers were dried over Na$_2$SO$_4$ and concentrated. The residue was purified by silica gel column chromatography (10%-20% ethyl acetate in petroleum ether) to obtain 35-5 (1.67 g). ESI-MS m/z: (M+H)$^+$=358.

Step E: Preparation of tert-butyl (S,Z)-3-(2-(3-(1-((tert-butylsulfinyl)imino)ethyl)-2-fluorophenyl)-2,2-difluoroethyl)azetidine-1-carboxylate (35-6). To a stirred solution of 35-5 (1.67 g, 1.0 eq., 4.67 mmol) and (S)-2-methylpropane-2-sulfinamide (1.13 g, 2.0 eq., 9.35 mmol) in dry THF (20 mL) was added tetraethyl titanate (2.13 g, 2.0 eq., 9.35 mmol) and the mixture was stirred for 16 h at 70° C. The mixture was diluted with H$_2$O and the solution extracted with DCM (3×40 mL). The combined organic layer was washed with saturated brine (50 mL), dried over Na$_2$SO$_4$ and concentrated. The residue was purified by silica gel column chromatography (25%-35% ethyl acetate in petroleum ether) to obtain 35-6 (1.95 g). ESI-MS m/z: (M+H)$^+$=461.

Step F: Preparation of tert-butyl 3-(2-(3-((R)-1-(((S)-tert-butylsulfinyl)amino)ethyl)-2-fluorophenyl)-2,2-difluoroethyl)azetidine-1-carboxylate (35-7). To a stirred solution of 35-6 (1.95 g, 1.0 eq., 4.23 mmol) in dry THF (25 mL) was added dropwise L-selectride (1.01 g, 1.25 eq., 5.29 mmol, 1M in THF) at −78° C. under nitrogen. The mixture was stirred for 3 h, then diluted with sat. Aqueous NH$_4$Cl and extracted with DCM (3×30 mL). The combined organic layer was washed with saturated brine (40 mL), dried over Na$_2$SO$_4$ and concentrated. The residue was purified by silica gel column chromatography (0%-55% ethyl acetate in petroleum ether) to obtain 35-7 (950 mg, de %=96.90%). ESI-MS m/z: (M+H)$^+$=463.

Step G: Preparation of tert-butyl (R)-3-(2-(3-(1-aminoethyl)-2-fluorophenyl)-2,2-difluoroethyl)azetidine-1-carboxylate (35-8). To a stirred solution of 35-7 (950 mg, 1.0 eq., 2.05 mmol) in MeOH (16 mL) was added HCl/dioxane (3.9 mL, 1.9 eq., 3.9 mmol, 1M) at 0° C. and the resulting mixture was stirred at 0° C. for 1 h. The mixture was diluted with sat. Aqueous NaHCO$_3$ and extracted with DCM (3×50 mL). The combined organic layer was washed with saturated brine (30 mL), dried over Na$_2$SO$_4$ and concentrated. The residue was purified by silica gel column chromatography (0%-10% MeOH in DCM) to obtain 35-8 (720 mg). ESI-MS m/z: (M+H)$^+$=359. $^1$H NMR (400 MHz, DMSO) δ 7.75 (t, J=6.7 Hz, 1H), 7.38-7.31 (m, 1H), 7.28 (t, J=7.7 Hz, 1H), 4.29 (q, J=6.6 Hz, 1H), 3.82-3.78 (m, J=8.3 Hz, 2H), 3.50 (d, J=5.6 Hz, 2H), 2.75-2.66 (m, 1H), 2.63-2.53 (m, 2H), 1.35 (s, 9H), 1.25 (d, J=6.6 Hz, 3H).

Step H: Preparation of tert-butyl (R)-3-(2-(3-(1-((6-(1,1-dioxidotetrahydro-2H-thiopyran-4-yl)-7-oxo-7,8-dihydropyrido[2,3-d]pyrimidin-4-yl)amino)ethyl)-2-fluorophenyl)-2,2-difluoroethyl)azetidine-1-carboxylate (35-9). To a stirred solution of 35-8 (150 mg, 1.0 eq., 0.42 mmol) and 9-1 (144 mg, 1.1 eq., 0.46 mmol) in dry DMSO (3 mL) was added KF (146 mg, 6.0 eq., 2.52 mmol) and the resulting solution was heated to 100° C. for 2 h under nitrogen. The mixture was diluted with water (30 mL) and extracted with ethyl acetate (3×20 mL). The combined organic layers were washed with brine, dried over Na$_2$SO$_4$ and concentrated. The residue was purified by com-flash chromatography on a silica gel column (0%-10% MeOH in DCM) to give 35-9 (270 mg). ESI-MS m/z: (M+H)$^+$=636.

Step I: Preparation of tert-butyl (R)-3-(2-(3-(1-((8-(6-(1,3-dioxolan-2-yl)hexyl)-6-(1,1-dioxidotetrahydro-2H-thiopyran-4-yl)-7-oxo-7,8-dihydropyrido[2,3-d]pyrimidin-4-yl)amino)ethyl)-2-fluorophenyl)-2,2-difluoroethyl)azetidine-1-carboxylate (35-10). To a stirred solution of 35-9 (250 mg, 1.0 eq., 0.39 mmol) and 11-6 (139 mg, 1.5 eq., 0.59 mmol) in DMSO (5 mL) was added K$_3$PO$_4$ (250 mg, 3.0 eq., 1.18 mmol), and the resulting solution was stirred at room temperature for 2 h. The mixture was diluted with ethyl acetate/water (20 mL/30 mL) and extracted with EA (3×30 mL). The combined organic layers were washed with brine, dried over Na$_2$SO$_4$ and concentrated. The residue was purified by com-flash chromatography on a silica gel column (0%-10% MeOH in DCM) to give 35-10 (240 mg). ESI-MS m/z: (M+H)$^+$=792.

Step J: Preparation of (R)-7-(4-((1-(3-(2-(azetidin-3-yl)-1,1-difluoroethyl)-2-fluorophenyl)ethyl)amino)-6-(1,1-dioxidotetrahydro-2H-thiopyran-4-yl)-7-oxopyrido[2,3-d]pyrimidin-8(7H)-yl)heptanal (35-11). To a solution of 35-10 (220 mg, 1.0 eq., 0.28 mmol) in THF (10 mL) was added HCl (20 mL, 2 M in water) at room temperature and the resulting solution was stirred at room temperature for 3 h. The mixture was diluted with NaHCO$_3$ and extracted with DCM (3×50 mL). The combined organic layers were washed with brine, dried over Na$_2$SO$_4$ and concentrated to give 35-11 (200 mg, crude), which was used in the next step without further purification. ESI-MS m/z: (M+H)$^+$=648.

Step K: Preparation of (3R)-1$^6$-(1,1-dioxidotetrahydro-2H-thiopyran-4-yl)-4$^2$,5,5-trifluoro-3-methyl-1$^7$,1$^8$-dihydro-2-aza-1(4,8)-pyrido[2,3-d]pyrimidina-7(3,1)-azetidina-4(1,3)-benzenacyclotetradecaphan-1$^7$-one (212). To a solution of 35-11 (200 mg, 1.0 eq., 0.31 mmol) in MeOH (200 mL) and 1,2-dichloroethane (100 mL) was added acetic acid (1 drop) and the mixture was stirred for 30 min at room temperature. Then, NaBH$_3$CN (49 mg, 2.5 eq., 0.78 mmol) was added to the above solution and the resulting solution was stirred at room temperature for 1 h. The mixture was concentrated under reduced pressure to give a residue, which was purified by prep-HPLC (formic acid condition) to give the title compound (30.46 mg). ESI-MS m/z: $(M+H)^+=632$. $^1$H NMR (400 MHz, DMSO) δ 8.56 (s, 1H), 8.38 (s, 1H), 8.23 (s, 1H), 7.71-7.69 (m, 1H), 7.35-7.20 (m, 2H), 5.80-5.67 (m, 1H), 4.66 (s, 1H), 4.09 (s, 1H), 3.42-3.35 (m, 2H), 3.22-3.13 (m, 3H), 2.21-1.91 (m, 6H), 1.77-0.66 (m, 20H).

Example 36: Synthesis of 4-((3R)-5,5-difluoro-3-methyl-1$^7$-oxo-1$^7$,1$^8$-dihydro-2-aza-1(4,8)-pyrido[2,3-d]pyrimidina-8(3,1)- azetidina-4(1,3)-benzenacyclotetradecaphane-1$^6$-yl)tetrahydro-2H-thiopyran-4-carbonitrile 1,1-dioxide (213)

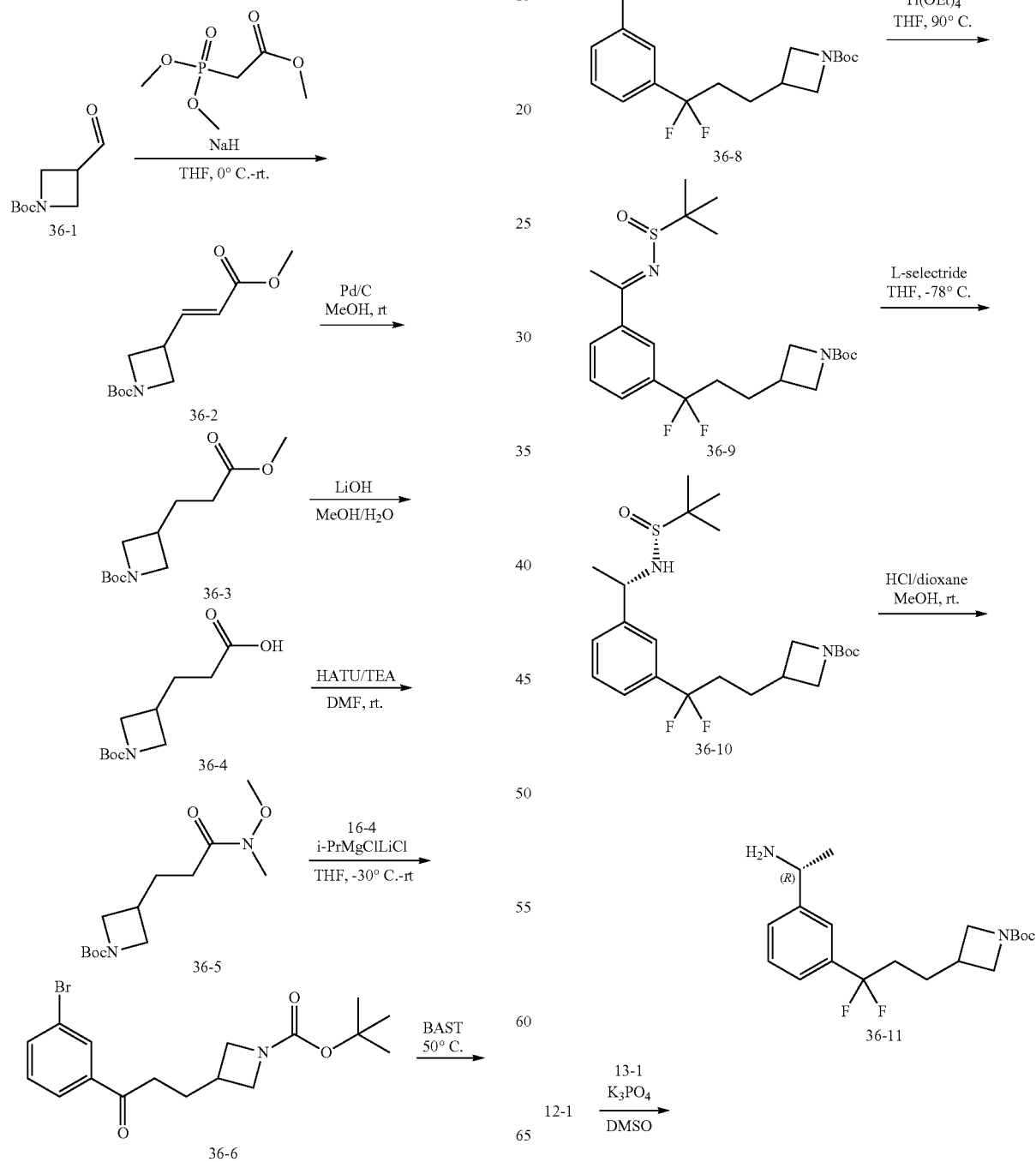

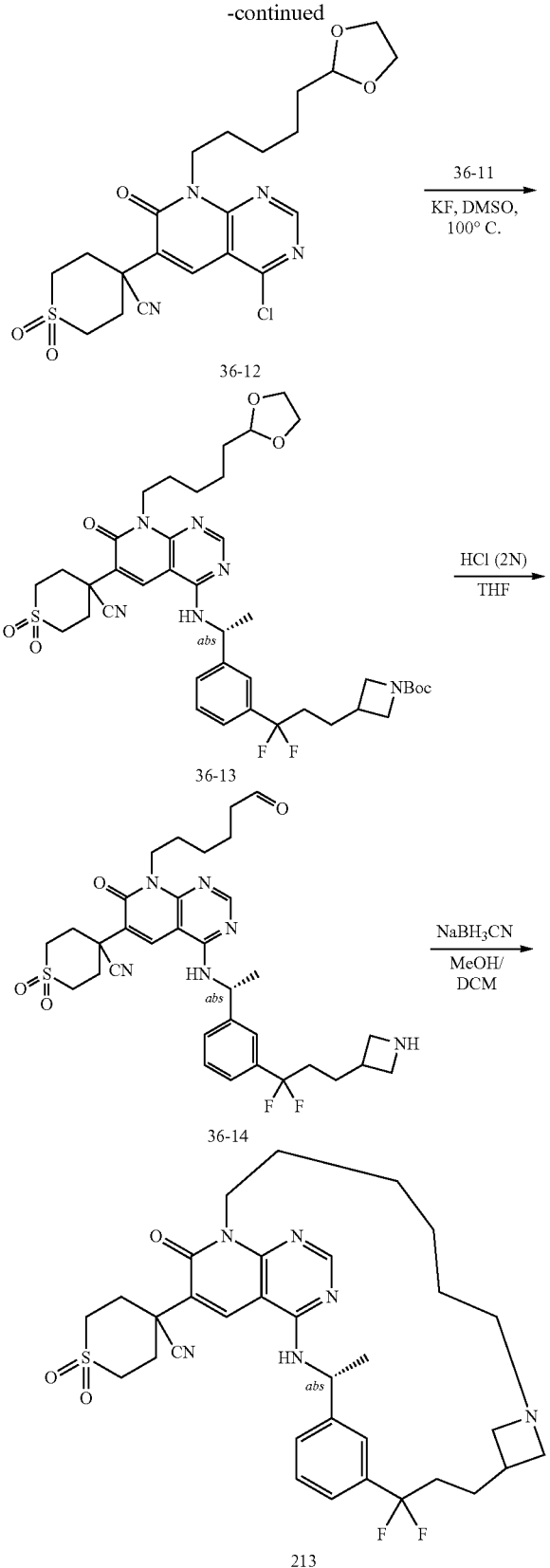

eq., 5.93 mmol) in THF (20 mL) was added sodium hydride (300 mg, 1.4 eq., 7.56 mmol, 60% in mineral oil) at 0° C. The reaction mixture was stirred 15 minutes, then tert-butyl 3-formylazetidine-1-carboxylate (36-1, 1.0 g, 1.0 eq., 5.4 mmol) was added and the reaction mixture was stirred at 0° C. for 90 minutes. After completion, the reaction mixture was diluted with water (20 mL) and extracted with ethyl acetate (3×50 mL). The combined organic layer was washed with brine (20 mL) and dried over anhydrous sodium sulfate. Removal of solvent under reduced pressure afforded the desired product (0.98 g), which was used in the next step without purification. ESI-MS m/z: (M−Boc+H)$^+$=186.

Step B: Preparation of tert-butyl 3-(3-methoxy-3-oxopropyl)azetidine-1-carboxylate (36-3). To a solution of 36-2 (0.98 g, 4.06 mmol) in MeOH (15 mL) was added Pd/C (300 mg, 10%). The reaction mixture was stirred under H$_2$ atmosphere for 2 hours, then filtered and concentrated in vacuo to give 36-3 (0.95 g) as a colorless oil. ESI-MS m/z: (M−Boc+H)$^+$=188.0.

Step C: Preparation of 3-(1-(tert-butoxycarbonyl)azetidin-3-yl)propanoic acid (36-4). To a solution of 36-3 (0.95 g, 3.9 mmol) in MeOH (25 mL) was added lithium hydroxide monohydrate (300 mg, 1.8 eq., 7.14 mmol) and water (2.5 mL). The reaction mixture was stirred for 16 hours at room temperature. The solution was concentrated and the residue was dissolved into ethyl acetate and neutralized with saturated critic acid. The solution was separated and the organic layer was extracted with ethyl acetate, washed with brine and concentrated to give 36-4 (820 mg) as a colorless oil. ESI-MS m/z: (M−Boc+H)$^+$=174.2.

Step D: Preparation of tert-butyl 3-(3-(methoxy(methyl)amino)-3-oxopropyl)azetidine-1-carboxylate (36-5). To a solution of 36-4 (0.48 g, 2.06 mmol) in DMF (5 mL) were added DIEA (0.53 g, 2 eq., 4.12 mmol), N,O-dimethylhydroxylamine hydrochloride (0.24 g, 1.2 eq., 2.47 mmol) and HATU (0.94 g, 1.2 eq., 2.47 mmol). The mixture was stirred at 25° C. for 2 hours. The resulting solution was poured into water (50 mL), extracted with ethyl acetate (30 mL×3), and the organic layers were dried over Na$_2$SO$_4$. After filtration, the solvent was removed and the residue was purified by reverse phase FC to give 36-5 (0.52 g) as a colorless oil. ESI-MS m/z: (M−Boc+H)$^+$=217.1.

Step E: Preparation of tert-butyl 3-(3-(3-bromophenyl)-3-oxopropyl)azetidine-1-carboxylate (36-6). To a solution of 16-4 (7.24 g, 3.5 eq., 25.6 mmol) in THF (10 mL) was added iPrMgCl·LiCl (26 mL, 3.5 eq., 1M) at −40° C., The solution was warmed slowly to 0° C. and stirred for 1 hour. The resulting solution was added dropwise to a solution of 36-5 (2 g, 7.3 mmol) in THF (5 mL) at 0° C. After addition, the solution was warmed to room temperature and stirred for 1 hour. The reaction was quenched with a saturated NH$_4$Cl and extracted with ethyl acetate (3×30 mL). The combined organic layers were washed with brine, dried over Na$_2$SO$_4$, concentrated and the residue was purified by FC (PE/EA=10%) to give 36-6 (1.5 g) as a colorless oil. ESI-MS m/z: (M−Boc+H)$^+$=312.1.

Step F: Preparation of tert-butyl 3-(3-(3-bromophenyl)-3,3-difluoropropyl)azetidine-1-carboxylate (36-7). A solution of 36-6 (1.4 g, 175 mmol) in BAST (5 mL) was heated to 50° C. and stirred for 3 days. The solution was added into an aqueous of NaHCO$_3$ at 0° C. The solution was extracted with DCM (3×30 mL) and the combined organic layers were dried over Na$_2$SO$_4$, concentrated in vacuo and the residue was purified by FC (PE/EA=10/1) to give 36-7 (1.0 g) as a yellow oil. ESI-MS m/z: (M−Boc+H)$^+$=390.1.

Step G: Preparation of tert-butyl 3-(3-(3-acetylphenyl)-3,3-difluoropropyl)azetidine-1-carboxylate (36-8). To a solu- Step A: Preparation of tert-butyl (E)-3-(3-methoxy-3-oxoprop-1-en-1-yl)azetidine-1-carboxylate (36-2). To a solution of ethyl 2-(diethoxyphosphoryl)acetate (1.08 g, 1.1 tion of 36-7 (3.6 g, 1 eq., 9.2 mmol) in dioxane (40 mL) were added tributyl(1-ethoxyvinyl)stannane (10 g, 3 eq., 27.6 mmol) and Pd (PPh$_3$)$_2$Cl$_2$ (645 mg, 0.1 eq., 0.92 mmol). The reaction mixture was heated to 90° C. and stirred for 3 hours. After cooling to room temperature, the solution was poured into aqueous KF (2 M, 250 ml). The resulting solution was extracted with EA (3×150 mL). The solution was dried over Na$_2$SO$_4$, concentrated and the residue was purified by FC to give the title compound (2.8) as a yellow oil. This compound was dissolved into MeCN (40 mL). To the solution was added TFA (7 mL) and the resulting mixture stirred for 3 hrs. The solution was treated with saturated NaHCO$_3$ at 0° C., then solvent was removed and the residue was extracted by EA. The solvent was removed and the residue was purified by FC to give 36-8 (1.7 g) as a yellow solid. ESI-MS m/z: (M−Boc+H)$^+$=254.0.

Step H: Preparation of tert-butyl (E)-3-(3-(3-(1-((tert-butylsulfinyl)imino)ethyl)phenyl)-3,3-difluoropropyl)azetidine-1-carboxylate (36-9). To a solution of 36-8 (500 mg, 1.28 mmol) in THF (10 mL) were added (S)-2-methylpropane-2-sulfmamide (232 mg, 1.5 eq., 1.92 mmol) and Ti(OEt)$_4$ (584 mg, 2 eq., 2.56 mmol). The reaction mixture was heated to 90° C. and stirred for 16 hours. After cooling to room temperature, the solution was poured into water (50 mL) and the resulting solution was extracted with ethyl acetate (3×30 mL). The combined organic layers were dried over Na$_2$SO$_4$, concentrated and the residue was purified by FC to give 36-9 (450 mg) as a yellow oil. ESI-MS m/z: (M−Boc+H)$^+$=457.0.

Step I: Preparation of tert-butyl 3-(3-(3-(((S)-1-(((R)-tert-butylsulfinyl)amino)ethyl)phenyl)-3,3-difluoropropyl)azetidine-1-carboxylate (36-10). To a solution of 36-9 (200 mg, 0.44 mmol) in THF (10 mL) was added L-Selectride (0.88 mL, 2 eq., 1 M) at −70° C. The solution was stirred at −70° C. for 60 mins, then quenched with saturated aqueous NH$_4$Cl. The solution was extracted by ethyl acetate (3×10 mL), dried over Na$_2$SO$_4$, concentrated in vacuo and the residue was purified by prep-TLC to give 36-10 (170 mg) as a colorless oil. ESI-MS m/z: (M−Boc+H)$^+$=459.2.

Step J: Preparation of tert-butyl (R)-3-(3-(3-(1-aminoethyl)phenyl)-3,3-difluoropropyl)azetidine-1-carboxylate (36-11). To a solution of 36-10 (200 mg, 0.087 mmol) in MeOH (2.8 mL) was added a solution of HCl/dioxane (4M, 0.7 mL) at room temperature. The reaction mixture was stirred for 2 hours, then treated with aqueous NaHCO$_3$. The solution was concentrated and the resulting solution was extracted with ethyl acetate (3×10 mL). The combined organic layers were dried over Na$_2$SO$_4$. After filtration, the solvent was removed to give 36-11 (150 mg) as a colorless oil. ESI-MS m/z: (M−Boc+H)$^+$=355.2.

Step K: Preparation of 4-(8-(5-(1,3-dioxolan-2-yl)pentyl)-4-chloro-7-oxo-7,8-dihydropyrido[2,3-d]pyrimidin-6-yl)tetrahydro-2H-thiopyran-4-carbonitrile 1,1-dioxide (36-12). To a solution of 12-1 (300 mg, 0.89 mmol) in DMSO (6 mL) were added K$_3$PO$_4$ (376 mg, 2 eq, 1.78 mmol) and 13-1 (298 mg, 1.5 eq., 1.33 mmol). The reaction mixture was stirred at room temperature for 4 hours. The resulting solution was poured into water (60 mL), extracted with ethyl acetate (3×30 mL), and the combined organic layers were dried over Na$_2$SO$_4$. After filtration, the solvent was removed and the residue was purified by FC to give 36-12 (230 mg) as a white solid. ESI-MS m/z: (M+H)$^+$=481.1.

Step L: Preparation of tert-butyl (R)-3-(3-(3-(1-((8-(5-(1,3-dioxolan-2-yl)pentyl)-6-(4-cyano-1,1-dioxidotetrahydro-2H-thiopyran-4-yl)-7-oxo-7,8-dihydropyrido[2,3-d]pyrimidin-4-yl)amino)ethyl)phenyl)-3,3-difluoropropyl)azetidine-1-carboxylate (36-13). To a solution of 36-12 (230 mg, 0.48 mmol) in DMSO (4 mL) were added 36-11 (170 mg, 1 eq., 0.48 mmol) and KF (84 mg, 3 eq., 1.44 mmol). The reaction mixture was heated to 100° C. and stirred for 2 hours under N$_2$ atmosphere. The solution was poured into water (40 mL) and extracted with ethyl acetate (3×30 mL). The combined organic layers were dried over Na$_2$SO$_4$, concentrated and the residue was purified by FC to give 36-13 (270 mg) as a colorless oil. ESI-MS m/z: (M+H)$^+$=799.4.

Step M: Preparation of (R)-4-(4-((1-(3-(3-(azetidin-3-yl)-1,1-difluoropropyl)phenyl)ethyl)amino)-7-oxo-8-(6-oxohexyl)-7,8-dihydropyrido[2,3-d]pyrimidin-6-yl)tetrahydro-2H-thiopyran-4-carbonitrile 1,1-dioxide (36-14). To a solution of 36-13 (100 mg, 0.126 mmol) in THF (10 mL) was added aqueous HCl (20 mL, 2N). The resulting solution was stirred at room temperature for 16 hours. The solution was diluted with DCM (50 mL) and then treated with a saturated NaHCO$_3$ to pH ~ 8. The solution was separated and the water phase was extracted with DCM (3×10 mL). The combined organic layers were dried over Na$_2$SO$_4$ and concentrated in vacuo to give crude 36-14 (60 mg), which was used directly in the next step without further purification. ESI-MS m/z: (M+1)$^+$=655.3.

Step N: Preparation of 4-((3R)-5,5-difluoro-3-methyl-1$^7$-oxo-1$^7$,1$^8$-dihydro-2-aza-1(4,8)-pyrido[2,3-d]pyrimidina-8(3,1)-azetidina-4(1,3)-benzenacyclotetradecaphane-1$^6$-yl)tetrahydro-2H-thiopyran-4-carbonitrile 1,1-dioxide (213). To a solution of 36-14 (100 mg, 0.15 mmol) in DCM (50 mL) and MeOH (100 mL) was added AcOH (9 drops). The solution was stirred at room temperature for 30 min, then to the solution was added NaBH$_3$CN (24 mg, 2.5 eq, 0.38 mmol). The resulting solution was stirred for 2 hours. The solvent was removed and the residue was dissolved in DCM (30 mL). The solution was washed with saturated NaHCO$_3$, dried over Na$_2$SO$_4$, concentrated and the residue was purified by prep-TLC to give 213 (30 mg) as a white solid. ESI-MS m/z: (M+1)$^+$=639.2. $^1$H NMR (400 MHz, DMSO-d$_6$): 8.64 (d, J=7.4 Hz, 1H), 8.40 (d, J=9.5 Hz, 2H), 7.60 (d, J=7.8 Hz, 1H), 7.55 (s, 1H), 7.48 (t, J=7.7 Hz, 1H), 7.32 (d, J=7.6 Hz, 1H), 5.51 (t, J=7.1 Hz, 1H), 4.39 (dd, J=40.3, 6.0 Hz, 2H), 3.49 (s, 2H), 3.08-2.76 (m, 4H), 2.12 (d, J=6.2 Hz, 1H), 2.08-1.89 (m, 6H), 1.85-1.77 (m, 1H), 1.64 (d, J=7.1 Hz, 5H), 1.34-1.06 (m, 8H), 1.00 (brs, 3H).

Example 37: Ras Sequence

```
Human K-Ras4b (SEQ ID NO. 1):
  1   MTEYKLVVVG AGGVGKSALT IQLIQNHFVD EYDPTIEDSY RKQVVIDGET

51   CLLDILDTAG QEEYSAMRDQ YMRTGEGFLC VFAINNTKSF EDIHHYREQI

101   KRVKDSEDVP MVLVGNKCDL PSRTVDTKQA QDLARSYGIP FIETSAKTRQ

151   GVDDAFYTLV REIRKHKEKM SKDGKKKKKK SKTKCVIM
```

```
Human SOS1 (SEQ ID NO. 3):
   1 MQAQQLPYEF SEENAPKWR GLLVPALKKV QGQVHPTLES NDDALQYVEE

51 LILQLLNMLC QAQPRSASDV EERVQKSFPH PIDKWAIADA QSAIEKRKRR

101 NPLSLPVEKI HPLLKEVLGY KIDHQVSVYI VAVLEYISAD ILKLVGNYVR

151 NIRHYEITKQ DIKVAMCADK VLMDMFHQDV EDINILSLTD EEPSTSGEQT

201 YYDLVKAFMA EIRQYIRELN LIIKVFREPF VSNSKLFSAN DVENIFSRIV

251 DIHELSVKLL GHIEDTVEMT DEGSPHPLVG SCFEDLAEEL AFDPYESYAR

301 DILRPGFHDR FLSQLSKPGA ALYLQSIGEG FKEAVQYVLP RLLLAPVYHC

351 LHYFELLKQL EEKSEDQEDK ECLKQAITAL LNVQSGMEKI CSKSLAKRRL

401 SESACRFYSQ QMKGKQLAIK KMNEIQKNID GWEGKDIGQC CNEFIMEGTL

451 TRVGAKHERH IFLFDGLMIC CKSNHGQPRL PGASNAEYRL KEKFFMRKVQ

501 INDKDDTNEY KHAFEIILKD ENSVIFSAKS AEEKNNWMAA LISLQYRSTL

551 ERMLDVTMLQ EEKEEQMRLP SADVYRFAEP DSEENIIFEE NMQPKAGIPI

601 IKAGTVIKLI ERLTYHMYAD PNFVRTFLTT YRSFCKPQEL LSLIIERFEI

651 PEPEPTEADR IAIENGDQPL SAELKRFRKE YIQPVQLRVL NVCRHWVEHH

701 FYDFERDAYL LQRMEEFIGT VRGKAMKKWV ESITKIIQRK KIARDNGPGH

751 NITFQSSPPT VEWHISRPGH IETFDLLTLH PIEIARQLTL LESDLYRAVQ

801 PSELVGSVWT KEDKEINSPN LLKMIRHTTN LTLWFEKCIV ETENLEERVA

851 VVSRIIEILQ VFQELNNFNG VLEVVSAMNS SPVYRLDHTF EQIPSRQKKI

901 LEEAHELSED HYKKYLAKLR SINPPCVPFF GIYLTNILKT EEGNPEVLKR

951 HGKELINFSK RRKVAEITGE IQQYQNQPYC LRVESDIKRF FENLNPMGNS

1001 MEKEFTDYLF NKSLEIEPRN PKPLPRFPKK YSYPLKSPGV RPSNPRPGTM

1051 RHPTPLQQEP RKISYSRIPE SETESTASAP NSPRTPLTPP PASGASSTTD

1101 VCSVFDSDHS SPFHSSNDTV FIQVTLPHGP RSASVSSISL TKGTDEVPVP

1151 PPVPPRRRPE SAPAESSPSK IMSKHLDSPP AIPPRQPTSK AYSPRYSISD

1201 RTSISDPPES PPLLPPREPV RTPDVFSSSP LHLQPPPLGK KSDHGNAFFP

1251 NSPSPFTPPP PQTPSPHGTR RHLPSPPLTQ EVDLHSIAGP PVPPRQSTSQ

1301 HIPKLPPKTY KREHTHPSMH RDGPPLLENA HSS

Human SOS2 (SEQ ID NO. 5):
   1 MQQAPQPYEF FSEENSPKWR GLLVSALRKV QEQVHPTLSA NEESLYYIEE

51 LIFQLLNKLC MAQPRTVQDV EERVQKTFPH PIDKWAIADA QSAIEKRKRR

101 NPLLLPVDKI HPSLKEVLGY KVDYHVSLYI VAVLEYISAD ILKLAGNYVF

151 NIRHYEISQQ DIKVSMCADK VLMDMFDQDD IGLVSLCEDE PSSSGELNYY

201 DLVRTEIAEE RQYLRELNMI IKVFREAFLS DRKLFKPSDI EKIFSNISDI

251 HELTVKLLGL IEDTVEMTDE SSPHPLAGSC FEDLAEEQAF DPYETLSQDI

301 LSPEFHEHFN KLMARPAVAL HFQSIADGFK EAVRYVLPRL MLVPVYHCWH

351 YFELLKQLKA CSEEQEDREC LNQAITALMN LQGSMDRIYK QYSPRRRPGD

401 PVCPFYSHQL RSKHLAIKKM NEIQKNIDGW EGKDIGQCCN EFIMEGPLTR

451 IGAKHERHIF LFDGLMISCK PNHGQTRLPG YSSAEYRLKE KFVMRKIQIC

501 DKEDTCEHKH AFELVSKDEN SIIFAAKSAE EKNNWMAALI SLHYRSTLDR

551 MLDSVLLKEE NEQPLRLPSP EVYRFVVKDS EENIVFEDNL QSRSGIPIIK
```

```
-continued
 601   GGTVVKLIER   LTYHMYADPN   FVRTFLTTYR   SFCKPQELLS   LLIERFEIPE

651   PEPTDADKLA   IEKGEQPISA   DLKRFRKEYV   QPVQLRILNV   FRHWVEHHFY

701   DFERDLELLE   RLESFISSVR   GKAMKKWVES   IAKIIRRKKQ   AQANGVSHNI

751   TFESPPPPIE   WHISKPGQFE   TFDLMTLHPI   EIARQLTLLE   SDLYRKVQPS

801   ELVGSVWTKE   DKEINSPNLL   KMIRHTTNLT   LWFEKCIVEA   ENFEERVAVL

851   SRIIEILQVF   QDLNNFNGVL   EIVSAVNSVS   VYRLDHTFEA   LQERKRKILD

901   EAVELSQDHF   KKYLVKLKSI   NPPCVPFFGI   YLTNILKTEE   GNNDFLKKKG

951   KDLINFSKRR   KVAEITGEIQ   QYQNQPYCLR   IEPDMRRFFE   NLNPMGSASE

1001   KEFTDYLFNK   SLEIEPRNCK   QPPRFPRKST   FSLKSPGIRP   NTGRHGSTSG

1051   TLRGHPTPLE   REPCKISFSR   IAETELESTV   SAPTSPNTPS   TPPVSASSDL

1101   SVFLDVDLNS   SCGSNSIFAP   VLLPHSKSFF   SSCGSLHKLS   EEPLIPPPLP

1151   PRKKFDHDAS   NSKGNMKSDD   DPPAIPPRQP   PPPKVKPRVP   VPTGAFDGPL

1201   HSPPPPPPRD   PLPDTPPPVP   LRPPEHFINC   PFNLQPPPLG   HLHRDSDWLR

1251   DISTCPNSPS   TPPSTPSPRV   PRRCYVLSSS   QNNLAHPPAP   PVPPRQNSSP

1301   HLPKLPPKTY   KRELSHPPLY   RLPLLENAET   PQ
```

Example 38: Protein Expression

DNA expression constructs encoding one or more protein sequences of interest (e.g., Kras fragments thereof, mutant variants thereof, etc.) and its corresponding DNA sequences are optimized for expression in E. coli and synthesized by, for example, the GeneArt Technology at Life Technologies. In some cases, the protein sequences of interest are fused with a tag (e.g., glutathione S-transferase (GST), histidine (His), or any other affinity tags) to facilitate recombinant expression and purification of the protein of interest. Such tag can be cleaved subsequent to purification. Alternatively, such tag may remain intact to the protein of interest and may not interfere with activities (e.g., target binding and/or phosphorylation) of the protein of interest A resulting expression construct is additionally encoded with (i) att-site sequences at the 5' and 3' ends for subcloning into various destination vectors using, for example, the Gateway Technology, as well as (ii) a Tobacco Etch Virus (TEV) protease site for proteolytic cleavage of one or more tag sequences. The applied destination vectors can be a pET vector series from Novagen (e.g., with ampicillin resistance gene), which provides an N-terminal fusion of a GST-tag to the integrated gene of interest and/or a pET vector series (e.g., with ampicillin resistance gene), which provides a N-terminal fusion of a HIS-tag to the integrated gene. To generate the final expression vectors, the expression construct of the protein of interest is cloned into any of the applied destination vectors. The expression vectors are transformed into E. coli strain, e.g., BL21 (DE3). Cultivation of the transformed strains for expression is performed in 10 L and 1 L fermenter. The cultures are grown, for example, in Terrific Broth media (MP Biomedicals, Kat. #1 13045032) with 200 µg/mL ampicillin at a temperature of 37° C. to a density of 0.6 (OD600), shifted to a temperature of ~27° C. (for K-Ras expression vectors) induced for expression with 100 mM IPTG, and further cultivated for 24 hours. After cultivation, the transformed E. coli cells are harvested by centrifugation and the resulting pellet is suspended in a lysis buffer, as provided below, and lysed by passing three-times through a high pressure device. The lysate is centrifuged (49000 g, 45 min, 4° C.) and the supernatant is used for further purification.

Example 39: Ras Protein Purification

A Ras (e.g., K-Ras wildtype or a mutant such as K-Ras G12D, K-Ras G12V or K-Ras G12C) construct or a variant thereof is tagged with GST. E. coli culture from a 10 L fermenter is lysed in lysis buffer (50 mM Tris HCl 7.5, 500 mM NaCl, 1 mM DTT, 0,5% CHAPS, Complete Protease Inhibitor Cocktail-(Roche)). As a first chromatography step, the centrifuged lysate is incubated with 50 mL Glutathione Agarose 4B (Macherey-Nagel; 745500.100) in a spinner flask (16 h, 10O). The Glutathione Agarose 4B loaded with protein is transferred to a chromatography column connected to a chromatography system, e.g., an Akta chromatography system. The column is washed with wash buffer (50 mM Tris HCl 7.5, 500 mM NaCl, 1 mM DTT) and the bound protein is eluted with elution buffer (50 mM Tris HCl 7.5, 500 mM NaCl, 1 mM DTT, 15 mM Glutathione). The main fractions of the elution peak (monitored by OD280) are pooled. For further purification by size-exclusion chromatography, the above eluate volume is applied to a column Superdex 200 HR prep grade (GE Healthcare) and the resulting peak fractions of the eluted fusion protein are collected. Native mass spectrometry analyses of the final purified protein construct can be performed to assess its homogeneous load with GDP.

Example 40: SOS Purification

A SOS construct or a variant thereof is His10-tagged (SEQ ID NO. 6). E. coli cultures are induced in a fermenter, harvested, and lysed in lysis buffer, for example, in 25 mM Tris HCl 7.5, 500 mM NaCl, 20 mM Imidazol, Complete EDTA-free (Roche)). For immobilized metal ion affinity chromatography (IMAC), the centrifuged lysate (50,000×g, 45 min, 40) is incubated with 30 mL Ni-NTA (Macherey-Nagel; #745400.100) in a spinner flask (16 h, 40) and subsequently transferred to a chromatography column connected to a chromatography system, e.g., an Akta chromatography system. The column is rinsed with wash buffer, e.g., in 25 mM Tris HCl 7.5, 500 mM NaCl, 20 mM Imidazol and the bound protein is eluted with a linear gradient (0-100%) of elution buffer (25 mM Tris HCl 7.5, 500 mM NaCl, 300 mM Imidazol). The main fractions of the elution peak (monitored by OD280) containing homogenous His10-hSOS is pooled.

Example 41: Ras-SOS Interaction Assay

The ability of any compound of the present disclosure to reduce a Ras protein signaling output by, e.g., interfering or disrupting interaction (or binding) between SOS1 and a Ras protein can be assessed in vitro. For example, the equilibrium interaction of human SOS1 (hSOS1) with human wildtype Kras or K-Ras mutant (e.g., hK-Ras G12C mutant, or hK-Ras G12C) can be assessed as a proxy or an indication for a subject compound's ability to inhibit SOS. Detection of such interaction is achieved by measuring homogenous time-resolved fluorescence resonance energy transfer (HTRF) from (i) a fluorescence resonance energy transfer (FRET) donor (e.g., antiGST-Europium) that is bound to GST-tagged K-Ras G12C to (ii) a FRET acceptor (e.g., anti-6His-XL665) bound to a His-tagged hSOS1.

The assay buffer can contain 5 mM HEPES pH 7.4, 150 mM NaCl, 10 mM EDTA, 1 mM DTT, 0.05% BSA, 0.0025% (v/v) Igepal and 100 mM KF. A Ras working solution is prepared in assay buffer containing typically 10 nM of the protein construct (e.g., GST-tagged hK-Ras G12C) and 2 nM of the FRET donor (e.g., antiGST-Eu(K) from Cisbio, France). A SOS1 working solution is prepared in assay buffer containing typically 10 nM of the protein construct (e.g., His-hSOS1) and 10 nM of the FRET acceptor (e.g., anti-6His-XL665 from Cisbio, France). An inhibitor control solution is prepared in assay buffer containing 10 nM of the FRET acceptor without the SOS1 protein.

A fixed reaction mixture with or without test compound is transferred into a 384-well plate. Ras working solution is added to all wells of the test plate. SOS1 working solution is added to all wells except for those that are subsequently filled with the inhibitor control solution. After approximately 60 min incubation, the fluorescence is measured with a M1000Pro plate reader (Tecan) using HTRF detection (excitation 337 nm, emission 1: 620 nm, emission 2: 665 nm). Compounds are tested in duplicate at different concentrations (for example, 10 µM, 2.5 µM, 0.63 µM, 0.16 µM, 0.04 µM, 0.01 µM test compound). The ratiometric data (i.e., emission 2 divided by emission 1) is used to calculate IC50 values against SOS1 using GraphPad Prism (GraphPad software).

Table 2 below shows the resulting IC50 values of the compounds exemplified in Table 1 against SOS1 using the Ras-SOS interaction assay as described above, wherein K-Ras G13D is utilized. The results demonstrate that compounds disclosed herein are capable of reducing Ras protein signaling by inhibiting SOS1-mediated signaling. Many of the exemplified compounds are potent SOS1 inhibitors, exhibiting an IC50 value against SOS1 less than about 500 nM, 400 nM, 300 nM, 200 nM, 100 nM, 80 nM, 60 nM, 50 nM, 40 nM, 30 nM, 20 nM, or even less than 10 nM. For example, compounds 54, 61, 101, 120, 138, 159, 166, 167, 168, 170, 171, 173, 174, 175, 176, 209, 210, 211, 212, and 213 exhibit IC50 values less than 50 nM, 40 nM, 30 nM, 20 nM, or 10 nM.

Table 2 shows the resulting IC50 values of selected compounds against SOS1 using the Ras-SOS interaction assay described herein. Compound numbers correspond to the numbers and structures provided in Table 1 and Examples 1-36. IC50 values were not determined for compounds of Table 1 that are not listed in Table 2.

TABLE 2

| | <100 nM (++) | 100 nM to 5 µM (+) |
|---|---|---|
| SOS1 IC$_{50}$ | 6, 8, 10, 11, 15, 16, 19, 20, 21, 22, 23, 24, 25, 26, 27, 28, 29, 30, 31, 32, 34, 35, 36, 38, 39, 40, 41, 42, 43, 45, 46, 47, 48, 49, 50, 51, 52, 53, 54, 55, 57, 58, 60, 61, 62, 63, 64, 65, 67, 69, 70, 71, 72, 73, 74, 75, 76, 77, 78, 79, 80, 83, 85, 86, 89, 90, 91, 92, 93, 94, 95, 97, 98, 100, 101, 104, 105, 106, 107, 108, 109, 110, 112, 113, 114, 116, 118, 119, 120, 121, 122, 123, 124, 125, 126, 127, 128, 129, 131, 132, 135, 137, 138, 140, 141, 142, 143, 144, 145, 146, 147, 149, 151, 152, 153, 154, 155, 156, 157, 158, 159, 160, 161, 162, 163, 164, 165, 166, 167, 168, 169, 170, 171, 173, 174, 175, 176, 177, 178, 179, 180, 181, 182, 186, 187, 188, 189, 190, 191, 192, 193, 194, 195, 196, 202, 203, 209, 210, 211, 212, 213 | 1, 2, 3, 4, 5, 7, 9, 12, 13, 14, 18, 37, 44, 56, 66, 82, 87, 88, 99, 102, 115, 130, 133, 136, 148, 150, 172 |

Table 3 shows comparative IC50 values of selected compounds against SOS1 using the Ras-SOS interaction assay described herein. Compound numbers correspond to the numbers and structures provided in Table 1 and Examples 1-36.

TABLE 3

| Compound | SOS1 IC$_{50}$ |
|---|---|
| Comparative Compound A | 11 nM |
| Compound 175 | 8 nM |
| Compound 176 | 7 nM |

Example 42: ERK Phosphorylation Assay

An ERK phosphorylation assay is used to examine the potency with which compounds disclosed herein inhibit the SOS1-mediated signaling and hence Ras signaling output in a Kras mutant cancer cell line. MIA PaCa-2 cells (ATCC CRL-1420) expressing K-Ras G12C are grown in DMEM/Ham's F12 medium supplemented with 10% fetal calf serum, glutamine and ~2.5% horse serum. Alternatively, other cell lines with aberrant Ras signaling output can be utilized. Non-limiting exemplary cell lines include NCI-H358 and H1975. Cells are plated in 96-well plates at a concentration of 40,000 cells/well and allowed to attach for at least 8 hours. Following, diluted solutions of test inhibitor compounds are added to the cell culture. After ~2 hours of incubation, the medium is removed and lysis buffer from AlphaLISA® SureFire® Ultra™ p-ERK 1/2 (Thr202/Tyr204) assay kit (Perkin Elmer ALSU-PERK-A10K) is added to the cells. The plate is agitated for 10 min at room temperature and 10 μL of the lysate is transferred to a 384-well Optiplate™ (Perkin Elmer) for assay. Thereafter ~5 μL of Acceptor Mix from the p-ERK AlphaLISA assay kit is added to wells and the plate is sealed with adhesive film. The samples are incubated for one hour at room temperature. Following, 5 μL of Donor Mix is added to the wells and plate is re-sealed with adhesive film and incubated for one hour at room temperature. The plate is then read on a multimode microplate reader (e.g., SPARK® Tecan) equipped with Alpha detection module. The data can be fitted to four-parameter dose-response curve using Prism version 9 (GraphPad) to calculate an IC50 for the inhibition of ERK phosphorylation. Certain compounds disclosed herein when assessed in this ERK phosphorylation assay exhibited IC50 values less than about 1 μM, about 500 nM, about 200 nM, about 100 nM, or 50 nM.

Example 43: Ras-SOS Cellular Growth Inhibition Assay

The ability of any compound of the present disclosure to inhibit SOS1-mediated signaling and hence Ras protein signaling can be demonstrated by inhibiting growth of a given Kras mutant cell line.

Growth of cells with K-Ras G12C mutation: MIA PaCa-2 (ATCC CRL-1420) and NCI-H1792 (ATCC CRL-5895) cell lines comprise a G12C mutation and can be used to assess Ras cellular signaling in vitro, e.g., in response to a subject compound of the present disclosure. This cellular assay can also be used to discern selective inhibition of subject compounds against certain types of Kras mutants, e.g., more potent inhibition against Kras G12D relative to Kras G12C mutant, by using MIA PaCa-2 (G12C driven tumor cell line) as a comparison. Cell culture medium (comprising, for example, MIA PaCa-2 cells) is prepared with DMEM/Ham's F12 (e.g., with stable Glutamine, 10% FCS, and 2.5% Horse Serum). NCI-H1792 culture medium is prepared with RPMI 1640 (e.g., with stable Glutamine) and 10% FCS. A CellTiter-Glo (CTG) luminescent based assay (Promega) is used to assess growth of the cells, as a measurement of the ability of the compounds herein to inhibit Ras signaling in the cells. The cells (e.g., 800-1200 per well) are seeded in their respective culture medium in standard tissue culture-treated ultra-low attachment surface 96-well format plates (Corning Costar #3474). The day after plating, cells are treated with a dilution series (e.g., a 9 point 3-fold dilution series) of the compounds herein (e.g., approximately 125 μL final volume per well). Cell viability can be monitored (e.g., approximately 5 days later) according to the manufacturer's recommended instructions, where the CellTiter-Glo reagent is added (e.g., approximately 65 μL), vigorously mixed, covered, and placed on a plate shaker (e.g., approximately for 20 min) to ensure sufficient cell lysis prior to assessment of luminescent signal. The IC50 values are determined using the four-parameter fit. The resulting IC50 value is a measurement of the ability of the compounds herein to reduce cell growth of Ras-driven cells as representative tumor cells. Many of the exemplified compounds are potent SOS1 inhibitors, inhibiting SOS1-mediated signaling, capable of reducing cell growth with an IC50 value less than about 1 μM, 500 nM, 400 nM, 300 nM, 200 nM, 100 nM, 80 nM, 60 nM, 50 nM, 40 nM, 30 nM, 20 nM, 10 nM or even less. For example, compounds 6, 9, 54, 61, 101, 120, 167, 170, 171, 173, 174, and 175 exhibit IC50 values less than about 1 μM, 500 nM, 400 nM, 300 nM, 200 nM, 100 nM, 80 nM, 60 nM, 50 nM, 40 nM, 30 nM, 20 nM, or even less than 10 nM, in inhibiting MIA PaCa-2 cell growth. The results demonstrate that the subject compounds are effective in inhibiting growth of tumor cells including cells comprising one or more Kras mutations, e.g., Ras-driven tumor cells carrying a Kras G12C mutation.

Example 44: EGFR-SOS Cellular Inhibition Assay

The ability of any compound of the present disclosure to inhibit SOS1-mediated signaling and hence Ras protein signaling can be demonstrated by inhibiting growth of a given EGFR mutant cell line.

Growth of cells with EGFR T790M L858R double mutation: The NCI-H1975 (ATCC CRL-5908) cell line comprises an EGFR T790M L858R double mutation and can be used to assess EGFR cellular signaling in vitro, e.g., in response to a subject compound of the present disclosure. NCI-H1975 culture medium is prepared with RPMI 1640 (e.g., with stable Glutamine) and 10% FCS. A CellTiter-Glo (CTG) luminescent based assay (Promega) is used to assess growth of the cells, as a measurement of the ability of the compounds herein to inhibit EGFR signaling in the cells. The cells (e.g., 800-1200 per well) are seeded in their respective culture medium in standard tissue culture-treated ultra-low attachment surface 96-well format plates (Corning Costar #3474). The day after plating, cells are treated with a dilution series (e.g., a 9 point 3-fold dilution series) of the compounds herein (e.g., approximately 125 μL final volume per well). Cell viability can be monitored (e.g., approximately 5 days later) according to the manufacturer's recommended instructions, where the CellTiter-Glo reagent is added (e.g., approximately 65 μL), vigorously mixed, covered, and placed on a plate shaker (e.g., approximately for 20 min) to ensure sufficient cell lysis prior to assessment of luminescent signal. The IC50 values are determined using the four-parameter fit. The resulting IC50 value is a measurement of the ability of the compounds herein to reduce growth of EGFR-driven tumor cells. See Table 4. Many of the exemplified compounds are potent SOS1 inhibitors, capable of reducing cell growth with an IC50 value less than about 1 μM, 500 nM, 400 nM, 300 nM, 200 nM, 100 nM, 80 nM, 60 nM, 50 nM, 40 nM, 30 nM, 20 nM, or even less than 10 nM. For example, compounds 6, 54, 61, 101, 120, 159, 167, 170, 171, 173, 174, 175, 176, 209, 210, 211, 212, and 213 exhibit IC50 values less than 500 nM, 400 nM, 300 nM, 200 nM, 100 nM, 80 nM, 60 nM, 50 nM, 40 nM, 30 nM, 20 nM, or even less than 10 nM, in inhibiting growth of an NCI-H1975 (ATCC CRL-5908) cell line comprising an EGFR T790M L858R double mutation.

Table 4 shows the resulting IC50 values of selected compounds against SOS1 using the cell proliferation assays described herein. Compound numbers correspond to the numbers and structures provided in Table 1 and Examples 1-36. IC50 values were not determined for compounds of Table 1 that are not listed in Table 4.

TABLE 4

| | <1 µM (+++) | 1 µM to 10 µM (++) | >10 µM (+) |
|---|---|---|---|
| H1975 IC$_{50}$ | 6, 7, 8, 9, 10, 11, 12, 15, 16, 19, 20, 21, 22, 23, 24, 26, 27, 28, 29, 30, 31, 32, 34, 35, 36, 38, 39, 40, 41, 42, 43, 46, 47, 48, 49, 50, 52, 53, 54, 55, 57, 58, 60, 61, 62, 63, 64, 65, 67, 70, 71, 72, 73, 74, 76, 77, 78, 79, 80, 83, 85, 86, 87, 89, 90, 91, 92, 94, 95, 97, 98, 100, 101, 104, 105, 106, 107, 108, 109, 110, 112, 113, 114, 116, 118, 119, 120, 121, 122, 123, 124, 125, 126, 127, 128, 129, 131, 132, 135, 137, 138, 140, 141, 142, 143, 144, 145, 146, 147, 149, 151, 152, 153, 154, 155, 156, 157, 158, 159, 160, 161, 162, 163, 164, 165, 166, 167, 169, 170, 171, 172, 173, 174, 175, 176, 177, 178, 179, 180, 181, 182, 186, 187, 188, 189, 190, 191, 202, 203, 209, 210, 211, 212, 213 | 3, 44, 130, 168 | 88 |

Example 45: In Vivo Ras Inhibition and Synergistic Reduction of Tumor Growth in a Ras-Driven Model The in vivo reduction in Ras signaling output by a subject compound alone and synergistic reduction of tumor growth in combination with another therapeutic agent are determined in a mouse tumor xenograft model.

Xenograft with K-Ras G12C mutation: In an example, tumor xenografts are established by administration of tumor cells with K-Ras G12C mutation (e.g., MIA PaCa-2 cells) into mice, e.g., injection of the tumor cells into the right flanks of female BomTacNMRI-Foxn1nu mice with an age between 6 to 8 weeks. In case of the subcutaneous (s.c.) MIA PaCa-2 xenograft mouse models, MIA PaCa-2 cells are grown in cell culture flasks in appropriate medium. Cultures are incubated at 37° C. and 5% $CO_2$ in a humidified atmosphere, with medium change or subcultivation performed 2-3 times a week. For injection, the cultured tumor cells are mixed with PBS including 5% FCS and Matrigel in a 1:1 ratio. About 0.5×10E7 cells in a volume of 100 µL is injected s.c. in each mouse to establish tumors. Mice are randomized into treatment groups of 6-10 mice, once tumors reach a desirable size (e.g., between about 88 to about 504 mm$^3$, or between about 103 to about 377 mm$^3$). Treatment with a subject compound of the present disclosure or with a control (e.g., vehicle control) may start on the day of randomization and can be continued until end of the study (e.g., 18 days). The test samples are administered intragastrically using a gavage needle at an application volume of 10 mL/kg in a volume of 10 mL/kg per mouse daily twice with a 6 h difference.

Mice are housed under standardized conditions at 21.5±1.5° C. and 55±10% humidity. Standardized irradiated diet and autoclaved tap water is provided ad libitum. In some cases, tags (e.g., ear tags, microchips implanted subcutaneously under isoflurane anesthesia) are used to identify each mouse. The tumor diameter is measured two or three times a week with a caliper. The volume of each tumor (in mm$^3$) is calculated according to the formula "tumor volume= ($\pi$*length*width$^2$)/6." To monitor side effects of treatment, mice are inspected daily for abnormalities and body weight is determined, e.g., daily. Animals are sacrificed at the end of the study. Animals with necrotic tumors or tumor sizes exceeding 1500 mm$^3$ are sacrificed early during the study for ethical reasons. A compound disclosed herein inhibited tumor growth alone at an appropriate dose, and further synergistically inhibited tumor growth when administered in conjunction with a KRAS G12C inhibitor.

Example 46: Metabolic (Microsomal) Stability Assay

The metabolic stability of a test compound is assayed at 37° C. using pooled liver microsomes (mouse or human liver microsomes). An aliquot of 10 µL of 50 µM test compound is mixed with 490 µL of 0.611 mg/mL liver microsomes, and then, 50 µL of the mixtures are dispensed to the 96 well tubes and warmed at 37° C. for 10 minutes. The reactions are initiated by adding 50 µL of the pre-warmed NADPH regeneration system solution (add 1.2 µL solution, 240 µL solution B, mix with 10.56 mL KPBS) and then incubated at 37° C. The final incubation solution contains 100 mM potassium phosphate (pH 7.4), 1.3 mM NADP+, 3.3 mM glucose 6-phosphate, 0.4 Unit/mL of glucose 6-phosphate dehydrogenase, 3.3 mM magnesium chloride, 0.3 mg/mL liver microsomes and 0.5 µM test article. After 0, 15, 30 and 60 minutes in a shaking incubator, the reactions are terminated by adding 100 µL of acetonitrile containing 200 nM buspirone as an internal standard. All incubations are conducted in duplicate. Plates are vortexed vigorously by using Fisher Scientific microplate vortex mixer (Henry Troemner, US). Samples are then centrifuged at 3500 rpm for 10 minutes (4° C.) using Sorvall Legend XRT Centrifuge (Thermo Scientific, GE). Supernatants (40 µL) are transferred into clean 96-deep well plates. Each well is added with 160 µL of ultrapure water (Milli-Q, Millipore Corporation) with 0.1% (v/v) formic acid (Fisher Chemical), mixed thoroughly and subjected to LC/MS/MS analysis in MRM positive ionization mode.

All the samples are measured using a mass spectrometer (QTrap 5500 quadrupole/ion trap) coupled with a Shimadzu HPLC system. The HPLC system consists of a Shimadzu series degasser, binary quaternary gradient pumps, column heater coupled to an autosampler, and a Phenomenex Gemini-NX, C18, 3.0 µm or Phenomenex Lunar, C8, 5.0 µM HPLC column (Phenomenex, Torrance, CA), and elute with a mobile phase gradient consisting of Solution A (0.1% formic acid water) and Solution B (0.1% formic acid acetonitrile). The column temperature is maintained at 40° C. All the analytes are detected with positive-mode electrospray ionization (ES+).

The half-life for the metabolic degradation of the test compound is calculated by plotting the time-course disappearance of the test compound during the incubation with liver microsomes. Each plot is fitted to a first-order equation for the elimination of the test compound (% remaining compound) versus time using non-linear regression (Equation 1).

$$\frac{C_t}{C_0} = e^{-kt} \quad \text{Equation 1}$$

where $C_t$ is the mean relative substrate concentration at time t and $C_0$ is the initial concentration (0.5 µM) at time 0. Note that the area ratio of the substrate peak to an internal standard peak is proportional to the analyte concentration and is used for regression analysis to derive a value of k.

The half-life $t_{1/2}$ for metabolic (microsome) stability is derived from the test compound elimination constant k using Equation 2 below.

$$t_{1/2} = \frac{0.693}{k} \quad \text{Equation 2}$$

Example 47: CYP2C19 Inhibition Assay

Some xenobiotics can inhibit cytochrome P450 (CYP) enzyme function, which alters their ability to metabolize drugs. Administration of a CYP inhibitor with a drug whose clearance is dependent on CYP metabolism can result in increased plasma concentrations of this concomitant drug, leading to potential toxicity. The inhibition of CYP2C19 by a test compound is assayed in human liver microsomes using S-Mephenytoin as a CYP2C19 substrate. The stock solution of the test compound or known CYP2C19 inhibitor as a positive control (10 mM) is diluted with KPBS to 40 µM. In a similar way, the stock solutions of the human liver microsomes and S-Mephenytoin are diluted with KPBS buffer. The pre-incubations are started by incubating a plate containing 25 µL human liver microsomes (final concentration of 0.2 mg/mL), 25 µL NADPH-generating system, and a 25 µL test compound (final concentration 10 µM) or the positive control for 30 min at 37±1° C. After the pre-incubation, 25 µL S-Mephenytoin (final concentration 200 µM) is added and incubated another 12 minutes at 37±1° C. for substrate metabolism. The reactions are terminated by addition of 100 µL of ice-cold acetonitrile containing an internal standard (buspirone). Precipitated proteins are removed by centrifugation at 3500 rpm for 10 minutes at 4° C. (Allegra 25R, Beckman Co. Fullerton, CA) and then an aliquot of the supernatant is transferred to an assay plate.

All the samples are determined by a mass spectrometer (QTrap 5500 quadrupole/ion trap) coupled with a Shimadzu HPLC system, following the manufacturer's instructions. The metabolism of S-Mephenytoin in human liver microsomes is monitored by LC/MS/MS as representative of CYP2C19 inhibitory activity. The amount of metabolite formed is assessed by the peak area ratio (metabolite/IS) and % inhibition at 10 µM is expressed as a percentage of the metabolite signal reduced compared to the control (i.e. an incubation that contained no inhibitor and represented 100% enzyme activity): % inhibition=(1−A/B)×100%, where A is the metabolite peak area ratio formed in the presence of test compound or inhibitor at 10 µM and B is the metabolite peak area ratio formed without test compound or inhibitor in the incubation.

Example 48: Mouse and Human Protein Binding Assay to Assess Free Drug Concentration The assay is to determine the plasma protein binding of the test compound in the plasma of human and animal species using a Rapid Equilibrium Dialysis (RED) device for equilibrium dialysis and LC-MS/MS for sample analysis. Test compound is spiked in. The stock solution of the test compound is prepared at 5 mM concentration. One µL of 5 mM working solution into 1000 µL plasma. The final concentration is 5 µM. The spiked plasma is placed on a rocker and gently agitated for approximately 20 minutes. A volume of 300 µL of the plasma sample containing 5 µM test compound from each species is added to designate RED device donor chambers followed by addition of 500 µL of potassium phosphate buffer to the corresponding receiver chambers in duplicate. The RED device is then sealed with sealing tape and shaken at 150 RPM for 4 hours at 37° C. Post-dialysis donor and receiver compartment samples are prepared for LC-MS/MS analysis, including spiking samples with an internal standard for the bioanalytical analysis. Warfarin and propranolol are purchased from Sigma-Aldrich (St. Louis, MO), and used as positive controls for low and high plasma protein binding, respectively.

All the samples are analyzed using an Agilent Technologies 6430 Triple Quad LC/MS system. The HPLC system consisted of Agilent 1290 Infinity Liquid Chromatograph coupled to an autosampler (Agilent 1290 Infinity LC Injector HTC), and a Phenomenex Gemini-NX, C18, 3.0 µm or Phenomenex Lunar, C8, 5.0 µM HPLC column (Phenomenex, Torrance, CA), and are eluted with a mobile phase gradient consisting of Solution A (0.1% formic acid water) and Solution B (0.1% formic acid acetonitrile). The column temperature is maintained at 40° C. All the analytes are detected with positive-mode electrospray ionization (ES+). The percentage of the test compound bound to plasma is calculated following Equation 3 and 4.

$$\% \text{ Free test compound} = \frac{\text{Peak ratio}\left(\frac{\text{test compound}}{\text{Internal standard}}\right)\text{, receiver compartment}}{\text{Peak ratio}\left(\frac{\text{test compound}}{\text{Internal standard}}\right)\text{, donor compartment}} * 100 \quad \text{Equation 3}$$

$$\% \text{ Plasma protein bound test compound} = \quad \text{Equation 4}$$

$$100 - \% \text{ Free test compound}$$

Example 49: hERG (Automated Patch-Clamp) Assay

The human ether-a-go-go related gene (hERG) encodes the voltage gated potassium channel in the heart (IKr) which is involved in cardiac repolarization. Inhibition of the hERG causes QT interval prolongation and can lead to potential fatal events in humans. It is thus important to assess hERG inhibition early in drug discovery. A hERG automated patch-clamp assay is done using a hERG CHO-K1 cell line using an incubation time of 5 min. The degree of hERG inhibition (%) is obtained by measuring the tail current amplitude, which is induced by a one second test pulse to −40 mV after a two second pulse to +20 mV, before and after drug incubation (the difference current is normalized to control and multiplied by 100 to obtain the percent of inhibition). The percent hERG inhibition is measured in the presence of 10 µM test compound.

Example 50: Rat Oral Exposure (% F)

A pharmacokinetic profile for a test compound is assessed by single dosing in jugular vein cannulated male Sprague-Dawley rats. Animal weights are typically over 200 grams, and animals are allowed to acclimate to their new environment for at least 3 days prior to the initiation of any studies. One set of animals is dosed intravenous (IV) with test compound, 2 mg/kg in 20% HP-beta-CD or 20% Captisol, pH adjusted to -5-6 by citric acid. IV dosing solution concentration is 0.4 mg/mL test compound. Time of blood sampling is 5 minutes, 15 minutes, 30 minutes, 90 minutes, 360 minutes, and 24 hours following IV dosing. Another set of animals is dosed oral (po) with test compound, 10 mg/kg in 20% HP-beta-CD or 20% Captisol, pH adjusted to -3-4 by citric acid. Oral dosing solution concentration is 1 mg/mL test compound. Time of blood sampling is 15 minutes, 30 minutes, 90 minutes, 180 minutes, 360 minutes and 24 hours following oral (po) dosing. Blood samples (~0.1 mL/sample) are collected via jugular catheter and placed in tubes containing EDTA-$K_2$ and stored on ice until centrifuged. The blood samples are centrifuged at approximately 6800 g for 6 minutes at 2-8° C. and the resulting plasma is separated and stored frozen at approximately −80° C.

All the plasma samples are analyzed using an Agilent Technologies 6430 Triple Quad LC/MS system, following the manufacturer instructions. All the analytes are detected with positive-mode electrospray ionization (ES+). A standard curve for each test compound is generated and used to measure test compound concentrations in the rat plasma samples. Based on the time course sampling, an area under the curve is calculated for the oral dose group and the intravenous dose group. Percentage rat bioavailability is calculated based on equation 5.

$$\% \ F(\text{rat}) = \frac{AUC_{po} * \text{Dose}_{IV}}{AUC_{IV} * \text{Dose}_{po}},$$

where F is bioavailability, $AUC_{po}$ is area under curve of oral drug, $AUC_{IV}$ is area under curve of intravenous drug, $\text{Dose}_{IV}$ is the intravenous dose and $\text{Dose}_{po}$ is the oral dose.

Example 51: Kinase Selectivity Assay

Eurofins DiscoverX (USA) commercially offers measurement on its KINOMEscan scanEDGE™ 97 Panel comprising of 97 potential kinase off-targets. The KINOMEscan™ screening platform employs an active site-directed competition binding assay to quantitatively measure interactions between test compounds and kinases. Test compound is screened at 10 µM, and results for primary screen binding interactions are reported as 'Percent control', where lower numbers indicate stronger binding to a kinase being examined.

$$\text{Percent control} = \left( \frac{\text{test compound signal} - \text{positive control signal}}{\text{negative control signal} - \text{positive control signal}} \right) * 100$$

where the negative control=DMSO (100% Ctrl) and the positive control=control compound (0% Ctrl).

Example 52: Mouse Oral Exposure (% F)

A pharmacokinetic profile for a test compound is assessed by single dosing in female CD-1 mice. Animal weights are typically between 20-50 grams, and animals are allowed to acclimate to their new environment for at least 3 days prior to the initiation of any studies. One set of animals is dosed intravenous (IV) with test compound, 2 mg/kg in 20% HP-beta-CD or 20% Captisol, pH adjusted to ~5-6 by citric acid at 10 mL/kg. Time of blood sampling is 5 minutes, 15 minutes, 30 minutes, 90 minutes, 360 minutes, and 24 hours following IV dosing. Another set of animals is dosed oral (po) with test compound, 10 mg/kg in 20% HP-beta-CD or 20% Captisol, pH adjusted to ~3-4 by citric acid at 10 mg/mL. Oral dosing solution concentration is 1 mg/mL test compound and 10 mL/kg. Time of blood sampling is 15 minutes, 30 minutes, 90 minutes, 180 minutes, 360 minutes and 24 hours following oral (po) dosing. Blood samples (~0.1 mL/sample) are collected via submandibular facial vein and placed in tubes containing EDTA-K2 and stored on ice until centrifuged. The blood samples are centrifuged at approximately 6800 g for 6 minutes at 2-8° C. and the resulting plasma is separated and stored frozen at approximately −80° C.

Plasma samples are analyzed using an Agilent Technologies 6430 Triple Quad LC/MS system, following the manufacturer instructions. All the analytes are detected with positive-mode electrospray ionization (ES+). A standard curve for each test compound is generated and used to measure test compound concentrations in the mouse plasma samples. Based on the time course sampling, an area under the curve is calculated for the oral dose group and the intravenous dose group. Percentage mouse bioavailability is calculated based on equation 6.

$$\% \ F(\text{mouse}) = \frac{AUC_{po} * \text{Dose}_{IV}}{AUC_{IV} * \text{Dose}_{po}}, \quad \text{Equation 6}$$

where F is bioavailability, $AUC_{po}$ is area under curve of oral drug, $AUC_{IV}$ is area under curve of intravenous drug, $\text{Dose}_{IV}$ is the intravenous dose and $\text{Dose}_{po}$ is the oral dose.

Table 5 shows the resulting oral exposure (% F) values of selected compounds in mice using the assay described above. Compound numbers correspond to the numbers and structures provided in Table 1 and Examples 1-36.

TABLE 5

|  | ≥4% |
| --- | --- |
| Mouse Oral Exposure (% F) | 175, 176 |

What is claimed is:

1. A compound of the formula:

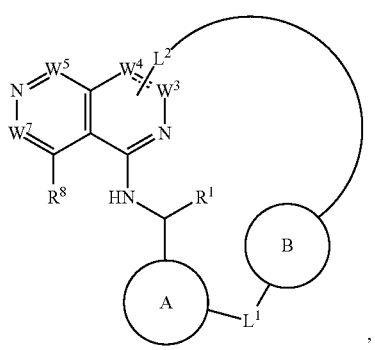

or a pharmaceutically acceptable salt or solvate thereof, wherein:

is selected from $C_{5-7}$ carbocycle and 5- to 7-membered heterocycle, each of which is optionally substituted with one or more $R^{11}$;

is absent or selected from $C_{3-8}$ carbocycle and 3- to 8-membered heterocycle, each of which is optionally substituted with one or more $R^{11a}$;

$L^1$ is selected from a bond, $C_{1-6}$ alkylene, and $C_{1-6}$ haloalkylene;

$L^2$ is selected from $C_{5-25}$ alkylene, $C_{5-25}$ alkenylene, $C_{5-25}$ alkynylene, 5- to 25-membered heteroalkylene, and 5- to 25-membered heteroalkenylene, each of which is optionally substituted with one or more $R^{11b}$, wherein $L^2$ is covalently bound to one of $W^3$, $W^4$, $W^5$, or $W^7$;

$W^2$ is selected from N and $C(R^2)$;

$W^3$ is selected from $N(R^{3b})$, N, $C(R^3)$, and C(O);

$W^4$ is selected from $N(R^{4b})$, N, $C(R^4)$, and C(O);

$W^5$ is selected from N and $C(R^5)$;

$W^7$ is $C(R^7)$;

$R^1$ is $C_{1-3}$ alkyl optionally substituted with one or more $R^{11c}$;

$R^2$ and $R^8$ are each independently selected from hydrogen, halogen, —CN, $C_{1-6}$ alkyl, $C_{2-6}$ alkenyl, $C_{2-6}$ alkynyl, $C_{3-10}$ carbocycle, 3- to 10-membered heterocycle, —$OR^{12}$, —$SR^{12}$, —$N(R^{12})(R^{13})$, —$C(O)OR^{12}$, —OC(O)N($R^{12}$)($R^{13}$), —$N(R^{14})C(O)N(R^{12})(R^{13})$, —$N(R^{14})C(O)OR^{15}$, —$N(R^{14})S(O)_2R^{15}$, —$C(O)R^{15}$, —$S(O)R^{15}$, —$OC(O)R^{15}$, —$C(O)N(R^{12})(R^{13})$, —C(O)C(O)N($R^{12}$)($R^{13}$), —$N(R^{14})C(O)R^{15}$, —$S(O)_2R^{15}$, —$S(O)_2N(R^{12})(R^{13})$, —$S(=O)(=NH)N(R^{12})(R^{13})$, —$CH_2C(O)N(R^{12})(R^{13})$, —$CH_2N(R^{14})C(O)R^{15}$, —$CH_2S(O)_2R^{15}$, and —$CH_2S(O)_2N(R^{12})(R^{13})$, wherein each $C_{1-6}$ alkyl, $C_{2-6}$ alkenyl, $C_{2-6}$ alkynyl, $C_{3-10}$ carbocycle, and 3- to 10-membered heterocycle is independently optionally substituted with one, two, or three $R^{20}$;

$R^3$, $R^4$, $R^5$, and $R^7$ are each independently selected from a bond to $L^2$, hydrogen, halogen, —CN, $C_{1-6}$ alkyl, $C_{2-6}$ alkenyl, $C_{2-6}$ alkynyl, $C_{3-10}$ carbocycle, 3- to 10-membered heterocycle, —$OR^{12}$, —$SR^{12}$, —$N(R^{12})(R^{13})$, —$C(O)OR^{12}$, —OC(O)N($R^{12}$)($R^{13}$), —$N(R^{14})C(O)N(R^{12})(R^{13})$, —$N(R^{14})C(O)OR^{15}$, —$N(R^{14})S(O)_2R^{15}$, —$C(O)R^{15}$, —$S(O)R^{15}$, —$OC(O)R^{15}$, —$C(O)N(R^{12})(R^{13})$, —C(O)C(O)N($R^{12}$)($R^{13}$), —$N(R^{14})C(O)R^{15}$, —$S(O)_2R^{15}$, —$S(O)_2N(R^{12})(R^{13})$, —$S(=O)(=NH)N(R^{12})(R^{13})$, —$CH_2C(O)N(R^{12})(R^{13})$, —$CH_2N(R^{14})C(O)R^{15}$, —$CH_2S(O)_2R^{15}$, and —$CH_2S(O)_2N(R^{12})(R^{13})$, wherein each $C_{1-6}$ alkyl, $C_{2-6}$ alkenyl, $C_{2-6}$ alkynyl, $C_{3-10}$ carbocycle, and 3- to 10-membered heterocycle is independently optionally substituted with one, two, or three $R^{20}$;

$R^{3b}$ and $R^{4b}$ are each independently selected from a bond to $L^2$, hydrogen, —CN, $C_{1-6}$ alkyl, $C_{2-6}$ alkenyl, $C_{2-6}$ alkynyl, $C_{3-10}$ carbocycle, 3- to 10-membered heterocycle, —$OR^{12}$, —$SR^{12}$, —$C(O)OR^{12}$, —OC(O)N($R^{12}$)($R^{13}$), —$C(O)R^{15}$, —$S(O)R^{15}$, —$OC(O)R^{15}$, —$C(O)N(R^{12})(R^{13})$, —C(O)C(O)N($R^{12}$)($R^{13}$), —$S(O)_2R^{15}$, —$S(O)_2N(R^{12})(R^{13})$, —$S(=O)(=NH)N(R^{12})(R^{13})$, —$CH_2C(O)N(R^{12})(R^{13})$, —$CH_2N(R^{14})C(O)R^{15}$, —$CH_2S(O)_2R^{15}$, and —$CH_2S(O)_2N(R^{12})(R^{13})$, wherein each $C_{1-6}$ alkyl, $C_{2-6}$ alkenyl, $C_{2-6}$ alkynyl, $C_{3-10}$ carbocycle and 3- to 10-membered heterocycle is independently optionally substituted with one, two, or three $R^{20}$;

$R^{11}$ and $R^{11a}$ are each independently selected at each occurrence from halogen, —CN, $C_{1-6}$ alkyl, $C_{2-6}$ alkenyl, $C_{2-6}$ alkynyl, $C_{3-10}$ carbocycle, 3- to 10-membered heterocycle, —$OR^{12}$, —$SR^{12}$, —$N(R^{12})(R^{13})$, —$C(O)OR^{12}$, —OC(O)N($R^{12}$)($R^{13}$), —$N(R^{14})C(O)N(R^{12})(R^{13})$, —$N(R^{14})C(O)OR^{15}$, —$N(R^{14})S(O)_2R^{15}$, —$C(O)R^{15}$, —$S(O)R^{15}$, —$OC(O)R^{15}$, —$C(O)N(R^{12})(R^{13})$, —C(O)C(O)N($R^{12}$)($R^{13}$), —$N(R^{14})C(O)R^{15}$, —$S(O)_2R^{15}$, —$S(O)_2N(R^{12})(R^{13})$, —$S(=O)(=NH)N(R^{12})(R^{13})$, —$CH_2C(O)N(R^{12})(R^{13})$, —$CH_2N(R^{14})C(O)R^{15}$, —$CH_2S(O)_2R^{15}$, —$CH_2S(O)_2N(R^{12})(R^{13})$, —$CH_2N(R^{12})S(O)_2(R^{13})$, and —$P(O)(R^{17})(R^{17a})$, wherein $C_{1-6}$ alkyl, $C_{2-6}$ alkenyl, $C_{2-6}$ alkynyl, $C_{3-10}$ carbocycle, and 3- to 10-membered heterocycle are optionally substituted with one, two, or three $R^{20}$;

$R^{11b}$ is independently selected at each occurrence from halogen, oxo, —CN, $C_{1-6}$ alkyl, $C_{2-6}$ alkenyl, $C_{2-6}$ alkynyl, $C_{3-10}$ carbocycle, 3- to 10-membered heterocycle, —OR$^{12}$, —SR$^{12}$, —N(R$^{12}$)(R$^{13}$), —C(O)OR$^{12}$, —OC(O)N(R$^{12}$)(R$^{13}$), —N(R$^{14}$)C(O)N(R$^{12}$)(R$^{13}$), —N(R$^{14}$)C(O)OR$^{15}$, —N(R$^{14}$)S(O)$_2$R$^{15}$, —C(O)R$^{15}$, —S(O)R$^{15}$, —OC(O)R$^{15}$, —C(O)N(R$^{12}$)(R$^{13}$), —C(O)C(O)N(R$^{12}$)(R$^{13}$), —N(R$^{14}$)C(O)R$^{15}$, —S(O)$_2$R$^{15}$, —S(O)$_2$N(R$^{12}$)(R$^{13}$), —S(=O)(=NH)N(R$^{12}$)(R$^{13}$), —CH$_2$C(O)N(R$^{12}$)(R$^{13}$), —CH$_2$N(R$^{14}$)C(O)R$^{15}$, —CH$_2$S(O)$_2$R$^{15}$, —CH$_2$S(O)$_2$N(R$^{12}$)(R$^{13}$), —CH$_2$N(R$^{12}$)S(O)$_2$(R$^{13}$), and —P(O)(R$^{17}$)(R$^{17a}$), wherein C$_{1-6}$ alkyl, C$_{2-6}$ alkenyl, C$_{2-6}$ alkynyl, C$_{3-10}$ carbocycle, and 3- to 10-membered heterocycle are optionally substituted with one, two, or three R$^{20}$;

R$^{11c}$ is independently selected at each occurrence from halogen, —OR$^{12}$, and —N(R$^{12}$)(R$^{13}$);

R$^{12}$ is independently selected at each occurrence from hydrogen, C$_{1-6}$ alkyl, C$_{1-6}$ haloalkyl, C$_{2-6}$ alkenyl, C$_{2-6}$ alkynyl, C$_{3-10}$ carbocycle, and 3- to 10-membered heterocycle, wherein C$_{1-6}$ alkyl, C$_{2-6}$ alkenyl, C$_{2-6}$ alkynyl, C$_{3-10}$ carbocycle, and 3- to 10-membered heterocycle are optionally substituted with one, two, or three R$^{20}$;

R$^{13}$ is independently selected at each occurrence from hydrogen, C$_{1-6}$ alkyl, and C$_{1-6}$ haloalkyl; or R$^{12}$ and R$^{13}$, together with the nitrogen atom to which they are attached, form a 3- to 10-membered heterocycle optionally substituted with one, two, or three R$^{20}$;

R$^{14}$ is independently selected at each occurrence from hydrogen, C$_{1-6}$ alkyl, and C$_{1-6}$ haloalkyl;

R$^{15}$ is independently selected at each occurrence from C$_{1-6}$ alkyl, C$_{2-6}$ alkenyl, C$_{2-6}$ alkynyl, C$_{3-10}$ carbocycle, and 3- to 10-membered heterocycle, wherein C$_{1-6}$ alkyl, C$_{2-6}$ alkenyl, C$_{2-6}$ alkynyl, C$_{3-10}$ carbocycle, and 3- to 10-membered heterocycle are optionally substituted with one, two, or three R$^{20}$;

R$^{17}$ and R$^{17a}$ are each independently selected at each occurrence from C$_{1-6}$ alkyl and C$_{3-6}$ cycloalkyl, wherein C$_{1-6}$ alkyl and C$_{3-6}$ cycloalkyl are optionally substituted with one, two or three R$^{20}$; or R$^{17}$ and R$^{17a}$, together with the phosphorous atom to which they are attached, form a 3- to 10-membered heterocycle;

R$^{20}$ is independently selected at each occurrence from halogen, oxo, =NH, —CN, C$_{1-6}$ alkyl, C$_{2-6}$ alkenyl, C$_{2-6}$ alkynyl, C$_{3-10}$ carbocycle, —CH$_2$—(C$_{3-10}$ carbocycle), 3- to 10-membered heterocycle, —CH$_2$-(3- to 10-membered heterocycle), —OR$^{21}$, —SR$^{21}$, —N(R$^{22}$)(R$^{23}$), —C(O)OR$^{22}$, —C(O)N(R$^{22}$)(R$^{23}$), —C(O)C(O)N(R$^{22}$)(R$^{23}$), —OC(O)N(R$^{22}$)(R$^{23}$), —N(R$^{24}$) C(O)N(R$^{22}$)(R$^{23}$), —N(R$^{24}$) C(O)OR$^{25}$, —N(R$^{24}$)C(O)R$^{25}$, —N(R$^{24}$)S(O)$_2$R$^{25}$, —C(O)R$^{25}$, —S(O)$_2$R$^{25}$, —S(O)$_2$N(R$^{22}$)(R$^{23}$), —OCH$_2$C(O)OR$^{22}$, and —OC(O)R$^{25}$, wherein C$_{1-6}$ alkyl, C$_{2-6}$ alkenyl, C$_{2-6}$ alkynyl, C$_{3-10}$ carbocycle, —CH$_2$-(C$_{3-10}$ carbocycle), 3- to 10-membered heterocycle, and —CH$_2$-(3- to 10-membered heterocycle) are optionally substituted with one, two, or three groups independently selected from halogen, oxo, =NH, —CN, C$_{1-6}$ alkyl, C$_{1-6}$ haloalkyl, C$_{1-6}$ alkoxy, C$_{1-6}$ haloalkoxy, —OR$^{21}$, —SR$^{21}$, —N(R$^{22}$)(R$^{23}$), —C(O)OR$^{22}$, —C(O)N(R$^{22}$)(R$^{23}$), —C(O)C(O)N(R$^{22}$)(R$^{23}$), —OC(O)N(R$^{22}$)(R$^{23}$), —N(R$^{24}$) C(O)N(R$^{22}$)(R$^{23}$), —N(R$^{24}$) C(O)OR$^{25}$, —N(R$^{24}$)C(O)R$^{25}$, —N(R$^{24}$)S(O)$_2$R$^{25}$, —C(O)R$^{25}$, —S(O)$_2$R$^{25}$, —S(O)$_2$N(R$^{22}$)(R$^{23}$), and —OC(O)R$^{25}$;

R$^{21}$ is independently selected at each occurrence from H, C$_{1-6}$ alkyl, C$_{1-6}$ haloalkyl, C$_{2-6}$ alkenyl, C$_{2-6}$ alkynyl, C$_{3-10}$ carbocycle, and 3- to 10-membered heterocycle, wherein C$_{3-10}$ carbocycle and 3- to 10-membered heterocycle are optionally substituted with one, two, or three groups independently selected from halogen and C$_{1-6}$ alkyl;

R$^{22}$ is independently selected at each occurrence from H, C$_{1-6}$ alkyl, C$_{1-6}$ haloalkyl, C$_{2-6}$ alkenyl, C$_{2-6}$ alkynyl, C$_{3-10}$ carbocycle, and 3- to 10-membered heterocycle, wherein C$_{3-10}$ carbocycle and 3- to 10-membered heterocycle are optionally substituted with one, two, or three groups independently selected from halogen and C$_{1-6}$ alkyl;

R$^{23}$ is independently selected at each occurrence from H and C$_{1-6}$ alkyl;

R$^{24}$ is independently selected at each occurrence from H and C$_{1-6}$ alkyl;

R$^{25}$ is independently selected at each occurrence from C$_{1-6}$ alkyl, C$_{2-6}$ alkenyl, C$_{2-6}$ alkynyl, C$_{3-10}$ carbocycle, and 3- to 10-membered heterocycle, wherein C$_{1-6}$ alkyl, C$_{3-10}$ carbocycle, and 3- to 10-membered heterocycle are optionally substituted with one, two, or three groups independently selected from halogen, C$_{1-6}$ alkyl, C$_{1-6}$ haloalkyl, C$_{1-6}$ alkoxy, C$_{3-10}$ carbocycle, and 3- to 10-membered heterocycle; and ------ indicates a single or double bond such that all valences are satisfied.

2. The compound of claim 1, wherein the compound is selected from

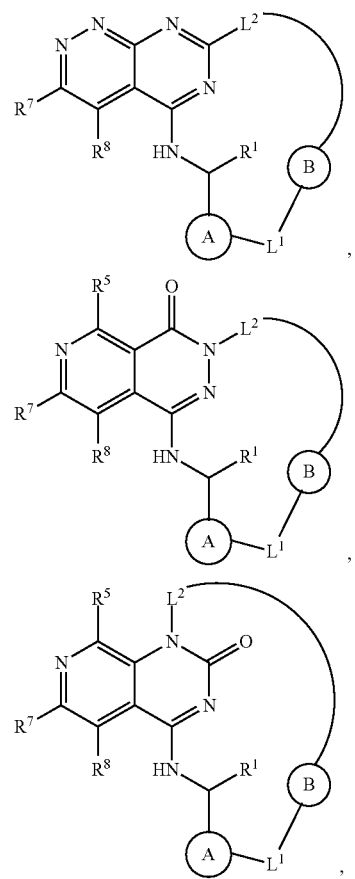

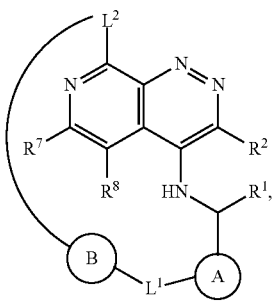
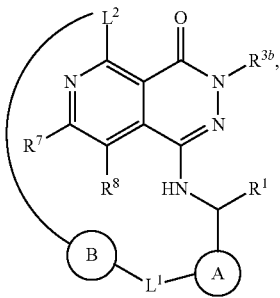
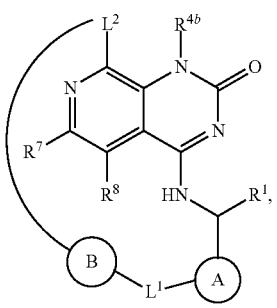
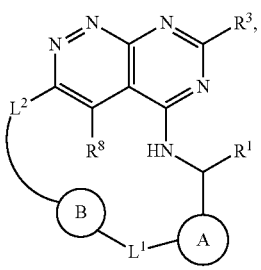
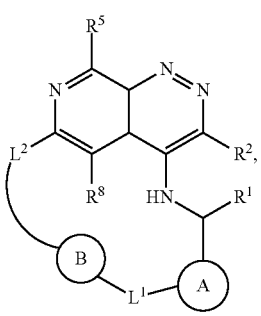

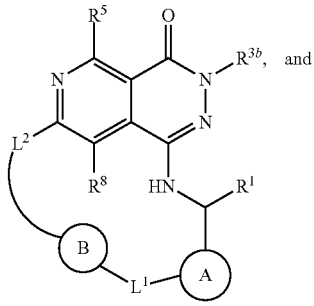
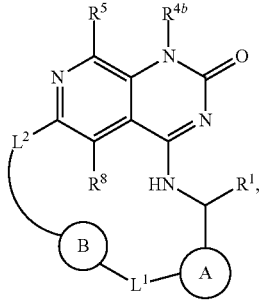

or a pharmaceutically acceptable salt or solvate thereof.

3. The compound, salt, or solvate of claim 1, wherein $R^1$ is —$CH_3$.

4. The compound, salt, or solvate of claim 1, wherein $R^{3b}$ is selected from hydrogen and —$CH_3$.

5. The compound, salt, or solvate of claim 1, wherein $R^7$ is selected from $C_{1-6}$ alkyl, $C_{3-10}$ cycloalkyl, 3- to 10-membered heterocycloalkyl, and —$N(R^{12})(R^{13})$, wherein $C_{1-6}$ alkyl, $C_{3-10}$ cycloalkyl, and 3- to 10-membered heterocycloalkyl are optionally substituted with one, two, or three $R^{20}$.

6. The compound, salt, or solvate of claim 1, wherein $R^7$ is selected from

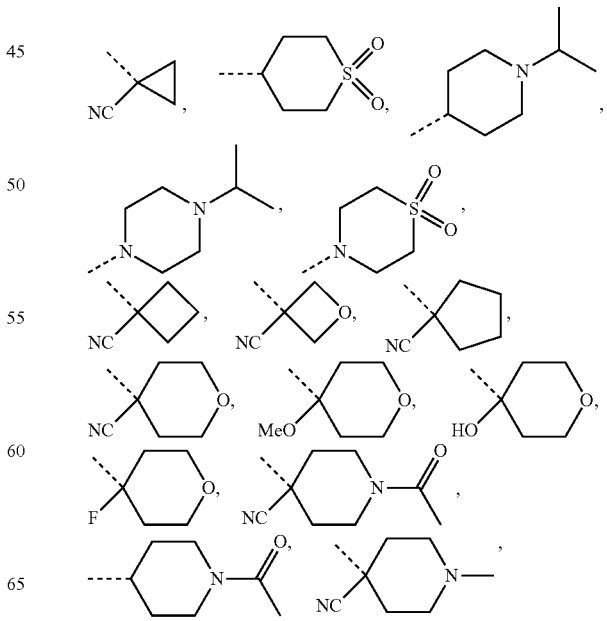

-continued

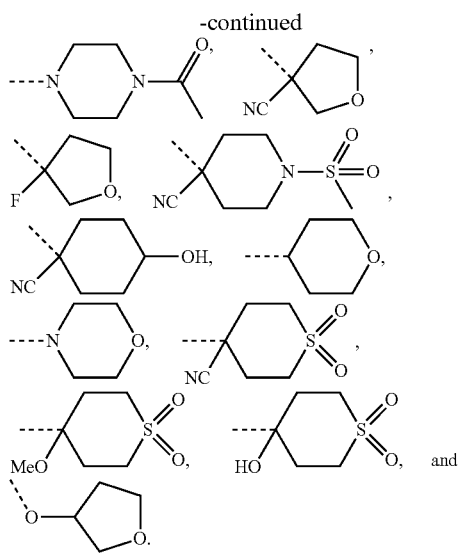

7. The compound, salt, or solvate of claim 1, wherein $R^8$ is hydrogen.

8. The compound, salt, or solvate of claim 1, wherein

Ⓐ is selected from

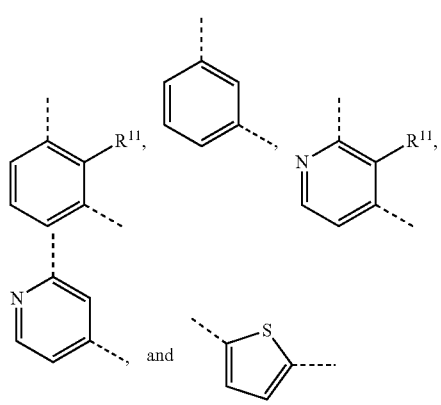

9. The compound, salt, or solvate of claim 8, wherein $R^{11}$ is selected from fluorine and —CH$_3$.

10. The compound, salt, or solvate of claim 1, wherein $L^1$ is C$_{1-3}$ haloalkylene.

11. The compound, salt, or solvate of claim 10, wherein $L^1$ is selected from —CF$_2$—, —CF$_2$CH$_2$—, and —CF$_2$CH$_2$CH$_2$—.

12. The compound, salt, or solvate of claim 1, wherein

Ⓑ is selected from absent, phenyl, and 4- to 8-membered heterocycle, wherein the phenyl and 4- to 8-membered heterocycle are optionally substituted with one or more $R^{11a}$.

13. The compound, salt, or solvate of claim 12, wherein

Ⓑ is selected from azetidine, pyrrolidine, and piperidine, each of which is optionally substituted with one or more —CH$_3$.

14. The compound, salt, or solvate of claim 1, wherein $L^2$ is selected from C$_{5-10}$ alkylene, C$_{5-10}$ alkenylene, 5- to 10-membered heteroalkylene, and 5- to 10-membered heteroalkenylene, each of which is optionally substituted with one or more $R^{11b}$.

15. The compound of claim 1, wherein the compound is selected from

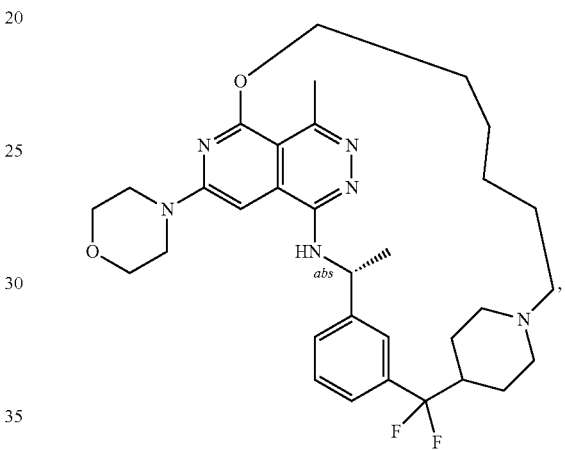

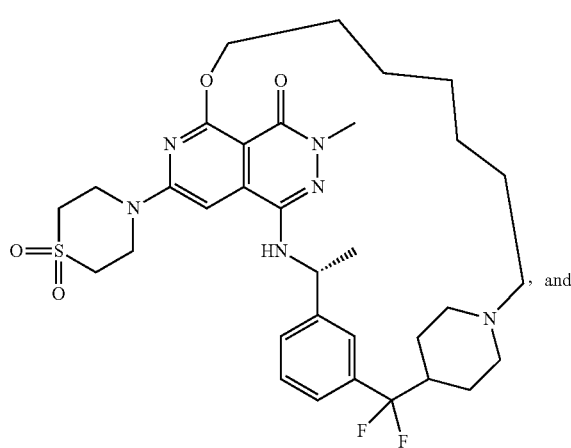

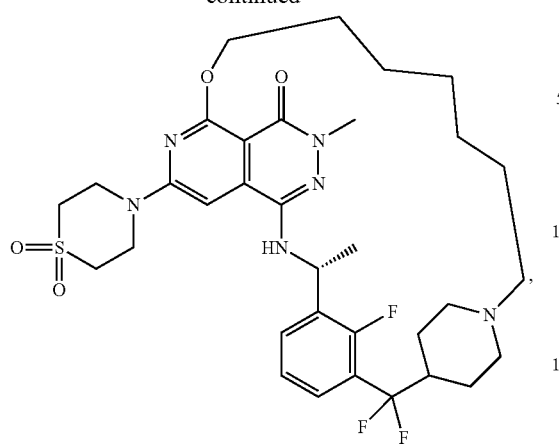
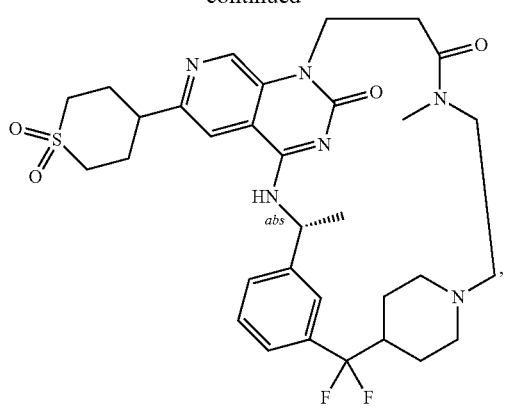
or a pharmaceutically acceptable salt or solvate thereof.
16. The compound of claim 1, wherein the compound is selected from
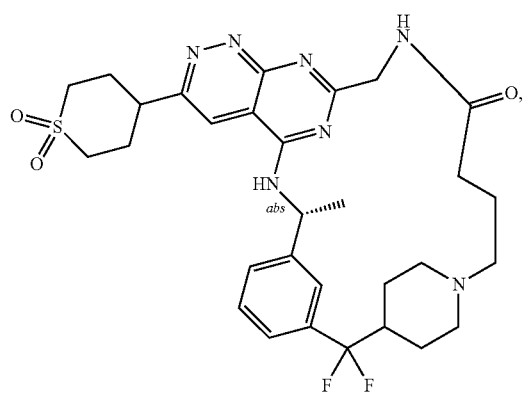
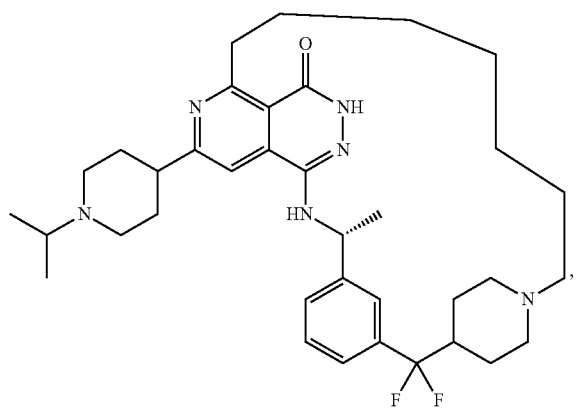
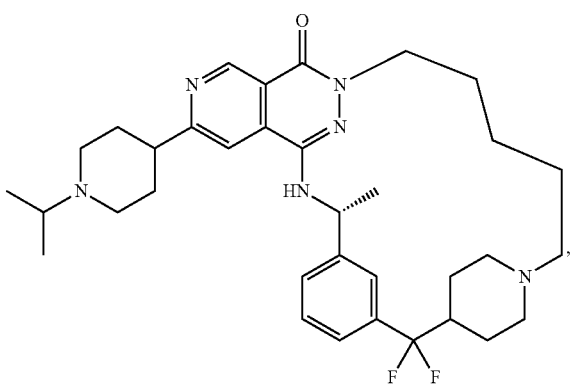
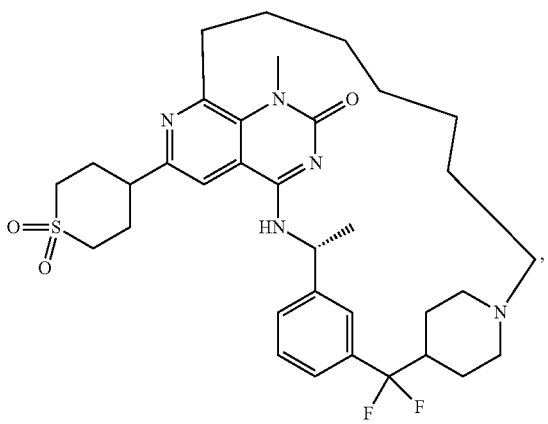

649
-continued

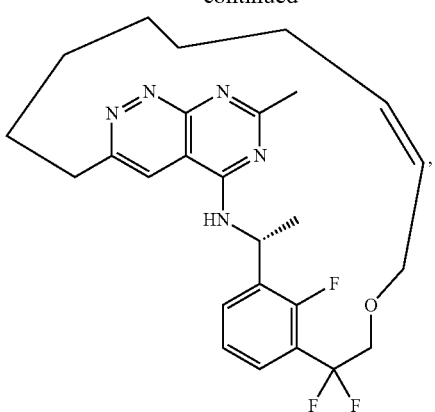

and

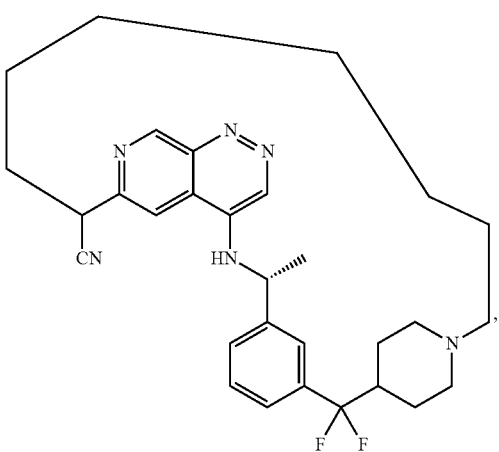

650
-continued

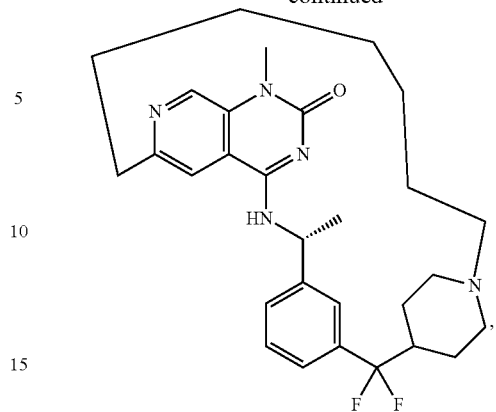

or a pharmaceutically acceptable salt or solvate thereof.

17. A pharmaceutical composition comprising a compound of claim 1, or a pharmaceutically acceptable salt or solvate thereof, and a pharmaceutically acceptable excipient.

18. A method of inhibiting cell growth, comprising administering to a cell expressing SOS1 an effective amount of a compound of claim 1, or a pharmaceutically acceptable salt or solvate thereof, thereby inhibiting growth of said cells.

19. The method of claim 18, wherein the cell is a cancer cell.

20. The method of claim 18, further comprising administering an additional agent to the cell.

21. The method of claim 20, wherein the additional agent is an inhibitor of one or more targets selected from MEK, EGFR, ALK, c-MET, ErbB2, PI3-kinase, SHP2, Bcr-Abl, and KRAS, or a mutant thereof.

* * * * *

SEQUENCE LISTING

```
Sequence total quantity: 6
SEQ ID NO: 1          moltype = AA  length = 188
FEATURE               Location/Qualifiers
```

```
source                  1..188
                        mol_type = protein
                        organism = Homo sapiens
SEQUENCE: 1
MTEYKLVVVG AGGVGKSALT IQLIQNHFVD EYDPTIEDSY RKQVVIDGET CLLDILDTAG   60
QEEYSAMRDQ YMRTGEGFLC VFAINNTKSF EDIHHYREQI KRVKDSEDVP MVLVGNKCDL  120
PSRTVDTKQA QDLARSYGIP FIETSAKTRQ GVDDAFYTLV REIRKHKEKM SKDGKKKKKK  180
SKTKCVIM                                                           188

SEQ ID NO: 2            moltype =   length =
SEQUENCE: 2
000

SEQ ID NO: 3            moltype = AA   length = 1333
FEATURE                 Location/Qualifiers
source                  1..1333
                        mol_type = protein
                        organism = Homo sapiens
SEQUENCE: 3
MQAQQLPYEF FSEENAPKWR GLLVPALKKV QGQVHPTLES NDDALQYVEE LILQLLNMLC   60
QAQPRSASDV EERVQKSFPH PIDKWAIADA QSAIEKRKRR NPLSLPVEKI HPLLKEVLGY  120
KIDHQVSVYI VAVLEYISAD ILKLVGNYVR NIRHYEITKQ DIKVAMCADK VLMDMFHQDV  180
EDINILSLTD EEPSTSGEQT YYDLVKAFMA EIRQYIRELN LIIKVFREPF VSNSKLFSAN  240
DVENIFSRIV DIHELSVKLL GHIEDTVEMT DEGSPHPLVG SCFEDLAEEL AFDPYESYAR  300
DILRPGFHDR FLSQLSKPGA ALYLQSIGEG FKEAVQYVLP RLLLAPVYHC LHYFELLKQL  360
EEKSEDQEDK ECLKQAITAL LNVQSGMEKI CSKSLAKRRL SESACRFYSQ QMKGKQLAIK  420
KMNEIQKNID GWEGKDIGQC CNEFIMEGTL TRVGAKHERH IFLFDGLMIC CKSNHGQPRL  480
PGASNAEYRL KEKFFMRKVQ INDKDDTNEY KHAFEIILKD ENSVIFSAKS AEEKNNWMAA  540
LISLQYRSTL ERMLDVTMLQ EEKEEQMRLP SADVYRFAEP DSEENIIFEE NMQPKAGIPI  600
IKAGTVIKLI ERLTYHMYAD PNFVRTFLTT YRSFCKPQEL LSLIIERFEI PEPEPTEADR  660
IAIENGDQPL SAELKRFRKE YIQPVQLRVL NVCRHWVEHH FYDFERDAYL LQRMEEFIGT  720
VRGKAMKKWV ESITKIIQRK KIARDNGPGH NITFQSSPPT VEWHISRPGH IETFDLLTLH  780
PIEIEIARQLTL LESDLYRAVQ PSELVGSVWT KEDKEINSPN LLKMIRHTTN LTLWFEKCIV  840
ETENLEERVA VVSRIIEILQ VFQELNNFNG VLEVVSAMNS SPVYRLDHTF EQIPSRQKKI  900
LEEAHELSED HYKKYLAKLR SINPPCVPFF GIYLTNILKT EEGNPEVLKR HGKELINFSK  960
RRKVAEITGE IQQYQNQPYC LRVESDIKRF FENLNPMGNS MEKEFTDYLF NKSLEIEPRN 1020
PKPLPRFPKK YSYPLKSPGV RPSNPRPGTM RHPTPLQQEP RKISYSRIPE SETESTASAP 1080
NSPRTPLTPP PASGASSTTD VCSVPDSDHS SPFHSSNDTV FIQVTLPHGP RSASVSSISL 1140
TKGTDEVPVP PPVPPRRRPE SAPAESSPSK IMSKHLDSPP AIPPRQPTSK AYSPRYSISD 1200
RTSISDPPES PPLLPPREPV RTPDVFSSSP LHLQPPPLGK KSDHGNAFFP NSPSPFTPPP 1260
PQTPSPHGTR RHLPSPPLTQ EVDLHSIAGP PVPPRQSTSQ HIPKLPPKTY KREHTHPSMH 1320
RDGPPLLENA HSS                                                   1333

SEQ ID NO: 4            moltype =   length =
SEQUENCE: 4
000

SEQ ID NO: 5            moltype = AA   length = 1332
FEATURE                 Location/Qualifiers
source                  1..1332
                        mol_type = protein
                        organism = Homo sapiens
SEQUENCE: 5
MQQAPQPYEF FSEENSPKWR GLLVSALRKV QEQVHPTLSA NEESLYYIEE LIFQLLNKLC   60
MAQPRTVQDV EERVQKTFPH PIDKWAIADA QSAIEKRKLL PLLLPVDKI HPSLKEVLGY  120
KVDYHVSLYI VAVLEYISAD ILKLAGNYVF NIRHYEISQQ DIKVSMCADK VLMDMFDQDD  180
IGLVSLCEDE PSSSGELNYY DLVRTEIAEE RQYLRELNMI IKVFREAFLS DRKLFKPSDI  240
EKIFSNISDI HELTVKLLGL IEDTVEMTDE SSPHPLAGSC FEDLAEEQAF DPYETLSQDI  300
LSPEFHEHFN KLMARPAVAL HFQSIADGPK EAVRYVLPML MLVPVYHCWH YFELLKQLKA  360
CSEEQEDREC LNQAITALMN LQGSMDRIYK QYSPRRRPGD PVCPFYSHQL RSKHLAIKKM  420
NEIQKNIDGW EGKDIGQCCN EFIMEGPLTR IGAKHERHIF LFDGLMISCK PNHGQTRLPG  480
YSSAEYRLKE KFVMRKIQIC DKEDTCEHKH AFELVSKDEN SIIFAAKSAE EKNNWMAALI  540
SLHYRSTLDR MLDSVLLKEE NEQPLRLPSP EVYRFVVKDS EENIVFEDNL QSRSGIPILK  600
GGTVVKLIER LTYHMYADPN FVRTFLTTYR SFCKPQELLS LLIERFEIPE PEPTDADKLA  660
IEKGEQPISA DLKRFRKEYV QPVQLRILNV FRHWVEHHFY DFERDLELLE RLESFISSVR  720
GKAMKKWVES IAKIIRRKKQ AQANGVSHNI TFESPPPPIE WHISKPGQFE TFDLMTLHPI  780
EIARQLTLLE SDLYRKVQPS ELVGSVWTKE DKEINSPNLL KMIRHTTNLT LWFEKCIVEA  840
ENFEERVAVL SRIIEILQVF QDLNNFNGVL EIVSAVNSVS VYRLDHTFEA LQERKRKILD  900
EAVELSQDHF KKYLVKLKSI NPPCVPFFGI YLTNILKTEE GNNDFLKKKG KDLINFSKRR  960
KVAEITGEIQ QYQNQPYCLR IEPDMRRFFE NLNPMGSASE KEFTDYLFNK SLEIEPRNCK 1020
QPPRFPRKST FSLKSPGIRP NTGRHGSTSG TLRGHPTPLE REPCKISFSR IAETELESTV 1080
SAPTSPNTPS TPPVSASSDL SVFLDVDLNS SCGSNSIFAP VLLPHSKSFF SSCGSLHKLS 1140
EEPLIPPPLP PRKKFDHDAS NSKGNMKSDD DPPAIPPRQP PPKVKPRVP VPTGAFDGPL 1200
HSPPPPPPRD PLPDTPPPVP LRPPEHFINC PFNLQPPPLG HLHRDSDWLR DISTCPNSPS 1260
TPPSTPSPRV PRRCYVLSSS QNNLAHPPAP PVPPRQNSSP HLPKLPPKTY KRELSHPPLY 1320
RLPLLENAET PQ                                                    1332

SEQ ID NO: 6            moltype = AA   length = 10
FEATURE                 Location/Qualifiers
```

```
REGION          1..10
                note = Description of Artificial Sequence: Synthetic 10xHis
                tag
source          1..10
                mol_type = protein
                organism = synthetic construct
SEQUENCE: 6
HHHHHHHHHH                                                                10
```

UNITED STATES PATENT AND TRADEMARK OFFICE
CERTIFICATE OF CORRECTION

Page 1 of 2

PATENT NO. : 12,195,465 B2
APPLICATION NO. : 18/497515
DATED : January 14, 2025
INVENTOR(S) : Wu et al.

It is certified that error appears in the above-identified patent and that said Letters Patent is hereby corrected as shown below:

In the Claims

Claim 1, Column 639, Line 15, should read:

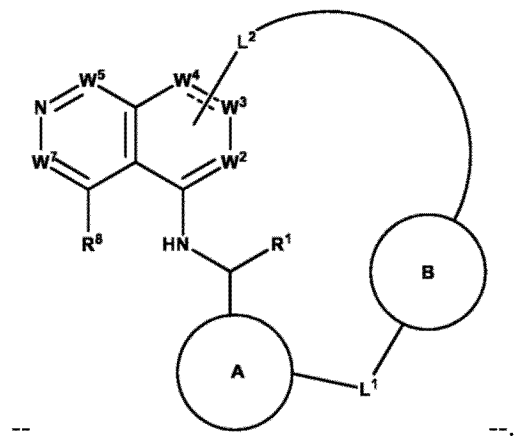

-- --.

Claim 1, Column 641, Line 48, delete "—N($R^{24}$) C(O)N($R^{22}$)($R^{23}$), —N($R^{24}$) C(O)O$R^{25}$," and insert -- —N($R^{24}$)C(O)N($R^{22}$)($R^{23}$), —N($R^{24}$) C(O)O$R^{25}$, --.

Claim 1, Column 641, Line 60, delete "—N($R^{24}$) C(O)N($R^{22}$)($R^{23}$), —N($R^{24}$) C(O)O$R^{25}$," and insert -- —N($R^{24}$)C(O)N($R^{22}$)($R^{23}$), —N($R^{24}$) C(O)O$R^{25}$, --.

Signed and Sealed this
Twenty-ninth Day of July, 2025

Coke Morgan Stewart
*Acting Director of the United States Patent and Trademark Office*

CERTIFICATE OF CORRECTION (continued)
U.S. Pat. No. 12,195,465 B2

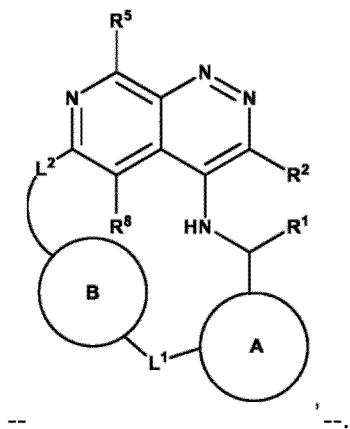

Claim 2, Column 643, Line 60, should read: